(12) United States Patent
Shimma et al.

(10) Patent No.: US 8,022,205 B2
(45) Date of Patent: Sep. 20, 2011

(54) PYRIMIDINE DERIVATIVES AS PI3K INHIBITOR AND USE THEREOF

(75) Inventors: Nobuo Shimma, Kamakura (JP); Hirosato Ebiike, Kamakura (JP); Jun Ohwada, Kamakura (JP); Hatsuo Kawada, Kamakura (JP); Kenji Morikami, Gotemba (JP); Mitsuaki Nakamura, Kamakura (JP); Miyuki Yoshida, Kamakura (JP); Nobuya Ishii, Kamakura (JP); Masami Hasegawa, Kamakura (JP); Shun Yamamoto, Kamakura (JP); Kohei Koyama, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 335 days.

(21) Appl. No.: 12/376,039

(22) PCT Filed: Aug. 7, 2007

(86) PCT No.: PCT/JP2007/065396
§ 371 (c)(1),
(2), (4) Date: Feb. 2, 2009

(87) PCT Pub. No.: WO2008/018426
PCT Pub. Date: Feb. 14, 2008

(65) Prior Publication Data
US 2010/0069629 A1   Mar. 18, 2010

(30) Foreign Application Priority Data

Aug. 8, 2006 (JP) ................................. 2006-216108
Apr. 27, 2007 (JP) ................................. 2007-118631

(51) Int. Cl.
C07D 401/04 (2006.01)
C07D 401/12 (2006.01)
C07D 405/04 (2006.01)
C07D 413/12 (2006.01)
(52) U.S. Cl. ......... 544/114; 544/320; 544/330; 544/331
(58) Field of Classification Search .................. 544/114, 544/320, 330, 331
See application file for complete search history.

(56) References Cited

U.S. PATENT DOCUMENTS 4,959,368 A   9/1990 Awaya et al.
5,378,700 A   1/1995 Sakuma et al.
7,423,148 B2 * 9/2008 Nuss et al. .................... 544/320

FOREIGN PATENT DOCUMENTS

| JP | 08-325268 A | 12/1996 |
| JP | 2006-514118 A | 4/2006 |
| WO | WO 91/05784 A1 | 5/1991 |
| WO | WO 02/059083 A2 | 8/2002 |
| WO | WO 2004/043367 A2 | 5/2004 |
| WO | WO 2004/048365 A1 | 6/2004 |
| WO | WO 2004/099209 A1 | 11/2004 |

OTHER PUBLICATIONS

Kiselyov et al., "Viehe's salt in a novel one pot synthesis of pyrimidines," Tetrahedron Letters, 2005, 46:1177-1179.
Vlahos et al., "A Specific Inhibitor of Phosphatidylinositol 3-Kinase, 2-(4-Morpholinyl)-8-phenyl-4H-1-benzopyran-4-one (LY294002)," J. Biol. Chem., Feb. 18, 1994, 269(7):5241-5248.
Yano et al., "Inhibition of Histamine Secretion by Wortmannin through the Blockade of Phosphatidylinositol 3-Kinase in RBL-2H3 Cells," J. Biol. Chem., Dec. 5, 1993, 268(34):25846-25856.
Supplementary European Search Report dated Mar. 1, 2011, in corresponding EP 07792065.0, 6 pages.

* cited by examiner

Primary Examiner — Susannah Chung
(74) Attorney, Agent, or Firm — Foley & Lardner LLP

(57) ABSTRACT

A drug is provided that is useful as a preventive or therapeutic for cancer as a result of having superior PI3K inhibitory effects as well as superior stability in the body and water-solubility.

A compound, or pharmaceutically acceptable salt thereof, represented by formula (I):

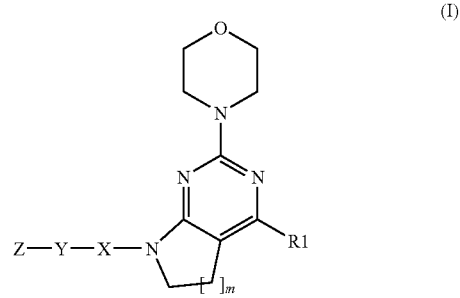

[wherein, X represents a single bond, etc.; Y represents a single bond, etc. (provided that X and Y are not simultaneously single bonds); Z represents a hydrogen atom, etc.; m represents an integer of 1 or 2; and $R^1$ represents a cyclic substituent].

18 Claims, No Drawings

PYRIMIDINE DERIVATIVES AS PI3K INHIBITOR AND USE THEREOF

CROSS-REFERENCE TO RELATED APPLICATIONS

This application is a National Stage application of PCT/JP2007/065396, filed Aug. 7, 2007, which claims priority from Japanese applications JP 2006-216108, filed Aug. 8, 2006, and JP 2007-118631, filed Apr. 27, 2007.

TECHNICAL FIELD

The present invention relates to a novel condensed pyrimidine derivative and a pharmaceutically acceptable salt thereof, a pharmaceutical composition containing the same, and synthetic intermediates and the like thereof.

BACKGROUND ART

Phosphatidylinositol 3-kinase (PI3K) is known as a kind of phosphorylases of phosphatidylinositol that phosphorylates 3-position of an inositol ring, and is expressed over a wide range throughout the body. The PI3K is known to be activated by stimulation including growth factors, hormones and the like, activate Akt and PDK1, and be involved in survival signals that inhibit cell death, cytoskeleton, glucose metabolism, vesicular transport and the like. In addition, the phosphatidylinositols phosphorylated at position 3 that are formed by PI3K function as messengers of these information transfer systems (Phosphatidylinositol 3-kinases in tumor progression. Eur. J. Biochem. 268, 487-498 (2001); Phosphoinositide 3-kinase: the key switch mechanism in insulin signaling. Biochem. J. 333, 471-490 (1998); Distinct roles of class I and class III phosphatidylinositol 3-kinase in phagosome formation and maturation. J. C. B., 155(1), 19-25 (2001) and the like).

PI3K is categorized into three classes consisting of Class I, Class II and Class III according to the type of phosphatidylinositols serving as a substrate.

Although Class 1 enzymes form phosphatidylinositol (3,4,5)-triphosphate [PI(3,4,5)P3] by using phosphatidylinositol (4,5)-bisphosphate [PI(4,5)P2] as a substrate in vivo, it is able to use phosphatidylinositol (PI) and phosphatidylinositol (4)-phosphate [PI(4)P] as a substrates in vitro. Further, Class I enzymes are categorized into Class Ia and Ib according to the activation mechanism. Class Ia includes the p110α, p110β and p110δ subtypes, and each forms a heterodimer complex with a regulatory subunit (p85) and is activated by a tyrosine kinase receptor and the like. Class 1b includes a p110γ subtype that is activated by the βγ subunit (Gβγ) of a trimer G protein, and forms a heterodimer with a regulatory subunit (p110).

Class II enzymes include the PI3KC2α, C2β and C2γ subtypes, that use PI and PI(4)P as substrates. These enzymes have a C2 domain on the C terminal, and regulatory subunits as observed for Class I enzymes have not yet to be discovered.

Class III enzymes only use PI as a substrate, and are reported to be involved in membrane transport control as a result of interaction between p150 and human Vps34, a human homolog of Vps34 isolated from yeast.

As a result of analyses using these PI3K knockout mice, p110δ in Class Ia has been reported to be involved in the differentiation and function of T cells and B cells, while p110γ in Class 1b has been reported to be involved in abnormalities of migration of eosinophils, mast cells, platelets and myocardial cells (Phosphoinositide 3-kinase signaling—which way to target? Trends in Pharmacological Science, 24(7), 366-376 (2003)).

On the basis of these results, the targeting of p110δ and p110γ of Class I is expected to be useful against autoimmune diseases, inflammations, asthma, heart disease and the like.

Recently, a gene amplification of PIK3CA encoding p110α, constitutive activation due to mutation, and high expression of p110α at the protein level have been reported in numerous types of cancers (and particularly ovarian cancer, colon cancer and breast cancer). As a result, inhibition of apoptosis by constitutive activation of survival signals is believed to be partially responsible for the mechanism of tumorigenesis (PIK3CA is implicated as an oncogene in ovarian cancer. Nature Genet. 21, 99-102, (1999); High frequency of mutations of the PIK3CA gene in human cancers. Science, 304, 554, (2004); Increased levels of phosphoinositol 3-Kinase activity in colorectal tumors. Cancer, 83, 41-47 (1998)).

In addition, the deletion or mutation of PTEN, a phospholipid phosphatase which hydrolizes PI(3,4,5)P3 that is one of the products of PI3K, has been reported in numerous cancers. Since PTEN functions as a suppressor of PI3K as a result of using PI(3,4,5)P3 as a substrate, deletion or mutation of PTEN is thought to lead to activation of PI3K in the PI3K signal.

On the basis of these reasons, useful anticancer action is expected to be obtained by inhibiting the activity of p110α in particular in cancers with elevated PI3K activity.

In this manner, Wortmannin (Non-Patent Document 1) and LY294002 (Non-Patent Document 2) are known to be specific inhibitors of PI3K, that are expected to be useful in the fields of immune diseases, anti-inflammatory agents, anticancer agents and the like.

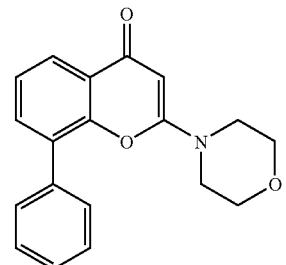

LY294002

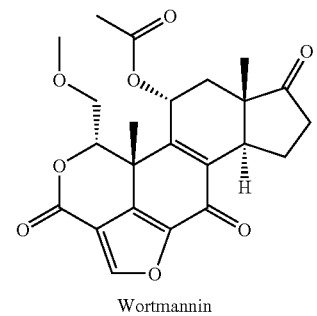

Wortmannin

Although numerous compounds having PI3K inhibitory action have recently been reported, none have yet to be used in clinical studies as pharmaceuticals in the form of anticancer agents, and have been limited to experimental studies on anticancer action based on the PI3K inhibitory action thereof, thus creating the desire for the prompt development of anticancer agents and the like having PI3K inhibitory action that are able to be used clinically.

On the other hand, compounds composed of a simple structure having a dimethylamino group at position 4 are known as multisubstituted bicyclic pyrimidines, and particularly 2-morpholin-4-yl-6,7-dihydro-5H-pyrrolo[2,3-d]pyrimidine derivatives (see Non-Patent Document 3). Although these derivatives have been suggested to have effect on hypoxemia accompanying respiratory diseases, their anticancer action or PI3K inhibitory action has neither been disclosed nor suggested.

Separate from this, 2-morpholin-4-yl-6,7-dihydro-5H-pyrrolo[2,3-d]pyrimidine derivatives having a nitrogen atom-mediated substituent or linear hydrocarbon group at 4-position have been reported to be effective against hypoxemia accompanying respiratory diseases (see Patent Document 1). However, their anticancer action or PI3K inhibitory action has neither been disclosed nor suggested.

In contrast, a compound of the present invention to be described to follow in the form of 2-morpholin-4-yl-6,7-dihydro-5H-pyrrolo[2,3-d]pyrimidine derivatives or 2-morpholin-4-yl-5,6,7,8-tetrahydro-pyrrido[2,3-d]pyrimidine derivatives having an unsaturated cyclic group directly bonded to a carbon atom at 4-position as in general formula (I) has heretofore not been known, and the usefulness of these derivatives as anticancer agents and the like having PI3K inhibitory action is also not known.

Patent Document 1: WO9105784

Non-Patent Document 1: H. Yano et al., J. Biol. Chem., 268, 25846, 1993

Non-Patent Document 2: C. J. Vlahos et al., J. Biol. Chem., 269, 5241, 1994

Non-Patent Document 3: Tetrahedron Letter 46 (2005), 1177-1179

DISCLOSURE OF THE INVENTION

Problems to be Solved by the Invention

As a result of conducting extensive studies to develop a compound that is useful as an anticancer agent having inhibitory activity on PI3K and superior safety, the inventors of the present invention found that a 2-morpholin-4-yl-6,7-dihydro-5H-pyrrolo[2,3-d]pyrimidine derivative or 2-morpholin-4-yl-5,6,7,8-tetrahydro-pyrrido[2,3-d]pyrimidine derivative, in which a specific unsaturated cyclic group is bonded directly to a carbon atom of said cyclic group at position 4 by using the encircled portion of general formula (I') indicated below as a matrix, has a superior PI3K inhibitory effect as well as superior stability in a body and water solubility allowing it to be a useful drug for the prevention or treatment of cancer, thereby leading to completion of the present invention. Further, the inventors also found the compounds useful as a synthesis intermediate, leading to completion of the present invention.

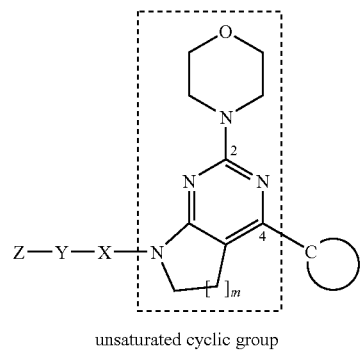

unsaturated cyclic group

Means for Solving the Problems

Namely, the present invention provides a compound indicated below, a pharmaceutical composition comprising that compound, and synthesis intermediates thereof.

The present invention relates to a compound, or pharmaceutically acceptable salt thereof, represented by formula (I):

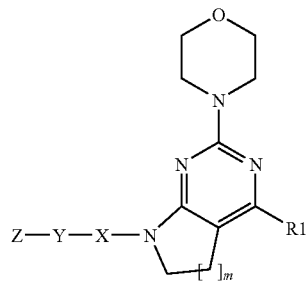

[wherein,

X represents a single bond, or a linking group selected from —CO—, —SO$_2$—, —CS— or —CH$_2$—;

Y represents a single bond or a divalent linking group derived from a ring selected from benzene, pyridine, pyrimidine, pyrazole, imidazole, oxazole, thiazole, furan, thiophene, quinoline, benzoimidazole, benzothiazole, benzopyrazole, naphthalene and benzothiophene (said linking group may be unsubstituted or substituted at 1 to 6 locations by a halogen atom, —C$_{1-6}$ alkyl or —OC$_{1-6}$ alkyl);

X and Y are not simultaneously single bonds;

Z represents a hydrogen atom or a substituent selected from the following group A:

Group A:
—C$_{1-6}$alkyl,
-ethynyl,
-halogenoC$_{1-6}$alkyl,
-Cyc,
—C$_{1-6}$alkylene-OR,
—C$_{1-6}$alkylene-COR,
—C$_{1-6}$alkylene-COOR,
—C$_{1-6}$alkylene-CONRR',
—C$_{1-6}$alkylene-NRR',
—C$_{1-6}$alkylene-Cyc,
—C$_{1-6}$alkylene-CO-Cyc,
—C$_{1-6}$alkylene-O—C$_{1-6}$alkylene-Cyc,
—C$_{1-6}$alkylene-SO$_2$R,
—C$_{1-6}$alkylene-SO$_2$-Cyc, -halogen,
—CN,
—SO$_2$R,
—SO$_2$—NRR',
—SO$_2$—NR-Cyc,
—SO$_2$—NR—C$_{1-6}$alkylene-Cyc,
—SO$_2$-Cyc,
—COR,
—CO-Cyc,
—CO-Cyc-C$_{1-6}$alkylene-Cyc,
—CO—C$_{1-6}$alkylene-Cyc,
—CO-Cyc-Cyc,
—COOR,
—CONRR',
—CONR—C$_{1-6}$alkylene-OR,
—CONR—C$_{1-6}$alkylene-CONR'R",
—CONR-Cyc,
—CONR—C$_{1-6}$alkylene-Cyc,
—OR,
—O-allyl,
—O-halogenoC$_{1-6}$alkyl,
—O—C$_{1-6}$alkylene-NRR',
—O—C$_{1-6}$alkylene-CONRR',
—O—C$_{1-6}$alkylene-NRCOR,
—NRR',
—NH—NH$_2$,
—NRCOR',
—NRCO-Cyc,
—NRCO—C$_{1-6}$alkylene-Cyc,
—NRCO—C$_{1-6}$alkylene-OR,
—NR—C$_{1-6}$alkylene-COOR,
—NR—C$_{1-6}$alkylene-CONR'R",
—NR—C$_{1-6}$alkylene-NR'R",
—NR—C$_{1-6}$alkylene-NR'COR",
—NR—C$_{1-6}$alkylene-OR',
—NR-Cyc,
—NR-Cyc-Cyc,
—NR-Cyc-CO-Cyc,
—NR-Cyc-CO—C$_{1-6}$alkylene-Cyc,
—NR-Cyc-NR'-Cyc,
—NR-Cyc-NR'—C$_{1-6}$alkylene-Cyc,
—NR—C$_{1-6}$alkylene-Cyc,
—NR—C$_{1-6}$alkylene-Cyc-CO-Cyc,
—NR—C$_{1-6}$alkylene-Cyc-NR'-Cyc,
—NRSO$_2$R',
—S—C$_{1-6}$alkylene-CO-Cyc,
—S—C$_{1-6}$alkylene-COOR',
—S—C$_{1-6}$alkylene-NRCOR', and
—S—C$_{1-6}$alkylene-CONRR';

m represents an integer of 1 or 2;

R$^1$ represents a cyclic substituent selected from the following group having n substituents T;

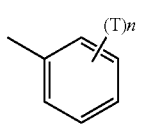
R$_1$a

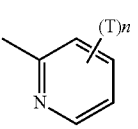
R$_1$b1

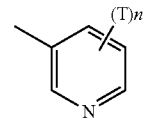
R$_1$b2

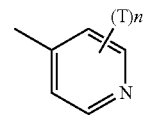
R$_1$b3

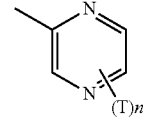
R$_1$c1

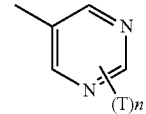
R$_1$c2

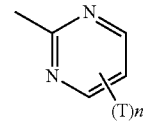
R$_1$c3

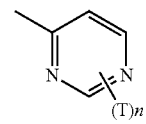
R$_1$c4

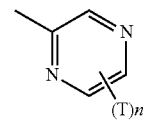
R$_1$c5

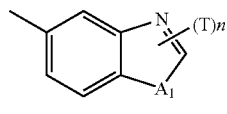
R$_1$d

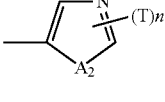
R$_1$e

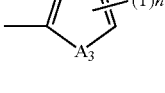
R$_1$f

A$_1$, A$_2$ and A$_3$ are respectively and independently selected from NH, S or O;

T represents a substituent selected from the following group B:

Group B:
-Cyc,
—C$_{1-6}$alkyl,
—C$_{1-6}$alkylene-OR,
—C$_{1-6}$alkylene-NRR',
—C$_{1-6}$alkylene-CONRR',
—C$_{1-6}$alkylene-NRCOR',
—C$_{1-6}$alkylene-Cyc,
—OR, —O-halogenoC$_{1-6}$alkyl,
—O—C$_{1-6}$alkylene-Cyc,
—O—COOR,
—O—COR,
—O—CONRR',
—NRR',
—NR—C$_{1-6}$alkylene-NR'R",
—NR—C$_{1-6}$alkylene-OR',
-halogen,
—CO-Cyc,
—CO-CyC-Cyc,
—CO—C$_{1-6}$alkylene-Cyc,
—COOR,
—COO—C$_{1-6}$alkylene-OR,
—COO—C$_{1-6}$alkylene-NRR',
—COO—C$_{1-6}$alkylene-Cyc,
—CONRR',
—CONR—C$_{1-6}$alkylene-OR',
—CONR—C$_{1-6}$alkylene-NR'R",
—CONR—C$_{1-6}$alkylene-CONR'R",
—CONR-Cyc,
—CONR—C$_{1-6}$alkylene-Cyc,
—SO$_2$NRR',
—NRSO$_2$R',
—CN, and
—NH—NH$_2$;

n represents an integer of 0, 1, 2, 3, 4 or 5 (T may be the same or different when n is 2 to 5);

in the aforementioned group A and group B,

R, R' and R" may be respectively and independently the same or different and represent a hydrogen atom or a —C$_{1-6}$ alkyl (said —C$_{1-6}$ alkyl may be substituted by a group selected from —OH, —O(C$_{1-6}$ alkyl), —COOH, —COO(C$_{1-6}$ alkyl), —CONH$_2$, —CONH(C$_{1-6}$ alkyl), —CON(C$_{1-6}$ alkyl)$_2$, —NHCO(C$_{1-6}$ alkyl), —NH$_2$, —NH(C$_{1-6}$ alkyl) and —N(C$_{1-6}$ alkyl)$_2$);

Cyc represents a hydrocarbon ring or nitrogen-containing heterocyclic ring (said hydrocarbon ring and nitrogen-containing heterocyclic ring may be substituted at 1 to 3 locations by a group selected from —R (R is not a hydrogen atom at this time), —CO—R', —COOR, —CONRR', —NRCOR', -halogeno C$_{1-6}$ alkyl, halogen atom, —OR, —O-halogeno C$_{1-6}$ alkyl, —NRR' and —SO$_2$R);

said C$_{1-6}$ alkylene in the groups A and B may be substituted at 1 to 3 locations by a group selected from —C$_{1-6}$ alkyl, —OH, —CONH$_2$, —NH$_2$, —NH(C$_{1-6}$ alkyl) and —N(C$_{1-6}$alkyl)$_2$; and R, R' and R" of said —NRR', —NR'R" or —CONRR' in the group A, group B and Cyc may form a 3- to 7-member nitrogen-containing saturated hydrocarbon ring together with an adjacent N].

The present invention also relates to a compound represented by general formula (II) that is useful as a synthesis intermediate of the compound of formula (I):

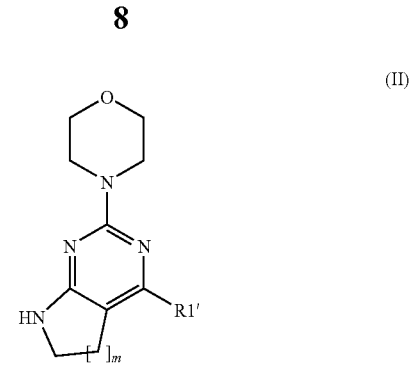

(II)

[wherein, m is the same as defined in formula (I), and R$^{1'}$ represents a group having the same meaning as R$^1$ of formula (I), or R$^1$ protected with a protecting group].

The present invention also relates to a pharmaceutical composition comprising as an active ingredient thereof the above compound of formula (I) or a pharmaceutically acceptable salt thereof; a PI3K inhibitor comprising as an active ingredient thereof the above compound of formula (I) or a pharmaceutically acceptable salt thereof; and a preventive agent or therapeutic agent of a proliferative disease comprising as an active ingredient thereof the above compound of formula (I) or a pharmaceutically acceptable salt thereof.

Effects of the Invention

Since the compound of the present invention represented by formula (I) has superior PI3K inhibitory effects, superior cell proliferation inhibitory action and superior stability in a body and water solubility, it can be used as a preventive agent or therapeutic agent for a proliferative disease such as cancer. In addition, some of the compounds among the compounds represented by formula (I) are also useful as synthesis intermediates of other compounds. In addition, the compound represented by formula (II) is useful as a synthesis intermediate of the compound of the present invention represented by formula (I).

BEST MODE FOR CARRYING OUT THE INVENTION

The following provides an explanation of the compound of the present invention, a production process thereof and a pharmaceutical containing that compound.

The terms used in the present specification are defined as described below.

In the present specification, —C$_{1-6}$ alkyl refers to a linear or branched, monovalent saturated hydrocarbon group having 1 to 6 carbon atoms, and a preferable example thereof is an alkyl group having 1 to 4 carbon atoms (—C$_{1-4}$alkyl). Specific examples include -methyl, -ethyl, -n-propyl, -isopropyl, -n-butyl, -isobutyl, -t-butyl, -sec-butyl, -n-pentyl, -n-hexyl, -1-methylpentyl, -2-methylpentyl, -3-methylpentyl, -4-methylpentyl, -1,1-dimethylbutyl, -1,2-dimethylbutyl, -1,3-dimethylbutyl, -2,2-dimethylbutyl, -2,3-dimethylbutyl, -3,3-dimethylbutyl, -1-ethylbutyl, -2-ethylbutyl, -1,1,2-trimethylpropyl and -1,2,2-trimethylpropyl, while particularly preferable examples include -methyl, -ethyl, n-propyl and isopropyl.

In the present specification, —C$_{1-6}$ alkylene refers to a linear, divalent saturated hydrocarbon group having 1 to 6 carbon atoms, and specific examples of —C$_{1-6}$ alkylene include methylene, ethylene, propylene, butylene, pentylene and hexylene, and preferably methylene, ethylene, propylene and butylene. In addition, the —$C_{1-6}$ alkylene may be substituted by a group selected from —$C_{1-6}$ alkyl, —OH, —$CONH_2$, —$NH_2$, —NH($C_{1-6}$ alkyl) and —N($C_{1-6}$ alkyl)$_2$. The —$C_{1-6}$alkylene is preferably substituted by a group selected from —OH, -methyl or -dimethylamino or is unsubstituted.

In the present specification, -allyl refers to -2-propenyl (—$CH_2$—CH=$CH_2$).

In the present specification, -halogen refers to a monovalent group derived from a halogen atom (for example, F, Cl, Br or I). Examples include —F, —Cl, —Br and —I, and preferably —F and —Cl.

A -halogeno-$C_{1-6}$ alkyl refers to the above —$C_{1-6}$ alkyl substituted with one or more of the above halogen atoms, and preferably a —$C_{1-4}$alkyl substituted with one or more —F or —Cl and more preferably one or more fluorine atoms, examples of which include -fluoro $C_{1-4}$alkyl such as —trifluoromethyl, -difluoromethyl, -monofluoromethyl, -pentafluoroethyl, -tetrafluoroethyl, -trifluoroethyl, -difluoroethyl, -monofluoroethyl, -heptafluoropropyl, -hexafluoropropyl, -pentafluoropropyl, -tetrafluoropropyl, -trifluoropropyl, -difluoropropyl, -monofluoropropyl, -nanofluorobutyl, -octafluorobutyl, -heptafluorobutyl, -hexafluorobutyl, -pentafluorobutyl, -tetrafluorobutyl, -trifluorobutyl, -difluorobutyl and -monofluorobutyl, and -chloro $C_{1-4}$alkyl groups such as -trichloromethyl, -dichloromethyl, -monochloromethyl, -pentachloroethyl, -tetrachloroethyl, -trichloroethyl, -dichloroethyl and -monochloroethyl. The -halogeno-$C_{1-6}$ alkyl is more preferably -trifluoromethyl, -2-fluoroethyl, -2,2,2-trifluoroethyl, -3,3,3-trifluoropropyl or -4-fluorobutyl.

In the present specification, unless specifically indicated otherwise, a hydrocarbon ring refers to an aromatic or non-aromatic monocyclic or bicyclic ring that can be present in the form of a monovalent or divalent hydrocarbon cyclic group. The number of atoms that compose the ring may be 3 to 10, and is preferably 6 to 10 when in the form of an unsaturated hydrocarbon ring, 3 to 6 when in the form of a saturated hydrocarbon ring, or 6 to 10 when in the form of a partially unsaturated hydrocarbon ring. Specific examples of hydrocarbon rings include aromatic hydrocarbon rings such as benzene or naphthalene; specific examples of non-aromatic hydrocarbon rings include saturated hydrocarbon rings such as cyclopropane, cyclobutane, cyclopentane, cyclohexane, spiro[2.3]hexane or spiro[3.3]heptane, and partially unsaturated hydrocarbon rings such as indane, tetrahydronaphthalene, cyclopropene, cyclobutene, cyclopentene or cyclohexene. A preferable example of a hydrocarbon ring is benzene.

In addition, a nitrogen-containing heterocyclic ring, unless specifically indicated otherwise, refers to an aromatic or non-aromatic monocyclic or bicyclic ring having 3 to 12 ring members, and preferably 5 to 6 ring members, which, in addition to ring members in the form of carbon atoms, may also contain at least one nitrogen atom, and may additionally contain 1 to 2 heteroatoms selected from nitrogen, oxygen and sulfur, and can also be present in the form of a monovalent or divalent nitrogen-containing heterocyclic group. Although the ring may be monocyclic or bicyclic, it is preferably monocyclic. Specific examples of such nitrogen-containing heterocyclic rings include aromatic heterocyclic rings such as pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, quinoline, isoquinoline, quinoxaline, quinazoline, phthalazine, purine or pteridine, and non-aromatic heterocyclic rings such as azirizine, azetidine, pyrrolidine, imidazoline, oxazoline, imidazolidine, oxazolidine, thiazine, piperidine, piperazine, morpholine or azepane. Preferable examples of nitrogen-containing heterocyclic rings include azirizine, azetidine, pyrrolidine, pyrazole, thiazole, pyridine, pyrimidine, piperidine, piperazine, morpholine and azepane, while particularly preferable examples include azirizine, azetidine, pyrrolidine, pyrazole, thiazole, pyridine, pyrimidine, morpholine, piperazine, piperidine and azepane.

In the present specification, groups typically used as protecting groups for —OH, groups used as protecting groups for primary amino and secondary amino, groups used as protecting groups for —COOH and groups used as protecting groups for —COH can be used as "protecting groups" without any particular limitations thereon.

Examples of protecting groups for —OH include $C_{1-6}$alkyl protecting groups such as a methyl, ethyl or t-butyl group; $C_{1-6}$ alkenyl protecting groups such as an allyl or vinyl group; acetal protecting groups such as a tetrahydropyran-2-yl (THP), tetrahydrothiopyran-2-yl, 1,4-dioxan-2-yl or tetrahydrofuran-2-yl group; alkylsilyl protecting groups such as a trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl, diphenylisopropylsilyl or phenyldiisopropylsilyl group; $C_{1-6}$alkylcarbonyl protecting groups such as an acetyl or propionyl group; phenylcarbonyl groups; $C_{1-6}$alkyloxycarbonyl protecting groups such as a methoxycarbonyl, ethoxycarbonyl or t-butoxycarbonyl group; $C_{1-6}$ alkoxymethyl protecting groups such as a methoxymethyl or ethoxymethyl group; $C_{1-6}$ alkoxyalkoxymethyl protecting groups such as a 2-methoxyethoxymethyl group; alkoxyethyl protecting groups such as a 1-ethoxyethyl group; benzyloxymethyl groups; benzyl protecting groups such as a benzyl, 4-methylbenzyl, 2-methoxybenzyl, 4-methoxybenzyl, 2,4-dimethoxybenzyl or o-nitrobenzyl group; and formyl groups. Among these, $C_{1-6}$ alkyl and acetal protecting groups are preferable, while t-butyl and tetrahydropyran-2-yl (THP) groups are more preferable.

Examples of groups used as protecting groups for primary amino and secondary amino include $C_{1-6}$alkoxycarbonyl protecting groups such as a methoxycarbonyl group; substituted $C_{1-6}$ alkyloxycarbonyl protecting groups such as a cyclopropylmethoxycarbonyl, 2,2,2-trichloroethoxycarbonyl, 2-iodoethoxycarbonyl, 2-trimethylsilylethoxycarbonyl, 2-methylthioethoxycarbonyl, 2-methylsulfonylethoxycarbonyl, isobutyroxycarbonyl or t-butoxycarbonyl (BOC) group; $C_{1-6}$ alkenyloxycarbonyl protecting groups such as a vinyloxycarbonyl or allyloxycarbonyl group; benzyloxycarbonyl (CBZ) groups; benzyloxycarbonyl protecting groups such as a p-methoxybenzyloxycarbonyl, 2,4-dichlorobenzyloxycarbonyl or p-cyanobenzyloxycarbonyl group; formyl groups; acetyl groups; substituted $C_{1-6}$ alkylcarbonyl protecting groups such as a dichloroacetyl, trichloroacetyl or trifluoroacetyl group; phthalimido groups (name of functional group after being protected); benzyl groups; and, benzyl protecting groups such as a 2-methoxybenzyl, 4-methoxybenzyl, 3,4-dimethoxybenzyl or 2,4-dimethoxybenzyl group. Among these, benzyl protecting groups, substituted $C_{1-6}$ alkyloxycarbonyl protecting groups and substituted $C_{1-6}$alkylcarbonyl protecting groups are preferable, while 4-methoxybenzyl, 2,4-dimethoxybenzyl, BOC and acetyl groups are more preferable.

Examples of groups used as protecting groups for —COOH include $C_{1-6}$ alkyl protecting groups such as a methyl, ethyl, t-butyl or allyl group; benzyl protecting groups such as a p-nitrobenzyl, p-bromobenzyl or benzyl group;

phenyl groups and p-nitrophenyl groups. Among these, $C_{1-6}$alkyl protecting groups are preferable, while a methyl group is more preferable.

Preferable examples of groups used as protecting groups for —COH include cycloacetal protecting groups such as a dimethoxymethyl, diethoxymethyl, 1,3-dioxan-2-yl or 1,3-dioxolan-2-yl group, while a 1,3-dioxan-2-yl or 1,3-dioxolan-2-yl group is more preferable.

Compound of Formula (I)

The compound of formula (I) of the present invention is represented by the aforementioned general formula. In the formula, X represents a single bond, or a linking group selected from —CO—, —SO$_2$—, —CS— or —CH$_2$—, preferably a single bond, —CO—, —CS— or —SO$_2$—, and more preferably a single bond, —CO— or —CS—.

In addition, Y represents a single bond or a divalent linking group derived from a ring selected from benzene, pyridine, pyrimidine, pyrazole, imidazole, oxazole, thiazole, furan, thiophene, quinoline, benzoimidazole, benzothiazole, benzopyrazole, naphthalene and benzothiophene (at this time, the substitution modes of the two linkers that bond X and Z in said linking group are arbitrary). Preferable examples of Y include a single bond or a divalent linking group derived from a ring selected from benzene, pyridine, pyrimidine, thiazole, thiophene, imidazole, quinoline or naphthalene, more preferable examples include a single bond or a divalent linking group derived from a ring selected from benzene, pyridine, pyrimidine, thiazole or imidazole, and even more preferable examples include a single bond or a divalent linking group derived from a ring selected from benzene, pyridine or pyrimidine. In addition, examples of preferable substitution positions in said linking group include divalent linking groups selected from the formulas indicated below (Ya, Yb$_1$, Yb$_2$, Yb$_3$, Yb$_4$, Yc$_1$, Yc$_2$, Yc$_3$, Yc$_4$, Yc$_5$, Yc$_6$, Yc$_7$, Yd, Ye, Yf, Yg, Yi$_1$, Yi$_2$ and Yh). In addition, said linking group may be unsubstituted or substituted at 1 to 6 arbitrary locations by a halogen atom, —C$_{1-6}$ alkyl or —OC$_{1-6}$ alkyl, and preferably by a chlorine atom, fluorine atom, -methyl or -methoxy. In addition, said linking group is more preferably unsubstituted or substituted at 1 or 2 locations by -fluoro, -methyl or -methoxy. Furthermore, an asterisk (*) in the following group of linking groups represents a bond with Z.

Ya

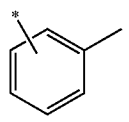

Yb$_1$

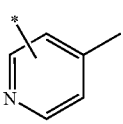

Yb$_2$

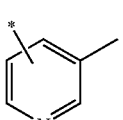

Yb$_3$

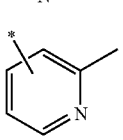

-continued

Yb$_4$

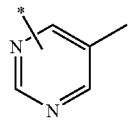

Yc$_1$

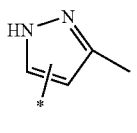

Yc$_2$

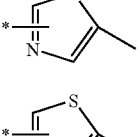

Yc$_3$

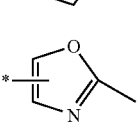

Yc$_4$

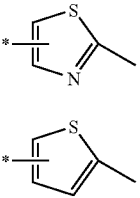

Yc$_5$


Yc$_6$

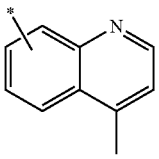

Yc$_7$

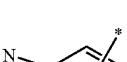
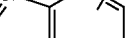

Yd

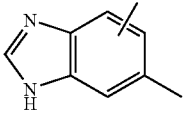

Ye

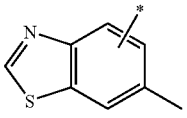

Yf

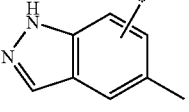

Yg

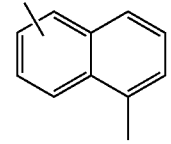

Yi$_1$

-continued

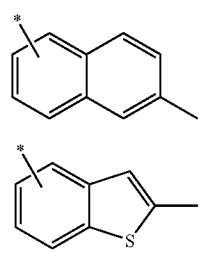

Yi$_2$

Yh

More preferable examples of Y include a single bond, Ya, Yb$_1$, Yb$_2$, Yb$_3$, Yb$_4$, Yc$_5$, Yc$_6$, Yf, Yd, Yi$_1$, Yc$_7$, further preferable examples include a single bond, Ya, Yb$_1$, Yb$_2$, Yb$_3$, Yb$_4$, Yc$_5$ and Yc$_7$, and particularly preferable examples include a single bond, Ya, Yb$_1$, Yb$_2$, Yb$_3$ and Yb$_4$.

In addition, more preferable examples of Y include a single bond or linking groups selected from Ya, Yb$_1$, Yb$_2$, Yb$_3$ and Yb$_4$ optionally substituted at 1 or 2 locations by -fluoro, -methyl or -methoxy.

Moreover, examples of other substitution modes of Y include the following preferable relationships for the relationship between the two linkers for bonding X and Z in the case Y is a linking group.

Ya, Yb$_1$, Yb$_2$, Yb$_3$ or Yb$_4$ (meta- or para-substituted); Yc$_1$ (3,5-substituted); Yc$_2$ (2,5-substituted); Yc$_3$ (2,5-substituted); Yc$_4$ (2,4- or 2,5-substituted); Yc$_5$ (2,4- or 2,5-substituted); Yc$_6$ (2,4- or 2,5-substituted); Yc$_7$ (2,4- or 2,5-substituted); Yd (4,6-, 4,7- or 4,8-substituted); Ye (2,6- or 4,6-substituted); Yf (2,6- or 4,6-substituted); Yg (5,3- or 5,7-substituted); Yi$_1$ (1,5-, 1,6- or 1,7-substituted); Yi$_2$ (2,5-, 2,6-, 2,7- or 2,8-substituted); and Yh (2,4-, 2,5-, 2,6- or 2,7-substituted).

However, X and Y are not simultaneously single bonds.

Z is a hydrogen atom or substituent selected from the following group A:

Group A: —C$_{1-6}$ alkyl, -ethynyl, -halogenoC$_{1-6}$ alkyl, -Cyc, —C$_{1-6}$ alkylene-OR, —C$_{1-6}$ alkylene-COR, —C$_{1-6}$ alkylene-COOR, —C$_{1-6}$ alkylene-CONRR', —C$_{1-6}$ alkylene-NRR', —C$_{1-6}$alkylene-Cyc, —C$_{1-6}$alkylene-CO-Cyc, —C$_{1-6}$alkylene-O—C$_{1-6}$ alkylene-Cyc, —C$_{1-6}$alkylene-SO$_2$R, —C$_{1-6}$ alkylene-SO$_2$-Cyc, -halogen, —CN, —SO$_2$R, —SO$_2$—NRR', —SO$_2$—NR-Cyc, —SO$_2$—NR—C$_{1-6}$alkylene-Cyc, —SO$_2$-Cyc, —COR, —CO-Cyc, —CO-Cyc-C$_{1-6}$alkylene-Cyc, —CO—C$_{1-6}$alkylene-Cyc, —CO-Cyc-Cyc, —COOR, —CONRR', —CONR—C$_{1-6}$ alkylene-OR', —CONR—C$_{1-6}$ alkylene-CONR'R", —CONR-Cyc, —CONR—C$_{1-6}$ alkylene-Cyc, —OR, —O-allyl, —O-halogenoC$_{1-6}$alkyl, —O—C$_{1-6}$alkylene-NRR', —O—C$_{1-6}$alkylene-CONRR', —O—C$_{1-6}$alkylene-NRCOR', —NRR', —NH—NH$_2$, —NRCOR', —NRCO-Cyc, —NRCO—C$_{1-6}$ alkylene-Cyc, —NRCO—C$_{1-6}$alkylene-OR', —NR—C$_{1-6}$ alkylene-COOR', —NR—C$_{1-6}$alkylene-CONR'R", —NR—C$_{1-6}$ alkylene-NR'R", —NR—C$_{1-6}$ alkylene-NR'COR", —NR—C$_{1-6}$ alkylene-OR', —NR-Cyc, —NR-Cyc-Cyc, —NR-Cyc-CO-Cyc, —NR-Cyc-CO—C$_{1-6}$ alkylene-Cyc, —NR-Cyc-NR'-Cyc, —NR-Cyc-NR'—C$_{1-6}$alkylene-Cyc, —NR—C$_{1-6}$ alkylene-Cyc, —NR—C$_{1-6}$ alkylene-Cyc-CO-Cyc, —NR—C$_{1-6}$ alkylene-Cyc-NR'-Cyc, —NRSO$_2$R', —S—C$_{1-6}$alkylene-CO-Cyc, —S—C$_{1-6}$ alkylene-COOR', —S—C$_{1-6}$alkylene-NRCOR', and —S—C$_{1-6}$alkylene-CONRR'.

Preferable examples of Z include a hydrogen atom or any of the following substituents: C$_{1-6}$ alkyl, -halogeno C$_{1-6}$ alkyl, -Cyc, —C$_{1-6}$ alkylene-COOR', —C$_{1-6}$ alkylene-CONRR', —C$_{1-6}$ alkylene-NRR', —C$_{1-6}$ alkylene-Cyc, -halogen, —CN, —SO$_2$R', —SO$_2$—NRR', —CO-Cyc, —CO-Cyc-Cyc, —COOR, —CONRR', —CONR—C$_{1-6}$ alkylene-Cyc, —OR, —O-halogeno C$_{1-6}$ alkyl, —O—C$_{1-6}$ alkylene-NRR', —NRR', —NR—C$_{1-6}$ alkylene-NR'R", —NR-Cyc-Cyc, —NR-Cyc-CO-Cyc, —NR—C$_{1-6}$ alkylene-Cyc, —NR—C$_{1-6}$ alkylene-OR', NHSO$_2$R', —S—C$_{1-6}$ alkylene-NRCOR' and —S—C$_{1-6}$ alkylene-CONRR'. More preferable examples of Z include a hydrogen atom or substituents selected from the following group A': —C$_{1-6}$ alkyl, -piperazinyl, -piperidino, -morpholino, -pyrrolidinyl, -dihydropyrrolyl, —C$_{1-6}$ alkylene-OH, —C$_{1-6}$ alkylene-COOH, —C$_{1-6}$ alkylene-COOCH$_3$, —C$_{1-6}$ alkylene-CONH$_2$, —C$_{1-6}$ alkylene-N(CH$_3$)$_2$, —C$_{1-6}$ alkylene-(phenyl), —C$_{1-6}$ alkylene-(naphthyl), —C$_{1-6}$ alkylene-(piperazinyl), -fluorine atom, —CN, —SO$_2$CH$_3$, —SO$_2$—NH$_2$, —CO— (piperazinyl), —CO-(morpholyl), —CO-((pyridyl)piperazinyl), —COOH, —COOCH$_3$, —COOCH$_2$CH$_3$, —CONH$_2$, —CONH—C$_{1-6}$ alkylene-(pyridyl), —OH, -trifluoromethoxy, —O—C$_{1-6}$ alkylene-N(CH$_3$)$_2$, —N(C$_{1-6}$ alkyl)$_2$, —NR—C$_{1-6}$ alkylene-N(CH$_3$)$_2$, —NR—C$_{1-6}$ alkylene-(morpholino), —NR—C$_{1-6}$ alkylene-(cyclopropyl), —NR—C$_{1-6}$ alkylene-(phenyl), —NR-((piperazyl)phenyl), —NR-(phenyl)-CO-(piperazinyl), —NR—C$_{1-6}$ alkylene-OH, —NR—C$_{1-6}$ alkylene-OCH$_3$, —NHSO$_2$(C$_{1-6}$ alkyl), —S—C$_{1-6}$ alkylene-NRCOCH$_3$ and —S—C$_{1-6}$ alkylene-CONH$_2$.

The aforementioned -piperazinyl, -piperidino, -morpholino, -pyrrolidinyl, -dihydropyrrolyl, -phenyl and -naphthyl may be respectively further substituted by —OH, -methyl, -ethyl, -n-propyl, -isopropyl, -trifluoromethyl, -2-fluoroethyl, -2,2,2-trifluoroethyl, -3,3,3-trifluoropropyl, -4-fluorobutyl, -dimethylamino, -hydroxymethyl, -acetyl or -phenyl.

Even more preferable examples of Z include -hydrogen atom, -chlorine atom, -fluorine atom, -hydroxy, —CN, -trifluoromethoxy, -methoxy, -2-(N,N-dimethylamino)-ethoxy, -methyl, -ethyl, -1-methyl-ethyl, -n-butyl, -t-butyl, -2,2-dimethyl-propyl, -n-hexyl, -2-hydroxyethyl, -2-hydroxy-propyl, -2-hydroxy-1-methyl-ethyl, -phenyl-ethyl, -4-fluoro-phenyl-methyl, -trifluoromethyl, -naphthylmethyl, -piperazin-1-yl-methyl, -4-methylpiperazin-1-ylmethyl, -4-n-propyl-piperazin-1-ylmethyl, -4-i-propyl-piperazin-1-ylmethyl, -4-(2'-fluoroethyl)-piperazin-1-ylmethyl, -4-(2',2',2'-trifluoroethyl)-piperazin-1-ylmethyl, -4-(3',3',3'-trifluoropropyl)-piperazin-1-ylmethyl, -4-(4'-fluorobutyl)-piperazin-1-ylmethyl, -3-methoxycarbonyl-n-propyl, -3-carboxyl-n-propyl, -3-carbamoyl-n-propyl, -2-methoxycarbonyl-ethyl, -morpholin-4-ylcarbonyl, -4-pyridin-3-yl-piperazin-1-ylcarbonyl, -carboxyl, -methoxycarbonyl, -ethoxycarbonyl, -carbamoyl, —N-pyridin-3-ylmethyl-carbamoyl, -2-carbamoyl-ethylthio, -2-acetylamino-ethylthio, -methylamino, -dimethylamino, -ethylamino, -n-butylamino, -3-hydroxy-n-propylamino, -phenylamino, -1-propylamino, -2-phenyl-ethylamino, -2,4-difluoro-phenylamino, -3,3-dimethyl-butylamino, -methyl(3-methylbutyl)amino, -3-(N,N-dimethylamino)-n-propylamino, -methyl(3-(N,N-dimethylamino)-n-butyl)amino, -methyl(2-(N,N-dimethylamino)-n-propyl)amino, -methyl(3-(N,N-dimethylamino)-n-propyl)amino, -methyl(2-(N,N-dimethylamino)-ethyl)amino, -methyl(2-methyl-propyl)amino, -2-hydroxyethylamino, -2-hydroxy-1-methyl-ethylamino, —N,N-(2-hydroxy)-n-propylamino, —N,N-(2-hydroxyethyl)-methylamino, —N,N-(2-methoxyethyl)methylamino, —N,N-ethyl(2-dimethylamino-ethyl)amino, -cyclohexylmethylamino, -4-(4-methylpiperazin-1-yl)-2,6-difluorophenylamino, -4-(4-ethylpiperazin-1-yl)-2,6-difluorophenylamino, -4-(4-ethylpiperazine-1-carbonyl)-2,6-difluorophenylamino, -5-(4-ethylpiperazine-1-carbonyl)-2-methylphenylamino, -3-morpholinyl-n-propylamino, -4-methyl-piperazinyl, -4-ethyl-piperazinyl, -4-acetyl-piperazinyl, -4-phenyl-piperazinyl, -4-dimethylamino-piperidino, —N-ethyl-piperidino, -3-hydroxy-piperidino, -4-hydroxy-piperidino, —N-morpholino, -2-hydroxymethyl-pyrrolidinyl, -3-hydroxy-N-pyrrolidinyl, -methylsulfonylamino, -methylsulfonyl, -aminosulfonyl, -cyclopropylmethyl(n-propyl)amino, -3,5-dimethyl-morpholino, -3-morpholino-n-propylamino, -2-benzocyclopentylamino, —N-dihydropyrrolyl-dihydropyrrolyl, and -cyclohexylamino.

In addition, m represents an integer of 1 or 2, and is preferably 1.

In addition, $R^1$ is a cyclic substituent selected from the following group having n substituents T.

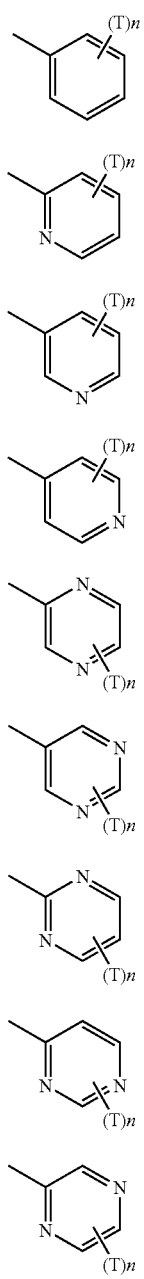

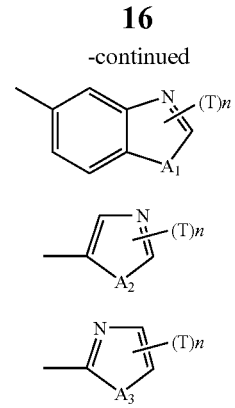

Here, $A_1$, $A_2$ and $A_3$ are respectively and independently selected from NH, S or O. Preferable examples of $A_1$ include S and NH. Preferable examples of $A_2$ include S and O. In addition, preferable examples of $A_3$ include S and O.

Preferable examples of $R^1$ include $R_1a$, $R_1b_1$, $R_1b_2$, $R_1b_3$, $R_1c_1$, $R_1c_2$, $R_1c_3$, $R_1c_4$, $R_1c_5$, $R_1d$, $R_1e$ and $R_1f$, more preferable examples include $R_1a$, $R_1b_1$, $R_1b_2$, $R_1b_3$, $R_1c_1$, $R_1c_2$, $R_1c_3$, $R_1c_4$ and $R_1c_5$, even more preferable examples include $R_1c_1$, $R_1c_2$, $R_1c_3$, $R_1c_4$ and $R_1c_5$, and a particularly preferable example is $R_1c_2$. At this time, n is preferably 0 or 1.

In addition, preferable examples of the mode relating to the substitution position of -(T)n in $R^1$ include the meta position (position 3 or position 5) and the para position (position 4) with respect to the substitution position of 2-morpholin-4-yl-6,7-dihydro-5H-pyrrolo[2,3-d]pyrimidine or 2-morpholin-4-yl-5,6,7,8-tetrahydro-5H-pyrrolo[2,3-d]pyrimidine of $R_1$ in the case $R_1$ is $R_1a$, $R_1b_1$, $R_1b_2$, $R_1b_3$, $R_1c_1$, $R_1c_2$ or $R_1c_3$, and preferably position 3 or position 4 in the case $R_1$ is $R_1e$ or $R_1f$. The following indicates examples of the substitution position of T in $R_1$.

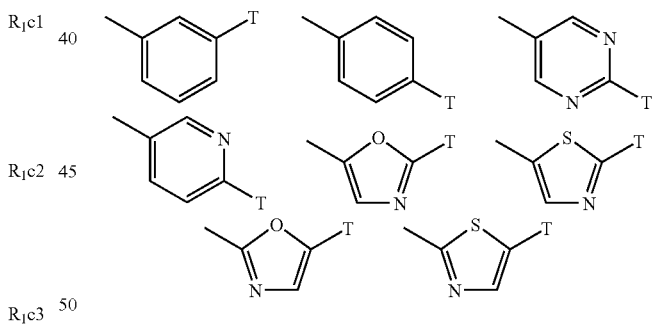

In the case $R_1$ is a group derived from pyridine, pyrimidine or thiazole in particular in $R_1$, these groups are preferably bonded to the matrix as -pyridin-3-yl, -pyrimidin-5-yl or -thiazol-2-yl, respectively.

In addition, T represents a substituent selected from the following group B.

Group B: -Cyc, —$C_{1-6}$ alkyl, —$C_{1-6}$ alkylene-OR, —$C_{1-6}$ alkylene-NRR', —$C_{1-6}$ alkylene-CONRR', —$C_{1-6}$ alkylene-NRCOR', —$C_{1-6}$ alkylene-Cyc, —OR, —O-halogen-$C_{1-6}$ alkyl, —O—$C_{1-6}$ alkylene-Cyc, —O—COOR, —O—COR, —O—CONRR', —NRR', —NR—$C_{1-6}$ alkylene-NR'R'', —NR—$C_{1-6}$ alkylene-OR', -halogen, —CO-Cyc, —CO-Cyc-Cyc, —CO—$C_{1-6}$ alkylene-Cyc, —COOR, —COO—$C_{1-6}$ alkylene-OR, —COO—$C_{1-6}$ alkylene-NRR', —COO—$C_{1-6}$ alkylene-Cyc, —CONRR', —CONR—$C_{1-6}$ alkylene-OR', —CONR—$C_{1-6}$ alkylene-NR'R'', —CONR—$C_{1-6}$ alkylene-CONR'R", —CONR-Cyc, —CONR—C$_{1-6}$ alkylene-Cyc, —SO$_2$NRR', —NRSO$_2$R', —CN and —NH—NH$_2$.

T is preferably -Cyc, —C$_{1-6}$ alkyl, —C$_{1-6}$ alkylene-(nitrogen-containing heterocyclic ring), —C$_{1-6}$ alkylene-OH, —C$_{1-6}$ alkylene-CONH(C$_{1-6}$ alkyl), —C$_{1-6}$ alkylene-NH$_2$, —C$_{1-6}$ -alkylene-N(C$_{1-6}$ alkyl)$_2$, —OH, —O—C$_{1-6}$ alkyl, —O-trifluoromethyl, —O—C$_{1-6}$ alkylene-(pyridyl), —O—C$_{1-6}$ alkylene-(phenyl), —O—COOR, —O—COCH$_3$, —O—CONH(C$_{1-6}$ alkyl), —NH$_2$, —NR—C$_{1-6}$ alkylene-N(C$_{1-6}$ alkyl)$_2$, —NR—C$_{1-6}$ alkylene-OH, —NR—C$_{1-6}$ alkylene-O(C$_{1-6}$ alkyl), -fluorine atom, —CO-Cyc, —CO—C$_{1-6}$ alkylene-Cyc, —COO(C$_{1-6}$ alkyl), —COO—C$_{1-6}$ alkylene-OH, —COO—C$_{1-6}$ alkylene-OCH$_3$, —COO—C$_{1-6}$ alkylene-N(C$_{1-6}$ alkyl)$_2$, —COO—C$_{1-6}$ alkylene-Cyc, —CONH$_2$, —CONH(C$_{1-6}$ alkyl), —CON(C$_{1-6}$ alkyl)$_2$, —CON(C$_{1-6}$ alkyl)(phenyl), —CON(C$_{1-6}$ alkyl)(C$_{3-6}$ cycloalkyl), —CON(C$_{1-6}$ alkyl)(cyclopropylmethyl), —CONR—C$_{1-6}$ alkylene-OH, —CONR—C$_{1-6}$ alkylene-OCH$_3$, —CONR—C$_{1-6}$ alkylene-N(C$_{1-6}$ alkyl)$_2$, —CONR—C$_{1-6}$ alkylene-CONH$_2$, —CONR-Cyc, —CONR—C$_{1-6}$ alkylene-Cyc, —SO$_2$NH$_2$, NHSO$_2$CH$_3$, —CN or —NH—NH$_2$, and the aforementioned Cyc may be further respectively substituted by —OH, -methyl, -ethyl, -dimethylamino, -hydroxymethyl, -acetyl, -phenyl or -pyrrolidinyl.

More preferable examples of T include a group selected from the following group B': —C$_{1-6}$ alkyl, —C$_{1-6}$ alkylene-OH, —C$_{1-6}$ alkylene-NH$_2$, —C$_{1-6}$ alkylene-CONH(C$_{1-6}$ alkyl), —OH, —O—C$_{1-6}$ alkyl, —O—C$_{1-6}$ alkylene-(nitrogen-containing heterocyclic ring), —O—C$_{1-6}$ alkylene-(phenyl), —O—COCH$_3$, —O—CONH(C$_{1-6}$ alkyl), —NH$_2$, -fluorine atom, —COO(C$_{1-6}$ alkyl), —COO—C$_{1-6}$ alkylene-OH, —COO—C$_{1-6}$ alkylene-OCH$_3$, —COO—C$_{1-6}$ alkylene-N(C$_{1-6}$ alkyl)$_2$, —CONH$_2$, —CONH(C$_{1-6}$ alkyl), —CON(C$_{1-6}$ alkyl)$_2$, —CON(C$_{1-6}$ alkyl)(phenyl), —CON(C$_{1-6}$ alkyl)(C$_{3-6}$ cycloalkyl), —CON(C$_{1-6}$ alkyl)(cyclopropylmethyl), —CONR—C$_{1-6}$ alkylene-OH, —CONR—C$_{1-6}$ alkylene-OCH$_3$, —CONR—C$_{1-6}$ alkylene-N(C$_{1-6}$ alkyl)$_2$, —CONR—C$_{1-6}$ alkylene-CONH$_2$, —CONR-Cyc, —CONR—C$_{1-6}$ alkylene-(nitrogen-containing heterocyclic ring), —CN, —NH—NH$_2$ and —NHSO$_2$CH$_3$.

Here, the nitrogen-containing heterocyclic ring in the above T indicates a saturated, partially unsaturated or aromatic monocyclic heterocyclic ring containing at least one nitrogen atom that, in addition to the nitrogen atom(s), may further contain 1 to 2 heteroatoms selected from an oxygen atom or sulfur atom. Examples of such nitrogen-containing heterocyclic rings include aromatic heterocyclic rings such as pyrrole, pyrazole, imidazole, triazole, oxazole, isoxazole, indazole, thiazole, pyridine, pyridazine, pyrimidine, pyrazine, oxazine or triazine, and non-aromatic heterocyclic rings such as azirizine, azetidine, pyrrolidine, imidazoline, oxazoline, imidazolidine, oxazolidine, thiazine, piperidine, piperazine, morpholine or azepane. Preferable examples of nitrogen-containing heterocyclic rings include azirizine, azetidine, pyrrolidine, pyrazole, thiazole, pyridine, pyrimidine, piperidine, piperazine, morpholine and azepane, while particularly preferable examples include azirizine, azetidine, pyrrolidine, pyrazole, thiazole, pyridine, pyrimidine, morpholine, piperazine, piperidine and azepane. Said nitrogen-containing heterocyclic ring may be further respectively substituted by —OH, -methyl, -ethyl, -dimethylamino, -hydroxymethyl or -acetyl.

Furthermore preferable examples of T include -hydroxy, -methoxy, -t-butoxy, -ethylaminocarbonyloxy, -methylcarbonyloxy, -2-(2-pyridyl)ethoxy, -2-(3-pyridyl)ethoxy, -3-(3-pyridyl)-n-propoxy, -4-pyridyl-methoxy, -benzyloxy, -fluorine atom, -amino, -hydrazino, -methyl, -hydroxymethyl, -aminomethyl, -diethylamino-methyl, -carboxyl, -methoxycarbonyl, -2-(N,N-dimethylamino)-ethoxy-carbonyl, -carbamoyl, -methylcarbamoyl, -phenylcarbamoyl, -dimethylcarbamoyl, -diethylcarbamoyl, -n-propylaminocarbonyl, -isobutylaminocarbonyl, -1-methyl-n-butylaminocarbonyl, -3,3-dimethyl-n-butylaminocarbonyl, —N-isopropyl-N-methylaminocarbonyl, —N-isobutyl-N-methylaminocarbonyl, —N-(3-methyl-n-butyl)-N-methylaminocarbonyl, -cyclopentylaminocarbonyl, -cyclohexylaminocarbonyl, —N-cyclopropylmethyl-N-n-propylaminocarbonyl, -2-benzocyclopentylaminocarbonyl, -3-hydroxy-n-propylamino, -2-hydroxy-1-phenyl-aminocarbonyl, —N-ethyl-N-(2-hydroxyethyl)aminocarbonyl, —N-methyl-N-(2-methoxyethyl)aminocarbonyl, -2-methoxy-ethylaminocarbonyl, -2-(N,N-dimethylamino)-ethylamino-carbonyl, -2-(N,N-dimethylamino)-methylamino-carbonyl, -2-(N,N-diethylamino)-ethylamino-carbonyl, -2-(N,N-dimethylamino)-n-propylamino-carbonyl, -2-N-morpholinylethylaminocarbonyl, -3-N-morpholinylpropylaminocarbonyl, —N-(3,5-dimethylmorpholinyl)aminocarbonyl, -(2-pyridyl)methylamino-carbonyl, -2-(2-pyridyl)ethylamino-carbonyl, -4-pyridyl-methylamino-carbonyl, -2-(4-pyridyl)ethylamino-carbonyl, -2-carbamoyl-methylamino-carbonyl, -2-carbamoyl-ethylamino-carbonyl, -benzylaminocarbonyl, -2-phenyl-ethylamino-carbonyl, —N-methyl-piperazyl-carbonyl, —N-ethyl-piperazino-carbonyl, -4-phenyl-piperazinocarbonyl, -4-hydroxypiperidino-carbonyl, -3-hydroxypyrrolidinyl-carbonyl, -2-(N-pyrolidinyl)ethyl-carbonyl, -2-hydroxymethyl-pyrrolidinyl-carbonyl, -4-(N-pyrrolidinyl)-piperidino-carbonyl, —N-(2,5-dihydro-1H-pyrrolyl-carbonyl, —N-azetidino-carbonyl, -4,5-dimethyl-thiazolyl-carbonyl, —CN, -cyclohexylmethylaminocarbonyl and -methylsulfonylamino, while particularly preferable examples include -hydroxy, -methoxy, -t-butoxy or -amino.

n represents an integer of 0, 1, 2, 3, 4 or 5, and in the case n is 2 to 5, groups T may be the same or different. n is preferably 0, 1 or 2, more preferably 0 or 1, and even more preferably 1.

A preferable mode of R$^1$ is a group selected from -3-methoxy-phenyl, -3-hydroxy-phenyl, -4-fluoro-3-hydroxy-phenyl, -2-fluoro-3-hydroxy-phenyl, -3-hydroxymethyl-phenyl, -3-benzyloxy-2,6-difluoro-phenyl, -4-aminomethyl-phenyl, -4-fluoro-3-hydroxymethyl-phenyl, —N-(2-dimethylamino-ethyl)-3-carbamoyl-phenyl, —N-(2-dimethylamino-ethyl)-4-carbamoyl-phenyl, —N-(2-pyridin-3-yl-ethyl)-3-carbamoyl-phenyl, N-methyl-3-carbamoylphenyl, -3-(2-dimethylamino-ethoxycarbonyl)-phenyl, —N-(1-methyl-butyl)-3-carbamoyl-phenyl, -3-(4-hydroxy-piperidin-1-yl)carbonyl-phenyl, —N-(2-diethylamino-ethyl)-4-carbamoyl-phenyl, -3-(2,6-dimethyl-morpholin-4-yl)carbonyl-phenyl, —N-(2-dimethylamino-ethyl)-N-methyl-3-carbamoyl-phenyl, -pyridin-3-yl, -pyridin-4-yl, -2-amino-pyridin-5-yl, -5-amino-pyridin-2-yl, -2-amino-piperidin-5-yl, -2-amino-3-methoxy-piperidin-5-yl, -2-methoxy-piperidin-5-yl, -2,4-dimethoxy-piperidin-5-yl or -1H-benzoimidazol-5-yl, more preferably a group selected from -3-hydroxy-phenyl, -4-aminomethyl-phenyl, -2-amino-piperidin-5-yl, -4-fluoro-3-hydroxy-phenyl, -4-fluoro-3-hydroxymethyl-phenyl, -2-amino-pyridin-5-yl, -5-amino-pyridin-2-yl, -2,4-dimethoxy-piperidin-5-yl, -1H-benzoimidazol-5-yl, -3-(2-dimethylamino-ethoxycarbonyl)-phenyl or —N-(2-dimethylamino-ethyl)-3-carbamoyl-phenyl, even more preferably a group selected from -3-hydroxy-phenyl or -2-amino-pyrimidin-5-yl, and particularly preferably -2-amino-pyrimidin-5-yl.

In addition, R, R' and R" in the aforementioned groups A and B may be the same or different and represent a hydrogen atom or —C$_{1-6}$ alkyl, and said —C$_{1-6}$ alkyl may be substituted by a group selected from —OH, —O(C$_{1-6}$ alkyl), —COOH, —COO(C$_{1-6}$ alkyl), —CONH$_2$, —CONH(C$_{1-6}$ alkyl), —CON(C$_{1-6}$ alkyl)$_2$, —NHCO(C$_{1-6}$ alkyl), —NH$_2$, —NH (C$_{1-6}$ alkyl) or —N(C$_{1-6}$alkyl)$_2$. In addition, R, R' and R" in group B may be the same or different and preferably represent a hydrogen atom or unsubstituted —C$_{1-6}$ alkyl.

In the aforementioned groups A and B. Cyc represents the aforementioned hydrocarbon ring or the aforementioned nitrogen-containing heterocyclic ring, -Cyc is a monovalent group derived from the aromatic or non-aromatic, monocyclic or bicyclic hydrocarbon ring or nitrogen-containing heterocyclic ring, and -Cyc- is a divalent group derived from the aromatic or non-aromatic, monocyclic or bicyclic hydrocarbon ring or nitrogen-containing heterocyclic ring. Said hydrocarbon ring and said nitrogen-containing heterocyclic ring may be substituted at 1 to 3 locations by a group selected from —R (R is not a hydrogen atom at this time), —CO—R, —COOR, —CONRR', —NRCOR', -halogeno C$_{1-6}$ alkyl, halogen atom, —OR, —O-halogeno C$_{1-6}$ alkyl, —NRR' or —SO$_2$R. In addition, the R, R' and R" of said —NRR', —NR'R" or —CONRR' in the aforementioned group A, group B and Cyc may also form a 3- to 7-member nitrogen-containing saturated hydrocarbon ring together with an adjacent N. Examples of this 3- to 7-member, nitrogen-containing saturated hydrocarbon ring include aziridine, azetidine, pyrrolidine, piperidine and azepane. In addition, this 3- to 7-member, nitrogen-containing saturated hydrocarbon ring may further contain 1 to 3 other heteroatoms such as a nitrogen atom, oxygen atom or sulfur atom, and this 3- to 7-member, nitrogen-containing saturated hydrocarbon ring is preferably a 5- to 6-member ring, examples of which include imidazolidine, oxazolidine, piperazine and morpholine.

Cyc is preferably unsubstituted, or may also be substituted at 1 to 3 locations by —OH, —O(C$_{1-6}$ alkyl), —O—C$_{1-6}$ alkylene-OH, —O(trifluoromethyl), —C$_{1-6}$ alkyl, —C$_{1-6}$ alkylene-OH, -trifluoromethyl, —COO(C$_{1-6}$ alkyl), —CONH$_2$, —CONH(C$_{1-6}$ alkyl), —CON(C$_{1-6}$ alkyl)$_2$, —NH$_2$, —NH(C$_{1-6}$ alkyl), —N(C$_{1-6}$ alkyl)$_2$, —N(C$_{1-6}$ alkyl) CO(C$_{1-6}$ alkyl), halogen atom, —SO$_2$(C$_{1-6}$ alkyl) or —CO (C$_{1-6}$ alkyl), and more preferably unsubstituted or substituted at 1 to 3 locations with a group selected from the group consisting of -methyl, -ethyl, —OH, —F, —Cl, -trifluoromethyl, -dimethylamino, -hydroxymethyl, -methoxy, -acetyl and -methoxycarbonyl.

Preferable examples of -Cyc include the groups indicated below.

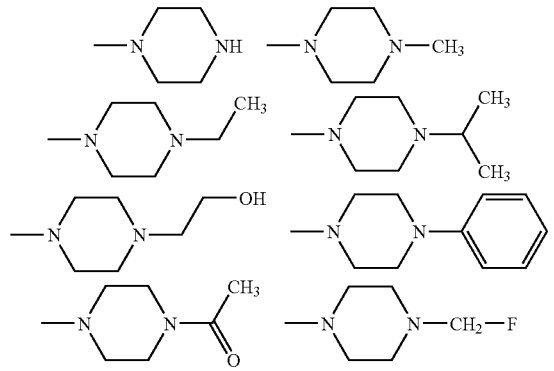

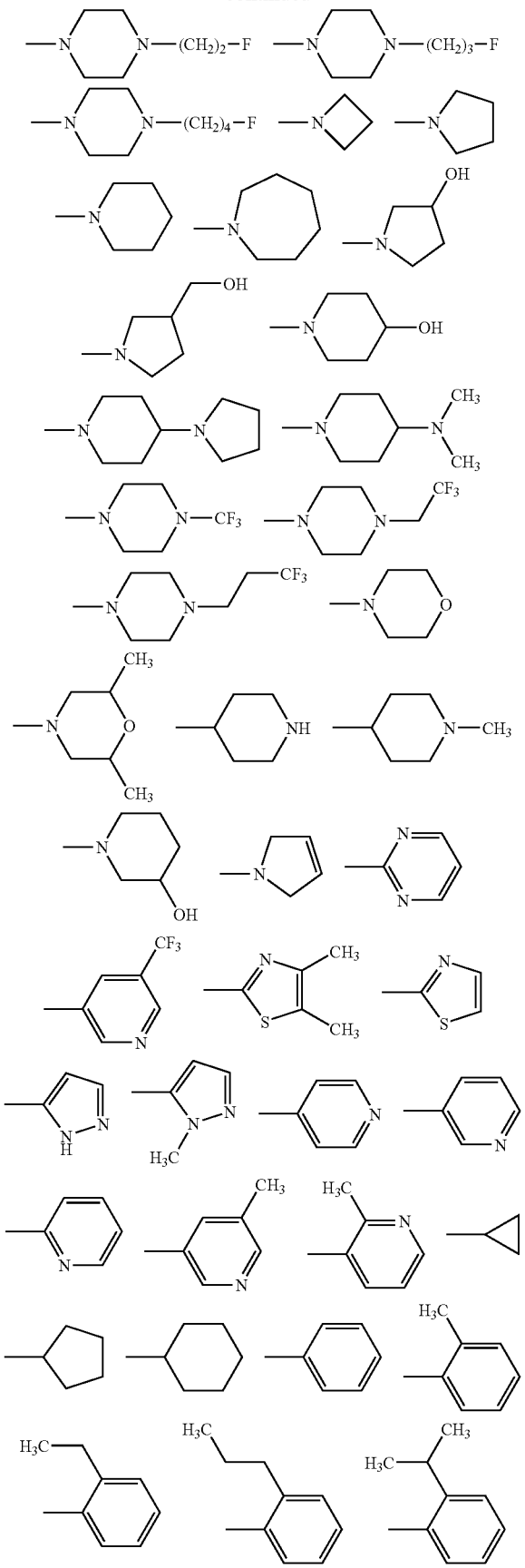

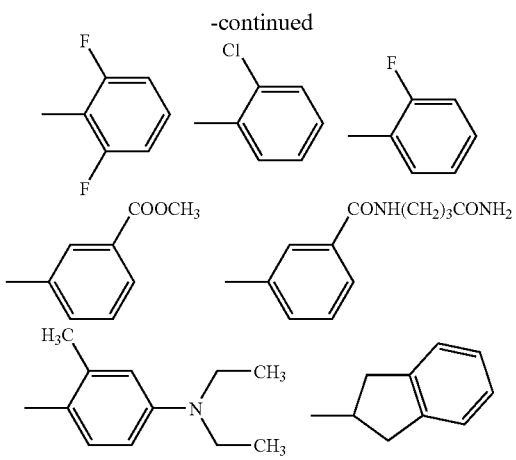

In addition, preferable modes of Cyc in group A as a portion of —Z in general formula (I) include hydrocarbon rings, specific examples of which include aromatic hydrocarbon rings such as benzene or naphthalene; and non-aromatic hydrocarbon rings including saturated hydrocarbon rings such as cyclopropane, cyclobutane, cyclopentane, cyclohexane, spiro[2.3]hexane or spiro[3.3]heptane, and partially unsaturated hydrocarbon rings such as indane, tetrahydronaphthalene, cyclopropene, cyclobutene, cyclopentene or cyclohexene. Preferable examples of hydrocarbon rings include benzene, naphthalene and cyclopropane, and more preferably benzene. In addition, specific examples of nitrogen-containing heterocyclic rings include aromatic heterocyclic rings such as pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, quinoline, isoquinoline, quinoxaline, quinazoline, phthalazine, purine or pteridine, and non-aromatic heterocyclic rings such as azirizine, azetidine, pyrrolidine, imidazoline, oxazoline, imidazolidine, oxazolidine, thiazine, piperidine, piperazine, morpholine or azepane. Preferable examples of nitrogen-containing heterocyclic rings include azirizine, azetidine, pyrrolidine, pyrazole, thiazole, pyridine, pyrimidine, morpholine, piperazine, piperidine and azepane, while particularly preferable examples include nitrogen-containing heterocyclic rings such as pyrazole, thiazole, pyridine, pyrimidine, morpholine, piperazine, piperidine and azepane. More preferable modes of the hydrocarbon ring and nitrogen-containing heterocyclic ring in Cyc include monovalent or divalent groups derived from benzene, naphthalene, cyclopropane, cyclobutane, cyclopentane, cyclohexane, indane, azirizine, azetidine, pyrrolidine, pyrazole, thiazole, pyrrole, dihydropyrrole, pyridine, pyrimidine, morpholine, piperazine, piperidine or azepane, and even more preferable modes include monovalent or divalent groups derived from benzene, pyrazole, thiazole, pyridine, pyrimidine, morpholine, piperazine, piperidine or azepane.

In addition, specific examples of preferable modes of Cyc in group B as a portion of -T in general formula (I) include hydrocarbon rings including aromatic hydrocarbon rings such as benzene or naphthalene; and non-aromatic hydrocarbon rings including saturated hydrocarbon rings such as cyclopropane, cyclobutane, cyclopentane, cyclohexane, spiro [2.3]hexane or spiro[3.3]heptane, and partially unsaturated hydrocarbon rings such as indane, tetrahydronaphthalene, cyclopropene, cyclobutene, cyclopentene or cyclohexene. Preferable examples of hydrocarbon rings include cyclopropane, cyclobutane, cyclopentane, cyclohexane, benzene, naphthalene and indane, and more preferably benzene. In addition, specific examples of nitrogen-containing heterocyclic rings include aromatic heterocyclic rings such as pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, quinoline, isoquinoline, quinoxaline, quinazoline, phthalazine, purine or pteridine, and non-aromatic heterocyclic rings such as azirizine, azetidine, pyrrolidine, imidazoline, oxazoline, imidazolidine, oxazolidine, thiazine, 2,5-dihydropyrrole, piperidine, piperazine, morpholine or azepane. Preferable examples of nitrogen-containing heterocyclic rings include monocyclic nitrogen-containing heterocyclic rings, and said monocyclic nitrogen-containing heterocyclic rings are as previously defined. Preferable examples of nitrogen-containing heterocyclic rings include azirizine, azetidine, pyrrolidine, pyrazole, thiazole, pyrrole, dihydropyrroles such as 2,5-dihydropyrrole, pyridine, pyrimidine, morpholine, piperazine, piperidine and azepane, and nitrogen-containing heterocyclic groups derived therefrom are preferable. More preferable modes of these Cyc include monovalent or divalent groups derived from benzene, aziridine, azetidine, pyrrolidine, pyrazole, thiazole, pyridine, pyrimidine, morpholine, piperazine or piperidine.

Preferable examples of Cyc in the aforementioned group A are either unsubstituted or may be further respectively substituted at 1 to 3 locations by —OH, —O($C_{1-6}$alkyl), —O—$C_{1-6}$ alkylene-OH, —$C_{1-6}$ alkyl, —$C_{1-6}$ alkylene-OH, -fluoro $C_{1-6}$ alkyl, —COO($C_{1-6}$ alkyl), —$CONH_2$, —CONH ($C_{1-6}$ alkyl), —CON($C_{1-6}$ alkyl)$_2$, —$NH_2$, —NH($C_{1-6}$ alkyl), —N($C_{1-6}$ alkyl)$_2$, —$SO_2$($C_{1-6}$ alkyl) or —CO($C_{1-6}$ alkyl).

Preferable examples of Cyc in the aforementioned group B are either unsubstituted or may be further respectively substituted at 1 to 3 locations by —OH, —O($C_{1-6}$alkyl), —$C_{1-6}$ alkyl, —$NH_2$, —NH($C_{1-6}$ alkyl), —N($C_{1-6}$ alkyl)$_2$ or —CO ($C_{1-6}$ alkyl), while more preferable examples are either unsubstituted or further substituted at 1 to 3 locations by —OH, -methyl, -ethyl, -dimethylamino, -hydroxymethyl or -acetyl.

In addition, in the aforementioned groups A and B, $C_{1-6}$ alkylene may be substituted at 1 to 3 locations by a group selected from —$C_{1-6}$ alkyl, —OH, —$CONH_2$, —$NH_2$, —NH ($C_{1-6}$alkyl) or —N($C_{1-6}$ alkyl)$_2$.

Among the compounds represented by general formula (I) of the present invention, preferable examples of one aspect of the compounds include compounds having the following combinations of substituents:

X is a single bond, —CO— or —CS—;

Y is a single bond or a divalent linking group derived from a ring selected from benzene, pyridine, pyrimidine, thiazole or imidazole;

Z is a hydrogen atom or a substituent selected from the following group A':

group A': —$C_{1-6}$ alkyl, -piperazinyl, -piperidino, -morpholino, -pyrrolidinyl, -dihydropyrrolyl, —$C_{1-6}$ alkylene-OH, —$C_{1-6}$ alkylene-COOH, —$C_{1-6}$ alkylene-COOCH$_3$, —$C_{1-6}$ alkylene-CONH$_2$, —$C_{1-6}$ alkylene-N(CH$_3$)$_2$, —$C_{1-6}$ alkylene-(phenyl), —$C_{1-6}$ alkylene-(naphthyl), -fluorine atom, —$C_{1-6}$ -alkylene-(piperazinyl), —CN, —SO$_2$CH$_3$, —SO$_2$—NH$_2$, —CO-(piperazinyl), —CO-(morpholyl), —CO-((pyridyl)piperazinyl), —COOH, —COOCH$_3$, —COOCH$_2$CH$_3$, —CONH$_2$, —CONH—$C_{1-6}$ alkylene-(pyridyl), —OH, -trifluoromethoxy, —O—$C_{1-6}$ alkylene-N (CH$_3$)$_2$, —N(C$_{1-6}$ alkyl)$_2$, —NR—$C_{1-6}$ alkylene-N(CH$_3$)$_2$, —NR—$C_{1-6}$ alkylene-(morpholino), —NR—$C_{1-6}$ alkylene- (cyclopropyl), —NR—$C_{1-6}$ alkylene-(phenyl), —NR-((piperazinyl)phenyl), —NR-(phenyl)-CO-(piperazinyl), —NR—$C_{1-6}$ alkylene-OH, —NR—$C_{1-6}$ alkylene-OCH$_3$, —NHSO$_2$($C_{1-6}$ alkyl), —S—$C_{1-6}$ alkylene-NRCOCH$_3$ and —S—$C_{1-6}$ alkylene-CONH$_2$ (the above -piperazinyl, -piperidino, -morpholino, -pyrrolidinyl, -dihydropyrrolyl, -phenyl and -naphthyl may be further respectively substituted by —OH, -methyl, -ethyl, -n-propyl, -isopropyl, -trifluoromethyl, -2-fluoroethyl, -2,2,2-trifluoroethyl, -3,3,3-trifluoropropyl, -4-fluorobutyl, -dimethylamino, -hydroxymethyl, -acetyl or -phenyl);

$R^1$ is $R_1a$, $R_1b_2$, $R_1b_3$, $R_1c_2$, $R_1e$ or $R_1f$, and $A_3$ is S or O at this time;

n is 0, 1 or 2;

m is 1; and

T represents a hydrogen atom or a substituent selected from the following group B':

group B': —$C_{1-6}$ alkyl, —$C_{1-6}$ alkylene-OH, —$C_{1-6}$ alkylene-NH$_2$, —$C_{1-6}$ alkylene-CONH($C_{1-6}$ alkyl), —OH, —O—$C_{1-6}$ alkyl, —O—$C_{1-6}$ alkylene-(nitrogen-containing heterocyclic monocyclic group), —O—$C_{1-6}$ alkylene-(phenyl), —O—COCH$_3$, —O—CONH($C_{1-6}$ alkyl), —NH$_2$, -fluorine atom, —COO($C_{1-6}$ alkyl), —COO—$C_{1-6}$ alkylene-OH, —COO—$C_{1-6}$ alkylene-OCH$_3$, —COO—$C_{1-6}$ alkylene-N($C_{1-6}$ alkyl)$_2$, —CONH$_2$, —CONH($C_{1-6}$ alkyl), —CON($C_{1-6}$ alkyl)$_2$, —CON($C_{1-6}$ alkyl)(phenyl), —CON($C_{1-6}$ alkyl)($C_{3-6}$ cycloalkyl), —CON($C_{1-6}$ alkyl)(cyclopropylmethyl), —CONR—$C_{1-6}$alkylene-OH, —CONR—$C_{1-6}$ alkylene-OCH$_3$, —CONR—$C_{1-6}$ alkylene-N($C_{1-6}$ alkyl)$_2$, —CONR—$C_{1-6}$ alkylene-CONH$_2$, —CONR-Cyc, —CONR—$C_{1-6}$ alkylene-(nitrogen-containing heterocyclic monocyclic ring), —CN, —NH—NH$_2$, and —NHSO$_2$CH$_3$ (the above nitrogen-containing heterocyclic monocyclic ring is a monocyclic heterocyclic ring containing at least one nitrogen atom, that may further contain an oxygen atom or a sulfur atom in addition to a nitrogen atom, and may be saturated, partially unsaturated or aromatic. The nitrogen-containing heterocyclic monocyclic ring may be further respectively substituted by —OH, -methyl, -ethyl, -dimethylamino, -hydroxymethyl, -acetyl, -phenyl or -pyrrolidinyl).

Among the compounds represented by general formula (I) of the present invention, preferable examples of another aspect of the compounds include compounds having the following combinations of substituents:

compounds in which X is a linking group selected from —CO—, —CS—, —SO$_2$— or —CH$_2$—; Y is a single bond; and Z is a hydrogen atom or a group selected from —$C_{1-6}$ alkyl, -Cyc, —OR, —NRR', —NR-Cyc, —NR—$C_{1-6}$ alkylene-Cyc, —COOR, —$C_{1-6}$ alkylene-COOR, —$C_{1-6}$ alkylene-CONRR' or —$C_{1-6}$ alkylene-NRR' (more preferably Z is a hydrogen atom or a group selected from -methyl, -ethyl, -t-butyl, -phenyl, -pyridyl, —NH—$C_{1-6}$alkyl, —N($C_{1-6}$ alkyl)$_2$, —NH-(phenyl which may be substituted with a group selected from —F, —CF$_3$or -methyl), —O—$C_{1-6}$alkyl, —$C_{1-6}$ alkyl-N($C_{1-6}$ alkyl)$_2$, —$C_{1-6}$ alkylene-COOH, —$C_{1-6}$ alkylene-COO—$C_{1-6}$ alkyl or —COO—$C_{1-6}$ alkyl); and compounds in which X is a linking group selected from —CO— or —CS—; Y is a single bond; and Z is a group selected from -Cyc, —$C_{1-6}$ alkylene-Cyc, —$C_{1-6}$ alkylene-CO-Cyc, —$C_{1-6}$alkylene-O—$C_{1-6}$ alkylene-Cyc, —$C_{1-6}$ alkylene-SO$_2$-Cyc, —NRCO-Cyc, —NRCO—$C_{1-6}$ alkylene-Cyc, —NR-Cyc, —NR-Cyc-Cyc, —NR-Cyc-CO-Cyc, —NR—$C_{1-6}$ alkylene-Cyc-CO-Cyc, —NR-Cyc-CO—$C_{1-6}$ alkylene-Cyc, —NR—$C_{1-6}$ alkylene-Cyc-NR'-Cyc, —NR—$C_{1-6}$ alkylene-Cyc-NR'-Cyc, —NR-Cyc-NR'—$C_{1-6}$ alkylene-Cyc or —NR—$C_{1-6}$ alkylene-Cyc.

Among compounds represented by general formula (I) of the present invention, still another aspect of the compounds preferably contains at least one aromatic hydrocarbon ring or aromatic heterocyclic ring in a side chain in —X—Y—Z. Examples of aromatic hydrocarbon rings include benzene and naphthalene, while examples of aromatic heterocyclic rings include pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, benzothiophene, benzofuran, quinoline, isoquinoline, quinoxaline, quinazoline, phthalazine, purine and pteridine. Preferable examples include benzene, pyrazole, thiazole, imidazole, pyridine, pyrimidine and benzimidazole, while more preferable examples include benzene, pyridine and pyrimidine. The aromatic ring is monovalent in the case of being located on the end of the side chain represented by —X—Y—Z, and divalent in the case of being located at an intermediate position in the side chain.

Examples of preferable aspects of —X—Y—Z that satisfy these conditions include compounds having the combinations of substituents indicated below:

[Pattern 1]

X is a single bond or a linking group selected from —CO— or —CS—;

Y is a divalent linking group derived from a ring selected from benzene, pyridine, pyrimidine, pyrazole, imidazole, oxazole, thiazole, furan, thiophene, quinoline, benzoimidazole, benzothiazole, benzopyrazole, naphthalene or benzothiophene, and preferably benzene, pyridine or pyrimidine; and Z is a hydrogen atom or a substituent selected from group A (where group A is the same as previously defined);

while a pattern that is more preferable than Pattern 1 is such that:

X is a single bond;

Y is a divalent linking group derived from a ring selected from benzene, pyridine or pyrimidine; and Z is a hydrogen atom or a substituent selected from group A (where group A is the same as previously defined);

[Pattern 2]

X is a linking group selected from —CO— or —CS—;

Y is a single bond; and

Z is a substituent selected from group $A_0$:

(Group $A_0$: -Cyc,

—$C_{1-6}$ alkylene-Cyc,

—$C_{1-6}$ alkylene-CO-Cyc,

—$C_{1-6}$ alkylene-O—$C_{1-6}$alkylene-Cyc,

—$C_{1-6}$ alkylene-SO$_2$-Cyc,

—NRCO-Cyc,

—NRCO—$C_{1-6}$ alkylene-Cyc,

—NR-Cyc,

—NR-Cyc-Cyc,

—NR-Cyc-CO-Cyc,

—NR—$C_{1-6}$ alkylene-Cyc-CO-Cyc,

—NR-Cyc-CO—$C_{1-6}$ alkylene-Cyc,

—NR-Cyc-NR'-Cyc,

—NR—$C_{1-6}$ alkylene-Cyc-NR'-Cyc,

—NR-Cyc-NR'—$C_{1-6}$ alkylene-Cyc, and

—NR—$C_{1-6}$ alkylene-Cyc;

and at this time, said Cyc is preferably an aromatic hydrocarbon ring or aromatic heterocyclic ring, and when 2 Cyc are present in a substituent of group A or group $A_0$, at least one is preferably an aromatic hydrocarbon ring or aromatic heterocyclic ring, and more preferably, -Cyc- is an aromatic hydrocarbon ring and -Cyc is a nitrogen-containing heterocyclic ring).

Specific examples of compounds represented by general formula (I) of the present invention and salts thereof include those compounds described below and those compounds described in the following tables (including free forms and salts thereof). However, the present invention should not be limited to these exemplifications.

4-(3-methoxy-phenyl)-2-morpholin-4-yl-7-pyridin-4-yl-6,7-dihydro-5H-pyrrolo[2,3-d]pyrimidine (A-01);
4-(3-methoxy-phenyl)-2-morpholin-4-yl-7-pyridin-3-yl-6,7-dihydro-5H-pyrrolo[2,3-d]pyrimidine (A-02);
5-[4-(3-methoxy-phenyl)-2-morpholin-4-yl-5,6-dihydro-pyrrolo[2,3-d]pyrimidin-7-yl]-pyridin-2-ol (A-03);
4-(3-methoxy-phenyl)-2-morpholin-4-yl-7-pyridin-3-ylmethyl-6,7-dihydro-5H-pyrrolo[2,3-d]pyrimidine (A-04);
7-(1H-indazol-5-yl)-4-(3-methoxy-phenyl)-2-morpholin-4-yl-6,7-dihydro-5H-pyrrolo[2,3-d]pyrimidine (A-05);
7-(1H-benzimidazol-5-yl)-4-(3-methoxy-phenyl)-2-morpholin-4-yl-6,7-dihydro-5H-pyrrolo[2,3-d]pyrimidine (A-06);
4-(3-methoxy-phenyl)-7-methyl-2-morpholin-4-yl-6,7-dihydro-5H-pyrrolo[2,3-d]pyrimidine (A-07);
4-(3-methoxy-phenyl)-7-(6-methoxy-pyridin-3-yl)-2-morpholin-4-yl-6,7-dihydro-5H-pyrrolo[2,3-d]pyrimidine (A-08);
3-(2-morpholin-4-yl-7-pyridin-4-yl-6,7-dihydro-5H-pyrrolo[2,3-d]pyrimidin-4-yl)-phenol (A-09);
3-(2-morpholin-4-yl-7-pyridin-3-yl-6,7-dihydro-5H-pyrrolo[2,3-d]pyrimidin-4-yl)-phenol (A-10);
5-[4-(3-hydroxy-phenyl)-2-morpholin-4-yl-5,6-dihydro-pyrrolo[2,3-d]pyrimidin-7-yl]-pyridin-2-ol (A-11);
3-(2-morpholin-4-yl-7-pyridin-3-ylmethyl-6,7-dihydro-5H-pyrrolo[2,3-d]pyrimidin-4-yl)-phenol trifluoroacetic acid salt (A-12);
3-[7-(1H-indazol-5-yl)-2-morpholin-4-yl-6,7-dihydro-5H-pyrrolo[2,3-d]pyrimidin-4-yl]-phenol (A-13);
3-[7-(1H-benzimidazol-5-yl)-2-morpholin-4-yl-6,7-dihydro-5H-pyrrolo[2,3-d]pyrimidin-4-yl]-phenol (A-14);
3-(7-methyl-2-morpholin-4-yl-6,7-dihydro-5H-pyrrolo[2,3-d]pyrimidin-4-yl)-phenol (A-15);
3-[7-(2-methyl-pyridin-4-yl)-2-morpholin-4-yl-6,7-dihydro-5H-pyrrolo[2,3-d]pyrimidin-4-yl]-phenol (A-16);
3-[7-(1-methyl-1H-pyrazol-3-yl)-2-morpholin-4-yl-6,7-dihydro-5H-pyrrolo[2,3-d]pyrimidin-4-yl]-phenol (A-17);
3-[4-(3-hydroxy-phenyl)-2-morpholin-4-yl-5,6-dihydro-pyrrolo[2,3-d]pyrimidin-7-yl]-benzonitrile (A-18);
3-[7-(2-methyl-quinolin-4-yl)-2-morpholin-4-yl-6,7-dihydro-5H-pyrrolo[2,3-d]pyrimidin-4-yl]-phenol (A-19);
3-[7-(3-dimethylamino-phenyl)-2-morpholin-4-yl-6,7-dihydro-5H-pyrrolo[2,3-d]pyrimidin-4-yl]-phenol (A-20);
3-[2-morpholin-4-yl-7-(4-trifluoromethoxy-phenyl)-6,7-dihydro-5H-pyrrolo[2,3-d]pyrimidin-4-yl]-phenol (A-21);
3-(2-morpholin-4-yl-7-o-tolyl-6,7-dihydro-5H-pyrrolo[2,3-d]pyrimidin-4-yl)-phenol (A-22);
3-[7-(2,4-dimethyl-phenyl)-2-morpholin-4-yl-6,7-dihydro-5H-pyrrolo[2,3-d]pyrimidin-4-yl]-phenol (A-23);
3-[7-(3-dimethylamino-propyl)-2-morpholin-4-yl-6,7-dihydro-5H-pyrrolo[2,3-d]pyrimidin-4-yl]-phenol (A-24);
3-[7-(4-isopropyl-phenyl)-2-morpholin-4-yl-6,7-dihydro-5H-pyrrolo[2,3-d]pyrimidin-4-yl]-phenol (A-25);
3-[7-(3-chloro-phenyl)-2-morpholin-4-yl-6,7-dihydro-5H-pyrrolo[2,3-d]pyrimidin-4-yl]-phenol trifluoroacetic acid salt (A-26);
3-[7-(4-chloro-3-methyl-phenyl)-2-morpholin-4-yl-6,7-dihydro-5H-pyrrolo[2,3-d]pyrimidin-4-yl]-phenol trifluoroacetic acid salt (A-27);
3-[7-(2-chloro-phenyl)-2-morpholin-4-yl-6,7-dihydro-5H-pyrrolo[2,3-d]pyrimidin-4-yl]-phenol trifluoroacetic acid salt (A-28);
3-(2-morpholin-4-yl-7-pyridin-2-yl-6,7-dihydro-5H-pyrrolo[2,3-d]pyrimidin-4-yl)-phenol (A-29);
3-[7-(5-methyl-pyridin-2-yl)-2-morpholin-4-yl-6,7-dihydro-5H-pyrrolo[2,3-d]pyrimidin-4-yl]-phenol (A-30);
3-[7-(4-chloro-phenyl)-2-morpholin-4-yl-6,7-dihydro-5H-pyrrolo[2,3-d]pyrimidin-4-yl]-phenol trifluoroacetic acid salt (A-31);
2-fluoro-5-(2-morpholin-4-yl-7-pyridin-4-yl-6,7-dihydro-5H-pyrrolo[2,3-d]pyrimidin-4-yl)-phenol trifluoroacetic acid salt (A-32);
2-fluoro-3-(2-morpholin-4-yl-7-pyridin-4-yl-6,7-dihydro-5H-pyrrolo[2,3-d]pyrimidin-4-yl)-phenol trifluoroacetic acid salt (A-33);
2-methyl-5-(2-morpholin-4-yl-7-pyridin-4-yl-6,7-dihydro-5H-pyrrolo[2,3-d]pyrimidin-4-yl)-phenol (A-34);
2-methyl-3-(2-morpholin-4-yl-7-pyridin-4-yl-6,7-dihydro-5H-pyrrolo[2,3-d]pyrimidin-4-yl)-phenol (A-35);
3-[4-(3-methoxy-phenyl)-2-morpholin-4-yl-5,6-dihydro-pyrrolo[2,3-d]pyrimidin-7-yl]-propan-1-ol (A-36);
2-morpholin-4-yl-4,7-di-pyridin-3-yl-6,7-dihydro-5H-pyrrolo[2,3-d]pyrimidine (A-37);
2-morpholin-4-yl-4-pyridin-3-yl-7-pyridin-4-yl-6,7-dihydro-5H-pyrrolo[2,3-d]pyrimidine (A-38);
N-methyl-3-(2-morpholin-4-yl-7-pyridin-3-yl-6,7-dihydro-5H-pyrrolo[2,3-d]pyrimidin-4-yl)-benzenesulfonamide (A-39);
N-methyl-3-(2-morpholin-4-yl-7-pyridin-4-yl-6,7-dihydro-5H-pyrrolo[2,3-d]pyrimidin-4-yl)-benzenesulfonamide (A-40);
3-{7-[2-(4-methyl-piperazin-1-yl)-pyridin-4-yl]-2-morpholin-4-yl-6,7-dihydro-5H-pyrrolo[2,3-d]pyrimidin-4-yl}-phenol (A-41);
3-{7-[2-(2-dimethylamino-ethoxy)-pyridin-4-yl]-2-morpholin-4-yl-6,7-dihydro-5H-pyrrolo[2,3-d]pyrimidin-4-yl}-phenol (A-42);
3-[7-(4-dimethylamino-3,4,5,6-tetrahydro-2H-[1,2']bipyridinyl-4'-yl)-2-morpholin-4-yl-6,7-dihydro-5H-pyrrolo[2,3-d]pyrimidin-4-yl]-phenol (A-43);
3-[2-morpholin-4-yl-7-(2-morpholin-4-yl-pyridin-4-yl)-6,7-dihydro-5H-pyrrolo[2,3-d]pyrimidin-4-yl]-phenol (A-44);
3-(7-{2-[(3-dimethylamino-propyl)-methyl-amino]-pyridin-4-yl}-2-morpholin-4-yl-6,7-dihydro-5H-pyrrolo[2,3-d]pyrimidin-4-yl)-phenol (A-45);
3-(7-{2-[(2-dimethylamino-ethyl)-methyl-amino]-pyridin-4-yl}-2-morpholin-4-yl-6,7-dihydro-5H-pyrrolo[2,3-d]pyrimidin-4-yl)-phenol (A-46);
3-[7-(4-dimethylamino-phenyl)-2-morpholin-4-yl-6,7-dihydro-5H-pyrrolo[2,3-d]pyrimidin-4-yl]-phenol (A-47);
N-{3-[4-(3-hydroxy-phenyl)-2-morpholin-4-yl-5,6-dihydro-pyrrolo[2,3-d]pyrimidin-7-yl]-phenyl}-methanesulfonamide trifluoroacetic acid salt (A-48);
3-(2-morpholin-4-yl-7-thiazol-2-yl-6,7-dihydro-5H-pyrrolo[2,3-d]pyrimidin-4-yl)-phenol (A-49);
3-[7-(4-methanesulfonyl-phenyl)-2-morpholin-4-yl-6,7-dihydro-5H-pyrrolo[2,3-d]pyrimidin-4-yl]-phenol (A-50);
4-[4-(3-hydroxy-phenyl)-2-morpholin-4-yl-5,6-dihydro-pyrrolo[2,3-d]pyrimidin-7-yl]-benzenesulfonamide (A-51);
3-(7-benzothiazol-6-yl-2-morpholin-4-yl-6,7-dihydro-5H-pyrrolo[2,3-d]pyrimidin-4-yl)-phenol trifluoroacetic acid salt (A-52);

3-[4-(3-hydroxy-phenyl)-2-morpholin-4-yl-5,6-dihydro-pyrrolo[2,3-d]pyrimidin-7-yl]-benzenesulfonamide (A-53);
3-(2-morpholin-4-yl-8-pyridin-4-yl-5,6,7,8-tetrahydro-pyrido[2,3-d]pyrimidin-4-yl)-phenol (A-54);
5-(2-morpholin-4-yl-7-pyridin-4-yl-6,7-dihydro-5H-pyrrolo[2,3-d]pyrimidin-4-yl)-pyrimidin-2-ylamine (B-01);
5-(2-morpholin-4-yl-7-pyridin-3-yl-6,7-dihydro-5H-pyrrolo[2,3-d]pyrimidin-4-yl)-pyrimidin-2-ylamine (B-02);
5-(2-morpholin-4-yl-7-pyridin-4-yl-6,7-dihydro-5H-pyrrolo[2,3-d]pyrimidin-4-yl)-pyridin-2-ylamine (B-03);
5-(2-morpholin-4-yl-7-pyridin-3-yl-6,7-dihydro-5H-pyrrolo[2,3-d]pyrimidin-4-yl)-pyridin-2-ylamine (B-04);
4-methoxy-5-(2-morpholin-4-yl-7-pyridin-3-yl-6,7-dihydro-5H-pyrrolo[2,3-d]pyrimidin-4-yl)-pyrimidin-2-ylamine (B-05);
2-fluoro-4-(2-morpholin-4-yl-7-pyridin-4-yl-6,7-dihydro-5H-pyrrolo[2,3-d]pyrimidin-4-yl)-phenylamine (B-06);
2,6-difluoro-4-(2-morpholin-4-yl-7-pyridin-4-yl-6,7-dihydro-5H-pyrrolo[2,3-d]pyrimidin-4-yl)-phenylamine (B-07);
4-(2,4-dimethoxy-pyrimidin-5-yl)-2-morpholin-4-yl-7-pyridin-4-yl-6,7-dihydro-5H-pyrrolo[2,3-d]pyrimidine (B-08);
4-(2,4-dimethoxy-pyrimidin-5-yl)-2-morpholin-4-yl-7-pyridin-3-yl-6,7-dihydro-5H-pyrrolo[2,3-d]pyrimidine (B-09);
4-(6-methoxy-pyridin-3-yl)-2-morpholin-4-yl-7-pyridin-3-yl-6,7-dihydro-5H-pyrrolo[2,3-d]pyrimidine (B-10);
4-(6-methoxy-pyridin-3-yl)-2-morpholin-4-yl-7-pyridin-4-yl-6,7-dihydro-5H-pyrrolo[2,3-d]pyrimidine (B-11);
4-(2-morpholin-4-yl-7-pyridin-3-yl-6,7-dihydro-5H-pyrrolo[2,3-d]pyrimidin-4-yl)-benzoic acid methyl ester (B-12);
4-(2-morpholin-4-yl-7-pyridin-3-yl-6,7-dihydro-5H-pyrrolo[2,3-d]pyrimidin-4-yl)-benzoic acid methyl ester hydrochloride (B-13);
4-(2-morpholin-4-yl-7-pyridin-3-yl-6,7-dihydro-5H-pyrrolo[2,3-d]pyrimidin-4-yl)-benzonitrile (B-14);
4-(2-morpholin-4-yl-7-pyridin-3-yl-6,7-dihydro-5H-pyrrolo[2,3-d]pyrimidin-4-yl)-benzonitrile hydrochloride (B-15);
4-(3-fluoro-phenyl)-2-morpholin-4-yl-7-pyridin-4-yl-6,7-dihydro-5H-pyrrolo[2,3-d]pyrimidine (B-16);
4-(5-methoxy-pyridin-3-yl)-2-morpholin-4-yl-7-pyridin-4-yl-6,7-dihydro-5H-pyrrolo[2,3-d]pyrimidine (B-17);
2-morpholin-4-yl-7-pyridin-4-yl-4-pyrimidin-5-yl-6,7-dihydro-5H-pyrrolo[2,3-d]pyrimidine (B-18);
N-[4-(2-morpholin-4-yl-7-pyridin-4-yl-6,7-dihydro-5H-pyrrolo[2,3-d]pyrimidin-4-yl)-phenyl]-methanesulfonamide (B-19);
[2,6-difluoro-3-(2-morpholin-4-yl-7-pyridin-4-yl-6,7-dihydro-5H-pyrrolo[2,3-d]pyrimidin-4-yl)-phenyl]-methanol (B-20);
4-(1H-benzimidazol-5-yl)-2-morpholin-4-yl-7-pyridin-3-yl-6,7-dihydro-5H-pyrrolo[2,3-d]pyrimidine (B-21);
4-(1H-benzimidazol-5-yl)-2-morpholin-4-yl-7-pyridin-4-yl-6,7-dihydro-5H-pyrrolo[2,3-d]pyrimidine (B-22);
[3-(2-morpholin-4-yl-7-pyridin-3-yl-6,7-dihydro-5H-pyrrolo[2,3-d]pyrimidin-4-yl)-phenyl]-methanol (B-23);
4-(2-methoxy-pyridin-3-yl)-2-morpholin-4-yl-7-pyridin-3-yl-6,7-dihydro-5H-pyrrolo[2,3-d]pyrimidine (B-24);
4-(3-benzyloxy-2,6-difluoro-phenyl)-2-morpholin-4-yl-7-pyridin-4-yl-6,7-dihydro-5H-pyrrolo[2,3-d]pyrimidine (B-25);
2,4-difluoro-3-(2-morpholin-4-yl-7-pyridin-4-yl-6,7-dihydro-5H-pyrrolo[2,3-d]pyrimidin-4-yl)-phenol (B-26);
4-(2-methoxy-pyrimidin-5-yl)-2-morpholin-4-yl-7-pyridin-4-yl-6,7-dihydro-5H-pyrrolo[2,3-d]pyrimidine (B-27);
2-morpholin-4-yl-4,7-di-pyridin-4-yl-6,7-dihydro-5H-pyrrolo[2,3-d]pyrimidine (B-28);
2-morpholin-4-yl-4-pyridin-4-yl-7-pyridin-3-yl-6,7-dihydro-5H-pyrrolo[2,3-d]pyrimidine (B-29);
[4-(2-morpholin-4-yl-7-pyridin-4-yl-6,7-dihydro-5H-pyrrolo[2,3-d]pyrimidin-4-yl)-phenyl]-methanol (B-30);
[4-(2-morpholin-4-yl-7-pyridin-3-yl-6,7-dihydro-5H-pyrrolo[2,3-d]pyrimidin-4-yl)-phenyl]-methanol (B-31);
4-(2-morpholin-4-yl-7-pyridin-4-yl-6,7-dihydro-5H-pyrrolo[2,3-d]pyrimidin-4-yl)-benzylamine hydrochloride (B-32);
4-(2-morpholin-4-yl-7-pyridin-3-yl-6,7-dihydro-5H-pyrrolo[2,3-d]pyrimidin-4-yl)-benzylamine hydrochloride (B-33);
2-fluoro-5-(2-morpholin-4-yl-7-pyridin-4-yl-6,7-dihydro-5H-pyrrolo[2,3-d]pyrimidin-4-yl)-benzonitrile (B-34);
[2-fluoro-5-(2-morpholin-4-yl-7-pyridin-4-yl-6,7-dihydro-5H-pyrrolo[2,3-d]pyrimidin-4-yl)-phenyl]-methanol (B-35);
[3-(2-morpholin-4-yl-7-pyridin-4-yl-6,7-dihydro-5H-pyrrolo[2,3-d]pyrimidin-4-yl)-phenyl]-methanol (B-36);
2-morpholin-4-yl-7-pyridin-4-yl-4-(3-trifluoromethoxy-phenyl)-6,7-dihydro-5H-pyrrolo[2,3-d]pyrimidine (B-37);
2-morpholin-4-yl-7-pyridin-4-yl-4-(4-trifluoromethoxy-phenyl)-6,7-dihydro-5H-pyrrolo[2,3-d]pyrimidine (B-38);
4-(2-morpholin-4-yl-7-pyridin-4-yl-6,7-dihydro-5H-pyrrolo[2,3-d]pyrimidin-4-yl)-phenol (B-39);
2-morpholin-4-yl-7-pyridin-4-yl-4-(3,4,5-trimethoxy-phenyl)-6,7-dihydro-5H-pyrrolo[2,3-d]pyrimidine (B-40);
2-morpholin-4-yl-4-phenyl-7-pyridin-4-yl-6,7-dihydro-5H-pyrrolo[2,3-d]pyrimidine (B-41);
5-(2-morpholin-4-yl-7-pyridin-3-yl-6,7-dihydro-5H-pyrrolo[2,3-d]pyrimidin-4-yl)-pyridin-2-ol (B-42);
5-(2-morpholin-4-yl-7-pyridin-4-yl-6,7-dihydro-5H-pyrrolo[2,3-d]pyrimidin-4-yl)-pyridin-2-ol (B-43);
3-(2-morpholin-4-yl-7-pyridin-3-yl-6,7-dihydro-5H-pyrrolo[2,3-d]pyrimidin-4-yl)-pyridin-2-ol (B-44);
5-(2-morpholin-4-yl-7-pyridin-4-yl-6,7-dihydro-5H-pyrrolo[2,3-d]pyrimidin-4-yl)-pyrimidin-2-ol (B-45);
3-(2-morpholin-4-yl-7-phenyl-6,7-dihydro-5H-pyrrolo[2,3-d]pyrimidin-4-yl)-phenol (B-46);
3-[7-(2,4-difluoro-phenyl)-2-morpholin-4-yl-6,7-dihydro-5H-pyrrolo[2,3-d]pyrimidin-4-yl]-phenol (B-47);
4-(3-methoxy-phenyl)-7-(4-methoxy-phenyl)-2-morpholin-4-yl-6,7-dihydro-5H-pyrrolo[2,3-d]pyrimidine (B-48);
7-(4-methoxy-benzyl)-4-(3-methoxy-phenyl)-2-morpholin-4-yl-6,7-dihydro-5H-pyrrolo[2,3-d]pyrimidine (B-49);
3-(2-morpholin-4-yl-7-pyridin-3-yl-6,7-dihydro-5H-pyrrolo[2,3-d]pyrimidin-4-yl)-benzenesulfonamide (B-50);
3-(2-morpholin-4-yl-7-pyridin-4-yl-6,7-dihydro-5H-pyrrolo[2,3-d]pyrimidin-4-yl)-benzenesulfonamide (B-51);
2-fluoro-4-(2-morpholin-4-yl-7-pyridin-3-yl-6,7-dihydro-5H-pyrrolo[2,3-d]pyrimidin-4-yl)-phenylamine (B-52);
2,6-difluoro-4-(2-morpholin-4-yl-7-pyridin-3-yl-6,7-dihydro-5H-pyrrolo[2,3-d]pyrimidin-4-yl)-phenylamine (B-53);
4-(2-morpholin-4-yl-7-pyridin-3-yl-6,7-dihydro-5H-pyrrolo[2,3-d]pyrimidin-4-yl)-phenylamine (B-54);
6-(2-morpholin-4-yl-7-pyridin-4-yl-6,7-dihydro-5H-pyrrolo[2,3-d]pyrimidin-4-yl)-pyridin-3-ylamine (B-55);
4-(3-hydroxyphenyl)-2-(morpholin-4-yl)-7-(ethylaminocarbonyl)-6,7-dihydro-5H-pyrrolo[2,3-d]pyrimidine (C-01);
1-[4-(3-hydroxy-phenyl)-2-morpholin-4-yl-5,6-dihydro-pyrrolo[2,3-d]pyrimidin-7-yl]-ethanone (C-02);

[4-(3-t-butoxyphenyl)-2-morpholin-4-yl-5,6-dihydropyrrolo[2,3-d]pyrimidin-7-yl]-phenylmethanone (C-03);

[4-(3-hydroxyphenyl)-2-morpholin-4-yl-5,6-dihydropyrrolo[2,3-d]pyrimidin-7-yl]-phenylmethanone (C-04);

1-[4-(3-hydroxyphenyl)-2-morpholin-4-yl-5,6-dihydropyrrolo[2,3-d]pyrimidin-7-yl]propan-1-one (C-05);

1-[4-(3-hydroxyphenyl)-2-morpholin-4-yl-5,6-dihydropyrrolo[2,3-d]pyrimidin-7-yl]-2,2-dimethyl-propan-1-one (C-06);

4-(3-t-butoxy-phenyl)-2-morpholin-4-yl-7-(toluene-4-sulfonyl)-6,7-dihydro-5H-pyrrolo[2,3-d]pyrimidine (C-07);

3-[2-morpholin-4-yl-7-(toluene-4-sulfonyl)-6,7-dihydro-5H-pyrrolo[2,3-d]pyrimidin-4-yl]-phenol (C-08);

4-(3-hydroxy-phenyl)-2-morpholin-4-yl-5,6-dihydro-pyrrolo[2,3-d]pyrimidine-7-carbaldehyde (C-09);

3-(7-methanesulfonyl-2-morpholin-4-yl-6,7-dihydro-5H-pyrrolo[2,3-d]pyrimidin-4-yl)-phenol (C-10);

3-(7-ethanesulfonyl-2-morpholin-4-yl-6,7-dihydro-5H-pyrrolo[2,3-d]pyrimidin-4-yl)-phenol (C-11);

3-[2-morpholin-4-yl-7-(toluene-2-sulfonyl)-6,7-dihydro-5H-pyrrolo[2,3-d]pyrimidin-4-yl]-phenol (C-12);

[4-(3-hydroxy-phenyl)-2-morpholin-4-yl-5,6-dihydro-pyrrolo[2,3-d]pyrimidin-7-yl]-acetic acid ethyl ester (C-13);

3-(7-benzenesulfonyl-2-morpholin-4-yl-6,7-dihydro-5H-pyrrolo[2,3-d]pyrimidin-4-yl)-phenol (C-14);

3-[2-morpholin-4-yl-7-(thiophene-2-sulfonyl)-6,7-dihydro-5H-pyrrolo[2,3-d]pyrimidin-4-yl]-phenol (C-15);

3-[7-(3-methoxy-benzenesulfonyl)-2-morpholin-4-yl-6,7-dihydro-5H-pyrrolo[2,3-d]pyrimidin-4-yl]-phenol (C-16);

4-(3-hydroxy-phenyl)-2-morpholin-4-yl-5,6-dihydro-pyrrolo[2,3-d]pyrimidine-7-carboxylic acid phenyl amide (C-17);

4-(3-hydroxy-phenyl)-2-morpholin-4-yl-5,6-dihydro-pyrrolo[2,3-d]pyrimidine-7-carboxylic acid (2,4-difluoro-phenyl)-amide (C-18);

4-(3-hydroxy-phenyl)-2-morpholin-4-yl-5,6-dihydro-pyrrolo[2,3-d]pyrimidine-7-carboxylic acid p-tolylamide (C-19);

4-(3-hydroxy-phenyl)-2-morpholin-4-yl-5,6-dihydro-pyrrolo[2,3-d]pyrimidine-7-carboxylic acid (4-trifluoromethyl-phenyl)-amide (C-20);

3-[7-(4-fluoro-benzenesulfonyl)-2-morpholin-4-yl-6,7-dihydro-5H-pyrrolo[2,3-d]pyrimidin-4-yl]-phenol (C-21);

3-[7-(2,4-difluoro-benzenesulfonyl)-2-morpholin-4-yl-6,7-dihydro-5H-pyrrolo[2,3-d]pyrimidin-4-yl]-phenol (C-22);

4-[4-(3-hydroxy-phenyl)-2-morpholin-4-yl-5,6-dihydro-pyrrolo[2,3-d]pyrimidine-7-sulfonyl]-benzonitrile (C-23);

3-[2-morpholin-4-yl-7-(toluene-3-sulfonyl)-6,7-dihydro-5H-pyrrolo[2,3-d]pyrimidin-4-yl]-phenol (C-24);

3-[7-(4-tert-butyl-benzenesulfonyl)-2-morpholin-4-yl-6,7-dihydro-5H-pyrrolo[2,3-d]pyrimidin-4-yl]-phenol (C-25);

3-[2-morpholin-4-yl-7-(4-trifluoromethyl-benzenesulfonyl)-6,7-dihydro-5H-pyrrolo[2,3-d]pyrimidin-4-yl]-phenol (C-26);

3-[2-morpholin-4-yl-7-(3-trifluoromethyl-benzenesulfonyl)-6,7-dihydro-5H-pyrrolo[2,3-d]pyrimidin-4-yl]-phenol (C-27);

3-[2-morpholin-4-yl-7-(4-trifluoromethoxy-benzenesulfonyl)-6,7-dihydro-5H-pyrrolo[2,3-d]pyrimidin-4-yl]-phenol (C-28);

[4-(3-hydroxy-phenyl)-2-morpholin-4-yl-5,6-dihydro-pyrrolo[2,3-d]pyrimidin-7-yl]-p-tolyl-methanone (C-29);

[4-(3-hydroxy-phenyl)-2-morpholin-4-yl-5,6-dihydro-pyrrolo[2,3-d]pyrimidin-7-yl]-m-tolyl-methanone (C-30);

[4-(3-hydroxy-phenyl)-2-morpholin-4-yl-5,6-dihydro-pyrrolo[2,3-d]pyrimidin-7-yl]-(4-trifluoromethyl-phenyl)-methanone (C-31);

2-(4-fluoro-phenyl)-1-[4-(3-hydroxy-phenyl)-2-morpholin-4-yl-5,6-dihydro-pyrrolo[2,3-d]pyrimidin-7-yl]-ethanone (C-32);

1-[4-(3-hydroxy-phenyl)-2-morpholin-4-yl-5,6-dihydro-pyrrolo[2,3-d]pyrimidin-7-yl]-3-phenyl-propan-1-one (C-33);

[4-(3-hydroxy-phenyl)-2-morpholin-4-yl-5,6-dihydro-pyrrolo[2,3-d]pyrimidin-7-yl]-(3-trifluoromethyl-phenyl)-methanone (C-34);

1-[4-(3-hydroxy-phenyl)-2-morpholin-4-yl-5,6-dihydro-pyrrolo[2,3-d]pyrimidin-7-yl]-2-phenyl-ethanone (C-35);

N-{4-[4-(3-hydroxy-phenyl)-2-morpholin-4-yl-5,6-dihydro-pyrrolo[2,3-d]pyrimidine-7-carbonyl]-phenyl}-acetamide (C-36);

[4-(3-hydroxy-phenyl)-2-morpholin-4-yl-5,6-dihydro-pyrrolo[2,3-d]pyrimidin-7-yl]-pyridin-2-yl-methanone (C-37);

(2,4-difluoro-phenyl)-[4-(3-hydroxy-phenyl)-2-morpholin-4-yl-5,6-dihydro-pyrrolo[2,3-d]pyrimidin-7-yl]-methanone (C-38);

[4-(3-hydroxy-phenyl)-2-morpholin-4-yl-5,6-dihydro-pyrrolo[2,3-d]pyrimidin-7-yl]-pyridin-4-yl-methanone (C-39);

[4-(3-hydroxy-phenyl)-2-morpholin-4-yl-5,6-dihydro-pyrrolo[2,3-d]pyrimidin-7-yl]-o-tolyl-methanone (C-40);

(4-tert-butyl-phenyl)-[4-(3-hydroxy-phenyl)-2-morpholin-4-yl-5,6-dihydro-pyrrolo[2,3-d]pyrimidin-7-yl]-methanone (C-41);

4-[4-(3-hydroxy-phenyl)-2-morpholin-4-yl-5,6-dihydro-pyrrolo[2,3-d]pyrimidine-7-carbonyl]-benzonitrile trifluoroacetic acid salt (C-42);

[4-(3-hydroxy-phenyl)-2-morpholin-4-yl-5,6-dihydro-pyrrolo[2,3-d]pyrimidin-7-yl]-naphthalen-2-yl-methanone trifluoroacetic acid salt (C-43);

[4-(3-hydroxy-phenyl)-2-morpholin-4-yl-5,6-dihydro-pyrrolo[2,3-d]pyrimidin-7-yl]-naphthalen-1-yl-methanone trifluoroacetic acid salt (C-44);

1-[4-(3-hydroxy-phenyl)-2-morpholin-4-yl-5,6-dihydro-pyrrolo[2,3-d]pyrimidin-7-yl]-3,3-dimethyl-butan-1-one (C-45);

1-[4-(3-hydroxy-phenyl)-2-morpholin-4-yl-5,6-dihydro-pyrrolo[2,3-d]pyrimidin-7-yl]-pentan-1-one (C-46);

4-[4-(3-hydroxy-phenyl)-2-morpholin-4-yl-5,6-dihydro-pyrrolo[2,3-d]pyrimidin-7-yl]-4-oxo-butyric acid methyl ester (C-47);

5-[4-(3-hydroxy-phenyl)-2-morpholin-4-yl-5,6-dihydro-pyrrolo[2,3-d]pyrimidin-7-yl]-5-oxo-pentanoic acid methyl ester (C-48);

1-[4-(3-hydroxy-phenyl)-2-morpholin-4-yl-5,6-dihydro-pyrrolo[2,3-d]pyrimidin-7-yl]-heptan-1-one (C-49);

4-(3-hydroxy-phenyl)-2-morpholin-4-yl-5,6-dihydro-pyrrolo[2,3-d]pyrimidine-7-carboxylic acid isopropylamide trifluoroacetic acid salt (C-50);

4-(3-hydroxy-phenyl)-2-morpholin-4-yl-5,6-dihydro-pyrrolo[2,3-d]pyrimidine-7-carboxylic acid phenethyl-amide trifluoroacetic acid salt (C-51);

1-[4-(3-hydroxy-phenyl)-2-morpholin-4-yl-5,6-dihydro-pyrrolo[2,3-d]pyrimidin-7-yl]-2-naphthalen-1-yl-ethanone (C-52);

[4-(3-hydroxy-phenyl)-2-morpholin-4-yl-5,6-dihydro-pyrrolo[2,3-d]pyrimidin-7-yl]-thiophen-2-yl-methanone trifluoroacetic acid salt (C-53);

benzo[b]thiophen-2-yl-[4-(3-hydroxy-phenyl)-2-morpholin-4-yl-5,6-dihydro-pyrrolo[2,3-d]pyrimidin-7-yl]-methanone trifluoroacetic acid salt (C-54);

4-(3-hydroxy-phenyl)-2-morpholin-4-yl-5,6-dihydro-pyrrolo[2,3-d]pyrimidine-7-carbothioic acid methyl amide trifluoroacetic acid salt (C-55);

4-(3-hydroxy-phenyl)-2-morpholin-4-yl-5,6-dihydro-pyrrolo[2,3-d]pyrimidine-7-carbothioic acid butyl amide trifluoroacetic acid salt (C-56);

3-[7-(butane-1-sulfonyl)-2-morpholin-4-yl-6,7-dihydro-5H-pyrrolo[2,3-d]pyrimidin-4-yl]-phenol (C-57);

1-[4-(2-amino-pyrimidin-5-yl)-2-morpholin-4-yl-5,6-dihydro-pyrrolo[2,3-d]pyrimidin-7-yl]-ethanone (D-01);

5-(7-methanesulfonyl-2-morpholin-4-yl-6,7-dihydro-5H-pyrrolo[2,3-d]pyrimidin-4-yl)-pyrimidin-2-ylamine (D-02);

4-(2-amino-pyrimidin-5-yl)-2-morpholin-4-yl-5,6-dihydro-pyrrolo[2,3-d]pyrimidine-7-carboxylic acid ethyl amide (D-03);

5-(7-ethyl-2-morpholin-4-yl-6,7-dihydro-5H-pyrrolo[2,3-d]pyrimidin-4-yl)-pyrimidin-2-ylamine (D-04);

5-(7-benzyl-2-morpholin-4-yl-6,7-dihydro-5H-pyrrolo[2,3-d]pyrimidin-4-yl)-pyrimidin-2-ylamine (D-05);

1-[4-(2-amino-pyrimidin-5-yl)-2-morpholin-4-yl-5,6-dihydro-pyrrolo[2,3-d]pyrimidin-7-yl]-propan-1-one (D-06);

4-[4-(2-amino-pyrimidin-5-yl)-2-morpholin-4-yl-5,6-dihydro-pyrrolo[2,3-d]pyrimidin-7-yl]-pyridine-2-carboxylic acid tert-butyl amide (D-07);

4-[4-(2-amino-pyrimidin-5-yl)-2-morpholin-4-yl-5,6-dihydro-pyrrolo[2,3-d]pyrimidin-7-yl]-benzoic acid methyl ester (D-08);

4-[4-(2-amino-pyrimidin-5-yl)-2-morpholin-4-yl-5,6-dihydro-pyrrolo[2,3-d]pyrimidin-7-yl]-benzoic acid sodium salt (D-09);

4-[4-(2-amino-pyrimidin-5-yl)-2-morpholin-4-yl-5,6-dihydro-pyrrolo[2,3-d]pyrimidin-7-yl]-benzamide (D-10);

1-[4-(2-amino-pyrimidin-5-yl)-2-morpholin-4-yl-5,6-dihydro-pyrrolo[2,3-d]pyrimidin-7-yl]-3-phenylpropan-1-one (D-11);

4-[4-(2-amino-pyrimidin-5-yl)-2-morpholin-4-yl-5,6-dihydro-pyrrolo[2,3-d]pyrimidin-7-yl]-4-oxo-butyric acid methyl ester (D-12);

4-(2-amino-pyrimidin-5-yl)-2-morpholin-4-yl-5,6-dihydro-pyrrolo[2,3-d]pyrimidine-7-carboxylic acid isopropylamide (D-13);

4-(2-amino-pyrimidin-5-yl)-2-morpholin-4-yl-5,6-dihydro-pyrrolo[2,3-d]pyrimidine-7-thiocarboxylic acid ethyl amide (D-14);

4-(2-amino-pyrimidin-5-yl)-2-morpholin-4-yl-5,6-dihydro-pyrrolo[2,3-d]pyrimidine-7-carboxylic acid ethyl ester (D-15);

{3-[4-(2-amino-pyrimidin-5-yl)-2-morpholin-4-yl-5,6-dihydro-pyrrolo[2,3-d]pyrimidin-7-yl]-4-fluoro-phenyl}-morpholin-4-yl-methanone (D-16);

4-(2-amino-pyrimidin-5-yl)-2-morpholin-4-yl-5,6-dihydro-pyrrolo[2,3-d]pyrimidine-7-carbothioic acid [5-(4-ethyl-piperazine-1-carbonyl)-2-methyl-phenyl]-amide (D-17);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-2,6-difluoro-phenyl]-amide (D-18);

4-[4-(2-amino-pyrimidin-5-yl)-2-morpholin-4-yl-5,6-dihydro-pyrrolo[2,3-d]pyrimidin-7-yl]-N-pyridin-3-ylmethyl-benzamide (D-19);

{4-[4-(2-amino-pyrimidin-5-yl)-2-morpholin-4-yl-5,6-dihydro-pyrrolo[2,3-d]pyrimidin-7-yl]-phenyl}-(4-pyridin-3-yl-piperazin-1-yl)-methanone (D-20);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-3-yl-piperazin-1-yl)-methanone (D-21);

{4-[4-(2-amino-pyrimidin-5-yl)-2-morpholin-4-yl-5,6-dihydro-pyrrolo[2,3-d]pyrimidin-7-yl]-3-fluoro-phenyl}-morpholin-4-yl-methanone (D-22);

4-(2-amino-pyrimidin-5-yl)-2-morpholin-4-yl-5,6-dihydro-pyrrolo[2,3-d]pyrimidine-7-carboxylic acid [4-(4-methyl-piperazin-1-yl)-2,6-difluoro-phenyl]-amide (D-23);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2,6-difluoro-phenyl]-amide (D-24);

{3-[4-(2-amino-pyrimidin-5-yl)-2-morpholin-4-yl-5,6-dihydro-pyrrolo[2,3-d]pyrimidin-7-yl]-4-methyl-phenyl}-morpholin-4-yl-methanone (D-25);

5-{7-[4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-26);

[4-(2-amino-pyrimidin-5-yl)-2-morpholin-4-yl-5,6-dihydro-pyrrolo[2,3-d]pyrimidin-7-yl]-phenyl-methanone (D-27);

4-(2-amino-pyrimidin-5-yl)-2-morpholin-4-yl-5,6-dihydro-pyrrolo[2,3-d]pyrimidine-7-carboxylic acid phenylamide (D-28);

{[4-(2-amino-pyrimidin-5-yl)-2-morpholin-4-yl-5,6-dihydro-pyrrolo[2,3-d]pyrimidine-7-carbonyl]-amino}-acetic acid ethyl ester (D-29);

3-{[4-(2-amino-pyrimidin-5-yl)-2-morpholin-4-yl-5,6-dihydro-pyrrolo[2,3-d]pyrimidine-7-carbonyl]-amino}-propionic acid ethyl ester (D-30);

4-(2-amino-pyrimidin-5-yl)-2-morpholin-4-yl-5,6-dihydro-pyrrolo[2,3-d]pyrimidine-7-carboxylic acid carbamoylmethyl-amide (D-31);

4-(2-amino-pyrimidin-5-yl)-2-morpholin-4-yl-5,6-dihydro-pyrrolo[2,3-d]pyrimidine-7-carboxylic acid (2-carbamoyl-ethyl)-amide (D-32);

{[4-(2-amino-pyrimidin-5-yl)-2-morpholin-4-yl-5,6-dihydro-pyrrolo[2,3-d]pyrimidine-7-carbonyl]-amino}-acetic acid (D-33);

3-{[4-(2-amino-pyrimidin-5-yl)-2-morpholin-4-yl-5,6-dihydro-pyrrolo[2,3-d]pyrimidine-7-carbonyl]-amino}-propionic acid (D-34);

4-[4-(2-amino-pyrimidin-5-yl)-2-morpholin-4-yl-5,6-dihydro-pyrrolo[2,3-d]pyrimidin-7-yl]-4-oxo-butyric acid (D-35);

5-[7-(5-bromo-pyridin-2-yl)-2-morpholin-4-yl-6,7-dihydro-5H-pyrrolo[2,3-d]pyrimidin-4-yl]-pyrimidin-2-ylamine (D-36);

5-[7-(6-fluoro-pyridin-3-yl)-2-morpholin-4-yl-6,7-dihydro-5H-pyrrolo[2,3-d]pyrimidin-4-yl]-pyrimidin-2-ylamine (D-37);

4-[4-(2-amino-pyrimidin-5-yl)-2-morpholin-4-yl-5,6-dihydro-pyrrolo[2,3-d]pyrimidin-7-yl]-4-oxo-butyramide (D-38);

4-(2-amino-pyrimidin-5-yl)-2-morpholin-4-yl-5,6-dihydro-pyrrolo[2,3-d]pyrimidine-7-carboxylic acid 2-methoxy-ethyl ester (D-39);

4-(2-amino-pyrimidin-5-yl)-2-morpholin-4-yl-5,6-dihydro-pyrrolo[2,3-d]pyrimidine-7-carboxylic acid allyl ester (D-40);

4-[4-(2-amino-pyrimidin-5-yl)-2-morpholin-4-yl-5,6-dihydro-pyrrolo[2,3-d]pyrimidin-7-yl]-N-(2-dimethylamino-ethyl)-benzamide (D-41);

{4-[4-(2-amino-pyrimidin-5-yl)-2-morpholin-4-yl-5,6-dihydro-pyrrolo[2,3-d]pyrimidin-7-yl]-phenyl}-(4-methyl-piperazin-1-yl)-methanone (D-42);

N-{4-[4-(2-amino-pyrimidin-5-yl)-2-morpholin-4-yl-5,6-dihydro-pyrrolo[2,3-d]pyrimidin-7-yl]-phenyl}-acetamide (D-43);
N-{4-[4-(2-amino-pyrimidin-5-yl)-2-morpholin-4-yl-5,6-dihydro-pyrrolo[2,3-d]pyrimidin-7-yl]-phenyl}-methanesulfonamide (D-44);
N-{3-[4-(2-amino-pyrimidin-5-yl)-2-morpholin-4-yl-5,6-dihydro-pyrrolo[2,3-d]pyrimidin-7-yl]-phenyl}-acetamide (D-45);
4-(2-amino-pyrimidin-5-yl)-2-morpholin-4-yl-5,6-dihydro-pyrrolo[2,3-d]pyrimidine-7-carbothioic acid (2-morpholin-4-yl-ethyl)-amide (D-46);
4-(2-amino-pyrimidin-5-yl)-2-morpholin-4-yl-5,6-dihydro-pyrrolo[2,3-d]pyrimidine-7-carboxylic acid (3-trifluoromethyl-phenyl)-amide (D-47);
N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-48);
5-{7-[6-(4-ethyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-49);
5-(7-ethanesulfonyl-2-morpholin-4-yl-6,7-dihydro-5H-pyrrolo[2,3-d]pyrimidin-4-yl)-pyrimidin-2-ylamine (D-50);
5-[2-morpholin-4-yl-7-(propane-1-sulfonyl)-6,7-dihydro-5H-pyrrolo[2,3-d]pyrimidin-4-yl]-pyrimidin-2-ylamine (D-51);
3-[4-(2-amino-pyrimidin-5-yl)-2-morpholin-4-yl-5,6-dihydro-pyrrolo[2,3-d]pyrimidin-7-yl]-benzoic acid methyl ester (D-52);
{3-[4-(2-amino-pyrimidin-5-yl)-2-morpholin-4-yl-5,6-dihydro-pyrrolo[2,3-d]pyrimidin-7-yl]-phenyl}-morpholin-4-yl-methanone (D-53);
{3-[4-(2-amino-pyrimidin-5-yl)-2-morpholin-4-yl-5,6-dihydro-pyrrolo[2,3-d]pyrimidin-7-yl]-phenyl}-(4-methyl-piperazin-1-yl)-methanone (D-54);
3-[4-(2-amino-pyrimidin-5-yl)-2-morpholin-4-yl-5,6-dihydro-pyrrolo[2,3-d]pyrimidin-7-yl]-N-(2-dimethylamino-ethyl)-benzamide (D-55);
4-{[4-(2-amino-pyrimidin-5-yl)-2-morpholin-4-yl-5,6-dihydro-pyrrolo[2,3-d]pyrimidine-7-carbonyl]-amino}-benzoic acid ethyl ester (D-56);
5-(2-morpholin-4-yl-7-phenyl-6,7-dihydro-5H-pyrrolo[2,3-d]pyrimidin-4-yl)-pyrimidin-2-ylamine (D-57);
5-[7-(2,4-difluoro-phenyl)-2-morpholin-4-yl-6,7-dihydro-5H-pyrrolo[2,3-d]pyrimidin-4-yl]-pyrimidin-2-ylamine (D-58);
4-(2-amino-pyrimidin-5-yl)-2-morpholin-4-yl-5,6-dihydro-pyrrolo[2,3-d]pyrimidine-7-carboxylic acid (2-morpholin-4-yl-ethyl)-amide (D-59);
4-(2-amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide (D-60);
4-(2-amino-pyrimidin-5-yl)-2-morpholin-4-yl-5,6-dihydro-pyrrolo[2,3-d]pyrimidine-7-carboxylic acid (2-piperidin-1-yl-ethyl)-amide (D-61);
5-{7-[3-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-62);
5-{7-[4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-63);
[4-(2-amino-pyrimidin-5-yl)-2-morpholin-4-yl-5,6-dihydro-pyrrolo[2,3-d]pyrimidin-7-yl]-piperidin-4-yl-methanone (D-64);
4-(2-amino-pyrimidin-5-yl)-2-morpholin-4-yl-5,6-dihydro-pyrrolo[2,3-d]pyrimidine-7-carboxylic acid (4-pyridin-3-yl-phenyl)-amide (D-65);
4-(2-amino-pyrimidin-5-yl)-2-morpholin-4-yl-5,6-dihydro-pyrrolo[2,3-d]pyrimidine-7-carboxylic acid (4-pyridin-4-yl-phenyl)-amide (D-66);
4-(2-amino-pyrimidin-5-yl)-2-morpholin-4-yl-5,6-dihydro-pyrrolo[2,3-d]pyrimidine-7-carboxylic acid piperidin-4-ylamide (D-67);
4-(2-amino-pyrimidin-5-yl)-2-morpholin-4-yl-5,6-dihydro-pyrrolo[2,3-d]pyrimidine-7-carboxylic acid (2-dimethylamino-ethyl)-amide (D-68);
5-{2-morpholin-4-yl-7-[2-(3-morpholin-4-yl-propylamino)-pyridin-4-yl]-6,7-dihydro-5H-pyrrolo[2,3-d]pyrimidin-4-yl}-pyrimidin-2-ylamine (D-69);
1-(4-{4-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-70);
5-{7-[6-(4-methyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-71);
5-{7-[6-(2-dimethylamino-ethoxy)-pyridin-3-yl]-2-morpholin-4-yl-6,7-dihydro-5H-pyrrolo[2,3-d]pyrimidin-4-yl}-pyrimidin-2-ylamine (D-72);
{5'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (D-73);
N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-74);
4'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-ol (D-75);
[4-(2-amino-pyrimidin-5-yl)-2-morpholin-4-yl-5,6-dihydro-pyrrolo[2,3-d]pyrimidin-7-yl]-(4-methyl-piperazin-1-yl)-methanone (D-76);
4-(2-amino-pyrimidin-5-yl)-2-morpholin-4-yl-5,6-dihydro-pyrrolo[2,3-d]pyrimidine-7-carboxylic acid (3-dimethylamino-propyl)-amide (D-77);
4-(2-amino-pyrimidin-5-yl)-2-morpholin-4-yl-5,6-dihydro-pyrrolo[2,3-d]pyrimidine-7-carboxylic acid (piperidin-4-ylmethyl)-amide (D-78);
{5-[4-(2-amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-79);
3-[4-(2-amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-80);
4-(2-amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-amide (D-81);
4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-amide (D-82);
{4-[4-(2-amino-pyrimidin-5-yl)-2-morpholin-4-yl-5,6-dihydro-pyrrolo[2,3-d]pyrimidin-7-yl]-phenyl}-(4-ethyl-piperazin-1-yl)-methanone (D-83);
4-[4-(2-amino-pyrimidin-5-yl)-2-morpholin-4-yl-5,6-dihydro-pyrrolo[2,3-d]pyrimidin-7-yl]-N-(2-dimethylamino-ethyl)-N-methyl-benzamide (D-84);
{5-[4-(2-amino-pyrimidin-5-yl)-2-morpholin-4-yl-5,6-dihydro-pyrrolo[2,3-d]pyrimidin-7-yl]-pyridin-2-yl}-morpholin-4-yl-methanone (D-85):
5-{7-[3-(morpholine-4-sulfonyl)-phenyl]-2-morpholin-4-yl-6,7-dihydro-5H-pyrrolo[2,3-d]pyrimidin-4-yl}-pyrimidin-2-ylamine (D-86);
5-{7-[4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-87);

4-(2-amino-pyrimidin-5-yl)-2-morpholin-4-yl-5,6-dihydro-pyrrolo[2,3-d]pyrimidine-7-carboxylic acid (1-methyl-piperidin-4-yl)-amide (D-88);

1-[4-(2-amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione (D-89);

1-[4-(2-amino-pyrimidin-5-yl)-2-morpholin-4-yl-5,6-dihydro-pyrrolo[2,3-d]pyrimidin-7-yl]-4-morpholin-4-yl-butane-1,4-dione (D-90);

4-[4-(2-amino-pyrimidin-5-yl)-2-morpholin-4-yl-5,6-dihydro-pyrrolo[2,3-d]pyrimidin-7-yl]-N-(3-dimethylamino-propyl)-benzamide (D-91);

4-[4-(2-amino-pyrimidin-5-yl)-2-morpholin-4-yl-5,6-dihydro-pyrrolo[2,3-d]pyrimidin-7-yl]-N-(3-dimethylamino-propyl)-N-methyl-benzamide (D-92);

4-[4-(2-amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-93);

4-[4-(2-amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-94);

{5-[4-(2-amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-95);

5-{7-[3-(4-ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-96);

5-{7-[4-(4-ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-97);

4-[4-(2-amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-98);

3-[4-(2-amino-pyrimidin-5-yl)-2-morpholin-4-yl-5,6-dihydro-pyrrolo[2,3-d]pyrimidin-7-yl]-N-(2-hydroxy-ethyl)-benzenesulfonamide (D-99);

4-[4-(2-amino-pyrimidin-5-yl)-2-morpholin-4-yl-5,6-dihydro-pyrrolo[2,3-d]pyrimidin-7-yl]-N-(2-hydroxy-ethyl)-benzenesulfonamide (D-100);

4-(2-amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-phenyl]-amide (D-101);

4-(2-amino-pyrimidin-5-yl)-2-morpholin-4-yl-5,6-dihydro-pyrrolo[2,3-d]pyrimidine-7-carboxylic acid [3-(morpholine-4-carbonyl)-phenyl]-amide (D-102);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-phenyl]-amide (D-103);

4-(2-amino-pyrimidin-5-yl)-2-morpholin-4-yl-5,6-dihydro-pyrrolo[2,3-d]pyrimidine-7-carboxylic acid [4-(morpholine-4-carbonyl)-phenyl]-amide (D-104);

4-(2-amino-pyrimidin-5-yl)-2-morpholin-4-yl-5,6-dihydro-pyrrolo[2,3-d]pyrimidine-7-carboxylic acid (3-morpholin-4-yl-phenyl)-amide (D-105);

4-(2-amino-pyrimidin-5-yl)-2-morpholin-4-yl-5,6-dihydro-pyrrolo[2,3-d]pyrimidine-7-carboxylic acid [3-(2-morpholin-4-yl-ethylamino)-phenyl]-amide (D-106);

4-(2-amino-pyrimidin-5-yl)-2-morpholin-4-yl-5,6-dihydro-pyrrolo[2,3-d]pyrimidine-7-carboxylic acid (4-morpholin-4-yl-phenyl)-amide (D-107);

4-(2-amino-pyrimidin-5-yl)-2-morpholin-4-yl-5,6-dihydro-pyrrolo[2,3-d]pyrimidine-7-carboxylic acid [4-(2-morpholin-4-yl-ethylamino)-phenyl]-amide (D-108);

1-(4-{5-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-109);

5-[2-morpholin-4-yl-7-(6-morpholin-4-yl-pyridin-3-yl)-6,7-dihydro-5H-pyrrolo[2,3-d]pyrimidin-4-yl]-pyrimidin-2-ylamine (D-110);

{4-[4-(2-amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-111);

{4-[4-(2-amino-pyrimidin-5-yl)-2-morpholin-4-yl-5,6-dihydro-pyrrolo[2,3-d]pyrimidin-7-yl]-phenyl}-piperazin-1-yl-methanone (D-112);

{4-[4-(2-amino-pyrimidin-5-yl)-2-morpholin-4-yl-5,6-dihydro-pyrrolo[2,3-d]pyrimidin-7-yl]-phenyl}-(4-isopropyl-piperazin-1-yl)-methanone (D-113);

5-[7-(1-benzyloxymethyl-1H-benzimidazol-5-yl)-2-morpholin-4-yl-6,7-dihydro-5H-pyrrolo[2,3-d]pyrimidin-4-yl]-pyrimidin-2-ylamine (D-114);

5-[7-(1H-benzimidazol-5-yl)-2-morpholin-4-yl-6,7-dihydro-5H-pyrrolo[2,3-d]pyrimidin-4-yl]-pyrimidin-2-ylamine (D-115);

N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (D-116);

{5-[4-(2-amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-117);

2-(4-{3-[4-(2-amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-118);

2-(4-{4-[4-(2-amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-119);

{2-[4-(2-amino-pyrimidin-5-yl)-2-morpholin-4-yl-5,6-dihydro-pyrrolo[2,3-d]pyrimidin-7-yl]-thiazol-4-yl}-(4-ethyl-piperazin-1-yl)-methanone (D-120);

{2-[4-(2-amino-pyrimidin-5-yl)-2-morpholin-4-yl-5,6-dihydro-pyrrolo[2,3-d]pyrimidin-7-yl]-thiazol-4-yl}-[4-(2-hydroxy-ethyl)-piperazin-1-yl]-methanone (D-121);

4-(2-amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide (D-122);

3-[4-(2-amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-123);

3-[4-(2-amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-124);

{3-[4-(2-amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-125);

5-[2-morpholin-4-yl-7-(4-morpholin-4-ylmethyl-phenyl)-6,7-dihydro-5H-pyrrolo[2,3-d]pyrimidin-4-yl]-pyrimidin-2-ylamine (D-126);

2-{4-[4-(2-amino-pyrimidin-5-yl)-2-morpholin-4-yl-5,6-dihydro-pyrrolo[2,3-d]pyrimidin-7-yl]-phenylsulfanyl}-1-(4-ethyl-piperazin-1-yl)-ethanone (D-127);

{5-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-128);

5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-ylamine (D-129);

{3-[4-(2-amino-pyrimidin-5-yl)-2-morpholin-4-yl-5,6-dihydro-pyrrolo[2,3-d]pyrimidin-7-yl]-4-methyl-phenyl}-(4-methyl-piperazin-1-yl)-methanone (D-130);

5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-ylamine (D-131);

5-{2-morpholin-4-yl-7-[3-(piperazine-1-sulfonyl)-phenyl]-6,7-dihydro-5H-pyrrolo[2,3-d]pyrimidin-4-yl}-pyrimidin-2-ylamine (D-132);

5-{2-morpholin-4-yl-7-[4-(piperazine-1-sulfonyl)-phenyl]-6,7-dihydro-5H-pyrrolo[2,3-d]pyrimidin-4-yl}-pyrimidin-2-ylamine (D-133);

1-[4-(2-{3-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-134);

4-(2-amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-methyl-amide (D-135);

5-(7-{3-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-136);

{4-[4-(2-amino-pyrimidin-5-yl)-2-morpholin-4-yl-5,6-dihydro-pyrrolo[2,3-d]pyrimidin-7-yl]-3-methyl-phenyl}-morpholin-4-yl-methanone (D-137);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-ethyl-piperazin-1-yl)-methanone (D-138);

4-[4-(2-amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzamide (D-139);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-methyl-piperazin-1-yl)-methanone (D-140);

{4-[4-(2-amino-pyrimidin-5-yl)-2-morpholin-4-yl-5,6-dihydro-pyrrolo[2,3-d]pyrimidin-7-yl]-3-fluoro-phenyl}-piperazin-1-yl-methanone (D-141);

{4-[4-(2-amino-pyrimidin-5-yl)-2-morpholin-4-yl-5,6-dihydro-pyrrolo[2,3-d]pyrimidin-7-yl]-3-methyl-phenyl}-(4-methyl-piperazin-1-yl)-methanone (D-142);

1-[4-(2-{4-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-143);

5-(7-{4-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-144);

{4-[4-(2-amino-pyrimidin-5-yl)-2-morpholin-4-yl-5,6-dihydro-pyrrolo[2,3-d]pyrimidin-7-yl]-3-fluoro-phenyl}-[4-(2-hydroxy-ethyl)-piperazin-1-yl]-methanone (D-145);

{4-[4-(2-amino-pyrimidin-5-yl)-2-morpholin-4-yl-5,6-dihydro-pyrrolo[2,3-d]pyrimidin-7-yl]-3-methyl-phenyl}-(4-ethyl-piperazin-1-yl)-methanone (D-146);

{4-[4-(2-amino-pyrimidin-5-yl)-2-morpholin-4-yl-5,6-dihydro-pyrrolo[2,3-d]pyrimidin-7-yl]-3-methyl-phenyl}-[4-(2-hydroxy-ethyl)-piperazin-1-yl]-methanone (D-147);

{3-[4-(2-amino-pyrimidin-5-yl)-2-morpholin-4-yl-5,6-dihydro-pyrrolo[2,3-d]pyrimidin-7-yl]-2-methyl-phenyl}-(4-methyl-piperazin-1-yl)-methanone (D-148);

5-{7-[2-fluoro-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-149);

5-{7-[4-(4-ethyl-piperazine-1-sulfonyl)-2-fluoro-phenyl]-2-morpholin-4-yl-6,7-dihydro-5H-pyrrolo[2,3-d]pyrimidin-4-yl}-pyrimidin-2-ylamine (D-150);

5-{7-[5-(4-ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-ylamine (D-151);

2-(4-{4-[4-(2-amino-pyrimidin-5-yl)-2-morpholin-4-yl-5,6-dihydro-pyrrolo[2,3-d]pyrimidin-7-yl]-3-fluoro-benzenesulfonyl}-piperazin-1-yl)-ethanol (D-152);

4-(2-amino-pyrimidin-5-yl)-2-morpholin-4-yl-5,6-dihydro-pyrrolo[2,3-d]pyrimidine-7-carboxylic acid {3-[4-(2-hydroxy-ethyl)-piperazin-1-yl]-phenyl}-methyl-amide (D-153);

4-(2-amino-pyrimidin-5-yl)-2-morpholin-4-yl-5,6-dihydro-pyrrolo[2,3-d]pyrimidine-7-carboxylic acid methyl-(3-piperazin-1-yl-phenyl)-amide (D-154);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-methyl-amide (D-155);

1-(4-{3-[4-(2-amino-pyrimidin-5-yl)-2-morpholin-4-yl-5,6-dihydro-pyrrolo[2,3-d]pyrimidin-7-yl]-4-fluoro-benzyl}-piperazin-1-yl)-ethanone (D-156);

{3-[4-(2-amino-pyrimidin-5-yl)-2-morpholin-4-yl-5,6-dihydro-pyrrolo[2,3-d]pyrimidin-7-yl]-2-methyl-phenyl}-morpholin-4-yl-methanone (D-157);

{3-[4-(2-amino-pyrimidin-5-yl)-2-morpholin-4-yl-5,6-dihydro-pyrrolo[2,3-d]pyrimidin-7-yl]-2-methyl-phenyl}-(4-ethyl-piperazin-1-yl)-methanone (D-158);

{3-[4-(2-amino-pyrimidin-5-yl)-2-morpholin-4-yl-5,6-dihydro-pyrrolo[2,3-d]pyrimidin-7-yl]-2-methyl-phenyl}-[4-(2-hydroxy-ethyl)-piperazin-1-yl]-methanone (D-159);

4-(2-amino-pyrimidin-5-yl)-2-morpholin-4-yl-5,6-dihydro-pyrrolo[2,3-d]pyrimidine-7-carboxylic acid methyl-[4-(4-methyl-piperazin-1-yl)-phenyl]-amide (D-160);

4-(2-amino-pyrimidin-5-yl)-2-morpholin-4-yl-5,6-dihydro-pyrrolo[2,3-d]pyrimidine-7-carboxylic acid methyl-(4-piperazin-1-yl-phenyl)-amide (D-161);

4-(2-amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazin-1-yl]-phenyl}-methyl-amide (D-162);

4-(2-amino-pyrimidin-5-yl)-2-morpholin-4-yl-5,6-dihydro-pyrrolo[2,3-d]pyrimidine-7-carboxylic acid methyl-phenyl-amide (D-163);

5-{7-[2-methyl-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-164);

5-{7-[4-(4-ethyl-piperazine-1-sulfonyl)-2-methyl-phenyl]-2-morpholin-4-yl-6,7-dihydro-5H-pyrrolo[2,3-d]pyrimidin-4-yl}-pyrimidin-2-ylamine (D-165);

2-(4-{4-[4-(2-amino-pyrimidin-5-yl)-2-morpholin-4-yl-5,6-dihydro-pyrrolo[2,3-d]pyrimidin-7-yl]-3-methyl-benzenesulfonyl}-piperazin-1-yl)-ethanol (D-166);

2-{4-[4-(2-amino-pyrimidin-5-yl)-2-morpholin-4-yl-5,6-dihydro-pyrrolo[2,3-d]pyrimidin-7-yl]-pyridin-2-ylamino}-ethanol (D-167);

3-{4-[4-(2-amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-168);

3-{4-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-169);

3-{4-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-170);

2-{3-[4-(2-amino-pyrimidin-5-yl)-2-morpholin-4-yl-5,6-dihydro-pyrrolo[2,3-d]pyrimidin-7-yl]-phenyl}-1-piperazin-1-yl-ethanone (D-171);

2-{4-[4-(2-amino-pyrimidin-5-yl)-2-morpholin-4-yl-5,6-dihydro-pyrrolo[2,3-d]pyrimidin-7-yl]-phenyl}-1-piperazin-1-yl-ethanone (D-172);

5-[7-(2-fluoro-5-morpholin-4-ylmethyl-phenyl)-2-morpholin-4-yl-6,7-dihydro-5H-pyrrolo[2,3-d]pyrimidin-4-yl]-pyrimidin-2-ylamine (D-173);

5-(2-morpholin-4-yl-7-o-tolyl-6,7-dihydro-5H-pyrrolo[2,3-d]pyrimidin-4-yl)-pyrimidin-2-ylamine (D-174);

5-{7-[2-fluoro-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-175);

5-{7-[2-methyl-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-176);

4-(2-amino-pyrimidin-5-yl)-2-morpholin-4-yl-5,6-dihydro-pyrrolo[2,3-d]pyrimidine-7-carboxylic acid methyl-[3-(4-methyl-piperazin-1-yl)-phenyl]-amide (D-177);

5-[7-(3-methyl-pyridin-2-yl)-2-morpholin-4-yl-6,7-dihydro-5H-pyrrolo[2,3-d]pyrimidin-4-yl]-pyrimidin-2-ylamine (D-178);

4-[4-(2-amino-pyrimidin-5-yl)-2-morpholin-4-yl-5,6-dihydro-pyrrolo[2,3-d]pyrimidin-7-yl]-N-[2-(2-hydroxy-ethoxy)-ethyl]-benzamide (D-179);

4-(2-amino-pyrimidin-5-yl)-2-morpholin-4-yl-5,6-dihydro-pyrrolo[2,3-d]pyrimidine-7-carboxylic acid o-tolylamide (D-180);

4-(2-amino-pyrimidin-5-yl)-2-morpholin-4-yl-5,6-dihydro-pyrrolo[2,3-d]pyrimidine-7-carboxylic acid (2-isopropyl-phenyl)-amide (D-181);

2-{3-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-182);

2-{4-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-183);

2-{3-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-184);

2-{4-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-185);

2-{3-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-186);

2-{4-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-187);

3-{4-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-188);

3-{3-[4-(2-amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-189);

3-{3-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-190);

3-{3-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-191);

3-{3-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-192);

5-[7-(4-methyl-pyridin-3-yl)-2-morpholin-4-yl-6,7-dihydro-5H-pyrrolo[2,3-d]pyrimidin-4-yl]-pyrimidin-2-ylamine (D-193);

4-(2-amino-pyrimidin-5-yl)-2-morpholin-4-yl-5,6-dihydro-pyrrolo[2,3-d]pyrimidine-7-carboxylic acid (4-{methyl-[3-(4-methyl-piperazin-1-yl)-propyl]-amino}-phenyl)-amide (D-194);

{3-[4-(2-amino-pyrimidin-5-yl)-2-morpholin-4-yl-5,6-dihydro-pyrrolo[2,3-d]pyrimidin-7-yl]-2-fluoro-phenyl}-morpholin-4-yl-methanone (D-195);

5-{7-[2-methyl-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-196);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzamide (D-197);

5-{7-[2-fluoro-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-198);

{4-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-199);

{4-[4-(2-amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-200);

{4-[4-(2-amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-201);

{4-[4-(2-amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-202);

{3-[4-(2-amino-pyrimidin-5-yl)-2-morpholin-4-yl-5,6-dihydro-pyrrolo[2,3-d]pyrimidin-7-yl]-4-fluoro-phenyl}-(4-ethyl-piperazin-1-yl)-methanone (D-203);

5-[7-(1-methyl-1H-imidazol-2-yl)-2-morpholin-4-yl-6,7-dihydro-5H-pyrrolo[2,3-d]pyrimidin-4-yl]-pyrimidin-2-ylamine (D-204);

4-[4-(2-amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzamide (D-205);

4-(2-amino-pyrimidin-5-yl)-2-morpholin-4-yl-5,6-dihydro-pyrrolo[2,3-d]pyrimidine-7-carboxylic acid {4-[methyl-(2-morpholin-4-yl-ethyl)-amino]-phenyl}-amide (D-206);

4-(2-amino-pyrimidin-5-yl)-2-morpholin-4-yl-5,6-dihydro-pyrrolo[2,3-d]pyrimidine-7-carboxylic acid {4-[methyl-(3-morpholin-4-yl-propyl)-amino]-phenyl}-amide (D-207);

4-(2-amino-pyrimidin-5-yl)-2-morpholin-4-yl-5,6-dihydro-pyrrolo[2,3-d]pyrimidine-7-carboxylic acid [4-(3-morpholin-4-yl-propylamino)-phenyl]-amide (D-208);

4-[4-(2-amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzenesulfonamide (D-209);

4-(2-amino-pyrimidin-5-yl)-2-morpholin-4-yl-5,6-dihydro-pyrrolo[2,3-d]pyrimidine-7-carbothioic acid o-tolylamide (D-210);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzenesulfonamide (D-211);

4-[4-(2-amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzenesulfonamide (D-212);

4-(2-amino-pyrimidin-5-yl)-2-morpholin-4-yl-5,6-dihydro-pyrrolo[2,3-d]pyrimidine-7-carboxylic acid (2-ethyl-phenyl)-amide (D-213);

4-(2-amino-pyrimidin-5-yl)-2-morpholin-4-yl-5,6-dihydro-pyrrolo[2,3-d]pyrimidine-7-carboxylic acid (2-propyl-phenyl)-amide (D-214);

4-(2-amino-pyrimidin-5-yl)-2-morpholin-4-yl-5,6-dihydro-pyrrolo[2,3-d]pyrimidine-7-carboxylic acid (2,6-difluoro-phenyl)-amide (D-215);

4-(2-amino-pyrimidin-5-yl)-2-morpholin-4-yl-5,6-dihydro-pyrrolo[2,3-d]pyrimidine-7-carbothioic acid phenylamide (D-216);

4-(2-amino-pyrimidin-5-yl)-2-morpholin-4-yl-5,6-dihydro-pyrrolo[2,3-d]pyrimidine-7-carboxylic acid (2-chloro-phenyl)-amide (D-217);

4-(2-amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide (D-218);

4-(2-amino-pyrimidin-5-yl)-2-morpholin-4-yl-5,6-dihydro-pyrrolo[2,3-d]pyrimidine-7-carboxylic acid [2-methyl-4-(morpholine-4-carbonyl)-phenyl]-amide (D-219);

4-(2-amino-pyrimidin-5-yl)-2-morpholin-4-yl-5,6-dihydro-pyrrolo[2,3-d]pyrimidine-7-carboxylic acid [2-methyl-4-(4-methyl-piperazine-1-carbonyl)-phenyl]-amide (D-220);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2-methyl-phenyl]-amide (D-221);

4-(2-amino-pyrimidin-5-yl)-2-morpholin-4-yl-5,6-dihydro-pyrrolo[2,3-d]pyrimidine-7-carbothioic acid (2-fluoro-phenyl)-amide (D-222);

4-(2-amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide (D-223);

4-(2-amino-pyrimidin-5-yl)-2-morpholin-4-yl-5,6-dihydro-pyrrolo[2,3-d]pyrimidine-7-carboxylic acid [5-(4-ethyl-piperazine-1-carbonyl)-2-methyl-phenyl]-amide (D-224);

4-(2-amino-pyrimidin-5-yl)-2-morpholin-4-yl-5,6-dihydro-pyrrolo[2,3-d]pyrimidine-7-carbothioic acid (2,6-difluoro-phenyl)-amide (D-225);

4-(2-amino-pyrimidin-5-yl)-2-morpholin-4-yl-5,6-dihydro-pyrrolo[2,3-d]pyrimidine-7-carboxylic acid methyl-(3-morpholin-4-yl-phenyl)-amide (D-226);

4-(2-amino-pyrimidin-5-yl)-2-morpholin-4-yl-5,6-dihydro-pyrrolo[2,3-d]pyrimidine-7-carboxylic acid methyl-{3-[methyl-(2-morpholin-4-yl-ethyl)-amino]-phenyl}-amide (D-227);

{5-[4-(2-amino-pyrimidin-5-yl)-2-morpholin-4-yl-5,6-dihydro-pyrrolo[2,3-d]pyrimidine-7-yl]-pyridin-3-yl}-morpholin-4-yl-methanone (D-228);

{5-[4-(2-amino-pyrimidin-5-yl)-2-morpholin-4-yl-5,6-dihydro-pyrrolo[2,3-d]pyrimidin-7-yl]-pyridin-3-yl}-(4-methyl-piperazin-1-yl)-methanone (D-229);

{5-[4-(2-amino-pyrimidin-5-yl)-2-morpholin-4-yl-5,6-dihydro-pyrrolo[2,3-d]pyrimidin-7-yl]-pyridin-3-yl}-(4-ethyl-piperazin-1-yl)-methanone (D-230);

4-(2-amino-pyrimidin-5-yl)-2-morpholin-4-yl-5,6-dihydro-pyrrolo[2,3-d]pyrimidine-7-carbothioic acid [4-(4-methyl-piperazine-1-carbonyl)-phenyl]-amide (D-231);

4-(2-amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-phenyl]-amide (D-232);

4-(2-amino-pyrimidin-5-yl)-2-morpholin-4-yl-5,6-dihydro-pyrrolo[2,3-d]pyrimidine-7-carbothioic acid [3-(4-methyl-piperazine-1-carbonyl)-phenyl]-amide (D-233);

4-[4-(2-amino-pyrimidin-5-yl)-2-morpholin-4-yl-5,6-dihydro-pyrrolo[2,3-d]pyrimidin-7-yl]-3-methyl-benzonitrile (D-234);

4-(2-amino-pyrimidin-5-yl)-2-morpholin-4-yl-5,6-dihydro-pyrrolo[2,3-d]pyrimidine-7-carbothioic acid [3-(4-ethyl-piperazine-1-carbonyl)-phenyl]-amide (D-235);

4-(2-amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide (D-236);

4-(2-amino-pyrimidin-5-yl)-2-morpholin-4-yl-5,6-dihydro-pyrrolo[2,3-d]pyrimidine-7-carboxylic acid (2-methyl-5-morpholin-4-yl-phenyl)-amide (D-237);

4-(2-amino-pyrimidin-5-yl)-2-morpholin-4-yl-5,6-dihydro-pyrrolo[2,3-d]pyrimidine-7-carboxylic acid [2-methyl-5-(4-methyl-piperazin-1-yl)-phenyl]-amide (D-238);

4-(2-amino-pyrimidin-5-yl)-2-morpholin-4-yl-5,6-dihydro-pyrrolo[2,3-d]pyrimidine-7-carboxylic acid [5-(4-ethyl-piperazin-1-yl)-2-methyl-phenyl]-amide (D-239);

4-(2-amino-pyrimidin-5-yl)-2-morpholin-4-yl-5,6-dihydro-pyrrolo[2,3-d]pyrimidine-7-carboxylic acid (2-methyl-4-morpholin-4-yl-phenyl)-amide (D-240);

4-(2-amino-pyrimidin-5-yl)-2-morpholin-4-yl-5,6-dihydro-pyrrolo[2,3-d]pyrimidine-7-carboxylic acid [2-methyl-4-(4-methyl-piperazin-1-yl)-phenyl]-amide (D-241);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-2-methyl-phenyl]-amide (D-242);

4-(2-amino-pyrimidin-5-yl)-2-morpholin-4-yl-5,6-dihydro-pyrrolo[2,3-d]pyrimidine-7-carboxylic acid [2-methyl-3-(morpholine-4-carbonyl)-phenyl]-amide (D-243);

4-(2-amino-pyrimidin-5-yl)-2-morpholin-4-yl-5,6-dihydro-pyrrolo[2,3-d]pyrimidine-7-carboxylic acid [2-methyl-3-(4-methyl-piperazine-1-carbonyl)-phenyl]-amide (D-244);

4-(2-amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-2-methyl-phenyl]-amide (D-245);

{4-[4-(2-amino-pyrimidin-5-yl)-2-morpholin-4-yl-5,6-dihydro-pyrrolo[2,3-d]pyrimidin-7-yl]-3-methyl-phenyl}-((2R,6S)-2,6-dimethyl-morpholin-4-yl)-methanone (D-246);

4-(2-amino-pyrimidin-5-yl)-2-morpholin-4-yl-5,6-dihydro-pyrrolo[2,3-d]pyrimidine-7-carbothioic acid [3-(morpholine-4-carbonyl)-phenyl]-amide (D-247);

5-{7-[5-(morpholine-4-sulfonyl)-pyridin-3-yl]-2-morpholin-4-yl-6,7-dihydro-5H-pyrrolo[2,3-d]pyrimidin-4-yl}-pyrimidin-2-ylamine (D-248);

5-{7-[5-(4-methyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-249);

5-{7-[5-(4-ethyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-250);

4-(2-amino-pyrimidin-5-yl)-2-morpholin-4-yl-5,6-dihydro-pyrrolo[2,3-d]pyrimidine-7-carbothioic acid [4-(morpholine-4-carbonyl)-phenyl]-amide (D-251);

4-(2-amino-pyrimidin-5-yl)-2-morpholin-4-yl-5,6-dihydro-pyrrolo[2,3-d]pyrimidine-7-carbothioic acid [2-methyl-4-(morpholine-4-carbonyl)-phenyl]-amide (D-252);

4-(2-amino-pyrimidin-5-yl)-2-morpholin-4-yl-5,6-dihydro-pyrrolo[2,3-d]pyrimidine-7-carbothioic acid [2-methyl-4-(4-methyl-piperazine-1-carbonyl)-phenyl]-amide (D-253);

4-(2-amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-2-methyl-phenyl]-amide (D-254);

4-(2-amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide (D-255);

4-(2-amino-pyrimidin-5-yl)-2-morpholin-4-yl-5,6-dihydro-pyrrolo[2,3-d]pyrimidine-7-carboxylic acid [2,6-difluoro-4-(4-methyl-piperazine-1-carbonyl)-phenyl]-amide (D-256);

4-(2-amino-pyrimidin-5-yl)-2-morpholin-4-yl-5,6-dihydro-pyrrolo[2,3-d]pyrimidine-7-carboxylic acid [2,6-difluoro-4-(morpholine-4-carbonyl)-phenyl]-amide (D-257);

4-[4-(2-amino-pyrimidin-5-yl)-2-morpholin-4-yl-5,6-dihydro-pyrrolo[2,3-d]pyrimidin-7-yl]-3-methyl-N-pyridin-4-yl-benzamide (D-258);

4-[4-(2-amino-pyrimidin-5-yl)-2-morpholin-4-yl-5,6-dihydro-pyrrolo[2,3-d]pyrimidin-7-yl]-3-methyl-N-pyridin-4-ylmethyl-benzamide (D-259);

4-methyl-5-(2-morpholin-4-yl-7-pyridin-3-yl-6,7-dihydro-5H-pyrrolo[2,3-d]pyrimidin-4-yl)-pyrimidin-2-ylamine (D-260);

4-methyl-5-(2-morpholin-4-yl-7-pyridin-4-yl-6,7-dihydro-5H-pyrrolo[2,3-d]pyrimidin-4-yl)-pyrimidin-2-ylamine (D-261);

4-(2-amino-pyrimidin-5-yl)-2-morpholin-4-yl-5,6-dihydro-pyrrolo[2,3-d]pyrimidine-7-carboxylic acid benzyl-methyl-amide (D-262);

4-(2-amino-pyrimidin-5-yl)-2-morpholin-4-yl-5,6-dihydro-pyrrolo[2,3-d]pyrimidine-7-carboxylic acid methyl-phenethyl-amide (D-263);

4-[4-(2-amino-pyrimidin-5-yl)-2-morpholin-4-yl-5,6-dihydro-pyrrolo[2,3-d]pyrimidin-7-yl]-N-pyridin-4-ylmethyl-benzamide (D-264);

{4-[4-(2-amino-pyrimidin-5-yl)-2-morpholin-4-yl-5,6-dihydro-pyrrolo[2,3-d]pyrimidin-7-yl]-phenyl}-(4-pyridin-4-yl-piperazin-1-yl)-methanone (D-265);

5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-266);

{4-[4-(2-amino-pyrimidin-5-yl)-2-morpholin-4-yl-5,6-dihydro-pyrrolo[2,3-d]pyrimidin-7-yl]-3-methyl-phenyl}-pyrrolidin-1-yl-methanone (D-267);

{4-[4-(2-amino-pyrimidin-5-yl)-2-morpholin-4-yl-5,6-dihydro-pyrrolo[2,3-d]pyrimidin-7-yl]-3-methyl-phenyl}-piperidin-1-yl-methanone (D-268);

4-methyl-piperazine-1-carboxylic acid {3-[4-(2-amino-pyrimidin-5-yl)-2-morpholin-4-yl-5,6-dihydro-pyrrolo[2,3-d]pyrimidin-7-yl]-phenyl}-amide (D-269);

4-[4-(2-amino-pyrimidin-5-yl)-2-morpholin-4-yl-5,6-dihydro-pyrrolo[2,3-d]pyrimidin-7-yl]-3-fluoro-N-thiazol-2-yl-benzamide (D-270);

4-[4-(2-amino-pyrimidin-5-yl)-2-morpholin-4-yl-5,6-dihydro-pyrrolo[2,3-d]pyrimidin-7-yl]-3-fluoro-N-pyridin-4-ylmethyl-benzamide (D-271);

{4-[4-(2-amino-pyrimidin-5-yl)-2-morpholin-4-yl-5,6-dihydro-pyrrolo[2,3-d]pyrimidin-7-yl]-3-methyl-phenyl}-azepan-1-yl-methanone (D-272);

4-(2-amino-pyrimidin-5-yl)-2-morpholin-4-yl-5,6-dihydro-pyrrolo[2,3-d]pyrimidine-7-carboxylic acid (2,6-difluoro-4-morpholin-4-yl-phenyl)-amide (D-273);

4-(2-amino-pyrimidin-5-yl)-2-morpholin-4-yl-5,6-dihydro-pyrrolo[2,3-d]pyrimidine-7-carboxylic acid (2-methyl-pyridin-3-yl)-amide (D-274);

4-(2-amino-pyrimidin-5-yl)-2-morpholin-4-yl-5,6-dihydro-pyrrolo[2,3-d]pyrimidine-7-carboxylic acid (pyridin-3-ylmethyl)-amide (D-275);

4-(2-amino-pyrimidin-5-yl)-2-morpholin-4-yl-5,6-dihydro-pyrrolo[2,3-d]pyrimidine-7-carboxylic acid (4-methyl-pyridin-3-yl)-amide (D-276);

N-{4-[4-(2-amino-pyrimidin-5-yl)-2-morpholin-4-yl-5,6-dihydro-pyrrolo[2,3-d]pyrimidin-7-yl]-phenyl}-isonicotinamide (D-277);

{4-[4-(2-amino-pyrimidin-5-yl)-2-morpholin-4-yl-5,6-dihydro-pyrrolo[2,3-d]pyrimidin-7-yl]-phenyl}-(4-pyridin-2-yl-piperazin-1-yl)-methanone (D-278);

4-[4-(2-amino-pyrimidin-5-yl)-2-morpholin-4-yl-5,6-dihydro-pyrrolo[2,3-d]pyrimidin-7-yl]-N-(2-pyridin-3-yl-ethyl)-benzamide (D-279);

4-(2-amino-pyrimidin-5-yl)-2-morpholin-4-yl-5,6-dihydro-pyrrolo[2,3-d]pyrimidine-7-carboxylic acid (2-methyl-2H-pyrazol-3-yl)-amide (D-280);

4-(2-amino-pyrimidin-5-yl)-2-morpholin-4-yl-5,6-dihydro-pyrrolo[2,3-d]pyrimidine-7-carboxylic acid (5-methyl-2-phenyl-2H-pyrazol-3-yl)-amide (D-281);

4-[4-(2-amino-pyrimidin-5-yl)-2-morpholin-4-yl-5,6-dihydro-pyrrolo[2,3-d]pyrimidin-7-yl]-N-pyridin-2-ylmethyl-benzamide (D-282);

4-(2-amino-pyrimidin-5-yl)-2-morpholin-4-yl-5,6-dihydro-pyrrolo[2,3-d]pyrimidine-7-carboxylic acid (2,6-dimethyl-phenyl)-amide (D-283);

{4-[4-(2-amino-pyrimidin-5-yl)-2-morpholin-4-yl-5,6-dihydro-pyrrolo[2,3-d]pyrimidin-7-yl]-phenyl}-(4-pyrimidin-2-yl-piperazin-1-yl)-methanone (D-284);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-2-yl-piperazin-1-yl)-methanone (D-285);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-4-yl-piperazin-1-yl)-methanone (D-286);

4-(2-amino-pyrimidin-5-yl)-2-morpholin-4-yl-5,6-dihydro-pyrrolo[2,3-d]pyrimidine-7-carboxylic acid 3-(4-methyl-piperazine-1-carbonyl)-benzylamide (D-287);

{4-[4-(2-amino-pyrimidin-5-yl)-2-morpholin-4-yl-5,6-dihydro-pyrrolo[2,3-d]pyrimidin-7-yl]-3-methyl-phenyl}-(4-pyridin-4-yl-piperazin-1-yl)-methanone (D-288);

4-(2-amino-pyrimidin-5-yl)-2-morpholin-4-yl-5,6-dihydro-pyrrolo[2,3-d]pyrimidine-7-carbothioic acid [2-methyl-5-(4-methyl-piperazin-1-yl)-phenyl]-amide (D-289);

4-(2-amino-pyrimidin-5-yl)-2-morpholin-4-yl-5,6-dihydro-pyrrolo[2,3-d]pyrimidine-7-carbothioic acid [5-(4-ethyl-piperazin-1-yl)-2-methyl-phenyl]-amide (D-290);

4-(2-amino-pyrimidin-5-yl)-2-morpholin-4-yl-5,6-dihydro-pyrrolo[2,3-d]pyrimidine-7-carbothioic acid [2-methyl-4-(4-methyl-piperazin-1-yl)-phenyl]-amide (D-291);

4-(2-amino-pyrimidin-5-yl)-2-morpholin-4-yl-5,6-dihydro-pyrrolo[2,3-d]pyrimidine-7-carbothioic acid [4-(4-ethyl-piperazin-1-yl)-2-methyl-phenyl]-amide (D-292);

4-(2-amino-pyrimidin-5-yl)-2-morpholin-4-yl-5,6-dihydro-pyrrolo[2,3-d]pyrimidine-7-carboxylic acid 4-(4-methyl-piperazine-1-carbonyl)-benzylamide (D-293);

4-(2-amino-pyrimidin-5-yl)-2-morpholin-4-yl-5,6-dihydro-pyrrolo[2,3-d]pyrimidine-7-carboxylic acid {2-[4-(4-methyl-piperazine-1-carbonyl)-phenyl]-ethyl}-amide (D-294);

4-(2-amino-pyrimidin-5-yl)-2-morpholin-4-yl-5,6-dihydro-pyrrolo[2,3-d]pyrimidine-7-carboxylic acid methyl-{2-[4-(4-methyl-piperazine-1-carbonyl)-phenyl]-ethyl}-amide (D-295);

5-(7-{4-[2-(4-methyl-piperazine-1-sulfonyl)-ethyl]-phenyl}-2-morpholin-4-yl-6,7-dihydro-5H-pyrrolo[2,3-d]pyrimidin-4-yl)-pyrimidin-2-ylamine (D-296);

4-(2-amino-pyrimidin-5-yl)-2-morpholin-4-yl-5,6-dihydro-pyrrolo[2,3-d]pyrimidine-7-carboxylic acid methyl-[4-(4-methyl-piperazine-1-carbonyl)-benzyl]-amide (D-297);

4-(2-amino-pyrimidin-5-yl)-2-morpholin-4-yl-5,6-dihydro-pyrrolo[2,3-d]pyrimidine-7-carboxylic acid methyl-[3-(4-methyl-piperazine-1-carbonyl)-benzyl]-amide (D-298);

4-(2-amino-pyrimidin-5-yl)-2-morpholin-4-yl-5,6-dihydro-pyrrolo[2,3-d]pyrimidine-7-carboxylic acid (4-diethylamino-2-methyl-phenyl)-amide (D-299);

{3-[4-(2-amino-pyrimidin-5-yl)-2-morpholin-4-yl-5,6-dihydro-pyrrolo[2,3-d]pyrimidin-7-yl]-4-methoxy-phenyl}-morpholin-4-yl-methanone (D-300);

4-[4-(2-amino-pyrimidin-5-yl)-2-morpholin-4-yl-5,6-dihydro-pyrrolo[2,3-d]pyrimidin-7-yl]-3-methyl-N-pyridin-3-ylmethyl-benzamide (D-301);

4-[4-(2-amino-pyrimidin-5-yl)-2-morpholin-4-yl-5,6-dihydro-pyrrolo[2,3-d]pyrimidin-7-yl]-3-methyl-N-(2-pyridin-3-yl-ethyl)-benzamide (D-302);

3-[4-(2-amino-pyrimidin-5-yl)-2-morpholin-4-yl-5,6-dihydro-pyrrolo[2,3-d]pyrimidin-7-yl]-4-methyl-N-pyridin-3-ylmethyl-benzamide (D-303);

3-[4-(2-amino-pyrimidin-5-yl)-2-morpholin-4-yl-5,6-dihydro-pyrrolo[2,3-d]pyrimidin-7-yl]-4-methyl-N-(2-pyridin-3-yl-ethyl)-benzamide (D-304);

4-[4-(2-amino-pyrimidin-5-yl)-2-morpholin-4-yl-5,6-dihydro-pyrrolo[2,3-d]pyrimidin-7-yl]-3-fluoro-N-pyridin-3-ylmethyl-benzamide (D-305);

4-[4-(2-amino-pyrimidin-5-yl)-2-morpholin-4-yl-5,6-dihydro-pyrrolo[2,3-d]pyrimidin-7-yl]-3-fluoro-N-(2-pyridin-3-yl-ethyl)-benzamide (D-306);

{4-[4-(2-amino-pyrimidin-5-yl)-2-morpholin-4-yl-5,6-dihydro-pyrrolo[2,3-d]pyrimidin-7-yl]-phenyl}-(4-morpholin-4-yl-piperidin-1-yl)-methanone (D-307);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-morpholin-4-yl-piperidin-1-yl)-methanone (D-308);

{4-[4-(2-amino-pyrimidin-5-yl)-2-morpholin-4-yl-5,6-dihydro-pyrrolo[2,3-d]pyrimidin-7-yl]-3-chloro-phenyl}-morpholin-4-yl-methanone (D-309);

{3-[4-(2-amino-pyrimidin-5-yl)-2-morpholin-4-yl-5,6-dihydro-pyrrolo[2,3-d]pyrimidin-7-yl]-4-chloro-phenyl}-morpholin-4-yl-methanone (D-310);

{4-[4-(2-amino-pyrimidin-5-yl)-2-morpholin-4-yl-5,6-dihydro-pyrrolo[2,3-d]pyrimidin-7-yl]-3-methyl-phenyl}-(4-pyridin-3-yl-piperazin-1-yl)-methanone (D-311);

4-(2-amino-pyrimidin-5-yl)-2-morpholin-4-yl-5,6-dihydro-pyrrolo[2,3-d]pyrimidine-7-carboxylic acid (4-methyl-biphenyl-3-yl)-amide (D-312);

4-(2-amino-pyrimidin-5-yl)-2-morpholin-4-yl-5,6-dihydro-pyrrolo[2,3-d]pyrimidine-7-carboxylic acid (2-methyl-5-pyridin-3-yl-phenyl)-amide (D-313);

5-[2-morpholin-4-yl-7-(5-trifluoromethyl-pyridin-3-yl)-6,7-dihydro-5H-pyrrolo[2,3-d]pyrimidin-4-yl]-pyrimidin-2-ylamine (D-314);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-3-ylmethyl-piperazin-1-yl)-methanone (D-315);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-4-ylmethyl-piperazin-1-yl)-methanone (D-316);

4-[4-(2-amino-pyrimidin-5-yl)-2-morpholin-4-yl-5,6-dihydro-pyrrolo[2,3-d]pyrimidin-7-yl]-N-methyl-N-pyridin-3-ylmethyl-benzamide (D-317);

4-[4-(2-amino-pyrimidin-5-yl)-2-morpholin-4-yl-5,6-dihydro-pyrrolo[2,3-d]pyrimidin-7-yl]-3-fluoro-N-methyl-N-pyridin-3-ylmethyl-benzamide (D-318);

4-[4-(2-amino-pyrimidin-5-yl)-2-morpholin-4-yl-5,6-dihydro-pyrrolo[2,3-d]pyrimidin-7-yl]-N-methyl-N-(2-pyridin-3-yl-ethyl)-benzamide (D-319);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-pyridin-3-yl-ethyl)-benzamide (D-320);

{4-[4-(2-amino-pyrimidin-5-yl)-2-morpholin-4-yl-5,6-dihydro-pyrrolo[2,3-d]pyrimidin-7-yl]-phenyl}-(4-pyridin-3-ylmethyl-piperazin-1-yl)-methanone (D-321);

{4-[4-(2-amino-pyrimidin-5-yl)-2-morpholin-4-yl-5,6-dihydro-pyrrolo[2,3-d]pyrimidin-7-yl]-phenyl}-(4-pyridin-4-ylmethyl-piperazin-1-yl)-methanone (D-322);

5-(2-morpholin-4-yl-4-pyridin-4-yl-5,6-dihydro-pyrrolo[2,3-d]pyrimidin-7-yl)-pyrimidin-2-ylamine (D-323);

{6-[4-(2-amino-pyrimidin-5-yl)-2-morpholin-4-yl-5,6-dihydro-pyrrolo[2,3-d]pyrimidin-7-yl]-naphthalen-2-yl}-(4-methyl-piperazin-1-yl)-methanone (D-324);

5-{7-[3-fluoro-4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-325);

5-{7-[2-fluoro-4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-326);

5-{2-morpholin-4-yl-7-[4-(4-propyl-piperazin-1-ylmethyl)-phenyl]-6,7-dihydro-5H-pyrrolo[2,3-d]pyrimidin-4-yl}-pyrimidin-2-ylamine (D-327);

5-{7-[4-(4-isopropyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-328);

5-(7-{4-[4-(2-fluoroethyl)-piperazin-1-ylmethyl]-phenyl}-2-morpholin-4-yl-6,7-dihydro-5H-pyrrolo[2,3-d]pyrimidin-4-yl)-pyrimidin-2-ylamine (D-329);

5-(7-{4-[4-(4-fluorobutyl)-piperazin-1-ylmethyl]-phenyl}-2-morpholin-4-yl-6,7-dihydro-5H-pyrrolo[2,3-d]pyrimidin-4-yl)-pyrimidin-2-ylamine (D-330);

5-(2-morpholin-4-yl-7-{4-[4-(3,3,3-trifluoropropyl)piperazin-1-ylmethyl]-phenyl}-6,7-dihydro-5H-pyrrolo[2,3-d]pyrimidin-4-yl)-pyrimidin-2-ylamine (D-332);

5-{7-[6-(4-methyl-piperazin-1-ylmethyl)naphthalen-2-yl]-2-morpholin-4-yl-6,7-dihydro-5H-pyrrolo[2,3-d]pyrimidin-4-yl}-pyrimidin-2-ylamine (D-333);

5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-334);

5-[7-(2-fluoro-4-morpholin-4-ylmethyl-phenyl)-2-morpholin-4-yl-6,7-dihydro-5H-pyrrolo[2,3-d]pyrimidin-4-yl]-pyrimidin-2-ylamine (D-335);

4-(3-ethylaminocarbonyloxyphenyl)-2-(morpholin-4-yl)-7-(pyridin-4-yl)-6,7-dihydro-5H-pyrrolo[2,3-d]pyrimidine (E-01);

4-(3-methylaminocarbonyloxyphenyl)-2-(morpholin-4-yl)-7-(pyridin-4-yl)-6,7-dihydro-5H-pyrrolo[2,3-d]pyrimidine (E-02);

4-(3-acetoxyphenyl)-2-(morpholin-4-yl)-7-(pyridin-4-yl)-6,7-dihydro-5H-pyrrolo[2,3-d]pyrimidine (E-03);

2-morpholin-4-yl-7-pyridin-4-yl-4-[3-(2-pyridin-2-ylethoxy)phenyl]-6,7-dihydro-5H-pyrrolo[2,3-d]pyrimidine (E-04);

2-morpholin-4-yl-7-pyridin-4-yl-4-[3-(3-pyridin-3-yl-propoxy)-phenyl]-6,7-dihydro-5H-pyrrolo[2,3-d]pyrimidine (E-05);

2-morpholin-4-yl-7-pyridin-4-yl-4-[3-(pyridin-4-ylmethoxy)-phenyl]-6,7-dihydro-5H-pyrrolo[2,3-d]pyrimidine (E-06);

3-(2-morpholin-4-yl-7-pyridin-4-yl-6,7-dihydro-5H-pyrrolo[2,3-d]pyrimidin-4-yl)benzonitrile (E-07);

3-(2-morpholin-4-yl-7-pyridin-4-yl-6,7-dihydro-5H-pyrrolo[2,3-d]pyrimidin-4-yl)benzylamine (E-08);

N-[3-(2-morpholin-4-yl-7-pyridin-4-yl-6,7-dihydro-5H-pyrrolo[2,3-d]pyrimidin-4-yl)benzyl]acetamide (E-9);

5-(2-morpholin-4-yl-7-pyridin-4-yl-6,7-dihydro-5H-pyrrolo[2,3-d]pyrimidin-4-yl)-2-pyrrolidin-1-ylmethylphenol (E-10);

2-diethylaminomethyl-5-(2-morpholin-4-yl-7-pyridin-4-yl-6,7-dihydro-5H-pyrrolo[2,3-d]pyrimidin-4-yl)phenol (E-11);

5-(2-morpholin-4-yl-7-pyridin-4-yl-6,7-dihydro-5H-pyrrolo[2,3-d]pyrimidin-4-yl)-2-piperidin-1-ylmethyl-phenol (E-12);

3-(2-morpholin-4-yl-7-pyridin-4-yl-6,7-dihydro-5H-pyrrolo[2,3-d]pyrimidin-4-yl)-phenylamine (F-01);

3-(2-morpholin-4-yl-7-pyridin-3-yl-6,7-dihydro-5H-pyrrolo[2,3-d]pyrimidin-4-yl)-benzoic acid methyl ester (G-01);

3-(2-morpholin-4-yl-7-pyridin-4-yl-6,7-dihydro-5H-pyrrolo[2,3-d]pyrimidin-4-yl)-benzoic acid methyl ester (G-02);

3-(2-morpholin-4-yl-7-pyridin-3-yl-6,7-dihydro-5H-pyrrolo[2,3-d]pyrimidin-4-yl)-benzoic acid (G-03);

3-(2-morpholin-4-yl-7-pyridin-4-yl-6,7-dihydro-5H-pyrrolo[2,3-d]pyrimidin-4-yl)-benzoic acid (G-04);

N-(2-dimethylaminoethyl)-3-(2-morpholin-4-yl-7-pyridin-3-yl-6,7-dihydro-5H-pyrrolo[2,3-d]pyrimidin-4-yl)-benzamide (G-05);

N-(2-morpholin-4-yl-ethyl)-3-(2-morpholin-4-yl-7-pyridin-3-yl-6,7-dihydro-5H-pyrrolo[2,3-d]pyrimidin-4-yl)-benzamide (G-06);

3-(2-morpholin-4-yl-7-pyridin-3-yl-6,7-dihydro-5H-pyrrolo[2,3-d]pyrimidin-4-yl)-N-(2-pyridin-3-yl-ethyl)-benzamide (G-07);

N-methyl-3-(2-morpholin-4-yl-7-pyridin-3-yl-6,7-dihydro-5H-pyrrolo[2,3-d]pyrimidin-4-yl)-benzamide (G-08);

3-(2-morpholin-4-yl-7-pyridin-3-yl-6,7-dihydro-5H-pyrrolo[2,3-d]pyrimidin-4-yl)-N-pyridin-3-ylmethyl-benzamide (G-09);

N-(2-dimethylamino-ethyl)-3-(2-morpholin-4-yl-7-pyridin-4-yl-6,7-dihydro-5H-pyrrolo[2,3-d]pyrimidin-4-yl)-benzamide (G-10);

3-(2-morpholin-4-yl-7-pyridin-3-yl-6,7-dihydro-5H-pyrrolo[2,3-d]pyrimidin-4-yl)-N-(2-pyridin-4-yl-ethyl)-benzamide (G-11);

N-(2-carbamoyl-ethyl)-3-(2-morpholin-4-yl-7-pyridin-3-yl-6,7-dihydro-5H-pyrrolo[2,3-d]pyrimidin-4-yl)-benzamide (G-12);

N-(2-morpholin-4-yl-ethyl)-3-(2-morpholin-4-yl-7-pyridin-3-yl-6,7-dihydro-5H-pyrrolo[2,3-d]pyrimidin-4-yl)-benzamide (G-13);

3-(2-morpholin-4-yl-7-pyridin-4-yl-6,7-dihydro-5H-pyrrolo[2,3-d]pyrimidin-4-yl)-N-(2-pyridin-3-yl-ethyl)-benzamide (G-14);

N-isobutyl-3-(2-morpholin-4-yl-7-pyridin-4-yl-6,7-dihydro-5H-pyrrolo[2,3-d]pyrimidin-4-yl)-benzamide (G-15);

3-(2-morpholin-4-yl-7-pyridin-4-yl-6,7-dihydro-5H-pyrrolo[2,3-d]pyrimidin-4-yl)-N-pyridin-3-ylmethyl-benzamide (G-16);

3-(2-morpholin-4-yl-7-pyridin-3-yl-6,7-dihydro-5H-pyrrolo[2,3-d]pyrimidin-4-yl)-N-propyl-benzamide (G-17);

3-(2-morpholin-4-yl-7-pyridin-4-yl-6,7-dihydro-5H-pyrrolo[2,3-d]pyrimidin-4-yl)-N-propyl-benzamide (G-18);

3-(2-morpholin-4-yl-7-pyridin-4-yl-6,7-dihydro-5H-pyrrolo[2,3-d]pyrimidin-4-yl)-N-(2-pyridin-4-yl-ethyl)-benzamide (G-19);

N-benzyl-3-(2-morpholin-4-yl-7-pyridin-3-yl-6,7-dihydro-5H-pyrrolo[2,3-d]pyrimidin-4-yl)-benzamide (G-20);

N-(2-methoxy-ethyl)-3-(2-morpholin-4-yl-7-pyridin-4-yl-6,7-dihydro-5H-pyrrolo[2,3-d]pyrimidin-4-yl)-benzamide (G-21);

N-(2-morpholin-4-yl-ethyl)-3-(2-morpholin-4-yl-7-pyridin-4-yl-6,7-dihydro-5H-pyrrolo[2,3-d]pyrimidin-4-yl)-benzamide (G-22);

N-carbamoylmethyl-3-(2-morpholin-4-yl-7-pyridin-4-yl-6,7-dihydro-5H-pyrrolo[2,3-d]pyrimidin-4-yl)-benzamide (G-23);

N-(2-carbamoyl-ethyl)-3-(2-morpholin-4-yl-7-pyridin-4-yl-6,7-dihydro-5H-pyrrolo[2,3-d]pyrimidin-4-yl)-benzamide (G-24);

3-(2-morpholin-4-yl-7-pyridin-4-yl-6,7-dihydro-5H-pyrrolo[2,3-d]pyrimidin-4-yl)-N-phenethyl-benzamide (G-25);

N-isobutyl-3-(2-morpholin-4-yl-7-pyridin-3-yl-6,7-dihydro-5H-pyrrolo[2,3-d]pyrimidin-4-yl)-benzamide (G-26);

3-(2-morpholin-4-yl-7-pyridin-3-yl-6,7-dihydro-5H-pyrrolo[2,3-d]pyrimidin-4-yl)-benzoic acid 2-dimethylamino-ethyl ester (G-27);

3-(2-morpholin-4-yl-7-pyridin-3-yl-6,7-dihydro-5H-pyrrolo[2,3-d]pyrimidin-4-yl)-benzamide (G-28);

4-(2-morpholin-4-yl-7-pyridin-4-yl-6,7-dihydro-5H-pyrrolo[2,3-d]pyrimidin-4-yl)-benzoic acid methyl ester hydrochloride (G-29);

N-(2-dimethylamino-ethyl)-4-(2-morpholin-4-yl-7-pyridin-3-yl-6,7-dihydro-5H-pyrrolo[2,3-d]pyrimidin-4-yl)-benzamide (G-30);

3-(2-morpholin-4-yl-7-pyridin-4-yl-6,7-dihydro-5H-pyrrolo[2,3-d]pyrimidin-4-yl)-benzamide (G-31);

4-(2-morpholin-4-yl-7-pyridin-3-yl-6,7-dihydro-5H-pyrrolo[2,3-d]pyrimidin-4-yl)-benzoic acid methyl ester (G-32);

4-(2-morpholin-4-yl-7-pyridin-3-yl-6,7-dihydro-5H-pyrrolo[2,3-d]pyrimidin-4-yl)-benzamide (G-33);

N-(2-morpholin-4-yl-ethyl)-4-(2-morpholin-4-yl-7-pyridin-3-yl-6,7-dihydro-5H-pyrrolo[2,3-d]pyrimidin-4-yl)-benzamide (G-34);

N-(2-morpholin-4-yl-ethyl)-4-(2-morpholin-4-yl-7-pyridin-4-yl-6,7-dihydro-5H-pyrrolo[2,3-d]pyrimidin-4-yl)-benzamide (G-35);

4-(2-morpholin-4-yl-7-pyridin-3-yl-6,7-dihydro-5H-pyrrolo[2,3-d]pyrimidin-4-yl)-benzamide (G-36);

3-(2-morpholin-4-yl-7-pyridin-4-yl-6,7-dihydro-5H-pyrrolo[2,3-d]pyrimidin-4-yl)-benzoic acid 2-dimethylamino-ethyl ester (G-37);

N,N-dimethyl-3-(2-morpholin-4-yl-7-pyridin-4-yl-6,7-dihydro-5H-pyrrolo[2,3-d]pyrimidin-4-yl)-benzamide trifluoroacetic acid salt (G-38);

N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-39);

3-(2-morpholin-4-yl-7-pyridin-4-yl-6,7-dihydro-5H-pyrrolo[2,3-d]pyrimidin-4-yl)-N-phenyl-benzamide trifluoroacetic acid salt (G-40);

N-(3-dimethylamino-propyl)-3-(2-morpholin-4-yl-7-pyridin-4-yl-6,7-dihydro-5H-pyrrolo[2,3-d]pyrimidin-4-yl)-benzamide trifluoroacetic acid salt (G-41);

N-carbamoylmethyl-3-(2-morpholin-4-yl-7-pyridin-3-yl-6,7-dihydro-5H-pyrrolo[2,3-d]pyrimidin-4-yl)-benzamide trifluoroacetic acid salt (G-42);

3-(2-morpholin-4-yl-7-pyridin-3-yl-6,7-dihydro-5H-pyrrolo[2,3-d]pyrimidin-4-yl)-N-phenyl-benzamide trifluoroacetic acid salt (G-43);

3-(2-morpholin-4-yl-7-pyridin-3-yl-6,7-dihydro-5H-pyrrolo[2,3-d]pyrimidin-4-yl)-N-phenethyl-benzamide (G-44);

N-(2-methoxy-ethyl)-3-(2-morpholin-4-yl-7-pyridin-3-yl-6,7-dihydro-5H-pyrrolo[2,3-d]pyrimidin-4-yl)-benzamide (G-45);

3-(2-morpholin-4-yl-7-pyridin-4-yl-6,7-dihydro-5H-pyrrolo[2,3-d]pyrimidin-4-yl)-N-(2-piperidin-1-yl-ethyl)-benzamide (G-46);

N-(3-hydroxy-propyl)-3-(2-morpholin-4-yl-7-pyridin-3-yl-6,7-dihydro-5H-pyrrolo[2,3-d]pyrimidin-4-yl)-benzamide (G-47);

N-(1-methyl-butyl)-3-(2-morpholin-4-yl-7-pyridin-3-yl-6,7-dihydro-5H-pyrrolo[2,3-d]pyrimidin-4-yl)-benzamide (G-48);

N-(2-methoxy-ethyl)-N-methyl-3-(2-morpholin-4-yl-7-pyridin-3-yl-6,7-dihydro-5H-pyrrolo[2,3-d]pyrimidin-4-yl)-benzamide (G-49);

(4-methyl-piperazin-1-yl)-[3-(2-morpholin-4-yl-7-pyridin-3-yl-6,7-dihydro-5H-pyrrolo[2,3-d]pyrimidin-4-yl)-phenyl]-methanone (G-50);

(4-hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone (G-51);

N-(3,3-dimethyl-butyl)-3-(2-morpholin-4-yl-7-pyridin-3-yl-6,7-dihydro-5H-pyrrolo[2,3-d]pyrimidin-4-yl)-benzamide (G-52);

N-cyclopropylmethyl-3-(2-morpholin-4-yl-7-pyridin-3-yl-6,7-dihydro-5H-pyrrolo[2,3-d]pyrimidin-4-yl)-N-propyl-benzamide (G-53);

N—((S)-2-hydroxy-1-phenyl-ethyl)-3-(2-morpholin-4-yl-7-pyridin-3-yl-6,7-dihydro-5H-pyrrolo[2,3-d]pyrimidin-4-yl)-benzamide (G-54);

N-(3-morpholin-4-yl-propyl)-3-(2-morpholin-4-yl-7-pyridin-3-yl-6,7-dihydro-5H-pyrrolo[2,3-d]pyrimidin-4-yl)-benzamide (G-55);

N-(3-dimethylamino-propyl)-3-(2-morpholin-4-yl-7-pyridin-3-yl-6,7-dihydro-5H-pyrrolo[2,3-d]pyrimidin-4-yl)-benzamide (G-56);

3-(2-morpholin-4-yl-7-pyridin-3-yl-6,7-dihydro-5H-pyrrolo[2,3-d]pyrimidin-4-yl)-N-pyridin-4-ylmethyl-benzamide (G-57);

N-cyclohexylmethyl-3-(2-morpholin-4-yl-7-pyridin-3-yl-6,7-dihydro-5H-pyrrolo[2,3-d]pyrimidin-4-yl)-benzamide (G-58);

N-(2-diethylamino-ethyl)-3-(2-morpholin-4-yl-7-pyridin-3-yl-6,7-dihydro-5H-pyrrolo[2,3-d]pyrimidin-4-yl)-benzamide (G-59);

N-isopropyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-60);

N-isobutyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-61);

N-ethyl-N-(2-hydroxy-ethyl)-3-(2-morpholin-4-yl-7-pyridin-3-yl-6,7-dihydro-5H-pyrrolo[2,3-d]pyrimidin-4-yl)-benzamide (G-62);

(3-hydroxy-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-63);

N-indan-2-yl-3-(2-morpholin-4-yl-7-pyridin-3-yl-6,7-dihydro-5H-pyrrolo[2,3-d]pyrimidin-4-yl)-benzamide (G-64);

azetidin-1-yl-[3-(2-morpholin-4-yl-7-pyridin-3-yl-6,7-dihydro-5H-pyrrolo[2,3-d]pyrimidin-4-yl)-phenyl]-methanone (G-65);

(4-ethyl-piperazin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-66);

N,N-diethyl-3-(2-morpholin-4-yl-7-pyridin-3-yl-6,7-dihydro-5H-pyrrolo[2,3-d]pyrimidin-4-yl)-benzamide (G-67);

((R)-2-hydroxymethyl-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-68);

[3-(2-morpholin-4-yl-7-pyridin-3-yl-6,7-dihydro-5H-pyrrolo[2,3-d]pyrimidin-4-yl)-phenyl]-(4-pyrrolidin-1-yl-piperidin-1-yl)-methanone (G-69);

(3-hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-70);

N-cyclopentyl-3-(2-morpholin-4-yl-7-pyridin-3-yl-6,7-dihydro-5H-pyrrolo[2,3-d]pyrimidin-4-yl)-benzamide (G-71);

(2,5-dihydro-pyrrol-1-yl)-[3-(2-morpholin-4-yl-7-pyridin-3-yl-6,7-dihydro-5H-pyrrolo[2,3-d]pyrimidin-4-yl)-phenyl]-methanone (G-72);

[3-(2-morpholin-4-yl-7-pyridin-3-yl-6,7-dihydro-5H-pyrrolo[2,3-d]pyrimidin-4-yl)-phenyl]-(4-phenyl-piperazin-1-yl)-methanone (G-73);

N-cyclohexyl-3-(2-morpholin-4-yl-7-pyridin-3-yl-6,7-dihydro-5H-pyrrolo[2,3-d]pyrimidin-4-yl)-benzamide (G-74);

(2,6-dimethyl-morpholin-4-yl)-[3-(2-morpholin-4-yl-7-pyridin-3-yl-6,7-dihydro-5H-pyrrolo[2,3-d]pyrimidin-4-yl)-phenyl]-methanone (G-75);

N-methyl-N-(3-methyl-butyl)-3-(2-morpholin-4-yl-7-pyridin-3-yl-6,7-dihydro-5H-pyrrolo[2,3-d]pyrimidin-4-yl)-benzamide trifluoroacetic acid salt (G-76);

N-(2-dimethylamino-ethyl)-N-ethyl-3-(2-morpholin-4-yl-7-pyridin-3-yl-6,7-dihydro-5H-pyrrolo[2,3-d]pyrimidin-4-yl)-benzamide trifluoroacetic acid salt (G-77);

azetidin-1-yl-[3-(2-morpholin-4-yl-7-pyridin-4-yl-6,7-dihydro-5H-pyrrolo[2,3-d]pyrimidin-4-yl)-phenyl]-methanone (G-78);

N-(3-hydroxy-propyl)-3-(2-morpholin-4-yl-7-pyridin-4-yl-6,7-dihydro-5H-pyrrolo[2,3-d]pyrimidin-4-yl)-benzamide (G-79);

N-cyclopentyl-3-(2-morpholin-4-yl-7-pyridin-4-yl-6,7-dihydro-5H-pyrrolo[2,3-d]pyrimidin-4-yl)-benzamide (G-80);

(3-hydroxy-pyrrolidin-1-yl)-[3-(2-morpholin-4-yl-7-pyridin-4-yl-6,7-dihydro-5H-pyrrolo[2,3-d]pyrimidin-4-yl)-phenyl]-methanone trifluoroacetic acid salt (G-81);

N-(2-methoxy-ethyl)-N-methyl-3-(2-morpholin-4-yl-7-pyridin-4-yl-6,7-dihydro-5H-pyrrolo[2,3-d]pyrimidin-4-yl)-benzamide (G-82);

(4-methyl-piperazin-1-yl)-[3-(2-morpholin-4-yl-7-pyridin-4-yl-6,7-dihydro-5H-pyrrolo[2,3-d]pyrimidin-4-yl)-phenyl]-methanone (G-83);

(4-hydroxy-piperidin-1-yl)-[3-(2-morpholin-4-yl-7-pyridin-4-yl-6,7-dihydro-5H-pyrrolo[2,3-d]pyrimidin-4-yl)-phenyl]-methanone trifluoroacetic acid salt (G-84);

N-methyl-N-(3-methyl-butyl)-3-(2-morpholin-4-yl-7-pyridin-4-yl-6,7-dihydro-5H-pyrrolo[2,3-d]pyrimidin-4-yl)-benzamide (G-85);

3-(2-morpholin-4-yl-7-pyridin-4-yl-6,7-dihydro-5H-pyrrolo[2,3-d]pyrimidin-4-yl)-N-pyridin-4-ylmethyl-benzamide (G-86);

(4-ethyl-piperazin-1-yl)-[3-(2-morpholin-4-yl-7-pyridin-4-yl-6,7-dihydro-5H-pyrrolo[2,3-d]pyrimidin-4-yl)-phenyl]-methanone (G-87);

N-(2-diethylamino-ethyl)-3-(2-morpholin-4-yl-7-pyridin-4-yl-6,7-dihydro-5H-pyrrolo[2,3-d]pyrimidin-4-yl)-benzamide trifluoroacetic acid salt (G-88);

N-(2-dimethylamino-ethyl)-N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-89);

3-(2-morpholin-4-yl-7-pyridin-4-yl-6,7-dihydro-5H-pyrrolo[2,3-d]pyrimidin-4-yl)-N-(2-pyrrolidin-1-yl-ethyl)-benzamide (G-90);

3-(2-morpholin-4-yl-7-pyridin-3-yl-6,7-dihydro-5H-pyrrolo[2,3-d]pyrimidin-4-yl)-N-(2-pyrrolidin-1-yl-ethyl)-benzamide (G-91);

N-(4,5-dimethyl-thiazol-2-yl)-3-(2-morpholin-4-yl-7-pyridin-3-yl-6,7-dihydro-5H-pyrrolo[2,3-d]pyrimidin-4-yl)-benzamide (G-92);

N-indan-2-yl-3-(2-morpholin-4-yl-7-pyridin-4-yl-6,7-dihydro-5H-pyrrolo[2,3-d]pyrimidin-4-yl)-benzamide (G-93);

(3-hydroxy-piperidin-1-yl)-[3-(2-morpholin-4-yl-7-pyridin-4-yl-6,7-dihydro-5H-pyrrolo[2,3-d]pyrimidin-4-yl)-phenyl]-methanone (G-94);

7-(2-chloro-pyridin-4-yl)-4-(3-methoxy-phenyl)-2-morpholin-4-yl-6,7-dihydro-5H-pyrrolo[2,3-d]pyrimidine trifluoroacetic acid salt (H-01);

3-{7-[2-(3-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-02);

3-{7-[2-(isobutyl-methyl-amino)-pyridin-4-yl]-2-morpholin-4-yl-6,7-dihydro-5H-pyrrolo[2,3-d]pyrimidin-4-yl}-phenol (H-03);

3-{7-[2-(4-ethyl-piperazin-1-yl)-pyridin-4-yl]-2-morpholin-4-yl-6,7-dihydro-5H-pyrrolo[2,3-d]pyrimidin-4-yl}-phenol (H-04);

4'-[4-(3-hydroxy-phenyl)-2-morpholin-4-yl-5,6-dihydropyrrolo[2,3-d]pyrimidin-7-yl]-3,4,5,6-tetrahydro-2H-[1,2']bipyridinyl-4-ol (H-05);

4-[4-(3-hydroxy-phenyl)-2-morpholin-4-yl-5,6-dihydropyrrolo[2,3-d]pyrimidin-7-yl]-pyridin-2-ol (H-06);

1-(4-{4-[4-(3-hydroxy-phenyl)-2-morpholin-4-yl-5,6-dihydro-pyrrolo[2,3-d]pyrimidin-7-yl]-pyridin-2-yl}-piperazin-1-yl)-ethanone (H-07);

3-{7-[2-(2-hydroxy-ethylamino)-pyridin-4-yl]-2-morpholin-4-yl-6,7-dihydro-5H-pyrrolo[2,3-d]pyrimidin-4-yl}-phenol trifluoroacetic acid salt (H-08);

3-{7-[2-(2-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-09);

3-{7-[2-(2-hydroxy-1-methyl-ethylamino)-pyridin-4-yl]-2-morpholin-4-yl-6,7-dihydro-5H-pyrrolo[2,3-d]pyrimidin-4-yl}-phenol trifluoroacetic acid salt (H-10);

4'-[4-(3-hydroxy-phenyl)-2-morpholin-4-yl-5,6-dihydro-pyrrolo[2,3-d]pyrimidin-7-yl]-3,4,5,6-tetrahydro-2H-[1,2']bipyridinyl-3-ol (H-11);

3-{7-[2-(3-dimethylamino-propylamino)-pyridin-4-yl]-2-morpholin-4-yl-6,7-dihydro-5H-pyrrolo[2,3-d]pyrimidin-4-yl}-phenol (H-12);

3-{7-[2-(3-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-13);

3-(7-{2-[(2-hydroxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-14);

3-(7-{2-[(2-methoxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-15);

3-(7-{2-[(2-dimethylamino-ethyl)-ethyl-amino]-pyridin-4-yl}-2-morpholin-4-yl-6,7-dihydro-5H-pyrrolo[2,3-d]pyrimidin-4-yl)-phenol trifluoroacetic acid salt (H-16);

3-{7-[2-((R)-2-hydroxymethyl-pyrrolidin-1-yl)-pyridin-4-yl]-2-morpholin-4-yl-6,7-dihydro-5H-pyrrolo[2,3-d]pyrimidin-4-yl}-phenol trifluoroacetic acid salt (H-17);

3-[2-morpholin-4-yl-7-(4-pyrrolidin-1-yl-3,4,5,6-tetrahydro-2H-[1,2']bipyridinyl-4'-yl)-6,7-dihydro-5H-pyrrolo[2,3-d]pyrimidin-4-yl]-phenol trifluoroacetic acid salt (H-18);

3-{7-[2-(cyclohexylmethyl-amino)-pyridin-4-yl]-2-morpholin-4-yl-6,7-dihydro-5H-pyrrolo[2,3-d]pyrimidin-4-yl}-phenol trifluoroacetic acid salt (H-19);

3-{7-[2-(3,3-dimethyl-butylamino)-pyridin-4-yl]-2-morpholin-4-yl-6,7-dihydro-5H-pyrrolo[2,3-d]pyrimidin-4-yl}-phenol trifluoroacetic acid salt (H-20);

3-{7-[2-(isobutyl-methyl-amino)-pyridin-4-yl]-2-morpholin-4-yl-6,7-dihydro-5H-pyrrolo[2,3-d]pyrimidin-4-yl}-phenol (H-21);

3-(7-{2-[methyl-(3-methyl-butyl)-amino]-pyridin-4-yl}-2-morpholin-4-yl-6,7-dihydro-5H-pyrrolo[2,3-d]pyrimidin-4-yl)-phenol (H-22);

1-{4-[4-(3-hydroxy-phenyl)-2-morpholin-4-yl-5,6-dihydro-pyrrolo[2,3-d]pyrimidin-7-yl]-pyridin-2-yl}-pyrrolidin-3-ol (H-23);

3-{2-morpholin-4-yl-7-[2-(4-phenyl-piperazin-1-yl)-pyridin-4-yl]-6,7-dihydro-5H-pyrrolo[2,3-d]pyrimidin-4-yl}-phenol trifluoroacetic acid salt (H-24);

3-{7-[2-(cyclopropylmethyl-propyl-amino)-pyridin-4-yl]-2-morpholin-4-yl-6,7-dihydro-5H-pyrrolo[2,3-d]pyrimidin-4-yl}-phenol trifluoroacetic acid salt (H-25);

3-{7-[2-(2,6-dimethyl-morpholin-4-yl)-pyridin-4-yl]-2-morpholin-4-yl-6,7-dihydro-5H-pyrrolo[2,3-d]pyrimidin-4-yl}-phenol trifluoroacetic acid salt (H-26);

3-{2-morpholin-4-yl-7-[2-(3-morpholin-4-yl-propylamino)-pyridin-4-yl]-6,7-dihydro-5H-pyrrolo[2,3-d]pyrimidin-4-yl}-phenol trifluoroacetic acid salt (H-27);

3-{7-[2-(indan-2-ylamino)-pyridin-4-yl]-2-morpholin-4-yl-6,7-dihydro-5H-pyrrolo[2,3-d]pyrimidin-4-yl}-phenol trifluoroacetic acid salt (H-28);

3-{7-[2-(2,5-dihydro-pyrrol-1-yl)-pyridin-4-yl]-2-morpholin-4-yl-6,7-dihydro-5H-pyrrolo[2,3-d]pyrimidin-4-yl}-phenol trifluoroacetic acid salt (H-29);

3-[7-(2-cyclohexylamino-pyridin-4-yl)-2-morpholin-4-yl-6,7-dihydro-5H-pyrrolo[2,3-d]pyrimidin-4-yl]-phenol trifluoroacetic acid salt (H-30);

5-[2-morpholin-4-yl-7-(2-morpholin-4-yl-pyridin-4-yl)-6,7-dihydro-5-pyrrolo[2,3-d]pyrimidin-4-yl]-pyrimidin-2-ylamine (H-31);

5-[7-(2-dimethylaminoethoxy-pyridin-4-yl)-2-morpholin-4-yl-6,7-dihydro-5H-pyrrolo[2,3-d]pyrimidin-4-yl]-pyrimidin-2-ylamine (H-32);

N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (H-33);

5-{7-[2-(4-ethyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-34);

{4'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (H-35);

5-{7-[2-(4-methyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-36);

N-{3-[4-(2-amino-pyrimidin-5-yl)-2-morpholin-4-yl-5,6-dihydro-pyrrolo[2,3-d]pyrimidin-7-yl]-phenyl}-methanesulfonamide (I-01).

| Example No. | Compound No. | Structural formula |
|---|---|---|
| Example 1-A-01 | (A-01) | 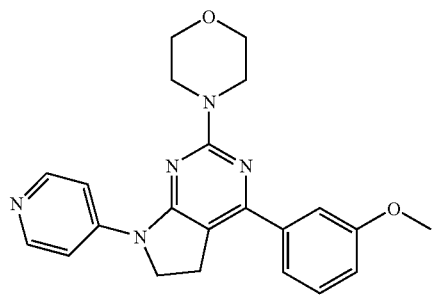 |

-continued

| Example No. | Compound No. | Structural formula |
|---|---|---|
| Example 1-A-02 | (A-02) | |
| Example 1-A-03 | (A-03) | |
| Example 1-A-04 | (A-04) | |
| Example 1-A-05 | (A-05) | |
| Example 1-A-06 | (A-06) | |

-continued
| Example No. | Compound No. | Structural formula |
|---|---|---|
| Example 1-A-07 | (A-07) | 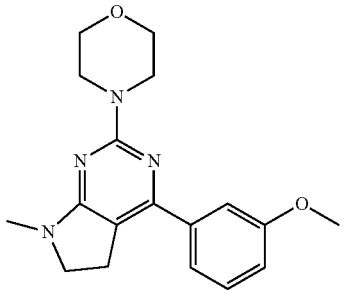 |
| Example 1-A-08 | (A-08) | 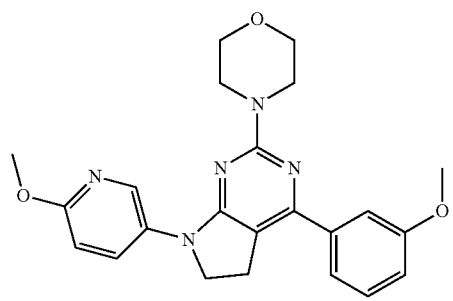 |
| Example 1-A-09 | (A-09) | 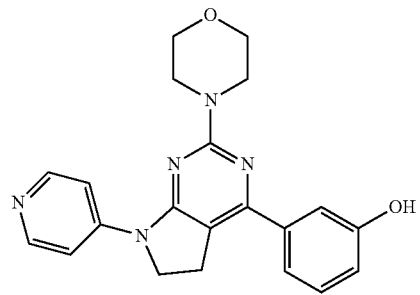 |
| Example 1-A-10 | (A-10) | 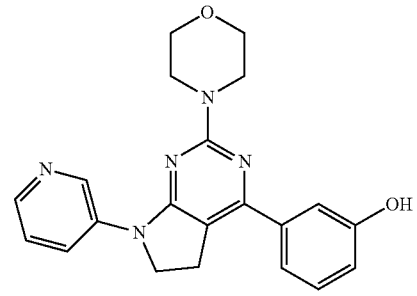 |
| Example 1-A-11 | (A-11) | 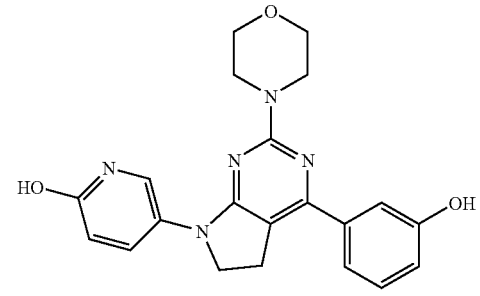 |

-continued
| Example No. | Compound No. | Structural formula |
|---|---|---|
| Example 1-A-12 | (A-12) | 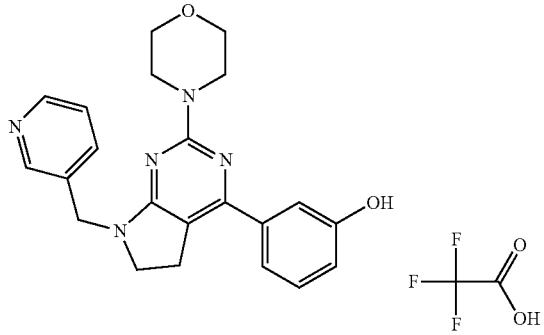 |
| Example 1-A-13 | (A-13) | 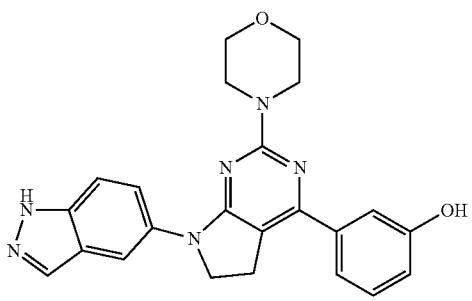 |
| Example 1-A-14 | (A-14) | 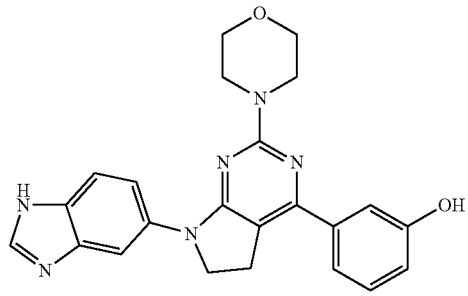 |
| Example 1-A-15 | (A-15) | 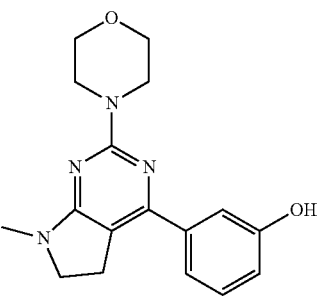 |
| Example 1-A-16 | (A-16) | 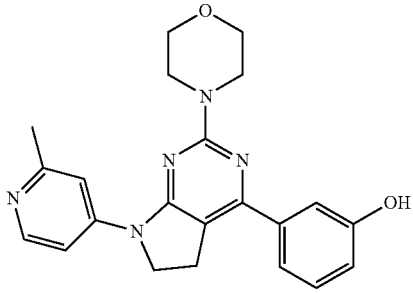 |

-continued

| Example No. | Compound No. | Structural formula |
|---|---|---|
| Example 1-A-17 | (A-17) | |
| Example 1-A-18 | (A-18) | |
| Example 1-A-19 | (A-19) | |
| Example 1-A-20 | (A-20) | |
| Example 1-A-21 | (A-21) | |

-continued
| Example No. | Compound No. | Structural formula |
|---|---|---|
| Example 1-A-22 | (A-22) | 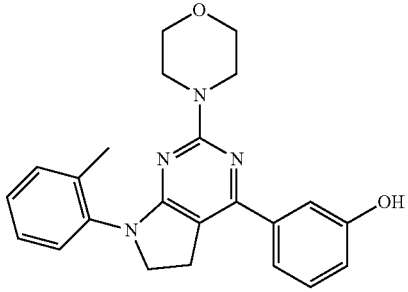 |
| Example 1-A-23 | (A-23) | 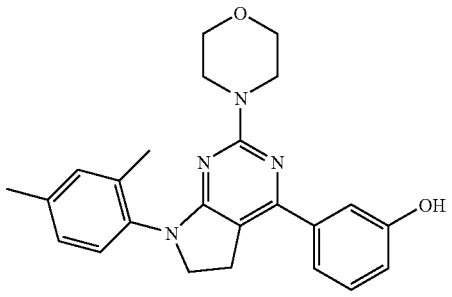 |
| Example 1-A-24 | (A-24) | 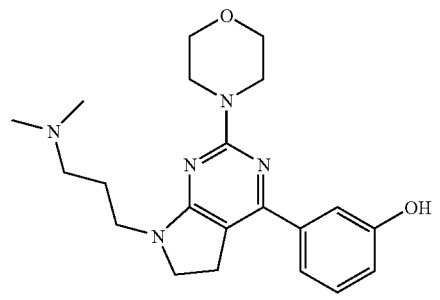 |
| Example 1-A-25 | (A-25) | 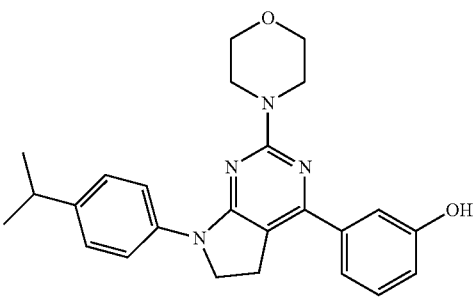 |
| Example 1-A-26 | (A-26) | 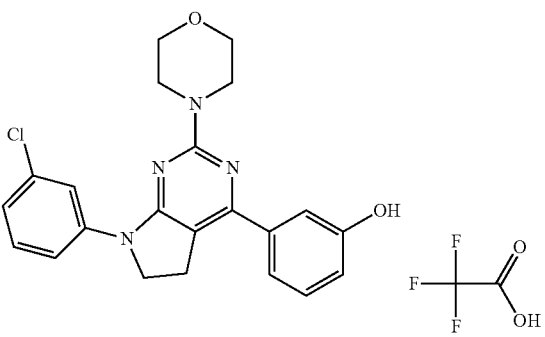 |

-continued
| Example No. | Compound No. | Structural formula |
|---|---|---|
| Example 1-A-27 | (A-27) | 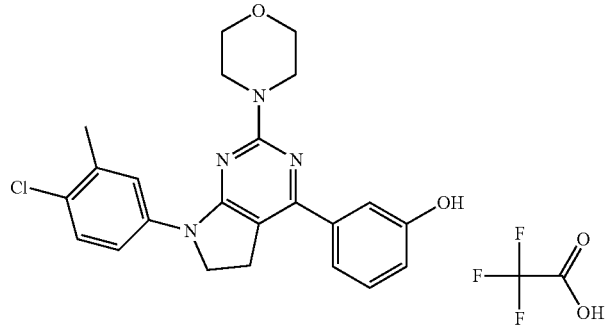 |
| Example 1-A-28 | (A-28) | 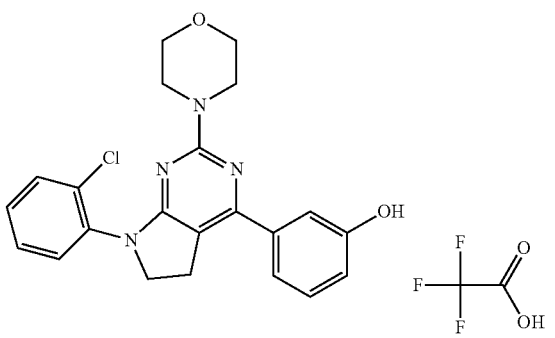 |
| Example 1-A-29 | (A-29) | 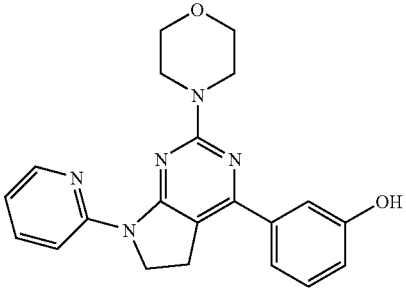 |
| Example 1-A-30 | (A-30) | 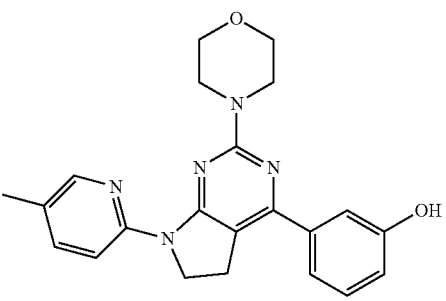 |

-continued
| Example No. | Compound No. | Structural formula |
|---|---|---|
| Example 1-A-31 | (A-31) | 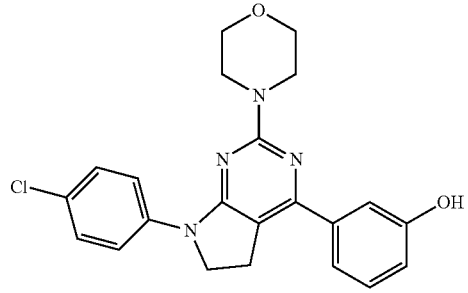 |
| Example 1-A-32 | (A-32) | 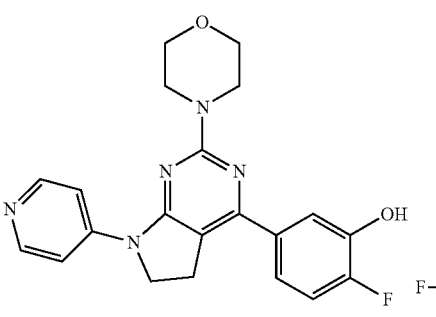 |
| Example 1-A-33 | (A-33) | 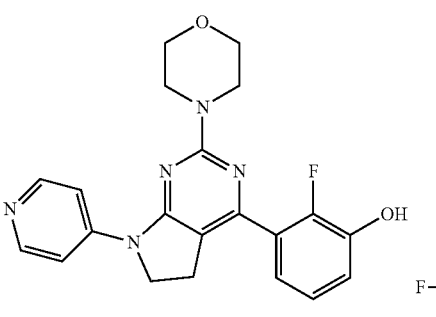 |
| Example 1-A-34 | (A-34) | 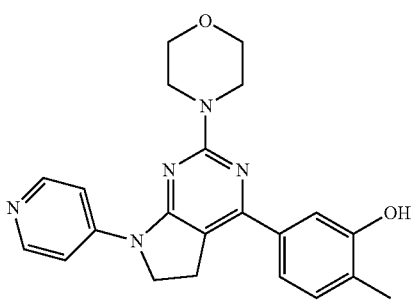 |

-continued

| Example No. | Compound No. | Structural formula |
|---|---|---|
| Example 1-A-35 | (A-35) | |
| Example 1-A-36 | (A-36) | |
| Example 1-A-37 | (A-37) | |
| Example 1-A-38 | (A-38) | |

-continued
| Example No. | Compound No. | Structural formula |
|---|---|---|
| Example 1-A-39 | (A-39) | 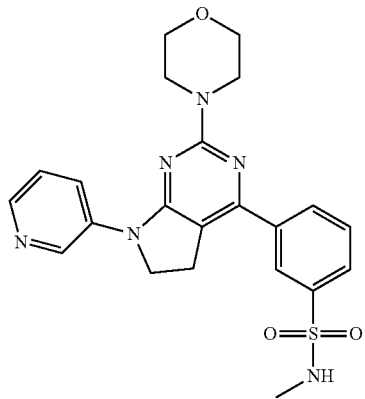 |
| Example 1-A-40 | (A-40) | 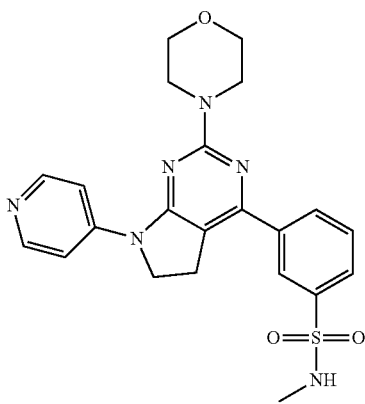 |
| Example 1-A-41 | (A-41) | 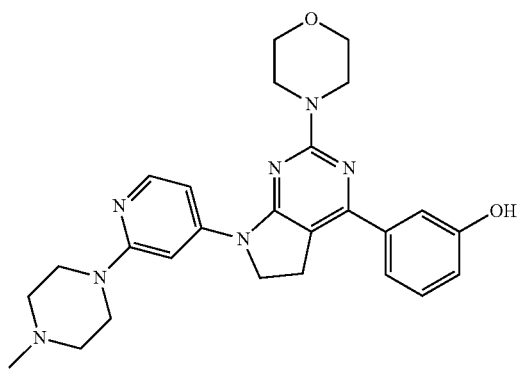 |

-continued
| Example No. | Compound No. | Structural formula |
|---|---|---|
| Example 1-A-42 | (A-42) | 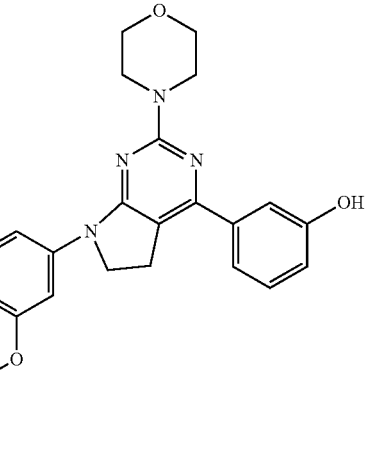 |
| Example 1-A-43 | (A-43) | 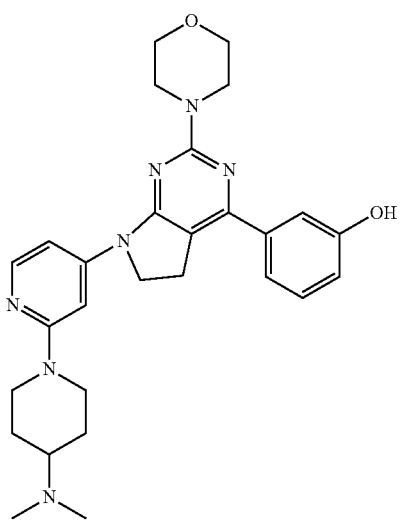 |
| Example 1-A-44 | (A-44) | 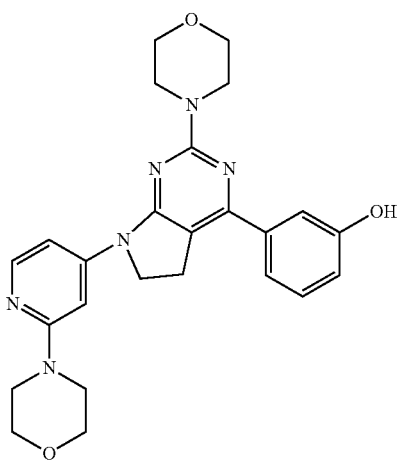 |

-continued
| Example No. | Compound No. | Structural formula |
|---|---|---|
| Example 1-A-45 | (A-45) | 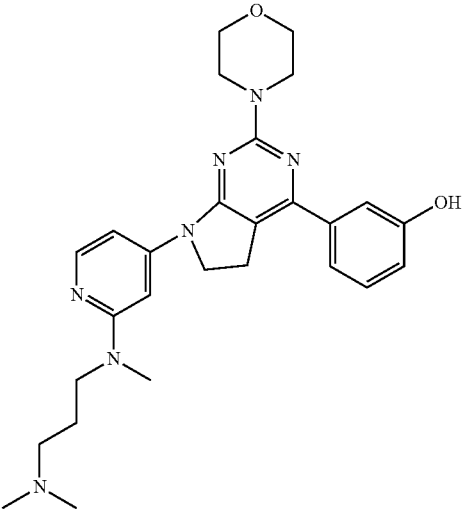 |
| Example 1-A-46 | (A-46) | 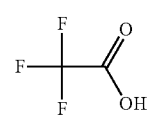 |
| Example 1-A-47 | (A-47) | 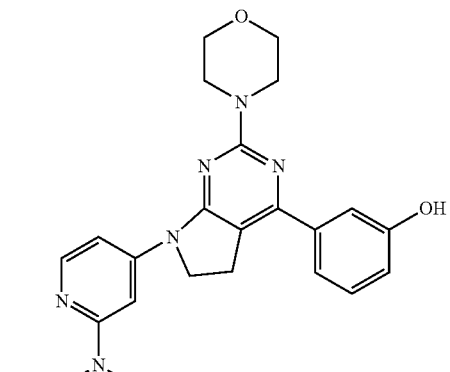 |

-continued

| Example No. | Compound No. | Structural formula |
|---|---|---|
| Example 1-A-48 | (A-48) | |
| Example 1-A-49 | (A-49) | |
| Example 1-A-50 | (A-50) | |
| Example 1-A-51 | (A-51) | |
| Example 1-A-52 | (A-52) | |

-continued
| Example No. | Compound No. | Structural formula |
|---|---|---|
| Example 1-A-53 | (A-53) | 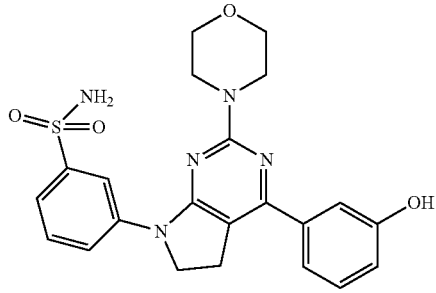 |
| Example 1-A-54 | (A-54) | 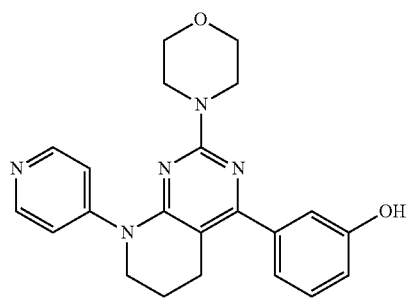 |
| Example No. | Compound No. | Structural formula |
|---|---|---|
| Example 1-B-01 | (B-01) | 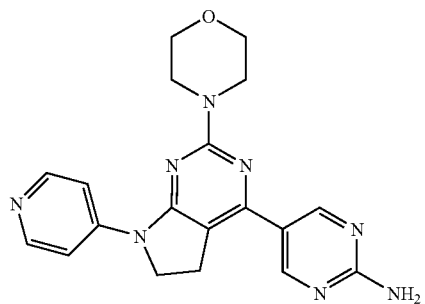 |
| Example 1-B-02 | (B-02) | 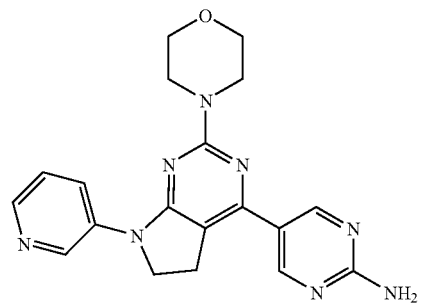 |

-continued
| Example No. | Compound No. | Structural formula |
|---|---|---|
| Example 1-B-03 | (B-03) | 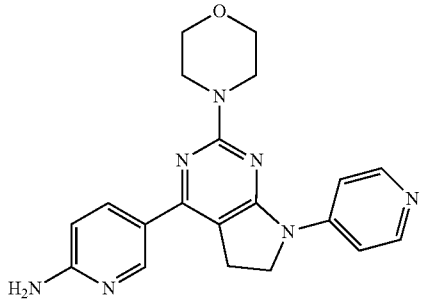 |
| Example 1-B-04 | (B-04) | 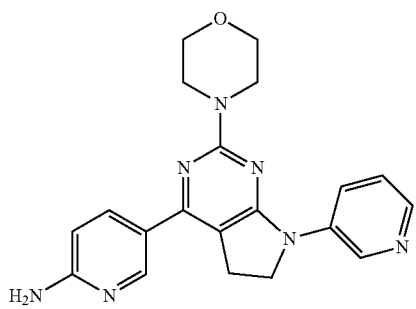 |
| Example 1-B-05 | (B-05) | 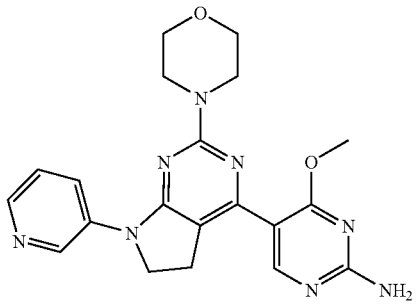 |
| Example 1-B-06 | (B-06) | 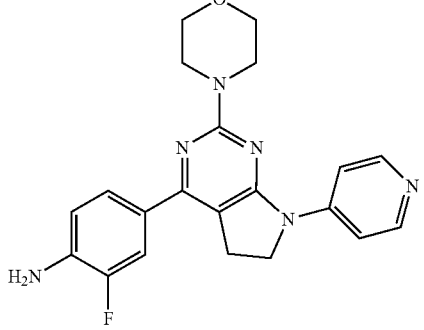 |

-continued
| Example No. | Compound No. | Structural formula |
|---|---|---|
| Example 1-B-07 | (B-07) | 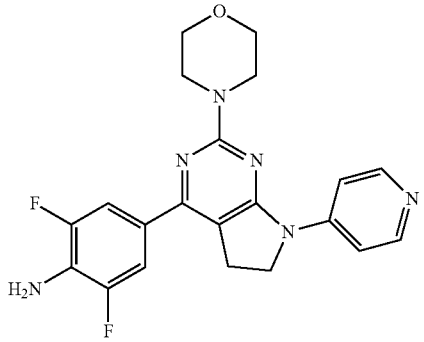 |
| Example 1-B-08 | (B-08) | 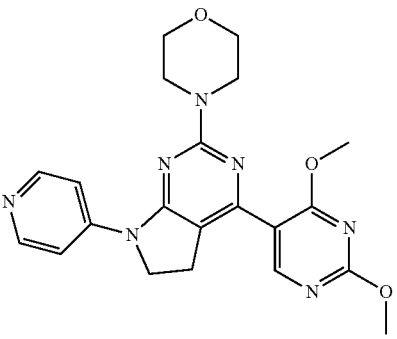 |
| Example 1-B-09 | (B-09) | 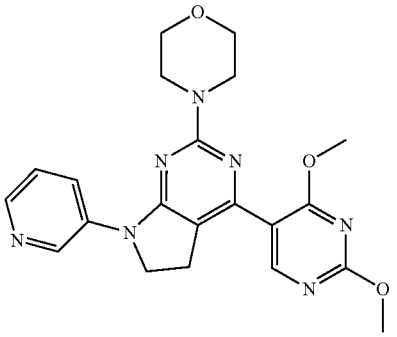 |
| Example 1-B-10 | (B-10) | 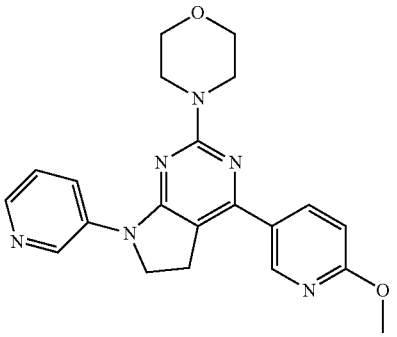 |

| Example No. | Compound No. | Structural formula |
| --- | --- | --- |
| Example 1-B-11 | (B-11) | |
| Example 1-B-12 | (B-12) | |
| Example 1-B-13 | (B-13) | HCl |
| Example 1-B-14 | (B-14) | |

-continued
| Example No. | Compound No. | Structural formula |
|---|---|---|
| Example 1-B-15 | (B-15) | 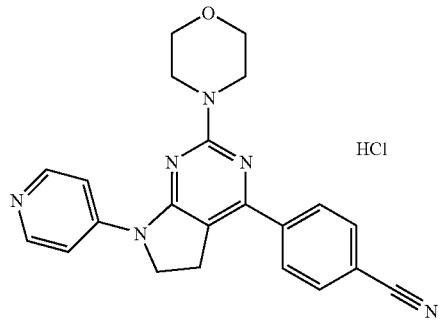 |
| Example 1-B-16 | (B-16) | 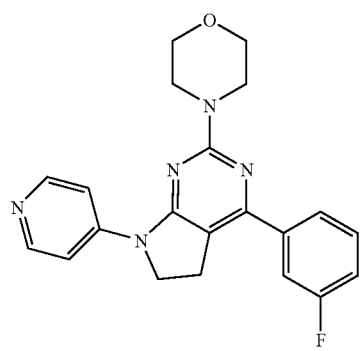 |
| Example 1-B-17 | (B-17) | 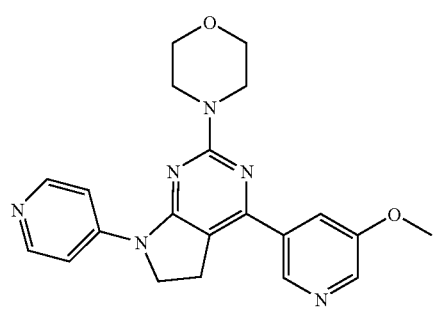 |
| Example 1-B-18 | (B-18) | 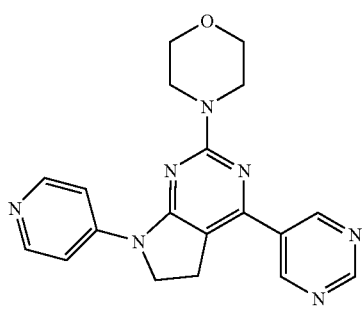 |

-continued
| Example No. | Compound No. | Structural formula |
|---|---|---|
| Example 1-B-19 | (B-19) | 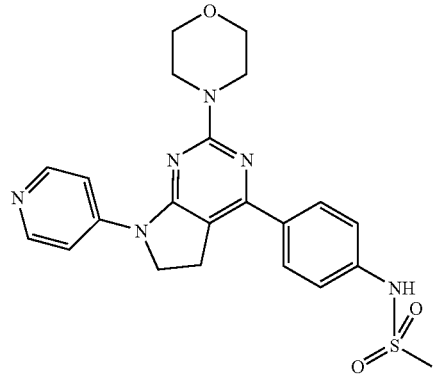 |
| Example 1-B-20 | (B-20) | 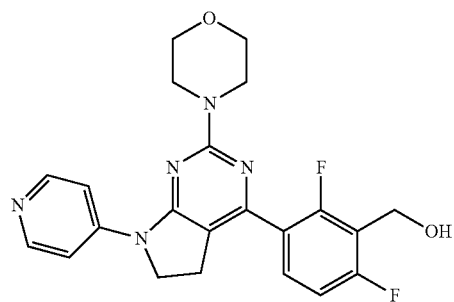 |
| Example 1-B-21 | (B-21) | 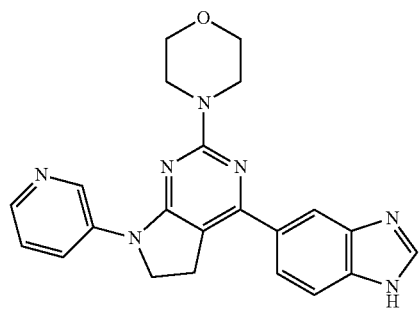 |
| Example 1-B-22 | (B-22) | 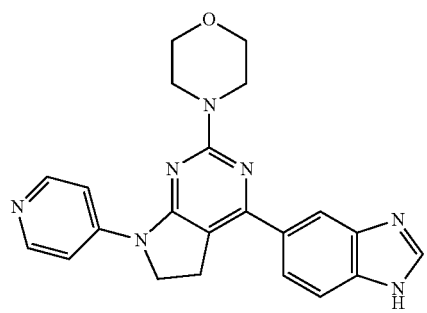 |

-continued

| Example No. | Compound No. | Structural formula |
|---|---|---|
| Example 1-B-23 | (B-23) | |
| Example 1-B-24 | (B-24) | |
| Example 1-B-25 | (B-25) | |
| Example 1-B-26 | (B-26) | |

-continued
| Example No. | Compound No. | Structural formula |
|---|---|---|
| Example 1-B-27 | (B-27) | 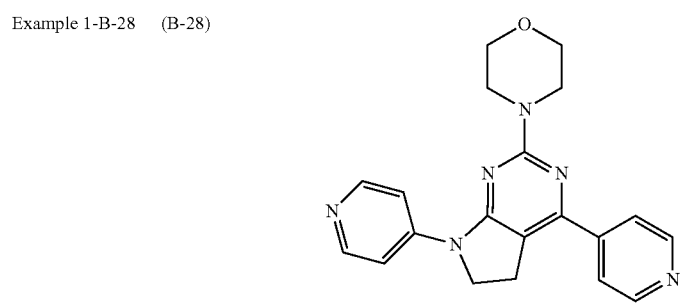 |
| Example 1-B-28 | (B-28) | 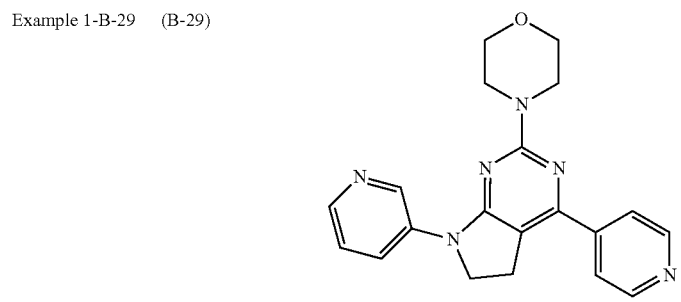 |
| Example 1-B-29 | (B-29) | |
| Example 1-B-30 | (B-30) | 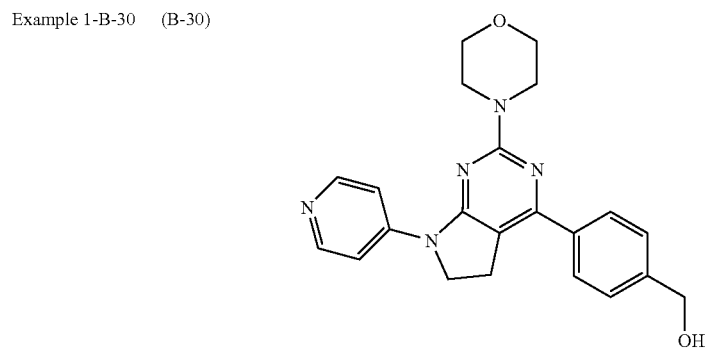 |

-continued

| Example No. | Compound No. | Structural formula |
|---|---|---|
| Example 1-B-31 | (B-31) | |
| Example 1-B-32 | (B-32) | HCl |
| Example 1-B-33 | (B-33) | HCl |
| Example 1-B-34 | (B-34) | |

-continued

| Example No. | Compound No. | Structural formula |
|---|---|---|
| Example 1-B-35 | (B-35) | |
| Example 1-B-36 | (B-36) | |
| Example 1-B-37 | (B-37) | |
| Example 1-B-38 | (B-38) | |
| Example 1-B-39 | (B-39) | |

-continued
| Example No. | Compound No. | Structural formula |
|---|---|---|
| Example 1-B-40 | (B-40) | 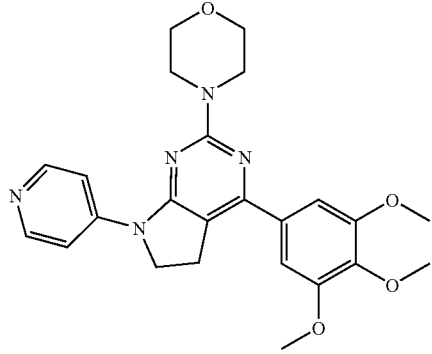 |
| Example 1-B-41 | (B-41) | 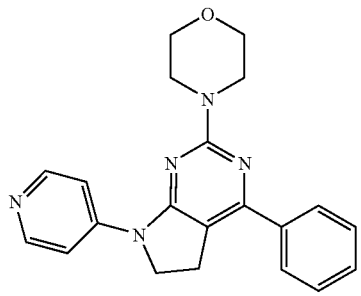 |
| Example 1-B-42 | (B-42) | 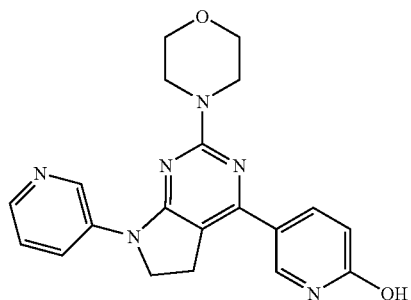 |
| Example 1-B-43 | (B-43) | 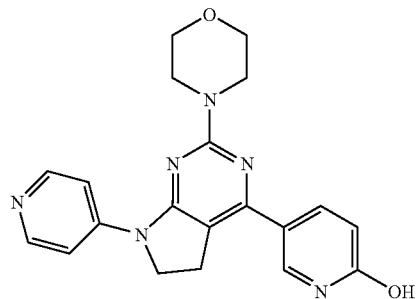 |

-continued

| Example No. | Compound No. | Structural formula |
|---|---|---|
| Example 1-B-44 | (B-44) | |
| Example 1-B-45 | (B-45) | |
| Example 1-B-46 | (B-46) | |
| Example 1-B-47 | (B-47) | |
| Example 1-B-48 | (B-48) | |

-continued
| Example No. | Compound No. | Structural formula |
|---|---|---|
| Example 1-B-49 | (B-49) | 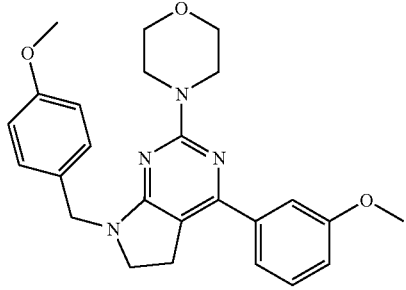 |
| Example 1-B-50 | (B-50) | 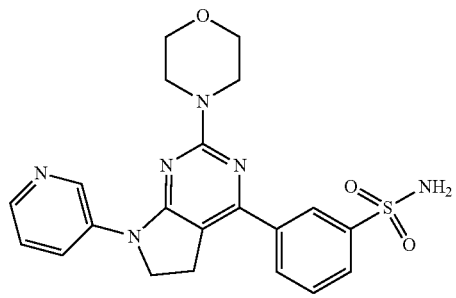 |
| Example 1-B-51 | (B-51) | 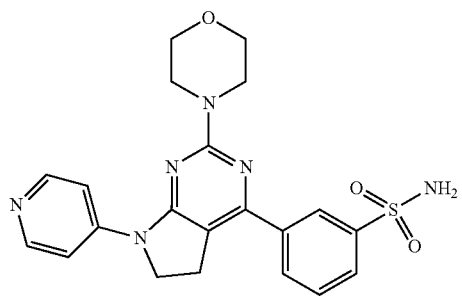 |
| Example 1-B-52 | (B-52) | 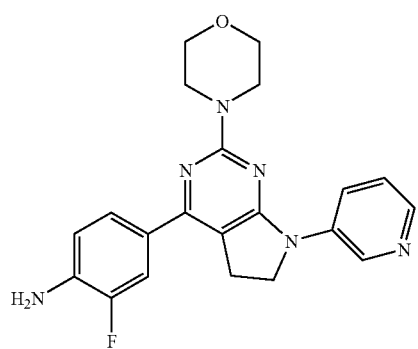 |

-continued
| Example No. | Compound No. | Structural formula |
|---|---|---|
| Example 1-B-53 | (B-53) | 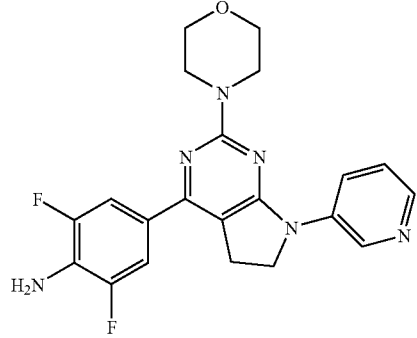 |
| Example 1-B-54 | (B-54) | 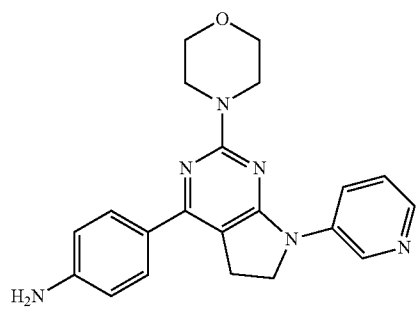 |
| Example 1-B-55 | (B-55) | 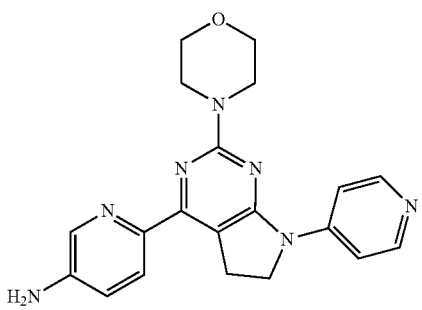 |
| Example No. | Compound No. | Structural formula |
|---|---|---|
| Example 1-C-01 | (C-01) | 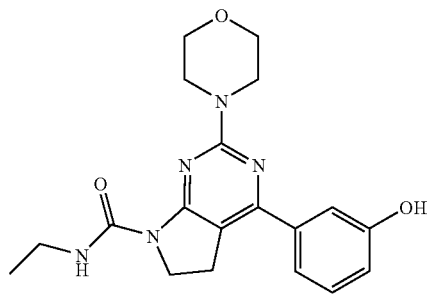 |

-continued

| Example No. | Compound No. | Structural formula |
|---|---|---|
| Example 1-C-02 | (C-02) | |
| Example 1-C-03 | (C-03) | |
| Example 1-C-04 | (C-04) | |
| Example 1-C-05 | (C-05) | |
| Example 1-C-06 | (C-06) | |

-continued

| Example No. | Compound No. | Structural formula |
|---|---|---|
| Example 1-C-07 | (C-07) | |
| Example 1-C-08 | (C-08) | |
| Example 1-C-09 | (C-09) | |
| Example 1-C-10 | (C-10) | |

-continued

| Example No. | Compound No. | Structural formula |
|---|---|---|
| Example 1-C-11 | (C-11) | |
| Example 1-C-12 | (C-12) | |
| Example 1-C-13 | (C-13) | |
| Example 1-C-14 | (C-14) | |
| Example 1-C-15 | (C-15) | |

-continued
| Example No. | Compound No. | Structural formula |
|---|---|---|
| Example 1-C-16 | (C-16) | 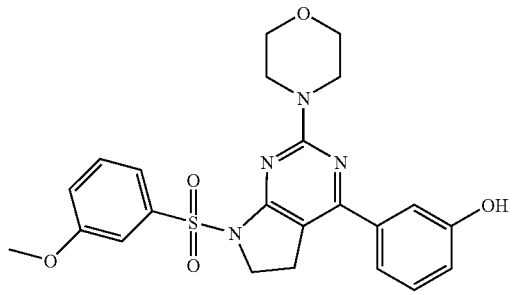 |
| Example 1-C-17 | (C-17) | 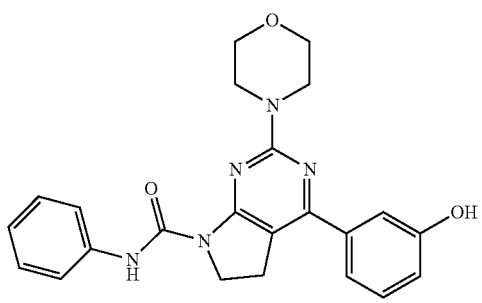 |
| Example 1-C-18 | (C-18) | 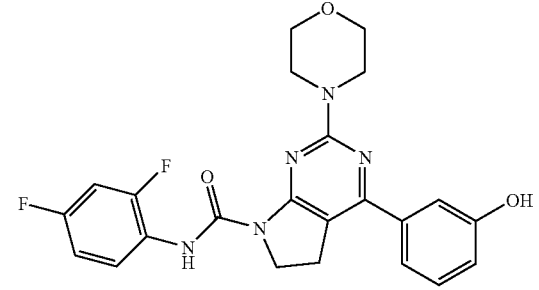 |
| Example 1-C-19 | (C-19) | 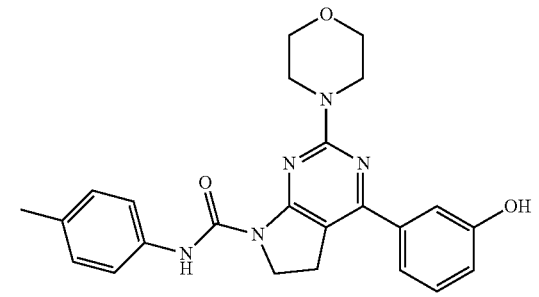 |
| Example 1-C-20 | (C-20) | 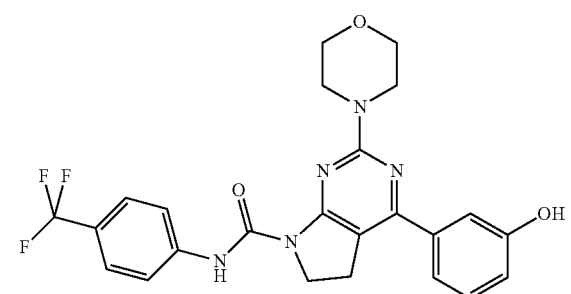 |

-continued

| Example No. | Compound No. | Structural formula |
|---|---|---|
| Example 1-C-21 | (C-21) | |
| Example 1-C-22 | (C-22) | |
| Example 1-C-23 | (C-23) | |
| Example 1-C-24 | (C-24) | |
| Example 1-C-25 | (C-25) | |

-continued

| Example No. | Compound No. | Structural formula |
|---|---|---|
| Example 1-C-26 | (C-26) | |
| Example 1-C-27 | (C-27) | |
| Example 1-C-28 | (C-28) | |
| Example 1-C-29 | (C-29) | |

-continued
| Example No. | Compound No. | Structural formula |
|---|---|---|
| Example 1-C-30 | (C-30) | 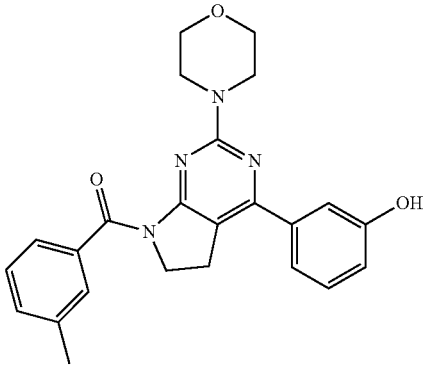 |
| Example 1-C-31 | (C-31) | 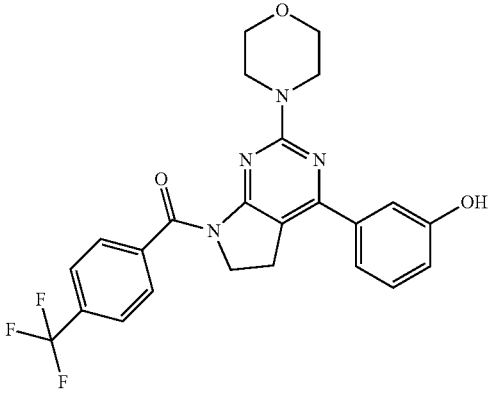 |
| Example 1-C-32 | (C-32) | 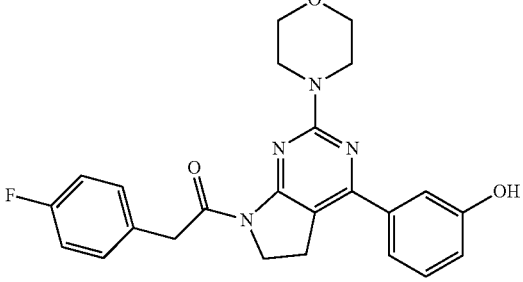 |
| Example 1-C-33 | (C-33) | 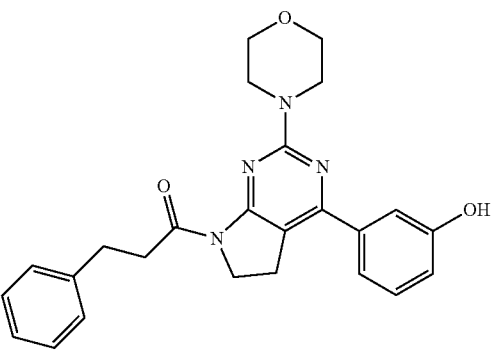 |

-continued
| Example No. | Compound No. | Structural formula |
|---|---|---|
| Example 1-C-34 | (C-34) | 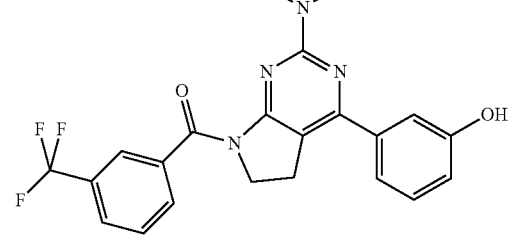 |
| Example 1-C-35 | (C-35) | 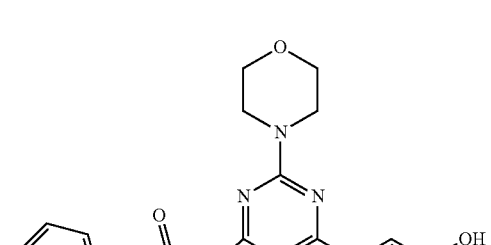 |
| Example 1-C-36 | (C-36) | 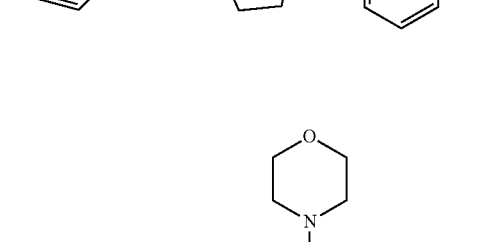 |
| Example 1-C-37 | (C-37) | 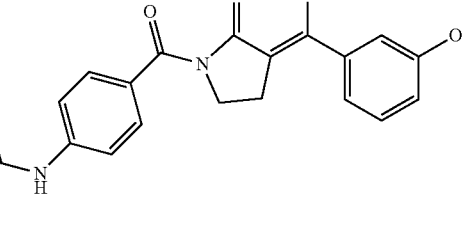 |

| Example No. | Compound No. | Structural formula |
|---|---|---|
| Example 1-C-38 | (C-38) | |
| Example 1-C-39 | (C-39) | |
| Example 1-C-40 | (C-40) | |
| Example 1-C-41 | (C-41) | |

-continued
| Example No. | Compound No. | Structural formula |
|---|---|---|
| Example 1-C-42 | (C-42) | 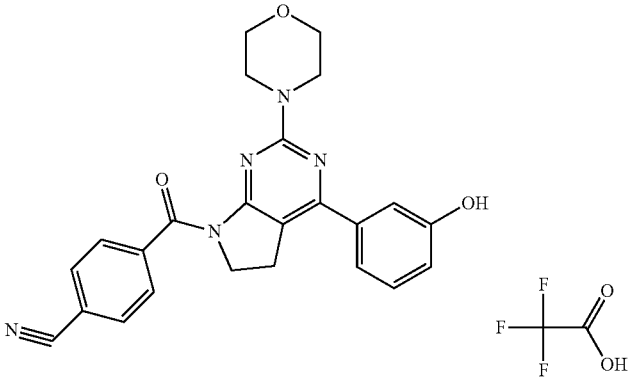 |
| Example 1-C-43 | (C-43) | 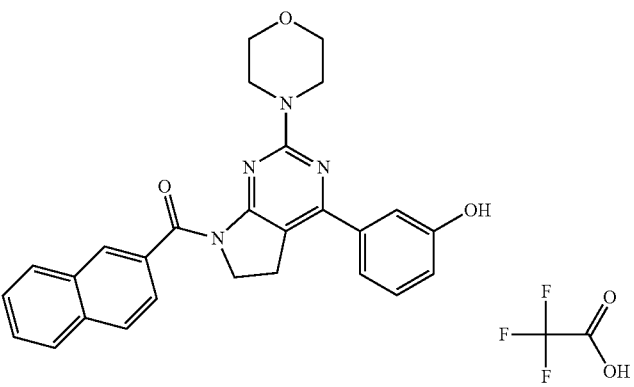 |
| Example 1-C-44 | (C-44) | 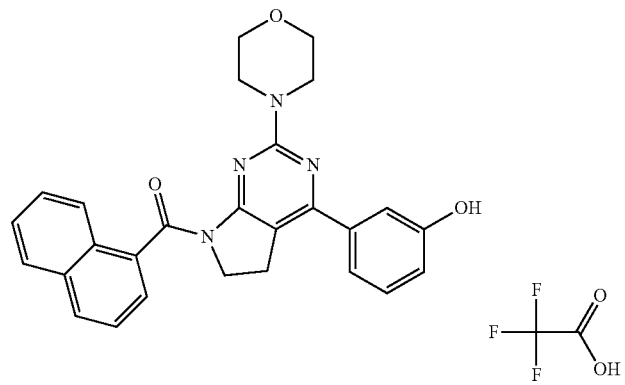 |
| Example 1-C-45 | (C-45) | 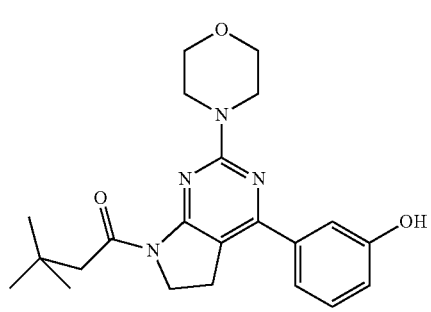 |

-continued

| Example No. | Compound No. | Structural formula |
|---|---|---|
| Example 1-C-46 | (C-46) | |
| Example 1-C-47 | (C-47) | |
| Example 1-C-48 | (C-48) | |
| Example 1-C-49 | (C-49) | |
| Example 1-C-50 | (C-50) | |

-continued
| Example No. | Compound No. | Structural formula |
|---|---|---|
| Example 1-C-51 | (C-51) | 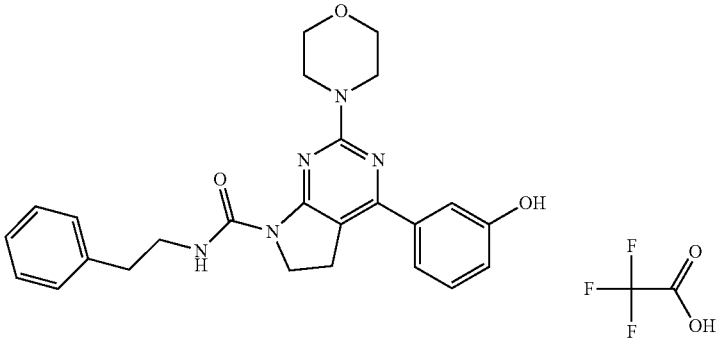 |
| Example 1-C-52 | (C-52) | 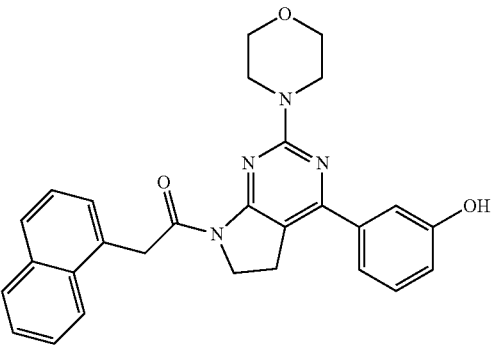 |
| Example 1-C-53 | (C-53) | 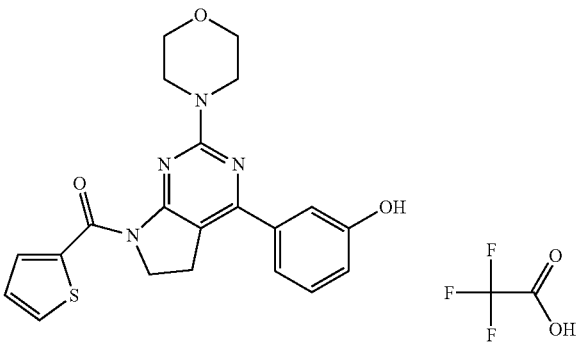 |
| Example 1-C-54 | (C-54) | 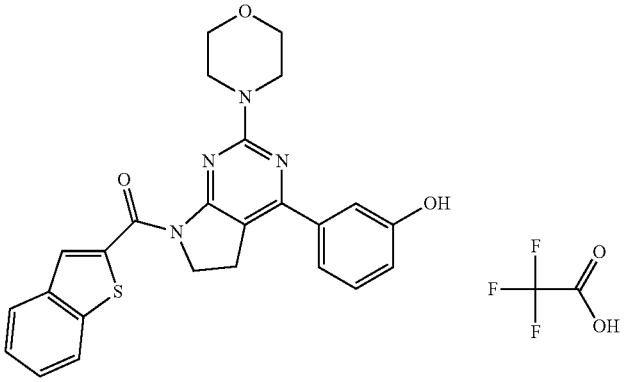 |

| Example No. | Compound No. | Structural formula |
|---|---|---|
| Example 1-C-55 | (C-55) | 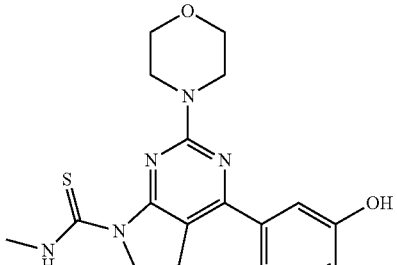 |
| Example 1-C-56 | (C-56) | 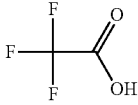 |
| Example 1-C-57 | (C-57) | 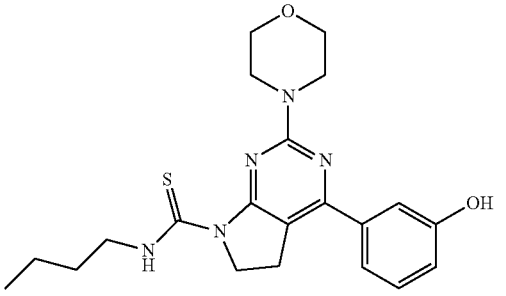 |
| Example No. | Compound No. | Structural formula |
|---|---|---|
| Example 1-D-01 | (D-01) | 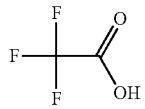 |

-continued

| Example No. | Compound No. | Structural formula |
|---|---|---|
| Example 1-D-02 | (D-02) | |
| Example 1-D-03 | (D-03) | |
| Example 1-D-04 | (D-04) | |
| Example 1-D-05 | (D-05) | |
| Example 1-D-06 | (D-06) | |

-continued
| Example No. | Compound No. | Structural formula |
|---|---|---|
| Example 1-D-07 | (D-07) | 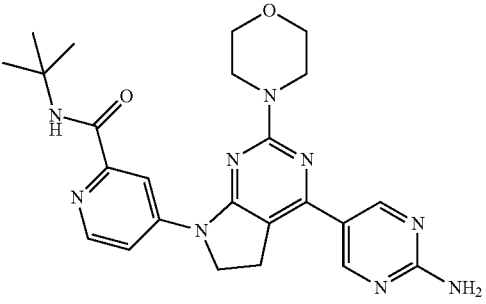 |
| Example 1-D-08 | (D-08) | 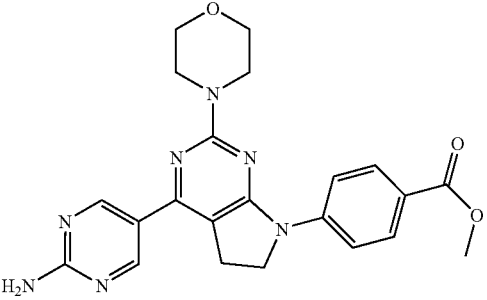 |
| Example 1-D-09 | (D-09) | 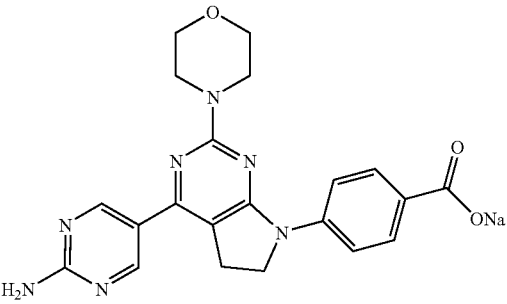 |
| Example 1-D-10 | (D-10) | 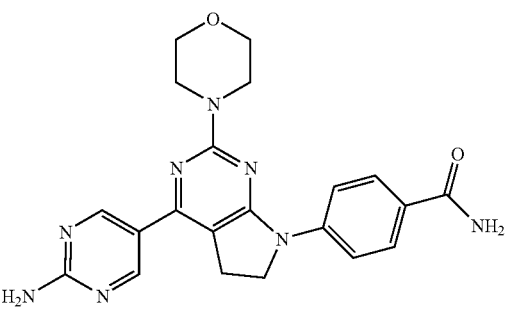 |

-continued

| Example No. | Compound No. | Structural formula |
|---|---|---|
| Example 1-D-11 | (D-11) | |
| Example 1-D-12 | (D-12) | |
| Example 1-D-13 | (D-13) | |
| Example 1-D-14 | (D-14) | |

-continued

| Example No. | Compound No. | Structural formula |
|---|---|---|
| Example 1-D-15 | (D-15) | |
| Example 1-D-16 | (D-16) | |
| Example 1-D-17 | (D-17) | |
| Example 1-D-18 | (D-18) | |

-continued

| Example No. | Compound No. | Structural formula |
|---|---|---|
| Example 1-D-19 | (D-19) | |
| Example 1-D-20 | (D-20) | |
| Example 1-D-21 | (D-21) | |
| Example 1-D-22 | (D-22) | |

-continued
| Example No. | Compound No. | Structural formula |
|---|---|---|
| Example 1-D-23 | (D-23) | 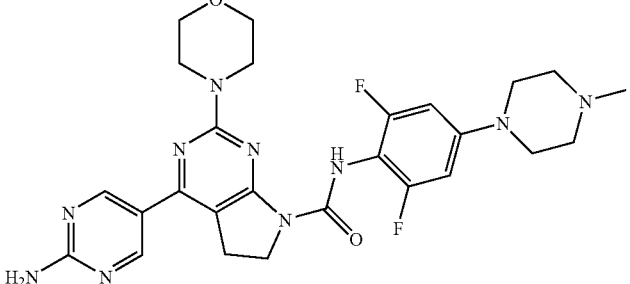 |
| Example 1-D-24 | (D-24) | 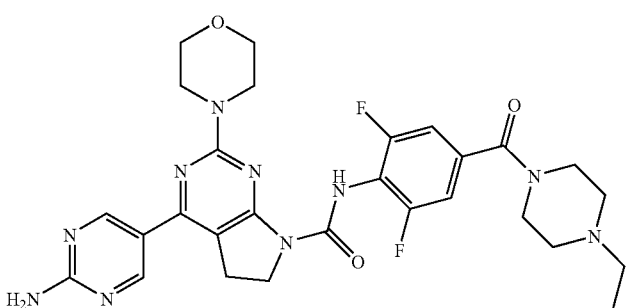 |
| Example 1-D-25 | (D-25) | 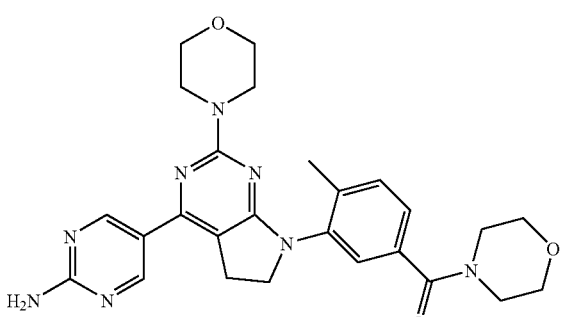 |
| Example 1-D-26 | (D-26) | 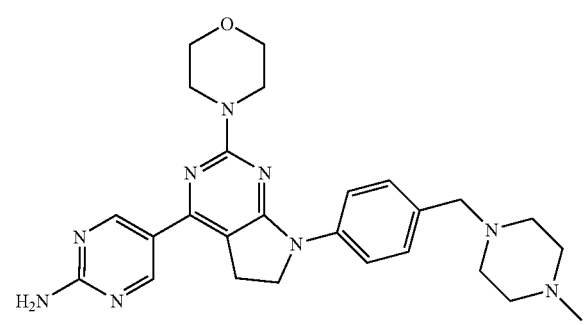 |

-continued

| Example No. | Compound No. | Structural formula |
|---|---|---|
| Example 1-D-27 | (D-27) | |
| Example 1-D-28 | (D-28) | |
| Example 1-D-29 | (D-29) | |
| Example 1-D-30 | (D-30) | |

| Example No. | Compound No. | Structural formula |
|---|---|---|
| Example 1-D-31 | (D-31) | |
| Example 1-D-32 | (D-32) | |
| Example 1-D-33 | (D-33) | |
| Example 1-D-34 | (D-34) | |

-continued
| Example No. | Compound No. | Structural formula |
|---|---|---|
| Example 1-D-35 | (D-35) | 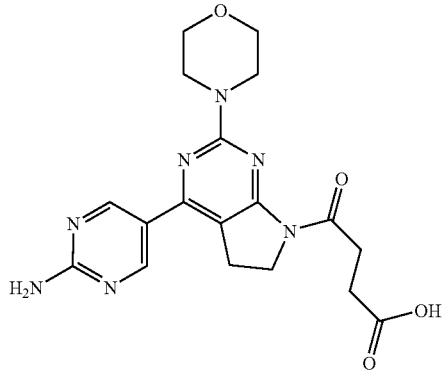 |
| Example 1-D-36 | (D-36) | 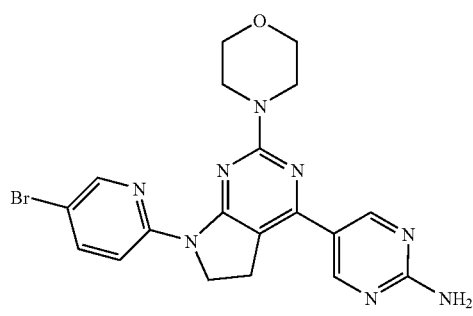 |
| Example 1-D-37 | (D-37) | 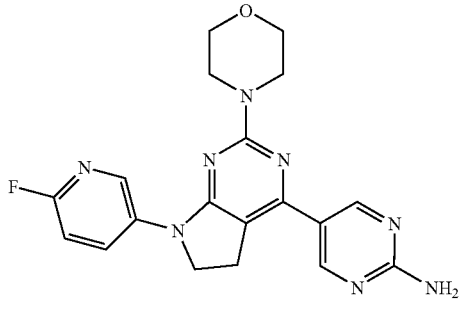 |
| Example 1-D-38 | (D-38) | 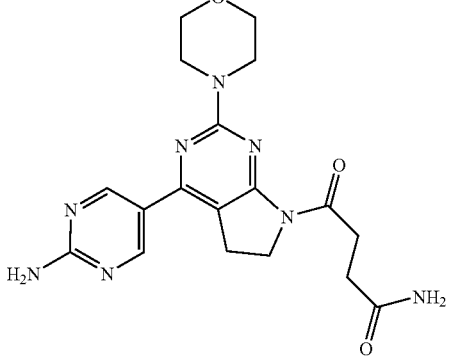 |

-continued

| Example No. | Compound No. | Structural formula |
|---|---|---|
| Example 1-D-39 | (D-39) | |
| Example 1-D-40 | (D-40) | |
| Example 1-D-41 | (D-41) | |
| Example 1-D-42 | (D-42) | |
| Example 1-D-43 | (D-43) | |

-continued

| Example No. | Compound No. | Structural formula |
|---|---|---|
| Example 1-D-44 | (D-44) | |
| Example 1-D-45 | (D-45) | |
| Example 1-D-46 | (D-46) | |
| Example 1-D-47 | (D-47) | |
| Example 1-D-48 | (D-48) | |

-continued

| Example No. | Compound No. | Structural formula |
|---|---|---|
| Example 1-D-49 | (D-49) | |
| Example 1-D-50 | (D-50) | |
| Example 1-D-51 | (D-51) | |
| Example 1-D-52 | (D-52) | |
| Example 1-D-53 | (D-53) | |

| Example No. | Compound No. | Structural formula |
|---|---|---|
| Example 1-D-54 | (D-54) | 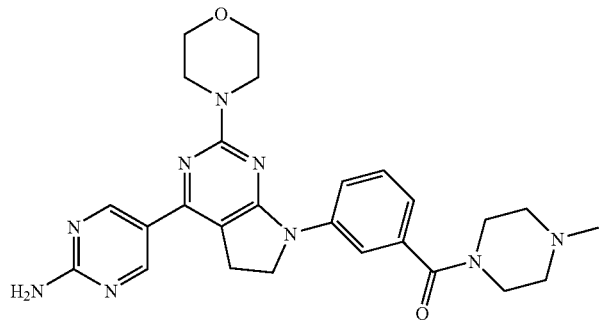 |
| Example 1-D-55 | (D-55) | 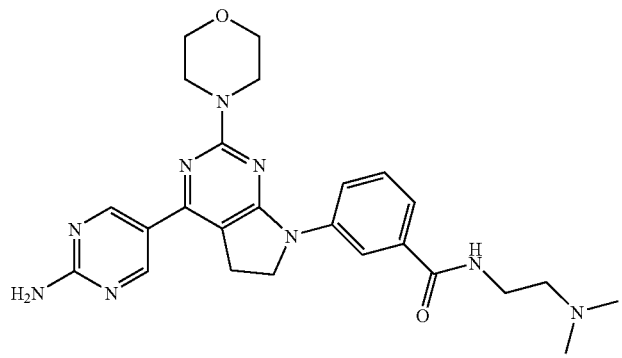 |
| Example 1-D-56 | (D-56) | 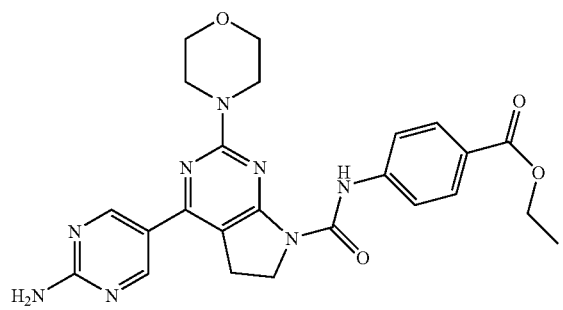 |
| Example 1-D-57 | (D-57) | 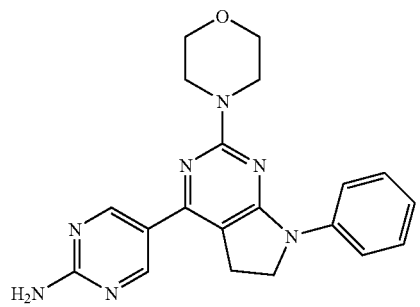 |

-continued
| Example No. | Compound No. | Structural formula |
|---|---|---|
| Example 1-D-58 | (D-58) | 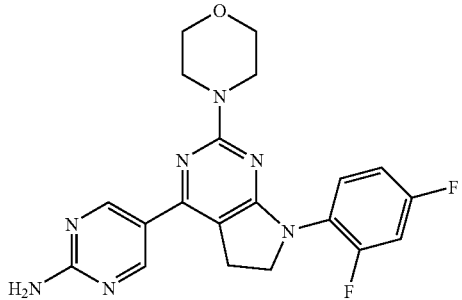 |
| Example 1-D-59 | (D-59) | 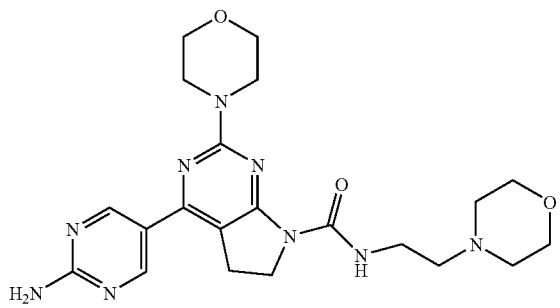 |
| Example 1-D-60 | (D-60) | 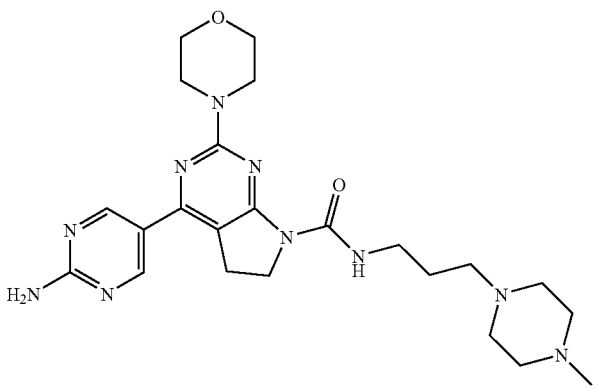 |
| Example 1-D-61 | (D-61) | 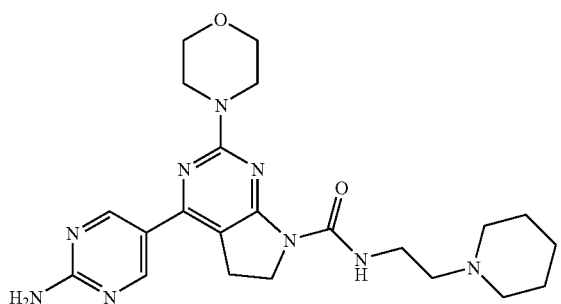 |

| Example No. | Compound No. | Structural formula |
|---|---|---|
| Example 1-D-62 | (D-62) | |
| Example 1-D-63 | (D-63) | |
| Example 1-D-64 | (D-64) | |
| Example 1-D-65 | (D-65) | |
| Example 1-D-66 | (D-66) | |

| Example No. | Compound No. | Structural formula |
|---|---|---|
| Example 1-D-67 | (D-67) | 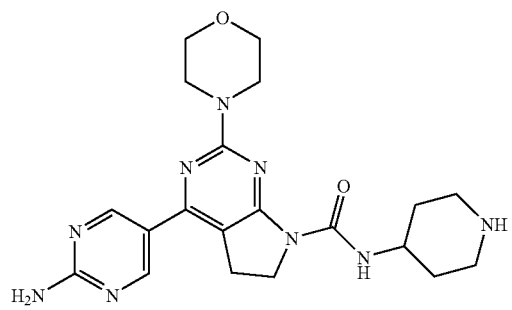 |
| Example 1-D-68 | (D-68) | 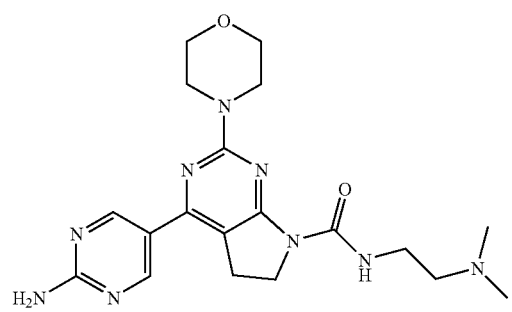 |
| Example 1-D-69 | (D-69) | 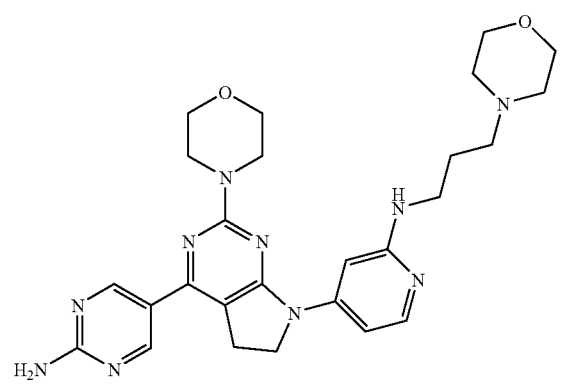 |
| Example 1-D-70 | (D-70) | 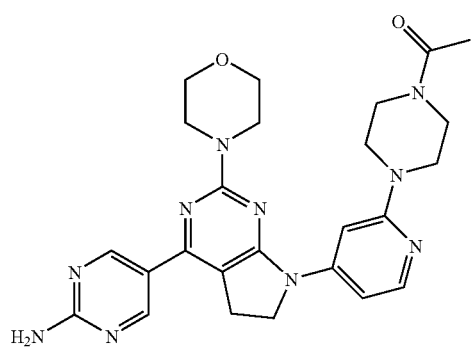 |

-continued

| Example No. | Compound No. | Structural formula |
|---|---|---|
| Example 1-D-71 | (D-71) | |
| Example 1-D-72 | (D-72) | |
| Example 1-D-73 | (D-73) | |
| Example 1-D-74 | (D-74) | |
| Example 1-D-75 | (D-75) | |

| Example No. | Compound No. | Structural formula |
|---|---|---|
| Example 1-D-76 | (D-76) | 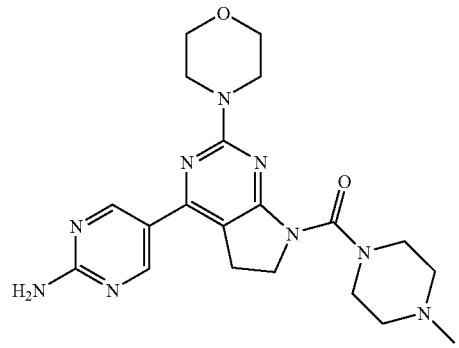 |
| Example 1-D-77 | (D-77) | 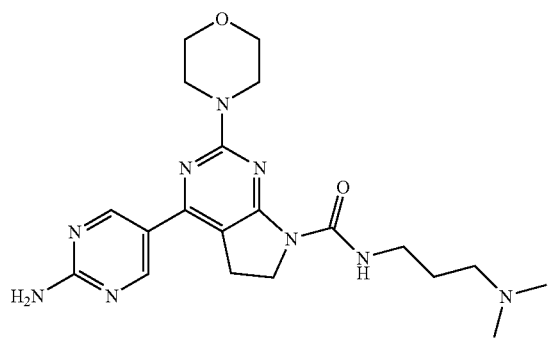 |
| Example 1-D-78 | (D-78) | 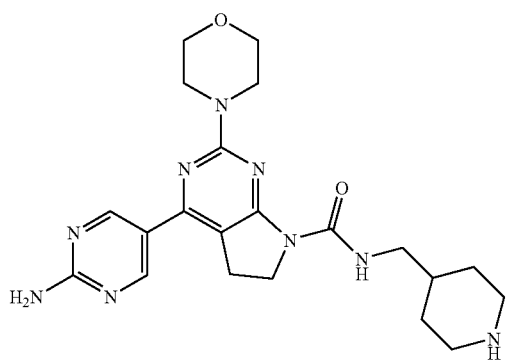 |
| Example 1-D-79 | (D-79) | 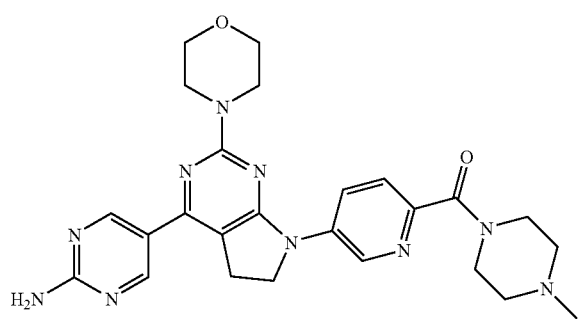 |

-continued

| Example No. | Compound No. | Structural formula |
|---|---|---|
| Example 1-D-80 | (D-80) | |
| Example 1-D-81 | (D-81) | |
| Example 1-D-82 | (D-82) | |
| Example 1-D-83 | (D-83) | |

-continued
| Example No. | Compound No. | Structural formula |
|---|---|---|
| Example 1-D-84 | (D-84) | 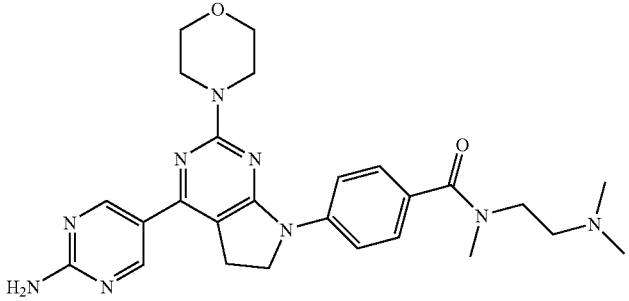 |
| Example 1-D-85 | (D-85) | 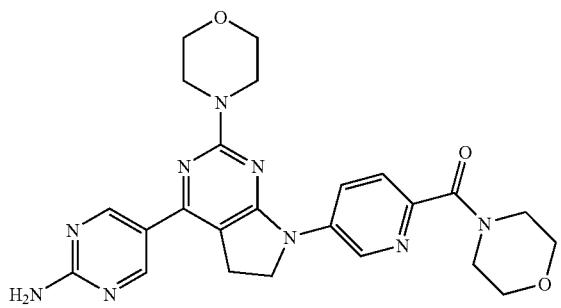 |
| Example 1-D-86 | (D-86) | 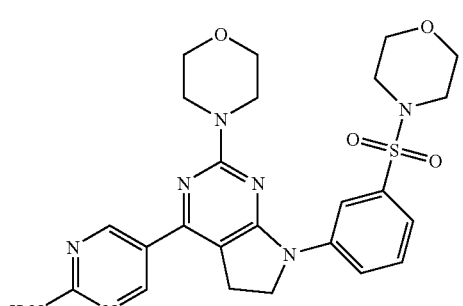 |
| Example 1-D-87 | (D-87) | 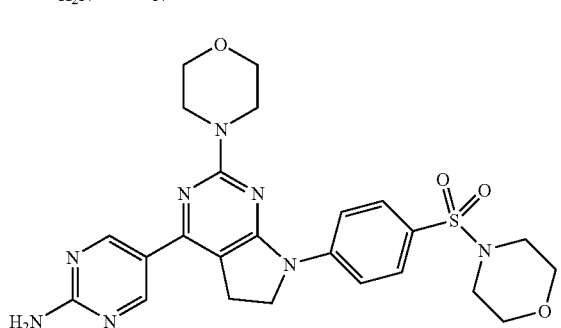 |
| Example 1-D-88 | (D-88) | 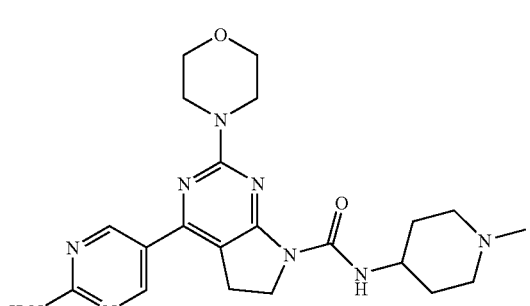 |

-continued

| Example No. | Compound No. | Structural formula |
|---|---|---|
| Example 1-D-89 | (D-89) | |
| Example 1-D-90 | (D-90) | |
| Example 1-D-91 | (D-91) | |
| Example 1-D-92 | (D-92) | |

| Example No. | Compound No. | Structural formula |
|---|---|---|
| Example 1-D-93 | (D-93) | |
| Example 1-D-94 | (D-94) | |
| Example 1-D-95 | (D-95) | |
| Example 1-D-96 | (D-96) | |

| Example No. | Compound No. | Structural formula |
|---|---|---|
| Example 1-D-97 | (D-97) | |
| Example 1-D-98 | (D-98) | |
| Example 1-D-99 | (D-99) | |
| Example 1-D-100 | (D-100) | |

-continued

| Example No. | Compound No. | Structural formula |
|---|---|---|
| Example 1-D-101 | (D-101) | |
| Example 1-D-102 | (D-102) | |
| Example 1-D-103 | (D-103) | |
| Example 1-D-104 | (D-104) | |
| Example 1-D-105 | (D-105) | |

-continued
| Example No. | Compound No. | Structural formula |
|---|---|---|
| Example 1-D-106 | (D-106) | 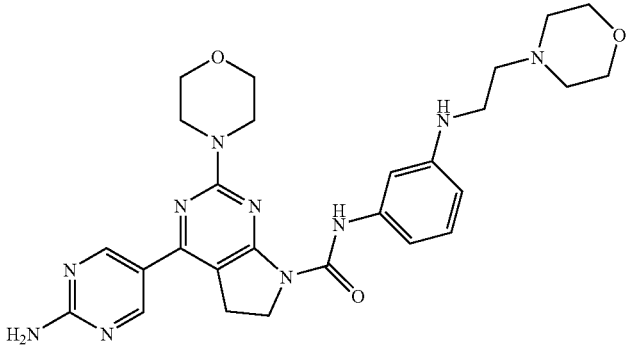 |
| Example 1-D-107 | (D-107) | 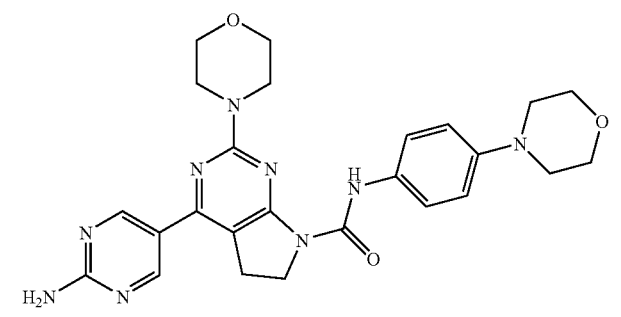 |
| Example 1-D-108 | (D-108) | 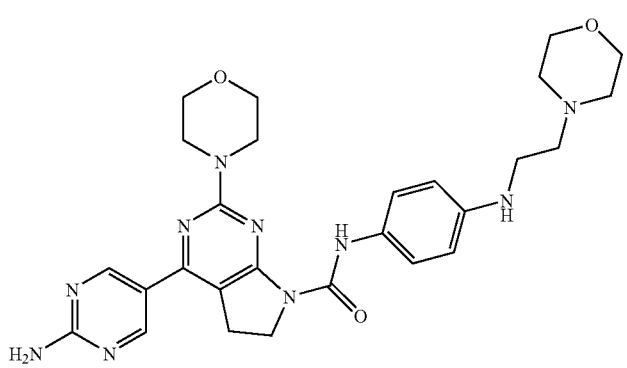 |
| Example 1-D-109 | (D-109) | 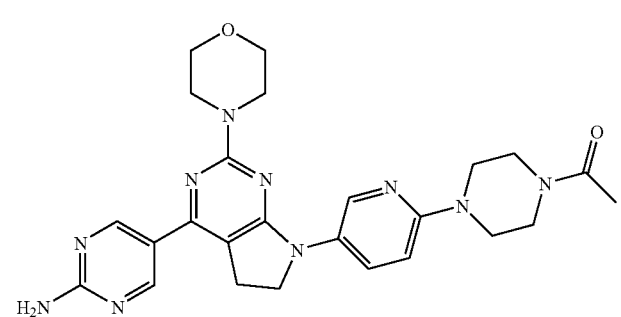 |

-continued

| Example No. | Compound No. | Structural formula |
|---|---|---|
| Example 1-D-110 | (D-110) | |
| Example 1-D-111 | (D-111) | |
| Example 1-D-112 | (D-112) | |
| Example 1-D-113 | (D-113) | |

-continued

| Example No. | Compound No. | Structural formula |
|---|---|---|
| Example 1-D-114 | (D-114) | |
| Example 1-D-115 | (D-115) | |
| Example 1-D-116 | (D-116) | |
| Example 1-D-117 | (D-117) | |

-continued

| Example No. | Compound No. | Structural formula |
|---|---|---|
| Example 1-D-118 | (D-118) | |
| Example 1-D-119 | (D-119) | |
| Example 1-D-120 | (D-120) | |
| Example 1-D-121 | (D-121) | |

-continued

| Example No. | Compound No. | Structural formula |
|---|---|---|
| Example 1-D-122 | (D-122) | |
| Example 1-D-123 | (D-123) | |
| Example 1-D-124 | (D-124) | |
| Example 1-D-125 | (D-125) | |
| Example 1-D-126 | (D-126) | |

| Example No. | Compound No. | Structural formula |
|---|---|---|
| Example 1-D-127 | (D-127) | 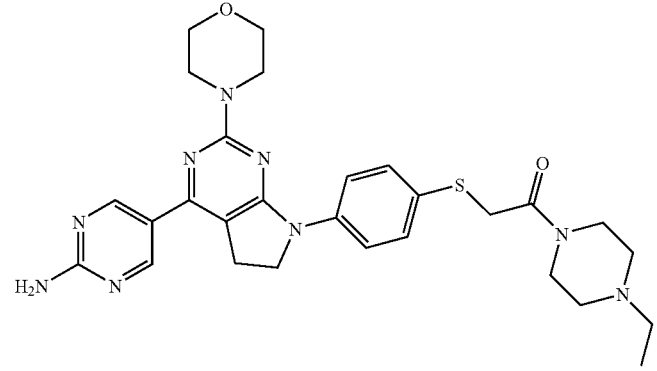 |
| Example 1-D-128 | (D-128) | 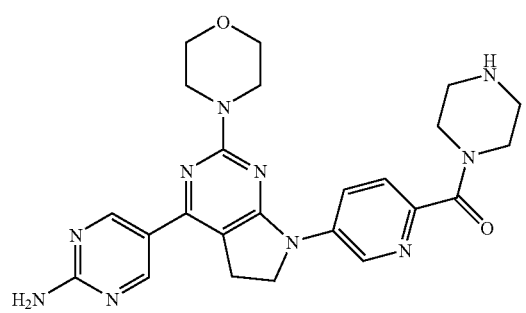 |
| Example 1-D-129 | (D-129) | 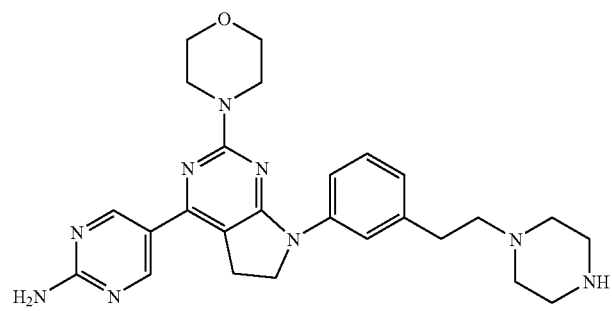 |
| Example 1-D-130 | (D-130) | 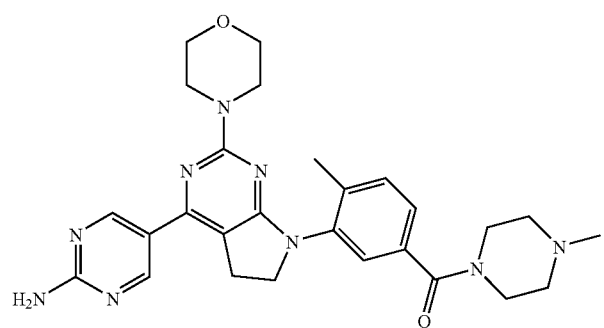 |

-continued

| Example No. | Compound No. | Structural formula |
|---|---|---|
| Example 1-D-131 | (D-131) | |
| Example 1-D-132 | (D-132) | |
| Example 1-D-133 | (D-133) | |
| Example 1-D-134 | (D-134) | |

-continued

| Example No. | Compound No. | Structural formula |
|---|---|---|
| Example 1-D-135 | (D-135) | |
| Example 1-D-136 | (D-136) | |
| Example 1-D-137 | (D-137) | |
| Example 1-D-138 | (D-138) | |

-continued

| Example No. | Compound No. | Structural formula |
|---|---|---|
| Example 1-D-139 | (D-139) | |
| Example 1-D-140 | (D-140) | |
| Example 1-D-141 | (D-141) | |
| Example 1-D-142 | (D-142) | |
| Example 1-D-143 | (D-143) | |

-continued

| Example No. | Compound No. | Structural formula |
|---|---|---|
| Example 1-D-144 | (D-144) | |
| Example 1-D-145 | (D-145) | |
| Example 1-D-146 | (D-146) | |
| Example 1-D-147 | (D-147) | |

-continued
| Example No. | Compound No. | Structural formula |
|---|---|---|
| Example 1-D-148 | (D-148) | 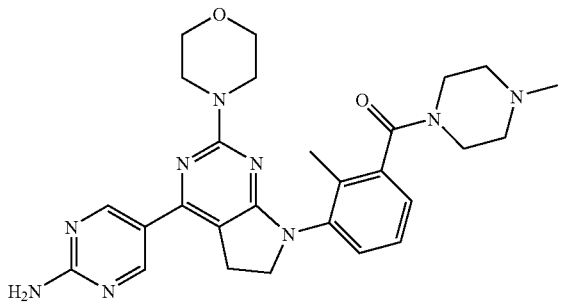 |
| Example 1-D-149 | (D-149) | 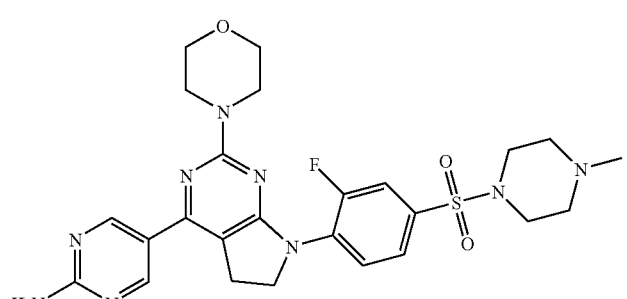 |
| Example 1-D-150 | (D-150) | 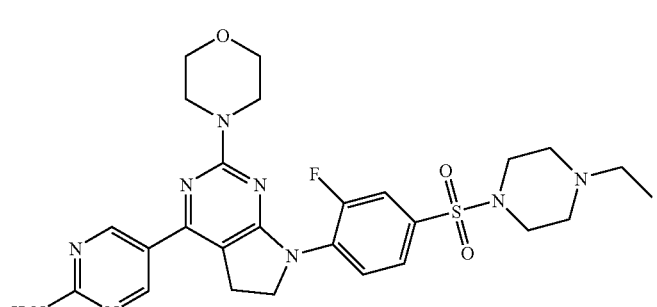 |
| Example 1-D-151 | (D-151) | 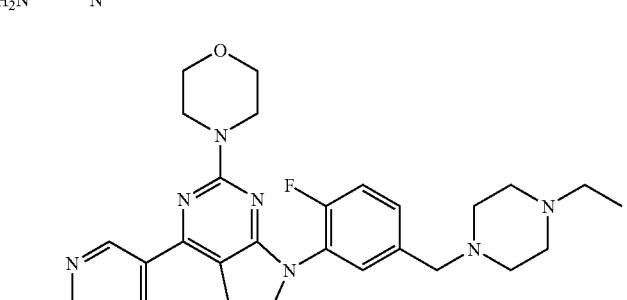 |
| Example 1-D-152 | (D-152) | 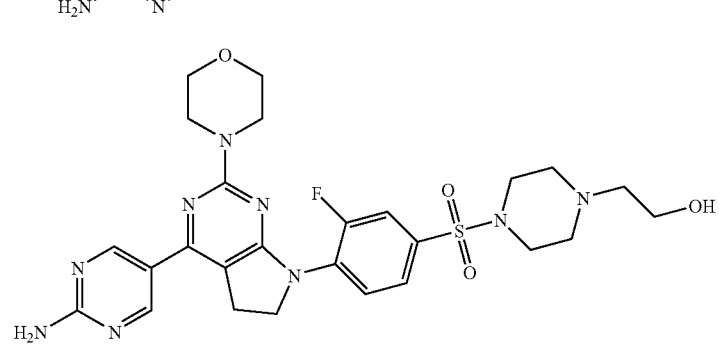 |

| Example No. | Compound No. | Structural formula |
|---|---|---|
| Example 1-D-153 | (D-153) | |
| Example 1-D-154 | (D-154) | |
| Example 1-D-155 | (D-155) | |
| Example 1-D-156 | (D-156) | |

-continued
| Example No. | Compound No. | Structural formula |
|---|---|---|
| Example 1-D-157 | (D-157) | 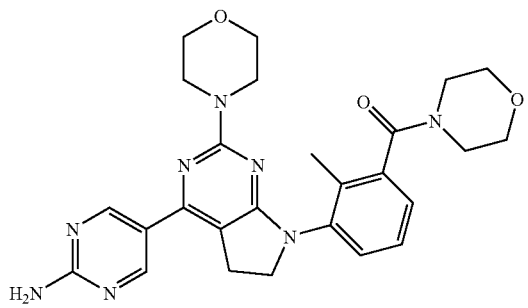 |
| Example 1-D-158 | (D-158) | 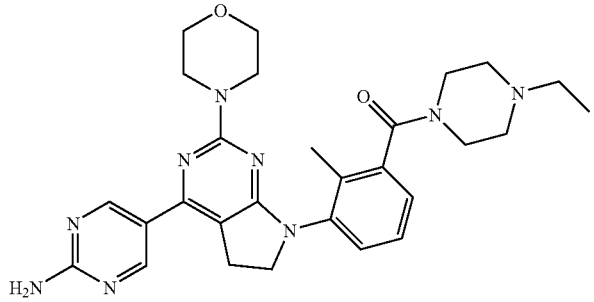 |
| Example 1-D-159 | (D-159) | 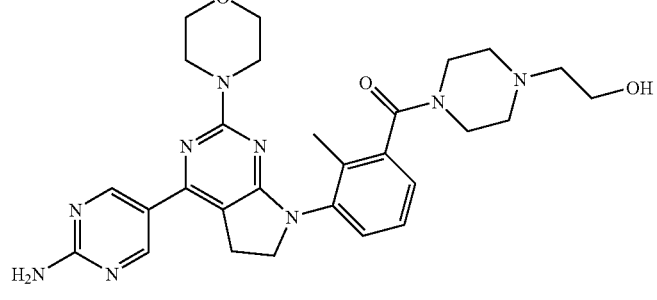 |
| Example 1-D-160 | (D-160) | 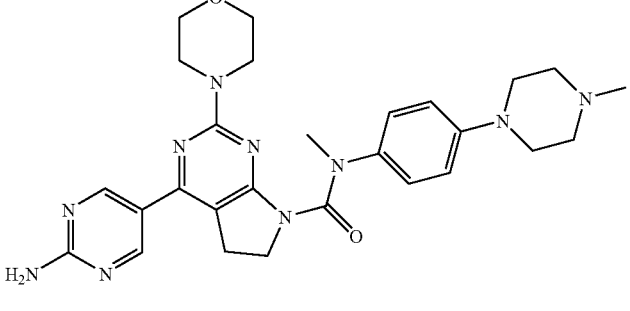 |
| Example 1-D-161 | (D-161) | 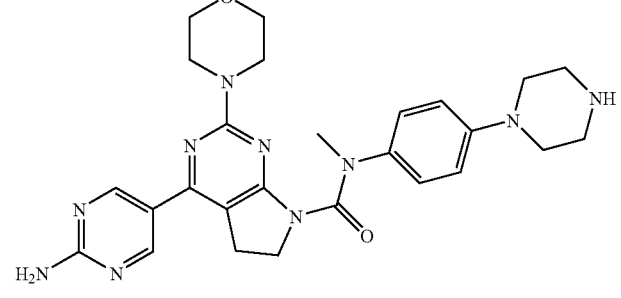 |

-continued

| Example No. | Compound No. | Structural formula |
|---|---|---|
| Example 1-D-162 | (D-162) | |
| Example 1-D-163 | (D-163) | |
| Example 1-D-164 | (D-164) | |
| Example 1-D-165 | (D-165) | |
| Example 1-D-166 | (D-166) | |

-continued
| Example No. | Compound No. | Structural formula |
|---|---|---|
| Example 1-D-167 | (D-167) | 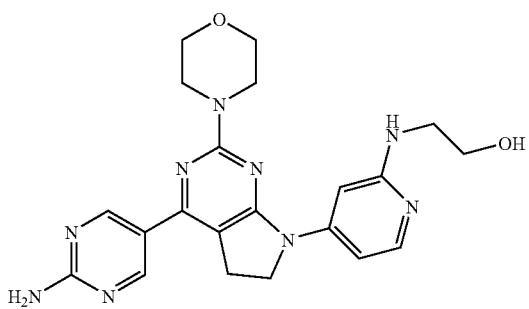 |
| Example 1-D-168 | (D-168) | 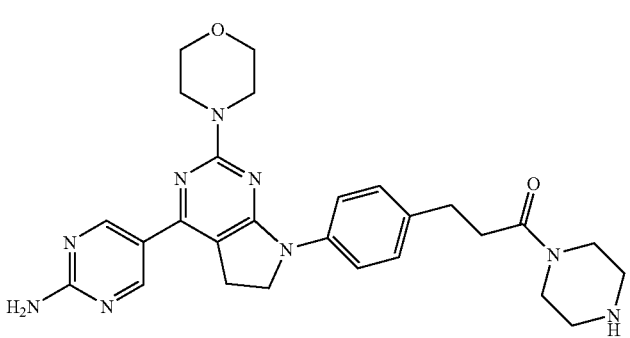 |
| Example 1-D-169 | (D-169) | 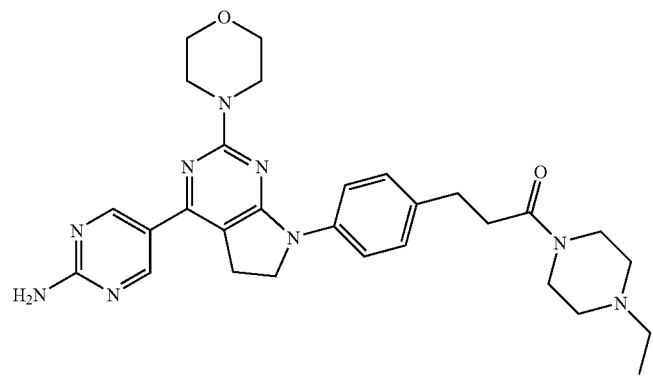 |
| Example 1-D-170 | (D-170) | 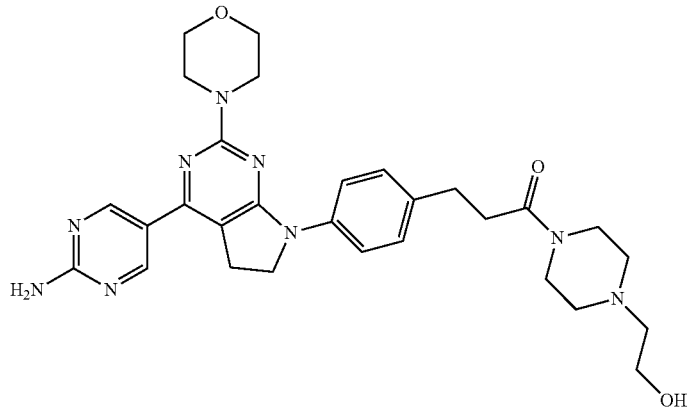 |

-continued

| Example No. | Compound No. | Structural formula |
|---|---|---|
| Example 1-D-171 | (D-171) | |
| Example 1-D-172 | (D-172) | |
| Example 1-D-173 | (D-173) | |
| Example 1-D-174 | (D-174) | |
| Example 1-D-175 | (D-175) | |

| Example No. | Compound No. | Structural formula |
|---|---|---|
| Example 1-D-176 | (D-176) | 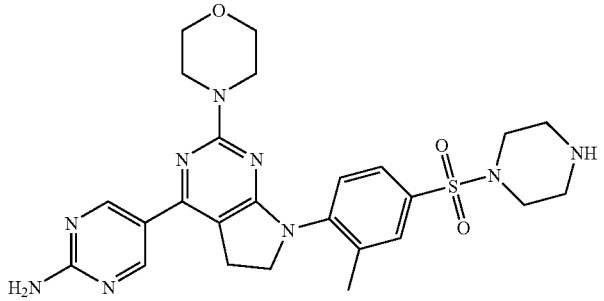 |
| Example 1-D-177 | (D-177) | 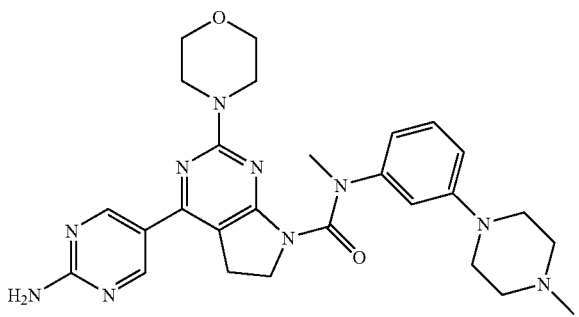 |
| Example 1-D-178 | (D-178) | 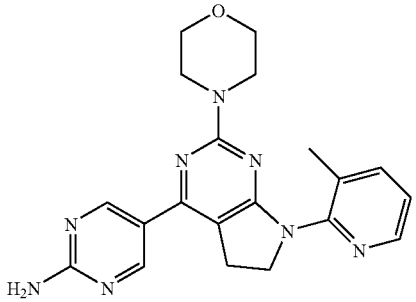 |
| Example 1-D-179 | (D-179) | 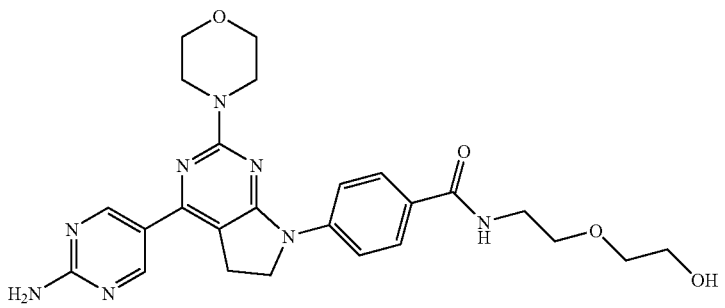 |
| Example 1-D-180 | (D-180) | 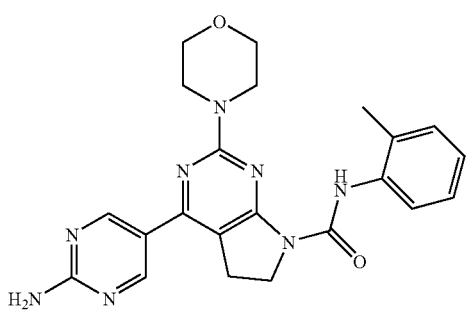 |

| Example No. | Compound No. | Structural formula |
|---|---|---|
| Example 1-D-181 | (D-181) | 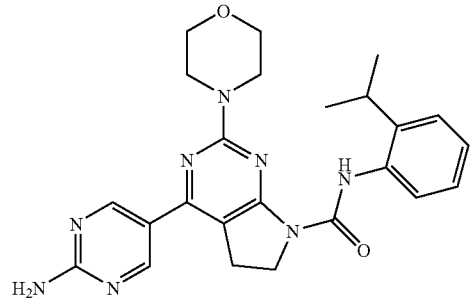 |
| Example 1-D-182 | (D-182) | 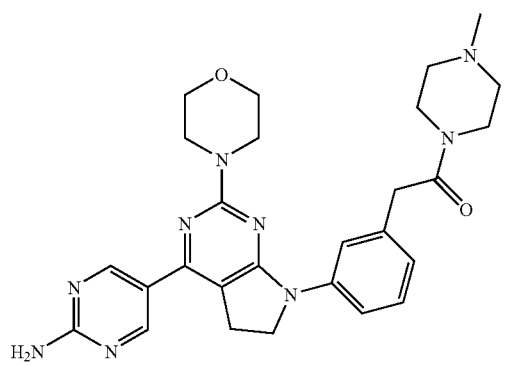 |
| Example 1-D-183 | (D-183) | 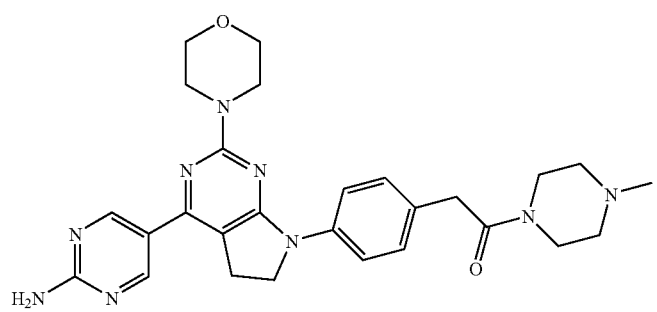 |
| Example 1-D-184 | (D-184) | 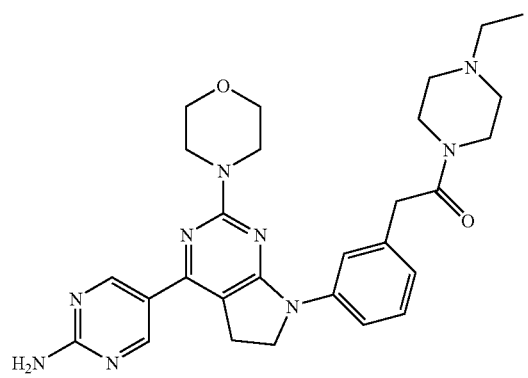 |

| Example No. | Compound No. | Structural formula |
|---|---|---|
| Example 1-D-185 | (D-185) | 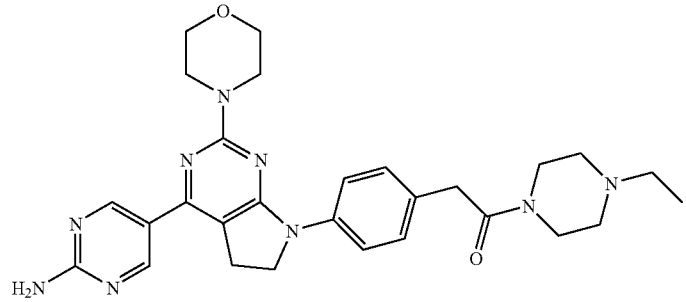 |
| Example 1-D-186 | (D-186) | 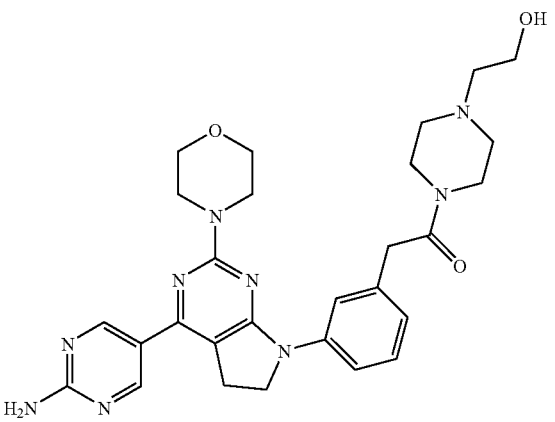 |
| Example 1-D-187 | (D-187) | 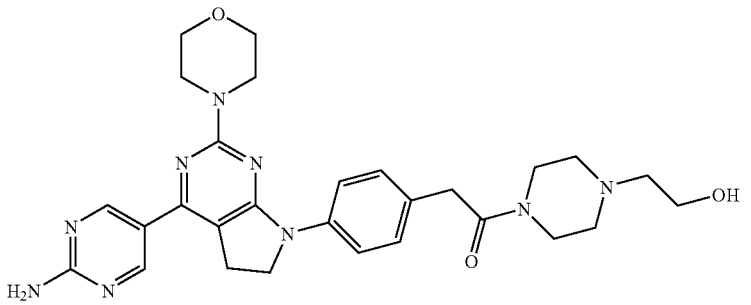 |
| Example 1-D-188 | (D-188) | 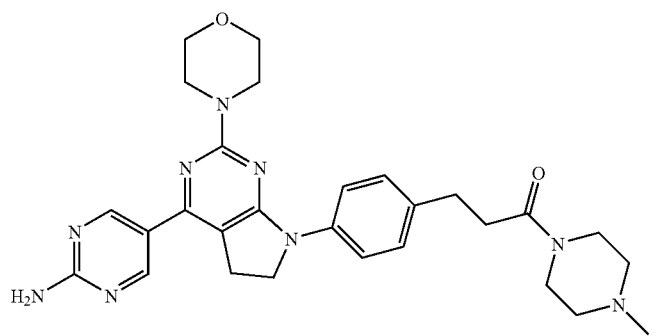 |

-continued
| Example No. | Compound No. | Structural formula |
|---|---|---|
| Example 1-D-189 | (D-189) | 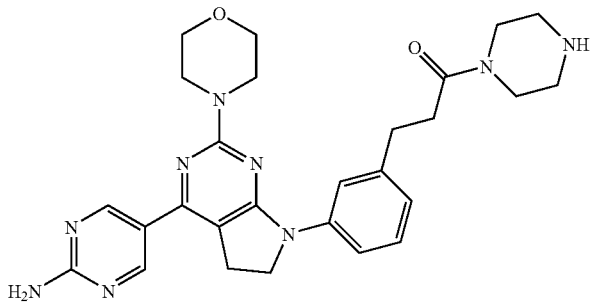 |
| Example 1-D-190 | (D-190) | 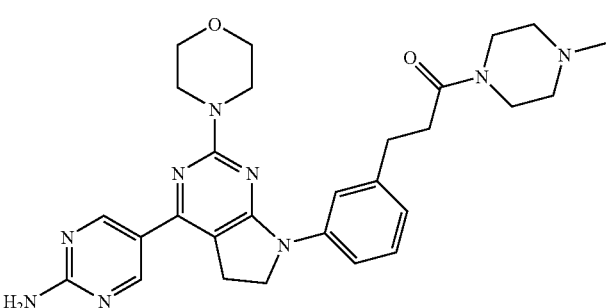 |
| Example 1-D-191 | (D-191) | 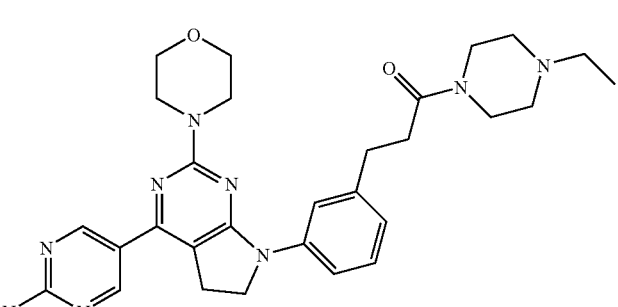 |
| Example 1-D-192 | (D-192) | 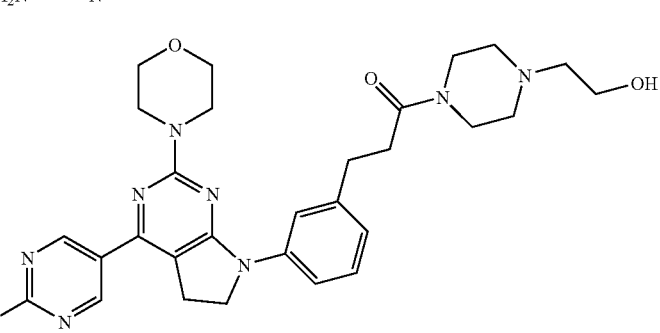 |
| Example 1-D-193 | (D-193) | 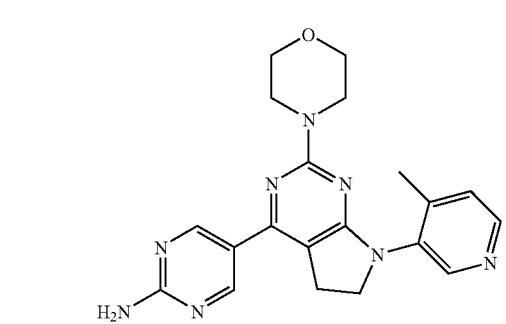 |

| Example No. | Compound No. | Structural formula |
|---|---|---|
| Example 1-D-194 | (D-194) | |
| Example 1-D-195 | (D-195) | |
| Example 1-D-196 | (D-196) | |
| Example 1-D-197 | (D-197) | |
| Example 1-D-198 | (D-198) | |

-continued
| Example No. | Compound No. | Structural formula |
|---|---|---|
| Example 1-D-199 | (D-199) | 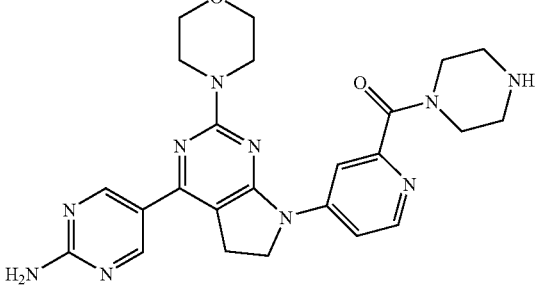 |
| Example 1-D-200 | (D-200) | 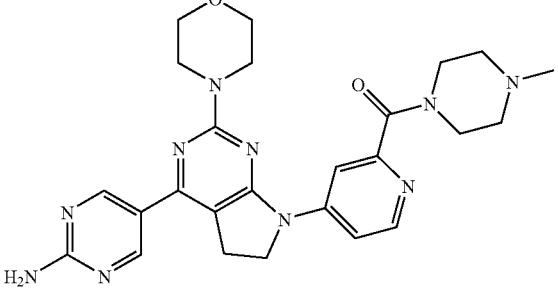 |
| Example 1-D-201 | (D-201) | 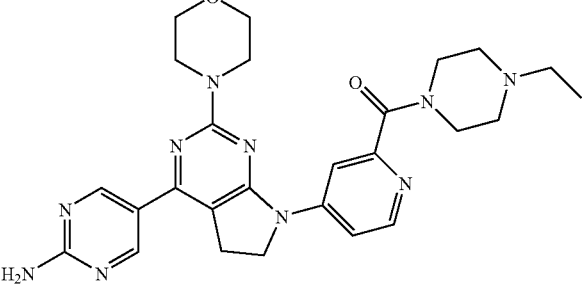 |
| Example 1-D-202 | (D-202) | 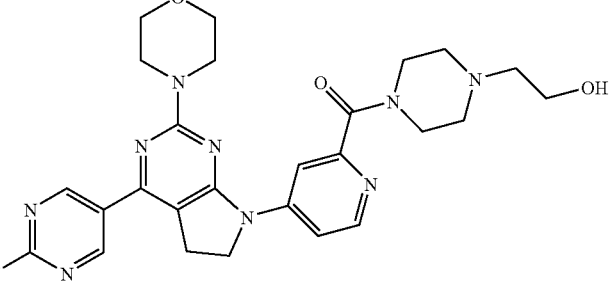 |
| Example 1-D-203 | (D-203) | 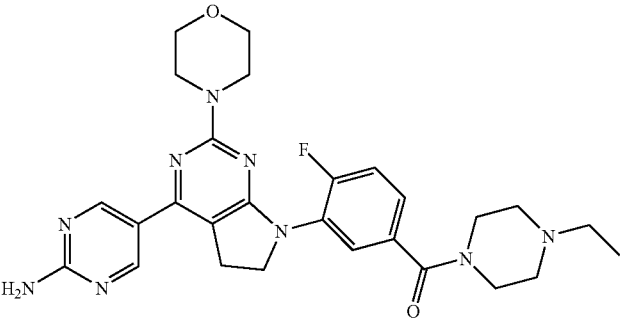 |

-continued
| Example No. | Compound No. | Structural formula |
|---|---|---|
| Example 1-D-204 | (D-204) | 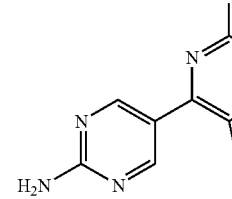 |
| Example 1-D-205 | (D-205) | 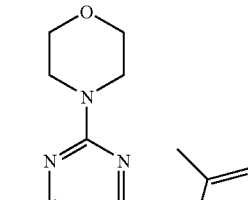 |
| Example 1-D-206 | (D-206) | 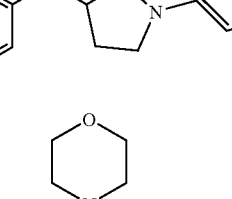 |
| Example 1-D-207 | (D-207) | 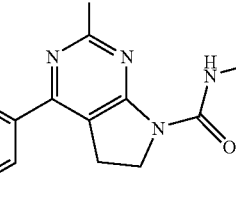 |
| Example 1-D-208 | (D-208) | 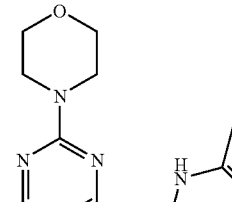 |

| Example No. | Compound No. | Structural formula |
|---|---|---|
| Example 1-D-209 | (D-209) | |
| Example 1-D-210 | (D-210) | |
| Example 1-D-211 | (D-211) | |
| Example 1-D-212 | (D-212) | |
| Example 1-D-213 | (D-213) | |

-continued

| Example No. | Compound No. | Structural formula |
|---|---|---|
| Example 1-D-214 | (D-214) | |
| Example 1-D-215 | (D-215) | |
| Example 1-D-216 | (D-216) | |
| Example 1-D-217 | (D-217) | |
| Example 1-D-218 | (D-218) | |

-continued
| Example No. | Compound No. | Structural formula |
|---|---|---|
| Example 1-D-219 | (D-219) | 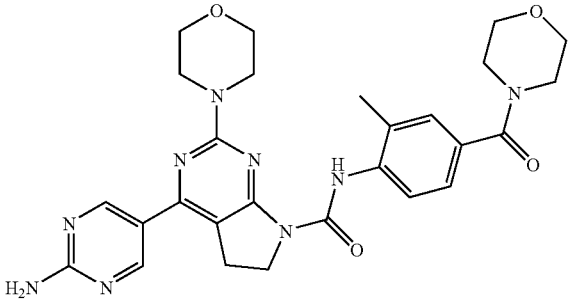 |
| Example 1-D-220 | (D-220) | 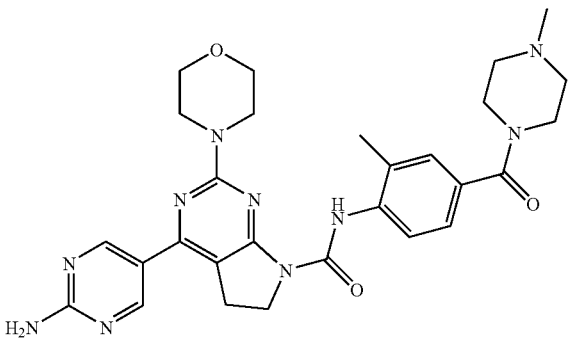 |
| Example 1-D-221 | (D-221) | 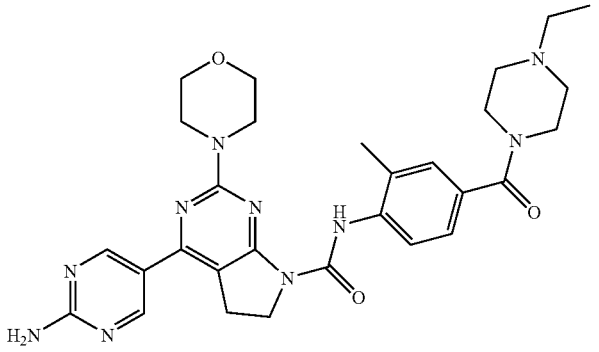 |
| Example 1-D-222 | (D-222) | 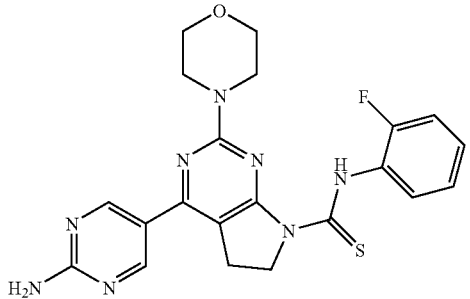 |

| Example No. | Compound No. | Structural formula |
|---|---|---|
| Example 1-D-223 | (D-223) | |
| Example 1-D-224 | (D-224) | |
| Example 1-D-225 | (D-225) | |
| Example 1-D-226 | (D-226) | |
| Example 1-D-227 | (D-227) | |

-continued

| Example No. | Compound No. | Structural formula |
|---|---|---|
| Example 1-D-228 | (D-228) | |
| Example 1-D-229 | (D-229) | |
| Example 1-D-230 | (D-230) | |
| Example 1-D-231 | (D-231) | |
| Example 1-D-232 | (D-232) | |

-continued

| Example No. | Compound No. | Structural formula |
|---|---|---|
| Example 1-D-233 | (D-233) | |
| Example 1-D-234 | (D-234) | |
| Example 1-D-235 | (D-235) | |
| Example 1-D-236 | (D-236) | |
| Example 1-D-237 | (D-237) | |

-continued
| Example No. | Compound No. | Structural formula |
|---|---|---|
| Example 1-D-238 | (D-238) | 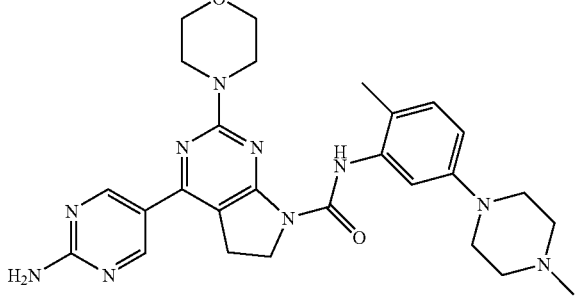 |
| Example 1-D-239 | (D-239) | 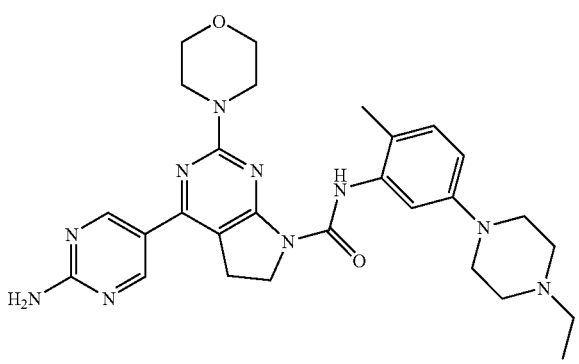 |
| Example 1-D-240 | (D-240) | 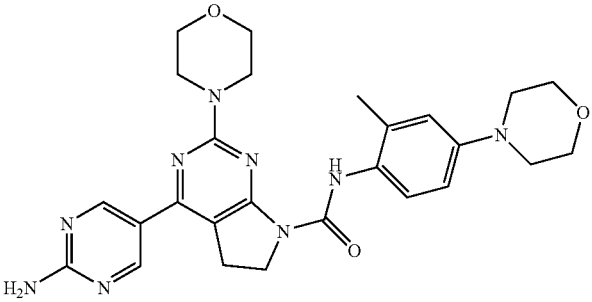 |
| Example 1-D-241 | (D-241) | 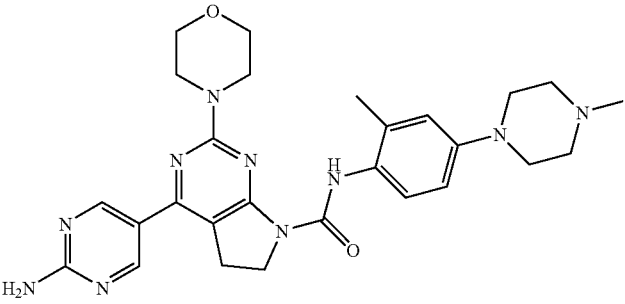 |

-continued

| Example No. | Compound No. | Structural formula |
|---|---|---|
| Example 1-D-242 | (D-242) | |
| Example 1-D-243 | (D-243) | |
| Example 1-D-244 | (D-244) | |
| Example 1-D-245 | (D-245) | |
| Example 1-D-246 | (D-246) | |

| Example No. | Compound No. | Structural formula |
|---|---|---|
| Example 1-D-247 | (D-247) | 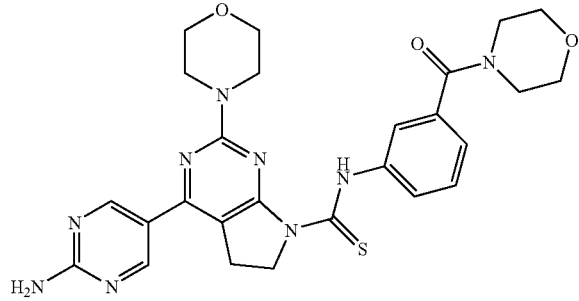 |
| Example 1-D-248 | (D-248) | 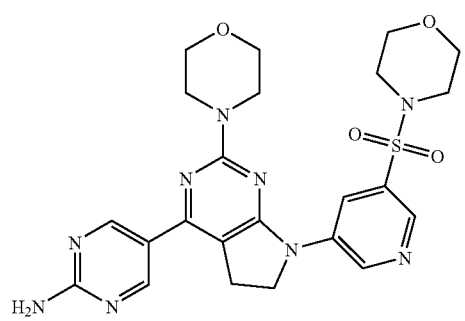 |
| Example 1-D-249 | (D-249) | 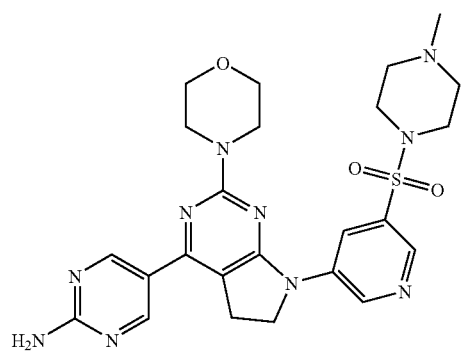 |
| Example 1-D-250 | (D-250) | 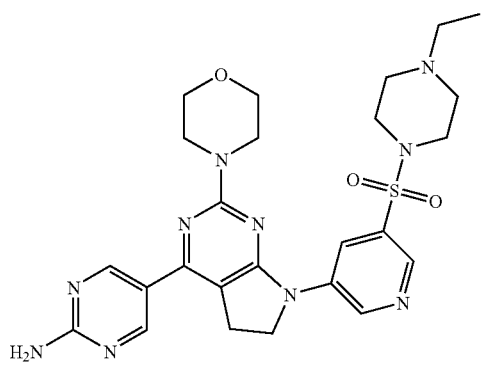 |

-continued

| Example No. | Compound No. | Structural formula |
|---|---|---|
| Example 1-D-251 | (D-251) | |
| Example 1-D-252 | (D-252) | |
| Example 1-D-253 | (D-253) | |
| Example 1-D-254 | (D-254) | |
| Example 1-D-255 | (D-255) | |

-continued

| Example No. | Compound No. | Structural formula |
|---|---|---|
| Example 1-D-256 | (D-256) | |
| Example 1-D-257 | (D-257) | |
| Example 1-D-258 | (D-258) | |
| Example 1-D-259 | (D-259) | |
| Example 1-D-260 | (D-260) | |

-continued
| Example No. | Compound No. | Structural formula |
|---|---|---|
| Example 1-D-261 | (D-261) | 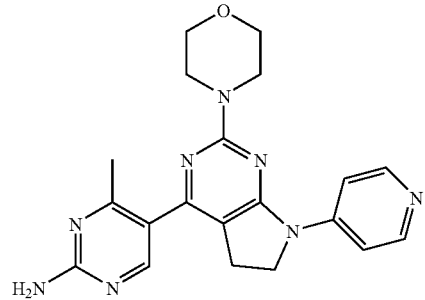 |
| Example 1-D-262 | (D-262) | 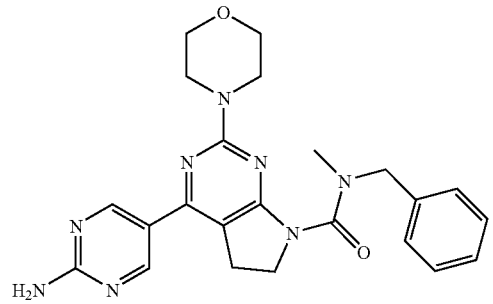 |
| Example 1-D-263 | (D-263) | 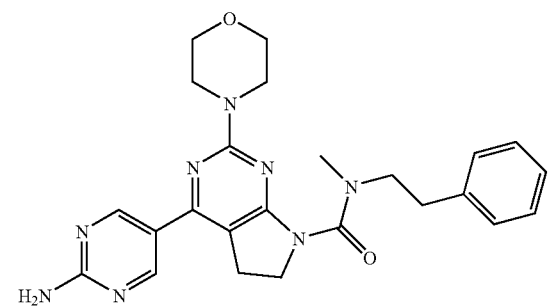 |
| Example 1-D-264 | (D-264) | 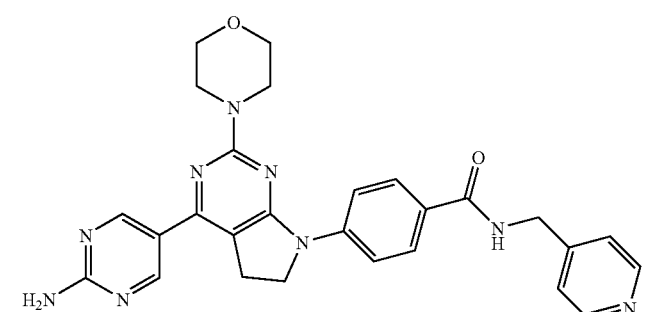 |

| Example No. | Compound No. | Structural formula |
|---|---|---|
| Example 1-D-265 | (D-265) | 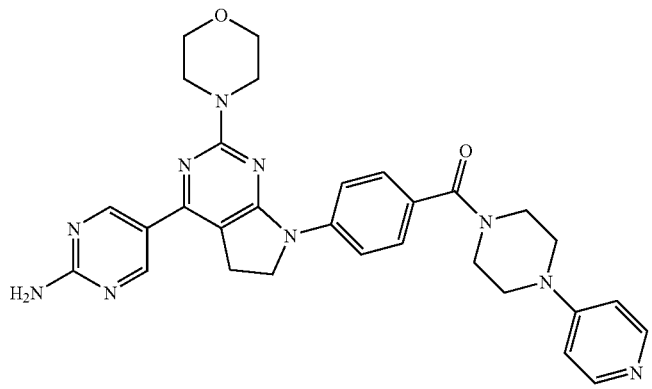 |
| Example 1-D-266 | (D-266) | 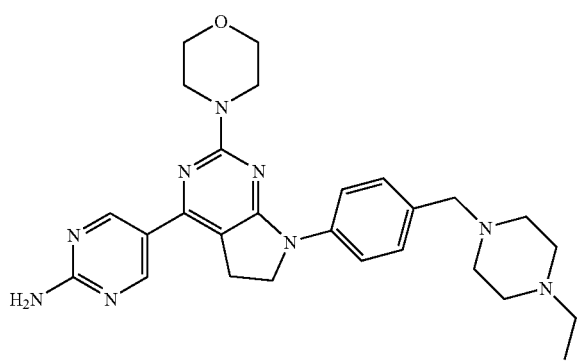 |
| Example 1-D-267 | (D-267) | 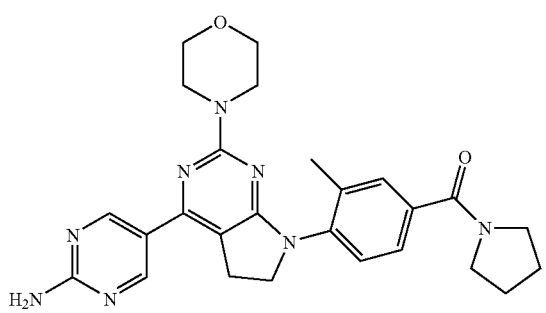 |
| Example 1-D-268 | (D-268) | 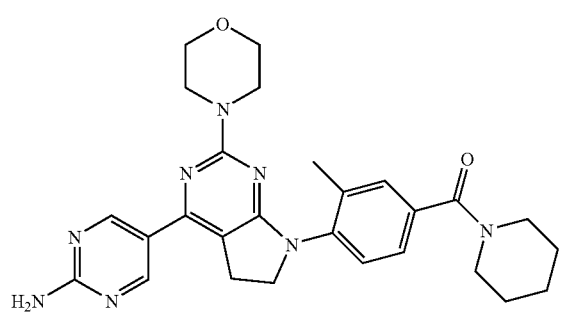 |

| Example No. | Compound No. | Structural formula |
|---|---|---|
| Example 1-D-269 | (D-269) | |
| Example 1-D-270 | (D-270) | |
| Example 1-D-271 | (D-271) | |
| Example 1-D-272 | (D-272) | |

-continued

| Example No. | Compound No. | Structural formula |
|---|---|---|
| Example 1-D-273 | (D-273) | |
| Example 1-D-274 | (D-274) | |
| Example 1-D-275 | (D-275) | |
| Example 1-D-276 | (D-276) | |

-continued

| Example No. | Compound No. | Structural formula |
|---|---|---|
| Example 1-D-277 | (D-277) | |
| Example 1-D-278 | (D-278) | |
| Example 1-D-279 | (D-279) | |
| Example 1-D-280 | (D-280) | |

-continued

| Example No. | Compound No. | Structural formula |
|---|---|---|
| Example 1-D-281 | (D-281) | |
| Example 1-D-282 | (D-282) | |
| Example 1-D-283 | (D-283) | |
| Example 1-D-284 | (D-284) | |

| Example No. | Compound No. | Structural formula |
|---|---|---|
| Example 1-D-285 | (D-285) | |
| Example 1-D-286 | (D-286) | |
| Example 1-D-287 | (D-287) | |
| Example 1-D-288 | (D-288) | |

-continued
| Example No. | Compound No. | Structural formula |
|---|---|---|
| Example 1-D-289 | (D-289) | 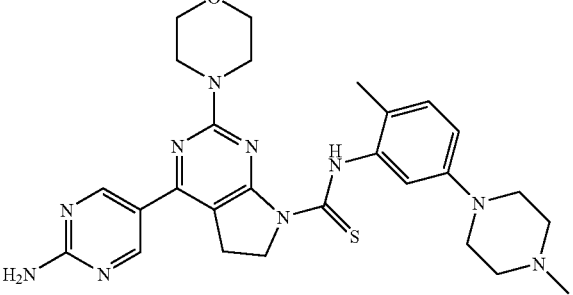 |
| Example 1-D-290 | (D-290) | 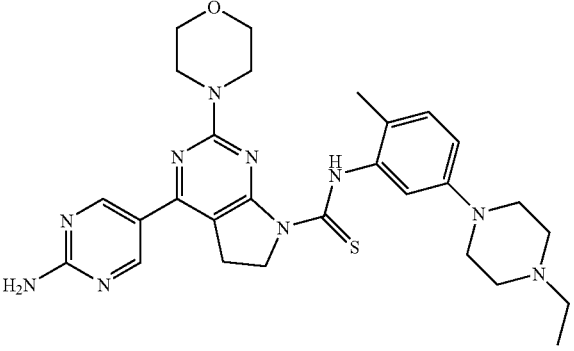 |
| Example 1-D-291 | (D-291) | 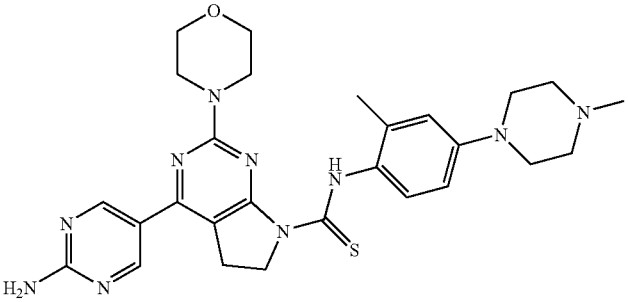 |
| Example 1-D-292 | (D-292) | 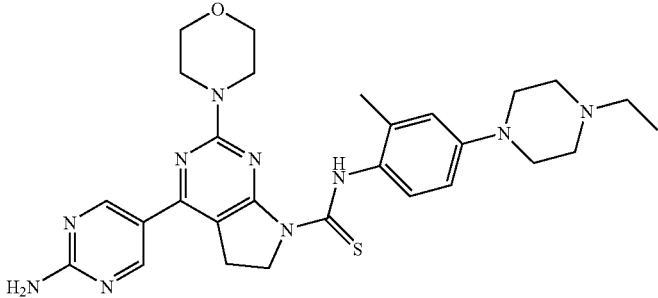 |

-continued
| Example No. | Compound No. | Structural formula |
|---|---|---|
| Example 1-D-293 | (D-293) | 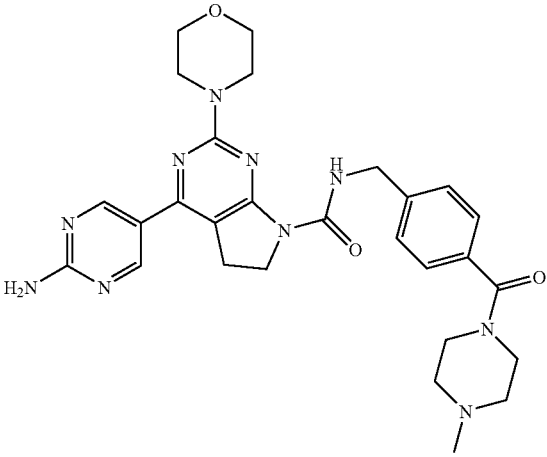 |
| Example 1-D-294 | (D-294) | 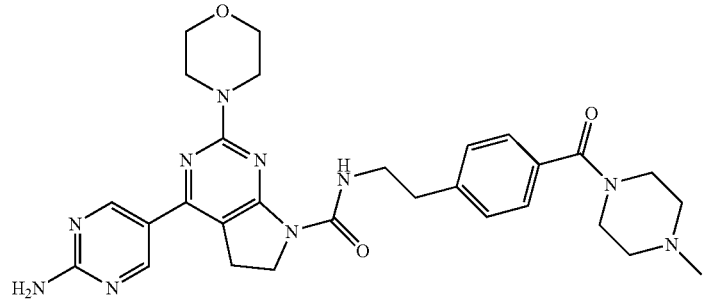 |
| Example 1-D-295 | (D-295) | 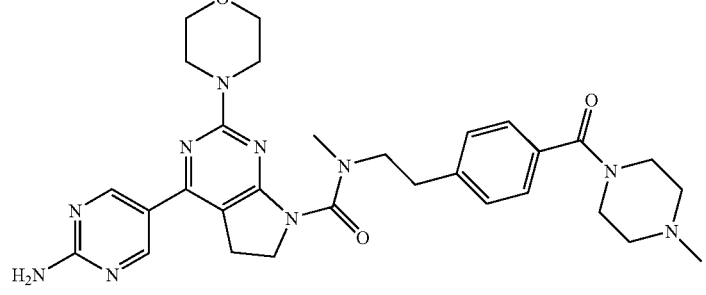 |
| Example 1-D-296 | (D-296) | 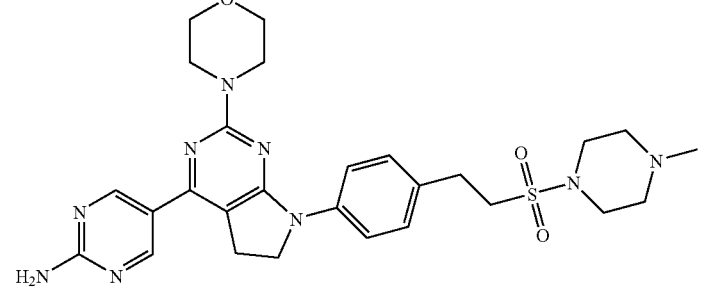 |

-continued
| Example No. | Compound No. | Structural formula |
|---|---|---|
| Example 1-D-297 | (D-297) | 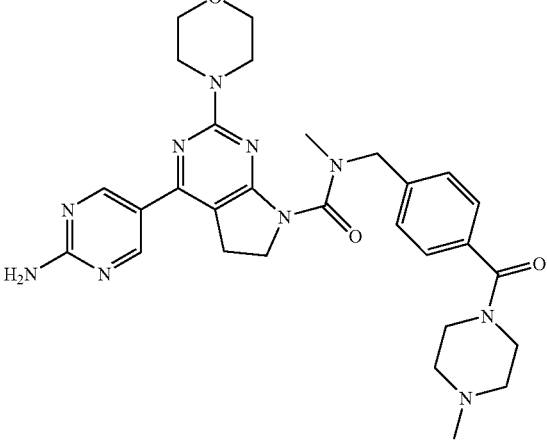 |
| Example 1-D-298 | (D-298) | 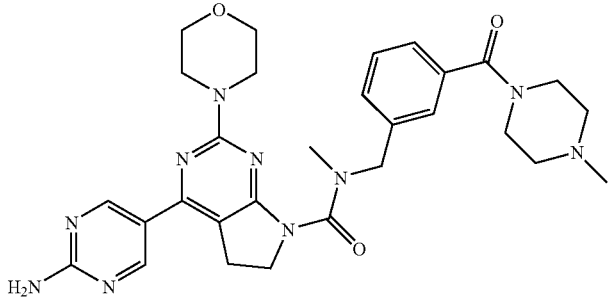 |
| Example 1-D-299 | (D-299) | 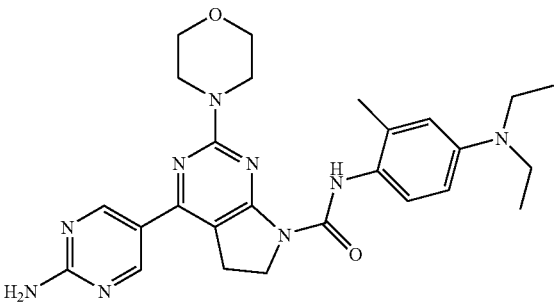 |
| Example 1-D-300 | (D-300) | 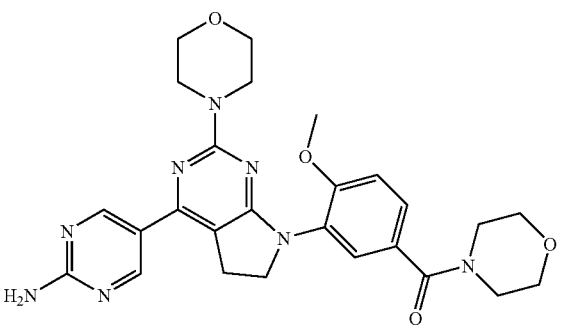 |

-continued
| Example No. | Compound No. | Structural formula |
|---|---|---|
| Example 1-D-301 | (D-301) | 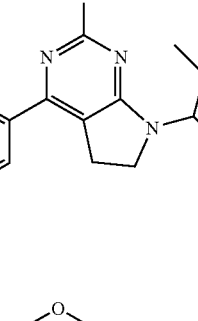 |
| Example 1-D-302 | (D-302) | 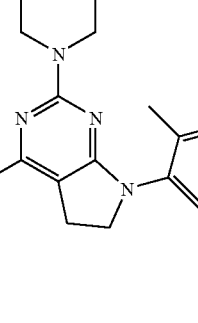 |
| Example 1-D-303 | (D-303) | 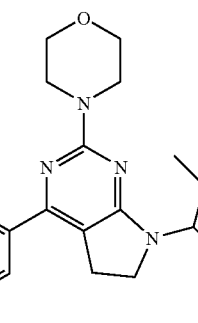 |
| Example 1-D-304 | (D-304) | 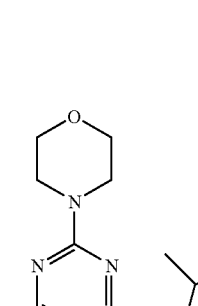 |

-continued

| Example No. | Compound No. | Structural formula |
|---|---|---|
| Example 1-D-305 | (D-305) | |
| Example 1-D-306 | (D-306) | |
| Example 1-D-307 | (D-307) | |
| Example 1-D-308 | (D-308) | |

-continued

| Example No. | Compound No. | Structural formula |
|---|---|---|
| Example 1-D-309 | (D-309) | |
| Example 1-D-310 | (D-310) | |
| Example 1-D-311 | (D-311) | |
| Example 1-D-312 | (D-312) | |

-continued

| Example No. | Compound No. | Structural formula |
|---|---|---|
| Example 1-D-313 | (D-313) | |
| Example 1-D-314 | (D-314) | |
| Example 1-D-315 | (D-315) | |
| Example 1-D-316 | (D-316) | |

-continued
| Example No. | Compound No. | Structural formula |
|---|---|---|
| Example 1-D-317 | (D-317) | 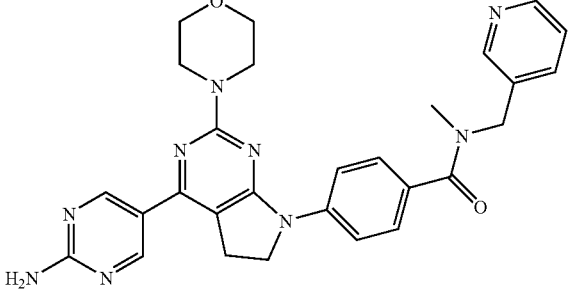 |
| Example 1-D-318 | (D-318) | 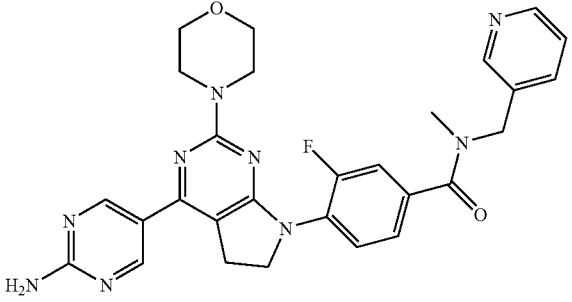 |
| Example 1-D-319 | (D-319) | 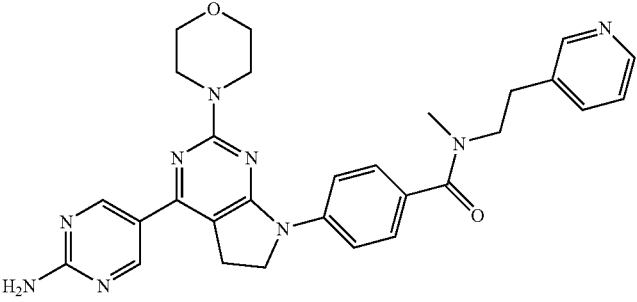 |
| Example 1-D-320 | (D-320) | 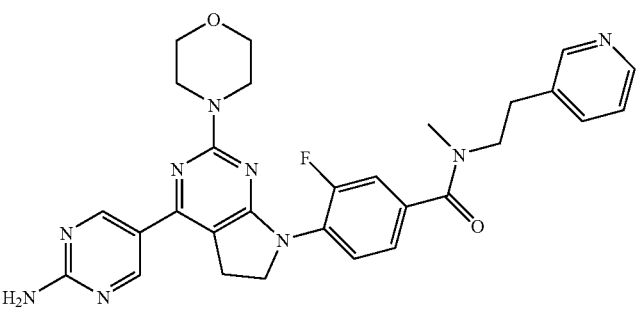 |

-continued

| Example No. | Compound No. | Structural formula |
|---|---|---|
| Example 1-D-321 | (D-321) | |
| Example 1-D-322 | (D-322) | |
| Example 1-D-323 | (D-323) | |
| Example 1-D-324 | (D-324) | |

| Example No. | Compound No. | Structural formula |
|---|---|---|
| Example 1-D-325 | (D-325) | |
| Example 1-D-326 | (D-326) | |
| Example 1-D-327 | (D-327) | |
| Example 1-D-328 | (D-328) | |
| Example 1-D-329 | (D-329) | |

-continued
| Example No. | Compound No. | Structural formula |
|---|---|---|
| Example 1-D-330 | (D-330) | 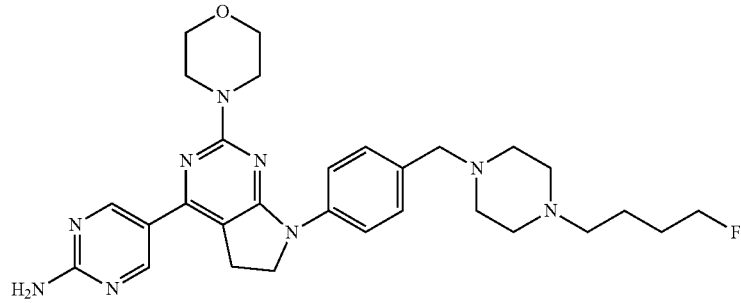 |
| Example 1-D-332 | (D-332) | 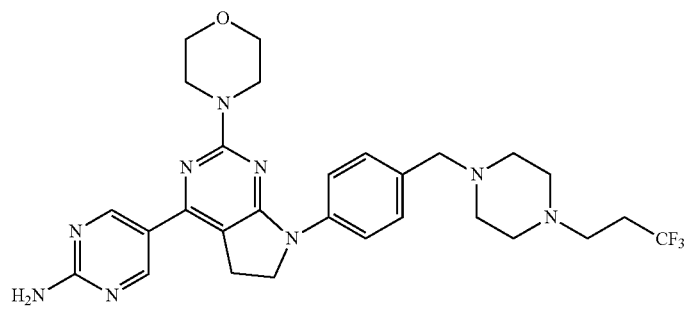 |
| Example 1-D-333 | (D-333) | 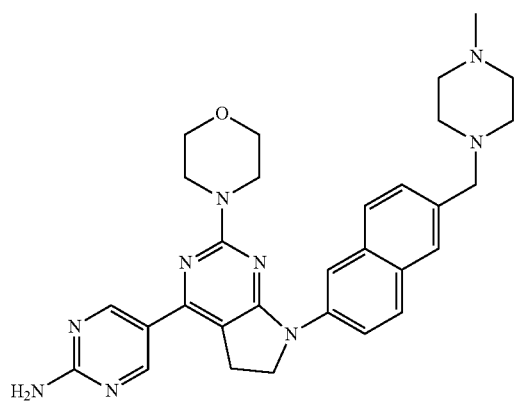 |
| Example 1-D-334 | (D-334) | 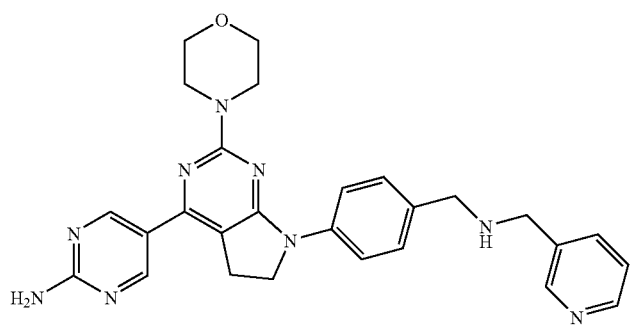 |

| Example No. | Compound No. | Structural formula |
|---|---|---|
| Example 1-D-335 | (D-335) | 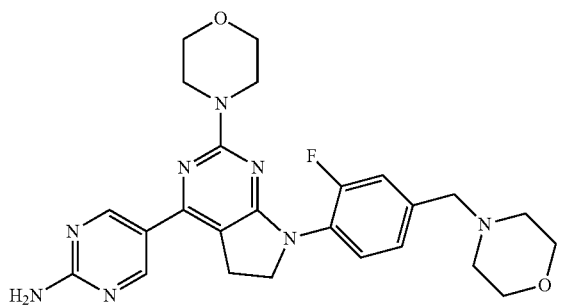 |
| Example No. | Compound No. | Structural formula |
|---|---|---|
| Example 1-E-01 | (E-01) | 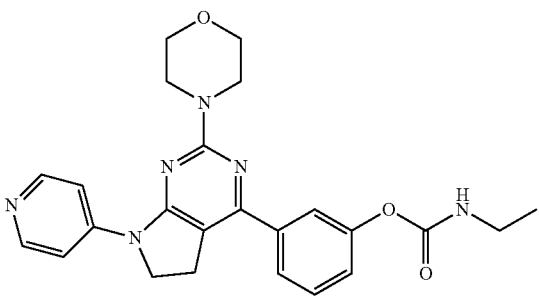 |
| Example 1-E-02 | (E-02) | 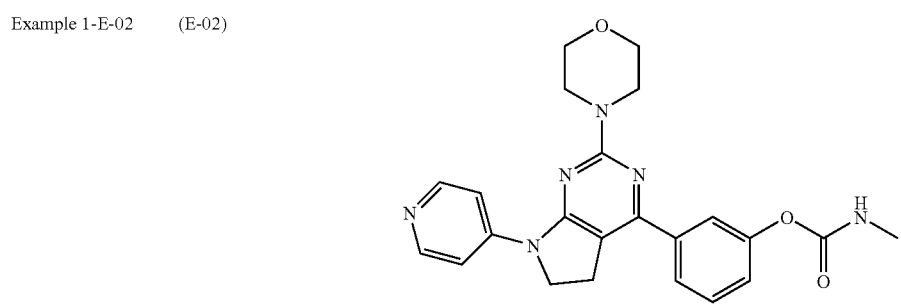 |
| Example 1-E-03 | (E-03) | 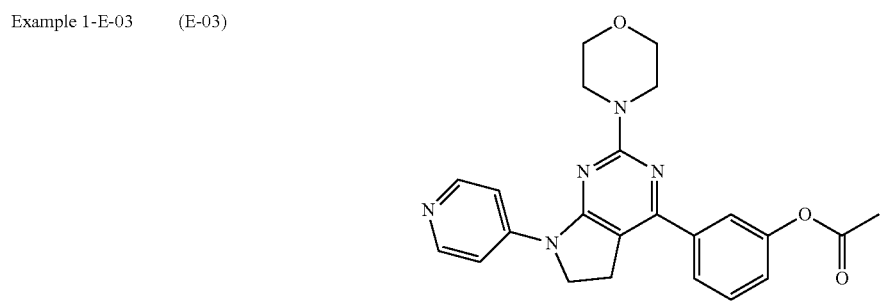 |

-continued

| Example No. | Compound No. | Structural formula |
|---|---|---|
| Example 1-E-04 | (E-04) | |
| Example 1-E-05 | (E-05) | |
| Example 1-E-06 | (E-06) | |
| Example 1-E-07 | (E-07) | |
| Example 1-E-08 | (E-08) | |

-continued
| Example No. | Compound No. | Structural formula |
|---|---|---|
| Example 1-E-09 | (E-09) | 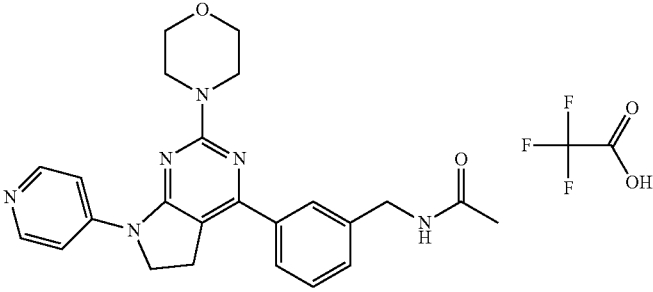 |
| Example 1-E-10 | (E-10) | 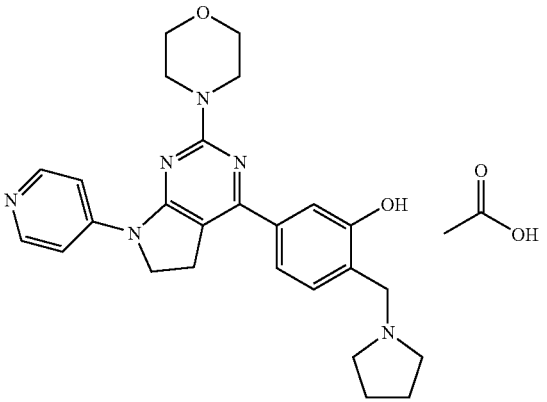 |
| Example 1-E-11 | (E-11) | 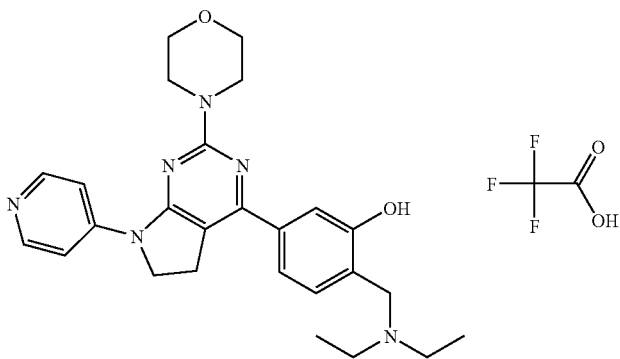 |
| Example 1-E-12 | (E-12) | 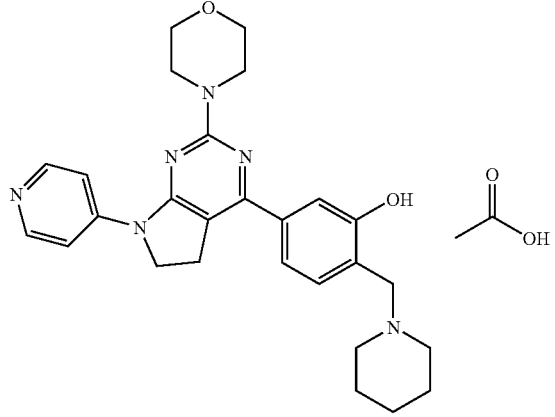 |

| Example No. | Compound No. | Structural formula |
|---|---|---|
| Example 1-F-01 | (F-01) | |

| Example No. | Compound No. | Structural formula |
|---|---|---|
| Example 1-G-01 | (G-01) | |
| Example 1-G-02 | (G-02) | |
| Example 1-G-03 | (G-03) | |

| Example No. | Compound No. | Structural formula |
|---|---|---|
| Example 1-G-04 | (G-04) | |
| Example 1-G-05 | (G-05) | |
| Example 1-G-06 | (G-06) | |
| Example 1-G-07 | (G-07) | |

-continued

| Example No. | Compound No. | Structural formula |
|---|---|---|
| Example 1-G-08 | (G-08) | |
| Example 1-G-09 | (G-09) | |
| Example 1-G-10 | (G-10) | |
| Example 1-G-11 | (G-11) | |

-continued

| Example No. | Compound No. | Structural formula |
|---|---|---|
| Example 1-G-12 | (G-12) | |
| Example 1-G-13 | (G-13) | |
| Example 1-G-14 | (G-14) | |
| Example 1-G-15 | (G-15) | |

-continued

| Example No. | Compound No. | Structural formula |
|---|---|---|
| Example 1-G-16 | (G-16) | |
| Example 1-G-17 | (G-17) | |
| Example 1-G-18 | (G-18) | |
| Example 1-G-19 | (G-19) | |

-continued

| Example No. | Compound No. | Structural formula |
|---|---|---|
| Example 1-G-20 | (G-20) | |
| Example 1-G-21 | (G-21) | |
| Example 1-G-22 | (G-22) | |
| Example 1-G-23 | (G-23) | |

-continued

| Example No. | Compound No. | Structural formula |
|---|---|---|
| Example 1-G-24 | (G-24) | |
| Example 1-G-25 | (G-25) | |
| Example 1-G-26 | (G-26) | |
| Example 1-G-27 | (G-27) | |

-continued

| Example No. | Compound No. | Structural formula |
|---|---|---|
| Example 1-G-28 | (G-28) | |
| Example 1-G-29 | (G-29) | HCl |
| Example 1-G-30 | (G-30) | |
| Example 1-G-31 | (G-31) | |

-continued

| Example No. | Compound No. | Structural formula |
|---|---|---|
| Example 1-G-32 | (G-32) | |
| Example 1-G-33 | (G-33) | |
| Example 1-G-34 | (G-34) | |
| Example 1-G-35 | (G-35) | |

-continued
| Example No. | Compound No. | Structural formula |
|---|---|---|
| Example 1-G-36 | (G-36) | 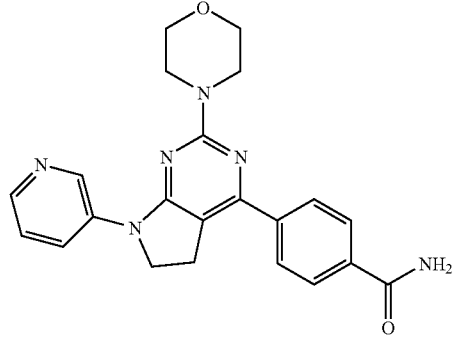 |
| Example 1-G-37 | (G-37) | 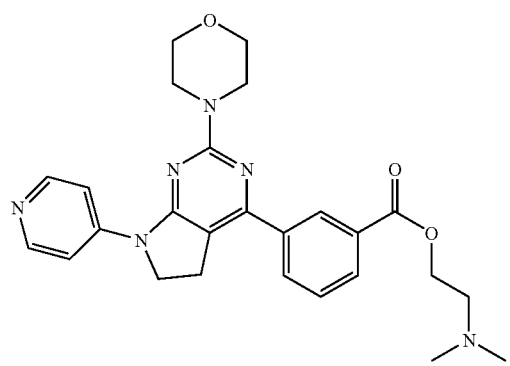 |
| Example 1-G-38 | (G-38) | 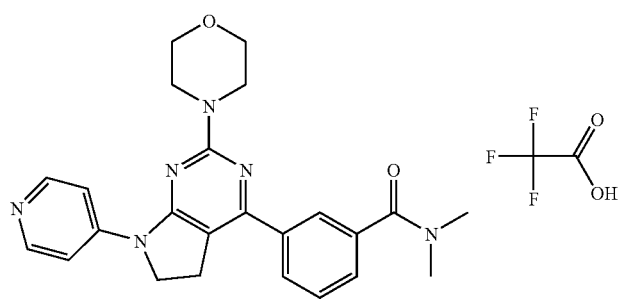 |
| Example 1-G-39 | (G-39) | 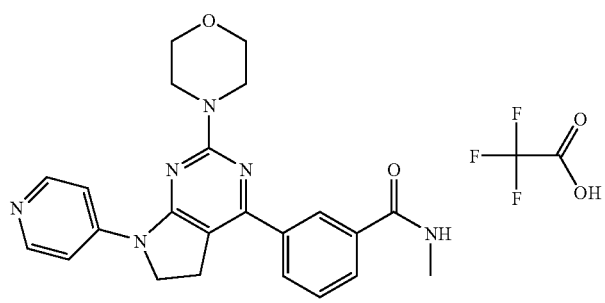 |

-continued
| Example No. | Compound No. | Structural formula |
|---|---|---|
| Example 1-G-40 | (G-40) | 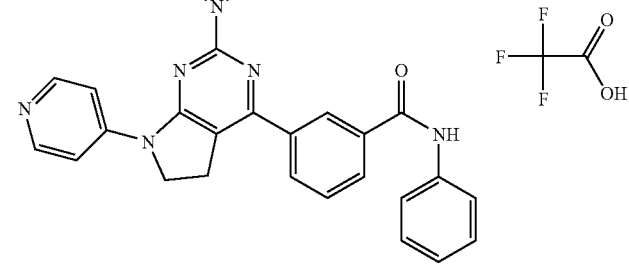 |
| Example 1-G-41 | (G-41) | 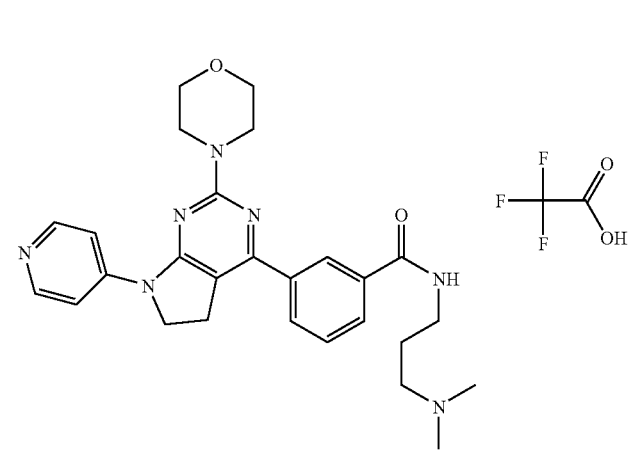 |
| Example 1-G-42 | (G-42) | 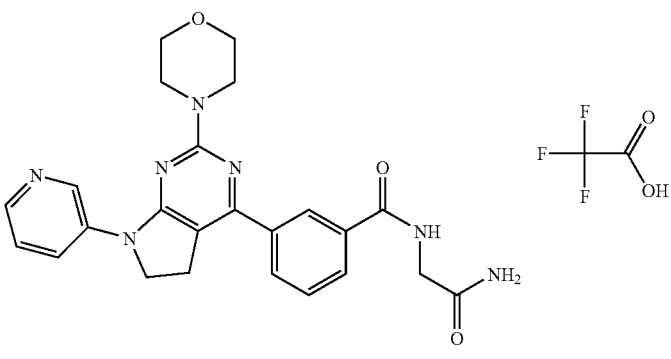 |
| Example 1-G-43 | (G-43) | 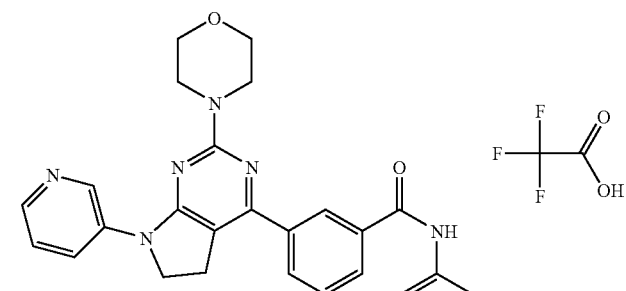 |

|Example No.|Compound No.|Structural formula|
|---|---|---|
|Example 1-G-44|(G-44)||
|Example 1-G-45|(G-45)||
|Example 1-G-46|(G-46)||
|Example 1-G-47|(G-47)||

-continued

| Example No. | Compound No. | Structural formula |
|---|---|---|
| Example 1-G-48 | (G-48) | |
| Example 1-G-49 | (G-49) | |
| Example 1-G-50 | (G-50) | |
| Example 1-G-51 | (G-51) | |
| Example 1-G-52 | (G-52) | |

-continued

| Example No. | Compound No. | Structural formula |
|---|---|---|
| Example 1-G-53 | (G-53) | |
| Example 1-G-54 | (G-54) | Chiral |
| Example 1-G-55 | (G-55) | |
| Example 1-G-56 | (G-56) | |
| Example 1-G-57 | (G-57) | |

-continued
| Example No. | Compound No. | Structural formula |
|---|---|---|
| Example 1-G-58 | (G-58) | 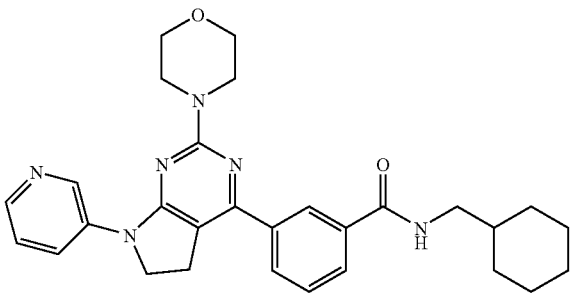 |
| Example 1-G-59 | (G-59) | 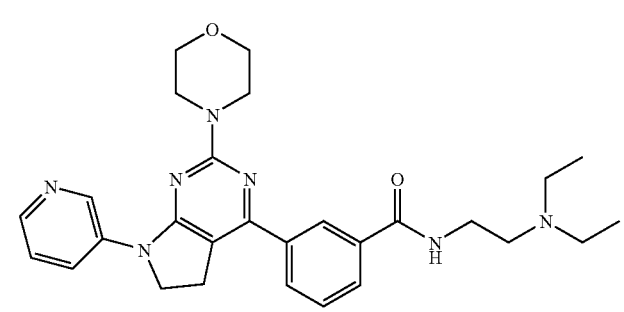 |
| Example 1-G-60 | (G-60) | 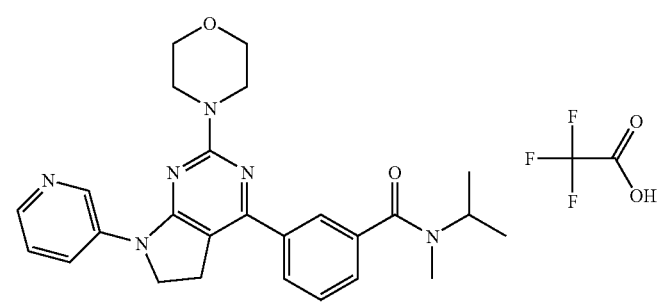 |
| Example 1-G-61 | (G-61) | 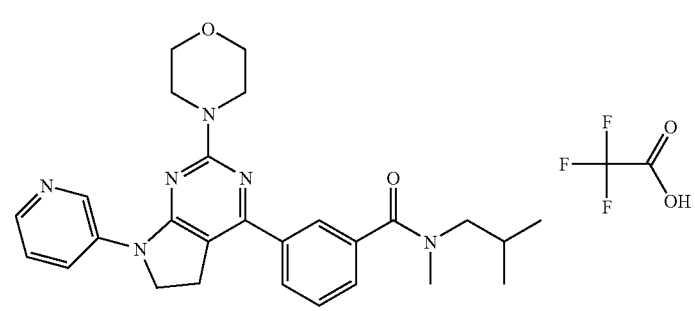 |
| Example 1-G-62 | (G-62) | 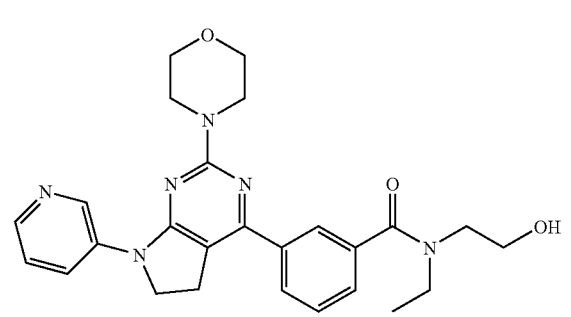 |

| Example No. | Compound No. | Structural formula |
|---|---|---|
| Example 1-G-63 | (G-63) | 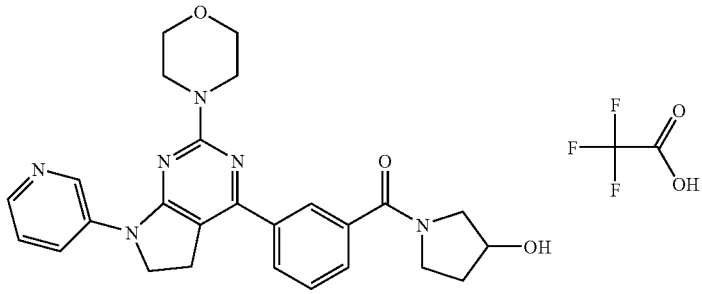 |
| Example 1-G-64 | (G-64) | 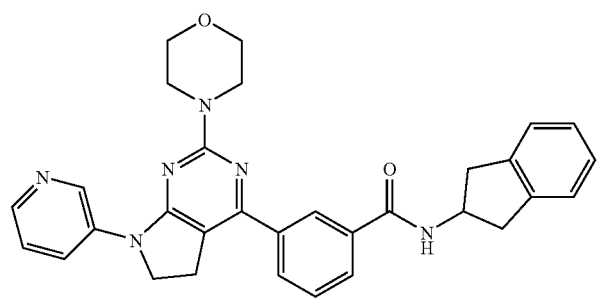 |
| Example 1-G-65 | (G-65) | 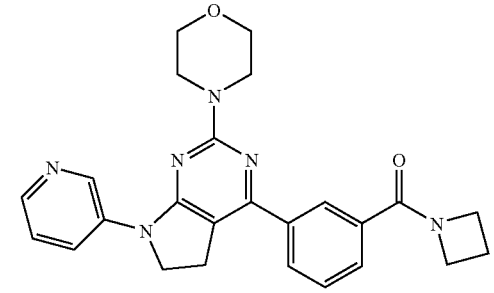 |
| Example 1-G-66 | (G-66) | 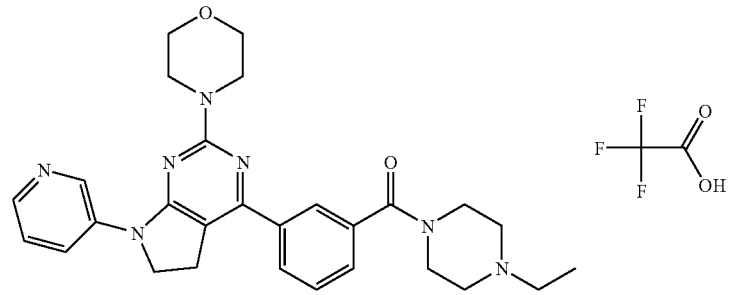 |
| Example 1-G-67 | (G-67) | 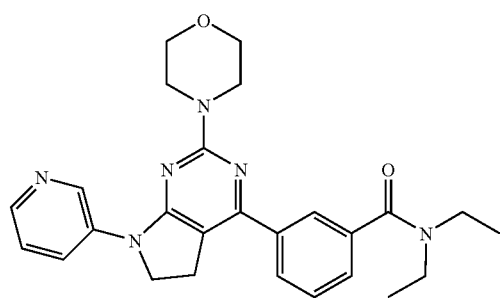 |

| Example No. | Compound No. | Structural formula |
|---|---|---|
| Example 1-G-68 | (G-68) | 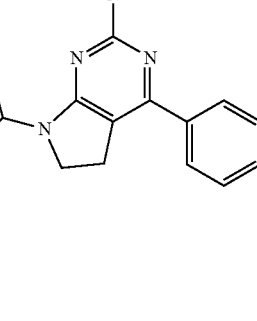 Chiral |
| Example 1-G-69 | (G-69) | 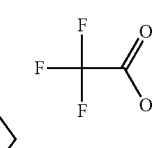 |
| Example 1-G-70 | (G-70) | 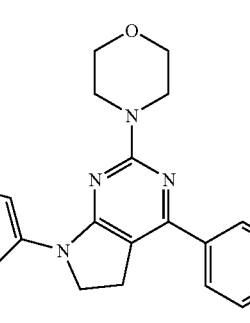 |
| Example 1-G-71 | (G-71) | 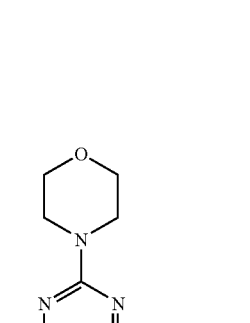 |

-continued

| Example No. | Compound No. | Structural formula |
|---|---|---|
| Example 1-G-72 | (G-72) | |
| Example 1-G-73 | (G-73) | |
| Example 1-G-74 | (G-74) | |
| Example 1-G-75 | (G-75) | |

-continued

| Example No. | Compound No. | Structural formula |
|---|---|---|
| Example 1-G-76 | (G-76) | |
| Example 1-G-77 | (G-77) | |
| Example 1-G-78 | (G-78) | |
| Example 1-G-79 | (G-79) | |
| Example 1-G-80 | (G-80) | |

-continued
| Example No. | Compound No. | Structural formula |
|---|---|---|
| Example 1-G-81 | (G-81) | 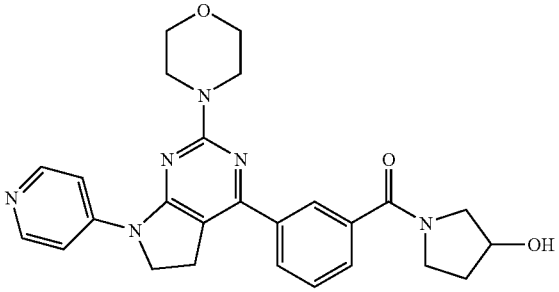 |
| Example 1-G-82 | (G-82) | 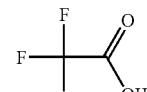 |
| Example 1-G-83 | (G-83) | 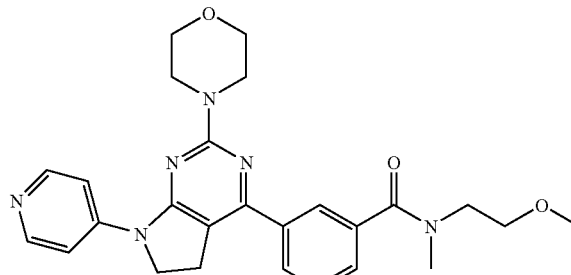 |
| Example 1-G-84 | (G-84) | 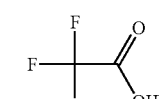 |
| Example 1-G-85 | (G-85) | 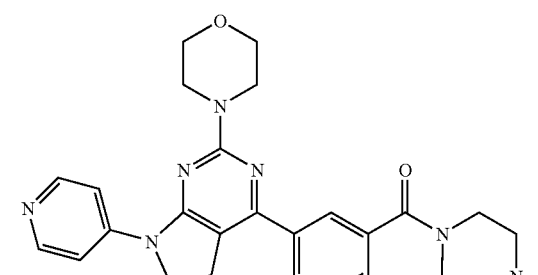 |

| Example No. | Compound No. | Structural formula |
|---|---|---|
| Example 1-G-86 | (G-86) | |
| Example 1-G-87 | (G-87) | |
| Example 1-G-88 | (G-88) | |
| Example 1-G-89 | (G-89) | |
| Example 1-G-90 | (G-90) | |

-continued

| Example No. | Compound No. | Structural formula |
|---|---|---|
| Example 1-G-91 | (G-91) | |
| Example 1-G-92 | (G-92) | |
| Example 1-G-93 | (G-93) | |
| Example 1-G-94 | (G-94) | |

| Example No. | Compound No. | Structural formula |
|---|---|---|
| Example 1-H-01 | (H-01) | 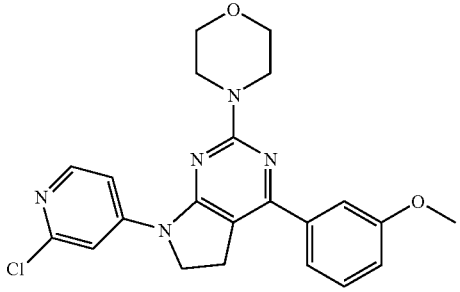 |
| Example 1-H-02 | (H-02) | 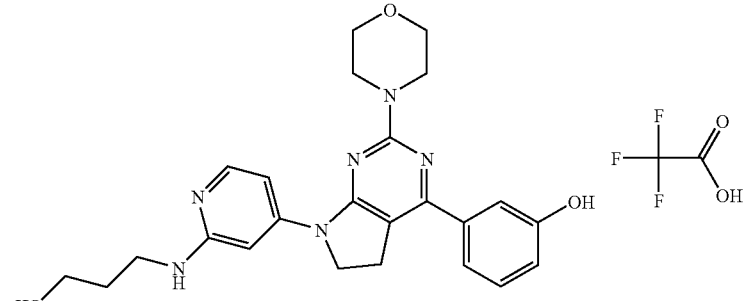 |
| Example 1-H-03 | (H-03) | 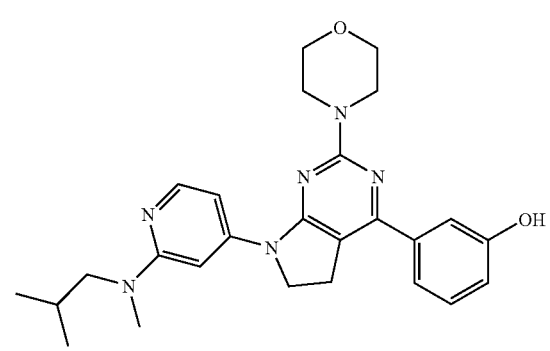 |
| Example 1-H-04 | (H-04) | 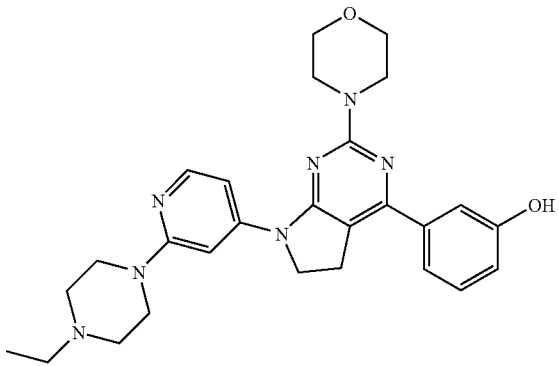 |

-continued

| Example No. | Compound No. | Structural formula |
|---|---|---|
| Example 1-H-05 | (H-05) | |
| Example 1-H-06 | (H-06) | |
| Example 1-H-07 | (H-07) | |
| Example 1-H-08 | (H-08) | |

| Example No. | Compound No. | Structural formula |
|---|---|---|
| Example 1-H-09 | (H-09) | 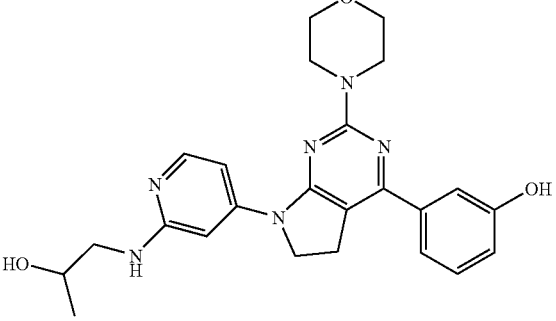 |
| Example 1-H-10 | (H-10) | 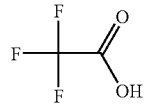 |
| Example 1-H-11 | (H-11) | 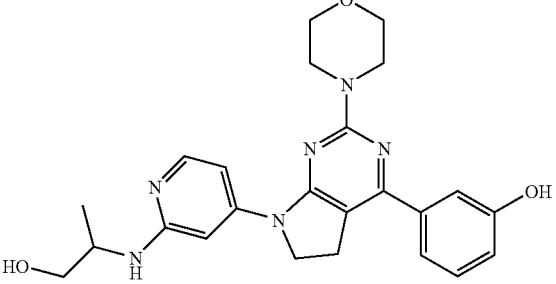 |
| Example 1-H-12 | (H-12) | 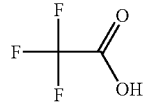 |

-continued

| Example No. | Compound No. | Structural formula |
|---|---|---|
| Example 1-H-13 | (H-13) | |
| Example 1-H-14 | (H-14) | |
| Example 1-H-15 | (H-15) | |
| Example 1-H-16 | (H-16) | |

| Example No. | Compound No. | Structural formula |
|---|---|---|
| Example 1-H-17 | (H-17) | 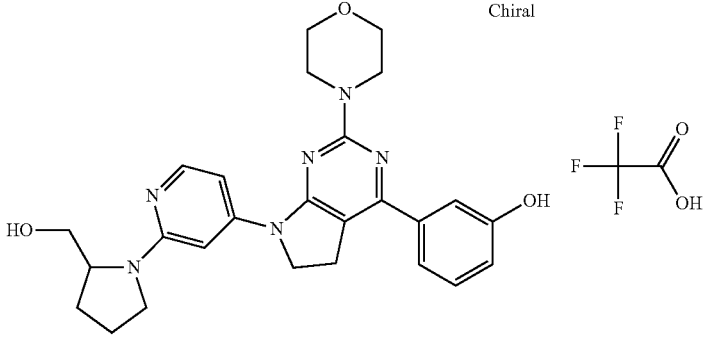 Chiral |
| Example 1-H-18 | (H-18) | 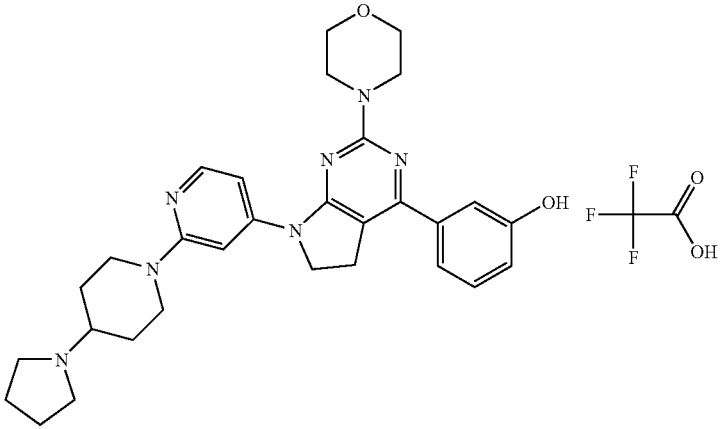 |
| Example 1-H-19 | (H-19) | 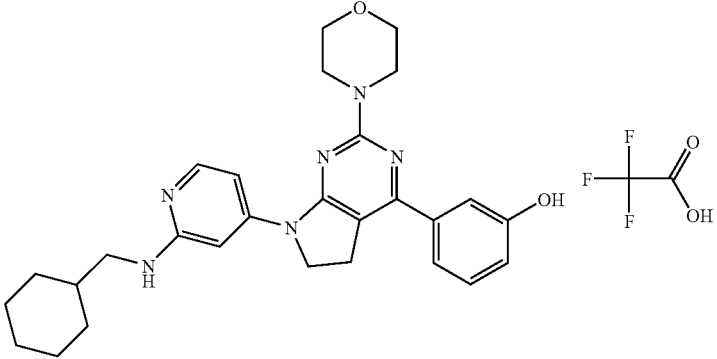 |
| Example 1-H-20 | (H-20) | 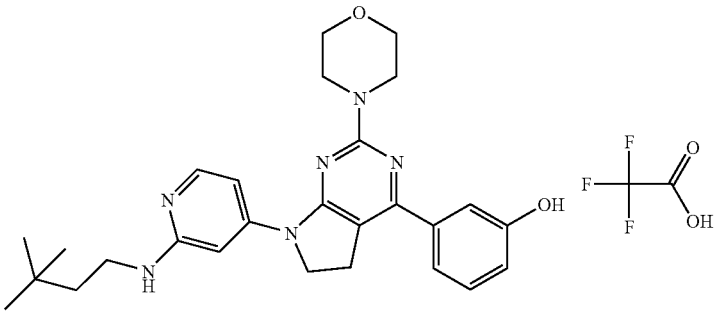 |

| Example No. | Compound No. | Structural formula |
|---|---|---|
| Example 1-H-21 | (H-21) | 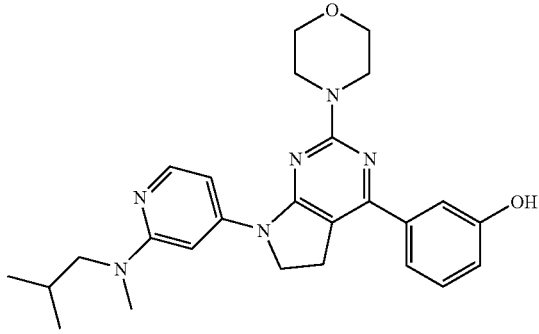 |
| Example 1-H-22 | (H-22) | 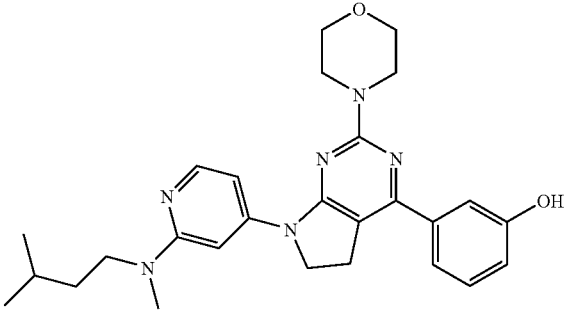 |
| Example 1-H-23 | (H-23) | 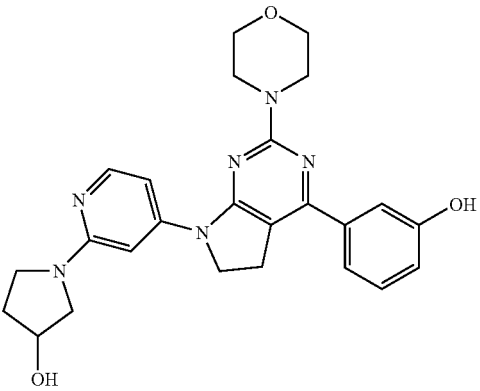 |
| Example 1-H-24 | (H-24) | 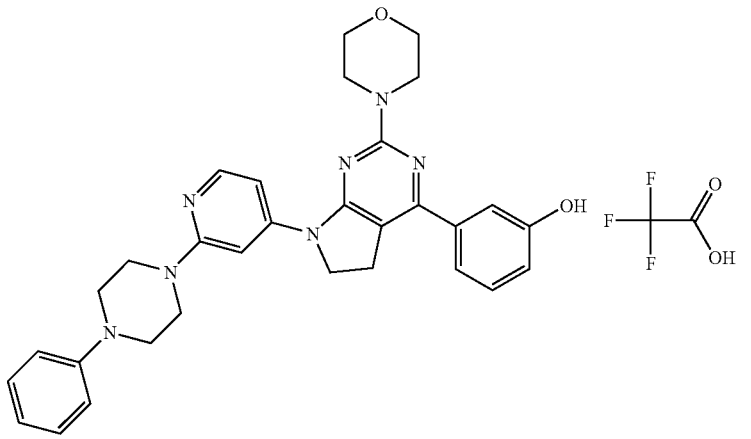 |

-continued
| Example No. | Compound No. | Structural formula |
|---|---|---|
| Example 1-H-25 | (H-25) | 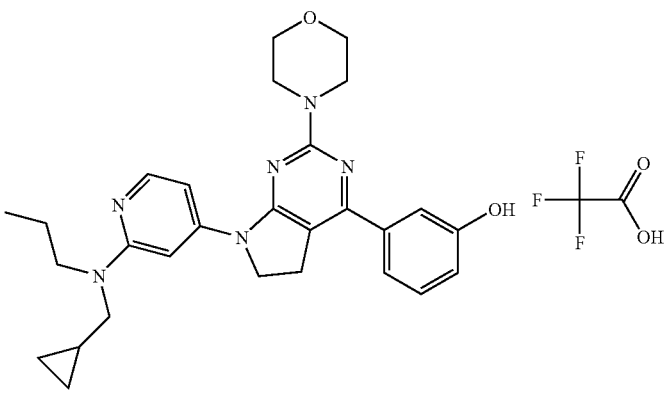 |
| Example 1-H-26 | (H-26) | 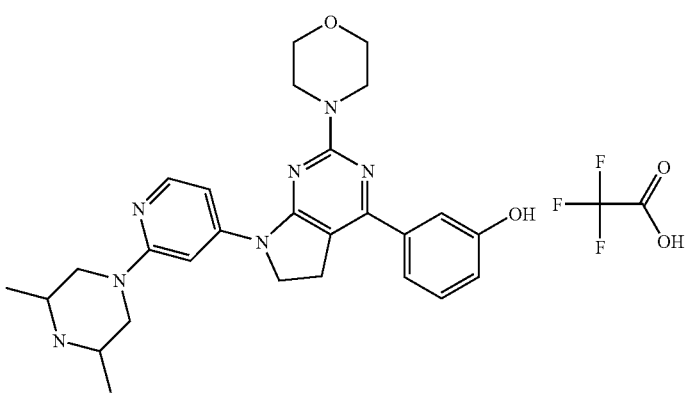 |
| Example 1-H-27 | (H-27) | 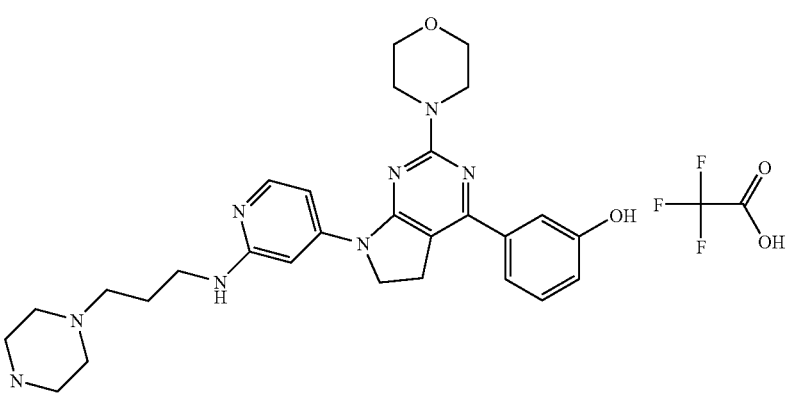 |
| Example 1-H-28 | (H-28) | 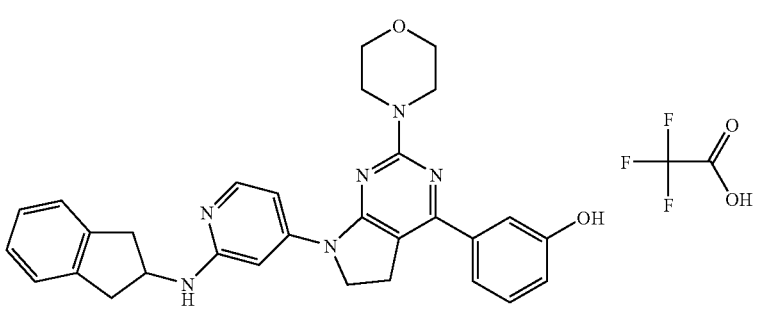 |

-continued
| Example No. | Compound No. | Structural formula |
|---|---|---|
| Example 1-H-29 | (H-29) | 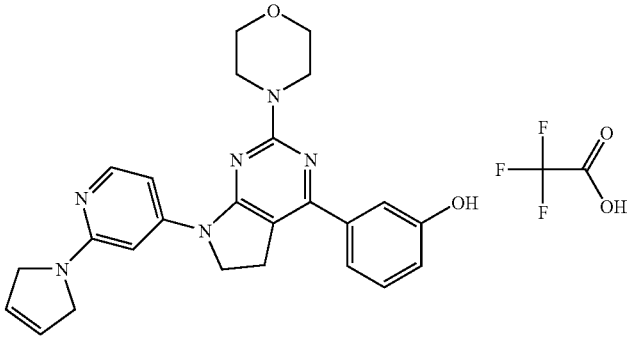 |
| Example 1-H-30 | (H-30) | 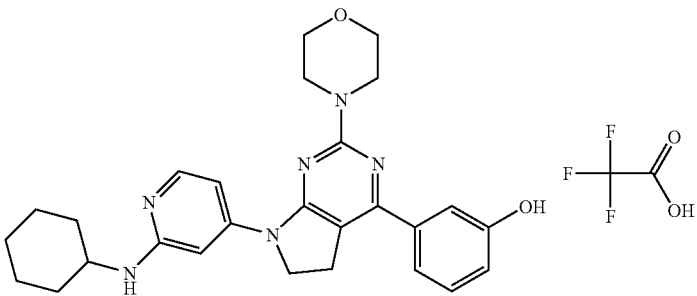 |
| Example 1-H-31 | (H-31) | 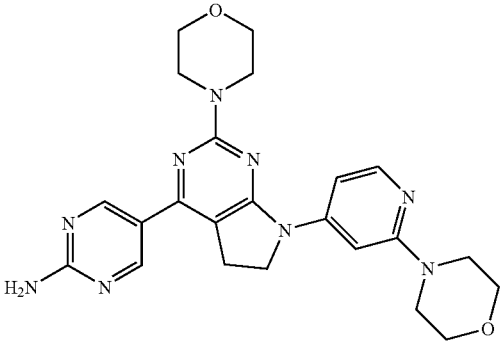 |
| Example 1-H-32 | (H-32) | 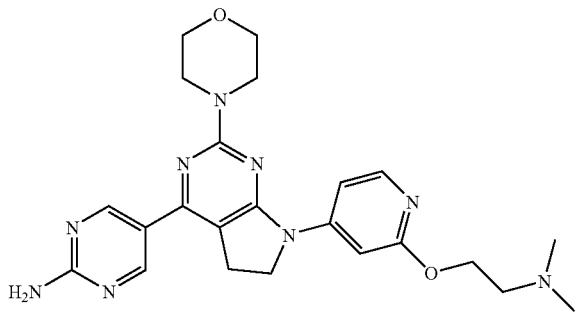 |

-continued

| Example No. | Compound No. | Structural formula |
|---|---|---|
| Example 1-H-33 | (H-33) | |
| Example 1-H-34 | (H-34) | |
| Example 1-H-35 | (H-35) | |
| Example 1-H-36 | (H-36) | |

| Example No. | Compound No. | Structural formula |
|---|---|---|
| Example 1-I-01 | (I-01) | 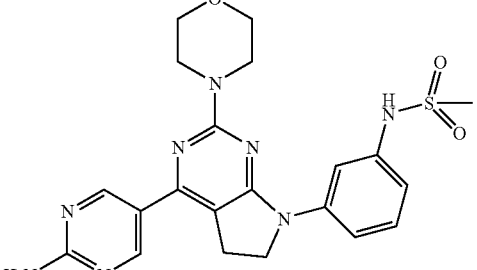 |

In addition, examples of preferable compounds among the compounds of formula (I) of the present invention include the following compound numbers: A-01, A-02, A-03, A-04, A-09, A-10, A-11, A-12, A-13, A-14, A-15, A-16, A-17, A-18, A-19, A-20, A-21, A-22, A-23, A-24, A-32, A-33, A-37, A-38, A-39, A-41, A-42, A-43, A-44, A-45, A-46, A-48, A-49, A-50, A-51, A-52, A-53, B-01, B-02, B-03, B-04, B-05, B-06, B-07, B-08, B-09, B-13, B-15, B-17, B-18, B-19, B-20, B-21, B-22, B-23, B-25, B-27, B-29, B-31, B-32, B-33, B-35, B-36, B-42, B-46, B-52, B-53, B-55, C-01, C-02, C-04, C-05, C-06, C-08, C-09, C-10, C-11, C-12, 13, C-14, C-15, C-16, C-17, C-18, C-19, C-20, C-21, C-22, C-23, C-24, C-25, C-26, C-27, C-28, C-29, C-30, C-31, C-32, C-33, C-34, C-35, C-36, C-37, C-38, C-39, C-40, C-41, C-42, C-44, C-45, C-46, C-47, C-48, C-49, C-50, C-51, C-52, C-53, C-55, C-56, C-57, D-01, D-02, D-03, D-04, D-05, D-06, D-07, D-08, D-09, D-10, D-11, D-12, D-13, D-14, D-15, D-16, D-17, D-18, D-19, D-20, D-21, D-22, D-23, D-24, D-25, D-26, D-27, D-28, D-29, D-30, D-31, D-32, D-33, D-34, D-35, D-36, D-37, D-38, D-39, D-40, D-41, D-42, D-43, D-44, D-45, D-46, D-47, D-48, D-49, D-50, D-51, D-52, D-53, D-54, D-55, D-56, D-57, D-58, D-59, D-60, D-61, D-62, D-63, D-64, D-65, D-66, D-67, D-68, D-69, D-70, D-71, D-72, D-73, D-74, D-75, D-76, D-77, D-78, D-79, D-80, D-81, D-82, D-83, D-84, D-85, D-86, D-87, D-88, D-89, D-90, D-91, D-92, D-93, D-94, D-95, D-96, D-97, D-98, D-99, D-100, D-101, D-102, D-103, D-104, D-105, D-106, D-107, D-108, D-109, D-110, D-111, D-112, D-113, D-114, D-115, D-116, D-117, D-118, D-119, D-120, D-121, D-122, D-123, D-124, D-125, D-126, D-127, D-128, D-129, D-130, D-131, D-132, D-133, D-134, D-135, D-136, D-137, D-138, D-139, D-140, D-141, D-142, D-143, D-144, D-145, D-146, D-147, D-148, D-149, D-150, D-151, D-152, D-153, D-154, D-155, D-156, D-157, D-158, D-159, D-160, D-161, D-162, D-163, D-164, D-165, D-166, D-167, D-168, D-169, D-170, D-171, D-172, D-173, D-174, D-175, D-176, D-177, D-178, D-179, D-180, D-181, D-182, D-183, D-184, D-185, D-186, D-187, D-188, D-189, D-190, D-191, D-192, D-193, D-194, D-195, D-196, D-197, D-198, D-199, D-200, D-201, D-202, D-203, D-204, D-205, D-206, D-207, D-208, D-209, D-210, D-211, D-212, D-213, D-214, D-215, D-216, D-217, D-218, D-219, D-220, D-221, D-222, D-223, D-224, D-225, D-226, D-227, D-228, D-229, D-230, D-231, D-232, D-233, D-234, D-235, D-236, D-237, D-238, D-239, D-240, D-241, D-242, D-243, D-244, D-245, D-246, D-247, D-248, D-249, D-250, D-251, D-252, D-253, D-254, D-255, D-256, D-257, D-258, D-259, D-260, D-261, D-262, D-263, D-264, D-265, D-266, D-267, D-268, D-269, D-270, D-271, D-272, D-273, D-274, D-275, D-276, D-277, D-278, D-279, D-280, D-281, D-282, D-283, D-284, D-285, D-286, D-287, D-288, D-289, D-290, D-291, D-292, D-293, D-294, D-295, D-296, D-297, D-298, D-299, D-300, D-301, D-302, D-303, D-304, D-305, D-306, D-307, D-308, D-309, D-310, D-311, D-312, D-313, D-314, D-315, D-316, D-317, D-318, D-319, D-320, D-321, D-322, D-323, D-324, D-325, D-326, D-327, D-328, D-329, D-330, D-332, D-333, D-334, D-335, E-01, E-02, E-03, E-04, E-05, E-07, F-01, G-01, G-03, G-05, G-06, G-07, G-08, G-09, G-10, G-11, G-12, G-13, G-27, G-28, G-29, G-40, G-42, G-43, G-44, G-45, G-47, G-48, G-49, G-50, G-51, G-52, G-53, G-54, G-55, G-56, G-57, G-58, G-59, G-60, G-61, G-62, G-63, G-64, G-65, G-66, G-67, G-68, G-69, G-70, G-71, G-72, G-73, G-74, G-75, G-76, G-77, G-78, G-80, G-81, G-82, G-83, G-84, G-85, G-87, G-89, G-91, G-92, G-93, G-94, H-02, H-03, H-04, H-05, H-06, H-07, H-08, H-09, H-10, H-11, H-12, H-13, H-14, H-15, H-16, H-17, H-18, H-19, H-20, H-21, H-22, H-23, H-24, H-25, H-26, H-27, H-28, H-29, H-30, H-31, H-32, H-33, H-34, H-35, H-36, I-01.

In addition, examples of more preferable compounds among the compounds of formula (I) of the present invention include the following compound numbers: A-01, A-03, A-09, A-10, A-11, A-13, A-14, A-16, A-17, A-18, A-19, A-20, A-32, A-33, A-41, A-42, A-43, A-44, A-45, A-46, A-48, A-49, A-50, A-51, A-52, A-53, B-01, B-02, B-03, B-04, B-05, B-08, B-09, B-18, B-22, B-23, B-25, B-27, B-29, B-32, B-33, B-35, B-36, B-52, B-53, B-55, C-01, C-02, C-04, C-05, C-06, C-09, C-10, C-11, C-12, C-29, C-30, C-32, C-33, C-34, C-35, C-36, C-37, C-38, C-39, C-40, C-41, C-42, C-44, C-45, C-46, C-47, C-48, C-49, C-50, C-51, C-55, C-56, C-57, D-01, D-02, D-03, D-04, D-05, D-06, D-07, D-08, D-09, D-10, D-11, D-12, D-13, D-14, D-15, D-16, D-17, D-18, D-19, D-20, D-21, D-22, D-23, D-24, D-25, D-26, D-27, D-28, D-29, D-30, D-31, D-32, D-33, D-34, D-35, D-36, D-37, D-38, D-39, D-40, D-41, D-42, D-43, D-44, D-45, D-46, D-47, D-48, D-49, D-50, D-51, D-52, D-53, D-54, D-55, D-56, D-57, D-58, D-59, D-60, D-61, D-62, D-63, D-64, D-65, D-66, D-67, D-68, D-69, D-70, D-71, D-72, D-73, D-74, D-75, D-76, D-77, D-78, D-79, D-80, D-81, D-82, D-83, D-84, D-85, D-86, D-87, D-88, D-89, D-90, D-91, D-92, D-93, D-94, D-95, D-96, D-97, D-98, D-99, D-100, D-101, D-102, D-103, D-104, D-105, D-106, D-107, D-108, D-109, D-110, D-111, D-112, D-113, D-114, D-115, D-116, D-117, D-118, D-119, D-120, D-121, D-122, D-123, D-124, D-125, D-126, D-127, D-128, D-129, D-130, D-131, D-132, D-133, D-134, D-135, D-136, D-137, D-138, D-139, D-140, D-141, D-142, D-143, D-144, D-145, D-146, D-147, D-148, D-149, D-150, D-151, D-152, D-153, D-154, D-155, D-156, D-157, D-158, D-159, D-160, D-161, D-162, D-163, D-164, D-165, D-166, D-167, D-168, D-169, D-170, D-171, D-172, D-173, D-174, D-175, D-176, D-177, D-178, D-179, D-180, D-181, D-182, D-183, D-184, D-185, D-186, D-187, D-188, D-189, D-190, D-191, D-192, D-193, D-194, D-195, D-196, D-197, D-198, D-199, D-200, D-201, D-202, D-203, D-204, D-205, D-206, D-207, D-208, D-209, D-210, D-211, D-212, D-213, D-214, D-215, D-216, D-217, D-218, D-219, D-220, D-221, D-222, D-223, D-224, D-225, D-226, D-227, D-228, D-229, D-230, D-231, D-232, D-233, D-234, D-235, D-236, D-237, D-238, D-239, D-240, D-241, D-242, D-243, D-244, D-245, D-246, D-247, D-248, D-249, D-250, D-251, D-252, D-253, D-254, D-255, D-256, D-257, D-258, D-259, D-260, D-261, D-262, D-263, D-264, D-265, D-266, D-267, D-268, D-269, D-270, D-271, D-272, D-273, D-274, D-275, D-276, D-277, D-278, D-279, D-280, D-281, D-282, D-283, D-284, D-285, D-286, D-287, D-288, D-289, D-290, D-291, D-292, D-293, D-294, D-295, D-296, D-297, D-298, D-299, D-300, D-301, D-302, D-303, D-304, D-305, D-306, D-307, D-308, D-309, D-310, D-311, D-312, D-313, D-314, D-315, D-316, D-317, D-318, D-319, D-320, D-321, D-322, D-323, D-324, D-325, D-326, D-327, D-328, D-329, D-330, D-332, D-333, D-334, D-335, G-05, G-07, G-08, G-09, G-10, G-11, G-27, G-49, G-51, G-59, G-67, G-75, G-77, H-02, H-03, H-04, H-05, H-06, H-07, H-08, H-09, H-10, H-11, H-12, H-13, H-14, H-15, H-16, H-17, H-18, H-20, H-21, H-22, H-23, H-24, H-25, H-26, H-27, H-29, H-30, H-31, H-32, H-33, H-34, H-35, H-36, I-01.

Moreover, examples of particularly preferable compounds include the following compound numbers: A-09, A-14, A-32, A-44, A-48, B-02, B-03, B-09, B-22, B-32, B-35, B-55, C-55, D-01, D-02, D-03, D-16, D-17, D-18, D-19, D-20, D-21, D-22, D-23, D-24, D-25, D-26, D-42, D-95, D-101, D-102, D-103, D-104, D-108, D-128, D-137, D-138, D-139, D-172, D-223, D-231, D-237, D-242, D-264, D-265, D-273, D-286, D-290, D-307, D-318, D-325, D-326, D-327, D-328, D-329, D-330, D-332, D-333, D-334, G-05, G-27, H-12, H-32, K-34.

Although stereoisomers and tautomers may exist for the compound of the present invention depending on the type of substituents, isolates or mixtures of these isomers are included in the present invention.

Stereoisomers include, for example, enantiomers, diastereomers and cis- and trans-geometrical isomers. In addition, racemic forms and the other mixtures thereof are included in these isomers. In particular, the compound of the formula (I) includes stereoisomers in the present invention.

In addition, several tautomeric forms such as enol and imine forms, keto and enamine forms and mixtures thereof may exist for the compound of the present invention and a pharmaceutically acceptable salt thereof. Tautomers are present in solution as a mixture of tautomer set. In solid forms, one of the tautomers is usually dominant. Although one of the tautomers may be described, all tautomers of the compound of the present invention are included in the present invention.

Moreover, atropisomers of the present invention are also included in the present invention. Atropisomers refer to Compound I represented by the formula (I) capable of being separated into isomers having limited rotation.

In addition, the compound as claimed in the present invention, whether it be in a free form or in the form of a pharmaceutically acceptable salt, is included in the present invention. There are no particular limitations on this "salt" provided it forms a salt with the compound represented by formula (I) as claimed in the present invention (also referred to as Compound I) and is a pharmaceutically acceptable salt, and examples thereof include an acid salt formed by Compound I of the present invention and an acid, and a basic salt formed by Compound I of the present invention an a base.

The acid used to prepare a pharmaceutically acceptable acid salt of Compound I of the present invention is preferably that which reacts with Compound I of the present invention and forms a non-toxic acid salt. Examples of acid salts include hydrochlorides, hydrobromides, hydroiodides, nitrates, sulfates, bisulfates, phosphates, acid phosphates, acetates, lactates, citrates, acid citrates, tartrates, bitartrates, succinates, oxalates, malates, fumarates, gluconates, malonates, saccharates, benzoates, mandelates, salicylates, trifluoroacetates, propionates, glutarates, methane sulfonates, ethane sulfonates, benzene sulfonates, p-toluene sulfonates and 1,1'-methylene-bis-2-hydroxy-3-naphthoates.

The base used to prepare a pharmaceutically acceptable basic salt of Compound I of the present invention is preferably that which reacts with Compound I of the present invention and forms a non-toxic basic salt. Examples of basic salts include alkaline metal salts such as sodium salts and potassium salts, alkaline earth metal salts such as calcium salts and magnesium salts, ammonium salts, water-soluble amine addition salts such as N-methylglucamine salts, a lower alkanol ammonium salts, and salts derived from other pharmaceutically acceptable bases of organic amines.

In addition, since Compound I of the present invention may absorb moisture, become adhered with moisture and form a hydrate if allowed to stand in air, such salts are included in the present invention as salts of Compound I.

Moreover, although Compound I of the present invention may also absorb some types of solvents resulting in the formation of a solvate, such salts are also included in the present invention as salts of Compound I.

Typical Process for Producing Compound of Formula (I)

Although the compound of the present invention represented by formula (I) can be produced according to ordinary organic synthesis means such as the process indicated below, the production process of compounds represented by formula (I) of the present invention is not limited thereto. Furthermore, in the production process indicated below, in the case defined groups are subjected to undesirable chemical conversion under the conditions of the process used, production can be carried out by using a means such as protection and deprotection of functional groups unless specifically stated otherwise in the description. An example of a procedure for selecting as well as attaching and removing protecting groups is the method described in Greene and Wuts, "Protective Groups in Organic Synthesis" (3rd edition, Wiley-VCH, Inc., 1999), and these methods may be suitably used depending on the reaction conditions. In addition, the order of the reaction steps, such as the introduction of substituents, can be changed as necessary. In addition, in the production process described below, a desired product can be obtained by carrying a functional group modification reaction at a suitable stage in a series of reaction steps after having carried out the reaction with a raw material having a functional group serving as a precursor. The functional group modification reaction can be carried out by the method described in, for example, Smith and March, "March's Advanced Organic Chemistry" (5th edition, Wiley-VCH, Inc., 2001) or Richard C. Larock, "Comprehensive Organic Transformations" (VCH Publishers, Inc., 1989). Commercially available products may be used for the raw material compounds used during production, or the raw material compounds may also be produced in accordance with ordinary methods as necessary.

Furthermore, in the following production process and explanation thereof, $R^{1'}$ refers to the previously defined $R^1$ or $R^1$ protected with a protecting group. Specific examples of $R^1$ protected with a protecting group include cyclic substituents in which —COOH, —OH, —CONH$_2$, —CONRH or a primary or secondary amino group, contained in substituents -Cyc, —$C_{1-6}$ alkylene-OR', —$C_{1-6}$ alkylene-NRR', —$C_{1-6}$ alkylene-CONRR', —$C_{1-6}$ alkylene-NRCOR', —$C_{1-6}$ alkylene-Cyc, —OR, —O—$C_{1-6}$ alkylene-Cyc, —O—COOR, —O—COR, —O—CONRR', —NRR', —NR—$C_{1-6}$ alkylene-NR'R", —NR—$C_{1-6}$ alkylene-OR', —CO-Cyc, —CO—$C_{1-6}$ alkylene-Cyc, —COOR, —COO—$C_{1-6}$ alkylene-OR, —COO—$C_{1-6}$ alkylene-NRR', —COO—$C_{1-6}$ alkylene-Cyc, —CONRR', —CONR—$C_{1-6}$ alkylene-OR', —CONR—$C_{1-6}$ alkylene-NR'R", —CONR—$C_{1-6}$alkylene-CONR'R", —CONR-Cyc, —CONR—$C_{1-6}$ alkylene-Cyc, —$SO_2$NRR', —$NRSO_2$R' and —NH—$NH_2$ (where R, R', R" and Cyc are the same as previously defined) among substituent T, is protected by a protecting group.

In addition, X', Y' and Z' either have the same meanings as the X, Y and Z defined in general formula (I), or indicate X, Y and Z protected with a protecting group depending on the case. In addition, L refers to a leaving group, and represents, for example, a halogen atom (preferably, chlorine, bromine, iodine atom) a sulfonyloxy leaving group such as a -methanesulfonyloxy, -trifluoromethanesulfonyloxy or -p-toluenesulfonyloxy, a $C_{1-4}$alkoxy group such as methoxy, ethoxy or t-butoxy, a $C_{1-4}$alkylcarbonyloxy group such as acetyloxy, propionyloxy or t-butylcarbonyloxy, or a $C_{1-4}$alkoxycarbonyloxy group such as methoxycarbonyloxy, ethoxycarbonyloxy or t-butoxycarbonyloxy (—O-Boc). In addition, Hal represents a halogen atom, examples of which include a chlorine atom, bromine atom and iodine atom, with a chlorine atom being preferable. In addition, PG represents a benzyl protecting group such as 2,4-dimethoxybenzyl or 4-methoxybenzyl, while $PG_2$represents a protecting group of, for example, a $C_1$-$C_6$alkylcarbonyl group such as an acetyl group, a $C_1$-$C_6$alkoxycarbonyl group such as a t-butoxycarbonyl group, an aryl $C_1$-$C_6$alkoxycarbonyl group such as a benzyloxycarbonyl group, or a $C_1$-$C_6$alkylsilyl group such as a t-butyldimethylsilyl group.

In addition, acylation refers to a reaction in which a desired substituent is added or substituted to a specific position through a carbonyl group.

In addition, compounds represented by general formula (I) described in the following reaction steps are compounds of the present invention represented by general formula (I) or said compounds in which substituents are protected with suitable protecting groups. Among the compounds represented by general formula (I), said compounds protected with a protecting group allow compounds of the present invention represented by general formula (I) to be obtained by suitably going through a deprotection step in accordance with ordinary methods. In addition, protection steps and deprotection steps in accordance with ordinary methods are suitably included in the following reaction steps.

In addition, T, n, m, X, Y, $R^1$and $R^1$a are the same as in previously defined formula (I).

[Typical Synthesis Method of Compound of Formula (I)]

Reaction Step 1A

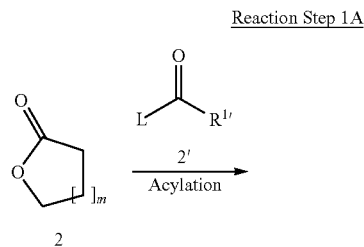

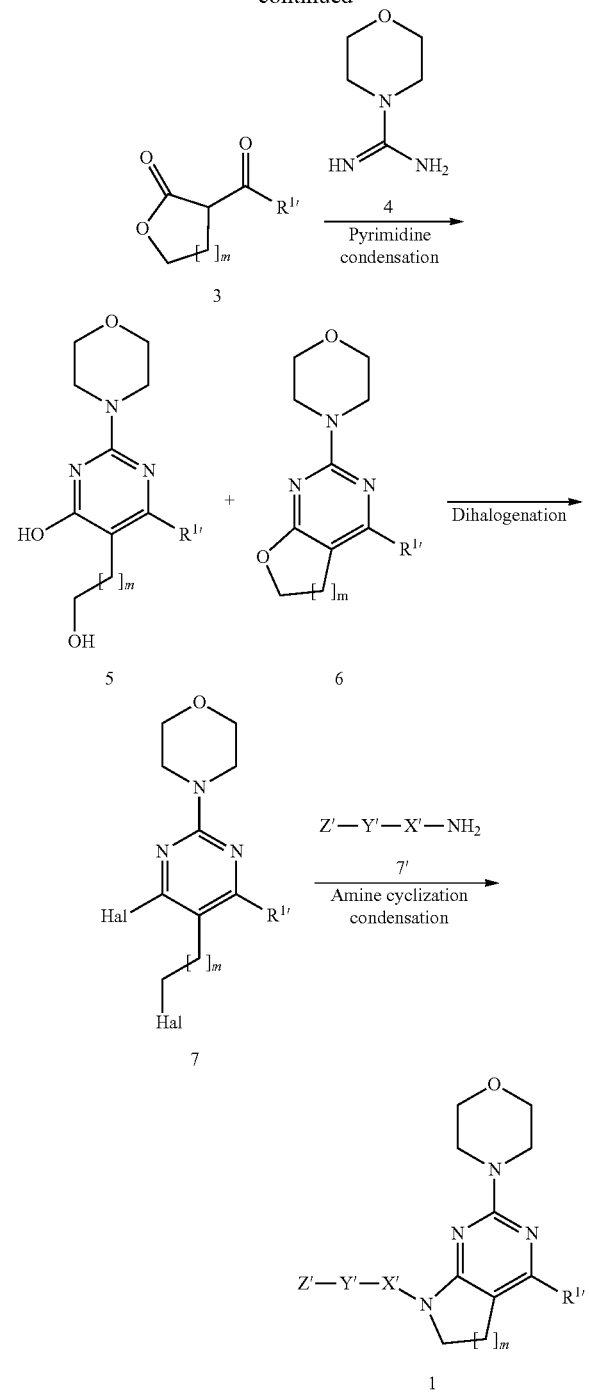

In the formulae, L is a leaving group, preferably a halogen atom, $C_{1-4}$alkoxy group or $C_{1-4}$alkylcarbonyloxy group, and more preferably a chlorine atom, methoxy group or methylcarbonyloxy group. In addition, Hal, X', Y', Z', m and $R^{1'}$ are the same as previously defined.

The present production process converts a pyrimidine derivative 5 or 6, obtained by condensing a 3-acyl-(γ or δ)-lactone derivative 3 and a guanidine derivative 4 (e.g., Lancaster Inc.) to a dihalogenated form 7 followed by cyclization and condensation with a primary amine to obtain Compound 1 of the present invention.

3-acyl-(γ or δ)-lactone derivative 3 can be easily prepared by acylating a commercially available (γ or δ)-lactone 2 using a known method (T. Miyadera, et al., Chem. Pharm. Bull. Jpn., Vol. 12, pp. 1344, 1964; K. Zbigniew, et al., J. Org. Chem., Vol. 52, pp. 4601, 1987; P. M. Pihko, et al., Synlett., Vol. 12, pp. 2115, 2004). Namely, a compound represented by formula 3 can be produced by reacting (γ or δ)-lactone 2 with an acylation agent 2' (such as carboxylic acid chloride, carboxylic acid ester or carboxylic acid anhydride) having a desired group $R^{1'}$ in a suitable solvent (such as tetrahydrofuran, dioxane, diethyl ether, dimethoxyethane, toluene or benzene, and preferably tetrahydrofuran, diethyl ether, toluene or benzene) in the presence of a suitable base (such as sodium methoxide, sodium ethoxide, potassium hydride, sodium hydride, potassium bis-trimethylsilylamide, sodium metal, sodium bis-trimethylsilylamide, lithium diisopropylamide or lithium bis-trimethylsilylamide, and preferably lithium diisopropylamide, lithium bis-trimethylsilylamide, sodium methoxide or sodium metal) and at a suitable temperature (although varying according to the types of solvent and base and the like, the reaction temperature is normally from −78° C. to room temperature and preferably −78 to 0° C.) Although varying according to the reaction temperature and the like, the reaction time is normally 1 minute to 24 hours and preferably 30 minutes to 5 hours.

Conversion from 3 obtained in the manner described above to pyrimidine derivative 5 or 6 can be carried out using a known aminic compound in the form of guanidine derivative 4 in compliance with a known condensation reaction (M. Samimi, et al., Tetrahedron Lett., Vol. 13, pp. 3457, 1972; A. Gangjee, et al., J. Med. Chem., Vol. 43, pp. 3837, 2000). Namely, a compound represented by formula 5 and formula 6 can be produced by reacting a compound represented by formula 3 with guanidine derivative 4 (including inorganic or organic acid salts thereof) in a suitable solvent (such as methanol, ethanol, t-butanol, tetrahydrofuran, dioxane, dimethoxyethanol, diethyl ether, dimethoxyethane, dimethylformamide, dimethylacetamide, dimethylsulfoxide, acetonitrile, toluene or benzene, and preferably methanol, ethanol, t-butanol, tetrahydrofuran, dimethoxyethanol or 1,4-dioxane) and in the presence of a suitable base (such as sodium hydroxide, potassium hydroxide, sodium methoxide, sodium ethoxide, potassium methoxide, potassium ethoxide, potassium t-butoxide, potassium hydride, sodium hydride, potassium bis-trimethylsilylamide, sodium bis-trimethylsilylamide, sodium metal, lithium bis-trimethylsilylamide, lithium diisopropylamide or triethylamine, and preferably sodium methoxide, sodium ethoxide, potassium methoxide, potassium ethoxide, potassium t-butoxide or triethylamine) and at a suitable temperature (although varying according to the types of solvent and base and the like, the reaction temperature is normally room temperature to 150° C. and preferably room temperature to 120° C.). The reaction mixture may be irradiated with microwaves to accelerate the reaction.

A compound represented by formula 7 can be produced by dihalogenating (and preferably dichlorinating) a pyrimidine derivative represented by formula 5 or 6, or a mixture thereof, according to a known method (A. Gangjee, et al., J. Med. Chem., Vol. 43, pp. 3837, 2000; P. Rajamanickam, et al., Indian J. Chem., Section B, Vol. 26B, pp. 910, 1987). Namely, a compound represented by formula 7 can be produced by reacting a pyrimidine derivative represented by formula 5 or 6 or a mixture thereof with a suitable halogenation agent (such as phosphorous oxychloride, thionyl chloride or Vilsmeier's reagent, and preferably phosphorous oxychloride or Vilsmeier's reagent) in a suitable solvent (such as dimethylsulfoxide, dichloromethane, tetrahydrofuran, dioxane, diethyl ether, dimethoxyethane, dimethylformamide, dimethylacetamide, dimethylsulfoxide, acetone, acetonitrile, toluene, benzene or nitrobenzene, and preferably dimethylformamide or dichloromethane) or in the absence of solvent, and at a suitable temperature (although varying according to the types of solvent and base and the like, the reaction temperature is, for example, room temperature to 150° C. and preferably room temperature to 120° C.). In addition, although varying according to the reaction temperature and the like, the reaction time is normally 30 minutes to 200 hours and preferably 5 to 100 hours. The reaction mixture may be irradiated with microwaves to accelerate the reaction.

A compound represented by formula 1 can be obtained by a known condensation reaction (A. Gangjee, et al., J. Med. Chem., Vol. 43, pp. 3837, 2000; C. A. Leach, et al., J. Med. Chem., Vol. 35, pp. 1845, 1992) of a compound represented by formula 7 with a suitable primary amine derivative 7' having desired groups —X'—Y'—Z' acquired commercially or synthesized. Namely, a compound represented by formula 1 can be produced by reacting a compound represented by formula 7 with a suitable primary amine derivative 7' having desired groups in a suitable solvent (such as tetrahydrofuran, dioxane, diethyl ether, dimethoxyethane, dimethylformamide, dimethylacetamide, dimethylsulfoxide, acetone, acetonitrile, toluene or benzene, and preferably toluene, 1,4-dioxane, or dimethoxyethane) in the presence of a suitable palladium catalyst (such as $PdCl_2$, $Pd(OAc)_2$, $Pd(OH)_2$, $Pd_2dba_3$, $PdCl_2[P(o-tol)_3]_2$, $Pd(O_2CCF_3)_2$, palladium carbon or palladium black, and preferably $PdCl_2$, $Pd(OAc)_2$, $Pd_2dba_3$, $PdCl_2[P(o-tol)_3]_2$ or $Pd(O_2CCF_3)_2$), a ligand (such as $PPh_3$, $P(o-tol)_3$, $P(t-Bu)_3$, dppf, BINAP, 2',6'-dimethoxy-2-(dicyclohexylphosphino)biphenyl (S-Phos), 2-dicyclohexylphosphino-2',4',6'-triisopropylbiphenyl (X-Phos), 4,5-bis(diphenylphosphino)-9,9-dimethylxanthene (Xantphos) or 1,3-bis(2,6-diisopropylphenyl)imidazole-2-ylidene), and a suitable base (such as sodium hydroxide, potassium hydroxide, sodium methoxide, sodium ethoxide, sodium t-butoxide, potassium t-butoxide, potassium bis-trimethylsilylamide, sodium bis-trimethylsilylamide, sodium metal, lithium bis-trimethylsilylamide, lithium diisopropylamide, cesium carbonate or potassium phosphate, and preferably cesium carbonate, sodium hydroxide, sodium t-butoxide, potassium phosphate or lithium bis-trimethylsilylamide). Although varying according to the types of solvent and base and the like, the reaction temperature is, for example, room temperature to 160° C. and preferably 100 to 160° C. In addition, although varying according to the reaction temperature and the like, the reaction time is normally 30 minutes to 10 hours and preferably 30 minutes to 5 hours. The reaction mixture may be irradiated with microwaves to accelerate the reaction.

Reaction Step 1B

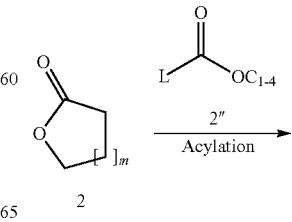

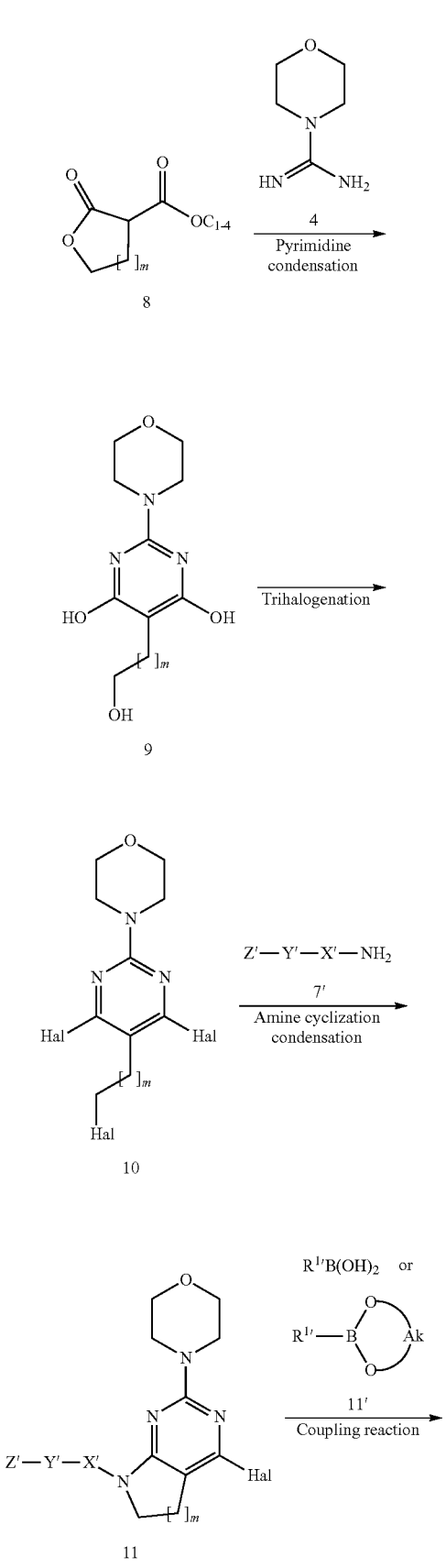

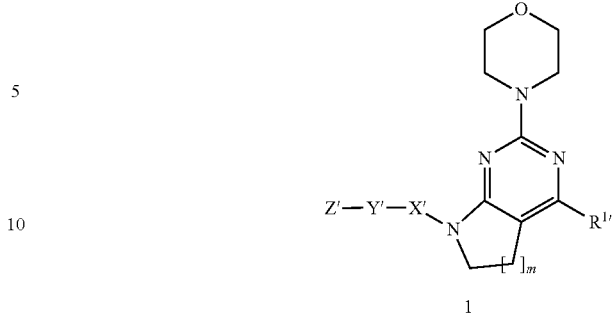

In the formulae, —OC$_{1-4}$ represents —C$_{1-4}$alkyloxy (and preferably -methoxy), -Ak- represents a linear or branched alkylene chain composed of 1 to 6 carbon atoms (and preferably -(1,1,2,2-trimethyl-ethylene)-), and L, m, Hal, X', Y', Z' and R$^{1'}$ are as previously defined.

The present production process is a process for obtaining compound 1 of the present invention by converting a trihydroxy derivative 9, obtained by condensing a 3-C$_{1-4}$alkoxycarbonyl-(γ or δ)-lactone 8 and guanidine derivative 4, to a trihalogen form (and preferably a trichloro form) 10, followed by carrying out a cyclization condensation reaction with a primary amine 7' having a desired group and a coupling reaction with a boronic acid derivative 11'.

The 3-C$_{1-4}$alkoxycarbonyl-(γ or δ)-lactone 8 can be produced by reacting with a suitable acylation agent (acylation agent 2" having a —C$_{1-4}$alkyloxy group instead of —R$^{1'}$ in acylation agent 2' in reaction step 1A (and at this time, L is preferably a chlorine atom, -methoxy or -methylcarbonyloxy), such as methyl chloroformate or dimethyl carbonate, can be used) in compliance with the method for obtaining 3 from 2 in reaction step 1A.

Conversion from the resulting 8 to the pyrimidine derivative 9 can be carried out by a condensation reaction with guanidine derivative 4 in compliance with the method for obtaining compound 5 or compound 6 from compound 3 of reaction step 1A (D. L. Dunn, et al., J. Org. Chem., Vol. 40, pp. 3713, 1975; K. Burdeska, et al., Helv. Chim. Acta., Vol. 64, pp. 113, 1981; P. Wang, et al., Huaxue Xuebao, Vol. 42, pp. 722, 1984). Namely, a compound represented by formula 9 can be produced by reacting a compound represented by formula 8 with guanidine derivative 4 (such as a guanidine derivative or inorganic acid salt or organic acid salt thereof) in a suitable solvent (such as methanol, ethanol, t-butanol, tetrahydrofuran, dimethoxyethanol or 1,4-dioxane) and in the presence of a suitable base (such as sodium methoxide, sodium ethoxide, potassium methoxide, potassium ethoxide, potassium t-butoxide or triethylamine) at a suitable temperature (from room temperature to the solvent boiling point).

A trihalogen form 10 represented by formula 10 can be produced in compliance with the reaction step for converting compound 5 or compound 6, or a mixture of compound 5 and compound 6, to 7 in reaction step 1A. Namely, a compound represented by formula 10 can be obtained by halogenating a compound represented by formula 9 in a suitable solvent (such as dimethylformamide or dichloromethane) or in the absence of solvent with a suitable halogenation agent (such as phosphorous oxychloride or thionyl chloride) at a suitable temperature (such as from room temperature to the solvent or reagent boiling point) (A. Gangjee, et al., J. Med. Chem., Vol. 43, pp. 3837, 2000; P. Rajamanickam, et al., Indian J. Chem., Section B, Vol. 26B, pp. 910, 1987).

A compound represented by formula 11 can be obtained by a condensation reaction with a compound represented by formula 10 and a primary amine 7' having the desired group —X'—Y'—Z' in compliance with the reaction step from compound 7 to compound 1 in reaction step 1A (A. Gangjee, et al., J. Med. Chem., Vol. 43, pp. 3837, 2000; C. A. Leach, et al., J. Med. Chem., Vol. 35, pp. 1845, 1992). Namely, a compound represented by formula II can be produced by reacting a compound represented by formula 10 with the primary amine 7' in a suitable solvent (such as toluene, 1,4-dioxane or dimethoxyethane), in the presence of a suitable palladium catalyst (such as $PdCl_2$, $Pd(OAc)_2$, $Pd_2dba_3$, $PdCl_2[P(o-tol)_3]_2$ or $Pd(O_2CCF_3)_2$), ligand (such as $PPh_3$, $P(o-tol)_3$, $P(t-Bu)_3$, dppf, BINAP, or 2',6'-dimethoxy-2-(dicyclohexylphosphino)biphenyl (S-Phos)), and a suitable base (such as cesium carbonate, sodium hydroxide, potassium t-butoxide, sodium hydride, potassium phosphate or lithium bis-trimethylsilylamide ($LiN(TMS)_2$) at a suitable temperature (room temperature to the solvent/reagent boiling point).

Furthermore, a compound represented by formula II can also be synthesized by carrying out a similar reaction in the absence of palladium catalyst and ligand in the reaction described above (E. Bisagni, et al., J. Org. Chem., Vol. 47, pp. 1500, 1982).

A compound represented by formula 1 can be obtained using a known condensation reaction between a compound represented by formula 11 and a boronic acid derivative having a desired group $R^{1'}$ represented by formula 11' (M. Havelkova, et al., Synlett., pp. 1145, 1999; G. Luo, et al., Tetrahedron Lett., Vol. 43, pp. 5739, 2002). Namely, in the reaction with boronic acid derivative 11', a compound represented by formula 1 can be produced by reacting a compound represented by formula 11 with the boronic acid derivative 11' (such as optionally substituted phenylboronic acid, optionally substituted heteroarylboronic acid or boronic acid ester such as arylboronic acid pinacol ester) in a suitable solvent (such as toluene, tetrahydrofuran, 1,4-dioxane or dimethoxyethane) and in the presence of a suitable palladium catalyst (such as $PdCl_2$, $Pd(OAc)_2$, $Pd_2dba_3$, $PdCl_2[P(o-tol)_3]_2$ or $Pd(O_2CCF_3)_2$), ligand (such as $PPh_3$, $P(o-tol)_3$, $P(t-Bu)_3$, dppf, BINAP, 2',6'-dimethoxy-2-(dicyclohexylphosphino)biphenyl (S-Phos), 1,3-bis(2,6-diisopropylphenyl)imidazol-2-ylidene)), and a suitable base (such as cesium carbonate, sodium hydroxide, potassium t-butoxide, potassium phosphate or lithium bis-trimethylsilylamide ($LiN(TMS)_2$) at a suitable temperature (0 to 110° C. and preferably 25 to 110° C.). In addition, a compound represented by formula 1 can also be produced by using a aryl zinc compound prepared with a known method instead of boronic acid (Metal-Catalyzed Cross-Coupling Reactions, 2nd ed., 2004, Vol. 2, pp. 815).

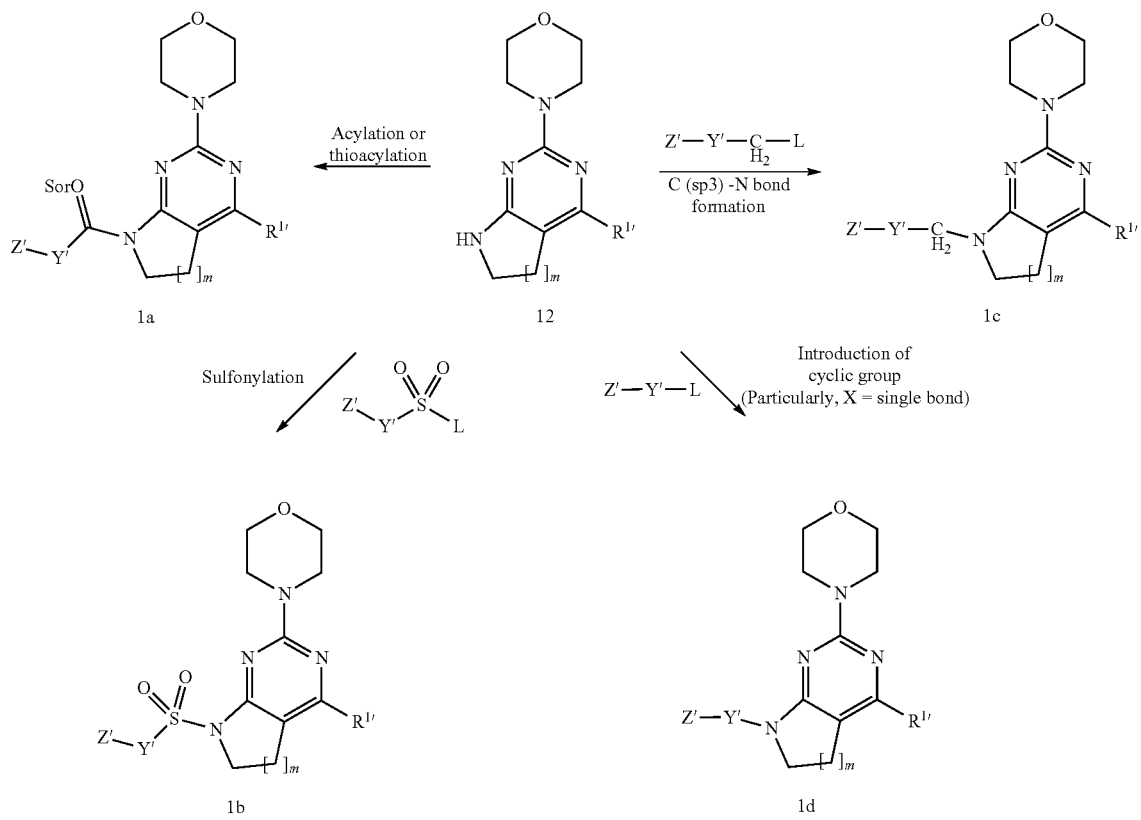

In the formulae, L, Y', Z', m and $R^{1'}$ are the same as previously defined. In addition, a "cyclic group" here refers to a desired cyclic group selected from the group of linking groups previously defined for Y.

The present production process is a typical production process for producing various variations of general formula (I) having groups represented by Z'—Y'—CO—, Z'—Y'—CS—, Z'—Y'—SO_2—, Z'—Y'—CH_2— or Z'—Y'— (at this time X' is a single bond) for the aforementioned groups Z'—Y'—X'—. Namely, this process allows the obtaining of compounds 1a to 1d by subjecting an amino compound represented by formula 12 able to be produced in a reaction step 3C to be described later to acylation, thioacylation, sulfonylation, C(sp3)-N bond formation reaction or cyclic group introduction reaction using known methods.

Production of Compounds Represented by Formula 1a (Part 1)

A compound represented by formula 1a can be easily prepared by acylating or thioacylating a compound represented by formula 12 (which can be prepared in reaction step 3C to be described later) by a known method (acylation reaction in the presence of a carboxylic halide, carboxylic anhydride or condensation agent (acid halide method, mixed acid anhydride method or condensation method)) (Reference: Experimental Chemistry Course, 4th ed. (Maruzen), Vol. 22, pp. 137; Tetrahedron, Vol. 57, pp. 1551, 2001).

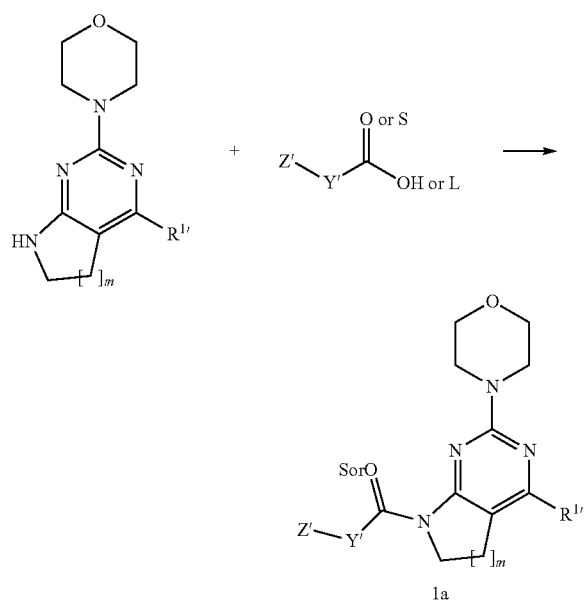

In the formulae, Y', Z', m and $R^{1'}$ are the same as previously defined, the L referred to here represents a leaving group (to be described in detail later), preferably represents a halogen atom, —$C_{1-4}$alkoxy or —$C_{1-4}$alkylcarbonyloxy, and more preferably a chlorine atom, -methoxy or -methylcarbonyloxy.

This reaction is achieved by reacting a compound represented by formula 12 with a carboxylic acid having a desired Z'—Y'— or a reactive derivative of said carboxylic acid (acid halide, mixed acid anhydride or active ester) in the step for producing compound 1a.

This reaction is carried out by, for example, an acid halide method, mixed acid anhydride method, active ester method or condensation method.

The acid halide method is achieved by producing an acid halide (L is a halogen atom and preferably a chlorine atom in the aforementioned formula Z'—Y'—CO-L or Z'—Y'—CS-L) by reacting a carboxylic acid (Z'—Y'—COOH), thiocarboxylic acid (Z'—Y'—CSOH) or dithiocarboxylic acid (Z'—Y'—CSSH) and the like having a desired Z'—Y'— with a halogenation agent (such as thionyl chloride, oxalic chloride or phosphorous pentachloride) in an inert solvent and then reacting this acid halide with a compound represented by formula 12 in an inert solvent. The reaction may be carried out in the presence of base at this time.

Examples of inert solvents used include dichloromethane, tetrahydrofuran, dioxane, diethyl ether, dimethoxyethane, acetone, acetonitrile, dimethylformamide, dimethylacetamide, dimethylsulfoxide, toluene and benzene, while preferable examples include dichloromethane, tetrahydrofuran, dimethoxyethane, dimethylformamide and acetonitrile.

Examples of bases used include triethylamine, diisopropylethylamine, pyridine, dimethylaminopyridine, potassium hydride, sodium hydride, potassium bis-trimethylsilylamide, sodium bis-trimethylsilylamide, sodium metal, potassium carbonate, cesium carbonate, lithium bis-trimethylsilylamide and lithium diisopropylamide, while preferable examples include triethylamine, diisopropyl ethylamine, pyridine, dimethylaminopyridine, potassium carbonate and cesium carbonate.

Although varying according to the types of solvent and base and the like, the reaction temperature is, for example, −20° C. to the boiling point of the solvent, and preferably room temperature to the boiling point of the solvent for both the reaction with halogenation agent and the reaction between the acid halide and compound 12. Although varying according to the reaction temperature and the like, the reaction time is 15 minutes to 100 hours and preferably 30 minutes to 80 hours.

The mixed acid anhydride method is achieved by reacting a $C_{1-6}$ alkyl halogenoformate or $C_{1-6}$ alkylcarboxylic anhydride (where, the $C_{1-6}$ alkyl represents a linear or branched alkyl group having 1 to 6 carbon atoms) with a carboxylic acid having a desired Z'—Y'— (such as Z'—Y'—COOH or Z'—Y'—CSOH) to produce a mixed acid anhydride (at this time L represents $C_{1-6}$ alkylcarbonyloxy and preferably methoxycarbonyloxy or ethoxycarbonyloxy in the aforementioned formula Z'—Y'—CO-L or Z'—Y'—CS-L) followed by reacting the mixed acid anhydride and a compound represented by formula 12. The reaction for producing the mixed acid anhydride is carried out by reacting a compound including a $C_{1-6}$ alkyl halogenocarbonate such as methyl chlorocarbonate, ethyl chlorocarbonate, isobutyl chlorocarbonate or hexyl chlorocarbonate (and preferably ethyl chlorocarbonate or isobutyl chlorocarbonate), a $C_{1-6}$alkyl carboxylic anhydride such as acetic anhydride or propionic anhydride (and preferably acetic anhydride), and is preferably carried out in an inert solvent in the presence of base.

The same bases and inert solvents used in the acid halide method of this step are used for the base and inert solvent. Although varying according to the type of solvent and the like, the reaction temperature is normally −20 to 50° C. (and preferably 0 to 30° C.). Although varying according to the reaction temperature and the like, the reaction time is normally 15 minutes to 24 hours (and preferably 30 minutes to 15 hours).

The condensation method is carried out by directly reacting a compound represented by formula 12 with a carboxylic acid (Z'—Y'—COOH), thiocarboxylic acid (Z'—Y'—CSOH) or dithiocarboxylic acid (Z'—Y'—CSSH) having a desired Z'—Y'— in an inert solvent, in the presence of a condensation agent and in the presence or absence of a base (and preferably in the presence of a base).

Examples of the inert solvents used include dichloromethane, tetrahydrofuran, dioxane, diethyl ether, dimethoxyethane, dimethylformamide, dimethylacetamide, dimethylsulfoxide, acetone, acetonitrile, toluene and benzene, while preferable examples include dichloromethane, tetrahydrofuran, dimethoxyethane, dimethylformamide and acetonitrile.

In addition, examples of the condensation agents used include 1,3-dicyclohexylcarbodiimide (DCC), 2-ethoxy-1-ethoxycarbonyl-1,2-dihydroquinoline (EEDQ), bromo-tris (pyrrolidino)-phosphonium hexafluorophosphate (PyBrOP), 1-ethyl-3-(3'-dimethylaminopropyl)carbodiimide hydrochloride (WSCI) or (benzotriazolyloxy)tripyrrolidino-phosphonium hexafluorophosphate (PyBOP), 3-hydroxy-4-oxo-3,4-dihydro-1,2,3-benzotriazine (HODhBt) and hydroxybenzotriazole (HOBt). In addition, other examples include the combination of 1-ethyl-3-(3'-dimethylaminopropyl) carbodiimide (EDC) and N-hydroxybenzotriazole (HOBt) and the combination of 1-ethyl-3-(3'-dimethylaminopropyl) carbodiimide hydrochloride (WSCI) and 3-hydroxy-4-oxo-3,4-dihydro-1,2,3-benzotriazine (HODhBt).

In addition, examples of bases used include diisopropylethylamine, triethylamine, pyridine, dimethylaminopyridine, potassium hydride, sodium hydride, potassium bistrimethylsilylamide, sodium bistrimethylsilylamide, sodium metal, potassium carbonate, cesium carbonate, lithium bistrimethylsilylamide, lithium diisopropylamide, and preferable examples include diisopropylethylamine, triethylamine, pyridine, potassium carbonate, cesium carbonate, sodium hydride.

This reaction allows production by reacting at a suitable reaction temperature (although varying according to the types of solvent and base and the like, the reaction temperature is, for example, 0° C. to the boiling point of the solvent and preferably room temperature to the boiling point of the solvent).

Production of Compounds Represented by Formula 1a (Part 2)

Production examples of compounds represented by formula 1a in particular those having a group Z'—Y'—CO— and group Z'—Y'—CS— in which Y' is a single bond (compounds represented by the following formula 1a') (method using isocyanate or thioisocyanate, method using a carbonylation agent or thiocarbonylation agent, or method using a carbamoyl halide or thiocarbamoyl halide)

Method Using Isocyanate or Thioisocyanate

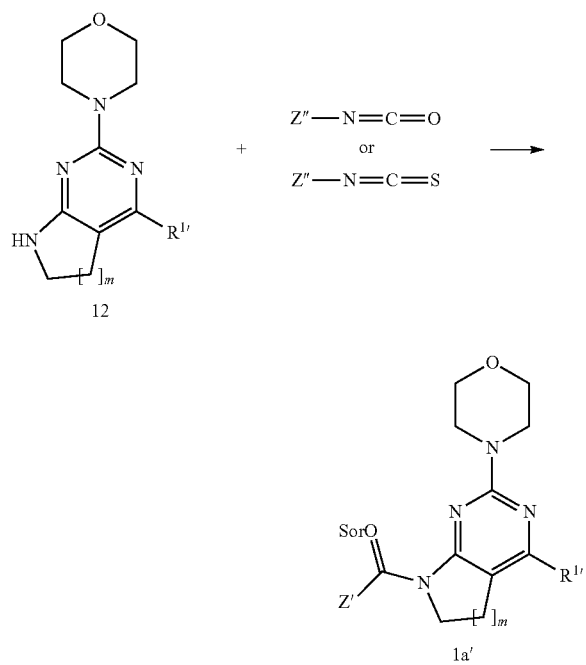

The reaction indicated in the above reaction formula (wherein, Y', m and R'' are the same as previously defined, and Z' and Z'' will be defined later) is a method for producing a compound represented by formula 1a' by reacting an isocyanate (Z''-N=C=O) or thioisocyanate (Z''-N=C=S) serving as a precursor able to be derived to a desired Z' with a compound represented by formula 12.

A compound represented by formula 1a' is particularly a compound represented by formula 1a in which Y' is a single bond and has a group Z'—CO— and a group Z'—CS—, and at this time, Z' particularly refers to a group among the groups of Z selected from the following groups: —NRR', —NR—$C_{1-6}$ alkylene-COOR', —NR—$C_{1-6}$ alkylene —CONR'R'', —NR—$C_{1-6}$alkylene-NR'R'', —NR—$C_{1-6}$ alkylene-NR'COR'', —NR—$C_{1-6}$ alkylene-OR', —NR-Cyc, —NR-Cyc-Cyc, —NR-Cyc-CO-Cyc, —NR-Cyc-CO—$C_{1-6}$alkylene-Cyc, —NR-Cyc-NR'-Cyc, —NR-Cyc-NR'—$C_{1-6}$ alkylene-Cyc, —NR—$C_{1-6}$ alkylene-Cyc, —NR—$C_{1-6}$ alkylene-Cyc-CO-Cyc and —NR—$C_{1-6}$ alkylene-Cyc-NR'-Cyc, or the above group protected with a suitable protecting group, and this method is a reaction for producing said compound.

This reaction can be carried out by reacting a compound represented by formula 12 with an isocyanate (Z''-N=C=O) or thioisocyanate (Z''-N=C=S) that is a precursor for deriving to a desired Z' (and at this time, examples of Z'' include —R (and this R is not a hydrogen atom), —$C_{1-6}$alkylene-COOR', —$C_{1-6}$ alkylene-CONR'R'', —$C_{1-6}$ alkylene-NR'R'', —$C_{1-6}$ alkylene-NR'COR'', —$C_{1-6}$ alkylene-OR', -Cyc, -Cyc-Cyc, -Cyc-CO-Cyc, -Cyc-CO—$C_{1-6}$ alkylene-Cyc, -Cyc-NR'-Cyc, -Cyc-NR'-$C_{1-6}$ alkylene-Cyc, —$C_{1-6}$ alkylene-Cyc, —$C_{1-6}$ alkylene-Cyc-CO-Cyc, —$C_{1-6}$ alkylene-Cyc-NR'-Cyc or the above groups protected with a suitable protecting group) in an inert solvent and in the presence of base.

Examples of inert solvents used include halogen-based solvents such as dichloromethane, chloroform, carbon tetrachloride or 1,2-dichloroethane, ether-based solvents such as diethyl ether, tetrahydrofuran, dioxane or dimethoxyethane, aromatic-based solvents such as benzene, toluene, xylene, quinoline or chlorobenzene, cyclohexane, dimethylsulfoxide, dimethylacetamide, dimethylimidazolidinone, dimethylformamide, N-methylpyrrolidone and acetonitrile, preferable examples include halogen-based solvents such as dichloromethane, chloroform, carbon tetrachloride or 1,2-dichloroethane, ether-based solvents such as diethyl ether, tetrahydrofuran, dioxane or dimethoxyethane, aromatic-based solvents such as benzene, toluene, xylene, quinoline or chlorobenzene, dimethylacetamide, dimethylformamide and N-methylpyrrolidone, and more preferable examples include 1,2-dichloroethane, tetrahydrofuran and toluene.

Examples of bases used include amines such as triethylamine, diisopropylethylamine, 1,8-diazabicyclo[5.4.0]-7-undecene, pyridine, dimethylaminopyridine and pyrazine, while preferable examples include triethylamine and dimethylaminopyridine. Although varying according to the type of solvent used and the like, the reaction temperature is normally −30 to 200° C. and preferably 20 to 120° C. Although varying according to the reaction temperature and the like, the reaction time is normally 10 minutes to 48 hours and preferably 30 minutes to 48 hours.

The compounds synthesized with the aforementioned reaction can also be synthesized by alternative methods. The following provides a description of those alternative methods.

[Alternative Method 1] Method Using Carbonylation Agent or Thiocarbonylation Agent

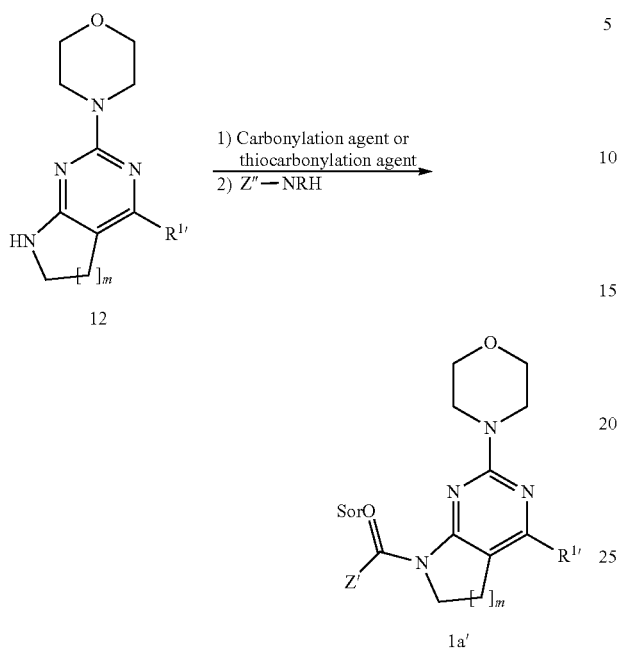

The reaction represented by the above reaction formula (wherein, Z', Z", m and R[1'] are the same as previously defined) is a reaction for producing a compound represented by the above formula 1a' by reacting a compound represented by formula 12 with an amine in the form of a precursor able to be derived to a desired Z'—(Z"—NHR) in an inert solvent and in the presence of a carbonylation agent or thiocarbonylation agent. In this reaction, Z"—NHR may be introduced to the compound represented by formula 12 after having reacted the carbonylation agent or thiocarbonylation agent, or the carbonylation agent or thiocarbonylation agent and Z"-NHR may be introduced simultaneously to the compound represented by formula 12. In addition, this reaction may also be carried out in the presence of base (and preferably in the presence of base).

Examples of the carbonylation agent include phosgene, triphosgene, carbonyldiimidazole, halogenoformic acid (and preferably chloroformic acid), halogenoformic acid $C_{1-6}$alkyl ester (preferably chloroformic acid $C_{1-6}$ alkyl ester, and more preferably methyl chloroformate or ethyl chloroformate), halogenoformic acid nitrophenyl ester (and preferably 4-nitrophenyl chloroformate), $C_{1-6}$ alkyl carboxylic acid anhydride (and preferably acetic anhydride), while preferable examples include phosgene, triphosgene, chloroformic acid, methyl chloroformate, ethyl chloroformate, 4-nitrophenyl chloroformate and acetic anhydride, and examples of thiocarbonylation agents include thiophosgene, with thiophosgene being used preferably.

In the amine serving as a precursor of a desired —Z'(Z"-NHR), Z" is at this time defined by the aforementioned method that uses isocyanate or thioisocyanate, and R is the same as previously defined.

The inert solvents and bases used are the same as those used in the method using isocyanate or thioisocyante described above, and although varying according to the type of solvent and the like, the reaction temperature is normally −30 to 200° C. and preferably 20 to 120° C. The reaction time is normally 10 minutes to 48 hours and preferably 30 minutes to 48 hours although varying according to the reaction temperature and the like.

[Alternative Method 2] Method Using Carbamoyl Derivative

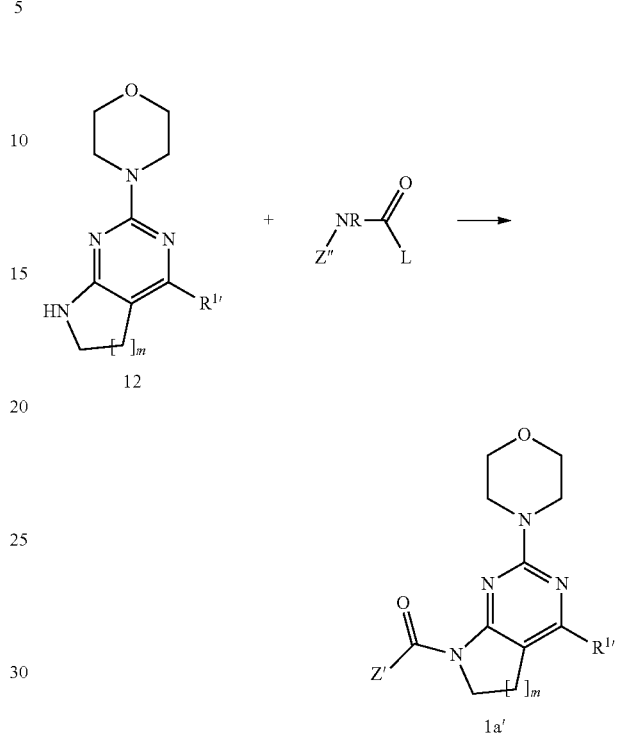

The reaction represented by the above reaction formula (wherein, Z', Z", m and R[1'] are the same as previously defined, and at this time, L is as described later) is a reaction for producing a compound represented by formula 1a' (and particularly a compound in which X=CO) by reacting a carbamoyl derivative in the form of a precursor able to be derived to a desired Z' and a compound represented by formula 12 in an inert solvent. At this time, the reaction may be carried out in the presence of base.

The carbamoyl derivative is represented by the above formula Z"-NR—CO-L and at this time, L is a halogen atom (and preferably a chlorine atom) or $C_{1-6}$ alkoxy. A preferable example of the carbamoyl derivative is carbamoyl chloride.

In addition, the inert solvents and bases used are the same as those used in the method using isocyanate or thioisocyante described above, and although varying according to the type of solvent and the like, the reaction temperature is normally −30 to 200° C. and preferably 20 to 120° C. The reaction time is normally 10 minutes to 48 hours and preferably 30 minutes to 48 hours although varying according to the reaction temperature and the like.

Production of Compounds Represented by Formula 1b

A compound represented by formula 1b can be easily prepared by sulfonylating a compound represented by formula 12 according to a known method (M. Loegers, et al., J. Am. Chem. Soc., Vol. 117, pp. 9139, 1995; H. Tanaka, et al., Bull. Chem. Soc. Jpn., Vol. 61, pp. 310, 1988; J. F. Rousseau, et al., Heterocycles, Vol. 55, pp. 2289, 2001). Namely, a compound represented by formula 1b can be produced by reacting compound 12 with a sulfonylation agent having a desired group —Y'—Z' (such as sulfonic acid chloride, sulfonic acid anhydride, sulfamoyl chloride, sulfonic acid imide or sulfamoyl ester, and preferably sulfonic acid chloride, sulfonic acid anhydride or sulfamoyl chloride) in a suitable solvent (such as dichloromethane, tetrahydrofuran, dioxane, diethyl ether, dimethoxyethane, dimethylformamide, dimethylacetamide, dimethylsulfoxide, acetone, acetonitrile, toluene or benzene, and preferably dichloromethane, tetrahydrofuran, dimethoxyethane, dimethylformamide or acetonitrile) in the presence of suitable a base (such as potassium hydride, sodium hydride, potassium bis-trimethylsilylamide, sodium bis-trimethylsilylamide, sodium metal, lithium bis-trimethylsilylamide, lithium diisopropylamide, triethylamine, potassium carbonate or cesium carbonate, and preferably triethylamine, potassium carbonate, cesium carbonate or sodium hydride) and at a suitable temperature (although varying according to the types of solvent, base and the like, the reaction temperature is, for example, 0° C. to the boiling point of the solvent, and preferably room temperature to the boiling point of the solvent). In addition, although varying according to the reaction temperature and the like, the reaction time is normally 30 minutes to 48 hours and preferably 30 minutes to 10 hours.

Production of Compounds Represented by Formula 1c

A compound 1c having a group Z'—Y'—CH$_2$— can be produced by subjecting Z'—Y'—CH$_2$-L having a desired group —Y'—Z' and a compound represented by formula 12 to a C—N bond formation reaction. This C—N bond formation reaction can be easily carried out by a known N-alkylation reaction (Handbook of Organic Chemistry Experimentation, 1st ed. (1990), Vol. 3, pp. 98). Namely, a compound represented by formula 1c can be produced by reacting compound 12 with a reagent Z'—Y'—CH$_2$-L having a desired group Z'—Y'— (wherein, L refers to a leaving group and particularly a halogen atom, sulfonic acid ester or dialkyl sulfate, and preferably an alkyl halide or sulfonic acid ester) in a suitable solvent (such as tetrahydrofuran, dioxane, diethyl ether, dimethoxyethane, dimethylformamide, dimethylacetoamide, dimethylsulfoxide, acetone, acetonitrile, toluene or benzene, and preferably tetrahydrofuran, dimethoxyethane, dimethylformamide, acetone or acetonitrile) in the presence of a suitable base (such as sodium hydroxide, potassium hydroxide, sodium methoxide, sodium ethoxide, potassium hydride, sodium hydride, potassium bis-trimethylsilylamide, sodium bis-trimethylsilylamide, sodium metal, lithium bis-trimethylsilylamide, lithium diisopropylamide, triethylamine, potassium carbonate, cesium carbonate or tributylphosphine, and preferably triethylamine, potassium carbonate, cesium carbonate, sodium hydroxide, sodium hydride or tributylphosphine) and at a suitable temperature (although varying according to the types of solvent, base and the like, the reaction temperature is, for example, 0° C. to the boiling point of the solvent and preferably room temperature to the boiling point of the solvent). In addition, although varying according to the reaction temperature and the like, the reaction time is normally 30 minutes to 48 hours and preferably 30 minutes to 10 hours.

Production of Compounds Represented by Formula 1d (Part 1)

A compound 1d having a group Z'—Y'—X'— in which X' is a single bond can be produced by introducing a cyclic group by a coupling reaction between a compound represented by formula 12 and Z'—Y'-L having a desired cyclic group selected from the group of linking groups for Y of general formula (I) (wherein, L refers to a leaving group and particularly a halogen atom or -trifluoromethanesulfonyloxy, and preferably a bromine atom, iodine atom or -trifluoromethanesulfonyloxy). In other words, this coupling reaction is a reaction for introducing a cyclic group by, for example, a known coupling reaction with a halogenated cyclic group (Org. Lett., Vol. 2, pp. 1101, 2000; Tetrahedron Lett., Vol. 42, pp. 7155, 2001). Namely, the compound 1d can be produced by reacting compound 12 with Z'—Y'-L in a suitable solvent (such as tetrahydrofuran, dioxane, diethyl ether, dimethoxyethane, dimethylformamide, dimethylacetamide, dimethylsulfoxide, acetone, acetonitrile, toluene or benzene, and preferably toluene, 1,4-dioxane, dimethoxyethane, tetrahydrofuran or dimethylformamide) in the presence of a suitable palladium catalyst (such as PdCl$_2$, Pd(OAc)$_2$, Pd$_2$dba$_3$, PdCl$_2$[P(o-tol)$_3$]$_2$, Pd(O$_2$CCF$_3$)$_2$, palladium carbon, palladium black or Pd(OH)$_2$, and preferably PdCl$_2$, Pd(OAc)$_2$, Pd$_2$dba$_3$, PdCl$_2$[P(o-tol)$_3$]$_2$ or Pd(O$_2$CCF$_3$)$_2$), a ligand (such as P(o-tol)$_3$, BINAP, DPPF, P(t-Bu)$_3$, 2-dicyclohexylphosphino-2'-(N,N-dimethylamino)biphenyl, 2-(di-t-butylphosphino) biphenyl, 2-(dicyclohexylphosphino)biphenyl, 2',6'-dimethoxy-2-(dicyclohexylphosphino)biphenyl, 2',4',6'-triisopropyl-2-(dicyclohexylphosphino)biphenyl, 4,5-bisdiphenylphosphanyl-9,9-dimethyl-9H-xanthene, 4,5-bis[bis(3,5-bistrifluoromethylphenyl)phosphanyl]-9,9-dimethyl-9H-xanthene or 1,3-diallyldihydroimidazolium salt, and preferably BINAP, 2',6'-dimethoxy-2-(dicyclohexylphosphino)biphenyl or 2',4',6'-triisopropyl-2-(dicyclohexylphosphino)biphenyl), and a suitable base (such as sodium hydroxide, potassium hydroxide, sodium methoxide, sodium ethoxide, potassium bis-trimethylsilylamide, sodium bis-trimethylsilylamide, lithium bis-trimethylsilylamide (LiN(TMS)$_2$), lithium diisopropylamide, cesium carbonate, potassium t-butoxide or potassium phosphate, and preferably cesium carbonate, sodium hydroxide, potassium t-butoxide, potassium phosphate or lithium bis-trimethylsilylamide) and at a suitable temperature (although varying according to the types of solvent, base and the like, the reaction temperature is, for example, 0° C. to the boiling point of the solvent and preferably room temperature to the boiling point of the solvent). In addition, although varying according to the reaction temperature and the like, the reaction time is normally 30 minutes to 100 hours and preferably 30 minutes to 24 hours.

Production of Compounds Represented by Formula 1d (Part 2)

A compound represented by formula id can also be produced by going through a two-step reaction in addition to the method described above.

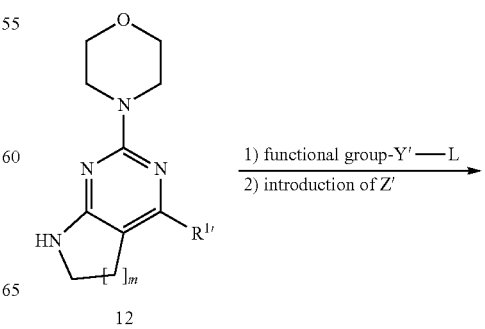

12

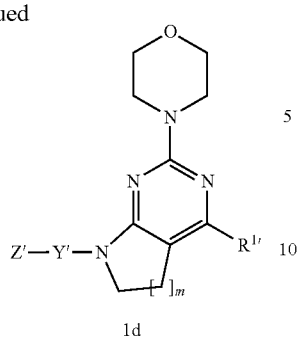

1d

The reaction represented by the above reaction formula [wherein, Y', Z', m, R[1'] and L are the same as previously defined, and at this time, L particularly represents a halogen atom or trifluoromethanesulfonyloxy (and preferably a bromine atom or iodine atom), and the functional group is as described below] is a reaction for producing a compound represented by formula Id by sequentially carrying out reactions for coupling a compound represented by formula 12 and a compound represented by (functional group)-Y'-L followed by introducing Z'.

The coupling reaction between a compound represented by formula 12 and a compound represented by (functional group)-Y'-L can be carried out in the same manner as the production process of a compound represented by formula Id (part 1) as previously described. The functional group in this (functional group)-Y'-L is a functional group capable of being involved in a reaction for introducing Z' (including various coupling reactions by, for example, an acid halide method, active ester method, condensation method or reductive amination method), examples of which include substituents containing a group such as a halogen (chloro, bromo or iodo), carboxyl, $C_{1-6}$ alkoxycarbonyl or formyl group (and at this time, the formyl group may be protected, and examples of protected formyl groups include di-$C_{1-6}$ alkoxymethyl and cycloacetal groups, while preferable examples include dimethoxymethyl, diethoxymethyl, 1,3-dioxan-2-yl and 1,3-dioxolan-2-yl groups). Preferable examples of functional groups capable of being involved in the reaction include chloro, carboxyl, methoxycarbonyl, ethoxycarbonyl and formyl groups (and these are preferably protected).

The reaction for continuously introducing Z' is achieved by carrying out a coupling reaction with a precursor derived to a desired Z' on a compound obtained in the coupling reaction between a compound represented by formula 12 and a compound represented by (functional group)-Y'-L.

For example, in the case the functional group capable of being involved in the reaction in the (functional group) is a carboxyl or $C_{1-6}$ alkoxycarbonyl (and preferably a carboxyl or methoxycarbonyl), this reaction is achieved by an esterification or amidation reaction (and can be carried out in the same manner as the aforementioned acylation reaction, namely an acid halide method, mixed acid anhydride method, active ester method, condensation method and the like) with Z''-OH or Z''-NHR (where Z'' is the same as previously defined, and R is as defined in claim 1).

In addition, in the case the functional group able to be involved in the reaction in the (functional group) is a formyl group, this reaction can be achieved by a coupling reaction in the form of, for example, a reductive amination reaction with Z''-NHR or Cyc' (and at this time, Cyc' is a nitrogen-containing saturated hydrocarbon ring, may further contain 1 to 3 other heteroatoms such as a nitrogen atom, oxygen atom or sulfur atom, and said nitrogen-containing saturated hydrocarbon ring preferably has 5 to 6 members, examples of which include imidazolidine, oxazolidine, piperazine and morpholine). If the reductive amidation reaction is carried out in the presence of Z''-NHR (and at this time, Z'' and R are the same as previously defined) in addition to a hydride reducing agent, reductive amination occurs and the corresponding amine is obtained. Examples of hydride reducing agents include sodium cyanoborohydride and sodium triacetoxyborohydride, and sodium triacetoxyborohydride is preferable.

Moreover, in the case the function group capable of being involved in the reaction in the (functional group) is a halogen (and preferably chloro), the reaction can be carried out by a coupling reaction with Z'—H (and at this time, an example of Z' is -Cyc, and at this time Cyc is preferably a nitrogen-containing saturated hydrocarbon ring, may further contain 1 to 3 other heteroatoms such as a nitrogen atom, oxygen atom or sulfur atom, and said nitrogen-containing saturated hydrocarbon ring preferably has 5 to 6 members, and is more preferably pyrimidine, piperazine or morpholine and the like) in the same manner as the production process of a compound represented by formula 1d (part 1).

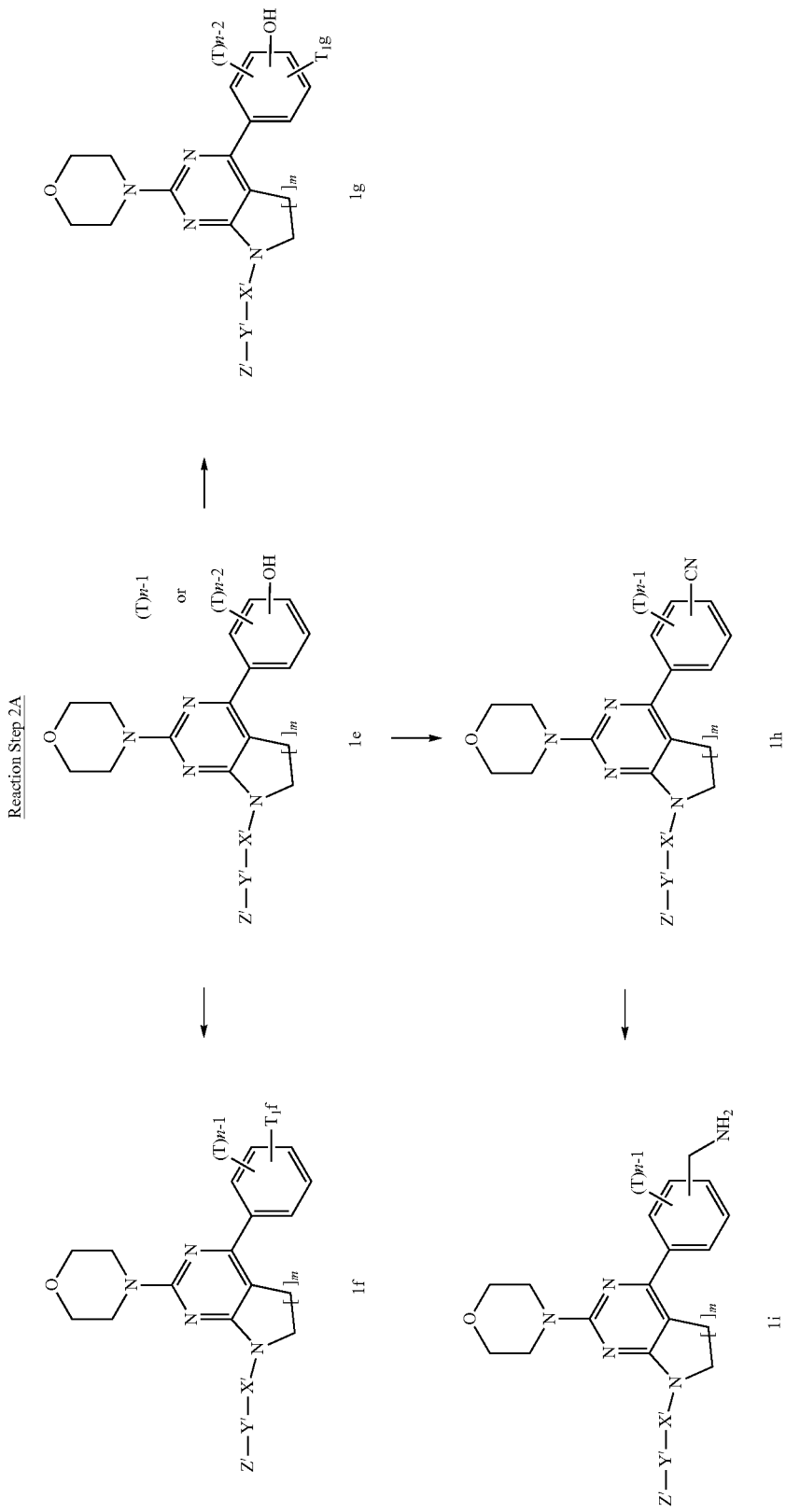

In the above formulae, X', Y', Z', T, n and m are the same as previously defined. In addition, -$T_1f$ represents particularly a group selected from —OR, —O-halogeno-$C_{1-6}$alkyl, —O—$C_{1-6}$ alkylene-Cyc, —O—COOR, —O—COR and —O—CONRR' (and at this time, R, R' and Cyc are the same as previously defined) among the previously defined T, or -sulfonyloxy. Further, -$T_1g$ represents particularly -halogen among the previously defined T, or —$CH_2$—NRR'.

This production process is a process for producing a compound in which $R_1$ in general formula (I) is $R_1a$ in particular. This process includes a method for obtaining compound 1f by applying to O-alkylation, acylation and sulfonylation reactions using known methods, a method for obtaining compound 1g by applying to a reaction for introducing an electrophilic substituent into an aromatic ring having a hydroxy substituent, and a method for obtaining a corresponding amino compound 1i by converting compound 1e to a cyano compound represented by formula 1h followed by reduction, with respect a hydroxy-substituted compound represented by formula 1e in particular among those compounds represented by general formula (I) capable of being synthesized in reaction step 1A to C.

Preparation of O-Alkylated Compound Represented by Formula 1f

An O-alkylated compound represented by formula 1f (a compound in which $R^1$ represents a phenyl group ($R_1a$) and a substituent-$T_1f$ thereof is —OR, —O-halogeno-$C_{1-6}$ alkyl or —O—$C_{1-6}$ alkylene-Cyc in particular among the previously defined T) can be produced by reacting a compound represented by formula 1e with an alkylation agent (such as an alkyl halide, sulfonic acid ester or epoxide) having a desired group (such as —R, -halogeno-$C_{1-6}$ alkyl or —$C_{1-6}$alkylene-Cyc) in a suitable solvent (such as methanol, ethanol, tetrahydrofuran, dimethoxyethane, dimethylformamide, acetone or acetonitrile), in the presence of a suitable base (such as triethylamine, potassium carbonate, cesium carbonate, sodium hydroxide, sodium hydride or tributylphosphine) and at a suitable temperature (0° C. to boiling point of the solvent). As an alternative method not using base, a compound represented by formula 1f can be synthesized by alkylation using a Mitsunobu reaction (Organic Reactions, New York, Vol. 42, pp. 335, 1992).

Preparation of O-Acylated Compound Represented by Formula 1f

An O-acylated compound represented by formula 1f (a compound wherein $R^1$ is a phenyl group ($R_1a$) and a substituent -$T_1f$ thereof is —O—COOR, —O—COR or —O—CONRR' in particular among the previously defined T) can be produced by reacting a compound represented by formula 1e with a desired acylation agent (such as carboxylic acid chloride, carboxylic acid anhydride, chloroformic acid ester, carbamoyl chloride or isocyanate) in a suitable solvent (such as tetrahydrofuran, dimethoxyethane, dichloromethane, dimethylformamide, acetone or acetonitrile) and in the presence of a suitable base (such as triethylamine, pyridine, potassium carbonate, cesium carbonate, sodium hydroxide or sodium hydride) at a suitable temperature (0 to 150° C.).

Production of O-Sulfonylated Compound Represented by Formula 1f

An O-sulfonylated compound represented by formula 1f (a compound wherein $R^1$ is a phenyl group ($R_1a$) and a substituent -$T_1f$ thereof is -sulfonyloxy in particular) can be produced by reacting compound 1e with a desired sulfonylation agent (such as sulfonic acid chloride, sulfonic acid anhydride or sulfamoyl chloride) in a suitable solvent (such as tetrahydrofuran, dimethoxyethane, dichloromethane, dimethylformamide, acetone or acetonitrile) and in the presence of a suitable base (such as triethylamine, pyridine, potassium carbonate, cesium carbonate, sodium hydroxide or sodium hydride) at a suitable temperature (0 to 150° C.). Compounds having an —O-sulfonyl group as a substituent of the phenyl group are useful as intermediate compounds for obtaining compounds of formula (I) of the present invention.

Preparation of Compounds Represented by Formula 1g

A compound represented by formula 1g (a compound wherein $R^1$ is a phenyl group ($R_1a$) and a substituent -$T_1g$ thereof is -halogen, —$CH_2$—NRR' or —$CH_2$-(nitrogen-containing heterocyclic ring) in particular among the previously defined T) can be synthesized by a known electrophilic substitution reaction on the aromatic ring having a hydroxy substituent of a compound represented by formula 1e (for example, Journal of Medicinal Chemistry, 46(23), 4933-4945, 2003). Namely, a halogenated compound represented by formula 1g can be obtained by reacting a compound represented by formula 1e with a suitable halogenation agent (such as a bromine molecule, N-bromosuccinimide (NBS), iodine molecule, iodine chloride, N-iodosuccinimide (NIS) or N-chlorosuccinimide (NCS)). In addition, a compound represented by formula 1g in which —$CH_2$—NRR' or —$CH_2$-(nitrogen-containing heterocyclic ring) has been introduced can be produced by reacting a desired secondary amine (such as dimethylamine, diethylamine, piperidine, pyrrolidine, N-methylpiperazine or morpholine) and formaldehyde in the presence of a suitable acid catalyst (such as hydrochloric acid, sulfuric acid, acetic acid, trifluoroacetic acid or methanesulfonic acid).

Preparation of Compounds Represented by Formula 1h

A compound represented by formula 1h (a compound in which $R^1$ is a phenyl group ($R_1a$) and a substituent T thereof is —CN in particular) can be produced by cyanating a hydroxy substituent of a compound represented by formula 1e using a known method. Namely, a compound represented by formula 1h can be produced by trifluoromethanesulfonylation of compound 1e with a trifluoromethanesulfonylation reagent (such as trifluoromethanesulfonic acid anhydride) in a suitable solvent (such as tetrahydrofuran) and in the presence of a suitable base (such as triethylamine or pyridine), and reacting the resulting trifluoromethanesulfonic acid ester with a cyanation agent (such as zinc cyanide or sodium cyanide) in a suitable solvent (such as dimethylformamide, dimethyl ether or tetrahydrofuran) and in the presence of a suitable palladium catalyst (such as $PdCl_2$, $Pd(OAc)_2$, $Pd_2dba_3$, $PdCl_2[P(o\text{-}tol)_3]_2$ or $Pd(O_2CCF_3)_2$) and a ligand (such as $P(o\text{-}tol)_3$, BINAP, DPPF, $P(t\text{-}Bu)_3$ or 2-dicyclohexylphosphino-2'-(N,N-dimethylamino)biphenyl) at a suitable temperature (room temperature to the boiling point of the solvent/reagents). The compound having a cyano group as the substituent, this compound is useful as an intermediate compound for obtaining a compound represented by formula (I) of the present invention.

Preparation of Compounds Represented by Formula 1i

Compound 1i in which substituent T is —$CH_2$—$NH_2$ in particular can be produced by carrying out reduction of the cyano group of compound 1h in a suitable solvent (such as methanol or tetrahydrofuran) and in the presence of a palladium catalyst (such as palladium carbon or palladium hydroxide) in a hydrogen atmosphere. The compound in which substituent T is —$CH_2$—$NH_2$ in particular is useful as an intermediate compound for obtaining a compound of formula (I) of the present invention.

Reaction Step 2B

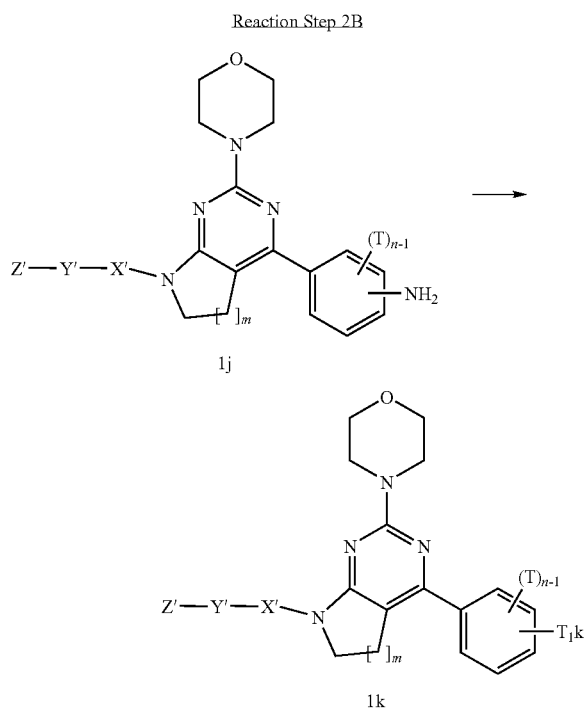

1j

1k

In the above formulae, X', Y', Z', m, n and T are the same as previously defined, and $T_1k$ is particularly —NRSO$_2$R' or —NRCOR' among the previously defined T (and at this time, R and R' are the same as defined in formula (I)).

This production process is a process for obtaining Compound 1k by subjecting an amino-substituted compound represented by formula 1j to an N-acylation (introduction of a —CO—C$_{1-6}$ alkyl group) or N-sulfonylation reaction using a known method. Production can be carried out using a known method similarly to the case of reaction step 1C (such as a condensation reaction using a carboxylic acid and the like and dicyclohexylcarbodiimide or using a water-soluble carbodiimide reagent and the like, or an acylation reaction using an acid anhydride or acid halide: Experimental Chemistry Course, 4th ed. (Maruzen), Vol. 22, pp. 137; Tetrahedron, Vol. 57, pp. 1551, 2001). A compound represented by formula 1k obtained in this manner is useful as a compound of formula (I) or as an intermediate compound for obtaining a compound of formula (I).

-continued

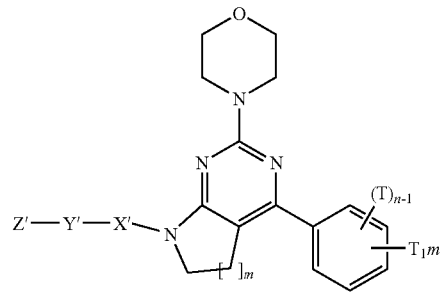

1m

In the above formulae, X', Y', Z', m, n and T are the same as previously defined, and -T$_1$m refers particularly to a group selected from —COOR, —COO—C$_{1-6}$ alkylene-OR, —COO—C$_{1-6}$alkylene-NRR', —COO—C$_{1-6}$ alkylene-Cyc, —CONRR', —CONR—C$_{1-6}$alkylene-OR', —CONR—C$_{1-6}$ alkylene-NR'R'', —CONR—C$_{1-6}$ alkylene-CONR'R'', —CONR-Cyc or —CONR—C$_{1-6}$ alkylene-Cyc among the previously defined T.

This production process is a process for producing a compound in which R$_1$ in general formula (I) is R$_1$a in particular. Among those compounds represented by general formula (I) able to be synthesized in compliance with reaction steps 1A to C, a compound represented by formula 1m can be obtained by carrying out an esterification or amidation reaction using a known method on a carboxylic acid compound represented by formula 1l. A compound represented by formula 1m can be produced by a condensation reaction (esterification or amidation reaction, Experimental Chemistry Course, 4th ed. (Maruzen), Vol. 22, pp. 137; Tetrahedron, Vol. 57, pp. 1551, 2001) between a carboxylic acid compound represented by formula 1l and an alcohol having a desired group (such as HOR, HO—C$_{1-6}$alkylene-OR, HO—C$_{1-6}$ alkylene-NRR' or HO—C$_{1-6}$ alkylene-Cyc) or an amine having a desired group (such as HNRR', HNR—C$_{1-6}$ alkylene-OR', HNR—C$_{1-6}$ alkylene-NR'R'', NHR—C$_{1-6}$ alkylene-CONR'R'', HNR-Cyc or HNR—C$_{1-6}$ alkylene-Cyc) using a condensation agent such as dicyclohexylcarbodiimide or water-soluble carbodiimide reagent.

Reaction Step 2C

Reaction Step 2D

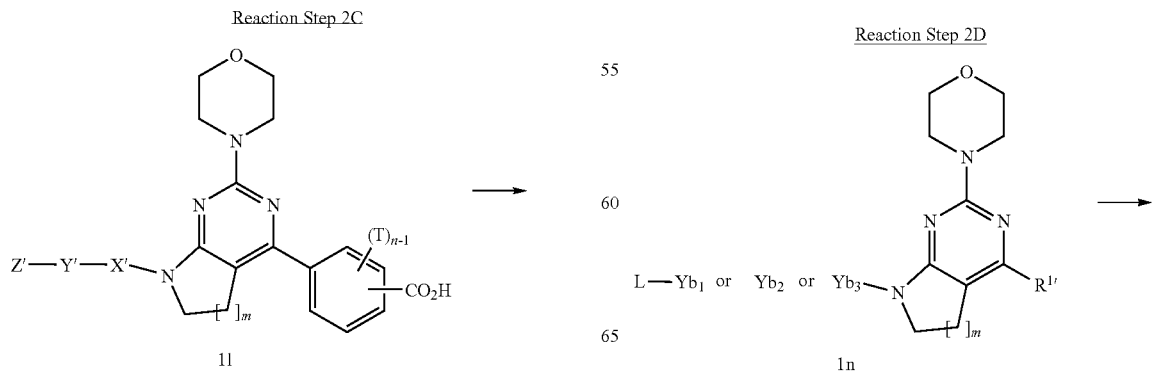

1l

1n

-continued

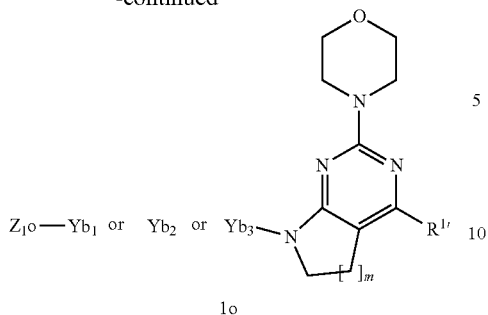

1o

In the above formulae, $Yb_1$, $Yb_2$, $Yb_3$, m, $R^{1\prime}$ and L are the same as previously defined, and $Z_1$o is particularly a group selected from —OR, —O-halogeno-$C_{1-6}$ alkyl, —NRR', —NR—$C_{1-6}$ alkylene-NR'R" or —NR—$C_{1-6}$ alkylene-OR' among the previously defined Z (and R, R' and R" are the same as previously defined).

This production process is a process for obtaining a compound represented by formula 1o by substituting an amino group (such as —NRR', —NR—$C_{1-6}$ alkylene-NR'R" or —NR—$C_{1-6}$alkylene-OR') or an alkoxy group (such as —OR, —O-halogeno-$C_{1-6}$ alkyl or —O—$C_{1-6}$ alkylene-Cyc) into a compound represented by formula in that is one aspect of a compound of formula (I), in which X is particularly a single bond and Y is particularly $Yb_1$, $Yb_2$ or $Yb_3$ having a leaving group L (and particularly preferably a halogen atom and the like) on the aromatic ring represented by $Yb_1$, $Yb_2$ or $Yb_3$ using a known substitution method (example of amino group substitution: E. Bisagni, et al., J. Org. Chem., Vol. 47, pp. 1500, 1982; example of alkoxy group substitution: L. W. Deady, et al., Australian J. Chem., Vol. 35, pp. 2025, 1982). In addition, an amino group-substituted compound 1m can also be produced by a coupling reaction with a desired amine using a palladium catalyst in the same manner as the production of Compound 1d in the previously described reaction step 1C.

Reaction Step 2E

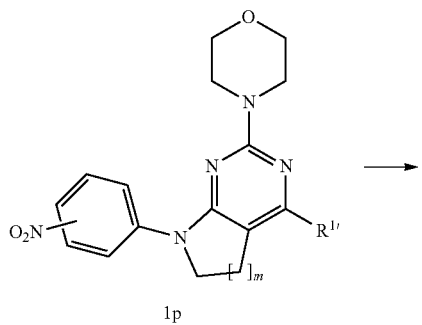

1p

-continued

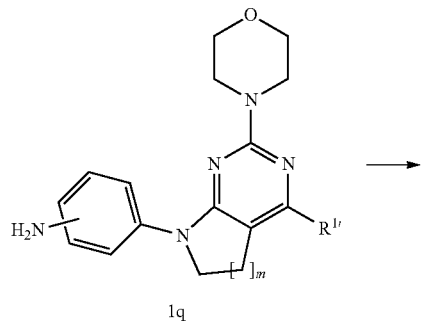

1q

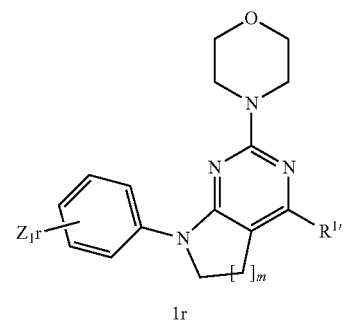

1r

In the above formulae, m and $R^{1\prime}$ are the same as previously defined, and $Z_1$r is particularly a group selected from —NRR', —NR—$C_{1-6}$ alkylene-NR'R", —NR—$C_{1-6}$alkylene-OR' or —$NRSO_2R'$ among the previously defined Z (and R, R' and R" are the same as previously defined).

This production process is a process for obtaining a corresponding amino compound 1q (one aspect of a compound of formula (I)) by reducing a nitro compound represented by formula 1p, and further obtaining a compound represented by formula 1r by amidation, carbamation, ureation or sulfonylation. These compounds can be produced using a known method similarly to the case of reaction step 1C. A compound represented by formula 1r obtained in this manner is useful as a compound of formula (I) or as an intermediate compound for obtaining a compound of formula (I).

Reaction Step 3A General synthetic process of synthetic block - substituted aniline

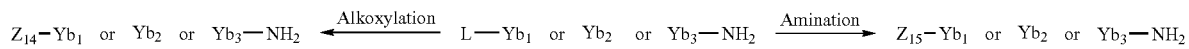

In the above formulae, $Yb_1$, $Yb_2$, $Yb_3$ and L are the same as previously defined, $Z_{14}$ particularly refers to —OR or —O-halogeno-$C_{1-6}$ alkyl among the previously defined Z, and $Z_{15}$ particularly refers to a group selected from —NRR', —NR—$C_{1-6}$ alkylene-NR'R" or —NR—$C_{1-6}$ alkylene-OR' among the previously defined Z (and R, R' and R" are the same as previously define).

This production process is a process for obtain a compound represented by formula 14 or formula 15, respectively, by substituting an amino group (such as —NRR', —NR—$C_{1-6}$ alkylene-NR'R" or —NR—$C_{1-6}$ alkylene-OR') or an alkoxy group (such as —OR, —O-halogeno-$C_{1-6}$ alkyl or —O—$C_{1-6}$alkylene-Cyc) into a compound having a leaving group (and particularly preferably a halogen atom) on the heterocyclic ring represented by formula 13 by a nucleophilic substitution reaction using a known method as explained in reaction step 2D.

Reaction Step 3B:
General synthetic process of synthetic block - boronic acid

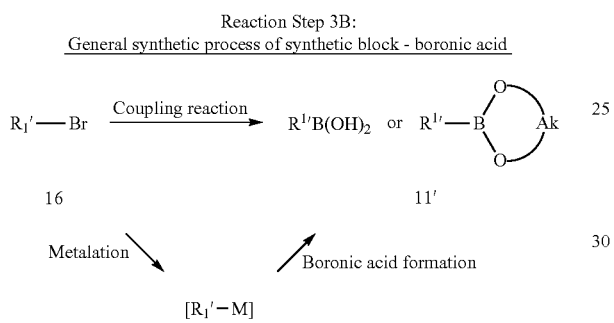

In the above formulae, $R^{1'}$ boronic acid or a boronic acid ester represented by formula 11', and Ak are as previously defined, and M represents a group selected from —Li, —Mg—Br or —Mg—Cl.

This production process is a process for obtaining a compound represented by formula 11' by converting a compound having a halogen atom such as a bromine atom on the ring of an aromatic compound represented by formula 16 to boronic acid using a known method (E. Tyrrell, et al., Synthesis, pp. 469, 2003; A. Suzuki et al., Chem. Rev., Vol. 95, pp. 2457, 1995).

Namely, production of boronic acid and boronic acid ester 11' by a coupling reaction on aromatic halogen compound 16 using a palladium catalyst can be carried out by reacting compound 16 with an alkoxydiborane (such as bis(pinacholate)diborane or bis(neopentylglycolate)diborane) in a suitable solvent (such as toluene, 1,4-dioxane, dimethoxyethane, tetrahydrofuran, dimethylsulfoxide or dimethylformamide) and in the presence of a suitable palladium catalyst (such as $PdCl_2$, $Pd(OAc)_2$, $Pd_2dba_3$, $PdCl_2[P(o\text{-tol})_3]_2$ or $Pd(O_2CCF_3)_2$), a ligand (such as $P(o\text{-tol})_3$, BINAP, DPPF, $P(t\text{-Bu})_3$, 2-dicyclohexylphosphino-2'-(N,N-dimethylamino)biphenyl), 2-(di-t-butylphosphino)biphenyl, 2-(dicyclohexylphoshino)biphenyl, 2',6'-dimethoxy-2-(dicyclohexylphosphino)biphenyl, 2',4',6'-triisopropyl-2-(dicyclohexylphosphino)biphenyl, or 1,3-diallyldihydroimidazolium salt) and a suitable base (such as sodium acetate, potassium acetate, cesium carbonate or potassium phosphate) at a suitable temperature (room temperature to the solvent/reagent boiling point).

In addition, boronic acid and boronic acid ester 11' can also be produced by treating compound 16 with an alkyl metal reagent (such as butyl lithium, isopropyl magnesium bromide or isopropyl magnesium chloride) in a suitable solvent (such as tetrahydrofuran, dimethyl ether or toluene) at a suitable temperature (−78° C. to room temperature) followed by reacting with a boronic acid ester (such as trimethyl boronate, triethyl boronate or triisopropyl boronate).

Reaction Step 3C: General synthetic process of synthetic block

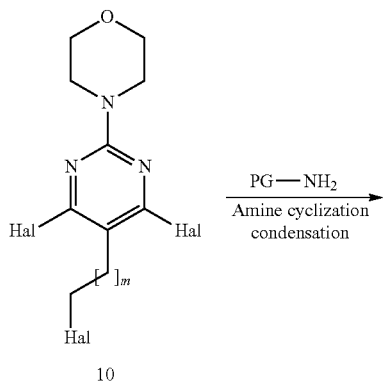

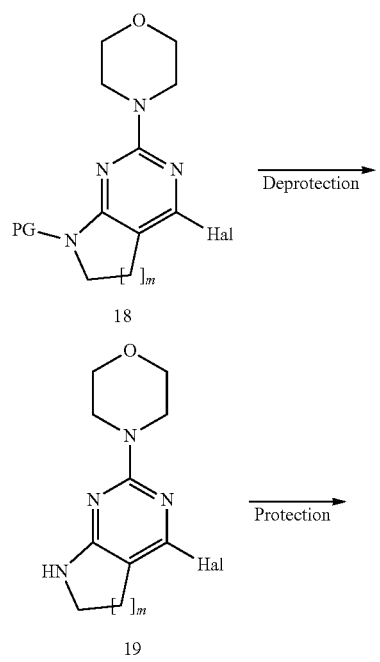

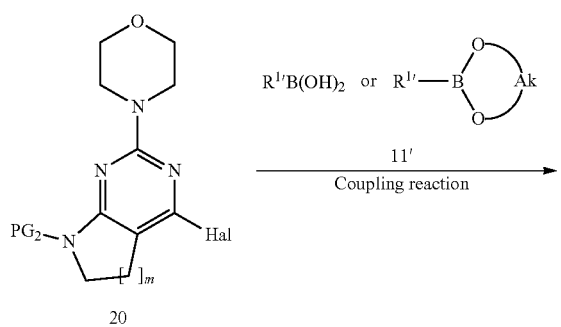

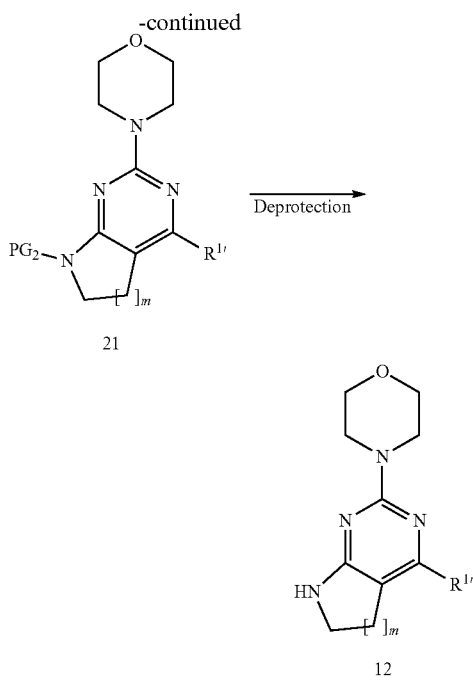

In the above formulae, m, R[1'] and Hal are the same as previously defined, PG and PG₂ represent protecting groups for amine compounds, and PG and PG₂ are not the same.

This production process is a process for obtaining a 2-morpholin-4-yl-6,7-dihydro-5H-pyrrolo[2,3-d]pyrimidine derivative or 2-morpholin-4-yl-5,6,7,8-tetrahydropyrido[2,3-d]pyrimidine derivative represented by formula 12 from a trihalogeno compound represented by formula 10.

A compound represented by formula 18 can be produced by a cyclization condensation reaction between a compound represented by formula 10 and an amine protected by PG (wherein examples of PG include amine protecting groups including carbamate-based protecting groups such as a methoxycarbonyl, ethoxycarbonyl, t-butoxycarbonyl, benzyloxycarbonyl or 9-fluorenylmethyloxycarbonyl (Fmoc) group, amide-based protecting groups such as a formyl, acetyl, chloroacetyl, trichloroacetyl, trifluoroacetyl or benzoyl group, hydrocarbon chain-based protecting groups such as a methyl or allyl group, and benzyl-based protecting groups such as a benzyl, 4-methoxybenzyl or 2,4-dimethoxybenzyl group, preferably benzyl-based protecting groups, and more preferably an amine protected with a 2,4-dimethoxybenzyl or 4-methoxybenzyl group) under similar conditions as the conversion step in reaction step 1B described above (compound 10→compound 11).

A compound represented by formula 19 can be produced by a de-PG (deprotection) reaction of a compound represented by formula 18. For example, in the case the PG of the compound represented by formula 18 is a benzyl-based protecting group (and preferably a 2,4-dimethoxybenzyl or 4-methoxybenzyl group), a compound represented by formula 19 can be produced by treating a compound represented by formula 18 with an acid (such as trifluoroacetic acid, sulfuric acid, hydrochloric acid, formic acid or acetic acid, and two or more types of acids may be used. Trifluoroacetic acid or sulfuric acid are preferred) in the presence of a solvent (such as dichloromethane or ethyl acetate) or in the absence of a solvent at a reaction temperature (normally, 0 to 120° C., preferably room temperature to 80° C.) (and a preferable treatment method is treatment with trifluoroacetic acid or treatment using ethyl acetate and sulfuric acid, and more preferably treatment with a solvent amount of trifluoroacetic acid, and even more preferably in the presence of a catalytic amount of concentrated sulfuric acid or N-acetylcysteine in an amount equal to or greater than the equivalent amount of the reactants), or by treating by catalytic hydrogen reduction using palladium carbon and the like.

A compound represented by formula 20 (wherein PG₂ represents an amine protecting group, examples of which include carbamate-based protecting groups such as a methoxycarbonyl, ethoxycarbonyl, t-butoxycarbonyl, benzyloxycarbonyl or 9-fluorenylmethyloxycarbonyl (Fmoc) group, amide-based protecting groups such as a formyl, acetyl, chloroacetyl, trichloroacetyl, trifluoroacetyl or benzoyl group, hydrocarbon chain-based protecting groups such as a methyl or allyl group, and benzyl-based protecting groups such as a benzyl, 4-methoxybenzyl or 2,4-dimethoxybenzyl group, preferably acyl-based protecting groups, and more preferably an acetyl group) can be produced by reacting a compound represented by formula 19 with a suitable acetylation agent (such as acetyl chloride or acetic anhydride) under the same conditions as the previously described reaction steps 1C, 2B and 2E.

A compound represented by formula 21 can be produced by coupling a compound represented by formula 20 with a desired boronic acid or boronic acid ester having a desired group R[1'] represented by formula 11' under the same conditions as the previously described reaction step 1B.

A compound represented by formula 12 can be obtained by a deprotection reaction of PG₂ of a compound represented by formula 21. For example, in the case PG₂ is an amide-based protecting group (and preferably an acetyl group), a compound represented by formula 12 can be produced by treating a compound represented by formula 18 with a base (such as sodium hydroxide, lithium hydroxide or sodium carbonate) in a solvent (such as methanol, ethanol, tetrahydrofuran or water) at a suitable reaction temperature (0 to 120° C. and preferably room temperature to 100° C.).

In addition, examples of R[1'] in the above production process include the groups indicated below.

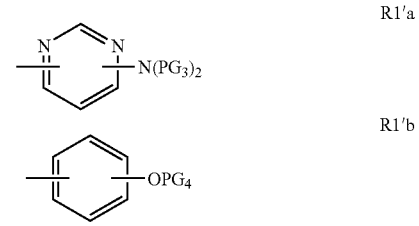

In the above formulae, PG₃ represents an amine protecting group, examples of which include carbamate-based protecting groups such as a methoxycarbonyl, ethoxycarbonyl, t-butoxycarbonyl, benzyloxycarbonyl or 9-fluorenylmethyloxycarbonyl (Fmoc) group, amide-based protecting groups such as a formyl, acetyl, chloroacetyl, trichloroacetyl, trifluoroacetyl or benzoyl group, hydrocarbon chain-based protecting groups such as a methyl or allyl group, and benzyl-based protecting groups such as a benzyl, 2-methoxybenzyl, 4-methoxybenzyl or 2,4-dimethoxybenzyl group, preferably benzyl-based protecting groups, and more preferably a 4-methoxybenzyl or 2,4-dimethoxybenzyl group. In addition, PG₄ represents a hydroxyl group protecting group, examples of which include ether-based protecting groups such as a methyl, t-butyl, methoxymethyl, methylthiomethyl, 2-methoxyethoxymethyl, benzyloxymethyl, tetrahydropyranyl (THP) or tetrahydrofuranyl group, silyl ether-based protecting groups such as a trimethylsilyl, triethylsilyl or t-butyldimethylsilyl group, ester-based protecting groups such as a formyl, acetyl, pivaloyl or benzoyl group, and carbonate-based protecting groups such as a methoxycarbonyl, ethoxycarbonyl or vinyloxycarbonyl group, and preferably an ether-based protecting group, and more preferably, a t-butyl group. In addition, $PG_3$ and $PG_4$ are preferably not the same as $PG_2$.

With respect to the reaction of $R^{1'}$ to $R^1$ (deprotection reactions) in general formulas (1), (1a), (1b), (1c), (1d) and (1e) in the production processes described above, in the case $R^{1'}$ is the aforementioned $R^{1'}a$, for example, deprotection can be carried out by a suitable deprotection reaction on an amine protecting group. For example, in the case $PG_3$ is a benzyl-based protecting group (and preferably a 4-methoxybenzyl or 2,4-dimethoxybenzyl group), this deprotection reaction can be carried out by a method comprising treating with an acid (such as trifluoroacetic acid, sulfuric acid, hydrochloric acid, formic acid or acetic acid, two different types of acids may be used, and trifluoroacetic acid or sulfuric acid is used preferably) in the presence of a solvent (such as dichloromethane or ethyl acetate) or in the absence of a solvent normally at a reaction temperature of 0 to 120° C. and preferably room temperature to 80° C. (with preferable examples of this treatment including treating with trifluoroacetic acid or treating with ethyl acetate and sulfuric acid, more preferably treating with a solvent amount of trifluoroacetic acid, and even more preferably treating with a catalytic amount of concentrated sulfuric acid or in the presence of N-acetylcysteine in an amount equal to or greater than the equivalent amount of the reactants), or by a method comprising treating by catalytic hydrogen reduction using palladium carbon and the like.

In addition, in the case $R^{1'}$ is the aforementioned $R^{1'}b$, the deprotection reaction can be carried out by a suitable deprotection reaction on a hydroxyl group protecting group. For example, in the case $PG_4$ is an ether-based protecting group (and preferably a t-butyl group), the deprotection reaction can be carried out by treating with an acid (such as trifluoroacetic acid, sulfuric acid, hydrochloric acid, formic acid or acetic acid, two different types of acids may be used, and trifluoroacetic acid or sulfuric acid is used preferably) in the presence of a solvent (such as dichloromethane or ethyl acetate) or in the absence of a solvent normally at a reaction temperature of 0 to 120° C. and preferably room temperature to 80° C. (with preferable examples of this treatment including treating with trifluoroacetic acid or treating with ethyl acetate and sulfuric acid, more preferably treating with a solvent amount of trifluoroacetic acid, and even more preferably treating with a catalytic amount of concentrated sulfuric acid).

All stereoisomers of compounds of the present invention represented by formula (I) (such as enantiomers and diastereomers (including cis- and trans-geometrical isomers)), racemic forms of the isomers, and other mixtures thereof are included in the compounds of the present invention and pharmaceutically acceptable salts thereof. In the present invention, Compound I particularly includes stereoisomers.

In addition, although several tautomeric forms such as enol and imine forms, keto and enamine forms and mixtures thereof may exist for the compounds of the present invention and pharmaceutically acceptable salts thereof, all tautomers of the compounds of the present invention are included in the present invention.

Moreover, atropisomers of the present invention are also included in the present invention. Atropisomers refer to compounds represented by general formula (I) capable of being separated into isomers having limited rotation.

These isomers can be separated by ordinary methods utilizing differences in physicochemical properties between isomers. For example, racemic compounds can be converted to three-dimensionally pure isomers using a typical optical resolution method such as optical resolution by deriving to a diastereomer salt with an optically active acid such as tartaric acid. Mixtures of diastereomers can be separated by using fractional crystallization or various types of chromatography (such as thin layer chromatography, column chromatography or gas chromatography).

In the case of obtaining a compound of formula (I) as claimed in the present invention in a free form, the free form can be converted to a salt optionally formed by a compound of formula (I) or a hydrate or solvate thereof in accordance with ordinary methods.

In addition, in the case of obtaining a compound of formula (I) as claimed in the present invention in the form of a salt, hydrate or solvate of a compound of formula (I), that salt, hydrate or solvate can be converted to a free form of a compound of formula (I) in accordance with ordinary methods.

Since a compound of formula (I) as claimed in the present invention, or pharmaceutically acceptable salt thereof, has superior PI3K inhibitory action, and particularly superior inhibitory action against the p110α of class Ia of PI3K, it is useful as a preventive agent or therapeutic agent of a proliferative disease, and is particularly useful as a preventive agent or therapeutic agent of cancer among the proliferative disease as a result of using a compound of the present invention alone or using concomitantly with various types of anticancer agents.

Herein, the "proliferative disease" refers to a disorder caused by deficiencies in the cellular signal transduction system or the signal transduction mechanism of a certain protein. The proliferative disease includes, for example, cancers, psoriasis, restenosis, autoimmune diseases, and atherosclerosis. Examples of cancer include solid cancers, while examples of solid cancers include colon cancer, prostate cancer and non-small cell lung cancer.

In addition, a compound of formula (I) of the present invention is also useful as a preventive agent or therapeutic agent (and particularly a therapeutic agent) of psoriasis, restenosis, autoimmune diseases and atherosclerosis, as well as diseases such as heart failure sequela, xenograft rejections, osteoarthritis, rheumatoid arthritis, respiratory diseases such as asthma, cystic fibrosis, hepatoma, cardiomegaly, Alzheimer's disease, diabetes, septic shock, HIV infection, inflammations caused by allergies and heart disease.

In particular, a compound of formula (I) of the present invention is useful as a preventive agent or therapeutic agent (and particularly a therapeutic agent) of cancers in which PI3K, and particularly the p110α in class Ia of PI3K, is highly expressed.

Moreover, the present invention also relates to methods for preventing or treating the proliferative diseases described above, for example, cancer. Another aspect of the present invention includes methods for preventing or treating solid or hematopoietic PI3K-related cancers.

These methods include a step in which a pharmaceutical composition containing as an active ingredient thereof a compound of formula (I) or a pharmaceutically acceptable salt thereof, is administered to a patient requiring such treatment or a patient suffering from such a disease or condition.

A pharmaceutical composition of the present invention can be formulated and administered orally or parenterally (such as intravenously, intramuscularly, subcutaneously, rectally, nasally, intracisternally, vaginally, abdominally, intracystically or locally). Examples of preparations for oral administration include tablets, capsules, granules, powders, pills, aqueous or non-aqueous oral solutions and suspensions. Examples of preparations for parenteral administration include injections, ointments, gels, creams, suppositories, oral or nasal sprays, emulsions, oily agents and suspending agents, as well as parenteral solutions filled into containers suitable for administration in individual small doses. In addition, the administration form can be adapted to various administration methods including controlled-release formulations in the manner of subcutaneous transplants.

The aforementioned preparations can be produced according to known methods using additives ordinarily used in pharmaceutical preparations, examples of which include vehicles, lubricants (coating agents), binders, disintegration agents, stabilizers, correctives, diluents, surfactants and emulsifiers.

Examples of vehicles include starches such as starch, potato starch and cornstarch, lactose, crystalline cellulose and calcium hydrogen phosphate.

Examples of coating agents include ethyl cellulose, hydroxypropyl cellulose, hydroxypropyl methyl cellulose, shellac, talc, Carnauba wax and paraffin.

Examples of binders include polyvinyl pyrrolidone, Macrogol and the same compounds as listed for the aforementioned vehicles.

Examples of disintegration agents include the same compounds as those listed for the aforementioned vehicles and chemically-modified starches and celluloses such as cross carmellose sodium, sodium carboxymethyl starch or crosslinked polyvinyl pyrrolidone.

Examples of stabilizers include paraoxybenzoic acid esters such as methyl paraben or propyl paraben; alcohols such as chlorobutanol, benzyl alcohol or phenylethyl alcohol; benzalkonium chloride; phenols such as phenol or cresol; thimerosal; dehydroacetic acid; and sorbic acid.

Examples of correctives include ordinarily used sweeteners, sour flavorings and fragrances.

Examples of surfactants and emulsifiers include Polysorbate 80, Polyoxyl 40 Stearate and Lauromacrogol.

In addition, examples of solvents able to be used for producing liquid preparations include ethanol, phenol, chlorocresol, purified water and distilled water.

In the case of using a pharmaceutical composition of the present invention as a PI3K inhibitor or therapeutic agent or preventive agent of a proliferative diseases such as cancer, the amount of compound of formula (I) of the present invention, or pharmaceutically acceptable salt, used can be suitably altered according to symptoms, age, body weight, relative state of health, presence of other drugs, administration method and the like. For example, the typical effective amount for a patient (warm-blooded animal and particularly a human) as a compound of formula (I) in the case of an oral preparation is preferably 0.1 to 1000 mg, and more preferably 1 to 100 mg, per kg of body weight per day. In the case of parenteral administration, the typical effective amount is preferably 0.1 to 1000 mg and more preferably 1 to 100 mg per kg of body weight per day. This amount is preferably administered once a day or divided into several administrations according to symptoms.

The pharmaceutical composition of the present invention can be used concomitantly with other radiotherapy, chemotherapy, vascularization inhibitors and anticancer agents.

EXAMPLES

Hereinbelow, the present invention is described in more detail by Examples, but the present invention is not limited to these Examples. In the present specification, "N" means "normality", and "M" means mol/L.

Further, NMR analysis was carried out using JNM-EX270 (270 MHz), JNM-GSX400 (400 MHz) from JEOL, Ltd. or NMR (400 MHz) from Bruker company, and NMR data is represented by ppm (parts per million). A deuterated lock signal from a sample solvent was referred to, with tetramethyl silane being set as an internal standard substance (0 ppm).

Mass spectrum data was obtained using JMS-DX303, JMS-SX/SX102A from JEOL Ltd. or Quttromicro from Micromass Ltd., and mass spectrum data provided with high performance liquid chromatography was obtained using a micromass (ZMD from Micromass Ltd.) equipped with 996-600E gradient high performance liquid chromatography from Waters Corporation or a micromass (ZQ from Micromass Ltd.) equipped with 2525 gradient high performance liquid chromatography from Waters Corporation.

For the condition for high performance liquid chromatography, any of the following conditions was used.

Condition 1 for High Performance Liquid Chromatography

Column: Combi ODS (ODS, 5 μm, 4.6 mm I.D.×50 mm, from Wako Pure Chemicals Industries, Ltd.), COSMOSIL (ODS, 5 μm, 4.6 mm I.D.×50 mm, from Nacalai Tesque, Inc.), Inertsil C18 (ODS, 5 μm, 4.6 mm I.D.×50 mm, from GL SCIENCES INC.), or SunFire C18 (ODS, 5 μm, 4.6 mm I.D.×50 mm, from Waters Corporation)

Mobile phase: a water containing 0.05% trifluoroacetic acid (A) and acetonitrile containing 0.05% trifluoroacetic acid (B)

Elution method: stepwise solvent gradient elution from 10% of B to 95% of B (3.5 min.), from 95% of B to 10% of B (1 min.), kept at 10% of B (0.5 min.)

Flow rate: 4.0 mL/min.

Condition 2 for High Performance Liquid Chromatography

Column: Combi ODS (ODS, 5 μm, 4.6 mm I.D.×50 mm, Wako Pure Chemicals Industries, Ltd.), COSMOSIL (ODS, 5 μm, 4.6 mm I.D.×50 mm, from Nacalai Tesque, Inc.), Inertsil C18 (ODS, 5 μm, 4.6 mm I.D.×50 mm, from GL SCIENCES INC.), or SunFire C18 (ODS, 5 μm, 4.6 mm I.D.×50 mm, from Waters Corporation)

Mobile Phase: a water containing 0.05% trifluoroacetic acid (A) and acetonitrile containing 0.05% trifluoroacetic acid (B)

Elution method: stepwise solvent gradient elution from 30% of B to 35% of B (0.2 min.), from 35% of B to 98% of B (3.3 min.), from 98% of B to 30% of B (1 min.), kept at 30% of B (0.5 min.)

Flow rate: 4.0 mL/min.

Condition 3 for High Performance Liquid Chromatography

Column: Combi ODS (ODS, 5 μm, 4.6 mm I.D.×50 mm, Wako Pure Chemicals Industries, Ltd.), or SunFire C18 (ODS, 5 μm, 4.6 mm I.D.×50 mm, from Waters Corporation)

Mobile Phase: a water containing 0.05% trifluoroacetic acid (A) and acetonitrile containing 0.05% trifluoroacetic acid (B)

Elution method: stepwise solvent gradient elution from 10% of B to 95% of B (2 min.), kept at 95% of B (1.5 min.), from 95% of B to 10% of B (1 min.), kept at 10% of B (0.5 min.)

Flow rate: 4.0 mL/min.

Organic synthesis reaction was carried out without further purifying a commercially available reagent.

Room temperature refers to a range of about 20 to 25° C.

All the water-prohibiting reactions were carried out under an argon atmosphere. Concentration or distilling off of a solvent under reduced pressure was, unless otherwise mentioned, carried out using a rotary evaporator.

In preparation of a compound, a functional group was protected by a protective group as necessary, and a protected form of a target molecule was prepared, followed by removal of the protective group. Selection and desorption operation of a protective group were carried out according to the method described, for example, in Greene and Wuts, "Protective Groups in Organic Synthesis", 3rd edition, John Wiley & Sons, 1999.

Condition for Microwave Reaction

All the microwave reactions were carried out according to CEM Explorer microwave system using a snap cap reaction vial. Setting of Powermax includes air cooling of a reaction vessel for avoiding temperature rise due to the microwave.

Further, for reagents or equipment to be used in Examples, the followings were used, unless otherwise mentioned.

SCX resin (BOND ELUT® SCX from VARIAN, Inc.)

Irradiation of ultrasonic wave: UT-105T from Sharp Corporation

WSCI (1-ethyl-3-(3'-dimethylaminopropyl)carbodiimide hydrochloride)

Deprotection Method

Further, typical deprotection methods to be used in the following 1-D-01 to 1-D-335 are shown below. In a case where a protective group is generally a weak group to an acid (e.g., PMB (4-methoxy-benzyl) group, BOC group, or THP (tetrahydropyran-2-yl) group, etc.), for a deprotection step, for example, deprotection methods by an acid as mentioned below can be used.

[Deprotection Method 1]

The concerned compound is dissolved in a solvent amount of TFA, and a catalytic amount of concentrated sulfuric acid is added, followed by stirring at 40° C. for a few hours. After completion of the reaction, TFA is concentrated followed by distilling off under reduced pressure, and water is added followed by neutralization with 1M NaOH aqueous solution. After the resulting solid is filtered off, stirring is carried out in, for example, dichloromethane or a mixed solvent of dichloromethane/hexane at room temperature, and the solid is filtered off again to obtain the desired compound.

[Deprotection Method 1']

The concerned compound is dissolved in a solvent amount of TFA, and a catalytic amount of concentrated sulfuric acid is added, followed by stirring at 40° C. for a few hours. After completion of the reaction, TFA is concentrated followed by distilling off under reduced pressure, and water is added followed by neutralization with 1M NaOH aqueous solution. After the resulting solid is filtered off, purification was carried out by silica gel chromatography, etc. (developing eluent: e.g., dichloromethane/2M ammonia methanol), to obtain the desired compound.

[Deprotection Method 2]

The concerned compound is dissolved in a solvent amount of TFA, followed by heating to reflux for a few hours. After completion of the reaction, the reaction mixture is concentrated under reduced pressure, and the resulting residue is purified by silica gel chromatography, etc. (developing solvent: e.g., dichloromethane/methanol), to obtain the desired compound.

[Deprotection Method 3]

The concerned compound is dissolved in a solvent amount of TFA, followed by addition of more than an equivalent amount of N-Acetylcysteine, followed by heating to reflux for a few hours. The reaction mixture is concentrated under reduced pressure, and the resulting residue is purified by silica gel column chromatography, etc., to obtain the desired compound.

Example 1-A-01

Synthesis of 4-(3-methoxy-phenyl)-2-morpholin-4-yl-7-pyridin-4-yl-6,7-dihydro-5H-pyrrolo[2,3-d]pyrimidine (A-01)

Step A 3-(3-Methoxybenzoyl)-dihydrofuran-2-one

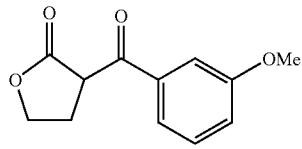

A solution of γ-butyrolactone (2 g, 23.3 mmol) in dehydrated tetrahydrofuran (250 ml) was cooled to −78° C. under a nitrogen atmosphere, and dehydrated tetrahydrofuran solution of 3-methoxybenzoyl chloride (4.17 g, 24.5 mmol) was added, followed by slow addition of lithium hexamethyldisilazide (LHMDS, 1M tetrahydrofuran solution, 46.6 ml, 46.6 mmol). After stirring for 1 hour, saturated sodium hydrogencarbonate aqueous solution (50 ml) was added at −78° C. followed by quenching. After extraction with ethyl acetate (200 ml), the organic layer was washed with brine (2×200 ml), dried over sodium sulfate, and subsequently the solvent was removed under reduced pressure, to obtain a crude product as a yellow oil. The crude was purified by silica gel column chromatography (hexane/ethyl acetate=50/50), to obtain the desired compound as a yellow solid (1.84 g, 36%).

$^1$H-NMR (400 MHz, CDCl$_3$) δ (ppm) 7.66 (1H, td, J=7.7, 1.1 Hz), 7.57 (1H, dd, J=2.5, 1.7 Hz), 7.42 (1H, t, J=8.0 Hz), 7.16 (1H, ddd, J=8.3, 2.7, 0.9 Hz), 4.48-4.58 (2H, m), 4.40-4.46 (1H, m), 3.86 (3H, s), 2.80-2.90 (1H, m), 2.48-2.57 (1H, m).

ESI (LC-MS positive mode) m/z 221 [M+H]$^+$.

Step B 5-(2-Hydroxyethyl)-6-(3-methoxyphenyl)-2-(morpholin-4-yl)-pyrimidin-4-ol and 4-(3-methoxyphenyl)-2-(morpholin-4-yl)-5,6-furo[2,3-d]pyrimidine

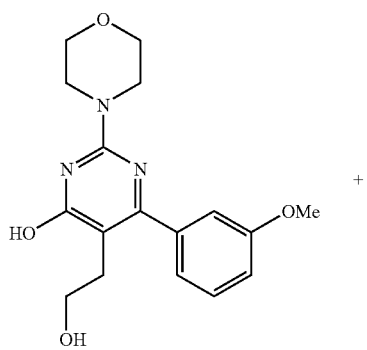

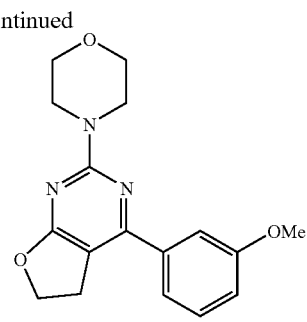

Morpholinoformamidine bromate salt (200 mg, 0.952 mmol), 3-(3-methoxybenzoyl)-dihydrofuran-2-one (419 mg, 1.904 mmol) and sodium t-butoxide (183 mg, 1.904 mmol) were added into a microwave reaction tube, followed by being dissolved in t-butanol (3 ml). After irradiation of microwave (200 W, 120° C.) for 1 hour, the solvent was removed under reduced pressure, to obtain a crude product as a brown solid. The crude was purified by silica gel column chromatography (DCM/MeOH=95/5), to obtain 5-(2-hydroxyethyl)-6-(3-methoxyphenyl)-2-(morpholin-4-yl)-pyrimidin-4-ol, and 4-(3-methoxyphenyl)-2-(morpholin-4-yl)-5,6-furo[2,3-d]pyrimidine as colorless solid.

5-(2-hydroxyethyl)-6-(3-methoxyphenyl)-2-(morpholin-4-yl)-pyrimidin-4-ol (88 mg, 28%): $^1$H-NMR (400 MHz, CDCl$_3$) δ (ppm) 7.33 (1H, t, 7.8 Hz), 6.97-7.03 (2H, m), 6.91-6.97 (1H, m), 3.82 (3H, s), 3.74-3.81 (6H, m), 3.67-3.73 (4H, m), 2.70 (2H, t, J=5.5 Hz); ESI (LC-MS positive mode) m/z 332 [M+H]$^+$.

4-(3-methoxyphenyl)-2-(morpholin-4-yl)-5,6-furo[2,3-d]pyrimidine (93 mg, 31%): $^1$H-NMR (400 MHz, CDCl$_3$) δ ppm) 7.51 (1H, dd, J=2.5, 1.6 Hz), 7.45 (1H, td, J=7.7, 1.2 Hz), 7.34 (1H, t, J=8.0 Hz), 6.96 (1H, ddd, J=8.2, 2.7, 0.9 Hz), 4.60 (2H, t, J=8.4 Hz), 3.84 (3H, s), 3.80-3.83 (4H, m), 3.70-3.77 (4H, m), 3.36 (2H, t, J=8.4 Hz); ESI (LC-MS positive mode) m/z 315 [M+H]$^+$.

Step C

4-Chloro-5-(2-chloroethyl)-6-(3-methoxyphenyl)-2-(morpholin-4-yl)-pyrimidine

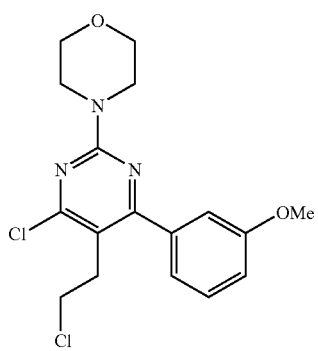

[Method C-1]

5-(2-Hydroxyethyl)-6-(3-methoxyphenyl)-2-(morpholin-4-yl)-pyrimidin-4-ol (220 mg, 0.66 mmol) was dissolved in phosphorus oxychloride (5 ml), followed by heating to 110° C. for 24 hours in a sealed tube. After concentration under reduced pressure, a crude was obtained as a brown oil. This was purified by silica gel column chromatography (hexane/ethyl acetate=90/10), to obtain the desired compound as a yellow oil (244 mg, 100%).

$^1$H-NMR (400 MHz, CDCl$_3$) δ (ppm) 7.40 (1H, t, J=8.1 Hz), 7.03-7.08 (1H, m), 6.97-7.03 (2H, m), 3.83 (3H, s), 3.75-3.81 (4H, m), 3.69-3.75 (4H, m), 3.55 (2H, t, J=8.0 Hz), 3.06 (2H, t, J=8.0 Hz).

ESI (LC-MS positive mode) m/z 368 [M+H]$^+$.

[Method C-2]

4-(3-Methoxyphenyl)-2-(morpholin-4-yl)-5,6-furo[2,3-d]pyrimidine (515 mg, 1.65 mmol) was dissolved in phosphorus oxychloride (12 ml), followed heating to 110° C. for 96 hours in a sealed tube. After concentration under reduced pressure, a crude was obtained as a brown oil. This was purified by silica gel column chromatography (hexane/ethyl acetate=90/10), to obtain the desired compound as a yellow oil (550 mg, 91%).

Step D 4-(3-Methoxy-phenyl)-2-morpholin-4-yl-7-pyridin-4-yl-6,7-dihydro-5H-pyrrolo[2,3-d]pyrimidine

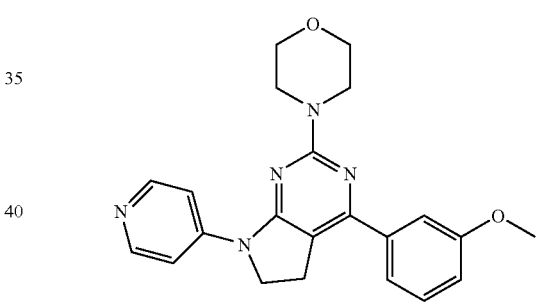

4-[4-Chloro-5-(2-chloroethyl)-6-(3-methoxyphenyl)-pyrimidin-2-yl]-morpholine (300 mg, 0.82 mmol), Pd$_2$(dba)$_3$ (37 mg, 0.04 mmol), 1,3-bis(2,6-diisopropylphenyl)imidazol-2-ylidene (53 mg, 0.12 mmol), sodium t-butoxide (183 mg, 1.904 mmol), and 4-aminopyridine (192 mg, 2.05 mmol) were added into a microwave reaction tube, and purged with nitrogen gas followed by dissolution in dioxane (3 ml). After irradiation of microwave (300 W, 160° C., powermax on) for 1 hour, the solvent was removed under reduced pressure, to obtain a crude product as a yellow oil. This was purified by silica gel column chromatography (dichloromethane/methanol=9/1), to obtain a product as a yellow crystal. This was recrystallized from methanol, to obtain the desired compound as a colorless crystal (150 mg, yield 39%).

$^1$H-NMR (400 MHz, CDCl$_3$) δ (ppm): 8.51 (2H, dd, J=4.9, 1.5 Hz), 7.73 (2H, dd, J=4.9, 1.5 Hz), 7.39 (1H, t, J=7.9 Hz), 7.44-7.50 (2H, m), 6.95-7.02 (1H, m), 4.05 (2H, m), 3.86 (11H, m), 3.36 (2H, m).

ESI (LC-MS positive mode) m/z 390 [M+H]$^+$.

Example 1-A-02

4-(3-Methoxy-phenyl)-2-morpholin-4-yl-7-pyridin-3-yl-6,7-dihydro-5H-pyrrolo[2,3-d]pyrimidine (A-02)

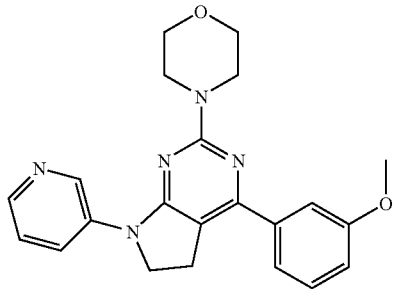

In the same manner as Example 1-A-01, from 4-[4-chloro-5-(2-chloroethyl)-6-(3-methoxyphenyl)-pyrimidin-2-yl]-morpholine and 3-aminopyridine, the desired compound was obtained.

$^1$H-NMR (400 MHz, CDCl$_3$) δ (ppm): 9.11 (1H, d, J=2.6 Hz), 8.29 (1H, dd, J=4.6, 1.1 Hz), 8.14 (1H, ddd, J=8.4, 2.6, 1.3 Hz), 7.47-7.51 (1H, m), 7.42-7.47 (1H, m), 7.37 (1H, t, J=7.9 Hz), 7.30, 1H, dd, J=8.5, 4.7 Hz), 6.97 (1H, dd, J=8.1, 1.9 Hz), 4.08 (2H, t, J=8.2 Hz), 3.82-3.89 (7H, m), 3.76-3.82 (4H, m), 3.36 (2H, t, J=8.2 Hz).

ESI (LC-MS positive mode) m/z 390 [M+H]$^+$.

Example 1-A-03

5-[4-(3-Methoxy-phenyl)-2-morpholin-4-yl-5,6-dihydro-pyrrolo[2,3-d]pyrimidin-7-yl]-pyridin-2-ol (A-03)

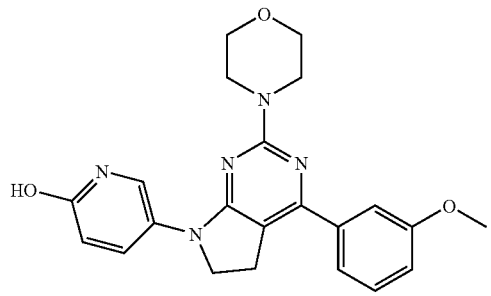

In the same manner as Example 1-A-01, from 4-[4-chloro-5-(2-chloroethyl)-6-(3-methoxyphenyl)-pyrimidin-2-yl]-morpholine and 2-hydroxy-pyridin-5-ylamine, the desired compound was obtained.

$^1$H-NMR (400 MHz, DMSO-d$_6$) δ (ppm): 8.01 (1H, dd, J=9.8, 3.0 Hz), 7.74 (1H, d, J=2.6 Hz), 7.42-7.50 (2H, m), 7.39 (1H, t, J=7.9 Hz), 7.01 (1H, ddd, J=8.1, 2.6, 1.0 Hz), 6.42 (1H, d, J=9.8 Hz), 3.94 (2H, t, J=8.2 Hz), 3.80 (3H, s), 3.65 (8H, s), 3.25 (2H, t, J=8.2 Hz).

ESI (LC-MS positive mode) m/z 406 ([M+H]$^+$).

Example 1-A-04

4-(3-Methoxy-phenyl)-2-morpholin-4-yl-7-pyridin-3-ylmethyl-6,7-dihydro-5H-pyrrolo[2,3-d]pyrimidine (A-04)

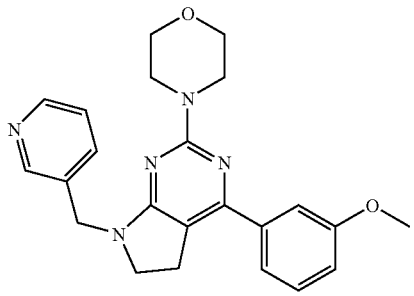

In the same manner as Example 1-A-01, from 4-[4-chloro-5-(2-chloroethyl)-6-(3-methoxyphenyl)-pyrimidin-2-yl]-morpholine and 3-aminomethylpyridine, the desired compound was obtained.

$^1$H-NMR (400 MHz, CD$_3$OD) δ (ppm): 8.74 (1H, s), 8.66 (1H, s), 8.16 (1H, d, J=7.9 Hz), 7.67-7.77 (1H, m), 7.49 (1H, t, J=8.1 Hz), 7.18-7.26 (2H, m), 7.15 (1H, ddd, J=8.3, 2.5, 0.8 Hz), 4.90 (2H, s), 3.75-3.89 (13H, m), 3.15 (2H, t, J=8.3 Hz).

ESI (LC-MS positive mode) m/z 404 ([M+H]$^+$).

Example 1-A-05

7-(1H-indazol-5-yl)-4-(3-methoxy-phenyl)-2-morpholin-4-yl-6,7-dihydro-5H-pyrrolo[2,3-d]pyrimidine (A-05)

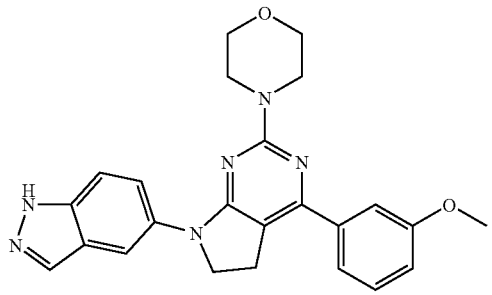

In the same manner as Example 1-A-01, from 4-[4-chloro-5-(2-chloroethyl)-6-(3-methoxyphenyl)-pyrimidin-2-yl]-morpholine and 1H-indazol-5-ylamine, the desired compound was obtained.

$^1$H-NMR (400 MHz, CDCl$_3$) δ (ppm): 10.10 (1H, s), 8.17 (1H, dd, J=9.1, 2.1 Hz), 8.05 (1H, d, J=1.0 Hz), 7.77 (1H, dd, J=2.0, 0.5 Hz), 7.48-7.54 (2H, m), 7.44-7.48 (1H, m), 7.37 (1H, t, J=7.9 Hz), 6.96 (1H, ddd, J=8.2, 2.6, 1.0 Hz), 4.13 (2H, t, J=8.2 Hz), 3.82-3.90 (7H, m), 3.76-3.82 (4H, m), 3.34 (2H, J=t, 8.2 Hz).

ESI (LC-MS positive mode) m/z 429 ([M+H]$^+$).

Example 1-A-06

7-(1H-benzimidazol-5-yl)-4-(3-methoxy-phenyl)-2-morpholin-4-yl-6,7-dihydro-5H-pyrrolo[2,3-d]pyrimidine (A-06)

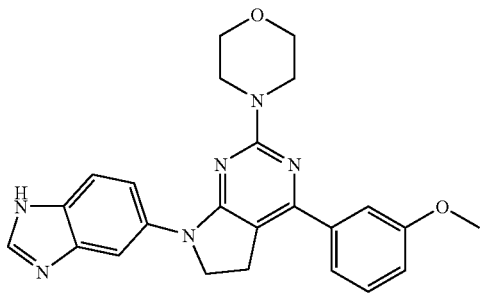

In the same manner as Example 1-A-01, from 4-[4-chloro-5-(2-chloroethyl)-6-(3-methoxyphenyl)-pyrimidin-2-yl]-morpholine and 1H-benzimidazol-5-ylamine, the desired compound was obtained.

$^1$H-NMR (400 MHz, DMSO-$d_6$) δ (ppm): 12.40 (1H, s), 7.74-8.25 (2H, m), 7.44-7.69 (4H, m), 7.40 (1H, t, J=7.9 Hz), 7.02 (1H, dd, J=7.6, 2.1 Hz), 4.14 (2H, t, J=8.2 Hz), 3.81 (3H, s), 3.72 (4H, s), 3.69 (4H, s), 3.30 (2H, t, J=8.3 Hz).

ESI (LC-MS positive mode) m/z 429 ([M+H]$^+$).

Example 1-A-07

4-(3-Methoxy-phenyl)-7-methyl-2-morpholin-4-yl-6,7-dihydro-5H-pyrrolo[2,3-d]pyrimidine (A-07)

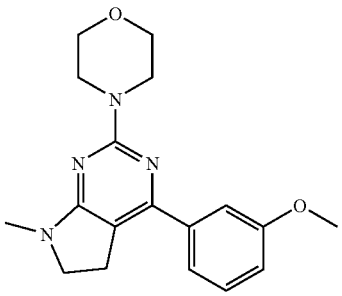

In the same manner as Example 1-A-01, from 4-[4-chloro-5-(2-chloroethyl)-6-(3-methoxyphenyl)-pyrimidin-2-yl]-morpholine and methylamine, the desired compound was obtained.

$^1$H-NMR (400 MHz, CD$_3$OD) δ (ppm): 7.43-7.52 (1H, m), 7.17-7.25 (2H, m), 7.13 (1H, ddd, J=8.4, 2.6, 0.9 Hz), 3.86 (3H, s), 3.73-3.85 (10H, m), 3.13 (3H, s), 3.06-3.14 (2H, m).

ESI (LC-MS positive mode) m/z 327 ([M+H]$^+$).

Example 1-A-08

4-(3-Methoxy-phenyl)-7-(6-methoxy-pyridin-3-yl)-2-morpholin-4-yl-6,7-dihydro-5H-pyrrolo[2,3-d]pyrimidine (A-08)

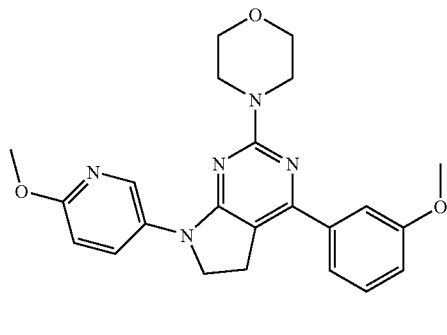

In the same manner as Example 1-A-01, from 4-[4-chloro-5-(2-chloroethyl)-6-(3-methoxyphenyl)-pyrimidin-2-yl]-morpholine and 2-methoxy-pyridin-5-ylamine, the desired compound was obtained.

$^1$H-NMR (400 MHz, CDCl$_3$) δ (ppm): 8.43 (1H, d, J=2.4 Hz), 8.19 (1H, dd, J=9.0, 2.9 Hz), 7.49 (1H, dd, J=2.5, 1.6 Hz), 7.44 (1H, dt, J=7.8, 1.3, 1.1 Hz), 7.36 (1H, t, J=7.9 Hz), 6.95 (1H, ddd, J=8.1, 2.7, 1.0 Hz), 6.78 (1H, dd, J=9.1, 0.5 Hz), 4.02 (2H, t, J=8.2 Hz), 3.93 (3H, s), 3.86 (3H, s), 3.80-3.85 (4H, m), 3.75-3.80 (4H, m), 3.32 (2H, t, J=8.3 Hz).

ESI (LC-MS positive mode) m/z 420 ([M+H]$^+$).

Example 1-A-09

3-(2-Morpholin-4-yl-7-pyridin-4-yl-6,7-dihydro-5H-pyrrolo[2,3-d]pyrimidin-4-yl)-phenol (A-09)

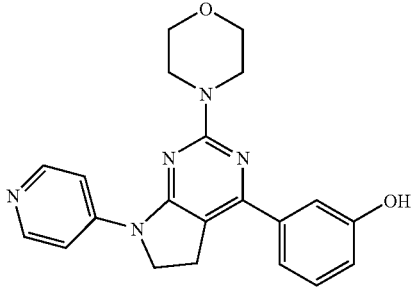

A solution of the compound A-01 (50 mg, 0.13 mmol) prepared in Example 1-A-01 in dimethylformamide (3 ml) was heated to 150° C., and a drop of sodium ethanethiolate (105 mg, 0.123 mmol) was added for every 15 minutes in 3 portions. After heating at 150° C. for 15 minutes followed by cooling, 1 ml of water was added followed by quenching. This was concentrated under reduced pressure, and purified by silica gel column chromatography (dichloromethane/methanol=94/6), to obtain a colorless crystal. This was washed with water, to obtain the desired compound (13 mg, 27%).

$^1$H-NMR (400 MHz, DMSO-$d_6$) δ (ppm): 9.60 (1H, s), 8.44 (2H, dd, J=4.9, 1.5 Hz), 7.81 (2H, dd, J=5.0, 1.6 Hz), 7.40 (1H, t, J=1.7 Hz), 7.34 (1H, d, J=8.1 Hz), 7.28 (1H, t, J=7.8 Hz), 6.85 (1H, ddd, J=7.9, 2.3, 1.0 Hz), 4.08 (2H, t, J=8.2 Hz), 3.66-3.79 (8H, m), 3.28 (2H, t, J=8.1 Hz).

ESI (LC-MS positive mode) m/z 376 ([M+H]$^+$).

Example 1-A-10

3-(2-Morpholin-4-yl-7-pyridin-3-yl-6,7-dihydro-5H-pyrrolo[2,3-d]pyrimidin-4-yl)-phenol (A-10)

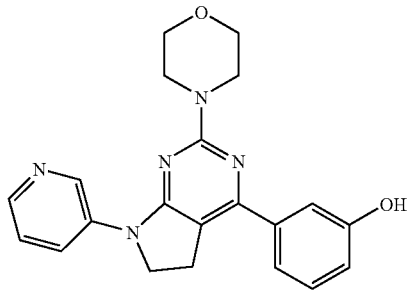

In the same manner as Example 1-A-09, the desired compound was obtained from Compound A-02.

¹H-NMR (400 MHz, DMSO-d₆) δ (ppm): 8.31 (1H, d, J=5.9 Hz), 7.78 (1H, dd, J=5.8, 1.9 Hz), 7.58 (1H, s), 7.40 (1H, s), 7.32-7.36 (1H, m), 7.28 (1H, t, J=7.9 Hz), 6.85 (1H, d, J=6.8 Hz), 4.07 (2H, t, J=8.1 Hz), 3.73 (8H, d, J=6.6 Hz), 3.25-3.32 (3H, m).

ESI (LC-MS positive mode) m/z 376 ([M+H]⁺).

Example 1-A-11

5-[4-(3-Hydroxy-phenyl)-2-morpholin-4-yl-5,6-dihydro-pyrrolo[2,3-d]pyrimidin-7-yl]-pyridin-2-ol (A-11)

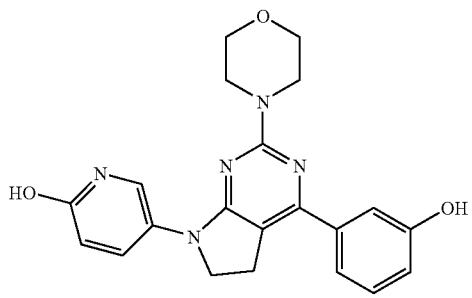

In the same manner as Example 1-A-09, the desired compound was obtained from Compound A-03.

¹H-NMR (400 MHz, DMSO-d₆) δ (ppm): 11.45 (1H, s), 9.52 (1H, s), 8.01 (1H, dd, J=9.8, 3.1 Hz), 7.73 (1H, d, J=2.7 Hz), 7.34-7.39 (1H, m), 7.31 (1H, d, J=7.9 Hz), 7.25 (1H, t, J=7.8 Hz), 6.81 (1H, ddd, J=7.9, 2.5, 1.1 Hz), 6.41 (1H, d, J=9.8 Hz), 3.94 (2H, t, J=8.1 Hz), 3.66 (8H, s), 3.22 (2H, t, J=8.2 Hz).

ESI (LC-MS positive mode) m/z 392 ([M+H]⁺).

Example 1-A-12

3-(2-Morpholin-4-yl-7-pyridin-3-ylmethyl-6,7-dihydro-5H-pyrrolo[2,3-d]pyrimidin-4-yl)-phenol trifluoroacetic acid salt (A-12)

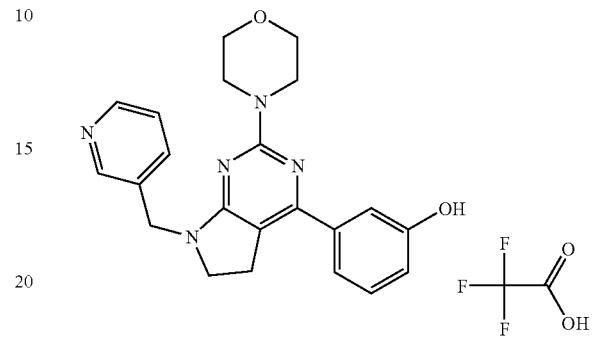

The reaction was carried out from Compound A-04 in the same manner as Example 1-A-09, and the resulting reaction crude product was further subjected to HPLC purification using an eluent containing trifluoroacetic acid, to obtain the desired compound as a trifluoroacetic acid salt.

¹H-NMR (400 MHz, CD₃OD) δ (ppm): 8.59-8.99 (2H, m), 8.41 (1H, d, J=8.0 Hz), 7.82-8.02 (1H, m), 7.38 (1H, t, J=8.0 Hz), 7.11 (1H, ddd, J=7.7, 1.7, 1.0 Hz), 7.06 (1H, t, J=2.0 Hz), 6.99 (1H, ddd, J=8.2, 2.4, 0.9 Hz), 4.96 (2H, s), 3.87 (2H, t, J=8.1 Hz), 3.71-3.84 (8H, m), 3.16 (2H, t, J=8.3 Hz).

ESI (LC-MS positive mode) m/z 390 ([M+H]⁺).

Example 1-A-13

3-[7-(1H-indazol-5-yl)-2-morpholin-4-yl-6,7-dihydro-5H-pyrrolo[2,3-d]pyrimidin-4-yl]-phenol (A-13)

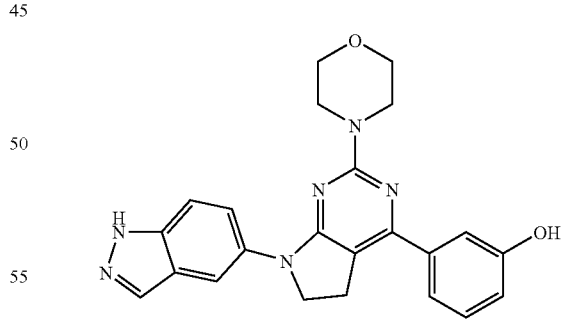

In the same manner as Example 1-A-09, the desired compound was obtained from Compound A-05.

¹H-NMR (400 MHz, CD₃OD) δ (ppm): 8.11 (1H, s), 8.01 (1H, d, J=1.4 Hz), 7.83 (1H, dd, J=9.1, 2.0 Hz), 7.64 (1H, d, J=9.1 Hz), 7.42 (1H, t, J=7.9 Hz), 7.17 (1H, ddd, J=7.7, 1.6, 0.9 Hz), 7.08-7.14 (1H, m), 7.02 (1H, ddd, J=8.2, 2.4, 0.8 Hz), 4.40 (2H, t, J=7.9 Hz), 3.77 (8H, s), 3.23-3.29 (2H, m).

ESI (LC-MS positive mode) m/z 415 ([M+H]⁺).

Example 1-A-14

3-[7-(1H-benzimidazol-5-yl)-2-morpholin-4-yl-6,7-dihydro-5H-pyrrolo[2,3-d]pyrimidin-4-yl]-phenol (A-14)

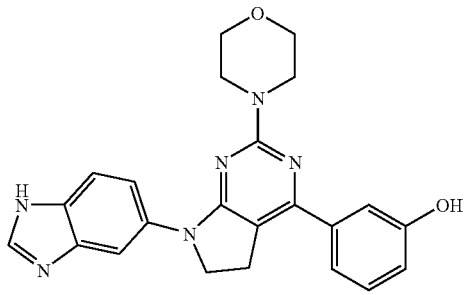

In the same manner as Example 1-A-09, the desired compound was obtained from Compound A-06.

$^1$H-NMR (400 MHz, DMSO-d$_6$) δ (ppm): 12.40 (1H, s), 9.54 (1H, s), 8.14-8.22 (1H, m), 7.93-8.13 (1H, m), 7.46-7.86 (2H, m), 7.37-7.43 (1H, m), 7.34 (1H, d, J=7.9 Hz), 7.27 (1H, t, J=7.8 Hz), 6.83 (1H, dd, J=7.5, 2.0 Hz), 4.14 (2H, t, J=8.1 Hz), 3.61-3.81 (8H, m), 3.28 (2H, t, J=8.1 Hz).

ESI (LC-MS positive mode) m/z 415 ([M+H]$^+$).

Example 1-A-15

3-(7-Methyl-2-morpholin-4-yl-6,7-dihydro-5H-pyrrolo[2,3-d]pyrimidin-4-yl)-phenol (A-15)

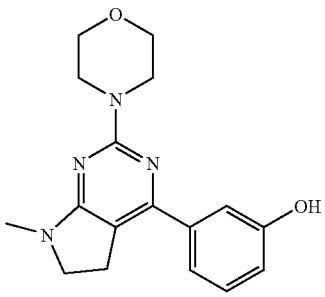

In the same manner as Example 1-A-09, the desired compound was obtained from Compound A-07.

$^1$H-NMR (400 MHz, CDCl$_3$) δ (ppm): 7.19-7.30 (3H, m), 6.93 (1H, d, J=8.1 Hz), 3.71-3.93 (10H, m), 3.11 (3H, s), 3.04-3.11 (1H, m), 2.66 (1H, s).

ESI (LC-MS positive mode) m/z 313 ([M+H]$^+$).

Example 1-A-16

3-[7-(2-Methyl-pyridin-4-yl)-2-morpholin-4-yl-6,7-dihydro-5H-pyrrolo[2,3-d]pyrimidin-4-yl]-phenol (A-16)

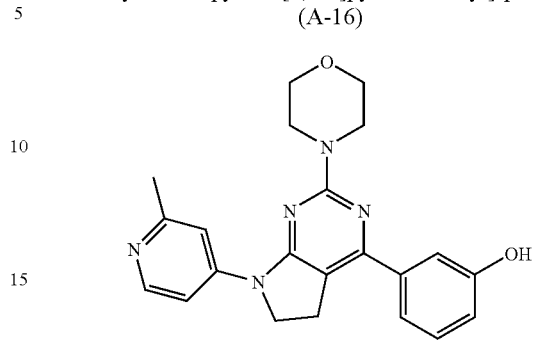

In the same manner as Example 1-A-01, from 4-[4-chloro-5-(2-chloroethyl)-6-(3-methoxyphenyl)-pyrimidin-2-yl]-morpholine and 4-amino-1-methylpyridine, 4-(3-methoxyphenyl)-7-(2-methyl-pyridin-4-yl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-d$_6$) δ (ppm): 8.31 (1H, d, J=5.9 Hz), 7.78 (1H, dd, J=5.8, 1.9 Hz), 7.58 (1H, s), 7.40 (1H, s), 7.32-7.36 (1H, m), 7.28 (1H, t, J=7.9 Hz), 6.85 (1H, d, J=6.8 Hz), 4.07 (2H, t, J=8.1 Hz), 3.73 (8H, d, J=6.6 Hz), 3.25-3.32 (3H, m).

ESI (LC-MS positive mode) m/z 390 ([M+H]$^+$).

Example 1-A-17

3-[7-(1-Methyl-1H-pyrazol-3-yl)-2-morpholin-4-yl-6,7-dihydro-5H-pyrrolo[2,3-d]pyrimidin-4-yl]-phenol (A-17)

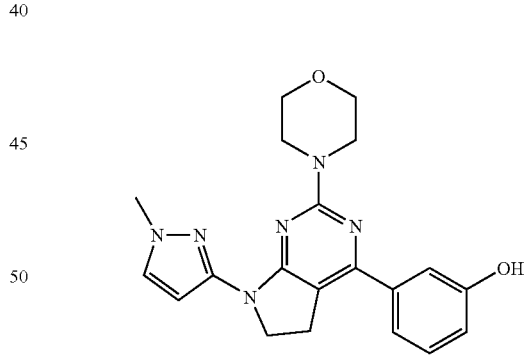

In the same manner as Example 1-A-01, from 4-[4-chloro-5-(2-chloroethyl)-6-(3-methoxyphenyl)-pyrimidin-2-yl]-morpholine and 1-methyl-1H-pyrazol-3-ylamine, 4-(3-methoxy-phenyl)-7-(1-methyl-1H-pyrazol-3-yl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-d$_6$) δ (ppm): 9.60 (1H, br.s.), 7.64 (1H, d, J=2.2 Hz), 7.40 (1H, s), 7.33-7.35 (1H, m), 7.26 (1H, t, J=7.9 Hz), 6.82 (1H, dd, J=7.9, 1.5 Hz), 6.78 (1H, d, J=2.2 Hz), 4.05 (2H, t, J=8.3 Hz), 3.78 (3H, s), 3.71 (8H, d, J=7.0 Hz), 3.26 (2H, t, J=8.3 Hz).

ESI (LC-MS positive mode) m/z 379 ([M+H]$^+$).

Example 1-A-18

3-[4-(3-Hydroxy-phenyl)-2-morpholin-4-yl-5,6-di-hydro-pyrrolo[2,3-d]pyrimidin-7-yl]-benzonitrile (A-18)

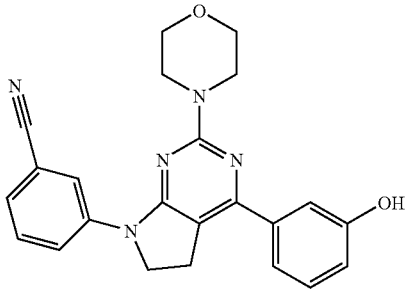

In the same manner as Example 1-A-01, from 4-[4-chloro-5-(2-chloroethyl)-6-(3-methoxyphenyl)-pyrimidin-2-yl]-morpholine and 3-cyanoaniline, 3-[4-(3-methoxy-phenyl)-2-morpholin-4-yl-5,6-dihydro-pyrrolo[2,3-d]pyrimidin-7-yl]-benzonitrile was obtained, and subsequently, further in the same manner as Example 1-A-09, the desired compound was obtained.

$^1$H-NMR (400 MHz, CDCl$_3$) δ (ppm): 8.19 (1H, s), 8.00 (1H, d, J=8.4 Hz), 7.41-7.54 (2H, m), 7.35-7.40 (1H, m), 7.28-7.34 (2H, m), 6.91 (1H, d, J=7.9 Hz), 4.06 (2H, t, J=8.2 Hz), 3.84 (8H, dd, J=14.4, 4.8 Hz), 3.34 (2H, t, J=8.1 Hz).

ESI (LC-MS positive mode) m/z 379 ([M+H]$^+$).

Example 1-A-19

3-[7-(2-Methyl-quinolin-4-yl)-2-morpholin-4-yl-6,7-dihydro-5H-pyrrolo[2,3-d]pyrimidin-4-yl]-phenol (A-19)

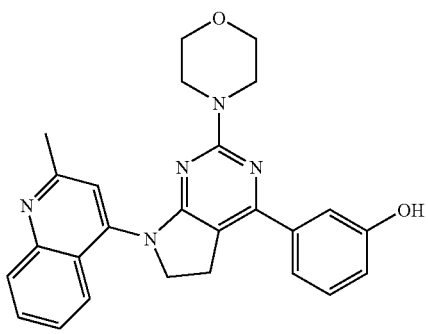

In the same manner as Example 1-A-01, from 4-[4-chloro-5-(2-chloroethyl)-6-(3-methoxyphenyl)-pyrimidin-2-yl]-morpholine and 2-methyl-quinolin-4-ylamine, 4-[4-(3-methoxy-phenyl)-2-morpholin-4-yl-5,6-dihydro-pyrrolo[2,3-d]pyrimidin-7-yl]-2-methyl-quinoline was obtained, and subsequently, further in the same manner as Example 1-A-09, the desired compound was obtained.

$^1$H-NMR (400 MHz, DMSO-d$_6$) δ (ppm): 7.92 (1H, d, J=8.1 Hz), 7.87 (1H, d, J=7.7 Hz), 7.70 (1H, t, J=7.0 Hz), 7.39-7.48 (3H, m), 7.34-7.38 (1H, m), 7.30 (1H, t, J=7.9 Hz), 6.86 (1H, dd, J=7.9, 1.3 Hz), 4.20 (2H, t, J=7.9 Hz), 3.45 (8H, dd, J=31.9, 3.9 Hz), 3.31-3.33 (2H, m), 2.65 (3H, s).

ESI (LC-MS positive mode) m/z 440 ([M+H]$^+$).

Example 1-A-20

3-[7-(3-Dimethylamino-phenyl)-2-morpholin-4-yl-6,7-dihydro-5H-pyrrolo[2,3-d]pyrimidin-4-yl]-phenol (A-20)

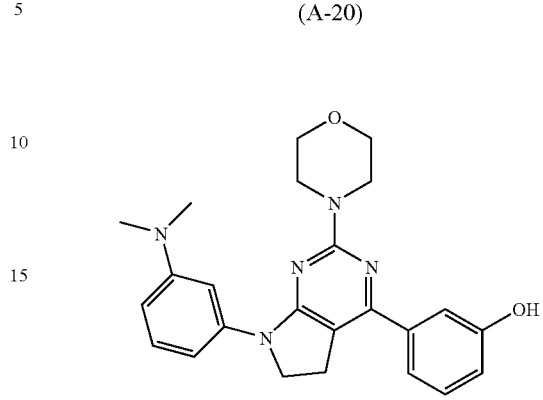

In the same manner as Example 1-A-01, from 4-[4-chloro-5-(2-chloroethyl)-6-(3-methoxyphenyl)-pyrimidin-2-yl]-morpholine and 3-N,N-dimethylaminoaniline, {3-[4-(3-methoxy-phenyl)-2-morpholin-4-yl-5,6-dihydro-pyrrolo[2,3-d]pyrimidin-7-yl]-phenyl}-dimethyl-amine was obtained, and subsequently, further in the same manner as Example 1-A-09, the desired compound was obtained.

$^1$H-NMR (400 MHz, CDCl$_3$) δ (ppm): 7.57 (1H, s), 7.42 (2H, d, J=7.8 Hz), 7.18-7.35 (2H, m), 6.87 (2H, d, J=7.9 Hz), 6.50 (1H, dd, J=8.1, 2.2 Hz), 4.09 (2H, t, J=7.9 Hz), 3.84 (8H, dd, J=19.5, 4.9 Hz), 3.28 (2H, t, J=7.3 Hz), 2.99 (6H, s).

ESI (LC-MS positive mode) m/z 418 ([M+H]$^+$).

Example 1-A-21

3-[2-Morpholin-4-yl-7-(4-trifluoromethoxy-phenyl)-6,7-dihydro-5H-pyrrolo[2,3-d]pyrimidin-4-yl]-phenol (A-21)

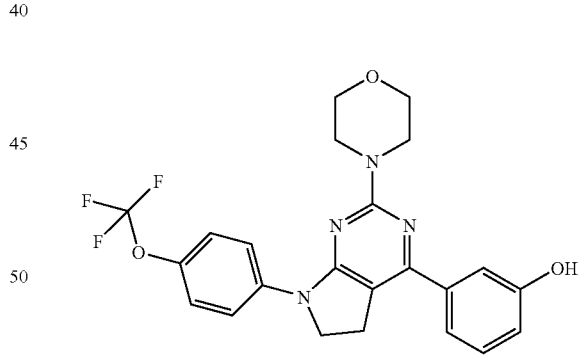

In the same manner as Example 1-A-01, from 4-[4-chloro-5-(2-chloroethyl)-6-(3-methoxyphenyl)-pyrimidin-2-yl]-morpholine and 4-trifluoromethoxyaniline, 4-(3-methoxy-phenyl)-2-morpholin-4-yl-7-(4-trifluoromethoxy-phenyl)-6,7-dihydro-5H-pyrrolo[2,3-d]pyrimidine was obtained, and subsequently, further in the same manner as Example 1-A-09, the desired compound was obtained.

$^1$H-NMR (400 MHz, CDCl$_3$) δ (ppm): 7.82 (2H, d, J=9.1 Hz), 7.47 (1H, s), 7.42 (1H, d, J=7.8 Hz), 7.33 (1H, t, J=7.9 Hz), 7.21-7.28 (2H, m), 6.90 (1H, d, J=8.0 Hz), 4.07 (2H, t, J=8.2 Hz), 3.85 (8H, dd, J=13.2, 4.6 Hz), 3.34 (2H, t, J=8.2 Hz).

ESI (LC-MS positive mode) m/z 459 ([M+H]$^+$).

Example 1-A-22

3-(2-Morpholin-4-yl-7-o-tolyl-6,7-dihydro-5H-pyrrolo[2,3-d]pyrimidin-4-yl)-phenol (A-22)

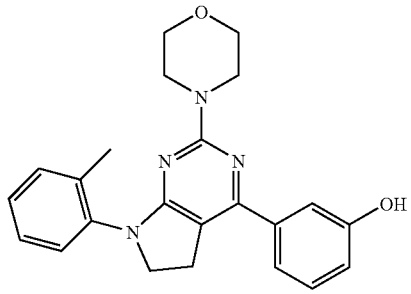

In the same manner as Example 1-A-01, from 4-[4-chloro-5-(2-chloroethyl)-6-(3-methoxyphenyl)-pyrimidin-2-yl]-morpholine and 2-methylaniline, 4-(3-methoxy-phenyl)-2-morpholin-4-yl-7-o-tolyl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-$d_6$) δ (ppm): 9.52 (1H, s), 7.39 (1H, s), 7.15-7.35 (6H, m), 6.83 (1H, d, J=7.9 Hz), 3.96 (2H, t, J=8.1 Hz), 3.55 (8H, d, J=7.0 Hz), 3.26-3.32 (2H, m), 2.21 (3H, s).

ESI (LC-MS positive mode) m/z 389 ([M+H]$^+$).

Example 1-A-23

3-[7-(2,4-Dimethyl-phenyl)-2-morpholin-4-yl-6,7-dihydro-5H-pyrrolo[2,3-d]pyrimidin-4-yl]-phenol (A-23)

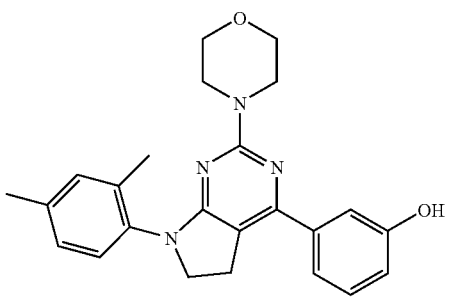

In the same manner as Example 1-A-01, from 4-[4-chloro-5-(2-chloroethyl)-6-(3-methoxyphenyl)-pyrimidin-2-yl]-morpholine and 2,4-dimethylaniline, 7-(2,4-dimethyl-phenyl)-4-(3-methoxy-phenyl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, CDCl$_3$) δ (ppm): 7.47 (1H, s), 7.40 (1H, d, J=7.7 Hz), 7.30 (1H, t, J=8.0 Hz), 7.09-7.17 (2H, m), 7.05 (1H, d, J=8.0 Hz), 6.86 (1H, d, J=8.1 Hz), 3.93 (2H, t, J=8.1 Hz), 3.72 (8H, s), 3.33 (2H, t, J=8.1 Hz), 2.36 (3H, s), 2.23 (3H, s).

ESI (LC-MS positive mode) m/z 389 ([M+H]$^+$).

Example 1-A-24

3-[7-(3-Dimethylamino-propyl)-2-morpholin-4-yl-6,7-dihydro-5H-pyrrolo[2,3-d]pyrimidin-4-yl]-phenol (A-24)

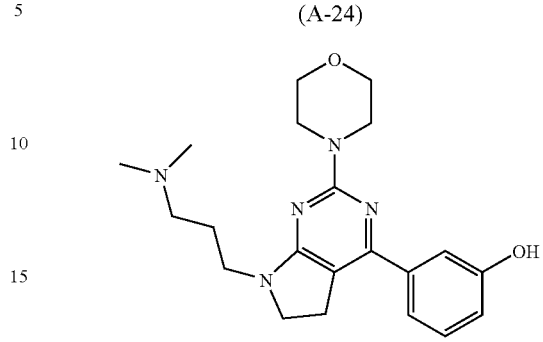

In the same manner as Example 1-A-01, from 4-[4-chloro-5-(2-chloroethyl)-6-(3-methoxyphenyl)-pyrimidin-2-yl]-morpholine and N,N-dimethyl-1,3-propanediamine, {3-[4-(3-methoxy-phenyl)-2-morpholin-4-yl-5,6-dihydro-pyrrolo[2,3-d]pyrimidin-7-yl]-propyl}-dimethyl-amine was obtained, and subsequently, further in the same manner as Example 1-A-09, the desired compound was obtained.

$^1$H-NMR (400 MHz, DMSO-$d_6$) δ (ppm): 9.48 (1H, brs), 7.35 (1H, s), 7.15-7.30 (2H, m), 6.79 (1H, d, J=8.9 Hz), 3.66 (8H, d, J=6.5 Hz), 3.56 (2H, t, J=8.1 Hz), 3.11 (2H, t, J=8.1 Hz), 2.27 (2H, t, J=7.0 Hz), 2.16 (6H, s), 1.63-1.75 (2H, m).

ESI (LC-MS positive mode) m/z 384 ([M+H]$^+$).

Example 1-A-25

3-[7-(4-Isopropyl-phenyl)-2-morpholin-4-yl-6,7-dihydro-5H-pyrrolo[2,3-d]pyrimidin-4-yl]-phenol (A-25)

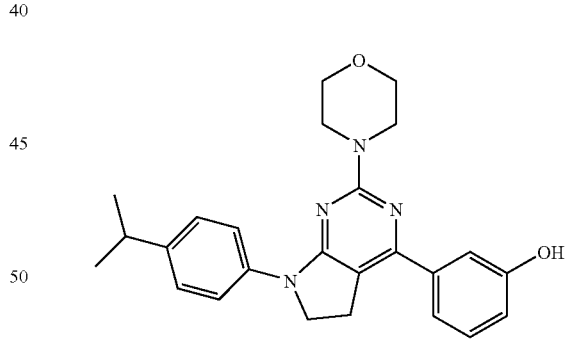

In the same manner as Example 1-A-01, from 4-[4-chloro-5-(2-chloroethyl)-6-(3-methoxyphenyl)-pyrimidin-2-yl]-morpholine and 4-isopropylaniline, 7-(4-isopropyl-phenyl)-4-(3-methoxy-phenyl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-$d_6$) δ (ppm): 9.54 (1H, s), 7.75 (2H, d, 8.8 Hz), 7.39 (1H, s), 7.31-7.36 (1H, m), 7.23-7.30 (3H, m), 6.83 (1H, dd, J=7.9, 1.5 Hz), 4.06 (2H, t, J=8.1 Hz), 3.70 (8H, d, J=5.1 Hz), 3.26 (2H, t, J=8.2 Hz), 2.81-2.92 (1H, m), 1.21 (3H, s), 1.19 (3H, s).

ESI (LC-MS positive mode) m/z 417 ([M+H]$^+$).

Example 1-A-26

3-[7-(3-Chloro-phenyl)-2-morpholin-4-yl-6,7-dihydro-5H-pyrrolo[2,3-d]pyrimidin-4-yl]-phenol trifluoroacetic acid salt (A-26)

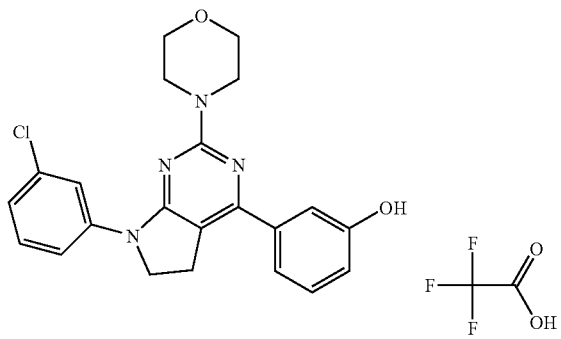

In the same manner as Example 1-A-01, from 4-[4-chloro-5-(2-chloroethyl)-6-(3-methoxyphenyl)-pyrimidin-2-yl]-morpholine and 3-chloroaniline, 7-(3-chloro-phenyl)-4-(3-methoxy-phenyl)-2-morpholin-4-yl-6,7-dihydro-5H-pyrrolo[2,3-d]pyrimidine was obtained, and subsequently, further in the same manner as Example 1-A-09 and by HPLC purification, the desired compound was obtained as a trifluoroacetic acid salt.

$^1$H-NMR (400 MHz, CD$_3$OD) δ (ppm): 7.72 (1H, s), 7.51-7.65 (3H, m), 7.39-7.46 (2H, m), 7.35 (1H, t, J=7.9 Hz), 6.91-7.02 (1H, m), 4.21-4.38 (2H, m), 3.62-3.88 (8H, m), 3.43-3.53 (2H, m).

ESI (LC-MS positive mode) m/z 409 ([M+H]$^+$).

Example 1-A-27

3-[7-(4-Chloro-3-methyl-phenyl)-2-morpholin-4-yl-6,7-dihydro-5H-pyrrolo[2,3-d]pyrimidin-4-yl]-phenol trifluoroacetic acid salt (A-27)

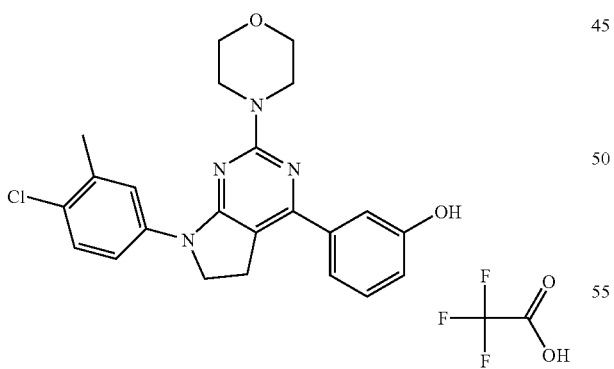

In the same manner as Example 1-A-01, from 4-[4-chloro-5-(2-chloroethyl)-6-(3-methoxyphenyl)-pyrimidin-2-yl]-morpholine and 4-chloro-3-methylaniline, 7-(4-chloro-3-methyl-phenyl)-4-(3-methoxy-phenyl)-2-morpholin-4-yl-6,7-dihydro-5H-pyrrolo[2,3-d]pyrimidine was obtained, and subsequently, further in the same manner as Example 1-A-09 and by HPLC purification, the desired compound was obtained as a trifluoroacetic acid salt.

$^1$H-NMR (400 MHz, CD$_3$OD) δ (ppm): 7.53-7.62 (2H, m), 7.39-7.45 (3H, m), 7.34 (1H, t, J=8.1 Hz), 6.96 (1H, dd, J=7.3, 2.7 Hz), 4.29 (2H, t, J=8.3 Hz), 3.63-3.87 (8H, m), 3.47 (2H, t, J=8.4 Hz), 2.46 (3H, s).

ESI (LC-MS positive mode) m/z 423 ([M+H]$^+$).

Example 1-A-28

3-[7-(2-Chloro-phenyl)-2-morpholin-4-yl-6,7-dihydro-5H-pyrrolo[2,3-d]pyrimidin-4-yl]-phenol trifluoroacetic acid salt (A-28)

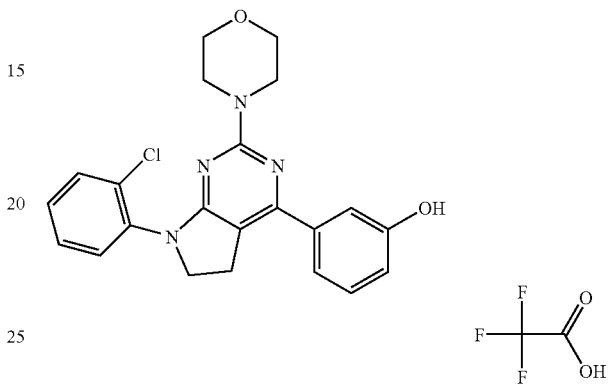

In the same manner as Example 1-A-01, from 4-[4-chloro-5-(2-chloroethyl)-6-(3-methoxyphenyl)-pyrimidin-2-yl]-morpholine and 2-chloroaniline, 7-(2-chloro-phenyl)-4-(3-methoxy-phenyl)-2-morpholin-4-yl-6,7-dihydro-5H-pyrrolo[2,3-d]pyrimidine was obtained, and subsequently, further in the same manner as Example 1-A-09, the reaction was carried out, followed by HPLC purification, to obtain the desired compound as a trifluoroacetic acid salt.

$^1$H-NMR (400 MHz, CD$_3$OD) δ (ppm): 7.76 (1H, dd, J=7.6, 1.7 Hz), 7.73 (1H, dd, J=8.1, 1.5 Hz), 7.60-7.67 (1H, m), 7.55-7.60 (1H, m), 7.41-7.47 (2H, m), 7.35 (1H, t, J=7.9 Hz), 6.95-7.00 (1H, m), 4.29-4.38 (1H, m), 4.18-4.29 (1H, m), 3.77-3.88 (4H, m), 3.65-3.72 (4H, m), 3.49-3.58 (2H, m).

ESI (LC-MS positive mode) m/z 409 ([M+H]$^+$).

Example 1-A-29

3-(2-Morpholin-4-yl-7-pyridin-2-yl-6,7-dihydro-5H-pyrrolo[2,3-d]pyrimidin-4-yl)-phenol (A-29)

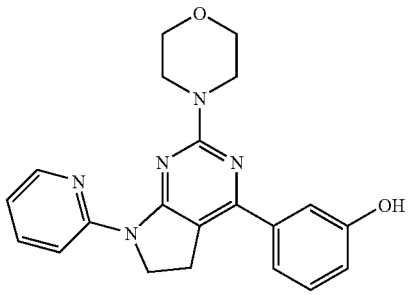

In the same manner as Example 1-A-01, from 4-[4-chloro-5-(2-chloroethyl)-6-(3-methoxyphenyl)-pyrimidin-2-yl]-morpholine and 2-aminopyrimidine, 4-(3-methoxy-phenyl)-2-morpholin-4-yl-7-pyridin-2-yl-6,7-dihydro-5H-pyrrolo[2,3-d]pyrimidine was obtained, and subsequently, further in the same manner as Example 1-A-09, the desired compound was obtained.

¹H-NMR (400 MHz, DMSO-d₆) δ (ppm): 9.57 (1H, s), 8.59 (1H, d, J=8.6 Hz), 8.36 (1H, d, J=3.8 Hz), 7.82 (1H, t, J=6.9 Hz), 7.41 (1H, s), 7.33-7.38 (1H, m), 7.28 (1H, t, J=7.9 Hz), 7.02 (1H, dd, J=7.1, 4.9 Hz), 6.85 (1H, dd, J=8.0, 1.6 Hz), 4.24 (2H, t, J=8.3 Hz).

ESI (LC-MS positive mode) m/z 376 ([M+H]⁺).

Example 1-A-30

3-[7-(5-Methyl-pyridin-2-yl)-2-morpholin-4-yl-6,7-dihydro-5H-pyrrolo[2,3-d]pyrimidin-4-yl]-phenol (A-30)

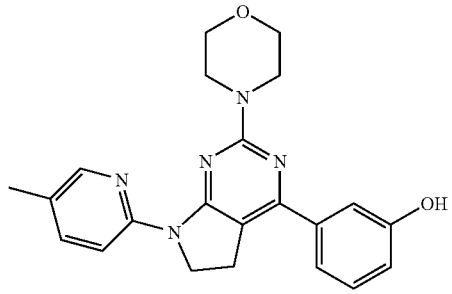

In the same manner as Example 1-A-01, from 4-[4-chloro-5-(2-chloroethyl)-6-(3-methoxyphenyl)-pyrimidin-2-yl]-morpholine and 2-amino-5-methylpyrimidine, 4-(3-methoxy-phenyl)-7-(5-methyl-pyridin-2-yl)-2-morpholin-4-yl-6,7-dihydro-5H-pyrrolo[2,3-d]pyrimidine was obtained, and subsequently, further in the same manner as Example 1-A-09, the desired compound was obtained.

¹H-NMR (400 MHz, DMSO-d₆) δ (ppm): 8.45 (1H, d, J=8.6 Hz), 8.16 (1H, s), 7.62 (1H, dd, J=8.6, 1.8 Hz), 7.30 (1H, s), 7.17 (2H, d, J=4.8 Hz), 6.67-6.81 (1H, m), 4.13 (2H, t, J=8.3 Hz), 3.69 (8H, d, J=6.2 Hz), 3.11-3.15 (2H, m), 2.24 (3H, s).

ESI (LC-MS positive mode) m/z 390 ([M+H]⁺).

Example 1-A-31

3-[7-(4-Chloro-phenyl)-2-morpholin-4-yl-6,7-dihydro-5H-pyrrolo[2,3-d]pyrimidin-4-yl]-phenol trifluoroacetic acid salt (A-31)

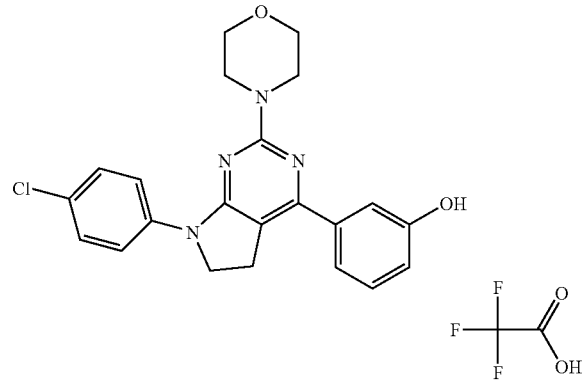

In the same manner as Example 1-A-01, from 4-[4-chloro-5-(2-chloroethyl)-6-(3-methoxyphenyl)-pyrimidin-2-yl]-morpholine and 4-chloroaniline, 7-(4-chloro-phenyl)-4-(3-methoxy-phenyl)-2-morpholin-4-yl-6,7-dihydro-5H-pyrrolo[2,3-d]pyrimidine was obtained. Further, in the same manner as Example 1-A-09, the reaction was carried out, followed by HPLC purification, to obtain the desired compound as a trifluoroacetic acid salt.

¹H-NMR (400 MHz, CD₃OD) δ (ppm): 7.61 (4H, d, J=2.9 Hz), 7.39-7.46 (2H, m), 7.34 (1H, t, J=8.1 Hz), 6.96 (1H, d, J=8.8 Hz), 4.30 (2H, t, J=8.3 Hz), 3.61-3.87 (8H, m), 3.48 (2H, t, J=8.1 Hz).

ESI (LC-MS positive mode) m/z 409 ([M+H]⁺).

Example 1-A-32

2-Fluoro-5-(2-morpholin-4-yl-7-pyridin-4-yl-6,7-dihydro-5H-pyrrolo[2,3-d]pyrimidin-4-yl)-phenol trifluoroacetic acid salt (A-32)

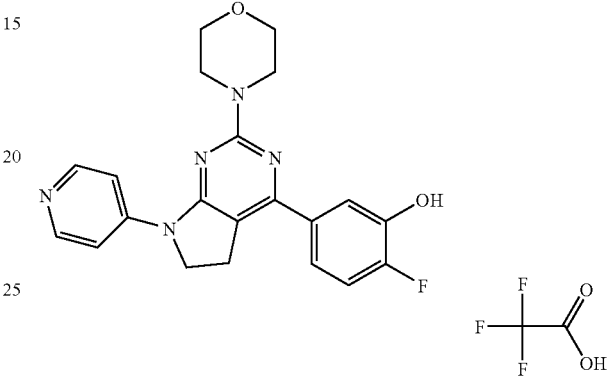

Using as an acid chloride of the starting material an acid chloride prepared from 4-fluoro-3-methoxy-benzoic acid and thionyl chloride instead of 3-methoxybenzoyl chloride, in the same manner as Example 1-A-01, 4-(4-fluoro-3-methoxy-phenyl)-2-morpholin-4-yl-7-pyridin-4-yl-6,7-dihydro-5H-pyrrolo[2,3-d]pyrimidine was obtained, from which, the reaction was carried out in the same manner as Example 1-A-09, followed by HPLC purification, to obtain the desired compound.

¹H-NMR (400 MHz, DMSO-d₆) δ (ppm): 10.19 (1H, brs), 8.65 (2H, d, J=7.3 Hz), 8.28 (2H, brs), 7.67 (1H, dd, J=8.7, 2.1 Hz), 7.36-7.47 (1H, m), 7.27 (1H, dd, J=11.0, 8.6 Hz), 4.23 (2H, t, J=8.1 Hz), 3.76 (8H, dd, J=17.7, 5.0 Hz), 3.33-3.39 (2H, m).

ESI (LC-MS positive mode) m/z 394 ([M+H]⁺).

Example 1-A-33

2-Fluoro-3-(2-morpholin-4-yl-7-pyridin-4-yl-6,7-dihydro-5H-pyrrolo[2,3-d]pyrimidin-4-yl)-phenol trifluoroacetic acid salt (A-33)

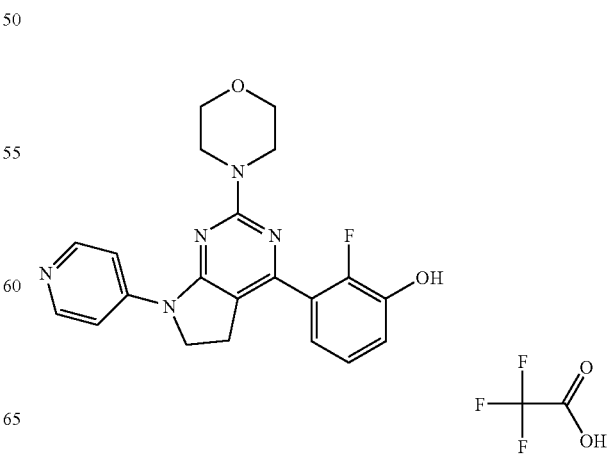

Using as an acid chloride of the starting material, an acid chloride prepared from 2-fluoro-3-methoxy-benzoic acid and thionyl chloride instead of 3-methoxybenzoyl chloride, in the same manner as Example 1-A-01, 4-(2-fluoro-3-methoxy-phenyl)-2-morpholin-4-yl-7-pyridin-4-yl-6,7-dihydro-5H-pyrrolo[2,3-d]pyrimidine was obtained, from which, the reaction was carried out in the same manner as Example 1-A-09, followed by HPLC purification, to obtain the desired compound.

$^1$H-NMR (400 MHz, DMSO-$d_6$) δ (ppm): 10.14 (1H, brs), 8.67 (2H, d, J=7.3 Hz), 8.29 (2H, brs), 7.03-7.19 (2H, m), 6.99 (1H, t, J=6.8 Hz), 4.22 (2H, t, J=8.1 Hz), 3.73 (8H, dd, J=13.9, 4.8 Hz), 3.05 (2H, t, J=8.1 Hz).

ESI (LC-MS positive mode) m/z 394 ([M+H]$^+$).

Example 1-A-34

2-Methyl-5-(2-morpholin-4-yl-7-pyridin-4-yl-6,7-dihydro-5H-pyrrolo[2,3-d]pyrimidin-4-yl)-phenol
(A-34)

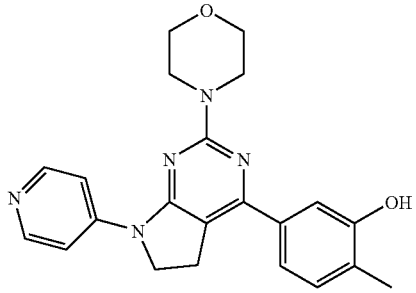

By using 4-methyl-3-methoxy-benzoic acid chloride for the reaction with γ-butyrolactone from Step A in Example 1-A-01, 2-morpholin-4-yl-7-pyridin-4-yl-4-(4-methyl-3-methoxy-phenyl)-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-$d_6$) δ (ppm): 9.49 (1H, brs), 8.44 (2H, d, J=6.3 Hz), 7.82 (2H, d, J=6.4 Hz), 7.49 (1H, s), 7.29 (1H, d, J=7.8 Hz), 7.17 (1H, d, J=8.0 Hz), 4.08 (2H, t, J=8.2 Hz), 3.74 (8H, d, J=7.7 Hz), 3.24-3.32 (3H, m), 2.17 (3H, s).

ESI (LC-MS positive mode) m/z 390 ([M+H]$^+$).

Example 1-A-35

2-Methyl-3-(2-Morpholin-4-yl-7-pyridin-4-yl-6,7-dihydro-5H-pyrrolo[2,3-d]pyrimidin-4-yl)-phenol
(A-35)

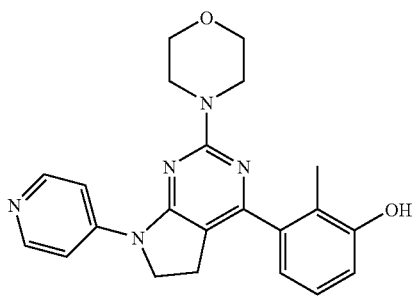

By using 2-methyl-3-methoxy-benzoic acid chloride for the reaction with γ-butyrolactone from Step A in Example 1-A-01, 2-morpholin-4-yl-7-pyridin-4-yl-4-(2-methyl-3-methoxy-phenyl)-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-$d_6$) δ (ppm): 9.50 (1H, brs), 8.45 (2H, d, J=6.0 Hz), 7.81 (2H, d, J=6.0 Hz), 7.05 (1H, t, J=7.7 Hz), 6.85 (1H, d, J=7.9 Hz), 6.73 (1H, d, J=7.3 Hz), 4.03 (2H, t, J=8.2 Hz), 3.68 (8H, s), 2.81-2.94 (2H, m), 2.04 (3H, s).

ESI (LC-MS positive mode) m/z 390 ([M+H]$^+$).

Example 1-A-36

3-[4-(3-Methoxy-phenyl)-2-morpholin-4-yl-5,6-dihydro-pyrrolo[2,3-d]pyrimidin-7-yl]-propan-1-ol
(A-36)

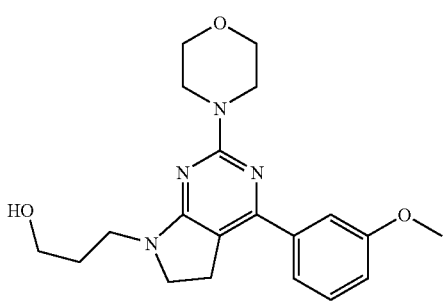

In the same manner as Example 1-A-01, from 4-[4-chloro-5-(2-chloroethyl)-6-(3-methoxyphenyl)-pyrimidin-2-yl]-morpholine and 3-aminopropane-1-ol, the desired compound was obtained.

$^1$H-NMR (400 MHz, CDCl$_3$) δ (ppm): 7.32-7.49 (3H, m), 6.92-6.96 (1H, m), 4.60 (1H, brt), 3.86 (3H, s), 3.78 (8H, m), 3.49-3.64 (6H, m), 3.23 (2H, t, J=8.1 Hz), 1.73-1.81 (2H, m).

ESI (LC-MS positive mode) m/z 371 ([M+H]$^+$).

Example 1-A-37

2-Morpholin-4-yl-4,7-di-pyridin-3-yl-6,7-dihydro-5H-pyrrolo[2,3-d]pyrimidine (A-37)

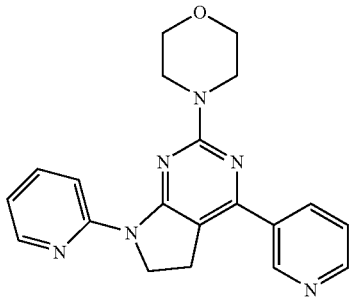

By using nicotinic acid chloride for the reaction with γ-butyrolactone from Step A in Example 1-A-01, 4-[4-chloro-5-(2-chloro-ethyl)-6-pyrimidin-3-yl-pyrimidin-2-yl]-morpholine was obtained, which was subsequently reacted with 3-aminopyridine, to obtain the desired compound.

$^1$H-NMR (400 MHz, CDCl$_3$) δ (ppm): 3.39 (2H, t, J=7.9 Hz), 3.79-3.90 (8H, m), 4.13 (2H, t, J=7.9 Hz), 7.33 (1H, dd, J=8.4, 4.8 Hz), 7.41 (1H, dd, J=8.1, 4.8 Hz), 8.15 (1H, dq, J=8.4, 1.3 Hz), 8.25 (1H, dt, J=8.1, 2.0 Hz), 8.30 (1H, m), 8.67 (1H, dd, J=4.8, 1.7 Hz), 9.14 (2H, m).

ESI (LC-MS positive mode) m/z 391 ([M+H]$^+$).

Example 1-A-38

2-Morpholin-4-yl-4-pyridin-3-yl-7-pyridin-4-yl-6,7-dihydro-5H-pyrrolo[2,3-d]pyrimidine (A-38)

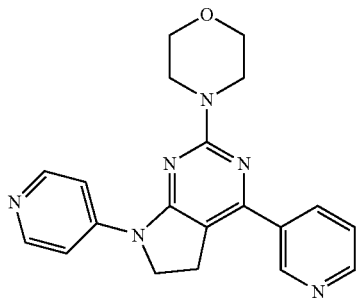

Using 4-aminopyridine instead of 3-aminopyridine, in the same manner as Example 1-A-37, the desired compound was obtained as a yellow solid (yield 9%).

$^1$H-NMR (400 MHz, CDCl$_3$) δ (ppm): 3.38 (2H, t, J=8.7 Hz), 3.80-3.92 (8H, m), 4.11 (2H, t, J=8.7 Hz), 7.43 (1H, ddd, J=8.1, 4.8, 0.8 Hz), 7.75 (2H, dd, J=5.0, 1.7 Hz), 8.26 (1H, dt, J=8.1, 2.3 Hz), 8.53 (2H, dd, J=5.0, 1.7 Hz), 8.67 (1H, dd, J=4.8, 1.7 Hz), 9.12 (1H, dd, J=2.3, 0.8 Hz)

ESI (LC-MS positive mode) m/z 391 ([M+H]$^+$).

Example 1-A-39

N-methyl-3-(2-morpholin-4-yl-7-pyridin-3-yl-6,7-dihydro-5H-pyrrolo[2,3-d]pyrimidin-4-yl)-benzenesulfonamide (A-39)

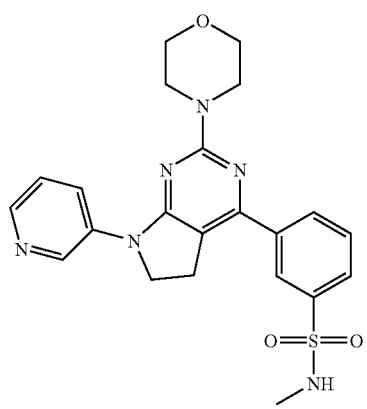

Using 3-[6-chloro-5-(2-chloro-ethyl)-2-morpholin-4-yl-pyrimidin-4-yl]-N-methyl-benzenesulfonamide instead of 4-[4-chloro-5-(2-chloro-ethyl)-6-phenyl-pyrimidin-2-yl]-morpholine, in the same manner as Example 1-A-37, the desired compound was obtained as a yellow solid (Yield 9%).

$^1$H-NMR (400 MHz, DMSO-d$_6$) δ (ppm): 9.10 (1H, d, J=2.6 Hz), 8.32 (1H, t, J=1.6 Hz), 8.28-8.24 (2H, m), 8.20 (1H, d, J=7.8 Hz), 7.87 (1H, dt, J=7.8, 1.6 Hz), 7.75 (1H, t, J=7.8 Hz), 7.62 (1H, q, J=4.9 Hz), 7.47-7.42 (1H, m), 4.17 (2H, t, J=8.2 Hz), 3.78-3.66 (8H, m), 3.38 (2H, t, J=8.2 Hz), 2.46 (3H, d, J=4.9 Hz).

ESI (LC-MS positive mode) m/z 453 ([M+H]$^+$).

Example 1-A-40

N-methyl-3-(2-morpholin-4-yl-7-pyridin-4-yl-6,7-dihydro-5H-pyrrolo[2,3-d]pyrimidin-4-yl)-benzenesulfonamide (A-40)

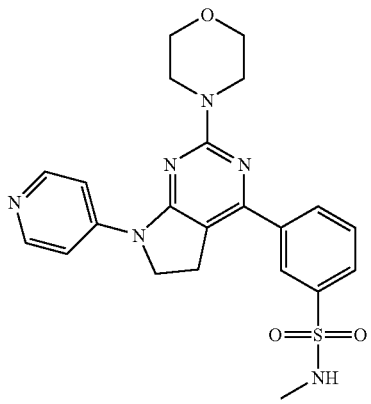

Using 4-aminopyridine instead of 3-aminopyridine, and 3-[6-chloro-5-(2-chloro-ethyl)-2-morpholin-4-yl-pyrimidin-4-yl]-N-methyl-benzenesulfonamide instead of 4-[4-chloro-5-(2-chloro-ethyl)-6-phenyl-pyrimidin-2-yl]-morpholine, in the same manner as Example 1-A-37, the desired compound was obtained as a yellow solid (yield 9%).

$^1$H-NMR (400 MHz, DMSO-d$_6$) δ (ppm): 8.49 (2H, d, J=5.4 Hz), 8.31 (1H, s), 8.20 (1H, d, J=7.9 Hz), 7.87 (2H, d, J=5.4 Hz), 7.76 (1H, td, J=7.9, 1.6 Hz), 7.63 (1H, q, J=5.4 Hz), 4.14 (2H, t, J=8.1 Hz), 3.78-3.72 (8H, m), 3.37 (2H, t, J=8.1 Hz), 2.45 (2H, d, J=4.9 Hz).

ESI (LC-MS positive mode) m/z 453 ([M+H]$^+$).

Example 1-A-41

3-{7-[2-(4-Methyl-piperazin-1-yl)-pyridin-4-yl]-2-morpholin-4-yl-6,7-dihydro-5H-pyrrolo[2,3-d]pyrimidin-4-yl}-phenol (A-41)

Step A 2-(4-Methyl-piperazin-1-yl)-pyridin-4-ylamine

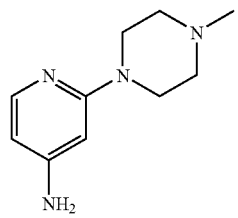

4-Amino-2-chloropyridine (180 mg, 1.4 mmol) was dissolved in 1-methylpiperazine (1 ml), followed by heating at 135° C. for 16 hours in a pressure vessel. After cooling to room temperature, methanol (2 ml) and diethyl ether (2 ml) were added, and the deposited precipitate was filtered off. The resulting solid was washed with cooled diethyl ether followed by drying, to obtain a colorless crystal powder (50 mg, 18.6% yield).

$^1$H-NMR (400 MHz, CD$_3$OD) δ (ppm) 7.63 (1H, d, J=5.95 Hz), 6.09 (1H, dd, J=5.95, 1.92 Hz), 5.99 (1H, d, J=1.92 Hz), 3.37-3.42 (4H, m), 2.52-2.58 (4H, m), 2.34 (3H, s).

Step B 4-(3-Methoxy-phenyl)-7-[2-(4-methyl-piperazin-1-yl)-pyridin-4-yl]-2-morpholin-4-yl-6,7-dihydro-5H-pyrrolo[2,3-d]pyrimidine

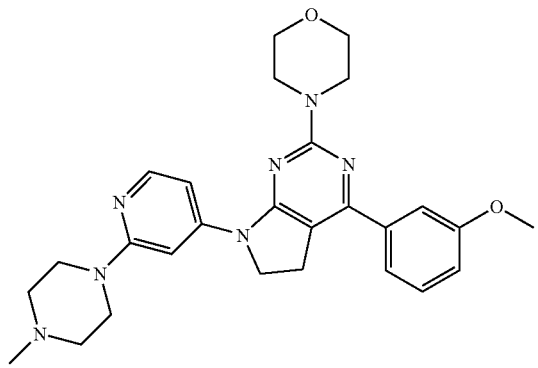

Sodium hydride (108 mg, 60% mineral oil dispersion, 2.72 mmol) was placed in a dried flask under a nitrogen atmosphere, followed by sequential addition of anhydrous tetrahydrofuran (10 ml) and 2-(4-methylpiperazin-1-yl)pyridin-4-ylamine (62 mg, 0.32 mmol) with a syringe, and the resulting mixture was heated to reflux for 2 hours. 4-[4-chloro-5-(2-chloroethyl)-6-(3-methoxyphenyl)-pyrimidin-2-yl]morpholine (100 mg, 0.27 mmol) was added, followed by heating to reflux for 16 hours. The reaction mixture was cooled, which was subsequently added dropwise slowly onto ice water, followed by extraction twice with ethyl acetate (10 ml). The organic layer was washed with brine (10 ml), and dried over sodium sulfate, followed by distilling off under reduced pressure, to obtain a crude product as a red oil (107 mg).

ESI (LC-MS positive mode) m/z 975 [2M+H].

Step C

3-{7-[2-(4-Methyl-piperazin-1-yl)-pyridin-4-yl]-2-morpholin-4-yl-6,7-dihydro-5H-pyrrolo[2,3-d]pyrimidin-4-yl}-phenol

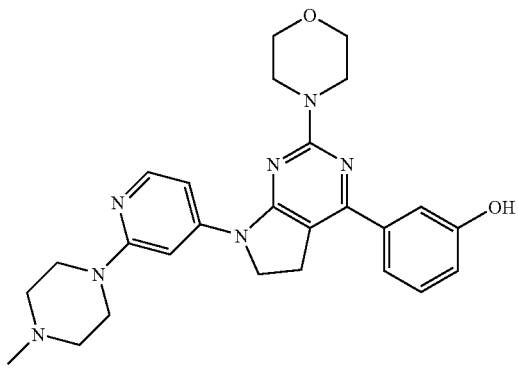

4-(3-Methoxyphenyl)-7-[2-(4-methylpiperazin-1-yl)-pyridin-4-yl]-2-morpholin-4-yl-6,7-dihydro-5H-pyrrolo[2,3-d]pyrimidine (107 mg, 0.22 mmol) was heated at 150° C. in dimethylformamide (1 ml), and sodium ethanethiolate (275 mg, 3.3 mmol) was added at 15 minutes intervals in 3 portions. After heating at 150° C. for further 15 minutes followed by cooling, water (1 ml) was added, followed by washing with ethyl acetate (2 ml). After the aqueous layer was left overnight, the deposited precipitate was filtered off, and washed with water followed by drying, whereby a colorless solid was obtained (18 mg, 17.3% yield).

$^1$H-NMR (400 MHz, DMSO-d$_6$) δ (ppm) 8.02 (1H, d, J=5.7 Hz), 7.38 (2H, d, J=8.4 Hz), 7.31-7.35 (1H, m), 7.28 (1H, t, J=7.8 Hz), 7.09 (1H, dd, J=5.9, 1.6 Hz), 6.85 (1H, dd, J=7.5, 1.8 Hz), 4.07 (2H, t, J=8.1 Hz), 3.73 (8H, dd, J=15.4, 4.8 Hz), 3.44-3.51 (4H, m), 3.24-3.30 (2H, m), 2.37-2.44 (4H, m), 2.22 (3H, s).

ESI (LC-MS positive mode) m/z 474 [M+H].

Example 1-A-42

3-{7-[2-(2-Dimethylamino-ethoxy)-pyridin-4-yl]-2-morpholin-4-yl-6,7-dihydro-5H-pyrrolo[2,3-d]pyrimidin-4-yl}-phenol (A-42)

Step A 2-(2-Dimethylamino-ethoxy)-pyridin-4-ylamine

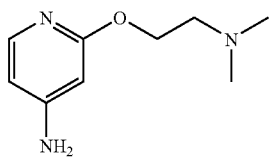

Sodium hydride (159 mg, 60% mineral oil dispersion, 3.98 mmol) was placed in a dried flask under a nitrogen atmosphere, followed by sequential addition of anhydrous toluene (10 ml) and 2-dimethylaminoethanol (177 mg, 2.0 mmol) with a syringe. After the resulting mixture was stirred at room temperature for 40 minutes, 4-amino-2-chloropyridine (203 mg, 1.59 mmol) was added, followed by heating to reflux for 16 hours. The reaction mixture was cooled, which was subsequently added dropwise slowly onto ice water, followed by extraction twice with ethyl acetate (10 ml). The organic layer was washed with brine (10 ml), and dried over sodium sulfate, followed by distilling off under reduced pressure, to obtain a crude product as a pale brown solid (180 mg).

$^1$H-NMR (400 MHz, CDCl$_3$) δ (ppm) 7.78 (1H, d, J=5.76 Hz), 6.18 (1H, dd, J=5.72, 2.06 Hz), 5.96 (1H, d, J=2.01 Hz), 4.34 (2H, t, J=5.67 Hz), 4.14 (2H, br.s.), 2.63-2.73 (2H, m), 2.31 (6H, s).

Step B (2-{4-[4-(3-Methoxy-phenyl)-2-morpholin-4-yl-5,6-dihydro-pyrrolo[2,3-d]pyrimidin-7-yl]-pyridin-2-yloxy}-ethyl)-dimethyl-amine

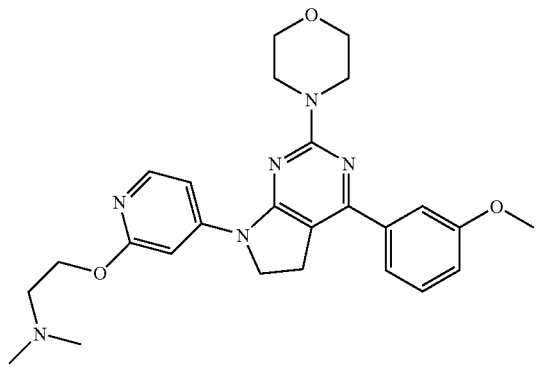

Sodium hydride (108 mg, 60% mineral oil dispersion, 2.72 mmol) was placed in a dried flask under a nitrogen atmosphere, followed by sequential addition of anhydrous tetrahydrofuran (10 ml) and 2-(4-methylpiperazin-1-yl)pyridin-4-ylamine (62 mg, 0.32 mmol) with a syringe. After the resulting mixture was stirred at room temperature for 2 hours, 4-[4-chloro-5-(2-chloroethyl)-6-(3-methoxyphenyl)-pyrimidin-2-yl]morpholine (100 mg, 0.27 mmol) was added, followed by heating to reflux for 4 hours. The reaction mixture was cooled, which was subsequently added dropwise slowly onto ice water, followed by extraction twice with ethyl acetate (10 ml). The organic layer was washed with brine (10 ml), and dried over sodium sulfate, followed by distilling off under reduced pressure, to obtain a crude product as a red oil (206 mg).

ESI (LC-MS positive mode) m/z 477 [M+H].

Step C

3-{7-[2-(2-Dimethylamino-ethoxy)-pyridin-4-yl]-2-morpholin-4-yl-6,7-dihydro-5H-pyrrolo[2,3-d]pyrimidin-4-yl}-phenol

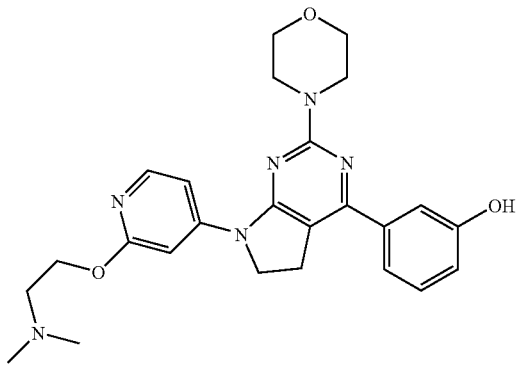

4-(3-Methoxyphenyl)-7-[2-(2-dimethylaminoethoxy)pyridin-4-yl]-2-morpholin-4-yl-6,7-dihydro-5H-pyrrolo[2,3-d]pyrimidine (206 mg) was heated to 150° C. in dimethylformamide (1 ml), and sodium ethanethiolate (275 mg, 3.3 mmol) was added at 15 minutes intervals in 3 portions. After heating at 150° C. for further 15 minutes followed by cooling, water (1 ml) was added, followed by extraction with ethyl acetate (2 ml). The organic layer was separated, followed by concentration under reduced pressure, the resulting oil was purified by preparative HPLC, to obtain a trifluoroacetic acid salt of the desired compound as a pale yellow solid (14 mg, 9% yield).

$^1$H-NMR (400 MHz, CD$_3$OD) δ (ppm) 8.17 (1H, d, J=6.0 Hz), 7.76 (1H, d, J=4.1 Hz), 7.37 (1H, t, J=8.1 Hz), 7.22-7.30 (3H, m), 6.97 (1H, d, J=7.9 Hz), 4.65-4.75 (2H, m), 4.24 (2H, t, J=8.1 Hz), 3.85 (8H, dd, J=11.6, 3.7 Hz), 3.57-3.68 (2H, m), 3.33-3.39 (2H, m), 3.01 (6H, s).

ESI (LC-MS positive mode) m/z 463 [M+H].

Example 1-A-43

3-[7-(4-Dimethylamino-3,4,5,6-tetrahydro-2H-[1,2']bipyridinyl-4'-yl)-2-morpholin-4-yl-6,7-dihydro-5H-pyrrolo[2,3-d]pyrimidin-4-yl]-phenol (A-43)

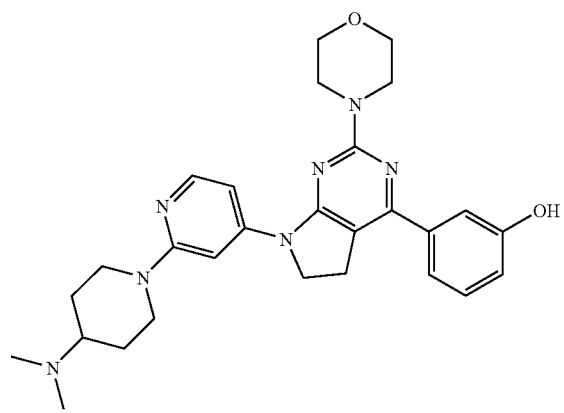

In the same manner as Example 1-A-41, using 4-dimethylaminopiperidine instead of 1-methylpiperazine, the desired compound was obtained.

$^1$H-NMR (400 MHz, CD$_3$OD) δ (ppm) 7.92 (1H, d, J=7.3 Hz), 7.81 (1H, br.s.), 7.57 (1H, br.s.), 7.42 (1H, s), 7.36-7.40 (1H, m), 7.31 (1H, t, J=7.8 Hz), 6.91 (1H, d, J=6.5 Hz), 4.18-4.36 (4H, m), 3.84 (8H, dd, J=19.3, 5.3 Hz), 3.52-3.66 (1H, m), 3.40 (2H, t, J=8.1 Hz), 3.24-3.29 (2H, m), 2.93 (6H, s), 2.28 (2H, d, J=13.4 Hz), 1.77-1.99 (2H, m).

ESI (LC-MS positive mode) m/z 502 [M+H].

Example 1-A-44

3-[2-Morpholin-4-yl-7-(2-morpholin-4-yl-pyridin-4-yl)-6,7-dihydro-5H-pyrrolo[2,3-d]pyrimidin-4-yl]-phenol (A-44)

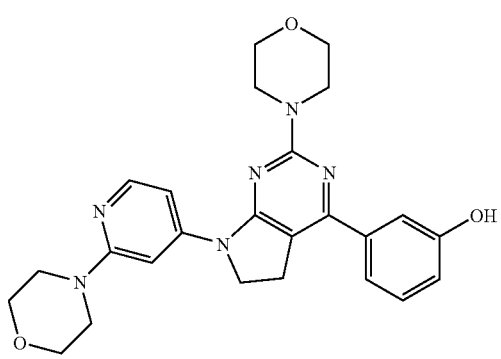

In the same manner as Example 1-A-41, using morpholine instead of 1-methylpiperazine, the desired compound was obtained.

¹H-NMR (400 MHz, CD₃OD) δ (ppm) 7.80-7.96 (2H, m), 7.35-7.51 (3H, m), 7.31 (1H, t, J=7.9 Hz), 6.90 (1H, d, J=8.1 Hz), 4.21 (2H, t, J=8.2 Hz), 3.72-3.94 (12H, m), 3.54-3.63 (4H, m), 3.39 (2H, t, J=8.2 Hz).

ESI (LC-MS positive mode) m/z 461 [M+H].

Example 1-A-45

3-(7-{2-[(3-Dimethylamino-propyl)-methyl-amino]-pyridin-4-yl}-2-morpholin-4-yl-6,7-dihydro-5H-pyrrolo[2,3-d]pyrimidin-4-yl)-phenol (A-45)

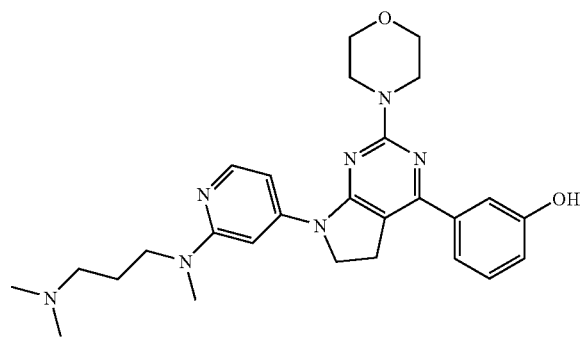

In the same manner as Example 1-A-41, using (3-dimethylaminopropyl)-methyl-amine instead of 1-methylpiperazine, the desired compound was obtained.

¹H-NMR (400 MHz, CD₃OD) δ (ppm) 7.87 (2H, s), 7.40 (1H, s), 7.37 (1H, d, J=8.0 Hz), 7.30 (1H, t, J=7.9 Hz), 7.10 (1H, br.s.), 6.90 (1H, d, J=9.4 Hz), 4.20 (2H, t, J=8.1 Hz), 3.83 (8H, dd, J=16.5, 5.1 Hz), 3.69 (2H, t, J=7.4 Hz), 3.36 (2H, t, J=8.1 Hz), 3.20-3.28 (5H, m), 2.93 (6H, s), 2.05-2.22 (2H, m).

ESI (LC-MS positive mode) m/z 490 [M+H].

Example 1-A-46

3-(7-{2-[(2-Dimethylamino-ethyl)-methyl-amino]-pyridin-4-yl}-2-morpholin-4-yl-6,7-dihydro-5H-pyrrolo[2,3-d]pyrimidin-4-yl)-phenol (A-46)

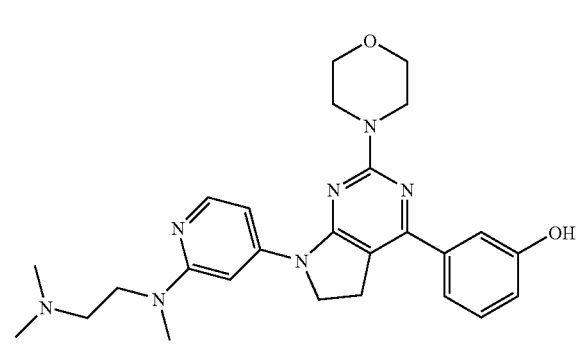

In the same manner as Example 1-A-41, using (2-dimethylaminoethyl)-methyl-amine instead of 1-methylpiperazine, the desired compound was obtained.

¹H-NMR (400 MHz, CD₃OD) δ (ppm) 7.90-8.07 (2H, m), 7.28-7.41 (3H, m), 7.05 (1H, br.s.), 6.96 (1H, d, J=8.3 Hz), 4.29 (2H, t, J=8.1 Hz), 4.05 (2H, t, J=7.1 Hz), 3.84 (8H, dd, J=18.0, 5.1 Hz), 3.48 (2H, t, J=7.2 Hz), 3.35 (2H, t, J=8.2 Hz), 3.27 (3H, s), 3.00 (6H, s).

ESI (LC-MS positive mode) m/z 476 [M+H].

Example 1-A-47

3-[7-(4-Dimethylamino-phenyl)-2-morpholin-4-yl-6,7-dihydro-5H-pyrrolo[2,3-d]pyrimidin-4-yl]-phenol (A-47)

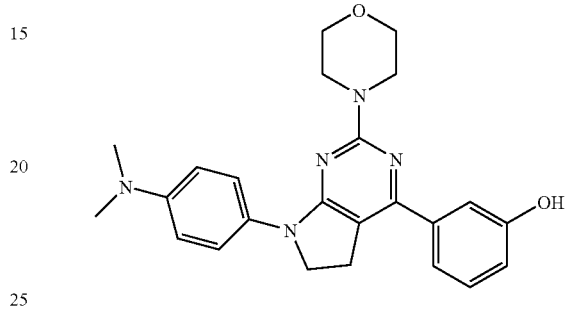

In the same manner as Example 1-A-01, from 4-[4-chloro-5-(2-chloroethyl)-6-(3-methoxyphenyl)-pyrimidin-2-yl]-morpholine and 4-dimethylaminoaniline, 4-(3-methoxy-phenyl)-7-(4-dimethylaminophenyl)-2-morpholin-4-yl-6,7-dihydro-5H-pyrrolo[2,3-d]pyrimidine was obtained, and subsequently, further in the same manner as Example 1-A-09, the desired compound was obtained.

¹H-NMR (400 MHz, DMSO-d₆) δ (ppm): 9.57 (1H, s), 8.78 (1H, s), 7.78 (1H, dd, J=8.3, 1.6 Hz), 7.58 (1H, t, J=8.0 Hz), 7.47 (1H, d, J=8.4 Hz), 7.41 (1H, s), 7.34-7.38 (3H, m), 7.29 (1H, t, J=7.9 Hz), 6.85 (1H, dd, J=7.9, 1.5 Hz), 4.12 (2H, t, J=8.2 Hz), 3.73 (8H, dd, J=29.4, 4.8 Hz), 3.28-3.33 (2H, m).

ESI (LC-MS positive mode) m/z 418 ([M+H]⁺).

Example 1-A-48

N-{3-[4-(3-hydroxy-phenyl)-2-morpholin-4-yl-5,6-dihydro-pyrrolo[2,3-d]pyrimidin-7-yl]-phenyl}-methane sulfonamide trifluoroacetic acid salt (A-48)

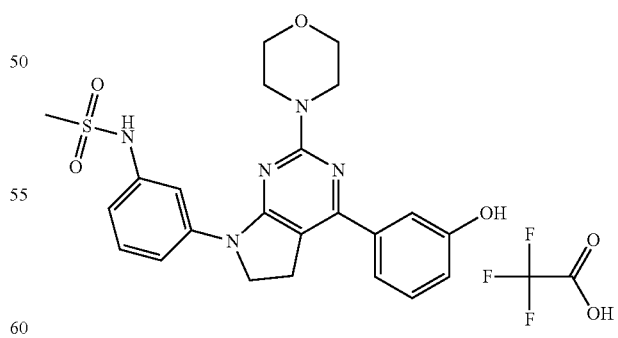

In the same manner as Example 1-A-01, from 4-[4-chloro-5-(2-chloroethyl)-6-(3-methoxyphenyl)-pyrimidin-2-yl]-morpholine and 3-methanesulfonylaminoaniline, 4-(3-methoxy-phenyl)-7-(3-methanesulfonylaminophenyl)-2-morpholin-4-yl-6,7-dihydro-5H-pyrrolo[2,3-d]pyrimidine was obtained, and subsequently, further in the same manner as Example 1-A-09, the reaction was carried out. The resulting reaction crude product was further subjected to HPLC purification using a developing solvent including trifluoroacetic acid, to obtain the desired compound as a trifluoroacetic acid salt.

$^1$H-NMR (400 MHz, CD$_3$OD) δ (ppm): 8.06 (1H, s), 7.33-7.48 (3H, m), 7.17 (1H, d, J=6.8 Hz), 7.12 (1H, t, J=2.0 Hz), 6.97-7.06 (2H, m), 4.32 (2H, t, J=8.0 Hz), 3.83 (8H, dd, J=20.8, 5.3 Hz), 3.22 (2H, t, J=8.0 Hz), 2.99 (3H, s).

ESI (LC-MS positive mode) m/z 468 ([M+H]$^+$).

Example 1-A-49

3-(2-Morpholin-4-yl-7-thiazol-2-yl-6,7-dihydro-5H-pyrrolo[2,3-d]pyrimidin-4-yl)-phenol (A-49)

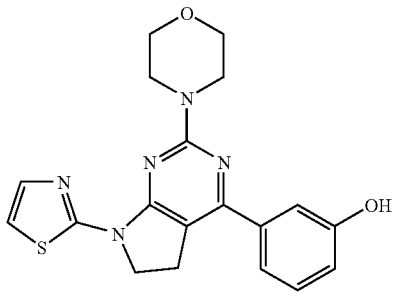

In the same manner as Example 1-A-01, from 4-[4-chloro-5-(2-chloroethyl)-6-(3-methoxyphenyl)-pyrimidin-2-yl]-morpholine and 2-aminothiazole, 4-(3-methoxy-phenyl)-7-(thiazol-2-yl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-d$_6$) δ (ppm): 9.68 (1H, brs), 7.42-7.56 (2H, m), 7.38 (1H, d, J=7.4 Hz), 7.21-7.33 (2H, m), 6.87 (1H, d, J=7.8 Hz), 4.31 (2H, t, J=8.1 Hz), 3.78 (8H, dd, J=41.2, 4.0 Hz), 3.36 (2H, m).

ESI (LC-MS positive mode) m/z 382 ([M+H]$^+$).

Example 1-A-50

3-[7-(4-Methanesulfonyl-phenyl)-2-morpholin-4-yl-6,7-dihydro-5H-pyrrolo[2,3-d]pyrimidin-4-yl]-phenol (A-50)

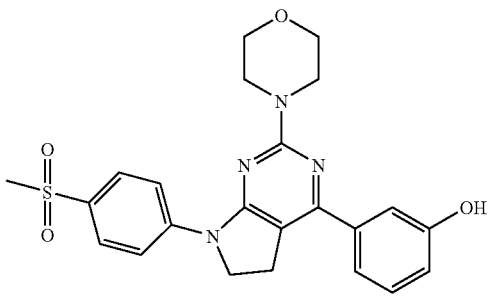

In the same manner as Example 1-A-01, from 4-[4-chloro-5-(2-chloroethyl)-6-(3-methoxyphenyl)-pyrimidin-2-yl]-morpholine and 4-methanesulfonylaniline, 4-(3-methoxy-phenyl)-7-(3-methanesulfonylphenyl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (DMSO-d$_6$) δ (ppm): 9.58 (1H, s), 8.11 (2H, d, J=9.1 Hz), 7.92 (2H, d, J=9.1 Hz), 7.38-7.43 (1H, m), 7.33-7.37 (1H, m), 7.29 (1H, t, J=7.8 Hz), 6.82-6.90 (1H, m), 4.14 (2H, t, J=8.1 Hz), 3.73 (8H, dd, J=15.2, 4.9 Hz), 3.28-3.33 (2H, m), 3.18 (3H, s).

ESI (LC-MS positive mode) m/z 453 [(M+H)$^+$].

Example 1-A-51

4-[4-(3-Hydroxy-phenyl)-2-morpholin-4-yl-5,6-dihydro-pyrrolo[2,3-d]pyrimidin-7-yl]-benzenesulfonamide (A-51)

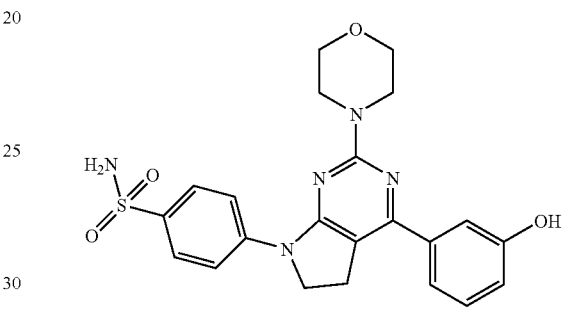

In the same manner as Example 1-A-01, from 4-[4-chloro-5-(2-chloroethyl)-6-(3-methoxyphenyl)-pyrimidin-2-yl]-morpholine and 4-aminobenzene sulfonamide, 4-(3-methoxy-phenyl)-7-(4-aminosulfonylphenyl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-d$_6$) δ (ppm): 9.59 (1H, s), 7.98-8.06 (2H, m), 7.83 (2H, d, J=8.9 Hz), 7.20-7.43 (5H, m), 6.85 (1H, d, J=9.5 Hz), 4.13 (2H, t, J=8.1 Hz), 3.67-3.80 (8H, m), 3.26-3.32 (2H, m).

ESI (LC-MS positive mode) m/z 454 ([M+H]$^+$).

Example 1-A-52

3-(7-Benzothiazol-6-yl-2-morpholin-4-yl-6,7-dihydro-5H-pyrrolo[2,3-d]pyrimidin-4-yl)-phenol trifluoroacetic acid salt (A-52)

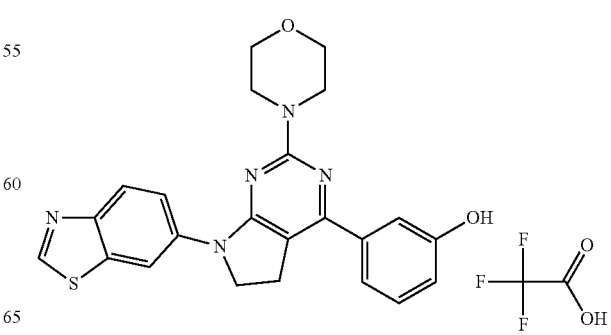

In the same manner as Example 1-A-01, from 4-[4-chloro-5-(2-chloroethyl)-6-(3-methoxyphenyl)-pyrimidin-2-yl]-morpholine and 6-aminobenzothiazole, 4-(3-methoxy-phenyl)-7-(benzothiazol-6-yl)-2-morpholin-4-yl-6,7-dihydro-5H-pyrrolo[2,3-d]pyrimidine was obtained, and subsequently, further in the same manner as Example 1-A-09, the reaction was carried out. The resulting reaction crude product was further subjected to HPLC purification using a developing solvent containing trifluoroacetic acid, to obtain the desired compound as a trifluoroacetic acid salt.

$^1$H-NMR (400 MHz, CD$_3$OD) δ (ppm): 9.28 (1H, s), 8.43 (1H, s), 8.05-8.20 (2H, m), 7.43 (1H, t, J=7.9 Hz), 7.19 (1H, d, J=7.7 Hz), 7.13 (1H, s), 7.03 (1H, d, J=9.7 Hz), 4.43 (2H, t, J=7.9 Hz), 3.82 (8H, s), 3.26-3.29 (2H, m).

ESI (LC-MS positive mode) m/z 432 ([M+H]$^+$).

Example 1-A-53

3-[4-(3-Hydroxy-phenyl)-2-morpholin-4-yl-5,6-dihydro-pyrrolo[2,3-d]pyrimidin-7-yl]-benzenesulfonamide (A-53)

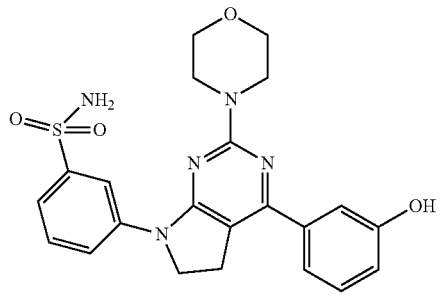

In the same manner as Example 1-A-01, from 4-[4-chloro-5-(2-chloroethyl)-6-(3-methoxyphenyl)-pyrimidin-2-yl]-morpholine and 3-aminobenzene sulfonamide, 4-(3-methoxy-phenyl)-7-(3-aminosulfonylphenyl)-2-morpholin-4-yl-6,7-dihydro-5H-pyrrolo[2,3-d]pyrimidine was obtained, and subsequently, further in the same manner as Example 1-A-09, the desired compound was obtained.

$^1$H-NMR (400 MHz, DMSO-d$_6$) δ (ppm): 9.56 (1H, s), 8.78 (1H, t, J=2.0 Hz), 7.78 (1H, dd, J=8.2, 2.2 Hz), 7.57 (1H, t, J=8.0 Hz), 7.45-7.49 (1H, m), 7.39-7.42 (1H, m), 7.33-7.37 (3H, m), 7.28 (1H, t, J=7.8 Hz), 6.83 (1H, dd, J=2.56, 0.91 Hz), 4.12 (2H, t, J=8.2 Hz), 3.66-3.79 (8H, m), 3.28-3.33 (2H, m).

ESI (LC-MS positive mode) m/z 454 ([M+H]$^+$).

Example 1-A-54

3-(2-Morpholin-4-yl-8-pyridin-4-yl-5,6,7,8-tetrahydro-pyrido[2,3-d]pyrimidin-4-yl)-phenol (A-54)

Step A 3-(3-Methoxybenzoyl)dihydropyran-2-one

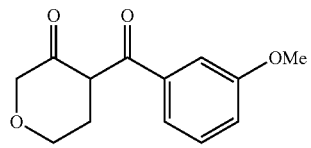

A solution of δ-valerolactone (2.0 g, 20 mmol) in anhydrous tetrahydrofuran (100 ml) was cooled to −78° C. under a nitrogen atmosphere, and 3-methoxybenzoyl chloride (3.58 g, 21 mmol) and lithium hexamethyldisilazide (40 ml, 1M tetrahydrofuran solution, 40 mmol) were added sequentially. Stirring was carried out for 2 hours, followed by treatment with saturated sodium bicarbonate water. The reaction mixture was extracted with ethyl acetate (100 ml), followed by washing with brine, and subsequently, the solvent was distilled off under reduced pressure, to obtain a brown crude product. Purification by silica gel column chromatography (hexane/ethyl acetate=1/1) afforded the desired compound as a pale yellow liquid.

$^1$H-NMR (400 MHz, CDCl$_3$) δ (ppm) 4.30-4.48 (2H, m), 3.80 (3H, s), 3.59 (1H, t, J=7.9 Hz), 2.11-2.35 (2H, m), 1.83-2.06 (2H, m).

ESI (LC-MS positive mode) m/z 235 ([M+H]$^+$).

Step B 5-(3-Hydroxypropyl)-6-(methoxyphenyl)-2-morpholin-4-yl-pyrimidin-4-ol

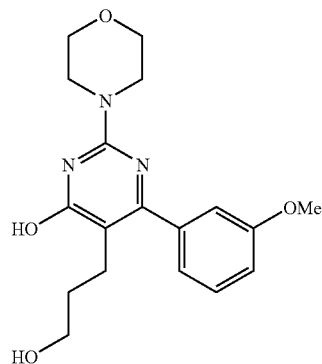

Morpholinoformamidine bromate salt (200 mg, 0.952 mmol), 3-(3-methoxybenzoyl)dihydropyran-2-one (544 mg, 3.6 mmol) and sodium t-butoxide (230 mg, 2.32 mmol) were added into a microwave reaction tube, and dissolved in t-BuOH (3 ml). After irradiation of microwave (200 W, 120° C.) for 1 hour, the solvent was removed under reduced pressure, to obtain a crude product as a brown solid. This was purified by silica gel column chromatography (dichloromethane/methanol=95/5), to obtain 5-(2-hydroxyethyl)-6-(3-methoxyphenyl)-2-(morpholin-4-yl)-pyrimidin-4-ol and 4-(3-methoxyphenyl)-2-(morpholin-4-yl)-5,6-furo[2,3-d]pyrimidine as colorless solid (Yield 16%).

ESI (LC-MS positive mode) m/z 346 ([M+H]$^+$).

Step C

4-Chloro-5-(3-chloropropyl)-6-(3-methoxyphenyl)-2-(morpholin-4-yl)-pyrimidine

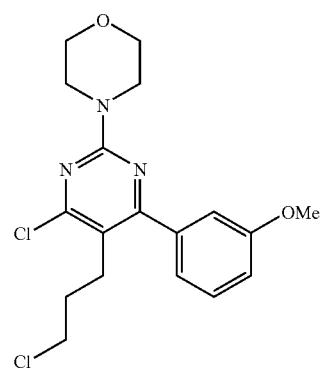

5-(3-Hydroxypropyl)-6-(3-methoxyphenyl)-2-(morpholin-4-yl)-pyrimidin-4-ol (1.03 g, 2.97 mmol) was dissolved in POCl$_3$ (8 ml), followed by heating to 110° C. for 24 hours in a sealed tube. After concentration under reduced pressure, the crude product was obtained as a brown oil. This was purified by silica gel column chromatography (hexane/ethyl acetate=90/10), to obtain the desired compound as a yellow oil (790 mg, 66%).

ESI (LC-MS positive mode) m/z 382 ([M+H]$^+$).

Step D 4-(3-Methoxyphenyl)-2-morpholin-4-yl-7-pyridin-4-yl-5,6,7,8-tetrahydro-pyrido[2,3-d]pyrimidine

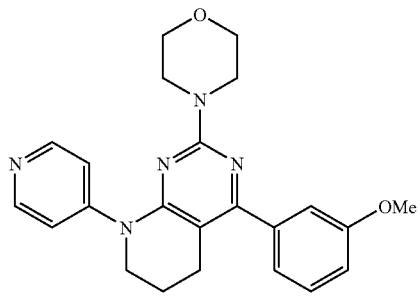

To a mixture of Pd(OAc)$_2$ (46 mg, 0.21 mmol), S-Phos (176 mg, 0.41 mmol) and 4-aminopyridine (233 mg, 2.48 mmol), deaerated 1,4-dioxane solution (48 ml) of 4-[4-chloro-5-(3-chloropropyl)-6-(3-methoxyphenyl)-pyrimidin-2-yl]-morpholine (790 mg, 2.07 mmol) was added. The mixture was heated to reflux for 18 hours followed by cooling, and water (50 ml) was added. The product was extracted three times with ethyl acetate (100 ml), and the extract was concentrated under reduced pressure. The resulting residue was recrystallized from ethyl acetate/heptane, to obtain the desired compound as a yellow crystal (500 mg, 69%).

ESI (LC-MS positive mode) m/z 404 [M+H]$^+$.

Step E 3-(2-Morpholin-4-yl-8-pyridin-4-yl-5,6,7,8-tetrahydro-pyrido[2,3-d]pyrimidin-4-yl)-phenol

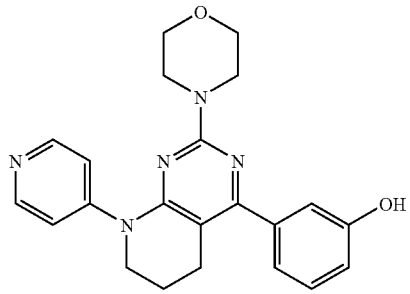

A solution of 4-(3-methoxyphenyl)-2-morpholin-4-yl-8-pyrimidin-4-yl-5,6,7,8-tetrahydropyrido[2,3-d]pyrimidine (0.50 g, 1.24 mmol) in dimethylformamide (5 ml) was heated to 150° C., and sodium ethanethiolate (1.04 g, 12.4 mmol) was added for every 15 minutes in 3 portions. After heating at 150° C. for 2 hours, sodium ethanethiolate (1.04 g, 12.4 mmol) was added, followed by heating for further 15 minutes. After cooling the reaction mixture, water (5 ml) and ethyl acetate (20 ml) were added, to filter off the deposited precipitate. The crude product was purified by silica column chromatography (dichloromethane/methanol=95/5), to obtain the desired compound as a pale brown solid (0.21 g, 43% yield).

$^1$H-NMR (400 MHz, DMSO-d$_6$) δ (ppm) 9.54 (1H, s), 8.47 (2H, d, J=6.0 Hz), 7.48 (2H, d, J=6.2 Hz), 7.24 (1H, t, J=7.9 Hz), 6.90-6.99 (2H, m), 6.82 (1H, dd, J=7.0, 2.0 Hz), 3.78-3.85 (2H, m), 3.54 (8H, dd, J=28.9, 4.8 Hz), 2.63 (2H, t, J=6.2 Hz), 1.82-1.95 (2H, m).

ESI (LC-MS positive mode) m/z 390 [M+H].

Example 1-B

4-Chloro-2-morpholin-4-yl-7-pyridin-3-yl-6,7-dihydro-5H-pyrrolo[2,3-d]pyrimidine to be used in the following Examples 1-B-05, 1-B-10, 1-B-12, 1-B-14, 1-B-21, 1-B-23, 1-B-24, 1-B-29, 1-B-31, 1-B-33, 1-B-50, and 1-B-51 was prepared according to Step A in Example 1-B-02 described below. Further, 4-chloro-2-morpholin-4-yl-7-pyridin-4-yl-6,7-dihydro-5H-pyrrolo[2,3-d]pyrimidine to be used in the following Examples 1-B-08, 1-B-11, 1-B-13, 1-B-15 to 20, 1-B-22, 1-B-25 to 28, 1-B-30, 1-B-32, 1-B-34 to 41, 1-B-43, 1-B-45, and 1-B-55 was prepared according to Step C in Example 1-B-01 described below.

Example 1-B-01

5-(2-Morpholin-4-yl-7-pyridin-4-yl-6,7-dihydro-5H-pyrrolo[2,3-d]pyrimidin-4-yl)-pyrimidin-2-ylamine (B-01)

Step A

2-Oxotetrahydrofuran-3-carboxylic acid methyl ester

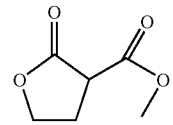

To a tetrahydrofuran solution (150 ml) of lithium hexamethyldisilazide prepared at −78° C. under an argon atmosphere from hexamethyl disilazane (55.4 ml, 262 mmol) and normal butyl lithium (2.62 M hexane solution, 100 ml, 262 mmol), a tetrahydrofuran solution (60 ml) of gamma butyrolactone (9.84 ml, 128 mmol) was added dropwise at −78° C. 10 minutes later, dimethyl carbonate (11.3 ml, 134 mmol) was added, followed by further stirring at room temperature for 10 hours. The reaction mixture was poured onto a mixture of concentrated hydrochloric acid (44 ml) and ice (500 g), followed by extraction twice with ethyl acetate. The extract was washed with brine, and subsequently dried over sodium sulfate. After filtering off the drying agent, the filtrate was concentrated under reduced pressure, to obtain the desired compound (pale brown oil, 15.1 g, 82%).

$^1$H-NMR (270 MHz, CDCl$_3$) δ (ppm): 4.29-4.37 (1H, m), 4.13-4.22 (1H, m), 3.66 (s, 3H), 3.42 (1H, dd, J=7.8, 9.4 Hz), 2.47-2.62 (1H, m), 2.29-2.42 (1H, m).

ESI (LC-MS positive mode) m/z 145 [(M+H)$^+$].

Step B

4-[4,6-Dichloro-5-(2-chloroethyl)-pyrimidin-2-yl]-morpholine

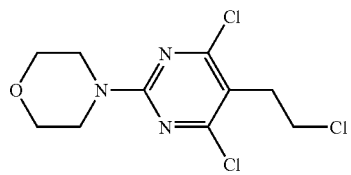

To 1M sodium methoxide solution prepared from sodium metal (3.19 g, 139 mmol) and methanol (140 ml), 2-oxotetrahydrofuran-3-carboxylic acid methyl ester (13.3 g, 92 mmol) and morpholinoformamidine hydrochloride (15.3 g, 92 mmol) were added, followed by refluxing for 2 hours. The reaction mixture was concentrated under reduced pressure, and the resulting residue was dissolved in phosphorus oxychloride (90 ml), followed by stirring at 100° C. for 10 hours. The reaction mixture was concentrated under reduced pressure, and ice (ca. 100 g) was added to the residue, which was neutralized with 5M aqueous sodium hydroxide solution, followed by extraction twice with ethyl acetate. The organic layer was washed with brine, and dried over sodium sulfate. The drying agent was filtered off and concentrated, and the resulting residue was purified by silica gel column chromatography (n-hexane/ethyl acetate=20/0 to 10/1), to obtain the desired compound (yellow powder, 8.4 g, 28%).

$^1$H-NMR (270 MHz, CDCl$_3$) δ (ppm): 3.20 (2H, t, J=7.9 Hz), 3.66 (2H, t, J=7.9 Hz), 3.70-3.81 (8H, m).

ESI (LC-MS positive mode) m/z 296 [(M+H)$^+$].

Step C

4-Chloro-2-morpholin-4-yl-7-pyridin-4-yl-6,7-dihydro-5H-pyrrolo[2,3-d]pyrimidine

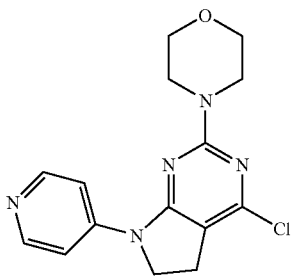

60% sodium hydride in oil (800 mg) was washed with hexane, and suspended in tetrahydrofuran (10 ml). A tetrahydrofuran solution (40 ml) of 4-aminopyridine (1.88 g) was added to the suspension with ice-cooling, followed by refluxing for 2 hours under an argon stream. After confirming the reaction mixture having turned blue, tetrahydrofuran solution (8 ml) of 4-[4,6-dichloro-5-(2-chloroethyl)-pyrimidin-2-yl]-morpholine (1.19 g) was added, followed by further stirring for 10 hours. The reaction mixture was poured onto ice water (50 ml), followed by extraction twice with ethyl acetate (20 ml), and the organic layer was washed with brine, followed by drying over sodium sulfate. The drying agent was filtered off and concentrated, and the resulting residue was purified by silica gel column chromatography (dichloromethane), to obtain the desired compound (pale yellow powder, 727 mg, 54%).

$^1$H-NMR (270 MHz, CDCl$_3$) δ (ppm): 8.51 (2H, dd, J=5.0, 1.6 Hz), 7.65 (2H, dd, J=5.0, 1.6 Hz), 4.07 (2H, t, J=8.1 Hz), 3.66-3.80 (8H, brs), 3.10 (2H, t, J=8.1 Hz).

ESI (LC-MS positive mode) m/z 318 [(M+H)$^+$].

Step D

5-(2-Morpholin-4-yl-7-pyridin-4-yl-6,7-dihydro-5H-pyrrolo[2,3-d]pyrimidin-4-yl)-pyrimidin-2-ylamine

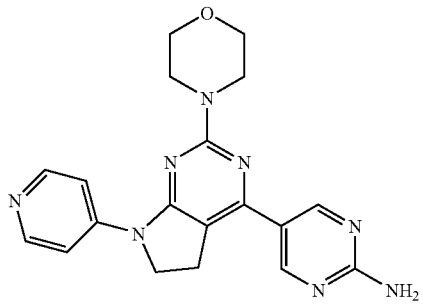

To 4-chloro-2-morpholin-4-yl-7-pyridin-4-yl-6,7-dihydro-5H-pyrrolo[2,3-d]pyrimidine (119 mg, 0.374 mmol) obtained from Step C, bis-(4-methoxybenzyl)-[5-(4,4,5,5-tetramethyl-[1,3,2]dioxaborolan-2-yl)-pyrimidin-2-yl]amine (207 mg, 0.449 mmol), palladium acetate (4.2 mg, 0.0187 mmol), S-Phos (15 mg, 0.0374 mmol) and potassium phosphate (159 mg, 0.748 mmol), dimethylformamide (3 ml) was added, followed by being degassed under ultrasonic irradiation. This was stirred at 100° C. for 5 hours, followed by extraction with ethyl acetate with the addition of water, and the organic layer was washed with brine. After drying over anhydrous sodium sulfate, concentration was carried out under reduced pressure, followed by purification by silica gel column chromatography (dichloromethane/methanol=100/1 to 40/1), to obtain bis-(4-methoxy-benzyl)-[5-(2-morpholin-4-yl-7-pyridin-4-yl-6,7-dihydro-5H-pyrrolo[2,3-d]pyrimidin-4-yl)-pyrimidin-2-yl]-amine (199 mg, yield 87%).

To the obtained bis-(4-methoxy-benzyl)-[5-(2-morpholin-4-yl-7-pyridin-4-yl-6,7-dihydro-5H-pyrrolo[2,3-d]pyrimidin-4-yl)-pyrimidin-2-yl]-amine, TFA (3 ml) and concentrated sulfuric acid (a few drops) were added, followed by stirring at 40° C. for 6 hours. This was concentrated under reduced pressure, and water was added, followed by neutralization with 1N aqueous sodium hydroxide solution. The resulting solid was purified by silica gel column chromatography (dichloromethane/2N ammonia methanol=40/1 to 10/1), to obtain the desired compound as a colorless solid (32.3 mg, yield 26%).

$^1$H-NMR (DMSO-d$_6$) δ: 8.83 (2H, s), 8.45 (2H, d, J=6.8 Hz), 7.82 (2H, d, J=6.8 Hz), 7.11 (2H, s), 4.09 (2H, t, J=8.5 Hz), 3.77-3.69 (8H, m), 3.32 (2H, t, J=8.5 Hz).

ESI (LC-MS positive mode) m/z 377 ([M+H]$^+$).

Example 1-B-02

5-(2-Morpholin-4-yl-7-pyridin-3-yl-6,7-dihydro-5H-pyrrolo[2,3-d]pyrimidin-4-yl)-pyrimidin-2-ylamine
(B-02)

Step A

4-Chloro-2-morpholin-4-yl-7-pyridin-3-yl-6,7-dihydro-5H-pyrrolo[2,3-d]pyrimidine

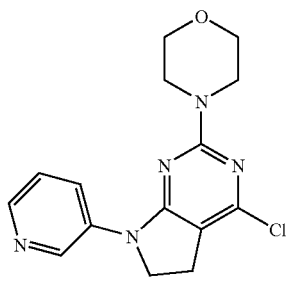

In the same manner as Example 1-B-01, from 4-[4,6-dichloro-5-(2-chloroethyl)-pyrimidin-2-yl]-morpholine (1.25 g) and 3-aminopyridine (1.97 g), the desired compound (pale yellow powder, 1.07 mg, 88%) was obtained.

$^1$H-NMR (270 MHz, CDCl$_3$) δ (ppm): 9.06 (1H, d, J=2.6 Hz), 8.31 (1H, dd, J=4.7, 1.4 Hz), 8.06 (1H, dq, J=8.5, 1.4 Hz), 7.31 (1H, ddd, J=8.5, 4.7, 0.7 Hz), 4.09 (2H, t, J=8.3 Hz), 3.81-3.73 (8H, m), 3.11 (2H, t, J=8.3 Hz).

ESI (LC-MS positive mode) m/z 318 [(M+H)$^+$].

Step B 5-(2-Morpholin-4-yl-7-pyridin-3-yl-6,7-dihydro-5H-pyrrolo[2,3-d]pyrimidin-4-yl)-pyrimidin-2-ylamine

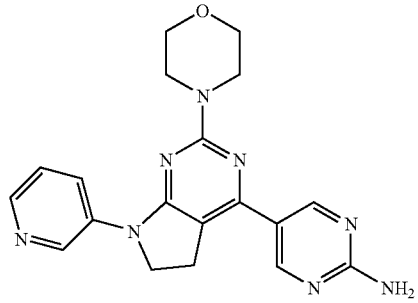

In the same manner as Step D in Example 1-B-01, from 4-chloro-2-morpholin-4-yl-7-pyridin-3-yl-6,7-dihydro-5H-pyrrolo[2,3-d]pyrimidine (119 mg, 0.374 mmol) and bis-(4-methoxybenzyl)-[5-(4,4,5,5-tetramethyl-[1,3,2]dioxaborolan-2-yl)-pyrimidin-2-yl]amine, the desired compound was obtained as a colorless solid (16.6 mg, yield 12%).

$^1$H-NMR (DMSO-d$_6$) δ: 9.08 (1H, s), 8.82 (2H, s), 8.25-8.23 (2H, brm), 7.41 (1H, dd, J=8.3, 4.9 Hz), 7.07 (2H, s), 4.12 (2H, t, J=9.0 Hz), 3.71 (8H, d, J=4.4 Hz), 3.33 (2H, t, J=9.0 Hz).

ESI (LC-MS positive mode) m/z 377 ([M+H]$^+$).

Example 1-B-03

5-(2-Morpholin-4-yl-7-pyridin-4-yl-6,7-dihydro-5H-pyrrolo[2,3-d]pyrimidin-4-yl)-pyridin-2-ylamine
(B-03)

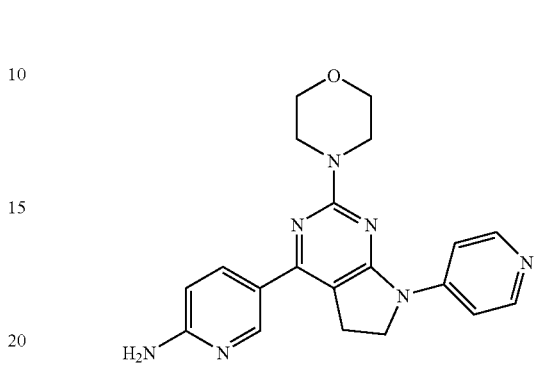

In the same manner as Step D in Example 1-B-01, using bis-(4-methoxybenzyl)-[5-(4,4,5,5-tetramethyl-[1,3,2]dioxaborolan-2-yl)-pyridin-2-yl]-amine as a boronic acid ester, the desired compound was obtained as a yellow solid.

$^1$H-NMR (DMSO-d$_6$) δ: 8.55 (1.0H, d, J=2.0 Hz), 8.53 (2.0H, d, J=6.3 Hz), 8.08-8.03 (3.0H, m), 6.59-6.55 (3.0H, m), 4.14 (2.0H, t, J=8.3 Hz), 3.73 (8.0H, d, J=8.3 Hz), 3.38-3.33 (2.0H, m).

ESI (LC-MS positive mode) m/z 376 ([M+H]$^+$).

Example 1-B-04

5-(2-Morpholin-4-yl-7-pyridin-3-yl-6,7-dihydro-5H-pyrrolo[2,3-d]pyrimidin-4-yl)-pyridin-2-ylamine
(B-04)

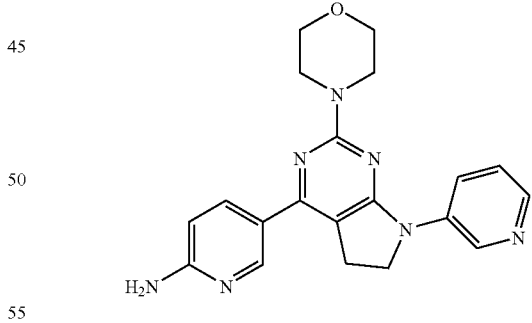

In the same manner as Step B in Example 1-B-02, using bis-(4-methoxybenzyl)-[5-(4,4,5,5-tetramethyl-[1,3,2]dioxaborolan-2-yl)-pyridin-2-yl]-amine as a boronic acid ester, the desired compound was obtained as a yellow solid.

$^1$H-NMR (DMSO-d$_6$) δ: 9.08 (1H, d, J=2.4 Hz), 8.52 (1H, d, J=2.4 Hz), 8.23 (2H, d, J=5.4 Hz), 8.09 (1H, dd, J=8.8, 2.0 Hz), 7.41 (1H, t, J=6.6 Hz), 6.67 (2H, brs), 6.62 (2H, d, J=8.8 Hz), 4.11 (2H, t, J=8.1 Hz), 3.71 (8H, d, J=3.4 Hz), 3.36-3.26 (2H, m).

ESI (LC-MS positive mode) m/z 376 ([M+H]$^+$).

Example 1-B-05

4-Methoxy-5-(2-morpholin-4-yl-7-pyridin-3-yl-6,7-dihydro-5H-pyrrolo[2,3-d]pyrimidin-4-yl)-pyrimidin-2-ylamine (B-05)

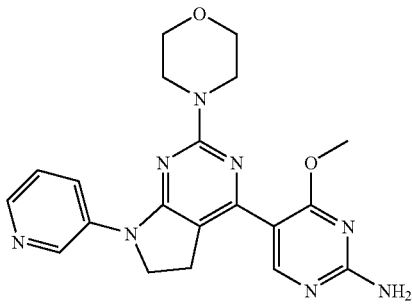

In the same manner as Step B in Example 1-B-02, using bis-(4-methoxybenzyl)-[4-methoxy-5-(4,4,5,5-tetramethyl-[1,3,2]dioxaborolan-2-yl)-pyrimidin-2-yl]-amine as a boronic acid ester, the desired compound was obtained as a yellow solid.

$^1$H-NMR (CDCl$_3$) δ: 9.08 (1H, s), 8.40 (1H, s), 8.32-8.26 (1H, m), 8.15 (1H, dq, J=8.5, 1.3 Hz), 7.30 (1H, t, J=6.3 Hz), 5.10 (2H, s), 4.04 (2H, t, J=8.3 Hz), 3.96 (3H, s), 3.83-3.76 (8H, m), 3.02 (2H, t, J=8.3 Hz).

ESI (LC-MS positive mode) m/z 407 ([M+H]$^+$).

Example 1-B-06

2-Fluoro-4-(2-morpholin-4-yl-7-pyridin-4-yl-6,7-dihydro-5H-pyrrolo[2,3-d]pyrimidin-4-yl)-phenylamine (B-06)

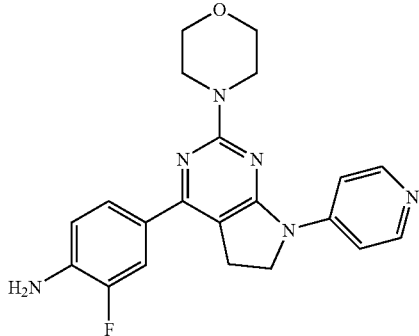

In the same manner as Step D in Example 1-B-01, using [2-fluoro-4-(4,4,5,5-tetramethyl-[1,3,2]dioxaborolan-2-yl)phenyl]-bis-(4-methoxybenzyl)-amine as a boronic acid, the desired compound was obtained as a yellow solid.

$^1$H-NMR (DMSO-d$_6$) δ: 8.43 (2H, d, J=6.3 Hz), 7.81 (2H, d, J=6.3 Hz), 7.67 (1H, d, J=12.7 Hz), 7.56 (1H, d, J=9.3 Hz), 6.84 (1H, t, J=9.3 Hz), 5.65 (2H, s), 4.08 (2H, t, J=8.3 Hz), 3.76-3.68 (8H, m), 3.36-3.31 (2H, brm).

ESI (LC-MS positive mode) m/z 393 ([M+H]$^+$).

Example 1-B-07

2,6-Difluoro-4-(2-morpholin-4-yl-7-pyridin-4-yl-6,7-dihydro-5H-pyrrolo[2,3-d]pyrimidin-4-yl)-phenylamine (B-07)

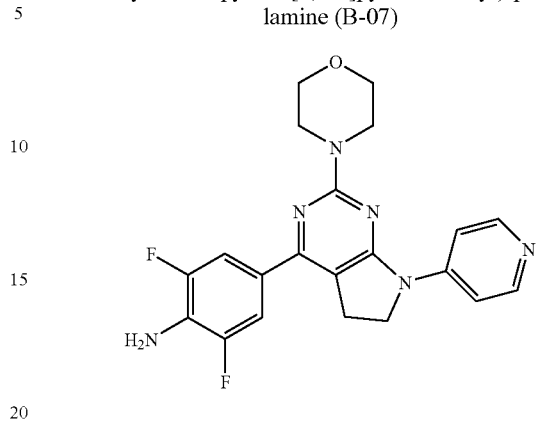

In the same manner as Step D in Example 1-B-01, using 2,6-difluoro-4-(4,4,5,5-tetramethyl-[1,3,2]dioxaborolan-2-yl)phenyl-bis-(4-methoxybenzyl)-amine as a boronic acid, the desired compound was obtained as a yellow solid.

$^1$H-NMR (DMSO-d$_6$) δ: 8.44 (2H, d, J=6.3 Hz), 7.82 (2H, d, J=6.3 Hz), 7.55 (2H, d, J=10.7 Hz), 5.73 (2H, s), 4.09 (2H, t, J=8.1 Hz), 3.75-3.70 (8H, brm), 3.35 (2H, t, J=8.1 Hz).

ESI (LC-MS positive mode) m/z 411 ([M+H]$^+$).

Example 1-B-08

4-(2,4-Dimethoxy-pyrimidin-5-yl)-2-morpholin-4-yl-7-pyridin-4-yl-6,7-dihydro-5H-pyrrolo[2,3-d]pyrimidine (B-08)

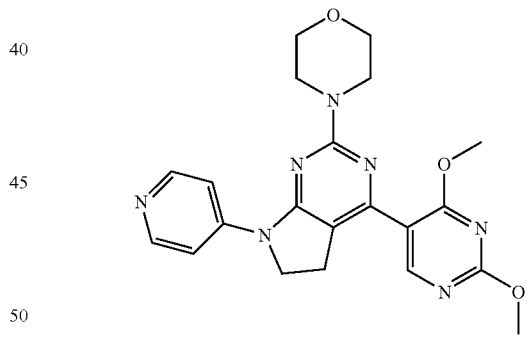

To 4-chloro-2-morpholin-4-yl-7-pyridin-4-yl-6,7-dihydro-5H-pyrrolo[2,3-d]pyrimidine (40 mg, 0.126 mmol), 2,4-dimethoxy-5-(4,4,5,5-tetramethyl-[1,3,2]dioxaborolan-2-yl)-pyrimidine (67 mg, 0.252 mmol), palladium acetate (1.4 mg, 0.0063 mmol), S-Phos (5.2 mg, 0.0126 mmol) and potassium phosphate (53.5 mg, 0.252 mmol), dimethylformamide (1 ml) was added, followed by being degassed under ultrasonic irradiation. This was stirred at 100° C. for 12 hours, followed by addition of water, and the resulting solid was filtered, which was washed with ethyl acetate, to obtain the desired compound as a colorless solid (15.7 mg, yield 30%).

$^1$H-NMR (CDCl$_3$) δ: 8.56 (1H, s), 8.51 (2H, d, J=6.8 Hz), 7.72 (2H, d, J=6.8 Hz), 4.06 (6H, s), 4.04 (2H, t, J=8.8 Hz), 3.85-3.78 (8H, m), 3.01 (2H, t, J=8.8 Hz).

ESI (LC-MS positive mode) m/z 422 ([M+H]$^+$).

Example 1-B-09

4-(2,4-Dimethoxy-pyrimidin-5-yl)-2-morpholin-4-yl-7-pyridin-3-yl-6,7-dihydro-5H-pyrrolo[2,3-d]pyrimidine (B-09)

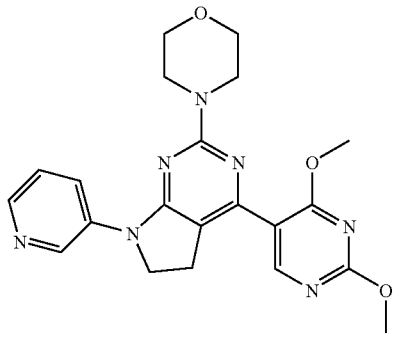

In the same manner as Example 1-B-08, using 4-chloro-2-morpholin-4-yl-7-pyridin-3-yl-6,7-dihydro-5H-pyrrolo[2,3-d]pyrimidine, the desired compound was obtained as a colorless solid.

$^1$H-NMR (CDCl$_3$) δ: 9.09 (1H, d, J=2.4 Hz), 8.57 (1H, s), 8.30 (1H, dd, J=4.9, 1.5 Hz), 8.14 (1H, dq, J=8.5, 1.5 Hz), 7.31 (1H, dd, J=8.5, 4.9 Hz), 4.06 (6H, s), 4.05 (2H, t, J=8.3 Hz), 3.84-3.74 (8H, m), 3.02 (2H, t, J=8.3 Hz).
ESI (LC-MS positive mode) m/z 422 ([M+H]$^+$).

Example 1-B-10

4-(6-Methoxy-pyridin-3-yl)-2-morpholin-4-yl-7-pyridin-3-yl-6,7-dihydro-5H-pyrrolo[2,3-d]pyrimidine (B-10)

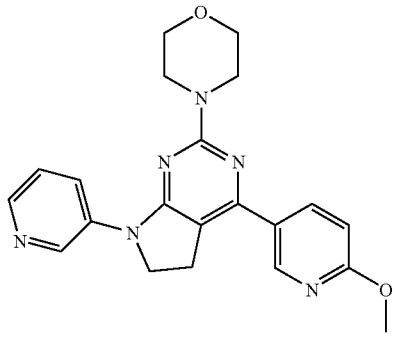

To 4-chloro-2-morpholin-4-yl-7-pyridin-3-yl-6,7-dihydro-5H-pyrrolo[2,3-d]pyrimidine (20 mg, 0.0629 mmol), 2-methoxy-5-(4,4,5,5-tetramethyl-1,3,2-dioxaborolan-2-yl)pyridine (29.6 mg, 0.126 mmol), palladium acetate (1.4 mg, 0.00630 mmol), S-Phos (5.2 mg, 0.0126 mmol) and potassium phosphate (26.7 mg, 0.126 mmol), dimethylformamide (1 ml) was added, followed by being degassed under ultrasonic irradiation. This was stirred at 100° C. for 3 hours, followed by extraction with ethyl acetate with the addition of water, and the organic layer was washed with brine. After drying over anhydrous sodium sulfate, concentration was carried out under reduced pressure, followed by elution with 2M ammonia methanol solution through SCX resin and then concentration.
Purification by silica gel column chromatography (chloroform) afforded the desired compound as a yellow powder.

$^1$H-NMR (CDCl$_3$) δ: 9.11 (1H, d, J=2.5 Hz), 8.72 (1H, d, J=2.3 Hz), 8.30 (1H, dd, J=4.5, 1.3 Hz), 8.23 (1H, dd, J=8.9, 2.5 Hz), 8.15 (1H, dq, J=8.4, 1.3 Hz), 7.32 (1H, dd, J=8.4, 4.5 Hz), 6.85 (1H, d, J=8.9 Hz), 4.11 (2H, t, J=8.2 Hz), 4.00 (3H, s), 3.87-3.78 (8H, m), 3.36 (2H, t, J=8.2 Hz).
ESI (LC-MS positive mode) m/z 391 ([M+H]$^+$).

Example 1-B-11

4-(6-Methoxy-pyridin-3-yl)-2-morpholin-4-yl-7-pyridin-4-yl-6,7-dihydro-5H-pyrrolo[2,3-d]pyrimidine (B-11)

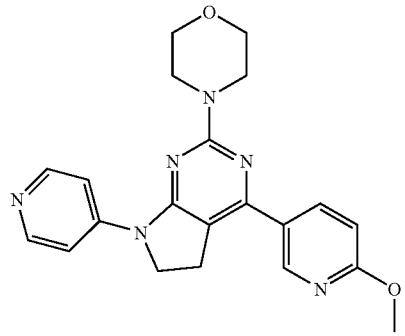

In the same manner as Example 1-B-10, using 4-chloro-2-morpholin-4-yl-7-pyridin-4-yl-6,7-dihydro-5H-pyrrolo[2,3-d]pyrimidine, and 2-methoxy-5-(4,4,5,5-tetramethyl-1,3,2-dioxaborolan-2-yl)pyridine as a boronic acid, the desired compound was obtained.

$^1$H-NMR (CDCl$_3$) δ: 8.71 (1H, dd, J=2.5, 0.6 Hz), 8.51 (2H, dd, J=4.9, 1.5 Hz), 8.23 (1H, dd, J=8.7, 2.5 Hz), 7.73 (2H, dd, J=4.9, 1.5 Hz), 6.85 (1H, dd, J=8.7, 0.6 Hz), 4.08 (2H, t, J=8.3 Hz), 4.00 (3H, s), 3.86-3.83 (8H, m), 3.35 (2H, t, J=8.3 Hz).
ESI (LC-MS positive mode) m/z 391 ([M+H]$^+$).

Example 1-B-12

4-(2-Morpholin-4-yl-7-pyridin-3-yl-6,7-dihydro-5H-pyrrolo[2,3-d]pyrimidin-4-yl)-benzoic acid methyl ester (B-12)

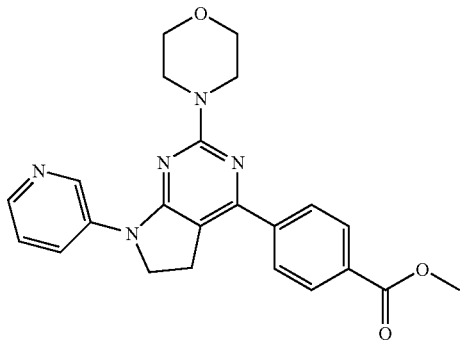

In the same manner as Example 1-B-10, using 4-chloro-2-morpholin-4-yl-7-pyridin-3-yl-6,7-dihydro-5H-pyrrolo[2,3-d]pyrimidine, and 4-methoxycarbonylphenylboronic acid as a boronic acid, the desired compound was obtained.

$^1$H-NMR (DMSO-d$_6$) δ: 3.37 (2H, t, J=8.2 Hz), 3.65-3.75 (8H, m), 3.89 (3H, s), 4.15 (2H, t, J=8.2 Hz), 7.43 (1H, m), 8.08 (4H, s), 8.23 (2H, m), 8.26 (1H, d, J=4.9 Hz), 9.10 (1H, d, J=2.7 Hz).
ESI (LC-MS positive mode) m/z 418 ([M+H]$^+$).

Example 1-B-13

4-(2-Morpholin-4-yl-7-pyridin-3-yl-6,7-dihydro-5H-pyrrolo[2,3-d]pyrimidin-4-yl)-benzoic acid methyl ester hydrochloride (B-13)

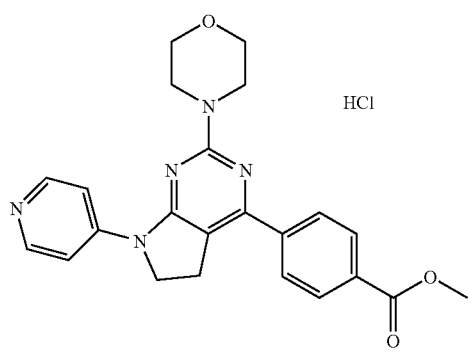

In the same manner as Example 1-B-10, using 4-chloro-2-morpholin-4-yl-7-pyridin-4-yl-6,7-dihydro-5H-pyrrolo[2,3-d]pyrimidine, and 4-methoxycarbonylphenylboronic acid as a boronic acid, the desired compound was synthesized, and further 1 equivalent of 1M hydrochloric acid was added, followed by stirring at room temperature, which was concentrated under reduced pressure, to obtain the desired compound.

$^1$H-NMR (DMSO-$d_6$) δ: 3.38-3.46 (2H, brs), 3.73-3.82 (8H, m), 3.90 (3H, s), 4.27 (2H, t, J=7.2 Hz), 8.11 (4H, s), 8.26-8.38 (2H, m), 8.68 (2H, d, J=7.4 Hz).

ESI (LC-MS positive mode) m/z 418 ([M+H]$^+$).

Example 1-B-14

4-(2-Morpholin-4-yl-7-pyridin-3-yl-6,7-dihydro-5H-pyrrolo[2,3-d]pyrimidin-4-yl)-benzonitrile (B-14)

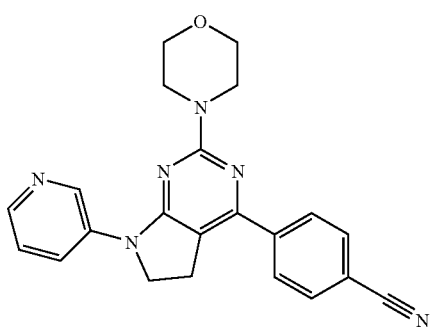

In the same manner as Example 1-B-10, using 4-chloro-2-morpholin-4-yl-7-pyridin-3-yl-6,7-dihydro-5H-pyrrolo[2,3-d]pyrimidine, and 4-(4,4,5,5-tetramethyl-1,3,2-dioxaborolan-2-yl)benzonitrile as a boronic acid, the desired compound was obtained.

$^1$H-NMR (DMSO-$d_6$) δ: 3.37 (2H, t, J=7.7 Hz), 3.67-3.77 (8H, m), 4.16 (2H, t, J=7.7 Hz), 7.44 (1H, dd, J=8.3, 4.9 Hz), 7.97 (2H, d, J=8.3 Hz), 8.12 (2H, d, J=8.3 Hz), 8.24-8.28 (2H, m), 9.09 (1H, d, J=2.5 Hz).

ESI (LC-MS positive mode) m/z 385 ([M+H]$^+$).

Example 1-B-15

4-(2-Morpholin-4-yl-7-pyridin-4-yl-6,7-dihydro-5H-pyrrolo[2,3-d]pyrimidin-4-yl)-benzonitrile hydrochloride (B-15)

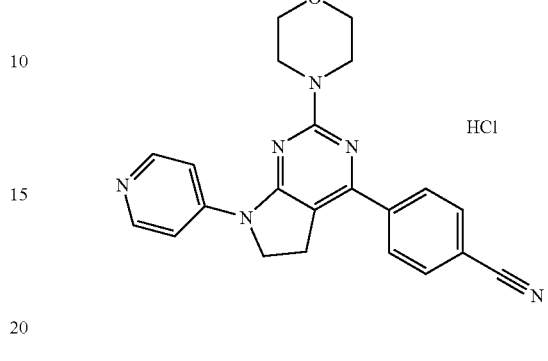

In the same manner as Example 1-B-10, using 4-chloro-2-morpholin-4-yl-7-pyridin-4-yl-6,7-dihydro-5H-pyrrolo[2,3-d]pyrimidine, and 4-(4,4,5,5-tetramethyl-1,3,2-dioxaborolan-2-yl)benzonitrile as a boronic acid, 4-(2-morpholin-4-yl-7-pyridin-4-yl-6,7-dihydro-5H-pyrrolo[2,3-d]pyrimidin-4-yl)-benzonitrile was obtained, and subsequently 1 equivalent of 1M hydrochloric acid was added, followed by stirring at room temperature, which was concentrated under reduced pressure, to obtain the desired compound.

$^1$H-NMR (DMSO-$d_6$) δ: 3.44 (2H, t, J=8.0 Hz), 3.70-3.84 (8H, m), 4.28 (2H, t, J=8.0 Hz), 8.02 (2H, d, J=8.3 Hz), 8.15 (2H, d, J=8.3 Hz), 8.32 (2H, m), 8.68 (2H, d, J=7.6 Hz).

ESI (LC-MS positive mode) m/z 385 ([M+H]$^+$).

Example 1-B-16

4-(3-fluoro-phenyl)-2-morpholin-4-yl-7-pyridin-4-yl-6,7-dihydro-5H-pyrrolo[2,3-d]pyrimidine (B-16)

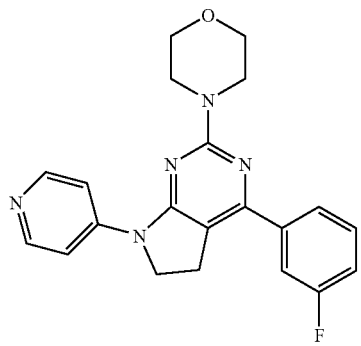

In the same manner as Example 1-B-10, using 4-chloro-2-morpholin-4-yl-7-pyridin-4-yl-6,7-dihydro-5H-pyrrolo[2,3-d]pyrimidine, and 3-fluorophenylboronic acid as a boronic acid, the desired compound was obtained.

$^1$H-NMR (CDCl$_3$) δ: 8.52 (2H, d, J=6.2 Hz), 7.74 (2H, d, J=6.2 Hz), 7.66 (2H, m), 7.46 (1H, m), 7.12 (1H, m), 4.09 (2H, t, J=7.8 Hz), 3.86 (8H, m), 3.36 (2H, t, J=7.8 Hz).

ESI (LC-MS positive mode) m/z 378 ([M+H]$^+$).

Example 1-B-17

4-(5-Methoxy-pyridin-3-yl)-2-morpholin-4-yl-7-pyridin-4-yl-6,7-dihydro-5H-pyrrolo[2,3-d]pyrimidine (B-17)

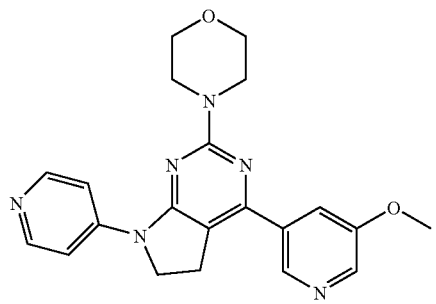

In the same manner as Example 1-B-10, using 4-chloro-2-morpholin-4-yl-7-pyridin-4-yl-6,7-dihydro-5H-pyrrolo[2,3-d]pyrimidine, and 3-methoxy-5-(4,4,5,5-tetramethyl-1,3,2-dioxaborolan-2-yl)pyridine as a boronic acid, the desired compound was obtained.

$^1$H-NMR (CDCl$_3$) δ: 8.68 (1H, m), 8.52 (2H, d, J=6.5 Hz), 8.37 (1H, d, J=2.7 Hz), 7.81 (1H, m), 7.73 (2H, d, J=6.5 Hz), 4.10 (2H, t, 7.8 Hz), 3.94 (3H, s), 3.85 (8H, m), 3.49 (2H, t, J=7.8 Hz).

ESI (LC-MS positive mode) m/z 391 ([M+H]$^+$).

Example 1-B-18

2-Morpholin-4-yl-7-pyridin-4-yl-4-pyrimidin-5-yl-6,7-dihydro-5H-pyrrolo[2,3-d]pyrimidine (B-18)

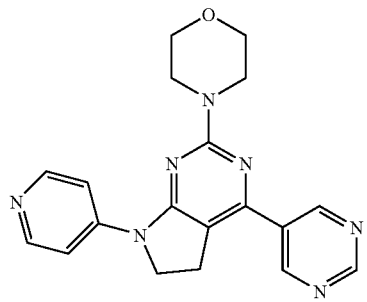

In the same manner as Example 1-B-10, using 4-chloro-2-morpholin-4-yl-7-pyridin-4-yl-6,7-dihydro-5H-pyrrolo[2,3-d]pyrimidine, and pyrimidin-5-boronic acid as a boronic acid, the desired compound was obtained.

$^1$H-NMR (CD$_3$OD) δ: 9.31 (2H, s), 9.24 (1H, s), 8.45 (2H, d, J=6.5 Hz), 7.87 (2H, d, J=6.5 Hz), 4.21 (2H, t, J=8.1 Hz), 3.87 (8H, m), 3.45 (2H, t, J=8.1 Hz).

ESI (LC-MS positive mode) m/z 362 ([M+H]$^+$).

Example 1-B-19

N-[4-(2-morpholin-4-yl-7-pyridin-4-yl-6,7-dihydro-5H-pyrrolo[2,3-d]pyrimidin-4-yl)-phenyl]-methane sulfonamide (B-19)

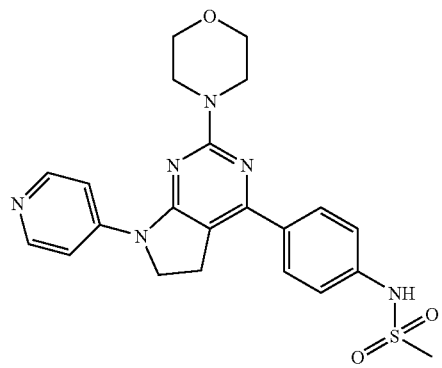

In the same manner as Example 1-B-10, using 4-chloro-2-morpholin-4-yl-7-pyridin-4-yl-6,7-dihydro-5H-pyrrolo[2,3-d]pyrimidine, and N-(4-(4,4,5,5-tetramethyl-1,3,2-dioxaborolan-2-yl)-phenyl)methane sulfonamide as a boronic acid, the desired compound was obtained as a colorless solid.

$^1$H-NMR (DMSO-d$_6$) δ: 8.49-8.43 (1H, brm), 7.96 (2H, d, J=7.8 Hz), 7.86-7.82 (2H, brm), 7.74-7.66 (2H, m), 7.33 (2H, d, J=9.8 Hz), 4.10 (2H, t, J=9.0 Hz), 3.78-3.70 (8H, m), 3.10-3.07 (2H, m), 3.07 (3H, s).

ESI (LC-MS positive mode) m/z 453 ([M+H]$^+$).

Example 1-B-20

[2,6-Difluoro-3-(2-morpholin-4-yl-7-pyridin-4-yl-6,7-dihydro-5H-pyrrolo[2,3-d]pyrimidin-4-yl)-phenyl]-methanol (B-20)

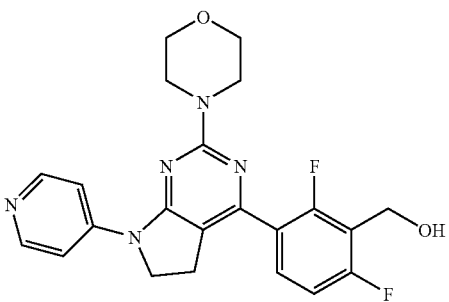

In the same manner as Example 1-B-10, using 4-chloro-2-morpholin-4-yl-7-pyridin-4-yl-6,7-dihydro-5H-pyrrolo[2,3-d]pyrimidine, and 2,4-difluoro-3-formylphenylboronic acid as a boronic acid, 2,6-difluoro-3-(2-morpholin-4-yl-7-pyridin-4-yl-6,7-dihydro-5H-pyrrolo[2,3-d]pyrimidin-4-yl)-benzaldehyde was obtained. Methanol and sodium borohydride were added, which was stirred at room temperature for 1 hour, followed by elution with 2M ammonia methanol solution through SCX resin and then concentration. Purification by preparative TLC afforded the desired compound as a colorless solid.

¹H-NMR (DMSO-d₆) δ: 8.49 (2H, d, J=6.8 Hz), 8.18 (1H, s), 7.95-7.86 (2H, brm), 7.65-7.51 (1H, m), 4.49 (2H, d, J=5.4 Hz), 4.10 (2H, t, J=8.8 Hz), 3.71 (8H, d, J=4.9 Hz), 3.00 (2H, t, J=8.8 Hz).
ESI (LC-MS positive mode) m/z 426 ([M+H]⁺).

Example 1-B-21

4-(1H-benzimidazol-5-yl)-2-morpholin-4-yl-7-pyridin-3-yl-6,7-dihydro-5H-pyrrolo[2,3-d]pyrimidine (B-21)

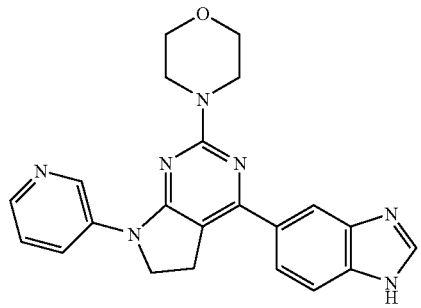

In the same manner as Example 1-B-10, using 4-chloro-2-morpholin-4-yl-7-pyridin-3-yl-6,7-dihydro-5H-pyrrolo[2,3-d]pyrimidine, and 5-(4,4,5,5-tetramethyl-[1,3,2]dioxaborolan-2-yl)-1H-benzimidazole as a boronic acid, the desired compound was obtained.
¹H-NMR (DMSO-d₆) δ: 9.55 (1H, d, J=1.6 Hz), 9.44 (1H, s), 8.71 (1H, d, J=9.2 Hz), 8.52 (1H, d, J=5.1 Hz), 8.37 (1H, s), 8.17 (1H, d, J=8.1 Hz), 8.00-7.92 (2H, m), 4.23 (2H, t, J=8.4 Hz), 3.82-3.73 (8H, m), 3.45 (2H, t, J=8.4 Hz).
ESI (LC-MS positive mode) m/z 400 ([M+H]⁺).

Example 1-B-22

4-(1H-benzimidazol-5-yl)-2-morpholin-4-yl-7-pyridin-4-yl-6,7-dihydro-5H-pyrrolo[2,3-d]pyrimidine (B-22)

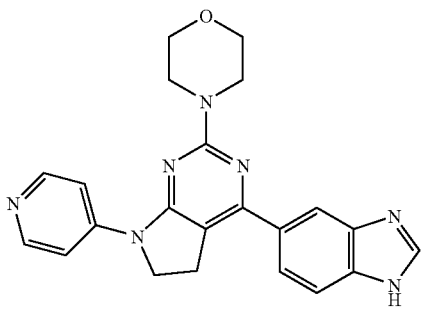

In the same manner as Example 1-B-10, using 4-chloro-2-morpholin-4-yl-7-pyridin-4-yl-6,7-dihydro-5H-pyrrolo[2,3-d]pyrimidine, and 5-(4,4,5,5-tetramethyl-[1,3,2]dioxaborolan-2-yl)-1H-benzimidazole as a boronic acid, 4-(1-benzyloxymethyl-1H-benzimidazol-5-yl)-2-morpholin-4-yl-7-pyridin-4-yl-6,7-dihydro-5H-pyrrolo[2,3-d]pyrimidine (16 mg, 21%) was obtained. Then, the obtained above compound was dissolved in chloroform (1 ml), and trimethylsilyliodide (23 μl, 5 equivalents) was added, followed by refluxing for 3 hours. The reaction mixture was concentrated under reduced pressure, and the resulting residue was dissolved in methanol (5 ml). Subsequently, a crystal was precipitated with ether (5 ml), and filtered off, to obtain the desired compound as a yellow solid (10 mg, 82%).
¹H-NMR (DMSO-d₆) δ: 9.45 (1H, s), 8.69 (2H, d, J=7.3 Hz), 8.35-8.30 (2H, m), 8.18-8.14 (2H, m), 7.94 (1H, dd, J=8.7, 2.8 Hz), 4.29 (2H, t, J=7.7 Hz), 3.83-3.75 (8H, m), 3.47 (2H, t, J=7.7 Hz).
ESI (LC-MS positive mode) m/z 400 ([M+H]⁺).

Example 1-B-23

[3-(2-Morpholin-4-yl-7-pyridin-3-yl-6,7-dihydro-5H-pyrrolo[2,3-d]pyrimidin-4-yl)-phenyl]-methanol (B-23)

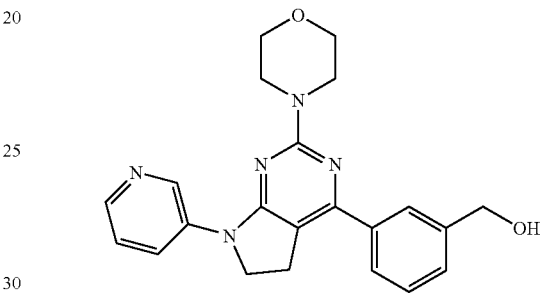

In the same manner as Example 1-B-10, using 4-chloro-2-morpholin-4-yl-7-pyridin-3-yl-6,7-dihydro-5H-pyrrolo[2,3-d]pyrimidine, and 3-(hydroxymethyl)phenylboronic acid as a boronic acid, the desired compound was obtained.
¹H-NMR (CDCl₃) δ: 8.48 (2.0H, d, J=6.1 Hz), 7.91 (1.1H, s), 7.81 (1.1H, d, J=6.8 Hz), 7.73 (1.8H, d, J=6.1 Hz), 7.49-7.43 (2.0H, m), 4.78 (2.0H, s), 4.04 (2.1H, t, J=8.3 Hz), 3.90-3.81 (8.4H, m), 3.34 (2.0H, t, J=8.3 Hz).
ESI (LC-MS positive mode) m/z 390 ([M+H]⁺).

Example 1-B-24

4-(2-Methoxy-pyridin-3-yl)-2-morpholin-4-yl-7-pyridin-3-yl-6,7-dihydro-5H-pyrrolo[2,3-d]pyrimidine (B-24)

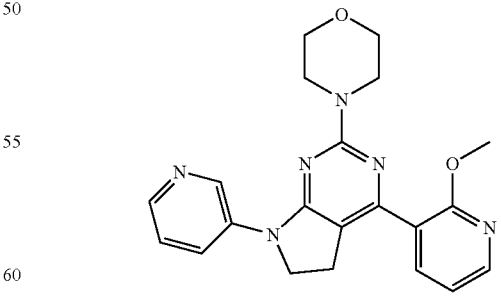

In the same manner as Example 1-B-10, using 4-chloro-2-morpholin-4-yl-7-pyridin-3-yl-6,7-dihydro-5H-pyrrolo[2,3-d]pyrimidine, and 2-methoxy-3-(4,4,5,5-tetramethyl-[1,3,2]dioxaborolan-2-yl)-pyridine as a boronic acid, the desired compound was obtained.

¹H-NMR (CDCl₃) δ: 9.11 (1H, d, J=2.5 Hz), 8.30 (1H, dd, J=4.6, 1.3 Hz), 8.25 (1H, dd, J=4.9, 2.5 Hz), 8.16 (1H, dq, J=8.5, 1.3 Hz), 7.89 (1H, dd, J=7.3, 1.9 Hz), 7.32 (1H, dd, J=8.5, 4.9 Hz), 7.02 (1H, dd, J=7.1, 4.9 Hz), 4.05 (2H, t, J=8.2 Hz), 4.01 (3H, s), 3.78-3.84 (8H, m), 3.03 (2H, t, J=8.2 Hz).
ESI (LC-MS positive mode) m/z 391 ([M+H]⁺).

Example 1-B-25

4-(3-Benzyloxy-2,6-difluoro-phenyl)-2-morpholin-4-yl-7-pyridin-4-yl-6,7-dihydro-5H-pyrrolo[2,3-d]pyrimidine (B-25)

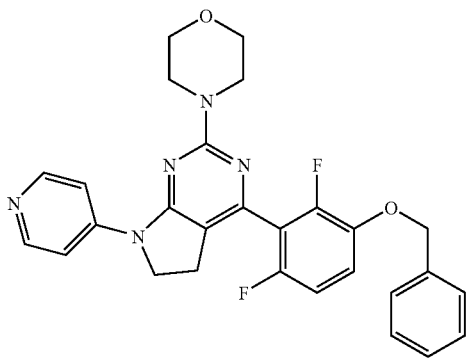

In the same manner as Example 1-B-10, using 4-chloro-2-morpholin-4-yl-7-pyridin-4-yl-6,7-dihydro-5H-pyrrolo[2,3-d]pyrimidine, and 3-benzyloxy-2,6-difluorophenylboronic acid as a boronic acid, the desired compound was obtained.
¹H-NMR (CDCl₃) δ: 8.51 (2H, d, J=6.5 Hz), 7.74 (2H, d, J=6.5 Hz), 7.40 (5H, m), 7.00 (1H, m), 6.87 (1H, m), 5.14 (2H, s), 4.05 (2H, t, J=7.8 Hz), 3.81 (8H, m), 2.98 (2H, t, J=7.8 Hz).
ESI (LC-MS positive mode) m/z 502 ([M+H]⁺).

Example 1-B-26

2,4-Difluoro-3-(2-morpholin-4-yl-7-pyridin-4-yl-6,7-dihydro-5H-pyrrolo[2,3-d]pyrimidin-4-yl)-phenol (B-26)

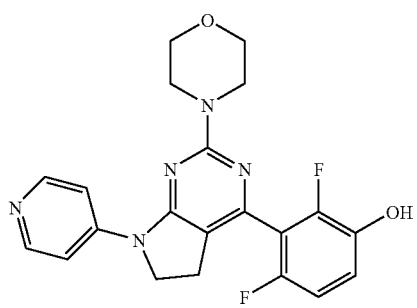

Compound B-25 obtained in Example 1-B-25 was dissolved in methanol, and a catalytic amount of palladium carbon was added, followed by stirring at room temperature under a hydrogen gas atmosphere. The palladium catalyst was filtered, and subsequently concentrated under reduced pressure. Purification by preparative TLC afforded the desired compound.

¹H-NMR (CD₃OD) δ: 8.43 (2H, d, J=6.5 Hz), 8.02 (2H, d, J=6.5 Hz), 7.01 (1H, m), 6.89 (1H, m), 4.15 (2H, t, J=7.8 Hz), 3.79 (8H, m), 2.99 (2H, t, J=7.8 Hz)
ESI (LC-MS positive mode) m/z 412 ([M+H]⁺).

Example 1-B-27

4-(2-Methoxy-pyrimidin-5-yl)-2-morpholin-4-yl-7-pyridin-4-yl-6,7-dihydro-5H-pyrrolo[2,3-d]pyrimidine (B-27)

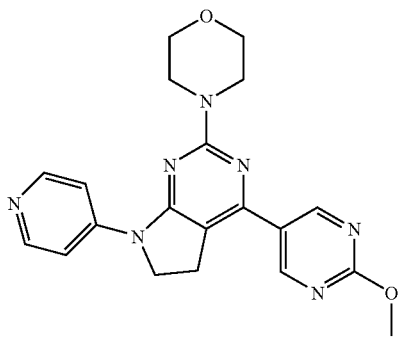

In the same manner as Example 1-B-10, using 4-chloro-2-morpholin-4-yl-7-pyridin-4-yl-6,7-dihydro-5H-pyrrolo[2,3-d]pyrimidine, and 2-methoxypyrimidin-5-boronic acid as a boronic acid, the desired compound was obtained.
¹H-NMR (CDCl₃) δ: 9.09 (2H, s), 8.53 (2H, d, 6.2 Hz), 7.73 (2H, d, 6.2 Hz), 4.13 (2H, t, 7.8 Hz), 4.08 (3H, s), 3.85 (8H, m), 3.35 (2H, t, 7.8 Hz).
ESI (LC-MS positive mode) m/z 392 ([M+H]⁺).

Example 1-B-28

2-Morpholin-4-yl-4,7-di-pyridin-4-yl-6,7-dihydro-5H-pyrrolo[2,3-d]pyrimidine (B-28)

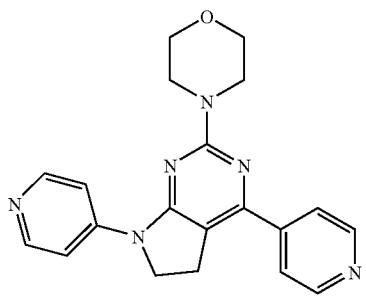

In the same manner as Example 1-B-10, using 4-(4,4,5,5-tetramethyl-1,3,2-dioxaborolan-2-yl)pyridine as a boronic acid, the desired compound was obtained.
¹H-NMR (CDCl₃) δ: 8.75 (2H, m), 8.53 (2H, m), 7.78 (2H, m), 7.74 (2H, m), 4.12 (2H, t, J=7.8 Hz), 3.86 (8H, m), 3.39 (2H, t, J=7.8 Hz).
ESI (LC-MS positive mode) m/z 361 ([M+H]⁺).

Example 1-B-29

2-Morpholin-4-yl-4-pyridin-4-yl-7-pyridin-3-yl-6,7-dihydro-5H-pyrrolo[2,3-d]pyrimidine (B-29)

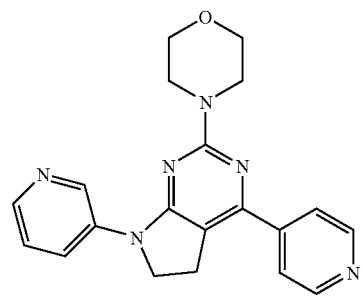

In the same manner as Example 1-B-10, using 4-chloro-2-morpholin-4-yl-7-pyridin-3-yl-6,7-dihydro-5H-pyrrolo[2,3-d]pyrimidine, and 4-(4,4,5,5-tetramethyl-1,3,2-dioxaborolan-2-yl)pyridine as a boronic acid, the desired compound was obtained.

$^1$H-NMR (CDCl$_3$) δ: 9.13 (1H, m), 8.73 (2H, m), 8.33 (1H, m), 8.16 (1H, m), 7.79 (2H, m), 7.34 (1H, m), 4.14 (2H, t, J=7.8 Hz), 3.86 (8H, m), 3.40 (2H, t, J=7.8 Hz)

ESI (LC-MS positive mode) m/z 361 ([M+H]$^+$).

Example 1-B-30

[4-(2-Morpholin-4-yl-7-pyridin-4-yl-6,7-dihydro-5H-pyrrolo[2,3-d]pyrimidin-4-yl)-phenyl]-methanol (B-30)

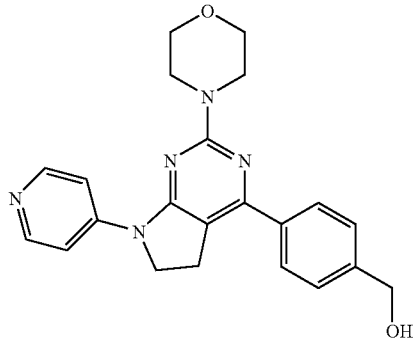

In the same manner as Example 1-B-10, using 4-chloro-2-morpholin-4-yl-7-pyridin-4-yl-6,7-dihydro-5H-pyrrolo[2,3-d]pyrimidine, and 4-(hydroxymethyl)phenylboronic acid as a boronic acid, the desired compound was obtained.

$^1$H-NMR (DMSO-d$_6$+TFA) δ: 8.65 (2H, d, J=7.3 Hz), 8.34 (2H, m), 7.95 (2H, d, J=8.1 Hz), 7.47 (2H, d, J=8.1 Hz), 4.61 (2H, s), 4.27 (2H, brt), 3.80 (8H, m), 3.44 (2H, brt).

ESI (LC-MS positive mode) m/z 390 ([M+H]$^+$).

Example 1-B-31

[4-(2-Morpholin-4-yl-7-pyridin-3-yl-6,7-dihydro-5H-pyrrolo[2,3-d]pyrimidin-4-yl)-phenyl]-methanol (B-31)

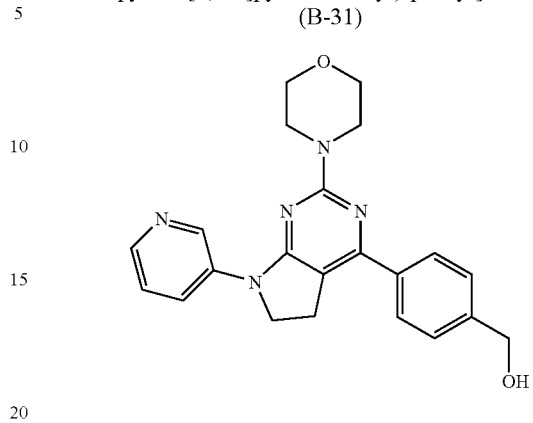

In the same manner as Example 1-B-10, using 4-chloro-2-morpholin-4-yl-7-pyridin-3-yl-6,7-dihydro-5H-pyrrolo[2,3-d]pyrimidine, and 4-(hydroxymethyl)phenylboronic acid as a boronic acid, the desired compound was obtained.

$^1$H-NMR (CDCl$_3$+TFA) δ: 9.59 (1H, m), 8.64-8.80 (2H, m), 8.13 (1H, m), 7.55 (4H, m), 4.84 (2H, brs), 4.44 (2H, brt), 3.92 (8H, m), 3.35 (2H, brt).

ESI (LC-MS positive mode) m/z 390 ([M+H]$^+$).

Example 1-B-32

4-(2-Morpholin-4-yl-7-pyridin-4-yl-6,7-dihydro-5H-pyrrolo[2,3-d]pyrimidin-4-yl)-benzylamine hydrochloride (B-32)

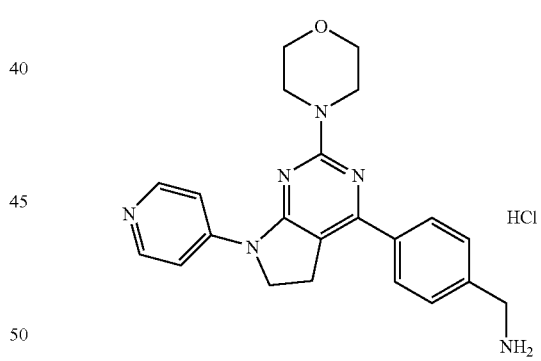

In the same manner as Example 1-B-10, using 4-chloro-2-morpholin-4-yl-7-pyridin-4-yl-6,7-dihydro-5H-pyrrolo[2,3-d]pyrimidine, and [4-(N-Boc-aminomethyl)phenyl]boronic acid as a boronic acid, 4-(4-tert-butoxycarbonylaminomethyl-phenyl)-2-(morpholin-4-yl)-7-(pyridin-4-yl)-6,7-dihydro-5H-pyrrolo[2,3-d]pyrimidine was obtained. This was dissolved in 1N hydrochloric acid-acetic acid, followed by stirring at room temperature for 40 minutes, and diethyl ether was added to the reaction mixture, to filter off a solid, whereby the desired compound was obtained.

$^1$H-NMR (DMSO-d$_6$+TFA) δ: ppm 8.58 (2H, d, J=7.3 Hz), 8.34 (2H, d, J=7.3 Hz), 8.01 (2H, d, J=8.4 Hz), 7.65 (2H, d, J=8.4 Hz), 4.29 (2H, brt), 4.16 (2H, s), 3.79 (8H, m), 3.40 (2H, brt).

ESI (LC-MS positive mode) m/z 389 ([M+H]$^+$).

Example 1-B-33

4-(2-Morpholin-4-yl-7-pyridin-3-yl-6,7-dihydro-5H-pyrrolo[2,3-d]pyrimidin-4-yl)-benzylamine hydrochloride (B-33)

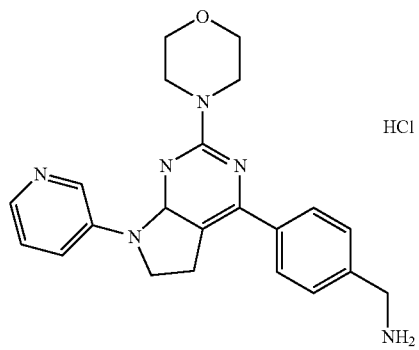

In the same manner as Example 1-B-10, using 4-chloro-2-morpholin-4-yl-7-pyridin-3-yl-6,7-dihydro-5H-pyrrolo[2,3-d]pyrimidine, and [4-(N-Boc-aminomethyl)phenyl]boronic acid as a boronic acid, 4-(4-tert-butoxycarbonylaminomethyl-phenyl)-2-(morpholin-4-yl)-7-(pyridin-3-yl)-6,7-dihydro-5H-pyrrolo[2,3-d]pyrimidine was obtained. This was dissolved in 1N hydrochloric acid-acetic acid, followed by stirring at room temperature for 40 minutes, and diethyl ether was added to the reaction mixture, to filter off a solid, whereby the desired compound was obtained.

$^1$H-NMR (DMSO-$d_6$+TFA) δ: ppm 9.63 (1H, m), 8.93 (1H, m), 8.69 (1H, m), 8.17 (1H, m), 7.92 (2H, m), 7.73 (2H, m), 4.45 (2H, m), 4.26 (2H, s), 3.83 (8H, m), 3.37 (2H, m).

ESI (LC-MS positive mode) m/z 389 ([M+H]$^+$).

Example 1-B-34

2-Fluoro-5-(2-morpholin-4-yl-7-pyridin-4-yl-6,7-dihydro-5H-pyrrolo[2,3-d]pyrimidin-4-yl)-benzonitrile (B-34)

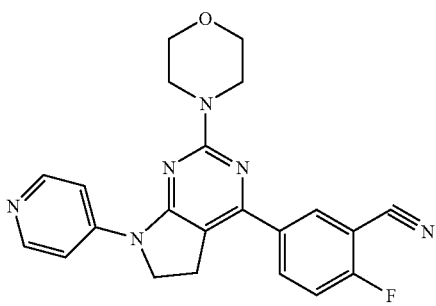

To 4-chloro-2-morpholin-4-yl-7-pyridin-4-yl-6,7-dihydro-5H-pyrrolo[2,3-d]pyrimidine (10 mg, 0.0315 mmol), 3-cyano-4-fluorophenylboronic acid (10.4 mg, 0.0630 mmol), palladium acetate (1.4 mg, 0.0063 mmol), S-Phos (5.2 mg, 0.0126 mmol) and sodium hydroxide (2.5 mg, 0.063 mmol), t-butanol (1 ml) was added, followed by being degassed under ultrasonic irradiation. This was stirred at 100° C. for 3 hours, followed by extraction with ethyl acetate with the addition of water, and the organic layer was washed with brine. After drying over anhydrous sodium sulfate, concentration was carried out under reduced pressure, followed by elution with 2M ammonia methanol solution through SCX resin and then concentration. Purification by preparative TLC afforded the desired compound as a colorless solid (3.1 mg, yield 12%).

$^1$H-NMR (CDCl$_3$) δ: 8.54 (2H, d, J=6.3 Hz), 8.22 (1H, dd, J=5.9, 2.4 Hz), 8.19-8.15 (1H, m), 7.74 (2H, d, J=6.3 Hz), 7.32 (1H, t, J=8.5 Hz), 4.12 (2H, t, J=8.2 Hz), 3.93-3.81 (8H, m), 3.36 (2H, t, J=8.2 Hz).

ESI (LC-MS positive mode) m/z 403 ([M+H]$^+$).

Example 1-B-35

[2-Fluoro-5-(2-morpholin-4-yl-7-pyridin-4-yl-6,7-dihydro-5H-pyrrolo[2,3-d]pyrimidin-4-yl)-phenyl]-methanol (B-35)

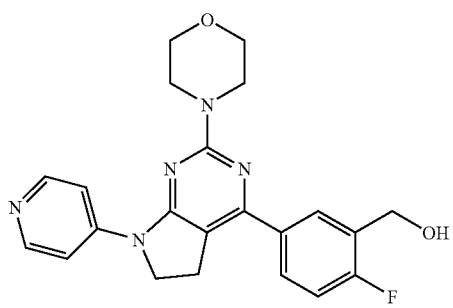

In the same manner as Example 1-B-34 (except not passing through SCX), using 4-fluoro-3-formylbenzeneboronic acid as a boronic acid, 2-fluoro-5-(2-morpholin-4-yl-7-pyridin-4-yl-6,7-dihydro-5H-pyrrolo[2,3-d]pyrimidin-4-yl)-benzaldehyde was obtained. This was dissolved in methanol (1 ml), and sodium borohydride (1.2 mg, 0.0315 mmol, 1.0 equivalent) was added, followed by stirring at room temperature for 30 minutes. To this, saturated aqueous ammonium chloride solution was added, followed by extraction with ethyl acetate, and the organic layer was washed using brine. After drying with anhydrous sodium sulfate, concentration was carried out under reduced pressure. Purification by preparative TLC afforded the desired compound as a colorless solid (7.0 mg, yield 27%).

$^1$H-NMR (DMSO-$d_6$) δ: 8.46 (2H, d, J=4.9 Hz), 8.08 (1H, d, J=7.8 Hz), 7.93-7.87 (1H, m), 7.83 (2H, d, J=4.9 Hz), 7.28 (1H, t, J=9.3 Hz), 5.39 (1H, s), 4.62 (2H, d, J=5.4 Hz), 4.11 (2H, t, J=8.3 Hz), 3.80-3.69 (8H, m), 3.37-3.33 (2H, m).

ESI (LC-MS positive mode) m/z 408 ([M+H]$^+$).

Example 1-B-36

[3-(2-Morpholin-4-yl-7-pyridin-4-yl-6,7-dihydro-5H-pyrrolo[2,3-d]pyrimidin-4-yl)-phenyl]-methanol (B-36)

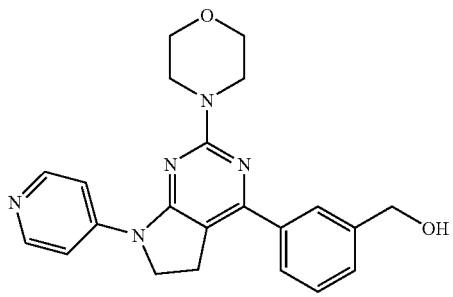

In the same manner as Example 1-B-34, using 3-(hydroxymethyl)phenylboronic acid as a boronic acid, the desired compound was obtained as a colorless solid.

$^1$H-NMR (CDCl$_3$) δ: 8.17 (2H, d, J=6.1 Hz), 7.59 (1H, s), 7.49 (1H, d, J=6.8 Hz), 7.41 (2H, d, J=6.1 Hz), 7.15 (1H, q, J=6.8 Hz), 7.14 (1H, s), 4.47 (2H, s), 3.73 (2H, t, J=8.3 Hz), 3.59-3.49 (8H, m), 3.03 (2H, t, J=8.3 Hz)

ESI (LC-MS positive mode) m/z 390 ([M+H]$^+$).

Example 1-B-37

2-Morpholin-4-yl-7-pyridin-4-yl-4-(3-trifluoromethoxy-phenyl)-6,7-dihydro-5H-pyrrolo[2,3-d]pyrimidine (B-37)

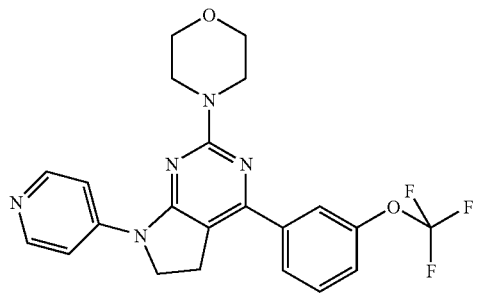

In the same manner as Example 1-B-34, using 3-(trifluoromethoxy)phenylboronic acid as a boronic acid, the desired compound was obtained as a yellow solid.

$^1$H-NMR (CDCl$_3$) δ: 8.52 (2H, d, J=5.6 Hz), 7.83 (1H, d, J=8.0 Hz), 7.78 (1H, s), 7.73 (2H, d, J=5.6 Hz), 7.50 (1H, t, J=8.0 Hz), 7.29 (2H, d, J=8.0 Hz), 4.09 (2H, t, J=8.2 Hz), 3.91-3.82 (8H, m), 3.36 (2H, t, J=8.2 Hz).

ESI (LC-MS positive mode) m/z 444 ([M+H]$^+$).

Example 1-B-38

2-Morpholin-4-yl-7-pyridin-4-yl-4-(4-trifluoromethoxy-phenyl)-6,7-dihydro-5H-pyrrolo[2,3-d]pyrimidine (B-38)

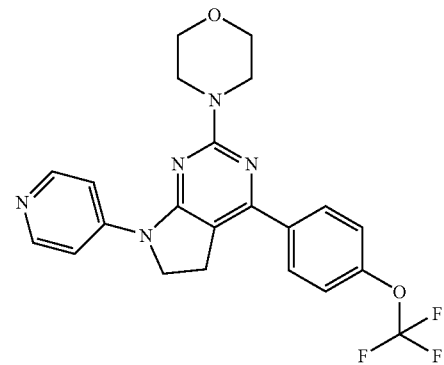

In the same manner as Example 1-B-34, using 4-(trifluoromethoxy)benzeneboronic acid as a boronic acid, the desired compound was obtained as a colorless solid.

$^1$H-NMR (CDCl$_3$) δ: 8.52 (2H, d, J=5.9 Hz), 7.95 (2H, d, J=8.5 Hz), 7.74 (2H, d, J=5.9 Hz), 7.31 (2H, d, J=8.5 Hz), 4.09 (2H, t, J=8.3 Hz), 3.90-3.81 (8H, m), 3.35 (2H, t, J=8.3 Hz).

ESI (LC-MS positive mode) m/z 444 ([M+H]$^+$).

Example 1-B-39

4-(2-Morpholin-4-yl-7-pyridin-4-yl-6,7-dihydro-5H-pyrrolo[2,3-d]pyrimidin-4-yl)-phenol (B-39)

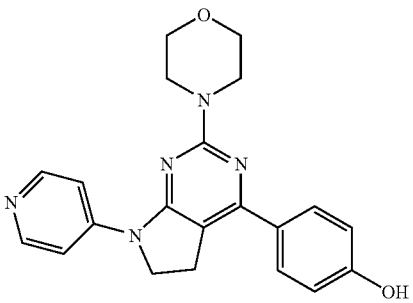

In the same manner as Example 1-B-34, using 4-hydroxyphenylboronic acid as a boronic acid, the desired compound was obtained as a yellow solid.

$^1$H-NMR (DMSO-d$_6$) δ: 9.86 (1H, s), 8.59-8.35 (2H, m), 7.85 (4H, d, J=8.8 Hz), 6.88 (2H, d, J=8.8 Hz), 4.08 (2H, t, J=8.5 Hz), 3.73 (8.0H, d, J=6.8 Hz), 3.30-3.27 (2H, m).

ESI (LC-MS positive mode) m/z 376 ([M+H]$^+$).

Example 1-B-40

2-Morpholin-4-yl-7-pyridin-4-yl-4-(3,4,5-trimethoxy-phenyl)-6,7-dihydro-5H-pyrrolo[2,3-d]pyrimidine (B-40)

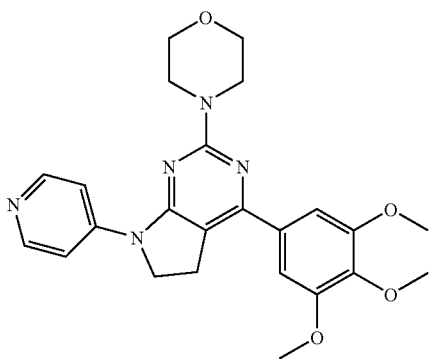

In the same manner as Example 1-B-34, using 3,4,5-trimethoxyphenylboronic acid as a boronic acid, the desired compound was obtained as a colorless solid.

$^1$H-NMR (CDCl$_3$) δ: 8.51 (2H, d, J=6.6 Hz), 7.74 (2H, d, J=6.6 Hz), 7.15 (2H, s), 4.08 (2H, t, J=8.2 Hz), 3.93 (6H, s), 3.91 (3H, s), 3.90-3.82 (8H, m), 3.37 (2H, t, J=8.2 Hz).

ESI (LC-MS positive mode) m/z 450 ([M+H]$^+$).

Example 1-B-41

2-Morpholin-4-yl-4-phenyl-7-pyridin-4-yl-6,7-dihydro-5H-pyrrolo[2,3-d]pyrimidine (B-41)

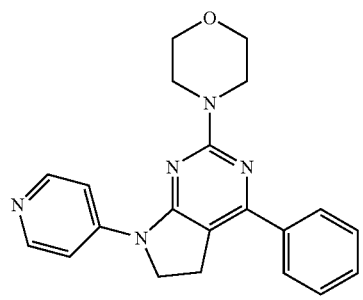

In the same manner as Example 1-B-34, using phenylboronic acid as a boronic acid, the desired compound was obtained as a colorless solid.

$^1$H-NMR (CDCl$_3$) δ: 8.51 (2H, d, J=5.7 Hz), 7.94-7.88 (2H, m), 7.75 (2H, d, J=5.7 Hz), 7.49-7.45 (3H, m), 4.07 (2H, t, J=8.5 Hz), 3.93-3.80 (8H, m), 3.37 (2H, t, J=8.5 Hz).

ESI (LC-MS positive mode) m/z 360 ([M+H]$^+$).

Example 1-B-42

5-(2-Morpholin-4-yl-7-pyridin-3-yl-6,7-dihydro-5H-pyrrolo[2,3-d]pyrimidin-4-yl)-pyridin-2-ol (B-42)

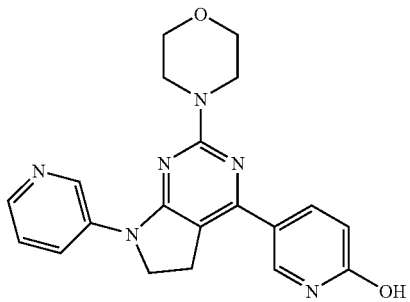

Compound B-10 obtained in Example 1-B-10 was dissolved in chloroform, trimethylsilyliodide (5 equivalents) was added, followed by refluxing for 3 hours. The reaction mixture was concentrated under reduced pressure, and the resulting residue was dissolved in methanol, to precipitate a crystal with ether, whereby the desired compound was obtained.

$^1$H-NMR (DMSO-d$_6$) δ: 9.46 (1H, s), 8.72 (1H, d, J=8.7 Hz), 8.52 (1H, d, J=5.4 Hz), 8.11 (1H, dd, J=9.6, 2.6 Hz), 8.04-7.98 (2H, m), 6.46 (1H, d, J=9.6 Hz), 6.46 (1H, d, J=9.6 Hz), 4.18 (2H, t, J=7.9 Hz), 3.72-3.78 (8H, m), 3.34 (2H, t, J=7.9 Hz).

ESI (LC-MS positive mode) m/z 377 ([M+H]$^+$).

Example 1-B-43

5-(2-Morpholin-4-yl-7-pyridin-4-yl-6,7-dihydro-5H-pyrrolo[2,3-d]pyrimidin-4-yl)-pyridin-2-ol (B-43)

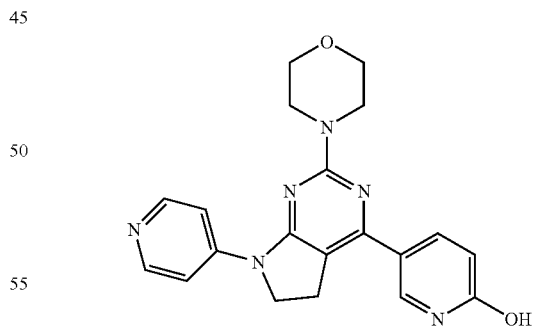

In the same manner as Example 1-B-42, using compound B-11 obtained in Example 1-B-11, the desired compound was obtained.

$^1$H-NMR (DMSO-d$_6$) δ: 12.06 (1H, s), 8.64 (2H, d, J=6.6 Hz), 8.29 (2H, brs), 8.14 (1H, dd, J=9.7, 2.3 Hz), 7.99 (1H, d, J=2.3 Hz), 6.46 (1H, d, J=9.7 Hz), 4.22 (2H, t, J=7.7 Hz), 3.73 (8H, m), 3.34 (2H, t, J=7.7 Hz).

ESI (LC-MS positive mode) m/z 377 ([M+H]$^+$).

Example 1-B-44

3-(2-Morpholin-4-yl-7-pyridin-3-yl-6,7-dihydro-5H-pyrrolo[2,3-d]pyrimidin-4-yl)-pyridin-2-ol (B-44)

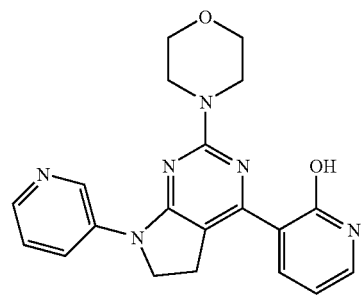

In the same manner as Example 1-B-10, using 2-methoxy-3-(4,4,5,5-tetramethyl-[1,3,2]dioxaborolan-2-yl)-pyridine as a boronic acid, 4-(2-methoxy-pyridin-3-yl)-2-morpholin-4-yl-7-pyridin-3-yl-6,7-dihydro-5H-pyrrolo[2,3-d]pyrimidine was obtained. This was demethylated in the same manner as Example 1-B-42, to obtain the desired compound.

$^1$H-NMR (DMSO-$d_6$) δ: 9.19 (1H, d, J=2.3 Hz), 8.53 (1H, dt, J=5.0, 1.5 Hz), 8.47 (1H, d, J=8.6 Hz), 8.19 (1H, dd, J=7.6, 1.5 Hz), 7.87 (1H, dd, J=6.8, 1.5 Hz), 7.78-7.72 (1H, m), 6.66 (1H, t, J=6.8 Hz), 4.36 (2H, t, J=7.8 Hz), 3.78-3.68 (8H, m), 3.37 (2H, t, J=7.8 Hz).

ESI (LC-MS positive mode) m/z 377 ([M+H]$^+$).

Example 1-B-45

5-(2-Morpholin-4-yl-7-pyridin-4-yl-6,7-dihydro-5H-pyrrolo[2,3-d]pyrimidin-4-yl)-pyrimidin-2-ol (B-45)

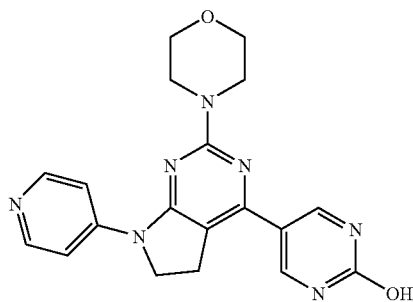

In the same manner as Example 1-B-10, using 4-chloro-2-morpholin-4-yl-7-pyridin-4-yl-6,7-dihydro-5H-pyrrolo[2,3-d]pyrimidine, and 2-methoxypyrimidin-5-boronic acid as a boronic acid, 4-(2-methoxy-pyrimidin-5-yl)-2-morpholin-4-yl-7-pyridin-4-yl-6,7-dihydro-5H-pyrrolo[2,3-d]pyrimidine was obtained. This was demethylated in the same manner as Example 1-B-42, to obtain the desired compound.

$^1$H-NMR (DMSO-$d_6$) δ: 8.48 (4H, m), 7.87 (2H, m), 4.11 (2H, t, 7.8 Hz), 3.72 (8H, m), 3.33 (2H, t, 7.8 Hz)

ESI (LC-MS positive mode) m/z 378 ([M+H]$^+$).

Example 1-B-46

3-(2-Morpholin-4-yl-7-phenyl-6,7-dihydro-5H-pyrrolo[2,3-d]pyrimidin-4-yl)-phenol (B-46)

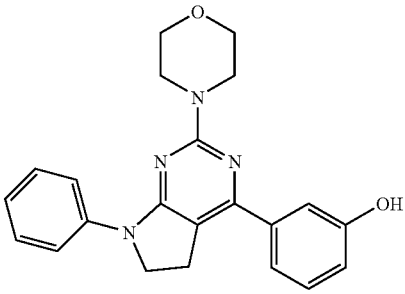

In the same manner as Step C in Example 1-B-01, using aniline as an amine, 4-chloro-2-morpholin-4-yl-7-phenyl-6,7-dihydro-5H-pyrrolo[2,3-d]pyrimidine was obtained (Yield 78%). Then, in the same manner as Example 1-B-10, using 3-hydroxyphenylboronic acid as a boronic acid, the desired compound was obtained (Yield 16%).

$^1$H-NMR (CDCl$_3$) δ: 7.80-7.76 (1H, m), 7.41-7.38 (2H, m), 7.35 (1H, d, J=6.8 Hz), 7.28 (1H, t, J=7.6 Hz), 7.12 (1H, dt, J=7.6, 1.3 Hz), 7.07 (1H, t, J=8.0 Hz), 6.90-6.78 (1.0H, m), 6.39 (1H, dd, J=8.0, 2.2 Hz), 6.33 (1H, t, J=2.2 Hz), 4.06 (2H, t, J=8.2 Hz), 3.89-3.81 (8H, m), 3.27 (2H, t, J=8.2 Hz).

ESI (LC-MS positive mode) m/z 375 ([M+H]$^+$).

Example 1-B-47

3-[7-(2,4-Difluoro-phenyl)-2-morpholin-4-yl-6,7-dihydro-5H-pyrrolo[2,3-d]pyrimidin-4-yl]-phenol (B-47)

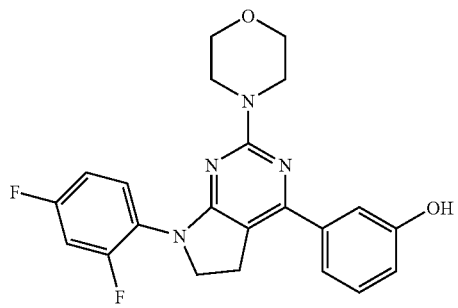

In the same manner as Step C in Example 1-B-01, using 2,4-difluoroaniline as an amine, 4-chloro-7-(2,4-difluorophenyl)-2-morpholin-4-yl-6,7-dihydro-5H-pyrrolo[2,3-d]pyrimidine was obtained (Yield 82%). Then, in the same manner as Example 1-B-10, using 3-hydroxyphenylboronic acid as a boronic acid, the desired compound was obtained (Yield 17%).

$^1$H-NMR (CDCl$_3$) δ: 7.58 (1H, m), 7.43 (1H, dt, J=7.3, 3.8 Hz), 7.32 (1H, t, J=7.3 Hz), 7.15-7.01 (1H, m), 6.87 (2H, m), 6.38 (1H, m), 4.03 (2H, t, J=8.3 Hz), 3.75 (8H, brs), 3.33 (2H, t, J=8.3 Hz).

ESI (LC-MS positive mode) m/z 393 ([M+H]$^+$).

Example 1-B-48

4-(3-Methoxy-phenyl)-7-(4-methoxy-phenyl)-2-morpholin-4-yl-6,7-dihydro-5H-pyrrolo[2,3-d]pyrimidine (B-48)

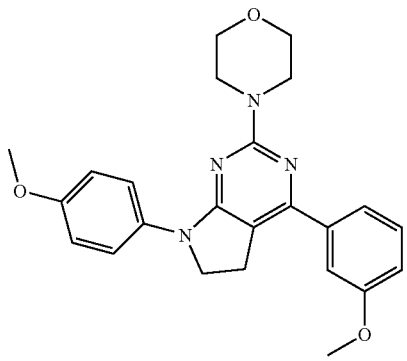

In the same manner as Step C in Example 1-B-01, using 4-methoxyaniline as an amine, 4-chloro-7-(2,4-difluoro-phenyl)-2-morpholin-4-yl-6,7-dihydro-5H-pyrrolo[2,3-d]pyrimidine was obtained (Yield 22%). Then, in the same manner as Example 1-B-10, using 3-methoxyphenylboronic acid as a boronic acid, the desired compound was obtained (Yield 37%).

$^1$H-NMR (CDCl$_3$) δ: 7.69 (2H, d, J=9.2 Hz), 7.51 (1H, t, J=2.4 Hz), 7.46 (1H, d, J=7.9 Hz), 7.36 (1H, t, J=7.9 Hz), 6.97-6.95 (1H, m), 6.94 (2H, d, J=9.2 Hz), 4.04 (2H, t, J=8.1 Hz), 3.87 (3H, s), 3.85-3.76 (8H, m), 3.82 (3H, s), 3.30 (2H, t, J=8.1 Hz).

ESI (LC-MS positive mode) m/z 419 ([M+H]$^+$).

Example 1-B-49

7-(4-Methoxy-benzyl)-4-(3-methoxy-phenyl)-2-morpholin-4-yl-6,7-dihydro-5H-pyrrolo[2,3-d]pyrimidine (B-49)

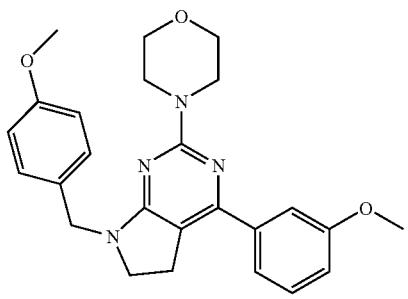

In the same manner as Step C in Example 1-B-01, using 4-methoxybenzylamine as an amine, 4-chloro-7-(4-methoxybenzyl)-2-morpholin-4-yl-6,7-dihydro-5H-pyrrolo[2,3-d]pyrimidine was obtained. Then, in the same manner as Example 1-B-10, using 3-methoxyphenylboronic acid as a boronic acid, the desired compound was obtained.

$^1$H-NMR (CDCl$_3$) δ: 7.50 (1H, t, J=1.8 Hz), 7.43 (1H, d, J=7.8 Hz), 7.33 (1H, t, J=7.8 Hz), 7.24 (2H, d, J=8.5 Hz), 6.92 (1H, dd, J=8.0, 2.7 Hz), 6.86 (2H, d, J=8.5 Hz), 4.55 (2H, s), 3.87-3.78 (8H, m), 3.85 (3H, s), 3.80 (3H, s), 3.44 (2H, t, J=8.0 Hz), 3.14 (2H, t, J=8.0 Hz).

ESI (LC-MS positive mode) m/z 433 ([M+H]$^+$).

Example 1-B-50

3-(2-Morpholin-4-yl-7-pyridin-3-yl-6,7-dihydro-5H-pyrrolo[2,3-d]pyrimidin-4-yl)-benzenesulfonamide (B-50)

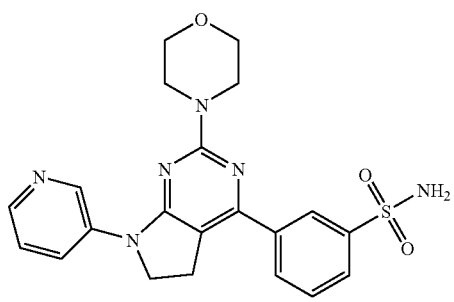

4-Chloro-2-morpholin-4-yl-7-pyridin-3-yl-6,7-dihydro-5H-pyrrolo[2,3-d]pyrimidine (48 mg), palladium acetate (1 mg), S-Phos (3.7 mg), N,N-bis-(4-methoxy-benzyl)-3-(4,4,5,5-tetramethyl-[1,3,2]dioxaborolan-2-yl)-benzenesulfonamide (118 mg) and potassium phosphate (64 mg) were dissolved in dimethylformamide (1.5 ml), and degassing under ultrasonic irradiation, and substitution with argon were repeated three times. The reaction mixture was stirred at 100° C. for 10 hours, and subsequently diluted with water/ethyl acetate (50 ml/50 ml). The organic layers were separated, and the aqueous layer was extracted with ethyl acetate (50 ml). The combined organic layers were washed with brine, and the organic layer was dried over sodium sulfate. After filtering off the drying agent, the filtrate was concentrated under reduced pressure, and the resulting residue was purified by preparative TLC (dichloromethane/methanol=20/1), to obtain a yellow crystal (20 mg, 20%).

This was dissolved in trifluoroacetic acid (2 ml), followed by stirring at 40° C. for 1 hour. To the reaction mixture, water (1 ml) was added, followed by neutralization with sodium hydrogencarbonate aqueous solution. The precipitate was filtered off, followed by recrystallization from methanol/ether, to obtain the desired compound as a gray powder (6 mg, 46%).

$^1$H-NMR (270 MHz, DMSO-d$_6$) δ (ppm): 9.10 (1H, d, J=2.1 Hz), 8.40 (1H, s), 8.27 (1H, d, J=5.1 Hz), 8.14 (1H, d, J=7.6 Hz), 7.91 (1H, d, J=7.6 Hz), 7.71 (1H, t, J=7.6 Hz), 7.49 (2H, s), 7.44 (2H, m), 4.17 (2H, t, J=8.2 Hz), 3.74 (8H, m), 3.37 (2H, t, J=8.2 Hz).

ESI (LC-MS positive mode) m/z 439 [(M+H)$^+$].

Example 1-B-51

3-(2-Morpholin-4-yl-7-pyridin-4-yl-6,7-dihydro-5H-pyrrolo[2,3-d]pyrimidin-4-yl)-benzenesulfonamide (B-51)

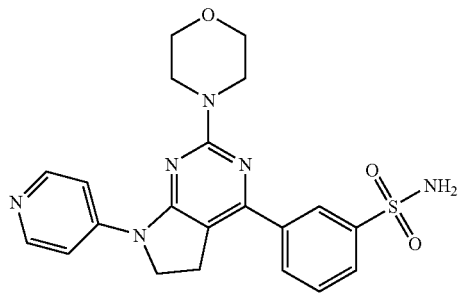

In the same manner as Example 1-B-50, from 4-chloro-2-morpholin-4-yl-7-pyridin-3-yl-6,7-dihydro-5H-pyrrolo[2,3-d]pyrimidine and N,N-bis-(4-methoxy-benzyl)-3-(4,4,5,5-tetramethyl-[1,3,2]dioxaborolan-2-yl)-benzenesulfonamide, the desired compound was obtained as a gray powder.

$^1$H-NMR (270 MHz, DMSO-$d_6$) δ (ppm): 8.47 (2H, d, J=6.1 Hz), 8.40 (1H, s), 8.15 (1H, d, J=7.3 Hz), 7.92 (1H, d, J=6.9 Hz), 7.84 (2H, d, J=6.1 Hz), 7.72 (1H, t, J=7.8 Hz), 7.50 (1H, s), 4.13 (2H, t, J=8.1 Hz), 3.79-3.70 (8H, m), 3.37 (2H, t, J=8.1 Hz).

ESI (LC-MS positive mode) m/z 439 [(M+H)$^+$].

Example 1-B-52

2-Fluoro-4-(2-morpholin-4-yl-7-pyridin-3-yl-6,7-dihydro-5H-pyrrolo[2,3-d]pyrimidin-4-yl)-phenylamine (B-52)

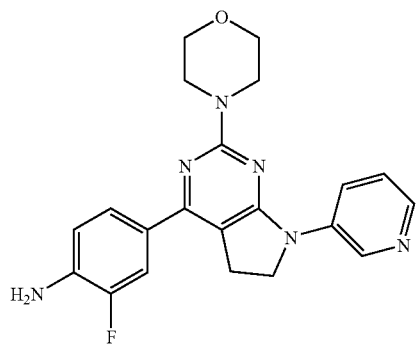

In the same manner as Step B in Example 1-B-02, using [2-fluoro-4-(4,4,5,5-tetramethyl-[1,3,2]dioxaborolan-2-yl)phenyl]-bis-(4-methoxybenzyl)-amine as a boronic acid, the desired compound was obtained.

$^1$H-NMR (DMSO-$d_6$) δ (ppm): 9.07 (1H, d, J=2.4 Hz), 8.23 (2H, dd, J=7.8, 2.4 Hz), 7.66 (1H, dd, J=13.7, 2.0 Hz), 7.55 (1H, dd, J=8.5, 1.7 Hz), 7.42-7.38 (1H, m), 6.84 (1H, t, J=8.8 Hz), 5.59 (2H, s), 4.10 (2H, t, J=8.3 Hz), 3.75-3.67 (8H, m), 3.33 (2H, t, J=8.3 Hz).

ESI (LC-MS positive mode) m/z 411 [(M+H)$^+$].

Example 1-B-53

2,6-Difluoro-4-(2-morpholin-4-yl-7-pyridin-3-yl-6,7-dihydro-5H-pyrrolo[2,3-d]pyrimidin-4-yl)-phenylamine (B-53)

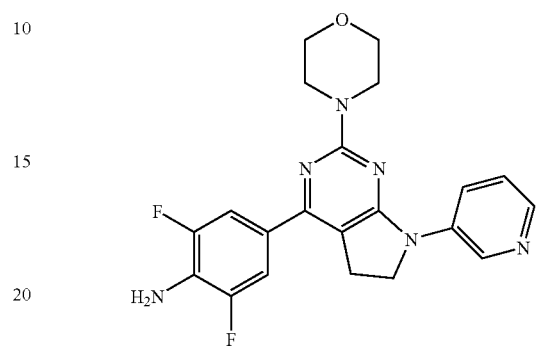

In the same manner as Step B in Example 1-B-02, using [2,6-difluoro-4-(4,4,5,5-tetramethyl-[1,3,2]dioxaborolan-2-yl)phenyl]-bis-(4-methoxybenzyl)-amine as a boronic acid, the desired compound was obtained.

$^1$H-NMR (DMSO-$d_6$) δ (ppm): 9.26 (1H, d, J=2.4 Hz), 8.45 (1H, d, J=8.5 Hz), 8.36 (1H, d, J=5.1 Hz), 7.68 (1H, dd, J=8.5, 5.1 Hz), 7.55 (2H, dd, J=8.3, 2.4 Hz), 4.15 (2H, t, J=8.3 Hz), 3.72 (8H, d, J=5.4 Hz), 3.38 (2H, t, J=8.3 Hz).

ESI (LC-MS positive mode) m/z 411 [(M+H)$^+$].

Example 1-B-54

4-(2-Morpholin-4-yl-7-pyridin-3-yl-6,7-dihydro-5H-pyrrolo[2,3-d]pyrimidin-4-yl)-phenylamine (B-54)

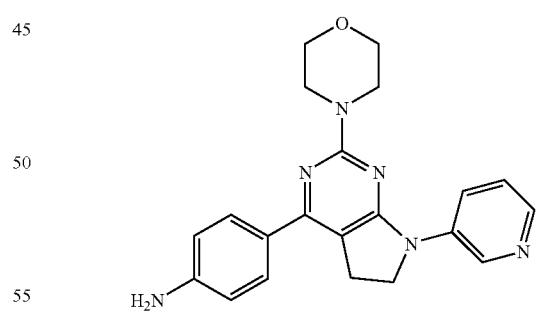

In the same manner as Example 1-B-08, using (4-aminophenyl)boronic acid hydrochloride as a boronic acid, the desired compound was obtained.

$^1$H-NMR (CDCl$_3$) δ (ppm): 9.03 (1H, d, J=2.4 Hz), 8.23 (1H, d, J=3.9 Hz), 8.10 (1H, dq, J=8.4, 1.3 Hz), 7.45 (2H, d, J=7.8 Hz), 7.32 (2H, t, J=8.1 Hz), 7.06 (1H, t, J=7.3 Hz), 4.02 (2H, t, J=8.5 Hz), 3.78 (8H, s), 2.86 (2H, t, J=8.5 Hz).

ESI (LC-MS positive mode) m/z 375 [(M+H)$^+$].

Example 1-B-55

6-(2-Morpholin-4-yl-7-pyridin-4-yl-6,7-dihydro-5H-pyrrolo[2,3-d]pyrimidin-4-yl)-pyridin-3-ylamine (B-55)

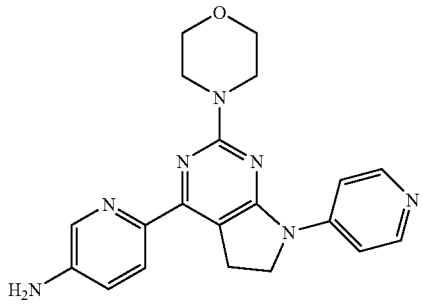

To a solution of n-butyl lithium (1.56M hexane solution, 0.23 ml, 0.363 mmol) in tetrahydrofuran (2 ml), at 0° C., isopropyl magnesium chloride (2M tetrahydrofuran solution, 0.09 ml, 0.182 mmol) was added, followed by stirring for 15 minutes. To this, a solution of (6-bromo-pyridin-3-yl)-bis-(4-methoxy-benzyl)-amine (50 mg, 0.121 mmol, 1.0 equivalent) in tetrahydrofuran (1 ml) was added, followed by stirring for 1.5 hours. Zinc chloride (1M diethyl ether solution, 0.55 ml, 0.545 mmol) was added, and the temperature was raised to room temperature, followed by stirring for 1 hour. 4-Chloro-2-morpholin-4-yl-7-pyridin-4-yl-6,7-dihydro-5H-pyrrolo[2,3-d]pyrimidine (38.4 mg, 0.121 mmol) was added, followed by refluxing for 2 hours. Water was added, followed by extraction with ethyl acetate, and the organic layer was washed with brine. After drying over sodium sulfate, concentration was carried out under reduced pressure. Purification by preparative TLC (dichloromethane/methanol=40/1) afforded bis-(4-methoxy-benzyl)-[6-(2-morpholin-4-yl-7-pyridin-4-yl-6,7-dihydro-5H-pyrrolo[2,3-d]pyrimidin-4-yl)-pyridin-3-yl]-amine (5.3 mg, yield 7%).

To this, TFA (1 ml) and concentrated sulfuric acid (1 drop) were added, followed by stirring at 40° C. for 1.5 hours. This was concentrated under reduced pressure, and water was added, followed by neutralization with 1M hydrochloric acid. The resulting solid was washed with water, to obtain the desired compound as a yellow solid (1.5 mg, yield 46%).

$^1$H-NMR (DMSO-d$_6$) δ (ppm): 8.41 (2H, brs), 8.10 (1H, d, J=8.3 Hz), 8.03 (1H, brs), 7.83-7.79 (2H, brm), 7.00 (1H, d, J=8.3 Hz), 5.77 (2H, s), 4.02 (2H, t, J=8.5 Hz), 3.78-3.67 (8H, brm), 3.45 (2H, t, J=8.5 Hz).

ESI (LC-MS positive mode) m/z 376 [(M+H)$^+$].

Example 1-C

In the following Examples 1-C-42, 1-C-43, 1-C-44, 1-C-50, 1-C-51, 1-C-53, 1-C-54, 1-C-55 and 1-C-56, the resulting reaction crude products were further subjected to HPLC purification using an eluent containing TFA, to obtain the desired compound as a trifluoroacetic acid salt. Further, 4-(3-t-butoxyphenyl)-2-morpholin-4-yl-6,7-dihydro-5H-pyrrolo[2,3-d]pyrimidine to be used in the following Examples 1-C-01, 1-C-03 and 1-C-07 was prepared according to Example 1-J-01 described later.

Example 1-C-01

4-(3-Hydroxyphenyl)-2-(morpholin-4-yl)-7-(ethylaminocarbonyl)-6,7-dihydro-5H-pyrrolo[2,3-d]pyrimidine (C-01)

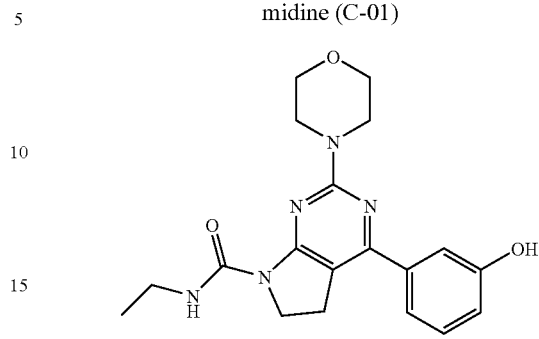

4-(3-t-Butoxyphenyl)-2-morpholin-4-yl-6,7-dihydro-5H-pyrrolo[2,3-d]pyrimidine (20 mg, 0.056 mmol) was dissolved in dimethylformamide (1 mL), and diisopropylethylamine (29 μL, 3 equivalents) and ethyl isocyanate (13 μL, 3 equivalents) were added, followed by stirring at 60° C. for 2 days. The reaction mixture was poured onto water, followed by extraction with ethyl acetate, and the organic layer was dried over sodium sulfate. After filtering off the drying agent, concentration was carried out under reduced pressure, and the resulting residue was stirred at room temperature for 30 minutes in trifluoroacetic acid. Concentration was carried out under reduced pressure, and the resulting residue was purified by silica gel column chromatography (ethyl acetate/hexane), to obtain the desired compound (colorless powder, 1.7 mg, 9%).

$^1$H-NMR (270 MHz, CD$_3$OD) δ (ppm): 8.99 (1H, m), 7.27-7.41 (3H, m), 6.92 (1H, m), 4.08 (2H, br), 3.82 (8H, m), 3.42 (2H, m), 3.25 (2H, br), 1.27 (3H, t, 7.3 Hz).

ESI (LC-MS positive mode) m/z 370 [(M+H)$^+$].

Example 1-C-02

1-[4-(3-Hydroxy-phenyl)-2-morpholin-4-yl-5,6-dihydro-pyrrolo[2,3-d]pyrimidin-7-yl]-ethanone (C-02)

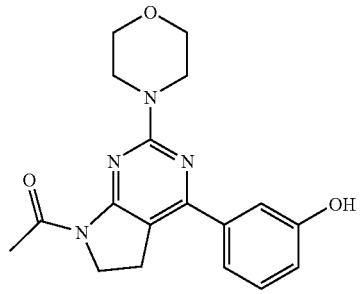

1-[4-(3-t-Butoxyphenyl)-2-morpholin-4-yl-5,6-dihydro-pyrrolo[2,3-d]pyrimidin-7-yl]-ethanone (20 mg) prepared according to Step E in Example 1-J-01 described later was dissolved in trifluoroacetic acid (500 μl), followed by stirring at room temperature for 30 minutes. The reaction mixture was concentrated under reduced pressure, and to the resulting residue, water (5 ml) and methanol (1 ml) were added, followed by neutralization with aqueous saturated sodium bicarbonate solution. The deposited precipitate was filtered off, followed by drying under reduced pressure, to obtain a colorless powder (11 mg, 64%).

¹H-NMR (270 MHz, DMSO-d₆) δ (ppm): 9.72 (1H, s), 7.37 (1H, d, J=1.8 Hz), 7.34-7.25 (2H, m), 6.86 (1H, dt, J=7.4, 1.8 Hz), 3.93 (2H, t, J=8.2 Hz), 3.74-3.67 (8H, m), 3.13 (2H, t, J=8.2 Hz), 2.58 (3H, s).

ESI (LC-MS positive mode) m/z 341 [(M+H)⁺].

Example 1-C-03

[4-(3-t-Butoxyphenyl)-2-morpholin-4-yl-5,6-dihydropyrrolo[2,3-d]pyrimidin-7-yl]-phenylmethanone (C-03)

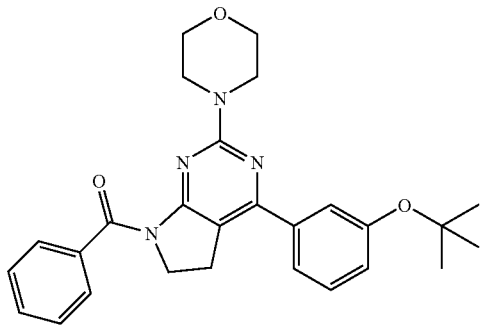

To an acetonitrile solution (2 ml) of 4-(3-t-butoxyphenyl)-2-morpholin-4-yl-6,7-dihydro-5H-pyrrolo[2,3-d]pyrimidine (36 mg), an acetonitrile solution (1 ml) of pyridine (25 μl, 3 equivalents), dimethylaminopyridine (ca. 2 mg, catalytic amount) and benzoyl chloride (28 mg, 2 equivalents) was added under ice cooling, followed by stirring at room temperature for 10 hours. To the reaction mixture, water (20 ml) was added, followed by extraction with ethyl acetate (10 ml×2). The organic layer was washed with aqueous ammonium chloride solution and brine, and subsequently dried over sodium sulfate. After filtering off the drying agent, the filtrate was concentrated under reduced pressure, and the resulting residue was purified by preparative TLC (n-hexane/ethyl acetate=2/1), to obtain the desired compound as a colorless powder (42 mg, 90%).

¹H-NMR (270 MHz, CDCl₃) δ (ppm): 7.58-7.65 (3H, m), 7.52 (1H, t, J=1.8 Hz), 7.29-7.48 (4H, m), 7.11-7.13 (1H, m), 4.26 (2H, t, J=8.4 Hz), 3.50-3.60 (8H, m), 3.30 (2H, t, J=8.4 Hz), 1.42 (9H, s).

ESI (LC-MS positive mode) m/z 459 [(M+H)⁺].

Example 1-C-04

[4-(3-Hydroxyphenyl)-2-morpholin-4-yl-5,6-dihydropyrrolo[2,3-d]pyrimidin-7-yl]-phenylmethanone (C-04)

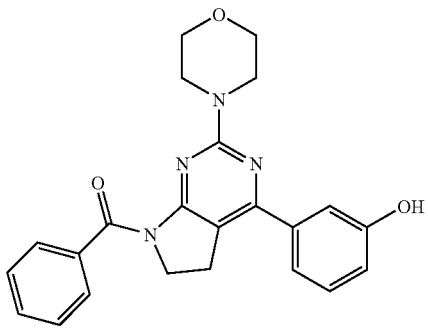

Compound C-03 (42 mg) obtained in Example 1-C-03 was dissolved in trifluoroacetic acid (1 ml). 30 minutes later, excessive amounts of solvent was concentrated under reduced pressure, and the residue was dissolved in methanol (1 ml), followed by addition of water (2 ml). The resulting suspension was neutralized with saturated sodium bicarbonate water, and the resulting precipitate was filtered off, and washed with water, and then with ether, to obtain a colorless powder (22 mg, 60%).

¹H-NMR (270 MHz, DMSO-d₆) δ (ppm): 7.49-7.44 (6H, m), 7.33 (1H, s), 7.27 (1H, d, J=5.1 Hz), 6.85 (1H, dd, J=7.1, 4.3 Hz), 4.10 (2H, t, J=7.9 Hz), 3.40-3.34 (8H, m), 3.21 (2H, t, J=8.0 Hz).

ESI (LC-MS positive mode) m/z 403 [(M+H)⁺].

Example 1-C-05

1-[4-(3-Hydroxyphenyl)-2-morpholin-4-yl-5,6-dihydropyrrolo[2,3-d]pyrimidin-7-yl]propan-1-one (C-05)

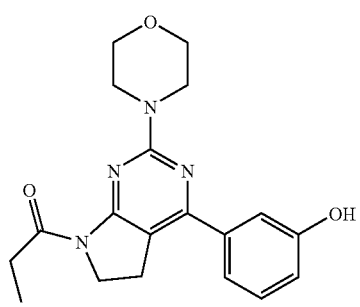

In the same manner as Examples 1-C-03 and 1-C-04, using propionyl chloride, the desired compound was obtained as a colorless powder.

¹H-NMR (270 MHz, DMSO-d₆) δ (ppm): 7.36 (1H, d, J=2.0 Hz), 7.32 (1H, d, J=7.4 Hz), 7.28 (1H, t, J=7.6 Hz), 6.86 (1H, d, J=7.4 Hz), 3.94 (2H, t, J=8.2 Hz), 3.70 (8H, brs), 3.14 (2H, t, J=8.2 Hz), 3.04 (2H, q, J=7.3 Hz), 1.11 (3H, t, J=7.3 Hz).

ESI (LC-MS positive mode) m/z 355 [(M+H)⁺].

Example 1-C-06

1-[4-(3-Hydroxyphenyl)-2-morpholin-4-yl-5,6-dihydropyrrolo[2,3-d]pyrimidin-7-yl]-2,2-dimethyl-propan-1-one (C-06)

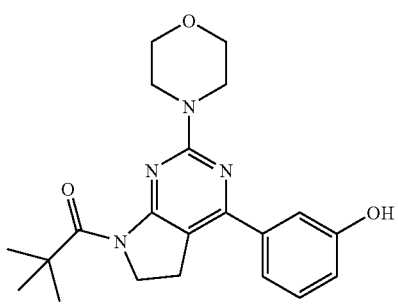

In the same manner as Examples 1-C-03 and 1-C-04, using pivaloyl chloride, the desired compound was obtained as a colorless powder.

¹H-NMR (270 MHz, CDCl₃) δ (ppm): 7.63 (1H, d J=7.7 Hz), 7.51 (1H, t, J=2.0 Hz), 7.41 (1H, d, J=7.7 Hz), 7.34 (1H, t, J=7.7 Hz), 7.30 (1H, d, J=0.7 Hz), 7.17 (1H, d, J=7.6 Hz), 7.10-7.13 (1H, m), 7.00 (1H, dd, J=8.2, 2.6 Hz), 4.25 (2H, t, J=8.2 Hz), 3.85 (3H, s), 3.56-3.64 (8H, m), 3.30 (2H, t, J=8.2 Hz), 1.42 (9H, s).

ESI (LC-MS positive mode) m/z 489 [(M+H)⁺].

Example 1-C-07

4-(3-t-Butoxy-phenyl)-2-morpholin-4-yl-7-(toluene-4-sulfonyl)-6,7-dihydro-5H-pyrrolo[2,3-d]pyrimidine (C-07)

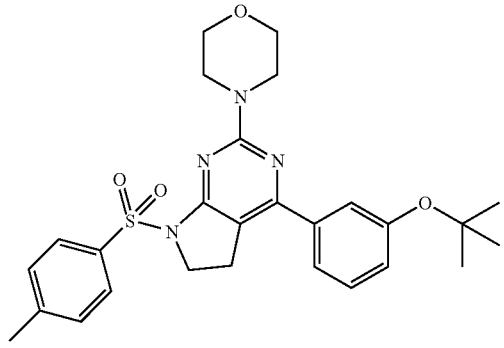

To a dimethylformamide solution (1 ml) of 4-(3-t-butoxyphenyl)-2-morpholin-4-yl-6,7-dihydro-5H-pyrrolo[2,3-d]pyrimidine (11 mg), sodium hydride (60% mineral oil dispersion, 1.5 mg, 1.2 equivalents) was added with ice cooling, followed by stirring at room temperature for 30 minutes. With ice cooling, tosyl chloride (6.6 mg, 1.1 equivalents) was added, followed by stirring at room temperature for 10 hours. To the reaction mixture, water (5 ml) was added, followed by extraction with ethyl acetate (5 ml×2). The organic layer was washed with aqueous ammonium chloride solution and brine, followed by drying over sodium sulfate. After filtering off the drying agent, the filtrate was concentrated under reduced pressure, and the resulting residue was purified by preparative TLC (n-hexane/ethyl acetate=2/1), to obtain the desired compound as a colorless powder (11 mg, 70%).

¹H-NMR (270 MHz, CDCl₃) δ (ppm): 7.95 (2H, d, J=8.4 Hz), 7.51 (1H, d, J=7.8 Hz), 7.39 (1H, t, J=2.0 Hz), 7.32 (1H, t, J=8.1 Hz), 7.28 (2H, d, J=8.4 Hz), 7.04 (1H, dd, J=8.1, 1.5 Hz), 4.08 (2H, t, J=8.2 Hz), 3.74-3.89 (8H, m), 3.19 (2H, t, J=8.2 Hz), 2.42 (3H, s), 1.35 (9H, s).

ESI (LC-MS positive mode) m/z 509 [(M+H)⁺].

Example 1-C-08

3-[2-Morpholin-4-yl-7-(toluene-4-sulfonyl)-6,7-dihydro-5H-pyrrolo[2,3-d]pyrimidin-4-yl]-phenol (C-08)

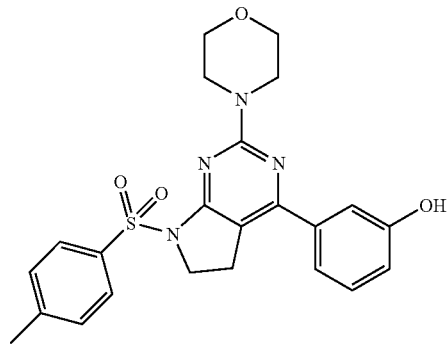

Compound C-07 (11 mg) obtained in Example 1-C-07 was dissolved in trifluoroacetic acid (1 ml). 30 minutes later, the solvent was removed under reduced pressure, and subsequently water (2 ml) was added to the residue. The resulting suspension was neutralized with aqueous saturated sodium bicarbonate, and the resulting precipitate was filtered off, and washed with water, and then with ether, to obtain a colorless powder (6 mg, 61%).

¹H-NMR (270 MHz, CDCl₃) δ (ppm): 7.95 (2H, d, J=8.2 Hz), 7.27-7.32 (6H, m), 6.86-6.91 (1H, m), 4.08 (2H, t, J=8.2), 3.85 (4H, m), 3.75-3.79 (4H, m), 3.18 (2H, t, J=8.2 Hz), 2.41 (3H, s).

ESI (LC-MS positive mode) m/z 453 [(M+H)⁺].

Example 1-C-09

4-(3-Hydroxy-phenyl)-2-morpholin-4-yl-5,6-dihydro-pyrrolo[2,3-d]pyrimidin-7-carbaldehyde (C-09)

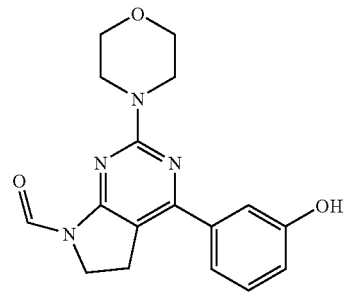

4-(3-t-Butoxy-phenyl)-2-morpholin-4-yl-5,6-dihydro-pyrrolo[2,3-d]pyrimidin-7-carbaldehyde (5 mg) obtained from Example 1-C-07 as a byproduct was treated with trifluoroacetic acid (1 ml), and the solvent was distilled off, which was subsequently diluted with water (1 ml), and extracted with dichloromethane (3 ml×3), followed by concentration under reduced pressure, to obtain a colorless powder (2 mg, 47%).

¹H-NMR (270 MHz, CDCl₃) δ (ppm): 9.35 (1H, s), 7.46-7.43 (2H, m), 7.34 (1H, t, J=7.5 Hz), 6.94 (1H, dq, J=7.8, 1.2 Hz), 4.04 (2H, t, J=8.1 Hz), 3.88-3.78 (8H, m), 3.29 (2H, t, J=8.1 Hz).

ESI (LC-MS positive mode) m/z 327 [(M+H)⁺].

Example 1-C-10

3-(7-Methanesulfonyl-2-morpholin-4-yl-6,7-dihydro-5H-pyrrolo[2,3-d]pyrimidin-4-yl)-phenol (C-10)

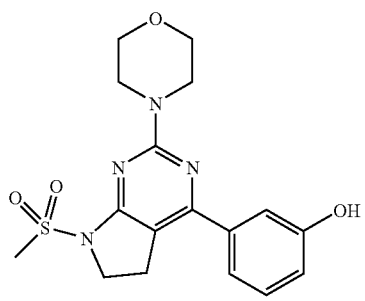

In the same manner as Examples 1-C-07 and 1-C-08, using methanesulfonyl chloride, the desired compound was obtained.

¹H-NMR (270 MHz, CDCl₃) δ (ppm): 7.33 (1H, m), 7.09 (1H, m), 7.00 (2H, m), 4.23 (2H, t, J=7.8 Hz), 3.82-3.96 (8H, m), 3.36 (3H, s), 3.17 (2H, t, J=7.8 Hz)

ESI (LC-MS positive mode) m/z 377 [(M+H)⁺].

Example 1-C-11

3-(7-Ethanesulfonyl-2-morpholin-4-yl-6,7-dihydro-5H-pyrrolo[2,3-d]pyrimidin-4-yl)-phenol (C-11)

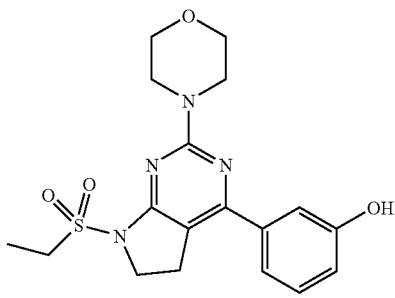

In the same manner as Examples 1-C-07 and 1-C-08, using ethanesulfonyl chloride, the desired compound was obtained according to the same method.

¹H-NMR (270 MHz, CDCl₃) δ (ppm): 7.33 (1H, m), 7.09 (1H, m), 6.99 (2H, m), 4.24 (2H, t, J=8.1 Hz), 3.82-3.95 (8H, m), 3.56 (2H, q, J=7.0 Hz), 3.18 (2H, t, J=8.1 Hz), 1.48 (3H, t, J=7.0 Hz)

ESI (LC-MS positive mode) m/z 391 [(M+H)⁺].

Example 1-C-12

3-[2-Morpholin-4-yl-7-(toluene-2-sulfonyl)-6,7-dihydro-5H-pyrrolo[2,3-d]pyrimidin-4-yl]-phenol (C-12)

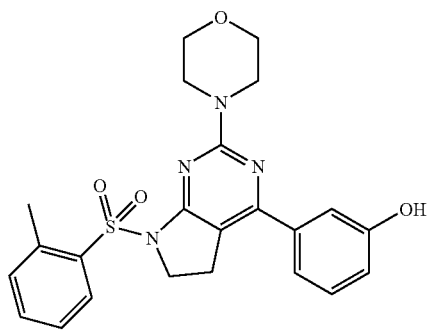

In the same manner as Examples 1-C-07 and 1-C-08, using o-tolylsulfonyl chloride, the desired compound was obtained.

¹H-NMR (270 MHz, DMSO-d₆) δ (ppm): 8.16 (2H, dd, J=7.8, 1.2 Hz), 7.92 (1H, d, J=8.4 Hz), 7.61 (1H, dt, J=7.6, 1.5 Hz), 7.44 (1H, t, J=8.2 Hz), 7.30-7.25 (2H, m), 6.86-6.84 (1H, m), 4.21 (2H, t, J=8.4 Hz), 3.66-3.56 (8H, m), 3.30 (2H, t, J=8.1 Hz), 2.55 (3H, s).

ESI (LC-MS positive mode) m/z 453 [(M+H)⁺].

Example 1-C-13

[4-(3-Hydroxy-phenyl)-2-morpholin-4-yl-5,6-dihydro-pyrrolo[2,3-d]pyrimidin-7-yl]-ethyl acetate ester (C-13)

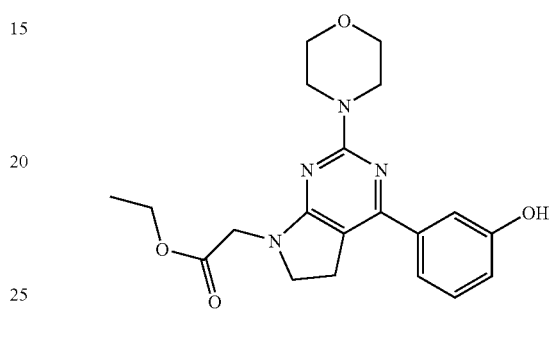

In the same manner as Examples 1-C-07 and 1-C-08, using ethyl bromoacetate, the desired compound was obtained.

¹H-NMR (270 MHz, CDCl₃) δ (ppm): 7.38-7.34 (2H, m), 7.26 (1H, t, J=4.0 Hz), 6.82 (1H, dq, J=8.0, 1.2 Hz), 4.23 (2H, q, J=7.1 Hz), 4.18 (2H, s), 3.81-3.77 (8H, m), 3.67 (2H, t, J=8.2 Hz), 3.19 (2H, t, J=8.1 Hz), 1.29 (3H, t, J=7.1 Hz).

ESI (LC-MS positive mode) m/z 385 [(M+H)⁺].

Example 1-C-14

3-(7-Benzenesulfonyl-2-morpholin-4-yl-6,7-dihydro-5H-pyrrolo[2,3-d]pyrimidin-4-yl)-phenol (C-14)

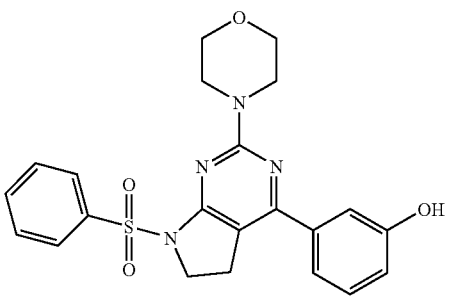

In the same manner as Examples 1-C-07 and 1-C-08, using phenylsulfonyl chloride, the desired compound was obtained.

¹H-NMR (DMSO-d₆) δ (ppm): 8.01-8.06 (2H, m), 7.70-7.75 (1H, m), 7.59-7.66 (2H, m), 7.22-7.29 (3H, m), 6.82-6.86 (1H, m), 4.09 (2H, t, J=8.05 Hz), 3.61-3.74 (8H, m), 3.20 (2H, t, J=8.14 Hz).

ESI (LC-MS positive mode) m/z 439 [(M+H)⁺].

Example 1-C-15

3-[2-Morpholin-4-yl-7-(thiophene-2-sulfonyl)-6,7-dihydro-5H-pyrrolo[2,3-d]pyrimidin-4-yl]-phenol (C-15)

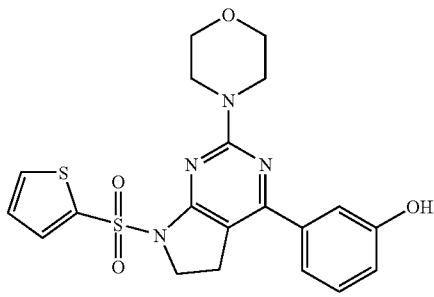

In the same manner as Examples 1-C-07 and 1-C-08, using thiophene-2-sulfonyl chloride, the desired compound was obtained.

$^1$H-NMR (DMSO-d$_6$) δ (ppm): 9.60 (1H, brs.), 8.05 (1H, dd, 5.03, J=1.37 Hz), 7.86 (1H, dd, 3.84, J=1.46 Hz), 7.21-7.32 (4H, m), 6.82-6.88 (1H, m), 3.99 (2H, t, J=8.05 Hz), 3.76-3.82 (4H, m), 3.67-3.71 (4H, m), 3.20 (2H, t, J=8.05 Hz).

ESI (LC-MS positive mode) m/z 445 [(M+H)$^+$].

Example 1-C-16

3-[7-(3-Methoxy-benzenesulfonyl)-2-morpholin-4-yl-6,7-dihydro-5H-pyrrolo[2,3-d]pyrimidin-4-yl]-phenol (C-16)

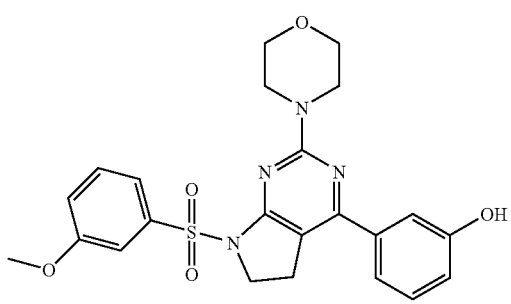

In the same manner as Examples 1-C-07 and 1-C-08, using 3-methoxy-benzenesulfonyl chloride, the desired compound was obtained.

$^1$H-NMR (DMSO-d$_6$) δ (ppm): 9.60 (1H, brs.), 7.44-7.70 (3H, m), 7.18-7.33 (4H, m), 6.70-6.91 (1H, m), 4.07 (2H, t, J=8.14 Hz), 3.82 (3H, s), 3.59-3.77 (8H, m), 3.19 (2H, t, J=8.05 Hz).

ESI (LC-MS positive mode) m/z 469 [(M+H)$^+$].

Example 1-C-17

4-(3-Hydroxy-phenyl)-2-morpholin-4-yl-5,6-dihydro-pyrrolo[2,3-d]pyrimidine-7-carboxylic acid phenylamide (C-17)

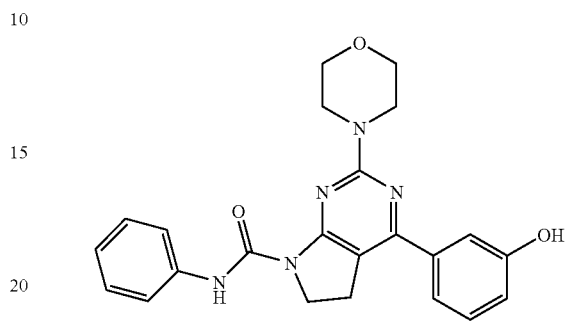

In the same manner as Examples 1-C-07 and 1-C-08, using phenylisocyanate, the desired compound was obtained.

$^1$H-NMR (DMSO-d$_6$) δ (ppm): 11.02 (1H, s), 9.63 (1H, s), 7.53 (2H, d, J=7.6 Hz), 7.40-7.45 (1H, m), 7.36 (3H, t, J=8.0 Hz), 7.30 (1H, t, J=7.8 Hz), 7.07 (1H, t, J=7.4 Hz), 6.88 (1H, dd, J=7.9, 1.5 Hz), 4.04 (2H, t, 8.4 Hz), 3.77 (8H, d, J=3.0 Hz), 3.21 (H, t, J=8.4 Hz).

ESI (LC-MS positive mode) m/z 418 [(M+H)$^+$].

Example 1-C-18

4-(3-Hydroxy-phenyl)-2-morpholin-4-yl-5,6-dihydro-pyrrolo[2,3-d]pyrimidine-7-carboxylic acid (2,4-difluoro-phenyl)-amide (C-18)

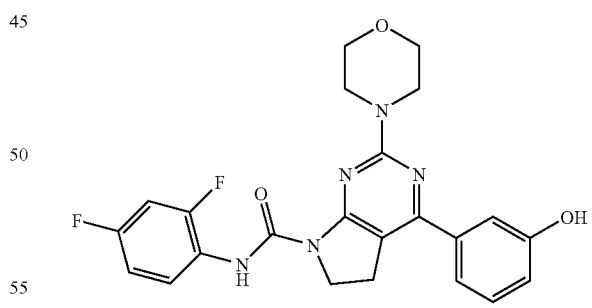

In the same manner as Examples 1-C-07 and 1-C-08, using 2,4-difluorophenylisocyanate, the desired compound was obtained.

$^1$H-NMR (DMSO-d$_6$) δ (ppm): 10.91 (1H, s), 9.63 (1H, brs.), 8.18-8.30 (1H, m), 7.32-7.45 (3H, m), 7.29 (1H, t, J=7.8 Hz), 7.10 (1H, t, J=8.8 Hz), 6.88 (1H, dd, J=7.9, 1.4 Hz), 4.04 (2H, t, J=8.4 Hz), 3.73 (8H, dd, J=20.9, 5.0 Hz), 3.19 (2H, t, J=8.4 Hz).

ESI (LC-MS positive mode) m/z 454 [(M+H)$^+$].

Example 1-C-19

4-(3-Hydroxy-phenyl)-2-morpholin-4-yl-5,6-dihydro-pyrrolo[2,3-d]pyrimidine-7-carboxylic acid p-tolylamide (C-19)

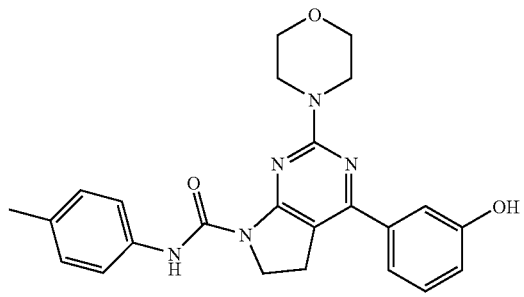

In the same manner as Examples 1-C-07 and 1-C-08, using 4-methylphenylisocyanate, the desired compound was obtained.

¹H-NMR (DMSO-d₆) δ (ppm): 10.94 (1H, s), 9.64 (1H, brs.), 7.38-7.46 (3H, m), 7.35-7.39 (1H, m), 7.30 (1H, t, J=7.9 Hz), 7.16 (2H, d, J=8.2 Hz), 6.88 (1H, dd, J=7.9, 1.5 Hz), 4.03 (2H, t, J=8.3 Hz), 3.76 (8H, brs.), 3.20 (2H, t, J=8.4 Hz), 2.27 (3H, s).

ESI (LC-MS positive mode) m/z 432 [(M+H)⁺].

Example 1-C-20

4-(3-Hydroxy-phenyl)-2-morpholin-4-yl-5,6-dihydro-pyrrolo[2,3-d]pyrimidine-7-carboxylic acid (4-trifluoromethyl-phenyl)-amide (C-20)

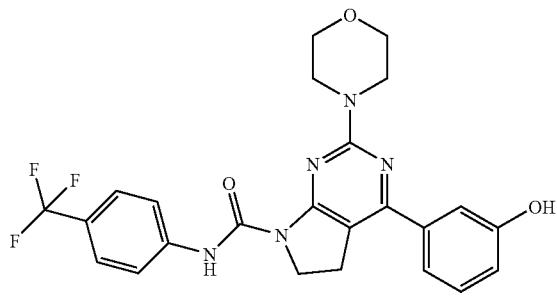

In the same manner as Examples 1-C-07 and 1-C-08, using 4-trifluoromethylphenylisocyanate, the desired compound was obtained.

¹H-NMR (DMSO-d₆) δ (ppm): 11.30 (1H, s), 9.64 (1H, brs.), 7.72 (4H, s), 7.42 (1H, s), 7.36 (1H, d, J=7.9 Hz), 7.29 (1H, t, J=7.8 Hz), 6.88 (1H, d, J=7.9, 1.4 Hz), 4.04 (2H, t, J=8.4 Hz), 3.83 (8H, brs.), 3.20 (2H, t, J=8.4 Hz).

ESI (LC-MS positive mode) m/z 486 [(M+H)⁺].

Example 1-C-21

3-[7-(4-Fluoro-benzenesulfonyl)-2-morpholin-4-yl-6,7-dihydro-5H-pyrrolo[2,3-d]pyrimidin-4-yl]-phenol (C-21)

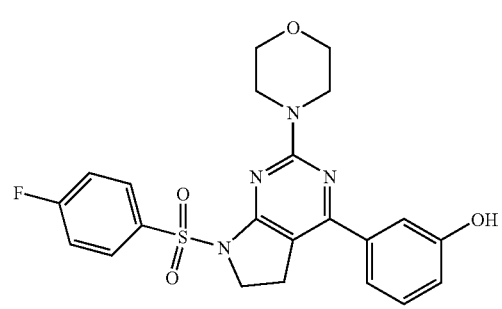

In the same manner as Examples 1-C-07 and 1-C-08, using 4-fluoro-benzenesulfonyl chloride, the desired compound was obtained.

¹H-NMR (DMSO-d₆) δ (ppm): 9.60 (1H, brs.), 8.06-8.15 (2H, m), 7.44-7.53 (2H, m), 7.21-7.30 (3H, m), 6.81-6.88 (1H, m), 4.09 (2H, t, J=8.05 Hz), 3.67 (8H, dd, J=16.83, 4.94 Hz), 3.20 (2H, t, J=8.05 Hz).

ESI (LC-MS positive mode) m/z 457 [(M+H)⁺].

Example 1-C-22

3-[7-(2,4-Difluoro-benzenesulfonyl)-2-morpholin-4-yl-6,7-dihydro-5H-pyrrolo[2,3-d]pyrimidin-4-yl]-phenol (C-22)

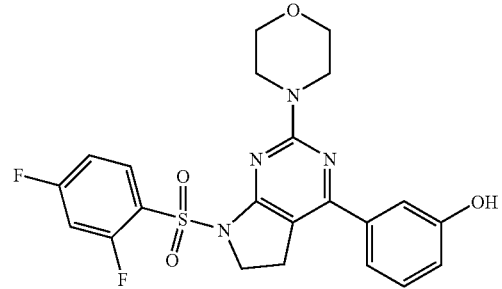

In the same manner as Examples 1-C-07 and 1-C-08, using 2,4-difluoro-benzenesulfonyl chloride, the desired compound was obtained.

¹H-NMR (DMSO-d₆) δ (ppm): 9.60 (1H, s), 8.15-8.25 (1H, m), 7.53-7.63 (1H, m), 7.35-7.43 (1H, m), 7.21-7.33 (3H, m), 6.81-6.89 (1H, m), 4.20 (2H, t, J=8.14 Hz), 3.56 (8H, s), 3.27 (2H, t, J=8.14 Hz).

ESI (LC-MS positive mode) m/z 475 [(M+H)⁺].

Example 1-C-23

4-[4-(3-Hydroxy-phenyl)-2-morpholin-4-yl-5,6-dihydro-pyrrolo[2,3-d]pyrimidine-7-sulfonyl]-benzonitrile (C-23)

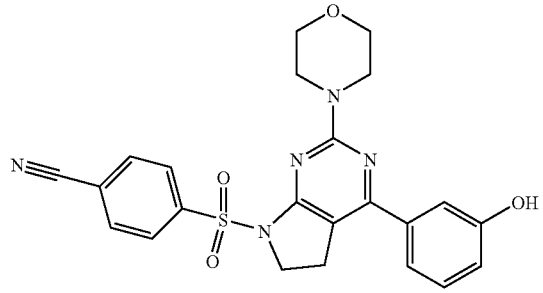

In the same manner as Examples 1-C-07 and 1-C-08, using 4-cyano-benzenesulfonyl chloride, the desired compound was obtained.

$^1$H-NMR (DMSO-d$_6$) δ (ppm): 9.61 (1H, s), 8.10-8.23 (4H, m), 7.23-7.30 (3H, m), 6.82-6.88 (1H, m), 4.14 (2H, t, J=8.14 Hz), 3.66 (8H, d, J=6.77 Hz), 3.22 (2H, t, J=8.14 Hz).

ESI (LC-MS positive mode) m/z 464 [(M+H)$^+$].

Example 1-C-24

3-[2-Morpholin-4-yl-7-(toluene-3-sulfonyl)-6,7-dihydro-5H-pyrrolo[2,3-d]pyrimidin-4-yl]-phenol (C-24)

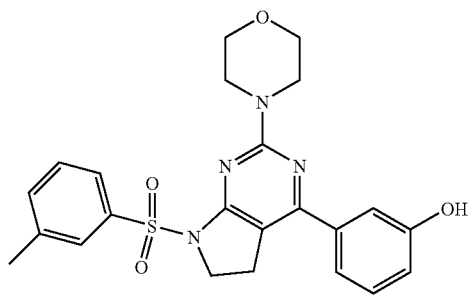

In the same manner as Examples 1-C-07 and 1-C-08, using 3-methyl-benzenesulfonyl chloride, the desired compound was obtained.

$^1$H-NMR (DMSO-d$_6$) δ (ppm): 9.60 (1H, brs.), 7.87 (1H, s), 7.79-7.85 (1H, m), 7.47-7.57 (2H, m), 7.21-7.30 (3H, m), 6.81-6.87 (1H, m), 4.08 (2H, t, J=8.05 Hz), 3.68 (8H, dd, J=16.92, 4.85 Hz), 3.19 (2H, t, J=8.14 Hz), 2.39 (3H, s).

ESI (LC-MS positive mode) m/z 453 [(M+H)$^+$].

Example 1-C-25

3-[7-(4-tert-Butyl-benzenesulfonyl)-2-morpholin-4-yl-6,7-dihydro-5H-pyrrolo[2,3-d]pyrimidin-4-yl]-phenol (C-25)

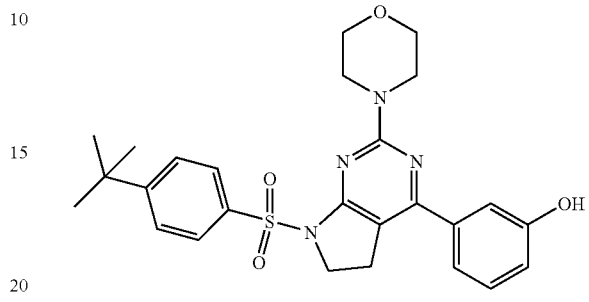

In the same manner as Examples 1-C-07 and 1-C-08, using 4-tert-butyl-benzenesulfonyl chloride, the desired compound was obtained.

$^1$H-NMR (DMSO-d$_6$) δ (ppm): 9.59 (1H, s), 7.94 (2H, d, J=8.60 Hz), 7.64 (2H, d, J=8.60 Hz), 7.20-7.30 (3H, m), 6.79-6.86 (1H, m), 4.06 (2H, t, J=8.14 Hz), 3.58-3.75 (8H, m), 3.19 (2H, t, J=8.14 Hz), 1.28 (9H, s).

ESI (LC-MS positive mode) m/z 495 [(M+H)$^+$].

Example 1-C-26

3-[2-Morpholin-4-yl-7-(4-trifluoromethyl-benzenesulfonyl)-6,7-dihydro-5H-pyrrolo[2,3-d]pyrimidin-4-yl]-phenol (C-26)

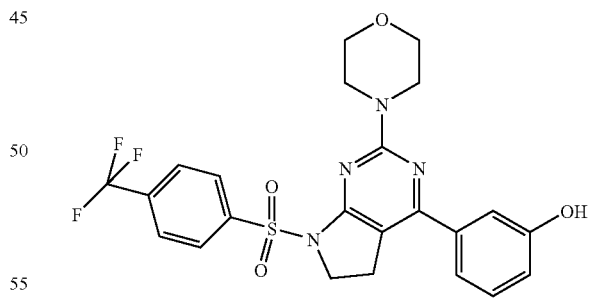

In the same manner as Examples 1-C-07 and 1-C-08, using 4-trifluoromethyl-benzenesulfonyl chloride, the desired compound was obtained.

$^1$H-NMR (DMSO-d$_6$) δ (ppm): 9.62 (1H, brs.), 8.25 (2H, d, J=8.23 Hz), 8.04 (2H, d, J=8.42 Hz), 7.21-7.32 (3H, m), 6.80-6.90 (1H, m), 4.14 (2H, t, J=8.14 Hz), 3.66 (8H, dd, J=17.11, 4.85 Hz), 3.22 (2H, t, J=8.05 Hz).

ESI (LC-MS positive mode) m/z 507 [(M+H)$^+$].

Example 1-C-27

3-[2-Morpholin-4-yl-7-(3-trifluoromethyl-benzene-sulfonyl)-6,7-dihydro-5H-pyrrolo[2,3-d]pyrimidin-4-yl]-phenol (C-27)

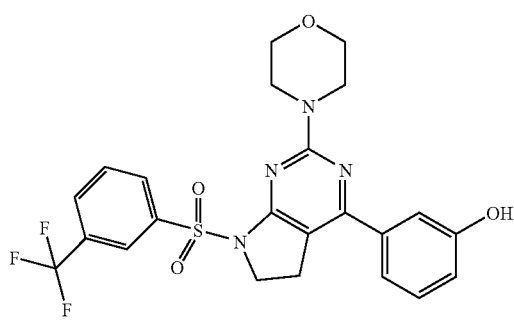

In the same manner as Examples 1-C-07 and 1-C-08, using 3-trifluoromethyl-benzenesulfonyl chloride, the desired compound was obtained.

$^1$H-NMR (DMSO-$d_6$) δ (ppm): 9.59 (1H, brs.), 8.31-8.37 (2H, m), 8.14 (1H, d, J=7.68 Hz), 7.90 (1H, t, J=7.78 Hz), 7.22-7.32 (3H, m), 6.81-6.88 (1H, m), 4.15 (2H, t, J=8.05 Hz), 3.65 (8H, d, J=1.83 Hz), 3.22 (2H, t, J=8.05 Hz).

ESI (LC-MS positive mode) m/z 507 [(M+H)$^+$].

Example 1-C-28

3-[2-Morpholin-4-yl-7-(4-trifluoromethoxy-benzene-sulfonyl)-6,7-dihydro-5H-pyrrolo[2,3-d]pyrimidin-4-yl]-phenol (C-28)

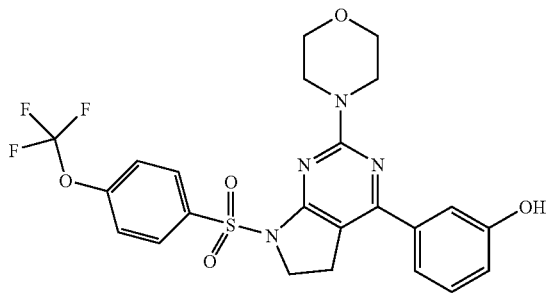

In the same manner as Examples 1-C-07 and 1-C-08, using 4-trifluoromethoxybenzenesulfonyl chloride, the desired compound was obtained.

$^1$H-NMR (DMSO-$d_6$) δ (ppm): 9.60 (1H, brs.), 8.14-8.22 (2H, m), 7.64 (2H, d, J=7.87 Hz), 7.21-7.32 (3H, m), 6.81-6.89 (1H, m), 4.12 (2H, t, J=8.05 Hz), 3.58-3.73 (8H, m), 3.22 (2H, t, J=8.14 Hz).

ESI (LC-MS positive mode) m/z 523 [(M+H)$^+$].

Example 1-C-29

[4-(3-Hydroxy-phenyl)-2-morpholin-4-yl-5,6-dihydro-pyrrolo[2,3-d]pyrimidin-7-yl]-p-tolyl-methanone (C-29)

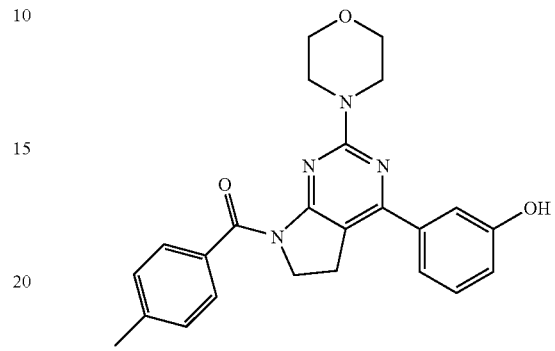

In the same manner as Examples 1-C-07 and 1-C-08, using 4-methyl-benzoyl chloride, the desired compound was obtained.

$^1$H-NMR (DMSO-$d_6$) δ (ppm): 9.62 (1H, s), 7.13-7.48 (7H, m), 6.78-6.93 (1H, m), 4.08 (2H, t, J=7.9 Hz), 2.97-3.53 (10H, m), 2.34 (3H, s).

ESI (LC-MS positive mode) m/z 417 [(M+H)$^+$].

Example 1-C-30

[4-(3-Hydroxy-phenyl)-2-morpholin-4-yl-5,6-dihydro-pyrrolo[2,3-d]pyrimidin-7-yl]-m-tolyl-methanone (C-30)

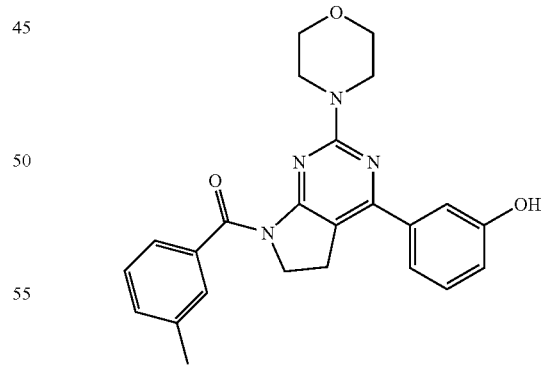

In the same manner as Examples 1-C-07 and 1-C-08, using 3-methylbenzoyl chloride, the desired compound was obtained.

$^1$H-NMR (DMSO-$d_6$) δ (ppm): 9.63 (1H, brs.), 7.15-7.42 (7H, m), 6.72-6.97 (1H, m), 4.09 (2H, t, J=8.0 Hz), 2.98-3.58 (10H, m), 2.32 (3H, s).

ESI (LC-MS positive mode) m/z 417 [(M+H)$^+$].

Example 1-C-31

[4-(3-Hydroxy-phenyl)-2-morpholin-4-yl-5,6-dihydro-pyrrolo[2,3-d]pyrimidin-7-yl]-(4-trifluoromethyl-phenyl)-methanone (C-31)

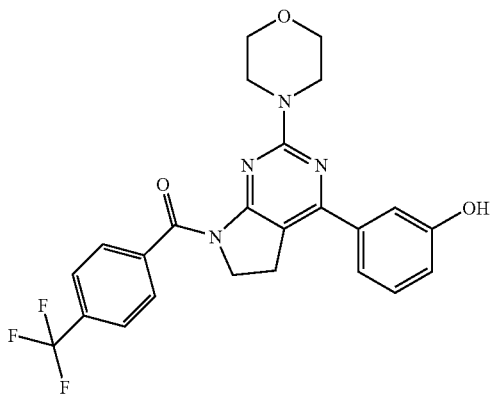

In the same manner as Examples 1-C-07 and 1-C-08, using 4-trifluoromethylbenzoyl chloride, the desired compound was obtained according to the same method.

$^1$H-NMR (DMSO-$d_6$) δ (ppm): 9.85 (1H, brs.), 7.82 (2H, d, J=8.2 Hz), 7.70 (2H, d, J=8.2 Hz), 7.22-7.39 (3H, m), 6.78-6.93 (1H, m), 4.12 (2H, t, J=8.0 Hz), 3.38 (8H, brs.), 3.22 (2H, t, J=8.0 Hz).

ESI (LC-MS positive mode) m/z 471 [(M+H)$^+$].

Example 1-C-32

2-(4-Fluoro-phenyl)-1-[4-(3-hydroxy-phenyl)-2-morpholin-4-yl-5,6-dihydro-pyrrolo[2,3-d]pyrimidin-7-yl]-ethanone (C-32)

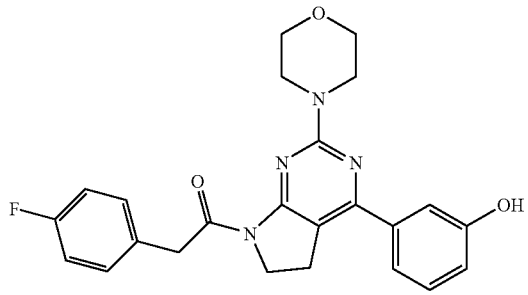

In the same manner as Examples 1-C-07 and 1-C-08, using (4-fluorophenyl)acetyl chloride, the desired compound was obtained.

$^1$H-NMR (DMSO-$d_6$) δ (ppm): 9.80 (1H, brs.), 7.21-7.46 (5H, m), 7.13 (2H, t, J=8.9 Hz), 6.82-6.92 (1H, m), 4.47 (2H, s), 3.96 (2H, t, J=8.2 Hz), 3.68 (8H, d, J=6.2 Hz), 3.14 (2H, t, J=8.1 Hz).

ESI (LC-MS positive mode) m/z 435 [(M+H)$^+$].

Example 1-C-33

1-[4-(3-Hydroxy-phenyl)-2-morpholin-4-yl-5,6-dihydro-pyrrolo[2,3-d]pyrimidin-7-yl]-3-phenyl-propan-1-one (C-33)

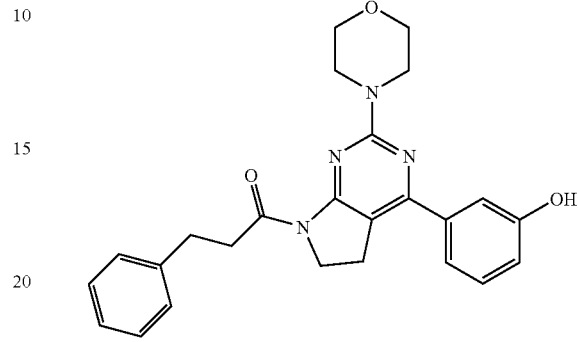

In the same manner as Examples 1-C-07 and 1-C-08, using 3-phenylpropionyl chloride, the desired compound was obtained.

$^1$H-NMR (DMSO-$d_6$) δ (ppm): 7.03-7.47 (8H, m), 6.73-6.92 (1H, m), 3.91 (2H, t, J=8.2 Hz), 3.59 (8H, brs.), 3.40 (2H, t, J=7.4 Hz), 3.09 (2H, t, J=8.2 Hz), 2.92 (2H, t, J=8.3 Hz).

ESI (LC-MS positive mode) m/z 431 [(M+H)$^+$].

Example 1-C-34

[4-(3-Hydroxy-phenyl)-2-morpholin-4-yl-5,6-dihydro-pyrrolo[2,3-d]pyrimidin-7-yl]-(3-trifluoromethyl-phenyl)-methanone (C-34)

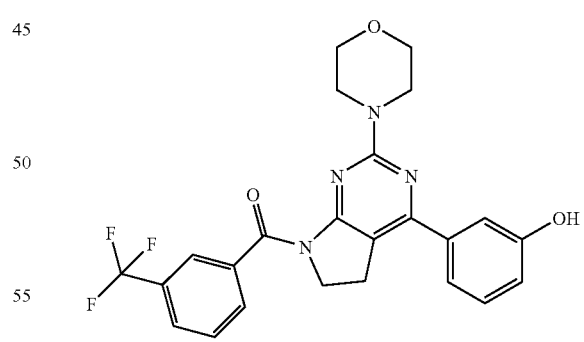

In the same manner as Examples 1-C-07 and 1-C-08, using 3-trifluoromethylbenzoyl chloride, the desired compound was obtained.

$^1$H-NMR (DMSO-$d_6$) δ (ppm): 9.85 (1H, brs.), 7.74-7.94 (3H, m), 7.69 (1H, t, J=7.7 Hz), 7.35 (1H, s), 7.24-7.31 (2H, m), 6.83-6.91 (1H, m), 4.12 (2H, t, J=8.1 Hz), 3.38 (8H, brs.), 3.22 (2H, t, J=8.1 Hz).

ESI (LC-MS positive mode) m/z 471 [(M+H)$^+$].

Example 1-C-35

1-[4-(3-Hydroxy-phenyl)-2-morpholin-4-yl-5,6-dihydro-pyrrolo[2,3-d]pyrimidin-7-yl]-2-phenyl-ethanone (C-35)

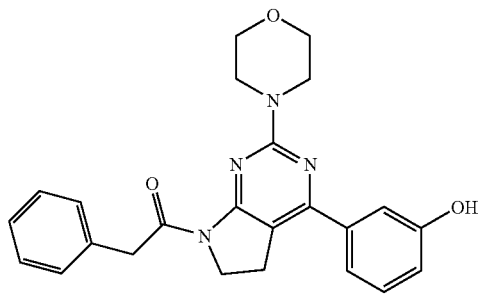

In the same manner as Examples 1-C-07 and 1-C-08, using phenylacetyl chloride, the desired compound was obtained.

$^1$H-NMR (DMSO-d$_6$) δ (ppm): 9.62 (1H, s), 7.19-7.42 (8H, m), 6.84-6.92 (2H, m), 4.49 (2H, s), 3.98 (2H, t, J=8.3 Hz), 3.67 (8H, dd, 20.5, J=5.0 Hz), 3.15 (2H, t, J=8.2 Hz).

ESI (LC-MS positive mode) m/z 417 [(M+H)$^+$].

Example 1-C-36

N-{4-[4-(3-Hydroxy-phenyl)-2-morpholin-4-yl-5,6-dihydro-pyrrolo[2,3-d]pyrimidine-7-carbonyl]-phenyl}-acetamide (C-36)

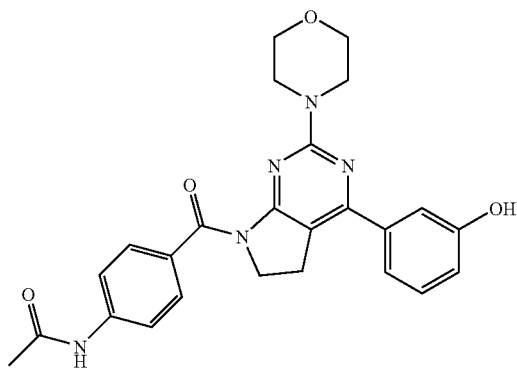

In the same manner as Examples 1-C-07 and 1-C-08, using 4-acetylaminobenzoyl chloride, the desired compound was obtained.

$^1$H-NMR (DMSO-d$_6$) δ (ppm): 10.14 (1H, s), 7.60 (2H, d, J=8.6 Hz), 7.46 (2H, d, J=8.7 Hz), 7.33 (1H, s), 7.26 (2H, d, J=4.9 Hz), 6.79-6.94 (1H, m), 4.05 (2H, t, J=8.0 Hz), 3.41 (8H, brs.), 3.18 (2H, t, J=8.0 Hz), 2.08 (3H, s).

ESI (LC-MS positive mode) m/z 460 [(M+H)$^+$].

Example 1-C-37

[4-(3-Hydroxy-phenyl)-2-morpholin-4-yl-5,6-dihydro-pyrrolo[2,3-d]pyrimidin-7-yl]-pyridin-2-yl-methanone (C-37)

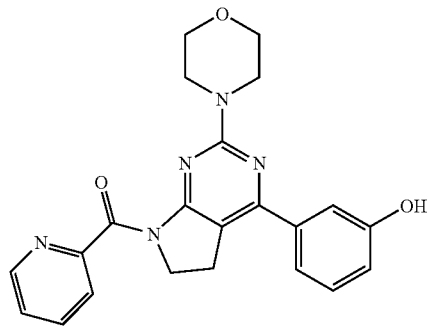

In the same manner as Examples 1-C-07 and 1-C-08, using pyridine-2-carbonyl chloride, the desired compound was obtained.

$^1$H-NMR (DMSO-d$_6$) δ (ppm): 9.64 (1H, s), 8.57 (1H, d, J=5.3 Hz), 7.93 (1H, t, J=7.7 Hz), 7.55 (1H, d, J=7.8 Hz), 7.47 (1H, dd, J=8.2, 5.4 Hz), 7.35 (1H, s), 7.24-7.33 (2H, m), 6.82-6.91 (1H, m), 4.13 (3H, t, J=8.0 Hz), 3.40 (8H, brs.), 3.25 (2H, t, J=8.1 Hz).

ESI (LC-MS positive mode) m/z 404 [(M+H)$^+$].

Example 1-C-38 (2,4-Difluoro-phenyl)-[4-(3-hydroxy-phenyl)-2-morpholin-4-yl-5,6-dihydro-pyrrolo[2,3-d]pyrimidin-7-yl]-methanone (C-38)

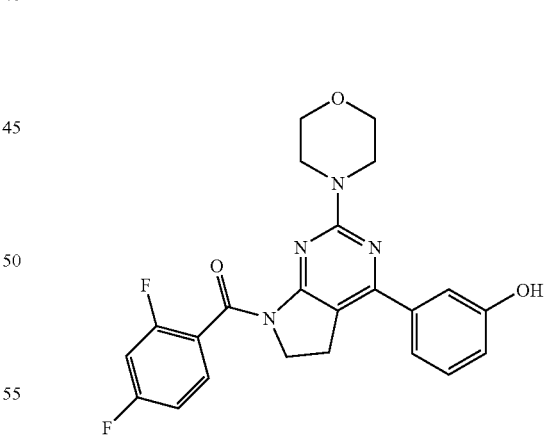

In the same manner as Examples 1-C-07 and 1-C-08, using 2,4-difluorobenzoyl chloride, the desired compound was obtained.

$^1$H-NMR (DMSO-d$_6$) δ (ppm): 9.67 (1H, brs.), 7.50-7.65 (1H, m), 7.24-7.44 (4H, m), 7.20 (1H, t, J=8.5 Hz), 6.83-6.92 (1H, m), 4.13 (2H, t, J=8.1 Hz), 3.46 (8H, brs.), 3.20-3.27 (2H, m).

ESI (LC-MS positive mode) m/z 439 [(M+H)$^+$].

Example 1-C-39

[4-(3-Hydroxy-phenyl)-2-morpholin-4-yl-5,6-dihydro-pyrrolo[2,3-d]pyrimidin-7-yl]-pyridin-4-yl-methanone (C-39)

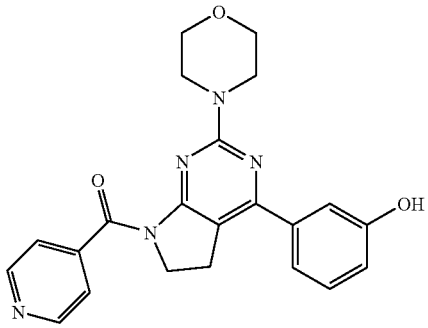

In the same manner as Examples 1-C-07 and 1-C-08, using pyridine-4-carbonyl chloride, the desired compound was obtained.

$^1$H-NMR (DMSO-d$_6$) δ (ppm): 9.64 (1H, s), 8.67 (2H, d, J=5.9 Hz), 7.45 (2H, d, J=5.9 Hz), 7.35 (1H, s), 7.25-7.32 (2H, m), 6.88 (1H, d, J=7.0 Hz), 4.12 (2H, t, J=8.1 Hz), 3.41 (8H, brs.), 3.23 (2H, t, J=8.1 Hz), ESI (LC-MS positive mode) m/z 404 [(M+H)$^+$].

Example 1-C-40

[4-(3-Hydroxy-phenyl)-2-morpholin-4-yl-5,6-dihydro-pyrrolo[2,3-d]pyrimidin-7-yl]-o-tolyl-methanone (C-40)

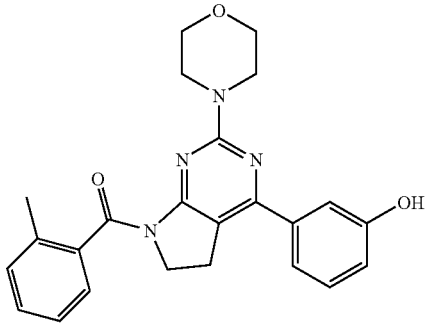

In the same manner as Examples 1-C-07 and 1-C-08, using 2-methylbenzoyl chloride, the desired compound was obtained.

$^1$H-NMR (DMSO-d$_6$) δ (ppm): 9.70 (1H, brs.), 7.12-7.41 (7H, m), 6.76-6.92 (1H, m), 4.14 (2H, t, J=8.1 Hz), 3.37 (8H, d, J=3.7 Hz), 3.23 (2H, t, J=8.4 Hz), 2.17 (3H, s).

ESI (LC-MS positive mode) m/z 417 [(M+H)$^+$].

Example 1-C-41 (4-tert-Butyl-phenyl)-[4-(3-hydroxy-phenyl)-2-morpholin-4-yl-5,6-dihydro-pyrrolo[2,3-d]pyrimidin-7-yl]-methanone (C-41)

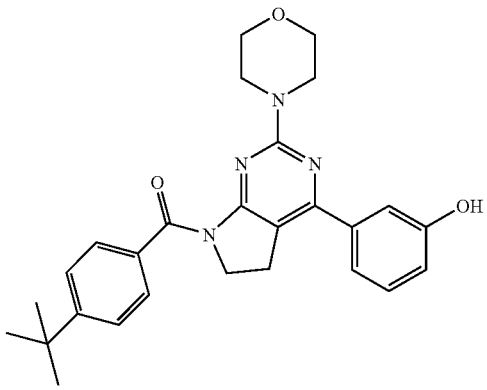

In the same manner as Examples 1-C-07 and 1-C-08, using 4-tert-butylbenzoyl chloride, the desired compound was obtained.

$^1$H-NMR (DMSO-d$_6$) δ (ppm): 9.60 (1H, s), 7.44 (4H, s), 7.23-7.37 (3H, m), 6.79-6.91 (1H, m), 4.09 (2H, t, J=8.1 Hz), 3.21 (2H, t, J=8.0 Hz), 3.09-3.50 (8H, m), 1.30 (9H, s).

ESI (LC-MS positive mode) m/z 459 [(M+H)$^+$].

Example 1-C-42

4-[4-(3-Hydroxy-phenyl)-2-morpholin-4-yl-5,6-dihydro-pyrrolo[2,3-d]pyrimidine-7-carbonyl]-benzonitrile trifluoroacetic acid salt (C-42)

In the same manner as Examples 1-C-07 and 1-C-08, using 4-cyanobenzoyl chloride, the desired compound was obtained.

$^1$H-NMR (DMSO-d$_6$) δ (ppm): 9.62 (1H, brs.), 7.95 (2H, d, J=8.5 Hz), 7.68 (2H, d, J=8.5 Hz), 7.19-7.41 (3H, m), 6.87 (1H, d, J=7.0 Hz), 4.13 (2H, t, J=8.1 Hz), 3.32-3.69 (8H, m), 3.24 (2H, t, J=8.0 Hz).

ESI (LC-MS positive mode) m/z 428 [(M+H)$^+$].

Example 1-C-43

[4-(3-Hydroxy-phenyl)-2-morpholin-4-yl-5,6-dihydro-pyrrolo[2,3-d]pyrimidin-7-yl]-naphthalen-2-yl-methanone trifluoroacetic acid salt (C-43)

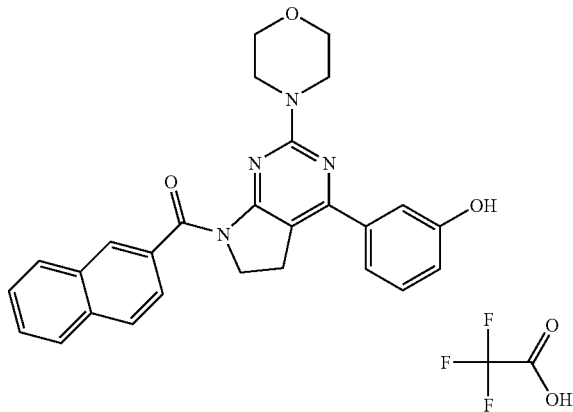

In the same manner as Examples 1-C-07 and 1-C-08, using naphthalene-2-carbonyl chloride, the desired compound was obtained.

$^1$H-NMR (DMSO-$d_6$) δ (ppm): 9.61 (1H, s), 8.10 (1H, s), 7.92-8.04 (3H, m), 7.53-7.65 (3H, m), 7.24-7.38 (3H, m), 6.79-6.94 (1H, m), 4.17 (2H, t, J=8.1 Hz), 3.26 (2H, t, J=8.1 Hz), 3.04 (8H, brs.).

ESI (LC-MS positive mode) m/z 453 [(M+H)$^+$].

Example 1-C-44

[4-(3-Hydroxy-phenyl)-2-morpholin-4-yl-5,6-dihydro-pyrrolo[2,3-d]pyrimidin-7-yl]-naphthalen-1-yl-methanone trifluoroacetic acid salt (C-44)

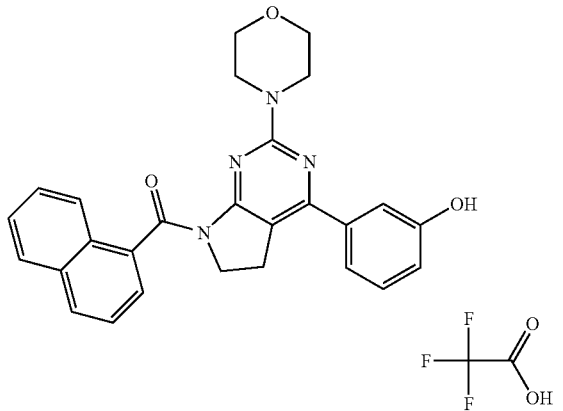

In the same manner as Examples 1-C-07 and 1-C-08, using naphthalene-1-carbonyl chloride, the desired compound was obtained.

$^1$H-NMR (DMSO-$d_6$) δ (ppm): 9.61 (1H, brs.), 7.99 (2H, dd, J=7.8, 4.3 Hz), 7.75 (1H, d, J=8.2 Hz), 7.44-7.60 (4H, m), 7.22-7.36 (3H, m), 6.81-6.92 (1H, m), 4.30 (2H, t, J=8.1 Hz), 3.54 (4H, brs.), 3.28 (2H, t, J=8.1 Hz), 3.11 (4H, brs.).

ESI (LC-MS positive mode) m/z 453 [(M+H)$^+$].

Example 1-C-45

1-[4-(3-Hydroxy-phenyl)-2-morpholin-4-yl-5,6-dihydro-pyrrolo[2,3-d]pyrimidin-7-yl]-3,3-dimethyl-butan-1-one (C-45)

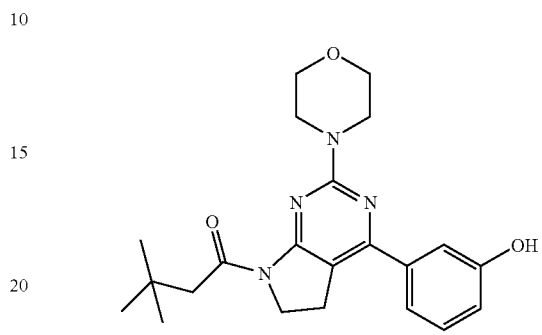

In the same manner as Examples 1-C-07 and 1-C-08, using 3,3-dimethylbutyryl chloride, the desired compound was obtained.

$^1$H-NMR (DMSO-$d_6$) δ (ppm): 9.61 (1H, s), 7.23-7.40 (3H, m), 6.87 (1H, d, J=7.7 Hz), 3.96 (2H, t, J=8.3 Hz), 3.72 (8H, dd, J=16.3, 4.9 Hz), 3.18 (2H, s), 3.12 (2H, t, J=8.3 Hz), 1.02 (9H, s).

ESI (LC-MS positive mode) m/z 397 [(M+H)$^+$].

Example 1-C-46

1-[4-(3-Hydroxy-phenyl)-2-morpholin-4-yl-5,6-dihydro-pyrrolo[2,3-d]pyrimidin-7-yl]-pentan-1-one (C-46)

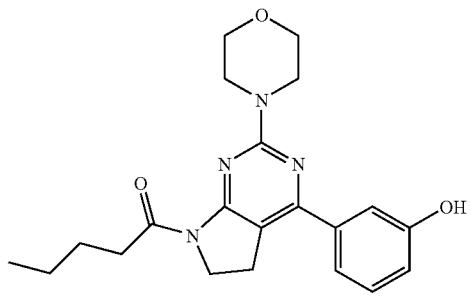

In the same manner as Examples 1-C-07 and 1-C-08, using pentanoyl chloride, the desired compound was obtained.

$^1$H-NMR (DMSO-$d_6$) δ (ppm): 9.62 (1H, brs.), 7.23-7.41 (3H, m), 6.87 (1H, d, J=7.7 Hz), 3.93 (2H, t, J=8.3 Hz), 3.70 (8H, d, J=7.6 Hz), 3.13 (2H, t, J=8.3 Hz), 3.05 (2H, t, J=15.1 Hz), 1.54-1.66 (2H, m), 1.26-1.42 (2H, m), 0.90 (3H, t, J=7.4 Hz).

ESI (LC-MS positive mode) m/z 383 [(M+H)$^+$].

Example 1-C-47

4-[4-(3-Hydroxy-phenyl)-2-morpholin-4-yl-5,6-di-hydro-pyrrolo[2,3-d]pyrimidin-7-yl]-4-oxo-butyric acid methyl ester (C-47)

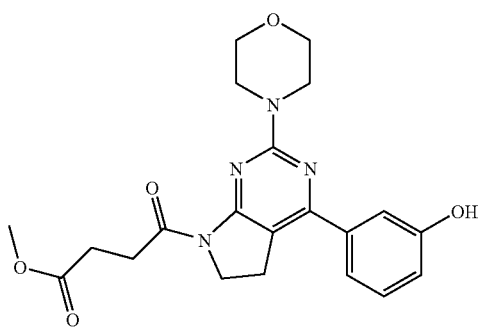

In the same manner as Examples 1-C-07 and 1-C-08, using 3-chlorocarbonyl-propionic acid methyl ester, the desired compound was obtained.

$^1$H-NMR (DMSO-d$_6$) δ (ppm): 9.62 (1H, brs.), 7.22-7.41 (3H, m), 6.87 (1H, d, J=7.8 Hz), 3.94 (2H, t, J=8.2 Hz), 3.71 (8H, dd, J=14.7, 4.7 Hz), 3.60 (3H, s), 3.28-3.32 (2H, m), 3.16 (2H, t, J=8.3 Hz), 2.64 (2H, t, J=6.6 Hz).

ESI (LC-MS positive mode) m/z 413 [(M+H)$^+$].

Example 1-C-48

5-[4-(3-Hydroxy-phenyl)-2-morpholin-4-yl-5,6-di-hydro-pyrrolo[2,3-d]pyrimidin-7-yl]-5-oxo-pen-tanoic acid methyl ester (C-48)

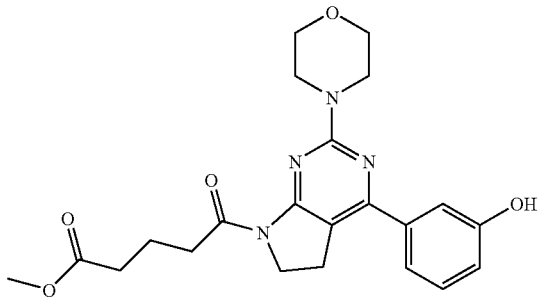

In the same manner as Examples 1-C-07 and 1-C-08, using 4-chlorocarbonyl-butyric acid methyl ester, the desired compound was obtained.

$^1$H-NMR (DMSO-d$_6$) δ (ppm): 9.61 (1H, s), 7.24-7.40 (3H, m), 6.87 (1H, d, J=7.7 Hz), 3.94 (2H, t, J=8.3 Hz), 3.70 (8H, d, J=3.6 Hz), 3.58 (3H, s), 3.01-3.21 (4H, m), 2.40 (2H, t, J=7.3 Hz), 1.80-1.94 (2H, m).

ESI (LC-MS positive mode) m/z 427 [(M+H)$^+$].

Example 1-C-49

1-[4-(3-Hydroxy-phenyl)-2-morpholin-4-yl-5,6-di-hydro-pyrrolo[2,3-d]pyrimidin-7-yl]-heptan-1-one (C-49)

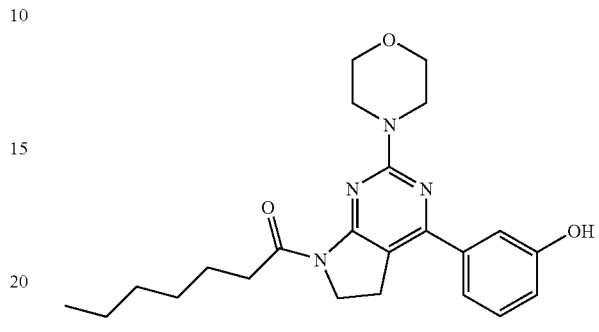

In the same manner as Examples 1-C-07 and 1-C-08, using heptanoyl chloride, the desired compound was obtained.

$^1$H-NMR (DMSO-d$_6$) δ (ppm): 9.62 (1H, brs.), 7.17-7.42 (3H, m), 6.86 (1H, d, J=7.7 Hz), 3.93 (2H, t, J=8.2 Hz), 3.70 (8H, d, J=7.8 Hz), 3.13 (2H, t, J=8.3 Hz), 3.04 (2H, t, J=7.6 Hz), 1.55-1.67 (2H, m), 1.30 (3H, t, J=13.3 Hz).

ESI (LC-MS positive mode) m/z 411 [(M+H)$^+$].

Example 1-C-50

4-(3-Hydroxy-phenyl)-2-morpholin-4-yl-5,6-dihy-dro-pyrrolo[2,3-d]pyrimidine-7-carboxylic acid iso-propylamide trifluoroacetic acid salt (C-50)

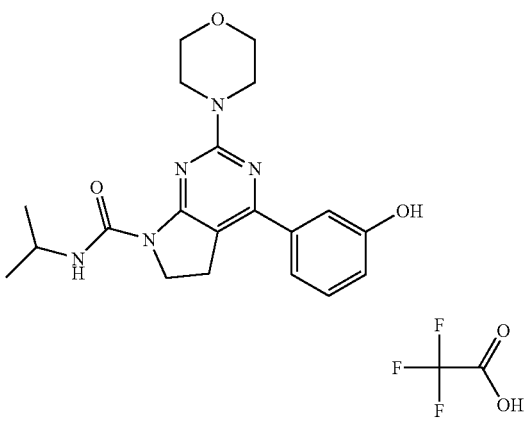

In the same manner as Examples 1-C-07 and 1-C-08, using isopropyl isocyanate, the desired compound was obtained.

$^1$H-NMR (DMSO-d$_6$) δ (ppm): 9.59 (1H, s), 8.69 (1H, d, J=7.0 Hz), 7.23-7.44 (3H, m), 6.86 (1H, d, J=7.8 Hz), 3.93 (2H, t, J=8.4 Hz), 3.81-3.90 (1H, m), 3.69 (8H, d, J=7.1 Hz), 3.15 (2H, t, J=8.4 Hz), 1.18 (6H, d, J=6.5 Hz).

ESI (LC-MS positive mode) m/z 384 [(M+H)$^+$].

Example 1-C-51

4-(3-Hydroxy-phenyl)-2-morpholin-4-yl-5,6-dihydro-pyrrolo[2,3-d]pyrimidine-7-carboxylic acid phenethyl-amide trifluoroacetic acid salt (C-51)

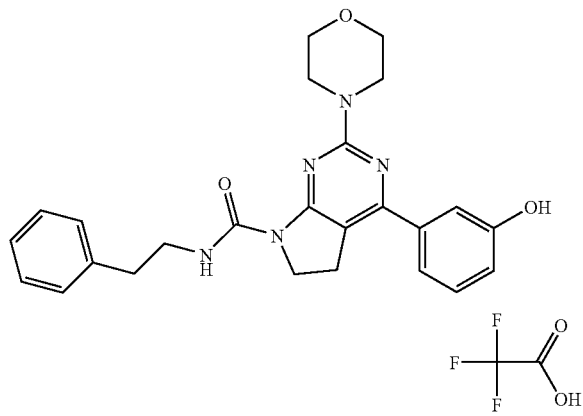

In the same manner as Examples 1-C-07 and 1-C-08, using 2-phenylethyl isocyanate, the desired compound was obtained.

$^1$H-NMR (DMSO-d$_6$) δ (ppm): 9.61 (1H, brs.), 8.61 (1H, t, J=5.8 Hz), 7.14-7.44 (8H, m), 6.86 (1H, d, J=7.7 Hz), 3.95 (2H, t, J=8.4 Hz), 3.31-3.65 (10H, m), 3.14 (2H, t, J=8.4 Hz), 2.81 (2H, J=t, 6.6 Hz).

ESI (LC-MS positive mode) m/z 446 [(M+H)$^+$].

Example 1-C-52

1-[4-(3-Hydroxy-phenyl)-2-morpholin-4-yl-5,6-dihydro-pyrrolo[2,3-d]pyrimidin-7-yl]-2-naphthalen-1-yl-ethanone (C-52)

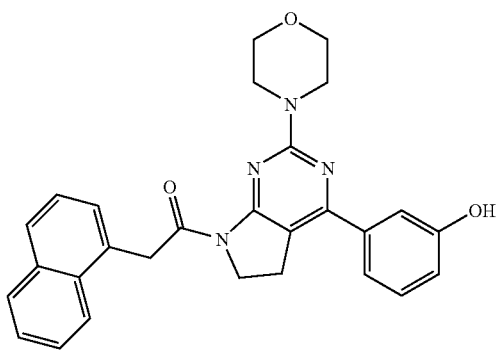

In the same manner as Examples 1-C-07 and 1-C-08, using naphthalen-1-yl-acetyl chloride, the desired compound was obtained.

$^1$H-NMR (DMSO-d$_6$) δ (ppm): 9.63 (1H, brs.), 7.90-8.03 (2H, m), 7.84 (1H, d, J=7.9 Hz), 7.22-7.59 (7H, m), 6.88 (1H, d, J=8.0 Hz), 4.91 (2H, s), 4.05 (2H, t, J=8.1 Hz), 3.49 (8H, dd, J=16.8, 4.0 Hz), 3.21 (2H, t, J=7.4 Hz).

ESI (LC-MS positive mode) m/z 467 [(M+H)$^+$].

Example 1-C-53

[4-(3-Hydroxy-phenyl)-2-morpholin-4-yl-5,6-dihydro-pyrrolo[2,3-d]pyrimidin-7-yl]-thiophen-2-yl-methanone trifluoroacetic acid salt (C-53)

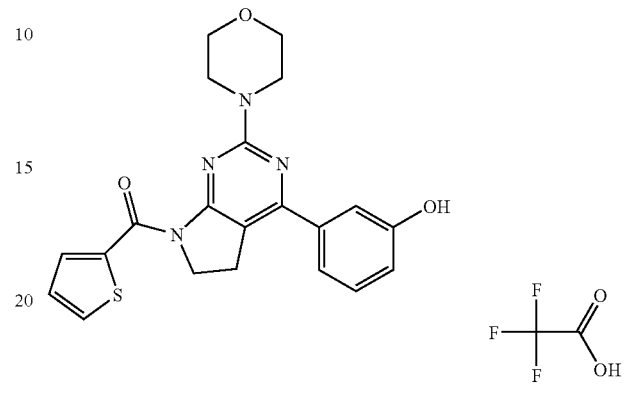

In the same manner as Examples 1-C-07 and 1-C-08, using thiophene-2-carbonyl chloride, the desired compound was obtained.

$^1$H-NMR (DMSO-d$_6$) δ (ppm): 9.61 (1H, brs.), 7.85 (1H, d, J=4.9 Hz), 7.70 (1H, d, J=4.9 Hz), 7.24-7.43 (3H, m), 7.15 (1H, dd, J=4.9, 3.8 Hz), 6.88 (1H, d, J=7.4 Hz), 4.09 (2H, t, J=8.0 Hz), 3.39-3.58 (8H, m), 3.20 (2H, t, J=8.0 Hz).

ESI (LC-MS positive mode) m/z 409 [(M+H)$^+$].

Example 1-C-54

Benzo[β]thiophen-2-yl-[4-(3-hydroxy-phenyl)-2-morpholin-4-yl-5,6-dihydro-pyrrolo[2,3-d]pyrimidin-7-yl]-methanone trifluoroacetic acid salt (C-54)

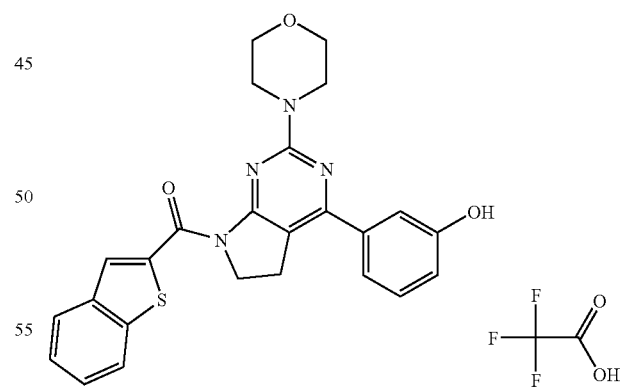

In the same manner as Examples 1-C-07 and 1-C-08, using benzo[β]thiophene-2-carbonyl chloride, the desired compound was obtained.

$^1$H-NMR (DMSO-d$_6$) δ (ppm): 9.63 (1H, s), 8.05 (1H, d, J=7.8 Hz), 7.98 (1H, s), 7.95 (1H, d, J=7.1 Hz), 7.41-7.53 (2H, m), 7.26-7.37 (3H, m), 6.88 (1H, d, J=7.4 Hz), 4.15 (2H, t, J=8.0 Hz), 3.14-3.32 (10H, m).

ESI (LC-MS positive mode) m/z 459 [(M+H)$^+$].

Example 1-C-55

4-(3-Hydroxy-phenyl)-2-morpholin-4-yl-5,6-dihydro-pyrrolo[2,3-d]pyrimidine-7-carbothioic acid methylamide trifluoroacetic acid salt (C-55)

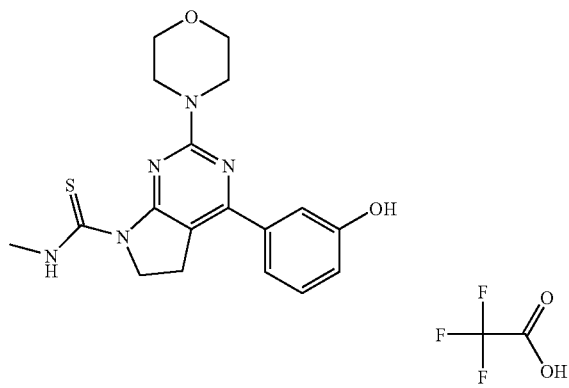

In the same manner as Examples 1-C-07 and 1-C-08, using isothiocyanatomethane, the desired compound was obtained.

$^1$H-NMR (DMSO-d$_6$) δ (ppm): 10.88 (1H, s), 9.63 (1H, brs.), 7.23-7.45 (3H, m), 6.88 (1H, d, J=7.9 Hz), 4.29 (2H, t, J=8.3 Hz), 3.70 (8H, d, J=3.0 Hz), 3.15-3.23 (2H, m), 3.14 (3H, d, J=4.5 Hz).

ESI (LC-MS positive mode) m/z 372 [(M+H)$^+$].

Example 1-C-56

4-(3-Hydroxy-phenyl)-2-morpholin-4-yl-5,6-dihydro-pyrrolo[2,3-d]pyrimidine-7-carbothioic acid butylamide trifluoroacetic acid salt (C-56)

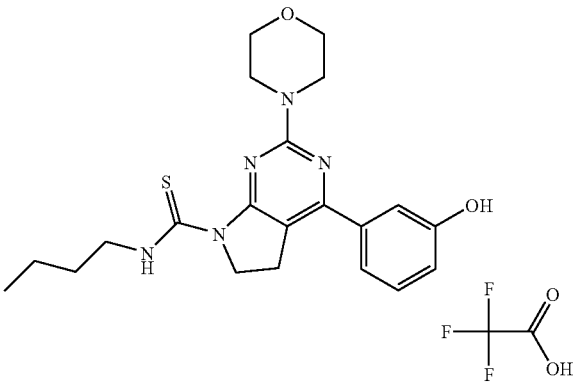

In the same manner as Examples 1-C-07 and 1-C-08, using isothiocyanatobutane, the desired compound was obtained.

$^1$H-NMR (DMSO-d$_6$) δ (ppm): 10.96 (1H, s), 7.23-7.45 (3H, m), 6.88 (1H, d, J=7.9 Hz), 4.28 (2H, t, J=8.7 Hz), 3.69 (8H, d, J=7.2 Hz), 3.59-3.65 (2H, m), 3.17 (2H, t, J=8.3 Hz), 1.56-1.67 (2H, m), 1.30-1.43 (2H, m), 0.91 (3H, t, J=7.4 Hz).

ESI (LC-MS positive mode) m/z 414 [(M+H)$^+$].

Example 1-C-57

3-[7-(Butane-1-sulfonyl)-2-morpholin-4-yl-6,7-dihydro-5H-pyrrolo[2,3-d]pyrimidin-4-yl]-phenol (C-57)

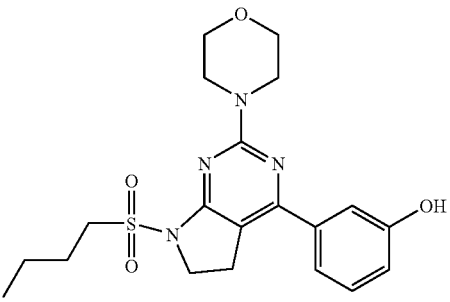

In the same manner as Examples 1-C-07 and 1-C-08, using butylsulfonyl chloride, the desired compound was obtained.

Example 1-D

Bis-(4-methoxy-benzyl)-[5-(2-morpholin-4-yl-6,7-dihydro-5H-pyrrolo[2,3-d]pyrimidin-4-yl)-pyrimidin-2-yl]-amine to be used in the following Examples 1-D-01, 1-D-02, 1-D-03, 1-D-04, 1-D-07, 1-D-08, 1-D-16, 1-D-17, 1-D-18, 1-D-19, 1-D-21, 1-D-23 to 1-D-335 was prepared according to Example 1-J-02 described later.

Example 1-D-01

1-[4-(2-Amino-pyrimidin-5-yl)-2-morpholin-4-yl-5,6-dihydro-pyrrolo[2,3-d]pyrimidin-7-yl]-ethanone (D-01)

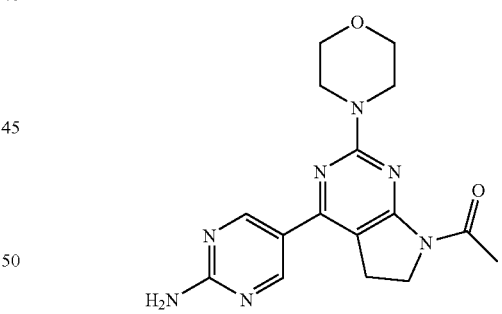

To dichloroethane solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol), pyridine (45 μl, 0.556 mmol) and N,N-dimethylaminopyridine (2.3 mg, 0.0185 mmol) were added, and further acetic anhydride (52 μl, 0.556 mmol) was added, followed by refluxing for 3 hours. This was cooled to room temperature, followed by addition of saturated aqueous ammonium chloride solution, and passed through Whatman tube. The resulting organic phase was concentrated under reduced pressure, to obtain 1-(4-{2-[bis-(4-methoxy-benzyl)-amino]-pyrimidin-5-yl}-2-morpholin-4-yl-5,6-dihydro-pyrrolo[2,3-d]pyrimidin-7-yl)-ethanone as a crude product. To this, TFA (2 ml) and concentrated sulfuric acid (2 drops) were added, followed by stirring at 40° C. for 4 hours. After concentration of TFA under reduced pressure, water was added, followed by neutralization with 1M aqueous sodium hydroxide solution. After filtering the solid, dichloromethane (5 ml) was added, followed by stirring at room temperature for 30 minutes, and the solid was filtered off, to obtain the desired compound as a colorless solid (29.3 mg, yield 46%).

$^1$H-NMR (DMSO-d$_6$) δ (ppm): 8.81 (2H, s), 7.15 (2H, s), 3.93 (2H, t, J=8.3 Hz), 3.73-3.65 (8H, m), 3.16 (2H, t, J=8.3 Hz), 2.57 (3H, s).

ESI (LC-MS positive mode) m/z 342 [(M+H)$^+$].

Example 1-D-02

5-(7-Methanesulfonyl-2-morpholin-4-yl-6,7-dihydro-5H-pyrrolo[2,3-d]pyrimidin-4-yl)-pyrimidin-2-ylamine (D-02)

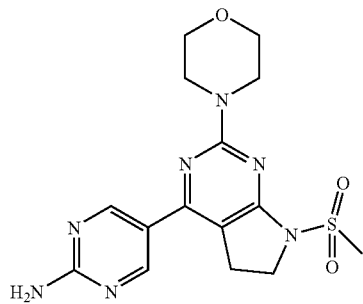

To tetrahydrofuran solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol), 60% sodium hydride (222 mg, 5.56 mmol) was added, followed by stirring at room temperature for 30 minutes. To this, mesyl chloride (430 µl, 5.56 mmol) was added, followed by refluxing for 6 hours. This was cooled to room temperature, followed by addition of saturated aqueous ammonium chloride solution, and passed through Whatman tube. The resulting organic phase was concentrated under reduced pressure, followed by purification by silica gel column chromatography (dichloromethane/methanol=200/1), to obtain [5-(7-methanesulfonyl-2-morpholin-4-yl-6,7-dihydro-5H-pyrrolo[2,3-d]pyrimidin-4-yl)-pyrimidin-2-yl]-bis-(4-methoxy-benzyl)-amine (80.2 mg, Yield 70%). To this, trifluoroacetic acid (1 ml) and concentrated sulfuric acid (2 drops) were added, followed by stirring at 40° C. for 3 hours. After concentration of trifluoroacetic acid under reduced pressure, water was added, followed by neutralization with 1M aqueous sodium hydroxide solution. The solid was filtered, followed by purification by silica gel column chromatography (dichloromethane/2M ammonia methanol=30/1), to obtain the desired compound as a yellow solid (14.9 mg, Yield 31%).

$^1$H-NMR (DMSO-d$_6$) δ (ppm): 8.79 (2H, s), 7.15 (2H, s), 3.98 (2H, t, J=8.3 Hz), 3.74-3.65 (8H, m), 3.23 (12H, t, J=8.3 Hz).

ESI (LC-MS positive mode) m/z 378 [(M+H)$^+$].

Example 1-D-03

4-(2-Amino-pyrimidin-5-yl)-2-morpholin-4-yl-5,6-dihydro-pyrrolo[2,3-d]pyrimidine-7-carboxylic acid ethylamide (D-03)

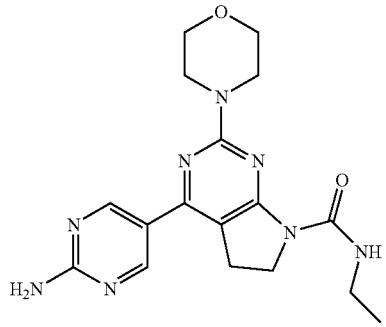

To dichloroethane solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol), triethylamine (780 µl, 5.56 mmol) and ethylisocyanate (780 µl, 5.56 mmol) were added, followed by refluxing for 6 hours. This was cooled to room temperature, followed by addition of saturated aqueous ammonium chloride solution, and passed through Whatman tube. The resulting organic layer was concentrated under reduced pressure, followed by purification by silica gel column chromatography (dichloromethane/methanol=100/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid ethylamide (110.1 mg, Yield 97%). To this, trifluoroacetic acid (1 ml) and concentrated sulfuric acid (2 drops) were added, followed by stirring at 40° C. for 3 hours. After concentration of TFA under reduced pressure, water was added, followed by neutralization with 1M aqueous sodium hydroxide solution. The solid was filtered, followed by purification by silica gel column chromatography (dichloromethane/2M ammonia methanol=50/1), to obtain the desired compound as a yellow solid (20.9 mg, Yield 31%).

$^1$H-NMR (DMSO-d$_6$) δ (ppm): 8.81 (2H, s), 8.62 (1H, t, J=4.9 Hz), 7.13 (2H, s), 3.94 (2H, t, J=8.5 Hz), 3.72-3.64 (8H, m), 3.37-3.33 (3H, m), 3.17 (2H, t, J=8.5 Hz), 1.14 (2H, t, J=7.1 Hz).

ESI (LC-MS positive mode) m/z 371 [(M+H)$^+$].

Example 1-D-04

5-(7-Ethyl-2-morpholin-4-yl-6,7-dihydro-5H-pyrrolo[2,3-d]pyrimidin-4-yl)-pyrimidin-2-ylamine (D-04)

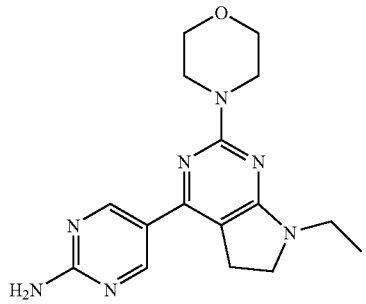

Bis-(4-methoxy-benzyl)-[5-(2-morpholin-4-yl-6,7-dihydro-5H-pyrrolo[2,3-d]pyrimidin-4-yl)-pyrimidin-2-yl]-amine (54 mg) was dissolved in dimethylformamide (5 ml), and sodium hydride (60% mineral oil dispersion, 5 mg) was added under ice cooling, followed by stirring at room temperature for 30 minutes. After dropwise addition of ethyl iodide (9 μl), the reaction mixture was further stirred for 10 hours, and subsequently diluted with water (20 ml), followed by extraction with ethyl acetate (10 ml×2). The combined organic layers were washed with brine, and dried with sodium sulfate. After filtering off the drying agent, the filtrate was concentrated under reduced pressure, and the resulting residue was purified by silica gel column chromatography (hexane/ethyl acetate=20/0 to 10/1), to obtain [5-(7-ethyl-2-morpholin-4-yl-6,7-dihydro-5H-pyrrolo[2,3-d]pyrimidin-4-yl)-pyrimidin-2-yl]-bis-(4-methoxy-benzyl)-amine as a colorless solid (49 mg, 86%). The above colorless solid was dissolved in trifluoroacetic acid (2 ml), and concentrated sulfuric acid (1 drop) was added, followed by stirring at 100° C. for 1 hour. The solvent was concentrated under reduced pressure, and the resulting residue was diluted with water (2 ml), to filter the resulting precipitate, followed by washing with water. The crude product was purified by amino silica gel column chromatography (dichloromethane), to obtain a colorless powder (18 mg, 64%).

$^1$H-NMR (CDCl$_3$) δ (ppm): 8.84 (2H, s), 5.23 (2H, s), 3.83-3.74 (8H, m), 3.59 (2H, t, J=8.1 Hz), 3.45 (2H, q, J=7.2 Hz), 3.13 (2H, t, J=8.1 Hz), 1.18 (2H, t, J=7.2 Hz).

ESI (LC-MS positive mode) m/z 328 [(M+H)$^+$].

Example 1-D-05

5-(7-Benzyl-2-morpholin-4-yl-6,7-dihydro-5H-pyrrolo[2,3-d]pyrimidin-4-yl)-pyrimidin-2-ylamine (D-05)

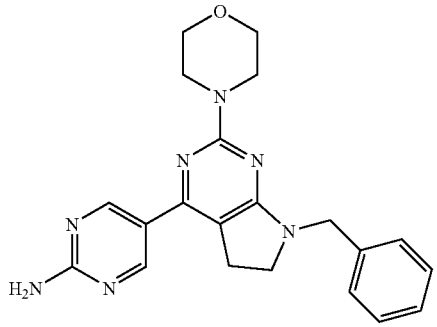

In the same manner as Example 1-D-04, using benzyl bromide, the desired compound was obtained as a colorless powder.

$^1$H-NMR (CDCl$_3$) δ (ppm): 8.86 (1H, s), 7.32 (5H, m), 5.22 (2H, s), 4.61 (2H, s), 3.85-3.76 (8H, m), 3.50 (2H, t, J=8.2 Hz), 3.12 (2H, t, J=8.2 Hz).

ESI (LC-MS positive mode) m/z 390 [(M+H)$^+$].

Example 1-D-06

1-[4-(2-Amino-pyrimidin-5-yl)-2-morpholin-4-yl-5,6-dihydro-pyrrolo[2,3-d]pyrimidin-7-yl]-propan-1-one (D-06)

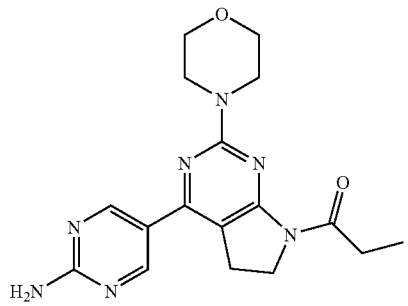

In the same manner as Example 1-D-01, using propionyl chloride, the desired compound was obtained.

$^1$H-NMR (CDCl$_3$) δ (ppm): 8.88 (2H, s), 5.28 (2H, s), 4.10 (2H, t, J=8.3 Hz), 3.75-3.80 (8H, m), 3.16 (2H, d, J=8.3 Hz), 3.10 (2H, q, J=7.3 Hz), 1.24 (2H, t, J=7.3 Hz).

ESI (LC-MS positive mode) m/z 356 [(M+H)$^+$].

Example 1-D-07

4-[4-(2-Amino-pyrimidin-5-yl)-2-morpholin-4-yl-5,6-dihydro-pyrrolo[2,3-d]pyrimidin-7-yl]-pyridine-2-carboxylic acid tert-butylamide (D-07)

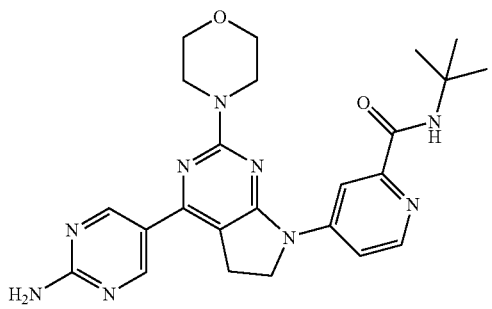

Bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg), palladium acetate (1.7 mg), S-Phos (6.2 mg), 4-chloropicolinic acid t-butylamide (64 mg) and potassium phosphate (64 mg) were stirred in dimethylformamide (1.5 ml) under an argon atmosphere at 100° C. for 2 days. The reaction mixture was cooled to room temperature, and subsequently diluted with water (20 ml), followed by extraction with ethyl acetate (10 ml). The organic layer was washed with brine, and dried over sodium sulfate. After filtering off the drying agent, the filtrate was concentrated under reduced pressure, and the resulting residue was purified by silica gel column chromatography (hexane/ethyl acetate=5/0 to 3/1), to obtain 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridine-2-carboxylic acid tert-butylamide as a pale yellow solid (44 mg, 41%). The above compound was dissolved in trifluoroacetic acid (3 ml), and refluxed for 5 hours in the presence of N-acetylcysteine (33 mg, 3.3 equivalents). The reaction mixture was concentrated under reduced pressure, and water (2 ml) was added to the resulting residue, followed by neutralization with saturated sodium bicarbonate water. The resulting precipitate was filtered and dried, and purified by amino silica gel column chromatography (dichloromethane), to obtain a colorless powder (17 mg, 58%).

$^1$H-NMR (DMSO-$d_6$) δ (ppm): 8.84 (2H, s), 8.47 (1H, m), 8.09-8.05 (1H, m), 7.16 (1H, s), 4.16 (2H, t, J=8.2 Hz), 3.72 (8H, m), 3.25 (2H, t, J=8.2 Hz), 1.42 (9H, s).

ESI (LC-MS positive mode) m/z 476 [(M+H)$^+$].

Example 1-D-08

4-[4-(2-Amino-pyrimidin-5-yl)-2-morpholin-4-yl-5,6-dihydro-pyrrolo[2,3-d]pyrimidin-7-yl]-benzoic acid methyl ester (D-08)

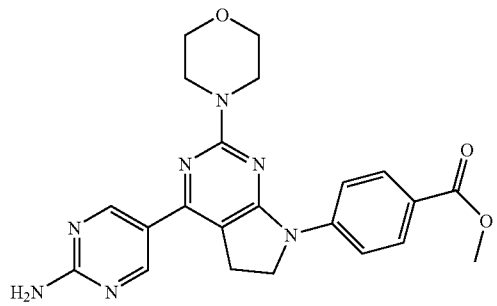

A solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg, 0.370 mmol), 4-bromobenzoic acid methyl ester (95 mg, 0.444 mmol), palladium acetate (10.0 mg, 0.0444 mmol), S-Phos (36.4 mg, 0.0888 mmol) and potassium phosphate (157 mg, 0.740 mmol) in dimethylformamide (3 ml) was degassed under ultrasonic irradiation, and stirred at 100° C. for 3 hours. To this, water was added, and the precipitate was filtered, which was subsequently dissolved in dichloromethane, and dried over sodium sulfate, followed by concentration under reduced pressure. Purification by silica gel column chromatography (dichloromethane/methanol=200/1) afforded 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid methyl ester as a yellow powder (143.5 mg, Yield 57%).

To a product of the previous reaction (43.5 mg), TFA (1 ml) and concentrated sulfuric acid (2 drops) were added, followed by stirring at 40° C. for 4 hours. Concentration was carried out under reduced pressure, and water was added, followed by neutralization with 1M aqueous sodium hydroxide solution. After the resulting solid was filtered, dichloromethane was added, followed by stirring at room temperature for 30 minutes, and the solid was filtered, to obtain the desired compound (17.6 mg, yield 63%).

$^1$H-NMR (DMSO-$d_6$) δ (ppm): 8.82 (2H, s), 7.99-7.98 (4H, brm), 7.08 (2H, s), 4.13 (2H, t, J=8.3 Hz), 3.83 (3H, s), 3.76-3.67 (8H, m), 3.32-3.29 (2H, brm).

ESI (LC-MS positive mode) m/z 434 [(M+H)$^+$].

Example 1-D-09

4-[4-(2-Amino-pyrimidin-5-yl)-2-morpholin-4-yl-5,6-dihydro-pyrrolo[2,3-d]pyrimidin-7-yl]-benzoic acid sodium salt (D-09)

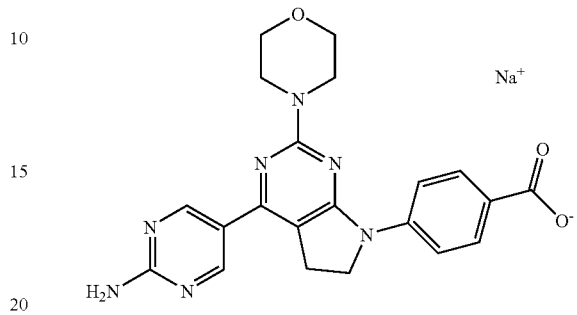

Tetrahydrofuran/5M aqueous sodium hydroxide solution/30% hydrogen peroxide solution=4/2/1 solution of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid methyl ester obtained in Example 1-D-08 was refluxed overnight, followed by neutralization with 6M hydrochloric acid. After filtering the precipitate, trifluoroacetic acid (1 ml) and concentrated sulfuric acid (2 drops) were added, followed by stirring at 40° C. for 4 hours. Concentration was carried out under reduced pressure, and water was added, followed by neutralization with 1M aqueous sodium hydroxide solution. After filtering the resulting solid, dichloromethane/hexane=9/1 was added, followed by stirring at room temperature for 30 minutes, to filter the solid. To this, 1M aqueous sodium hydroxide solution corresponding to 1 equivalent of sodium hydroxide was added, followed by stirring at room temperature for 10 minutes, and subsequently concentration was carried out under reduced pressure, to obtain the desired compound.

$^1$H-NMR (DMSO-$d_6$) δ (ppm): 8.81 (2H, s), 7.85 (2H, d, J=8.8 Hz), 7.70 (2H, d, J=8.8 Hz), 7.03 (2H, s), 4.09 (2H, t, J=7.8 Hz), 3.75-3.65 (8H, m).

ESI (LC-MS positive mode) m/z 420 [(M+H)$^+$].

Example 1-D-10

4-[4-(2-Amino-pyrimidin-5-yl)-2-morpholin-4-yl-5,6-dihydro-pyrrolo[2,3-d]pyrimidin-7-yl]-benzamide (D-10)

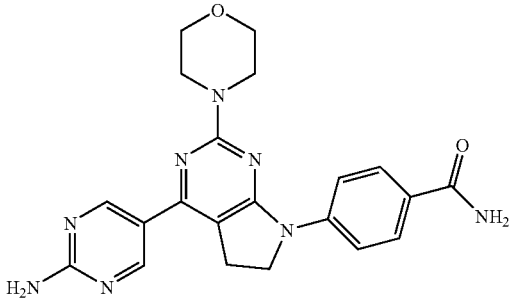

To a solution of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (30 mg, 0.0468 mmol) obtained in Example 1-D-09 in dimethylformamide (1 ml), Hunig's base (41 µl, 0.234 mmol), HOBt monohydrate (8.3 mg, 0.0468 mmol), WSC hydrochloride (17.6 mg, 0.0702 mmol) and ammonium chloride (5.0 mg, 0.0936 mmol) were added, followed by stirring at 80° C. for 3 hours. To this, water (5 ml) was added, and the solid was filtered off. To this, trifluoroacetic acid (1 ml) and concentrated sulfuric acid (2 drops) were added, followed by stirring at 40° C. for 3 hours. After concentration of TFA under reduced pressure, water was added, followed by neutralization with 1M aqueous sodium hydroxide solution. The solid was filtered, and subsequently suspended in dichloromethane/hexane=9/1, which was stirred at room temperature for 30 minutes, followed by filtering the solid, to obtain the desired compound.

$^1$H-NMR (DMSO-$d_6$) δ (ppm): 8.82 (2H, s), 7.95-7.82 (4H, m), 7.22-7.06 (2H, m), 4.14 (2H, t, J=8.5 Hz), 3.76-3.67 (8H, m), 3.31 (2H, t, J=8.5 Hz).

ESI (LC-MS positive mode) m/z 419 [(M+H)$^+$].

Example 1-D-11

1-[4-(2-Amino-pyrimidin-5-yl)-2-morpholin-4-yl-5,6-dihydro-pyrrolo[2,3-d]pyrimidin-7-yl]-3-phenyl-propan-1-one (D-11)

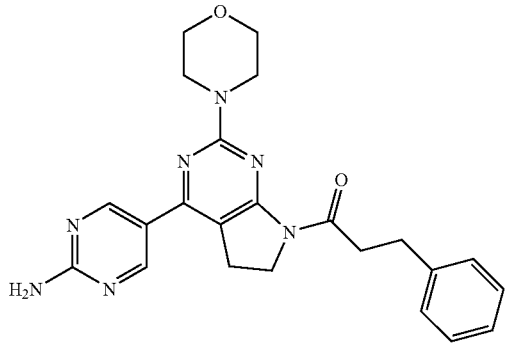

In the same manner as Example 1-D-01, using 3-phenyl-propanoyl chloride, the desired compound was obtained.

$^1$H-NMR (TFA-d) δ (ppm): 9.22 (2H, s), 7.30-7.15 (5H, m), 4.34 (2H, br.t), 4.02-3.91 (8H, m), 3.33 (4H, m), 3.07 (2H, br.t).

ESI (LC-MS positive mode) m/z 432 [(M+H)$^+$].

Example 1-D-12

4-[4-(2-Amino-pyrimidin-5-yl)-2-morpholin-4-yl-5,6-dihydro-pyrrolo[2,3-d]pyrimidin-7-yl]-4-oxo-butyric acid methyl ester (D-12)

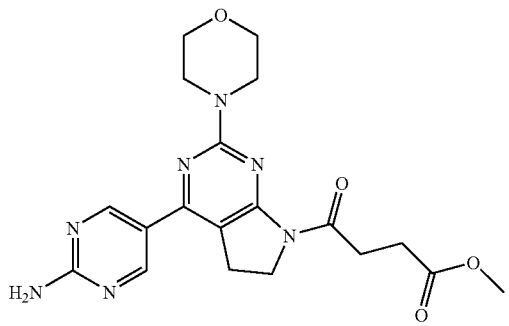

In the same manner as Example 1-D-01, using methyl 4-chloro-4-oxobutylate, the desired compound was obtained.

$^1$H-NMR (TFA-d) δ (ppm): 9.25 (2H, s), 4.42 (2H, m), 4.04 (8H, m), 3.81 (3H, s), 3.38-3.27 (4H, m), 2.90 (2H, m).

ESI (LC-MS positive mode) m/z 414 [(M+H)$^+$].

Example 1-D-13

4-(2-Amino-pyrimidin-5-yl)-2-morpholin-4-yl-5,6-dihydro-pyrrolo[2,3-d]pyrimidine-7-carboxylic acid isopropylamide (D-13)

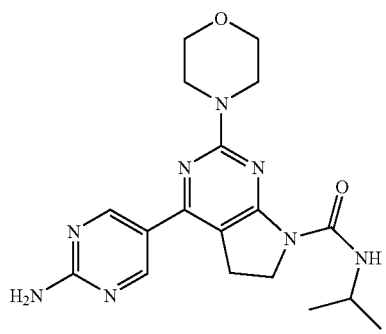

In the same manner as Example 1-D-03, using isopropyl-isocyanate, the desired compound was obtained.

$^1$H-NMR (CDCl$_3$) δ (ppm): 8.89 (2H, s), 8.71 (1H, d, J=7.3 Hz), 5.32 (2H, s), 4.13 (2H, t, J=8.1 Hz), 4.07 (1H, m), 3.79 (8H, m), 3.17 (2H, t, J=8.1 Hz), 1.25 (6H, d, J=6.5 Hz).

ESI (LC-MS positive mode) m/z 385 [(M+H)$^+$].

Example 1-D-14

4-(2-Amino-pyrimidin-5-yl)-2-morpholin-4-yl-5,6-dihydro-pyrrolo[2,3-d]pyrimidin-7-thiocarboxylic acid ethylamide (D-14)

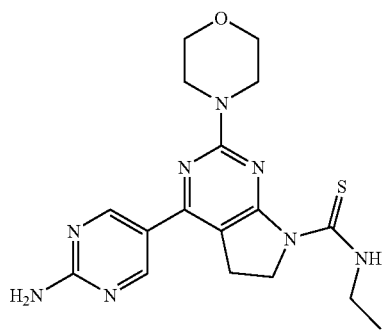

In the same manner as Example 1-D-03, using ethylthio-isocyanate, the desired compound was obtained.

$^1$H-NMR (TFA-d) δ (ppm): 9.20 (2H, s), 4.59 (2H, br.t), 4.07-3.95 (8H, m), 3.71 (2H, m), 3.29 (2H, br.t), 1.30 (2H, t, J=7.3 Hz).

ESI (LC-MS positive mode) m/z 387 [(M+H)$^+$].

Example 1-D-15

4-(2-Amino-pyrimidin-5-yl)-2-morpholin-4-yl-5,6-dihydro-pyrrolo[2,3-d]pyrimidine-7-carboxylic acid ethyl ester (D-15)

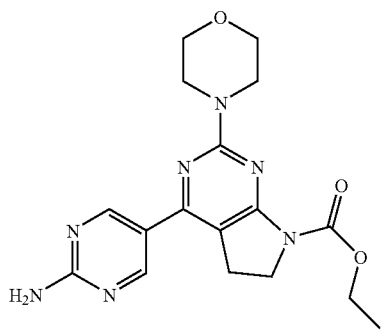

In the same manner as Example 1-D-01, using ethyl chloroformate, the desired compound was obtained.

$^1$H-NMR (CDCl$_3$) δ (ppm): 8.88 (2H, s), 5.28 (2H, s), 4.33 (2H, q, J=7.3 Hz), 4.07 (2H, t, J=8.6 Hz), 3.89-3.76 (8H, m), 3.18 (2H, t, J=8.6 Hz), 1.38 (2H, t, J=7.3 Hz).

ESI (LC-MS positive mode) m/z 372 [(M+H)$^+$].

Example 1-D-16

{3-[4-(2-Amino-pyrimidin-5-yl)-2-morpholin-4-yl-5,6-dihydro-pyrrolo[2,3-d]pyrimidin-7-yl]-4-fluoro-phenyl}-morpholin-4-yl-methanone (D-16)

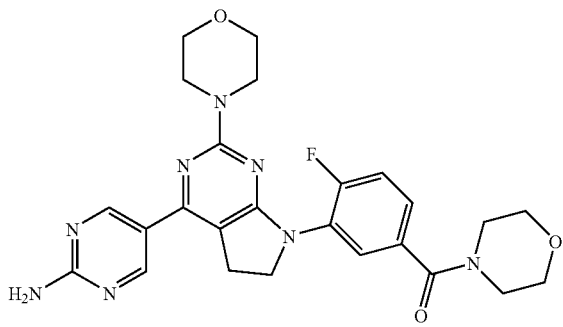

To dichloromethane solution (4 ml) of 3-bromo-4-fluorobenzoic acid (200 mg, 0.694 mmol), WSCI (262 mg, 1.37 mmol), morpholine (95.5 μl, 1.10 mmol) and N,N-dimethylaminopyridine (112 mg, 0.917 mmol) were added, followed by stirring at room temperature for 15 hours. This was diluted with ethyl acetate (10 ml), and the organic layer was dried sequentially with saturated aqueous ammonium chloride solution (10 ml) and saturated aqueous sodium chloride solution (10 ml). The organic layer was dried over anhydrous sodium sulfate, and concentrated under reduced pressure, whereby a crude product of (3-bromo-4-fluoro-phenyl)-morpholin-4-yl-methanone was obtained as a colorless solid (274 mg).

A dimethylformamide solution (2 ml) of the obtained (3-bromo-4-fluoro-phenyl)-morpholin-4-yl-methanone crude product (56.1 mg), bis-(4-methoxy-benzyl)-[5-(2-morpholin-4-yl-6,7-dihydro-5H-pyrrolo[2,3-d]pyrimidin-4-yl)-pyrimidin-2-yl]-amine (70.0 mg, 0.130 mmol), palladium acetate (2.9 mg, 0.013 mmol), X-Phos (12.4 mg, 0.0261 mmol) and potassium phosphate (55.1 mg, 0.260 mmol) was degassed under ultrasonic irradiation, followed by stirring at 100° C. for 6 hours under a nitrogen atmosphere. The reaction mixture was cooled to room temperature, followed by dilution with dichloromethane (10 ml), which was washed with saturated aqueous sodium chloride solution (10 ml). The organic layer was dried over sodium sulfate, followed by concentration under reduced pressure, and the residue was purified by silica gel column chromatography (dichloromethane/methanol=50/1), to obtain [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-fluoro-phenyl]-morpholin-4-yl-methanone as a pale brown solid (90.0 mg, 93%).

This was dissolved in TFA (2 ml), and N-acetylcysteine (43.3 mg, 0.265 mmol) was added, followed by refluxing for 5 hours. The reaction mixture was concentrated under reduced pressure, and the resulting residue was purified by silica gel column chromatography (dichloromethane/methanol=20/1), to obtain {3-[4-(2-amino-pyrimidin-5-yl)-2-morpholin-4-yl-5,6-dihydro-pyrrolo[2,3-d]pyrimidin-7-yl]-4-fluoro-phenyl}-morpholin-4-yl-methanone as a yellow powder (44.0 mg, 67%).

$^1$H-NMR (DMSO-d$_6$) δ (ppm): 8.78 (2H, s), 7.70 (1H, dd, J=7.4, 1.8 Hz), 7.48-7.18 (4H, m), 4.12 (2H, t, J=7.7 Hz), 3.83-3.50 (16H, m), 3.33 (2H, t, J=7.7 Hz).

ESI (LC-MS positive mode) m/z 507 (M+H)$^+$.

Example 1-D-17

4-(2-Amino-pyrimidin-5-yl)-2-morpholin-4-yl-5,6-dihydro-pyrrolo[2,3-d]pyrimidine-7-carbothioic acid [5-(4-ethyl-piperazine-1-carbonyl)-2-methyl-phenyl]-amide (D-17)

Step A (4-ethyl-piperazin-1-yl)-(4-methyl-3-nitro-phenyl)-methanone

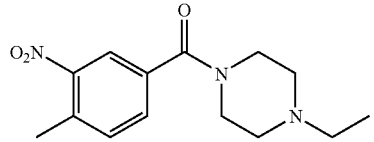

To 4-methyl-3-nitro-benzoic acid (730 mg, 4.03 mmol), WSCI (930 mg, 4.85 mmol), HOBt (110 mg, 0.674 mmol) and N-ethylpiperazine (608 μl, 4.79 mmol), dichloromethane (8 ml) was added, followed by stirring for 13 hours. The reaction mixture was washed with aqueous ammonium chloride solution, and subsequently dried over sodium sulfate. After filtering sodium sulfate, the filtrate was concentrated under reduced pressure, to obtain (4-ethyl-piperazin-1-yl)-(4-methyl-3-nitro-phenyl)-methanone (1.06 g, 95%).

ESI (LC-MS positive mode) m/z 278 (M+H)$^+$.

Step B (4-Ethyl-piperazin-1-yl)-(3-amino-4-methyl-phenyl)-methanone

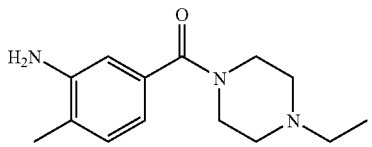

(4-Ethyl-piperazin-1-yl)-(4-methyl-3-nitro-phenyl)-methanone (1.06 g, 3.82 mmol) obtained in Step A was stirred for 16 hours in methanol (20 ml) under a hydrogen atmosphere in the presence of 10% palladium carbon. After the reaction mixture was filtered, the filtrate was concentrated under reduced pressure, to obtain (4-ethyl-piperazin-1-yl)-(3-amino-4-methyl-phenyl)-methanone (1.0 g, quant.).

ESI (LC-MS positive mode) m/z 248 (M+H)$^+$.

Step C 4-(2-Amino-pyrimidin-5-yl)-2-morpholin-4-yl-5,6-dihydro-pyrrolo[2,3-d]pyrimidine-7-carbothioic acid [5-(4-ethyl-piperazine-1-carbonyl)-2-methyl-phenyl]-amide (D-17)

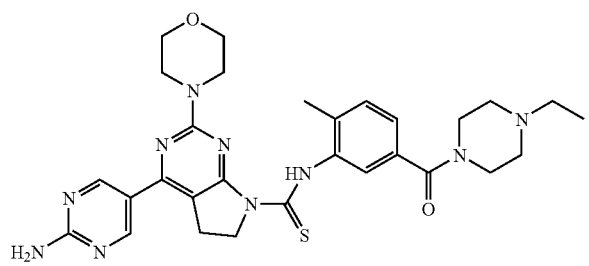

A dichloromethane solution (3 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol), pyridine (30 μl, 0.37 mmol) and thiophosgene (28 μl, 0.37 mmol) was stirred for 40 minutes. This was concentrated and dried under reduced pressure, and subsequently (4-ethyl-piperazin-1-yl)-(3-amino-4-methyl-phenyl)-methanone (90 mg, 0.390 mmol) obtained in Step B was added, followed by stirring in dichloromethane (3 ml) for 16 hours. The reaction mixture was washed with aqueous ammonium chloride solution, and subsequently dried over sodium sulfate. The drying agent was removed, followed by concentration and drying. To this, TFA (2 ml) was added, followed by stirring at 80° C. for 4 hours. After TFA was removed under reduced pressure, dichloromethane was added, followed by washing with sodium hydrogencarbonate aqueous solution. The organic layer was dried over sodium sulfate, filtered and concentrated, to obtain a crude product. Purification by silica gel column chromatography (dichloromethane/methanol=10/1) afforded 4-(2-amino-pyrimidin-5-yl)-2-morpholin-4-yl-5,6-dihydro-pyrrolo[2,3-d]pyrimidine-7-carbothioic acid [5-(4-ethyl-piperazine-1-carbonyl)-2-methyl-phenyl]-amide (42 mg, 39%) as a pale yellow powder.

$^1$H-NMR (CDCl$_3$) δ (ppm): 12.5 (1H, s), 8.91 (2H, s), 7.54 (1H, s), 7.30 (2H, s), 5.32 (2H, s), 4.58 (2H, t, J=8.1 Hz), 3.75-3.61 (12H, m), 3.25 (2H, t, J=8.1 Hz), 2.49-2.41 (6H, m), 2.32 (3H, s), 1.10 (3H, t, J=7.3 Hz).

ESI (LC-MS positive mode) m/z 589 (M+H)$^+$.

Example 1-D-18

4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-2,6-difluoro-phenyl]-amide (D-18)

Step A

N,N-di-Boc-4-bromo-2,6-difluoro-phenylamine

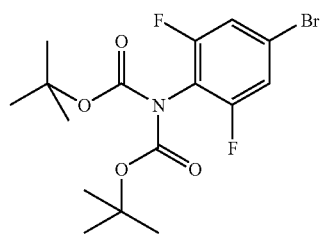

4-Bromo-2,6-difluoro-phenylamine (10 g, 48 mmol) was dissolved in DMF (100 ml), and (Boc)$_2$O (23.1 g, 106 mmol) and DMAP (176 mg, 1.44 mmol) were added, followed by stirring at room temperature for 14 hours. 200 ml of water was added, and the resulting solid was filtered, to obtain a crude product as a colorless solid (18.3 g, 93%).

$^1$H-NMR (CDCl$_3$) δ (ppm): 7.14 (2H, ddd, J=11.2, 3.2, 2.1 Hz), 1.43 (18H, s).

ESI (LC-MS positive mode) m/z 408, 410 (M+H)$^+$.

Step B

N-Boc-4-(4-ethyl-piperazin-1-yl)-2,6-difluoro-phenylamine

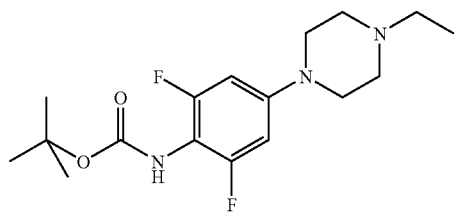

To a solution of N,N-di-Boc-4-bromo-2,6-difluoro-phenylamine (9.0 g, 22.0 mmol) obtained in Step A, palladium acetate (49 mg, 0.218 mmol), S-Phos (181 mg, 0.441 mmol), and tert-butoxy potassium (4.45 g, 39.7 mmol) in toluene (100 ml), 1-ethyl-piperazine (4.20 ml, 33.1 mmol) was added, followed by stirring at 60° C. for 14 hours. After cooling to room temperature, 100 ml of water was added, followed by extraction with ethyl acetate (100 ml×2). The organic layer was dried over sodium sulfate, and the solvent was distilled off under reduced pressure. This was purified by silica gel column chromatography (dichloromethane/methanol=100/1 to 10/1), whereby the desired compound was obtained (2.4 g, 32%).

$^1$H-NMR (CDCl$_3$) δ: 6.42 (2H, dt, J=17.4, 3.3 Hz), 5.74 (1H, s), 3.21-3.15 (4H, m), 2.60-2.54 (4H, m), 2.46 (2H, q, J=7.3 Hz), 1.49 (9H, s), 1.12 (3H, t, J=7.3 Hz).
ESI (LC-MS positive mode) m/z 342 (M+H)$^+$.

Step C 4-(4-Ethyl-piperazin-1-yl)-2,6-difluoro-phenylamine

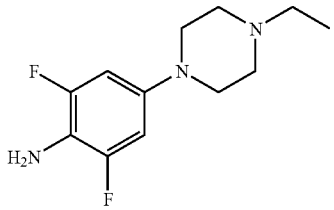

To a solution of N-Boc-4-(4-ethyl-piperazin-1-yl)-2,6-difluoro-phenylamine (2.4 g, 7.03 mmol) obtained in Step B in ethyl acetate (20 ml), 6M–HCl aqueous solution (10 ml) was added, followed by stirring at room temperature for 1 hour. To this, 5M-NaOH aqueous solution was added to adjust the pH to 8, followed by extraction with ethyl acetate (50 ml×2). The organic layer was dried over sodium sulfate, and the solvent was distilled off under reduced pressure. This was purified by silica gel column chromatography (dichloromethane/methanol=50/1 to 20/1), followed by further dissolution in a minimum amount of dichloromethane. n-Hexane was added, and an oily component was removed, to obtain the desired compound as a brown solid (1.33 g, 78%).
$^1$H-NMR (CDCl$_3$) δ: 6.44 (2H, ddd, J=20.4, 10.7, 2.9 Hz), 3.37 (2H, s), 3.07-3.04 (4H, m), 2.61-2.55 (4H, m), 2.46 (2H, q, J=7.2 Hz), 1.12 (3H, t, J=7.2 Hz).
ESI (LC-MS positive mode) m/z 242 (M+H)$^+$.

Step D 4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-2,6-difluoro-phenyl]-amide (D-18)

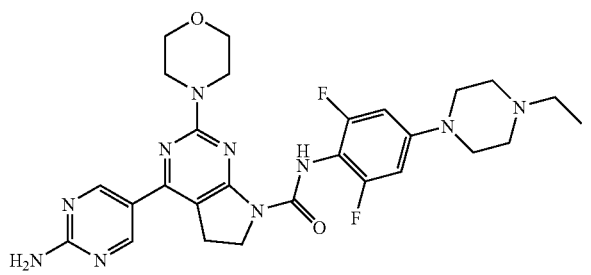

To a solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (2.48 g, 4.59 mmol) in dichloromethane (50 ml), pyridine (743 µl, 9.19 mmol) was added, followed by cooling to 0° C. To this, triphosgene (2.73 g, 9.19 mmol) was added, which was raised to room temperature, followed by stirring for 1 hour. The solvent was distilled off under reduced pressure, and dissolved again in dichloromethane (50 ml), to which a solution of 4-(4-ethyl-piperazin-1-yl)-2,6-difluoro-phenylamine (1.33 g, 5.51 mmol) obtained in Step C in dichloromethane (50 ml) was added dropwise over 30 minutes, followed by stirring for 1 hour. Dichloromethane (100 ml) was added, followed by further stirring at room temperature for 19 hours. 100 ml of Dichloromethane was added, followed by adsorption to silica gel, and subsequently the solvent was distilled off under reduced pressure. This was purified by silica gel column chromatography (dichloromethane/methanol=50/1 to 10/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazin-1-yl)-2,6-difluoro-phenyl]-amide as a crude product. This was dissolved in TFA (45 ml), and N-acetylcysteine (1.49 g, 9.15 mmol) was added, followed by refluxing for 6 hours. After the solvent was distilled off under reduced pressure, 5M-NaOH aqueous solution was added to adjust the pH to 8, and the resulting solid was washed with aqueous sodium bicarbonate (50 ml), water (50 ml) and methanol (50 ml), followed by purification by silica gel column chromatography (dichloromethane/methanol=100/1 to 10/1), to obtain the desired compound as a colorless solid (1.34 g, 52%).
$^1$H-NMR (DMSO-D$_6$) δ: 10.15 (1H, s), 8.84 (2H, s), 7.22 (2H, s), 6.73 (2H, d, J=11.7 Hz), 4.01 (2H, t, J=8.0 Hz), 3.67 (8H, s), 3.26 (2H, t, J=8.0 Hz), 3.22-3.16 (4H, m), 2.48-2.44 (4H, m), 2.36 (2H, q, J=7.1 Hz), 1.03 (3H, t, J=7.1 Hz).
ESI (LC-MS positive mode) m/z 567 (M+H)$^+$.

Example 1-D-19

4-[4-(2-Amino-pyrimidin-5-yl)-2-morpholin-4-yl-5,6-dihydro-pyrrolo[2,3-d]pyrimidin-7-yl]-N-pyridin-3-ylmethyl-benzamide (D-19)

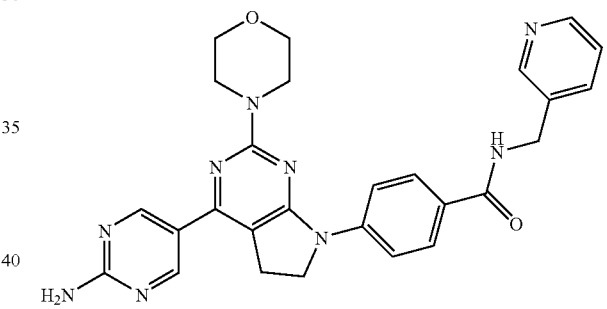

Step A 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid

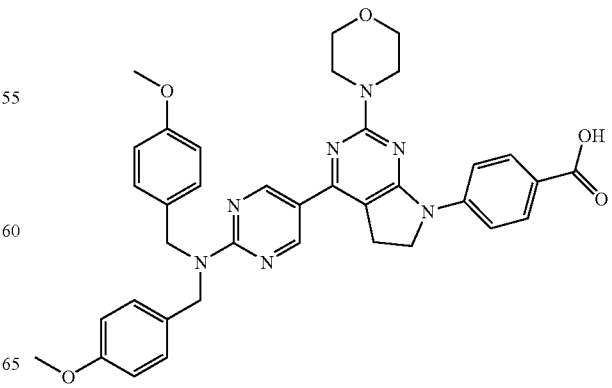

499

A dimethylformamide solution (15 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (700 mg, 1.30 mmol), 4-bromobenzoic acid (313 mg, 1.56 mmol), tris(dibenzylideneacetone) dipalladium (29.7 mg, 0.0324 mmol), X-Phos (61.8 mg, 0.130 mmol) and potassium phosphate (881 mg, 4.15 mmol) was degassed under ultrasonic irradiation, and stirred at 100° C. for 16 hours under a nitrogen atmosphere. After the reaction mixture was cooled to room temperature, 6M hydrochloric acid (2 ml) and water (15 ml) were added, followed by stirring at room temperature for 1 hour. The precipitated solid was filtered, and ethyl acetate (10 ml) was added, followed by irradiation of ultrasonic wave. The solid was filtered, and washed with ethyl acetate, whereby 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid was obtained as a yellow solid (855 mg, 100%).

ESI (LC-MS positive mode) m/z 660 (M+H)⁺.

Step B

4-[4-(2-Amino-pyrimidin-5-yl)-2-morpholin-4-yl-5,6-dihydro-pyrrolo[2,3-d]pyrimidin-7-yl]-N-pyridin-3-ylmethyl-benzamide (D-19)

To a DMF solution (2 ml) of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A, 3-(aminomethyl)pyridine (18.4 μl, 0.182 mmol), WSCI (34.9 mg, 0.182 mol), HOBt (12.3 mg, 0.0909 mmol) and N-ethyldiisopropylamine (63.4 μl, 0.364 mmol) were added, followed by stirring at room temperature for 20 hours. The reaction mixture was diluted with dichloromethane (10 ml), and washed with water (10 ml). The organic layer was dried over sodium sulfate, and concentrated under reduced pressure, whereby a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-pyridin-3-ylmethyl-benzamide was obtained as a brown solid (115 mg).

This was dissolved in TFA (2 ml), and N-acetylcysteine (32.7 mg, 0.200 mmol) was added, followed by refluxing for 16 hours. The reaction mixture was concentrated under reduced pressure, and the resulting residue was purified by silica gel column chromatography (dichloromethane/methanol=15/1), to obtain 4-[4-(2-amino-pyrimidin-5-yl)-2-morpholin-4-yl-5,6-dihydro-pyrrolo[2,3-d]pyrimidin-7-yl]-N-pyridin-3-ylmethyl-benzamide as a yellow powder (34.0 mg, 73%).

¹H-NMR (DMSO-d₆) δ (ppm): 9.04 (1H, m), 8.82 (2H, s), 8.64 (1H, s), 8.55 (1H, d, J=4.3 Hz), 7.95 (4H, s), 7.87 (1H, m), 7.52 (1H, m), 7.14 (2H, brs), 4.53 (2H, d, J=4.3 Hz), 4.13 (2H, t, J=8.2 Hz), 3.78-3.66 (8H, m), 3.32 (2H, t, J=8.2 Hz).

ESI (LC-MS positive mode) m/z 510 (M+H)⁺.

500

Example 1-D-20

{4-[4-(2-Amino-pyrimidin-5-yl)-2-morpholin-4-yl-5,6-dihydro-pyrrolo[2,3-d]pyrimidin-7-yl]-phenyl}-(4-pyridin-3-yl-piperazin-1-yl)-methanone (D-20)

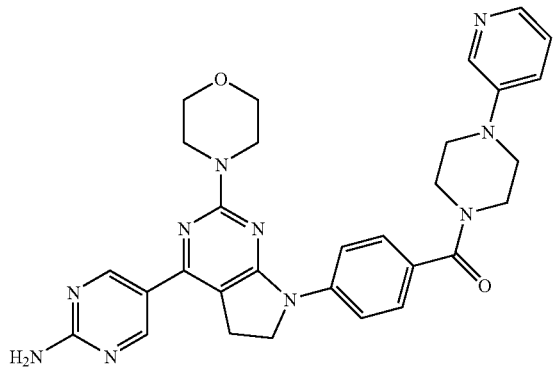

Step A

1-Pyridin-3-yl-piperazine

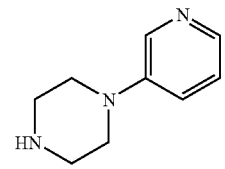

A toluene solution (6 ml) of 3-bromopyridine (300 mg, 1.89 mmol), piperazine-1-carboxylic acid tert-butyl ester (389 mg, 2.09 mmol), tris(dibenzylideneacetone)dipalladium (43.4 mg, 0.0474 mmol), Xantphos (54.9 mg, 0.0949 mmol) and potassium tert butoxide (469 mg, 4.18 mmol) was degassed under ultrasonic irradiation, and stirred at 80° C. for 17 hours under a nitrogen atmosphere. After the reaction mixture was cooled to room temperature, water (20 ml) was added, followed by extraction twice with dichloromethane (20 ml). The organic layer was dried over sodium sulfate, followed by concentration under reduced pressure, and the residue was purified by silica gel column chromatography (dichloromethane/methanol=30/1), to obtain a crude product of 4-pyridin-3-yl-piperazine-1-carboxylic acid tert-butyl ester as a yellow liquid (510 mg).

To this, TFA (5 ml) was added, followed by stirring at room temperature for 2 hours. The reaction mixture was concentrated under reduced pressure, and the residue was adsorbed to SCX resin, and washed with methanol (20 ml), followed by elution with 2M ammonia methanol solution (20 ml). The eluent was concentrated under reduced pressure, to obtain 1-pyridin-3-yl-piperazine as a yellow liquid (181 mg, 58%).
ESI (LC-MS positive mode) m/z 164 (M+H)⁺.
(It is also possible to synthesize this compound with reference to Chem. Pharm. Bull. 49(19)1314-1320)

Step B

{4-[4-(2-Amino-pyrimidin-5-yl)-2-morpholin-4-yl-5,6-dihydro-pyrrolo[2,3-d]pyrimidin-7-yl]-phenyl}-(4-pyridin-3-yl-piperazin-1-yl)-methanone (D-20)

To a DMF solution (2 ml) of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A in Example 1-D-19, 1-pyridin-3-yl-piperazine (29.7 mg, 0.182 mmol), WSCI (34.9 mg, 0.182 mol), HOBt (12.3 mg, 0.0909 mmol) and N-ethyldiisopropylamine (63.4 µl, 0.364 mmol) were added, followed by stirring at room temperature for 14 hours. The reaction mixture was diluted with dichloromethane (10 ml), and washed with water (10 ml). The organic layer was dried over sodium sulfate, and concentrated under reduced pressure, whereby a crude product of (4-{2-[bis-(4-methoxy-benzyl)-amino]-pyrimidin-5-yl}-2-morpholin-4-yl-5,6-dihydro-pyrrolo[2,3-d]pyrimidin-7-yl)-(4-pyridin-3-yl-piperazin-1-yl)-methanone was obtained as a brown solid (121 mg).

This was dissolved in TFA (2 ml), and N-acetylcysteine (32.7 mg, 0.200 mmol) was added, followed by refluxing for 16 hours. The reaction mixture was concentrated under reduced pressure, and the resulting residue was purified by silica gel column chromatography (dichloromethane/methanol=15/1), to obtain {4-[4-(2-amino-pyrimidin-5-yl)-2-morpholin-4-yl-5,6-dihydro-pyrrolo[2,3-d]pyrimidin-7-yl]-phenyl}-(4-pyridin-3-yl-piperazin-1-yl)-methanone as a yellow powder (39.7 mg, 77%).
¹H-NMR (DMSO-d₆) δ (ppm): 9.16 (2H, s), 8.78-8.47 (2H, m), 8.27 (2H, d, J=8.9 Hz), 8.23-7.94 (2H, m), 7.85 (2H, d, J=8.9 Hz), 7.46 (2H, brs), 4.53-3.59 (20H, m).
ESI (LC-MS positive mode) m/z 565 (M+H)⁺.

Example 1-D-21

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-pyridin-3-yl-piperazin-1-yl)-methanone (D-21)

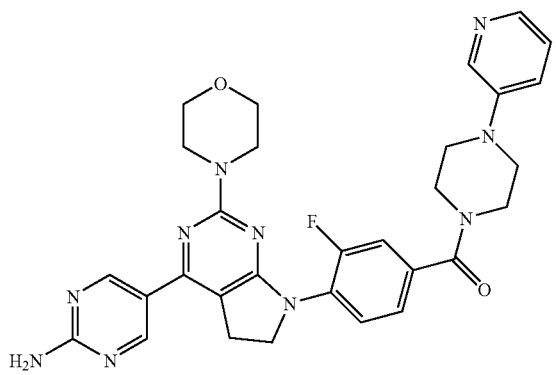

Step A 4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid

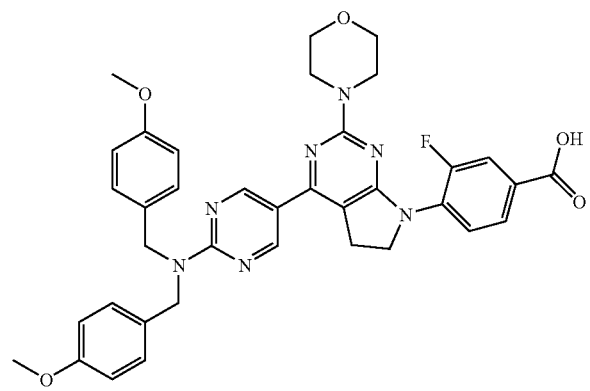

A dimethylformamide solution (15 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (700 mg, 1.30 mmol), 4-bromo-3-fluorobenzoic acid (341 mg, 1.56 mmol), tris(dibenzylideneacetone)dipalladium (29.7 mg, 0.0324 mmol), X-Phos (61.8 mg, 0.130 mmol) and potassium phosphate (881 mg, 4.15 mmol) was degassed under ultrasonic irradiation, followed by stirring at 100° C. for 24 hours under a nitrogen atmosphere. After the reaction mixture was cooled to room temperature, 6M hydrochloric acid (2 ml) and water (15 ml) were added, followed by stirring at room temperature for 1 hour. The precipitated solid was filtered, and ethyl acetate (15 ml) was added, followed by irradiation of ultrasonic wave. The solid was filtered, and washed with ethyl acetate, whereby 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid was obtained as a yellow solid (679 mg, 77%).
ESI (LC-MS positive mode) m/z 678 (M+H)⁺.

Step B

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-pyridin-3-yl-piperazin-1-yl)-methanone (D-21)

To a DMF solution (2 ml) of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A, 1-pyridin-3-yl-piperazine (38.5 mg, 0.235 mmol) obtained in Step A in Example 1-D-20, WSCI (45.3 mg, 0.236 mol), HOBt (16.0 mg, 0.118 mmol) and N-ethyldiisopropylamine (102 µl, 0.472 mmol) were added, followed by stirring at room temperature for 15 hours. The reaction mixture was diluted with dichloromethane (10 ml), and washed with water (10 ml). The organic layer was dried over sodium sulfate, and concentrated under reduced pressure, whereby a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-phenyl]-(4-pyridin-3-yl-piperazin-1-yl)-methanone was obtained as a brown solid (145 mg).

This was dissolved in TFA (2 ml), and N-acetylcysteine (42.4 mg, 0.260 mmol) was added, followed by refluxing for 20 hours. The reaction mixture was concentrated under reduced pressure, and the resulting residue was purified by silica gel column chromatography (dichloromethane/methanol=15/1), to obtain {4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-3-yl-piperazin-1-yl)-methanone as a yellow powder (60.2 mg, 88%).

$^1$H-NMR (DMSO-$d_6$) (ppm): 8.81 (2H, s), 8.44 (1H, d, J=2.5 Hz), 8.20 (1H, d, J=4.9 Hz), 7.90 (1H, dd, J=8.7, 2.5 Hz), 7.78 (1H, t, J=7.9 Hz), 7.71 (1H, dd, J=8.7, 11.5 Hz), 7.46 (1H, d, J=11.5 Hz), 7.34 (1H, d, J=7.9 Hz), 7.16 (2H, brs), 4.12 (2H, t, J=8.2 Hz), 3.77-3.41 (16H, m), 3.31 (2H, t, J=8.2 Hz).

ESI (LC-MS positive mode) m/z 583 (M+H)$^+$.

Example 1-D-22

{4-[4-(2-Amino-pyrimidin-5-yl)-2-morpholin-4-yl-5,6-dihydro-pyrrolo[2,3-d]pyrimidin-7-yl]-3-fluoro-phenyl}-morpholin-4-yl-methanone (D-22)

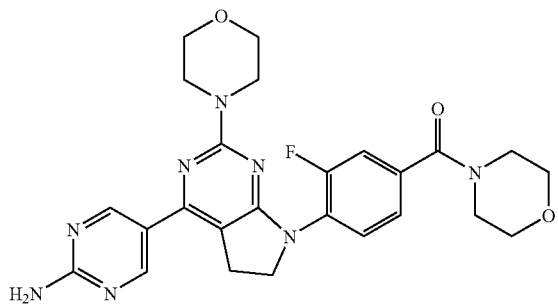

To a 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (120 mg, 0.177 mmol) obtained in Step A in 1-D-21, WSCI (68 mg, 0.35 mmol), HOBt (24 mg, 0.15 mmol) and morpholine (31 μl, 0.35 mmol), dichloromethane (4 ml) was added, followed by stirring for 1 hour. The reaction mixture was washed with water, and subsequently dried over sodium sulfate. The drying agent was removed, followed by concentration and drying. To this, TFA (2 ml) was added, followed by stirring at 80° C. for 4 hours. After TFA was removed under reduced pressure, dichloromethane was added, followed by washing with aqueous sodium hydrogencarbonate solution. The organic layer was dried over sodium sulfate, filtered and concentrated, to obtain a crude product. Purification by silica gel column chromatography (dichloromethane/methanol=10/1) afforded {4-[4-(2-amino-pyrimidin-5-yl)-2-morpholin-4-yl-5,6-dihydro-pyrrolo[2,3-d]pyrimidin-7-yl]-3-fluoro-phenyl}-morpholin-4-yl-methanone as a colorless solid (86 mg, 96%).

$^1$H-NMR (DMSO-$d_6$) δ (ppm): 8.81 (2H, s), 7.75 (1H, t, J=8.1 Hz), 7.41 (1H, m), 7.29 (1H, m), 7.09 (2H, s), 4.13-4.06 (2H, m), 3.71-3.45 (10H, m), 3.36-3.33 (8H, m).

ESI (LC-MS positive mode) m/z 507 (M+H)$^+$.

Example 1-D-23

4-(2-Amino-pyrimidin-5-yl)-2-morpholin-4-yl-5,6-dihydro-pyrrolo[2,3-d]pyrimidine-7-carboxylic acid [4-(4-methyl-piperazin-1-yl)-2,6-difluoro-phenyl]-amide (D-23)

Step A 4-(4-Methyl-piperazin-1-yl)-2,6-difluoro-phenylamine

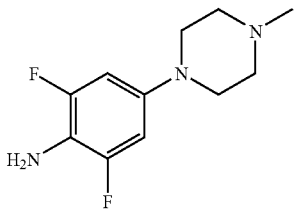

To a solution of N,N-di-Boc-4-bromo-2,6-difluoro-phenylamine (5.59 g, 13.7 mmol) obtained in Step A in Example 1-D-18, palladium acetate (308 mg, 1.37 mmol), S-Phos (1.12 g, 27.4 mmol) and cesium carbonate (8.93 g, 27.4 mmol) in toluene (100 ml), 1-methyl-piperazine (6.08 ml, 54.8 mmol) was added, followed by stirring at 100° C. for 16 hours. After cooling to room temperature, 100 ml of ethyl acetate was added, which was washed with water (100 ml) and saturated aqueous ammonium chloride solution (100 ml). The organic layer was dried over sodium sulfate, and subsequently the solvent was distilled off under reduced pressure. This was purified by silica gel column chromatography (dichloromethane/methanol=50/1 to 25/1), whereby a mixture of N-Boc-4-(4-methyl-piperazin-1-yl)-2,6-difluoro-phenylamine and 1-Boc-4-methylpiperazine was obtained. This was dissolved in ethyl acetate (60 ml), and 6M–HCl aqueous solution (30 ml) was added, followed by stirring at room temperature for 3 hours. To this, 5M-NaOH aqueous solution was added to adjust the pH to 8, followed by extraction with ethyl acetate (100 ml×2), and the organic layer was washed with brine. After the organic layer was dried over sodium sulfate, the solvent was distilled off under reduced pressure. This was purified by silica gel column chromatography (dichloromethane/methanol=50/1 to 20/1), to obtain the desired compound as a brown solid (2.16 g, 69%).

$^1$H-NMR (CDCl$_3$) δ: 6.51-6.38 (2H, m), 3.38 (2H, s), 3.09-3.03 (4H, m), 2.58-2.52 (4H, m), 2.34 (3H, s).

ESI (LC-MS positive mode) m/z 228 (M+H)$^+$.

Step B 4-(2-Amino-pyrimidin-5-yl)-2-morpholin-4-yl-5,6-dihydro-pyrrolo[2,3-d]pyrimidine-7-carboxylic acid [4-(4-methyl-piperazin-1-yl)-2,6-difluoro-phenyl]-amide (D-23)

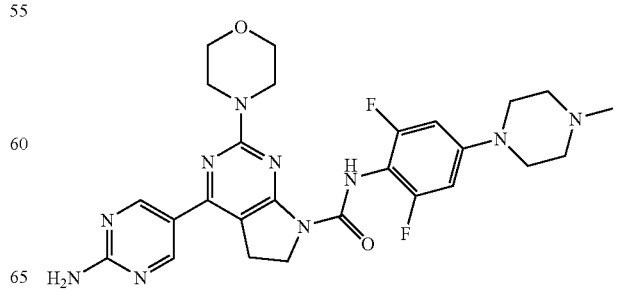

To a solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (2.40 g, 4.45 mmol) in dichloromethane (40 ml), pyridine (719 μl, 8.89 mmol) was added, followed by cooling to 0° C. To this, triphosgene (2.64 g, 8.89 mmol) was added, and the temperature was raised to room temperature, followed by stirring for 2 hours. The solvent was distilled off under reduced pressure, followed by dissolution again in dichloromethane (50 ml). A solution of 4-(4-methyl-piperazin-1-yl)-2,6-difluoro-phenylamine (1.52 g, 6.67 mmol) obtained in the above Step A in dichloromethane (40 ml) was added dropwise to it over 15 minutes, followed by stirring for 1 hour. Dichloromethane (250 ml) was added, followed by adsorption to silica gel, and subsequently the solvent was distilled off under reduced pressure. This was purified by silica gel column chromatography (dichloromethane/methanol=50/1 to 10/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-methyl-piperazin-1-yl)-2,6-difluoro-phenyl]-amide as a crude product. This was dissolved in TFA (40 ml), and N-acetylcysteine (1.45 g, 8.90 mmol) was added, followed by refluxing for 13 hours. After the solvent was distilled off under reduced pressure, 5M-NaOH aqueous solution was added to adjust the pH to 8, and the resulting solid was washed with water (50 ml) and methanol (50 ml), followed by purification by silica gel column chromatography (dichloromethane/methanol=50/1 to 10/1), and further washing with methanol (100 ml), to obtain the desired compound as a colorless solid (1.46 g, 59%).

¹H-NMR (DMSO-D₆) δ: 10.15 (1H, s), 8.84 (2H, s), 7.23 (2H, s), 6.74 (2H, d, J=11.7 Hz), 4.01 (2H, t, J=8.2 Hz), 3.67 (8H, s), 3.29-3.18 (6H, m), 2.46-2.40 (4H, m), 2.22 (3H, s).

ESI (LC-MS positive mode) m/z 553 (M+H)⁺.

Example 1-D-24

4-(2-Amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2,6-difluoro-phenyl]-amide (D-24)

Step A 3,5-difluoro-4-(4-methoxy-benzylamino)-benzonitrile

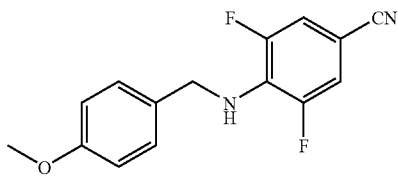

To acetonitrile solution (500 ml) of 3,4,5-trifluoro-benzonitrile (15.0 g, 95.5 mmol), N-ethyldiisopropylamine (33.3 ml, 191 mmol) and 4-methoxy-benzylamine (24.9 ml, 191 mmol) were added, followed by refluxing for 21 hours. The solvent was distilled off under reduced pressure, followed by dissolution in ethyl acetate (500 ml), which was washed with saturated aqueous sodium chloride solution (200 ml). After the organic layer was dried over sodium sulfate, the solvent was distilled off under reduced pressure. This was purified by silica gel column chromatography (dichloromethane), to obtain the desired compound (26.2 g, quant.).

¹H-NMR (CDCl₃) δ: 7.28-7.21 (2H, m), 7.10 (2H, dd, J=7.3, 2.5 Hz), 6.92-6.85 (2H, m), 4.55 (2H, d, J=6.1 Hz), 4.34 (1H, brs), 3.80 (3H, s).

ESI (LC-MS positive mode) m/z 275 (M+H)⁺.

Step B 3,5-Difluoro-4-(4-methoxy-benzylamino)-benzoic acid

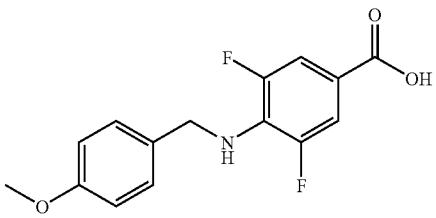

To 3,5-difluoro-4-(4-methoxy-benzylamino)-benzonitrile (26.2 g, 95.5 mmol) obtained in Step A, methanol (300 ml) and 5M-NaOH aqueous solution (150 ml) were added, followed by heating to reflux for 58 hours. The solvent was distilled off under reduced pressure, and dichloromethane (200 ml) was added, followed by extraction with 1M-NaOH aqueous solution (200 ml×3). To the aqueous layer, 6M-HCl aqueous solution was added to adjust the pH to 6, followed by extraction with ethyl acetate (300 ml×2). After the organic layer was dried over sodium sulfate, the solvent was distilled off under reduced pressure. The resulting solid was washed with n-hexane, and the desired compound was obtained as a colorless solid (25.6 g, 91%).

¹H-NMR (CDCl₃) δ: 7.54 (2H, dd, J=8.4, 2.1 Hz), 7.26 (2H, d, J=8.7 Hz), 6.89 (2H, d, J=8.7 Hz), 4.57 (2H, s), 3.81 (3H, s).

ESI (LC-MS positive mode) m/z 292 (M−H)⁺.

Step C

[3,5-difluoro-4-(4-methoxy-benzylamino)-phenyl]-(4-ethyl-piperazin-1-yl)-methanone

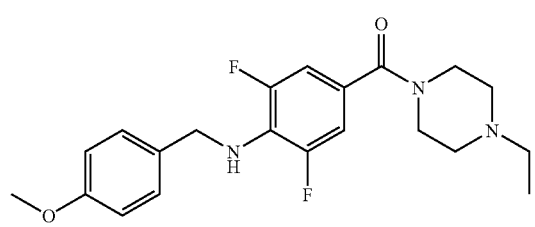

To a solution of 3,5-difluoro-4-(4-methoxy-benzylamino)-benzoic acid (9.00 g, 30.7 mmol) obtained in Step B in acetonitrile (150 ml), N-ethyldiisopropylamine (16.0 ml, 92.1 mmol), HOBt (4.15 g, 30.7 mmol) and WSCI (5.88 g, 30.7 mmol) were added, followed by stirring at room temperature for 10 minutes. To this, 1-ethyl-piperazine (4.68 ml, 368 mmol) was added, followed by stirring at room temperature for 62 hours. N-Ethyldiisopropylamine (5.35 ml, 30.7 mmol), HOBt (2.07 g, 15.3 mmol) and WSCI (2.94 g, 15.3 mmol) were added at room temperature, followed by stirring for 22 hours. The solvent was distilled off under reduced pressure, followed by dissolution in ethyl acetate (300 ml), which was washed with saturated aqueous sodium chloride solution (100 ml) and saturated sodium hydrogencarbonate aqueous solution (100 ml). Subsequently, the organic layer was dried over sodium sulfate, and the solvent was distilled off under reduced pressure. This was purified by silica gel column chromatography (dichloromethane/methanol=50/1 to 25/1), to obtain the desired compound as a brown oil (11.8 g, 99%).

$^1$H-NMR (CDCl$_3$) δ: 7.25 (2H, dd, J=6.4, 2.0 Hz), 6.93 (2H, dd, J=8.1, 2.0 Hz), 6.90-6.85 (2H, m), 4.48 (2H, s), 3.80 (3H, s), 3.63 (4H, s), 2.49-2.41 (6H, m), 1.10 (3H, t, J=7.2 Hz).

ESI (LC-MS positive mode) m/z 390 (M+H)$^+$.

Step D (4-Amino-3,5-difluoro-phenyl)-(4-ethyl-piperazin-1-yl)-methanone

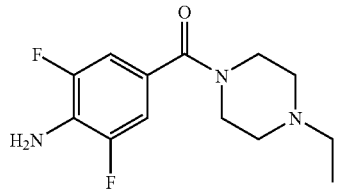

To a solution of [3,5-difluoro-4-(4-methoxy-benzylamino)-phenyl]-(4-ethyl-piperazin-1-yl)-methanone (11.8 g, 30.4 mmol) obtained in Step C in methanol (150 ml), palladium black was added, followed by stirring for 24 hours under a hydrogen gas atmosphere. Acetic acid (15 ml) was added, followed by further stirring for 17 hours at room temperature. This was filtered through Celite, and the solvent was distilled off under reduced pressure. This was purified by silica gel column chromatography (dichloromethane/methanol=100/1 to 10/1), to obtain the desired compound as a brown solid (7.42 g, 91%).

$^1$H-NMR (CDCl$_3$) δ: 6.96 (2H, dd, J=6.6, 2.1 Hz), 3.95 (2H, s), 3.63 (4H, brs), 2.51-2.39 (6H, m), 1.10 (3H, t, J=7.2 Hz).

ESI (LC-MS positive mode) m/z 270 (M+H)$^+$.

Step E 4-(2-Amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2,6-difluoro-phenyl]-amide (D-24)

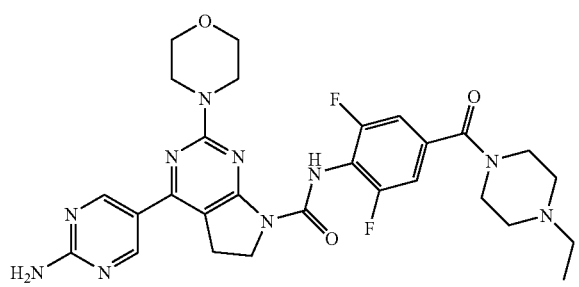

To a solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (2.50 g, 4.63 mmol) in dichloromethane (50 ml), pyridine (749 ml, 9.27 mmol) was added, and triphosgene (2.75 g, 9.27 mmol) was added under ice cooling. After stirring at room temperature for 1 hour, the solvent was distilled off under reduced pressure. To this, dichloroethane (100 ml) was added, and (4-amino-3,5-difluoro-phenyl)-(4-ethyl-piperazin-1-yl)-methanone (4.99 g, 18.5 mmol) obtained in Step D was added, followed by refluxing for 14 hours. The solvent was distilled off under reduced pressure, followed by purification by silica gel column chromatography (dichloromethane/methanol=50/1 to 10/1), to obtain a mixture of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazine-1-carbonyl)-2,6-difluoro-phenyl]-amide and (4-amino-3,5-difluoro-phenyl)-(4-ethyl-piperazin-1-yl)-methanone. This was dissolved in TFA (40 ml), and N-acetylcysteine (1.13 g, 6.95 mmol) was added, followed by refluxing for 14 hours. The solvent was distilled off under reduced pressure. 5M-NaOH aqueous solution was added to adjust the pH to 8, and 500 ml of water was added, followed by extraction with dichloromethane (1 l×3). The solvent was distilled off under reduced pressure. This was purified by silica gel column chromatography (dichloromethane/methanol=40/1 to 10/1), followed by further washing with methanol (100 ml), to obtain the desired compound as a yellow solid (1.31 g, 51%).

$^1$H-NMR (CDCl$_3$) δ: 10.88 (1H, s), 8.91 (2H, s), 7.07 (2H, dd, J=11.2, 3.6 Hz), 5.33 (2H, s), 4.23 (2H, t, J=8.4 Hz), 3.84-3.73 (10H, brm), 3.56-3.49 (2H, brm), 3.26 (2H, t, J=8.4 Hz), 2.59-2.38 (6H, m), 1.11 (3H, t, J=7.2 Hz).

ESI (LC-MS positive mode) m/z 595 (M+H)$^+$.

Example 1-D-25

{3-[4-(2-Amino-pyrimidin-5-yl)-2-morpholin-4-yl-5,6-dihydro-pyrrolo[2,3-d]pyrimidin-7-yl]-4-methyl-phenyl}-morpholin-4-yl-methanone (D-25)

Step A (3-Bromo-4-methyl-phenyl)-morpholin-4-yl-methanone

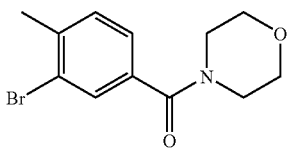

To dichloromethane solution (2 ml) of 3-bromo-4-methyl-benzoic acid (50 mg, 0.23 mmol), WSCI (67 mg, 0.348 mmol), morpholine (24 μl, 0.278 mmol) and N,N-dimethylaminopyridine (28 mg, 0.232 mmol) were added, followed by stirring at room temperature for 16 hours. To the reaction mixture, saturated aqueous ammonium chloride solution was added, followed by extraction twice with ethyl acetate (10 ml). The organic layer was washed with brine (10 ml), and dried over sodium sulfate, followed by distilling off under reduced pressure, and the resulting residue was purified by silica gel column chromatography (dichloromethane/methanol=50/1), whereby (3-bromo-4-methyl-phenyl)-morpholin-4-yl-methanone was obtained as a yellow brown solid (68 mg, 100%).

$^1$H-NMR (CDCl$_3$) δ (ppm): 7.59 (1H, d, J=1.5 Hz), 7.26 (1H, s), 7.25 (1H, d, J=1.5 Hz), 3.69 (8H, s), 2.42 (3H, s).

ESI (LC-MS positive mode) m/z 284, 286 (M)$^+$.

Step B

{3-[4-(2-Amino-pyrimidin-5-yl)-2-morpholin-4-yl-5,6-dihydro-pyrrolo[2,3-d]pyrimidin-7-yl]-4-methyl-phenyl}-morpholin-4-yl-methanone (D-25)

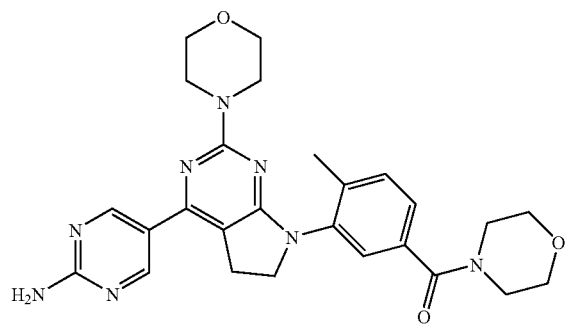

A solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg, 0.093 mmol), (3-bromo-4-methyl-phenyl)-morpholin-4-yl-methanone (68 mg, 0.232 mmol) obtained in Step A, $Pd_2dba_3$ (8.5 mg, 0.0093 mmol), S-Phos (7.6 mg, 0.0186 mmol) and potassium phosphate (39 mg, 0.186 mmol) in dimethylformamide (1 ml) was degassed under ultrasonic irradiation, followed by stirring at 100° C. for 4 hours. After the reaction mixture was cooled to room temperature, saturated aqueous ammonium chloride solution was added, followed by extraction twice with ethyl acetate (10 ml). The organic layer was washed with brine (10 ml), and dried over sodium sulfate, followed by distilling off under reduced pressure, and the resulting residue was purified by silica gel column chromatography (dichloromethane/methanol=50/1), whereby [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-methyl-phenyl]-morpholin-4-yl-methanone was obtained as a brown oil (70 mg, 100%).

This was dissolved in TFA (2 ml), followed by refluxing for 4 hours in the presence of N-acetylcysteine (30 mg, 0.184 mmol). The reaction mixture was concentrated under reduced pressure, and the resulting residue was purified by amino silica gel column chromatography (dichloromethane/acetone=5/1 to 2/1), whereby the desired compound was obtained as a yellow brown powder (20 mg, 43%).

$^1$H-NMR (CDCl$_3$) δ (ppm): 8.89 (2H, s), 7.33 (2H, d, J=8.2 Hz), 7.27 (1H, d, J=0.7 Hz), 7.25 (2H, dd, J=7.7, 1.5 Hz), 5.39 (2H, s), 3.98 (2H, t, J=8.2 Hz), 3.68 (16H, brs), 3.32 (2H, t, J=8.2 Hz), 2.29 (3H, s).

ESI (LC-MS positive mode) m/z 503 (M+H)$^+$.

Example 1-D-26

5-{7-[4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-26)

Step A 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzaldehyde

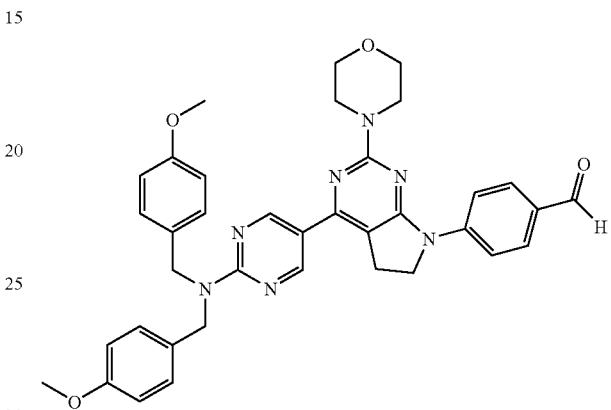

A solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (300 mg, 0.556 mmol), 2-(4-bromo-phenyl)-[1,3]dioxolane (178 mg, 0.778 mmol), $Pd_2dba_3$ (13 mg, 0.014 mmol), X-Phos (27 mg, 0.056 mmol) and potassium phosphate (236 mg, 1.112 mmol) in dimethylformamide (5 ml) was degassed under ultrasonic irradiation followed by stirring at 100° C. for 14 hours. The reaction mixture was cooled to room temperature, and saturated aqueous ammonium chloride solution was added, followed by extraction twice with ethyl acetate (50 ml). The organic layer was washed with brine (50 ml), and dried over sodium sulfate, followed by distilling off under reduced pressure, whereby a crude product of {5-[7-(4-[1,3]dioxolane-2-yl-phenyl)-2-morpholin-4-yl-6,7-dihydro-5H-pyrrolo[2,3-d]pyrimidin-4-yl]-pyrimidin-2-yl}-bis-(4-methoxy-benzyl)-amine was obtained as a brown oil (367 mg, 96%).

This was dissolved in THF (6 ml), and 1M hydrochloric acid (2 ml) was added, followed by stirring at room temperature for 3 hours. To the reaction mixture, saturated aqueous ammonium chloride solution was added, followed by extraction twice with ethyl acetate (50 ml). The organic layer was washed with brine (50 ml), and dried over sodium sulfate, followed by distilling off under reduced pressure, and the resulting residue was purified by silica gel column chromatography (dichloromethane/methanol=30/1), whereby the desired compound was obtained as a dark brown powder (345 mg, 96% 2 steps).

$^1$H-NMR (DMSO-D$_6$) δ (ppm): 9.87 (1H, s), 8.99 (2H, s), 8.06 (2H, d, J=8.8 Hz), 7.91 (2H, d, J=8.8 Hz), 7.21 (4H, d, J=8.3 Hz), 6.89 (4H, d, J=8.3 Hz), 4.79 (4H, s), 3.73 (6H, s), 3.34 (4H, s).

ESI (LC-MS positive mode) m/z 644 (M+H)$^+$.

The desired compound in Step A can also be synthesized by the following method.

A solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg, 0.093 mmol), 4-bromo-benzaldehyde (22 mg, 0.121 mmol), Pd$_2$dba$_3$ (8.5 mg, 0.0093 mmol), S-Phos (7.6 mg, 0.0186 mmol) and potassium phosphate (39 mg, 0.186 mmol) in dimethylformamide (1 ml) was degassed under ultrasonic irradiation, followed by stirring at 100° C. for 16 hours. The reaction mixture was cooled to room temperature, and saturated aqueous ammonium chloride solution was added, followed by extraction twice with ethyl acetate (10 ml). The organic layer was washed with brine (10 ml), and dried over sodium sulfate, followed by distilling off under reduced pressure, and the resulting residue was washed with ether, whereby the desired compound was obtained as a dark brown powder (29 mg, 49%).

Step B

5-{7-[4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-26)

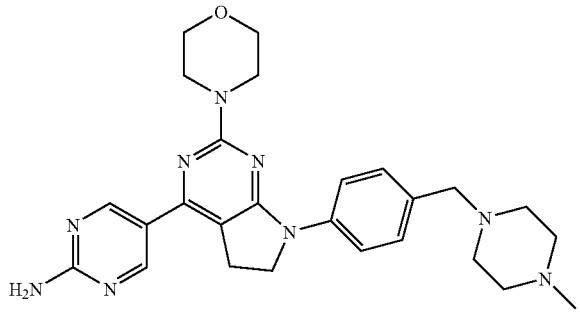

To a solution of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzaldehyde (76 mg, 0.118 mmol) in dichloromethane (2 ml), 1-methylpiperazine (40 µl, 0.354 mmol), sodium triacetoxy borohydride (100 mg, 472 mmol) and acetic acid (12.6 µl, 0.236 mmol) were added, followed by stirring at room temperature for 40 hours. To the reaction mixture, saturated aqueous ammonium chloride solution was added, followed by extraction twice with ethyl acetate (10 ml). The organic layer was washed with brine (10 ml), and dried over sodium sulfate, followed by distilling off under reduced pressure, and the resulting residue was purified by silica gel column chromatography (dichloromethane/2M-ammonia methanol=100/1 to 30/1), whereby bis-(4-methoxy-benzyl)-(5-{7-[4-(4-methyl-piperazin-1-ylmethyl)-phenyl]-2-morpholin-4-yl-6,7-dihydro-5H-pyrrolo[2,3-d]pyrimidin-4-yl}-pyrimidin-2-yl)-amine was obtained as a brown powder (44 mg, 51%).

This was dissolved in TFA (1 ml), followed by refluxing for 4 hours in the presence of N-acetylcysteine (20 mg, 120 mmol). The reaction mixture was concentrated under reduced pressure, and the resulting residue was purified by silica gel column chromatography (dichloromethane/2M-ammonia methanol=100/1 to 10/1), whereby the desired compound was obtained as a yellow brown powder (26 mg, 90%).

$^1$H-NMR (DMSO-D$_6$) δ (ppm): 8.81 (2H, s), 7.82 (2H, d, J=8.3 Hz), 7.33 (2H, d, J=8.3 Hz), 7.08 (2H, s), 4.08 (2H, t, J=7.3 Hz), 3.70 (4H, s), 3.56 (2H, s), 3.34 (10H, brs), 3.00 (4H, s), 2.63 (3H, s).

ESI (LC-MS positive mode) m/z 488 (M+H)$^+$.

Example 1-D-27

[4-(2-Amino-pyrimidin-5-yl)-2-morpholin-4-yl-5,6-dihydro-pyrrolo[2,3-d]pyrimidin-7-yl]-phenyl-methanone (D-27)

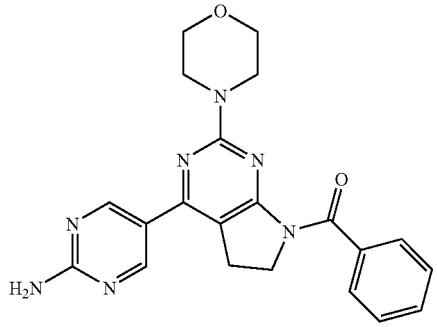

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and benzoyl chloride (32 µl) instead of acetic anhydride, in the same manner as Example 1-D-01, a crude product of (4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl-methanone was obtained, and then the PMB groups were removed according to Deprotection method 1, to obtain the desired compound (D-27) as a yellow solid (3.8 mg, 20%).

$^1$H-NMR (DMSO-d$_6$) δ: 8.79 (2H, s), 7.49-7.39 (5H, m), 7.15 (2H, s), 4.11 (2H, t, J=8.1 Hz), 3.42-3.27 (8H m), 3.24 (2H, t, J=8.1 Hz).

ESI (LC-MS positive mode) m/z 404 (M+H)$^+$.

Example 1-D-28

4-(2-Amino-pyrimidin-5-yl)-2-morpholin-4-yl-5,6-dihydro-pyrrolo[2,3-d]pyrimidine-7-carboxylic acid phenylamide (D-28)

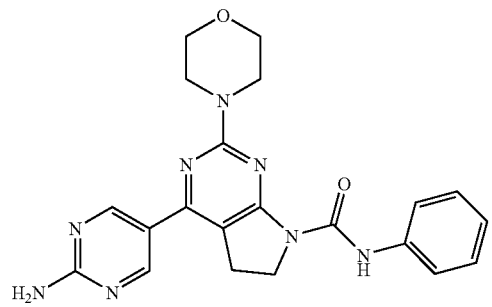

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and phenylisocyanate (30 µl) instead of ethylisocyanate, in the same manner as Example 1-D-03, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid phenylamide was obtained, and then the PMB groups were removed according to Deprotection method 1', to obtain the desired compound (D-28) as a yellow solid (4.2 mg, 25%).

¹H-NMR (DMSO-d₆) δ: 8.85 (2H, s), 7.53 (2H, d, J=7.8 Hz), 7.36 (2H, t, J=8.1 Hz), 7.19 (2H, s), 7.07 (1H, t, J=7.6 Hz), 4.05 (2H, t, J=8.5 Hz), 3.79-3.73 (8H, m), 3.23 (2H, t, J=8.5 Hz).

ESI (LC-MS positive mode) m/z 419 (M+H)⁺.

Example 1-D-29

{[4-(2-Amino-pyrimidin-5-yl)-2-morpholin-4-yl-5,6-dihydro-pyrrolo[2,3-d]pyrimidine-7-carbonyl]-amino}-acetic acid ethyl ester (D-29)

Step A

[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-acetic acid ethyl ester

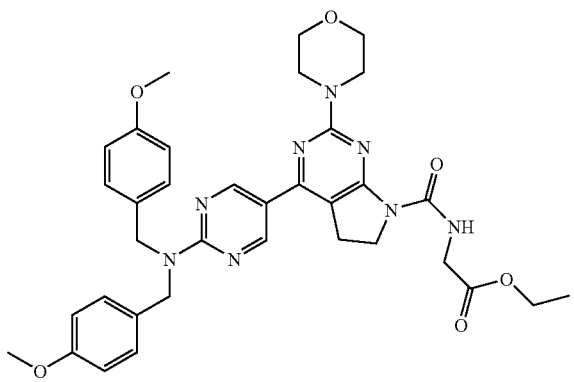

To a dichloroethane solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg), triethylamine (260 μl) and isocyanato-acetic acid ethyl ester (208 μl) were added, followed by refluxing for 3 hours. After this was cooled to room temperature, saturated aqueous ammonium chloride solution was added, and passed through Whatman tube. The resulting organic layer was concentrated under reduced pressure, followed by purification by silica gel column chromatography (dichloromethane/methanol=/) column chromatography (dichloromethane/methanol=1/0 to 100/1), to obtain a crude product of the desired compound (127 mg, quant.).

Step B

{[4-(2-Amino-pyrimidin-5-yl)-2-morpholin-4-yl-5,6-dihydro-pyrrolo[2,3-d]pyrimidine-7-carbonyl]-amino}-acetic acid ethyl ester (D-29)

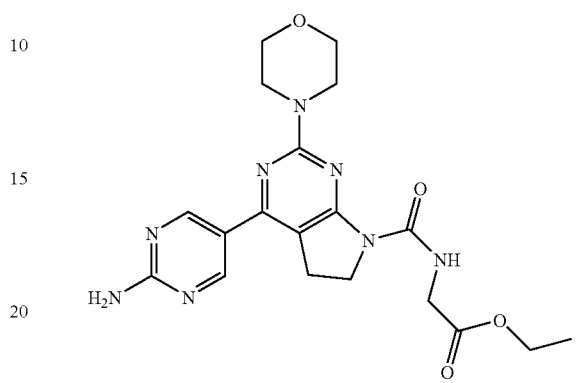

Using [(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-acetic acid ethyl ester (30 mg) obtained in Step A, the PMB groups were removed according to Deprotection method 1, to obtain the desired compound (D-29) as a yellow solid (8.5 mg, yield 31%).

¹H-NMR (DMSO-d₆) δ: 8.98 (1H, t, J=5.4 Hz), 8.82 (2H, s), 7.15 (2H, s), 4.15 (2H, q, J=7.3 Hz), 4.11 (2H, d, J=3.9 Hz), 3.95 (2H, t, J=8.5 Hz), 3.71 (8H, dd, J=16.6, 4.9 Hz), 3.20 (2H, t, J=8.5 Hz), 1.21 (3H, t, J=7.3 Hz).

ESI (LC-MS positive mode) m/z 429 (M+H)⁺.

Example 1-D-30

3-{[4-(2-Amino-pyrimidin-5-yl)-2-morpholin-4-yl-5,6-dihydro-pyrrolo[2,3-d]pyrimidine-7-carbonyl]-amino}-propionic acid ethyl ester (D-30)

Step A

3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid ethyl ester

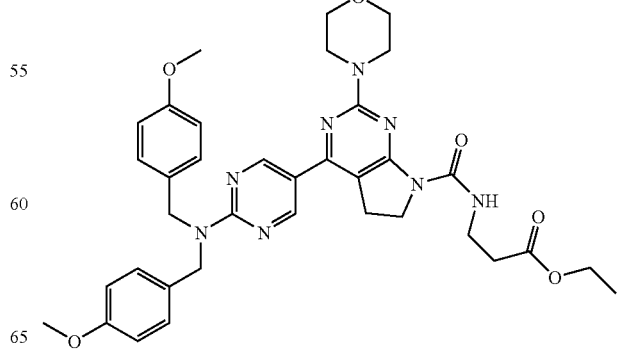

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 3-isocyanato-propionic acid ethyl ester (244 μl) instead of isocyanato-acetic acid ethyl ester, in the same manner as Example 1-D-29 in Step A, a crude product of the desired compound was obtained (114 mg, quant.).

Step B

3-{[4-(2-Amino-pyrimidin-5-yl)-2-morpholin-4-yl-5,6-dihydro-pyrrolo[2,3-d]pyrimidine-7-carbonyl]-amino}-propionic acid ethyl ester (D-30)

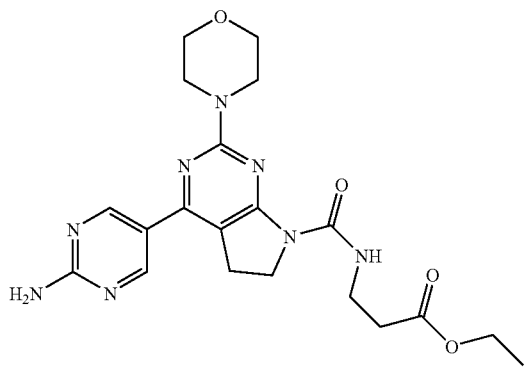

Using 3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid ethyl ester (30 mg) obtained in Step A, the PMB groups were removed according to Deprotection method 1, the desired compound (D-30) was obtained as a yellow solid (3.7 mg, 19%).
$^1$H-NMR (DMSO-$d_6$) δ: 8.80 (2H, s), 7.15 (2H, s), 4.07 (2H, q, J=7.3 Hz), 3.94 (2H, t, J=8.5 Hz), 3.70 (8H, s), 3.51 (2H, q, J=6.1 Hz), 3.17 (2H, t, J=8.5 Hz), 2.56 (2H, t, J=6.1 Hz), 1.17 (3H, t, J=7.3 Hz).
ESI (LC-MS positive mode) m/z 443 (M+H)$^+$.

Example 1-D-31

4-(2-Amino-pyrimidin-5-yl)-2-morpholin-4-yl-5,6-dihydro-pyrrolo[2,3-d]pyrimidine-7-carboxylic acid carbamoylmethyl-amide (D-31)

Step A

[(4-{2-[Bis-(4-methoxy-benzyl)-amino]-pyrimidin-5-yl}-2-morpholin-4-yl-5,6-dihydro-pyrrolo[2,3-d]pyrimidine-7-carbonyl)-amino]-acetic acid

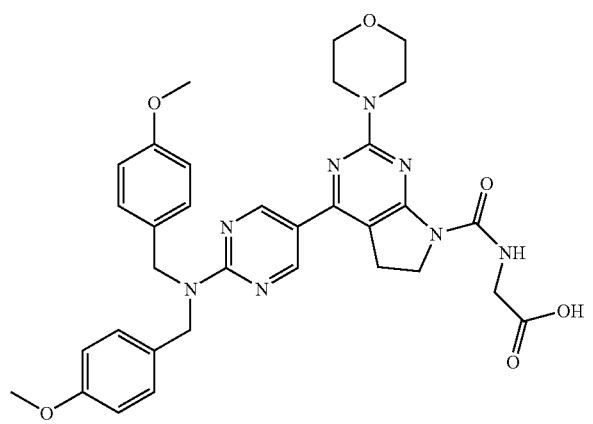

To a THF solution (3 ml) of [(4-{2'-[bis-(4-methoxy-benzyl)-amino]-[2,5']bipyrimidinyl-5-yl}-2-morpholin-4-yl-5,6-dihydro-pyrrolo[2,3-d]pyrimidine-7-carbonyl)-amino]-acetic acid ethyl ester (97 mg) obtained in Step A in Example 1-D-29, 5M-NaOH aqueous solution (1.5 ml) was added, followed by refluxing for 1 hour. The resulting solid was filtered, to obtain a crude product of the desired compound (51 mg, 54%).

Step B

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid carbamoyl methyl-amide

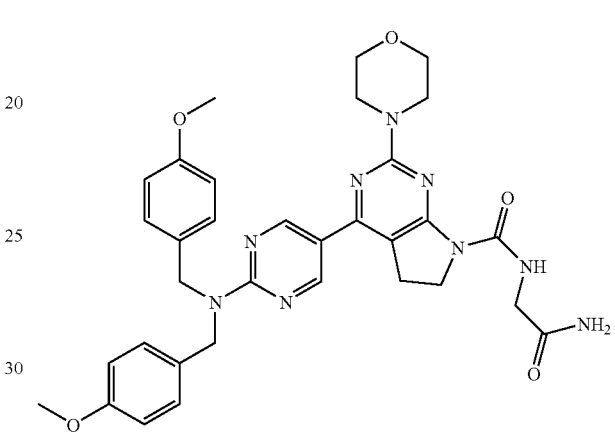

To a DMF solution (1 ml) of [(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-acetic acid (30 mg) obtained in Step A, ammonium chloride (5.0 mg), N-ethyldiisopropylamine (41 μl), HOBt (6.3 mg) and WSCI (13.4 mg) was added, followed by stirring at 80° C. for 3 hours. To this, water was added, and the resulting solid was filtered, to obtain a crude product of the desired compound (27 mg, 91%).

Step C 4-(2-Amino-pyrimidin-5-yl)-2-morpholin-4-yl-5,6-dihydro-pyrrolo[2,3-d]pyrimidine-7-carboxylic acid carbamoyl methyl-amide (D-31)

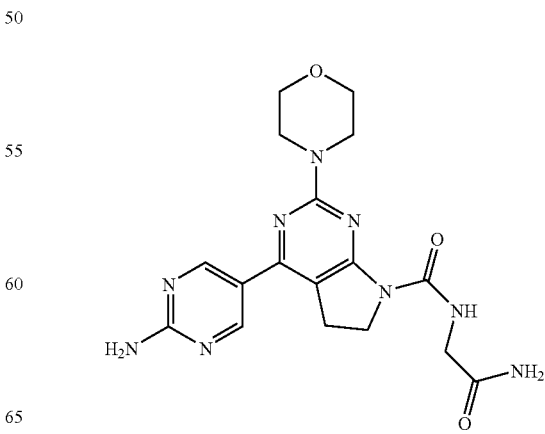

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid carbamoyl methyl-amide (27 mg) obtained in Step B, the PMB groups were removed according to Deprotection method 1, to obtain the desired compound (D-31) as a yellow powder (13.8 mg, yield 81%).

$^1$H-NMR (DMSO-d$_6$) δ: 9.10 (1H, t, J=4.4 Hz), 8.81 (2H, s), 7.54 (1H, brs), 7.23 (1H, brs), 7.13 (2H, s), 3.94 (2H, t, J=8.5 Hz), 3.90 (2H, d, J=4.4 Hz), 3.81 (4H, t, J=4.4 Hz), 3.67 (4H, t, J=4.4 Hz), 3.18 (2H, t, J=8.5 Hz).

ESI (LC-MS positive mode) m/z 400 (M+H)$^+$.

Example 1-D-32

4-(2-Amino-pyrimidin-5-yl)-2-morpholin-4-yl-5,6-dihydro-pyrrolo[2,3-d]pyrimidine-7-carboxylic acid (2-carbamoyl-ethyl)-amide (D-32)

Step A

3-[(4-{2-[Bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid

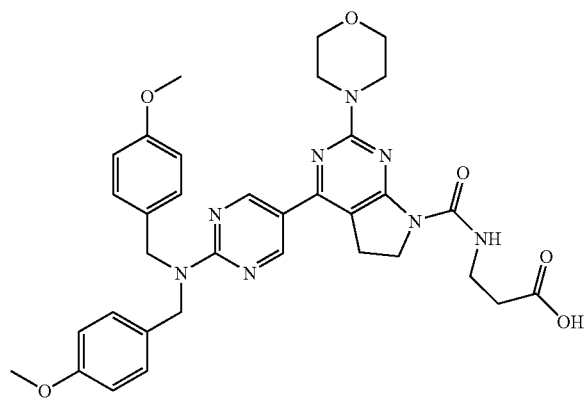

To a THF solution (3 ml) of 3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid ethyl ester (84 mg) obtained in Step A in Example 1-D-30, 5M-NaOH aqueous solution (1.5 ml) was added, followed by refluxing for 1 hour. The resulting solid was filtered, to obtain a crude product of the desired compound (78.2 mg, 97%)

Step B

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (2-carbamoyl-ethyl)-amide

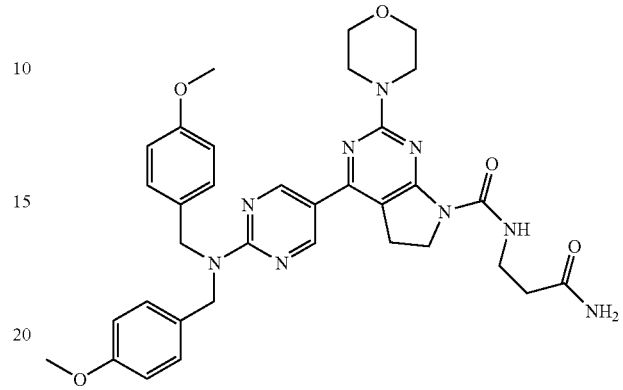

To a DMF solution (1 ml) of 3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid (40 mg) obtained in Step A, ammonium chloride (6.5 mg), N-ethyldiisopropylamine (53 µl), HOBt (8.3 mg) and WSCI (17.6 mg) were added, followed by stirring at 80° C. for 3 hours. To this, water was added and the resulting solid was filtered, to obtain a crude product of the desired compound (33.5 mg, 84%).

Step C 4-(2-Amino-pyrimidin-5-yl)-2-morpholin-4-yl-5,6-dihydro-pyrrolo[2,3-d]pyrimidine-7-carboxylic acid (2-carbamoyl-ethyl)-amide (D-32)

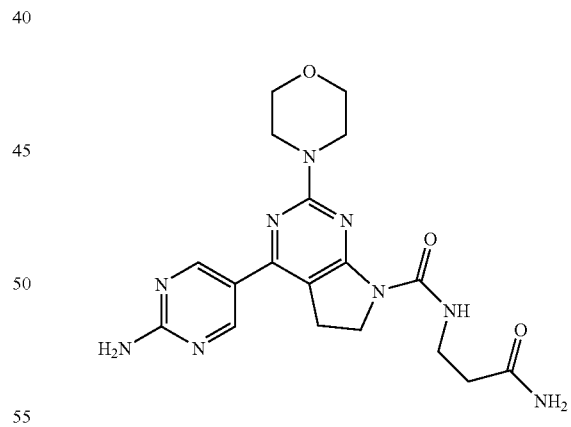

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-carbamoyl-ethyl)-amide (33.5 mg) obtained in Step B, the PMB groups were removed according to Deprotection method 1, to obtain the desired compound (D-32) as a yellow powder (17.5 mg, yield 83%).

$^1$H-NMR (DMSO-d$_6$) δ: 8.80 (2H, s), 8.75 (1H, t, J=5.6 Hz), 7.34 (1H, brs), 7.13 (2H, s), 6.83 (1H, brs), 3.93 (2H, t, J=8.5 Hz), 3.69 (8H, brs), 3.48-3.43 (2H, m), 3.16 (2H, t, J=8.5 Hz), 2.33-2.31 (2H, m).

ESI (LC-MS positive mode) m/z 414 (M+H)$^+$.

Example 1-D-33

{[4-(2-Amino-pyrimidin-5-yl)-2-morpholin-4-yl-5,6-dihydro-pyrrolo[2,3-d]pyrimidine-7-carbonyl]-amino}-acetic acid (D-33)

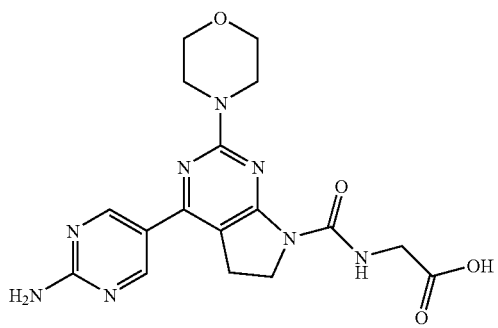

Using [(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-acetic acid (20 mg) obtained in Step A in Example 1-D-31, the PMB groups were removed according to Deprotection method 1, the desired compound (D-33) was obtained as a yellow solid (10.8 mg, yield 86%).

$^1$H-NMR (DMSO-d$_6$) δ: 9.02 (1H, s), 8.81 (2H, s), 7.14 (2H, s), 3.97-3.91 (4H, m), 3.80-3.75 (4H, m), 3.69-3.65 (4H, m), 3.18 (2H, t, J=8.3 Hz).

ESI (LC-MS positive mode) m/z 401 (M+H)$^+$.

Example 1-D-34

3-{[4-(2-Amino-pyrimidin-5-yl)-2-morpholin-4-yl-5,6-dihydro-pyrrolo[2,3-d]pyrimidine-7-carbonyl]-amino}-propionic acid (D-34)

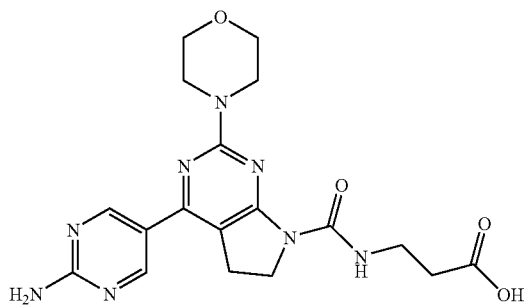

Using 3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-propionic acid (38 mg) obtained in Step A in Example 1-D-32, the PMB groups were removed according to Deprotection method 1, to obtain the desired compound (D-34) as a yellow solid (12.5 mg, yield 52%).

$^1$H-NMR (DMSO-d$_6$) δ: 8.80 (2H, s), 7.13 (2H, s), 3.93 (2H, t, J=8.5 Hz), 3.68 (8H, brs), 3.44-3.46 (2H, m), 3.15 (2H, t, J=8.5 Hz), 2.45 (2H, t, J=5.9 Hz).

ESI (LC-MS positive mode) m/z 415 (M+H)$^+$.

Example 1-D-35

4-[4-(2-Amino-pyrimidin-5-yl)-2-morpholin-4-yl-5,6-dihydro-pyrrolo[2,3-d]pyrimidin-7-yl]-4-oxo-butyric acid (D-35)

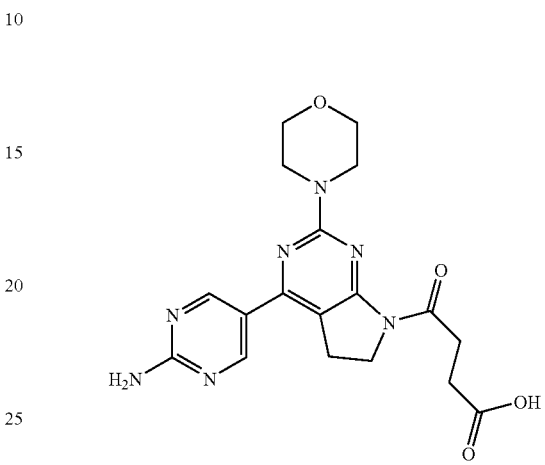

A dichloroethane solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol) and succinic anhydride (36 mg, 0.37 mmol) was stirred at 80° C. for 15 hours. Dichloroethane was removed under reduced pressure, and methanol was added to the residue, followed by filtering the suspended mixture, whereby 100 mg of a crude product of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butyric acid was obtained as a colorless solid. ESI (LC-MS positive mode) m/z 640 (M+H)$^+$.

The obtained 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butyric acid crude product (40 mg) was dissolved in TFA (2 ml), followed by refluxing for 4.5 hours. The reaction mixture was concentrated under reduced pressure. To the resulting residue, sodium hydrogencarbonate aqueous solution was added, followed by washing with dichloromethane. The aqueous layer was neutralized with 1M–HCl aqueous solution, and the resulting precipitate was filtered, followed by washing with water, to obtain 4-[4-(2-amino-pyrimidin-5-yl)-2-morpholin-4-yl-5,6-dihydro-pyrrolo[2,3-d]pyrimidin-7-yl]-4-oxo-butyric acid as a colorless powder (16 mg, 67%).

$^1$H-NMR (DMSO-D$_6$) δ: 9.05 (2H, s), 4.12 (2H, t, J=8.2 Hz), 3.93-3.73 (8H, m), 3.36 (2H, t, J=6.4 Hz), 2.72-2.67 (2H, m), 3.20 (2H, t, J=8.2 Hz), 2.72-2.64 (2H, m).

ESI (LC-MS positive mode) m/z 400 (M+H)$^+$.

Examples 1-D-36 and 1-D-37

5-[7-(5-Bromo-pyridin-2-yl)-2-morpholin-4-yl-6,7-dihydro-5H-pyrrolo[2,3-d]pyrimidin-4-yl]-pyrimidin-2-ylamine (D-36)

5-[7-(6-Fluoro-pyridin-3-yl)-2-morpholin-4-yl-6,7-dihydro-5H-pyrrolo[2,3-d]pyrimidin-4-yl]-pyrimidin-2-ylamine (D-37)

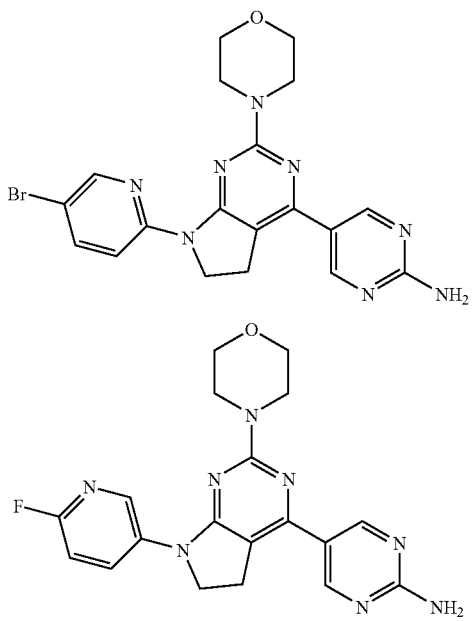

From bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and 2-fluoro-5-bromopyridine (30 µl), in the same manner as Step B in Example 1-D-25, crude products of {5-[7-(5-bromo-pyridin-2-yl)-2-morpholin-4-yl-6,7-dihydro-5H-pyrrolo[2,3-d]pyrimidin-4-yl]-pyrimidin-2-yl}-bis-(4-methoxy-benzyl)-amine and {5-[7-(6-fluoro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine were obtained, and then for each products the PMB groups were removed according to Deprotection method 3, to obtain the desired compound (D-36) as a colorless powder (5 mg, 32%) and as a colorless powder (D-37: 7 mg, 63%).

D-36:

$^1$H-NMR (DMSO-$d_6$) δ (ppm): 8.83 (2H, s), 8.57 (1H, d, J=8.7 Hz), 8.46 (1H, d, J=2.5 Hz), 8.02 (1H, dd, J=8.7, 2.5 Hz), 4.20 (3H, t, J=7.9 Hz), 3.72 (8H, m), 3.26 (2H, t, J=7.9 Hz).

ESI (LC-MS positive mode) m/z 455, 457 (M+H)$^+$.

D-37:

$^1$H-NMR (DMSO-$d_6$) δ (ppm): 8.82 (2H, d, J=1.2 Hz), 8.62 (1H, s), 8.49 (1H, t, J=7.9 Hz), 7.24 (1H, m), 7.12 (2H, s), 4.11 (2H, t, J=8.2 Hz), 3.70 (8H, s), 3.37 (2H, t, J=8.2 Hz).

ESI (LC-MS positive mode) m/z 395 (M+H)$^+$.

Example 1-D-38

4-[4-(2-Amino-pyrimidin-5-yl)-2-morpholin-4-yl-5,6-dihydro-pyrrolo[2,3-d]pyrimidin-7-yl]-4-oxo-butylamide (D-38)

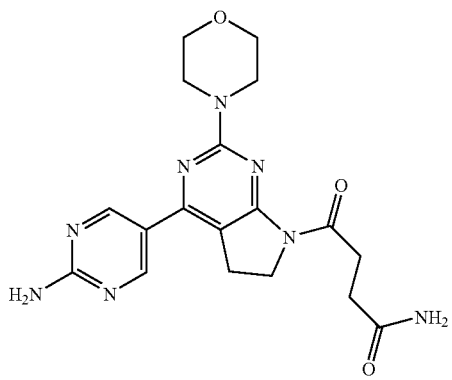

Using 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butyric acid (50 mg, 0.078 mmol) obtained in Example 1-D-35 and ammonium chloride (0.23 mmol) instead of morpholine, in the same manner as Example 1-D-22, a crude product of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butylamide was obtained as a colorless solid.

ESI (LC-MS positive mode) m/z 639 (M+H)$^+$.

The obtained 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butylamide crude product was deprotected according to the above deprotection reaction method 2, i.e., dissolved in TFA (2 ml), followed by refluxing for 4 hours. The reaction mixture was concentrated under reduced pressure, and the resulting residue was purified by silica gel column chromatography (dichloromethane/methanol=10/1), to obtain 4-[4-(2-amino-pyrimidin-5-yl)-2-morpholin-4-yl-5,6-dihydro-pyrrolo[2,3-d]pyrimidin-7-yl]-4-oxo-butylamide (3 mg, 10%) as a colorless powder.

$^1$H-NMR(CF$_3$COOD) δ: 9.28 (2H, brs), 4.50-4.41 (2H, m), 4.19-3.89 (10H, m), 3.55-3.34 (2H, m), 3.11-2.76 (2H, m).

ESI (LC-MS positive mode) m/z 399 (M+H)$^+$.

Example 1-D-39

4-(2-Amino-pyrimidin-5-yl)-2-morpholin-4-yl-5,6-dihydro-pyrrolo[2,3-d]pyrimidine-7-carboxylic acid 2-methoxy-ethyl ester (D-39)

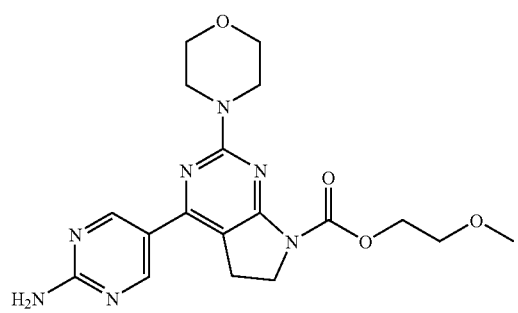

In the same manner as Example 1-D-01, using bis-(4-methoxy-benzyl)-[5-(2-morpholin-4-yl-6,7-dihydro-5H-pyrrolo[2,3-d]pyrimidin-4-yl)-pyrimidin-2-yl]-amine (40 mg) and 2-methoxy-ethyl chloroformate (0.021 ml) instead of acetic anhydride, a colorless oily crude product (60 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid 2-methoxy-ethyl ester was obtained. The obtained colorless oily crude product (60 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid 2-methoxy-ethyl ester was subjected to deprotection reaction according to the above deprotection reaction method 2, to obtain 4-(2-amino-pyrimidin-5-yl)-2-morpholin-4-yl-5,6-dihydro-pyrrolo[2,3-d]pyrimidine-7-carboxylic acid 2-methoxy-ethyl ester as a colorless solid (21 mg, 72%).

$^1$H-NMR (CDCl$_3$) δ: 8.89 (2H, s), 5.34 (2H, brs), 4.42 (2H, t, J=4.5 Hz), 4.09 (2H, t, J=8.4 Hz), 3.91-3.74 (8H, m), 3.70 (2H, t, J=4.5 Hz), 3.40 (3H, s), 3.19 (2H, t, J=8.6 Hz).

ESI (LC-MS positive mode) m/z 402 (M+H)$^+$.

Example 1-D-40

4-(2-Amino-pyrimidin-5-yl)-2-morpholin-4-yl-5,6-dihydro-pyrrolo[2,3-d]pyrimidine-7-carboxylic acid allyl ester (D-40)

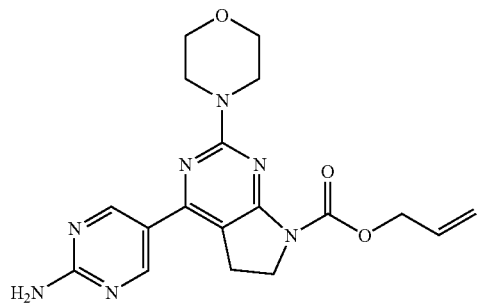

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (41.4 mg, 0.0769 mmol) and allyl chloroformate (17 μl, 0.160 mmol) instead of acetic anhydride, in the same manner as Example 1-D-01, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid allyl ester was obtained, and deprotection was further carried out according to the above deprotection reaction method 1, to obtain the desired compound (D-40) as a colorless powder (27.0 mg, 92%).

$^1$H-NMR (CDCl$_3$) δ (ppm): 8.89 (2H, s), 6.01 (2H, ddt, J=17.3, 10.4, 5.6 Hz), 5.42 (2H, ddt, J=17.3, 1.5, 1.5 Hz), 5.29 (2H, ddt, J=10.4, 1.5, 1.3 Hz), 4.78 (2H, ddd, J=5.6, 1.5, 1.3 Hz), 4.10 (2H, t, J=8.6 Hz), 3.89-3.73 (8H, m), 3.19 (2H, t, J=8.6 Hz).

ESI (LC-MS positive mode) m/z 384 (M+H)$^+$.

Example 1-D-41

4-[4-(2-Amino-pyrimidin-5-yl)-2-morpholin-4-yl-5,6-dihydro-pyrrolo[2,3-d]pyrimidin-7-yl]-N-(2-dimethylamino-ethyl)-benzamide (D-41)

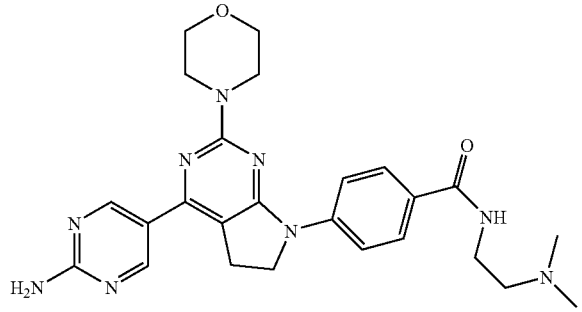

Using 4-(4-{2-[bis-(4-methoxy-benzyl)-amino]-pyrimidin-5-yl}-2-morpholin-4-yl-5,6-dihydro-pyrrolo[2,3-d]pyrimidine-7-yl)-benzoic acid (53.4 mg) obtained in Step A in Example 1-D-19 and N,N-dimethyl ethylenediamine (18 μl) instead of 3-(aminomethyl)pyridine, in the same manner as Step B in Example 1-D-19, 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(2-dimethylamino-ethyl)-benzamide was obtained as a crude product. Then the PMB groups were removed according to Deprotection method 3, to obtain the desired compound (D-41) as a colorless solid (21.7 mg, 55%).

$^1$H-NMR (DMSO-d$_6$) δ: 8.82 (2H, s), 8.25 (1H, t, J=5.6 Hz), 7.95-7.86 (4H, m), 7.07 (2H, s), 4.12 (2H, t, J=8.3 Hz), 3.77-3.75 (8H, m), 3.38-3.25 (4H, m), 2.40 (2H, t, J=6.8 Hz), 2.18 (6H, s).

ESI (LC-MS positive mode) m/z 490 (M+H)$^+$.

Example 1-D-42

{4-[4-(2-Amino-pyrimidin-5-yl)-2-morpholin-4-yl-5,6-dihydro-pyrrolo[2,3-d]pyrimidin-7-yl]-phenyl}-(4-methyl-piperazin-1-yl)-methanone (D-42)

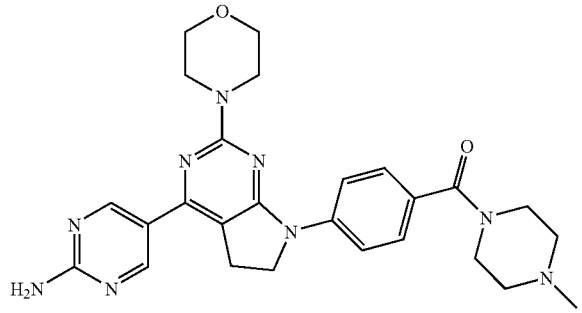

Using 4-(4-{2-[bis-(4-methoxy-benzyl)-amino]-pyrimidin-5-yl}-2-morpholin-4-yl-5,6-dihydro-pyrrolo[2,3-d]pyrimidine-7-yl)-benzoic acid (53.4 mg) obtained in Step A in Example 1-D-19 and 1-methyl-piperazine (18 μl) instead of 3-(aminomethyl)pyridine, in the same manner as Step B in Example 1-D-19, [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-(4-methyl-piperazin-1-yl)-methanone was obtained as a crude product. Then the PMB groups were removed according to Deprotection method 3 in Example, to obtain the desired compound (D-42) as a colorless solid (9.0 mg, 22%).

¹H-NMR (DMSO-d₆) δ: 8.80 (2H, s), 7.89 (2H, d, J=8.8 Hz), 7.42 (2H, d, J=8.8 Hz), 7.04 (2H, s), 4.10 (2H, t, J=8.3 Hz), 3.74-3.65 (8H, m), 3.55-3.45 (4H, brm), 3.45-3.42 (2H, m), 2.34-2.27 (4H, brm), 2.18 (3H, s).
ESI (LC-MS positive mode) m/z 502 (M+H)⁺.

Example 1-D-43

N-{4-[4-(2-amino-pyrimidin-5-yl)-2-morpholin-4-yl-5,6-dihydro-pyrrolo[2,3-d]pyrimidin-7-yl]-phenyl}-acetamide (D-43)

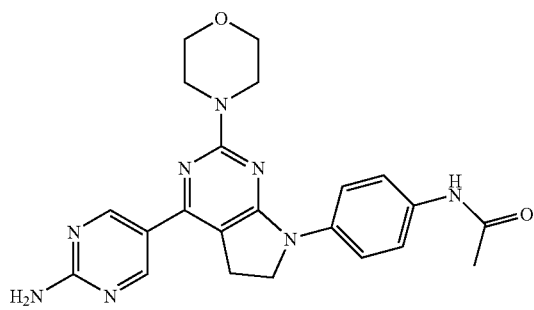

From bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and acetyl-(4-bromo-phenyl)-carbamic acid tert-butyl ester (prepared from N-(4-bromo-phenyl)-acetamide and di-t butyl carbonate in acetonitrile in the presence of DMAP, 94 mg) instead of 4-bromobenzoic acid methyl ester in Example 1-D-08, in the same manner as Example 1-D-08, a crude product of acetyl-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-carbamic acid tert-butyl ester was obtained, and then the PMB groups were removed according to Deprotection method 1, to obtain the desired compound (D-43) as a pale yellow powder (7 mg, 17%).
¹H-NMR (DMSO-d₆) δ (ppm): 9.87 (1H, s), 8.80 (2H, s), 7.74 (2H, J=9.2 Hz), 7.58 (2H, J=9.2 Hz), 7.06 (2H, s), 4.05 (2H, t, J=7.6 Hz), 3.69 (8H, brs), 3.27 (2H, t, J=7.6 Hz), 2.03 (3H, s).
ESI (LC-MS positive mode) m/z 433 (M+H)⁺.

Example 1-D-44

N-{4-[4-(2-amino-pyrimidin-5-yl)-2-morpholin-4-yl-5,6-dihydro-pyrrolo[2,3-d]pyrimidin-7-yl]-phenyl}-methane sulfonamide (D-44)

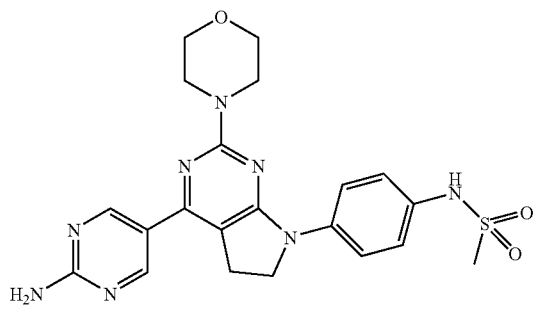

From bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and mesyl-(4-bromo-phenyl)-carbamic acid tert-butyl ester (prepared from N-(4-bromo-phenyl)-methane sulfonamide and di-t butyl carbonate in acetonitrile in the presence of DMAP, 105 mg) instead of 4-bromobenzoic acid methyl ester in Example 1-D-08, in the same manner as Example 1-D-08, a crude product of mesyl-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-carbamic acid tert-butyl ester was obtained, and then the PMB groups were removed according to Deprotection method 1, to obtain the desired compound (D-44) as a pale yellow powder (12 mg, 10%).
¹H-NMR (DMSO-d₆) δ (ppm): 9.56 (1H, s), 8.81 (2H, s), 7.82 (2H, d, J=8.9 Hz), 7.24 (2H, d, J=8.9 Hz), 7.08 (2H, s), 4.06 (2H, t, J=8.5 Hz), 3.70 (8H, brs), 3.29 (2H, t, J=8.5 Hz), 2.95 (3H, s).
ESI (LC-MS positive mode) m/z 469 (M+H)⁺.

Example 1-D-45

N-{3-[4-(2-amino-pyrimidin-5-yl)-2-morpholin-4-yl-5,6-dihydro-pyrrolo[2,3-d]pyrimidin-7-yl]-phenyl}-acetamide (D-45)

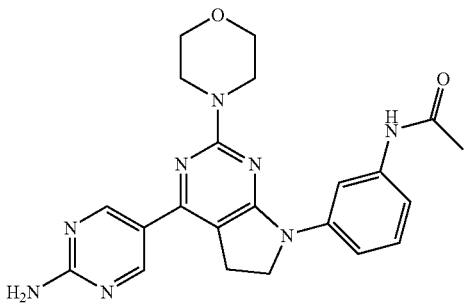

From bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and acetyl-(3-bromo-phenyl)-carbamic acid tert-butyl ester (prepared from N-(3-bromo-phenyl)-acetamide and di-t butyl carbonate in acetonitrile in the presence of DMAP, 94 mg) instead of 4-bromobenzoic acid methyl ester in Example 1-D-08, in the same manner as Example 1-D-08, a crude product of acetyl-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-carbamic acid tert-butyl ester was obtained, and then the PMB groups were removed according to Deprotection method 1, to obtain the desired compound (D-45) as a pale yellow powder (5 mg, 8%).
¹H-NMR (DMSO-d₆) δ (ppm): 9.92 (1H, s), 8.81 (2H, s), 8.30 (1H, s), 7.48 (1H, d, J=8.1 Hz), 7.28 (1H, t, J=8.1 Hz), 7.12 (1H, s), 7.09 (2H, s), 4.05 (2H, t, J=8.3 Hz), 3.75-3.63 (8H, m), 3.26 (2H, t, J=8.3 Hz), 2.05 (3H, s).
ESI (LC-MS positive mode) m/z 433 (M+H)⁺.

Example 1-D-46

4-(2-Amino-pyrimidin-5-yl)-2-morpholin-4-yl-5,6-dihydro-pyrrolo[2,3-d]pyrimidine-7-carbothioic acid (2-morpholin-4-yl-ethyl)-amide (D-46)

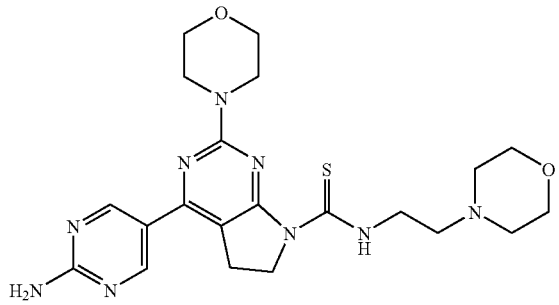

In the same manner as Example 1-D-03, using bis-(4-methoxy-benzyl)-[5-(2-morpholin-4-yl-6,7-dihydro-5H-pyrrolo[2,3-d]pyrimidin-4-yl)-pyrimidin-2-yl]-amine (40 mg) and (2-morpholin-4-yl-ethyl)-thioisocyanate (0.38 ml) instead of ethyl isocyanate, a crude product of 4-(2-bis-(4-methoxy-benzyl)-amino-pyrimidin-5-yl)-2-morpholin-4-yl-5,6-dihydro-pyrrolo[2,3-d]pyrimidine-7-carbothioic acid was obtained. Using a crude product (18 mg) of this 4-(2-bis-(4-methoxy-benzyl)-amino-pyrimidin-5-yl)-2-morpholin-4-yl-5,6-dihydro-pyrrolo[2,3-d]pyrimidine-7-carbothioic acid, deprotection was carried out according to the above Deprotection reaction method 2, to obtain 4-(2-amino-pyrimidin-5-yl)-2-morpholin-4-yl-5,6-dihydro-pyrrolo[2,3-d]pyrimidine-7-carbothioic acid (2-morpholin-4-yl-ethyl)-amide as a colorless powder (7 mg, 21%).

$^1$H-NMR (DMSO-D$_6$) δ: 11.02 (1H, brs), 8.84 (2H, s), 7.27 (2H, brs), 4.30 (2H, t, J=8.4 Hz), 4.19-3.32 (20H, m), 3.23 (2H, t, J=8.4 Hz).

ESI (LC-MS positive mode) m/z 472 (M+H)$^+$.

Example 1-D-47

4-(2-Amino-pyrimidin-5-yl)-2-morpholin-4-yl-5,6-dihydro-pyrrolo[2,3-d]pyrimidine-7-carboxylic acid (3-trifluoromethyl-phenyl)-amide (D-47)

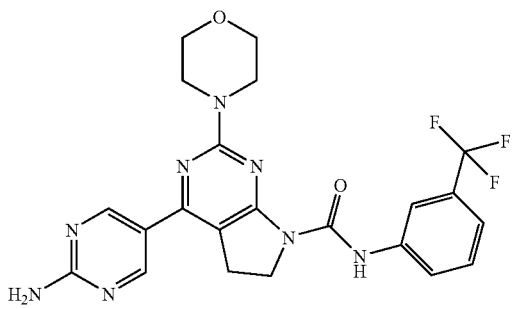

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (54 mg) and 3-trifluoromethyl-phenyl isocyanate (56.1 μl) instead of ethyl isocyanate, in the same manner as in Example 1-D-03, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-trifluoromethyl-phenyl)-amide was obtained, and then the PMB groups were removed according to Deprotection method 1', to obtain the desired compound (D-47) as a colorless solid (8.2 mg, 17%).

$^1$H-NMR (TFA-d$_1$) δ: 9.26 (2H, s), 7.76-7.71 (2H, m), 7.68-7.64 (2H, m), 4.59 (2H, t, J=7.8 Hz), 4.26-4.14 (9H, m), 3.42 (2H, t, J=7.8 Hz).

ESI (LC-MS positive mode) m/z 487 (M+H)$^+$.

Example 1-D-48

N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-48)

Step A

{5-[7-(6-Chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine

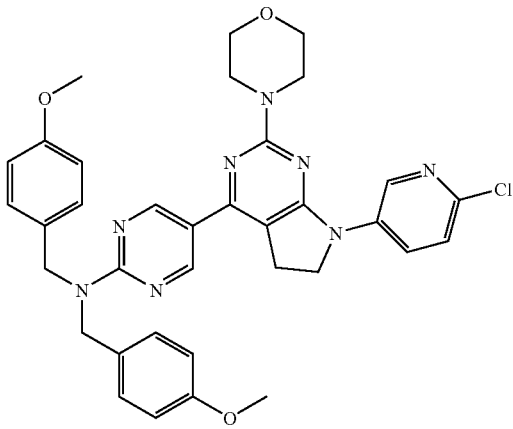

A toluene solution (10 ml) of 2-chloro-5-iodopyridine (67 mg, 0.27 mmol), bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.18 mmol), Pd$_2$(dba)$_3$·CHCl$_3$ (19 mg, 0.018 mmol), BINAP (17 mg, 0.02 mmol) and cesium carbonate (181 mg, 0.55 mmol) was degassed under ultrasonic irradiation, followed by stirring at 100° C. for 14 hours under a nitrogen atmosphere. The reaction mixture was cooled to room temperature, and diluted with water, followed by extraction with ethyl acetate. The organic layer was washed with saturated aqueous sodium chloride solution, dried over magnesium sulfate, and subsequently magnesium sulfate was filtered off. The filtrate was concentrated under reduced pressure, and the residue was purified by silica gel column chromatography (hexane/ethyl acetate=3/1), to obtain {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine as a yellow solid (43 mg, 36%).

$^1$H-NMR (CDCl$_3$) δ (ppm): 8.99 (s, 2H), 8.92 (d, 1H, J=3.1 Hz), 8.14 (dd, 1H, J=3.1 Hz, J=8.8 Hz), 7.61 (dd, 1H, J=3.1 Hz, J=8.8 Hz), 7.17 (d, 4H, J=8.7 Hz), 6.86 (d, 4H, J=8.7 Hz), 4.81 (s, 4H), 4.11 (m, 2H), 3.80 (S, 14H), 3.36 (t, 2H, J=8.0 Hz).

Step B

N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-48)

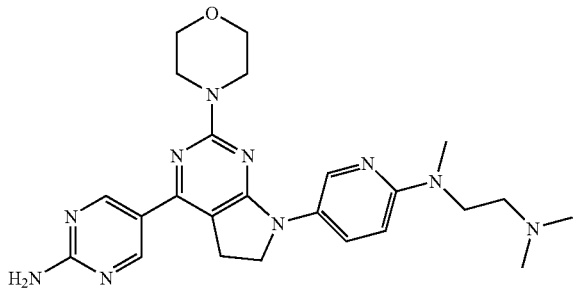

A toluene solution (60 ml) of {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.30 mmol) obtained in Step A, N,N,N'-trimethyl ethylenediamine (60 µl, 46 mmol), Pd$_2$(dba)$_3$·CHCl$_3$ (20 mg, 0.019 mmol), sodium-tert-butoxide (44 mg, 0.45 mmol) and 2,8,9-triisobutyl-2,5,8,9-tetraaza-1-phosphabicyclo[3.3.3]undecane (31 mg, 0.092 mmol) was degassed under ultrasonic irradiation, followed by refluxing for 14 hours under a nitrogen atmosphere. The reaction mixture was cooled to room temperature, and diluted with water, followed by extraction with dichloromethane. The organic layer was dried over magnesium sulfate, and subsequently magnesium sulfate was filtered off. Subsequently, the filtrate was concentrated under reduced pressure, and the residue was purified by silica gel column chromatography (dichloromethane/methanol=30/1), to obtain a crude product of N-[5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-N,N',N'-trimethyl-ethane-1,2-diamine as a pale yellow solid (110 mg). Then the PMB groups were removed according to the above Deprotection method 2, to obtain the desired compound as a yellow powder (40 mg, 54%).

$^1$H-NMR (CDCl$_3$) δ (ppm): 8.84 (2H, s), 8.38 (1H, d, J=2.6 Hz), 8.06 (1H, dd, J=2.6, 9.5 Hz), 6.63 (1H, d, J=9.1 Hz), 4.09 (2H, t, J=8.2 Hz), 3.80 (8H, s), 3.71 (2H, t, J=7.2 Hz), 3.30 (2H, t, J=8.2 Hz), 3.08 (3H, s), 2.67 (2H, t, J=7.2 Hz), 2.42 (6H, s).

ESI (LC-MS positive mode) m/z 477 (M+H)$^+$.

Example 1-D-49

5-{7-[6-(4-Ethyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-49)

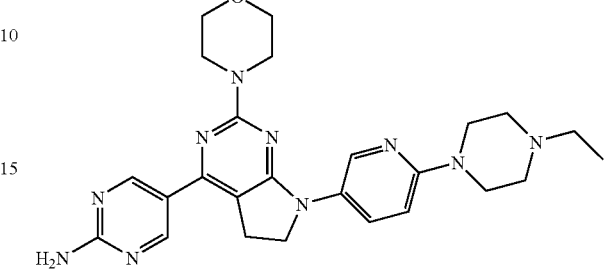

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.307 mmol) obtained in Step A in Example 1-D-48 and N-ethylpiperazine (59 µl, 0.461 mmol) instead of N,N,N'-trimethyl ethylenediamine, in the same manner as Example 1-D-48, a crude product of (5-{7-[6-(4-ethyl-piperazin-1-yl)-pyridin-3-yl]-2-morpholin-4-yl-6,7-dihydro-5H-pyrrolo[2,3-d]pyrimidin-4-yl}-pyrimidin-2-yl)-bis-(4-methoxy-benzyl)-amine was obtained as a yellow solid (160 mg), and then the PMB groups were removed according to the above Deprotection method 2, to obtain the desired compound (D-49) as a yellow powder (61 mg, 57%).

$^1$H-NMR (CDCl$_3$) δ (ppm): 8.88 (2H, s), 8.50 (1H, d, J=2.9 Hz), 8.07 (1H, dd, J=2.8, 9.1 Hz), 6.47 (1H, d, J=8.9 Hz), 5.34 (2H, s), 4.06 (2H, t, J=8.2 Hz), 3.80 (8H, s), 3.56 (4H, t, J=5.0 Hz), 3.28 (2H, t, J=8.0 Hz), 2.64 (4H, t, J=5.0 Hz), 2.52 (2H, q, J=7.2 Hz), 2.42 (3H, t, J=7.3 Hz).

ESI (LC-MS positive mode) m/z 489 (M+H)$^+$.

Example 1-D-50

5-(7-Ethanesulfonyl-2-morpholin-4-yl-6,7-dihydro-5H-pyrrolo[2,3-d]pyrimidin-4-yl)-pyrimidin-2-ylamine (D-50)

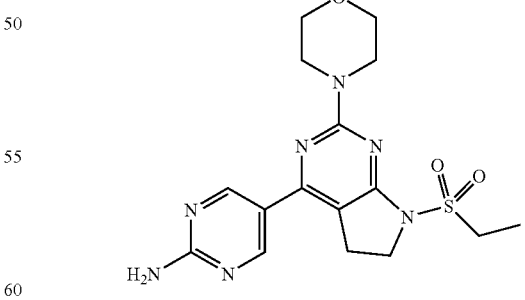

In the same manner as Example 1-D-02, using bis-(4-methoxy-benzyl)-[5-(2-morpholin-4-yl-6,7-dihydro-5H-pyrrolo[2,3-d]pyrimidin-4-yl)-pyrimidin-2-yl]-amine (40 mg) and ethanesulfonyl chloride (0.70 ml) instead of mesyl chloride, a crude product of bis-(4-methoxy-benzyl)-[5-(7-ethanesulfonyl-2-morpholin-4-yl-6,7-dihydro-5H-pyrrolo

[2,3-d]pyrimidin-4-yl)-pyrimidin-2-yl]-amine was obtained. Using this crude product (10 mg), the PMB groups were removed according to the above Deprotection method 2, to obtain 5-(7-ethanesulfonyl-2-morpholin-4-yl-6,7-dihydro-5H-pyrrolo[2,3-d]pyrimidin-4-yl)-pyrimidin-2-ylamine as a colorless powder (4 mg, 65%).

$^1$H-NMR (DMSO-D$_6$) δ: 8.79 (2H, s), 7.20 (2H, s), 4.00 (2H, t, J=8.3 Hz), 3.73 (2H, q, J=7.3 Hz), 3.72-3.63 (8H, m), 3.26 (2H, t, J=8.3 Hz), 1.24 (2H, t, J=7.3 Hz).

ESI (LC-MS positive mode) m/z 392 (M+H)$^+$.

Example 1-D-51

5-[2-Morpholin-4-yl-7-(propane-1-sulfonyl)-6,7-dihydro-5H-pyrrolo[2,3-d]pyrimidin-4-yl]-pyrimidin-2-ylamine (D-51)

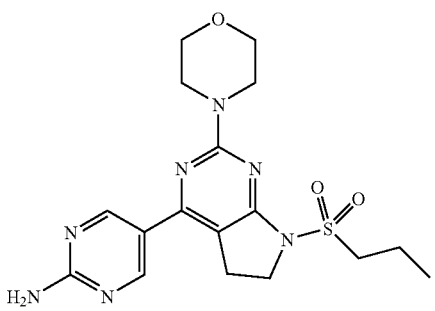

In the same manner as Example 1-D-02, using bis-(4-methoxy-benzyl)-[5-(2-morpholin-4-yl-6,7-dihydro-5H-pyrrolo[2,3-d]pyrimidin-4-yl)-pyrimidin-2-yl]-amine (40 mg) and propane-1-sulfonyl chloride (0.70 ml) instead of mesyl chloride, a crude product of bis-(4-methoxy-benzyl)-[5-[2-morpholin-4-yl-7-(propane-1-sulfonyl)-6,7-dihydro-5H-pyrrolo[2,3-d]pyrimidin-4-yl]-pyrimidin-2-yl]-amine was obtained. Using a crude product (12 mg) of this bis-(4-methoxy-benzyl)-[5-[2-morpholin-4-yl-7-(propane-1-sulfonyl)-6,7-dihydro-5H-pyrrolo[2,3-d]pyrimidin-4-yl]-pyrimidin-2-yl]-amine, the PMB groups were removed according to the above Deprotection method 2, to obtain 5-[2-morpholin-4-yl-7-(propane-1-sulfonyl)-6,7-dihydro-5H-pyrrolo[2,3-d]pyrimidin-4-yl]-pyrimidin-2-ylamine as a colorless powder (5.4 mg, 77%).

$^1$H-NMR (DMSO-D$_6$) δ: 8.79 (2H, s), 7.19 (2H, s), 3.99 (1H, t, J=8.2 Hz), 3.73-3.64 (8H, m), 3.57 (2H, t, J=7.7 Hz), 3.25 (2H, t, J=8.2 Hz), 1.80-1.69 (2H, m), 0.97 (3H, t, J=7.5 Hz).

ESI (LC-MS positive mode) m/z 406 (M+H)$^+$.

Example 1-D-52

3-[4-(2-Amino-pyrimidin-5-yl)-2-morpholin-4-yl-5,6-dihydro-pyrrolo[2,3-d]pyrimidin-7-yl]-benzoic acid methyl ester (D-52)

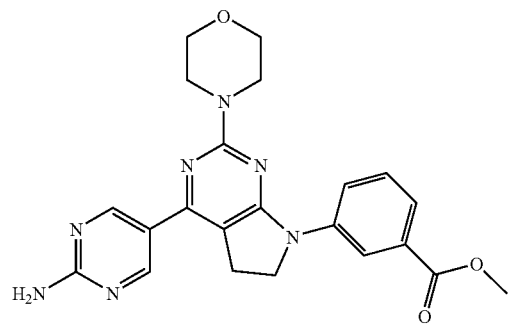

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (15.0 mg, 0.0278 mmol) and 3-bromobenzoic acid methyl ester (7.1 mg, 0.033 mmol) instead of 4-bromobenzoic acid methyl ester, in the same manner as Example 1-D-08, a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid methyl ester was obtained, and then the PMB groups were removed according to the above Deprotection method 2, to obtain the desired compound (D-52) as a yellow powder (10.4 mg, 86%).

$^1$H-NMR (DMSO-d$_6$) δ (ppm): 9.00 (1H, s), 8.80 (2H, s), 7.74 (1H, d, J=8.1 Hz), 7.60 (1H, d, J=7.3 Hz), 7.51 (1H, dd, J=8.1, 7.3 Hz), 7.16 (2H, brs), 4.10 (2H, t, J=7.6 Hz), 3.84 (3H, s), 3.79-3.66 (8H, m), 3.28 (2H, t, J=7.6 Hz).

ESI (LC-MS positive mode) m/z 434 (M+H)$^+$.

Example 1-D-53

{3-[4-(2-Amino-pyrimidin-5-yl)-2-morpholin-4-yl-5,6-dihydro-pyrrolo[2,3-d]pyrimidin-7-yl]-phenyl}-morpholin-4-yl-methanone (D-53)

Step A 3-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-benzoic acid

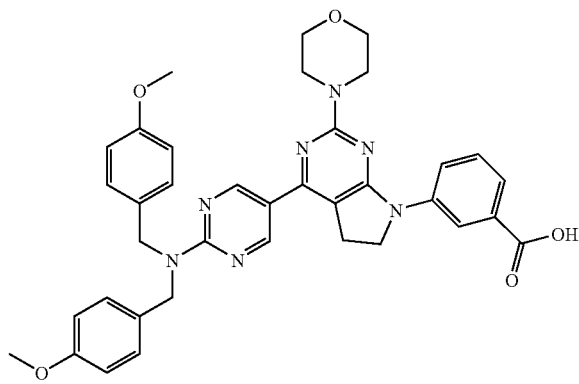

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid methyl ester (224 mg, 0.332 mmol) obtained in Example 1-D-52, in the same manner as Example 1-D-09, hydrolysis was carried out, to obtain 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid as a yellow solid (207.5 mg, 95%).

ESI (LC-MS positive mode) m/z 660 (M+H)⁺.

Step B

{3-[4-(2-Amino-pyrimidin-5-yl)-2-morpholin-4-yl-5, 6-dihydro-pyrrolo[2,3-d]pyrimidin-7-yl]-phenyl}-morpholin-4-yl-methanone (D-53)

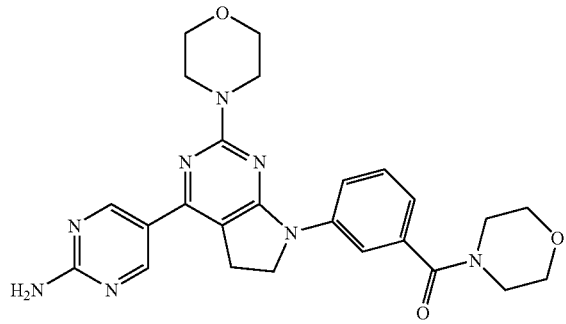

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (38.2 mg, 0.0579 mmol) obtained in Step A instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and morpholine (10.1 μl, 0.116 mmol) instead of 3-(aminomethyl)pyridine, in the same manner as Step B in Example 1-D-19, amidation was carried out, to obtain a crude product of {3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-morpholin-4-yl-methanone as a yellow liquid (37 mg), and then the PMB groups were removed according to the above Deprotection method 2, to obtain the desired compound (D-53) as a yellow powder (22.3 mg, 78%).

¹H-NMR (DMSO-d₆) δ (ppm): 8.81 (2.0H, s), 7.90 (1H, d, J=7.6 Hz), 7.89 (1H, brs), 7.47 (1H, dd, J=8.1, 7.6 Hz), 7.20 (2H, brs), 7.07 (1H, d, J=8.1 Hz), 4.13 (2H, t, J=8.1 Hz), 3.78-3.37 (16H, m), 3.30 (2H, t, J=8.2 Hz).

ESI (LC-MS positive mode) m/z 489 (M+H)⁺.

Example 1-D-54

{3-[4-(2-Amino-pyrimidin-5-yl)-2-morpholin-4-yl-5, 6-dihydro-pyrrolo[2,3-d]pyrimidin-7-yl]-phenyl}-(4-methyl-piperazin-1-yl)-methanone (D-54)

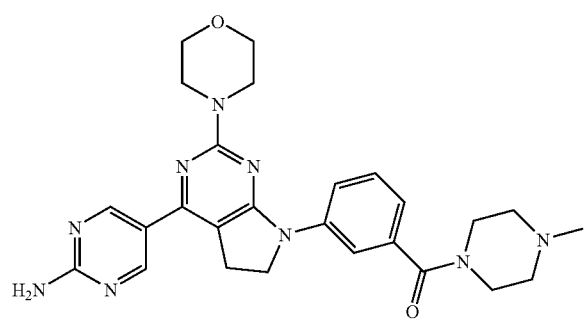

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (38.2 mg, 0.0579 mmol) obtained in Step A in Example 1-D-53 instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and N-methylpiperazine (13.0 μl, 0.116 mmol) instead of 3-(aminomethyl)pyridine, in the same manner as Step B in Example 1-D-19, amidation was carried out, to obtain a crude product of {3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-methyl-piperazin-1-yl)-methanone as a yellow liquid (31 mg), and then the PMB groups were removed according to the above Deprotection method 2, to obtain the desired compound (D-54) as a yellow powder (20.0 mg, 68%).

¹H-NMR (DMSO-d₆) δ (ppm): 8.82 (2H, s), 8.02 (1H, d, J=8.1 Hz), 7.87 (1H, s), 7.50 (1H, dd, J=8.2, 7.6 Hz), 7.18-7.04 (3H, m), 4.11 (2H, t, J=7.9 Hz), 3.79-3.65 (8H, m), 3.43-2.99 (10H, m), 2.83 (3H, s).

ESI (LC-MS positive mode) m/z 502 (M+H)⁺.

Example 1-D-55

3-[4-(2-Amino-pyrimidin-5-yl)-2-morpholin-4-yl-5, 6-dihydro-pyrrolo[2,3-d]pyrimidin-7-yl]-N-(2-dimethylamino-ethyl)-benzamide (D-55)

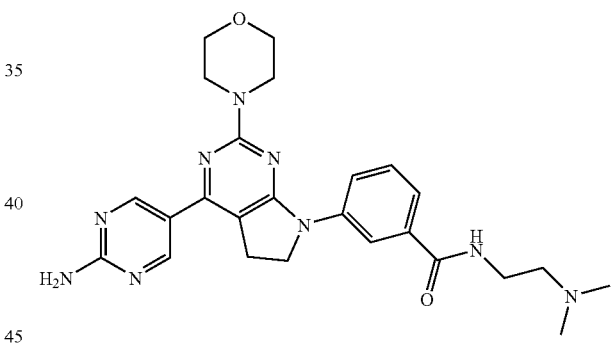

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (38.2 mg, 0.0579 mmol) obtained in Step A in Example 1-D-53 instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and N,N-dimethyl ethylenediamine (15.1 μl, 0.116 mmol) instead of 3-(aminomethyl)pyridine, in the same manner as Step B in Example 1-D-19, amidation was carried out, to obtain a crude product of 3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-dimethylamino-ethyl)-benzamide as a yellow liquid (29 mg), and then the PMB groups were removed according to the above Deprotection method 2, to obtain the desired compound (D-55) as a yellow powder (17.2 mg, 61%).

¹H-NMR (DMSO-d₆) δ (ppm): 8.83 (2H, s), 8.77-7.44 (4H, m), 7.11 (2H, brs), 5.01 (1H, m), 4.13 (2H, t, J=7.3 Hz), 3.83-3.17 (14H, m), 2.87 (6H, s).

ESI (LC-MS positive mode) m/z 490 (M+H)⁺.

Example 1-D-56

4-{[4-(2-Amino-pyrimidin-5-yl)-2-morpholin-4-yl-5,6-dihydro-pyrrolo[2,3-d]pyrimidine-7-carbonyl]-amino}-benzoic acid ethyl ester (D-56)

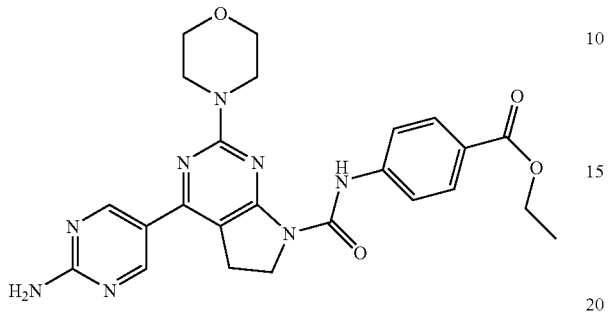

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 4-isocyanate-benzoic acid ethyl ester (206 μl) instead of ethyl isocyanate, in the same manner as Example 1-D-03, a crude product of 4-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-benzoic acid ethyl ester was obtained. Further, using this compound (20 mg), the PMB groups were removed according to the above Deprotection method 1', to obtain the desired compound (D-56) as a colorless solid (8.6 mg, 64%).

$^1$H-NMR (TFA-d$_1$) δ: 9.11 (2H, s), 8.08 (2H, d, J=8.6 Hz), 7.50 (2H, d, J=8.6 Hz), 4.48-4.37 (4H, m), 4.13-4.00 (8H, m), 3.26 (2H, t, J=6.9 Hz), 1.39 (3H, t, J=7.3 Hz).

ESI (LC-MS positive mode) m/z 491 (M+H)$^+$.

Example 1-D-57

5-(2-Morpholin-4-yl-7-phenyl-6,7-dihydro-5H-pyrrolo[2,3-d]pyrimidin-4-yl)-pyrimidin-2-ylamine (D-57)

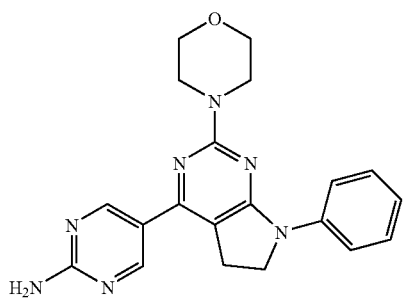

Using 4-[4,6-dichloro-5-(2-chloroethyl)-pyrimidin-2-yl]-morpholine (100 mg) and aniline (233 mg) instead of 4-aminopyridine, in the same manner as Step C in Example 1-B-01, 4-chloro-2-morpholin-4-yl-7-phenyl-6,7-dihydro-5H-pyrrolo[2,3-d]pyrimidine was obtained as an ivory powder (123 mg, 78%).

Using this compound (63.4 mg), in the same manner as Step D in Example 1-B-01, bis-(4-methoxy-benzyl)-[5-(2-morpholin-4-yl-7-phenyl-6,7-dihydro-5H-pyrrolo[2,3-d]pyrimidin-4-yl)-pyrimidin-2-yl]-amine was obtained as a crude product, and then the PMB groups were removed according to the above Deprotection method 1', to obtain the desired compound (D-57) as a yellow solid (19.4 mg, 25%).

$^1$H-NMR (TFA-d$_1$) δ: 9.10 (2H, s), 7.59-7.42 (4H, m), 7.35 (1H, t, J=7.7 Hz), 4.41 (2H, t, J=7.4 Hz), 4.08-3.89 (8H, m), 3.31 (2H, t, J=7.4 Hz).

ESI (LC-MS positive mode) m/z 376 (M+H)$^+$.

Example 1-D-58

5-[7-(2,4-Difluoro-phenyl)-2-morpholin-4-yl-6,7-dihydro-5H-pyrrolo[2,3-d]pyrimidin-4-yl]-pyrimidin-2-ylamine (D-58)

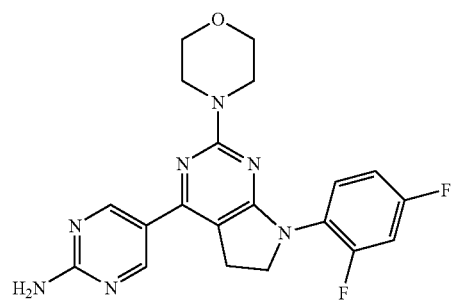

Using 4-[4,6-dichloro-5-(2-chloroethyl)-pyrimidin-2-yl]-morpholine (100 mg) and 2,4-difluoroaniline (323 mg) instead of 4-aminopyridine, in the same manner as Step C in Example 1-B-01, 4-chloro-7-(2,4-difluoro-phenyl)-2-morpholin-4-yl-6,7-dihydro-5H-pyrrolo[2,3-d]pyrimidine was obtained as an ivory powder (145 mg, 82%).

Using this compound (70.6 mg), in the same manner as Step D in Example 1-B-01, {5-[7-(2,4-difluoro-phenyl)-2-morpholin-4-yl-6,7-dihydro-5H-pyrrolo[2,3-d]pyrimidin-4-yl]-pyrimidin-2-yl}-bis-(4-methoxy-benzyl)-amine was obtained as a crude product, and then the PMB groups were removed according to the above Deprotection method 1', to obtain the desired compound (D-58) as a colorless solid (15.4 mg, 18%).

$^1$H-NMR (TFA-d$_1$) δ: 9.04 (2H, s), 7.40-7.26 (1H, m), 6.99-6.87 (2H, m), 4.23 (2H, t, J=7.3 Hz), 3.94-3.74 (8H, m), 3.29 (2H, t, J=7.3 Hz).

ESI (LC-MS positive mode) m/z 412 (M+H)$^+$.

Example 1-D-59

4-(2-Amino-pyrimidin-5-yl)-2-morpholin-4-yl-5,6-dihydro-pyrrolo[2,3-d]pyrimidine-7-carboxylic acid (2-morpholin-4-yl-ethyl)-amide (D-59)

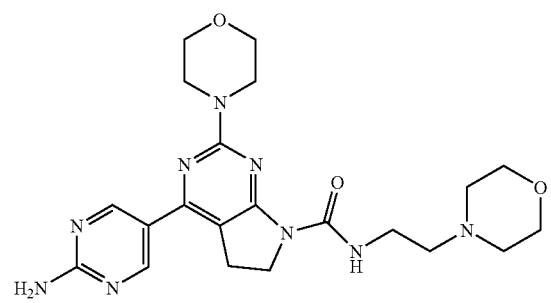

A dichloroethane solution (5 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg), pyridine (45 μl), N,N-dimethylaminopyridine (5 mg) and chloroformate-4-nitro-phenyl ester (112 mg) was stirred at room temperature for 26 hours. To this, (2-morpholin-4-yl-ethyl)-amine (0.04 ml) and triethylamine (0.05 ml) were added, followed by stirring at room temperature for 1 hour. The reaction mixture was washed with water, and the organic layer was dried over sodium sulfate. The drying agent was removed by filtration and the filtrate was concentrated under reduced pressure, to obtain a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-morpholin-4-yl-ethyl)-amide. Using a crude product of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-morpholin-4-yl-ethyl)-amide (60 mg), the PMB groups were removed according to the above Deprotection method 2, to obtain 4-(2-amino-pyrimidin-5-yl)-2-morpholin-4-yl-5,6-dihydro-pyrrolo[2,3-d]pyrimidine-7-carboxylic acid (2-morpholin-4-yl-ethyl)-amide as a colorless powder (40 mg, 100%).

$^1$H-NMR (DMSO-D$_6$) δ: 8.83 (2H, s), 8.76-8.76 (1H, m), 7.21 (2H, brs), 3.96 (2H, t, J=7.6 Hz), 3.75-3.30 (20H, m), 3.21 (2H, t, J=7.6 Hz).

ESI (LC-MS positive mode) m/z 456 (M+H)$^+$.

Example 1-D-60

4-(2-Amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide (D-60)

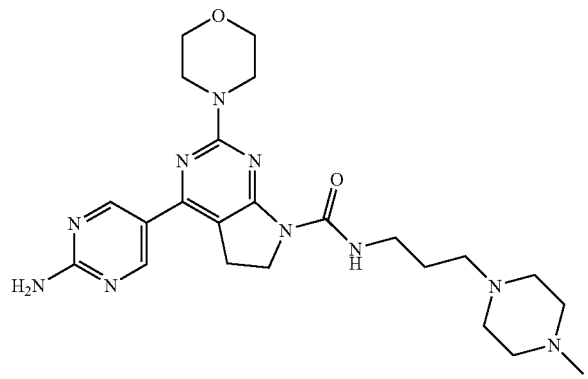

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and [3-(4-methyl-piperazin-1-yl)-propyl]-amine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide was obtained. Using a crude product of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide (37 mg), the PMB groups were removed according to the above Deprotection method 2, to obtain 4-(2-amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide as a colorless powder (15 mg, 63%).

$^1$H-NMR (CD$_3$OD) δ: 9.01 (1H, t, J=5.8 Hz), 8.86 (2H, s), 4.89 (2H, brs), 4.05 (2H, t, J=8.1 Hz), 3.49-3.26 (8H, m), 3.41-3.45 (2H, m), 3.29-3.32 (13H, m), 3.21 (2H, t, J=8.1 Hz), 1.92-1.74 (2H, m).

ESI (LC-MS positive mode) m/z 483 (M+H)$^+$.

Example 1-D-61

4-(2-Amino-pyrimidin-5-yl)-2-morpholin-4-yl-5,6-dihydro-pyrrolo[2,3-d]pyrimidine-7-carboxylic acid (2-piperidin-1-yl-ethyl)-amide (D-61)

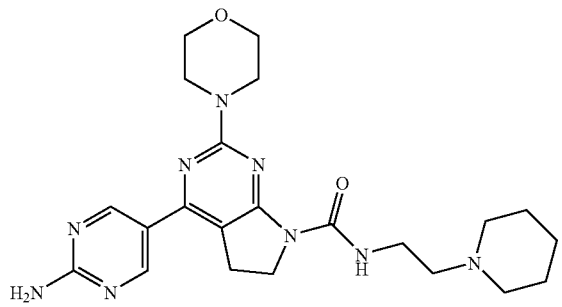

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (2-piperidin-1-yl-ethyl)-amine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-piperidin-1-yl-ethyl)-amide was obtained. Using a crude product (31 mg) of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-piperidin-1-yl-ethyl)-amide, the PMB groups were removed according to the above Deprotection method 2,4-(2-amino-pyrimidin-5-yl)-2-morpholin-4-yl-5,6-dihydro-pyrrolo[2,3-d]pyrimidine-7-carboxylic acid (2-piperidin-1-yl-ethyl)-amide was obtained as a colorless powder (21 mg, 100%).

$^1$H-NMR (DMSO-D$_6$) δ: 8.82 (2H, s), 8.78 (1H, t, J=5.4 Hz), 7.18 (2H, brs), 3.98 (2H, t, J=8.1 Hz), 3.37-3.31 (12H, m), 3.21 (10H, t, J=8.1 Hz), 3.00-2.84 (6H, m), 1.92-1.63 (6H, m).

ESI (LC-MS positive mode) m/z 454 (M+H)$^+$.

Example 1-D-62

5-{7-[3-(4-Methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-62)

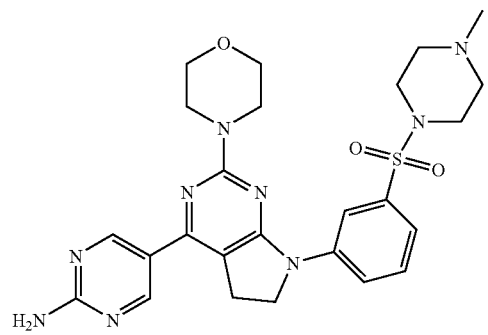

From bis-(4-methoxy-benzyl)-[5-(2-morpholin-4-yl-6,7-dihydro-5H-pyrrolo[2,3-d]pyrimidin-4-yl)-pyrimidin-2-yl]-amine (88 mg) and 1-(3-bromo-benzenesulfonyl)-4-methyl-piperazine (prepared from 3-bromo-benzenesulfonyl chloride and N-methylpiperazine in acetonitrile, 53 mg) instead of 4-bromobenzoic acid methyl ester in Example 1-D-08, in the same manner as Example 1-D-08, a crude product of bis-(4-methoxy-benzyl)-(5-{7-[3-(4-methyl-piperazine-1-sulfonyl)-phenyl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 1, to obtain the desired compound (D-62) as a colorless powder (9 mg, 7%).

$^1$H-NMR (CD$_3$OD) δ (ppm): 9.05 (1H, d, J=2.1 Hz), 8.87 (2H, s), 7.69 (2H, s), 7.61 (1H, d, J=1.2 Hz), 7.59 (1H, d, J=2.5 Hz), 7.37-7.40 (1H, m), 4.18 (2H, t, J=8.2 Hz), 3.80-3.91 (8H, m), 3.38 (2H, t, J=8.2 Hz), 3.08 (4H, m), 2.56 (4H, m), 2.30 (3H, s).

ESI (LC-MS positive mode) m/z 538 (M+H)$^+$.

Example 1-D-63

5-{7-[4-(4-Methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-63)

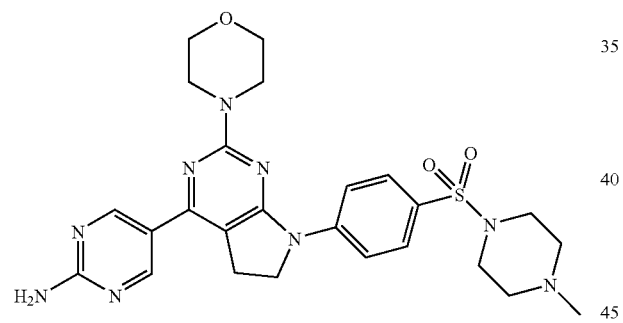

From bis-(4-methoxy-benzyl)-[5-(2-morpholin-4-yl-6,7-dihydro-5H-pyrrolo[2,3-d]pyrimidin-4-yl)-pyrimidin-2-yl]-amine (44 mg) and 1-(4-bromo-benzenesulfonyl)-4-methyl-piperazine (prepared from 4-bromo-benzenesulfonyl chloride and N-methylpiperazine in acetonitrile, 26 mg) instead of 4-bromobenzoic acid methyl ester in Example 1-D-08, in the same manner as Example 1-D-08, a crude product of bis-(4-methoxy-benzyl)-(5-{7-[4-(4-methyl-piperazine-1-sulfonyl)-phenyl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 1, to obtain the desired compound (D-63) as a colorless powder (4 mg, 9%)

$^1$H-NMR (CD$_3$OD) δ (ppm): 8.88 (2H, s), 8.07 (2H, d, J=9.1 Hz), 7.78 (2H, d, J=9.1 Hz), 7.60 (2H, s), 4.20 (2H, t, J=8.4 Hz), 3.88-3.83 (8H, m), 3.38 (2H, t, J=8.4 Hz), 3.18-3.11 (4H, m), 2.76-2.68 (4H, m), 2.42 (3H, s).

ESI (LC-MS positive mode) m/z 538 (M+H)$^+$.

Example 1-D-64

[4-(2-Amino-pyrimidin-5-yl)-2-morpholin-4-yl-5,6-dihydro-pyrrolo[2,3-d]pyrimidin-7-yl]-piperidin-4-yl-methanone (D-64)

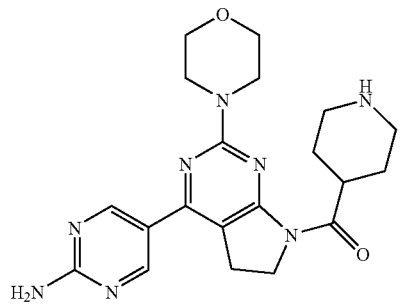

From bis-(4-methoxy-benzyl)-[5-(2-morpholin-4-yl-6,7-dihydro-5H-pyrrolo[2,3-d]pyrimidin-4-yl)-pyrimidin-2-yl]-amine (87 mg) and 4-(4-bromo-phenylcarbamoyl)-piperidine-1-carboxylic acid tert-butyl ester (prepared from 4-bromoaniline, WSCI and piperidine-1,4-dicarboxylic acid mono-tert-butyl ester, and then di-tert-butyl carbonate, 80 mg), in the same manner as Example 1-D-08, a crude product of 4-(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-piperidine-1-carboxylic acid tert-butyl ester was obtained, and then the PMB groups and BOC group were removed according to the above Deprotection method 1, to obtain the desired compound (D-64) as a colorless powder (11 mg, 10%).

$^1$H-NMR (CD$_3$OD) δ (ppm): 8.86 (2H, s), 7.49 (1H, s), 4.10 (2H, t, J=8.3 Hz), 3.86-3.82 (8H, m), 3.21-3.17 (3H, m), 2.68 (1H, td, J=12.4, 2.6 Hz), 1.98-1.27 (7H, m).

ESI (LC-MS positive mode) m/z 411 (M+H)$^+$.

Example 1-D-65

4-(2-Amino-pyrimidin-5-yl)-2-morpholin-4-yl-5,6-dihydro-pyrrolo[2,3-d]pyrimidine-7-carboxylic acid (4-pyridin-3-yl-phenyl)-amide (D-65)

Step A

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (4-iodo-phenyl)-amide

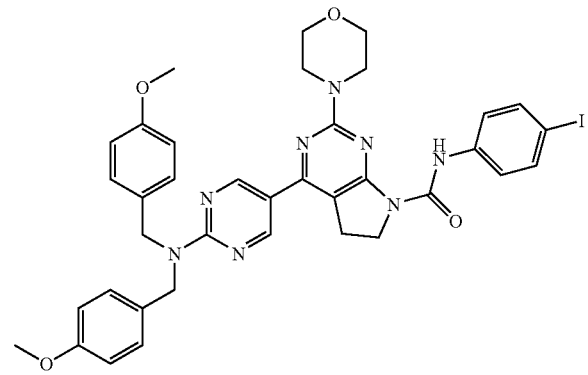

To dichloroethane solution (2 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg), DMAP (2.4 mg) and 1-iodo-4-isocyanato-benzene (120 mg) were added, followed by refluxing for 3 hours. This was cooled to room temperature, followed by addition of water, and passed through Whatman tube, to obtain the desired compound as a crude product (70.2 mg, 45%).

Step B 4-(2-Amino-pyrimidin-5-yl)-2-morpholin-4-yl-5,6-dihydro-pyrrolo[2,3-d]pyrimidine-7-carboxylic acid (4-pyridin-3-yl-phenyl)-amide (D-65)

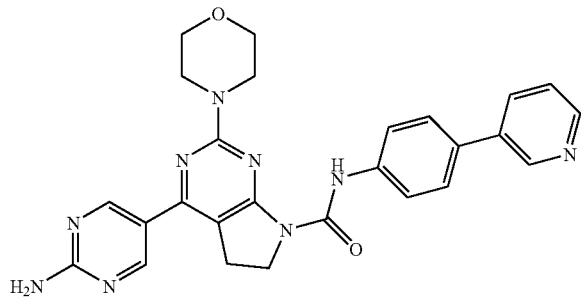

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (4-iodo-phenyl)-amide (35 mg) obtained in Step A, pyridin-3-boronic acid (11 mg), palladium acetate (1.0 mg), S-Phos (3.7 mg) and potassium phosphate (9.5 mg) were stirred at 100° C. for 3 hours in DMF (4.5 ml). To this, water was added, and the solid was filtered, followed by purification by silica gel column chromatography (dichloromethane/methanol=100/1 to 50/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-pyridin-3-yl-phenyl)-amide as a crude product. To this, N-Acetylcysteine (11 mg) was added, followed by refluxing for 4 hours in TFA (1 ml). TFA was distilled off, followed by purification by silica gel column chromatography (dichloromethane/methanol=100/1 to 50/1), to obtain the desired compound (D-65) as a colorless solid (5.0 mg, 23%, deprotection method according to the above Deprotection method 3).

$^1$H-NMR (TFA-d$_1$) δ: 9.13 (2H, s), 8.96 (1H, s), 8.77 (1H, d, J=7.7 Hz), 8.70 (1H, d, J=5.4 Hz), 8.10 (1H, t, J=7.0 Hz), 7.74-7.61 (5H, m), 4.51-4.39 (2.0H, brm), 4.14-3.99 (8H, m), 3.36-3.21 (2H, brm).

ESI (LC-MS positive mode) m/z 496 (M+H)$^+$.

Example 1-D-66

4-(2-Amino-pyrimidin-5-yl)-2-morpholin-4-yl-5,6-dihydro-pyrrolo[2,3-d]pyrimidine-7-carboxylic acid (4-pyridin-4-yl-phenyl)-amide (D-66)

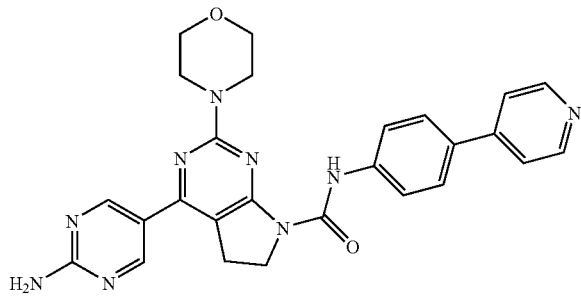

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-iodo-phenyl)-amide (25 mg) obtained in Step A in Example 1-D-65 and 4-(4,4,5,5-tetramethyl-[1,3,2]dioxaborolan-2-yl)-pyridine (13 mg) instead of pyridin-3-boronic acid, in the same manner as Step B in Example 1-D-65, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid-4-pyridin-4-yl-phenyl)-amide was obtained. Further, in the same manner as Step B in Example 1-D-65 according to the above Deprotection method 3, the PMB groups were removed, to obtain the desired compound (D-66) as a colorless solid (8.9 mg, 40%).

$^1$H-NMR (TFA-d$_1$) δ: 9.12 (2H, s), 8.68 (2H, d, J=6.6 Hz), 8.22 (2H, d, J=6.6 Hz), 7.89 (2H, d, J=8.0 Hz), 7.69 (2H, d, J=8.0 Hz), 4.49-4.38 (2H, brm), 4.16-3.99 (8H, m), 3.35-3.21 (2H, brm).

ESI (LC-MS positive mode) m/z 496 (M+H)$^+$.

Example 1-D-67

4-(2-Amino-pyrimidin-5-yl)-2-morpholin-4-yl-5,6-dihydro-pyrrolo[2,3-d]pyrimidine-7-carboxylic acid piperidin-4-ylamide (D-67)

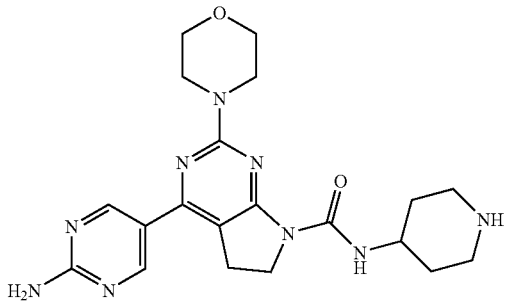

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 4-amino-1-tert-butoxycarbonyl-piperidine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid 1-tert-butoxycarbonyl-piperidin-4-ylamide was obtained. Using a crude product (46 mg) of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid 1-tert-butoxycarbonyl-piperidin-4-ylamide, according to the above Deprotection method 2, 4-(2-amino-pyrimidin-5-yl)-2-morpholin-4-yl-5,6-dihydro-pyrrolo[2,3-d]pyrimidine-7-carboxylic acid piperidin-4-ylamide was obtained as a colorless powder (12 mg, 48%).

$^1$H-NMR (CD$_3$OD) δ: 9.15 (1H, d, J=6.6 Hz), 8.87 (2H, s), 7.68 (2H, s), 4.11 (2H, t, J=8.2 Hz), 3.86-3.74 (8H, m), 3.55-3.01 (4H, m), 3.25 (2H, t, J=8.2 Hz), 2.35-2.26 (1H, m), 1.90-1.59 (2H, m), 1.32-1.20 (2H, m).

ESI (LC-MS positive mode) m/z 426 (M+H)$^+$.

Example 1-D-68

4-(2-Amino-pyrimidin-5-yl)-2-morpholin-4-yl-5,6-dihydro-pyrrolo[2,3-d]pyrimidine-7-carboxylic acid (2-dimethylamino-ethyl)-amide (D-68)

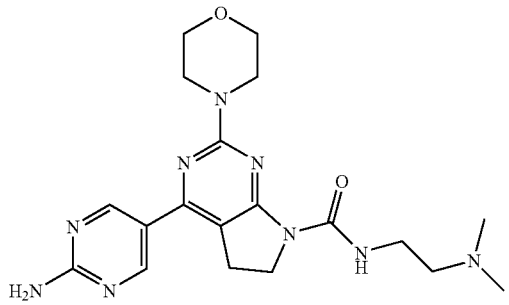

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (2-dimethylamino-ethyl)-amine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-dimethylamino-ethyl)-amide was obtained. Using a crude product (37 mg) of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2-dimethylamino-ethyl)-amide, according to the above Deprotection method 2,4-(2-amino-pyrimidin-5-yl)-2-morpholin-4-yl-5,6-dihydro-pyrrolo[2,3-d]pyrimidine-7-carboxylic acid (2-dimethylamino-ethyl)-amide was obtained as a colorless powder (23 mg, 100%).

$^1$H-NMR (DMSO-D$_6$) δ: 8.82 (2H, s), 8.77 (1H, t, J=5.6 Hz), 7.20 (2H, s), 3.96 (2H, t, J=8.2 Hz), 3.75-3.58 (8H, m), 3.21 (2H, t, J=8.2 Hz), 2.85-2.70 (4H, m).

ESI (LC-MS positive mode) m/z 414 (M+H)$^+$.

Example 1-D-69

5-{2-Morpholin-4-yl-7-[2-(3-morpholin-4-yl-propylamino)-pyridin-4-yl]-6,7-dihydro-5H-pyrrolo[2,3-d]pyrimidin-4-yl}-pyrimidin-2-ylamine (D-69)

Step A

{5-[7-(2-Chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine

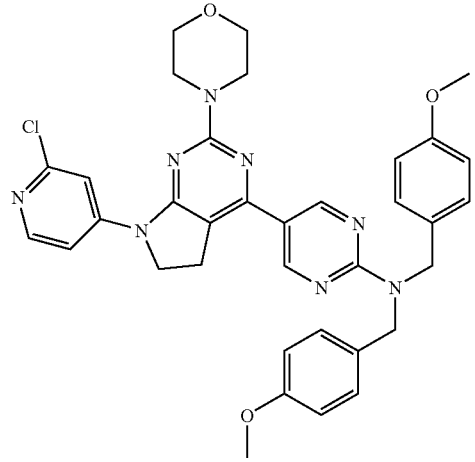

Bis-(4-methoxybenzyl)-[5-(2-morpholin-4-yl-6,7-dihydro-5H-pyrrolo[2,3-d]pyrimidin-4-yl)-pyrimidin-2-yl]-amine (1.65 g, 3.05 mmol) was suspended in dimethylformamide (20 ml), followed by addition of 2-chloro-4-iodopyridine (805 mg, 3.36 mmol), palladium acetate (35 mg, 0.156 mmol), triphenyl phosphine (81 mg, 0.309 mmol) and potassium phosphate (1.95 g, 14.1 mmol), and argon gas was blown for 10 minutes while irradiating ultrasonic wave. The reaction mixture was stirred at 100° C. for 1 hour, and cooled to room temperature, followed by addition of water (50 ml). The mixture was extracted with ethyl acetate (100 ml) and dichloromethane (100 ml), and the combined organic layers were washed with brine, followed by drying over sodium sulfate. After filtering off the drying agent, the filtrate was concentrated under reduced pressure, and the resulting residue was purified by silica gel column chromatography (dichloromethane/methanol=50/1), followed by suspension of the residue in ethyl acetate/hexane (10 ml/50 ml). The precipitate was filtered, and washed with hexane, followed by drying under reduced pressure, to obtain {5-[7-(2-chloropyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine as a yellow powder (1.75 g, 88%).

$^1$H-NMR (300 MHz, CDCl$_3$) δ (ppm): 8.99 (2H, s), 8.27 (1H, d, J=5.7 Hz), 7.82 (1H, d, J=1.9 Hz), 7.71 (1H, dd, J=1.9, 5.7 Hz), 7.20 (4H, d, J=8.4 Hz), 6.86 (4H, d, J=8.4 Hz), 4.84 (4H, s), 4.08 (2H, t, J=8.4 Hz), 3.81-3.89 (8H, m), 3.80 (6H, s), 3.36 (2H, t, J=8.4 Hz).

ESI (LC-MS positive mode) m/z 651 [(M+H)$^+$].

Step B

5-{2-Morpholin-4-yl-7-[2-(3-morpholin-4-yl-propylamino)-pyridin-4-yl]-6,7-dihydro-5H-pyrrolo[2,3-d]pyrimidin-4-yl}-pyrimidin-2-ylamine (D-69)

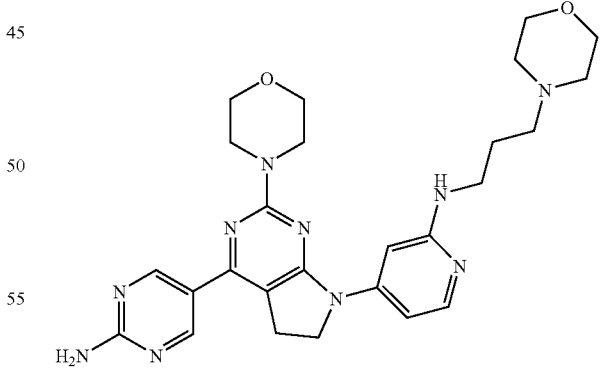

Using {5-[7-(2-chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.31 mmol) obtained in Step A instead of {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine, and N-(3-aminopropyl)morpholine (54 μl, 0.37 mmol) instead of N,N,N'-trimethyl ethylenediamine, in the same manner as Step B in Example 1-D-48, amination was carried out, to obtain a crude product of bis-(4-methoxy-benzyl)-(5-{2-morpholin-4-yl-7-[2-(3-morpholin-4-yl-propylamino)-pyridin-4-yl]-6,7-dihydro-5H-pyrrolo[2,3-d]pyrimidin-4-yl}-pyrimidin-2-yl)-amine as a yellow solid (100 mg), and then the PMB groups were removed according to the above Deprotection method 2, to obtain the desired compound (D-69) as a yellow powder (27 mg, 17%).

¹H-NMR (CDCl₃) δ (ppm): 8.89 (2H, s), 8.04 (1H, d, J=5.8 Hz), 7.02 (1H, dd, J=1.9, 6.1 Hz), 6.93 (1H, d, J=1.9 Hz), 5.24 (2H, s), 4.08 (2H, m), 3.83 (8H, m), 3.73 (4H, m), 3.34 (2H, m), 3.28 (2H, m), 2.47 (6H, m), 1.82 (2H, m), 1.25 (1H, s).

ESI (LC-MS positive mode) m/z 519 (M+H)⁺.

Example 1-D-70

1-(4-{4-[4-(2-Amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-70)

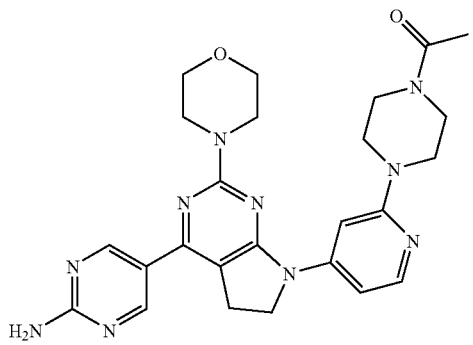

Using {5-[7-(2-chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.31 mmol) obtained in Step A in Example 1-D-69 instead of {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine, and N-acetylpiperazine (59 mg, 0.46 mmol) instead of N,N,N'-trimethyl ethylenediamine, in the same manner as Example 1-D-48, amination was carried out, to obtain a crude product of 1-{4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-piperazin-1-yl}-ethanone as a yellow solid (194 mg, 85%), and then the PMB groups were removed according to the above Deprotection method 2, to obtain the desired compound (D-70) as a yellow powder (71 mg, 46%).

¹H-NMR (CDCl₃) δ (ppm): 8.89 (2H, s), 8.13 (1H, d, J=5.7 Hz), 7.34 (1H, d, J=1.5 Hz), 7.02 (1H, dd, J=1.9, 6.1 Hz), 5.26 (2H, s), 4.09 (2H, m), 3.88 (8H, s), 3.76 (2H, m), 3.67 (2H, m), 3.50 (2H, m), 3.30 (2H, m), 2.15 (3H, s).

ESI (LC-MS positive mode) m/z 503 (M+H)⁺.

Example 1-D-71

5-{7-[6-(4-Methyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-71)

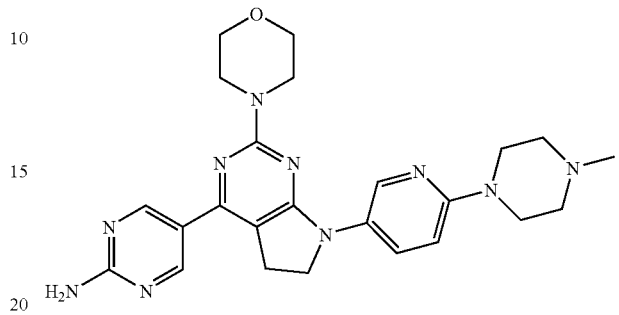

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.31 mmol) obtained in Step A in Example 1-D-48 and N-methylpiperazine (46 mg, 0.46 mmol) instead of N,N,N'-trimethyl ethylenediamine, in the same manner as Example 1-D-48, amination was carried out, to obtain a crude product of bis-(4-methoxy-benzyl)-(5-{7-[6-(4-methyl-piperazin-1-yl)-pyridin-3-yl]-2-morpholin-4-yl-6,7-dihydro-5H-pyrrolo[2,3-d]pyrimidin-4-yl}-pyrimidin-2-yl)-amine as a colorless solid (220 mg), and then the PMB groups were removed according to the above Deprotection method 2, to obtain the desired compound (D-71) as a yellow solid (35 mg, 24%).

¹H-NMR (CDCl₃) δ (ppm): 8.84 (2H, s), 8.51 (1H, d, J=2.6 Hz), 8.08 (1H, dd, J=2.6, 9.1 Hz), 6.78 (1H, d, J=9.1 Hz), 4.08 (2H, t, J=8.0 Hz), 3.57 (4H, m), 3.44 (2H, m), 3.30 (2H, t, J=8.4 Hz), 2.67 (4H, m), 2.42 (3H, s).

ESI (LC-MS positive mode) m/z 475 (M+H)⁺.

Example 1-D-72

5-{7-[6-(2-Dimethylamino-ethoxy)-pyridin-3-yl]-2-morpholin-4-yl-6,7-dihydro-5H-pyrrolo[2,3-d]pyrimidin-4-yl}-pyrimidin-2-ylamine (D-72)

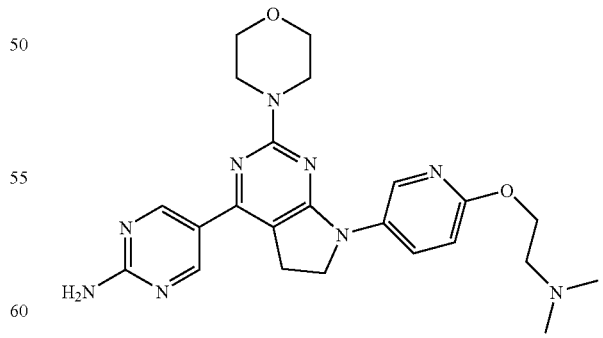

To a toluene solution (2 ml) of N,N-dimethylethanolamine (139 μl, 0.138 mmol) and {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (150 mg, 0.23 mmol) obtained in Step A in Example 1-D-48, 60% oily NaH (46 mg) was added, followed by refluxing for 4 hours. The reaction mixture was cooled to room temperature, and diluted with water, followed by extraction with ethyl acetate. The organic layer was dried over magnesium sulfate, followed by filtering off the magnesium sulfate, and subsequently the filtrate was concentrated under reduced pressure. The residue was purified by silica gel column chromatography (dichloromethane/methanol=50/1), to obtain a crude product of (5-{7-[6-(2-dimethylamino-ethoxy)-pyridin-3-yl]-2-morpholin-4-yl-6,7-dihydro-5H-pyrrolo[2,3-d]pyrimidin-4-yl}-pyrimidin-2-yl)-bis-(4-methoxy-benzyl)-amine as a yellow solid (67 mg), and then the PMB groups were removed according to the above Deprotection method 2, to obtain the desired compound (D-72) as a yellow powder (12 mg, 29%).

¹H-NMR (CDCl₃) δ (ppm): 8.84 (2H, s), 8.47 (1H, d, J=2.6 Hz), 8.20 (1H, dd, J=2.6, 9.1 Hz), 6.86 (1H, d, J=9.1 Hz), 4.44 (2H, m), 4.11 (4H, m), 3.81 (8H, m), 3.33 (2H, m), 2.83 (2H, t, J=5.7 Hz), 2.39 (6H, s).

ESI (LC-MS positive mode) m/z 464 (M+H)⁺.

Example 1-D-73

{5'-[4-(2-Amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (D-73)

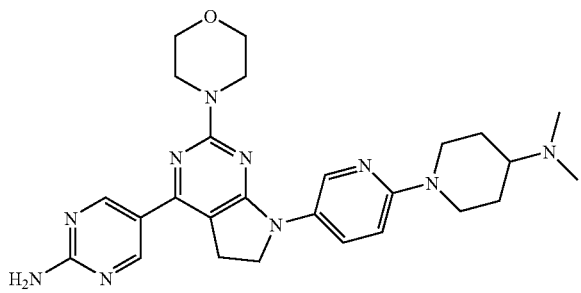

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.31 mmol) obtained in Step A in Example 1-D-48 and 4-dimethylaminopiperidine (59 mg, 0.46 mmol) instead of N,N,N'-trimethyl ethylenediamine, in the same manner as Example 1-D-48, amination was carried out, to obtain a crude product of [5'-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3,4,5,6-tetrahydro-2H-[1,2']bipyridinyl-4-yl]-dimethyl-amine as a yellow solid (197 mg), and then the PMB groups were removed according to the above Deprotection method 2, to obtain the desired compound (D-73) as a yellow powder (32 mg, 24%).

¹H-NMR (CDCl₃) δ (ppm): 8.84 (2H, s), 8.48 (1H, d, J=2.7 Hz), 8.07 (1H, dd, J=2.7, 9.5 Hz), 6.81 (1H, d, J=9.2 Hz), 4.28 (2H, m), 4.05 (2H, m), 3.80 (8H, s), 3.72 (2H, s), 3.30 (2H, t, J=8.4 Hz), 2.84 (2H, m), 2.47 (1H, m), 2.36 (6H, s), 2.00 (2H, m), 1.60 (2H, m).

ESI (LC-MS positive mode) m/z 503 (M+H)⁺.

Example 1-D-74

N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-74)

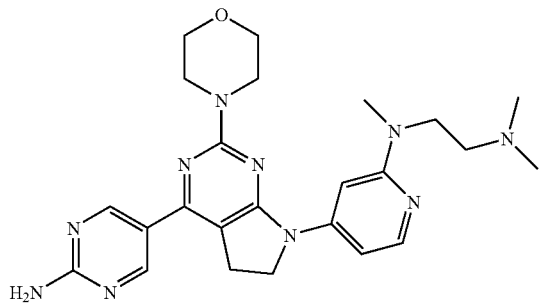

Using {5-[7-(2-chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine (100 mg, 0.154 mmol) obtained in Step A in Example 1-D-69 instead of {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine, and N,N,N'-trimethyl ethylenediamine (30 μl, 0.23 mmol), in the same manner as Example 1-D-48, amination was carried out, to obtain a crude product of N-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-N,N',N'-trimethyl-ethane-1,2-diamine as a dark brown solid (55 mg), and then the PMB groups were removed according to the above Deprotection method 2, to obtain the desired compound (D-74) as a yellow powder (25 mg, 68%).

¹H-NMR (CDCl₃) δ (ppm): 8.88 (2H, s), 8.08 (1H, d, J=5.7 Hz), 7.13 (1H, d, J=1.5 Hz), 6.90 (1H, dd, J=1.5, 5.7 Hz), 5.24 (2H, s), 4.09 (2H, t, J=8.2 Hz), 3.81 (10H, m), 3.28 (2H, t, J=8.2 Hz), 3.09 (3H, s), 2.62 (2H, t, J=7.2 Hz), 2.37 (6H, s).

ESI (LC-MS positive mode) m/z 477 (M+H)⁺.

Example 1-D-75

4'-[4-(2-Amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-ol (D-75)

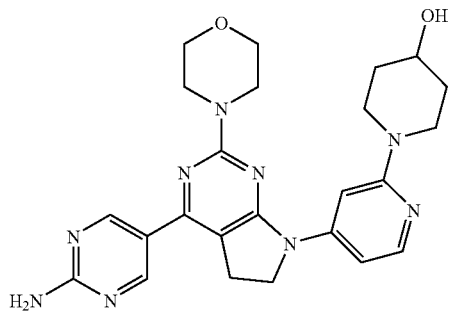

Using {5-[7-(2-chloro-pyridin-4-yl)-2-morpholin-4-yl-6,7-dihydro-5H-pyrrolo[2,3-d]pyrimidin-4-yl]-pyrimidin-2- yl}-bis-(4-methoxy-benzyl)-amine (200 mg, 0.307 mmol) obtained in Step A in Example 1-D-69 instead of {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine, and 4-[(tetrahydro-2-H-pyran-2-yl)oxy] piperidine (86 mg, 0.46 mmol) instead of N,N,N'-trimethyl ethylenediamine, in the same manner as Example 1-D-48, a crude product of bis-(4-methoxy-benzyl)-(5-{2-morpholin-4-yl-7-[4-(tetrahydro-pyran-2-yloxy)-3,4,5,6-tetrahydro-2H-[1,2']bipyridinyl-4'-yl]-6,7-dihydro-5H-pyrrolo[2,3-d]pyrimidin-4-yl}-pyrimidin-2-yl)-amine was obtained as a yellow amorphous (180 mg), and then the PMB groups and THP group were removed according to the above Deprotection method 2, to obtain the desired compound (D-75) as a pale yellow powder (35 mg, 33%).

¹H-NMR (CDCl₃) δ (ppm): 8.81 (2H, s), 7.99 (1H, d, J=5.7 Hz), 7.45 (1H, m), 7.09 (2H, s), 6.92 (1H, dd, J=1.5, 5.7 Hz), 4.68 (1H, d, J=3.8 Hz), 4.02 (4H, m), 3.71 (8H, m), 3.25 (2H, m), 3.07 (3H, m), 1.77 (2H, m), 1.37 (2H, m).

ESI (LC-MS positive mode) m/z 476 (M+H)⁺.

Example 1-D-76

[4-(2-Amino-pyrimidin-5-yl)-2-morpholin-4-yl-5,6-dihydro-pyrrolo[2,3-d]pyrimidin-7-yl]-(4-methyl-piperazin-1-yl)-methanone (D-76)

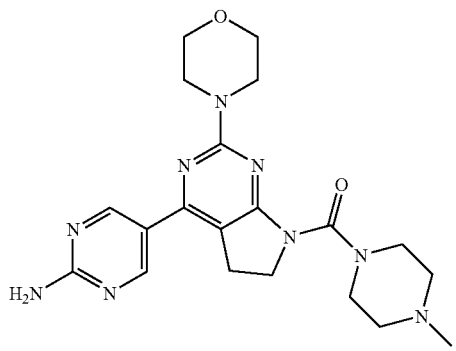

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 1-methyl-piperazine (0.04 ml) instead of (2-morpholin-4-yl-ethyl)-amine, a crude product of [4-(2-bis-(4-methoxy-benzyl)-amino-pyrimidin-5-yl)-2-morpholin-4-yl-5,6-dihydro-pyrrolo[2,3-d]pyrimidin-7-yl]-(4-methyl-piperazin-1-yl)-methanone was obtained. Using a crude product (48 mg) of this [4-(2-bis-(4-methoxy-benzyl)-amino-pyrimidin-5-yl)-2-morpholin-4-yl-5,6-dihydro-pyrrolo[2,3-d]pyrimidin-7-yl]-(4-methyl-piperazin-1-yl)-methanone, according to the above Deprotection method 2, [4-(2-amino-pyrimidin-5-yl)-2-morpholin-4-yl-5,6-dihydro-pyrrolo[2,3-d]pyrimidin-7-yl]-(4-methyl-piperazin-1-yl)-methanone was obtained as a colorless powder (23 mg, 77%).

¹H-NMR (DMSO-D₆) δ: 8.78 (2H, s), 7.14 (2H, s), 3.83 (2H, t, J=8.2 Hz), 3.74-3.62 (8H, m), 3.35 (5H, m), 3.24-3.09 (4H, m), 2.83-2.68 (4H, m).

ESI (LC-MS positive mode) m/z 426 (M+H)⁺.

Example 1-D-77

4-(2-Amino-pyrimidin-5-yl)-2-morpholin-4-yl-5,6-dihydro-pyrrolo[2,3-d]pyrimidine-7-carboxylic acid (3-dimethylamino-propyl)-amide (D-77)

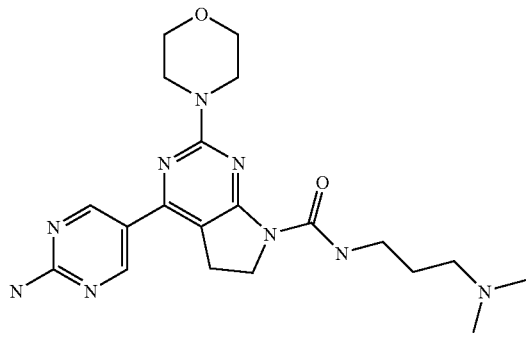

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 3-dimethylamino-propyl-amine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (3-dimethylamino-propyl)-amide was obtained. Using a crude product (33 mg) of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (3-dimethylamino-propyl)-amide, according to the above Deprotection method 2,4-(2-amino-pyrimidin-5-yl)-2-morpholin-4-yl-5,6-dihydro-pyrrolo[2,3-d]pyrimidine-7-carboxylic acid (3-dimethylamino-propyl)-amide was obtained as a colorless powder (15 mg, 71%).

¹H-NMR (DMSO-D₆) δ: 8.82 (2H, s), 8.71 (1H, t, J=5.3 Hz), 7.20 (2H, s), 3.95 (2H, t, J=8.1 Hz), 3.72-3.67 (8H, m), 3.42-3.38 (2H, m), 3.19 (2H, t, J=8.1 Hz), 3.01 (2H, t, J=6.6 Hz), 2.72 (6H, s), 1.92-1.78 (2H, m).

ESI (LC-MS positive mode) m/z 428 (M+H)⁺.

Example 1-D-78

4-(2-Amino-pyrimidin-5-yl)-2-morpholin-4-yl-5,6-dihydro-pyrrolo[2,3-d]pyrimidine-7-carboxylic acid (piperidin-4-ylmethyl)-amide (D-78)

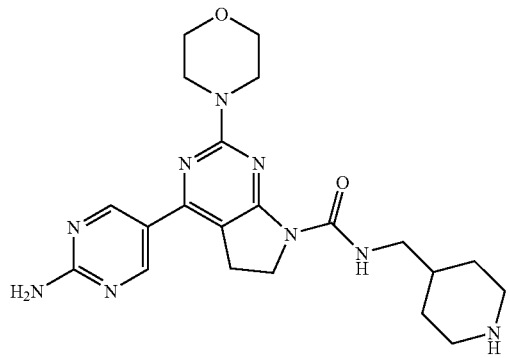

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 4-aminomethyl-1-tert-butoxycarbonyl-piperidine (0.04 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (1-tert-butoxycarbonyl-piperidin-4-ylmethyl)-amide was obtained. Using a crude product (29 mg) of this 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (1-tert-butoxycarbonyl-piperidin-4-ylmethyl)-amide, according to the above Deprotection method 2, 4-(2-amino-pyrimidin-5-yl)-2-morpholin-4-yl-5,6-dihydro-pyrrolo[2,3-d]pyrimidine-7-carboxylic acid (piperidin-4-ylmethyl)-amide was obtained as a colorless powder (9.2 mg, 58%).

$^1$H-NMR (DMSO-D$_6$) δ: 8.81 (2H, s), 8.76 (1H, t, J=5.6 Hz), 7.20 (2H, s), 3.94 (2H, t, J=7.6 Hz), 3.72-3.66 (8H, m), 3.33-3.14 (6H, m), 2.90-2.74 (2H, m), 1.89-1.68 (1H, m), 1.40-1.18 (4H, m).

ESI (LC-MS positive mode) m/z 440 (M+H)$^+$.

Example 1-D-79

{5-[4-(2-Amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-79)

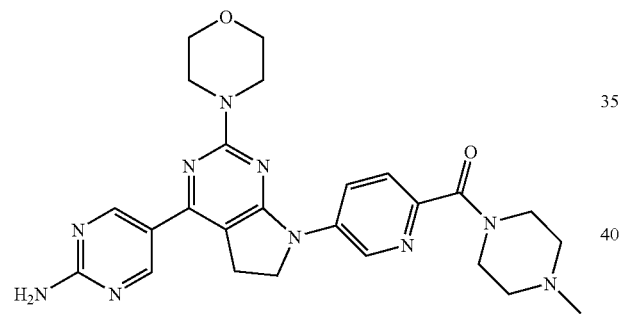

Step A

To a toluene solution (300 ml) at −78° C. in which 2,5-dibromopyridine (4.7 g) was dissolved, n-butyl lithium hexane solution (1.6 M) was added dropwise, followed by stirring at −78° C. for 3 hours. To the reaction mixture, dry ice (ca. 50 g) was added, and followed by further stirring at room temperature for 10 hours. Water (100 ml) was added, and the aqueous layer washed with ethyl acetate (100 ml×2) was neutralized with 5M-HCl aqueous solution under ice cooling, and the resulting precipitate was filtered and dried, to obtain 5-bromo-pyridine-2-carboxylic acid as a colorless powder (2.0 g, 50%). Then, 5-bromo-pyridine-2-carboxylic acid (202 mg), N-methylpiperazine (124 μl), WSCI (230 mg), HOBt (149 mg) and triethylamine (140 μl) were dissolved in acetonitrile (10 ml), followed by stirring at room temperature for 10 hours. To the reaction mixture, water (10 ml) was added, followed by extraction with ethyl acetate (10 ml). The organic layer was washed with saturated aqueous sodium chloride solution, followed by drying over sodium sulfate. After filtering off the sodium sulfate, the filtrate was concentrated under reduced pressure, and the resulting residue was purified by amino silica gel column chromatography (dichloromethane), to obtain (5-bromo-pyridin-2-yl)-(4-methyl-piperazin-1-yl)-methanone as a yellow oil (70 mg, 25%).

$^1$H-NMR (CDCl$_3$) δ (ppm): 8.65 (1H, d, J=2.3 Hz), 7.94 (1H, dd, J=8.2, 2.3 Hz), 7.58 (1H, d, J=8.2 Hz), 3.82 (2H, t, J=5.0 Hz), 3.62 (2H, t, J=5.0 Hz), 2.52 (2H, t, J=5.0 Hz), 2.41 (2H, t, J=5.0 Hz), 2.33 (3H, s).

ESI (LC-MS positive mode) m/z 284 (M+H)$^+$.

Step B

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and (5-bromo-pyridin-2-yl)-(4-methyl-piperazin-1-yl)-methanone (52 mg) obtained in the above Step A instead of 4-bromobenzoic acid methyl ester in Example 1-D-08, in the same manner as Example 1-D-08, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(4-methyl-piperazin-1-yl)-methanone was obtained, and the PMB groups were removed according to the above Deprotection method 1, to obtain the desired compound (D-79) as a colorless powder (26 mg, 35%).

$^1$H-NMR (DMSO-d$_6$) δ (ppm): 9.05 (1H, d, J=2.0 Hz), 8.83 (2H, s), 8.38 (1H, dd, J=9.0, 2.0 Hz), 7.65 (1H, d, J=9.0 Hz), 7.13 (2H, s), 4.15 (2H, t, J=8.1 Hz), 3.71 (8H, brs), 3.59 (4H, m), 3.34 (2H, t, J=8.1 Hz), 2.33 (4H, m), 2.20 (3H, s).

ESI (LC-MS positive mode) m/z 503 (M+H)$^+$.

Example 1-D-80

3-[4-(2-Amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-80)

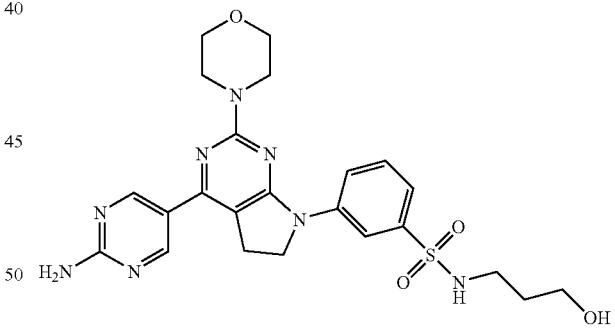

Step A

3-Bromo-N-(3-hydroxy-propyl)-benzenesulfonamide (266 mg) obtained from the reaction of pyridine, 3-aminopropanol and 3-bromobenzenesulfonyl chloride in acetonitrile was left to act in di-tert-butyl carbonate (226 mg) and acetonitrile (5 ml) in the presence of DMAP (10 mg), to obtain 3-bromo-N-Boc-N-(3-hydroxy-propyl)-benzenesulfonamide as a colorless oil (267 mg, 72%).

$^1$H-NMR (CDCl$_3$) δ (ppm): 7.77 (4H, d, J=8.7 Hz), 7.67 (4H, d, J=8.7 Hz), 3.98 (2H, t, J=6.4 Hz), 3.72 (2H, t, J=5.8 Hz), 2.02-1.93 (2H, m), 1.37 (9H, s).

ESI (LC-MS positive mode) m/z 394, 396 (M+H)$^+$.

Step B

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and 3-bromo-N-Boc-N-(3-hydroxy-propyl)-benzenesulfonamide (71 mg) obtained in the above Step A instead of 4-bromobenzoic acid methyl ester in Example 1-D-08, in the same manner as Example 1-D-08, to obtain a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(3-hydroxy-propyl)-benzenesulfonamide, and then the PMB groups were removed according to Deprotection method 1, to obtain the desired compound (D-80) as a colorless powder (9 mg, 13%).

$^1$H-NMR (DMSO-$d_6$) δ (ppm): 8.84 (1H, s), 8.83 (2H, s), 7.72 (1H, d, J=9.1 Hz), 7.60 (1H, t, J=7.8 Hz), 7.49 (1H, brs), 7.41 (1H, d, J=7.7 Hz), 7.12 (2H, s), 4.43 (1H, t, J=6.1 Hz), 4.13 (2H, t, J=7.9 Hz), 3.78-3.65 (8H, m), 3.25 (2H, brs), 3.18-3.20 (2H, m), 2.83-2.75 (2H, m), 1.57-1.47 (2H, m).

ESI (LC-MS positive mode) m/z 513 (M+H)$^+$.

Example 1-D-81

4-(2-Amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-amide (D-81)

Step A

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (3-iodo-phenyl)-amide

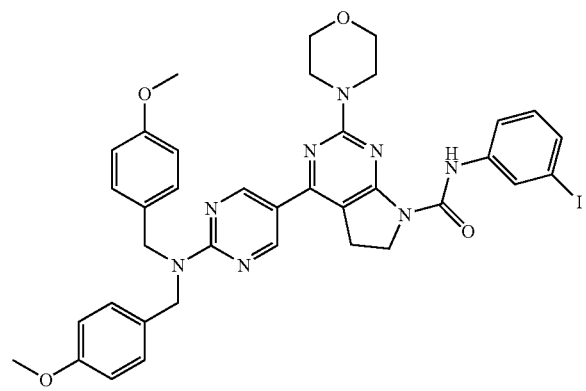

To a dichloroethane solution (10 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (540 mg), DMAP (12.2 mg) and 1-iodo-3-isocyanato-benzene (490 mg) were added, followed by refluxing for 17 hours. This was cooled to room temperature, and dichloromethane (40 ml) was added. After washing with saturated aqueous ammonium chloride solution (30 ml), the organic layer was dried over sodium sulfate. After the sodium sulfate was filtered off, the solvent was distilled off under reduced pressure, followed by silica gel column chromatography (hexane/dichloromethane/ethyl acetate=4/4/1 to 1/2/1), to obtain the desired compound as a crude product (404 mg, 51%).

Step B 4-(2-Amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-amide (D-81)

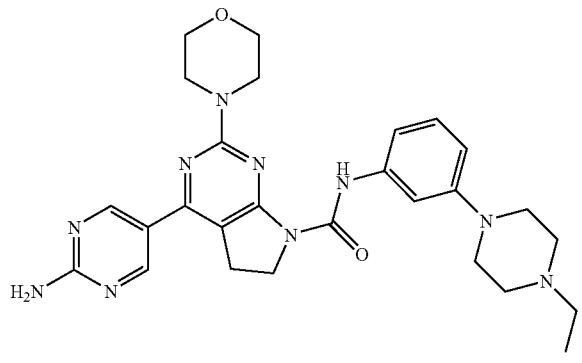

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (3-iodo-phenyl)-amide (48 mg) obtained in Step A, 1-ethyl-piperazine (77.5 μl), tris(dibenzylideneacetone)dipalladium (5.5 mg), S-Phos (5.0 mg) and potassium phosphate (26.0 mg) were stirred in DMF (5 ml) at 100° C. for 3 hours. To this, water was added, to filter the solid, which was dissolved in dichloromethane, followed by drying over sodium sulfate. After the sodium sulfate was filtered off, the solvent was distilled off under reduced pressure, followed by purification by silica gel column chromatography (dichloromethane/methanol=100/1 to 20/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(4-ethyl-piperazin-1-yl)-phenyl]-amide as a crude product. To this compound (23.1 mg), N-Acetylcysteine (10 mg) was added, followed by refluxing in TFA (1 ml) for 6 hours. TFA was distilled off, followed by purification by silica gel column chromatography (dichloromethane/2M-ammonia methanol=1/0 to 20/1), and further the resulting solid was washed with saturated sodium hydrogencarbonate aqueous solution (3 ml), water (3 ml) and acetonitrile (3 ml), to obtain the desired compound (D-81) as a yellow solid (12.5 mg, 79%).

$^1$H-NMR (TFA-$d_1$) δ: 9.11 (2H, s), 8.48 (1H, s), 7.64-7.55 (1H, m), 7.48-7.42 (1H, m), 7.26-7.19 (1H, m), 4.48-4.34 (4H, m), 4.31-4.12 (4H, m), 4.12-3.99 (8H, m), 3.91 (2H, t, J=12.6 Hz), 3.50 (2H, q, J=7.3 Hz), 3.28 (2H, t, J=7.4 Hz), 1.46 (3H, t, J=7.3 Hz).

ESI (LC-MS positive mode) m/z 531 (M+H)$^+$.

Example 1-D-82

4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-amide (D-82)

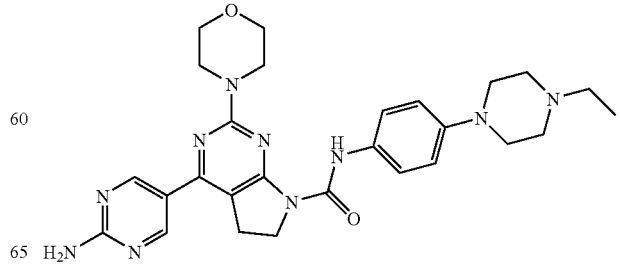

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-iodo-phenyl)-amide (100 mg) obtained in Step A in Example 1-D-65 instead of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-iodo-phenyl)-amide, in the same manner as Step B in Example 1-D-81, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazin-1-yl)-phenyl]-amide was obtained as a crude product. Further, in the same manner as steps in Example 1-D-81, the desired compound (D-82) was obtained as a yellow solid (10.9 mg, 16%).

$^1$H-NMR (TFA-d$_1$) δ: 9.11 (2H, s), 7.75-7.63 (4H, m), 4.47-4.27 (4H, m), 4.23-4.11 (4H, m), 4.11-3.96 (8H, m), 3.89 (2H, t, J=12.5 Hz), 3.48 (2H, q, J=7.3 Hz), 3.26 (2H, t, J=7.5 Hz), 1.45 (3H, t, J=7.3 Hz).

ESI (LC-MS positive mode) m/z 531 (M+H)$^+$.

Example 1-D-83

{4-[4-(2-Amino-pyrimidin-5-yl)-2-morpholin-4-yl-5,6-dihydro-pyrrolo[2,3-d]pyrimidin-7-yl]-phenyl}-(4-ethyl-piperazin-1-yl)-methanone (D-83)

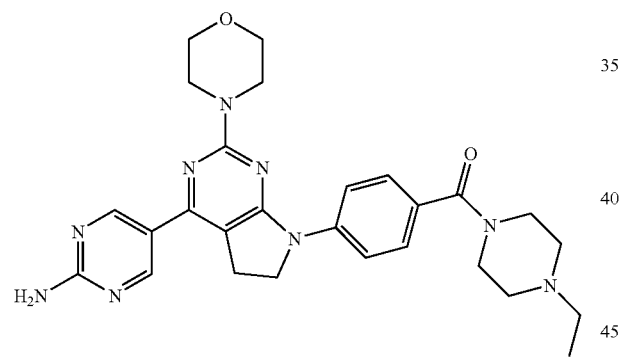

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (48.0 mg, 0.0728 mmol) obtained in Step A in Example 1-D-19 and N-ethylpiperazine (37.0 μl, 0.291 mmol) instead of 3-(aminomethyl)pyridine, in the same manner as Step B in Example 1-D-19, amidation was carried out, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-ethyl-piperazin-1-yl)-methanone as a brown solid (37 mg), and then the PMB groups were removed according to the above Deprotection method 2, to obtain the desired compound (D-83) as a yellow powder (25.0 mg, 67%).

$^1$H-NMR (DMSO-d$_6$) δ (ppm): 8.82 (2H, s), 7.93 (2H, d, J=8.2 Hz), 7.50 (2H, d, J=8.2 Hz), 7.11 (2H, s), 4.12 (2H, t, J=7.4 Hz), 3.95-2.61 (20H, m), 1.17 (3H, t, J=7.4 Hz).

ESI (LC-MS positive mode) m/z 490 (M+H)$^+$.

Example 1-D-84

4-[4-(2-Amino-pyrimidin-5-yl)-2-morpholin-4-yl-5,6-dihydro-pyrrolo[2,3-d]pyrimidin-7-yl]-N-(2-dimethylamino-ethyl)-N-methyl-benzamide (D-84)

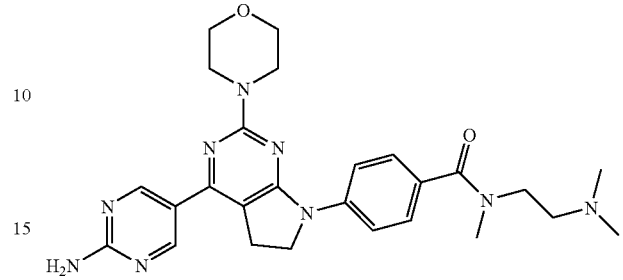

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (46.5 mg, 0.0705 mmol) obtained in Step A in Example 1-D-19 and N,N,N'-trimethyl ethylenediamine (36.7 μl, 0.282 mmol) instead of 3-(aminomethyl)pyridine, in the same manner as Step B in Example 1-D-19, amidation was carried out, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-dimethylamino-ethyl)-N-methyl-benzamide as a yellow liquid (29.7 mg), and then the PMB groups were removed according to the above Deprotection method 2, to obtain the desired compound (D-84) as a colorless powder (14.0 mg, 39%).

$^1$H-NMR (CDCl$_3$) δ (ppm): 8.88 (2H, s), 7.81 (2H, d, J=8.6 Hz), 7.48 (2H, d, J=8.6 Hz), 5.32 (2H, brs), 4.11 (2H, t, J=8.1 Hz), 3.94-3.72 (10H, m), 3.29 (2H, t, J=8.1 Hz), 3.09 (3H, s), 2.68-2.06 (8H, m).

ESI (LC-MS positive mode) m/z 504 (M+H)$^+$.

Example 1-D-85

{5-[4-(2-Amino-pyrimidin-5-yl)-2-morpholin-4-yl-5,6-dihydro-pyrrolo[2,3-d]pyrimidin-7-yl]-pyridin-2-yl}-morpholin-4-yl-methanone (D-85)

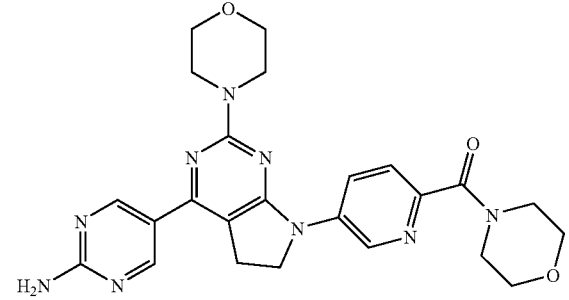

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and (5-bromo-pyridin-2-yl)-morpholin-4-yl-methanone (45 mg) obtained in the same manner as Step A in Example 1-D-79 instead of 4-bromobenzoic acid methyl ester in Example 1-D-08, in the same manner as Example 1-D-08, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-morpholin-4-yl-methanone was obtained, and then the PMB groups were removed according to the above Deprotection method 1, to obtain the desired compound (D-85) as a colorless powder (37 mg, 50%).

$^1$H-NMR (DMSO-d$_6$) δ (ppm): 9.05 (1H, d, J=2.1 Hz), 8.83 (2H, s), 8.39 (1H, dd, J=8.1, 2.5 Hz), 7.69 (1H, d, J=8.2 Hz), 7.12 (2H, s), 4.16 (2H, t, J=8.2 Hz), 3.78-3.56 (16H, m), 3.28 (2H, brs).

ESI (LC-MS positive mode) m/z 490 (M+H)$^+$.

Example 1-D-86

5-{7-[3-(Morpholine-4-sulfonyl)-phenyl]-2-morpholin-4-yl-6,7-dihydro-5H-pyrrolo[2,3-d]pyrimidin-4-yl}-pyrimidin-2-ylamine (D-86)

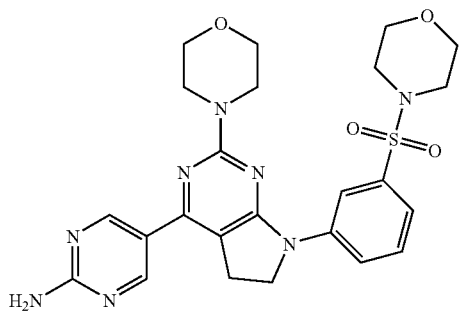

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (44 mg) and 4-(3-bromo-benzenesulfonyl)-morpholine (prepared from 3-bromobenzenesulfonyl chloride, morpholine and pyridine in acetonitrile, 51 mg) instead of 4-bromobenzoic acid methyl ester in Example 1-D-08, in the same manner as Example 1-D-08, a crude product of bis-(4-methoxy-benzyl)-(5-{7-[3-(morpholine-4-sulfonyl)-phenyl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 1, to obtain the desired compound (D-86) as a yellow powder (59 mg, 73%).

$^1$H-NMR (DMSO-d$_6$) δ (ppm): 8.96 (1H, s), 8.83 (2H, s), 7.73-7.64 (2H, m), 7.35 (1H, d, J=7.1 Hz), 7.12 (2H, s), 4.16 (2H, t, J=8.0 Hz), 3.76-3.65 (12H, m) 3.37 (2H, brs), 2.88-2.85 (4H, m).

ESI (LC-MS positive mode) m/z 525 (M+H)$^+$.

Example 1-D-87

5-{7-[4-(Morpholine-4-sulfonyl)-phenyl]-2-morpholin-4-yl-6,7-dihydro-5H-pyrrolo[2,3-d]pyrimidin-4-yl}-pyrimidin-2-ylamine (D-87)

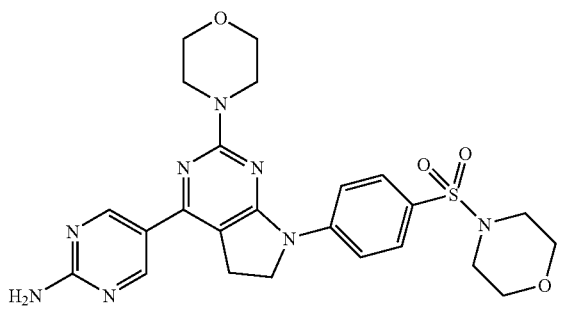

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (44 mg) and 4-(4-bromo-benzenesulfonyl)-morpholine (prepared from 4-bromobenzenesulfonyl chloride, morpholine and pyridine in acetonitrile, 51 mg) instead of 4-bromobenzoic acid methyl ester in Example 1-D-08, in the same manner as Example 1-D-08, a crude product of bis-(4-methoxy-benzyl)-(5-{7-[4-(morpholine-4-sulfonyl)-phenyl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 1, to obtain the desired compound (D-87) as a yellow powder (53 mg, 68%).

$^1$H-NMR (DMSO-d$_6$) δ (ppm): 8.84 (2H, s), 8.14 (2H, d, J=8.6 Hz), 7.74 (2H, d, J=8.6 Hz), 7.13 (2H, s), 4.15 (2H, t, J=8.5 Hz), 3.78-3.60 (12H, m), 3.29 (2H, brs), 2.86 (4H, brs).

ESI (LC-MS positive mode) m/z 525 (M+H)$^+$.

Example 1-D-88

4-(2-Amino-pyrimidin-5-yl)-2-morpholin-4-yl-5,6-dihydro-pyrrolo[2,3-d]pyrimidine-7-carboxylic acid (1-methyl-piperidin-4-yl)-amide (D-88)

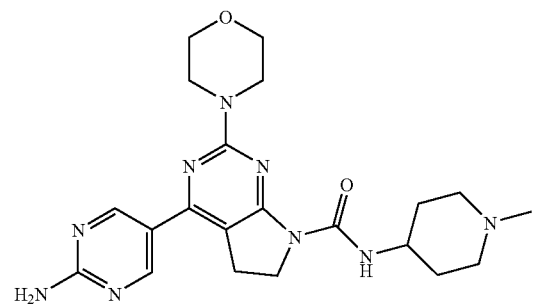

In the same manner as Example 1-D-59, using bis-(4-methoxy-benzyl)-[5-(2-morpholin-4-yl-6,7-dihydro-5H-pyrrolo[2,3-d]pyrimidin-4-yl)-pyrimidin-2-yl]-amine (60 mg) and 4-amino-1-methyl-piperidine (0.03 ml) instead of (2-morpholin-4-yl-ethyl)-amine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (1-methyl-piperidin-4-yl)-amide was obtained. Using this crude product (70 mg), according to the above Deprotection method 2,4-(2-amino-pyrimidin-5-yl)-2-morpholin-4-yl-5,6-dihydro-pyrrolo[2,3-d]pyrimidine-7-carboxylic acid (1-methyl-piperidin-4-yl)-amide was obtained as a colorless powder (32 mg, 86%).

$^1$H-NMR (DMSO-D$_6$) δ: 8.82 (2H, s), 8.81-8.77 (1H, m), 7.21 (2H, s), 3.94 (8H, t, J=7.9 Hz), 3.76-3.58 (8H, m), 3.33 (3H, s), 3.24-3.15 (3H, m), 2.79-2.67 (4H, m), 2.27-2.07 (4H, m).

ESI (LC-MS positive mode) m/z 440 (M+H)$^+$.

Example 1-D-89

1-[4-(2-Amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione (D-89)

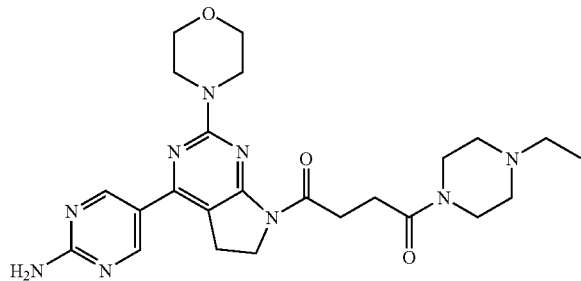

Using 4-[4-(2-Bis-(4-methoxy-benzyl)-amino-pyrimidin-5-yl)-2-morpholin-4-yl-5,6-dihydro-pyrrolo[2,3-d]pyrimidin-7-yl]-4-oxo-butyric acid (70 mg) obtained in Example 1-D-35 and 1-ethyl-piperazine (0.025 ml) instead of morpholine, in the same manner as Example 1-D-22, a crude product of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione was obtained as a colorless oil. Using this crude product (73 mg) of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione, according to the above Deprotection method 2, 1-[4-(2-amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione was obtained as a colorless powder (49 mg, 100%).

$^1$H-NMR (DMSO-$d_6$) (ppm): 8.82 (2H, s), 7.19 (2H, brs), 3.93 (2H, t, J=8.2 Hz), 3.71-3.33 (12H, m), 3.18 (2H, t, J=8.2 Hz), 2.72-2.49 (10H, m), 1.20 (3H, br.t).

ESI (LC-MS positive mode) m/z 496 (M+H)$^+$.

Example 1-D-90

1-[4-(2-Amino-pyrimidin-5-yl)-2-morpholin-4-yl-5,6-dihydro-pyrrolo[2,3-d]pyrimidin-7-yl]-4-morpholin-4-yl-butane-1,4-dione (D-90)

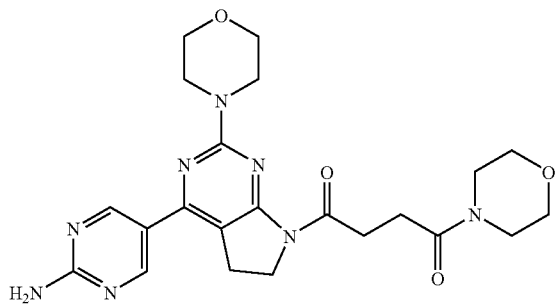

Using 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-oxo-butyric acid (70 mg) obtained in Example 1-D-35 and morpholine (0.025 ml), in the same manner as Example 1-D-22, a crude product of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-morpholin-4-yl-butane-1,4-dione was obtained as a colorless solid. Using this crude product (70 mg) of 4-[4-(2-bis-(4-methoxy-benzyl)-amino-pyrimidin-5-yl)-2-morpholin-4-yl-5,6-dihydro-pyrrolo[2,3-d]pyrimidin-7-yl]-4-morpholin-4-yl-butane-1,4-dione, according to the above Deprotection method 2, 1-[4-(2-amino-pyrimidin-5-yl)-2-morpholin-4-yl-5,6-dihydro-pyrrolo[2,3-d]pyrimidin-7-yl]-4-morpholin-4-yl-butane-1,4-dione was obtained as a colorless powder (28 mg, 61%).

$^1$H-NMR (CDCl$_3$) δ (ppm): 9.77 (2H, br.s), 8.28 (2H, br.s), 4.14 (2H, m), 3.77-3.63 (16H, m), 3.48 (2H, m), 3.19 (2H, m), 2.80 (2H, m).

ESI (LC-MS positive mode) m/z 469 (M+H)$^+$.

Example 1-D-91

4-[4-(2-Amino-pyrimidin-5-yl)-2-morpholin-4-yl-5,6-dihydro-pyrrolo[2,3-d]pyrimidin-7-yl]-N-(3-dimethylamino-propyl)-benzamide (D-91)

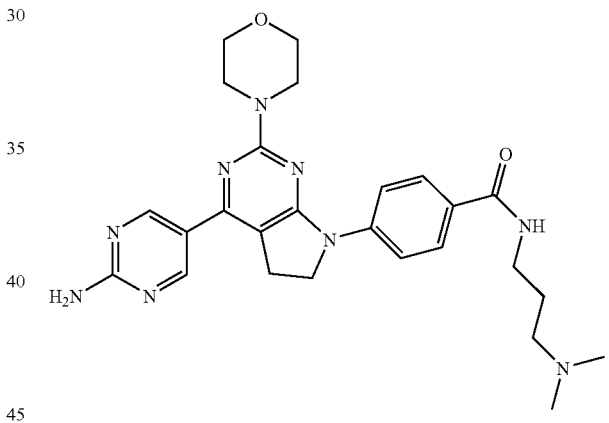

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (50.0 mg, 0.0758 mmol) obtained in Step A in Example 1-D-19 and N,N-dimethyl-1,3-propanediamine (19.0 μl, 0.152 mmol) instead of 3-(aminomethyl)pyridine, in the same manner as Step B in Example 1-D-19, a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(3-dimethylamino-propyl)-benzamide was obtained as a yellow solid (41.5 mg), and then the PMB groups were removed according to the above Deprotection method 2, to obtain the desired compound (D-91) as a colorless powder (25.8 mg, 68%).

$^1$H-NMR (DMSO-$d_6$) δ (ppm): 8.82 (2H, s), 8.43 (1H, t, J=5.6 Hz), 7.91 (2H, d, J=9.1 Hz), 7.88 (2H, d, J=9.1 Hz), 7.10 (2H, s), 4.12 (2H, t, J=8.2 Hz), 3.76-3.22 (14H, m), 2.33 (6H, s), 1.77-1.65 (2H, m).

ESI (LC-MS positive mode) m/z 504 (M+H)$^+$.

Example 1-D-92

4-[4-(2-Amino-pyrimidin-5-yl)-2-morpholin-4-yl-5,6-dihydro-pyrrolo[2,3-d]pyrimidin-7-yl]-N-(3-dimethylamino-propyl)-N-methyl-benzamide (D-92)

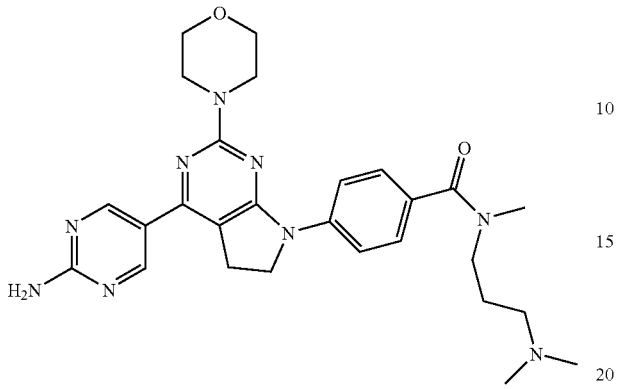

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (50.0 mg, 0.0758 mmol) obtained in Step A in Example 1-D-19 and N,N,N'-trimethyl-1,3-propanediamine (22.2 μl, 0.152 mmol) instead of 3-(aminomethyl)pyridine, amidation was conducted in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(3-dimethylamino-propyl)-N-methyl-benzamide as a yellow liquid (37.5 mg), and then the PMB groups were removed according to the above Deprotection method 2, to obtain the desired compound (D-92) as a yellow powder (25.5 mg, 65%).

$^1$H-NMR (DMSO-d$_6$) δ (ppm): 8.82 (2H, s), 7.89 (2H, d, J=8.4 Hz), 7.43 (2H, d, J=8.4 Hz), 7.10 (2H, s), 4.11 (2H, t, J=8.6 Hz), 3.82-3.58 (10H, m), 2.96 (3H, s), 2.32-1.54 (10H, m), 1.28-0.79 (2H, m).

ESI (LC-MS positive mode) m/z 518 (M+H)$^+$.

Example 1-D-93

4-[4-(2-Amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-93)

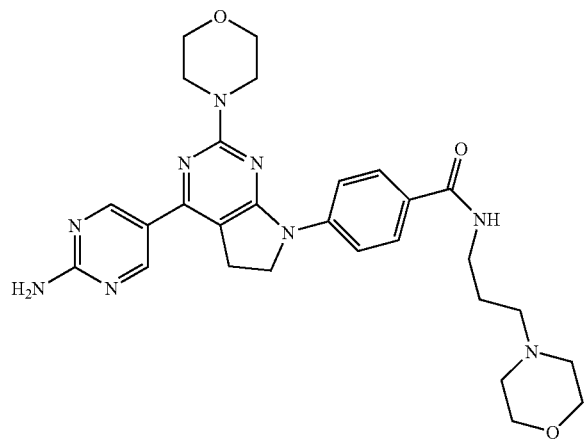

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (50.0 mg, 0.0758 mmol) obtained in Step A in Example 1-D-19 and N-(3-aminopropyl)morpholine (22.1 μl, 0.152 mmol) instead of 3-(aminomethyl)pyridine, amidation was conducted in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(3-morpholin-4-yl-propyl)-benzamide as a yellow solid (44.8 mg), and then the PMB groups were removed according to the above Deprotection method 2, to obtain the desired compound (D-93) as a yellow powder (29.3 mg, 71%).

$^1$H-NMR (DMSO-d$_6$) δ (ppm): 8.82 (2H, s), 8.41 (1H, m), 7.93 (2H, d, J=9.2 Hz), 7.89 (2H, d, J=9.2 Hz), 7.11 (2H, s), 4.12 (2H, t, J=7.7 Hz), 3.79-3.49 (18H, m), 2.48-2.24 (4H, m), 1.77-1.59 (2H, m).

ESI (LC-MS positive mode) m/z 546 (M+H)$^+$.

Example 1-D-94

4-[4-(2-Amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-94)

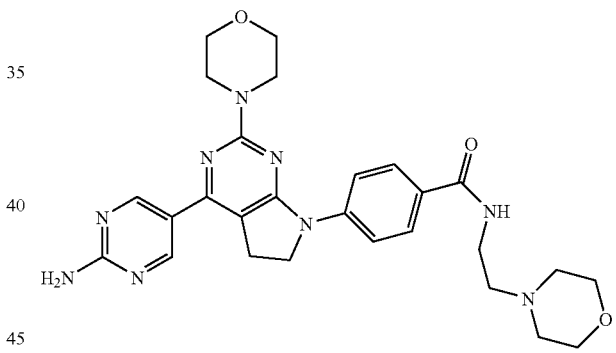

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (50.0 mg, 0.0758 mmol) obtained in Step A in Example 1-D-19 and N-(aminoethyl)morpholine (19.7 mg, 0.152 mmol) instead of 3-(aminomethyl)pyridine, amidation was conducted in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-morpholin-4-yl-ethyl)-benzamide as a yellow solid (33.0 mg), and then the PMB groups were removed according to the above Deprotection method 2, to obtain the desired compound (D-94) as a yellow powder (20.7 mg, 51%).

$^1$H-NMR (DMSO-d$_6$) δ (ppm): 8.83 (2H, s), 7.95 (2H, d, J=8.9 Hz), 7.89 (2H, d, J=8.9 Hz), 7.29 (1H, m), 7.11 (2H, s), 4.13 (2H, t, J=7.9 Hz), 3.80-3.52 (22H, m).

ESI (LC-MS positive mode) m/z 532 (M+H)$^+$.

Example 1-D-95

{5-[4-(2-Amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-95)

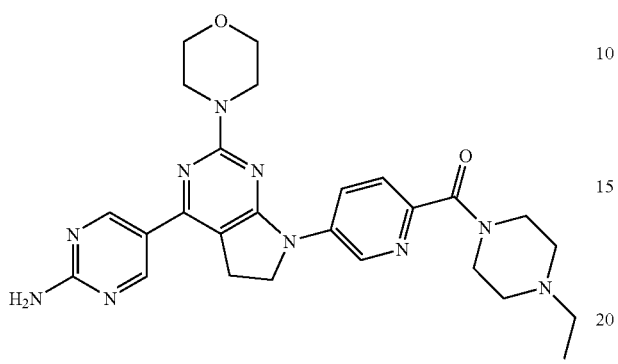

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (5-bromo-pyridin-2-yl)-(4-ethyl-piperazin-1-yl)-methanone (61 mg) obtained in the same manner as Step A in Example 1-D-79 instead of 4-bromobenzoic acid methyl ester in Example 1-D-08, in the same manner as Example 1-D-08, to obtain a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(4-ethyl-piperazin-1-yl)-methanone, and then the PMB groups were removed according to the above Deprotection method 1, to obtain the desired compound (D-95) as a milky white powder (52 mg, 54%).

$^1$H-NMR (DMSO-$d_6$) δ (ppm): 9.04 (1H, d, J=2.5 Hz), 8.83 (2H, s), 8.37 (1H, dd, J=8.9, 2.5 Hz), 7.64 (1H, d, J=8.9 Hz), 7.13 (2H, s), 4.15 (2H, t, J=8.4 Hz), 3.71 (8.0H, brs), 3.64-3.54 (4H, m), 3.37 (2H, brs), 2.46-2.42 (4H, m), 2.35 (2H, q, J=7.0 Hz), 1.01 (3H, t, J=7.0 Hz).

ESI (LC-MS positive mode) m/z 517 (M+H)$^+$.

Example 1-D-96

5-{7-[3-(4-Ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-96)

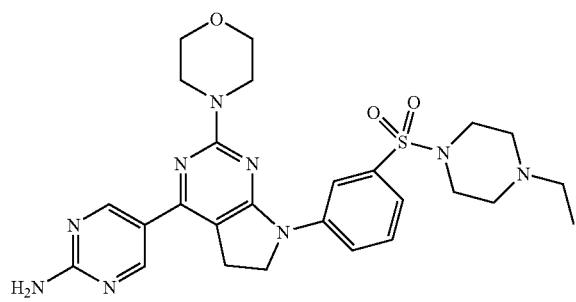

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 1-(3-bromo-benzenesulfonyl)-4-ethyl-piperazine (prepared from 3-bromo-benzenesulfonyl chloride and N-ethylpiperazine in acetonitrile, 68 mg) instead of 4-bromobenzoic acid methyl ester in Example 1-D-08, in the same manner as Example 1-D-08, a crude product of (5-{7-[3-(4-ethyl-piperazine-1-sulfonyl)-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to the above Deprotection method 1, to obtain the desired compound (D-96) as an ivory powder (45 mg, 43%).

$^1$H-NMR (DMSO-$d_6$) δ (ppm): 8.94 (1H, s), 8.83 (2H, s), 7.70-7.63 (2H, m), 7.34 (1H, d, J=6.9 Hz), 7.12 (2H, s), 4.15 (2H, t, J=7.5 Hz), 3.75-3.70 (8H, m), 3.30 (2H, brs), 2.88 (4H, brs), 2.41 (4H, brs), 2.28 (2H, q, J=7.0 Hz), 0.91 (3H, t, J=7.0 Hz).

ESI (LC-MS positive mode) m/z 552 (M+H)$^+$.

Example 1-D-97

5-{7-[4-(4-Ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-97)

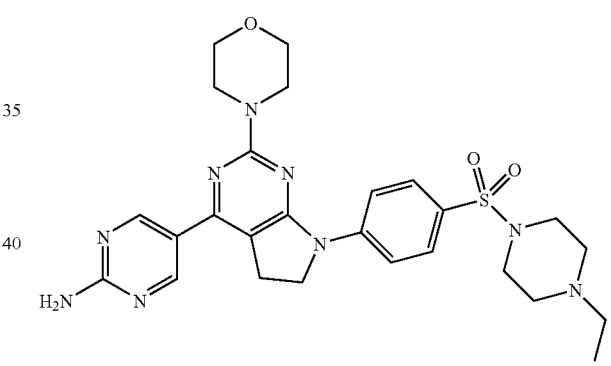

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 1-(4-bromo-benzenesulfonyl)-4-ethyl-piperazine (prepared from 4-bromo-benzenesulfonyl chloride and N-ethylpiperazine in acetonitrile, 68 mg) instead of 4-bromobenzoic acid methyl ester in Example 1-D-08, in the same manner as Example 1-D-08, a crude product of (5-{7-[4-(4-ethyl-piperazine-1-sulfonyl)-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to the above Deprotection method 1, to obtain the desired compound (D-96) as an ivory powder (70 mg, 69%).

$^1$H-NMR (DMSO-$d_6$) δ (ppm): 8.83 (2H, s), 8.12 (2H, d, J=9.1 Hz), 7.73 (2H, d, J=9.1 Hz), 7.13 (2H, s), 4.15 (2H, t, J=8.1 Hz), 3.77-3.66 (8H, m), 3.38 (2H, brs), 2.86 (4H, brs), 2.41 (4H, brs), 2.29 (2H, dd, J=14.8, 7.1 Hz), 0.92 (3H, t, J=7.1 Hz).

ESI (LC-MS positive mode) m/z 552 (M+H)$^+$.

Example 1-D-98

4-[4-(2-Amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-98)

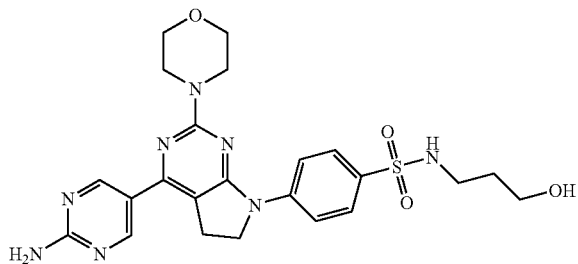

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (120 mg) and 4-bromo-N-Boc-N-(3-hydroxy-propyl)-benzenesulfonamide (105 mg) obtained in the same manner as Example 1-D-80 instead of 4-bromobenzoic acid methyl ester in Example 1-D-08, in the same manner as Example 1-D-08, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(3-hydroxy-propyl)-benzenesulfonamide was obtained, and then the PMB groups were removed according to the above Deprotection method 1, to obtain the desired compound (D-98) as a yellow powder (19 mg, 17%).

$^1$H-NMR (DMSO-d$_6$) δ (ppm): 8.83 (2H, s), 8.06 (2H, d, J=8.9 Hz), 7.78 (2H, d, J=8.9 Hz), 7.37 (1H, t, J=4.9 Hz), 7.13 (2H, s), 4.42 (1H, t, J=5.1 Hz), 4.14 (2H, t, J=8.0 Hz), 3.74-3.70 (10H, brm), 3.30 (2H, brs), 2.77 (2H, dd, J=13.4, 6.7 Hz), 1.58-1.48 (2H, m).

ESI (LC-MS positive mode) m/z 513 (M+H)$^+$.

Example 1-D-99

3-[4-(2-Amino-pyrimidin-5-yl)-2-morpholin-4-yl-5,6-dihydro-pyrrolo[2,3-d]pyrimidin-7-yl]-N-(2-hydroxy-ethyl)-benzenesulfonamide (D-99)

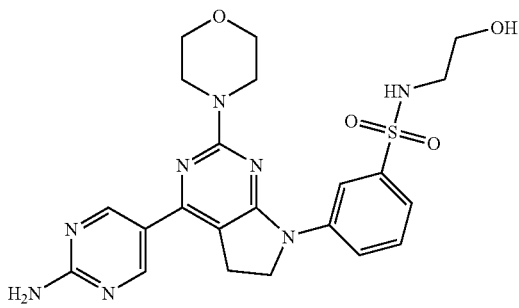

Using 3-bromo-N-Boc-N-(2-hydroxy-ethyl)-benzenesulfonamide (113 mg) instead of 4-bromo-N-Boc-N-(3-hydroxy-propyl)-benzenesulfonamide in Example 1-D-98, in the same manner as Example 1-D-98, a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(2-hydroxy-ethyl)-benzenesulfonamide was obtained, and then the PMB groups were removed according to Deprotection method 1, to obtain the desired compound (D-99) as a yellow powder (14 mg, 13%).

$^1$H-NMR (DMSO-d$_6$) δ (ppm): 9.05 (1H, s), 8.85 (1H, s), 8.83 (2H, s), 7.73 (1H, d, J=8.2 Hz), 7.60 (1H, t, J=7.9 Hz), 7.42 (1H, d, J=8.2 Hz), 7.12 (2H, s), 4.71 (1H, t, J=5.5 Hz), 4.13 (2H, t, J=8.3 Hz), 3.79-3.65 (8H, m), 3.38 (2H, t, J=5.8 Hz), 3.30 (2H, brs), 2.52-2.49 (2H, m).

ESI (LC-MS positive mode) m/z 499 (M+H)$^+$.

Example 1-D-100

4-[4-(2-Amino-pyrimidin-5-yl)-2-morpholin-4-yl-5,6-dihydro-pyrrolo[2,3-d]pyrimidin-7-yl]-N-(2-hydroxy-ethyl)-benzenesulfonamide (D-100)

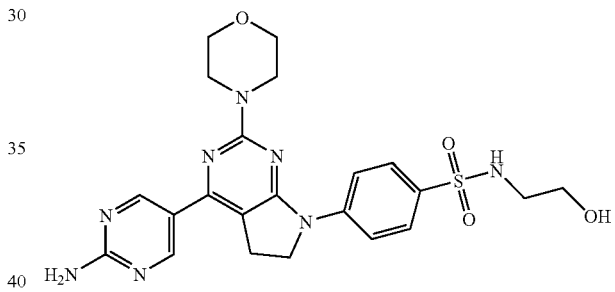

In the same manner as Example 1-D-98, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(2-hydroxy-ethyl)-benzenesulfonamide was obtained, which was further treated in the same manner as Example 1-D-98, to obtain the desired compound (D-100) as a yellow powder (8 mg, 7%). Using 4-bromo-N-Boc-N-(2-hydroxy-ethyl)-benzenesulfonamide (106 mg) instead of 4-bromo-N-Boc-N-(3-hydroxy-propyl)-benzenesulfonamide in Example 1-D-98, the same operation as Example 1-D-98 was carried out, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-(2-hydroxy-ethyl)-benzenesulfonamide, and then the PMB groups were removed according to Deprotection method 1, to obtain the desired compound (D-100) as a yellow powder (8 mg, 7%).

$^1$H-NMR (CD$_3$OD) δ (ppm): 8.48 (2H, s), 7.61 (2H, d, J=9.1 Hz), 7.48 (2H, d, J=9.1 Hz), 3.80 (2H, t, J=8.0 Hz), 3.56 (2H, brs), 3.50-3.45 (8H, m), 3.24 (2H, t, J=5.3 Hz), 2.65 (2H, t, J=5.3 Hz).

ESI (LC-MS positive mode) m/z 499 (M+H)$^+$.

Example 1-D-101

4-(2-Amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-phenyl]-amide (D-101)

Step A (4-Ethyl-piperazin-1-yl)-(3-nitro-phenyl)-methanone

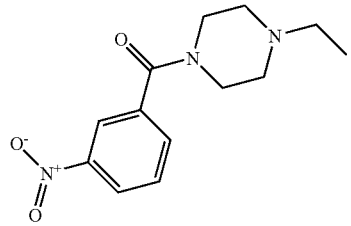

To a DMF solution (10 ml) of 3-nitro-benzoic acid (334 mg) and N-ethyldiisopropylamine (1 ml), HOBt (270 mg) and WSCI (575 mg) were added, followed by stirring at room temperature for 10 minutes. To this, 1-ethyl-piperazine (305 μl) was added, followed by stirring at room temperature for 22 hours. Brine (30 ml) was added, followed by extraction with ethyl acetate (30 ml×2), and the organic layer was dried over sodium sulfate. After the sodium sulfate was filtered off, the solvent was distilled off under reduced pressure, followed by purification by silica gel column chromatography (dichloromethane/methanol=100/1 to 20/1), to obtain the desired compound (365.3 mg, 69%).

Step B (3-Amino-phenyl)-(4-ethyl-piperazin-1-yl)-methanone

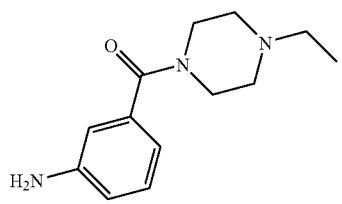

To methanol solution (5 ml) of (4-ethyl-piperazin-1-yl)-(3-nitro-phenyl)-methanone (365.3 mg) obtained in Step A, palladium black was added, followed by stirring at room temperature for 14 hours under a hydrogen gas atmosphere. This was filtered through Celite, and subsequently the solvent was distilled off under reduced pressure, to obtain the desired compound as a crude product (241.8 mg, 51%).

Step C 4-(2-Amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-phenyl]-amide (D-101)

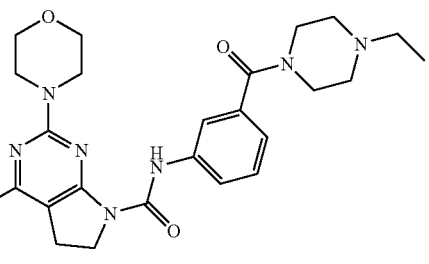

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and (3-amino-phenyl)-(4-ethyl-piperazin-1-yl)-methanone (93.3 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(4-ethyl-piperazine-1-carbonyl)-phenyl]-amide was obtained as a crude product. Then the PMB groups were removed according to Deprotection method 3, to obtain the desired compound (D-101) as a colorless solid (51.4 mg, 46%).

$^1$H-NMR (DMSO-$d_6$) δ: 11.12 (1H, s), 8.92 (2H, s), 7.81 (1H, s), 7.49-7.44 (2H, m), 7.20-7.15 (1H, m), 4.06 (2H, t, J=7.9 Hz), 3.83-3.71 (8H, m), 3.62-2.98 (10H, brm), 2.49-2.48 (2H, brm), 1.23 (3H, t, J=7.3 Hz).

ESI (LC-MS positive mode) m/z 559 (M+H)$^+$.

Example 1-D-102

4-(2-Amino-pyrimidin-5-yl)-2-morpholin-4-yl-5,6-dihydro-pyrrolo[2,3-d]pyrimidine-7-carboxylic acid [3-(morpholine-4-carbonyl)-phenyl]-amide (D-102)

Step A

Morpholin-4-yl-(3-nitro-phenyl)-methanone

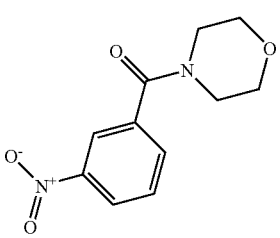

Using 3-nitro-benzoic acid (334 mg) and morpholine (209 µl) instead of 1-ethyl-piperazine, in the same manner as Step A in Example 1-D-101, the desired compound was obtained (340 mg, 72%).

Step B (3-Amino-phenyl)-morpholin-4-yl-methanone

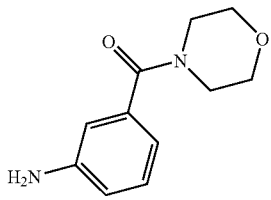

Using morpholin-4-yl-(3-nitro-phenyl)-methanone (340 mg) obtained in Step A instead of (4-ethyl-piperazin-1-yl)-(3-nitro-phenyl)-methanone, in the same manner as Step B in Example 1-D-101, the desired compound was obtained as a crude product (206.5 mg, 69%).

Step C 4-(2-Amino-pyrimidin-5-yl)-2-morpholin-4-yl-5,6-dihydro-pyrrolo[2,3-d]pyrimidine-7-carboxylic acid [3-(morpholine-4-carbonyl)-phenyl]-amide (D-102)

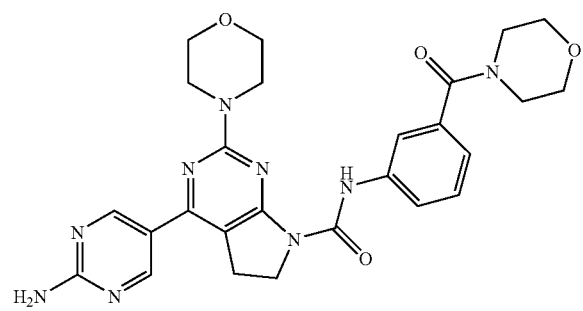

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and (3-amino-phenyl)-morpholin-4-yl-methanone (82.5 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(morpholine-4-carbonyl)-phenyl]-amide was obtained as a crude product. Then the PMB groups were removed according to Deprotection method 3, to obtain the desired compound (D-102) as a colorless solid (48.8 mg, 46%).

$^1$H-NMR (TFA-d$_1$) δ: 9.16 (2H, s), 7.93 (1H, s), 7.61-7.53 (1H, m), 7.47-7.36 (2H, m), 4.47 (2H, t, J=7.9 Hz), 4.17-4.02 (12H, m), 4.02-3.95 (2H, brm), 3.81-3.74 (2H, brm), 3.32 (2H, t, J=7.9 Hz).

ESI (LC-MS positive mode) m/z 532 (M+H)$^+$.

Example 1-D-103

4-(2-Amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-phenyl]-amide (D-103)

Step A (4-Ethyl-piperazin-1-yl)-(4-nitro-phenyl)-methanone

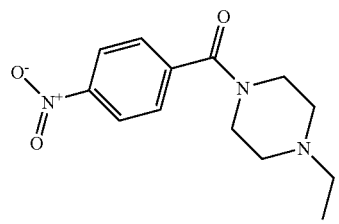

Using 4-nitro-benzoic acid (334 mg) instead of 3-nitro-benzoic acid, in the same manner as Step A in Example 1-D-101, the desired compound was obtained as a crude product (256.4 mg, 49%).

Step B (4-Amino-phenyl)-(4-ethyl-piperazin-1-yl)-methanone

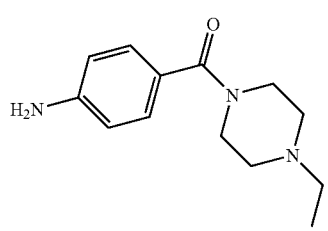

Using (4-ethyl-piperazin-1-yl)-(4-nitro-phenyl)-methanone (256.4 mg) obtained in Step A instead of (4-ethyl-piperazin-1-yl)-(3-nitro-phenyl)-methanone, in the same manner as Step B in Example 1-D-101, the desired compound was obtained as a crude product (240.9 mg, quant.).

Step C 4-(2-Amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-phenyl]-amide (D-103)

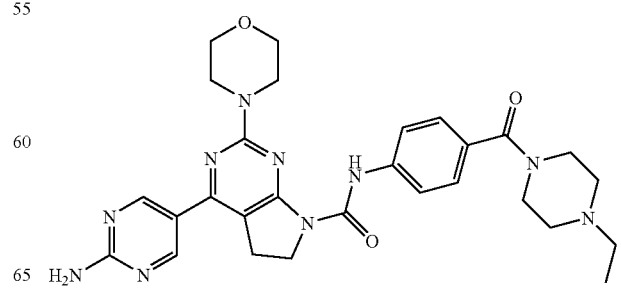

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and (4-amino-phenyl)-(4-ethyl-piperazin-1-yl)-methanone (93.3 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazine-1-carbonyl)-phenyl]-amide was obtained as a crude product. Then the PMB groups were removed according to Deprotection method 3, to obtain the desired compound (D-103) as a colorless solid (13.9 mg, 12%).

$^1$H-NMR (DMSO-d$_6$) δ: 11.16 (1H, s), 8.98 (2H, s), 7.64 (2H, d, J=8.6 Hz), 7.51 (2H, d, J=8.6 Hz), 4.08 (2H, t, J=8.0 Hz), 3.84-3.72 (8H, brm), 3.57-3.46 (4H, brm), 3.33-3.01 (6H, m), 2.62-2.57 (2H, brm), 1.24 (3H, t, J=7.3 Hz).

ESI (LC-MS positive mode) m/z 559 (M+H)$^+$.

Example 1-D-104

4-(2-Amino-pyrimidin-5-yl)-2-morpholin-4-yl-5,6-dihydro-pyrrolo[2,3-d]pyrimidine-7-carboxylic acid [4-(morpholine-4-carbonyl)-phenyl]-amide (D-104)

Step A

Morpholin-4-yl-(4-nitro-phenyl)-methanone

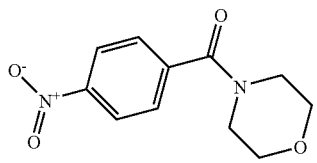

Using 4-nitro-benzoic acid (334 mg) instead of 3-nitro-benzoic acid, and morpholine (209 μl) instead of 1-ethyl-piperazine, in the same manner as Step A in Example 1-D-101, the desired compound was obtained (363.5 mg, 77%).

Step B (4-Amino-phenyl)-morpholin-4-yl-methanone

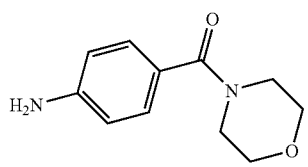

Using (4-amino-phenyl)-morpholin-4-yl-methanone (363.5 mg) obtained in Step A instead of (4-ethyl-piperazin-1-yl)-(3-nitro-phenyl)-methanone, in the same manner as Step B in Example 1-D-101, the desired compound was obtained as a crude product (241.8 mg, 77%).

Step C 4-(2-Amino-pyrimidin-5-yl)-2-morpholin-4-yl-5,6-dihydro-pyrrolo[2,3-d]pyrimidine-7-carboxylic acid [4-(morpholine-4-carbonyl)-phenyl]-amide (D-104)

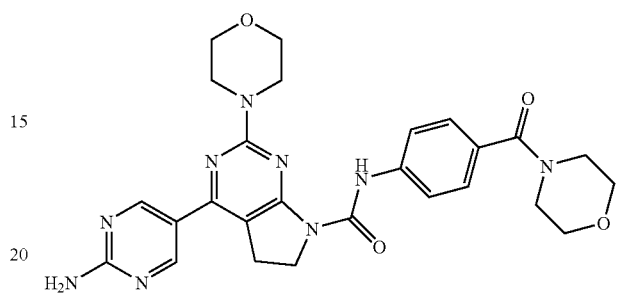

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and (4-amino-phenyl)-morpholin-4-yl-methanone (82.5 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(morpholine-4-carbonyl)-phenyl]-amide was obtained as a crude product. Then the PMB groups were removed according to Deprotection method 3, to obtain the desired compound (D-104) as a yellow solid (26.4 mg, 25%).

$^1$H-NMR (TFA-d$_1$) δ: 9.12 (2H, s), 7.65-7.53 (4H, m), 4.43 (2H, t, J=7.2 Hz), 4.14-3.99 (12H, m), 3.98-3.88 (2H, m), 3.81-3.69 (2H, m), 3.27 (2H, t, J=7.2 Hz).

ESI (LC-MS positive mode) m/z 532 (M+H)$^+$.

Example 1-D-105

4-(2-Amino-pyrimidin-5-yl)-2-morpholin-4-yl-5,6-dihydro-pyrrolo[2,3-d]pyrimidine-7-carboxylic acid (3-morpholin-4-yl-phenyl)-amide (D-105)

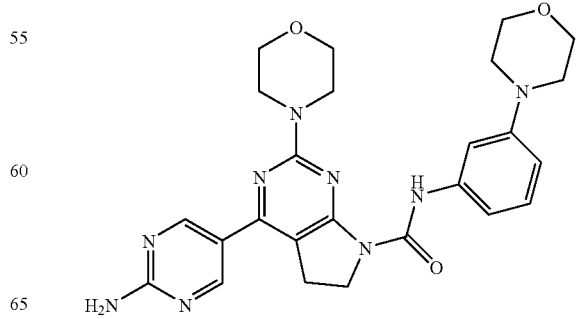

Step A 4-(3-Nitro-phenyl)-morpholine

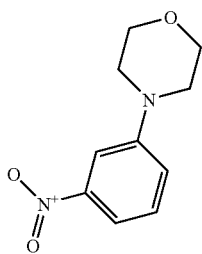

To a toluene solution (10 ml) of 1-bromo-3-nitro-benzene (303 mg), palladium acetate (9.0 mg), BINAP (37 mg) and cesium carbonate (978 mg), morpholine (209 μl) was added, degassed under ultrasonic irradiation. This was stirred at 100° C. for 6 hours, followed by addition of water (20 ml), which was extracted with ethyl acetate (20 ml×2), and the organic layer was dried over sodium sulfate. After the sodium sulfate was filtered off, the solvent was distilled off under reduced pressure, followed by purification by silica gel column chromatography (dichloromethane/methanol=100/1 to 20/1), to obtain the desired compound (236.7 mg, 57%).

Step B

3-Morpholin-4-yl-phenylamine

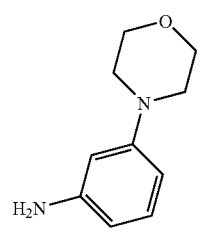

Using 4-(3-nitro-phenyl)-morpholine (236.7 mg) obtained in Step A instead of (4-ethyl-piperazin-1-yl)-(3-nitro-phenyl)-methanone, in the same manner as Step B in Example 1-D-101, the desired compound was obtained (61.4 mg, 30%).

Step C 4-(2-Amino-pyrimidin-5-yl)-2-morpholin-4-yl-5,6-dihydro-pyrrolo[2,3-d]pyrimidine-7-carboxylic acid (3-morpholin-4-yl-phenyl)-amide (D-105)

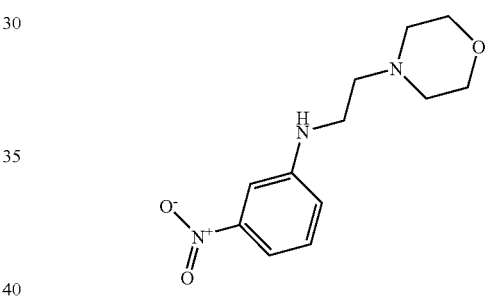

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and 3-morpholin-4-yl-phenylamine (61.4 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-morpholin-4-yl-phenyl)-amide was obtained as a crude product. Then the PMB groups were removed according to Deprotection method 3, to obtain the desired compound (D-105) as a colorless solid (37.4 mg, 37%).

$^1$H-NMR (CDCl$_3$) δ: 11.13 (1H, s), 9.19 (2H, s), 8.37-8.29 (2H, m), 7.37-7.31 (1H, m), 7.17-7.09 (1H, m), 4.29 (2H, t, J=8.1 Hz), 4.20-4.13 (4H, brm), 3.93-3.89 (8H, brm), 3.78-3.71 (4H, m), 3.31 (2H, t, J=8.1 Hz).

ESI (LC-MS positive mode) m/z 504 (M+H)$^+$.

Example 1-D-106

4-(2-Amino-pyrimidin-5-yl)-2-morpholin-4-yl-5,6-dihydro-pyrrolo[2,3-d]pyrimidine-7-carboxylic acid [3-(2-morpholin-4-yl-ethylamino)-phenyl]-amide (D-106)

Step A (2-Morpholin-4-yl-ethyl)-(3-nitro-phenyl)-amine

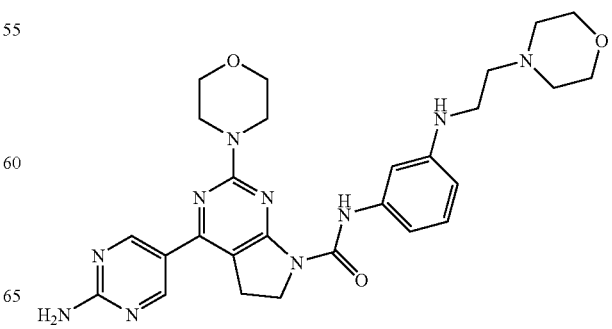

Using 1-bromo-3-nitro-benzene (303 mg) and 2-morpholin-4-yl-ethylamine (315 μl) instead of morpholine, in the same manner as Step A in Example 1-D-105, the desired compound was obtained (374.6 mg, 74%).

Step B 4-(2-Amino-pyrimidin-5-yl)-2-morpholin-4-yl-5,6-dihydro-pyrrolo[2,3-d]pyrimidine-7-carboxylic acid [3-(2-morpholin-4-yl-ethylamino)-phenyl]-amide (D-106)

To a DMF solution (5 ml) of (2-morpholin-4-yl-ethyl)-(3-nitro-phenyl)-amine (374.6 mg) obtained in Step A, di-tert-butyl dicarbonate (650 mg) and DMAP (18.2 mg) were added, followed by stirring at 50° C. for 20 hours. Water (20 ml) was added, followed by extraction with ethyl acetate (20 ml×2), and the organic layer was dried over sodium sulfate. The sodium sulfate was filtered off, and the solvent was distilled off under reduced pressure, to obtain (2-morpholin-4-yl-ethyl)-(3-nitro-phenyl)-carbamic acid tert-butyl ester as a crude product.

Using this crude product instead of (4-ethyl-piperazin-1-yl)-(3-nitro-phenyl)-methanone, in the same manner as Step B in Example 1-D-101, (3-amino-phenyl)-(2-morpholin-4-yl-ethyl)-carbamic acid tert-butyl ester was obtained as a crude product.

Using this crude product instead of 4-(4-ethyl-piperazin-1-yl)-2,6-difluoro-phenylamine, and using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg), in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(2-morpholin-4-yl-ethylamino)-phenyl]-amide was obtained as a crude product. Then the PMB groups were removed according to Deprotection method 3, to obtain the desired compound (D-106) as a yellow solid (17 mg, 16%)

$^1$H-NMR (TFA-$d_1$) δ: 9.31 (2H, s), 8.59 (1H, s), 7.79-7.70 (1H, m), 7.62-7.54 (1H, m), 7.42-7.36 (1H, m), 4.60 (2H, t, J=7.7 Hz), 4.52-4.40 (4H, m), 4.33-4.20 (8H, m), 4.19-3.97 (6H, m), 3.60 (2H, t, J=12.0 Hz), 3.48 (2H, t, J=7.7 Hz).

ESI (LC-MS positive mode) m/z 547 (M+H)$^+$.

Example 1-D-107

4-(2-Amino-pyrimidin-5-yl)-2-morpholin-4-yl-5,6-dihydro-pyrrolo[2,3-d]pyrimidine-7-carboxylic acid (4-morpholin-4-yl-phenyl)-amide (D-107)

Step A 4-(4-Nitro-phenyl)-morpholine

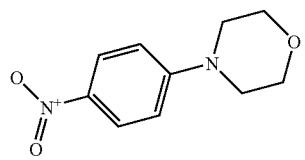

Using 1-iodo-4-nitro-benzene (498 mg) instead of 1-Bromo-3-nitro-benzene, in the same manner as Step A in Example 1-D-105, the desired compound was obtained (109.1 mg, 26%).

Step B

4-Morpholin-4-yl-phenylamine

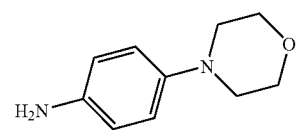

Using 4-morpholin-4-yl-phenylamine (109.1 mg) obtained in Step A instead of (4-ethyl-piperazin-1-yl)-(3-nitro-phenyl)-methanone, in the same manner as Step B in Example 1-D-101, the desired compound was obtained (45.4 mg, 49%).

Step C 4-(2-Amino-pyrimidin-5-yl)-2-morpholin-4-yl-5,6-dihydro-pyrrolo[2,3-d]pyrimidine-7-carboxylic acid (4-morpholin-4-yl-phenyl)-amide (D-107)

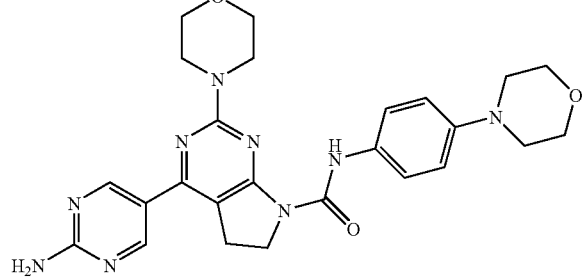

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and 4-morpholin-4-yl-phenylamine (45.4 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-morpholin-4-yl-phenyl)-amide was obtained as a crude product. Then the PMB groups were removed according to Deprotection method 3, to obtain the desired compound (D-107) as a yellow solid (20 mg, 20%).

$^1$H-NMR (CDCl$_3$) δ: 9.20 (2H, s), 7.68 (2H, d, J=9.1 Hz), 7.57 (2H, d, J=9.1 Hz), 4.30 (2H, t, J=8.4 Hz), 4.20-4.12 (4H, brm), 3.97-3.88 (8H, brm), 3.74-3.66 (4H, brm), 3.30 (2H, t, J=8.4 Hz).

ESI (LC-MS positive mode) m/z 504 (M+H)$^+$.

Example 1-D-108

4-(2-Amino-pyrimidin-5-yl)-2-morpholin-4-yl-5,6-dihydro-pyrrolo[2,3-d]pyrimidine-7-carboxylic acid [4-(2-morpholin-4-yl-ethylamino)-phenyl]-amide (D-108)

Step A (2-Morpholin-4-yl-ethyl)-(4-nitro-phenyl)-amine

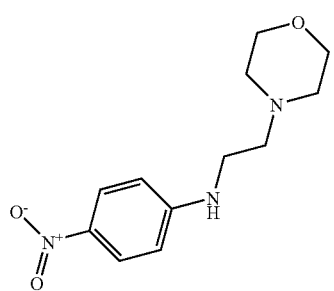

Using 1-iodo-4-nitro-benzene (498 mg) instead of 1-bromo-3-nitro-benzene, and 2-morpholin-4-yl-ethylamine (315 μl) instead of morpholine, in the same manner as Step A in Example 1-D-105, the desired compound was obtained (301.1 mg, 60%).

Step B 4-(2-Amino-pyrimidin-5-yl)-2-morpholin-4-yl-5,6-dihydro-pyrrolo[2,3-d]pyrimidine-7-carboxylic acid [4-(2-morpholin-4-yl-ethylamino)-phenyl]-amide (D-108)

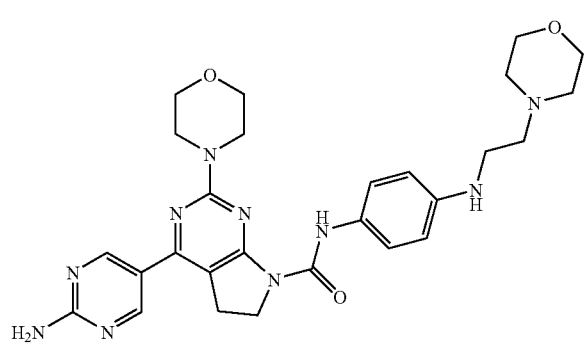

To a DMF solution (5 ml) of (2-morpholin-4-yl-ethyl)-(4-nitro-phenyl)-amine (301.1 mg) obtained in Step A, di-tert-butyl dicarbonate (544 mg) and DMAP (18.2 mg) were added, followed by stirring at 50° C. for 20 hours. Water (20 ml) was added, followed by extraction with ethyl acetate (20 ml×2), and the organic layer was dried over sodium sulfate. The sodium sulfate was filtered off, and the solvent was distilled off under reduced pressure, to obtain (2-morpholin-4-yl-ethyl)-(4-nitro-phenyl)-carbamic acid tert-butyl ester as a crude product.

Using this crude product instead of (4-ethyl-piperazin-1-yl)-(3-nitro-phenyl)-methanone, in the same manner as Step B in Example 1-D-101, (4-amino-phenyl)-(2-morpholin-4-yl-ethyl)-carbamic acid tert-butyl ester was obtained as a crude product.

Using this crude product instead of 4-(4-ethyl-piperazin-1-yl)-2,6-difluoro-phenylamine, and using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg), in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(2-morpholin-4-yl-ethylamino)-phenyl]-amide was obtained as a crude product. Then the PMB groups were removed according to Deprotection method 3, to obtain the desired compound (D-108) as a yellow solid (9.3 mg, 9%)

$^1$H-NMR (TFA-d$_1$) δ: 8.94 (2H, s), 7.50 (2H, d, J=8.6 Hz), 7.41 (2H, d, J=8.6 Hz), 4.25 (2H, t, J=7.7 Hz), 4.15-3.95 (4H, m), 3.94-3.79 (8H, m), 3.76-3.55 (6H, m), 3.22 (2H, t, J=10.8 Hz), 3.09 (2H, t, J=7.7 Hz).

ESI (LC-MS positive mode) m/z 547 (M+H)$^+$.

Example 1-D-109

1-(4-{5-[4-(2-Amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-109)

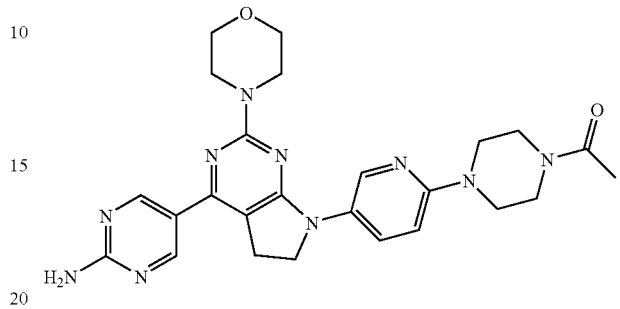

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.307 mmol) obtained in Step A in Example 1-D-48 and N-acetylpiperazine (59 mg, 0.461 mmol) instead of N,N,N'-trimethyl ethylenediamine, in the same manner as Example 1-D-48, amination was carried out, to obtain a crude product of 1-{4-[5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-piperazin-1-yl}-ethanone as a yellow solid (120 mg), and then the PMB groups were removed according to the above Deprotection method 2, to obtain the desired compound (D-109) as a yellow powder (46 mg, 57%).

$^1$H-NMR (CDCl$_3$) δ (ppm): 8.80 (2H, s), 8.54 (1H, d, J=2.9 Hz), 8.10 (1H, dd, J=2.7, 9.3 Hz), 7.05 (2H, s), 6.94 (1H, d, J=9.2 Hz), 4.05 (2H, t, J=8.3 Hz), 3.68 (8H, s), 3.49 (8H, m), 3.27 (2H, m), 2.05 (3H, s).

ESI (LC-MS positive mode) m/z 503 (M+H)$^+$.

Example 1-D-110

5-[2-Morpholin-4-yl-7-(6-morpholin-4-yl-pyridin-3-yl)-6,7-dihydro-5H-pyrrolo[2,3-d]pyrimidin-4-yl]-pyrimidin-2-ylamine (D-110)

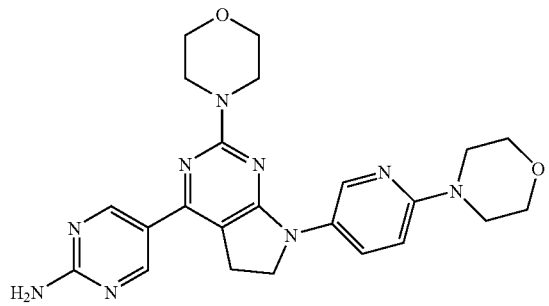

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.307 mmol) obtained in Step A in Example 1-D-48 and morpholine (40.2 mg, 0.462 mmol) instead of N,N,N'-trimethyl ethylenediamine, in the same manner as Step B in Example 1-D-48, amination was carried out, to obtain a crude product of bis-(4-methoxy-benzyl)-{5-[2-morpholin-4-yl-7-(6-morpholin-4-yl-pyridin-3-yl)-6,7-dihydro-5H-pyrrolo[2,3-d]pyrimidin-4-yl]-pyrimidin-2-yl}-amine as a yellow solid (160 mg), and then the PMB groups were removed according to the above Deprotection method 2, to obtain the desired compound (D-110) as a yellow powder (56 mg, 53%).

$^1$H-NMR (CDCl$_3$) δ (ppm): 8.88 (2H, s), 8.52 (1H, d, J=2.6 Hz), 8.09 (1H, dd, J=2.8, 9.2 Hz), 6.72 (1H, d, J=9.3 Hz), 5.22 (2H, s), 4.07 (2H, t, J=8.2 Hz), 3.83 (12H, s), 3.48 (4H, m), 3.29 (2H, t, J=8.2 Hz).

ESI (LC-MS positive mode) m/z 462 (M+H)$^+$.

Example 1-D-111

{4-[4-(2-Amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-111)

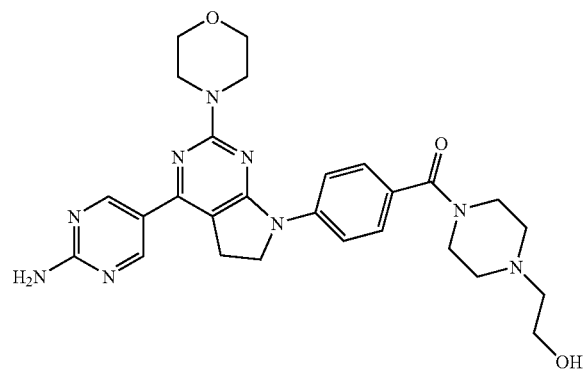

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (70.0 mg, 0.106 mmol) obtained in Step A in Example 1-D-19 and 1-piperazineethanol (26.0 μl, 0.212 mmol) instead of 3-(aminomethyl)pyridine, in the same manner as Step B in Example 1-D-19, amidation was carried out, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-[4-(2-hydroxy-ethyl)-piperazin-1-yl]-methanone as a yellow solid (68.1 mg), and then the PMB groups were removed according to the above Deprotection method 3, to obtain the desired compound (D-111) as a yellow powder (24.7 mg, 44%).

$^1$H-NMR (CDCl$_3$) δ (ppm): 8.89 (2H, s), 7.84 (2H, d, J=8.9 Hz), 7.47 (2H, d, J=8.9 Hz), 5.25 (2H, s), 4.12 (2H, t, J=8.3 Hz), 3.88-3.77 (12H, m), 3.66 (2H, t, J=5.3 Hz), 3.31 (2H, t, J=8.3 Hz), 2.59 (2H, t, J=5.3 Hz), 2.60-2.50 (4H, brm), 1.63 (1H, brs).

ESI (LC-MS positive mode) m/z 532 (M+H)$^+$.

Example 1-D-112

{4-[4-(2-Amino-pyrimidin-5-yl)-2-morpholin-4-yl-5,6-dihydro-pyrrolo[2,3-d]pyrimidin-7-yl]-phenyl}-piperazin-1-yl-methanone (D-112)

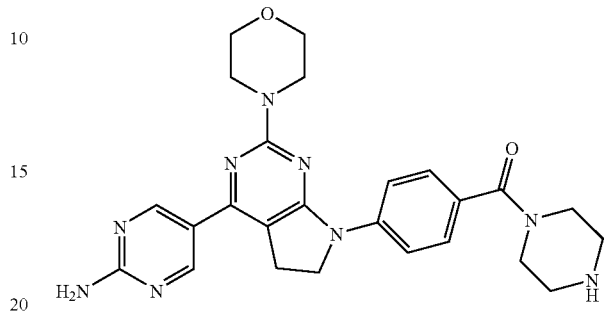

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (70.4 mg, 0.107 mmol) obtained in Step A in Example 1-D-19 and 1-Boc-piperazine (31.7 mg, 0.170 mmol) instead of 3-(aminomethyl)pyridine, in the same manner as Step B in Example 1-D-19, amidation was carried out, to obtain a crude product of 4-{4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-benzoyl}-piperazine-1-carboxylic acid tert-butyl ester as a yellow solid (74.2 mg), and then the PMB groups and BOC group were removed according to the above Deprotection method 3, to obtain the desired compound (D-112) as a colorless powder (41.4 mg, 80%).

$^1$H-NMR (CDCl$_3$) δ (ppm): 8.89 (2H, s), 7.84 (2H, d, J=8.4 Hz), 7.47 (2H, d, J=8.4 Hz), 5.22 (2H, s), 4.12 (1H, t, J=8.2 Hz), 3.89-3.52 (12H, m), 3.31 (2H, t, J=8.2 Hz), 2.94-2.87 (4H, brm), 1.58 (1H, brs).

ESI (LC-MS positive mode) m/z 488 (M+H)$^+$.

Example 1-D-113

{4-[4-(2-Amino-pyrimidin-5-yl)-2-morpholin-4-yl-5,6-dihydro-pyrrolo[2,3-d]pyrimidin-7-yl]-phenyl}-(4-isopropyl-piperazin-1-yl)-methanone (D-113)

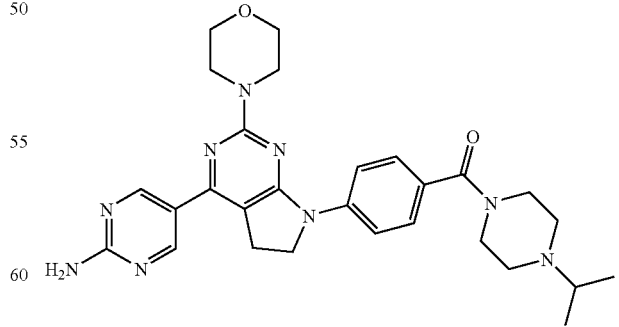

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid obtained in Step A in Example 1-D-19 and 1-isopropylpiperazine (30.4 μl, 0.212 mmol) instead of 3-(aminomethyl)pyridine, in the same manner as Step B in Example 1-D-19, amidation was carried out, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-isopropyl-piperazin-1-yl)-methanone as a yellow solid (64.4 mg), and then the PMB groups were removed according to the above Deprotection method 3, to obtain the desired compound (D-113) as a colorless powder (38.7 mg, 69%).

$^1$H-NMR (CDCl$_3$) δ (ppm): 8.89 (2H, s), 7.83 (2H, d, J=8.7 Hz), 7.48 (2H, d, J=8.7 Hz), 5.25 (2H, s), 4.12 (2H, t, J=8.1 Hz), 3.89-3.65 (12H, m), 3.31 (2H, t, J=8.1 Hz), 2.91-2.49 (5H, m), 1.09 (6H, d, J=6.6 Hz).

ESI (LC-MS positive mode) m/z 530 (M+H)$^+$.

Example 1-D-114

5-[7-(1-Benzyloxymethyl-1H-benzimidazol-5-yl)-2-morpholin-4-yl-6,7-dihydro-5H-pyrrolo[2,3-d]pyrimidin-4-yl]-pyrimidin-2-ylamine (D-114)

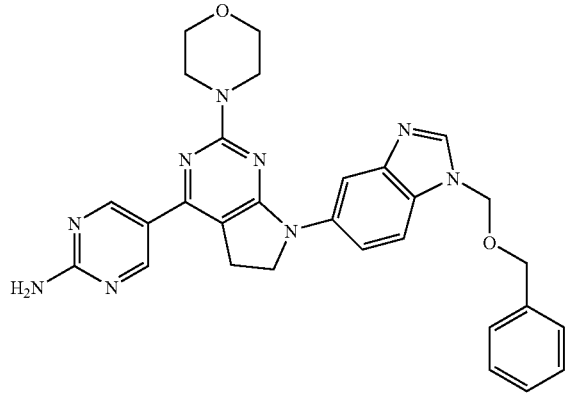

Example 1-D-115

5-[7-(1H-benzimidazol-5-yl)-2-morpholin-4-yl-6,7-dihydro-5H-pyrrolo[2,3-d]pyrimidin-4-yl]-pyrimidin-2-ylamine (D-115)

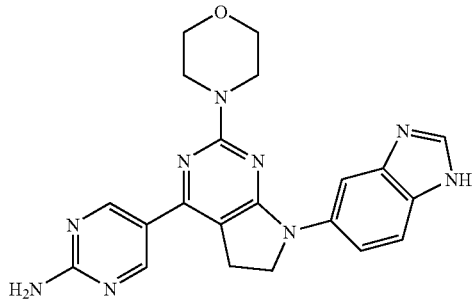

From bis-(4-methoxy-benzyl)-[5-(2-morpholin-4-yl-6,7-dihydro-5H-pyrrolo[2,3-d]pyrimidin-4-yl)-pyrimidin-2-yl]-amine (142 mg) and 1-benzyloxymethyl-5-bromo-1H-benzimidazole (prepared from 5-bromobenzimidazole, 60% oily sodium hydride and benzyloxymethyl chloride, 100 mg) instead of (3-bromo-4-methyl-phenyl)-morpholin-4-yl-methanone, in the same manner as Example 1-D-25, a crude product of {5-[7-(1-benzyloxymethyl-1H-benzimidazol-5-yl)-2-morpholin-4-yl-6,7-dihydro-5H-pyrrolo[2,3-d]pyrimidin-4-yl]-pyrimidin-2-yl}-bis-(4-methoxy-benzyl)-amine was obtained, and then the PMB groups were removed according to the above Deprotection method 1, followed by purification by amino silica gel column chromatography (dichloromethane/2M-ammonia methanol=100/1 to 20/1), to obtain the desired compound (D-114) as an ivory powder (5 mg, 4%) and the desired compound (D-115) as an ivory powder (22 g, 17%).

D-114:

$^1$H-NMR (CDCl$_3$) δ (ppm): 8.91 (2H, s), 8.44 (1H, d, J=2.0 Hz), 7.89 (1H, s), 7.81 (1H, d, J=8.7 Hz), 7.53 (1H, dd, J=8.7, 2.0 Hz), 7.40-7.26 (5H, m), 5.57 (2H, s), 5.23 (2.0H, s), 4.44 (2H, s), 4.21 (2H, t, J=8.2 Hz), 3.82-3.72 (8H, m), 3.33 (2H, t, J=8.2 Hz).

ESI (LC-MS positive mode) m/z 536 (M+H)$^+$.

D-115:

$^1$H-NMR (DMSO-d$_6$) δ (ppm): 12.40 (1H, s), 8.82 (2H, s), 8.17 (1H, brs), 8.12 (1H, brs), 7.95 (1H, brs), 7.62-7.59 (1H, m), 7.07 (2H, s), 4.15 (2H, t, J=8.0 Hz), 3.70 (8H, brs), 3.30 (2H, brs).

ESI (LC-MS positive mode) m/z 416 (M+H)$^+$.

Example 1-D-116

N-{5-[4-(2-Amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (D-116)

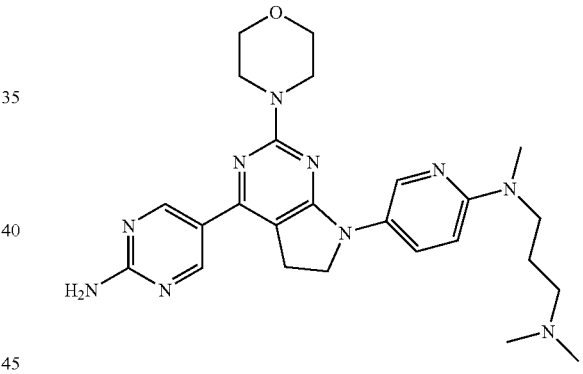

Using {5-[7-(6-chloro-pyridin-3-yl)-2-morpholin-4-yl-6,7-dihydro-5H-pyrrolo[2,3-d]pyrimidin-4-yl]-pyrimidin-2-yl}-bis-(4-methoxy-benzyl)-amine (200 mg, 0.307 mmol) obtained in Step A in Example 1-D-48 and N,N,N'-trimethyl-1,3-propanediamine (67 μl, 0.46 mmol) instead of N,N,N'-trimethyl ethylenediamine, in the same manner as Step B in Example 1-D-48, amination was carried out, to obtain a crude product of N-[5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-N,N',N'-trimethyl-propan-1,3-diamine as a pale yellow solid (162 mg), and then the PMB groups were removed according to the above Deprotection method 2, to obtain the desired compound (D-116) as a colorless powder (67 mg, 57%).

$^1$H-NMR (CDCl$_3$) δ (ppm): 8.87 (2H, s), 8.35 (1H, d, J=2.6 Hz), 8.04 (1H, dd, J=2.6, 9.1 Hz), 6.59 (1H, d, J=9.1 Hz), 5.25 (2H, s), 4.04 (2H, t, J=8.0 Hz), 3.79 (10H, s), 3.57 (2H, t, J=7.2 Hz), 3.26 (2H, t, J=8.3 Hz), 3.05 (3H, s), 2.38 (2H, t, J=6.8 Hz), 2.28 (s, 6H).

ESI (LC-MS positive mode) m/z 491 (M+H)$^+$.

Example 1-D-117

{5-[4-(2-Amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-117)

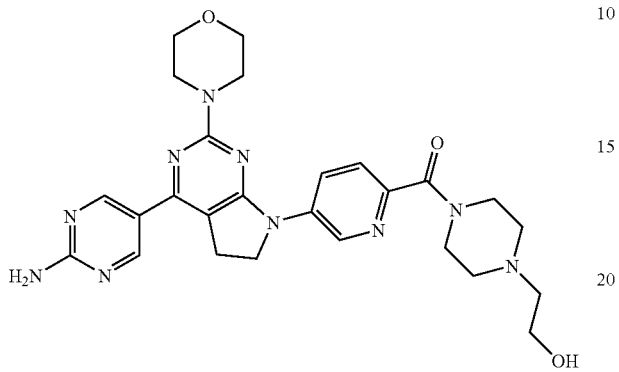

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (5-bromo-pyridin-2-yl)-[4-(2-hydroxy-ethyl)-piperazin-1-yl]-methanone (70 mg) obtained in the same manner as Step A in Example 1-D-79 instead of 4-bromobenzoic acid methyl ester in Example 1-D-08, in the same manner as Example 1-D-08, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-[4-(2-hydroxy-ethyl)-piperazin-1-yl]-methanone was obtained, and then the PMB groups were removed according to Deprotection method 1, to obtain the desired compound (D-117) as a yellow powder (23 mg, 23%).

$^1$H-NMR (DMSO-$d_6$) δ (ppm): 9.05 (1H, d, J=2.3 Hz), 8.83 (2H, s), 8.37 (1H, dd, J=8.6, 2.3 Hz), 7.65 (1H, d, J=8.6 Hz), 7.13 (2H, s), 4.44 (1H, t, J=5.1 Hz), 4.16 (2H, t, J=7.9 Hz), 3.74-3.70 (8H, brm), 3.65-3.62 (2H, m), 3.29 (2H, brs), 2.42 (2H, t, J=6.2 Hz).

ESI (LC-MS positive mode) m/z 533 (M+H)$^+$.

Example 1-D-118

2-(4-{3-[4-(2-Amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-118)

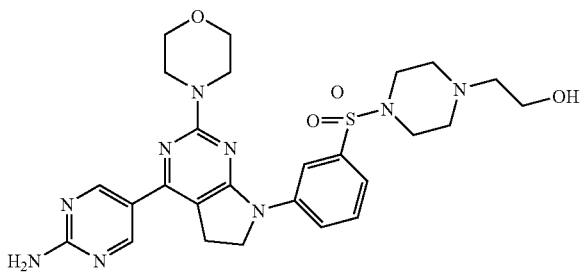

Using 3-bromo-benzenesulfonyl-4-(2-hydroxyethyl)piperazine instead of 4-bromo-N-Boc-N-(3-hydroxy-propyl)-benzenesulfonamide in Example 1-D-98, in the same manner as Example 1-D-98, a crude product of 2-{4-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzenesulfonyl]-piperazin-1-yl}-ethanol was obtained, and then the PMB groups were removed according to Deprotection method 1, to obtain the desired compound (D-118) as a yellow powder (14 mg, 13%).

$^1$H-NMR (DMSO-$d_6$) δ (ppm): 8.94 (1H, s), 8.83 (2H, s), 7.73-7.67 (2H, m), 7.34 (1H, d, J=6.8 Hz), 7.12 (2H, s), 4.35 (1H, t, J=5.4 Hz), 4.15 (2H, t, J=7.7 Hz), 3.76-3.69 (8H, m), 3.41-3.39 (4H, m), 3.29 (2H, brs), 2.88 (4H, brs), 2.34 (2H, t, J=6.0 Hz).

ESI (LC-MS positive mode) m/z 568 (M+H)$^+$.

Example 1-D-119

2-(4-{4-[4-(2-Amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-119)

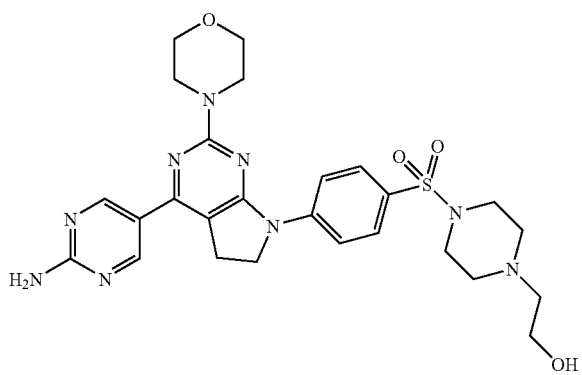

Using 4-bromo-benzenesulfonyl-4-(2-hydroxyethyl)piperazine instead of 4-bromo-N-Boc-N-(3-hydroxy-propyl)-benzenesulfonamide in Example 1-D-98, in the same manner as Example 1-D-98, a crude product of 2-{4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzenesulfonyl]-piperazin-1-yl}-ethanol was obtained, and then the PMB groups were removed according to Deprotection method 1, to obtain the desired compound (D-119) as a yellow powder (28 mg, 27%).

$^1$H-NMR (DMSO-$d_6$) δ (ppm): 8.83 (2H, s), 8.12 (2H, d, J=8.7 Hz), 7.73 (2H, d, J=8.7 Hz), 7.13 (1H, s), 4.36 (1H, t, J=5.4 Hz), 4.15 (2H, t, J=8.0 Hz), 3.73-3.71 (8H, m), 3.41 (4H, q, J=5.3 Hz), 3.28 (2H, brs), 2.86 (4H, brs), 2.35 (2H, t, J=5.9 Hz)

ESI (LC-MS positive mode) m/z 568 (M+H)$^+$.

Example 1-D-120

{2-[4-(2-Amino-pyrimidin-5-yl)-2-morpholin-4-yl-5,6-dihydro-pyrrolo[2,3-d]pyrimidin-7-yl]-thiazol-4-yl}-(4-ethyl-piperazin-1-yl)-methanone (D-120)

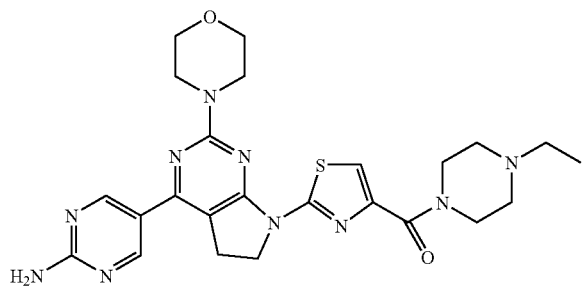

Step A

From bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-bromo-thiazole-4-carboxylic acid ethyl ester (96 mg), in the same manner as Example 1-D-08, a crude product of 2-(4-{2-[bis-(4-methoxy-benzyl)-amino]-pyrimidin-5-yl}-2-morpholin-4-yl-5,6-dihydro-pyrrolo[2,3-d]pyrimidin-7-yl)-thiazole-4-carboxylic acid ethyl ester was obtained, and then 5M-NaOH aqueous solution was left to act in THF, to obtain 2-(4-{2-[bis-(4-methoxy-benzyl)-amino]-pyrimidin-5-yl}-2-morpholin-4-yl-5,6-dihydro-pyrrolo[2,3-d]pyrimidin-7-yl)-thiazole-4-carboxylic acid as an ivory powder (154 mg, 63%).

$^1$H-NMR (DMSO-$d_6$) δ (ppm): 9.03 (2H, s), 7.77 (1H, s), 7.21 (2H, d, J=8.2 Hz), 6.89 (2H, d, J=8.2 Hz), 4.34 (2H, t, J=8.2 Hz), 3.83-3.81 (8H, m), 3.42 (2H, t, J=8.2 Hz).

ESI (LC-MS positive mode) m/z 667 (M+H)$^+$.

Step B

To 2-(4-{2-[bis-(4-methoxy-benzyl)-amino]-pyrimidin-5-yl}-2-morpholin-4-yl-5,6-dihydro-pyrrolo[2,3-d]pyrimidin-7-yl)-thiazole-4-carboxylic acid (77 mg), N-ethylpiperazine (36 μl), WSCI (68 mg), HOBt (48 mg) and triethylamine (48 μl) were left to act in DMF (3 ml), to obtain a crude product of [2-(4-{2-[bis-(4-methoxy-benzyl)-amino]-pyrimidin-5-yl}-2-morpholin-4-yl-5,6-dihydro-pyrrolo[2,3-d]pyrimidin-7-yl)-thiazol-4-yl]-(4-ethyl-piperazin-1-yl)-methanone, and then the PMB groups were removed according to Deprotection method 3, to obtain the desired compound (D-120) as an ivory powder (38 mg, 63%).

$^1$H-NMR (DMSO-$d_6$) δ (ppm): 8.86 (2H, s), 7.62 (1H, s), 7.19 (2H, s), 4.30 (2H, t, J=7.8 Hz), 3.82-3.71 (8H, m), 3.61 (4H, brs), 3.38 (2H, brs), 2.41 (4H, brs), 2.35 (2H, q, J=14.5 Hz), 1.01 (3H, t, J=7.1 Hz).

ESI (LC-MS positive mode) m/z 523 (M+H)$^+$.

Example 1-D-121

{2-[4-(2-Amino-pyrimidin-5-yl)-2-morpholin-4-yl-5,6-dihydro-pyrrolo[2,3-d]pyrimidin-7-yl]-thiazol-4-yl}-[4-(2-hydroxy-ethyl)-piperazin-1-yl]-methanone (D-121)

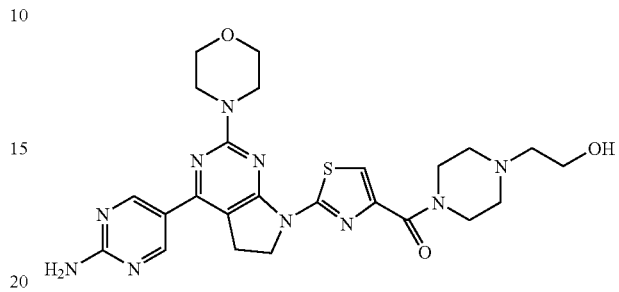

Using N-2-hydroxyethylpiperazine instead of N-ethylpiperazine in Step B in Example 1-D-120, in the same manner as Step B in Example 1-D-120, a crude product of [2-(4-{2-[bis-(4-methoxy-benzyl)-amino]-pyrimidin-5-yl}-2-morpholin-4-yl-5,6-dihydro-pyrrolo[2,3-d]pyrimidin-7-yl)-thiazol-4-yl]-[4-(2-hydroxy-ethyl)-piperazin-1-yl]-methanone was obtained, and then the PMB groups were removed according to Deprotection method 1, to obtain the desired compound (D-121) as an ivory powder (20 mg, 29%).

$^1$H-NMR (DMSO-$d_6$) δ (ppm): 8.86 (2H, s), 7.62 (1H, s), 7.19 (2H, s), 4.45 (1H, t, J=5.8 Hz), 4.30 (2H, t, J=7.6 Hz), 3.86-3.68 (8H, m), 3.61 (4H, brs), 3.51 (2H, dd, J=11.9, 5.8 Hz), 3.39 (2H, t, J=7.6 Hz), 2.48 (4H, brs), 2.43 (2H, m).

ESI (LC-MS positive mode) m/z 539 (M+H)$^+$.

Example 1-D-122

4-(2-Amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide (D-122)

Step A

[4-(2-Hydroxy-ethyl)-piperazin-1-yl]-(4-nitro-phenyl)-methanone

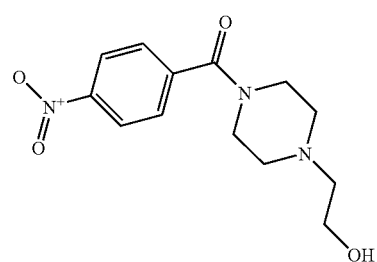

Using 4-nitro-benzoic acid (320 mg) instead of 3-nitro-benzoic acid, and 2-piperazin-1-yl-ethanol (282 μl) instead of 1-ethyl-piperazine, in the same manner as Step A in Example 1-D-101, the desired compound was obtained as a crude product.

Step B (4-Amino-phenyl)-[4-(2-hydroxy-ethyl)-piperazin-1-yl]-methanone

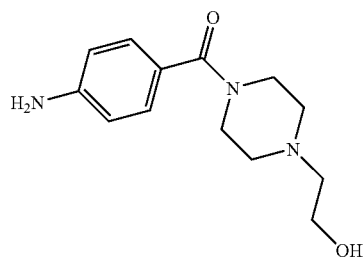

Using [4-(2-hydroxy-ethyl)-piperazin-1-yl]-(4-nitro-phenyl)-methanone obtained in Step A instead of (4-ethyl-piperazin-1-yl)-(3-nitro-phenyl)-methanone, in the same manner as Step B in Example 1-D-101, the desired compound was obtained as a crude product (275 mg, 59%).

Step C 4-(2-Amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide (D-122)

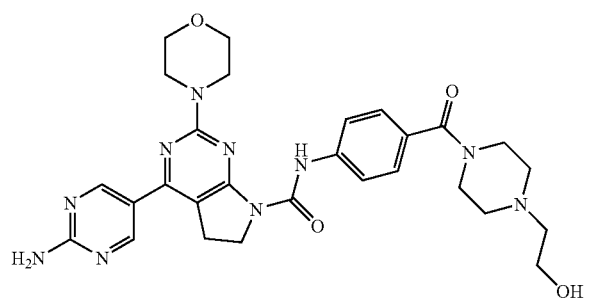

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and (4-amino-phenyl)-[4-(2-hydroxy-ethyl)-piperazin-1-yl]-methanone (99.7 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide was obtained as a crude product. Then the PMB groups were removed according to Deprotection method 3, to obtain the desired compound (D-122) as a yellow solid (8.8 mg, 8%).

$^1$H-NMR (TFA-d$_1$) δ: 9.21 (2H, s), 7.68 (2H, d, J=8.1 Hz), 7.62 (2H, d, J=8.1 Hz), 4.53 (2H, t, J=6.6 Hz), 4.36-3.83 (16H, brm), 3.69-3.59 (2H, brm), 3.52-3.30 (4H, brm).

ESI (LC-MS positive mode) m/z 575 (M+H)$^+$.

Example 1-D-123

3-[4-(2-Amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-123)

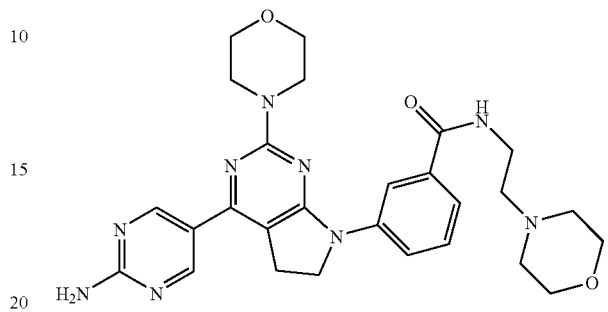

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (69.6 mg, 0.105 mmol) obtained in Step A in Example 1-D-53 instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and N-(2-aminoethyl)morpholine (27.5 mg, 0.211 mmol) instead of 3-(aminomethyl)pyridine, in the same manner as Step B in Example 1-D-19, amidation was carried out, to obtain a crude product of 3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-morpholin-4-yl-ethyl)-benzamide as a yellow solid (81.0 mg), and then the PMB groups were removed according to the above Deprotection method 3, to obtain the desired compound (D-123) as a yellow powder (34.2 mg, 60%).

$^1$H-NMR (CDCl$_3$) δ (ppm): 8.90 (2H, s), 8.18 (1H, s), 7.37-7.18 (4H, m), 5.22 (2H, s), 4.21-4.10 (2H, m), 3.92-3.54 (14H, m), 3.36-3.27 (2H, m), 2.67-2.49 (6H, m).

ESI (LC-MS positive mode) m/z 532 (M+H)$^+$.

Example 1-D-124

3-[4-(2-Amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-124)

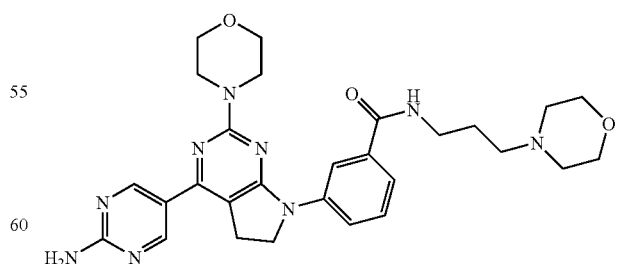

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (69.6 mg, 0.105 mmol) obtained in Step A in Example 1-D-53 instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and N-(3-aminopropyl)morpholine (31.0 µl, 0.212 mmol) instead of 3-(aminomethyl)pyridine, in the same manner as Step B in Example 1-D-19, amidation was carried out, to obtain a crude product of 3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-morpholin-4-yl-ethyl)-benzamide as a yellow solid (66.5 mg), and then the PMB groups were removed according to the above Deprotection method 3, to obtain the desired compound (D-124) as a colorless powder (23.0 mg, 40%).

$^1$H-NMR (CDCl$_3$) δ (ppm): 8.90 (2H, s), 8.26 (1H, brs), 8.11 (1H, d, J=7.9 Hz), 7.94 (1H, m), 7.45 (1H, dd, J=7.9, 6.4 Hz), 7.40 (1H, d, J=6.4 Hz), 5.23 (2H, s), 4.17 (2H, t, J=8.2 Hz), 3.90-3.77 (8H, m), 3.72-3.64 (4H, m), 3.63-3.54 (2H, m), 3.31 (2H, t, J=8.2 Hz), 2.61-2.45 (6H, m), 1.87-1.73 (2H, m).

ESI (LC-MS positive mode) m/z 546 (M+H)$^+$.

Example 1-D-125

{3-[4-(2-Amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-125)

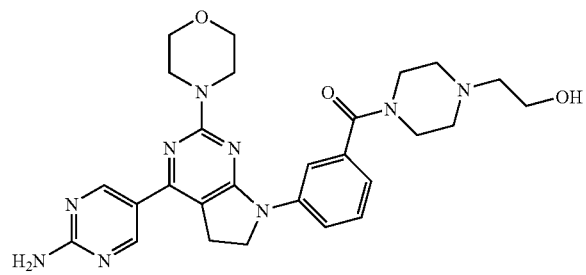

Using 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (68.1 mg, 0.103 mmol) obtained in Step A in Example 1-D-53 instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid, and 1-piperazineethanol (26.0 µl, 0.211 mmol) instead of 3-(aminomethyl)pyridine, amidation was carried out in the same manner as Step B in Example 1-D-19, to obtain a crude product of {3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-[4-(2-hydroxy-ethyl)-piperazin-1-yl]-methanone as a yellow solid (74.4 mg), and then the PMB groups were removed according to the above Deprotection method 3, to obtain the desired compound (D-125) as a yellow powder (31.7 mg, 58%).

$^1$H-NMR (CDCl$_3$) δ (ppm): 8.89 (2H, s), 8.00 (1H, d, J=8.9 Hz), 7.76 (1H, s), 7.42 (1H, dd, J=8.9, 7.4 Hz), 7.05 (1H, d, J=7.4 Hz), 5.24 (2H, s), 4.12 (2H, t, J=7.8 Hz), 3.87-3.77 (8H, m), 3.73-3.45 (6H, m), 3.30 (2H, t, J=7.8 Hz), 2.73-2.44 (6H, m), 1.60 (1H, brs).

ESI (LC-MS positive mode) m/z 532 (M+H)$^+$.

Example 1-D-126

5-[2-Morpholin-4-yl-7-(4-morpholin-4-ylmethyl-phenyl)-6,7-dihydro-5H-pyrrolo[2,3-d]pyrimidin-4-yl]-pyrimidin-2-ylamine (D-126)

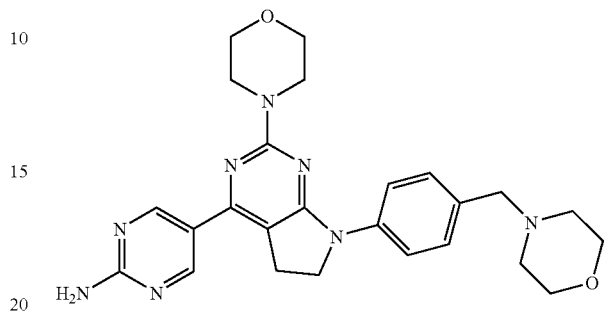

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzaldehyde (70 mg) and morpholine (14 µl) instead of 1-methylpiperazine, in the same manner as Step B in Example 1-D-26, a crude product of bis-(4-methoxy-benzyl)-{5-[2-morpholin-4-yl-7-(4-morpholin-4-ylmethyl-phenyl)-6,7-dihydro-5H-pyrrolo[2,3-d]pyrimidin-4-yl]-pyrimidin-2-yl}-amine was obtained, and then the PMB groups were removed according to the above Deprotection method 3, to obtain the desired compound (D-126) as a pale brown powder (26 mg, 50%).

$^1$H-NMR (DMSO-d$_6$) δ (ppm): 8.82 (2H, s), 7.95 (2H, d, J=8.6 Hz), 7.51 (2H, d, J=8.6 Hz), 7.09 (2H, s), 4.27 (2H, s), 4.11 (2H, s), 3.68-3.55 (14H, m), 3.35 (2H, s), 3.19 (2H, s).

ESI (LC-MS positive mode) m/z 475 (M+H)$^+$.

Example 1-D-127

2-{4-[4-(2-Amino-pyrimidin-5-yl)-2-morpholin-4-yl-5,6-dihydro-pyrrolo[2,3-d]pyrimidin-7-yl]-phenylsulfanyl}-1-(4-ethyl-piperazin-1-yl)-ethanone (D-127)

Step A (4-Bromo-phenylsulfanyl)-acetic acid

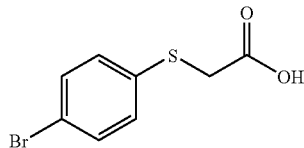

4-Bromo-phenylamine (172 mg) was dissolved in 1M-HCl aqueous solution (2 ml), and sodium nitrite (82.8 mg) was added at 0° C. After stirring at 0° C. for 30 minutes, a methanol solution of mercaptoacetic acid methyl ester (127 mg) was added, and saturated sodium hydrogencarbonate aqueous solution was further added, to adjust the pH to 5. After stirring at room temperature for 1 hour, stirring was further carried out at 60° C. for 2 hours. This was extracted with ethyl acetate (10 ml×2), and the organic layer was dried over sodium sulfate. After the sodium sulfate was filtered off, the solvent was distilled off under reduced pressure. This was purified by silica gel column chromatography (hexane/ethyl acetate=20/1), to obtain (4-bromo-phenylsulfanyl)-acetic acid methyl ester as a crude product. This was further stirred in 10 ml of methanol and 5M-NaOH aqueous solution at room temperature for 1 hour. After the water vessel was washed with ethyl acetate (30 ml), 1M–HCl aqueous solution was added to adjust the pH to 3. This was extracted with ethyl acetate (30 ml×2), and the organic layer was dried over sodium sulfate. After the sodium sulfate was filtered off, the solvent was distilled off under reduced pressure, to obtain the desired compound as a crude product (151 mg, 62%).

Step B 2-(4-Bromo-phenylsulfanyl)-1-(4-ethyl-piperazin-1-yl)-ethanone

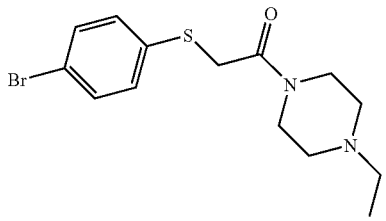

Using (4-bromo-phenylsulfanyl)-acetic acid (60 mg) obtained in Step A instead of 3-nitro-benzoic acid, in the same manner as Step A in Example 1-D-101, the desired compound was obtained (49 mg, 60%).

Step C

2-{4-[4-(2-Amino-pyrimidin-5-yl)-2-morpholin-4-yl-5,6-dihydro-pyrrolo[2,3-d]pyrimidin-7-yl]-phenylsulfanyl}-1-(4-ethyl-piperazin-1-yl)-ethanone (D-127)

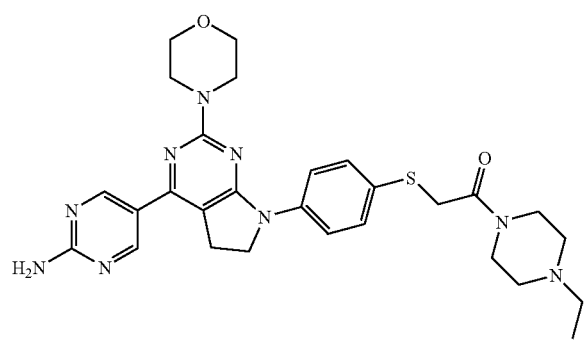

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (64.7 mg) and 2-(4-bromo-phenylsulfanyl)-1-(4-ethyl-piperazin-1-yl)-ethanone (49.4 mg) obtained in Step B instead of 4-chloro-picolinic acid t-butylamide, in the same manner as in Example 1-D-07, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide was obtained as a crude product. Further, in the same manner as Example 1-D-07, the desired compound (D-127) was obtained as a brown solid (17.5 mg, 29%).

$^1$H-NMR (DMSO-$d_6$) δ: 8.81 (2H, s), 7.80 (2H, d, J=8.7 Hz), 7.44 (2H, d, J=8.7 Hz), 7.08 (2H, brs), 4.07 (2H, t, J=7.4 Hz), 3.89 (2H, s), 3.75-3.65 (8H, brm), 3.51-3.38 (4H, m), 2.38-2.24 (8H, m), 0.99 (3H, t, J=7.1 Hz).

ESI (LC-MS positive mode) m/z 562 (M+H)$^+$.

Example 1-D-128

{5-[4-(2-Amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-128)

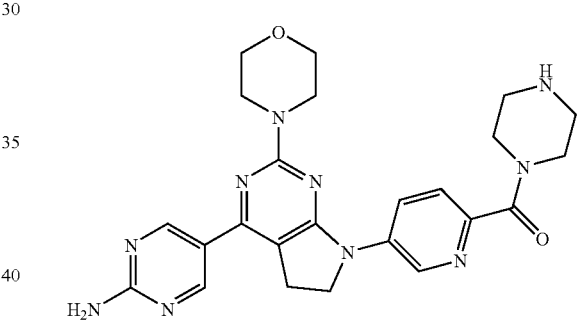

From bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 4-(5-bromo-pyridine-2-carbonyl)-piperazine-1-carboxylic acid tert-butyl ester (prepared in the same manner as Step A in Example 1-D-79, 76 mg), instead of 4-bromobenzoic acid methyl ester in Example 1-D-08, in the same manner as Example 1-D-08, a crude product of 4-[5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridine-2-carbonyl]-piperazine-1-carboxylic acid tert-butyl ester was obtained, and then the PMB groups and BOC group were removed according to the above Deprotection method 1, to obtain the desired compound (D-128) as a yellow solid (47 mg, 39%).

$^1$H-NMR (DMSO-$d_6$) δ (ppm): 9.04 (1H, d, J=2.2 Hz), 8.83 (2H, s), 8.36 (1H, dd, J=8.4, 2.2 Hz), 7.64 (1H, d, J=8.4 Hz), 7.13 (2H, s), 5.76 (1H, d, J=1.2 Hz), 4.15 (2H, t, J=7.8 Hz), 3.59-3.48 (4H, m), 3.34 (2H, t, J=7.8 Hz), 2.79-2.71 (4H, m).

ESI (LC-MS positive mode) m/z 489 (M+H)$^+$.

Example 1-D-129

5-{2-Morpholin-4-yl-7-[3-(2-piperazin-1-yl-ethyl)-phenyl]-6,7-dihydro-5H-pyrrolo[2,3-d]pyrimidin-4-yl}-pyrimidin-2-ylamine (D-129)

Step A 3-(2-(4-tert-butoxycarbonyl-piperazin-1-yl)-ethyl)-1-bromo-benzene

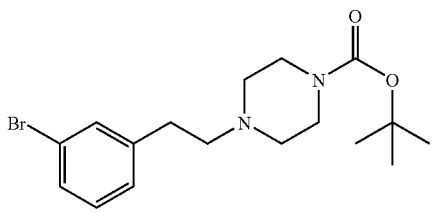

To 3-(2-bromo-ethyl)-1-bromo-benzene (0.15 ml, 1 mmol), 1-tert-butoxycarbonyl-piperazine (186 mg) and potassium carbonate (280 mg), acetonitrile (4 ml) was added, followed by stirring for 4 days. To the reaction mixture, ethyl acetate was added, which was washed with ammonium chloride solution, followed by drying over sodium sulfate. After filtering off the drying agent, the filtrate was concentrated under reduced pressure, to obtain 3-(2-(4-tert-butoxycarbonyl-piperazin-1-yl)-ethyl)-1-bromo-benzene as a colorless oil (340 mg, 92%).

ESI (LC-MS positive mode) m/z 371 (M+H)+.

Step B

5-{2-Morpholin-4-yl-7-[3-(2-piperazin-1-yl-ethyl)-phenyl]-6,7-dihydro-5H-pyrrolo[2,3-d]pyrimidin-4-yl}-pyrimidin-2-ylamine (D-129)

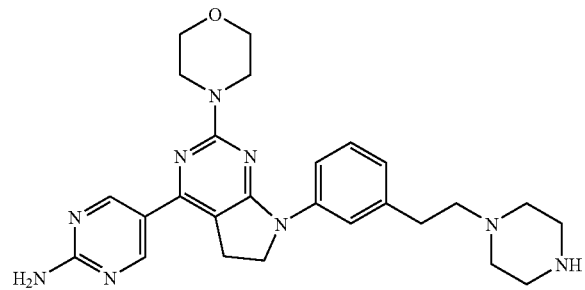

In the same manner as Example 1-D-08, using bis-(4-methoxy-benzyl)-[5-(2-morpholin-4-yl-6,7-dihydro-5H-pyrrolo[2,3-d]pyrimidin-4-yl)-pyrimidin-2-yl]-amine (380 mg) and 3-(2-(4-tert-butoxycarbonyl-piperazin-1-yl)-ethyl)-1-bromo-benzene (320 mg) obtained in the above Step A instead of 4-bromobenzoic acid methyl ester, a crude product of 5-{2-morpholin-4-yl-7-[3-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine was obtained. Using a crude product (45 mg) of this 5-{2-morpholin-4-yl-7-[3-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine, according to the above Deprotection method 2, 5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-ylamine was obtained as a pale yellow powder (2 mg).

1H-NMR (DMSO-D6) δ: 8.82 (2H, s), 8.54 (1H, m), 7.86 (1H, s), 7.54 (1H, m), 7.29 (1H, t, J=7.8 Hz), 7.08 (2H, s), 6.92 (1H, m), 4.08 (2H, t, J=7.6 Hz), 3.72 (8H, m), 3.39-2.50 (14H, m).

ESI (LC-MS positive mode) m/z 488 (M+H)+.

Example 1-D-130

{3-[4-(2-Amino-pyrimidin-5-yl)-2-morpholin-4-yl-5,6-dihydro-pyrrolo[2,3-d]pyrimidin-7-yl]-4-methyl-phenyl}-(4-methyl-piperazin-1-yl)-methanone (D-130)

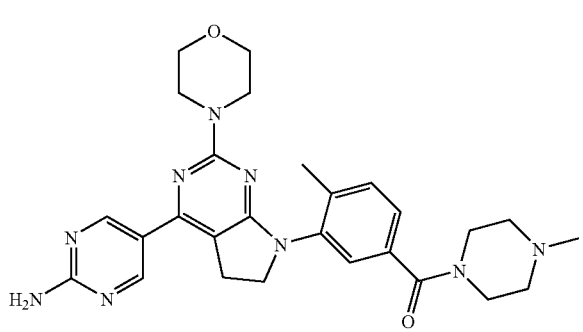

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-bromo-4-methyl-phenyl)-(4-methyl-piperazin-1-yl)-methanone (160 mg) instead of 4-chloropicolinic acid t-butylamide, in the same manner as Example 1-D-07, a crude product of [[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-methyl-phenyl]-(4-methyl-piperazin-1-yl)-methanone was obtained, and then the PMB groups were removed according to the above Deprotection method 3, to obtain the desired compound (D-130) as a pale yellow oil (84 mg, 44%).

1H-NMR (CDCl3) δ (ppm): 8.89 (2H, s), 7.32-7.24 (3H, m), 5.49 (2H, s), 3.98 (2H, t, J=8.2 Hz), 3.68 (16H, s), 3.31 (2H, t, J=8.1 Hz), 2.32 (3H, s), 2.29 (3H, s).

ESI (LC-MS positive mode) m/z 516 (M+H)+.

Example 1-D-131

5-{2-Morpholin-4-yl-7-[4-(2-piperazin-1-yl-ethyl)-phenyl]-6,7-dihydro-5H-pyrrolo[2,3-d]pyrimidin-4-yl}-pyrimidin-2-ylamine (D-131)

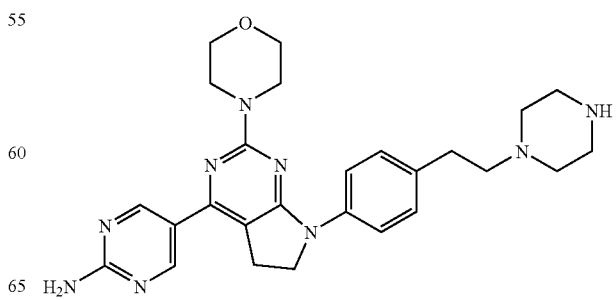

In the same manner as Example 1-D-129, using bis-(4-methoxy-benzyl)-[5-(2-morpholin-4-yl-6,7-dihydro-5H-pyrrolo[2,3-d]pyrimidin-4-yl)-pyrimidin-2-yl]-amine (590 mg) and 4-(2-(4-tert-butoxycarbonyl-piperazin-1-yl)-ethyl)-1-bromo-benzene (580 mg) obtained in the same manner as Step A in Example 1-D-129 using 4-(2-bromo-ethyl)-1-bromo-benzene instead of 3-(2-bromo-ethyl)-1-bromo-benzene, a crude product of 5-{2-morpholin-4-yl-7-[4-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine was obtained. Using a crude product (99 mg) of this 5-{2-morpholin-4-yl-7-[4-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine, according to the above Deprotection method 2, 5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-ylamine was obtained as a colorless powder (28 mg, 49%).

$^1$H-NMR (DMSO-D$_6$) δ: 8.80 (2H, s), 7.73 (2H, d, J=8.9 Hz), 7.23 (2H, d, J=8.9 Hz), 7.07 (2H, s), 4.06 (2H, t, J=8.6 Hz), 3.69 (8H, m), 3.30 (2H, m), 2.69-2.34 (12H, m).

ESI (LC-MS positive mode) m/z 488 (M+H)$^+$.

Example 1-D-132

5-{2-Morpholin-4-yl-7-[3-(piperazine-1-sulfonyl)-phenyl]-6,7-dihydro-5H-pyrrolo[2,3-d]pyrimidin-4-yl}-pyrimidin-2-ylamine (D-132)

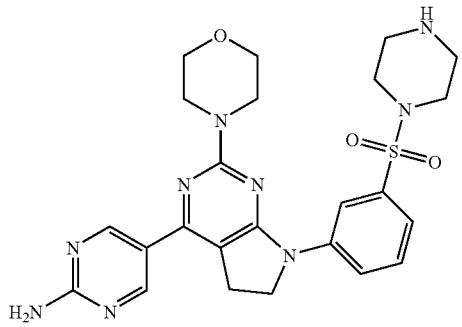

From 4-(3-bromo-benzenesulfonyl)-piperazine-1-carboxylic acid tert-butyl ester (prepared from 3-bromobenzenesulfonyl chloride and piperazine-1-carboxylic acid tert-butyl ester, 83 mg) instead of 1-(3-bromo-benzenesulfonyl)-4-ethyl-piperazine in Example 1-D-96, a crude product of 4-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzenesulfonyl]-piperazine-1-carboxylic acid tert-butyl ester was obtained, and then the PMB groups and BOC group were removed according to the above Deprotection method 1, to obtain the desired compound (D-132) as a yellow powder (32 mg, 33%).

$^1$H-NMR (DMSO-d$_6$) δ (ppm): 8.95 (1H, brs), 8.83 (2H, s), 7.83-7.81 (1H, m), 7.68-7.66 (1H, m), 7.34 (1H, d, J=6.4 Hz), 7.13 (2H, s), 5.76 (1H, s), 4.15 (2H, t, J=7.7 Hz), 3.76-3.69 (8H, m), 3.37 (1H, brs), 2.87-2.75 (8H, m).

ESI (LC-MS positive mode) m/z 524 (M+H)$^+$.

Example 1-D-133

5-{2-Morpholin-4-yl-7-[4-(piperazine-1-sulfonyl)-phenyl]-6,7-dihydro-5H-pyrrolo[2,3-d]pyrimidin-4-yl}-pyrimidin-2-ylamine (D-133)

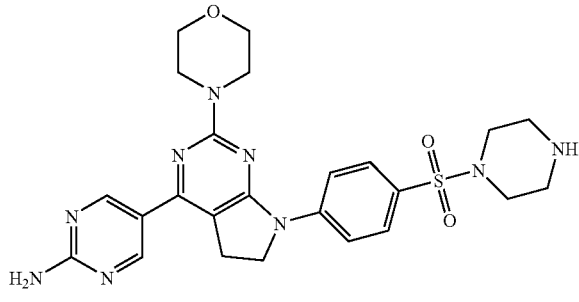

From 4-(4-bromo-benzenesulfonyl)-piperazine-1-carboxylic acid tert-butyl ester (prepared from 4-bromobenzenesulfonyl chloride and piperazine-1-carboxylic acid tert-butyl ester, 83 mg) instead of 4-(3-bromo-benzenesulfonyl)-piperazine-1-carboxylic acid tert-butyl ester in Example 1-D-132, a crude product of 4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzenesulfonyl]-piperazine-1-carboxylic acid tert-butyl ester was obtained, and then the PMB groups and BOC group were removed according to Deprotection method 1, to obtain the desired compound (D-133) as a yellow powder (50 mg, 46%).

$^1$H-NMR (DMSO-d$_6$) δ (ppm): 8.83 (2H, s), 8.12 (2H, d, J=9.1 Hz), 7.72 (2H, d, J=8.7 Hz), 7.13 (2H, s), 5.76 (1H, d, J=13 Hz), 4.14 (2H, t, J=7.6 Hz), 3.75-3.69 (8H, m), 3.36 (2H, brs), 2.77-2.70 (8H, m).

ESI (LC-MS positive mode) m/z 524 (M+H)$^+$.

Example 1-D-134

1-[4-(2-{3-[4-(2-Amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-134)

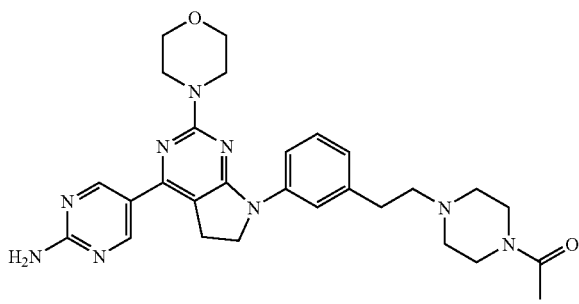

A crude product (195 mg) of 5-{2-morpholin-4-yl-7-[3-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine obtained in Step B in Example 1-D-129 was stirred in an acetic acid solution of 1M-hydrochloric acid at room temperature for 30 minutes.

The reaction mixture was poured onto sodium hydrogencarbonate aqueous solution, followed by extraction with dichloromethane. The organic layer was dried over sodium sulfate, and then sodium sulfate was removed by filtration. The filtrate was concentrated under reduced pressure, whereby a crude product of 5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine was obtained as a colorless solid (160 mg, 94%). ESI (LC-MS positive mode) m/z 728 (M+H)+.

This crude product (80 mg) of 5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine was dissolved in dichloromethane (2 ml), and acetyl chloride (0.015 ml) and triethylamine (0.03 ml) were added, followed by stirring at room temperature for 1 hour. The reaction mixture was washed with water, and the organic layer was dried over sodium sulfate, followed by distilling off under reduced pressure, whereby a crude product of 5-{2-morpholin-4-yl-7-[3-(2-(4-acetyl-piperazine)-1-yl-ethyl)-phenyl]-6,7-dihydro-5H-pyrrolo[2,3-d]pyrimidin-4-yl}-pyrimidin-2-yl-bis-(4-methoxy-benzyl)-amine was obtained as a colorless oil (85 mg, 100%). Using this crude product (85 mg) of 5-{2-morpholin-4-yl-7-[3-(2-(4-acetyl-piperazine)-1-yl-ethyl)-phenyl]-6,7-dihydro-5H-pyrrolo[2,3-d]pyrimidin-4-yl}-pyrimidin-2-yl-bis-(4-methoxy-benzyl)-amine, according to the above Deprotection method 2, 1-[4-(2-{3-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone was obtained as a colorless powder (48 mg, 83%).

$^1$H-NMR (DMSO-D$_6$) δ (ppm): 8.80 (2H, s), 7.80 (1H, m), 7.54 (1H, m), 7.27 (1H, m), 7.07 (2H, br.s), 6.89 (1H, m), 4.05 (2H, m), 3.68 (8H, m), 3.41-3.30 (6H, m), 2.73-2.36 (8H, m), 1.98 (3H, s).

ESI (LC-MS positive mode) m/z 530 (M+H)+.

Example 1-D-135

4-(2-Amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-methyl-amide (D-135)

Step A

N-(3-Bromo-phenyl)-acetamide

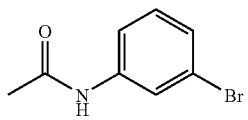

To a dichloromethane solution (15 ml) of 3-bromoaniline (1 g), acetic anhydride (659 μl) was added, followed by stirring at room temperature for 14 hours. This was washed with water (20 ml), and the organic layer was dried over sodium sulfate. After filtering off the sodium sulfate, the solvent was distilled off under reduced pressure. This was purified by silica gel column chromatography (dichloromethane/methanol=200/1), to obtain the desired compound (1.19 g, 96%).

Step B

N-(3-Bromo-phenyl)-N-methyl-acetamide

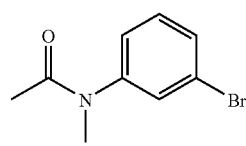

To a DMF solution (15 ml) of N-(3-bromo-phenyl)-acetamide (1.19 g) obtained in Step A, 60% oily sodium hydride (279 mg) was added, followed by stirring at room temperature for 10 minutes. To this, methyl iodide (434 μl) was added, followed by stirring at room temperature for 21 hours. To this, water (30 ml) was added, followed by extraction with ethyl acetate (30 ml×2), and the organic layer was dried over sodium sulfate. The sodium sulfate was filtered off, followed by purification by silica gel column chromatography (dichloromethane/methanol=200/1), to obtain the desired compound (1.20 g, 94%).

Step C

N-[3-(4-Ethyl-piperazin-1-yl)-phenyl]-N-methyl-acetamide

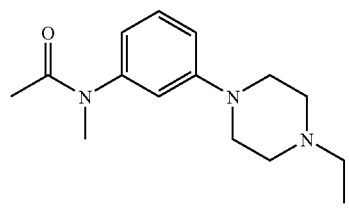

To a DMF solution (2.5 ml) of N-(3-bromo-phenyl)-N-methyl-acetamide (114 mg) obtained in Step B, palladium acetate (1.1 mg), S-Phos (4.1 mg) and potassium phosphate (212.3 mg), 1-ethylpiperazine (76.2 μl) was added, and then the mixture was degassed under ultrasonic irradiation. This was stirred at 100° C. for 5 hours, followed by addition of water (10 ml), which was extracted with ethyl acetate (10 ml×2), and the organic layer was dried over sodium sulfate. After the sodium sulfate was filtered off, the solvent was distilled off under reduced pressure, followed by purification by silica gel column chromatography (dichloromethane/methanol=20/1 to 10/1), to obtain the desired compound (104.9 mg, 80%).

Step D

[3-(4-Ethyl-piperazin-1-yl)-phenyl]-methyl-amine

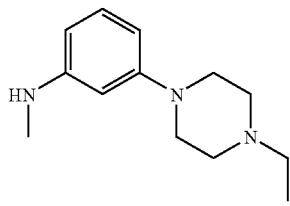

To N-[3-(4-ethyl-piperazin-1-yl)-phenyl]-N-methyl-acetamide (104.9 mg) obtained in Step C, water (2 ml) and concentrated sulfuric acid (0.4 ml) were added, followed by stirring at 80° C. for 8 hours. To this, 5M-NaOH aqueous solution was added, to adjust the pH to 9, followed by extraction with ethyl acetate (10 ml×2), and the organic layer was dried over sodium sulfate. The sodium sulfate was filtered off, followed by purification by silica gel column chromatography (dichloromethane/methanol=20/1 to 10/1), to obtain the desired compound (76.1 mg, 86%).

Step E 4-(2-Amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-methyl-amide (D-135)

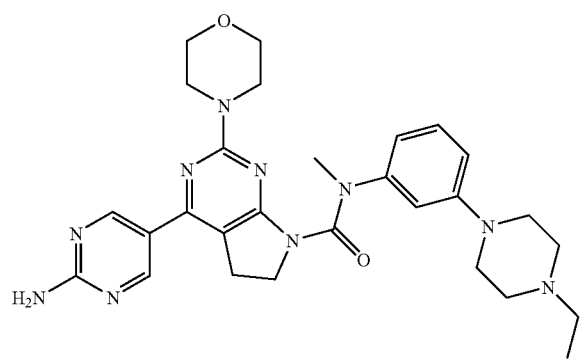

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and [3-(4-ethyl-piperazin-1-yl)-phenyl]-methyl-amine (52.6 mg) obtained in Step D instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(4-ethyl-piperazin-1-yl)-phenyl]-methyl-amide was obtained as a crude product. Further, using this compound (125 mg), the PMB groups were removed according to Deprotection method 3, to obtain the desired compound (D-135) as a yellow solid (54 mg, 53%).

$^1$H-NMR (CDCl$_3$) δ: 8.80 (2H, s), 7.18 (1H, t, J=8.0 Hz), 6.80-6.68 (3H, m), 5.22 (2H, brs), 3.84 (2H, t, J=8.2 Hz), 3.80-3.71 (8H, brm), 3.42 (3H, s), 3.19-3.13 (4H, brm), 3.06 (2H, t, J=8.2 Hz), 2.60-2.54 (4H, brm), 2.46 (2H, q, J=7.3 Hz), 1.12 (3H, t, J=7.3 Hz).

ESI (LC-MS positive mode) m/z 545 (M+H)$^+$.

Example 1-D-136

5-(7-{3-[2-(4-Methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-136)

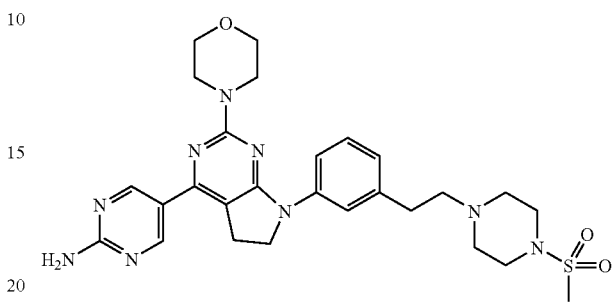

In the same manner as Example 1-D-134, using a crude product (80 mg) of 5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine obtained in Example 1-D-134 and methanesulfonyl chloride (0.017 ml) instead of acetyl chloride, a crude product of 5-(7-{3-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-yl-bis-(4-methoxy-benzyl)-amine was obtained as a pale yellow solid (82 mg, 93%). Using this crude product (82 mg) of 5-(7-{3-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-yl-bis-(4-methoxy-benzyl)-amine, according to the above Deprotection method 2,5-(7-{3-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine was obtained as a colorless powder (28 mg, 49%).

$^1$H-NMR (DMSO-D$_6$) δ (ppm): 8.80 (2H, s), 7.79 (1H, s), 7.58 (1H, m), 7.27 (1H, m), 7.07 (2H, br.s), 6.90 (1H, m), 4.07 (2H, m), 3.69 (8H, m), 3.32-3.10 (6H, m), 2.86 (3H, s) 2.76-2.48 (8H, m).

ESI (LC-MS positive mode) m/z 566 (M+H)$^+$.

Example 1-D-137

{4-[4-(2-Amino-pyrimidin-5-yl)-2-morpholin-4-yl-5,6-dihydro-pyrrolo[2,3-d]pyrimidin-7-yl]-3-methyl-phenyl}-morpholin-4-yl-methanone (D-137)

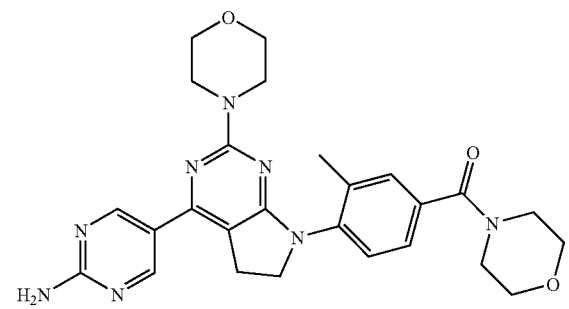

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-bromo-3-methyl-phenyl)-morpholin-4-yl-methanone (159 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-morpholin-4-yl-methanone was obtained, and then the PMB groups were removed according to the above Deprotection method 3, to obtain the desired compound (D-137) as a brown powder (58 mg, 62%).

$^1$H-NMR (CDCl$_3$) δ (ppm): 8.89 (2H, s), 7.37 (1H, s), 7.27 (2H, d, J=0.5 Hz), 5.40 (2H, s), 3.99 (2H, t, J=8.2 Hz), 3.69 (16H, s), 3.32 (2H, t, J=8.2 Hz), 2.29 (3H, s).

ESI (LC-MS positive mode) m/z 503 (M+H)$^+$

Example 1-D-138

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-ethyl-piperazin-1-yl)-methanone (D-138)

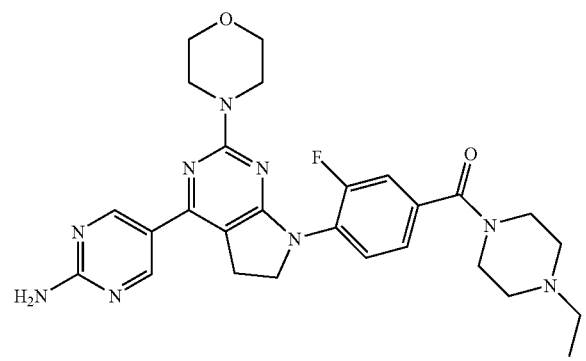

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (65.6 mg, 0.0968 mmol) obtained in Step A in Example 1-D-21 and N-ethylpiperazine (24.6 μl, 0.194 mmol) instead of 1-pyridin-3-yl-piperazine, amidation was carried out in the same manner as Step B in Example 1-D-21, and a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-phenyl}-(4-ethyl-piperazin-1-yl)-methanone was obtained as a yellow solid (64.2 mg). Then the PMB groups were removed according to the above Deprotection method 3, to obtain the desired compound (D-138) as a yellow powder (39.2 mg, 76%).

$^1$H-NMR (CDCl$_3$) δ (ppm): 8.94 (2H, s), 7.87 (1H, t, J=8.4 Hz), 7.32-7.24 (2H, m), 6.67 (2H, brs), 4.19 (2H, t, J=8.1 Hz), 3.76-3.73 (8H, m), 3.32 (2H, q, J=7.4 Hz), 3.12 (2H, t, J=8.1 Hz), 2.21-2.17 (8H, m), 1.41 (3H, t, J=7.4 Hz).

ESI (LC-MS positive mode) m/z 534 (M+H)$^+$.

Example 1-D-139

4-[4-(2-Amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzamide (D-139)

Step A

Methyl-(2-morpholin-4-yl-ethyl)-amine

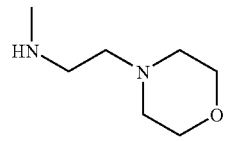

To a dichloromethane solution (25 ml) of ice-cooled N-(2-aminoethyl)morpholine (690 mg, 5.30 mmol), di tert-butyl dicarbonate (1.27 g, 5.83 mmol) was added, followed by stirring at room temperature for 15 hours. The reaction mixture was diluted with ethyl acetate (20 ml), and washed sequentially with saturated aqueous ammonium chloride solution (20 ml) and brine. After the organic layer was dried over sodium sulfate, the sodium sulfate was filtered off, and the filtrate was concentrated under reduced pressure, to obtain a crude product of (2-morpholin-4-yl-ethyl)-carbamic acid tert-butyl ester as a yellow liquid (1.22 g).

This was dissolved in DMF (20 ml), and under ice cooling 60% oily sodium hydride (640 mg) was added, followed by stirring at room temperature for 20 minutes. The reaction mixture was ice-cooled, and methyl iodide (396 μl, 6.36 mmol) was added, followed by stirring for 3 hours. The reaction mixture was diluted with ethyl acetate (50 ml), and washed sequentially with saturated aqueous ammonium chloride solution (30 ml) and brine (30 ml×5). After the organic layer was dried over sodium sulfate, the sodium sulfate was filtered off, and the filtrate was concentrated under reduced pressure, to obtain a crude product of methyl-(2-morpholin-4-yl-ethyl)-carbamic acid tert-butyl ester as a yellow liquid (1.50 g).

This was dissolved in TFA (20 ml), followed by stirring at room temperature for 50 minutes. The reaction mixture was concentrated under reduced pressure, and the residue was adsorbed to SCX resin, and washed with methanol (50 ml), followed by elution with 2M ammonia methanol solution. The eluate was concentrated under reduced pressure, to obtain methyl-(2-morpholin-4-yl-ethyl)-amine as a yellow liquid (608 mg, 80%).

$^1$H-NMR (CDCl$_3$) δ (ppm): 3.80-3.57 (4H, m), 3.71 (2H, t, J=4.5 Hz), 2.74-2.27 (10H, m).

ESI (LC-MS positive mode) m/z 145 (M+H)$^+$.

Step B

4-[4-(2-Amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzamide (D-139)

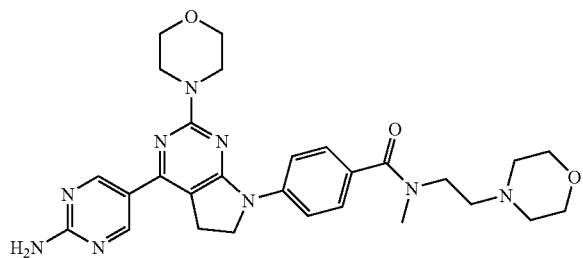

Using methyl-(2-morpholin-4-yl-ethyl)-amine (29.8 mg, 0.206 mmol) obtained in Step A instead of 3-(aminomethyl)pyridine, and 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (68.1 mg, 0.103 mmol) obtained in Step A in Example 1-D-19, in the same manner as Step B in Example 1-D-19, amidation was carried out, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-methyl-N-(2-morpholin-4-yl-ethyl)-benzamide as a yellow solid (70.2 mg), and then the PMB groups were removed according to the above Deprotection method 3, to obtain the desired compound (D-139) as a yellow powder (42.0 mg, 75%).

$^{1}$H-NMR (CDCl$_3$) δ (ppm): 8.92 (2H, s), 7.85 (2H, d, J=8.7 Hz), 7.57 (2H, d, J=8.7 Hz), 5.98 (2H, s), 4.14 (2H, t, J=8.1 Hz), 4.04-3.75 (14H, m), 3.41-3.30 (2H, m), 3.31 (2H, t, J=8.1 Hz), 3.09 (3H, s), 1.78-1.74 (4H, brm).

ESI (LC-MS positive mode) m/z 546 (M+H)$^+$.

Example 1-D-140

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-methyl-piperazin-1-yl)-methanone (D-140)

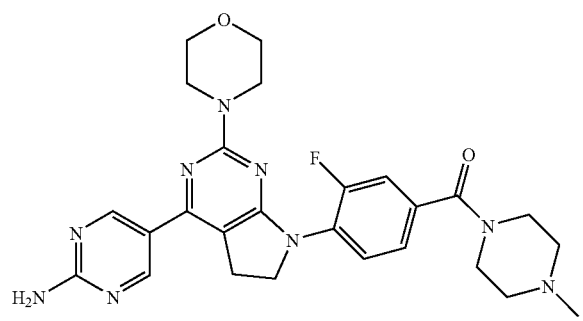

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (65.6 mg, 0.0968 mmol) obtained in Step A in Example 1-D-21 and N-methylpiperazine (20.9 µl, 0.194 mmol) instead of 1-pyridin-3-yl-piperazine, amidation was carried out in the same manner as Step B in Example 1-D-21, a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-methyl-piperazin-1-yl)-methanone was obtained as a yellow solid (85.0 mg), and then the PMB groups and BOC group were removed according to the above Deprotection method 3, to obtain the desired compound (D-140) as a yellow powder (25.0 mg, 50%).

$^{1}$H-NMR (CDCl$_3$) δ (ppm): 8.89 (2H, s), 7.80 (1H, t, J=7.7 Hz), 7.28-7.20 (2H, m), 5.27 (2H, s), 4.14 (2H, t, J=8.1 Hz), 3.82-3.79 (8H, m), 3.31 (2H, t, J=8.1 Hz), 2.52-2.39 (4H, m), 2.34 (3H, s), 1.72-1.66 (4H, m).

ESI (LC-MS positive mode) m/z 520 (M+H)$^+$.

Example 1-D-141

{4-[4-(2-Amino-pyrimidin-5-yl)-2-morpholin-4-yl-5,6-dihydro-pyrrolo[2,3-d]pyrimidin-7-yl]-3-fluoro-phenyl}-piperazin-1-yl-methanone (D-141)

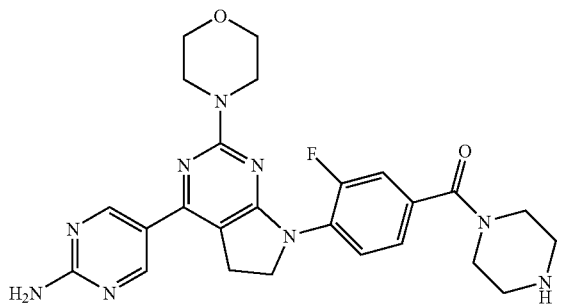

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (65.6 mg, 0.0968 mmol) obtained in Step A in Example 1-D-21 and 1-Boc-piperazine (36.1 mg, 0.194 mmol) instead of 1-pyridine-3-yl-piperazine, amidation was carried out in the same manner as Step B in Example 1-D-21, a crude product of 4-{4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-benzoyl}-piperazine-1-carboxylic acid tert-butyl ester was obtained as a yellow solid (89.9 mg), and then the PMB groups and BOC group were removed according to the above Deprotection method 3, to obtain the desired compound (D-141) as a yellow powder (29.6 mg, 60%).

$^{1}$H-NMR (CDCl$_3$) δ (ppm): 8.89 (2H, s), 7.80 (1H, t, J=8.1 Hz), 7.27-7.20 (2H, m), 5.27 (2H, s), 4.14 (2H, t, J=8.2 Hz), 3.92-3.50 (12H, m), 3.31 (2H, t, J=8.2 Hz), 3.01-2.86 (4H, m), 1.76 (1H, brs).

ESI (LC-MS positive mode) m/z 506 (M+H)$^+$.

Example 1-D-142

{4-[4-(2-Amino-pyrimidin-5-yl)-2-morpholin-4-yl-5,6-dihydro-pyrrolo[2,3-d]pyrimidin-7-yl]-3-methyl-phenyl}-(4-methyl-piperazin-1-yl)-methanone (D-142)

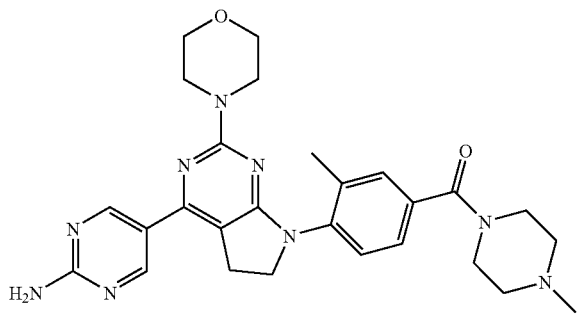

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-bromo-3-methyl-phenyl)-(4-methyl-piperazin-1-yl)-methanone (167 mg) instead of 4-chloropicolinic acid t-butylamide, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-(4-methyl-piperazin-1-yl)-methanone was obtained, and then the PMB groups were removed according to the above Deprotection method 3, to obtain the desired compound (D-142) as a pale yellow powder (25 mg, 26%).

$^1$H-NMR (CDCl$_3$) δ (ppm): 8.89 (2H, s), 7.36 (1H, s), 7.27 (2H, s), 5.37 (2H, s), 3.99 (2H, t, J=8.2 Hz), 3.69 (16H, brs), 3.32 (2H, t, J=8.2 Hz), 2.35 (3H, s), 2.29 (3H, s).

ESI (LC-MS positive mode) m/z 516 (M+H)$^+$.

Example 1-D-143

1-[4-(2-{4-[4-(2-Amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-143)

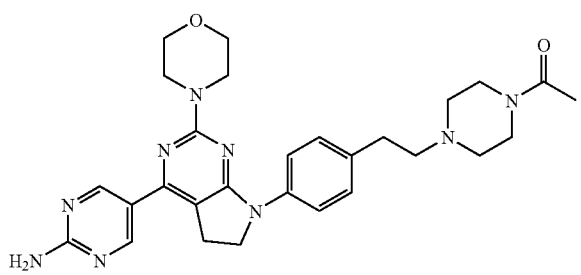

In the same manner as Example 1-D-134, using a crude product (627 mg) of 5-{2-morpholin-4-yl-7-[4-(2-(4-tert-butoxycarbonyl)-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine obtained in Example 1-D-131, a crude product of 5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine was obtained as a colorless solid (480 mg, 87%). Using a crude product (80 mg) of 5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine, acetylation was carried out in the same manner as Example 1-D-134, to obtain a crude product (88 mg) of 5-{2-morpholin-4-yl-7-[4-(2-(4-acetyl-piperazine)-1-yl-ethyl)-phenyl]-6,7-dihydro-5H-pyrrolo[2,3-d]pyrimidin-4-yl}-pyrimidin-2-yl-bis-(4-methoxy-benzyl)-amine. Using a crude product (84 mg) of 5-{2-morpholin-4-yl-7-[4-(2-(4-acetyl-piperazine)-1-yl-ethyl)-phenyl]-6,7-dihydro-5H-pyrrolo[2,3-d]pyrimidin-4-yl}-pyrimidin-2-yl-bis-(4-methoxy-benzyl)-amine, according to the above Deprotection method 2, 1-[4-(2-{4-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone was obtained as a colorless powder (39 mg, 68%).

$^1$H-NMR (DMSO-d$_6$) δ (ppm): 8.80 (2H, s), 7.74 (2H, d, J=8.4 Hz), 7.24 (2H, d, J=8.4 Hz), 7.06 (2H, s), 4.06 (2H, t, J=8.9 Hz), 3.69 (8H, m), 3.43-3.25 (6H, m), 2.75-2.36 (8H, m), 1.98 (3H, m).

ESI (LC-MS positive mode) m/z 530 (M+H)$^+$.

Example 1-D-144

5-(7-{4-[2-(4-Methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-144)

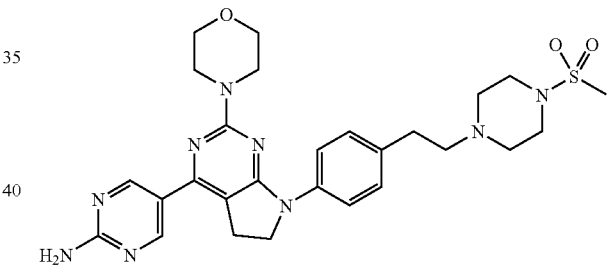

In the same manner as Example 1-D-143, using a crude product (80 mg) of 5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-yl-bis-(4-methoxy-benzyl)-amine obtained in Example 1-D-143 and methanesulfonyl chloride (0.012 ml) instead of acetyl chloride, a crude product of 5-(7-{4-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-yl-bis-(4-methoxy-benzyl)-amine was obtained as a colorless solid (88 mg, 100%). Using a crude product (88 mg) of 5-(7-{4-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-yl-bis-(4-methoxy-benzyl)-amine, according to the above Deprotection method 2,5-(7-{4-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine was obtained as a colorless powder (26 mg, 43%).

$^1$H-NMR (DMSO-d$_6$) δ (ppm): 8.79 (2H, s), 7.73 (2H, d, J=8.4 Hz), 7.24 (2H, d, J=8.4 Hz), 7.05 (2H, s), 4.05 (2H, t, J=7.8 Hz), 3.68 (8H, m), 3.31-3.07 (6H, m), 2.86 (3H, m), 2.74-2.48 (8H, m).

ESI (LC-MS positive mode) m/z 566 (M+H)$^+$.

Example 1-D-145

{4-[4-(2-Amino-pyrimidin-5-yl)-2-morpholin-4-yl-5,6-dihydro-pyrrolo[2,3-d]pyrimidin-7-yl]-3-fluoro-phenyl}-[4-(2-hydroxy-ethyl)-piperazin-1-yl]-methanone (D-145)

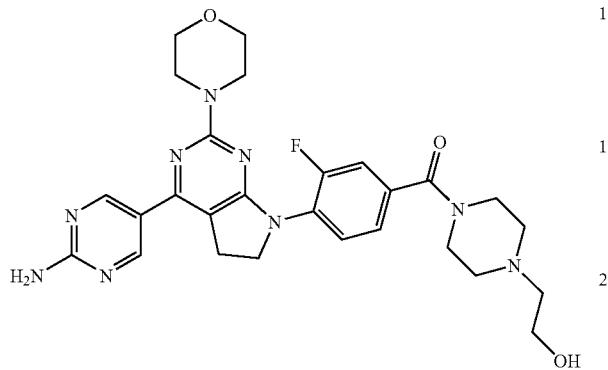

Using 4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (70.4 mg, 0.104 mmol) obtained in Step A in Example 1-D-21 and 1-piperazineethanol (25.5 μl, 0.208 mmol) instead of 1-pyridine-3-yl-piperazine, amidation was carried out in the same manner as Step B in Example 1-D-21, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-[4-(2-hydroxy-ethyl)-piperazin-1-yl]-methanone as a yellow solid (83.2 mg), and then the PMB groups were removed according to the above Deprotection method 3, to obtain the desired compound (D-145) as a yellow powder (24.5 mg, 43%).

$^1$H-NMR (CDCl$_3$) δ (ppm): 8.89 (2H, s), 7.81 (1H, t, J=7.9 Hz), 7.38-7.03 (2H, m), 5.26 (2H, s), 4.15 (2H, t, J=8.1 Hz), 3.84-3.63 (14H, m), 3.32 (2H, t, J=8.1 Hz), 2.73-2.30 (4H, m), 2.61 (4H, t, J=5.1 Hz), 1.64 (1H, brs).

ESI (LC-MS positive mode) m/z 550 (M+H)$^+$.

Example 1-D-146

{4-[4-(2-Amino-pyrimidin-5-yl)-2-morpholin-4-yl-5,6-dihydro-pyrrolo[2,3-d]pyrimidin-7-yl]-3-methyl-phenyl}-(4-ethyl-piperazin-1-yl)-methanone (D-146)

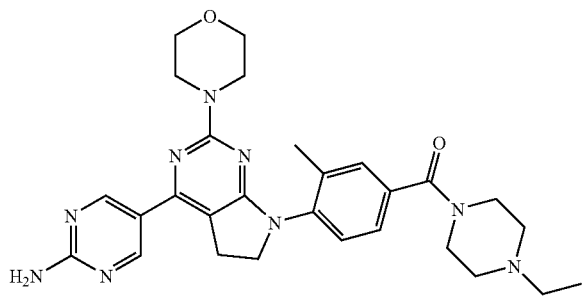

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-bromo-3-methyl-phenyl)-(4-ethyl-piperazin-1-yl)-methanone (162 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-(4-ethyl-piperazin-1-yl)-methanone was obtained, and then the PMB groups were removed according to the above Deprotection method 3, to obtain the desired compound (D-146) as a pale yellow powder (25 mg, 12%).

$^1$H-NMR (CDCl$_3$) δ (ppm): 8.89 (2H, s), 7.36 (1H, s), 7.27 (2H, s), 5.33 (2H, s), 3.99 (2H, t, J=8.2 Hz), 3.69 (16H, brs), 3.32 (2H, t, J=8.2 Hz), 2.48 (2H, dd, J=14.3, 7.2 Hz), 2.29 (3H, s), 1.12 (3H, t, J=7.2 Hz).

ESI (LC-MS positive mode) m/z 530 (M+H)$^+$.

Example 1-D-147

{4-[4-(2-Amino-pyrimidin-5-yl)-2-morpholin-4-yl-5,6-dihydro-pyrrolo[2,3-d]pyrimidin-7-yl]-3-methyl-phenyl}-[4-(2-hydroxy-ethyl)-piperazin-1-yl]-methanone (D-147)

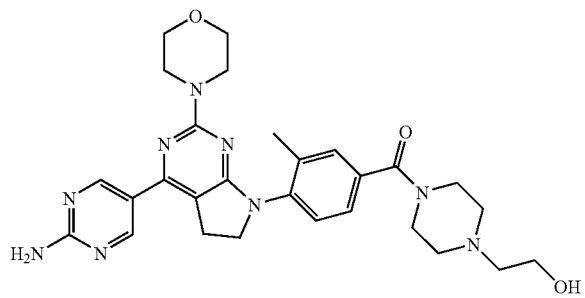

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-bromo-3-methyl-phenyl)-[4-(2-hydroxy-ethyl)-piperazin-1-yl]-methanone (168 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-[4-(2-hydroxy-ethyl)-piperazin-1-yl]-methanone was obtained, and then the PMB groups were removed according to the above Deprotection method 3, to obtain the desired compound (D-147) as a pale yellow powder (28 mg, 28%).

$^1$H-NMR (CDCl$_3$) δ (ppm): 8.89 (2H, s), 7.37 (1H, s), 7.27 (2H, s), 5.40 (2H, s), 3.99 (2H, t, J=8.2 Hz), 3.69 (18H, brs), 3.32 (2H, t, J=8.2 Hz), 2.67 (2H, dd, J=10.3, 5.4 Hz), 2.29 (3H, s).

ESI (LC-MS positive mode) m/z 546 (M+H)$^+$.

Example 1-D-148

{3-[4-(2-Amino-pyrimidin-5-yl)-2-morpholin-4-yl-5,6-dihydro-pyrrolo[2,3-d]pyrimidin-7-yl]-2-methyl-phenyl}-(4-methyl-piperazin-1-yl)-methanone (D-148)

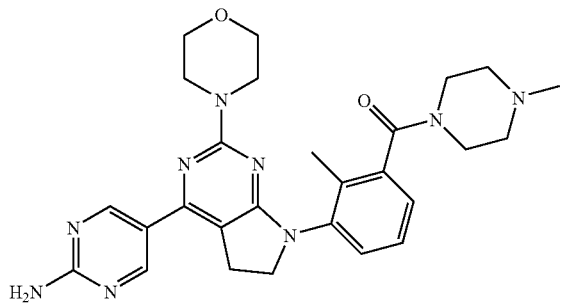

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-bromo-2-methyl-phenyl)-(4-methyl-piperazin-1-yl)-methanone (174 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-2-methyl-phenyl]-(4-methyl-piperazin-1-yl)-methanone was obtained, and then the PMB groups were removed according to the above Deprotection method 3, to obtain the desired compound (D-148) as a pale yellow powder (54 mg, 56%).

$^1$H-NMR (CDCl$_3$) δ (ppm): 8.89 (2H, s), 7.29-7.28 (2H, m), 7.13 (1H, dd, J=5.0, 3.0 Hz), 5.43 (2H, s), 3.96 (2H, t, J=7.6 Hz), 3.67 (18H, brs), 3.33 (2H, t, J=7.6 Hz), 2.32 (3H, s), 2.19 (3H, s).
ESI (LC-MS positive mode) m/z 516 (M+H)$^+$.

Example 1-D-149

5-{7-[2-Fluoro-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-149)

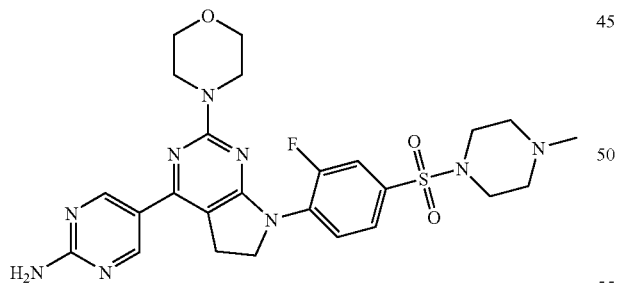

Using 1-(4-bromo-3-fluoro-benzenesulfonyl)-4-methyl-piperazine (prepared from 4-bromo-3-fluoro-benzenesulfonyl chloride and N-methylpiperazine, 68 mg) instead of 1-(3-bromo-benzenesulfonyl)-4-ethyl-piperazine used in Example 1-D-96, a crude product of (5-{7-[2-fluoro-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to Deprotection method 1, to obtain the desired compound (D-149) as a yellow powder (50 mg, 46%).

$^1$H-NMR (DMSO-d$_6$) δ (ppm): 8.81 (2H, s), 8.05 (1H, t, J=8.1 Hz), 7.66 (1H, dd, J=11.4, 1.9 Hz), 7.59 (1H, dd, J=8.7, 1.9 Hz), 7.12 (2H, s), 4.17 (2H, t, J=7.9 Hz), 3.63 (8H, brs), 3.36 (2H, brs), 2.96 (4H, brs), 2.36 (4H, brs), 2.15 (3H, s).
ESI (LC-MS positive mode) m/z 556 (M+H)$^+$.

Example 1-D-150

5-{7-[4-(4-Ethyl-piperazine-1-sulfonyl)-2-fluoro-phenyl]-2-morpholin-4-yl-6,7-dihydro-5H-pyrrolo[2,3-d]pyrimidin-4-yl}-pyrimidin-2-ylamine (D-150)

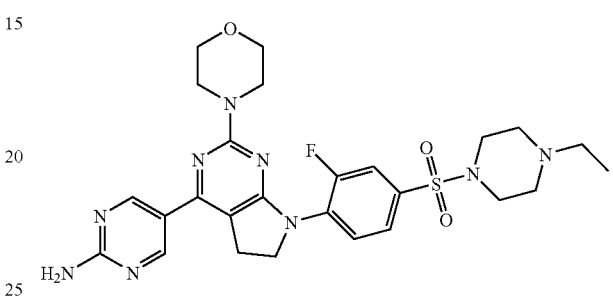

Using 1-(4-bromo-3-fluoro-benzenesulfonyl)-4-ethyl-piperazine (prepared from 4-bromo-3-fluoro-benzenesulfonyl chloride and N-ethylpiperazine, 71 mg) instead of 1-(3-bromo-benzenesulfonyl)-4-ethyl-piperazine used in Example 1-D-96, a crude product of (5-{7-[4-(4-ethyl-piperazine-1-sulfonyl)-2-fluoro-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to Deprotection method 1, to obtain the desired compound (D-150) as a yellow powder (76 mg, 71%).

$^1$H-NMR (DMSO-d$_6$) δ (ppm): 8.82 (2H, s), 8.06 (1H, t, J=8.1 Hz), 7.62 (2H, ddd, J=17.7, 10.0, 1.8 Hz), 7.12 (2H, s), 4.17 (2H, t, J=7.9 Hz), 3.40-3.33 (8H, m), 3.31 (2H, brs), 2.95 (4H, brs), 2.42 (4H, brs), 2.31 (2H, q, J=7.1 Hz), 0.94 (3H, t, J=7.1 Hz).
ESI (LC-MS positive mode) m/z 570 (M+H)$^+$.

Example 1-D-151

5-{7-[5-(4-Ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-ylamine (D-151)

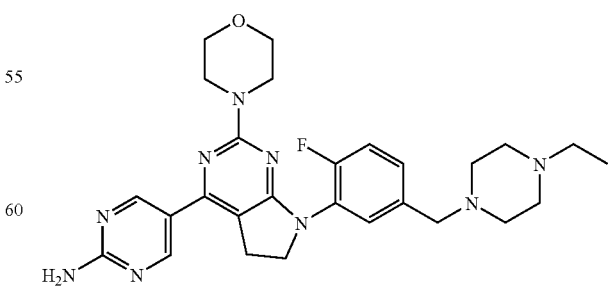

In the same manner as Step A in Example 1-D-26, using bis-(4-methoxy-benzyl)-[5-(2-morpholin-4-yl-6,7-dihydro-5H-pyrrolo[2,3-d]pyrimidin-4-yl)-pyrimidin-2-yl]-amine (215 mg) and 4-fluoro-3-bromo-benzaldehyde (113 mg) instead of 2-(4-bromo-phenyl)-[1,3]dioxolane, a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-fluoro-benzaldehyde was obtained as a colorless solid (260 mg). Using a crude product (130 mg) of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-fluoro-benzaldehyde, in the same manner as Step B in Example 1-D-26, using 1-ethylpiperazine (0.05 ml) instead of 1-methylpiperazine, a crude product of 5-{7-[5-(4-ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-yl-bis-(4-methoxy-benzyl)-amine was obtained as a colorless solid (57 mg). Using a crude product (57 mg) of 5-{7-[5-(4-ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-yl-bis-(4-methoxy-benzyl)-amine, according to the above Deprotection method 2, 5-{7-[5-(4-ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-ylamine was obtained as a colorless powder (26 mg, 68%).

$^1$H-NMR (CDCl$_3$) δ: 8.89 (2H, s), 7.62 (1H, m), 7.15-7.04 (2H, m), 5.24 (2H, s), 4.11 (2H, t, J=7.3 Hz), 3.74 (8H, s), 3.30 (2H, t, J=7.3 Hz), 2.50-2.38 (10H, m), 1.08 (3H, t, J=7.3 Hz).

ESI (LC-MS positive mode) m/z 520 (M+H)$^+$.

Example 1-D-152

2-(4-{4-[4-(2-Amino-pyrimidin-5-yl)-2-morpholin-4-yl-5,6-dihydro-pyrrolo[2,3-d]pyrimidin-7-yl]-3-fluoro-benzenesulfonyl}-piperazin-1-yl)-ethanol (D-152)

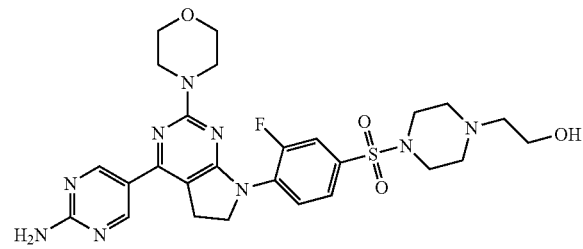

Using 2-[4-(4-bromo-3-fluoro-benzenesulfonyl)-piperazin-1-yl]-ethanol (prepared from 4-bromo-3-fluoro-benzenesulfonyl chloride and 2-piperazin-1-yl-ethanol, 74 mg) instead of 1-(3-bromo-benzenesulfonyl)-4-ethyl-piperazine used in Example 1-D-96, a crude product of (2-{4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzenesulfonyl]-piperazin-1-yl}-ethanol was obtained, and then the PMB groups were removed according to Deprotection method 1, to obtain the desired compound (D-152) as a yellow powder (68 mg, 63%).

$^1$H-NMR (DMSO-d$_6$) δ (ppm): 8.81 (2H, s), 8.06 (1H, t, J=8.1 Hz), 7.65 (1H, d, J=11.0 Hz), 7.59 (1H, d, J=8.1 Hz), 7.12 (2H, s), 4.17 (2H, t, J=5.9 Hz), 3.63 (8H, brs), 3.43 (2H, t, J=5.9 Hz), 3.33 (4H, brs), 2.94 (4H, brs), 2.36 (2H, t, J=6.1 Hz).

ESI (LC-MS positive mode) m/z 586 (M+H)$^+$.

Example 1-D-153

4-(2-Amino-pyrimidin-5-yl)-2-morpholin-4-yl-5,6-dihydro-pyrrolo[2,3-d]pyrimidine-7-carboxylic acid {3-[4-(2-hydroxy-ethyl)-piperazin-1-yl]-phenyl}-methyl-amide (D-153)

Step A (3-Bromo-phenyl)-methyl-amine

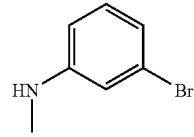

Using N-(3-bromo-phenyl)-N-methyl-acetamide (228 mg) obtained in Step B in Example 1-D-135 instead of N-[3-(4-ethyl-piperazin-1-yl)-phenyl]-N-methyl-acetamide, in the same manner as Step D in Example 1-D-135, the desired compound was obtained as a crude product (167 mg, 90%).

Step B

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide

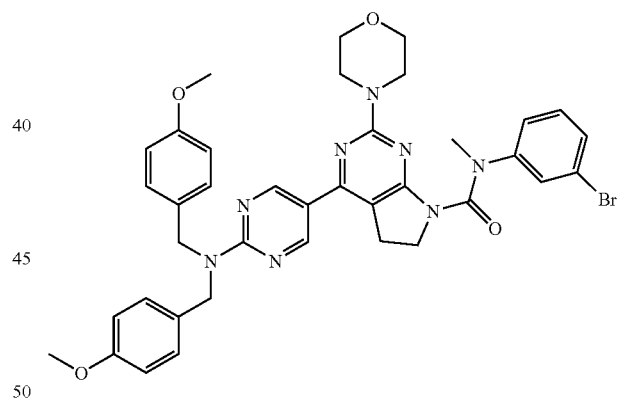

To a solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (324 g) in dichloromethane (3.0 ml), pyridine (194 μl) was added, followed by cooling to 0° C. To the resulting mixture, triphosgene (356 g) was added, and then the reaction mixture was warmed to room temperature, followed by stirring for 1 hour. The solvent was distilled under reduced pressure, and then the residue was dissolved in dichloromethane (2.0 ml). This was added to a solution of (3-bromo-phenyl)-methyl-amine (134 mg) obtained in Step A in dichloromethane (2.0 ml), followed by stirring for 1 hour. Water (5 ml) was added, followed by passing through Whatman tube, and the solvent was distilled off under reduced pressure. The residue was purified by silica gel column chromatography (dichloromethane/methanol=200/1 to 100/1), to obtain the desired compound (204 mg, 45%).

Step C 4-(2-Amino-pyrimidin-5-yl)-2-morpholin-4-yl-5,6-dihydro-pyrrolo[2,3-d]pyrimidine-7-carboxylic acid {3-[4-(2-hydroxy-ethyl)-piperazin-1-yl]-phenyl}-methyl-amide (D-153)

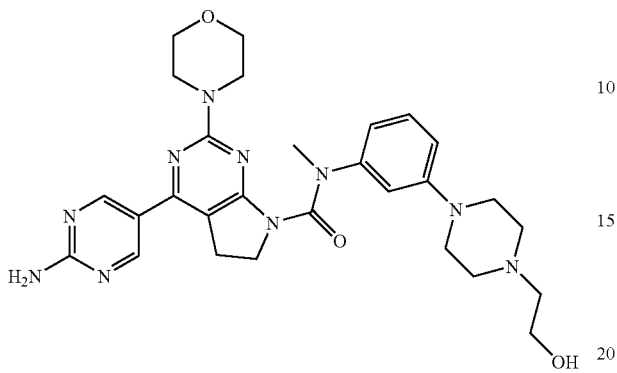

To a DMF solution (2.0 ml) of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide (70.5 mg) obtained in Step B, tris(dibenzylideneacetone) dipalladium (4.3 mg), S-Phos (3.8 mg) and potassium phosphate (39.8 mg), 2-piperazin-1-yl-ethanol (23 μl) was added, and degassed under ultrasonic irradiation. After this was stirred at 100° C. for 4 hours, water (10 ml) was added, followed by extraction with ethyl acetate (10 ml×2), and the organic layer was dried over sodium sulfate. After the sodium sulfate was filtered off, the solvent was distilled off under reduced pressure, followed by purification by silica gel column chromatography, to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {3-[4-(2-hydroxy-ethyl)-piperazin-1-yl]-phenyl}-methyl-amide. The PMB groups were removed according to Deprotection method 3, to obtain the desired compound (D-153) as a colorless solid (7.2 mg, 14%).

$^1$H-NMR (DMSO-d$_6$) δ: 8.71 (2H, s), 7.14-7.06 (2H, m), 6.84-6.80 (1H, brm), 6.71-6.64 (2H, m), 3.85 (2H, t, J=7.7 Hz), 3.65-3.59 (8H, brm), 3.54-3.47 (2H, m), 3.32 (3H, s), 3.13-3.03 (6H, brm), 2.51-2.49 (4H, brm), 2.40 (2H, t, J=6.3 Hz).

ESI (LC-MS positive mode) m/z 561 (M+H)$^+$.

Example 1-D-154

4-(2-Amino-pyrimidin-5-yl)-2-morpholin-4-yl-5,6-dihydro-pyrrolo[2,3-d]pyrimidine-7-carboxylic acid methyl-(3-piperazin-1-yl-phenyl)-amide (D-154)

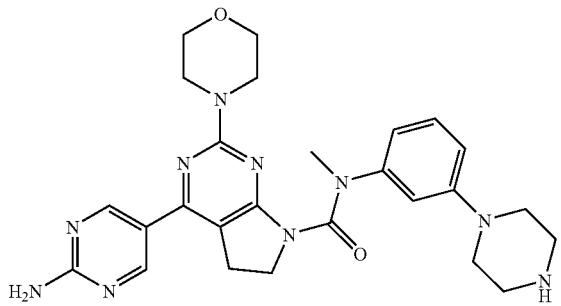

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide (70.5 mg) and N-Boc-piperazine (34.9 mg) instead of 2-piperazin-1-yl-ethanol, in the same manner as Step C in Example 1-D-153, 4-{3-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-methyl-amino]-phenyl}-piperazine-1-carboxylic acid tert-butyl ester was obtained as a crude product. Further, PMB group and BOC group were removed according to Deprotection method 3, to obtain the desired compound (D-154) as a yellow solid (37.9 mg, 78%).

$^1$H-NMR (DMSO-d$_6$) δ: 8.71 (2H, s), 7.14-7.06 (3H, m), 6.82-6.78 (1H, m), 6.71-6.62 (2H, brm), 3.84 (2H, t, J=8.1 Hz), 3.67-3.57 (8H, brm), 3.34 (3H, s), 3.08 (2H, t, J=8.1 Hz), 3.01-2.93 (4H, brm), 2.83-2.75 (4H, brm).

ESI (LC-MS positive mode) m/z 517 (M+H)$^+$.

Example 1-D-155

4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-methyl-amide (D-155)

Step A

N-(4-Bromo-phenyl)-acetamide

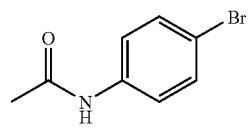

Using 4-bromoaniline (1 g) instead of 3-bromoaniline, in the same manner as Step A in Example 1-D-135, the desired compound was obtained (1.15 g, 93%).

Step B

N-(4-Bromo-phenyl)-N-methyl-acetamide

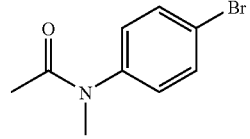

Using N-(4-bromo-phenyl)-acetamide (1.15 g) obtained in Step A instead of N-(3-bromo-phenyl)-acetamide, in the same manner as Step B in Example 1-D-135, the desired compound was obtained (1.19 g, 96%).

Step C

N-[4-(4-ethyl-piperazin-1-yl)-phenyl]-N-methyl-acetamide

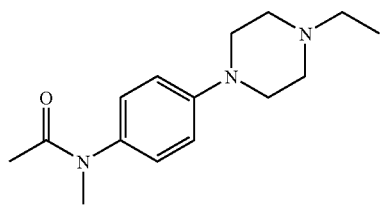

Using N-(4-bromo-phenyl)-N-methyl-acetamide (114 mg) obtained in Step B instead of N-(3-bromo-phenyl)-N-methyl-acetamide, in the same manner as Step C in Example 1-D-135, the desired compound was obtained (84.3 mg, 65%).

Step D

[4-(4-Ethyl-piperazin-1-yl)-phenyl]-methyl-amine

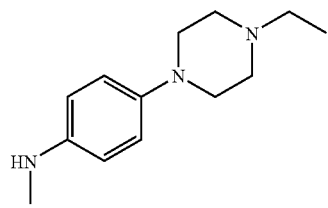

Using N-[4-(4-ethyl-piperazin-1-yl)-phenyl]-N-methyl-acetamide (84.3 mg) obtained in Step C instead of N-[3-(4-ethyl-piperazin-1-yl)-phenyl]-N-methyl-acetamide, in the same manner as Step D in Example 1-D-135, the desired compound was obtained (51.7 mg, 73%).

Step E 4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-methyl-amide (D-155)

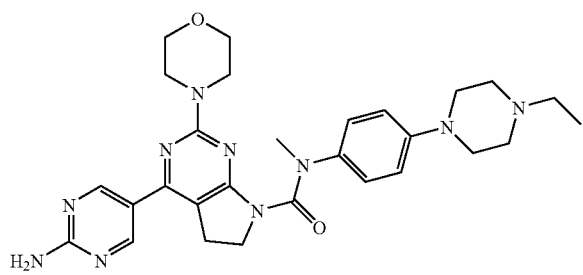

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and [4-(4-ethyl-piperazin-1-yl)-phenyl]-methyl-amine (51.7 mg) obtained in Step D instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazin-1-yl)-phenyl]-methyl-amide was obtained as a crude product. The PMB groups were removed according to Deprotection method 3, to obtain the desired compound (D-155) as a colorless solid (54.8 mg, 50%).

$^1$H-NMR (DMSO-d$_6$) δ: 8.72 (2H, s), 7.17-7.06 (4H, m), 6.85 (2H, d, J=8.9 Hz), 3.79 (2H, t, J=8.2 Hz), 3.69-3.60 (8H, brm), 3.27 (3H, s), 3.13-3.03 (6H, brm), 2.48-2.42 (4H, brm), 2.33 (2H, q, J=7.2 Hz), 1.01 (3H, t, J=7.2 Hz).

ESI (LC-MS positive mode) m/z 545 (M+H)$^+$.

Example 1-D-156

1-(4-{3-[4-(2-Amino-pyrimidin-5-yl)-2-morpholin-4-yl-5,6-dihydro-pyrrolo[2,3-d]pyrimidin-7-yl]-4-fluoro-benzyl}-piperazin-1-yl)-ethanone (D-156)

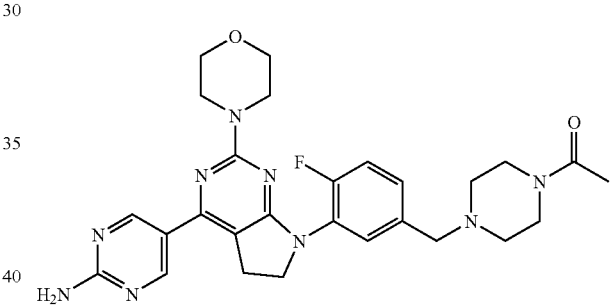

In the same manner as Example 1-D-151, using a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-fluoro-benzaldehyde (130 mg) and 1-acetylpiperazine (50 mg) instead of 1-ethylpiperazine, a crude product of 5-{7-[5-(4-acetyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-yl-bis-(4-methoxy-benzyl)-amine was obtained as colorless solid (63 mg). Using the crude product (63 mg) of 5-{7-[5-(4-acetyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-yl-bis-(4-methoxy-benzyl)-amine, according to the above Deprotection method 2, 1-(4-{3-[4-(2-amino-pyrimidin-5-yl)-2-morpholin-4-yl-5,6-dihydro-pyrrolo[2,3-d]pyrimidin-7-yl]-4-fluoro-benzyl}-piperazin-1-yl)-ethanone was obtained as a colorless powder (30 mg, 70%).

$^1$H-NMR (CDCl$_3$) δ (ppm): 8.89 (2H, s), 7.63 (1H, m), 7.25-7.06 (2H, m), 5.24 (2H, s), 4.12 (2H, t, J=7.3 Hz), 3.74 (8H, s), 3.62-3.28 (6H, m), 2.42-2.39 (4H, m), 2.08 (3H, s).

ESI (LC-MS positive mode) m/z 534 (M+H)$^+$.

Example 1-D-157

{3-[4-(2-Amino-pyrimidin-5-yl)-2-morpholin-4-yl-5,6-dihydro-pyrrolo[2,3-d]pyrimidin-7-yl]-2-methyl-phenyl}-morpholin-4-yl-methanone (D-157)

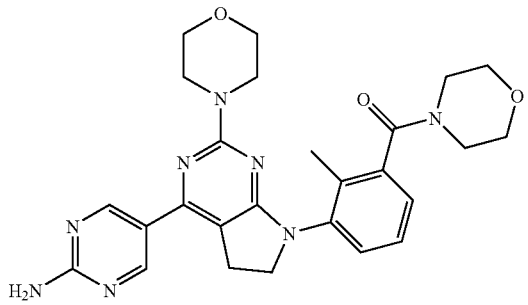

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-bromo-2-methyl-phenyl)-morpholin-4-yl-methanone (164 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-2-methyl-phenyl]-morpholin-4-yl-methanone was obtained, and then the PMB groups were removed according to Deprotection method 3, to obtain the desired compound (D-157) as a pale brown powder (50 mg, 54%).

$^1$H-NMR (CDCl$_3$) δ (ppm): 8.89 (2H, s), 7.30-7.28 (2H, m), 7.14 (1H, dd, J=5.6, 3.3 Hz), 5.59 (2H, s), 3.86-3.76 (2H, m), 3.67 (14H, s), 3.32 (2H, t, J=8.4 Hz), 2.20 (3H, s).

ESI (LC-MS positive mode) m/z 503 (M+H)$^+$.

Example 1-D-158

{3-[4-(2-Amino-pyrimidin-5-yl)-2-morpholin-4-yl-5,6-dihydro-pyrrolo[2,3-d]pyrimidin-7-yl]-2-methyl-phenyl}-(4-ethyl-piperazin-1-yl)-methanone (D-158)

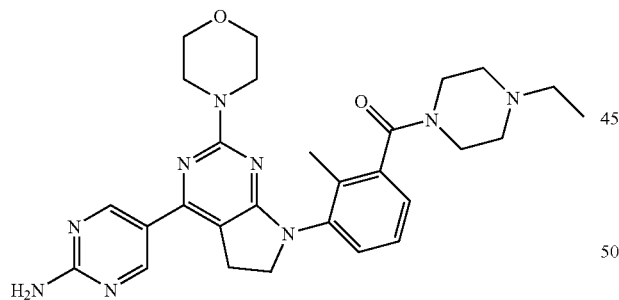

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-bromo-2-methyl-phenyl)-(4-ethyl-piperazin-1-yl)-methanone (156 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-2-methyl-phenyl]-(4-ethyl-piperazin-1-yl)-methanone was obtained, and then the PMB groups were removed according to Deprotection method 3, to obtain the desired compound (D-158) as a pale yellow powder (53 mg, 54%).

$^1$H-NMR (CDCl$_3$) δ (ppm): 8.89 (2H, s), 7.29-7.28 (2H, m), 7.14 (1H, dd, J=5.8, 3.1 Hz), 5.62 (2H, s), 3.87 (2H, t, J=4.9 Hz), 3.67 (16H, s), 3.32 (2H, t, J=8.0 Hz), 2.45 (2H, q, J=7.2 Hz), 2.19 (3H, s), 1.10 (3H, t, J=7.3 Hz).

ESI (LC-MS positive mode) m/z 530 (M+H)$^+$.

Example 1-D-159

{3-[4-(2-Amino-pyrimidin-5-yl)-2-morpholin-4-yl-5,6-dihydro-pyrrolo[2,3-d]pyrimidin-7-yl]-2-methyl-phenyl}-[4-(2-hydroxy-ethyl)-piperazin-1-yl]-methanone (D-159)

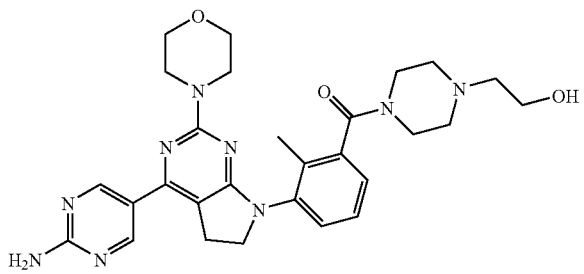

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-bromo-2-methyl-phenyl)-[4-(2-hydroxy-ethyl)-piperazin-1-yl]-methanone (188 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-2-methyl-phenyl]-[4-(2-hydroxy-ethyl)-piperazin-1-yl]-methanone was obtained, and then the PMB groups were removed according to the above Deprotection method 3, to obtain the desired compound (D-159) as a pale yellow powder (23 mg, 23%).

$^1$H-NMR (CDCl$_3$) δ (ppm): 8.89 (2H, s), 7.30-7.28 (1H, m), 7.13 (2H, dd, J=5.7, 3.2 Hz), 5.42 (2H, s), 3.87 (2H, t, J=4.5 Hz), 3.67 (24H, s), 3.33 (2H, t, J=8.1 Hz), 2.60 (2H, q, J=5.3 Hz), 2.20 (3H, s).

ESI (LC-MS positive mode) m/z 546 (M+H)$^+$.

Example 1-D-160

4-(2-Amino-pyrimidin-5-yl)-2-morpholin-4-yl-5,6-dihydro-pyrrolo[2,3-d]pyrimidine-7-carboxylic acid methyl-[4-(4-methyl-piperazin-1-yl)-phenyl]-amide (D-160)

Step A (4-Bromo-phenyl)-methyl-amine

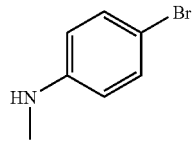

Using N-(4-bromo-phenyl)-N-methyl-acetamide (228 mg) obtained in Step B in Example 1-D-155 instead of N-[3-(4-ethyl-piperazin-1-yl)-phenyl]-N-methyl-acetamide, in the same manner as Step D in Example 1-D-135, the desired compound was obtained as a crude product (180 mg, 97%).

Step B

4-{2-[Bis-(4-methoxy-benzyl)-amino]-pyrimidin-5-yl}-2-morpholin-4-yl-5,6-dihydro-pyrrolo[2,3-d]pyrimidine-7-carboxylic acid (4-bromo-phenyl)-methyl-amide

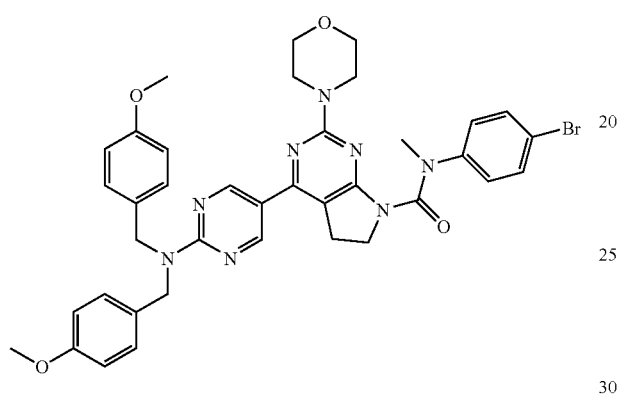

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (324 g) and (4-bromo-phenyl)-methyl-amine (134 mg) obtained in Step A instead of (3-bromo-phenyl)-methyl-amine, in the same manner as Step B in Example 1-D-153, the desired compound was obtained (363 mg, 81%).

Step C 4-(2-Amino-pyrimidin-5-yl)-2-morpholin-4-yl-5,6-dihydro-pyrrolo[2,3-d]pyrimidine-7-carboxylic acid methyl-[4-(4-methyl-piperazin-1-yl)-phenyl]-amide (D-160)

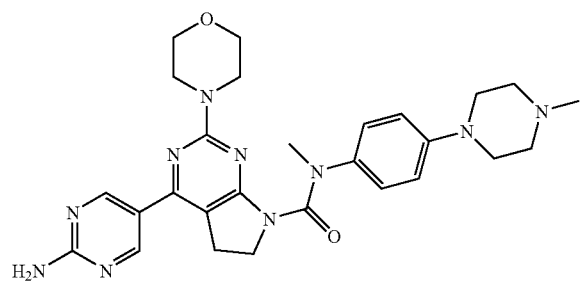

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-bromo-phenyl)-methyl-amide (121 mg) obtained in Step B instead of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide, and 1-methyl-piperazine (35.7 μl) instead of 2-piperazin-1-yl-ethanol, in the same manner as Step C in Example 1-D-153, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-[4-(4-methyl-piperazin-1-yl)-phenyl]-amide was obtained. The PMB groups were removed according to Deprotection method 3, to obtain the desired compound (D-160) as a brown solid (54 mg, 63%).

$^1$H-NMR (DMSO-$d_6$) δ: 8.71 (2H, s), 7.16-7.06 (4H, m), 6.85 (2H, d, J=8.9 Hz), 3.79 (2H, t, J=8.0 Hz), 3.69-3.60 (8H, brm), 3.27 (3H, s), 3.13-3.03 (6H, brm), 2.44-2.36 (3H, brm), 2.19 (3H, s).

ESI (LC-MS positive mode) m/z 531 (M+H)$^+$.

Example 1-D-161

4-(2-Amino-pyrimidin-5-yl)-2-morpholin-4-yl-5,6-dihydro-pyrrolo[2,3-d]pyrimidine-7-carboxylic acid methyl-(4-piperazin-1-yl-phenyl)-amide (D-161)

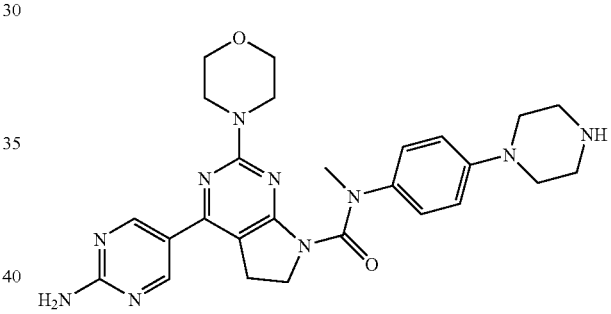

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-bromo-phenyl)-methyl-amide (121 mg) obtained in Step B in Example 1-D-160 instead of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide, and N-Boc-piperazine (60 mg) instead of 2-piperazin-1-yl-ethanol, in the same manner as Step C in Example 1-D-153, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-(4-piperazin-1-yl-phenyl)-amide was obtained. The PMB groups were removed according to Deprotection method 3, to obtain the desired compound (D-161) as a yellow solid (56.1 mg, 67%).

$^1$H-NMR (DMSO-$d_6$) δ: 8.72 (2H, s), 7.16-7.05 (4H, m), 6.83 (2H, d, J=9.1 Hz), 3.78 (2H, t, J=8.1 Hz), 3.70-3.60 (8H, brm), 3.27 (3H, s), 3.07 (2H, t, J=8.1 Hz), 3.02-2.95 (4H, brm), 2.82-2.75 (4H, brm).

ESI (LC-MS positive mode) m/z 517 (M+H)$^+$.

Example 1-D-162

4-(2-Amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazin-1-yl]-phenyl}-methyl-amide (D-162)

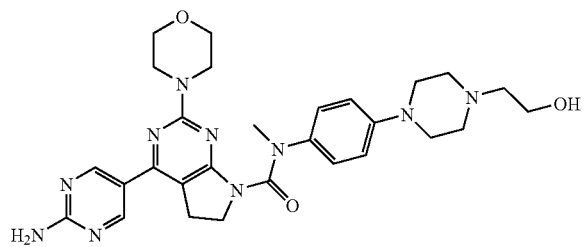

Example 1-D-163

4-(2-Amino-pyrimidin-5-yl)-2-morpholin-4-yl-5,6-dihydro-pyrrolo[2,3-d]pyrimidine-7-carboxylic acid methyl-phenyl-amide (D-163)

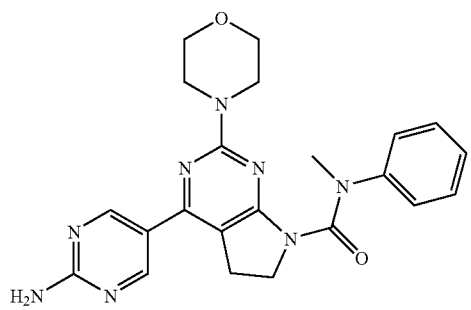

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-bromo-phenyl)-methyl-amide (121 mg) obtained in Step B in Example 1-D-160 instead of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide, in the same manner as Step C in Example 1-D-153, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid{4-[4-(2-hydroxy-ethyl)-piperazin-1-yl]-phenyl}-methyl-amide was obtained. The PMB groups were removed according to Deprotection method 3, to obtain the desired compound (D-162) as a colorless solid (17.1 mg, 38%)) and the desired compound (D-163) as a colorless solid (15.4 mg, 11%).

D-162:
$^1$H-NMR (DMSO-$d_6$) δ: 8.72 (2H, s), 7.16-7.07 (4H, m), 6.84 (2H, d, J=9.1 Hz), 3.79 (2H, t, J=7.9 Hz), 3.70-3.59 (8H, brm), 3.27 (3H, s), 3.13-3.03 (6H, brm), 2.52-2.49 (6H, brm), 2.40 (2H, t, J=6.3 Hz).
ESI (LC-MS positive mode) m/z 561 (M+H)$^+$.

D-163:
$^1$H-NMR (DMSO-$d_6$) δ: 8.71 (2H, s), 7.32-7.27 (4H, m), 7.14-7.11 (1H, m), 7.11-7.08 (2H, m), 3.87 (2H, t, J=8.2 Hz), 3.64-3.59 (8H, brm), 3.35 (3H, s), 3.09 (2H, t, J=8.2 Hz).
ESI (LC-MS positive mode) m/z 433 (M+H)$^+$

Example 1-D-164

5-{7-[2-Methyl-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-164)

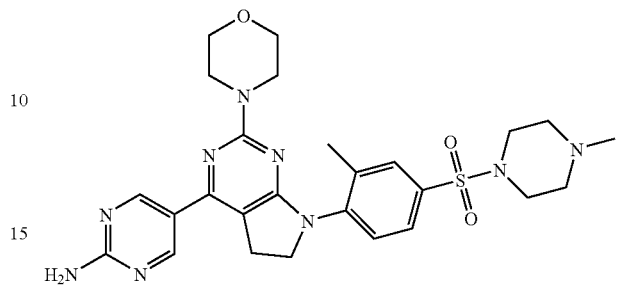

Using 1-(4-bromo-3-methyl-benzenesulfonyl)-4-methyl-piperazine (prepared from 4-bromo-3-methyl-benzenesulfonyl chloride and N-methylpiperazine, 68 mg) instead of 1-(3-bromo-benzenesulfonyl)-4-ethyl-piperazine used in Example 1-D-96, in the same manner as Example 1-D-08, a crude product of bis-(4-methoxy-benzyl)-(5-{7-[2-methyl-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 3, to obtain the desired compound (D-164) as a yellow powder (64 mg, 63%).
$^1$H-NMR (DMSO-$d_6$) δ (ppm): 8.81 (2H, s), 7.67 (1H, s), 7.59 (1H, s), 7.59 (1H, s), 7.08 (2H, s), 4.05 (2H, t, J=8.1 Hz), 3.56 (2H, brs), 3.42-3.31 (8H, m), 2.93 (4H, s), 2.35 (4H, brs), 2.32 (3H, s), 2.14 (3H, s).
ESI (LC-MS positive mode) m/z 552 (M+H)$^+$.

Example 1-D-165

5-{7-[4-(4-Ethyl-piperazine-1-sulfonyl)-2-methyl-phenyl]-2-morpholin-4-yl-6,7-dihydro-5H-pyrrolo[2,3-d]pyrimidin-4-yl}-pyrimidin-2-ylamine (D-165)

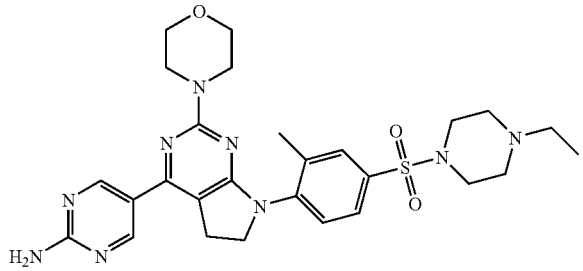

Using 1-(4-bromo-3-methyl-benzenesulfonyl)-4-ethyl-piperazine (prepared from 4-bromo-3-methyl-benzenesulfonyl chloride and N-ethylpiperazine, 71 mg) instead of 1-(4-bromo-3-methyl-benzenesulfonyl)-4-methyl-piperazine used in Example 1-D-164, in the same manner as Example 1-D-08, a crude product of (5-{7-[4-(4-ethyl-piperazine-1-sulfonyl)-2-methyl-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and the PMB groups were removed according to the above Deprotection method 3, to obtain the desired compound (D-165) as a yellow powder (77 mg, 73%).

$^1$H-NMR (DMSO-d$_6$) δ (ppm): 8.81 (2H, s), 7.67 (1H, s), 7.59 (2H, s), 7.08 (2H, s), 4.05 (2H, t, J=7.6 Hz), 3.56 (8H, brs), 3.34 (2H, brs), 2.92 (4H, brs), 2.41 (4H, brs), 2.32 (3H, s), 2.29 (2H, q, J=7.1 Hz), 0.93 (3H, t, J=7.1 Hz)
ESI (LC-MS positive mode) m/z 566 (M+H)$^+$.

Example 1-D-166

2-(4-{4-[4-(2-Amino-pyrimidin-5-yl)-2-morpholin-4-yl-5,6-dihydro-pyrrolo[2,3-d]pyrimidin-7-yl]-3-methyl-benzenesulfonyl}-piperazin-1-yl)-ethanol (D-166)

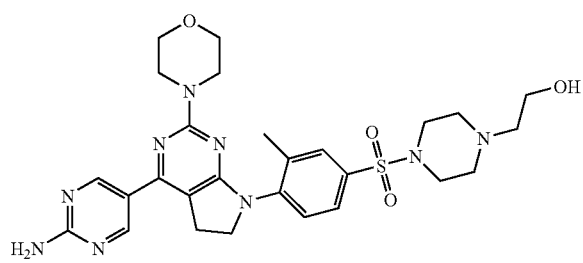

Using 2-[4-(4-bromo-3-methyl-benzenesulfonyl)-piperazin-1-yl]-ethanol (prepared from 4-bromo-3-methyl-benzenesulfonyl chloride and 2-piperazin-1-yl-ethanol, 74 mg) instead of 1-(4-bromo-3-methyl-benzenesulfonyl)-4-methyl-piperazine used in Example 1-D-164, in the same manner as Example 1-D-08, a crude product of (5-{7-[4-(4-ethyl-piperazine-1-sulfonyl)-2-methyl-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to the above Deprotection method 3, to obtain the desired compound (D-166) as a yellow powder (35 mg, 33%).
$^1$H-NMR (DMSO-d$_6$) δ (ppm): 8.81 (2H, s), 7.67 (1H, s), 7.59 (2H, s), 7.08 (2H, s), 4.39 (1H, t, J=5.4 Hz), 4.05 (2H, t, J=8.2 Hz), 3.56 (8H, s), 3.42 (2H, dd, J=11.9, 5.4 Hz), 3.34 (2H, brs), 2.34 (2H, dd, J=11.9, 5.4 Hz), 2.32 (3H, s).
ESI (LC-MS positive mode) m/z 582 (M+H)$^+$.

Example 1-D-167

2-{4-[4-(2-Amino-pyrimidin-5-yl)-2-morpholin-4-yl-5,6-dihydro-pyrrolo[2,3-d]pyrimidin-7-yl]-pyridin-2-ylamino}-ethanol (D-167)

Step A

[tert-Butoxycarbonyl-(4-chloro-pyridin-2-yl)-amino]-acetic acid methyl ester

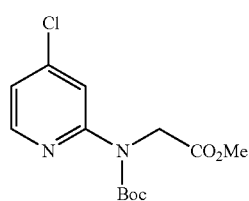

To a DMF suspension (1 ml) of (4-chloro-pyridin-2-yl)-carbamic acid tert-butyl ester (100 mg, 0.437 mmol), NaH (60% mineral oil dispersion, 68 mg) was added with ice cooling, followed by stirring at room temperature for 30 minutes. To the reaction mixture, bromoacetic acid methyl ester (0.19 ml, 2.06 mmol) was added, followed by stirring at room temperature for 1 hour. The reaction mixture was quenched with saturated aqueous ammonium chloride solution, followed by extraction with ethyl acetate (20 ml×2). The organic layers were combined, and washed with saturated aqueous sodium chloride solution. After the organic layer was dried over magnesium sulfate, the magnesium sulfate was filtered off, and the filtrate was concentrated under reduced pressure. The residue was purified by silica gel column chromatography (hexane/ethyl acetate=10:1), to obtain [tert-butoxycarbonyl-(4-chloro-pyridin-2-yl)-amino]-acetic acid methyl ester as a colorless liquid (380 mg, 97%).
$^1$H-NMR (CDCl$_3$) δ (ppm): 8.18 (1H, d, J=5.3 Hz), 8.01 (1H, m), 6.99 (1H, dd, J=1.9 Hz, 5.3 Hz), 4.73 (2H, s), 3.75 (3H, s), 1.53 (9H, s).
ESI (LC-MS positive mode) m/z 201 (M−100)$^+$.

Step B

{[4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-tert-butoxycarbonyl-amino}-acetic acid methyl ester

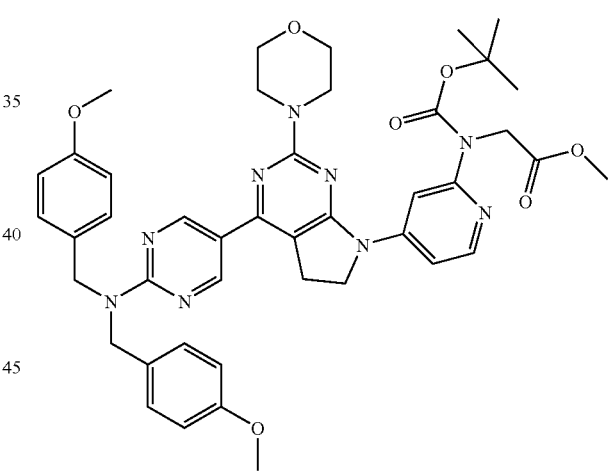

A DMF solution (4 ml) of [tert-butoxycarbonyl-(4-chloro-pyridin-2-yl)-amino]-acetic acid methyl ester (200 mg, 0.667 mmol) obtained in Step A, bis-(4-methoxy-benzyl)-[5-(2-morpholin-4-yl-6,7-dihydro-5H-pyrrolo[2,3-d]pyrimidin-4-yl)-pyrimidin-2-yl]-amine (300 mg, 0.556 mmol), palladium acetate (12.5 mg, 0.0556 mmol), S-Phos (46 mg, 0.111 mmol) and potassium phosphate (354 mg, 1.67 mmol) was deaerated under irradiation of ultrasonic wave, followed by stirring at 100° C. for 1 hour under a nitrogen atmosphere. The reaction mixture was cooled to room temperature, and diluted with water, followed by extraction with dichloromethane (30 ml×2). The organic layers were combined, and washed with saturated aqueous sodium chloride solution. After the organic layer was dried over magnesium sulfate, the magnesium sulfate was filtered off, and the filtrate was concentrated under reduced pressure, followed by purification of the residue by silica gel column chromatography (dichlo-

Step C

[4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(2-hydroxy-ethyl)-carbamic acid tert-butyl ester

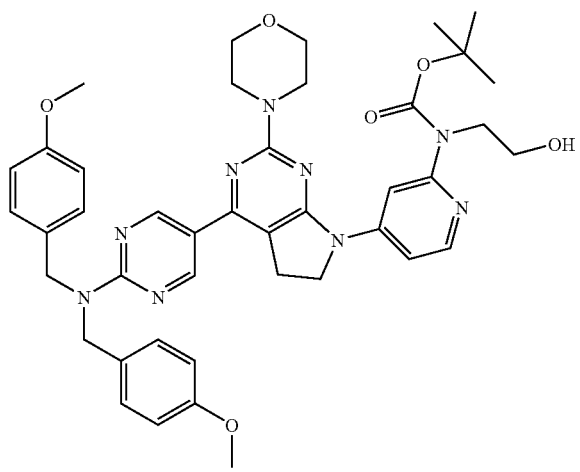

A THF solution (5 ml) of {[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-tert-butoxycarbonyl-amino}-acetic acid methyl ester (135 mg, 0.168 mmol) obtained in Step B was cooled to −40°, and 1.0M diethyl ether solution (0.20 ml, 0.20 mmol) of lithium aluminium hydride was added, which was gradually raised to 0° C. over 1 hour. The reaction mixture was quenched with aqueous potassium sodium tartrate solution, followed by extraction with dichloromethane (15 ml×2). The organic layers were combined, and washed with saturated aqueous sodium chloride solution. After the organic layer was dried over magnesium sulfate, the magnesium sulfate was filtered off, and the filtrate was concentrated under reduced pressure, and the residue was purified by silica gel column chromatography (dichloromethane/methanol=50:1), to obtain [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(2-hydroxy-ethyl)-carbamic acid tert-butyl ester as a yellow solid (73 mg, 56%).

$^1$H-NMR (CDCl$_3$) δ (ppm): 8.99 (2H, s), 8.14 (2H, m), 7.52 (1H, m), 7.19 (4H, m), 6.86 (4H, m), 4.84 (4H, s), 4.11 (2H, m), 3.87 (18H, m), 3.33 (2H, m), 1.53 (9H, s).

ESI (LC-MS positive mode) m/z 776 (M+H)$^+$.

Step D

2-{4-[4-(2-Amino-pyrimidin-5-yl)-2-morpholin-4-yl-5,6-dihydro-pyrrolo[2,3-d]pyrimidin-7-yl]-pyridin-2-ylamino}-ethanol (D-167)

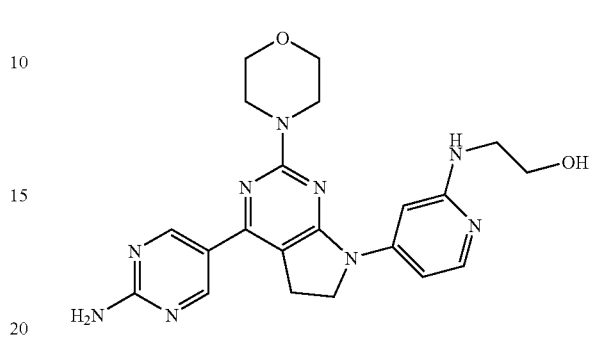

Using [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(2-hydroxy-ethyl)-carbamic acid tert-butyl ester (73 mg, 0.094 mmol) obtained in Step C, PMB group and BOC group were removed according to the above Deprotection method 2, to obtain the desired compound (D-167) as a yellow powder (20 mg, 51%).

$^1$H-NMR (TFA-d) δ (ppm): 9.27 (2H, s), 8.02 (2H, m), 7.21 (1H, m), 4.82 (1H, m), 4.59 (2H, m), 4.21 (8H, m), 4.06 (2H, m), 3.84 (1H, m), 3.53 (2H, m).

ESI (LC-MS positive mode) m/z 436 (M+H)$^+$.

Example 1-D-168

3-{4-[4-(2-Amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-168)

Step A

3-[4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-phenyl]-propionic acid

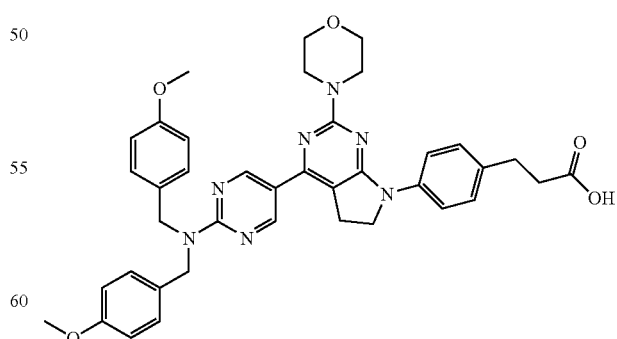

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 3-(4-bromo-phenyl)-propionic acid (47 mg), in the same manner as Step A in Example 1-D-19, 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-propionic acid was obtained as a crude product (65 mg).

Step B

3-{4-[4-(2-Amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-168)

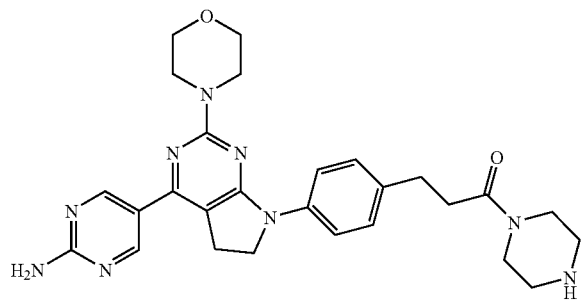

Using 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-propionic acid (61 mg) and piperazine-1-carboxylic acid tert-butyl ester (20 mg) instead of 3-(aminomethyl)pyridine, in the same manner as Step B in Example 1-D-19, 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-tert-butyl-piperazin-1-yl)-propan-1-one was obtained, and further PMB group and BOC group were removed according to the above Deprotection method 2, to obtain the desired compound (D-168) as a pale yellow powder (14 mg, 31%).

$^{1}$H-NMR (CDCl$_3$+CD$_3$OD) δ (ppm): 8.86 (2H, s), 7.70 (2H, m), 7.25 (2H, m), 4.10 (2H, m), 3.82 (8H, m), 3.62 (2H, m), 3.42 (2H, m), 3.27 (2H, m), 2.95 (2H, m), 2.66 (6H, m).

ESI (LC-MS positive mode) m/z 516 (M+H)$^+$.

Example 1-D-169

3-{4-[4-(2-Amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-169)

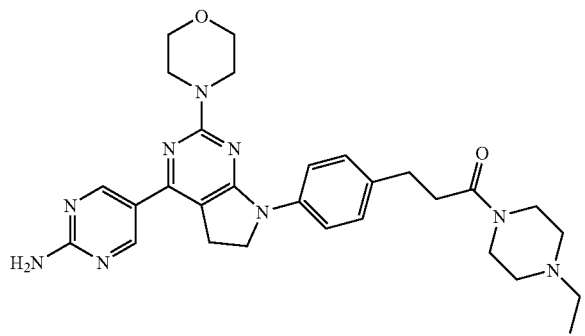

Using 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-propionic acid (100 mg) obtained in Step A in Example 1-D-168 and 1-ethyl-piperazine (22 μl) instead of 3-(aminomethyl)pyridine, in the same manner as Step B in Example 1-D-19, 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-ethyl-piperazin-1-yl)-propan-1-one was obtained, and then the PMB groups were removed according to the above Deprotection method 2, to obtain the desired compound (D-169) as a pale yellow powder (18 mg, 23%).

$^{1}$H-NMR (CDCl$_3$+CD$_3$OD) δ (ppm): 8.86 (2H, s), 7.71 (2H, d, J=8.4 Hz), 7.24 (2H, d, J=8.4 Hz), 4.10 (2H, d, J=8.0 Hz), 3.82 (8H, m), 3.66 (2H, m), 3.46 (2H, m), 3.28 (2H, d, J=8.0 Hz), 2.95 (2H, m), 2.64 (2H, m), 2.40 (6H, m), 1.10 (3H, t, J=7.3 Hz).

ESI (LC-MS positive mode) m/z 544 (M+H)$^+$.

Example 1-D-170

3-{4-[4-(2-Amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-170)

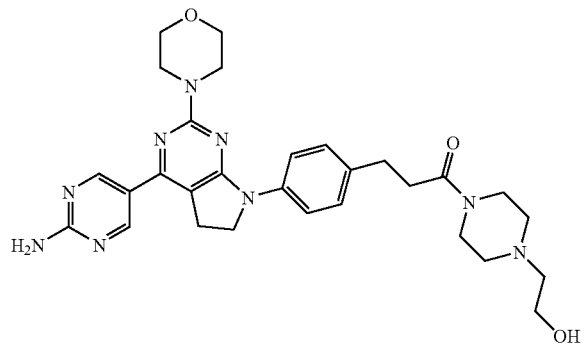

Using 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-propionic acid (100 mg) obtained in Step A in Example 1-D-168 and 2-piperazin-1-yl-ethanol (23 mg) instead of 3-(aminomethyl)pyridine, in the same manner as Step B in Example 1-D-19, 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-[4-(2-hydroxy-ethyl)-piperazin-1-yl]-propan-1-one was obtained, and then the PMB groups were removed according to the above Deprotection method 2, to obtain the desired compound (D-170) as a pale yellow powder (20 mg, 25%).

$^{1}$H-NMR (CDCl$_3$+CD$_3$OD) δ (ppm): 8.86 (2H, s), 7.70 (2H, d, J=8.8 Hz), 7.24 (2H, d, J=8.8 Hz), 4.09 (2H, d, J=8.2 Hz), 3.82 (8H, m), 3.65 (4H, m), 3.44 (2H, m), 3.27 (2H, d, J=8.2 Hz), 2.95 (2H, m), 2.66 (2H, m), 2.49 (6H, m).

ESI (LC-MS positive mode) m/z 560 (M+H)$^+$.

Example 1-D-171

2-{3-[4-(2-Amino-pyrimidin-5-yl)-2-morpholin-4-yl-5,6-dihydro-pyrrolo[2,3-d]pyrimidin-7-yl]-phenyl}-1-piperazin-1-yl-ethanone (D-171)

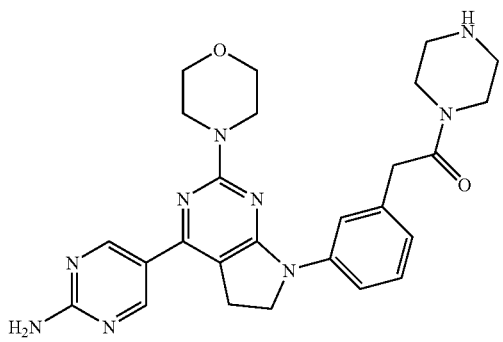

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and 4-[2-(3-bromo-phenyl)-acetyl]-piperazine-1-carboxylic acid tert-butyl ester (128 mg) instead of 4-chloropicolinic acid t-butylamide, in the same manner as Example 1-D-07, a crude product of 4-{2-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-acetyl}-piperazine-1-carboxylic acid tert-butyl ester was obtained, and further PMB group and BOC group were removed according to the above Deprotection method 2, to obtain the desired compound (D-171) as a colorless powder (4 mg, 3%).

$^1$H-NMR (CDCl$_3$+CD$_3$OD) δ (ppm): 8.85 (s, 2H), 7.76 (s, 1H), 7.70 (d, 1H, J=8.7 Hz), 7.34 (t, 1H, J=8.0 Hz), 6.93 (d, 1H, J=7.6 Hz), 4.12 (t, 2H, 8.2 Hz), 3.83-3.52 (m, 12H), 3.45 (t, 2H, J=4.7 Hz), 3.28 (t, 2H, 8.2 Hz), 2.81 (t, 2H, J=4.7 Hz), 2.65 (t, 2H, J=4.7 Hz).

ESI (LC-MS positive mode) m/z 502 (M+H)$^+$.

Example 1-D-172

2-{4-[4-(2-Amino-pyrimidin-5-yl)-2-morpholin-4-yl-5,6-dihydro-pyrrolo[2,3-d]pyrimidin-7-yl]-phenyl}-1-piperazin-1-yl-ethanone D-172)

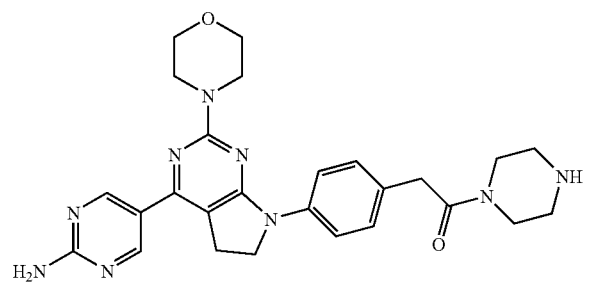

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and 4-[2-(4-bromo-phenyl)-acetyl]-piperazine-1-carboxylic acid tert-butyl ester (132 mg) instead of 4-chloropicolinic acid t-butylamide, in the same manner as Example 1-D-07, a crude product of 4-{2-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-acetyl}-piperazine-1-carboxylic acid tert-butyl ester was obtained, and further PMB group and BOC group were removed according to the above Deprotection method 2, to obtain the desired compound (D-172) as a colorless powder (5 mg, 3%).

$^1$H-NMR (CDCl$_3$+CD$_3$OD) δ (ppm): 8.84 (s, 2H), 7.78 (d, 2H, 8.7 Hz), 7.27 (d, 2H, J=8.3 Hz), 4.11 (t, 2H, J=8.0 Hz), 3.90-3.57 (m, 12H), 3.47 (m, 2H), 3.29 (t, 2H, J=8.0 Hz), 2.82 (t, 2H, J=4.7 Hz), 2.69 (t, 2H, J=4.7 Hz).

ESI (LC-MS positive mode) m/z 502 (M+H)$^+$.

Example 1-D-173

5-[7-(2-Fluoro-5-morpholin-4-ylmethyl-phenyl)-2-morpholin-4-yl-6,7-dihydro-5H-pyrrolo[2,3-d]pyrimidin-4-yl]-pyrimidin-2-ylamine (D-173)

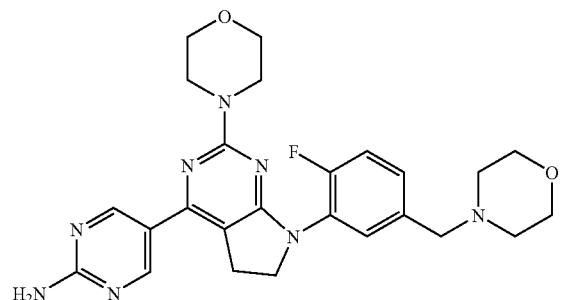

In the same manner as Step B in Example 1-D-26, using 4-fluoro-3-bromo-benzaldehyde (270 mg) and morpholine (0.23 ml), reductive amination was carried out, to obtain a crude product of 2-fluoro-5-morpholin-4-ylmethyl-bromobenzene as a colorless oil (344 mg). In the same manner as Example 1-D-08, bis-(4-methoxy-benzyl)-[5-(2-morpholin-4-yl-6,7-dihydro-5H-pyrrolo[2,3-d]pyrimidin-4-yl)-pyrimidin-2-yl]-amine (92 mg) and using a crude product (66 mg) of 2-fluoro-5-morpholin-4-ylmethyl-bromobenzene obtained in the above step instead of 4-bromobenzoic acid methyl ester, a crude product of 5-[7-(2-fluoro-5-morpholin-4-ylmethyl-phenyl)-2-morpholin-4-yl-6,7-dihydro-5H-pyrrolo[2,3-d]pyrimidin-4-yl]-pyrimidin-2-yl-bis-(4-methoxy-benzyl)-amine was obtained. Using a crude product (90 mg) of 5-[7-(2-fluoro-5-morpholin-4-ylmethyl-phenyl)-2-morpholin-4-yl-6,7-dihydro-5H-pyrrolo[2,3-d]pyrimidin-4-yl]-pyrimidin-2-yl-bis-(4-methoxy-benzyl)-amine, according to the above Deprotection method 2, 5-[7-(2-fluoro-5-morpholin-4-ylmethyl-phenyl)-2-morpholin-4-yl-6,7-dihydro-5H-pyrrolo[2,3-d]pyrimidin-4-yl]-pyrimidin-2-ylamine was obtained as a colorless powder (5.4 mg).

$^1$H-NMR (DMSO-d$_6$) δ (ppm): 8.82 (2H, s), 7.77 (1H, m), 7.50-7.40 (2H, m), 7.15 (2H, s), 4.34 (2H, s), 4.06 (2H, t, J=7.3 Hz), 3.94-3.12 (18H, m).

ESI (LC-MS positive mode) m/z 493 (M+H)$^+$.

Example 1-D-174

5-(2-Morpholin-4-yl-7-o-tolyl-6,7-dihydro-5H-pyrrolo[2,3-d]pyrimidin-4-yl)-pyrimidin-2-ylamine (D-174)

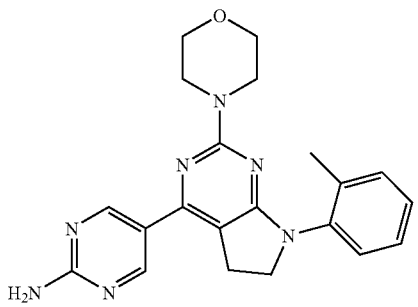

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 1-bromo-2-methyl-benzene (13 µl) instead of 4-chloropicolinic acid t-butylamide, in the same manner as in Example 1-D-07, a crude product of bis-(4-methoxy-benzyl)-[5-(2-morpholin-4-yl-7-o-tolyl-6,7-dihydro-5H-pyrrolo[2,3-d]pyrimidin-4-yl)-pyrimidin-2-yl]-amine was obtained, and then the PMB groups were removed according to the above Deprotection method 3, to obtain the desired compound (D-174) as a pale yellow powder (9 mg, 25%).

$^1$H-NMR (DMSO-$d_6$) δ (ppm): 8.80 (1H, s), 8.74 (1H, s), 7.32-7.17 (2H, m), 7.08-7.02 (1H, m), 6.82 (1H, d, J=8.4 Hz), 3.34 (18H, s), 3.14 (2H, t, J=8.2 Hz), 2.20 (3H, s).

ESI (LC-MS positive mode) m/z 390 (M+H)$^+$.

Example 1-D-175

5-{7-[2-Fluoro-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-175)

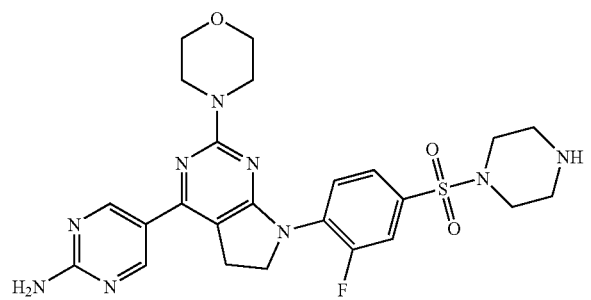

Using 4-(4-bromo-3-fluoro-benzenesulfonyl)-piperazine-1-carboxylic acid tert-butyl ester (prepared from 4-bromo-3-fluoro-benzenesulfonyl chloride and piperazine-1-carboxylic acid tert-butyl ester, 87 mg) instead of 1-(3-bromo-benzenesulfonyl)-4-ethyl-piperazine used in Example 1-D-96, in the same manner as Example 1-D-96, a crude product of 4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzenesulfonyl]-piperazine-1-carboxylic acid tert-butyl ester was obtained, and further PMB group and BOC group were removed according to the above Deprotection method 3, to obtain the desired compound (D-175) as an ivory powder (30 mg, 30%).

$^1$H-NMR (CDCl$_3$) δ (ppm): 8.90 (2H, s), 8.06 (1H, t, J=8.1 Hz), 7.54 (2H, dd, J=10.2, 1.3 Hz), 5.29 (1H, brs), 4.21 (2H, t, J=8.2 Hz), 3.77 (8H, brs), 3.33 (2H, t, J=8.3 Hz), 3.07-3.05 (4H, m), 2.97-2.95 (4H, m).

ESI (LC-MS positive mode) m/z 542 (M+H)$^+$.

Example 1-D-176

5-{7-[2-Methyl-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-176)

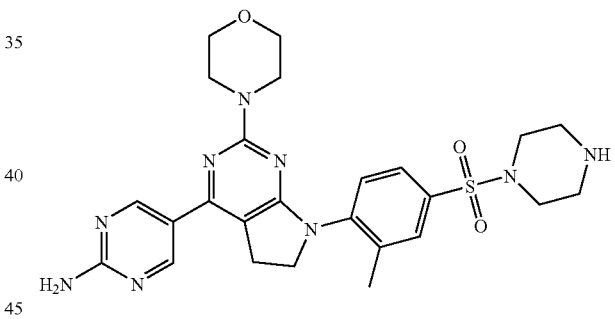

Using 4-(4-bromo-3-methyl-benzenesulfonyl)-piperazine-1-carboxylic acid tert-butyl ester (prepared from 4-bromo-3-methyl-benzenesulfonyl chloride and piperazine-1-carboxylic acid tert-butyl ester, 86 mg) instead of 1-(3-bromo-benzenesulfonyl)-4-ethyl-piperazine used in Example 1-D-96, in the same manner as Example 1-D-96, a crude product of 4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-benzenesulfonyl]-piperazine-1-carboxylic acid tert-butyl ester was obtained, and further PMB group and BOC group were removed according to the above Deprotection method 3, to obtain the desired compound (D-176) as an ivory powder (83 mg, 77%).

$^1$H-NMR (CDCl$_3$) δ (ppm): 8.89 (2H, s), 7.67 (1H, d, J=2.1 Hz), 7.61 (1H, dd, J=8.2, 2.1 Hz), 7.40 (1H, d, J=8.2 Hz), 5.39 (2H, s), 4.02 (2H, t, J=8.1 Hz), 3.71 (8H, s), 3.34 (2H, t, J=8.1 Hz), 3.07-3.05 (4H, m), 2.97-2.95 (4H, m), 2.35 (3H, s).

ESI (LC-MS positive mode) m/z 538 (M+H)$^+$.

Example 1-D-177

4-(2-Amino-pyrimidin-5-yl)-2-morpholin-4-yl-5,6-dihydro-pyrrolo[2,3-d]pyrimidine-7-carboxylic acid methyl-[3-(4-methyl-piperazin-1-yl)-phenyl]-amide (D-177)

Step A

N-methyl-N-[3-(4-methyl-piperazin-1-yl)-phenyl]-acetamide

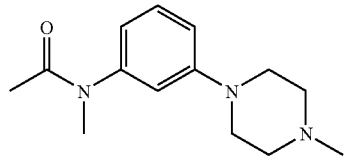

Using 1-methylpiperazine (60 μl) instead of 1-ethylpiperazine, in the same manner as Step C in Example 1-D-135, the desired compound was obtained (35.8 mg, 29%).

Step B

Methyl-[3-(4-methyl-piperazin-1-yl)-phenyl]-amine

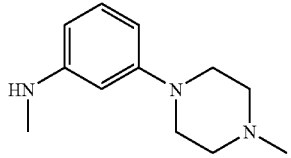

Using N-methyl-N-[3-(4-methyl-piperazin-1-yl)-phenyl]-acetamide (35.8 mg) obtained in Step A instead of N-[3-(4-ethyl-piperazin-1-yl)-phenyl]-N-methyl-acetamide, in the same manner as Step D in Example 1-D-135, the desired compound was obtained (29.2 mg, 98%).

Step C 4-(2-Amino-pyrimidin-5-yl)-2-morpholin-4-yl-5,6-dihydro-pyrrolo[2,3-d]pyrimidine-7-carboxylic acid methyl-[3-(4-methyl-piperazin-1-yl)-phenyl]-amide (D-177)

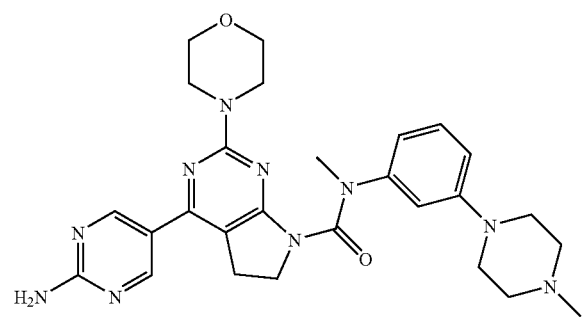

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (72 mg) and methyl-[3-(4-methyl-piperazin-1-yl)-phenyl]-amine (29.2 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-[3-(4-methyl-piperazin-1-yl)-phenyl]-amide was obtained as a crude product. The PMB groups were removed according to Deprotection method 3, to obtain the desired compound (D-177) as a colorless solid (17.2 mg, 23%).

$^1$H-NMR (CDCl$_3$) δ: 8.80 (2H, s), 7.22-7.14 (1H, m), 6.81-6.68 (3H, m), 3.84 (2H, t, J=8.1 Hz), 3.80-3.71 (8H, brm), 3.42 (3H, s), 3.19-3.12 (4H, brm), 3.06 (2H, t, J=8.1 Hz), 2.58-2.50 (4H, brm), 2.34 (3H, s).

ESI (LC-MS positive mode) m/z 531 (M+H)$^+$

Example 1-D-178

5-[7-(3-Methyl-pyridin-2-yl)-2-morpholin-4-yl-6,7-dihydro-5H-pyrrolo[2,3-d]pyrimidin-4-yl]-pyrimidin-2-ylamine (D-178)

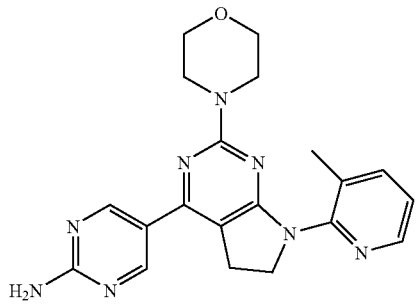

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 2-bromo-3-methylpyridine (35 mg) instead of 4-bromobenzoic acid methyl ester used in Example 1-D-8, in the same manner as Example 1-D-08, a crude product of bis-(4-methoxy-benzyl)-{5-[7-(3-methyl-pyridin-2-yl)-2-morpholin-4-yl-6,7-dihydro-5H-pyrrolo[2,3-d]pyrimidin-4-yl]-pyrimidin-2-yl}-amine was obtained, and then PMB group was removed according to the above Deprotection method 3, to obtain the desired compound (D-178) as a yellow solid (20 mg, 28%).

$^1$H-NMR (CDCl$_3$) δ (ppm): 8.89 (2H, s), 7.67 (1H, d, J=2.1 Hz), 7.61 (1H, dd, J=8.2, 2.1 Hz), 7.40 (1H, d, J=8.2 Hz), 5.39 (2H, s), 4.02 (2H, t, J=8.1 Hz), 3.71 (8H, s), 3.34 (2H, t, J=8.1 Hz), 3.07-3.05 (4H, m), 2.97-2.95 (4H, m), 2.35 (3H, s).

ESI (LC-MS positive mode) m/z 391 (M+H)$^+$.

Example 1-D-179

4-[4-(2-Amino-pyrimidin-5-yl)-2-morpholin-4-yl-5,6-dihydro-pyrrolo[2,3-d]pyrimidin-7-yl]-N-[2-(2-hydroxy-ethoxy)-ethyl]-benzamide (D-179)

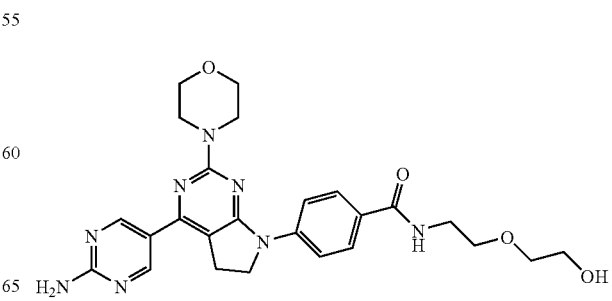

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (38 mg) obtained in Step A in Example 1-D-19 and 2-(2-aminoethoxy)ethanol (6 μl) instead of 3-(aminomethyl)pyridine, in the same manner as Step B in Example 1-D-19, 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-[2-(2-hydroxy-ethoxy)-ethyl]-benzamide was obtained, and further PMB group was removed according to the above Deprotection method 3, to obtain the desired compound (D-179) as a colorless powder (3 mg, 10%).

¹H-NMR (CDCl₃) δ (ppm): 8.89 (2H, s), 7.84 (2H, d, J=6.1 Hz), 7.71 (2H, dd, J=5.9, 3.2 Hz), 7.53 (2H, dd, J=5.5, 3.4 Hz), 6.74 (1H, d, J=8.2 Hz), 6.60 (1H, s), 4.54 (2H, t, J=4.6 Hz), 4.22 (2H, dd, J=5.8, 3.1 Hz), 4.13 (2H, t, J=7.3 Hz), 3.84-3.74 (14H, m).

ESI (LC-MS positive mode) m/z 507 (M+H)⁺.

Example 1-D-180

4-(2-Amino-pyrimidin-5-yl)-2-morpholin-4-yl-5,6-dihydro-pyrrolo[2,3-d]pyrimidine-7-carboxylic acid ortho-tolylamide (D-180)

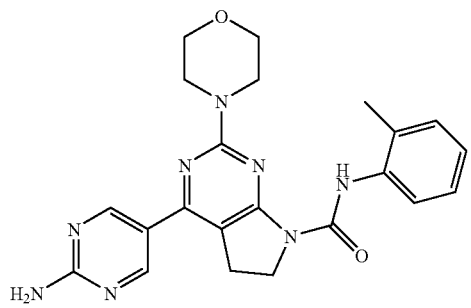

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and o-tolylamine (25.7 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid o-tolylamide was obtained as a crude product. Further PMB group was removed according to Deprotection method 3, to obtain the desired compound (D-180) as a colorless solid (58.6 mg, 68%).

¹H-NMR (CDCl₃) δ: 10.36 (1H, s), 8.91 (2H, s), 7.67-7.62 (1H, m), 7.25-7.20 (2H, m), 7.16-7.08 (1H, m), 4.23 (2H, t, J=8.6 Hz), 3.85-3.75 (8H, brm), 3.24 (2H, t, J=8.6 Hz), 2.33 (3H, s).

ESI (LC-MS positive mode) m/z 433 (M+H)⁺

Example 1-D-181

4-(2-Amino-pyrimidin-5-yl)-2-morpholin-4-yl-5,6-dihydro-pyrrolo[2,3-d]pyrimidine-7-carboxylic acid (2-isopropyl-phenyl)-amide (D-181)

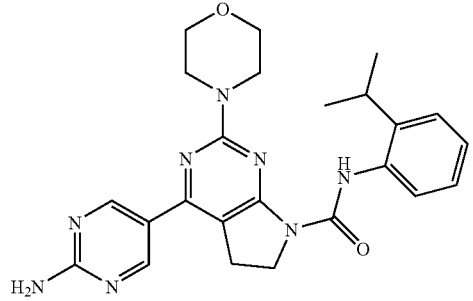

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and 2-isopropyl-phenylamine (32.5 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-isopropyl-phenyl)-amide was obtained as a crude product. Further PMB group was removed according to Deprotection method 3, to obtain the desired compound (D-181) as a colorless solid (52.5 mg, 57%).

¹H-NMR (CDCl₃) δ: 10.37 (1H, s), 8.91 (2H, s), 7.55-7.51 (1H, m), 7.35-7.30 (1H, m), 7.25-7.20 (2H, m), 4.23 (2H, t, J=8.4 Hz), 3.78-3.75 (8H, brm), 3.29-3.19 (3H, m), 1.23 (6H, d, J=6.9 Hz).

ESI (LC-MS positive mode) m/z 461 (M+H)⁺

Example 1-D-182

2-{3-[4-(2-Amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-182)

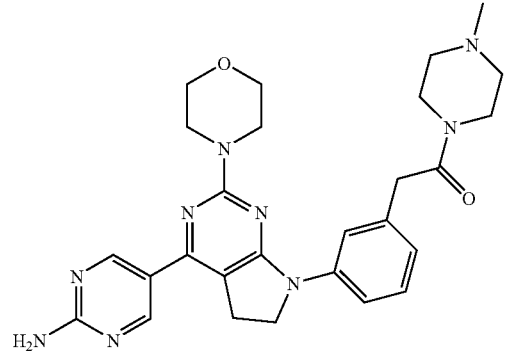

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(3-bromo-phenyl)-1-(4-methyl-piperazin-1-yl)-ethanone (126 mg) instead of 4-chloropicolinic acid t-butylamide, in the same manner as Example 1-D-07, a crude product of 2-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-methyl-piperazin-1-yl)-ethanone was obtained, and further PMB group was removed according to the above Deprotection method 2, to obtain the desired compound (D-182) as a yellow powder (36 mg, 19%).

$^1$H-NMR (CDCl$_3$) δ (ppm): 8.88 (2H, s), 7.77 (1H, s), 7.69 (1H, d, J=8.3 Hz), 7.32 (1H, t, J=8.0 Hz), 6.92 (1H, d, J=7.6 Hz), 5.25 (2H, s), 4.10 (2H, t, J=8.0 Hz), 3.80 (10H, m), 3.65 (2H, t, J=4.9 Hz), 3.47 (2H, m), 3.26 (2H, t, J=8.2 Hz), 2.35 (2H, t, J=4.9 Hz), 2.23 (5H, m).

ESI (LC-MS positive mode) m/z 516 (M+H)$^+$.

Example 1-D-183

2-{4-[4-(2-Amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-183)

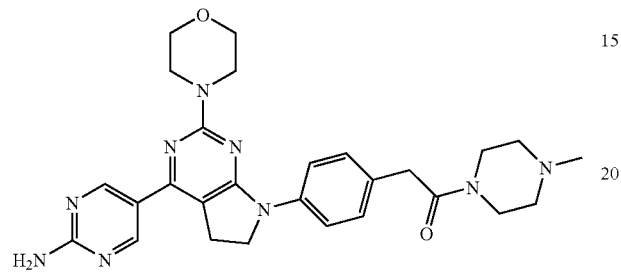

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(4-bromo-phenyl)-1-(4-methyl-piperazin-1-yl)-ethanone (130 mg) instead of 4-chloropicolinic acid t-butylamide, in the same manner as Example 1-D-07, a crude product of 2-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-methyl-piperazin-1-yl)-ethanone was obtained, and further PMB group was removed according to the above Deprotection method 2, to obtain the desired compound (D-183) as a yellow powder (35 mg, 19%).

$^1$H-NMR (CDCl$_3$) δ (ppm): 8.88 (2H, s), 7.76 (2H, d, J=8.7 Hz), 7.27 (2H, d, 8.7 Hz), 5.20 (2H, s), 4.09 (2H, t, J=8.3 Hz), 3.85 (8H, m), 3.71 (2H, s), 3.67 (2H, m), 3.49 (2H, t, J=5.3 Hz), 3.27 (2H, t, J=8.7 Hz), 2.37 (2H, m), 2.26 (5H, m).

ESI (LC-MS positive mode) m/z 516 (M+H)$^+$.

Example 1-D-184

2-{3-[4-(2-Amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-184)

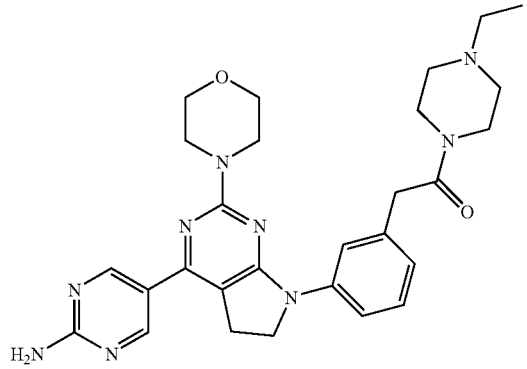

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(3-bromo-phenyl)-1-(4-ethyl-piperazin-1-yl)-ethanone (137 mg) instead of 4-chloropicolinic acid t-butylamide, in the same manner as Example 1-D-07, a crude product of 2-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-ethyl-piperazin-1-yl)-ethanone was obtained, and further PMB group was removed according to the above Deprotection method 2, to obtain the desired compound (D-184) as a pale yellow powder (112 mg, 60%).

$^1$H-NMR (CDCl$_3$) δ (ppm): 8.88 (2H, s), 7.77 (1H, s), 7.69 (1H, d, J=8.0 Hz), 7.32 (1H, t, J=8.0 Hz), 6.92 (1H, d, J=7.9 Hz), 5.26 (2H, s), 4.09 (2H, t, J=8.2 Hz), 3.83 (8H, m), 3.75 (2H, s), 3.66 (2H, t, J=4.9 Hz), 3.47 (2H, t, J=4.9 Hz), 3.26 (2H, t, J=8.2 Hz), 2.39 (4H, m), 2.27 (2H, t, J=4.9 Hz), 1.05 (3H, t, J=7.0 Hz).

ESI (LC-MS positive mode) m/z 530 (M+H)$^+$.

Example 1-D-185

2-{4-[4-(2-Amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-185)

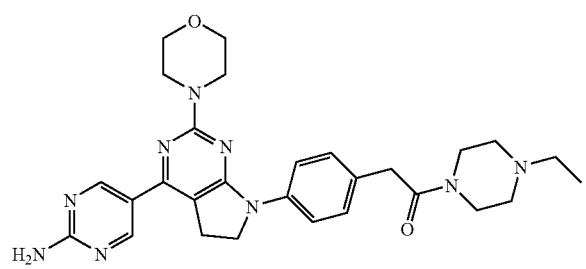

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(4-bromo-phenyl)-1-(4-ethyl-piperazin-1-yl)-ethanone (137 mg) instead of 4-chloropicolinic acid t-butylamide, in the same manner as Example 1-D-07, a crude product of 2-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-ethyl-piperazin-1-yl)-ethanone was obtained, and further PMB group was removed according to the above Deprotection method 2, to obtain the desired compound (D-185) as a yellow powder (92 mg, 47%).

$^1$H-NMR (CDCl$_3$) δ (ppm): 8.88 (2H, s), 7.76 (2H, d, J=8.7 Hz), 7.27 (2H, d, J=8.7 Hz), 5.24 (2H, s), 4.09 (2H, t, J=8.2 Hz), 3.81 (8H, m), 3.71 (2H, s), 3.67 (2H, t, J=4.9 Hz), 3.50 (2H, m), 3.27 (2H, t, J=8.2 Hz), 2.39 (4H, m), 2.29 (2H, t, J=4.9 Hz), 1.06 (3H, t, J=7.2 Hz).

ESI (LC-MS positive mode) m/z 530 (M+H)$^+$.

Example 1-D-186

2-{3-[4-(2-Amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-186)

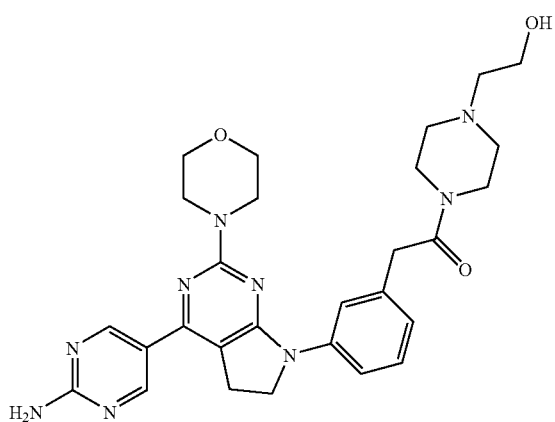

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(3-bromo-phenyl)-1-[4-(2-hydroxy-ethyl)-piperazin-1-yl]-ethanone (143 mg) instead of 4-chloropicolinic acid t-butylamide, in the same manner as Example 1-D-07, a crude product of 2-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-[4-(2-hydroxy-ethyl)-piperazin-1-yl]-ethanone was obtained, and further PMB group was removed according to the above Deprotection method 2, to obtain the desired compound (D-186) as a yellow powder (56 mg, 28%).

$^1$H-NMR (CDCl$_3$) δ (ppm): 8.88 (2H, s), 7.80 (1H, s), 7.68 (1H, d, J=8.0 Hz), 7.32 (1H, t, J=7.8 Hz), 6.92 (1H, d, J=7.2 Hz), 5.24 (2H, s), 4.09 (2H, t, J=8.2 Hz), 3.83 (8H, m), 3.75 (2H, s), 3.66 (2H, t, J=4.9 Hz), 3.60 (2H, t, J=5.1 Hz), 3.46 (2H, t, J=4.7 Hz), 3.27 (2H, t, J=8.2 Hz), 2.49 (4H, m), 2.34 (2H, t, J=4.7 Hz).

ESI (LC-MS positive mode) m/z 546 (M+H)$^+$.

Example 1-D-187

2-{4-[4-(2-Amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-187)

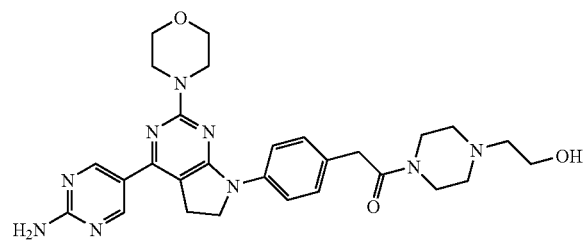

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 2-(4-bromo-phenyl)-1-(4-ethyl-piperazin-1-yl)-ethanone (143 mg) instead of 4-chloropicolinic acid t-butylamide, in the same manner as Example 1-D-07, a crude product of 2-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-[4-(2-hydroxy-ethyl)-piperazin-1-yl]-ethanone was obtained, and further PMB group was removed according to the above Deprotection method 2, to obtain the desired compound (D-187) as a pale brown powder (19 mg, 11%).

$^1$H-NMR (CDCl$_3$) δ (ppm): 8.88 (2H, s), 7.77 (2H, d, J=8.3 Hz), 7.27 (2H, d, J=8.3 Hz), 5.19 (2H, s), 4.09 (2H, t, J=8.2 Hz), 3.82 (8H, m), 3.72 (2H, s), 3.67 (2H, t, J=4.9 Hz), 3.61 (2H, t, J=5.1 Hz), 3.49 (2H, t, J=4.9 Hz), 3.27 (2H, t, J=8.2 Hz), 2.50 (4H, m), 2.37 (2H, t, J=4.7 Hz).

ESI (LC-MS positive mode) m/z 546 (M+H)$^+$.

Example 1-D-188

3-{4-[4-(2-Amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-188)

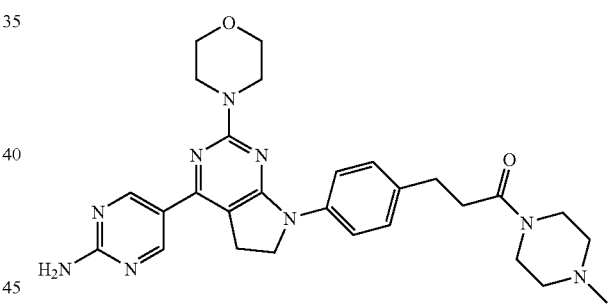

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 3-(4-bromo-phenyl)-1-(4-methyl-piperazin-1-yl)-propan-1-one (174 mg) instead of 4-chloropicolinic acid t-butylamide, in the same manner as Example 1-D-07, a crude product of 3-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-methyl-piperazin-1-yl)-propan-1-one was obtained, and further PMB group was removed according to the above Deprotection method 2, to obtain the desired compound (D-188) as a pale yellow powder (70 mg, 36%).

$^1$H-NMR (CDCl$_3$) δ (ppm): 8.88 (2H, s), 7.70 (2H, d, J=8.8 Hz), 7.24 (2H, d, J=8.8 Hz), 5.22 (2H, s), 4.09 (2H, t, 8.2 Hz), 3.81 (8H, m), 3.68 (2H, m), 3.46 (2H, m), 3.27 (2H, t, J=8.2 Hz), 2.97 (2H, t, J=7.8 Hz), 2.63 (2H, t, J=7.8 Hz), 2.38 (4H, m), 2.31 (3H, s).

ESI (LC-MS positive mode) m/z 530 (M+H)$^+$.

Example 1-D-189

3-{3-[4-(2-Amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-189)

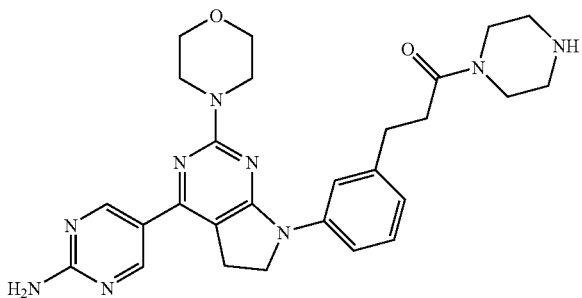

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 4-[3-(3-bromo-phenyl)-propionyl]-piperazine-1-carboxylic acid tert-butyl ester (220 mg) instead of 4-chloropicolinic acid t-butylamide, in the same manner as Example 1-D-07, a crude product of 4-{3-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-propionyl}-piperazine-1-carboxylic acid tert-butyl ester was obtained, and further PMB group and BOC group were removed according to the above Deprotection method 2, to obtain the desired compound (D-189) as a pale yellow powder (50 mg, 8%).

$^1$H-NMR (CDCl$_3$) δ (ppm): 8.89 (2H, s), 7.66 (2H, m), 7.31 (1H, m), 6.93 (1H, d, J=7.6 Hz), 5.23 (2H, s), 4.10 (2H, t, J=8.2 Hz), 3.82 (8H, m), 3.61 (2H, m), 3.37 (2H, m), 3.28 (2H, t, J=8.3 Hz), 3.00 (2H, t, J=8.0 Hz), 2.82 (2H, m), 2.75 (2H, m), 2.64 (2H, t, J=8.0 Hz).

ESI (LC-MS positive mode) m/z 516 (M+H)$^+$.

Example 1-D-190

3-{3-[4-(2-Amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-190)

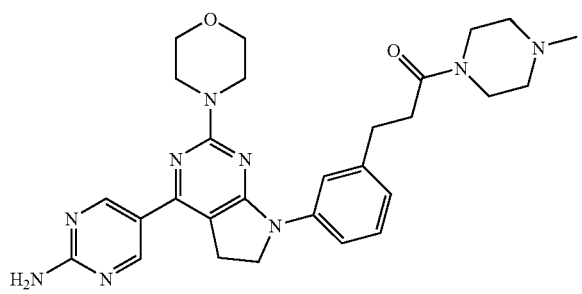

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 3-(3-bromo-phenyl)-1-(4-methyl-piperazin-1-yl)-propan-1-one (173 mg) instead of 4-chloropicolinic acid t-butylamide, in the same manner as Example 1-D-07, a crude product of 3-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-methyl-piperazin-1-yl)-propan-1-one was obtained, and further PMB group was removed according to the above Deprotection method 2, to obtain the desired compound (D-190) as a pale brown powder (110 mg, 58%).

$^1$H-NMR (CDCl$_3$) δ (ppm): 8.89 (2H, s), 7.65 (2H, m), 7.31 (1H, m), 6.93 (1H, d, J=7.6 Hz), 5.24 (2H, s), 4.10 (2H, t, J=8.2 Hz), 3.82 (8H, m), 3.66 (2H, m), 3.42 (2H, m), 3.27 (2H, t, J=8.2 Hz), 3.00 (2H, t, J=7.8 Hz), 2.64 (2H, t, J=7.8 Hz), 2.38 (2H, m), 2.29 (5H, m).

ESI (LC-MS positive mode) m/z 530 (M+H)$^+$.

Example 1-D-191

3-{3-[4-(2-Amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-191)

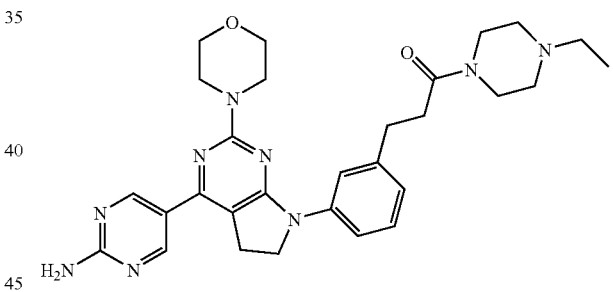

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 3-(3-bromo-phenyl)-1-(4-ethyl-piperazin-1-yl)-propan-1-one (181 mg) instead of 4-chloropicolinic acid t-butylamide, in the same manner as Example 1-D-07, a crude product of 3-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-(4-ethyl-piperazin-1-yl)-propan-1-one was obtained, and further PMB group was removed according to the above Deprotection method 2, to obtain the desired compound (D-191) as a pale brown powder (115 mg, 60%).

$^1$H-NMR (CDCl$_3$) δ (ppm): 8.89 (2H, s), 7.65 (2H, m), 7.31 (1H, m), 6.93 (1H, d, J=7.6 Hz), 5.23 (2H, s), 4.10 (2H, t, J=8.2 Hz), 3.82 (8H, m), 3.68 (2H, m), 3.44 (2H, m), 3.27 (2H, t, J=8.2 Hz), 3.00 (2H, t, J=7.8 Hz), 2.65 (2H, t, J=7.8 Hz), 2.39 (6H, m), 1.09 (3H, t, J=7.0 Hz).

ESI (LC-MS positive mode) m/z 544 (M+H)$^+$.

Example 1-D-192

3-{3-[4-(2-Amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-192)

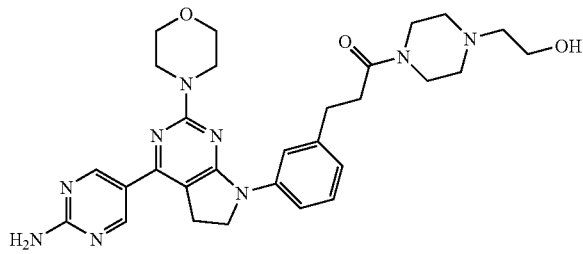

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg) and 3-(3-bromo-phenyl)-1-[4-(2-hydroxy-ethyl)-piperazin-1-yl]-propan-1-one (180 mg) instead of 4-chloropicolinic acid t-butylamide, in the same manner as Example 1-D-07, a crude product of 3-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-1-[4-(2-hydroxy-ethyl)-piperazin-1-yl]-propan-1-one was obtained, and further PMB group was removed according to the above Deprotection method 2, to obtain the desired compound (D-192) as a pale yellow powder (95 mg, 48%).

¹H-NMR (CDCl₃) δ (ppm): 8.89 (2H, s), 7.66 (2H, m), 7.31 (1H, m), 6.93 (1H, d, J=8.0 Hz), 5.23 (2H, s), 4.10 (2H, t, J=8.2 Hz), 3.82 (8H, m), 3.66 (4H, m), 3.43 (2H, m), 3.28 (2H, t, J=8.2 Hz), 3.00 (2H, t, J=7.6 Hz), 2.65 (2H, t, J=7.8 Hz), 2.55 (2H, t, J=5.3 Hz), 2.49 (2H, m), 2.41 (2H, m).

ESI (LC-MS positive mode) m/z 560 (M+H)⁺.

Example 1-D-193

5-[7-(4-methyl-pyridin-3-yl)-2-morpholin-4-yl-6,7-dihydro-5H-pyrrolo[2,3-d]pyrimidin-4-yl]-pyrimidin-2-ylamine (D-193)

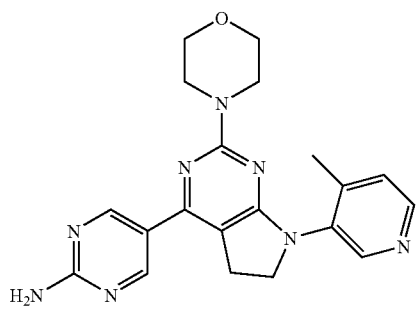

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 3-bromo-4-methylpyridine (35 mg) instead of 4-bromobenzoic acid methyl ester used in Example 1-D-8, in the same manner as Example 1-D-08, a crude product of bis-(4-methoxy-benzyl)-{5-[7-(3-methyl-pyridin-2-yl)-2-morpholin-4-yl-6,7-dihydro-5H-pyrrolo[2,3-d]pyrimi-din-4-yl]-pyrimidin-2-yl}-amine was obtained, and then PMB group was removed according to the above Deprotection method 3, to obtain the desired compound (D-193) as a yellow solid (25 mg, 22%).

¹H-NMR (CDCl₃) δ (ppm): 8.90 (2H, s), 8.51 (1H, s), 8.39 (1H, d, J=4.9 Hz), 7.23 (1H, d, J=4.9 Hz), 5.35 (2H, s), 4.03 (2H, t, J=8.2 Hz), 3.68 (8H, s), 3.35 (2H, t, J=8.2 Hz), 2.29 (3H, s).

ESI (LC-MS positive mode) m/z 391 (M+H)⁺.

Example 1-D-194

4-(2-Amino-pyrimidin-5-yl)-2-morpholin-4-yl-5,6-dihydro-pyrrolo[2,3-d]pyrimidine-7-carboxylic acid (4-{methyl-[3-(4-methyl-piperazin-1-yl)-propyl]-amino}-phenyl)-amide (D-194)

Step A

[3-(4-Methyl-piperazin-1-yl)-propyl]-(4-nitro-phenyl)-amine

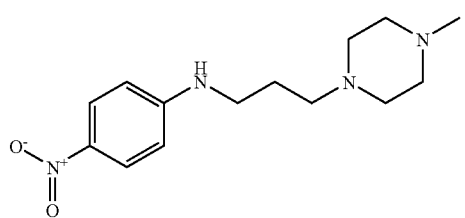

Using 1-iodo-4-nitro-benzene (500 mg) instead of 1-bromo-3-nitro-benzene, and 3-(4-methyl-piperazin-1-yl)-propylamine (379 mg) instead of morpholine, in the same manner as Step A in Example 1-D-105, the desired compound was obtained (432 mg, 77%).

Step B

Methyl-[3-(4-methyl-piperazin-1-yl)-propyl]-(4-nitro-phenyl)-amine

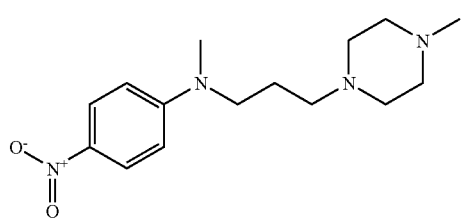

Using [3-(4-methyl-piperazin-1-yl)-propyl]-(4-nitro-phenyl)-amine (111 mg) obtained in Step A instead of N-(3-bromo-phenyl)-N-methyl-acetamide, in the same manner as Step B in Example 1-D-135, the desired compound was obtained (78.7 mg, 67%).

Step C

N-methyl-N-[3-(4-methyl-piperazin-1-yl)-propyl]-benzene-1,4-diamine

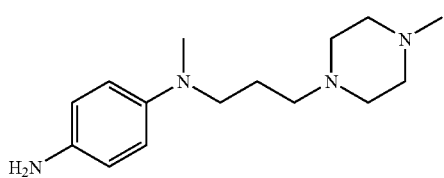

Using methyl-[3-(4-methyl-piperazin-1-yl)-propyl]-(4-nitro-phenyl)-amine (78.7 mg) obtained in Step B instead of (4-ethyl-piperazin-1-yl)-(3-nitro-phenyl)-methanone, in the same manner as Step B in Example 1-D-101, the desired compound was obtained (53.5 mg, 76%).

Step D

4-(2-Amino-pyrimidin-5-yl)-2-morpholin-4-yl-5,6-dihydro-pyrrolo[2,3-d]pyrimidine-7-carboxylic acid (4-{methyl-[3-(4-methyl-piperazin-1-yl)-propyl]-amino}-phenyl)-amide (D-194)

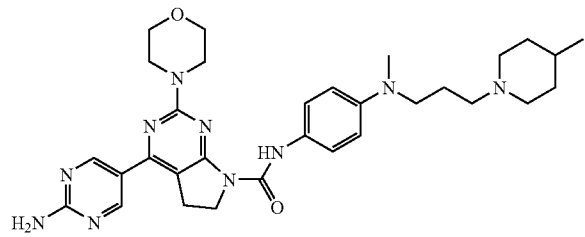

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and N-methyl-N-[3-(4-methyl-piperazin-1-yl)-propyl]-benzene-1,4-diamine (53.5 mg) obtained in Step C instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-{methyl-[3-(4-methyl-piperazin-1-yl)-propyl]-amino}-phenyl)-amide was obtained as a crude product. The PMB groups were removed according to Deprotection method 3, to obtain the desired compound (D-194) as a yellow solid (21.8 mg, 19%).

$^1$H-NMR (CD$_3$OD) δ: 10.70 (1H, s), 8.84 (2H, s), 7.31 (2H, d, J=9.1 Hz), 7.21 (2H, s), 6.71 (2H, d, J=9.1 Hz), 4.02 (2H, t, J=8.3 Hz), 3.77-3.70 (8H, brm), 3.30 (2H, t, J=7.4 Hz), 3.22 (2H, t, J=8.3 Hz), 2.83 (3H, s), 2.44-2.17 (8H, brm), 2.28 (2H, t, J=7.0 Hz), 2.19 (3H, s), 1.68-1.55 (2H, m).

ESI (LC-MS positive mode) m/z 588 (M+H)$^+$

Example 1-D-195

{3-[4-(2-Amino-pyrimidin-5-yl)-2-morpholin-4-yl-5,6-dihydro-pyrrolo[2,3-d]pyrimidin-7-yl]-2-fluoro-phenyl}-morpholin-4-yl-methanone (D-195)

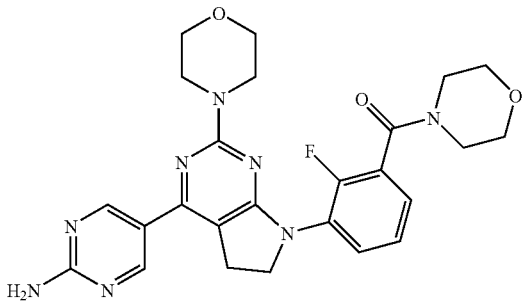

Using 3-bromo-2-fluorobenzoic acid (200 mg, 0.913 mmol) instead of 3-bromo-4-fluorobenzoic acid, and morpholine (95.5 μl, 1.10 mmol), amidation was carried out in the same manner as Example 1-D-16, to obtain a crude product (265 mg) of (3-bromo-2-fluoro-phenyl)-morpholin-4-yl-methanone. Using the obtained crude product (56.1 mg) of (3-bromo-2-fluoro-phenyl)-morpholin-4-yl-methanone instead of (3-bromo-4-fluoro-phenyl)-morpholin-4-yl-methanone, and bis-(4-methoxy-benzyl)-[5-(2-morpholin-4-yl-6,7-dihydro-5H-pyrrolo[2,3-d]pyrimidin-4-yl)-pyrimidin-2-yl]-amine (70.0 mg, 0.130 mmol), amination was carried out in the same manner as Example 1-D-16, to obtain a crude product of {3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-2-fluoro-phenyl}-morpholin-4-yl-methanone as a yellow solid (110 mg), and then the PMB groups were removed according to the above Deprotection method 3, to obtain the desired compound (D-195) as a yellow powder (15.0 mg, 23%).

$^1$H-NMR (CDCl$_3$) δ (ppm): 8.89 (2H, s), 7.76 (1H, dt, J=3.0, 7.7 Hz), 7.31-7.19 (2H, m), 5.23 (2H, s), 4.28-3.96 (4H, m), 3.87-3.37 (14H, m), 3.32 (2H, t, J=8.6 Hz).

ESI (LC-MS positive mode) m/z 507 (M+H)$^+$.

Example 1-D-196

5-{7-[2-methyl-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-196)

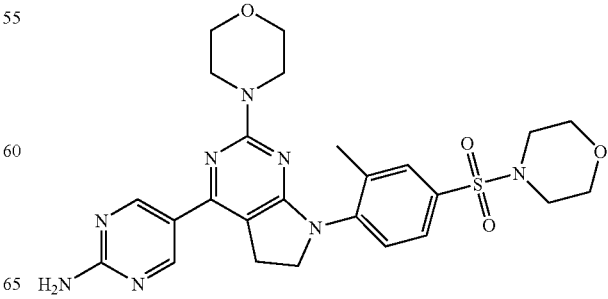

647

Using 4-(4-bromo-3-methyl-benzenesulfonyl)-morpholine (prepared from 4-bromo-3-methyl-benzenesulfonyl chloride and morpholine, 66 mg) instead of 4-bromo-N-Boc-N-(3-hydroxy-propyl)-benzenesulfonamide in Example 1-D-98, an operation was carried out in the same manner as Example 1-D-98, to obtain a crude product of bis-(4-methoxy-benzyl)-(5-{7-[2-methyl-4-(morpholine-4-sulfonyl)-phenyl]-2-morpholin-4-yl-6,7-dihydro-5H-pyrrolo[2,3-d]pyrimidin-4-yl}-pyrimidin-2-yl)-amine, and then the PMB groups were removed according to the above Deprotection method 3, to obtain the desired compound (D-196) as a pale yellow powder (81 mg, 80%).

$^1$H-NMR (CDCl$_3$) δ (ppm): 8.90 (2H, s), 7.68 (1H, d, J=2.1 Hz), 7.62 (1H, dd, J=8.4, 2.1 Hz), 7.43 (1H, d, J=8.4 Hz), 5.66 (2H, s), 4.04 (2H, t, J=8.1 Hz), 3.78 (4H, t, J=4.5 Hz), 3.70 (8H, s), 3.35 (2H, t, J=8.1 Hz), 3.07 (4H, t, J=4.5 Hz), 2.36 (3H, s).

ESI (LC-MS positive mode) m/z 539 (M+H)$^+$.

Example 1-D-197

4-[4-(2-Amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzamide (D-197)

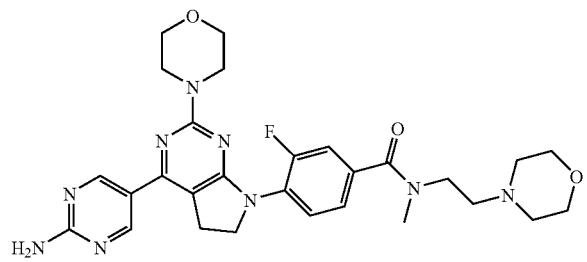

Using methyl-(2-morpholin-4-yl-ethyl)-amine (98.8 mg, 0.685 mmol) obtained in Step A in Example 1-D-139 instead of morpholine, and 4-bromo-3-fluorobenzoic acid (100 mg, 0.457 mmol) instead of 3-bromo-4-fluorobenzoic acid, in the same manner as Example 1-D-16, amidation was carried out, to obtain a crude product (153 mg) of 4-bromo-3-fluoro-N-methyl-N-(2-morpholin-4-yl-ethyl)-benzamide.

Using the obtained crude product (68 mg) of 4-bromo-3-fluoro-N-methyl-N-(2-morpholin-4-yl-ethyl)-benzamide instead of (3-bromo-4-fluoro-phenyl)-morpholin-4-yl-methanone, and bis-(4-methoxy-benzyl)-[5-(2-morpholin-4-yl-6,7-dihydro-5H-pyrrolo[2,3-d]pyrimidin-4-yl)-pyrimidin-2-yl]-amine (70.0 mg, 0.130 mmol), amination was carried out in the same manner as Example 1-D-16, to obtain a crude product of {4-(4-[2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-N-methyl-N-(2-morpholin-4-yl-ethyl)-benzamide as a yellow solid (161 mg), and then the PMB groups were removed according to the above Deprotection method 3, to obtain the desired compound (D-197) as a yellow powder (35.5 mg, 49%).

$^1$H-NMR (CDCl$_3$) δ (ppm): 8.91 (2H, s), 7.81 (1H, dd, J=8.6, 7.6 Hz), 7.36 (1H, dd, J=6.4, 1.8 Hz), 7.32 (1H, dd, J=8.6, 1.8 Hz), 6.25 (2H, s), 4.17 (2H, t, J=8.1 Hz), 4.06-4.02 (6H, m), 3.80-3.70 (8H, m), 3.41-3.33 (2H, m), 3.31 (2H, t, J=8.1 Hz), 3.07 (3H, s), 2.72-2.68 (4H, m).

ESI (LC-MS positive mode) m/z 564 (M+H)$^+$.

Example 1-D-198

5-{7-[2-Fluoro-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-198)

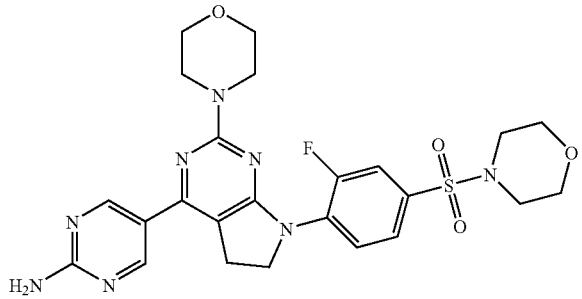

Using 4-(4-bromo-3-fluoro-benzenesulfonyl)-morpholine (prepared from 4-bromo-3-fluoro-benzenesulfonyl chloride and morpholine, 66 mg) instead of 1-(3-bromo-benzenesulfonyl)-4-ethyl-piperazine used in Example 1-D-96, in the same manner as Example 1-D-96, a crude product of (5-{7-[2-fluoro-4-(morpholine-4-sulfonyl)-phenyl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to the above Deprotection method 3, to obtain the desired compound (D-198) as a pale yellow powder (48 mg, 53%).

$^1$H-NMR (CDCl$_3$) δ (ppm): 8.90 (2H, s), 8.11 (1H, t, J=7.9 Hz), 7.56 (1H, s), 7.53 (1H, s), 5.41 (2H, s), 4.23 (2H, t, J=7.2 Hz), 3.80 (4H, brs), 3.77 (8H, brs), 3.33 (2H, t, J=8.2 Hz), 3.08-3.06 (4H, m).

ESI (LC-MS positive mode) m/z 543 (M+H)$^+$.

Example 1-D-199

{4-[4-(2-Amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-199)

Step A 4-(4-Chloro-pyridine-2-carbonyl)-piperazine-1-carboxylic acid tert-butyl ester

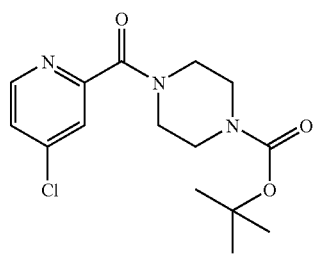

To a dichloromethane solution (4 ml) of 4-chloropicolinic acid chloride (175 mg, 0.994 mmol), N-ethyldiisopropylamine (346 µl, 1.99 mol) and N-Boc-piperazine (278 mg, 1.49 mmol) were added, followed by stirring at room temperature for 12 hours. The reaction mixture was concentrated under reduced pressure, and the residue was purified by silica gel column chromatography (dichloromethane/methanol=60/1), to obtain 4-(4-chloro-pyridine-2-carbonyl)-piperazine-1-carboxylic acid tert-butyl ester (166 mg, 51%).

¹H-NMR (CDCl₃) δ (ppm): 8.48 (d, 1H, J=5.4 Hz), 7.67 (d, 1H, J=2.1 Hz), 7.37 (dd, 1H, J=2.1 Hz, J=5.3 Hz), 3.77 (t, 2H, J=4.6 Hz), 3.51 (m, 6H), 1.48 (s, 9H).

ESI (LC-MS positive mode) m/z 326 (M+H)⁺.

Step B

{4-[4-(2-Amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-199)

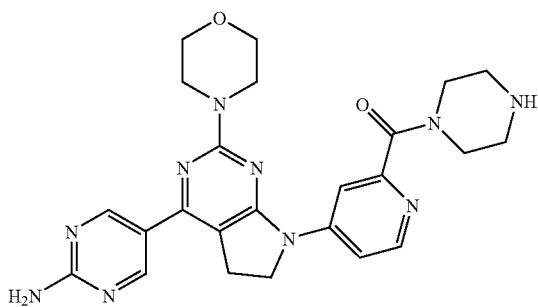

Using 4-(4-chloro-pyridine-2-carbonyl)-piperazine-1-carboxylic acid tert-butyl ester (163 mg, 0.500 mmol) obtained in Step A instead of 4-chloropicolinic acid t-butylamide, and bis-(4-methoxy-benzyl)-[5-(2-morpholin-4-yl-6,7-dihydro-5H-pyrrolo[2,3-d]pyrimidin-4-yl)-pyrimidin-2-yl]-amine (245 mg, 445 mmol), in the same manner as Example 1-D-07, amination was carried out, to obtain a crude product of 4-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridine-2-carbonyl]-piperazine-1-carboxylic acid tert-butyl ester as a yellow solid (239 mg), and further PMB group and BOC group were removed according to the above Deprotection method 2, to obtain the desired compound (D-199) as a yellow powder (67 mg, 49%).

¹H-NMR (CDCl₃+MeOH-d₄) δ (ppm): 8.87 (2H, s), 8.45 (1H, d, J=5.8 Hz), 8.11 (1H, dd, J=2.1, 5.8 Hz), 7.79 (1H, d, J=2.1 Hz), 4.14 (2H, t, J=8.2 Hz), 3.85 (10H, m), 3.61 (2H, t, J=4.6 Hz), 3.35 (2H, t, J=8.2 Hz), 3.03 (2H, t, J=4.6 Hz), 2.92 (2H, t, J=4.6 Hz).

ESI (LC-MS positive mode) m/z 489 (M+H)⁺.

Example 1-D-200

{4-[4-(2-Amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-200)

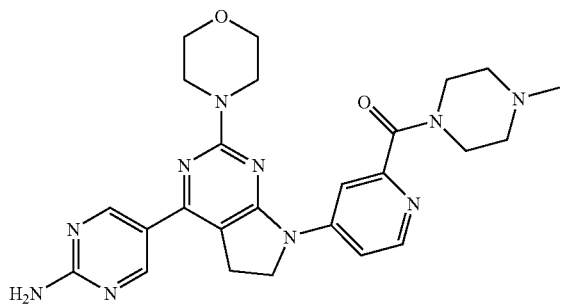

Using 4-chloropicolinic acid chloride and N-methylpiperazine instead of N-Boc-piperazine, amidation was carried out in the same manner as Step A in Example 1-D-199, to obtain (4-chloro-pyridin-2-yl)-(4-methyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (215 mg, 0.398 mmol), and the obtained (4-chloro-pyridin-2-yl)-(4-methyl-piperazin-1-yl)-methanone (105 mg, 0.438 mmol) instead of 4-chloropicolinic acid t-butylamide, amination was carried out in the same manner as Example 1-D-07, to obtain a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(4-methyl-piperazin-1-yl)-methanone as a yellow solid (285 mg), and then the PMB groups were removed according to the above Deprotection method 2, to obtain the desired compound (D-200) as a yellow powder (69 mg, 38%).

¹H-NMR (CDCl₃) δ (ppm): 8.89 (2H, s), 8.47 (1H, d, J=6.0 Hz), 8.09 (1H, dd, J=2.1, 6.0 Hz), 7.79 (1H, d, J=2.1 Hz), 5.28 (2H, s), 4.12 (2H, t, J=8.8 Hz), 3.85 (10H, m), 3.69 (2H, m), 3.33 (2H, t, J=8.8 Hz), 2.57 (2H, m), 2.47 (2H, m), 2.36 (3H, s).

ESI (LC-MS positive mode) m/z 503 (M+H)⁺.

Example 1-D-201

{4-[4-(2-Amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-201)

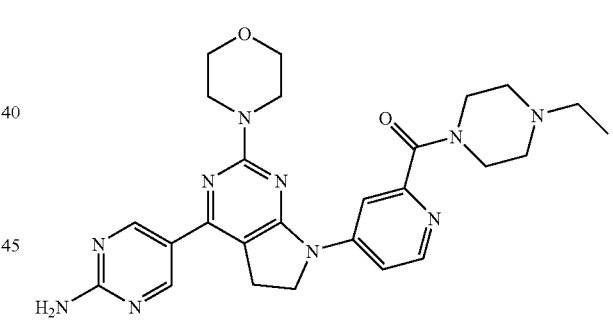

Using 4-chloropicolinic acid chloride and N-ethylpiperazine instead of N-Boc-piperazine, amidation was carried out in the same manner as Step A in Example 1-D-199, to obtain (4-chloro-pyridin-2-yl)-(4-ethyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (232 mg, 0.430 mmol), and the obtained (4-chloro-pyridin-2-yl)-(4-ethyl-piperazin-1-yl)-methanone (120 mg, 0.473 mmol) instead of 4-chloropicolinic acid t-butylamide, amination was carried out in the same manner as Example 1-D-07, to obtain a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-(4-ethyl-piperazin-1-yl)-methanone as a yellow solid (225 mg), and then the PMB groups were removed according to the above Deprotection method 2, to obtain the desired compound (D-201) as a yellow powder (85 mg, 57%).

$^1$H-NMR (CDCl$_3$) δ (ppm): 8.90 (2H, s), 8.47 (1H, d, J=6.0 Hz), 8.09 (1H, dd, J=2.1, 6.0 Hz), 7.79 (1H, d, J=2.1 Hz), 5.27 (2H, s), 4.12 (2H, t, J=8.2 Hz), 3.84 (10H, m), 3.72 (2H, m), 3.34 (2H, t, J=8.2 Hz), 2.55 (6H, m), 1.15 (3H, t, J=6.3 Hz).

ESI (LC-MS positive mode) m/z 517 (M+H)$^+$.

Example 1-D-202

{4-[4-(2-Amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-202)

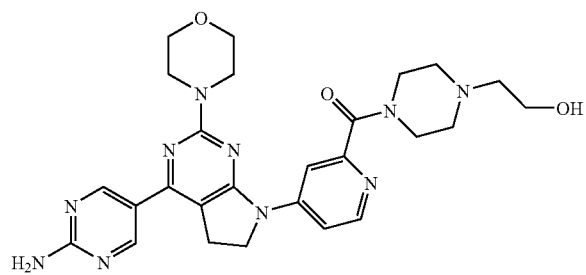

Using 4-chloropicolinic acid chloride and 4-(2-hydroxyethyl)piperazine instead of N-Boc-piperazine, amidation was carried out in the same manner as Step A in Example 1-D-199, to obtain (4-chloro-pyridin-2-yl)-[4-(2-hydroxy-ethyl)-piperazin-1-yl]-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (282 mg, 0.52 mmol), and (4-chloro-pyridin-2-yl)-[4-(2-hydroxy-ethyl)-piperazin-1-yl]-methanone (175 mg, 0.65 mmol) instead of 4-chloropicolinic acid t-butylamide, amination was carried out in the same manner as Example 1-D-07, to obtain a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-2-yl]-[4-(2-hydroxy-ethyl)-piperazin-1-yl]-methanone as a colorless solid (210 mg), and then the PMB groups were removed according to the above Deprotection method 2, to obtain the desired compound (D-202) as a colorless powder (114 mg, 80%).

$^1$H-NMR (CDCl$_3$) δ (ppm): 8.89 (2H, s), 8.48 (1H, d, J=5.7 Hz), 8.10 (1H, dd, J=2.2, 6.1 Hz), 7.78 (1H, d, J=2.2 Hz), 5.29 (2H, s), 4.11 (2H, t, J=8.2 Hz), 3.85 (10H, m), 3.66 (4H, m), 3.33 (2H, t, J=8.2 Hz), 2.59 (7H, m).

ESI (LC-MS positive mode) m/z 533 (M+H)$^+$.

Example 1-D-203

{3-[4-(2-Amino-pyrimidin-5-yl)-2-morpholin-4-yl-5,6-dihydro-pyrrolo[2,3-d]pyrimidin-7-yl]-4-fluoro-phenyl}-(4-ethyl-piperazin-1-yl)-methanone (D-203)

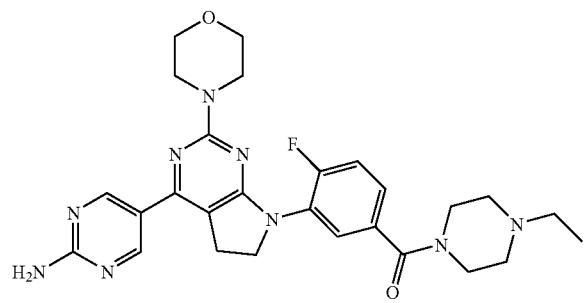

Using 3-bromo-4-fluorobenzoic acid (200 mg, 0.913 mmol) and N-ethylpiperazine (232 μl, 1.10 mmol) instead of morpholine, amidation was carried out in the same manner as Example 1-D-16, to obtain a crude product (292 mg) of (3-bromo-4-fluoro-phenyl)-(4-ethyl-piperazin-1-yl)-methanone. Using a crude product (81.8 mg) of the obtained (3-bromo-4-fluoro-phenyl)-(4-ethyl-piperazin-1-yl)-methanone instead of (3-bromo-4-fluoro-phenyl)-morpholin-4-yl-methanone, and bis-(4-methoxy-benzyl)-[5-(2-morpholin-4-yl-6,7-dihydro-5H-pyrrolo[2,3-d]pyrimidin-4-yl)-pyrimidin-2-yl]-amine (70.0 mg, 0.130 mmol), amination was carried out in the same manner as Example 1-D-16, to obtain a crude product of {3-[4-{2-[bis-(4-methoxy-benzyl)-amino]-pyrimidin-5-yl}-2-morpholin-4-yl-5,6-dihydro-pyrrolo[2,3-d]pyrimidin-7-yl]-4-fluoro-phenyl}-(4-ethyl-piperazin-1-yl)-methanone as a yellow solid (152 mg), and then the PMB groups were removed according to the above Deprotection method 3, to obtain the desired compound (D-203) as a yellow powder (48.5 mg, 70%).

$^1$H-NMR (CDCl$_3$) δ (ppm): 8.91 (2H, s), 7.80 (1H, d, J=7.3 Hz), 7.28-7.19 (2H, m), 6.22 (2H, s), 4.13 (2H, t, J=7.4 Hz), 3.78-3.69 (8H, m), 3.51-3.47 (4H, m), 3.32 (2H, t, J=7.4 Hz), 3.09 (2H, q, J=7.6 Hz), 2.74-2.66 (4H, m), 1.38 (3H, t, J=7.6 Hz).

ESI (LC-MS positive mode) m/z 534 (M+H)$^+$.

Example 1-D-204

5-[7-(1-Methyl-1H-imidazol-2-yl)-2-morpholin-4-yl-6,7-dihydro-5H-pyrrolo[2,3-d]pyrimidin-4-yl]-pyrimidin-2-ylamine (D-204)

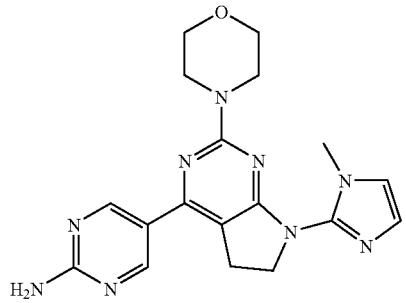

A solution of bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg, 0.185 mmol), 2-bromo-1-methyl-1H-imidazole (36 μl, 0.370 mmol), copper iodide (7 mg, 0.037 mmol), N,N'-dimethyl ethylenediamine (36 μl, 0.370 mmol) and potassium carbonate (51 mg, 0.370 mmol) in dioxane (3 ml) was deaerated under irradiation of ultrasonic wave, followed by stirring at 100° C. for 18 hours. After the reaction mixture was cooled to room temperature, saturated aqueous ammonium chloride solution was added, followed by extraction twice with ethyl acetate (50 ml). The organic layer was washed with saturated aqueous sodium chloride solution (50 ml), and dried over sodium sulfate. After the sodium sulfate was filtered off, the filtrate was concentrated under reduced pressure, and the resulting residue was purified by silica gel column chromatography (dichloromethane/methanol=50/1), whereby a crude product of bis-(4-methoxy-benzyl)-{5-[7-(3-methyl-3H-imidazol-4-yl)-2-morpholin-4-yl-6,7-dihydro-5H-pyrrolo[2,3-d]pyrimidin-4-yl]-pyrimidin-2-yl}-amine was obtained as a brown oil (142 mg).

This was dissolved in TFA (2 ml), followed by refluxing for 4 hours in the presence of N-acetylcysteine (60 mg, 0.370 mmol). The reaction mixture was concentrated under reduced pressure, and the resulting residue was purified by silica gel column chromatography (dichloromethane/0.8N-ammonia methanol=100/1 to 10/1), whereby the desired compound (D-204) was obtained as a pale yellow powder (86 mg, yield 70%).

$^1$H-NMR (DMSO-d$_6$) δ (ppm): 8.84 (1H, d, J=1.5 Hz), 7.47 (1H, s), 7.38 (1H, s), 7.21 (1H, s), 5.76 (2H, d, J=1.6 Hz), 4.16 (2H, t, J=7.9 Hz), 3.69 (3H, s), 3.63 (8H, s), 3.39 (2, t, J=7.7 Hz).

ESI (LC-MS positive mode) m/z 380 (M+H)$^+$.

Example 1-D-205

4-[4-(2-Amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzamide (D-205)

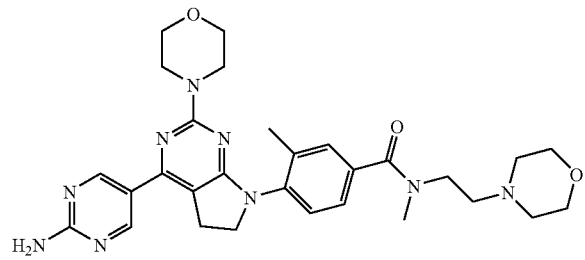

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 4-bromo-3,N-dimethyl-N-(2-morpholin-4-yl-ethyl)-benzamide (114 mg) instead of 4-chloropicolinic acid t-butylamide, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3,N-dimethyl-N-(2-morpholin-4-yl-ethyl)-benzamide was obtained, and further PMB group was removed according to the above Deprotection method 3, to obtain the desired compound (D-205) as a brown oil (68 mg, 66%).

$^1$H-NMR (CD$_3$OD) δ (ppm): 8.83 (2H, s), 7.40-7.29 (3H, m), 4.00 (2H, t, J=8.0 Hz), 3.80 (4H, s), 3.62 (14H, brs), 3.35 (3H, s), 3.07 (2H, s), 2.93 (2H, s), 2.28 (3H, s).

ESI (LC-MS positive mode) m/z 560 (M+H)$^+$.

Example 1-D-206

4-(2-Amino-pyrimidin-5-yl)-2-morpholin-4-yl-5,6-dihydro-pyrrolo[2,3-d]pyrimidine-7-carboxylic acid {4-[methyl-(2-morpholin-4-yl-ethyl)-amino]-phenyl}-amide (D-206)

Step A (2-Morpholin-4-yl-ethyl)-(4-nitro-phenyl)-amine

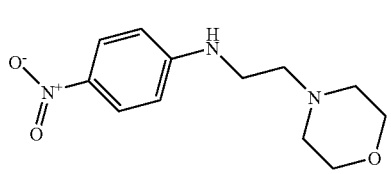

Using 1-iodo-4-nitro-benzene (500 mg) instead of 1-bromo-3-nitro-benzene, and 2-morpholin-4-yl-ethylamine (316 mg) instead of morpholine, in the same manner as Step A in Example 1-D-105, the desired compound was obtained (315 mg, 62%).

Step B

Methyl-(2-morpholin-4-yl-ethyl)-(4-nitro-phenyl)-amine

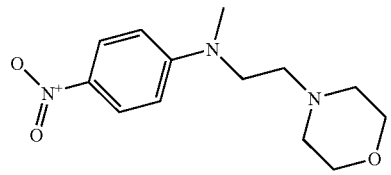

Using (2-morpholin-4-yl-ethyl)-(4-nitro-phenyl)-amine (126 mg) obtained in Step A instead of N-(3-bromo-phenyl)-N-methyl-acetamide, in the same manner as Step B in Example 1-D-135, the desired compound was obtained (125 mg, 94%).

Step C

N-methyl-N-(2-morpholin-4-yl-ethyl)-benzene-1,4-diamine

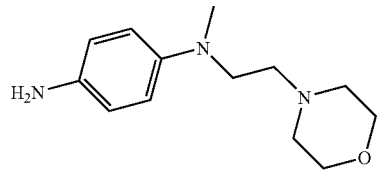

Using methyl-(2-morpholin-4-yl-ethyl)-(4-nitro-phenyl)-amine (125 mg) obtained in Step B instead of (4-ethyl-piperazin-1-yl)-(3-nitro-phenyl)-methanone, in the same manner as Step B in Example 1-D-101, the desired compound was obtained (91.1 mg, 82%).

Step D 4-(2-Amino-pyrimidin-5-yl)-2-morpholin-4-yl-5,6-dihydro-pyrrolo[2,3-d]pyrimidine-7-carboxylic acid {4-[methyl-(2-morpholin-4-yl-ethyl)-amino]-phenyl}-amide (D-206)

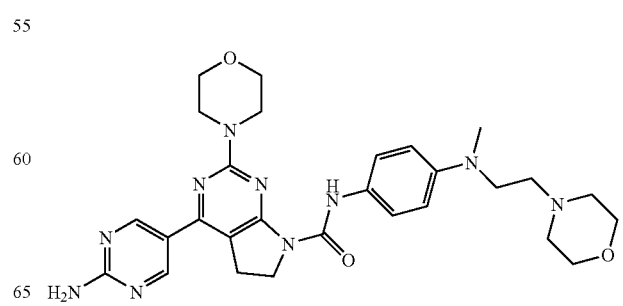

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and N-methyl-N-(2-morpholin-4-yl-ethyl)-benzene-1,4-diamine (56.5 mg) obtained in Step C instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {4-[methyl-(2-morpholin-4-yl-ethyl)-amino]-phenyl}-amide was obtained as a crude product. The PMB groups were removed according to Deprotection method 3, to obtain the desired compound (D-206) as a yellow solid (64 mg, 57%).

$^1$H-NMR (DMSO-$d_6$) δ: 10.76 (1H, s), 8.90 (2H, s), 7.39 (2H, d, J=8.9 Hz), 6.83 (2H, d, J=8.9 Hz), 4.04 (2H, t, J=8.3 Hz), 3.90-3.60 (16H, brm), 3.39-3.18 (6H, brm), 2.89 (3H, s).

ESI (LC-MS positive mode) m/z 561 (M+H)$^+$

Example 1-D-207

4-(2-Amino-pyrimidin-5-yl)-2-morpholin-4-yl-5,6-dihydro-pyrrolo[2,3-d]pyrimidine-7-carboxylic acid {4-[methyl-(3-morpholin-4-yl-propyl)-amino]-phenyl}-amide (D-207)

Step A (3-Morpholin-4-yl-propyl)-(4-nitro-phenyl)-amine

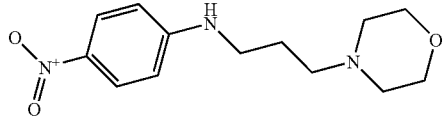

Using 1-iodo-4-nitro-benzene (500 mg) instead of 1-bromo-3-nitro-benzene, and 3-morpholin-4-yl-propylamine (353 mg) instead of morpholine, in the same manner as Step A in Example 1-D-105, the desired compound was obtained (219 mg, 41%).

Step B

Methyl-(3-morpholin-4-yl-propyl)-(4-nitro-phenyl)-amine

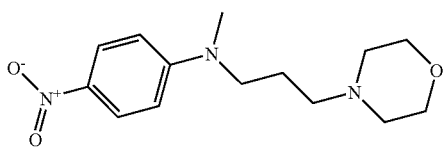

Using (3-morpholin-4-yl-propyl)-(4-nitro-phenyl)-amine (133 mg) obtained in Step A instead of N-(3-bromo-phenyl)-N-methyl-acetamide, in the same manner as Step B in Example 1-D-135, the desired compound was obtained as a crude product.

Step C

N-methyl-N-(3-morpholin-4-yl-propyl)-benzene-1,4-diamine

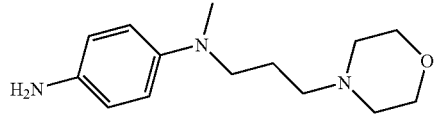

Using methyl-(3-morpholin-4-yl-propyl)-(4-nitro-phenyl)-amine obtained in Step B instead of (4-ethyl-piperazin-1-yl)-(3-nitro-phenyl)-methanone, in the same manner as Step B in Example 1-D-101, the desired compound was obtained (117 mg, 94%).

Step D 4-(2-Amino-pyrimidin-5-yl)-2-morpholin-4-yl-5,6-dihydro-pyrrolo[2,3-d]pyrimidine-7-carboxylic acid {4-[methyl-(3-morpholin-4-yl-propyl)-amino]-phenyl}-amide (D-207)

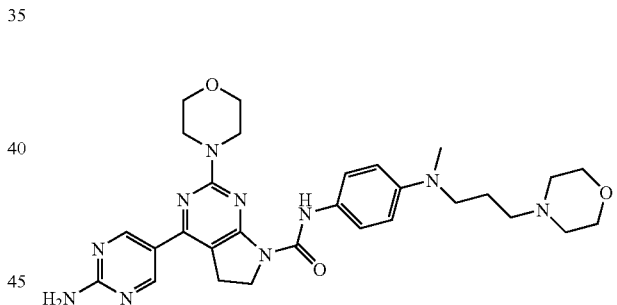

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and N-methyl-N-(3-morpholin-4-yl-propyl)-benzene-1,4-diamine (59.8 mg) obtained in Step C instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {4-[methyl-(3-morpholin-4-yl-propyl)-amino]-phenyl}-amide was obtained as a crude product. The PMB groups were removed according to Deprotection method 3, to obtain the desired compound (D-207) as a yellow solid (49.3 mg, 43%).

$^1$H-NMR (DMSO-$d_6$) δ: 10.81 (1H, s), 8.89 (2H, s), 7.42 (2H, d, J=8.5 Hz), 6.93 (2H, d, J=8.5 Hz), 4.04 (2H, t, J=8.1 Hz), 3.82-3.68 (12H, brm), 3.39 (2H, t, J=6.9 Hz), 3.30-3.09 (8H, brm), 2.93 (3H, s), 1.94-1.81 (2H, m).

ESI (LC-MS positive mode) m/z 575 (M+H)$^+$

Example 1-D-208

4-(2-Amino-pyrimidin-5-yl)-2-morpholin-4-yl-5,6-dihydro-pyrrolo[2,3-d]pyrimidine-7-carboxylic acid [4-(3-morpholin-4-yl-propylamino)-phenyl]-amide (D-208)

Step A (3-Morpholin-4-yl-propyl)-(4-nitro-phenyl)-carbamic acid tert-butyl ester

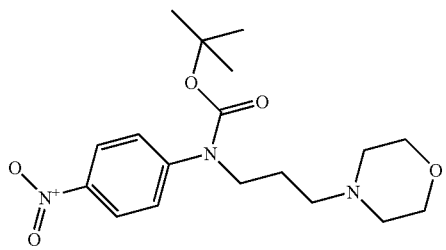

To an acetonitrile solution (3 ml) of (3-morpholin-4-yl-propyl)-(4-nitro-phenyl)-amine (86.7 mg) obtained in Step A in Example 1-D-207, di-tert-butyl dicarbonate (85.6 mg) and DMAP (4.0 mg) were added, followed by stirring at room temperature for 6.5 hours. Saturated aqueous sodium chloride solution (10 ml) was added, followed by extraction with ethyl acetate (20 ml×2), and the organic layer was dried over sodium sulfate. After the sodium sulfate was filtered off, the solvent was distilled off under reduced pressure, followed by purification by silica gel column chromatography, to obtain the desired compound (118 mg, 99%).

Step B (4-Amino-phenyl)-(3-morpholin-4-yl-propyl)-carbamic acid tert-butyl ester

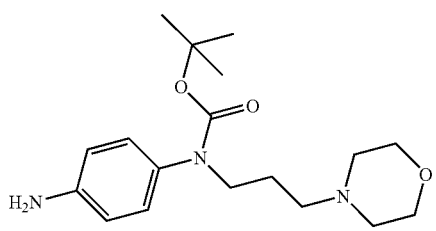

Using (3-Morpholin-4-yl-propyl)-(4-nitro-phenyl)-carbamic acid tert-butyl ester (118 mg) obtained in Step A instead of (4-ethyl-piperazin-1-yl)-(3-nitro-phenyl)-methanone, in the same manner as Step B in Example 1-D-101, the desired compound was obtained (59.3 mg, 55%).

Step C 4-(2-Amino-pyrimidin-5-yl)-2-morpholin-4-yl-5,6-dihydro-pyrrolo[2,3-d]pyrimidine-7-carboxylic acid [4-(3-morpholin-4-yl-propylamino)-phenyl]-amide (D-208)

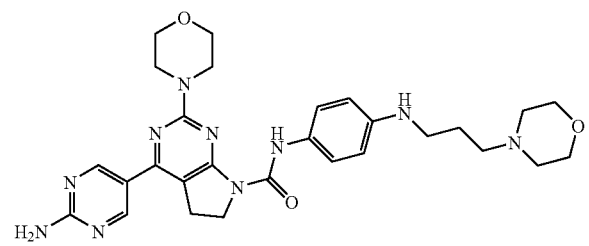

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and (4-amino-phenyl)-(3-morpholin-4-yl-propyl)-carbamic acid tert-butyl ester (59.3 mg) obtained in Step B instead of 4-(4-ethyl-piperazin-1-yl)-2,6-difluoro-phenylamine, in the same manner as Step D in Example 1-D-18, {4-[(4-{2-[bis-(4-methoxy-benzyl)-amino]-pyrimidin-5-yl}-2-morpholin-4-yl-5,6-dihydro-pyrrolo[2,3-d]pyrimidine-7-carbonyl)-amino]-phenyl}-(3-morpholin-4-yl-propyl)-carbamic acid tert-butyl ester was obtained as a crude product. The PMB groups were removed according to Deprotection method 3, to obtain the desired compound (D-208) as a yellow solid (36.4 mg, 43%).

$^1$H-NMR (DMSO-$d_6$) δ: 10.82 (0H, s), 8.89 (2H, s), 7.41 (2H, d, J=8.7 Hz), 6.89 (2H, d, J=8.7 Hz), 4.04 (2H, t, J=8.2 Hz), 3.87-3.68 (12H, brm), 3.33-3.14 (10H, brm), 2.01-1.87 (2H, m).

ESI (LC-MS positive mode) m/z 561 (M+H)$^+$

Example 1-D-209

4-[4-(2-Amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzenesulfonamide (D-209)

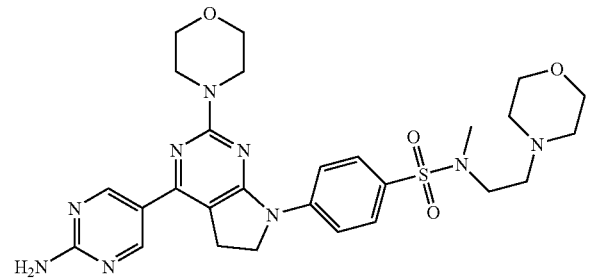

Using 4-bromo-N-methyl-N-(2-morpholin-4-yl-ethyl)-benzenesulfonamide (prepared from 4-bromo-benzenesulfonyl chloride and methyl-(2-morpholin-4-yl-ethyl)-amine, 70 mg) instead of 1-(3-bromo-benzenesulfonyl)-4-ethyl-piperazine used in Example 1-D-96, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N- methyl-N-(2-morpholin-4-yl-ethyl)-benzenesulfonamide was obtained, and then the PMB groups were removed according to the above Deprotection method 3, to obtain the desired compound (D-209) as a pale yellow amorphous (17 mg, 16%).

¹H-NMR (CDCl₃) δ (ppm): 8.90 (2H, s), 7.96 (2H, d, J=8.9 Hz), 7.81 (2H, d, J=8.9 Hz), 5.28 (2H, s), 4.14 (2H, t, J=8.7 Hz), 3.85-3.82 (8H, m), 3.70-3.69 (4H, m), 3.33 (2H, t, J=8.7 Hz), 3.18 (2H, t, J=6.8 Hz), 2.82 (3H, s), 2.57 (2H, t, J=6.8 Hz), 2.49-2.48 (4H, m).

ESI (LC-MS positive mode) m/z 582 (M+H)⁺.

Example 1-D-210

4-(2-Amino-pyrimidin-5-yl)-2-morpholin-4-yl-5,6-dihydro-pyrrolo[2,3-d]pyrimidine-7-carbothioic acid o-tolylamide (D-210)

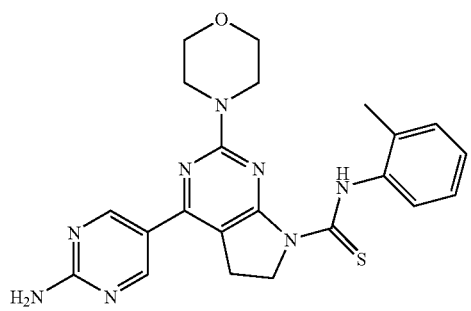

To a DMF solution (2 ml) of ice-cooled bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol), 60% oily NaH (18 mg) was added, followed by stirring at room temperature for 30 minutes. To the reaction mixture, o-tolyl isothiocyanate (59.8 μl, 0.445 mmol) was added, followed by further stirring for 2 hours. The reaction mixture was ice-cooled, and quenched with water (1 ml). This was diluted with dichloromethane (10 ml), and washed with water (10 ml×2). After the organic layer was dried over sodium sulfate, the sodium sulfate was filtered off, and the filtrate was concentrated under reduced pressure, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid o-tolylamide as a brown solid (134 mg). The PMB groups were removed according to the above Deprotection method 3, to obtain the desired compound (D-210) as a yellow powder (35.9 mg, 54%).

¹H-NMR (CDCl₃) δ (ppm): 12.41 (1H, s), 8.92 (2H, s), 7.45-7.25 (4H, m), 5.56 (2H, brs), 4.59 (2H, t, J=8.4 Hz), 3.84-3.58 (8H, m), 3.24 (2H, t, J=8.4 Hz), 2.32 (3H, s).

ESI (LC-MS positive mode) m/z 449 (M+H)⁺.

Example 1-D-211

4-[4-(2-Amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzenesulfonamide (D-211)

Using 4-bromo-3-fluoro-N-methyl-N-(2-morpholin-4-yl-ethyl)-benzenesulfonamide (prepared from 4-bromo-3-fluoro-benzenesulfonyl chloride and methyl-(2-morpholin-4-yl-ethyl)-amine, 73 mg) instead of 1-(3-bromo-benzenesulfonyl)-4-ethyl-piperazine used in Example 1-D-96, an operation was carried out in the same manner as Example 1-D-96, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-N-methyl-N-(2-morpholin-4-yl-ethyl)-benzenesulfonamide, and then the PMB groups were removed according to the above Deprotection method 3, to obtain the desired compound (D-211) as an ivory powder (12 mg, 11%).

¹H-NMR (CDCl₃) δ (ppm): (1H, d, J=4.8 Hz), 8.89 (2H, s), 8.06 (1H, t, J=8.2 Hz), 7.64-7.57 (1H, m), 5.33 (2H, s), 4.21 (2H, t, J=7.3 Hz), 3.78-3.75 (12H, m), 3.34-3.28 (4H, m), 2.87 (3H, s), 2.68-2.61 (6H, m).

ESI (LC-MS positive mode) m/z 600 (M+H)⁺.

Example 1-D-212

4-[4-(2-Amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzenesulfonamide (D-212)

Using 4-bromo-3-methyl-N-methyl-N-(2-morpholin-4-yl-ethyl)-benzenesulfonamide (prepared from 4-bromo-3-methyl-benzenesulfonyl chloride and methyl-(2-morpholin- 4-yl-ethyl)-amine, 70 mg) instead of 1-(3-bromo-benzenesulfonyl)-4-ethyl-piperazine used in Example 1-D-96, an operation was carried out in the same manner as Example 1-D-96, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-methyl-N-(2-morpholin-4-yl-ethyl)-benzenesulfonamide, and then the PMB groups were removed according to the above Deprotection method 3, to obtain the desired compound (D-212) as an ivory powder (7 mg, 10%).

$^1$H-NMR (CDCl$_3$) δ (ppm): 8.89 (2H, s), 7.71 (1H, d, J=2.1 Hz), 7.65 (1H, dd, J=8.4, 2.1 Hz), 7.42 (1H, d, J=8.4 Hz), 4.03 (2H, t, J=8.0 Hz), 3.93 (4H, brs), 3.70 (8H, brs), 3.48 (2H, t, J=6.4 Hz), 3.34 (2H, t, J=8.0 Hz), 2.95 (6H, brs), 2.90 (3H, s), 2.36 (3H, s).

ESI (LC-MS positive mode) m/z 596 (M+H)$^+$.

Example 1-D-213

4-(2-Amino-pyrimidin-5-yl)-2-morpholin-4-yl-5,6-dihydro-pyrrolo[2,3-d]pyrimidine-7-carboxylic acid (2-ethyl-phenyl)-amide (D-213)

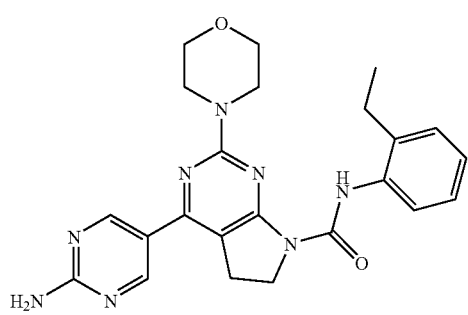

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and 2-ethyl-phenylamine (21.8 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-ethyl-phenyl)-amide was obtained as a crude product. The PMB groups were removed according to Deprotection method 3, to obtain the desired compound (D-213) as a colorless solid (39.3 mg, 56%).

$^1$H-NMR (DMSO-d$_6$) δ: 10.30 (1H, s), 8.85 (2H, s), 7.52 (2H, d, J=6.9 Hz), 7.33-7.12 (5H, m), 4.05 (2H, t, J=8.5 Hz), 3.74-3.63 (8H, brm), 3.24 (2H, t, J=8.5 Hz), 2.63 (2H, q, J=7.5 Hz), 1.16 (3H, t, J=7.5 Hz).

ESI (LC-MS positive mode) m/z 447 (M+H)$^+$

Example 1-D-214

4-(2-Amino-pyrimidin-5-yl)-2-morpholin-4-yl-5,6-dihydro-pyrrolo[2,3-d]pyrimidine-7-carboxylic acid (2-propyl-phenyl)-amide (D-214)

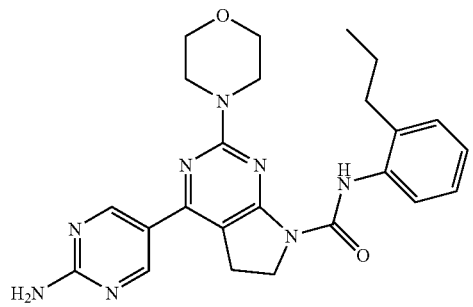

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and 2-propyl-phenylamine (24.3 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-propyl-phenyl)-amide was obtained as a crude product. The PMB groups were removed according to Deprotection method 3, to obtain the desired compound (D-214) as a colorless solid (45.7 mg, 66%).

$^1$H-NMR (DMSO-d$_6$) δ: 10.31 (1H, s), 8.85 (2H, s), 7.50 (1H, d, J=6.8 Hz), 7.30-7.10 (5H, m), 4.05 (2H, t, J=8.6 Hz), 3.74-3.64 (8H, brm), 3.25 (2H, t, J=8.6 Hz), 2.59 (2H, t, J=7.8 Hz), 1.55 (2H, td, J=7.8, 7.3 Hz), 0.86 (3H, t, J=7.3 Hz).

ESI (LC-MS positive mode) m/z 461 (M+H)$^+$

Example 1-D-215

4-(2-Amino-pyrimidin-5-yl)-2-morpholin-4-yl-5,6-dihydro-pyrrolo[2,3-d]pyrimidine-7-carboxylic acid (2,6-difluoro-phenyl)-amide (D-215)

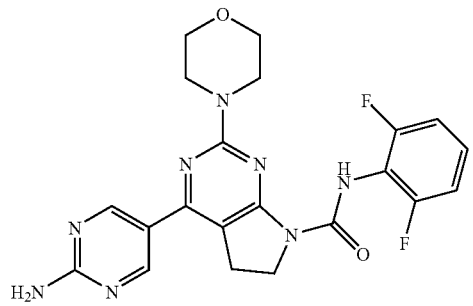

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and 2,6-difluoro-phenylamine (23.2 mg), in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2,6-difluoro-phenyl)-amide was obtained as a crude product. The PMB groups were removed according to Deprotection method 3, to obtain the desired compound (D-215) as a colorless solid (37.8 mg, 55%).

¹H-NMR (DMSO-d₆) δ: 10.51 (1H, s), 8.85 (2H, s), 7.42-7.30 (1H, m), 7.27-7.16 (4H, m), 4.04 (2H, t, J=8.4 Hz), 3.74-3.64 (8H, brm), 3.26 (2H, t, J=8.4 Hz).
ESI (LC-MS positive mode) m/z 455 (M+H)⁺

Example 1-D-216

4-(2-Amino-pyrimidin-5-yl)-2-morpholin-4-yl-5,6-dihydro-pyrrolo[2,3-d]pyrimidine-7-carbothioic acid phenylamide (D-216)

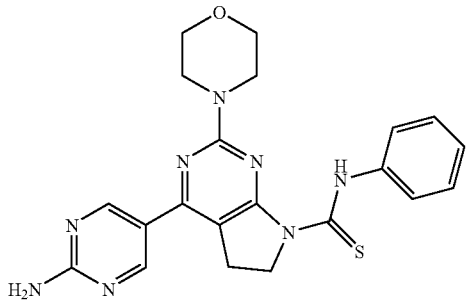

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and phenyl isothiocyanate (53.0 μl, 0.447 mmol) instead of o-tolyl isothiocyanate, thiourea was formed in the same manner as Example 1-D-210, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid phenylamide as a brown solid (155 mg), and then the PMB groups were removed according to the above Deprotection method 3, to obtain the desired compound (D-216) as a yellow powder (34.5 mg, 55%).
¹H-NMR (CDCl₃) δ (ppm): 12.95 (1H, s), 8.91 (2H, s), 7.61 (1H, d, J=7.6 Hz), 7.42 (2H, t, J=7.6 Hz), 7.27 (1H, d, J=7.6 Hz), 5.31 (2H, brs), 4.59 (2H, t, J=8.2 Hz), 3.80-3.77 (8H, m), 3.23 (2H, t, J=8.2 Hz).
ESI (LC-MS positive mode) m/z 435 (M+H)⁺.

Example 1-D-217

4-(2-Amino-pyrimidin-5-yl)-2-morpholin-4-yl-5,6-dihydro-pyrrolo[2,3-d]pyrimidine-7-carboxylic acid (2-chloro-phenyl)-amide (D-217)

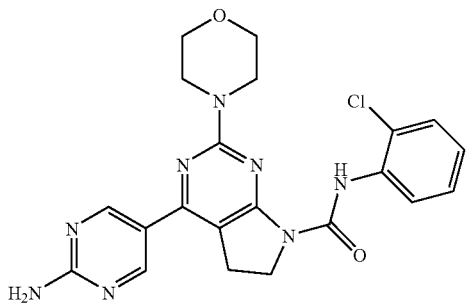

To a DMF solution (2 ml) of ice-cooled bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol), 60% oily NaH (18 mg) was added, followed by stirring at room temperature for 15 minutes. To the reaction mixture, 2-chlorophenylisocyanate (53.4 μl, 0.445 mmol) was added, followed by further stirring for 1 hour. The reaction mixture was ice-cooled, and quenched with water (1 ml). This was diluted with dichloromethane (10 ml), and washed with water (10 ml×2). After the organic layer was dried over sodium sulfate, the sodium sulfate was filtered off, and the filtrate was concentrated under reduced pressure, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-chloro-phenyl)-amide as a brown solid (115 mg), and then the PMB groups were removed according to the above Deprotection method 3, to obtain the desired compound (D-217) as a colorless powder (39.2 mg, 58%).
¹H-NMR (DMSO-d₆) δ (ppm): 10.77 (1H, s), 8.85 (2H, s), 7.99 (1H, d, J=8.1 Hz), 7.54 (1H, d, J=8.1 Hz), 7.37 (1H, t, J=8.1 Hz), 7.23 (2H, s), 7.16 (1H, t, J=8.1 Hz), 4.07 (2H, t, J=7.6 Hz), 3.81-3.65 (8H, m), 3.25 (2H, t, J=7.6 Hz).
ESI (LC-MS positive mode) m/z 453 (M+H)⁺.

Example 1-D-218

4-(2-Amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide (D-218)

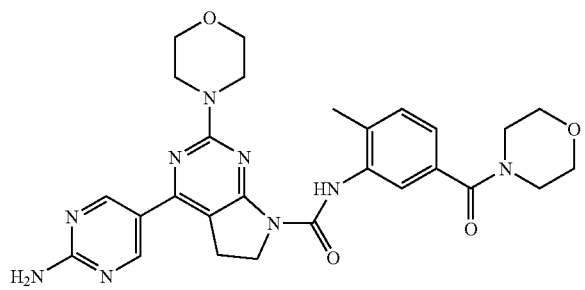

In the same manner as Example 1-D-17, using 4-methyl-3-nitro-benzoic acid (730 mg, 4.03 mmol) and morpholine (420 μl, 4.79 mmol) instead of 1-ethylpiperazine, amidation and reduction reaction were carried out, to obtain a crude product of (morpholin-1-yl)-(3-amino-4-methyl-phenyl)-methanone as a colorless solid (880 mg). In the same manner as Step D in Example 1-D-18, using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and a crude product (82 mg) of (morpholin-1-yl)-(3-amino-4-methyl-phenyl)-methanone obtained in the above step instead of 4-(4-ethyl-piperazin-1-yl)-2,6-difluoro-phenylamine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide was obtained. Using a crude product (100 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide, according to the above Deprotection method 2,4-(2-amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide was obtained as a colorless powder (20 mg, 20%).
¹H-NMR (DMSO-d₆) (ppm): 8.73 (2H, s), 7.51 (1H, s), 7.15 (1H, m), 7.00 (1H, m), 4.06 (2H, m), 3.71-3.31 (16H, m), 2.97 (2H, m), 2.12 (3H, s).
ESI (LC-MS positive mode) m/z 546 (M+H)⁺.

Example 1-D-219

4-(2-Amino-pyrimidin-5-yl)-2-morpholin-4-yl-5,6-dihydro-pyrrolo[2,3-d]pyrimidine-7-carboxylic acid [2-methyl-4-(morpholine-4-carbonyl)-phenyl]-amide (D-219)

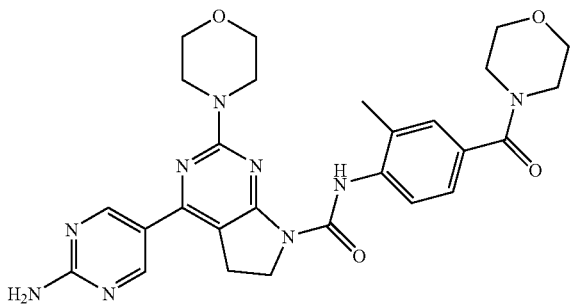

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-amino-3-methyl-phenyl)-morpholin-4-yl-methanone (25 mg) instead of 4-(4-ethyl-piperazin-1-yl)-2,6-difluoro-phenylamine, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-4-(morpholine-4-carbonyl)-phenyl]-amide was obtained, and then the PMB groups were removed according to the above Deprotection method 3, to obtain the desired compound (D-219) as a grayish white powder (20 mg, 39%).

$^1$H-NMR (DMSO-d$_6$) δ (ppm): 10.37 (1H, s), 8.85 (2H, s), 7.73 (1H, d, J=8.2 Hz), 7.30-7.26 (3H, m), 4.06 (2H, t, J=8.3 Hz), 3.70 (2H, d, J=4.0 Hz), 3.60 (2H, s), 3.33 (12H, s), 3.25 (2H, t, J=8.3 Hz), 3.17 (1H, d, J=5.3 Hz), 2.31 (3H, s).

ESI (LC-MS positive mode) m/z 546 (M+H)$^+$.

Example 1-D-220

4-(2-Amino-pyrimidin-5-yl)-2-morpholin-4-yl-5,6-dihydro-pyrrolo[2,3-d]pyrimidine-7-carboxylic acid [2-methyl-4-(4-methyl-piperazine-1-carbonyl)-phenyl]-amide (D-220)

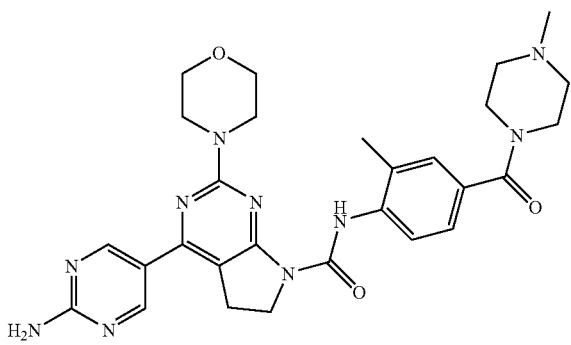

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-amino-3-methyl-phenyl)-(4-methyl-piperazin-1-yl)-methanone (26 mg) instead of 4-(4-ethyl-piperazin-1-yl)-2,6-difluoro-phenylamine, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-4-(4-methyl-piperazine-1-carbonyl)-phenyl]-amide was obtained, and then the PMB groups were removed according to the above Deprotection method 3, to obtain the desired compound (D-220) as a grayish white powder (11 mg, 21%).

$^1$H-NMR (DMSO-d$_6$) δ (ppm): 10.39 (1H, s), 8.85 (2H, s), 7.74 (1H, s), 7.33-7.26 (3H, m), 5.76 (1H, s), 4.06 (2H, t, J=8.2 Hz), 3.71 (4H, s), 3.35 (13H, s), 3.18 (2H, s), 2.66 (2H, s), 2.32 (3H, s).

ESI (LC-MS positive mode) m/z 559 (M+H)$^+$.

Example 1-D-221

4-(2-Amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2-methyl-phenyl]-amide (D-221)

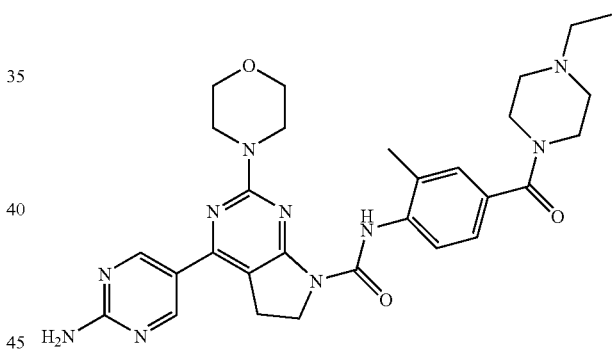

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-amino-3-methyl-phenyl)-(4-ethyl-piperazin-1-yl)-methanone (28 mg) instead of 4-(4-ethyl-piperazin-1-yl)-2,6-difluoro-phenylamine, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazine-1-carbonyl)-2-methyl-phenyl]-amide was obtained, and then the PMB groups were removed according to the above Deprotection method 3, to obtain the desired compound (D-221) as a grayish white powder (10 mg, 19%).

$^1$H-NMR (DMSO-d$_6$) δ (ppm): 10.48 (1H, s), 8.91 (2H, s), 7.73 (1H, d, J=8.2 Hz), 7.33 (1H, d, J=1.5 Hz), 7.28-7.24 (2H, m), 5.39 (1H, d, J=4.0 Hz), 4.23 (2H, t, J=8.5 Hz), 3.78 (16H, s), 3.25 (2H, t, J=8.5 Hz), 2.50 (2H, dd, J=13.7, 6.9 Hz), 2.34 (3H, s), 1.13 (3H, t, J=7.1 Hz).

ESI (LC-MS positive mode) m/z 573 (M+H)$^+$.

Example 1-D-222

4-(2-Amino-pyrimidin-5-yl)-2-morpholin-4-yl-5,6-dihydro-pyrrolo[2,3-d]pyrimidine-7-carbothioic acid (2-fluoro-phenyl)-amide (D-222)

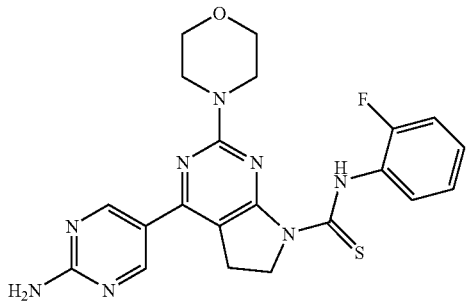

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and 2-fluorophenyl isothiocyanate (54.6 μl, 0.445 mmol) instead of o-tolyl isothiocyanate, thiourea was formed in the same manner as Example 1-D-210, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid (2-fluoro-phenyl)-amide as a brown solid (120 mg), and then the PMB groups were removed according to the above Deprotection method 3, to obtain the desired compound (D-222) as a yellow powder (54.5 mg, 80%).

$^1$H-NMR (DMSO-$d_6$) δ (ppm): 12.74 (1H, s), 8.87 (2H, s), 8.03 (1H, dt, J=7.9, 1.8 Hz), 7.51-7.06 (5H, m), 4.38 (2H, t, J=8.1 Hz), 3.71-3.65 (8H, m), 3.26 (2H, t, J=8.2 Hz).

ESI (LC-MS positive mode) m/z 453 (M+H)$^+$.

Example 1-D-223

4-(2-Amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide (D-223)

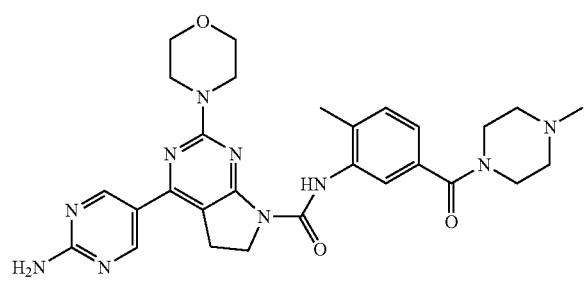

In the same manner as Example 1-D-218, using 1-methyl-piperazine (0.53 ml) instead of morpholine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide was obtained. Using a crude product (123 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide, according to the above Deprotection method 2, 4-(2-amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide was obtained as a colorless powder (29 mg, 34%).

$^1$H-NMR (DMSO-$d_6$) δ (ppm): 10.4 (1H, s), 8.85 (2H, s), 7.68 (1H, s), 7.33 (1H, m), 7.23 (2H, s), 7.10 (1H, m), 4.06 (2H, m), 3.70 (8H, m), 3.33-3.25 (6H, m), 2.52-2.31 (7H, m), 2.20 (3H, s).

ESI (LC-MS positive mode) m/z 559 (M+H)$^+$.

Example 1-D-224

4-(2-Amino-pyrimidin-5-yl)-2-morpholin-4-yl-5,6-dihydro-pyrrolo[2,3-d]pyrimidine-7-carboxylic acid [5-(4-ethyl-piperazine-1-carbonyl)-2-methyl-phenyl]-amide (D-224)

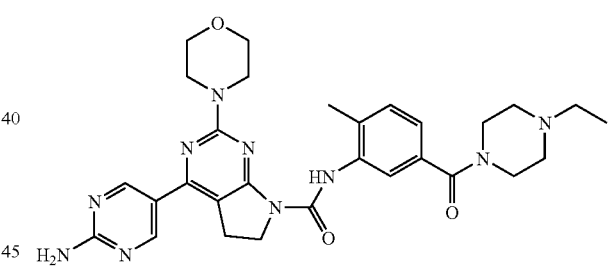

In the same manner as Example 1-D-218, using 1-ethyl-piperazine (0.6 ml) instead of morpholine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(4-ethyl-piperazine-1-carbonyl)-phenyl]-amide was obtained. Using a crude product (126 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid [2-methyl-5-(4-ethyl-piperazine-1-carbonyl)-phenyl]-amide, according to the above Deprotection method 2, 4-(2-amino-pyrimidin-5-yl)-2-morpholin-4-yl-5,6-dihydro-pyrrolo[2,3-d]pyrimidine-7-carboxylic acid [5-(4-ethyl-piperazine-1-carbonyl)-2-methyl-phenyl]-amide was obtained as a colorless powder (82 mg, 93%).

$^1$H-NMR (DMSO-$D_6$) δ: 10.4 (1H, s), 8.85 (2H, s), 7.68 (1H, s), 7.33 (1H, m), 7.23 (2H, s), 7.10 (1H, m), 4.07 (2H, m), 3.70 (8H, m), 3.39-3.24 (6H, m), 2.52-2.31 (9H, m), 1.00 (3H, t, J=7.0 Hz).

ESI (LC-MS positive mode) m/z 573 (M+H)$^+$.

Example 1-D-225

4-(2-Amino-pyrimidin-5-yl)-2-morpholin-4-yl-5,6-dihydro-pyrrolo[2,3-d]pyrimidine-7-carbothioic acid (2,6-difluoro-phenyl)-amide (D-225)

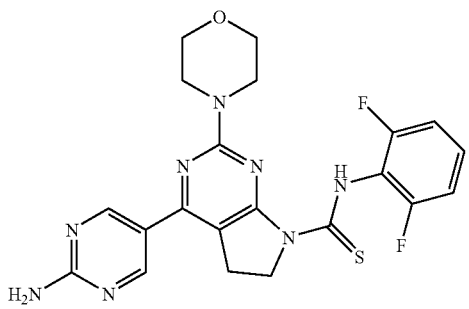

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and 2,6-difluorophenyl isothiocyanate (57.0 µl, 0.441 mmol) instead of o-tolyl isothiocyanate, thiourea was formed in the same manner as Example 1-D-210, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid (2,6-difluoro-phenyl)-amide as a yellow solid (108 mg), and then the PMB groups were removed according to the above Deprotection method 3, to obtain the desired compound (D-225) as a yellow powder (59.4 mg, 85%).

$^1$H-NMR (DMSO-$d_6$) δ (ppm): 12.21 (1H, s), 8.87 (2H, s), 7.50-7.16 (3H, m), 5.76 (2H, brs), 4.35 (2H, t, J=7.9 Hz), 3.87-3.37 (8H, m), 3.28 (2H, t, J=7.9 Hz).

ESI (LC-MS positive mode) m/z 471 (M+H)$^+$.

Example 1-D-226

4-(2-Amino-pyrimidin-5-yl)-2-morpholin-4-yl-5,6-dihydro-pyrrolo[2,3-d]pyrimidine-7-carboxylic acid methyl-(3-morpholin-4-yl-phenyl)-amide (D-226)

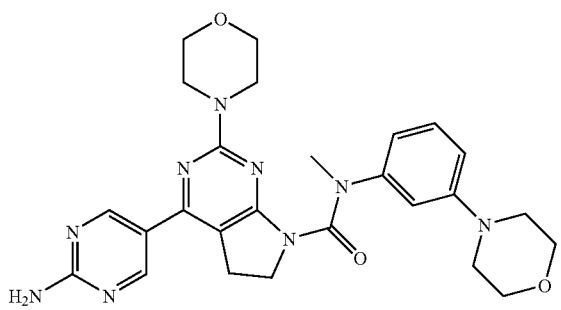

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide (112 mg) and morpholine (15.5 mg) instead of 2-piperazin-1-yl-ethanol, in the same manner as Step C in Example 1-D-153, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-morpholin-4-yl-phenyl)-amide was obtained as a crude product. The PMB groups were removed according to Deprotection method 3, to obtain the desired compound (1-D-226) as a yellow solid (47.3 mg, 61%).

$^1$H-NMR (CDCl$_3$) δ: 8.82 (2H, s), 7.21 (1H, t, J=8.1 Hz), 6.83-6.67 (3H, m), 5.92 (2H, brs), 3.94-3.68 (14H, m), 3.43 (3H, s), 3.14-3.03 (6H, m).

ESI (LC-MS positive mode) m/z 518 (M+H)$^+$

Example 1-D-227

4-(2-Amino-pyrimidin-5-yl)-2-morpholin-4-yl-5,6-dihydro-pyrrolo[2,3-d]pyrimidine-7-carboxylic acid methyl-{3-[methyl-(2-morpholin-4-yl-ethyl)-amino]-phenyl}-amide (D-227)

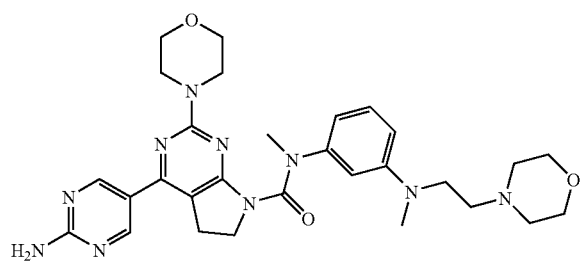

Using 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (3-bromo-phenyl)-methyl-amide (112 mg) and methyl-(2-morpholin-4-yl-ethyl)-amine (25.8 mg) obtained in Step A in Example 1-D-139 instead of 2-piperazin-1-yl-ethanol, in the same manner as Step C in Example 1-D-153, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {3-[methyl-(2-morpholin-4-yl-ethyl)-amino]-phenyl}-amide was obtained as a crude product. The PMB groups were removed according to Deprotection method 3, to obtain the desired compound (D-227) as a brown solid (18.6 mg, 22%).

$^1$H-NMR (CDCl$_3$) δ: 8.80 (2H, s), 7.15 (1H, t, J=7.8 Hz), 6.62-6.47 (3H, m), 5.24 (2H, brs), 3.88-3.65 (14H, m), 3.46-3.37 (5H, m), 3.07 (2H, t, J=8.0 Hz), 2.91 (3H, s), 2.51-2.39 (6H, m).

ESI (LC-MS positive mode) m/z 575 (M+H)$^+$

Example 1-D-228

{5-[4-(2-Amino-pyrimidin-5-yl)-2-morpholin-4-yl-5,6-dihydro-pyrrolo[2,3-d]pyrimidin-7-yl]-pyridin-3-yl}-morpholin-4-yl-methanone (D-228)

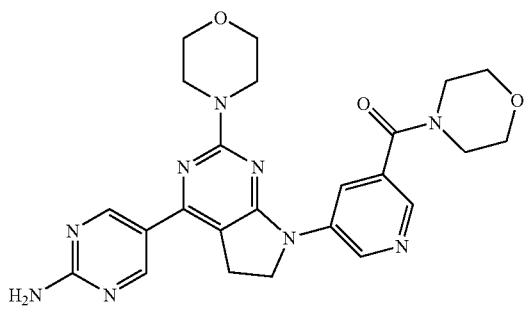

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (5-bromo-pyridin-3-yl)-morpholin-4-yl-methanone (38 mg) instead of 4-chloropicolinic acid t-butylamide, in the same manner as Example 1-D-07, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-3-yl]-morpholin-4-yl-methanone was obtained, and then the PMB groups were removed according to the above Deprotection method 3, to obtain the desired compound (D-228) as a yellow powder (45 mg, 100%).

$^1$H-NMR (DMSO-$d_6$) δ (ppm): 9.21 (1H, d, J=2.8 Hz), 8.83 (2H, s), 8.28 (2H, d, J=1.3 Hz), 8.23 (2H, t, J=2.2 Hz), 5.76 (1H, s), 4.14 (2H, t, J=8.0 Hz), 3.71 (14H, s), 3.55-3.51 (2H, m), 3.34 (2H, t, J=8.6 Hz).

ESI (LC-MS positive mode) m/z 490 (M+H)$^+$.

Example 1-D-229

{5-[4-(2-Amino-pyrimidin-5-yl)-2-morpholin-4-yl-5,6-dihydro-pyrrolo[2,3-d]pyrimidin-7-yl]-pyridin-3-yl}-(4-methyl-piperazin-1-yl)-methanone (D-229)

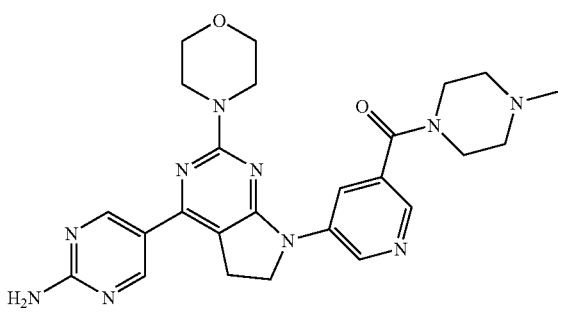

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (5-bromo-pyridin-3-yl)-(4-methyl-piperazin-1-yl)-methanone (40 mg, prepared according to Step A in Example 1-D-25) instead of 4-chloropicolinic acid t-butylamide, in the same manner as Example 1-D-07, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-3-yl]-(4-methyl-piperazin-1-yl)-methanone was obtained, and then the PMB groups were removed according to the above Deprotection method 3, to obtain the desired compound (D-229) as a pale yellow powder (42 mg, 91%).

$^1$H-NMR (DMSO-$d_6$) δ (ppm): 9.18 (1H, s), 8.83 (2H, s), 8.26 (2H, s), 7.13 (1H, s), 5.76 (1H, s), 4.14 (2H, t, J=8.0 Hz), 3.71 (8H, s), 3.34 (10H, s), 2.40 (3H, s).

ESI (LC-MS positive mode) m/z 503 (M+H)$^+$.

Example 1-D-230

{5-[4-(2-Amino-pyrimidin-5-yl)-2-morpholin-4-yl-5,6-dihydro-pyrrolo[2,3-d]pyrimidin-7-yl]-pyridin-3-yl}-(4-ethyl-piperazin-1-yl)-methanone (D-230)

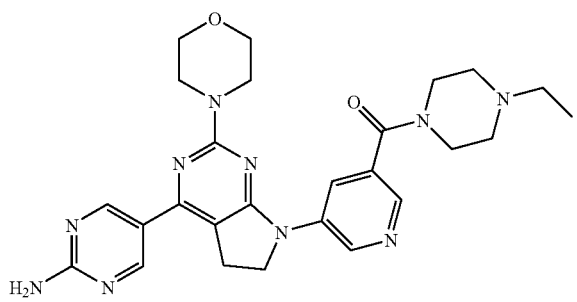

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (5-bromo-pyridin-3-yl)-(4-ethyl-piperazin-1-yl)-methanone (42 mg, prepared according to Step A in Example 1-D-25) instead of 4-chloropicolinic acid t-butylamide, in the same manner as Example 1-D-07, a crude product of [5-(4-{2-[bis-(4-methoxy-benzyl)-amino]-pyrimidin-5-yl}-2-morpholin-4-yl-5,6-dihydro-pyrrolo[2,3-d]pyrimidin-7-yl)-pyridin-3-yl]-(4-ethyl-piperazin-1-yl)-methanone was obtained, and then the PMB groups were removed according to the above Deprotection method 3, to obtain the desired compound (D-230) as a pale yellow powder (46 mg, 96%).

$^1$H-NMR (DMSO-$d_6$) δ (ppm): 9.16 (1H, s), 8.83 (2H, d, J=1.0 Hz), 8.25 (2H, s), 7.13 (1H, s), 5.76 (1H, d, J=1.3 Hz), 4.15 (2H, t, J=8.0 Hz), 3.71 (8H, s), 3.34 (8H, s), 2.44 (2H, s), 1.04 (3H, s).

ESI (LC-MS positive mode) m/z 517 (M+H)$^+$.

Example 1-D-231

4-(2-Amino-pyrimidin-5-yl)-2-morpholin-4-yl-5,6-dihydro-pyrrolo[2,3-d]pyrimidine-7-carbothioic acid [4-(4-methyl-piperazine-1-carbonyl)-phenyl]-amide (D-231)

Step A (4-Methyl-piperazin-1-yl)-(4-nitro-phenyl)-methanone

Using 4-nitro-benzoic acid (1 g) instead of 3-nitro-benzoic acid, and 1-methyl-piperazine (797 μl) instead of 1-ethyl-piperazine, in the same manner as Step A in Example 1-D-101, the desired compound was obtained as a crude product.

Step B (4-Amino-phenyl)-(4-methyl-piperazin-1-yl)-methanone

Using (4-methyl-piperazin-1-yl)-(4-nitro-phenyl)-methanone obtained in Step A instead of (4-ethyl-piperazin-1-yl)-(3-nitro-phenyl)-methanone, in the same manner as Step B in Example 1-D-101, the desired compound was obtained as a crude product (291 mg, 22%).

Step C 4-(2-Amino-pyrimidin-5-yl)-2-morpholin-4-yl-5,6-dihydro-pyrrolo[2,3-d]pyrimidine-7-carbothioic acid [4-(4-methyl-piperazine-1-carbonyl)-phenyl]-amide (D-231)

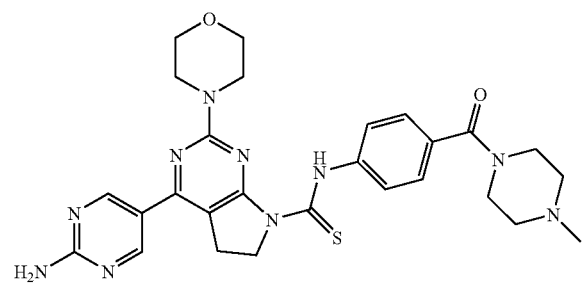

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and (4-amino-phenyl)-(4-methyl-piperazin-1-yl)-methanone (39.5 mg) obtained in Step B instead of 4-(4-ethyl-piperazin-1-yl)-2,6-difluoro-phenylamine, and thiophosgene (22.9 μl) instead of triphosgene, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [4-(4-methyl-piperazine-1-carbonyl)-phenyl]-amide was obtained as a crude product. The PMB groups were removed according to Deprotection method 3, to obtain the desired compound (D-231) as a yellow solid (28.1 mg, 33%).

$^1$H-NMR (DMSO-$d_6$) δ: 13.10 (1H, s), 8.88 (2H, s), 7.82 (2H, d, J=8.4 Hz), 7.52 (2H, d, J=8.4 Hz), 4.38 (2H, t, J=8.4 Hz), 3.74-3.67 (8H, brm), 3.52-3.38 (4H, brm), 3.26 (2H, t, J=8.4 Hz), 3.17-3.04 (4H, brm), 2.83 (3H, s).

ESI (LC-MS positive mode) m/z 561 (M+H)$^+$

Example 1-D-232

4-(2-Amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-phenyl]-amide (D-232)

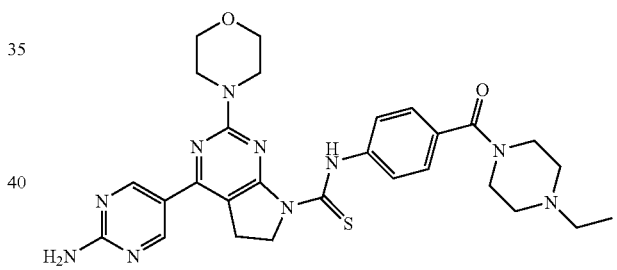

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and (4-amino-phenyl)-(4-ethyl-piperazin-1-yl)-methanone (42 mg) obtained in Step B in Example 1-D-103 instead of 4-(4-ethyl-piperazin-1-yl)-2,6-difluoro-phenylamine, and thiophosgene (22.9 μl) instead of triphosgene, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [4-(4-ethyl-piperazine-1-carbonyl)-phenyl]-amide was obtained as a crude product. The PMB groups were removed according to Deprotection method 3, to obtain the desired compound (D-232) as a colorless solid (54.1 mg, 62%).

$^1$H-NMR (DMSO-$d_6$) δ: 13.11 (1H, s), 8.90 (2H, s), 7.83 (2H, d, J=8.6 Hz), 7.54 (2H, d, J=8.6 Hz), 4.39 (2H, t, J=8.0 Hz), 3.72 (8H, s), 3.59-3.44 (4H, brm), 3.28 (2H, t, J=8.0 Hz), 3.22-3.01 (6H, m), 1.23 (3H, t, J=7.3 Hz).

ESI (LC-MS positive mode) m/z 575 (M+H)$^+$

Example 1-D-233

4-(2-Amino-pyrimidin-5-yl)-2-morpholin-4-yl-5,6-dihydro-pyrrolo[2,3-d]pyrimidine-7-carbothioic acid [3-(4-methyl-piperazine-1-carbonyl)-phenyl]-amide (D-233)

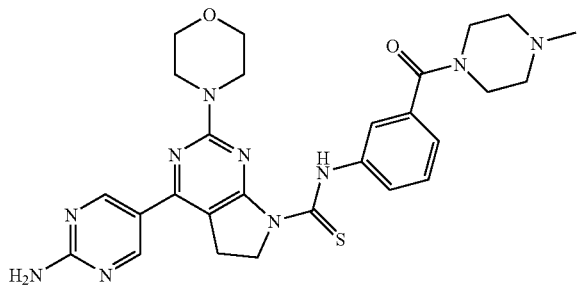

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and (3-amino-phenyl)-(4-methyl-piperazin-1-yl)-methanone (56 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [3-(4-methyl-piperazine-1-carbonyl)-phenyl]-amide was obtained, and then the PMB groups were removed according to the above Deprotection method 3, to obtain the desired compound (D-233) as an ivory powder (11 mg, 13%).

$^1$H-NMR (DMSO-$d_6$) δ (ppm): 13.07 (1H, s), 8.87 (2H, s), 7.80 (1H, s), 7.65 (1H, d, J=8.1 Hz), 7.49 (1H, t, J=7.7 Hz), 7.29 (2H, s), 7.25-7.23 (1H, m), 4.38 (2H, t, J=8.1 Hz), 3.70 (8H, brs), 3.61 (4H, brs), 3.27 (2H, t, J=8.1 Hz), 2.33 (4H, brs), 2.20 (3H, s).

ESI (LC-MS positive mode) m/z 561 (M+H)$^+$.

Example 1-D-234

4-[4-(2-Amino-pyrimidin-5-yl)-2-morpholin-4-yl-5,6-dihydro-pyrrolo[2,3-d]pyrimidin-7-yl]-3-methyl-benzonitrile (D-234)

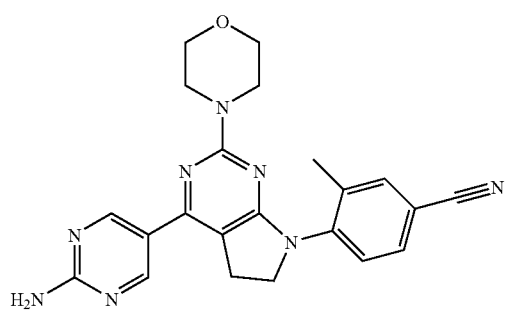

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (300 mg) and 3-methyl-4-bromobenzonitrile (120 mg) instead of 4-bromobenzoic acid methyl ester used in Example 1-D-8, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-benzonitrile was obtained, and then the PMB groups were removed according to the above Deprotection method 3 using 54 mg of the crude product, to obtain the desired compound (D-234) as an ivory powder (32 mg, 94%).

$^1$H-NMR (DMSO-$d_6$) δ (ppm): 8.80 (2H, s), 7.81 (1H, d, J=1.6 Hz), 7.71 (1H, dd, J=8.4, 1.6 Hz), 7.54 (1H, d, J=8.4 Hz), 7.07 (2H, s), 4.03 (2H, t, J=8.3 Hz), 3.56 (8H, brs), 3.31 (2H, brs), 2.26 (3H, s).

ESI (LC-MS positive mode) m/z 415 (M+H)$^+$.

Example 1-D-235

4-(2-Amino-pyrimidin-5-yl)-2-morpholin-4-yl-5,6-dihydro-pyrrolo[2,3-d]pyrimidine-7-carbothioic acid [3-(4-ethyl-piperazine-1-carbonyl)-phenyl]-amide (D-235)

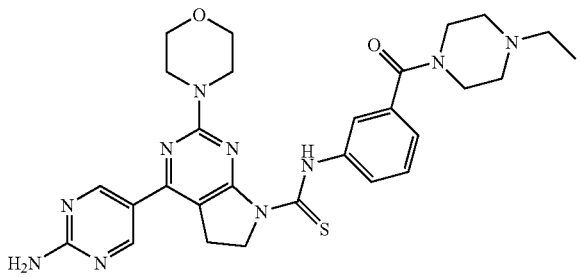

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (81 mg) and (3-amino-phenyl)-(4-ethyl-piperazin-1-yl)-methanone (105 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [3-(4-methyl-piperazine-1-carbonyl)-phenyl]-amide was obtained, and then the PMB groups were removed according to the above Deprotection method 3, to obtain the desired compound (D-235) as a pale yellow powder (22 mg, 26%).

$^1$H-NMR (DMSO-$d_6$) δ (ppm): 13.07 (1H, s), 8.87 (2H, s), 7.80 (1H, s), 7.66 (1H, d, J=7.3 Hz), 7.49 (1H, t, J=7.8 Hz), 7.29 (2H, s), 7.26-7.23 (1H, m), 4.38 (2H, t, J=8.2 Hz), 3.70 (8H, s), 3.66-3.63 (2H, m), 3.42 (4H, brs), 3.27 (2H, brs), 2.40 (4H, brs), 1.02 (3H, t, J=7.2 Hz).

ESI (LC-MS positive mode) m/z 575 (M+H)$^+$.

Example 1-D-236

4-(2-Amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide (D-236)

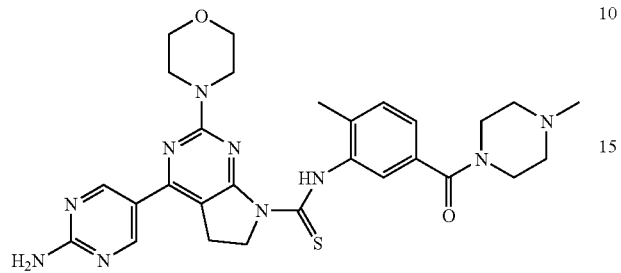

In the same manner as Example 1-D-17, using 1-methyl-piperazine instead of 1-ethylpiperazine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide was obtained. Using a crude product (82 mg) of 4-(2-bis-(4-methoxy-benzyl)-amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide, according to the above Deprotection method 2,4-(2-amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide was obtained as a colorless powder (7 mg).

$^1$H-NMR (DMSO-$d_6$) δ (ppm): 12.5 (1H, s), 8.87 (2H, s), 7.45 (1H, s), 7.39 (1H, m), 7.29 (2H, s), 7.23 (1H, m), 4.39 (2H, m), 3.65 (8H, m), 3.60-3.24 (6H, m), 2.31-2.20 (7H, m), 2.18 (3H, s).

ESI (LC-MS positive mode) m/z 575 (M+H)$^+$.

Example 1-D-237

4-(2-Amino-pyrimidin-5-yl)-2-morpholin-4-yl-5,6-dihydro-pyrrolo[2,3-d]pyrimidine-7-carboxylic acid (2-methyl-5-morpholin-4-yl-phenyl)-amide (D-237)

Step A 4-(4-Methyl-3-nitro-phenyl)-morpholine

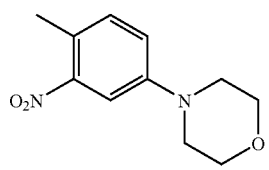

To 4-bromo-1-methyl-2-nitro-benzene (500 mg), tris(dibenzylideneacetone)dipalladium (120 mg) and potassium phosphate (928 mg), morpholine (242 mg), S-Phos (95 mg) and deaerated DMF (5 ml) were added, followed by irradiation of ultrasonic wave for 5 minutes. This was stirred at 110° C. for 5 hours. After cooling to room temperature, water was added, followed by extraction with ethyl acetate, and the organic layer was washed with brine, and dried over magnesium sulfate. After the magnesium sulfate was filtered off, the solvent was distilled off under reduced pressure, followed by purification by silica gel column chromatography (hexane/ethyl acetate=4/1), to obtain the desired compound as an orange solid (478 mg, 93%).

Step B

2-Methyl-5-morpholin-4-yl-phenylamine

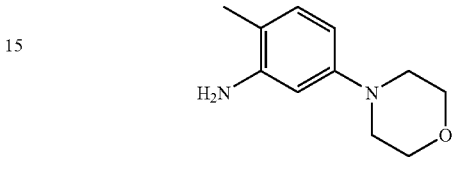

To a methanol solution (10 ml) of 4-(4-methyl-3-nitro-phenyl)-morpholine (22 mg) obtained in Step A, zinc (65 mg) and ammonium chloride (16 mg) were added, followed by stirring at room temperature for 3 hours. After filtration through Celite, the solvent was distilled off under reduced pressure, followed by purification by silica gel column chromatography (dichloromethane/methanol=30/1), to obtain the desired compound as a colorless solid (17 mg, 90%).

Step C 4-(2-Amino-pyrimidin-5-yl)-2-morpholin-4-yl-5,6-dihydro-pyrrolo[2,3-d]pyrimidine-7-carboxylic acid (2-methyl-5-morpholin-4-yl-phenyl)-amide (D-237)

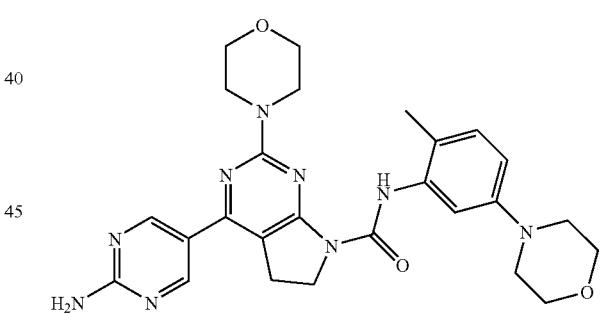

To a dichloromethane/saturated sodium hydrogencarbonate water=1/1 solution (14 ml) of bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg), phosgene (20%-toluene solution, 0.41 ml) was added dropwise, followed by stirring at room temperature for 1 hour. The organic layer was extracted, and dried over magnesium sulfate. After the magnesium sulfate was filtered off, the solvent was distilled off under reduced pressure. To this, dichloromethane (7 ml) was added, and 2-methyl-5-morpholin-4-yl-phenylamine (59 mg) obtained in Step B and triethylamine (58 μl) were added, followed by stirring at room temperature overnight. To this, water and 1M-HCl aqueous solution were added, followed by extraction with dichloromethane/methanol=50/1, and the organic layer was dried over sodium sulfate. After the sodium sulfate was filtered off, the solvent was distilled off under reduced pressure, followed by purification by silica gel column chromatography (dichloromethane/methanol=50/1), to obtain 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-methyl-5-morpholin-4-yl-phenyl)-amide as a crude product. The PMB groups were removed according to Deprotection method 2, to obtain the desired compound (D-237) as an ivory solid (131 mg, 91%).

$^1$H-NMR (CDCl$_3$) δ: 10.30 (1H, s), 8.90 (2H, s), 7.35 (1H, d, J=2.6 Hz), 7.12 (1H, d, J=8.3 Hz), 6.69 (1H, dd, J=2.6 Hz, 8.3 Hz), 5.32 (2H, s), 4.22 (2H, t, J=8.3 Hz), 3.80 (12H, m), 3.20 (6H, m), 2.24 (3H, s)

LCMS (ESI+) m/z 518.14 (M+H)$^+$

Example 1-D-238

4-(2-Amino-pyrimidin-5-yl)-2-morpholin-4-yl-5,6-dihydro-pyrrolo[2,3-d]pyrimidine-7-carboxylic acid [2-methyl-5-(4-methyl-piperazin-1-yl)-phenyl]-amide (D-238)

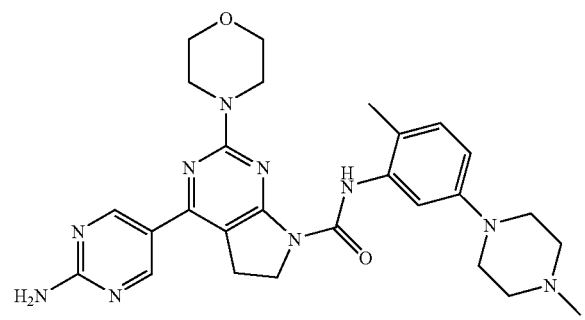

Using 2-methyl-5-(4-methyl-piperazin-1-yl)-phenylamine (69 mg) obtained using 1-methyl-piperazine instead of morpholine in the same manner as Step A and Step B in Example 1-D-237, instead of 2-methyl-5-morpholin-4-yl-phenylamine, from bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg), in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-5-(4-methyl-piperazin-1-yl)-phenyl]-amide was obtained as a crude product. The PMB groups were removed according to Deprotection method 2, to obtain the desired compound (D-238) as an ivory solid (82 mg, 56%).

$^1$H-NMR (CDCl$_3$) δ: 10.30 (1H, s), 8.90 (2H, s), 7.34 (1H, d, J=2.2 Hz), 7.10 (1H, d, J=8.3 Hz), 6.71 (1H, dd, J=8.3 Hz, 2.2 Hz), 5.27 (2H, s), 4.22 (2H, t, J=8.5 Hz), 3.78 (8H, m), 3.20 (6H, m), 2.56 (4H, m), 2.34 (3H, s), 2.23 (3H, s)

LCMS (ESI+) m/z 531.19 (M+H)$^+$

Example 1-D-239

4-(2-Amino-pyrimidin-5-yl)-2-morpholin-4-yl-5,6-dihydro-pyrrolo[2,3-d]pyrimidine-7-carboxylic acid [5-(4-ethyl-piperazin-1-yl)-2-methyl-phenyl]-amide (D-239)

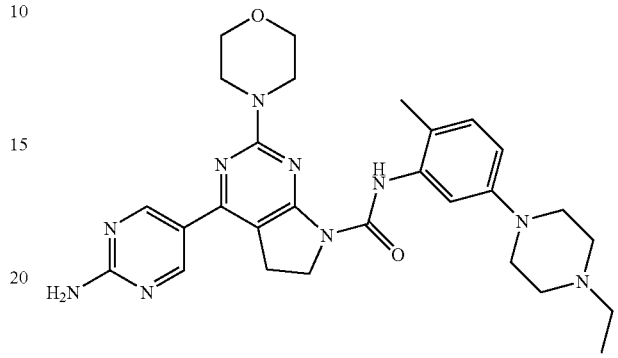

Using 5-(4-ethyl-piperazin-1-yl)-2-methyl-phenylamine (73 mg) obtained using 1-ethyl-piperazine instead of morpholine in the same manner as Step A and Step B in Example 1-D-237, instead of 2-methyl-5-morpholin-4-yl-phenylamine, from bis-(4-methoxy-benzyl)-[5-(2-morpholin-4-yl-6,7-dihydro-5H-pyrrolo[2,3-d]pyrimidin-4-yl)-pyrimidin-2-yl]-amine (200 mg), in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [5-(4-ethyl-piperazin-1-yl)-2-methyl-phenyl]-amide was obtained as a crude product. The PMB groups were removed according to Deprotection method 2, to obtain the desired compound (D-239) as an ivory solid (62 mg, 41%).

$^1$H-NMR (CDCl$_3$) δ: 10.20 (1H, s), 8.90 (2H, s), 7.34 (1H, d, J=2.6 Hz), 7.10 (1H, d, J=8.3 Hz), 6.71 (1H, dd, J=8.3 Hz, 2.6 Hz), 5.31 (2H, s), 4.22 (2H, t, J=8.3 Hz), 3.77 (8H, m), 3.22 (6H, m), 2.59 (4H, m), 2.48 (2H, q, J=7.2 Hz), 2.23 (3H, s), 1.12 (3H, t, J=7.2 Hz)

LCMS (ESI+) m/z 545.15 (M+H)$^+$

Example 1-D-240

4-(2-Amino-pyrimidin-5-yl)-2-morpholin-4-yl-5,6-dihydro-pyrrolo[2,3-d]pyrimidine-7-carboxylic acid (2-methyl-4-morpholin-4-yl-phenyl)-amide (D-240)

Step A 4-(3-Methyl-4-nitro-phenyl)-morpholine

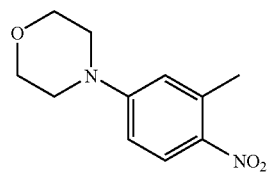

To a DMSO solution (8 ml) of 4-fluoro-2-methyl-1-nitrobenzene (500 mg), potassium carbonate (668 mg) and morpholine (0.42 ml) were added, followed by stirring at 80° C. for 18 hours. This was cooled to room temperature, and water (30 ml) was added, followed by extraction with ethyl acetate (50 ml×2). The organic layer was washed with saturated aqueous sodium chloride solution, followed by drying over magnesium sulfate. After the magnesium sulfate was filtered off, the solvent was distilled off under reduced pressure, to obtain the desired compound as a yellow solid (680 mg, 95%).

Step B

2-Methyl-4-morpholin-4-yl-phenylamine

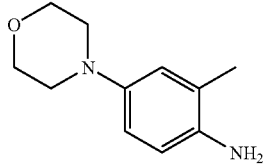

Using 4-(3-methyl-4-nitro-phenyl)-morpholine (680 mg) obtained in Step A instead of 4-(4-methyl-3-nitro-phenyl)-morpholine, in the same manner as Step B in Example 1-D-237, the desired compound was obtained as a brown solid (550 mg, 94%).

Step C 4-(2-Amino-pyrimidin-5-yl)-2-morpholin-4-yl-5,6-dihydro-pyrrolo[2,3-d]pyrimidine-7-carboxylic acid (2-methyl-4-morpholin-4-yl-phenyl)-amide (D-240)

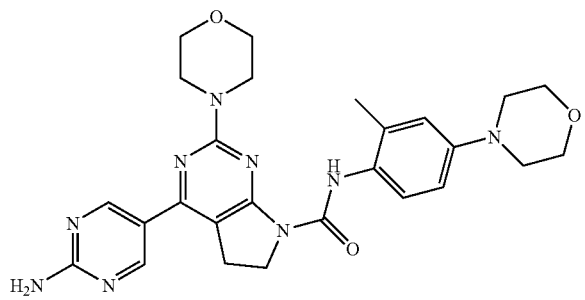

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 2-methyl-4-morpholin-4-yl-phenylamine (39 mg) obtained in Step B instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-methyl-4-morpholin-4-yl-phenyl)-amide was obtained as a crude product. Using 195 mg of this compound, PMB group was removed according to Deprotection method 2, to obtain the desired compound (D-240) (90 mg, 63%).
$^1$H-NMR (CDCl$_3$) δ: 10.23 (1H, s), 8.91 (2H, s), 7.47 (1H, m), 6.82 (2H, m), 5.31 (2H, s), 4.22 (2H, t, J=8.2 Hz), 3.88 (4H, m), 3.77 (8H, m), 3.23 (2H, t, J=8.2 Hz), 3.15 (4H, m), 2.30 (3H, s)
LCMS (ESI+) m/z 518.1 (M+H)$^+$ Example 1-D-241

4-(2-Amino-pyrimidin-5-yl)-2-morpholin-4-yl-5,6-dihydro-pyrrolo[2,3-d]pyrimidine-7-carboxylic acid [2-methyl-4-(4-methyl-piperazin-1-yl)-phenyl]-amide (D-241)

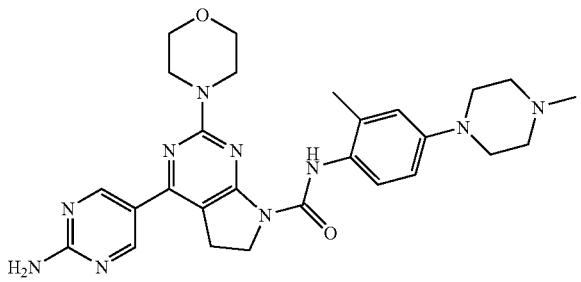

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg), and 2-methyl-4-(4-methyl-piperazin-1-yl)-phenylamine (63 mg) obtained using 1-methyl-piperazine instead of morpholine in the same manner as Step A and Step B in Example 1-D-240, instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-4-(4-methyl-piperazin-1-yl)-phenyl]-amide was obtained as a crude product. The PMB groups were removed according to Deprotection method 2, to obtain the desired compound (D-241) (110 mg, 75%).
$^1$H-NMR (CDCl$_3$) δ: 10.21 (1H, s), 8.90 (2H, s), 7.43 (1H, d, J=8.7 Hz), 6.82 (2H, m), 5.29 (2H, s), 4.21 (2H, t, J=8.5 Hz), 3.77 (8H, m), 3.22 (6H, m), 2.61 (4H, m), 2.38 (3H, s), 2.28 (3H, s)
LCMS (ESI+) m/z 531.2 (M+H)$^+$ Example 1-D-242

4-(2-Amino-pyrimidin-5-yl)-2-morpholin-4-yl-5,6-dihydro-pyrrolo[2,3-d]pyrimidine-7-carboxylic acid [4-(4-ethyl-piperazin-1-yl)-2-methyl-phenyl]-amide (D-242)

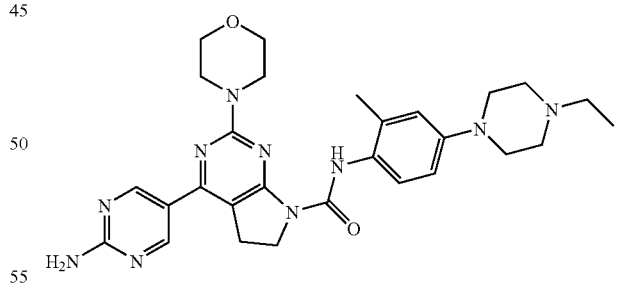

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg), and 4-(4-ethyl-piperazin-1-yl)-2-methyl-phenylamine (67 mg) obtained using 1-ethyl-piperazine instead of morpholine in the same manner as Step A and Step B in Example 1-D-240, instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [4-(4-ethyl-piperazin-1-yl)-2-methyl-phenyl]-amide was obtained as a crude product. The PMB groups were removed according to Deprotection method 2, to obtain the desired compound (D-242) (110 mg, 76%).

$^1$H-NMR (CDCl$_3$) δ: 10.20 (1H, s), 8.90 (2H, s), 7.43 (1H, d, J=8.8 Hz), 6.82 (2H, m), 5.32 (2H, s), 4.22 (2H, t, J=8.5 Hz), 3.77 (8H, m), 3.22 (6H, m), 2.62 (4H, m), 2.49 (2H, q, J=7.2 Hz), 2.29 (3H, s), 1.14 (3H, t, J=7.2 Hz)

LCMS (ESI+) m/z 545.2 (M+H)$^+$

Example 1-D-243

4-(2-Amino-pyrimidin-5-yl)-2-morpholin-4-yl-5,6-dihydro-pyrrolo[2,3-d]pyrimidine-7-carboxylic acid [2-methyl-3-(morpholine-4-carbonyl)-phenyl]-amide (D-243)

Step A (2-Methyl-3-nitro-phenyl)-morpholin-4-yl-methanone

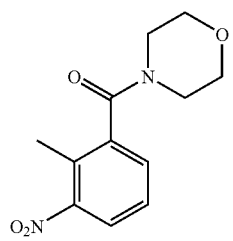

To a DMF solution (10 ml) of 2-methyl-3-nitro-benzoic acid (500 mg) and morpholine (361 mg), WSCI (793 mg), HOBt (560 mg) and N-ethyldiisopropylamine (1.44 ml) were added, followed by stirring at room temperature. To this, water was added, followed by extraction with ethyl acetate, which was subsequently washed with saturated aqueous sodium chloride solution, and the organic layer was dried over sodium sulfate. After the sodium sulfate was filtered off, the solvent was distilled off under reduced pressure, followed by purification by silica gel column chromatography (dichloromethane/methanol=40/1 to 10/1), to obtain the desired compound (587 mg, 85%).

Step B (3-amino-2-methyl-phenyl)-morpholin-4-yl-methanone

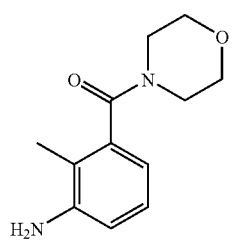

Using (2-methyl-3-nitro-phenyl)-morpholin-4-yl-methanone (587 mg) obtained in Step A instead of 4-(4-methyl-3-nitro-phenyl)-morpholine, in the same manner as Step B in Example 1-D-237, the desired compound was obtained (385 mg, 75%).

Step C 4-(2-Amino-pyrimidin-5-yl)-2-morpholin-4-yl-5,6-dihydro-pyrrolo[2,3-d]pyrimidine-7-carboxylic acid [2-methyl-3-(morpholine-4-carbonyl)-phenyl]-amide (D-243)

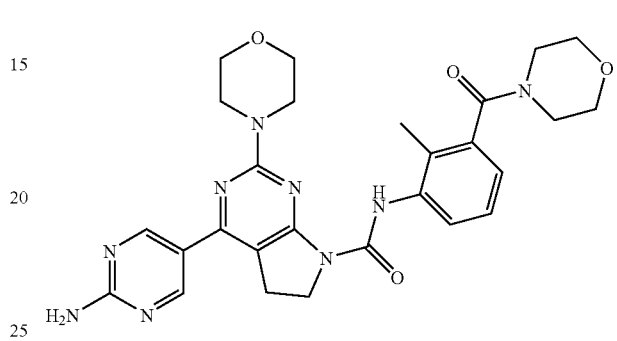

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and (3-amino-2-methyl-phenyl)-morpholin-4-yl-methanone (67 mg) obtained in Step B instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-3-(morpholine-4-carbonyl)-phenyl]-amide was obtained as a crude product. The PMB groups were removed according to Deprotection method 2, to obtain the desired compound (D-243) (60 mg, 40%).

$^1$H-NMR (CDCl$_3$) δ: 10.44 (1H, s), 8.91 (2H, s), 7.66 (1H, d, J=8.1 Hz), 7.30 (1H, d, J=7.6 Hz), 7.03 (1H, d, J=7.5 Hz), 5.30 (2H, s), 4.22 (2H, t, J=8.5 Hz), 3.82 (12H, m), 3.57 (2H, m), 3.26 (4H, m), 2.27 (3H, s)

LCMS (ESI+) m/z 546.2 (M+H)$^+$

Example 1-D-244

4-(2-Amino-pyrimidin-5-yl)-2-morpholin-4-yl-5,6-dihydro-pyrrolo[2,3-d]pyrimidine-7-carboxylic acid [2-methyl-3-(4-methyl-piperazine-1-carbonyl)-phenyl]-amide (D-244)

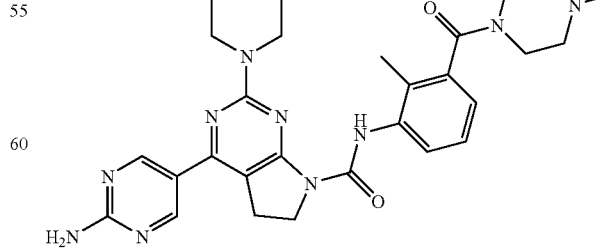

Using bis-(4-methoxy-benzyl)-[5-(2-morpholin-4-yl-6,7-dihydro-5H-pyrrolo[2,3-d]pyrimidin-4-yl)-pyrimidin-2-yl]- amine (150 mg), and (3-amino-2-methyl-phenyl)-(4-methyl-piperazin-1-yl)-methanone (71 mg) obtained using 1-methyl-piperazine instead of morpholine in the same manner as Step A and Step B in Example 1-D-243, instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2-methyl-3-(4-methyl-piperazine-1-carbonyl)-phenyl]-amide was obtained as a crude product. The PMB groups were removed according to Deprotection method 2, to obtain the desired compound (D-244) (45 mg, 29%).

$^1$H-NMR (CDCl$_3$) δ: 10.42 (1H, s), 8.91 (2H, s), 7.66 (1H, d, J=7.9 Hz), 7.29 (1H, d, J=7.8 Hz), 7.03 (1H, d, J=7.4 Hz), 5.28 (2H, s), 4.23 (2H, t, J=8.4 Hz), 3.81 (10H, m), 3.57 (2H, m), 3.25 (4H, m), 2.28 (8H, m)

LCMS (ESI+) m/z 559.2 (M+H)$^+$

Example 1-D-245

4-(2-Amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-2-methyl-phenyl]-amide (D-245)

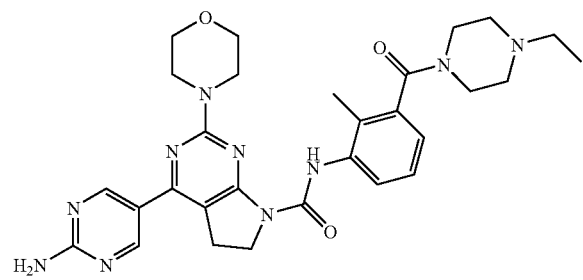

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg), and (3-amino-2-methyl-phenyl)-(4-ethyl-piperazin-1-yl)-methanone (76 mg) obtained using 1-ethyl-piperazine instead of morpholine in the same manner as Step A and Step B in Example 1-D-243, instead of 2-methyl-5-morpholin-4-yl-phenylamine, in the same manner as Step C in Example 1-D-237, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [3-(4-ethyl-piperazine-1-carbonyl)-2-methyl-phenyl]-amide was obtained as a crude product. The PMB groups were removed according to Deprotection method 2, to obtain the desired compound (D-245) (45 mg, 28%).

$^1$H-NMR (CDCl$_3$) δ: 10.42 (1H, s), 8.91 (2H, s), 7.65 (1H, d, J=8.2 Hz), 7.29 (1H, d, J=7.8 Hz), 7.03 (1H, d, J=7.4 Hz), 5.28 (2H, s), 4.22 (2H, t, J=8.3 Hz), 3.82 (10H, m), 3.26 (4H, m), 2.52 (2H, m), 2.44 (2H, q, J=7.2 Hz), 2.26 (3H, s), 1.09 (3H, t, J=7.1 Hz)

LCMS (ESI+) m/z 573.2 (M+H)$^+$

Example 1-D-246

{4-[4-(2-Amino-pyrimidin-5-yl)-2-morpholin-4-yl-5,6-dihydro-pyrrolo[2,3-d]pyrimidin-7-yl]-3-methyl-phenyl}-((2R,6S)-2,6-dimethyl-morpholin-4-yl)-methanone (D-246)

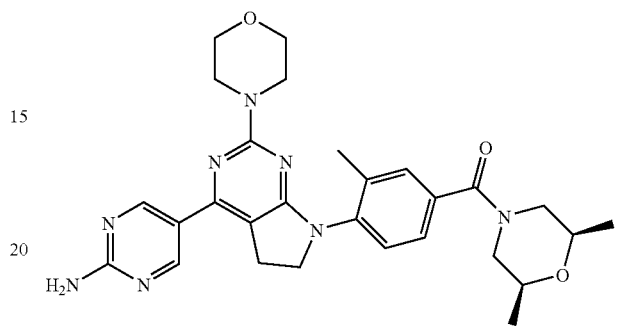

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-bromo-3-methyl-phenyl)-((2R,6S)-2,6-dimethyl-morpholin-4-yl)-methanone (44 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-((2R,6S)-2,6-dimethyl-morpholin-4-yl)-methanone was obtained, and then the PMB groups were removed according to the above Deprotection method 3, to obtain the desired compound (D-246) as a pale yellow powder (22 mg, 45%).

$^1$H-NMR (CD$_3$OD) δ (ppm): 8.70 (2H, s), 7.43-7.38 (3H, m), 4.20 (2H, t, J=8.4 Hz), 3.67 (14H, brs), 3.35 (2H, t, J=8.4 Hz), 2.31 (3H, s), 1.29-1.08 (6H, m).

ESI (LC-MS positive mode) m/z 531 (M+H)$^+$.

Example 1-D-247

4-(2-Amino-pyrimidin-5-yl)-2-morpholin-4-yl-5,6-dihydro-pyrrolo[2,3-d]pyrimidine-7-carbothioic acid [3-(morpholine-4-carbonyl)-phenyl]-amide (D-247)

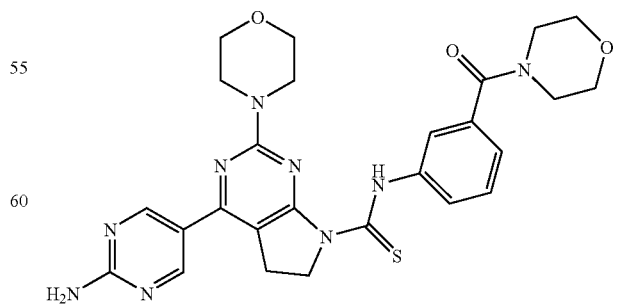

Using bis-(4-methoxy-benzyl)-[5-(2-morpholin-4-yl-6,7-dihydro-5H-pyrrolo[2,3-d]pyrimidin-4-yl)-pyrimidin-2-yl]- amine (81 mg) and (3-amino-phenyl)-morpholin-4-yl-methanone (34 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [3-(morpholine-4-carbonyl)-phenyl]-amide was obtained, and then the PMB groups were removed according to the above Deprotection method 3, to obtain the desired compound (D-247) as a pale yellow powder (50 mg, 61%).

$^1$H-NMR (DMSO-$d_6$) δ (ppm): 13.07 (1H, s), 8.87 (2H, s), 7.82 (1H, s), 7.66 (1H, d, J=8.6 Hz), 7.50 (1H, t, J=7.7 Hz), 7.28-7.24 (1H, m), 7.28 (2H, s), 4.39 (2H, t, J=7.8 Hz), 3.27 (2H, brs), 3.71 (8H, s), 3.62 (8H, brs).

ESI (LC-MS positive mode) m/z 548 (M+H)$^+$.

Example 1-D-248

5-{7-[5-(Morpholine-4-sulfonyl)-pyridin-3-yl]-2-morpholin-4-yl-6,7-dihydro-5H-pyrrolo[2,3-d]pyrimidin-4-yl}-pyrimidin-2-ylamine (D-248)

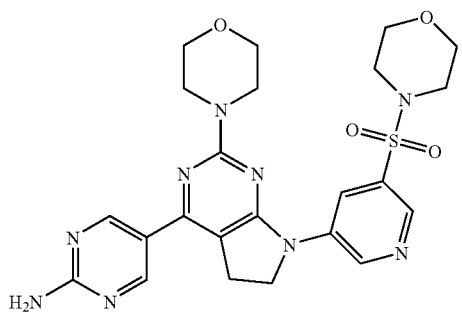

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 4-(5-bromo-pyridine-3-sulfonyl)-morpholine (prepared from 5-bromo-pyridine-3-sulfonyl chloride and morpholine, 60 mg) instead of 4-bromobenzoic acid methyl ester used in Example 1-D-8, in the same manner as Example 1-D-07, a crude product of bis-(4-methoxy-benzyl)-(5-{7-[5-(morpholine-4-sulfonyl)-pyridin-3-yl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 3, to obtain the desired compound (D-248) as an ivory powder (65 mg, 67%).

$^1$H-NMR (DMSO-$d_6$) δ (ppm): 9.18 (1H, d, J=2.1 Hz), 8.99 (1H, d, J=2.3 Hz), 8.84 (2H, s), 8.52 (1H, d, J=1.8 Hz), 7.12 (2H, s), 4.23 (2H, t, J=7.8 Hz), 3.74-3.66 (12H, m), 3.37 (2H, t, J=7.8 Hz), 2.97-2.93 (4H, m).

ESI (LC-MS positive mode) m/z 526 (M+H)$^+$.

Example 1-D-249

5-{7-[5-(4-Methyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-249)

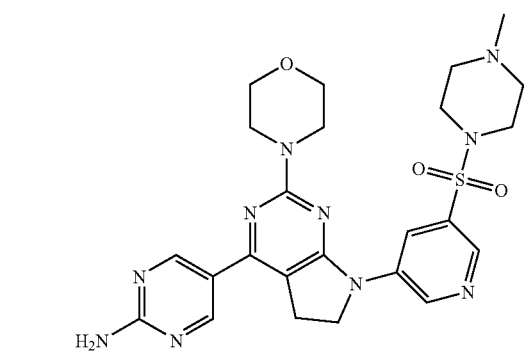

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 1-(5-bromo-pyridine-3-sulfonyl)-4-methyl-piperazine (prepared from 5-bromo-pyridine-3-sulfonyl chloride and N-methylpiperazine, 65 mg) instead of 4-bromobenzoic acid methyl ester used in Example 1-D-8, in the same manner as Example 1-D-07, a crude product of bis-(4-methoxy-benzyl)-(5-{7-[5-(4-methyl-piperazine-1-sulfonyl)-pyridin-3-yl]-2-morpholin-4-yl-6,7-dihydro-5H-pyrrolo[2,3-d]pyrimidin-4-yl}-pyrimidin-2-yl)-amine was obtained, and then the PMB groups were removed according to the above Deprotection method 3, to obtain the desired compound (D-249) as a milky white powder (66 mg, 66%).

$^1$H-NMR (DMSO-$d_6$) δ (ppm): 9.17 (1H, s), 8.97 (1H, d, J=1.8 Hz), 8.84 (2H, s), 8.52 (1H, s), 7.12 (2H, s), 4.22 (2H, t, J=8.0 Hz), 3.75-3.70 (8H, m), 3.37 (2H, t, J=8.0 Hz), 2.97 (4H, brs), 2.38 (4H, brs), 2.15 (3H, s).

ESI (LC-MS positive mode) m/z 539 (M+H)$^+$.

Example 1-D-250

5-{7-[5-(4-Ethyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-250)

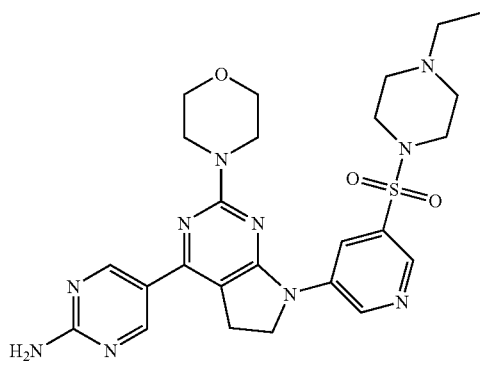

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 1-(5-bromo-pyridine-3-sulfonyl)-4- ethyl-piperazine (prepared from 5-bromo-pyridine-3-sulfonyl chloride and N-ethylpiperazine, 70 mg) instead of 4-bromobenzoic acid methyl ester used in Example 1-D-8, in the same manner as Example 1-D-07, a crude product of (5-{7-[5-(4-ethyl-piperazine-1-sulfonyl)-pyridin-3-yl]-2-morpholin-4-yl-6,7-dihydro-5H-pyrrolo[2,3-d]pyrimidin-4-yl}-pyrimidin-2-yl)-bis-(4-methoxy-benzyl)-amine was obtained, and then the PMB groups were removed according to the above Deprotection method 3, to obtain the desired compound (D-250) as a milky white powder (46 mg, 45%).

$^1$H-NMR (DMSO-d$_6$) δ (ppm): 9.18 (1H, s), 8.96 (1H, d, J=2.1 Hz), 8.84 (2H, s), 8.51 (1H, s), 7.17 (2H, s), 4.22 (2H, t, J=7.8 Hz), 3.75-3.69 (8H, m), 3.37 (2H, t, J=7.8 Hz), 2.95 (4H, brs), 2.43 (4H, brs), 2.30 (2H, q, J=7.1 Hz), 0.92 (3H, t, J=7.1 Hz).

ESI (LC-MS positive mode) m/z 553 (M+H)$^+$.

Example 1-D-251

4-(2-Amino-pyrimidin-5-yl)-2-morpholin-4-yl-5,6-dihydro-pyrrolo[2,3-d]pyrimidine-7-carbothioic acid [4-(morpholine-4-carbonyl)-phenyl]-amide (D-251)

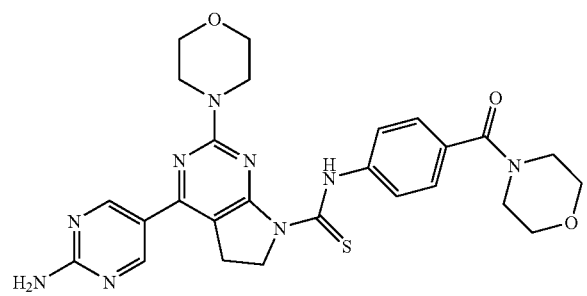

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and (4-amino-phenyl)-morpholin-4-yl-methanone (37.1 mg) obtained in Step B in Example 1-D-104 instead of 4-(4-ethyl-piperazin-1-yl)-2,6-difluoro-phenylamine, and thiophosgene (22.9 µl) instead of triphosgene, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [4-(morpholine-4-carbonyl)-phenyl]-amide was obtained as a crude product. Further, in the same manner as Step D in Example 1-D-18, the desired compound (D-251) was obtained as a colorless solid (40.1 mg, 68%).

$^1$H-NMR (TFA-d$_1$) δ: 9.18 (2H, s), 7.71 (2H, d, J=8.3 Hz), 7.60 (2H, d, J=8.3 Hz), 4.74 (2H, t, J=7.7 Hz), 4.12-4.04 (8H, brm), 4.01-3.95 (6H, brm), 3.82-3.77 (2H, brm), 3.33-3.26 (2H, brm).

ESI (LC-MS positive mode) m/z 548 (M+H)$^+$

Example 1-D-252

4-(2-Amino-pyrimidin-5-yl)-2-morpholin-4-yl-5,6-dihydro-pyrrolo[2,3-d]pyrimidine-7-carbothioic acid [2-methyl-4-(morpholine-4-carbonyl)-phenyl]-amide (D-252)

Using (bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and (4-amino-3-methyl-phenyl)-morpholin-4-yl-methanone (49.0 mg, 0.222 mmol) instead of (4-ethyl-piperazine-1-yl)-(3-amino-4-methyl-phenyl)-methanone, thiourea was formed in the same manner as Step C in Example 1-D-17, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-4-(morpholine-4-carbonyl)-phenyl]-amide as a brown solid (80.2 mg), and then the PMB groups were removed according to the above Deprotection method 3, to obtain the desired compound (D-252) as a yellow powder (24.9 mg, 30%).

$^1$H-NMR (CDCl$_3$) δ (ppm): 12.54 (1H, s), 8.91 (2H, s), 7.53 (1H, d, J=8.1 Hz), 7.37 (1H, s), 7.28 (1H, d, J=8.1 Hz), 5.50 (2H, brs), 4.58 (2H, t, J=7.9 Hz), 3.84-3.64 (12H, m), 3.25 (2H, t, J=7.9 Hz), 2.34 (3H, s), 2.14-1.91 (4H, m).

ESI (LC-MS positive mode) m/z 562 (M+H)$^+$.

Example 1-D-253

4-(2-Amino-pyrimidin-5-yl)-2-morpholin-4-yl-5,6-dihydro-pyrrolo[2,3-d]pyrimidine-7-carbothioic acid [2-methyl-4-(4-methyl-piperazine-1-carbonyl)-phenyl]-amide (D-253)

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and (4-amino-3-methyl-phenyl)-(4-methyl-piperazin-1-yl)-methanone (51.9 mg, 0.222 mmol) instead of (4-ethyl-piperazine-1-yl)-(3-amino-4-methyl-phenyl)-methanone, thiourea was formed in the same manner as Step C in Example 1-D-17, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-4-(4-methyl-piperazine-1-carbonyl)-phenyl]-amide as a brown solid (64.2 mg), and then the PMB groups were removed according to the above Deprotection method 3, to obtain the desired compound (D-253) as a yellow powder (32.7 mg, 38%).

$^1$H-NMR (CDCl$_3$) δ (ppm): 12.57 (1H, s), 8.92 (2H, s), 7.58 (1H, d, J=8.1 Hz), 7.39 (1H, s), 7.31 (1H, d, J=8.1 Hz), 5.47 (2H, brs), 4.58 (2H, t, J=8.1 Hz), 3.86-3.42 (16H, m), 3.26 (2H, t, J=8.1 Hz), 2.81 (3H, s), 2.35 (3H, s).

ESI (LC-MS positive mode) m/z 575 (M+H)$^+$.

Example 1-D-254

4-(2-Amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-2-methyl-phenyl]-amide (D-254)

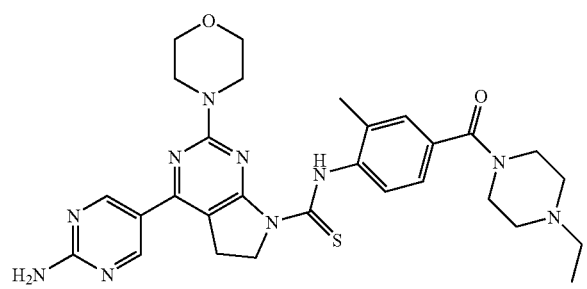

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and (4-amino-3-methyl-phenyl)-(4-ethyl-piperazin-1-yl)-methanone (55.0 mg, 0.222 mmol) instead of (4-ethyl-piperazine-1-yl)-(3-amino-4-methyl-phenyl)-methanone, thiourea was formed in the same manner as Step C in Example 1-D-17, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [4-(4-ethyl-piperazine-1-carbonyl)-2-methyl-phenyl]-amide as a brown solid (68.4 mg), and then the PMB groups were removed according to the above Deprotection method 3, to obtain the desired compound (D-254) as a yellow powder (33.7 mg, 39%).

$^1$H-NMR (CDCl$_3$) δ (ppm): 12.57 (1H, s), 8.92 (2H, s), 7.58 (1H, d, J=8.1 Hz), 7.39 (1H, s), 7.31 (1H, d, J=8.1 Hz), 5.44 (2H, brs), 4.58 (2H, t, J=8.1 Hz), 3.75-3.72 (16H, m), 3.26 (2H, t, J=8.1 Hz), 3.10 (2H, q, J=6.9 Hz), 2.35 (3H, s), 1.39 (1H, t, J=6.9 Hz).

ESI (LC-MS positive mode) m/z 589 (M+H)$^+$.

Example 1-D-255

4-(2-Amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide (D-255)

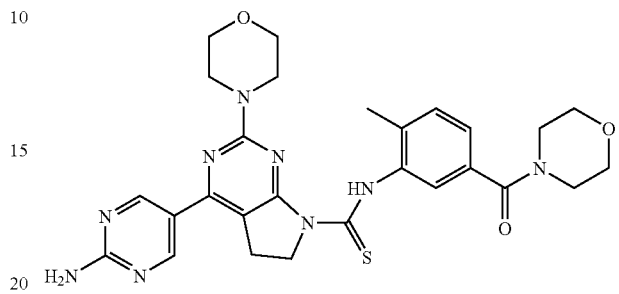

In the same manner as Example 1-D-17, using bis-(4-methoxy-benzyl)-[5-(2-morpholin-4-yl-6,7-dihydro-5H-pyrrolo[2,3-d]pyrimidin-4-yl)-pyrimidin-2-yl]-amine and (4-amino-3-methyl-phenyl)-(morpholine-4-yl)-methanone instead of (4-ethyl-piperazine-1-yl)-(3-amino-4-methyl-phenyl)-methanone, a crude product of 4-(2-bis-(4-methoxy-benzyl)-amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide was obtained. Using a crude product (150 mg) of 4-(2-bis-(4-methoxy-benzyl)-amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide, according to the above Deprotection method 2, 4-(2-amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide was obtained as a colorless powder (68 mg, 65%).

$^1$H-NMR (DMSO-d$_6$) (ppm): 12.4 (1H, s), 8.85 (2H, s), 7.49 (1H, s), 7.41 (1H, m), 7.26 (1H, m), 7.25 (2H, s), 4.35 (2H, m), 3.65-3.45 (16H, m), 3.30 (2H, m), 2.26 (3H, s).

ESI (LC-MS positive mode) m/z 562 (M+H)$^+$.

Example 1-D-256

4-(2-Amino-pyrimidin-5-yl)-2-morpholin-4-yl-5,6-dihydro-pyrrolo[2,3-d]pyrimidine-7-carboxylic acid [2,6-difluoro-4-(4-methyl-piperazine-1-carbonyl)-phenyl]-amide (D-256)

Step A

[3,5-Difluoro-4-(4-methoxy-benzylamino)-phenyl]-(4-methyl-piperazin-1-yl)-methanone

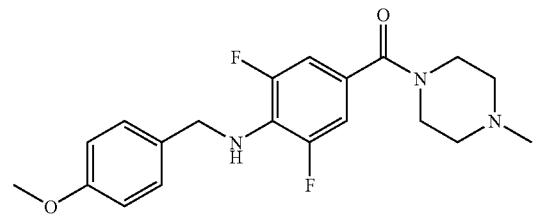

Using 3,5-difluoro-4-(4-methoxy-benzylamino)-benzoic acid (95.4 mg) obtained in Step B in Example 1-D-24 and 1-methyl-piperazine (43.3 μl) instead of 1-ethyl-piperazine, in the same manner as Step C in Example 1-D-24, the desired compound was obtained as a crude product (82 mg, 67%).

Step B (4-Amino-3,5-difluoro-phenyl)-(4-methyl-piperazin-1-yl)-methanone

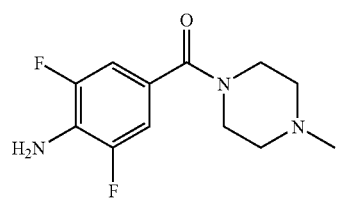

Using [3,5-difluoro-4-(4-methoxy-benzylamino)-phenyl]-(4-methyl-piperazin-1-yl)-methanone (82 mg) obtained in Step A instead of [3,5-difluoro-4-(4-methoxy-benzylamino)-phenyl]-(4-ethyl-piperazin-1-yl)-methanone, in the same manner as Step D in Example 1-D-24, the desired compound was obtained (46 mg, 82%).

Step C 4-(2-Amino-pyrimidin-5-yl)-2-morpholin-4-yl-5,6-dihydro-pyrrolo[2,3-d]pyrimidine-7-carboxylic acid [2,6-difluoro-4-(4-methyl-piperazine-1-carbonyl)-phenyl]-amide (D-256)

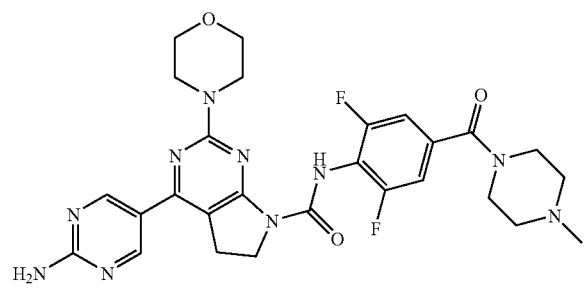

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and (4-amino-3,5-difluoro-phenyl)-(4-methyl-piperazin-1-yl)-methanone (46 mg) obtained in Step B instead of (4-amino-3,5-difluoro-phenyl)-(4-ethyl-piperazin-1-yl)-methanone, in the same manner as Step E in Example 1-D-24, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2,6-difluoro-4-(4-methyl-piperazine-1-carbonyl)-phenyl]-amide was obtained as a crude product. The PMB groups were removed according to Deprotection method 3, to obtain the desired compound (D-256) as a colorless solid (3.0 mg, 3%).
$^1$H-NMR (DMSO-d$_6$) δ: 10.59 (1H, s), 8.85 (2H, s), 7.27 (2H, t, J=5.8 Hz), 7.23 (2H, brs), 4.04 (2H, t, J=8.2 Hz), 3.78-3.52 (10H, brm), 3.30-3.20 (4H, brm), 2.41-2.26 (4H, brm), 2.20 (3H, s).
ESI (LC-MS positive mode) m/z 581 (M+H)$^+$ Example 1-D-257

4-(2-Amino-pyrimidin-5-yl)-2-morpholin-4-yl-5,6-dihydro-pyrrolo[2,3-d]pyrimidine-7-carboxylic acid [2,6-difluoro-4-(morpholine-4-carbonyl)-phenyl]-amide (D-257)

Step A

[3,5-Difluoro-4-(4-methoxy-benzylamino)-phenyl]-morpholin-4-yl-methanone

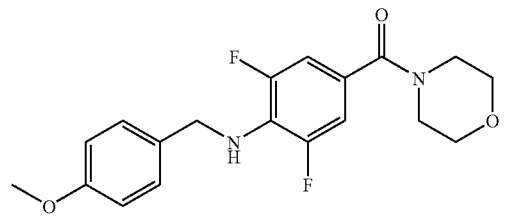

Using 3,5-difluoro-4-(4-methoxy-benzylamino)-benzoic acid (95.4 mg) obtained in Step B in Example 1-D-24 and morpholine (33.8 μl) instead of 1-ethyl-piperazine, in the same manner as Step C in Example 1-D-24, the desired compound was obtained as a crude product (111 mg, 94%).

Step B (4-Amino-3,5-difluoro-phenyl)-morpholin-4-yl-methanone

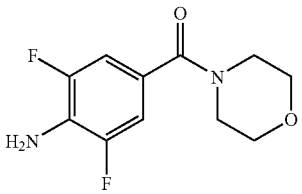

Using [3,5-difluoro-4-(4-methoxy-benzylamino)-phenyl]-morpholin-4-yl-methanone (111 mg) obtained in Step A instead of [3,5-difluoro-4-(4-methoxy-benzylamino)-phenyl]-(4-ethyl-piperazin-1-yl)-methanone, in the same manner as Step D in Example 1-D-24, the desired compound was obtained (58.5 mg, 79%).

Step C 4-(2-Amino-pyrimidin-5-yl)-2-morpholin-4-yl-5,6-dihydro-pyrrolo[2,3-d]pyrimidine-7-carboxylic acid [2,6-difluoro-4-(morpholine-4-carbonyl)-phenyl]-amide (D-257)

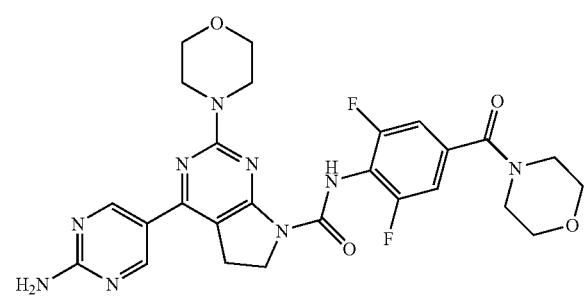

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and (4-amino-3,5-difluoro-phenyl)-morpholin-4-yl-methanone (43.6 mg) obtained in Step B instead of (4-amino-3,5-difluoro-phenyl)-(4-ethyl-piperazin-1-yl)-methanone, in the same manner as Step E in Example 1-D-24, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid [2,6-difluoro-4-(morpholine-4-carbonyl)-phenyl]-amide was obtained as a crude product. The PMB groups were removed according to Deprotection method 3, to obtain the desired compound (D-257) as a colorless solid (12.1 mg, 14%).

$^1$H-NMR (DMSO-$d_6$) δ: 10.59 (1H, s), 8.84 (2H, s), 7.30 (2H, d, J=8.4 Hz), 7.21 (1H, s), 4.03 (2H, t, J=8.2 Hz), 3.74-3.55 (16H, brm), 3.26-3.21 (2H, m).

ESI (LC-MS positive mode) m/z 568 (M+H)$^+$

Example 1-D-258

4-[4-(2-Amino-pyrimidin-5-yl)-2-morpholin-4-yl-5,6-dihydro-pyrrolo[2,3-d]pyrimidin-7-yl]-3-methyl-N-pyridin-4-yl-benzamide (D-258)

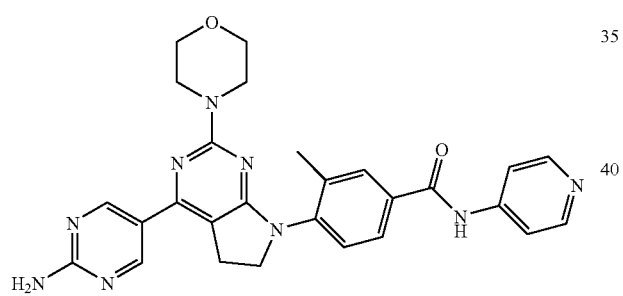

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and 4-bromo-3-methyl-N-pyridin-4-yl-benzamide (41 mg) instead of 4-chloropicolinic acid t-butylamide, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-N-pyridin-4-yl-benzamide was obtained, and then the PMB groups were removed according to the above Deprotection method 3, to obtain the desired compound (D-258) as a pale yellow powder (22 mg, 9%).

$^1$H-NMR (DMSO-$d_6$) δ (ppm): 11.12 (1H, s), 8.80 (1H, s), 8.64 (1H, d, J=5.8 Hz), 8.09 (1H, d, J=6.8 Hz), 7.94 (1H, s), 7.88 (1H, d, J=8.3 Hz), 7.52 (1H, d, J=8.3 Hz), 7.33 (1H, s), 7.14 (1H, s), 7.04 (1H, s), 6.95 (1H, s), 4.05 (2H, t, J=8.1 Hz), 3.56 (4H, s), 3.39 (6H, s), 2.31 (3H, s).

ESI (LC-MS positive mode) m/z 510 (M+H)$^+$.

Example 1-D-259

4-[4-(2-Amino-pyrimidin-5-yl)-2-morpholin-4-yl-5,6-dihydro-pyrrolo[2,3-d]pyrimidin-7-yl]-3-methyl-N-pyridin-4-ylmethyl-benzamide (D-259)

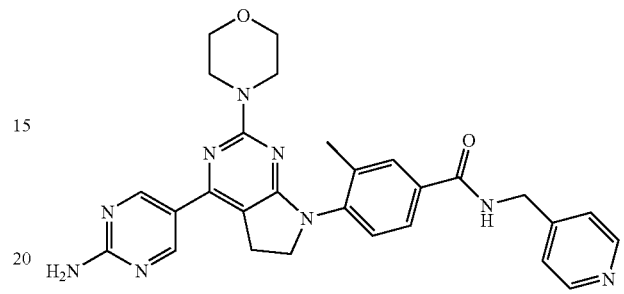

Step A 4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-3-methyl-benzoic acid Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 4-bromo-3-methylbenzoic acid (60 mg) instead of 4-bromobenzoic acid, in the same manner as Step A in Example 1-D-19, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-benzoic acid (31 mg, 25%) was obtained.

Step B

4-[4-(2-Amino-pyrimidin-5-yl)-2-morpholin-4-yl-5,6-dihydro-pyrrolo[2,3-d]pyrimidin-7-yl]-3-methyl-N-pyridin-4-ylmethyl-benzamide (D-259)

4-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-3-methyl-benzoic acid obtained above the step A (31 mg) and 4-(aminomethyl)-pyridine (6 μl) were treated in the same manner as Step B in Example 1-D-19 to give a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-N-pyridin-4-ylmethyl-benzamide, and then the PMB groups were removed according to the above Deprotection method 3, to obtain the desired compound (D-259) as a pale brown oil (10 mg, 10%).

$^1$H-NMR (CD$_3$OD) δ (ppm): 8.83 (2H, s), 8.51 (2H, s), 7.86 (1H, d, J=1.8 Hz), 7.78 (1H, d, J=8.2 Hz), 7.45-7.41 (3H, m), 5.49 (2H, d, J=0.3 Hz), 4.64 (2H, s), 4.08 (2H, t, J=8.0 Hz), 3.64 (8H, brs), 3.39 (2H, t, J=8.0 Hz), 2.33 (3H, s).

ESI (LC-MS positive mode) m/z 524 (M+H)$^+$.

Example 1-D-260

4-Methyl-5-(2-morpholin-4-yl-7-pyridin-3-yl-6,7-dihydro-5H-pyrrolo[2,3-d]pyrimidin-4-yl)-pyrimidin-2-ylamine (D-260)

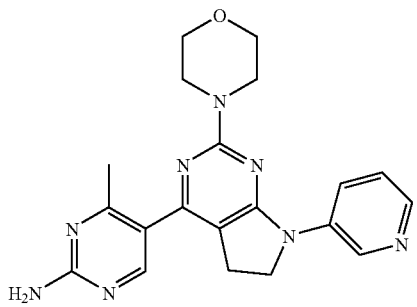

Step A

To a solution of (5-bromo-4-methyl-pyrimidin-2-yl)-bis-(4-methoxy-benzyl)-amine (1.28 g) obtained through the reaction of 5-bromo-4-methyl-pyrimidin-2-ylamine and 4-methoxybenzyl chloride in DMF in the presence of 60% oily sodium hydride, and boric acid triisopropyl (1.94 ml) in THF/toluene (4.2 ml/17 ml), at −78° C., n-butyl lithium-hexane solution (1.6 M, 4.5 ml) was added dropwise, followed by stirring at −78° C. for 1 hour. To the reaction mixture, water (10 ml) was added, and a colorless precipitate resulting from the addition of concentrated HCl (500 μl) was filtered, to obtain 2-{bis-(4-methoxy-benzyl)-amino}-4-methyl-pyrimidin-5-boronic acid. Then, the resulting colorless precipitate (787 mg), pinacol (248 mg) and magnesium sulfate (248 mg) were stirred in dichloromethane (10 ml) for 1 hour, followed by filtering off insolubles, and the filtrate was concentrated under reduced pressure, to obtain bis-(4-methoxy-benzyl)-[4-methyl-5-(4,4,5,5-tetramethyl-[1,3,2]dioxaborolan-2-yl)-pyrimidin-2-yl]-amine (275 mg, 29%) as a colorless amorphous.

Step B

Using 4-chloro-2-morpholin-4-yl-7-pyridin-3-yl-6,7-dihydro-5H-pyrrolo[2,3-d]pyrimidine (64 mg) obtained in Step A in Example 1-B-02 and bis-(4-methoxy-benzyl)-[4-methyl-5-(4,4,5,5-tetramethyl-[1,3,2]dioxaborolan-2-yl)-pyrimidin-2-yl]-amine (105 mg) obtained in Step A in Example 1-D-260 instead of bis-(4-methoxybenzyl)-[5-(4,4,5,5-tetramethyl-[1,3,2]dioxaborolan-2-yl)-pyrimidin-2-yl]amine used in Step D in Example 1-B-01, the same operation as Step D in Example 1-B-01 was carried out, to obtain the desired compound (D-260) as a pale yellow powder (34 g, 43%).

$^1$H-NMR (DMSO-$d_6$) δ (ppm): 9.07 (1H, d, J=2.3 Hz), 8.23 (1H, s), 8.23 (1H, dd, J=8.7, 3.0 Hz), 7.69 (1H, td, J=5.4, 2.7 Hz), 7.42 (1H, dd, J=8.7, 4.8 Hz), 6.77 (2H, s), 4.08 (2H, t, J=8.2 Hz), 3.67 (8H, brs), 3.04 (2H, t, J=8.2 Hz), 2.33 (3H, s).

ESI (LC-MS positive mode) m/z 391 (M+H)$^+$.

Example 1-D-261

4-Methyl-5-(2-morpholin-4-yl-7-pyridin-4-yl-6,7-dihydro-5H-pyrrolo[2,3-d]pyrimidin-4-yl)-pyrimidin-2-ylamine (D-261)

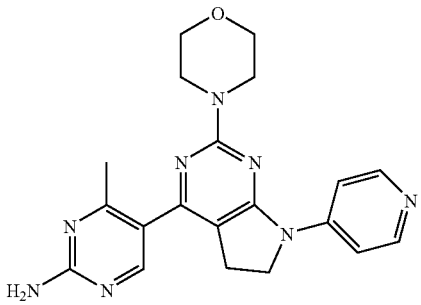

Using 4-chloro-2-morpholin-4-yl-7-pyridin-4-yl-6,7-dihydro-5H-pyrrolo[2,3-d]pyrimidine (64 mg) obtained in Step C in Example 1-B-01 and bis-(4-methoxy-benzyl)-[4-methyl-5-(4,4,5,5-tetramethyl-[1,3,2]dioxaborolan-2-yl)-pyrimidin-2-yl]-amine (105 mg) obtained in Step A in Example 1-D-260 instead of bis-(4-methoxy-benzyl)-[5-(4,4,5,5-tetramethyl-[1,3,2]dioxaborolan-2-yl)-pyrimidin-2-yl]amine used in Step D in Example 1-B-01, the same operation as Step D in Example 1-B-01 was carried out, to obtain the desired compound (D-261) as a colorless powder (19 mg, 25%).

$^1$H-NMR (DMSO-$d_6$) δ (ppm): 8.45 (2H, d, J=6.4 Hz), 8.24 (2H, s), 7.81 (2H, d, J=6.4 Hz), 6.79 (2H, s), 4.05 (2H, t, J=8.2 Hz), 3.69 (8H, s), 3.04 (2H, t, J=8.2 Hz), 2.32 (3H, s).

ESI (LC-MS positive mode) m/z 391 (M+H)$^+$.

Example 1-D-262

4-(2-Amino-pyrimidin-5-yl)-2-morpholin-4-yl-5,6-dihydro-pyrrolo[2,3-d]pyrimidine-7-carboxylic acid benzyl-methyl-amide (D-262)

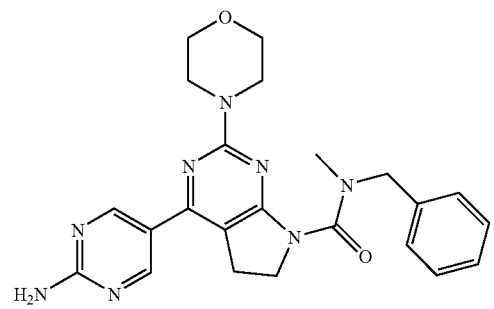

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80 mg) and N-methylbenzylamine (69 μl) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid benzyl-methyl-amide was obtained, and then the PMB groups were removed according to the above Deprotection method 3, to obtain the desired compound (D-262) as a colorless powder (20 mg, 30%).

$^{1}$H-NMR (DMSO-$d_{6}$) δ (ppm): 8.76 (2H, s), 7.36-7.29 (5H, m), 7.09 (2H, s), 4.61 (2H, s), 3.84 (2H, t, J=8.0 Hz), 3.57-3.50 (8H, m), 3.15 (2H, t, J=8.1 Hz), 2.91 (3H, s).

ESI (LC-MS positive mode) m/z 447 (M+H)$^{+}$.

Example 1-D-263

4-(2-Amino-pyrimidin-5-yl)-2-morpholin-4-yl-5,6-dihydro-pyrrolo[2,3-d]pyrimidine-7-carboxylic acid methyl-phenethyl-amide (D-263)

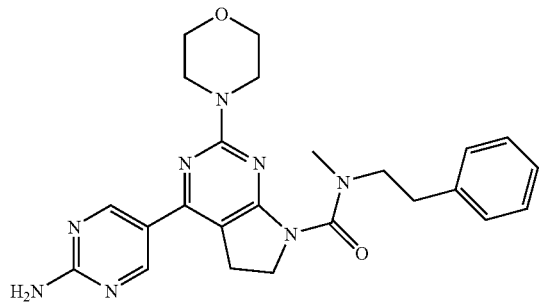

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80 mg) and N-methylphenethylamine (78 μl) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-phenethyl-amide was obtained, and then the PMB groups were removed according to the above Deprotection method 3, to obtain the desired compound (D-263) as a colorless powder (37 mg, 56%).

$^{1}$H-NMR (DMSO-$d_{6}$) δ (ppm): 8.76 (2H, s), 7.33-7.18 (5H, m), 7.08 (2H, s), 3.62-3.58 (12H, m), 3.07 (2H, t, J=7.7 Hz), 2.99 (3H, s), 2.86 (2H, t, J=7.1 Hz).

ESI (LC-MS positive mode) m/z 461 (M+H)$^{+}$.

Example 1-D-264

4-[4-(2-Amino-pyrimidin-5-yl)-2-morpholin-4-yl-5,6-dihydro-pyrrolo[2,3-d]pyrimidin-7-yl]-N-pyridin-4-ylmethyl-benzamide (D-264)

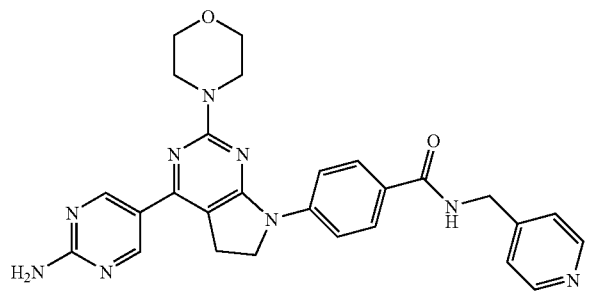

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (80.0 mg, 0.121 mmol) obtained in Step A in Example 1-D-19 and 4-(aminomethyl)pyridine (18.5 μl, 0.182 mmol) instead of 3-(aminomethyl)pyridine, amidation was carried out in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-pyridin-4-ylmethyl-benzamide as a brown solid (119 mg), and then the PMB groups were removed according to the above Deprotection method 3, to obtain the desired compound (D-264) as a yellow powder (46.7 mg, 76%).

$^{1}$H-NMR (DMSO-$d_{6}$) δ (ppm): 8.83 (2H, s), 8.17 (2H, d, J=8.7 Hz), 8.01 (2H, d, J=8.7 Hz), 7.55 (2H, d, J=3.6 Hz), 7.25 (2H, d, J=3.6 Hz), 7.11-7.06 (3H, m), 4.16 (2H, t, J=7.9 Hz), 3.78-3.69 (8H, m), 3.39-3.24 (4H, m).

ESI (LC-MS positive mode) m/z 510 (M+H)$^{+}$.

Example 1-D-265

{4-[4-(2-Amino-pyrimidin-5-yl)-2-morpholin-4-yl-5,6-dihydro-pyrrolo[2,3-d]pyrimidin-7-yl]-phenyl}-(4-pyridin-4-yl-piperazin-1-yl)-methanone (D-265)

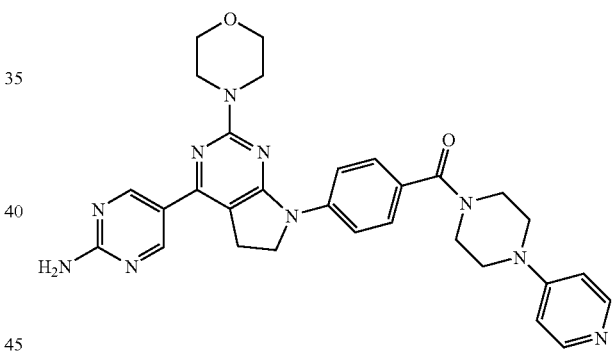

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (80.0 mg, 0.121 mmol) obtained in Step A in Example 1-D-19 and 1-(4-pyridyl)piperazine (29.7 mg, 0.182 mmol) instead of 3-(aminomethyl)pyridine, amidation was carried out in the same manner as Step B in Example 1-D-19, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-pyridin-4-yl-piperazin-1-yl)-methanone as a brown solid (116 mg), and then the PMB groups were removed according to the above Deprotection method 3, to obtain the desired compound (D-265) as a yellow powder (47.4 mg, 69%).

$^{1}$H-NMR (CDCl$_{3}$) δ (ppm): 8.90 (2H, s), 8.32 (2H, d, J=5.1 Hz), 7.87 (2H, d, J=8.9 Hz), 7.52 (2H, d, J=8.9 Hz), 6.68 (2H, d, J=5.1 Hz), 5.22 (2H, s), 4.13 (2H, t, J=8.3 Hz), 3.84-3.82 (8H, m), 3.42-3.38 (4H, m), 3.32 (2H, t, J=8.3 Hz), 1.62-1.58 (4H, m).

ESI (LC-MS positive mode) m/z 565 (M+H)$^{+}$.

Example 1-D-266

5-{7-[4-(4-Ethyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-266)

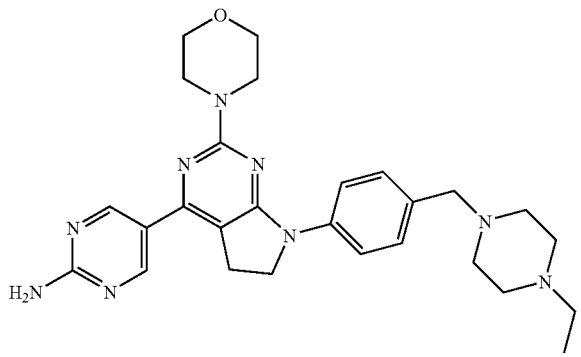

In the same manner as Example 1-D-26, using 1-ethylpiperazine instead of 1-methylpiperazine, a crude product of 5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-yl-bis-(4-methoxy-benzyl)-amine was obtained. Using a crude product (117 mg) of 5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-yl-bis-(4-methoxy-benzyl)-amine, according to the above Deprotection method 2, 5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-ylamine was obtained as a colorless powder (61 mg, 77%).

$^1$H-NMR (DMSO-D$_6$) δ (ppm): 8.81 (2H, s), 7.79 (2H, d, J=7.3 Hz), 7.29 (2H, d, J=7.3 Hz), 7.05 (2H, s), 4.08 (2H, m), 3.70 (8H, s), 3.41-3.25 (4H, m), 2.55-2.28 (10H, m), 0.97 (3H, br.t).

ESI (LC-MS positive mode) m/z 502 (M+H)$^+$.

Example 1-D-267

{4-[4-(2-Amino-pyrimidin-5-yl)-2-morpholin-4-yl-5,6-dihydro-pyrrolo[2,3-d]pyrimidin-7-yl]-3-methyl-phenyl}-pyrrolidin-1-yl-methanone (D-267)

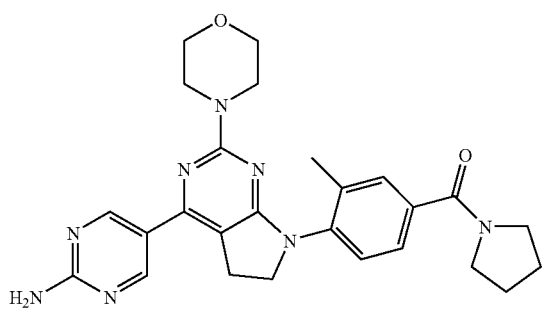

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-bromo-3-methyl-phenyl)-pyrrolidin-1-yl-methanone (38 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-pyrrolidin-1-yl-methanone was obtained, and then the PMB groups were removed according to the above Deprotection method 3, to obtain the desired compound (D-267) as a pale yellow powder (7 mg, 16%).

$^1$H-NMR (CDCl$_3$) δ (ppm): 8.86 (2H, s), 8.83 (1H, s), 7.98 (1H, s), 7.46 (1H, s), 7.38 (1H, d, J=7.3 Hz), 7.27 (1H, d, J=8.1 Hz), 4.00 (2H, t, J=8.2 Hz), 3.69 (8H, s), 3.50 (2H, t, J=6.2 Hz), 3.32 (2H, t, J=7.8 Hz), 3.22 (2H, t, J=7.7 Hz), 2.28 (3H, s), 2.01-1.89 (4H, m).

ESI (LC-MS positive mode) m/z 487 (M+H)$^+$.

Example 1-D-268

{4-[4-(2-Amino-pyrimidin-5-yl)-2-morpholin-4-yl-5,6-dihydro-pyrrolo[2,3-d]pyrimidin-7-yl]-3-methyl-phenyl}-piperidin-1-yl-methanone (D-268)

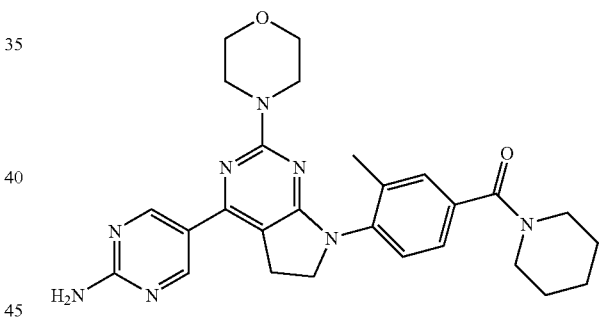

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-bromo-3-methyl-phenyl)-piperidin-1-yl-methanone (40 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-piperidin-1-yl-methanone was obtained, and then the PMB groups were removed according to the above Deprotection method 3, to obtain the desired compound (D-268) as a pale brown powder (14 mg, 30%).

$^1$H-NMR (CDCl$_3$) δ (ppm): 8.87 (3H, s), 7.99 (1H, s), 7.32-7.28 (3H, m), 3.99 (2H, t, J=7.9 Hz), 3.69 (8H, s), 3.41 (2H, s), 3.32 (2H, t, J=7.8 Hz), 3.21 (2H, t, J=7.8 Hz), 2.28 (3H, s), 1.69-1.58 (6H, m).

ESI (LC-MS positive mode) m/z 501 (M+H)$^+$.

Example 1-D-269

4-Methyl-piperazine-1-carboxylic acid {3-[4-(2-amino-pyrimidin-5-yl)-2-morpholin-4-yl-5,6-dihydro-pyrrolo[2,3-d]pyrimidin-7-yl]-phenyl}-amide (D-269)

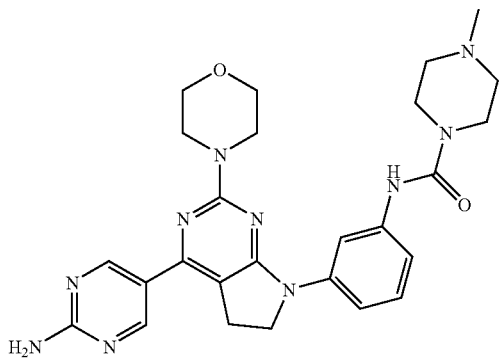

Using {5-[7-(3-amino-phenyl)-2-morpholin-4-yl-6,7-dihydro-5H-pyrrolo[2,3-d]pyrimidin-4-yl]-pyrimidin-2-yl}-bis-(4-methoxy-benzyl)-amine (15 mg) instead of bis-(4-methoxy-benzyl)-[5-(2-morpholin-4-yl-6,7-dihydro-5H-pyrrolo[2,3-d]pyrimidin-4-yl)-pyrimidin-2-yl]-amine, and N-methylpiperazine (3.2 μl) instead of 4-(4-ethyl-piperazin-1-yl)-2,6-difluoro-phenylamine, in the same manner as Step D in Example 1-D-18, a crude product of 4-methyl-piperazine-1-carboxylic acid [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-amide was obtained, and then the PMB groups were removed according to the above Deprotection method 3, to obtain the desired compound (D-269) as a pale brown powder (12 mg, 100%).

$^1$H-NMR (DMSO-d$_6$) δ (ppm): 8.84 (1H, s), 8.81 (2H, s), 8.31 (1H, s), 7.35-7.14 (4H, m), 4.05 (2H, t, J=8.0 Hz), 3.72 (4H, dd, J=17.1, 4.7 Hz), 3.40 (14H, brs), 2.82 (3H, s).

ESI (LC-MS positive mode) m/z 517 (M+H)$^+$.

Example 1-D-270

4-[4-(2-Amino-pyrimidin-5-yl)-2-morpholin-4-yl-5,6-dihydro-pyrrolo[2,3-d]pyrimidin-7-yl]-3-fluoro-N-thiazol-2-yl-benzamide (D-270)

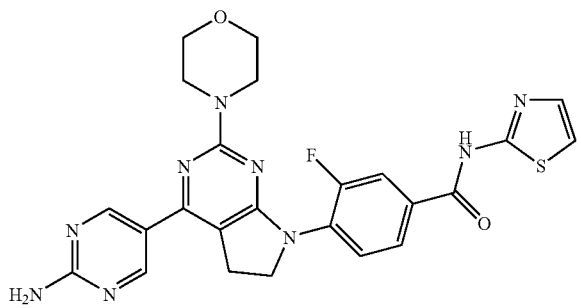

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 2-aminothiazole (23.6 mg, 0.236 mmol) instead of 1-pyridine-3-yl-piperazine, amidation was carried out in the same manner as Step B in Example 1-D-21, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-N-thiazol-2-yl-benzamide as a yellow solid (132 mg), and then the PMB groups were removed according to the above Deprotection method 3, to obtain the desired compound (D-270) as a yellow powder (37.8 mg, 62%).

$^1$H-NMR (DMSO-d$_6$) δ (ppm): 8.81 (2H, s), 8.05 (1H, dd, J=12.7, 2.0 Hz), 8.00 (1H, dd, J=7.7, 2.0 Hz), 7.88 (1H, t, J=7.7 Hz), 7.58 (1H, d, J=3.6 Hz), 7.30 (1H, d, J=3.6 Hz), 7.22 (1H, m), 5.76 (2H, s), 4.18 (2H, t, J=7.7 Hz), 3.66-3.62 (8H, m), 3.35 (2H, t, J=7.7 Hz).

ESI (LC-MS positive mode) m/z 520 (M+H)$^+$.

Example 1-D-271

4-[4-(2-Amino-pyrimidin-5-yl)-2-morpholin-4-yl-5,6-dihydro-pyrrolo[2,3-d]pyrimidin-7-yl]-3-fluoro-N-pyridin-4-ylmethyl-benzamide (D-271)

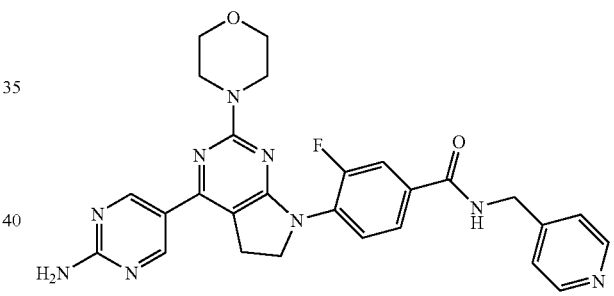

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 4-(aminomethyl)pyridine (24.0 μl, 0.236 mmol) instead of 1-pyridine-3-yl-piperazine, amidation was carried out in the same manner as Step B in Example 1-D-21, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-N-pyridin-4-ylmethyl-benzamide as a yellow solid (134 mg), and then the PMB groups were removed according to the above Deprotection method 3, to obtain the desired compound (D-271) as a yellow powder (49.4 mg, 79%).

$^1$H-NMR (DMSO-d$_6$) δ (ppm): 9.18 (1H, t, J=5.8 Hz), 8.81 (2H, s), 8.51 (2H, d, J=5.9 Hz), 7.88-7.76 (3H, m), 7.32 (2H, d, J=5.9 Hz), 7.08 (2H, brs), 4.50 (2H, d, J=5.8 Hz), 4.12 (2H, t, J=7.6 Hz), 3.63-3.60 (8H, m), 3.32-3.31 (2H, m).

ESI (LC-MS positive mode) m/z 528 (M+H)$^+$.

Example 1-D-272

{4-[4-(2-Amino-pyrimidin-5-yl)-2-morpholin-4-yl-5,6-dihydro-pyrrolo[2,3-d]pyrimidin-7-yl]-3-methyl-phenyl}-azepan-1-yl-methanone (D-272)

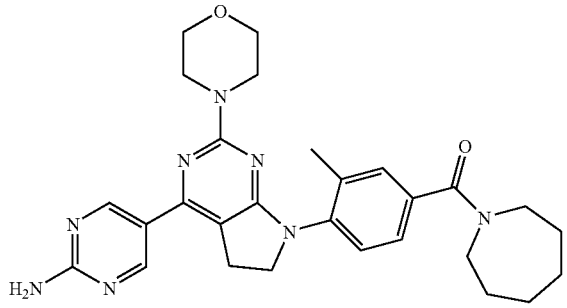

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and azepan-1-yl-(4-bromo-3-methyl-phenyl)-methanone (41 mg) instead of 4-chloropicolinic acid t-butylamide, in the same manner as Example 1-D-07, a crude product of azepan-1-yl-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-methanone was obtained, and then the PMB groups were removed according to the above Deprotection method 3, to obtain the desired compound (D-272) as a pale brown powder (16 mg, 33%).

$^1$H-NMR (CD$_3$OD) δ (ppm): 8.84 (2H, s), 7.36 (1H, s), 7.32 (1H, d, J=3.3 Hz), 7.25 (1H, dd, J=8.1, 2.0 Hz), 4.01 (2H, t, J=8.2 Hz), 3.67 (2H, t, J=5.9 Hz), 3.46 (2H, t, J=5.4 Hz), 3.35 (10H, brs), 2.28 (3H, s), 1.84-1.64 (8H, m).

ESI (LC-MS positive mode) m/z 515 (M+H)$^+$.

Example 1-D-273

4-(2-Amino-pyrimidin-5-yl)-2-morpholin-4-yl-5,6-dihydro-pyrrolo[2,3-d]pyrimidine-7-carboxylic acid (2,6-difluoro-4-morpholin-4-yl-phenyl)-amide (D-273)

Step A (2,6-Difluoro-4-morpholin-4-yl-phenyl)-carbamic acid tert-butyl ester

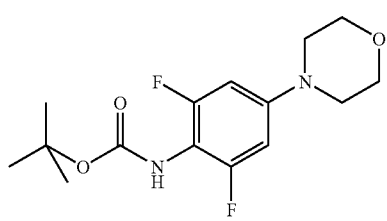

Using N,N-di-Boc-4-bromo-2,6-difluoro-phenylamine (408 mg) obtained in Step A in Example 1-D-18 and morpholine (130 μl) instead of 1-ethyl-piperazine, in the same manner as Step B in Example 1-D-18, the desired compound was obtained as a crude product.

Step B 2,6-Difluoro-4-morpholin-4-yl-phenylamine

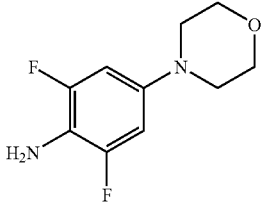

Using (2,6-difluoro-4-morpholin-4-yl-phenyl)-carbamic acid tert-butyl ester obtained in Step A instead of N-Boc-4-(4-ethyl-piperazin-1-yl)-2,6-difluoro-phenylamine, in the same manner as Step C in Example 1-D-18, the desired compound was obtained (49.5 mg, 23%).

Step C 4-(2-Amino-pyrimidin-5-yl)-2-morpholin-4-yl-5,6-dihydro-pyrrolo[2,3-d]pyrimidine-7-carboxylic acid (2,6-difluoro-4-morpholin-4-yl-phenyl)-amide (D-273)

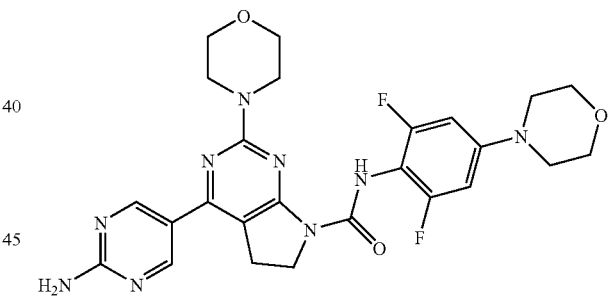

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (91.6 mg) and 2,6-difluoro-4-morpholin-4-yl-phenylamine (49.5 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2,6-difluoro-4-morpholin-4-yl-phenyl)-amide was obtained as a crude product. The PMB groups were removed according to Deprotection method 3, to obtain the desired compound (D-273) as a yellow solid (33.6 mg, 31%).

$^1$H-NMR (DMSO-d$_6$) δ: 10.15 (1H, s), 8.83 (2H, s), 7.18 (2H, s), 6.74 (2H, d, J=11.5 Hz), 4.01 (2H, t, J=8.3 Hz), 3.75-3.63 (12H, m), 3.23 (2H, t, J=8.3 Hz), 3.19-3.12 (4H, brm).

ESI (LC-MS positive mode) m/z 540 (M+H)$^+$

Example 1-D-274

4-(2-Amino-pyrimidin-5-yl)-2-morpholin-4-yl-5,6-dihydro-pyrrolo[2,3-d]pyrimidine-7-carboxylic acid (2-methyl-pyridin-3-yl)-amide (D-274)

Step A

3-Isocyanato-2-methyl-pyridine

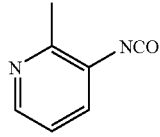

To an acetonitrile solution (5 ml) of 2-methylnicotinic acid (400 mg, 2.92 mmol) and DMF (11.2 μl, 0.156 mmol), oxalyl dichloride (501 μl, 5.83 mmol) was added dropwise, followed by stirring at room temperature for 2 hours. The reaction mixture was concentrated under reduced pressure, to obtain a crude product of 2-methylnicotinic acid chloride as a yellow liquid (470 mg).

This was dissolved in acetonitrile, and sodium azide (227.5 mg, 3.50 mmol) was added, followed by stirring at room temperature for 1 hour. To the reaction mixture, water (40 ml) was added, followed by extraction five times with dichloromethane (30 ml). The extracts were combined, followed by drying over sodium sulfate. Subsequently, the sodium sulfate was filtered off, and the filtrate was concentrated under reduced pressure, whereby a crude product of 2-methyl-nicotinoyl azide was obtained as a yellow solid (490 mg).

To this, toluene (5 ml) was added, followed by stirring at 50° C. for 3 hours under a nitrogen atmosphere. The reaction mixture was cooled to room temperature, and concentrated under reduced pressure, whereby a crude product of 3-isocyanate-2-methyl-pyridine was obtained as an ivory solid (313 mg).

ESI (LC-MS positive mode) m/z 135 (M+H)⁺.

Step B 4-(2-Amino-pyrimidin-5-yl)-2-morpholin-4-yl-5,6-dihydro-pyrrolo[2,3-d]pyrimidine-7-carboxylic acid (2-methyl-pyridin-3-yl)-amide (D-274)

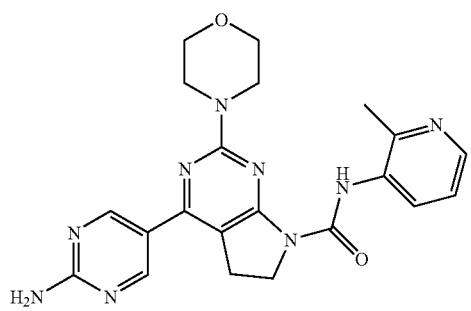

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and a crude product (59.7 mg) of 3-isocyanato-2-methyl-pyridine obtained in Step A instead of 2-chlorophenyl isocyanate, urea was formed in the same manner as Example 1-D-217, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-methyl-pyridin-3-yl)-amide as a yellow solid (103 mg), and then the PMB groups were removed according to the above Deprotection method 3, to obtain the desired compound (D-274) as a yellow powder (14.4 mg, 22%).

$^1$H-NMR (CDCl$_3$) δ (ppm): 10.69 (1H, s), 8.92 (2H, s), 8.47 (1H, d, J=4.9 Hz), 8.41 (1H, d, J=8.6 Hz), 7.43 (1H, dd, J=4.9, 8.6 Hz), 5.68 (2H, brs), 4.24 (2H, t, J=8.3 Hz), 4.04-3.69 (8H, m), 3.27 (2H, t, J=8.3 Hz), 2.70 (3H, s).

ESI (LC-MS positive mode) m/z 434 (M+H)⁺.

Example 1-D-275

4-(2-Amino-pyrimidin-5-yl)-2-morpholin-4-yl-5,6-dihydro-pyrrolo[2,3-d]pyrimidine-7-carboxylic acid (pyridin-3-ylmethyl)-amide (D-275)

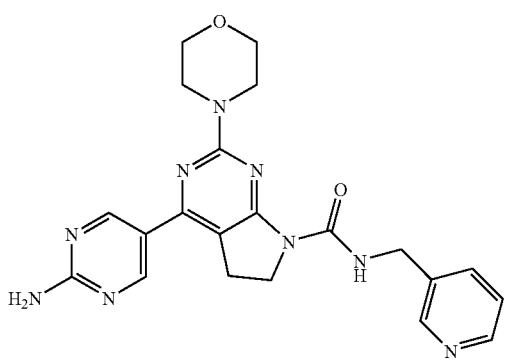

In the same manner as Step D in Example 1-D-18, using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 3-aminomethyl-pyridine (0.03 ml) instead of 4-(4-ethyl-piperazin-1-yl)-2,6-difluoro-phenylamine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (pyridin-3-ylmethyl)-amide was obtained. Using a crude product (85 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (pyridin-3-ylmethyl)-amide, according to the above Deprotection method 2,4-(2-amino-pyrimidin-5-yl)-2-morpholin-4-yl-5,6-dihydro-pyrrolo[2,3-d]pyrimidine-7-carboxylic acid (pyridin-3-ylmethyl)-amide was obtained as a yellow powder (24 mg, 44%).

$^1$H-NMR (DMSO-d$_6$) δ (ppm): 9.00 (2H, s), 8.90-8.10 (4H, m), 7.48-7.18 (4H, m), 4.71 (2H, s), 3.99 (2H, m), 3.68 (8H, m), 3.25 (2H, m).

ESI (LC-MS positive mode) m/z 434 (M+H)⁺.

Example 1-D-276

4-(2-Amino-pyrimidin-5-yl)-2-morpholin-4-yl-5,6-dihydro-pyrrolo[2,3-d]pyrimidine-7-carboxylic acid (4-methyl-pyridin-3-yl)-amide (D-276)

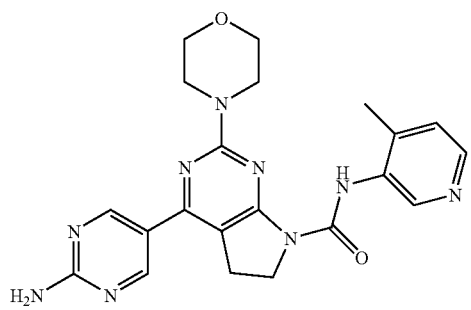

Using 4-methylnicotinic acid instead of 2-methylnicotinic acid, in the same manner as Step A in Example 1-D-274, a crude product of 3-isocyanato-4-methyl-pyridine was obtained. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.0 mg, 0.148 mmol) and the obtained crude product (59.7 mg) of 3-isocyanato-4-methyl-pyridine instead of 2-chlorophenyl isocyanate, urea was formed in the same manner as Example 1-D-217, to obtain a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-methyl-pyridin-3-yl)-amide as a yellow solid (132 mg), and then the PMB groups were removed according to the above Deprotection method 3, to obtain the desired compound (D-276) as a yellow powder (51.0 mg, 79%).

$^1$H-NMR (DMSO-$d_6$) δ (ppm): 10.59 (1H, s), 9.07 (1H, s), 8.86 (2H, s), 8.49 (1H, d, J=5.6 Hz), 7.77 (1H, d, J=5.6 Hz), 7.29 (2H, brs), 4.08 (2H, t, J=7.9 Hz), 3.79-3.60 (8H, m), 3.27 (2H, t, J=7.9 Hz), 2.47 (3H, s).

ESI (LC-MS positive mode) m/z 434 (M+H)$^+$.

Example 1-D-277

N-{4-[4-(2-Amino-pyrimidin-5-yl)-2-morpholin-4-yl-5,6-dihydro-pyrrolo[2,3-d]pyrimidin-7-yl]-phenyl}-isonicotinamide (D-277)

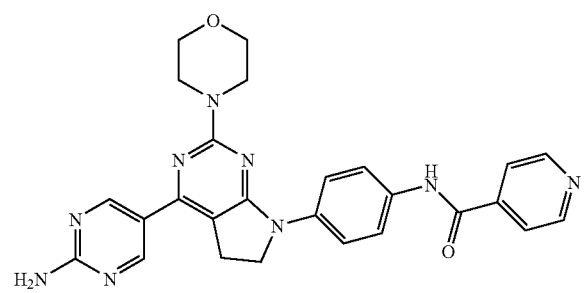

Using {5-[7-(4-amino-phenyl)-2-morpholin-4-yl-6,7-dihydro-5H-pyrrolo[2,3-d]pyrimidin-4-yl]-pyrimidin-2-yl}-bis-(4-methoxy-benzyl)-amine (15 mg) instead of bis-(4-methoxy-benzyl)-[5-(2-morpholin-4-yl-6,7-dihydro-5H-pyrrolo[2,3-d]pyrimidin-4-yl)-pyrimidin-2-yl]-amine, and isonicotinic acid (3.8 mg) instead of 4-chloropicolinic acid t-butylamide, in the same manner as Step B in Example 1-D-19, a crude product of N-[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-isonicotineamide was obtained, and then the PMB groups were removed according to the above Deprotection method 3, to obtain the desired compound (D-277) as an orange powder (12 mg, 100%).

$^1$H-NMR (DMSO-$d_6$) δ (ppm): 10.50 (2H, s), 8.79 (4H, s), 7.87 (2H, d, J=4.8 Hz), 7.82-7.77 (4H, m), 7.08 (1H, s), 4.08 (2H, t, J=8.1 Hz), 3.69 (8H, brs), 3.26 (2H, t, J=8.2 Hz).

ESI (LC-MS positive mode) m/z 496 (M+H)$^+$.

Example 1-D-278

{4-[4-(2-Amino-pyrimidin-5-yl)-2-morpholin-4-yl-5,6-dihydro-pyrrolo[2,3-d]pyrimidin-7-yl]-phenyl}-(4-pyridin-2-yl-piperazin-1-yl)-methanone (D-278)

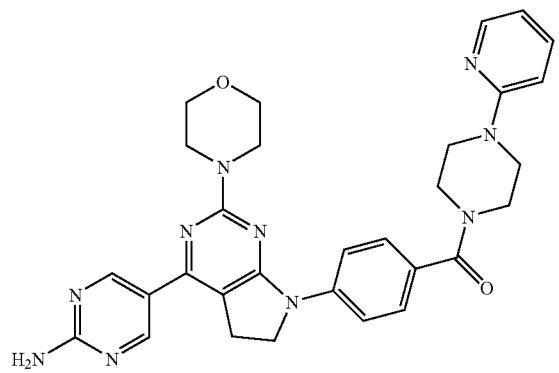

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A in Example 1-D-19 and 1-(2-pyridyl)piperazine (27.7 μl, 0.182 mmol) instead of 3-(aminomethyl)pyridine, amidation was carried out in the same manner as Step B in Example 1-D-19, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-pyridin-2-yl-piperazin-1-yl)-methanone as a brown solid (88.2 mg), and then the PMB groups were removed according to the above Deprotection method 3, to obtain the desired compound (D-278) as a yellow powder (47.4 mg, 100%).

$^1$H-NMR (DMSO-$d_6$) δ (ppm): 8.82 (2H, s), 8.11 (1H, dd, J=5.8, 1.8 Hz), 7.94 (2H, d, J=8.6 Hz), 7.81-7.78 (1H, m), 7.53 (2H, d, J=8.6 Hz), 7.26 (2H, brs), 7.11 (1H, d, J=8.9 Hz), 6.83 (1H, t, J=5.8 Hz), 4.16 (2H, t, J=7.8 Hz), 3.80-3.63 (8H, m), 3.32 (2H, t, J=7.9 Hz).

ESI (LC-MS positive mode) m/z 565 (M+H)$^+$.

Example 1-D-279

4-[4-(2-Amino-pyrimidin-5-yl)-2-morpholin-4-yl-5,6-dihydro-pyrrolo[2,3-d]pyrimidin-7-yl]-N-(2-pyridin-3-yl-ethyl)-benzamide (D-279)

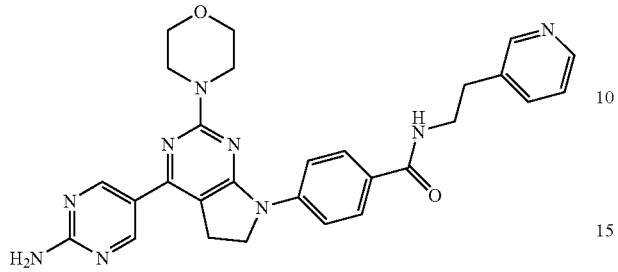

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A in Example 1-D-19 and 3-(2-aminoethyl)pyridine (21.4 µl, 0.182 mmol) instead of 3-(aminomethyl)pyridine, amidation was carried out in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-(2-pyridin-3-yl-ethyl)-benzamide as a brown solid (72.0 mg), and then the PMB groups were removed according to the above Deprotection method 3, to obtain the desired compound (D-279) as a yellow powder (40.4 mg, 85%).

$^1$H-NMR (DMSO-$d_6$) δ (ppm): 8.82 (2H, s), 8.68 (1H, s), 8.63 (1H, d, J=5.1 Hz), 8.48 (1H, dd, J=7.7, 5.1 Hz), 8.12 (1H, d, J=7.7 Hz), 7.92 (2H, d, J=9.1 Hz), 7.85 (2H, d, J=9.1 Hz), 7.70 (1H, t, J=6.4 Hz), 7.15 (2H, brs), 4.13 (2H, t, J=7.7 Hz), 3.79-3.67 (8H, m), 3.57 (2H, dt, J=6.4, 6.9 Hz), 3.32 (2H, t, J=7.7 Hz), 2.99 (2H, t, J=6.9 Hz).

ESI (LC-MS positive mode) m/z 524 (M+H)$^+$.

Example 1-D-280

4-(2-Amino-pyrimidin-5-yl)-2-morpholin-4-yl-5,6-dihydro-pyrrolo[2,3-d]pyrimidine-7-carboxylic acid (2-methyl-2H-pyrazol-3-yl)-amide (D-280)

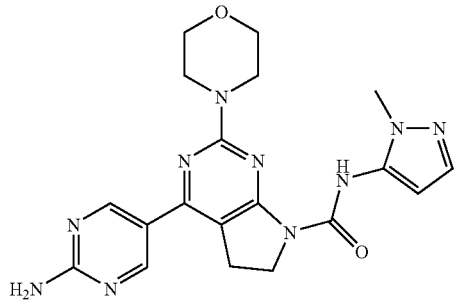

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and 2-methyl-2H-pyrazol-3-ylamine (23.3 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-methyl-2H-pyrazol-3-yl)-amide was obtained as a crude product. The PMB groups were removed according to Deprotection method 3, to obtain the desired compound (D-280) as a colorless solid (27.9 mg, 33%).

$^1$H-NMR (DMSO-$d_6$) δ: 10.56 (1H, s), 8.82 (2H, d, J=10.2 Hz), 7.35 (1H, d, J=1.8 Hz), 7.22 (2H, s), 6.23 (1H, d, J=1.8 Hz), 4.03 (2H, t, J=8.7 Hz), 3.75-3.64 (11H, m), 3.24 (2H, t, J=8.7 Hz).

ESI (LC-MS positive mode) m/z 423 (M+H)$^+$

Example 1-D-281

4-(2-Amino-pyrimidin-5-yl)-2-morpholin-4-yl-5,6-dihydro-pyrrolo[2,3-d]pyrimidine-7-carboxylic acid (5-methyl-2-phenyl-2H-pyrazol-3-yl)-amide (D-281)

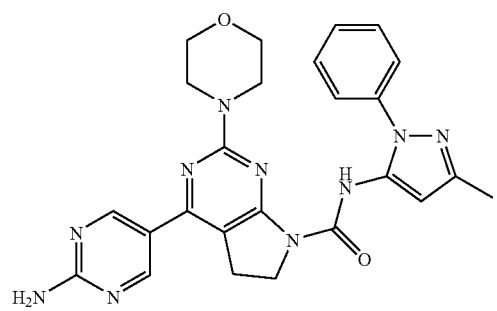

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (108 mg) and 5-methyl-2-phenyl-2H-pyrazol-3-ylamine (41.6 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (5-methyl-2-phenyl-2H-pyrazol-3-yl)-amide was obtained as a crude product. The PMB groups were removed according to Deprotection method 3, to obtain the desired compound (D-281) as a colorless solid (21.4 mg, 28%).

$^1$H-NMR (DMSO-$d_6$) δ: 10.88 (1H, s), 8.79 (2H, s), 7.59-7.36 (5H, m), 7.22 (2H, s), 6.31 (1H, s), 4.04 (2H, t, J=8.3 Hz), 3.48-3.36 (8H, brm), 3.22 (2H, t, J=8.3 Hz), 2.21 (3H, s).

ESI (LC-MS positive mode) m/z 499 (M+H)$^+$

Example 1-D-282

4-[4-(2-Amino-pyrimidin-5-yl)-2-morpholin-4-yl-5,6-dihydro-pyrrolo[2,3-d]pyrimidin-7-yl]-N-pyridin-2-ylmethyl-benzamide (D-282)

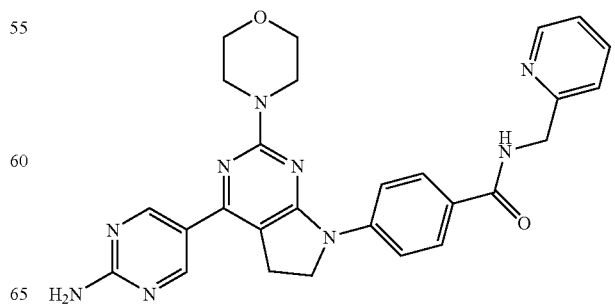

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A in Example 1-D-19 and 2-(aminomethyl)pyridine (18.4 μl, 0.182 mmol) instead of 3-(aminomethyl)pyridine, amidation was carried out in the same manner as Step B in Example 1-D-19, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-N-pyridin-2-ylmethyl-benzamide as a brown solid (119 mg), and then the PMB groups were removed according to the above Deprotection method 3, to obtain the desired compound (D-282) as a yellow powder (41.8 mg, 90%).

$^1$H-NMR (DMSO-d$_6$) δ (ppm): 9.12 (1H, t, J=5.6 Hz), 8.82 (2H, s), 8.63 (1H, d, J=4.6 Hz), 8.02 (1H, m), 7.97 (4H, s), 7.55 (1H, d, J=8.2 Hz), 7.51 (1H, m), 7.22 (2H, brs), 4.65 (2H, d, J=5.6 Hz), 4.16 (2H, t, J=8.0 Hz), 3.77-3.67 (8H, m), 3.32 (2H, t, J=8.0 Hz).

ESI (LC-MS positive mode) m/z 510 (M+H)$^+$.

Example 1-D-283

4-(2-Amino-pyrimidin-5-yl)-2-morpholin-4-yl-5,6-dihydro-pyrrolo[2,3-d]pyrimidine-7-carboxylic acid (2,6-dimethyl-phenyl)-amide (D-283)

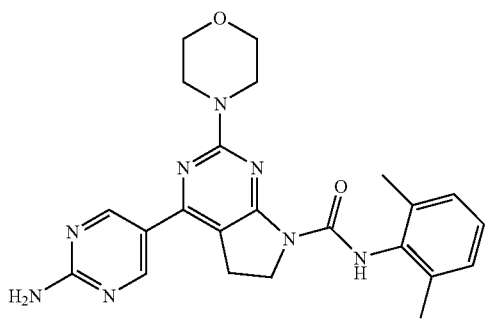

In the same manner as Example 1-D-18, using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 2,6-dimethyl-aniline (34 mg) instead of 4-(4-ethyl-piperazin-1-yl)-2,6-difluoro-phenylamine, a crude product of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2,6-dimethyl-phenyl)-amide was obtained. Using a crude product (126 mg) of 4-(2-bis-(4-methoxy-benzyl)-amino-pyrimidin-5-yl)-2-morpholin-4-yl-5,6-dihydro-pyrrolo[2,3-d]pyrimidine-7-carboxylic acid (2,6-dimethyl-phenyl)-amide, according to the above Deprotection method 2, 4-(2-amino-pyrimidin-5-yl)-2-morpholin-4-yl-5,6-dihydro-pyrrolo[2,3-d]pyrimidine-7-carboxylic acid (2,6-dimethyl-phenyl)-amide was obtained as a colorless powder (82 mg, 100%).

$^1$H-NMR (CDCl$_3$) δ (ppm): 10.2 (1H, s), 8.91 (2H, s), 7.13 (3H, s), 5.28 (2H, s), 4.23 (2H, t, J=8.1 Hz), 3.76 (8H, s), 3.25 (2H, t, J=8.1 Hz), 2.31 (6H, s).

ESI (LC-MS positive mode) m/z 447 (M+H)$^+$.

Example 1-D-284

{4-[4-(2-Amino-pyrimidin-5-yl)-2-morpholin-4-yl-5,6-dihydro-pyrrolo[2,3-d]pyrimidin-7-yl]-phenyl}-(4-pyrimidin-2-yl-piperazin-1-yl)-methanone (D-284)

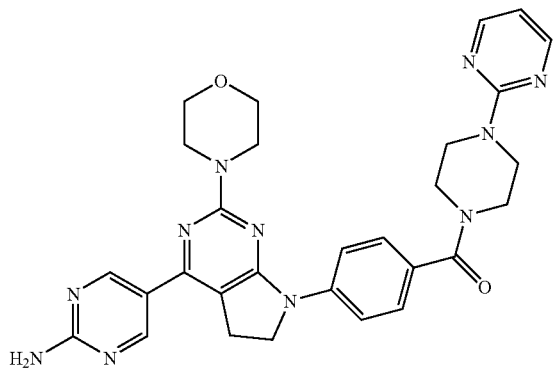

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (60.0 mg, 0.0909 mmol) obtained in Step A in Example 1-D-19 and 1-(2-pyrimidyl)piperazine dihydrochloride (43.1 mg, 0.182 mmol) instead of 3-(aminomethyl)pyridine, amidation was carried out in the same manner as Step B in Example 1-D-19, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-pyrimidin-2-yl-piperazin-1-yl)-methanone as a brown solid (131 mg), and then the PMB groups were removed according to the above Deprotection method 3, to obtain the desired compound (D-284) as a yellow powder (40.7 mg, 79%).

$^1$H-NMR (DMSO-d$_6$) δ (ppm): 8.82 (2H, s), 8.39 (2H, d, J=4.6 Hz), 7.93 (2H, d, J=8.4 Hz), 7.51 (2H, d, J=8.4 Hz), 7.12 (2H, brs), 6.67 (1H, t, J=4.6 Hz), 4.14 (2H, t, J=7.9 Hz), 3.86-3.52 (18H, m).

ESI (LC-MS positive mode) m/z 566 (M+H)$^+$.

Example 1-D-285

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-pyridin-2-yl-piperazin-1-yl)-methanone (D-285)

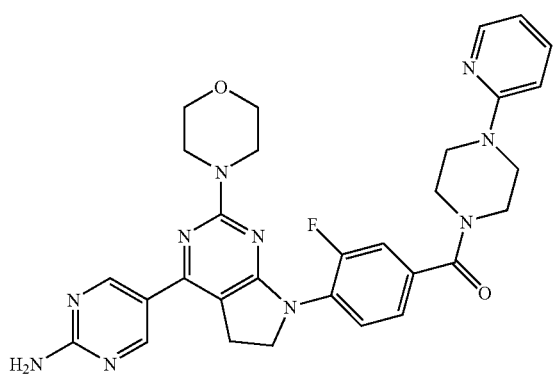

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 1-(2-pyridyl)piperazine (38.5 mg, 0.236 mmol) instead of 1-pyridine-3-yl-piperazine, amidation was carried out in the same manner as Step B in Example 1-D-21, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-phenyl}-(4-pyridin-2-yl-piperazin-1-yl)-methanone as a yellow solid (139 mg), and then the PMB groups were removed according to the above Deprotection method 3, to obtain the desired compound (D-285) as a yellow powder (54.8 mg, 80%).

$^{1}$H-NMR (DMSO-$d_6$) δ (ppm): 8.80 (2H, s), 8.12 (1H, dd, J=5.3, 1.6 Hz), 7.81-7.72 (2H, m), 7.48 (1H, dd, J=11.7, 1.6 Hz), 7.37 (1H, dd, J=8.4, 1.6 Hz), 7.26 (2H, brs), 7.07 (1H, d, J=8.6 Hz), 6.84-6.77 (1H, m), 4.11 (2H, t, J=7.9 Hz), 3.73-3.56 (8H, m), 3.34 (2H, t, J=7.9 Hz).

ESI (LC-MS positive mode) m/z 583 (M+H)$^+$.

Example 1-D-286

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-pyridin-4-yl-piperazin-1-yl)-methanone (D-286)

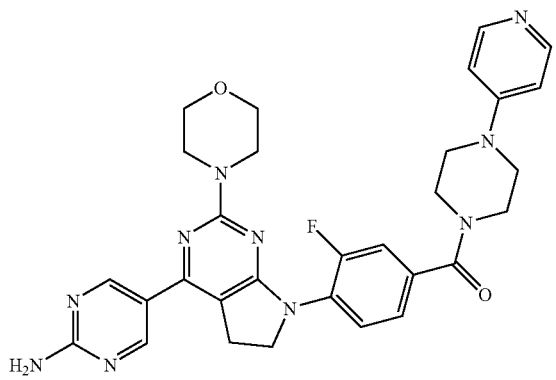

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 1-(4-pyridyl)piperazine (38.5 mg, 0.236 mmol) instead of 1-pyridine-3-yl-piperazine, amidation was carried out in the same manner as Step B in Example 1-D-21, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-phenyl}-(4-pyridin-4-yl-piperazin-1-yl)-methanone as a yellow solid (142 mg), and then the PMB groups were removed according to the above Deprotection method 3, to obtain the desired compound (D-286) as a yellow powder (51.2 mg, 74%).

$^{1}$H-NMR (DMSO-$d_6$) δ (ppm): 8.81 (2H, s), 8.19 (1H, d, J=6.4 Hz), 7.77 (1H, t, J=8.1 Hz), 7.45 (1H, dd, J=11.9, 1.8 Hz), 7.34 (1H, dd, J=8.1, 1.8 Hz), 7.10 (2H, brs), 6.85 (2H, d, J=6.4 Hz), 4.10 (1H, t, J=7.7 Hz), 3.71-3.38 (18H, m).

ESI (LC-MS positive mode) m/z 583 (M+H)$^+$.

Example 1-D-287

4-(2-Amino-pyrimidin-5-yl)-2-morpholin-4-yl-5,6-dihydro-pyrrolo[2,3-d]pyrimidine-7-carboxylic acid 3-(4-methyl-piperazine-1-carbonyl)-benzylamide (D-287)

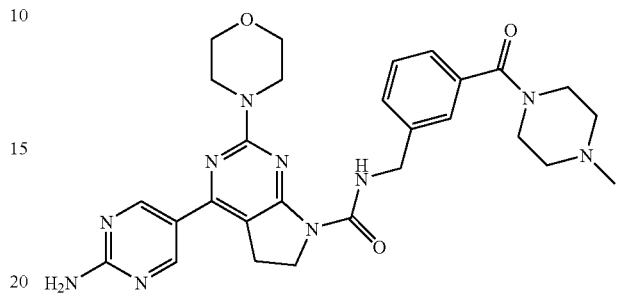

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-aminomethyl-phenyl)-(4-methyl-piperazin-1-yl)-methanone (70 mg) instead of 4-(4-ethyl-piperazin-1-yl)-2,6-difluoro-phenylamine, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid 3-(4-methyl-piperazine-1-carbonyl)-benzylamide was obtained, and then the PMB groups were removed according to the above Deprotection method 3, to obtain the desired compound (D-287) as a colorless powder (27 mg, 26%).

$^{1}$H-NMR (DMSO-$d_6$) δ (ppm): 9.03 (1H, t, J=5.2 Hz), 8.80 (2H, s), 7.45 (2H, d, J=4.9 Hz), 7.37 (1H, s), 7.32 (1H, t, J=4.4 Hz), 7.19 (2H, s), 4.51 (2H, d, J=5.3 Hz), 3.96 (2H, t, J=8.3 Hz), 3.53-3.40 (16H, m), 3.17 (2H, t, J=8.2 Hz), 2.29 (3H, s).

ESI (LC-MS positive mode) m/z 559 (M+H)$^+$.

Example 1-D-288

{4-[4-(2-Amino-pyrimidin-5-yl)-2-morpholin-4-yl-5,6-dihydro-pyrrolo[2,3-d]pyrimidin-7-yl]-3-methyl-phenyl}-(4-pyridin-4-yl-piperazin-1-yl)-methanone (D-288)

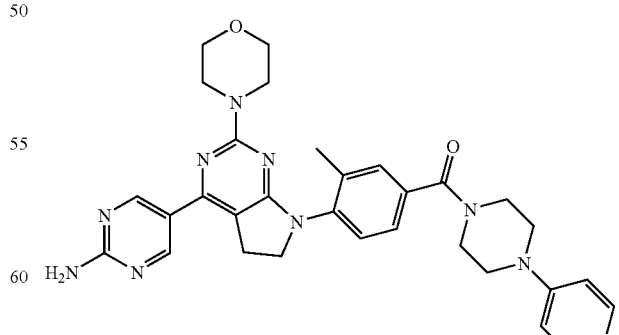

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (50 mg) and (4-bromo-3-methyl-phenyl)-(4-pyridin- 4-yl-piperazin-1-yl)-methanone (50 mg) obtained in the same manner instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-(4-pyridin-4-yl-piperazin-1-yl)-methanone was obtained, and then the PMB groups were removed according to the above Deprotection method 3, to obtain the desired compound (D-288) as a colorless oil (3 mg, 6%).

$^1$H-NMR (CD$_3$OD) δ (ppm): 8.65 (2H, s), 8.19 (2H, d, J=7.7 Hz), 7.53 (1H, s), 7.47 (2H, s), 7.19 (2H, d, J=7.7 Hz), 4.23 (2H, t, J=7.9 Hz), 3.87 (10H, brs), 3.68 (8H, brs), 3.36 (2H, t, J=8.1 Hz), 2.34 (3H, s).

ESI (LC-MS positive mode) m/z 579 (M+H)$^+$.

Example 1-D-289

4-(2-Amino-pyrimidin-5-yl)-2-morpholin-4-yl-5,6-dihydro-pyrrolo[2,3-d]pyrimidine-7-carbothioic acid [2-methyl-5-(4-methyl-piperazin-1-yl)-phenyl]-amide (D-289)

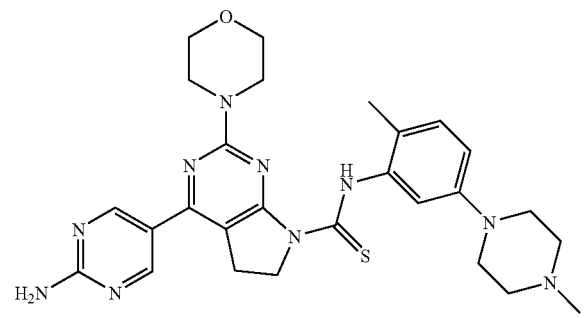

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and 2-methyl-5-(4-methyl-piperazin-1-yl)-phenylamine (69 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-5-(4-methyl-piperazin-1-yl)-phenyl]-amide was obtained, and then the PMB groups were removed according to the above Deprotection method 1, to obtain the desired compound (D-289) as an ivory solid (41 mg, 27%).

$^1$H-NMR (CDCl$_3$) δ (ppm): 12.3 (1H, s), 8.90 (2H, s), 7.18 (1H, d, J=8.3 Hz), 7.04 (1H, d, J=2.6 Hz), 6.83 (1H, dd, J=2.6, 8.3 Hz), 5.31 (2H, s), 4.58 (2H, t, J=8.3 Hz), 3.72 (8H, m), 3.22 (6H, m), 2.56 (2H, t, J=4.9 Hz), 2.34 (3H, s), 2.22 (3H, s)

ESI (LC-MS positive mode) m/z 547 (M+H)$^+$.

Example 1-D-290

4-(2-Amino-pyrimidin-5-yl)-2-morpholin-4-yl-5,6-dihydro-pyrrolo[2,3-d]pyrimidine-7-carbothioic acid [5-(4-ethyl-piperazin-1-yl)-2-methyl-phenyl]-amide (D-290)

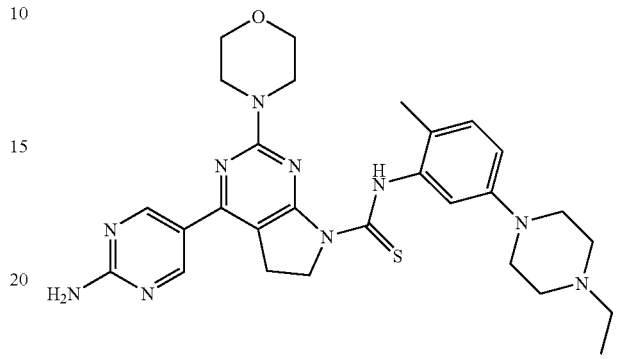

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and 2-methyl-5-(4-ethyl-piperazin-1-yl)-phenylamine (73 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-5-(4-ethyl-piperazin-1-yl)-phenyl]-amide was obtained, and then the PMB groups were removed according to the above Deprotection method 1, to obtain the desired compound (D-290) as an ivory solid (65 mg, 42%).

$^1$H-NMR (CDCl$_3$) δ (ppm): 12.3 (1H, s), 8.90 (2H, s), 7.17 (1H, d, J=8.3 Hz), 7.04 (1H, d, J=2.6 Hz), 6.84 (1H, dd, J=8.3, 2.6 Hz), 5.33 (2H, s), 4.58 (2H, m), 3.73 (8H, m), 3.25 (6H, m), 2.59 (4H, m), 2.45 (2H, m), 2.22 (3H, s), 1.11 (3H, t, J=7.2 Hz)

ESI (LC-MS positive mode) m/z 561 (M+H)$^+$.

Example 1-D-291

4-(2-Amino-pyrimidin-5-yl)-2-morpholin-4-yl-5,6-dihydro-pyrrolo[2,3-d]pyrimidine-7-carbothioic acid [2-methyl-4-(4-methyl-piperazin-1-yl)-phenyl]-amide (D-291)

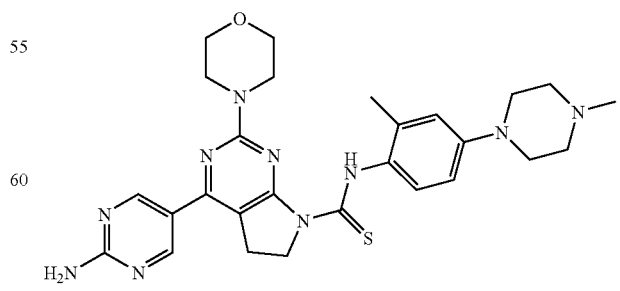

Using bis-(4-methoxy-benzyl)-[5-(2-morpholin-4-yl-6,7-dihydro-5H-pyrrolo[2,3-d]pyrimidin-4-yl)-pyrimidin-2-yl]- amine (150 mg) and 2-methyl-4-(4-methyl-piperazin-1-yl)-phenylamine (69 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-4-(4-methyl-piperazin-1-yl)-phenyl]-amide was obtained, and then the PMB groups were removed according to the above Deprotection method 1, to obtain the desired compound (D-291) as a yellow solid (35 mg, 23%).

$^1$H-NMR (CDCl$_3$) δ (ppm): 12.25 (1H, s), 8.91 (2H, s), 7.26 (1H, m), 6.81 (2H, m), 5.29 (2H, s), 4.58 (2H, t, J=8.4 Hz), 3.73 (8H, m), 3.23 (6H, m), 2.56 (4H, m), 2.35 (3H, s), 2.28 (3H, s)

ESI (LC-MS positive mode) m/z 547 (M+H)$^+$.

Example 1-D-292

4-(2-Amino-pyrimidin-5-yl)-2-morpholin-4-yl-5,6-dihydro-pyrrolo[2,3-d]pyrimidine-7-carbothioic acid [4-(4-ethyl-piperazin-1-yl)-2-methyl-phenyl]-amide (D-292)

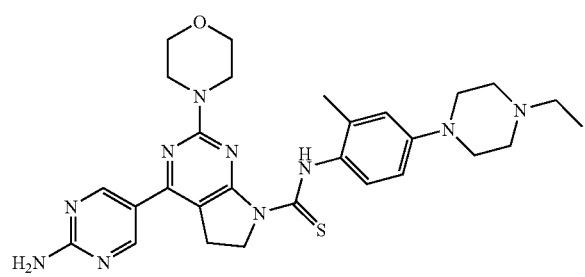

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (150 mg) and 2-methyl-4-(4-ethyl-piperazin-1-yl)-phenylamine (73 mg) instead of (4-ethyl-piperazin-1-yl)-(3-amino-4-methyl-phenyl)-methanone in Step C in Example 1-D-17, in the same manner as Step C in Example 1-D-17, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carbothioic acid [2-methyl-4-(4-ethyl-piperazin-1-yl)-phenyl]-amide was obtained, and then the PMB groups were removed according to the above Deprotection method 1, to obtain the desired compound (D-292) as a pale yellow solid (42 mg, 27%).

$^1$H-NMR (CDCl$_3$) δ (ppm): 12.25 (1H, s), 8.91 (2H, s), 7.26 (1H, m), 6.81 (2H, m), 5.29 (2H, s), 4.58 (2H, t, J=8.4 Hz), 3.73 (8H, m), 3.23 (6H, m), 2.59 (4H, m), 2.49 (2H, q, J=7.2 Hz), 2.27 (3H, s), 1.13 (3H, t, J=7.2 Hz)

ESI (LC-MS positive mode) m/z 561 (M+H)$^+$.

Example 1-D-293

4-(2-Amino-pyrimidin-5-yl)-2-morpholin-4-yl-5,6-dihydro-pyrrolo[2,3-d]pyrimidine-7-carboxylic acid 4-(4-methyl-piperazine-1-carbonyl)-benzylamide (D-293)

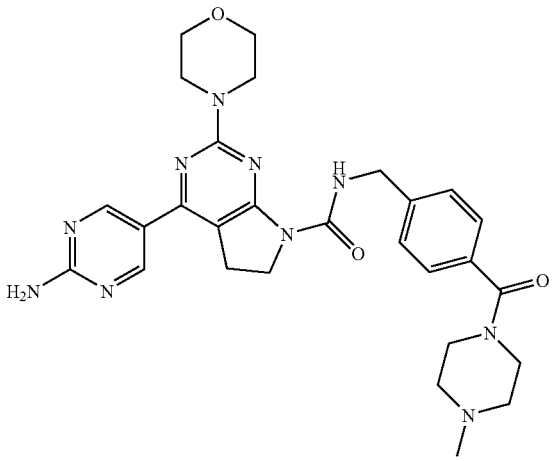

4-(Tert-butoxycarbonylamino-methyl)-benzoic acid was reacted with WSCI, HOBt, triethylamine and N-methylpiperazine in dichloromethane, to obtain a crude product of [4-(4-methyl-piperazine-1-carbonyl)-benzyl]-carbamic acid tert-butyl ester, and then treated with TFA, to obtain (4-aminomethyl-phenyl)-(4-methyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-aminomethyl-phenyl)-(4-methyl-piperazin-1-yl)-methanone (159 mg) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid 4-(4-methyl-piperazine-1-carbonyl)-benzylamide was obtained, and then the PMB groups were removed according to the above Deprotection method 3, to obtain the desired compound (D-293) as a colorless powder (64 mg, 62%).

$^1$H-NMR (DMSO-d$_6$) δ (ppm): 9.04 (1H, t, J=5.4 Hz), 8.81 (2H, s), 7.40 (4H, dd, J=13.3, 8.3 Hz), 4.49 (2H, d, J=5.3 Hz), 3.97 (2H, t, J=8.6 Hz), 3.76-3.69 (8H, m), 3.49 (4H, brs), 3.20 (2H, t, J=8.6 Hz), 2.30 (4H, brs), 2.19 (3H, s).

ESI (LC-MS positive mode) m/z 559 (M+H)$^+$.

Example 1-D-294

4-(2-Amino-pyrimidin-5-yl)-2-morpholin-4-yl-5,6-dihydro-pyrrolo[2,3-d]pyrimidine-7-carboxylic acid {2-[4-(4-methyl-piperazine-1-carbonyl)-phenyl]-ethyl}-amide (D-294)

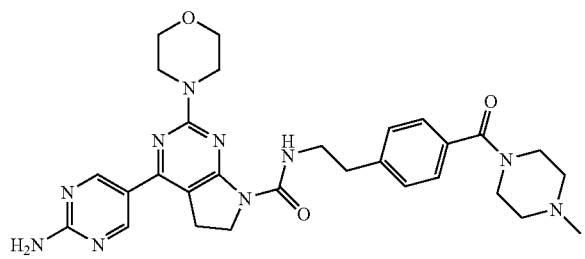

4-(2-Tert-butoxycarbonylamino-ethyl)-benzoic acid was reacted with WSCI, HOBt, triethylamine and N-methylpiperazine in dichloromethane, to obtain a crude product of {2-[4-(4-methyl-piperazine-1-carbonyl)-phenyl]-ethyl}-carbamic acid tert-butyl ester, and then treated with TFA, to obtain [4-(2-amino-ethyl)-phenyl]-(4-methyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and [4-(2-amino-ethyl)-phenyl]-(4-methyl-piperazin-1-yl)-methanone (39 mg) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid {2-[4-(4-methyl-piperazine-1-carbonyl)-phenyl]-ethyl}-amide was obtained, and then the PMB groups were removed according to the above Deprotection method 3, to obtain the desired compound (D-294) as a colorless powder (121 mg, 97%).

$^1$H-NMR (DMSO-$d_6$) δ (ppm): 8.79 (2H, s), 8.68-8.64 (1H, m), 7.31 (2H, s), 7.07 (4H, dd, J=14.7, 7.4 Hz), 4.40 (2H, t, J=7.0 Hz), 3.94 (2H, t, J=7.0 Hz), 3.66-3.43 (12H, m), 3.17 (2H, t, J=7.5 Hz), 2.87 (2H, t, J=7.5 Hz), 2.27 (4H, brs), 2.18 (3H, s), 1.88 (2H, t, J=7.5 Hz).

ESI (LC-MS positive mode) m/z 573 (M+H)$^+$.

Example 1-D-295

4-(2-Amino-pyrimidin-5-yl)-2-morpholin-4-yl-5,6-dihydro-pyrrolo[2,3-d]pyrimidine-7-carboxylic acid methyl-{2-[4-(4-methyl-piperazine-1-carbonyl)-phenyl]-ethyl}-amide (D-295)

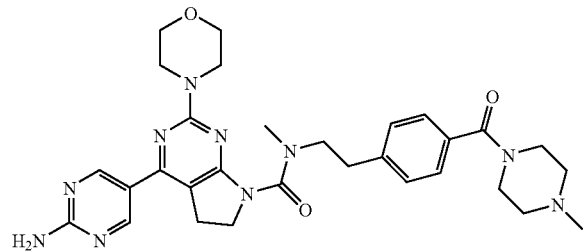

4-(2-Tert-butoxycarbonylamino-ethyl)-benzoic acid was reacted with WSCI, HOBt, triethylamine and N-methylpiperazine in dichloromethane, to obtain {2-[4-(4-methyl-piperazine-1-carbonyl)-phenyl]-ethyl}-carbamic acid tert-butyl ester, and then it was reacted with sodium hydride and methyl iodide in DMF, to obtain a crude product of methyl-{2-[4-(4-methyl-piperazine-1-carbonyl)-phenyl]-ethyl}-carbamic acid tert-butyl ester. Then, this was treated with TFA, to obtain [4-(2-methylamino-ethyl)-phenyl]-(4-methyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and [4-(2-methylamino-ethyl)-phenyl]-(4-methyl-piperazin-1-yl)-methanone (211 mg) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-{2-[4-(4-methyl-piperazine-1-carbonyl)-phenyl]-ethyl}-amide was obtained, and then the PMB groups were removed according to the above Deprotection method 3, to obtain the desired compound (D-295) as a colorless powder (26 mg, 24%).

$^1$H-NMR (CDCl$_3$) δ (ppm): 8.84 (2H, s), 7.31 (4H, dt, J=19.9, 8.0 Hz), 5.51 (2H, s), 3.80-3.76 (12H, m), 3.66 (2H, t, J=7.5 Hz), 3.46 (4H, brs), 3.10 (3H, s), 3.09 (2H, t, J=7.5 Hz), 2.97 (2H, t, J=7.5 Hz), 2.43 (4H, brs), 2.32 (3H, s).

ESI (LC-MS positive mode) m/z 587 (M+H)$^+$.

Example 1-D-296

5-(7-{4-[2-(4-Methyl-piperazine-1-sulfonyl)-ethyl]-phenyl}-2-morpholin-4-yl-6,7-dihydro-5H-pyrrolo[2,3-d]pyrimidin-4-yl)-pyrimidin-2-ylamine (D-296)

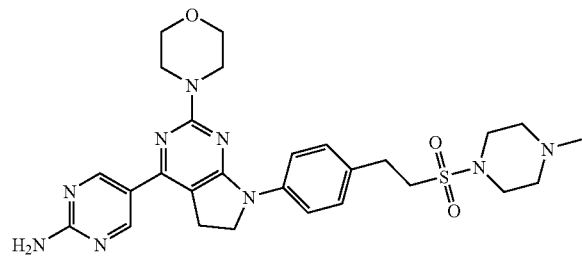

Step A

Methanesulfonic acid 2-(4-bromo-phenyl)-ethyl ester (1.39 g) prepared from 2-(4-bromo-phenyl)-ethanol and methanesulfonyl chloride, and Na$_2$SO$_3$ (816 mg) were reacted in ethanol/water (1/1), to obtain a crude product of 2-(4-bromo-phenyl)-ethanesulfonic acid sodium salt as a colorless plate-like crystal. Then, thionyl chloride (3 ml) was left to react in the presence of DMF (500 μl), to obtain 2-(4-bromo-phenyl)-ethanesulfonyl chloride, and further N-methylpiperazine (73 μl) was left to react in dichloromethane (2 ml) in the presence of triethylamine (54 μl), to obtain 1-[2-(4-bromo-phenyl)-ethanesulfonyl]-4-methyl-piperazine as a yellow solid (94 mg, 24%).

Step B

From bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 1-[2-(4-bromo-phenyl)-ethanesulfonyl]-4-methyl-piperazine (94 mg) obtained in Step A in Example 1-D-296 instead of 4-bromobenzoic acid methyl ester used in Example 1-D-8, in the same manner as Example 1-D-08, a crude product of bis-(4-methoxy-benzyl)-[5-(7-{4-[2-(4-methyl-piperazine-1-sulfonyl)-ethyl]-phenyl}-2-morpholin-4-yl-6,7-dihydro-5H-pyrrolo[2,3-d]pyrimidin-4-yl)-pyrimidin-2-yl]-amine was obtained, and then the PMB groups were removed according to the above Deprotection method 3, to obtain the desired compound (D-296) as a colorless solid (11 mg, 5%).

$^1$H-NMR (CDCl$_3$) δ (ppm): 8.89 (2H, s), 7.74 (4H, d, J=9.4 Hz), 5.23 (2H, s), 4.09 (2H, t, J=8.8 Hz), 3.89-3.77 (8H, m), 3.32-3.27 (12H, m), 3.15 (4H, brs), 2.50 (4H, brs), 2.33 (3H, s).

ESI (LC-MS positive mode) m/z 566 (M+H)$^+$.

Example 1-D-297

4-(2-Amino-pyrimidin-5-yl)-2-morpholin-4-yl-5,6-dihydro-pyrrolo[2,3-d]pyrimidine-7-carboxylic acid methyl-[4-(4-methyl-piperazine-1-carbonyl)-benzyl]-amide (D-297)

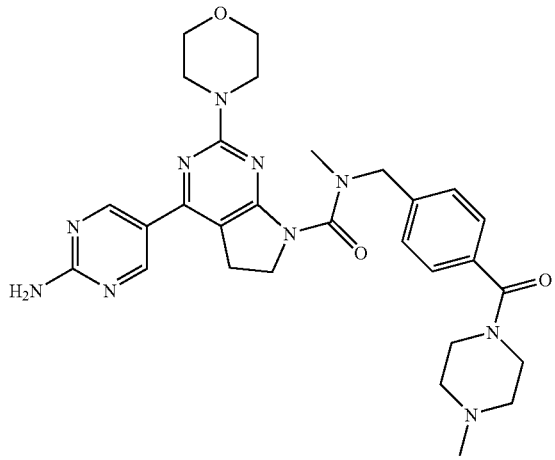

A crude product of [4-(4-methyl-piperazine-1-carbonyl)-benzyl]-carbamic acid tert-butyl ester obtained in Example 1-D-293, sodium hydride and methyl iodide were treated in DMF, and further treated with TFA, to obtain (4-methylaminomethyl-phenyl)-(4-methyl-piperazin-1-yl)-methanone. Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (4-methylaminomethyl-phenyl)-(4-methyl-piperazin-1-yl)-methanone (126 mg) instead of 4-(4-ethyl-piperazin-1-yl)-2,6-difluoro-phenylamine used in Step D in Example 1-D-18, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-[4-(4-methyl-piperazine-1-carbonyl)-benzyl]-amide was obtained, and then the PMB groups were removed according to the above Deprotection method 3, to obtain the desired compound (D-297) as a colorless powder (6 mg, 6%).

$^1$H-NMR (CDCl$_3$) δ (ppm): 8.85 (2H, s), 7.40 (4H, dd, J=10.8, 7.5 Hz), 5.32 (2H, s), 4.69 (2H, s), 4.00 (2H, t, J=8.0 Hz), 3.73-3.69 (8H, m), 3.46 (4H, brs), 3.15 (2H, t, J=8.0 Hz), 2.99 (4H, brs), 2.46 (3H, s).

ESI (LC-MS positive mode) m/z 573 (M+H)$^+$.

Example 1-D-298

4-(2-Amino-pyrimidin-5-yl)-2-morpholin-4-yl-5,6-dihydro-pyrrolo[2,3-d]pyrimidine-7-carboxylic acid methyl-[3-(4-methyl-piperazine-1-carbonyl)-benzyl]-amide (D-298)

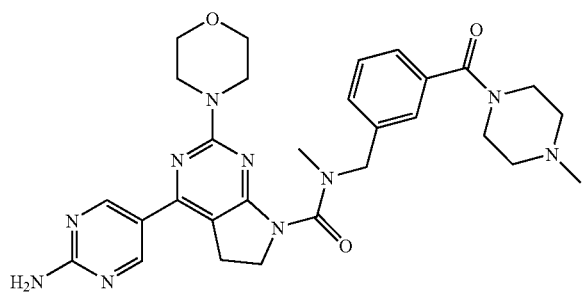

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and (3-methylaminomethyl-phenyl)-(4-methyl-piperazin-1-yl)-methanone (74 mg) instead of 4-(4-ethyl-piperazin-1-yl)-2,6-difluoro-phenylamine, in the same manner as Step D in Example 1-D-18, a crude product of 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid methyl-[3-(4-methyl-piperazine-1-carbonyl)-benzyl]-amide was obtained, and then the PMB groups were removed according to the above Deprotection method 3, to obtain the desired compound (D-298) as a colorless powder (12 mg, 11%).

$^1$H-NMR (CD$_3$OD) δ (ppm): 8.85 (1H, s), 8.82 (2H, s), 7.48-7.45 (3H, m), 7.37 (2H, d, J=5.9 Hz), 4.73 (2H, s), 4.58 (2H, d, J=5.8 Hz), 3.94-3.93 (2H, t, J=8.2 Hz), 3.74 (2H, brs), 3.62-3.56 (12H, m), 3.19 (2H, t, J=7.6 Hz), 3.08 (3H, s), 2.23 (3H, s).

ESI (LC-MS positive mode) m/z 573 (M+H)$^+$.

Example 1-D-299

4-(2-Amino-pyrimidin-5-yl)-2-morpholin-4-yl-5,6-dihydro-pyrrolo[2,3-d]pyrimidine-7-carboxylic acid (4-diethylamino-2-methyl-phenyl)-amide (D-299)

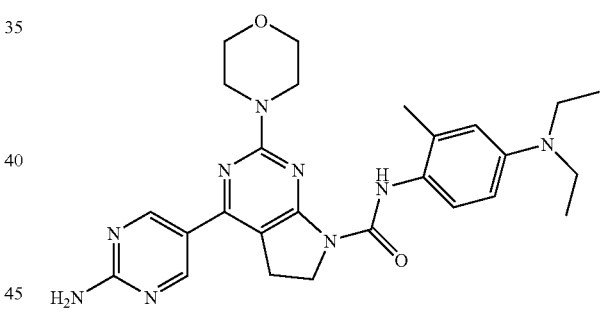

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and 2-amino-5-(diethylamino)toluene monohydrochloride (48.3 mg) instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-diethylamino-2-methyl-phenyl)-amide was obtained as a crude product. The PMB groups were removed according to Deprotection method 3, to obtain the desired compound (D-299) as a yellow solid (46.9 mg, 62%).

$^1$H-NMR (CDCl$_3$) δ: 10.12 (1H, s), 8.91 (2H, s), 7.32 (1H, d, J=8.1 Hz), 6.62-6.52 (2H, m), 5.29 (2H, brs), 4.22 (2H, t, J=8.4 Hz), 3.79-3.75 (8H, brm), 3.34 (4H, q, J=7.1 Hz), 3.22 (2H, t, J=8.4 Hz), 2.27 (3H, s), 1.16 (6H, t, J=7.1 Hz).

ESI (LC-MS positive mode) m/z 504 (M+H)$^+$

Example 1-D-300

{3-[4-(2-Amino-pyrimidin-5-yl)-2-morpholin-4-yl-5,6-dihydro-pyrrolo[2,3-d]pyrimidin-7-yl]-4-methoxy-phenyl}-morpholin-4-yl-methanone (D-300)

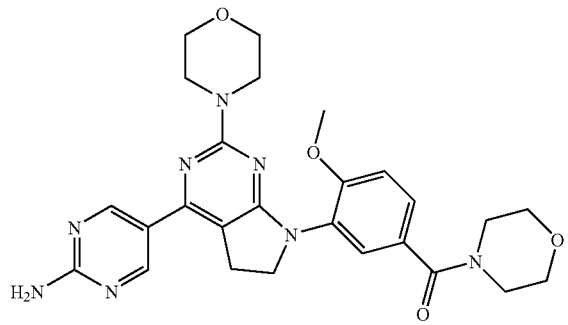

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and (3-bromo-4-methoxy-phenyl)-morpholin-4-yl-methanone (59 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-methoxy-phenyl]-morpholin-4-yl-methanone was obtained, and then the PMB groups were removed according to the above Deprotection method 3, to obtain the desired compound (D-300) as a pale brown powder (67 mg, 100%).

$^1$H-NMR (DMSO-$d_6$) δ (ppm): 8.80 (2H, s), 7.46 (1H, d, J=2.1 Hz), 7.34 (1H, dd, J=8.6, 2.1 Hz), 7.18 (1H, d, J=8.6 Hz), 7.05 (2H, s), 3.97 (2H, t, J=8.4 Hz), 3.85 (3H, s), 3.56 (16H, brs), 3.29 (2H, t, J=8.4 Hz).

ESI (LC-MS positive mode) m/z 519 (M+H)$^+$.

Example 1-D-301

4-[4-(2-Amino-pyrimidin-5-yl)-2-morpholin-4-yl-5,6-dihydro-pyrrolo[2,3-d]pyrimidin-7-yl]-3-methyl-N-pyridin-3-ylmethyl-benzamide (D-301)

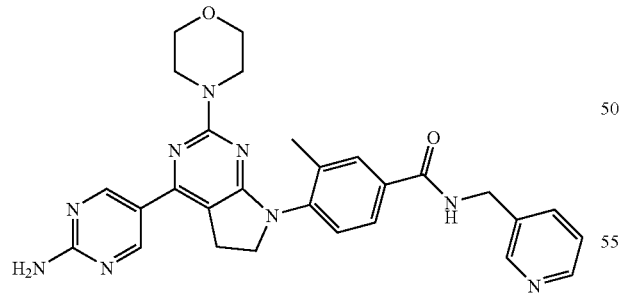

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and 4-bromo-3-methyl-N-pyridin-3-ylmethyl-benzamide (60 mg) instead of 4-chloropicolinic acid t-butylamide, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-N-pyridin-3-ylmethyl-benzamide was obtained, and then the PMB groups were removed according to the above Deprotection method 3, to obtain the desired compound (D-301) as a grayish white powder (32 mg, 47%).

$^1$H-NMR (CDCl$_3$) δ (ppm): 8.80 (2H, s), 8.52 (1H, d, J=1.6 Hz), 8.40 (1H, dd, J=4.9, 1.5 Hz), 7.82 (1H, t, J=1.9 Hz), 7.78 (2H, dd, J=2.9, 1.9 Hz), 7.69 (1H, dd, J=8.2, 1.8 Hz), 7.49 (1H, s), 7.34 (1H, dd, J=7.8, 4.9 Hz), 7.30 (1H, d, J=8.4 Hz), 4.52 (4H, s), 4.01 (2H, t, J=8.2 Hz), 3.63 (8H, s), 2.28 (3H, s).

ESI (LC-MS positive mode) m/z 524 (M+H)$^+$.

Example 1-D-302

4-[4-(2-Amino-pyrimidin-5-yl)-2-morpholin-4-yl-5,6-dihydro-pyrrolo[2,3-d]pyrimidin-7-yl]-3-methyl-N-(2-pyridin-3-yl-ethyl)-benzamide (D-302)

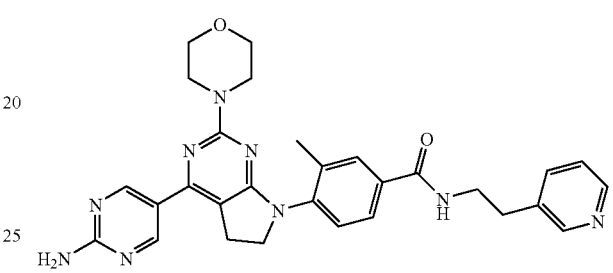

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and 4-bromo-3-methyl-N-(2-pyridin-3-yl-ethyl)-benzamide (62 mg) instead of 4-chloropicolinic acid t-butylamide, in the same manner as Example 1-D-07, a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-N-(2-pyridin-3-yl-ethyl)-benzamide was obtained, and then the PMB groups were removed according to the above Deprotection method 3, to obtain the desired compound (D-302) as a pale brown powder (29 mg, 41%).

$^1$H-NMR (CDCl$_3$) δ (ppm): 8.81 (2H, s), 8.42 (1H, d, J=1.6 Hz), 8.37 (2H, dd, J=4.9, 1.6 Hz), 7.74 (1H, t, J=1.9 Hz), 7.70 (2H, d, J=2.0 Hz), 7.61 (1H, dd, J=8.7, 4.3 Hz), 7.33 (1H, dd, J=7.7, 5.5 Hz), 7.29 (1H, d, J=8.4 Hz), 4.01 (2H, t, J=8.1 Hz), 3.64 (10H, brs), 3.32 (2H, t, J=8.2 Hz), 2.95 (2H, t, J=7.2 Hz), 2.85 (1H, d, J=0.7 Hz), 2.28 (3H, s).

ESI (LC-MS positive mode) m/z 538 (M+H)$^+$.

Example 1-D-303

3-[4-(2-Amino-pyrimidin-5-yl)-2-morpholin-4-yl-5,6-dihydro-pyrrolo[2,3-d]pyrimidin-7-yl]-4-methyl-N-pyridin-3-ylmethyl-benzamide (D-303)

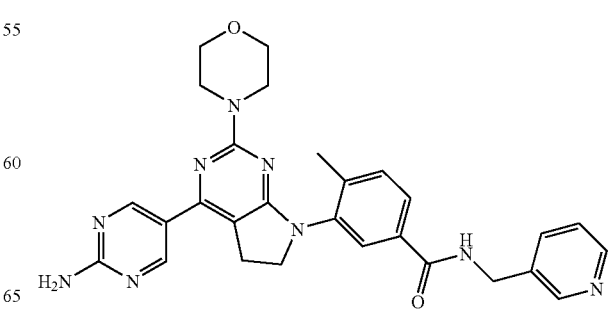

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and 3-bromo-4-methyl-N-pyridin-3-ylmethyl-benzamide (60 mg) instead of 4-chloropicolinic acid t-butylamide, in the same manner as Example 1-D-07, a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-methyl-N-pyridin-3-ylmethyl-benzamide was obtained, and then the PMB groups were removed according to the above Deprotection method 3, to obtain the desired compound (D-303) as a grayish white powder (27 mg, 40%).

$^1$H-NMR (CDCl$_3$) δ (ppm): 8.80 (2H, s), 8.50 (1H, d, J=1.5 Hz), 8.39 (1H, dd, J=4.9, 1.6 Hz), 7.79 (1H, dd, J=2.1, 1.6 Hz), 7.77-7.75 (2H, m), 7.67 (1H, dd, J=7.8, 1.9 Hz), 7.51 (1H, s), 7.34-7.32 (3H, m), 4.03 (2H, t, J=8.1 Hz), 3.62 (10H, brs), 3.32 (2H, t, J=7.6 Hz), 2.27 (3H, s).

ESI (LC-MS positive mode) m/z 524 (M+H)$^+$.

Example 1-D-304

3-[4-(2-Amino-pyrimidin-5-yl)-2-morpholin-4-yl-5,6-dihydro-pyrrolo[2,3-d]pyrimidin-7-yl]-4-methyl-N-(2-pyridin-3-yl-ethyl)-benzamide (D-304)

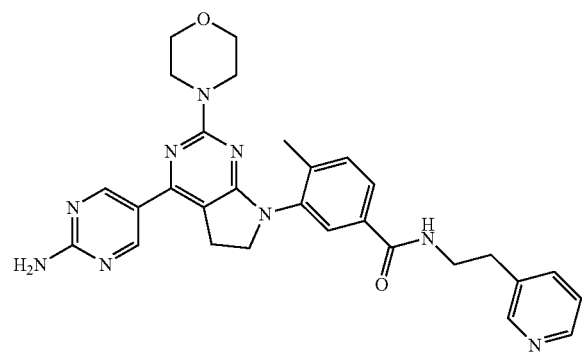

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and 3-bromo-4-methyl-N-(2-pyridin-3-yl-ethyl)-benzamide (62 mg) instead of 4-chloropicolinic acid t-butylamide, in the same manner as Example 1-D-07, a crude product of 3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-methyl-N-(2-pyridin-3-yl-ethyl)-benzamide was obtained, and then the PMB groups were removed according to the above Deprotection method 3, to obtain the desired compound (D-304) as a pale brown powder (22 mg, 32%).

$^1$H-NMR (CDCl$_3$) δ (ppm): 8.82 (2H, s), 8.40 (1H, d, J=1.5 Hz), 8.35 (2H, dd, J=5.0, 1.6 Hz), 7.72 (1H, t, J=1.9 Hz), 7.69 (2H, d, J=1.8 Hz), 7.59 (1H, dd, J=7.9, 1.8 Hz), 7.35-7.30 (2H, m), 4.03 (2H, t, J=8.2 Hz), 3.63 (8H, brs), 3.60 (2H, t, J=7.3 Hz), 3.34 (2H, t, J=7.5 Hz), 2.94 (2H, t, J=7.3 Hz), 2.27 (3H, s).

ESI (LC-MS positive mode) m/z 538 (M+H)$^+$.

Example 1-D-305

4-[4-(2-Amino-pyrimidin-5-yl)-2-morpholin-4-yl-5,6-dihydro-pyrrolo[2,3-d]pyrimidin-7-yl]-3-fluoro-N-pyridin-3-ylmethyl-benzamide (D-305)

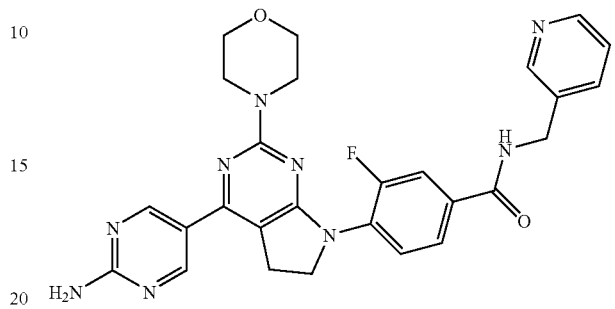

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 3-(aminomethyl)pyridine (24.0 μl, 0.237 mmol) instead of 1-pyridine-3-yl-piperazine, amidation was carried out in the same manner as Step B in Example 1-D-21, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-N-pyridin-3-ylmethyl-benzamide as a yellow solid (152 mg), and then the PMB groups were removed according to the above Deprotection method 3, to obtain the desired compound (D-305) as a yellow powder (47.9 mg, 77%).

$^1$H-NMR (DMSO-d$_6$) δ (ppm): 9.16 (1H, t, J=5.6 Hz), 8.81 (2H, s), 8.56 (1H, brs), 8.47 (1H, d, J=4.8 Hz), 7.85-7.69 (4H, m), 7.37 (1H, dd, J=7.9, 4.9 Hz), 7.10 (2H, brs), 4.50 (2H, d, J=5.6 Hz), 4.11 (2H, t, J=8.1 Hz), 3.65-3.58 (10H, m).

ESI (LC-MS positive mode) m/z 528 (M+H)$^+$.

Example 1-D-306

4-[4-(2-Amino-pyrimidin-5-yl)-2-morpholin-4-yl-5,6-dihydro-pyrrolo[2,3-d]pyrimidin-7-yl]-3-fluoro-N-(2-pyridin-3-yl-ethyl)-benzamide (D-306)

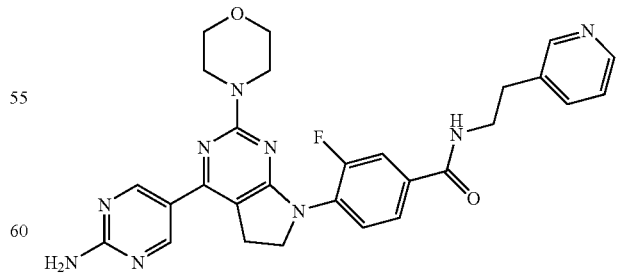

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 3-(2-aminoethyl)

pyridine (27.7 μl, 0.236 mmol) instead of 1-pyridine-3-yl-piperazine, amidation was carried out in the same manner as Step B in Example 1-D-21, to obtain a crude product of 4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-N-(2-pyridin-3-yl-ethyl)-benzamide as a yellow solid (171 mg), and then the PMB groups were removed according to the above Deprotection method 3, to obtain the desired compound (D-306) as a yellow powder (49.8 mg, 78%).

$^1$H-NMR (DMSO-$d_6$) δ (ppm): 8.81 (2H, s), 8.65 (1H, t, J=5.3 Hz), 8.46 (1H, brs), 8.42 (1H, d, J=4.6 Hz), 7.83-7.62 (4H, m), 7.32 (2H, dd, J=7.7, 4.6 Hz), 7.09 (2H, brs), 4.10 (2H, t, J=7.7 Hz), 3.71-3.23 (12H, m), 2.88 (2H, t, J=6.9 Hz).

ESI (LC-MS positive mode) m/z 542 (M+H)$^+$.

Example 1-D-307

{4-[4-(2-Amino-pyrimidin-5-yl)-2-morpholin-4-yl-5,6-dihydro-pyrrolo[2,3-d]pyrimidin-7-yl]-phenyl}-(4-morpholin-4-yl-piperidin-1-yl)-methanone (D-307)

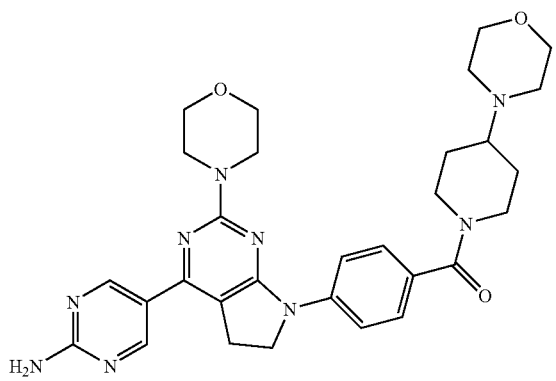

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (80.0 mg, 0.121 mmol) obtained in Step A in Example 1-D-19 and 4-morpholinopiperidine (41.3 mg, 0.242 mmol) instead of 3-(aminomethyl)pyridine, amidation was carried out in the same manner as Step B in Example 1-D-19, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-phenyl}-(4-morpholin-4-yl-piperidin-1-yl)-methanone as a yellow solid (82.0 mg), and then the PMB groups were removed according to the above Deprotection method 3, to obtain the desired compound (D-307) as a yellow powder (32.0 mg, 55%).

$^1$H-NMR (DMSO-$d_6$) δ (ppm): 8.82 (2H, s), 7.89 (2H, d, J=8.6 Hz), 7.43 (2H, d, J=8.6 Hz), 7.10 (2H, brs), 4.11 (2H, t, J=8.1 Hz), 3.76-3.53 (12H, m), 3.30 (2H, t, J=8.1 Hz), 3.10-2.88 (5H, m), 2.55-2.34 (4H, m), 1.87-1.25 (4H, m).

ESI (LC-MS positive mode) m/z 572 (M+H)$^+$.

Example 1-D-308

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-morpholin-4-yl-piperidin-1-yl)-methanone (D-308)

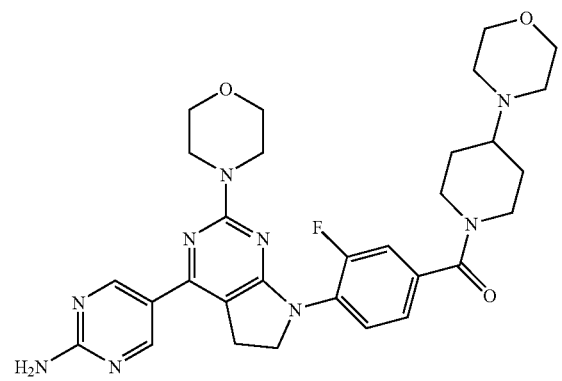

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and 4-morpholinopiperidine (40.2 mg, 0.236 mmol) instead of 1-pyridine-3-yl-piperazine, amidation was carried out in the same manner as Step B in Example 1-D-21, to obtain a crude product of {4-[4-{2-[bis-(4-methoxy-benzyl)-amino]-pyrimidin-5-yl}-2-morpholin-4-yl-5,6-dihydro-pyrrolo[2,3-d]pyrimidin-7-yl]-3-fluoro-phenyl}-(4-morpholin-4-yl-piperidin-1-yl)-methanone as a brown solid (136 mg), and then the PMB groups were removed according to the above Deprotection method 3, to obtain the desired compound (D-308) as a yellow powder (61.8 mg, 89%).

$^1$H-NMR (DMSO-$d_6$) δ (ppm): 8.81 (2H, s), 7.77 (1H, t, J=8.1 Hz), 7.40 (1H, dd, J=11.9, 1.8 Hz), 7.29 (1H, dd, J=8.1, 1.8 Hz), 7.11 (2H, brs), 4.10 (2H, t, J=8.1 Hz), 3.76-3.38 (12H, m), 3.34 (2H, t, J=8.1 Hz), 3.24-3.05 (5H, m), 2.52-2.41 (4H, m), 2.14-1.51 (4H, m).

ESI (LC-MS positive mode) m/z 590 (M+H)$^+$.

Example 1-D-309

{4-[4-(2-Amino-pyrimidin-5-yl)-2-morpholin-4-yl-5,6-dihydro-pyrrolo[2,3-d]pyrimidin-7-yl]-3-chloro-phenyl}-morpholin-4-yl-methanone (D-309)

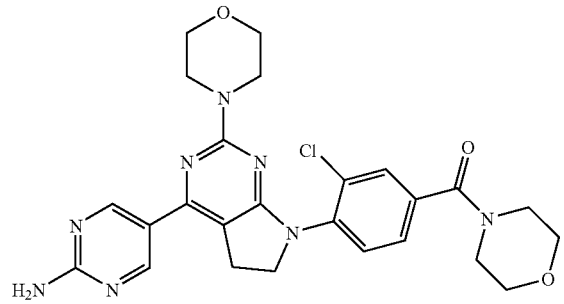

731

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and (4-bromo-3-chloro-phenyl)-morpholin-4-yl-methanone (59 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-chloro-phenyl]-morpholin-4-yl-methanone was obtained, and then the PMB groups were removed according to the above Deprotection method 3, to obtain the desired compound (D-309) as a pale brown powder (42 mg, 62%).

$^1$H-NMR (CDCl$_3$) δ (ppm): 8.93 (2H, s), 7.57 (1H, d, J=1.8 Hz), 7.50 (1H, d, J=8.1 Hz), 7.38 (2H, dd, J=8.2, 1.9 Hz), 5.30 (1H, s), 4.11 (2H, t, J=7.2 Hz), 3.70 (16H, brs), 3.34 (2H, t, J=8.1 Hz).

ESI (LC-MS positive mode) m/z 523 (M+H)$^+$.

Example 1-D-310

{3-[4-(2-Amino-pyrimidin-5-yl)-2-morpholin-4-yl-5,6-dihydro-pyrrolo[2,3-d]pyrimidin-7-yl]-4-chloro-phenyl}-morpholin-4-yl-methanone (D-310)

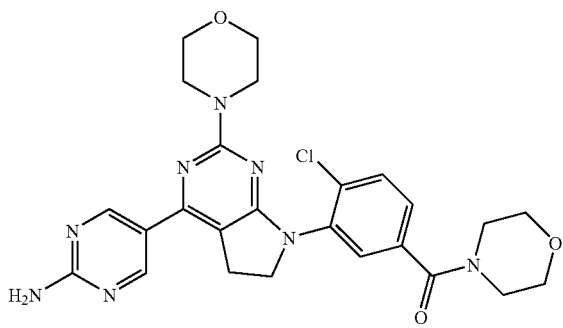

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and (3-bromo-4-chloro-phenyl)-morpholin-4-yl-methanone (59 mg) instead of 4-chloropicolinic acid t-butylamide, in the same manner as Example 1-D-07, a crude product of [3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-4-chloro-phenyl]-morpholin-4-yl-methanone was obtained, and then the PMB groups were removed according to the above Deprotection method 3, to obtain the desired compound (D-310) as a pale brown powder (16 mg, 24%).

$^1$H-NMR (CDCl$_3$) δ (ppm): 8.92 (2H, s), 7.55 (1H, d, J=8.2 Hz), 7.52 (1H, d, J=2.0 Hz), 7.31 (1H, dd, J=8.2, 2.0 Hz), 5.30 (1H, s), 4.08 (2H, t, J=8.2 Hz), 3.69 (16H, brs), 3.33 (2H, t, J=8.2 Hz).

ESI (LC-MS positive mode) m/z 523 (M+H)$^+$.

Example 1-D-311

{4-[4-(2-Amino-pyrimidin-5-yl)-2-morpholin-4-yl-5,6-dihydro-pyrrolo[2,3-d]pyrimidin-7-yl]-3-methyl-phenyl}-(4-pyridin-3-yl-piperazin-1-yl)-methanone (D-311)

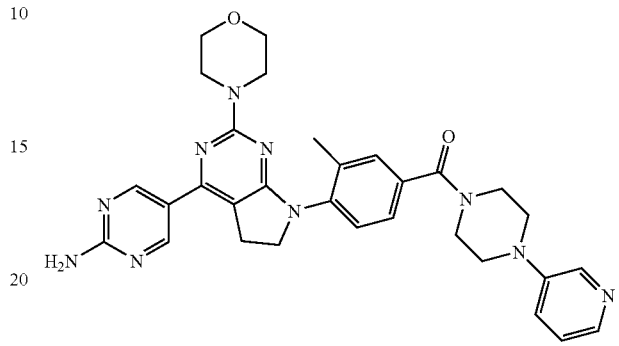

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (70 mg) and (4-bromo-3-methyl-phenyl)-(4-pyridin-3-yl-piperazin-1-yl)-methanone (70 mg) instead of 4-chloropicolinic acid t-butylamide, in the same manner as Example 1-D-07, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-methyl-phenyl]-(4-pyridin-3-yl-piperazin-1-yl)-methanone was obtained, and then the PMB groups were removed according to the above Deprotection method 3, to obtain the desired compound (D-311) as a yellow powder (41 mg, 55%).

$^1$H-NMR (CDCl$_3$) δ (ppm): 8.90 (2H, s), 8.36 (1H, s), 8.17 (1H, s), 7.41-7.24 (5H, m), 5.52 (1H, s), 5.30 (1H, s), 4.01 (2H, t, J=8.1 Hz), 3.70 (12H, brs), 3.33 (2H, t, J=8.4 Hz), 3.30 (4H, brs), 2.31 (3H, s).

ESI (LC-MS positive mode) m/z 579 (M+H)$^+$.

Example 1-D-312

4-(2-Amino-pyrimidin-5-yl)-2-morpholin-4-yl-5,6-dihydro-pyrrolo[2,3-d]pyrimidine-7-carboxylic acid (4-methyl-biphenyl-3-yl)-amide (D-312)

Step A

4-Methyl-3-nitro-biphenyl

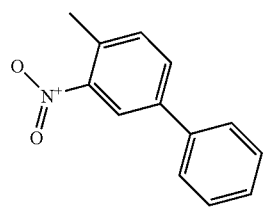

To a DMF solution (5.0 ml) of 4-bromo-2-methyl-1-nitro-benzene (500 mg), palladium acetate (10.4 mg), S-Phos (38.0 mg) and potassium phosphate (983 mg), phenylboronic acid-pinacol ester (496 mg) was added, and then the mixture was degassed under ultrasonic irradiation. After the mixture was stirred at 100° C. for 18 hours, water (20 ml) was added, followed by extraction with ethyl acetate (20 ml×2), and the organic layer was dried over sodium sulfate. After the sodium sulfate was filtered off, the solvent was distilled off under reduced pressure, followed by purification by silica gel column chromatography (hexane/ethyl acetate=100/1), to obtain the desired compound (457 mg, 93%).

Step B

4-Methyl-biphenyl-3-ylamine

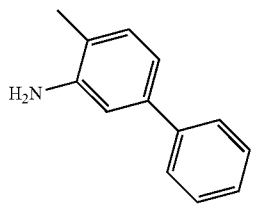

Using 4-methyl-3-nitro-biphenyl obtained in Step A instead of (4-ethyl-piperazin-1-yl)-(3-nitro-phenyl)-methanone, in the same manner as Step B in Example 1-D-101, the desired compound was obtained (292 mg, 74%).

Step C 4-(2-Amino-pyrimidin-5-yl)-2-morpholin-4-yl-5,6-dihydro-pyrrolo[2,3-d]pyrimidine-7-carboxylic acid (4-methyl-biphenyl-3-yl)-amide (D-312)

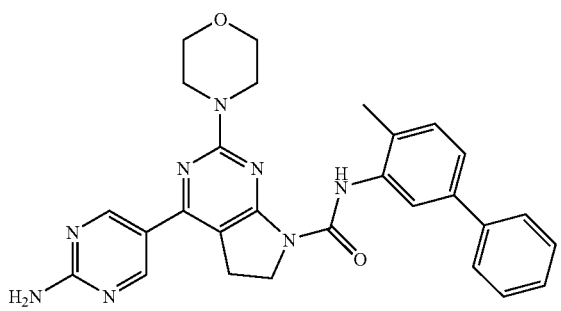

Using bis-(4-methoxy-benzyl)-[5-(2-morpholin-4-yl-6,7-dihydro-5H-pyrrolo[2,3-d]pyrimidin-4-yl)-pyrimidin-2-yl]-amine (80.9 mg) and 4-methyl-biphenyl-3-ylamine (33.0 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (4-methyl-biphenyl-3-yl)-amide was obtained as a crude product. The PMB groups were removed according to Deprotection method 3, to obtain the desired compound (D-312) as a yellow solid (57.4 mg, 76%).

$^1$H-NMR (DMSO-$d_6$) δ: 10.39 (1H, s), 8.86 (2H, s), 7.92 (1H, d, J=1.6 Hz), 7.63 (2H, d, J=7.1 Hz), 7.47 (2H, t, J=7.4 Hz), 7.42-7.33 (3H, m), 7.23 (2H, s), 4.07 (2H, t, J=8.3 Hz), 3.77-3.65 (8H, brm), 3.26 (2H, t, J=8.3 Hz), 2.31 (3H, s).

ESI (LC-MS positive mode) m/z 509 (M+H)$^+$

Example 1-D-313

4-(2-Amino-pyrimidin-5-yl)-2-morpholin-4-yl-5,6-dihydro-pyrrolo[2,3-d]pyrimidine-7-carboxylic acid (2-methyl-5-pyridin-3-yl-phenyl)-amide (D-313)

Step A 3-(4-Methyl-3-nitro-phenyl)-pyridine

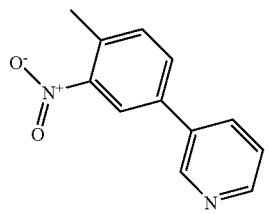

Using 4-bromo-2-methyl-1-nitro-benzene (500 mg) and tetrakistriphenylphosphine palladium (26.7 mg) instead of S-Phos, and pyridin-3-boronic acid-1,3-propanediol cyclic ester (396 mg) instead of phenylboronic acid-pinacol ester, in the same manner as Step A in Example 1-D-312, the desired compound was obtained (195 mg, 39%).

Step B

2-Methyl-5-pyridin-3-yl-phenylamine

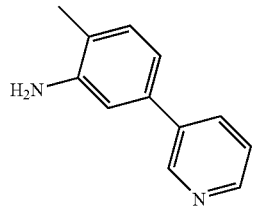

Using 3-(4-methyl-3-nitro-phenyl)-pyridine obtained in Step A instead of (4-ethyl-piperazin-1-yl)-(3-nitro-phenyl)-methanone, in the same manner as Step B in Example 1-D-101, the desired compound was obtained (136 mg, 81%).

Step C 4-(2-Amino-pyrimidin-5-yl)-2-morpholin-4-yl-5,6-dihydro-pyrrolo[2,3-d]pyrimidine-7-carboxylic acid (2-methyl-5-pyridin-3-yl-phenyl)-amide (D-313)

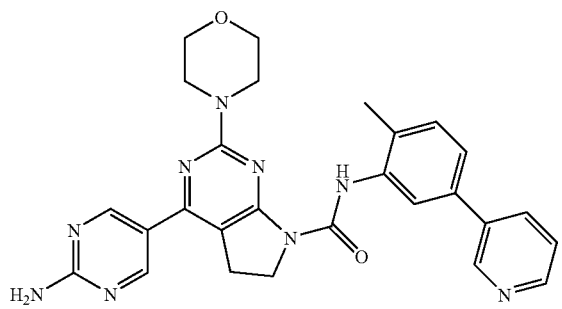

Using bis-(4-methoxy-benzyl)-[5-(2-morpholin-4-yl-6,7-dihydro-5H-pyrrolo[2,3-d]pyrimidin-4-yl)-pyrimidin-2-yl]- amine (80.9 mg) and 2-methyl-5-pyridin-3-yl-phenylamine (33.2 mg) obtained in Step B instead of 4-(4-ethyl-piperazin-1-yl)-2,6-difluoro-phenylamine, in the same manner as Step D in Example 1-D-18, 4-{2-[bis-(4-methoxy-benzyl)-amino]-pyrimidin-5-yl}-2-morpholin-4-yl-5,6-dihydro-pyrrolo[2,3-d]pyrimidine-7-carboxylic acid (2-methyl-5-pyridin-3-yl-phenyl)-amide was obtained as a crude product. The PMB groups were removed according to Deprotection method 3, to obtain the desired compound (D-313) as a yellow solid (41.2 mg, 54%).

$^1$H-NMR (DMSO-d$_6$) δ: 10.42 (1H, s), 8.97-8.91 (1H, m), 8.86 (2H, s), 8.64 (1H, d, J=5.1 Hz), 8.21 (1H, d, J=8.4 Hz), 8.00 (1H, s), 7.63 (1H, dd, J=8.1, 4.8 Hz), 7.55-7.39 (2H, m), 7.25 (2H, s), 4.07 (2H, t, J=8.2 Hz), 3.78-3.65 (8H, brm), 3.26 (2H, t, J=8.2 Hz), 2.34 (3H, s).

ESI (LC-MS positive mode) m/z 510 (M+H)$^+$

Example 1-D-314

5-[2-Morpholin-4-yl-7-(5-trifluoromethyl-pyridin-3-yl)-6,7-dihydro-5H-pyrrolo[2,3-d]pyrimidin-4-yl]-pyrimidin-2-ylamine (D-314)

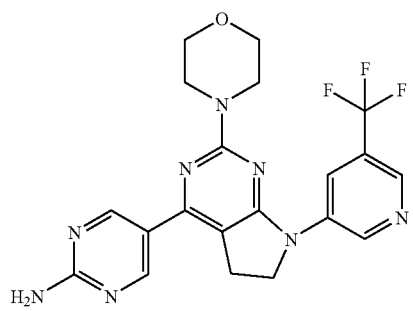

In the same manner as Example 1-D-08, using bis-(4-methoxy-benzyl)-[5-(2-morpholin-4-yl-6,7-dihydro-5H-pyrrolo[2,3-d]pyrimidin-4-yl)-pyrimidin-2-yl]-amine (100 mg) and 3-bromo-5-trifluoro-methyl-pyridine (63 mg) instead of 4-bromobenzoic acid methyl ester, a crude product of bis-(4-methoxy-benzyl)-5-[2-morpholin-4-yl-7-(5-trifluoromethyl-pyridin-3-yl)-6,7-dihydro-5H-pyrrolo[2,3-d]pyrimidin-4-yl]-pyrimidin-2-ylamine was obtained. Using a crude product (99 mg) of bis-(4-methoxy-benzyl)-5-[2-morpholin-4-yl-7-(5-trifluoromethyl-pyridin-3-yl)-6,7-dihydro-5H-pyrrolo[2,3-d]pyrimidin-4-yl]-pyrimidin-2-ylamine, according to the above Deprotection method 2, 5-[2-morpholin-4-yl-7-(5-trifluoromethyl-pyridin-3-yl)-6,7-dihydro-5H-pyrrolo[2,3-d]pyrimidin-4-yl]-pyrimidin-2-ylamine was obtained as a light gray powder (43 mg, 68%).

$^1$H-NMR (DMSO-D$_6$) δ: 9.17 (1H, m), 8.88 (1H, m), 8.84 (2H, s), 8.60 (1H, m), 7.14 (2H, s), 4.20 (2H, m), 3.71 (8H, m), 3.36 (2H, m).

ESI (LC-MS positive mode) m/z 445 (M+H)$^+$.

Example 1-D-315

{4-[4-(2-Amino-pyrimidin-5-yl)-2-morpholin-4-yl-5,6-dihydro-pyrrolo[2,3-d]pyrimidin-7-yl]-3-fluoro-phenyl}-(4-pyridin-3-ylmethyl-piperazin-1-yl)-methanone (D-315)

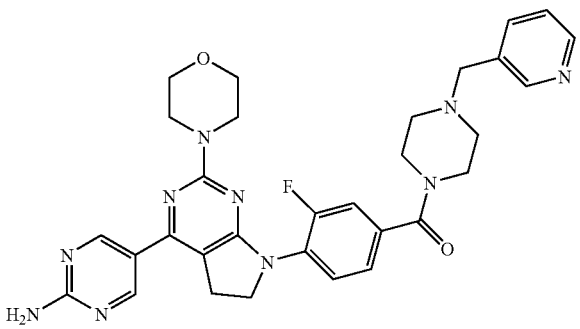

Step A

Piperazine-1-carboxylic acid tert-butyl ester (930 mg), 3-chloromethyl-pyridine hydrochloride (902 mg) and cesium carbonate (3.6 g) were reacted in DMF (5 ml), followed by further treatment with TFA, to obtain 1-pyridin-3-ylmethyl-piperazine (767 mg, 87%) as a pale brown oil.

Step B

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (54 mg) and 1-pyridin-3-ylmethyl-piperazine (22 mg) obtained in Step A in Example 1-D-315 instead of 3-(aminomethyl)pyridine used in Step B in Example 1-D-19, treatment was carried out in the same manner as Step B in Example 1-D-19, to obtain a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-phenyl]-(4-pyridin-3-ylmethyl-piperazin-1-yl)-methanone, and then the PMB groups were removed according to the above Deprotection method 3, to obtain the desired compound (D-315) as a yellow powder (32.0 mg, 83%).

$^1$H-NMR (DMSO-d$_6$) δ (ppm): 8.80 (2H, s), 8.51 (1H, d, J=1.8 Hz), 8.48 (1H, dd, J=4.8, 1.6 Hz), 7.75-7.71 (2H, m), 7.38-7.35 (2H, m), 7.26 (1H, dd, J=8.2, 1.6 Hz), 7.09 (2H, s), 4.08 (2H, t, J=8.0 Hz), 3.74 (2H, s), 3.68-3.62 (10H, m), 3.55 (4H, brs), 2.42 (4H, brs).

ESI (LC-MS positive mode) m/z 597 (M+H)$^+$.

Example 1-D-316

{4-[4-(2-Amino-pyrimidin-5-yl)-2-morpholin-4-yl-5, 6-dihydro-pyrrolo[2,3-d]pyrimidin-7-yl]-3-fluoro-phenyl}-(4-pyridin-4-ylmethyl-piperazin-1-yl)-methanone (D-316)

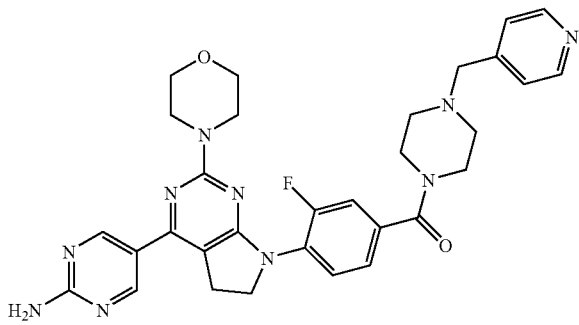

Using 1-pyridin-4-ylmethyl-piperazine (31 mg) instead of 1-pyridin-3-ylmethyl-piperazine used in Example 1-D-315, in the same manner as Example 1-D-315, a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-phenyl]-(4-pyridin-4-ylmethyl-piperazin-1-yl)-methanone was obtained, and then the PMB groups were removed according to the above Deprotection method 3, to obtain the desired compound (D-316) as a yellow powder (20 mg, 50%).

$^1$H-NMR (DMSO-$d_6$) δ (ppm): 8.80 (2H, s), 8.52 (2H, dd, J=6.6, 2.1 Hz), 7.74 (1H, t, J=8.4 Hz), 7.39 (1H, d, J=1.8 Hz), 7.35 (2H, dd, J=6.6, 2.1 Hz), 7.27 (1H, dd, J=8.4, 1.8 Hz), 7.09 (2H, s), 4.08 (2H, t, J=8.2 Hz), 3.74 (2H, s), 3.67 (2H, brs), 3.61 (8H, s), 3.56 (4H, s), 2.43 (4H, brs).

ESI (LC-MS positive mode) m/z 597 (M+H)$^+$.

Example 1-D-317

4-[4-(2-Amino-pyrimidin-5-yl)-2-morpholin-4-yl-5, 6-dihydro-pyrrolo[2,3-d]pyrimidin-7-yl]-N-methyl-N-pyridin-3-ylmethyl-benzamide (D-317)

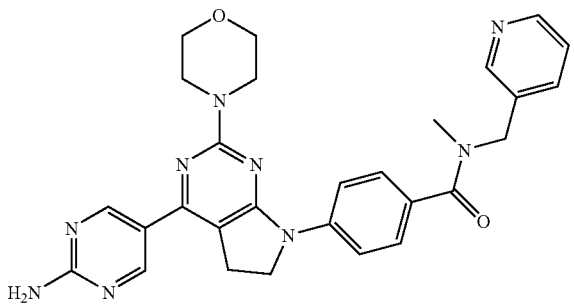

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (80.0 mg, 0.121 mmol) obtained in Step A in Example 1-D-19 and N-methyl-N-(3-pyridylmethyl)amine (22.2 mg, 0.182 mmol) instead of 3-(aminomethyl)pyridine, the amidation was carried out in the same manner as Step B in Example 1-D-19, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-methyl-N-pyridin-3-ylmethyl-benzamide as a yellow solid (119 mg), and then the PMB groups were removed according to the above Deprotection method 3, to obtain the desired compound (D-317) as a yellow powder (42.0 mg, 66%).

$^1$H-NMR (DMSO-$d_6$) δ (ppm): 8.83-8.81 (3H, m), 8.52 (1H, d, J=5.1 Hz), 7.91 (2H, d, J=8.1 Hz), 7.73 (1H, m), 7.52 (2H, d, J=8.1 Hz), 7.41 (1H, m), 7.12-7.08 (3H, m), 4.67 (2H, brs), 4.11 (2H, t, J=7.4 Hz), 3.76-3.58 (8H, m), 3.32-3.28 (2H, m), 2.94 (3H, s).

ESI (LC-MS positive mode) m/z 524 (M+H)$^+$.

Example 1-D-318

4-[4-(2-Amino-pyrimidin-5-yl)-2-morpholin-4-yl-5, 6-dihydro-pyrrolo[2,3-d]pyrimidin-7-yl]-3-fluoro-N-methyl-N-pyridin-3-ylmethyl-benzamide (D-318)

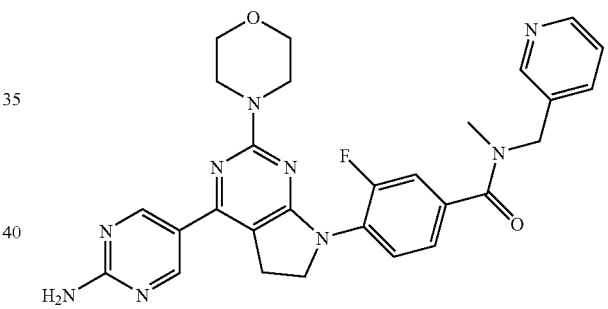

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and N-methyl-N-(3-pyridylmethyl)amine (21.6 mg, 0.177 mmol) instead of 1-pyridine-3-yl-piperazine, the amidation was carried out in the same manner as Step B in Example 1-D-21, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-N-methyl-N-pyridin-3-ylmethyl-benzamide as a yellow solid (92.8 mg), and then the PMB groups were removed according to the above Deprotection method 3, to obtain the desired compound (D-318) as a yellow powder (38.0 mg, 59%).

$^1$H-NMR (DMSO-$d_6$) δ (ppm): 8.81 (2H, s), 8.58 (1H, m), 8.52 (1H, dd, J=4.6, 1.5 Hz), 7.75 (2H, m), 7.54-7.31 (2H, m), 7.41 (1H, dd, J=7.7, 4.6 Hz), 7.09 (2H, brs), 4.69 (2H, brs), 4.09 (2H, t, J=7.7 Hz), 3.64-3.58 (8H, m), 3.33 (2H, t, J=7.7 Hz), 2.93 (3H, s).

ESI (LC-MS positive mode) m/z 542 (M+H)$^+$.

Example 1-D-319

4-[4-(2-Amino-pyrimidin-5-yl)-2-morpholin-4-yl-5,6-dihydro-pyrrolo[2,3-d]pyrimidin-7-yl]-N-methyl-N-(2-pyridin-3-yl-ethyl)-benzamide (D-319)

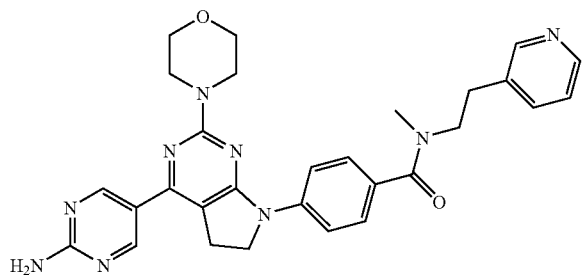

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (80.0 mg, 0.121 mmol) obtained in Step A in Example 1-D-19 and (2-pyridin-3-ylethylene)methylamine (24.8 mg, 0.182 mmol) instead of 3-(aminomethyl)pyridine, the amidation was carried out in the same manner as Step B in Example 1-D-19, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-N-methyl-N-(2-pyridin-3-yl-ethyl)-benzamide as a yellow solid (80.0 mg), and then the PMB groups were removed according to the above Deprotection method 3, to obtain the desired compound (D-319) as a yellow powder (55.5 mg, 72%).

$^1$H-NMR (DMSO-$d_6$) δ (ppm): 8.82 (2H, s), 8.71-7.01 (6H, m), 7.84 (2H, d, J=8.4 Hz), 7.16 (2H, d, J=8.4 Hz), 4.10 (2H, t, J=8.2 Hz), 3.87-3.55 (12H, m), 3.30 (2H, t, J=8.2 Hz), 3.00 (3H, s).

ESI (LC-MS positive mode) m/z 538 (M+H)$^+$.

Example 1-D-320

4-[4-(2-Amino-pyrimidin-5-yl)-2-morpholin-4-yl-5,6-dihydro-pyrrolo[2,3-d]pyrimidin-7-yl]-3-fluoro-N-methyl-N-(2-pyridin-3-yl-ethyl)-benzamide (D-320)

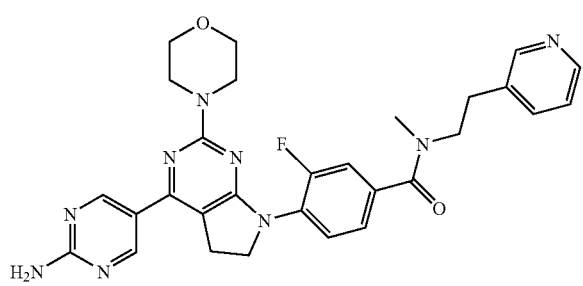

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid (80.0 mg, 0.118 mmol) obtained in Step A in Example 1-D-21 and (2-pyridin-3-ylethylene)methylamine (24.1 mg, 0.177 mmol) instead of 1-pyridine-3-yl-piperazine, the amidation was carried out in the same manner as Step B in Example 1-D-21, to obtain a crude product of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-N-methyl-N-(2-pyridin-3-yl-ethyl)-benzamide as a yellow solid (90.0 mg), and then the PMB groups were removed according to the above Deprotection method 3, to obtain the desired compound (D-320) as a yellow powder (65.0 mg, 95%).

$^1$H-NMR (DMSO-$d_6$) δ (ppm): 8.81 (2H, s), 8.57-8.17 (3H, m), 7.79-7.20 (3H, m), 7.08 (2H, brs), 6.93-6.93 (1H, m), 4.07 (2H, t, J=7.9 Hz), 3.71-3.41 (10H, m), 3.33 (3H, s), 3.32 (2H, t, J=7.9 Hz), 3.08-2.82 (2H, m).

ESI (LC-MS positive mode) m/z 556 (M+H)$^+$.

Example 1-D-321

{4-[4-(2-Amino-pyrimidin-5-yl)-2-morpholin-4-yl-5,6-dihydro-pyrrolo[2,3-d]pyrimidin-7-yl]-phenyl}-(4-pyridin-3-ylmethyl-piperazin-1-yl)-methanone (D-321)

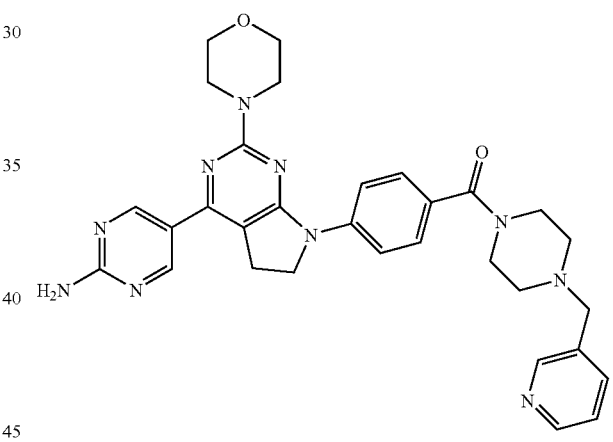

Using 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-benzoic acid (66 mg) instead of 4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-3-fluoro-benzoic acid used in Step B in Example 1-D-315, the same operation as Step B in Example 1-D-315 was carried out, to obtain a crude product of [4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-(4-pyridin-3-ylmethyl-piperazin-1-yl)-methanone, and then the PMB groups were removed according to the above Deprotection method 3, to obtain the desired compound (D-321) as a yellow solid (22 mg, 37%).

$^1$H-NMR (CDCl$_3$) δ (ppm): 8.88 (2.0H, s), 8.56 (1H, s), 8.53 (1H, d, J=5.1 Hz), 7.82 (2H, d, J=7.6 Hz), 7.69-7.66 (1H, m), 7.46 (2H, d, J=7.6 Hz), 7.27 (1H, dd, J=7.4, 5.9 Hz), 5.33 (2H, s), 5.30 (2H, s), 4.11 (2H, t, J=7.8 Hz), 3.81 (8H, s), 3.66 (4H, brs), 3.29 (2H, t, J=8.0 Hz), 2.48 (4H, brs).

ESI (LC-MS positive mode) m/z 579 (M+H)$^+$.

Example 1-D-322

{4-[4-(2-Amino-pyrimidin-5-yl)-2-morpholin-4-yl-5,6-dihydro-pyrrolo[2,3-d]pyrimidin-7-yl]-phenyl}-(4-pyridin-4-ylmethyl-piperazin-1-yl)-methanone (D-322)

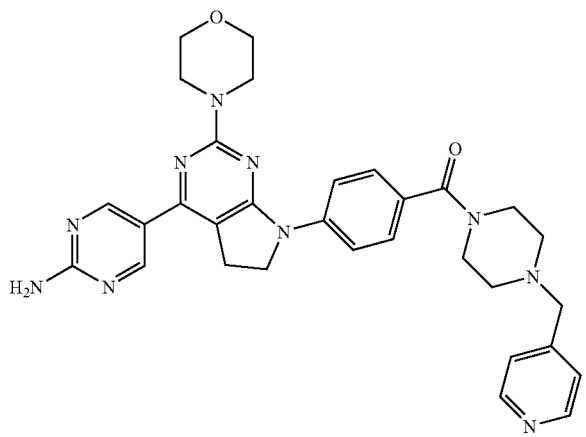

Using 1-pyridin-4-ylmethyl-piperazine (35 mg) instead of 1-pyridin-3-ylmethyl-piperazine used in Example 1-D-321, the same operation as Example 1-D-321 was carried out, to obtain a crude product of [[4-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-(4-pyridin-4-ylmethyl-piperazin-1-yl)-methanone, and then the PMB groups were removed according to the above Deprotection method 3, to obtain the desired compound (D-322) as a yellow solid (22 mg, 37%).

$^1$H-NMR (CDCl$_3$) δ (ppm): 8.89 (2H, s), 8.56 (2H, dd, J=4.5, 1.6 Hz), 7.83 (2H, d, J=8.7 Hz), 7.47 (2H, d, J=8.7 Hz), 7.28 (2H, dd, J=4.5, 1.6 Hz), 5.30 (2H, s), 5.25 (2H, s), 4.11 (2H, t, J=8.3 Hz), 3.84-3.78 (8H, m), 3.68 (4H, brs), 3.30 (2H, t, J=8.3 Hz), 2.49 (4H, brs).

ESI (LC-MS positive mode) m/z 579 (M+H)$^+$.

Example 1-D-323

5-(2-Morpholin-4-yl-4-pyridin-4-yl-5,6-dihydro-pyrrolo[2,3-d]pyrimidin-7-yl)-pyrimidin-2-ylamine (D-323)

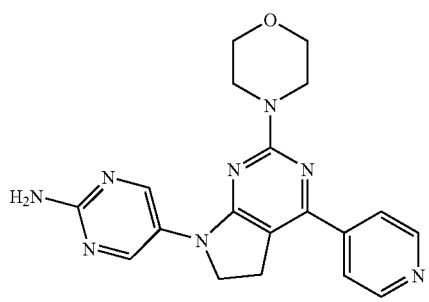

Step A 1-(2-Morpholin-4-yl-4-pyridin-4-yl-5,6-dihydro-pyrrolo[2,3-d]pyrimidin-7-yl)-ethanone

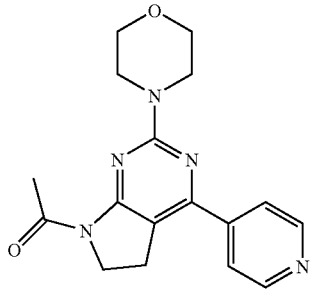

1-(4-Chloro-2-morpholin-4-yl-5,6-dihydro-pyrrolo[2,3-d]pyrimidin-7-yl)-ethanone (J-01-D, 217 mg), 4-(4,4,5,5-tetramethyl-[1,3]dioxaborolan-2-yl)-pyridine (189 mg), palladium acetate (8.6 mg), S-Phos (32 mg) and potassium phosphate (326 mg) were suspended in DMF (7.6 ml), followed by stirring at 100° C. for 3 hours. To the reaction mixture, water (50 ml) was added, followed by extraction five times with ethyl acetate/THF (40 ml/10 ml). The combined extracts were washed with saturated aqueous sodium chloride solution, followed by drying over sodium sulfate. After the sodium sulfate was filtered off, the filtrate was concentrated under reduced pressure, and the resulting residue was purified by silica gel column chromatography (dichloromethane/methanol=100/0 to 50/1), to obtain the desired compound (D-323) as a pale yellow powder (282 mg, 100%).

$^1$H-NMR (CDCl$_3$) δ (ppm): 8.69 (2H, dd, J=6, 1.6 Hz), 7.72 (2H, dd, J=4.6, 1.6 Hz), 4.07 (2H, t, J=8.3 Hz), 3.80-3.75 (8H, m), 3.18 (2H, t, J=8.3 Hz), 2.67 (3H, s).

ESI (LC-MS positive mode) m/z 326 (M+H)$^+$.

Step B

2-Morpholin-4-yl-4-pyridin-4-yl-6,7-dihydro-5H-pyrrolo[2,3-d]pyrimidine

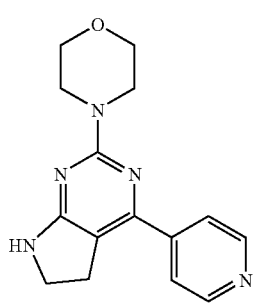

1-(2-Morpholin-4-yl-4-pyridin-4-yl-5,6-dihydro-pyrrolo[2,3-d]pyrimidin-7-yl)-ethanone (282 mg) obtained in the above Step A was dissolved in methanol (9 ml), and 5M-NaOH aqueous solution (0.381 ml) was added, followed by refluxing for 3 hours. The reaction mixture was neutralized with 5M-HCl aqueous solution, concentrated under reduced pressure, and subsequently diluted with water (10 ml), followed by extraction with dichloromethane. The organic layer was concentrated under reduced pressure, and the resulting residue was purified by silica gel column chromatography (ethyl acetate/hexane=1/2 to 2/1), to obtain the desired compound as a colorless powder (44 mg, 18%).

¹H-NMR (CDCl₃) δ (ppm): 8.70 (1H, dd, J=4.5, 1.6 Hz), 7.77 (2H, dd, J=4.5, 1.6 Hz), 4.83 (1H, s), 3.80-3.76 (8H, m), 3.68 (2H, t, J=4.0 Hz), 3.29 (2H, t, J=4.0 Hz).

ESI (LC-MS positive mode) m/z 284 (M+H)⁺.

Step C

Bis-(t-butoxycarbonyl)-[5-(2-morpholin-4-yl-4-pyridin-4-yl-5,6-dihydro-pyrrolo[2,3-d]pyrimidin-7-yl)-pyrimidin-2-yl]-amine

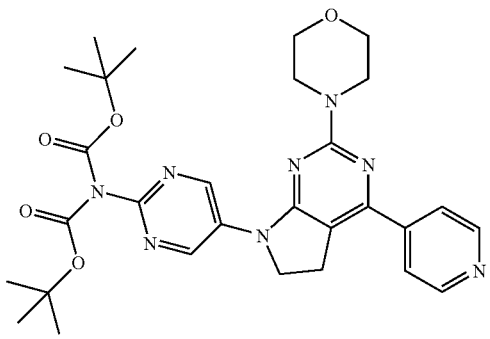

2-Morpholin-4-yl-4-pyridin-4-yl-6,7-dihydro-5H-pyrrolo[2,3-d]pyrimidine (52 mg) obtained in the above Step B, (5-bromo-pyrimidin-2-yl)-bis-(t-butoxycarbonyl)-amine (83 mg), palladium acetate (2.1 mg), S-Phos (7.5 mg) and potassium phosphate (78 mg) were dissolved in DMF (2 ml), followed by stirring at 100° C. for 10 hours. To the reaction mixture, water (20 ml) was added, followed by extraction with ethyl acetate (10 ml×2). The combined extracts were washed with saturated aqueous sodium chloride solution, followed by drying over sodium sulfate. After the sodium sulfate was filtered off, the filtrate was concentrated under reduced pressure, and the resulting residue was purified by preparative TLC (dichloromethane/2M ammonia methanol solution=20/1), to obtain the desired compound as a yellow solid (24 mg, 23%).

¹H-NMR (CDCl₃) δ (ppm): 9.32 (2H, s), 8.75 (1H, dd, J=4.6, 1.5 Hz), 7.78 (2H, dd, J=4.6, 1.5 Hz), 4.15 (2H, t, J=8.6 Hz), 3.92-3.68 (8H, m), 3.46 (2H, t, J=8.6 Hz), 1.48 (18H, s).

ESI (LC-MS positive mode) m/z 577 (M+H)⁺.

Step D

Bis-(t-butoxycarbonyl)-[5-(2-morpholin-4-yl-4-pyridin-4-yl-5,6-dihydro-pyrrolo[2,3-d]pyrimidin-7-yl)-pyrimidin-2-yl]-amine obtained in the above Step C was stirred in TFA (2 ml) at room temperature for 15 minutes. The reaction mixture was concentrated under reduced pressure, and the resulting residue was purified by amino preparative TLC (dichloromethane/ammonia methanol solution=20/1), to obtain the desired compound (D-323) as a yellow powder (11 mg, 70%).

¹H-NMR (CDCl₃) δ (ppm): 8.79 (2H, s), 8.72 (2H, dd, J=4.6, 1.6 Hz), 7.78 (2H, dd, J=4.6, 1.6 Hz), 4.93 (2H, s), 4.06 (2H, t, J=8.2 Hz), 3.83-3.79 (8H, m), 3.39 (2H, t, J=8.2 Hz).

ESI (LC-MS positive mode) m/z 377 (M+H)⁺.

Example 1-D-324

{6-[4-(2-Amino-pyrimidin-5-yl)-2-morpholin-4-yl-5,6-dihydro-pyrrolo[2,3-d]pyrimidin-7-yl]-naphthalen-2-yl}-(4-methyl-piperazin-1-yl)-methanone (D-324)

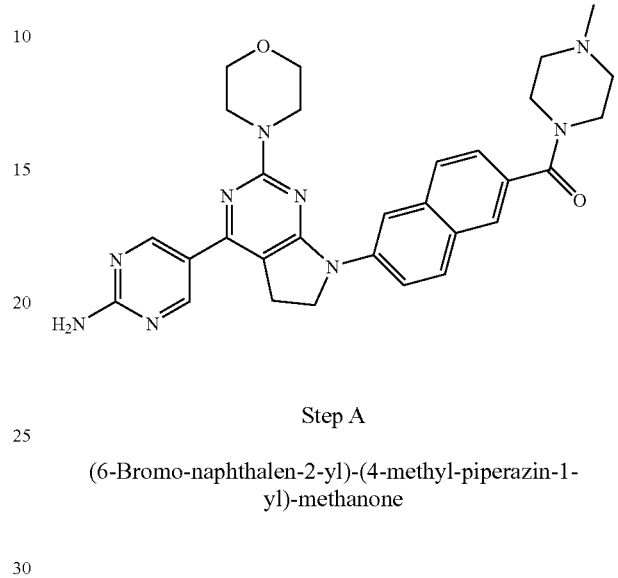

Step A (6-Bromo-naphthalen-2-yl)-(4-methyl-piperazin-1-yl)-methanone

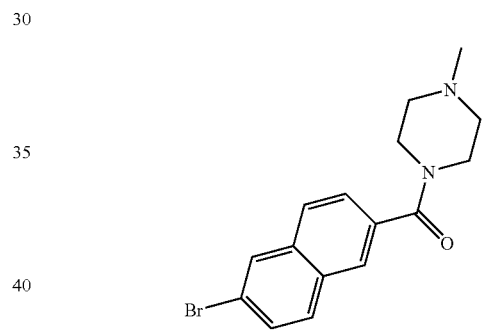

6-Bromo-naphthalen-2-carboxylic acid (502 mg) was suspended in dichloromethane (10 ml). To the suspension was added oxalyl chloride (515 µl), and then DMF (3 drops) with ice-cooling, followed by further stirring at room temperature for 1 hour. The reaction mixture was concentrated under reduced pressure, and the resulting residue was dissolved in acetonitrile (10 ml). N-Methylpiperazine (446 µl) and triethylamine (558 µl) were added to the solution with ice-cooling, followed by further stirring at room temperature for 1 hour. To the reaction mixture, 15% ammonium chloride water (100 ml) was added, and the resulting precipitate was filtered, washed with water, and dried under reduced pressure, to obtain the desired compound as an ivory powder (528 mg, 79%).

¹H-NMR (CDCl₃) δ (ppm): 8.03 (1H, d, J=1.8 Hz), 7.87 (1H, brs), 7.79 (1H, d, J=8.4 Hz), 7.74 (1H, d, J=8.9 Hz), 7.60 (1H, dd, J=8.4, 2.0 Hz), 7.52 (1H, dd, J=8.9, 1.8 Hz), 3.83 (2H, brs), 3.50 (2H, brs), 2.51 (4H, brs), 2.34 (3H, s).

ESI (LC-MS positive mode) m/z 333, 335 (M+H)⁺.

Step B

Using bis-(4-methoxy-benzyl)-[5-(2-morpholin-4-yl-6,7-dihydro-5H-pyrrolo[2,3-d]pyrimidin-4-yl)-pyrimidin-2-yl]- amine (100 mg) and (6-bromo-naphthalen-2-yl)-(4-methyl-piperazin-1-yl)-methanone (68 mg) obtained in the above Step A instead of 4-chloropicolinic acid t-butylamide in Example 1-D-07, in the same manner as Example 1-D-07, a crude product of [6-(4-{2-[bis-(4-methoxy-benzyl)-amino]-pyrimidin-5-yl}-2-morpholin-4-yl-5,6-dihydro-pyrrolo[2,3-d]pyrimidin-7-yl)-naphthalen-2-yl]-(4-methyl-piperazin-1-yl)-methanone was obtained, and then the PMB groups were removed according to the above Deprotection method 2, to obtain the desired compound (D-324) as a pale yellow powder (21 mg, 21%).

$^1$H-NMR (Acetone-$d_6$) δ (ppm): 8.91 (2H, s), 8.49 (1H, d, J=10.6 Hz), 7.95 (1H, d, J=10.6 Hz), 7.89 (1H, d, J=3.5 Hz), 7.83 (1H, d, J=9.2 Hz), 7.68 (2H, m), 7.49 (1H, d, J=9.7 Hz), 5.98 (2H, s), 4.30 (2H, t, J=8.1 Hz), 3.84 (8H, m), 3.71-3.60 (4H, m), 3.40 (2H, t, J=8.1 Hz), 2.50 (4H, brs), 2.35 (3H, s).

The following compounds (D-325 to D-330, and D-332 to D-335) were prepared in the same manner as Step B in Example 1-D-26, by using desired aldehyde derivatives that were prepared in the same manner as Step A in Example 1-D-26, and desired compounds for coupling (desired piperazine derivatives, morpholine derivative or amine derivatives).

| Example No. | Compound No. | Structure formula | Physical data |
|---|---|---|---|
| 1-D-325 | D-325 | | $^1$H-NMR (DMSO-$d_6$ + TFA) δ (ppm): 8.90 (2H, s), 7.95-7.60 (3H, m), 4.32 (2H, s), 4.20 (2H, m), 3.80-3.10 (18H, m), 2.89 (3H, s). ESI (LC-MS positive mode) m/z 506 (M + H)$^+$. |
| 1-D-326 | D-326 | | $^1$H-NMR (CD$_3$OD) δ (ppm): 8.83 (2H, s), 7.60 (2H, t, J = 8.2 Hz), 7.26-7.21 (3H, m), 4.07 (2H, t, J = 8.2 Hz), 3.65 (2H, s), 3.32 (10H, brs), 2.87 (3H, s). ESI (LC-MS positive mode) m/z 506 (M + H)$^+$. |
| 1-D-327 | D-327 | | $^1$H-NMR (DMSO-d6) δ (ppm): 8.81 (2H, s), 7.81 (2H, d, J = 8.1 Hz), 7.31 (2H, d, J = 8.1 Hz), 7.07 (2H, s), 4.08 (2H, t, J = 8.1 Hz), 3.70 (8H, brs), 3.33-2.50 (14H, m), 1.50 (2H, m), 0.86 (3H, t, J = 7.3 Hz). ESI (LC-MS positive mode) m/z 516 (M + H)$^+$. |
| 1-D-328 | D-328 | | $^1$H-NMR (DMSO-d6) δ (ppm): 8.81 (2H, s), 7.79 (2H, d, J = 8.7 Hz), 7.28 (2H, d, J = 8.7 Hz), 7.06 (2H, s), 4.08 (2H, t, J = 8.1 Hz), 3.70 (8H, brs), 3.35-2.40 (13H, m), 0.95 (6H, d, J = 6.6 Hz). ESI (LC-MS positive mode) m/z 516 (M + H)$^+$. |

| Example No. | Compound No. | Structure formula | Physical data |
|---|---|---|---|
| 1-D-329 | D-329 | | $^1$H-NMR (DMSO-d$_6$) δ: 8.81 (2H, s), 7.79 (2H, d, J = 8.7 Hz), 7.29 (2H, d, J = 8.7 Hz), 7.07 (2H, s), 4.51 (2H, dt, J = 47.9, 4.9 Hz), 4.08 (2H, t, J = 8.2 Hz), 3.77-3.70 (8H, m), 3.42 (2H, s), 3.29 (2H, brs), 2.66-2.38 (10H, m). ESI (LC-MS positive mode) m/z 520 (M + H)$^+$. |
| 1-D-330 | D-330 | | $^1$H-NMR (DMSO-d6) δ (ppm): 8.82 (2H, s), 7.94 (2H, d, J = 8.9 Hz), 7.55 (2H, d, J = 8.9 Hz), 4.57 (2H, m), 4.39 (1H, t, J = 5.4 Hz), 4.30 (2H, m), 4.20 (1H, m), 3.80-3.67 (8H, m), 3.32 (2H, m), 3.19 (2H, m), 1.73 (4H, m). ESI (LC-MS positive mode) m/z 549 (M + H)$^+$ |
| 1-D-332 | D-332 | | $^1$H-NMR (CDCl$_3$) δ (ppm): 8.89 (2H, s), 7.78 (2H, d, J = 8.5 Hz), 7.35 (2H, d, J = 8.5 Hz), 5.23 (2H, s), 4.10 (2H, t, J = 8.3 Hz), 3.84-3.80 (10H, m), 3.29 (2H, t, J = 8.3 Hz), 2.66-2.63 (6H, m), 2.32-2.27 (1H, m), 1.69-1.57 (4H, m). ESI (LC-MS positive mode) m/z 570 (M + H)$^+$. |
| 1-D-333 | D-333 | | $^1$H-NMR (DMSO-d$_6$) δ: 8.84 (2H, s), 8.37 (1H, d, J = 9.1 Hz), 8.02 (1H, brs), 7.91 (1H, d, J = 9.1 Hz), 7.83 (1H, d, J = 8.6 Hz), 7.75 (1H, brs), 7.45 (1H, d, J = 8.2 Hz), 7.10 (2H, s), 4.21 (2H, t, J = 8.1 Hz), 3.73-3.55 (8H, m), 3.38-3.07 (6H, br), 2.70 (4H, brs), 2.55 (3H, s). ESI (LC-MS positive mode) m/z 538 (M + H)$^+$. |

| Example No. | Compound No. | Structure formula | Physical data |
|---|---|---|---|
| 1-D-334 | D-334 | | $^1$H-NMR (CDCl$_3$) δ (ppm): 8.89 (2H, s), 8.59 (1H, d, J = 1.6 Hz), 8.51 (1H, dd, J = 4.7, 1.7 Hz), 7.77-7.69 (2H, m), 7.36 (2H, d, J = 8.6 Hz), 7.27 (1H, dd, J = 8.5, 3.9 Hz), 7.07 (1H, t, J = 4.0 Hz), 6.87-6.60 (2H, m), 4.10 (2H, t, J = 8.4 Hz), 3.86-3.74 (12H, brm), 3.27 (2H, t, J = 8.2 Hz). ESI (LC-MS positive mode) m/z 496 (M + H)$^+$. |
| 1-D-335 | D-335 | | $^1$H-NMR (CDCl$_3$) δ (ppm): 7.31-6.91 (3H, m), 3.71 (4H, t, J = 4.7 Hz), 3.49 (2H, s), 2.44 (4H, t, J = 4.6 Hz). ESI (LC-MS positive mode) m/z 274, 276 (M + H)$^+$. |

Example 1-E

Example 1-E-01

4-(3-Ethylaminocarbonyloxyphenyl)-2-(morpholin-4-yl)-7-(pyridin-4-yl)-6,7-dihydro-5H-pyrrolo[2,3-d]pyrimidine (E-01)

Compound A-09 (4-(3-hydroxyphenyl)-2-(morpholin-4-yl)-7-(pyridin-4-yl)-6,7-dihydro-5H-pyrrolo[2,3-d]pyrimidine (34 mg, 0.09 mmol) obtained in Example 1-A-09 was dissolved in dimethylformamide (1 mL), and diisopropylethylamine (32 μL) and ethyl isocyanate (32 μL) were added, followed by stirring at 60° C. for 12 hours. The reaction mixture was poured onto water, followed by extraction with dichloromethane, and the organic layer was dried over sodium sulfate. After the drying agent was filtered off, followed by concentration under reduced pressure, and the resulting residue was purified by silica gel column chromatography (dichloromethane/methanol), to obtain the desired compound (colorless powder, 22 mg, 55%).

$^1$H-NMR (400 MHz, DMSO-d$_6$) δ (ppm) 8.63 (2H, d, J=6.4 Hz), 8.00 (3H, d, J=6.4 Hz), 7.93 (1H, d, J=7.8 Hz), 7.81 (1H, s), 7.68 (1H, t, J=7.9 Hz), 7.40 (1H, d, J=9.8 Hz), 4.27 (2H, t, J=8.2 Hz), 3.91 (8H, d, J=7.1 Hz), 3.46-3.51 (2H, m), 3.22-3.35 (2H, m), 1.28 (3H, t, J=7.2 Hz).

ESI (LC-MS positive mode) m/z 447 [M+H].

Example 1-E-02

4-(3-Methylaminocarbonyloxyphenyl)-2-(morpholin-4-yl)-7-(pyridin-4-yl)-6,7-dihydro-5H-pyrrolo[2,3-d]pyrimidine (E-02)

In the same manner as Example 1-E-01, using methyl isocyanate, the desired compound was obtained.

$^1$H-NMR (400 MHz, DMSO-d$_6$) δ (ppm) 8.45 (2H, d, J=6.1 Hz), 7.82 (2H, d, J=6.4 Hz), 7.69-7.78 (2H, m), 7.63 (1H, s), 7.50 (1H, t, J=7.9 Hz), 7.21 (1H, d, J=8.1 Hz), 4.08 (2H, t, J=8.2 Hz), 3.73 (8H, d, J=6.6 Hz), 3.27-3.34 (2H, m), 2.68 (3H, d, J=4.6 Hz).

ESI (LC-MS positive mode) m/z 433 [M+H].

Example 1-E-03

4-(3-Acetoxyphenyl)-2-(morpholin-4-yl)-7-(pyridin-4-yl)-6,7-dihydro-5H-pyrrolo[2,3-d]pyrimidine (E-03)

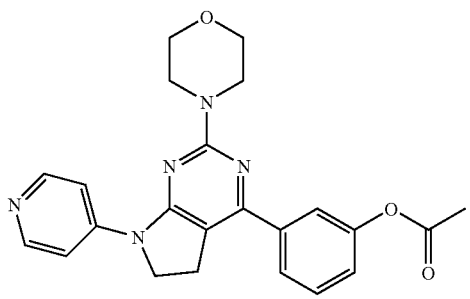

Compound A-09 (30 mg, 0.08 mmol) was dissolved in acetic anhydride (1 mL) and pyridine (1 mL), followed by stirring at 50° C. for 3 hours. The reaction mixture was poured onto water, followed by extraction with dichloromethane, and the organic layer was dried over sodium sulfate. The drying agent was filtered off, followed by concentration under reduced pressure, and the resulting residue was purified by silica gel column chromatography (dichloromethane/methanol), to obtain the desired compound (colorless powder, 21 mg, 64%).

$^1$H-NMR (400 MHz, DMSO-d$_6$) δ (ppm) 8.45 (2H, d, J=6.4 Hz), 7.81 (3H, m), 7.68 (1H, s), 7.55 (1H, t, J=8.0 Hz), 7.24 (1H, d, J=9.5 Hz), 4.09 (2H, t, J=8.2 Hz), 3.73 (8H, d, J=7.9 Hz), 3.27-3.34 (2H, m), 2.31 (3H, s).

ESI (LC-MS positive mode) m/z 418 [M+H].

Example 1-E-04

2-Morpholin-4-yl-7-pyridin-4-yl-4-[3-(2-pyridin-2-ylethoxy)phenyl]-6,7-dihydro-5H-pyrrolo[2,3-d]pyrimidine (E-04)

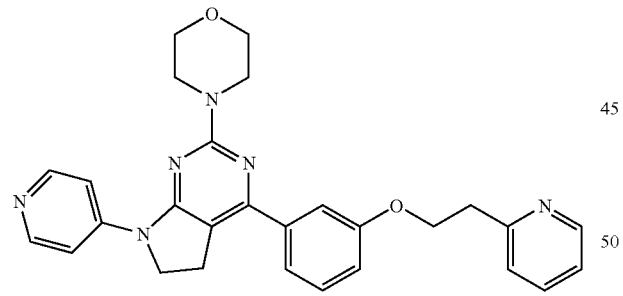

Compound A-09 (40 mg, 0.107 mmol), 2-(2-hydroxyethyl)pyridine (14.4 mg, 0.117 mmol) and triphenylphosphine (31 mg, 0.117 mmol) were mixed in anhydrous tetrahydrofuran (1 ml), followed by cooling to 0° C. under a nitrogen atmosphere. DIAD (24 mg, 0.177 mmol) was added dropwise, and the reaction mixture was heated to 50° C. over 72 hours. 2-(2-Hydroxyethyl)pyridine (14.4 mg, 0.117 mmol), triphenylphosphine (31 mg, 0.117 mmol) and DIAD (24 mg, 0.177 mmol) were added again, followed by heating to 50° C. over 24 hours. The mixture was cooled to room temperature, and subsequently diluted with ethyl acetate (2 ml), followed by extraction with 1M hydrochloric acid (2 ml×3). The aqueous layer was neutralized with saturated aqueous sodium hydrogencarbonate solution, followed by extraction twice with ethyl acetate (20 ml). The organic layer was dried over magnesium sulfate, followed by concentration under reduced pressure, and the residue was purified by preparative HPLC, whereby the desired compound was obtained as trifluoroacetic acid salt (6.7 mg, 13% yield).

$^1$H-NMR (400 MHz, CD$_3$OD) δ (ppm) 8.78 (1H, d, J=6.7 Hz), 8.48-8.59 (3H, m), 8.41 (2H, br.s.), 8.08 (1H, d, J=8.1 Hz), 7.92 (1H, t, J=6.8 Hz), 7.50-7.56 (2H, m), 7.43 (1H, t, J=8.2 Hz), 7.07 (1H, d, J=9.1 Hz), 4.51 (2H, t, J=5.9 Hz), 4.28 (2H, t, J=7.8 Hz), 3.73-3.95 (8H, m), 3.57 (2H, t, J=5.9 Hz), 3.44 (2H, t, J=8.5 Hz).

ESI (LC-MS positive mode) m/z 481 [M+H].

Example 1-E-05

2-Morpholin-4-yl-7-pyridin-4-yl-4-[3-(3-pyridin-3-yl-propoxy)-phenyl]-6,7-dihydro-5H-pyrrolo[2,3-d]pyrimidine (E-05)

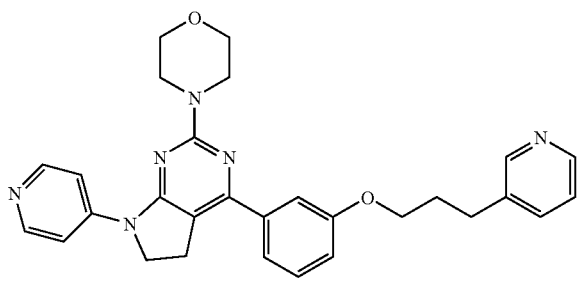

In the same manner as Example 1-E-04, using 3-pyridinepropanol, the desired compound was obtained.

$^1$H-NMR (400 MHz, CD$_3$OD) δ (ppm) 8.78 (1H, s), 8.69 (1H, d, J=5.3 Hz), 8.54 (2H, d, J=7.6 Hz), 8.49 (1H, d, J=8.1 Hz), 8.41 (2H, br.s.), 7.96 (1H, dd, J=8.0, 5.7 Hz), 7.49-7.55 (2H, m), 7.42 (1H, t, J=8.1 Hz), 7.05 (1H, dd, J=8.2, 1.6 Hz), 4.29 (2H, t, J=7.8 Hz), 4.14 (2H, t, J=5.9 Hz), 3.78-3.94 (8H, m), 3.45 (2H, t, J=8.6 Hz), 3.11 (2H, t, J=7.5 Hz), 2.18-2.30 (2H, m).

ESI (LC-MS positive mode) m/z 495 (M+H).

Example 1-E-06

2-Morpholin-4-yl-7-pyridin-4-yl-4-[3-(pyridin-4-ylmethoxy)-phenyl]-6,7-dihydro-5H-pyrrolo[2,3-d]pyrimidine (E-06)

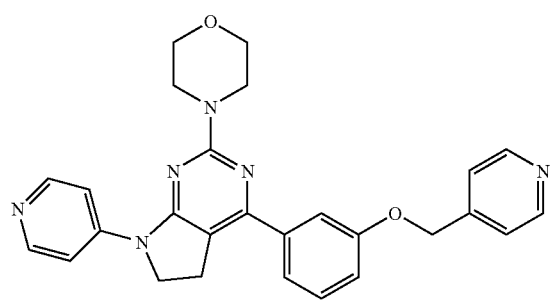

In the same manner as Example 1-E-04, using 4-pyridinemethanol, the desired compound was obtained.

$^1$H-NMR (400 MHz, CD$_3$OD) δ (ppm) 8.56-8.80 (4H, m), 8.32 (2H, br.s.), 7.63-7.75 (2H, m), 7.54-7.59 (2H, m), 7.48

(1H, t, J=8.1 Hz), 7.20 (1H, d, J=8.2 Hz), 5.38 (2H, s), 4.23 (2H, t, J=8.1 Hz), 3.74 (8H, d, J=3.9 Hz), 3.32-3.41 (2H, m).

ESI (LC-MS positive mode) m/z 467 (M+H).

Example 1-E-07

3-(2-Morpholin-4-yl-7-pyridin-4-yl-6,7-dihydro-5H-pyrrolo[2,3-d]pyrimidin-4-yl)benzonitrile (E-07)

Step A 3-(2-Morpholin-4-yl-7-pyridin-4-yl-6,7-dihydro-5H-pyrrolo[2,3-d]pyrimidin-4-yl)phenyl trifluoromethanesulfonic acid ester

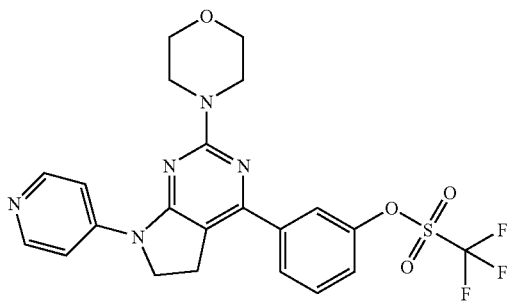

Compound A-09 (250 mg, 1.60 mmol) prepared in Example 1-A-09, N-phenyl-bis-trifluoromethanesulfonimide (247 mg, 0.69 mmol) and potassium carbonate (221 mg, 1.60 mmol) were mixed in tetrahydrofuran (3.75 ml), followed by irradiation of microwave (200 W, 120° C., 230 psi) for 30 minutes. The reaction mixture was diluted with dichloromethane (10 ml), followed by filtration. The filtrate was concentrated under reduced pressure, followed by addition of methanol, and the deposited precipitate was filtered. The precipitate was dried, to obtain the desired compound as a colorless solid (231 mg, 85% yield).

$^1$H-NMR (400 MHz, CDCl$_3$) δ (ppm) 8.50 (2H, d, J=6.6 Hz), 8.17 (2H, br.s.), 7.94 (1H, d, J=7.8 Hz), 7.85 (1H, s), 7.61 (1H, t, J=8.1 Hz), 7.41 (1H, dd, J=8.4, 1.8 Hz), 4.23 (2H, t, J=7.8 Hz), 3.88 (8H, d, J=4.4 Hz), 3.47 (2H, t, J=8.1 Hz).

ESI (LC-MS positive mode) m/z 508 (M+H).

Step B 3-(2-Morpholin-4-yl-7-pyridin-4-yl-6,7-dihydro-5H-pyrrolo[2,3-d]pyrimidin-4-yl)benzonitrile

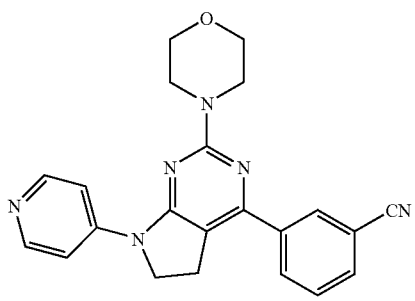

3-(2-Morpholin-4-yl-7-pyridin-4-yl-6,7-dihydro-5H-pyrrolo[2,3-d]pyrimidin-4-yl)phenyl trifluoromethanesulfonic acid ester (231 mg, 0.46 mmol) obtained in Step A, zinc cyanide (32 mg, 0.27 mmol), Pd2 (dba) 3 (21 mg, 0.023 mmol) and DPPF (30 mg, 0.055 mmol) were mixed in dimethylformamide (4.6 ml), followed by irradiation of microwave (150 W, 200° C., 230 psi) for 50 minutes. The reaction mixture was cooled, and diluted with ethyl acetate (10 ml). The organic layer was washed with saturated aqueous sodium hydrogencarbonate solution, and dried over sodium sulfate, followed by concentration under reduced pressure, whereby the desired compound was obtained as a brown solid (116 mg, 66% yield).

$^1$H-NMR (400 MHz, CDCl$_3$) δ (ppm) 8.59 (2H, d, J=7.0 Hz) 8.15-8.23 (3H, m) 8.11 (1H, d, J=8.0 Hz) 7.76 (1H, d, J=8.0 Hz) 7.61 (1H, t, J=7.9 Hz) 4.22 (2H, t, J=8.1 Hz) 3.85 (8H, d, J=5.9 Hz) 3.45 (2H, t, J=8.1 Hz).

ESI (LC-MS positive mode) m/z 385 (M+H).

Example 1-E-08

3-(2-Morpholin-4-yl-7-pyridin-4-yl-6,7-dihydro-5H-pyrrolo[2,3-d]pyrimidin-4-yl)benzylamine (E-08)

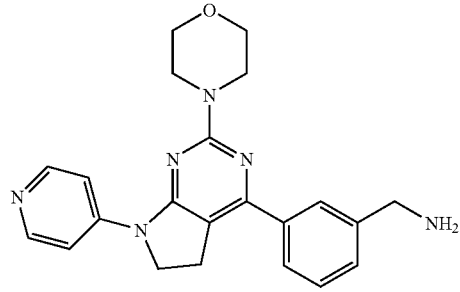

To a solution of compound E-07 (15 mg, 0.039 mmol) obtained in Example 1-E-07 in anhydrous tetrahydrofuran (0.5 ml), under a nitrogen atmosphere at 0° C., lithium aluminum hydride (0.086 ml, 1M tetrahydrofuran solution, 0.086 mmol) was added. After the reaction mixture was stirred at 0° C. for 30 minutes, the temperature was raised to room temperature, followed by further stirring for 5 hours. To the mixture, water was added, followed by filtration through Celite and extraction with ethyl acetate. The organic layer was washed with brine, and dried over sodium sulfate, followed by concentration under reduced pressure. The residue was purified by preparative HPLC, to obtain the desired compound (6.7 mg, 34% yield).

$^1$H-NMR (400 MHz, CD$_3$OD) δ (ppm) 8.55 (2H, d, J=3.7 Hz), 8.42 (2H, br.s.), 8.13 (1H, s), 8.03 (1H, d, J=6.6 Hz), 7.55-7.66 (2H, m), 4.31 (2H, t, J=7.9 Hz), 4.24 (2H, s), 3.86 (8H, dd, J=30.8, 4.9 Hz), 3.49 (2H, t, J=8.1 Hz).

ESI (LC-MS positive mode) m/z 389 (M+H).

Example 1-E-09

N-[3-(2-Morpholin-4-yl-7-pyridin-4-yl-6,7-dihydro-5H-pyrrolo[2,3-d]pyrimidin-4-yl)benzyl]acetamide (E-9)

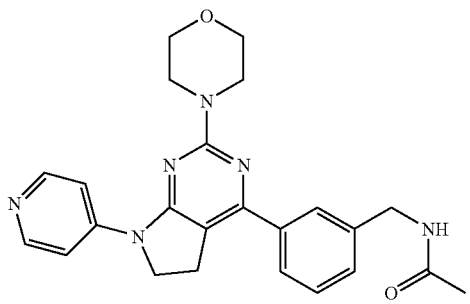

To a solution of Compound E-08 (36 mg, 0.093 mmol) obtained in Example 1-E-08 in dichloromethane (0.5 ml), acetic anhydride (11 mg, 0.10 mmol) and triethylamine (10 mg, 0.10 mmol) were added, followed by stirring for 3 hours. The reaction mixture was concentrated under reduced pressure, and the residue was purified by preparative HPLC, to obtain the desired compound (17 mg, 33% yield).

$^1$H-NMR (400 MHz, CD$_3$OD) δ (ppm) 8.53 (2H, d, J=7.3 Hz), 8.40 (2H, br.s.), 7.93 (1H, s), 7.88 (1H, d, J=7.8 Hz), 7.48 (1H, t, J=7.7 Hz), 7.38-7.44 (1H, m), 4.44 (2H, s), 4.29 (2H, t, J=8.1 Hz), 3.86 (8H, dd, J=26.4, 4.9 Hz), 3.38-3.54 (2H, m), 2.02 (3H, s).

ESI (LC-MS positive mode) m/z 430 (M+H).

Example 1-E-10

5-(2-Morpholin-4-yl-7-pyridin-4-yl-6,7-dihydro-5H-pyrrolo[2,3-d]pyrimidin-4-yl)-2-pyrrolidin-1-ylmethylphenol (E-10)

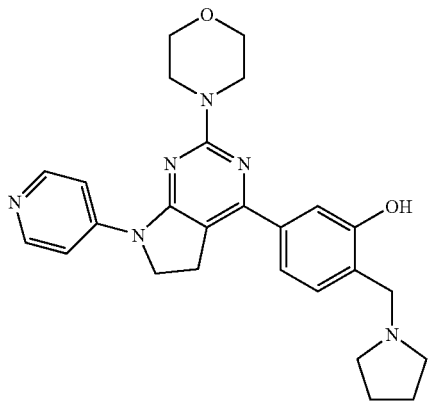

Compound A-09 (60 mg, 0.16 mmol) prepared in Example 1-A-09, formaldehyde (39 mg, 37% aqueous solution, 0.48 mmol), acetic acid (0.03 ml, 0.48 mmol) and pyrrolidine (34 mg, 0.48 mmol) were dissolved in 1,4-dioxane (4 ml) in a microwave tube, followed by irradiation of microwave (300 W, 200° C., 250 psi) for 50 minutes. The mixture was concentrated under reduced pressure, and the residue was purified by silica gel column chromatography (methanol/dichloromethane=5/95), whereby the desired compound was obtained (23.1 mg, 32% yield).

$^1$H-NMR (400 MHz, DMSO-d$_6$) δ (ppm) 8.44 (2H, d, J=5.7 Hz) 7.81 (2H, d, J=6.2 Hz) 7.37 (1H, s) 7.32 (1H, d, J=7.9 Hz) 7.22 (1H, d, J=7.9 Hz) 4.02-4.11 (2H, m) 3.80 (2H, s) 3.73 (8H, d, J=6.6 Hz) 3.29 (2H, t, J=8.1 Hz) 2.59 (4H, s) 1.76 (4H, d, J=4.9 Hz).

ESI (LC-MS positive mode) m/z 459 (M+H).

Example 1-E-11

2-Diethylaminomethyl-5-(2-morpholin-4-yl-7-pyridin-4-yl-6,7-dihydro-5H-pyrrolo[2,3-d]pyrimidin-4-yl)phenol (E-11)

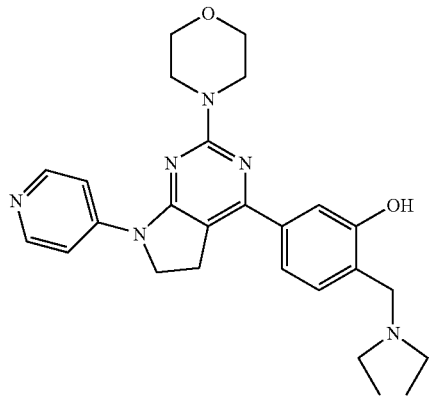

In the same manner as Example 1-E-10, using diethylamine, the desired compound was obtained.

$^1$H-NMR (400 MHz, CD$_3$OD) δ (ppm) 8.55 (2H, d, J=7.6 Hz), 8.42 (2H, br.s.), 7.67 (1H, s), 7.51-7.58 (1H, m), 7.45-7.52 (1H, m), 4.39 (2H, s), 4.25-4.35 (2H, m), 3.73-3.96 (8H, m), 3.43-3.51 (2H, m), 3.20-3.29 (4H, m), 1.39 (6H, t, J=7.3 Hz).

ESI (LC-MS positive mode) m/z 461 (M+H).

Example 1-E-12

5-(2-Morpholin-4-yl-7-pyridin-4-yl-6,7-dihydro-5H-pyrrolo[2,3-d]pyrimidin-4-yl)-2-piperidin-1-ylmethyl-phenol (E-12)

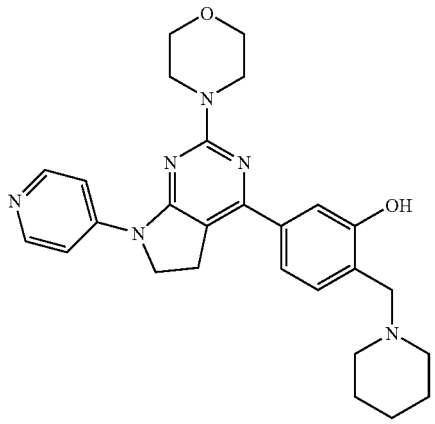

In the same manner as Example 1-E-10, using piperidine, the desired compound was obtained.

$^1$H-NMR (400 MHz, DMSO-d$_6$) δ (ppm) 8.45 (2H, d, J=5.7 Hz), 7.82 (2H, d, J=5.3 Hz), 7.27-7.38 (2H, m), 7.18

(1H, d, J=8.4 Hz), 4.08 (2H, t, J=7.8 Hz), 3.73 (8H, d, J=8.1 Hz), 3.66 (2H, s), 3.56 (4H, s), 3.12-3.50 (2H, m), 1.54 (4H, s), 1.44 (2H, s).

ESI (LC-MS positive mode) m/z 473 (M+H).

Example 1-F

Example 1-F-01

3-(2-Morpholin-4-yl-7-pyridin-4-yl-6,7-dihydro-5H-pyrrolo[2,3-d]pyrimidin-4-yl)-phenylamine (F-01)

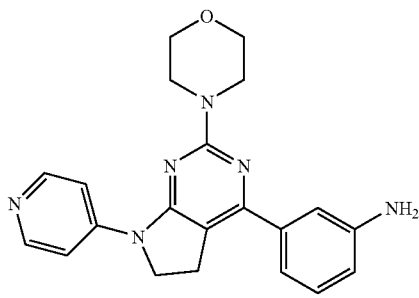

Palladium acetate (9 mg, 10 mol %), S-Phos (33 mg, 20 mol %), potassium phosphate (340 mg, 4 equivalents) and 3-aminophenylboronic acid hydrate (189 mg, 3 equivalents) were weighed in a two-neck flask equipped with Dimroth condenser, and heated with a drier under reduced pressure, followed by several repetitive argon substitution. A dimethylformamide solution (4 ml) of 4-chloro-2-morpholin-4-yl-7-pyridin-4-yl-6,7-dihydro-5H-pyrrolo[2,3-d]pyrimidine was added with a syringe, followed by stirring at 110° C. for 10 hours. The reaction mixture was added to water, followed by extraction twice with ethyl acetate, and the organic layer was washed with brine, and subsequently dried over sodium sulfate. The drying agent was filtered off, followed by concentration under reduced pressure, and the resulting residue was purified by silica gel column chromatography (dichloromethane/ammonia-methanol), to obtain the desired compound (yellow powder, 62 mg, 41%) was obtained.

1H-NMR (270 MHz, CDCl$_3$) δ (ppm): 2.85 (2H, t, J=8.9 Hz), 3.84 (8H, brs), 3.99 (2H, t, J=8.9 Hz), 6.14 (1H, s), 7.06 (1H, t, J=7.4 Hz), 7.23 (1H, t, J=7.4 Hz), 7.47 (1H, d, J=7.4 Hz), 7.65 (2H, dd, J=5.0, 1.5 Hz), 8.43 (2H, dd, J=5.0, 1.5 Hz).

ESI (LC-MS positive mode) m/z 375 (M+H).

Example 1-G

4-Chloro-2-morpholin-4-yl-7-pyridin-3-yl-6,7-dihydro-5H-pyrrolo[2,3-d]pyrimidine to be used in the following Example 1-G-01 was prepared according to Step A in Example 1-B-02 described above. Further, 4-chloro-2-morpholin-4-yl-7-pyridin-4-yl-6,7-dihydro-5H-pyrrolo[2,3-d] pyrimidine to be used in the following Example 1-G-02 was prepared according to Step C in Example 1-B-01 described above. Furthermore, in the following Examples 1-G-38 to 43, 1-G-46, 1-G-60, 1-G-61, 1-G-63, 1-G-66, 1-G-68, 1-G-70, 1-G-76, 1-G-77, 1-G-81, 1-G-82, 1-G-84, 1-G-88 and 1-G-89, a resulting reaction crude product was subjected to HPLC purification using a eluent containing trifluoroacetic acid, to obtain the desired compound as trifluoroacetic acid salt.

Example 1-G-01

3-(2-Morpholin-4-yl-7-pyridin-3-yl-6,7-dihydro-5H-pyrrolo[2,3-d]pyrimidin-4-yl)-benzoic acid methyl ester (G-01)

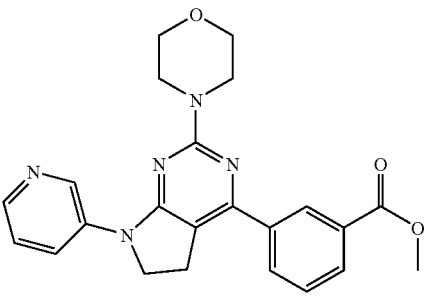

4-Chloro-2-morpholin-4-yl-7-pyridin-3-yl-6,7-dihydro-5H-pyrrolo[2,3-d]pyrimidine (317 mg, 1.00 mmol), palladium acetate (11 mg, 5 mol %), S-Phos (41 mg, 10 mol %) and 3-methoxycarbonylphenylboronic acid (637 mg) were dissolved in dimethylformamide (10 ml). Then, argon substitution was carried out three times under ultrasonic irradiation in reduced pressure. The reaction mixture was stirred at 100° C. for 2 hours, and the reaction mixture was allowed to cool to room temperature, and then poured onto water (100 ml). The reaction mixture was extracted twice with ethyl acetate/tetrahydrofuran (4/1, 100 ml), and the combined organic layers were washed with brine, followed by drying over sodium sulfate. After the drying agent was filtered off, the filtrate was concentrated under reduced pressure, and the resulting residue was purified by silica gel column chromatography (dichloromethane/methanol=100/0 to 50/1), to obtain a colorless solid (374 mg, 90%).

$^1$H-NMR (270 MHz, CDCl$_3$) δ (ppm): 9.12 (1H, d, J=2.7 Hz), 8.54 (1H, d, J=1.6 Hz), 8.31 (1H, dd, J=4.6, 1.6 Hz), 8.05-8.18 (3H, m), 7.55 (1H, t, J=7.6 Hz), 7.32 (1H, dd, J=8.4, 4.6 Hz), 4.11 (2H, t, J=8.4 Hz), 3.96 (3H, s), 3.77-3.89 (8H, m), 3.40 (2H, t, J=8.4 Hz).

ESI (LC-MS positive mode) m/z 418 [(M+H)$^+$].

Example 1-G-02

3-(2-Morpholin-4-yl-7-pyridin-4-yl-6,7-dihydro-5H-pyrrolo[2,3-d]pyrimidin-4-yl)-benzoic acid methyl ester (G-02)

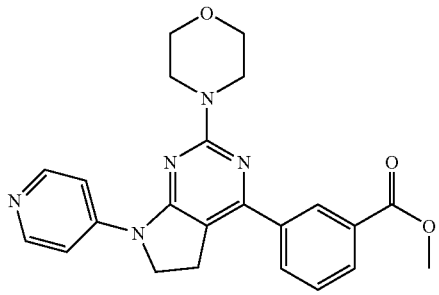

Using 4-chloro-2-morpholin-4-yl-7-pyridin-4-yl-6,7-dihydro-5H-pyrrolo[2,3-d]pyrimidine (378 mg), in the same manner as in the above, reaction and extraction were carried out. The extracts were concentrated under reduced pressure, and to the resulting residue, dichloromethane (5 ml) and then ether (50 ml) were added, followed by sonication. The precipitate was filtered, and washed with ether, to obtain an ivory powder (197 mg, 68%).

¹H-NMR (270 MHz, DMSO-d$_6$) δ (ppm): 8.27-8.49 (2H, m), 8.24 (2H, t, 7.6 Hz), 8.06 (1H, d, J=7.8 Hz), 7.85 (1H, d, J=6.8 Hz), 7.67 (2H, t, J=7.6 Hz), 4.12 (2H, t, J=8.4 Hz), 3.90 (3H, s), 3.72-3.85 (8H, m), 3.35 (2H, t, J=8.4 Hz).

ESI (LC-MS positive mode) m/z 418 [(M+H)$^+$].

Example 1-G-03

3-(2-Morpholin-4-yl-7-pyridin-3-yl-6,7-dihydro-5H-pyrrolo[2,3-d]pyrimidin-4-yl)-benzoic acid (G-03)

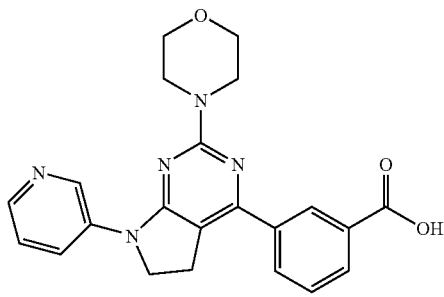

Compound G-01 (84 mg) obtained in Example 1-G-01 was added to methanol (1 ml) containing 5M aqueous sodium hydroxide solution (200 μl, 5 equivalents), followed by refluxing for 2 hours. Neutralization with 1M hydrochloric acid, filtration of the resulting precipitate, and washing with ether afforded a yellow powder (72 mg, 89%).

¹H-NMR (270 MHz, DMSO-d$_6$) δ (ppm): 13.2 (1H, s), 9.11 (1H, d, J=2.4 Hz), 8.51 (1H, s), 8.19-8.25 (3H, m), 8.03 (1H, d, J=7.6 Hz), 7.65 (1H, t, J=7.6 Hz), 7.42-7.46 (1H, m), 4.15 (2H, t, J=8.4 Hz), 3.73-3.78 (8H, m), 3.37 (2H, t, J=8.4 Hz).

ESI (LC-MS positive mode) m/z 404 [(M+H)$^+$].

Example 1-G-04

3-(2-Morpholin-4-yl-7-pyridin-4-yl-6,7-dihydro-5H-pyrrolo[2,3-d]pyrimidin-4-yl)-benzoic acid (G-04)

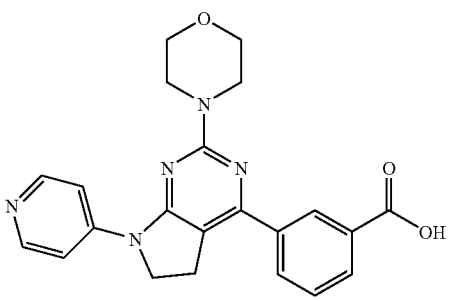

Using Compound G-02 (222 mg) obtained in Example 1-G-O$_2$, in the same manner as Example 1-G-03, a yellow powder (175 mg, 92%) was obtained.

¹H-NMR (270 MHz, DMSO-d$_6$) δ (ppm): 8.51-8.54 (3H, m), 8.22 (1H, d, J=7.8 Hz), 8.05 (1H, d, J=7.8 Hz), 7.67 (2H, d, J=6.8 Hz), 7.66 (1H, t, J=7.8 Hz), 4.16 (2H, t, J=8.4 Hz), 3.74-3.78 (8H, m), 3.38 (2H, t, J=8.4 Hz).

ESI (LC-MS positive mode) m/z 404 [(M+H)$^+$].

Example 1-G-05

N-(2-dimethylaminoethyl)-3-(2-morpholin-4-yl-7-pyridin-3-yl-6,7-dihydro-5H-pyrrolo[2,3-d]pyrimidin-4-yl)-benzamide (G-05)

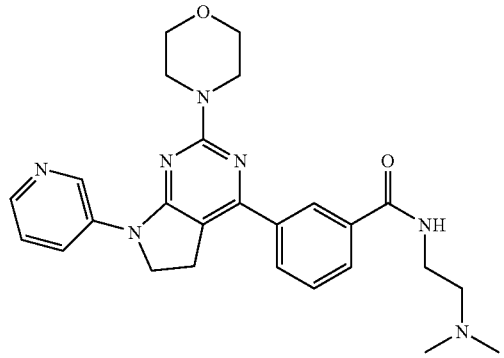

Compound G-03 (30 mg) obtained in Example 1-G-03, WSCI (43 mg, 3 equivalents), HOBt (30 mg, 3 equivalents) and N,N-dimethyl ethylenediamine (25 μl, 3 equivalents) were added to dimethylformamide (3.7 ml), followed by stirring for 10 hours. To the reaction mixture, water (10 ml) was added, followed by extraction with ethyl acetate, which was washed with brine, and subsequently dried over sodium sulfate. After the drying agent was filtered off, the filtrate was concentrated under reduced pressure, and the resulting residue was purified by preparative TLC (dichloromethane/ammonia-methanol=10/1), to obtain a pale yellow amorphous (3 mg, 9%).

¹H-NMR (270 MHz, CDCl$_3$) δ (ppm): 9.13 (1H, d, J=2.5 Hz), 8.38 (1H, t, J=1.8 Hz), 8.30 (1H, dd, J=4.6, 1.3 Hz), 8.11-8.16 (1H, m), 8.03-8.06 (1H, m), 7.81-7.84 (1H, m), 7.53 (1H, t, J=7.6 Hz), 7.26-7.34 (1H, m), 6.98 (1H, br), 4.10 (2H, t, J=8.6 Hz), 3.78-3.89 (8H, m), 3.54 (2H, q, J=6.1 Hz), 3.40 (2H, t, J=8.6 Hz), 2.54 (2H, t, J=6.1 Hz), 2.28 (6H, s).

ESI (LC-MS positive mode) m/z 474 [(M+H)$^+$].

Example 1-G-06

N-(2-morpholin-4-yl-ethyl)-3-(2-morpholin-4-yl-7-pyridin-3-yl-6,7-dihydro-5H-pyrrolo[2,3-d]pyrimidin-4-yl)-benzamide (G-06)

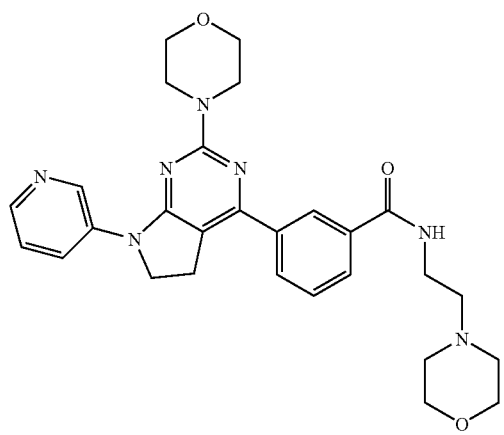

Compound G-03 (30 mg) obtained in Example 1-G-03, WSCI (43 mg, 3 equivalents), HOBt (30 mg, 3 equivalents) and 2-morpholin-4-yl-ethylamine (30 μl, 3 equivalents) were added to dimethylformamide, followed by stirring at room temperature for 10 hours. To the reaction mixture, water (20 ml) was added, and the resulting precipitate was filtered, followed by washing with ether, to obtain a yellow powder (17 mg, 17%).

$^1$H-NMR (270 MHz, DMSO-$d_6$) δ (ppm): 9.13 (1H, d, J=2.7 Hz), 8.38 (1H, s), 8.19-8.27 (2H, m), 8.07 (1H, d, J=7.8 Hz), 7.90 (1H, d, J=7.6 Hz), 7.55 (1H, t, J=7.8 Hz), 7.34-7.39 (1H, m), 4.16 (2H, t, J=8.4 Hz), 3.78-3.83 (8H, m), 3.54 (4H, m), 3.40-3.51 (4H, m), 2.58 (2H, m), 2.41 (4H, m).

ESI (LC-MS positive mode) m/z 516 [(M+H)$^+$].

Example 1-G-07

3-(2-Morpholin-4-yl-7-pyridin-3-yl-6,7-dihydro-5H-pyrrolo[2,3-d]pyrimidin-4-yl)-N-(2-pyridin-3-yl-ethyl)-benzamide (G-07)

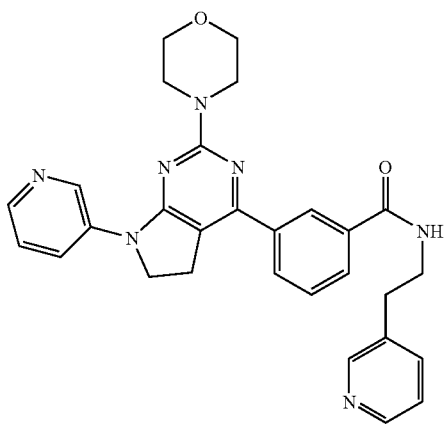

In the same manner as Example 1-G-05, from Compound G-03, WSCI, HOBt and 2-pyridin-3-yl-ethylamine, the desired compound was obtained.

$^1$H-NMR (400 MHz, DMSO-$d_6$) δ (ppm): 9.10 (1H, s), 8.68 (1H, t, J=6.0 Hz), 8.47 (1H, s), 8.42 (1H, d, J=4.8 Hz), 8.22-8.33 (3H, m), 8.08 (1H, d, J=7.6 Hz), 7.86 (1H, d, J=7.9 Hz), 7.68 (1H, d, J=7.8 Hz), 7.59 (1H, t, J=7.7 Hz), 7.43 (1H, dd, J=7.9, 5.2 Hz), 7.33 (1H, dd, J=7.7, 4.9 Hz), 4.15 (2H, t, J=8.1 Hz), 3.73 (8H, d, J=7.8 Hz), 3.50-3.60 (2H, m), 3.36-3.42 (2H, m), 2.90 (2H, t, J=7.0 Hz).

ESI (LC-MS positive mode) m/z 508 [(M+H)$^+$].

Example 1-G-08-N-methyl-3-(2-morpholin-4-yl-7-pyridin-3-yl-6,7-dihydro-5H-pyrrolo[2,3-d]pyrimidin-4-yl)-benzamide (G-08)

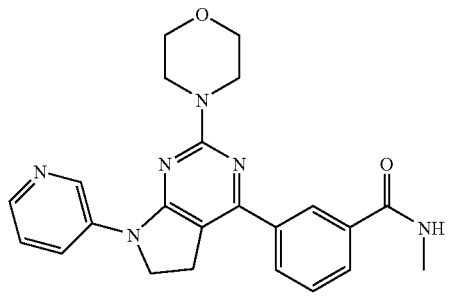

In the same manner as Example 1-G-05, from Compound G-03, WSCI, HOBt, methylamine hydrochloride and triethylamine, the desired compound was obtained.

$^1$H-NMR (400 MHz, DMSO-$d_6$) δ (ppm): 9.10 (1H, s), 8.55 (1H, d, J=4.5 Hz), 8.34 (1H, s), 8.25 (2H, d, J=5.3 Hz), 8.07 (1H, d, J=7.8 Hz), 7.90 (1H, d, J=7.7 Hz), 7.59 (1H, t, J=7.7 Hz), 7.43 (1H, d, J=13.0 Hz), 4.14 (2H, t, J=8.1 Hz), 3.73 (8H, dd, J=13.7, 4.3 Hz), 3.40-3.47 (2H, m), 2.81 (3H, d, J=4.4 Hz).

ESI (LC-MS positive mode) m/z 417 [(M+H)$^+$].

Example 1-G-09

3-(2-Morpholin-4-yl-7-pyridin-3-yl-6,7-dihydro-5H-pyrrolo[2,3-d]pyrimidin-4-yl)-N-pyridin-3-ylmethyl-benzamide (G-09)

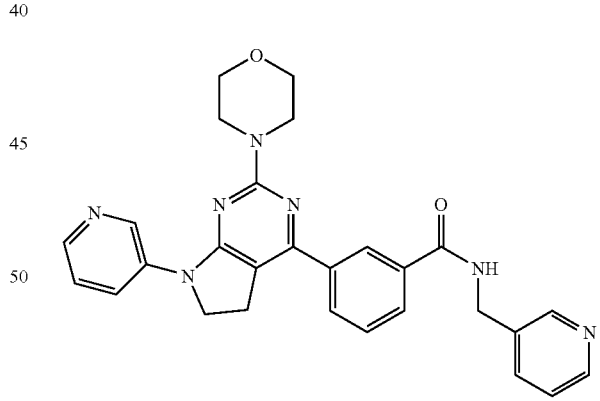

In the same manner as Example 1-G-05, from Compound G-03, WSCI, HOBt and 3-aminomethylpyridine, the desired compound was obtained.

$^1$H-NMR (250 MHz, DMSO-$d_6$) δ (ppm): 9.24 (1H, t, J=5.8 Hz), 9.09 (1H, s), 8.57 (1H, s), 8.47 (1H, d, J=4.5 Hz), 8.41 (1H, s), 8.25 (2H, d, J=5.4 Hz), 8.10 (1H, d, J=7.8 Hz), 7.97 (1H, d, J=7.9 Hz), 7.75 (1H, d, J=7.9 Hz), 7.61 (1H, t, J=7.8 Hz), 7.27-7.50 (2H, m), 4.53 (2H, d, J=5.7 Hz), 4.13 (2H, t, J=8.1 Hz), 3.72 (8H, d, J=3.0 Hz), 3.30-3.34 (2H, m).

ESI (LC-MS positive mode) m/z 494 [(M+H)$^+$].

Example 1-G-10

N-(2-dimethylamino-ethyl)-3-(2-morpholin-4-yl-7-pyridin-4-yl-6,7-dihydro-5H-pyrrolo[2,3-d]pyrimidin-4-yl)-benzamide (G-10)

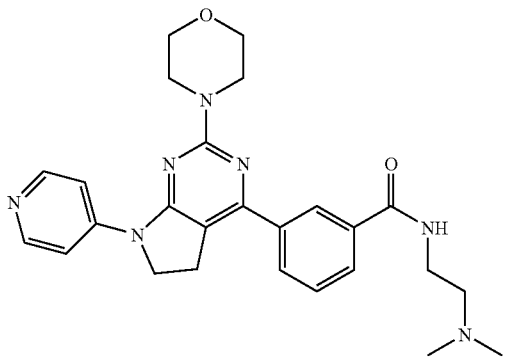

In the same manner as Example 1-G-05, from Compound G-04, WSCI, HOBt and N,N-dimethyl ethylenediamine, the desired compound was obtained.

$^1$H-NMR (270 MHz, CDCl$_3$) δ (ppm): 8.52 (2H, d, J=6.8 Hz), 8.38 (1H, t, J=1.7 Hz), 8.05 (1H, d, J=8.3 Hz), 7.82 (1H, d, J=7.8 Hz), 7.74 (2H, d, J=6.8 Hz), 7.54 (1H, t, J=7.8 Hz), 6.96 (1H, s), 4.08 (2H, t, J=7.8 Hz), 3.87 (8H, m), 3.55 (2H, dd, J=11.2, 5.9 Hz), 3.40 (2H, t, J=7.8 Hz), 2.55 (2H, t, J=5.1 Hz), 2.28 (6H, s).

ESI (LC-MS positive mode) m/z 474 [(M+H)$^+$].

Example 1-G-11

3-(2-Morpholin-4-yl-7-pyridin-3-yl-6,7-dihydro-5H-pyrrolo[2,3-d]pyrimidin-4-yl)-N-(2-pyridin-4-yl-ethyl)-benzamide (G-11)

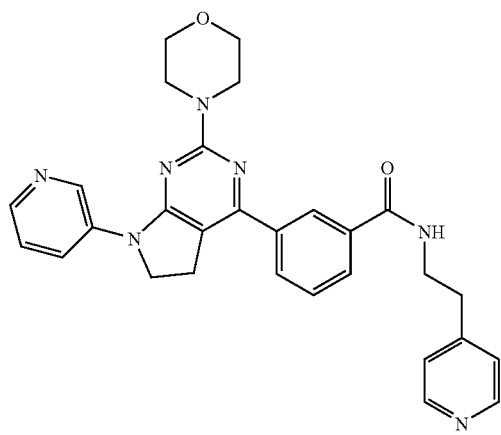

In the same manner as Example 1-G-05, from Compound G-03, from WSCI, HOBt and 2-pyridin-4-yl-ethylamine, the desired compound was obtained.

$^1$H-NMR (400 MHz, DMSO-d$_6$) δ (ppm): 9.09 (1H, s), 8.69 (1H, t, J=5.2 Hz), 8.47 (2H, d, J=5.5 Hz), 8.21-8.33 (3H, m), 8.07 (1H, d, J=7.7 Hz), 7.86 (1H, d, J=7.7 Hz), 7.58 (1H, t, J=7.8 Hz), 7.43 (1H, dd, J=8.1, 4.9 Hz), 7.29 (2H, d, J=5.5 Hz), 4.14 (2H, t, J=8.1 Hz), 3.72 (8H, d, J=6.3 Hz), 3.52-3.61 (2H, m), 3.29-3.34 (2H, m), 2.90 (2H, t, J=6.6 Hz).

ESI (LC-MS positive mode) m/z 508 [(M+H)$^+$].

Example 1-G-12

N-(2-carbamoyl-ethyl)-3-(2-morpholin-4-yl-7-pyridin-3-yl-6,7-dihydro-5H-pyrrolo[2,3-d]pyrimidin-4-yl)-benzamide (G-12)

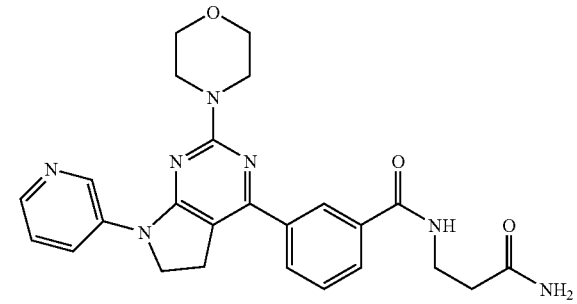

In the same manner as Example 1-G-05, from Compound G-03, WSCI, HOBt and 3-aminopropionamide, the desired compound was obtained.

$^1$H-NMR (250 MHz, DMSO-d$_6$) δ (ppm): 9.10 (1H, s), 8.64 (1H, t, J=5.4 Hz), 8.35 (1H, s), 8.26 (2H, d, J=5.4 Hz), 8.08 (1H, d, J=7.9 Hz), 7.91 (1H, d, J=7.9 Hz), 7.59 (1H, t, J=7.8 Hz), 7.32-7.47 (2H, m), 6.87 (1H, brs), 4.14 (2H, t, J=8.1 Hz), 3.73 (8H, d, J=3.3 Hz), 3.42-3.54 (2H, m), 3.35-3.40 (2H, m), 2.37 (2H, t, J=7.2 Hz).

ESI (LC-MS positive mode) m/z 474 [(M+H)$^+$].

Example 1-G-13

N-(2-Morpholin-4-yl-ethyl)-3-(2-morpholin-4-yl-7-pyridin-3-yl-6,7-dihydro-5H-pyrrolo[2,3-d]pyrimidin-4-yl)-benzamide (G-13)

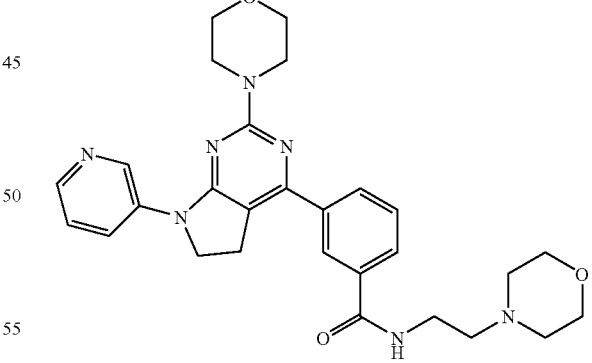

In the same manner as Example 1-G-05, from Compound G-03, WSCI, HOBt and 2-morpholin-4-yl-ethylamine, the desired compound was obtained.

$^1$H-NMR (270 MHz, DMSO-d$_6$) δ (ppm): 2.41 (4H, m), 2.58 (2H, m), 3.40-3.51 (4H, m), 3.54 (4H, m), 3.78-3.83 (8H, m), 4.16 (2H, t, J=8.4 Hz), 7.34-7.39 (1H, m), 7.55 (1H, t, J=7.8 Hz), 7.90 (1H, d, J=7.6 Hz), 8.07 (1H, d, J=7.8 Hz), 8.19-8.27 (2H, m), 8.38 (1H, s), 9.13 (1H, d, J=2.7 Hz).

ESI (LC-MS positive mode) m/z 516 [(M+H)$^+$].

Example 1-G-14

3-(2-Morpholin-4-yl-7-pyridin-4-yl-6,7-dihydro-5H-pyrrolo[2,3-d]pyrimidin-4-yl)-N-(2-pyridin-3-yl-ethyl)-benzamide (G-14)

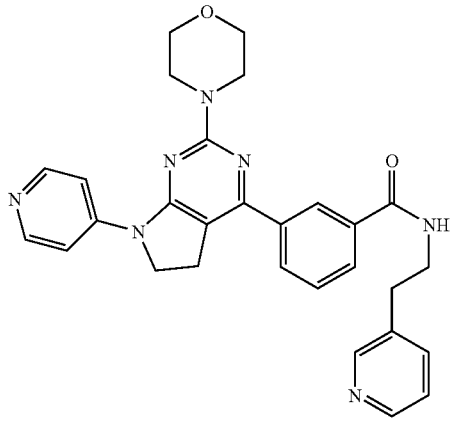

In the same manner as Example 1-G-05, from Compound G-04, WSCI, HOBt and 2-pyridin-3-yl-ethylamine, the desired compound was obtained.

$^1$H-NMR (250 MHz, DMSO-d$_6$) δ (ppm): 8.70 (1H, t, J=5.4 Hz), 8.39-8.51 (4H, m), 8.30 (1H, s), 8.08 (1H, d, J=7.9 Hz), 7.81-7.92 (3H, m), 7.68 (1H, d, J=7.8 Hz), 7.59 (1H, t, J=7.8 Hz), 7.32 (1H, dd, J=7.8, 4.8 Hz), 4.11 (2H, t, J=8.0 Hz), 3.75 (8H, d, J=3.7 Hz), 3.54 (2H, q, J=6.5 Hz), 2.89 (2H, t, J=6.8 Hz), 2.37 (2H, t, J=8.0 Hz).

ESI (LC-MS positive mode) m/z 508 [(M+H)$^+$].

Example 1-G-15

N-isobutyl-3-(2-morpholin-4-yl-7-pyridin-4-yl-6,7-dihydro-5H-pyrrolo[2,3-d]pyrimidin-4-yl)-benzamide (G-15)

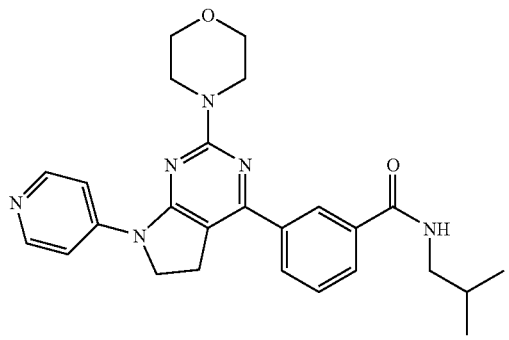

In the same manner as Example 1-G-05, from Compound G-04, WSCI, HOBt and 2-methylpropylamine, the desired compound was obtained.

$^1$H-NMR (250 MHz, DMSO-d$_6$) δ (ppm): 8.60 (1H, t, J=5.7 Hz), 8.46 (2H, d, J=6.3 Hz), 8.37 (1H, s), 8.08 (1H, d, J=7.9 Hz), 7.93 (1H, d, J=8.0 Hz), 7.83 (2H, d, J=6.4 Hz), 7.59 (1H, t, J=7.8 Hz), 4.11 (2H, t, J=8.6 Hz), 3.75 (8H, d, J=5.5 Hz), 3.11 (2H, t, J=6.4 Hz), 1.75-1.96 (1H, m), 0.90 (6H, d, J=6.6 Hz).

ESI (LC-MS positive mode) m/z 459 [(M+H)$^+$].

Example 1-G-16

3-(2-Morpholin-4-yl-7-pyridin-4-yl-6,7-dihydro-5H-pyrrolo[2,3-d]pyrimidin-4-yl)-N-pyridin-3-ylmethyl-benzamide (G-16)

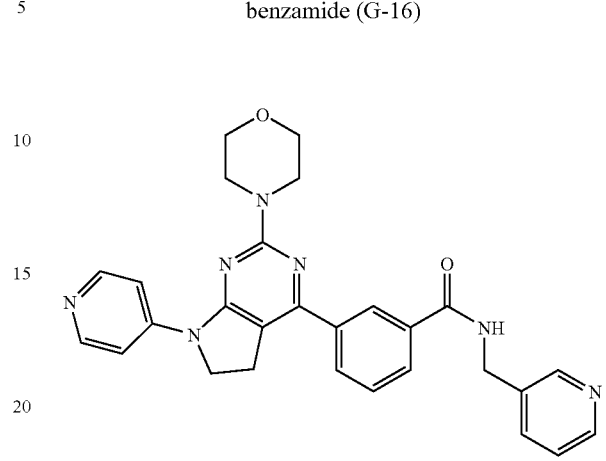

In the same manner as Example 1-G-05, from Compound G-04, WSCI, HOBt and 3-aminomethylpyridine, the desired compound was obtained.

$^1$H-NMR (360 MHz, DMSO-d$_6$) δ (ppm): 9.22 (1H, t, J=5.8 Hz), 8.57 (1H, s), 8.44-8.50 (3H, m), 8.41 (1H, s), 8.10 (1H, d, J=7.7 Hz), 7.98 (1H, d, J=7.9 Hz), 7.83 (2H, d, J=6.1 Hz), 7.75 (1H, d, J=7.9 Hz), 7.62 (1H, t, J=7.8 Hz), 7.37 (1H, dd, J=7.7, 5.0 Hz), 4.53 (2H, d, J=5.6 Hz), 4.11 (2H, t, J=8.1 Hz), 3.75 (8H, d, J=10.2 Hz), 3.35-3.43 (2H, m).

ESI (LC-MS positive mode) m/z 494 [(M+H)$^+$].

Example 1-G-17

3-(2-Morpholin-4-yl-7-pyridin-3-yl-6,7-dihydro-5H-pyrrolo[2,3-d]pyrimidin-4-yl)-N-propyl-benzamide (G-17)

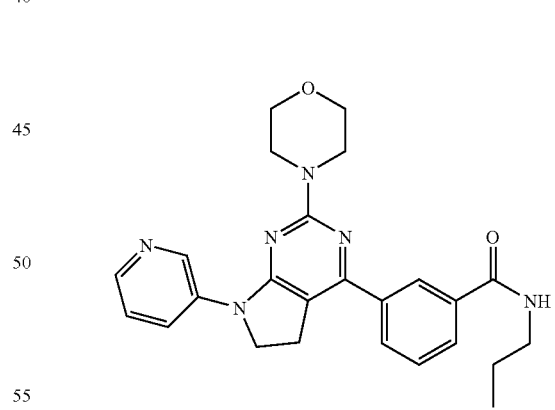

In the same manner as Example 1-G-05, from Compound G-03 prepared in Example 1-G-03, WSCI, HOBt and propylamine, the desired compound was obtained.

$^1$H-NMR (400 MHz, DMSO-d$_6$) δ (ppm): 9.10 (1H, s), 8.58 (1H, t, J=5.7 Hz), 8.36 (1H, s), 8.26 (2H, d, J=5.3 Hz), 8.07 (1H, d, J=7.8 Hz), 7.91 (1H, d, J=7.8 Hz), 7.59 (1H, t, J=7.7 Hz), 7.43 (1H, dd, J=8.1, 5.0 Hz), 4.15 (2H, t, J=8.1 Hz), 3.73 (8H, dd, J=13.5, 3.8 Hz), 3.37-3.42 (2H, m), 3.25 (2H, q, J=6.6 Hz), 1.46-1.65 (2H, m), 0.90 (3H, t, J=7.4 Hz).

ESI (LC-MS positive mode) m/z 445 [(M+H)$^+$].

Example 1-G-18

3-(2-Morpholin-4-yl-7-pyridin-4-yl-6,7-dihydro-5H-pyrrolo[2,3-d]pyrimidin-4-yl)-N-propyl-benzamide (G-18)

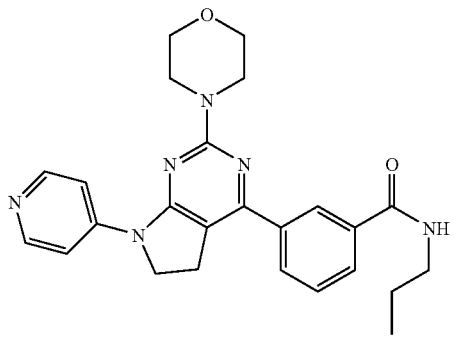

In the same manner as Example 1-G-05, from Compound G-04 prepared in Example 1-G-04, WSCI, HOBt and propylamine, the desired compound was obtained.

$^1$H-NMR (360 MHz, DMSO-$d_6$) δ (ppm): 8.57 (1H, t, J=5.5 Hz), 8.46 (2H, d, J=6.5 Hz), 8.36 (1H, s), 8.08 (1H, d, J=7.9 Hz), 7.92 (1H, d, J=7.9 Hz), 7.83 (2H, d, J=6.5 Hz), 7.59 (1H, t, J=7.8 Hz), 4.11 (2H, t, J=8.1 Hz), 3.75 (8H, dd, J=14.9, 4.7 Hz), 3.33-3.42 (2H, m), 3.20-3.29 (2H, m), 1.45-1.66 (2H, m), 0.91 (3H, t, J=7.3 Hz).

ESI (LC-MS positive mode) m/z 445 [(M+H)$^+$].

Example 1-G-19

3-(2-Morpholin-4-yl-7-pyridin-4-yl-6,7-dihydro-5H-pyrrolo[2,3-d]pyrimidin-4-yl)-N-(2-pyridin-4-yl-ethyl)-benzamide (G-19)

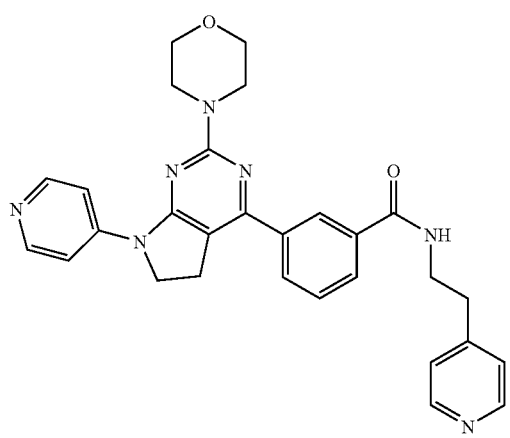

In the same manner as Example 1-G-05, from Compound G-04 prepared in Example 1-G-04, WSCI, HOBt and 2-pyridin-4-yl-ethylamine, the desired compound was obtained.

$^1$H-NMR (250 MHz, DMSO-$d_6$) δ (ppm): 8.70 (1H, t, J=5.4 Hz), 8.47 (4H, d, J=4.5 Hz), 8.29 (1H, s), 8.08 (1H, d, J=8.1 Hz), 7.80-7.92 (3H, m), 7.59 (1H, t, J=7.8 Hz), 7.29 (2H, d, J=5.9 Hz), 4.11 (2H, t, J=8.1 Hz), 3.75 (8H, d, J=3.3 Hz), 3.50-3.63 (2H, m), 3.26-3.33 (2H, m), 2.86-2.95 (2H, m).

ESI (LC-MS positive mode) m/z 508 [(M+H)$^+$].

Example 1-G-20

N-benzyl-3-(2-morpholin-4-yl-7-pyridin-3-yl-6,7-dihydro-5H-pyrrolo[2,3-d]pyrimidin-4-yl)-benzamide (G-20)

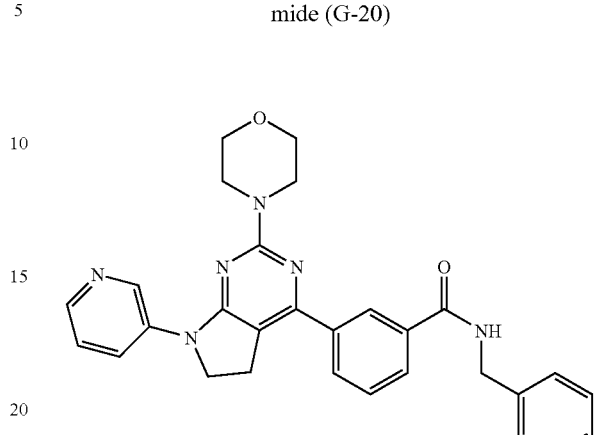

In the same manner as Example 1-G-05, from Compound G-03 prepared in Example 1-G-03, WSCI, HOBt and benzylamine, the desired compound was obtained.

$^1$H-NMR (400 MHz, DMSO-$d_6$) δ (ppm): 9.18 (1H, t, J=5.7 Hz), 9.10 (1H, s), 8.43 (1H, d, J=5.3 Hz), 8.26 (2H, d, J=5.3 Hz), 8.10 (1H, d, J=8.0 Hz), 7.98 (1H, d, J=7.7 Hz), 7.61 (1H, t, J=7.7 Hz), 7.39-7.49 (1H, m), 7.34 (4H, d, J=4.2 Hz), 7.22-7.29 (1H, m), 4.52 (2H, d, J=6.0 Hz), 4.15 (2H, t, J=8.2 Hz), 3.73 (8H, dd, J=14.0, 3.8 Hz), 3.36-3.42 (2H, m).

ESI (LC-MS positive mode) m/z 493 [(M+H)$^+$].

Example 1-G-21

N-(2-methoxy-ethyl)-3-(2-morpholin-4-yl-7-pyridin-4-yl-6,7-dihydro-5H-pyrrolo[2,3-d]pyrimidin-4-yl)-benzamide (G-21)

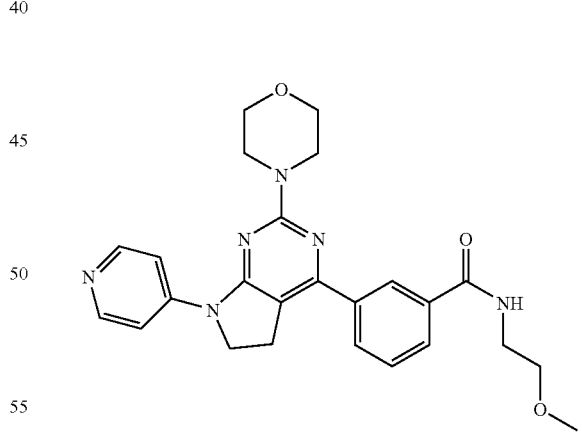

In the same manner as Example 1-G-05, from Compound G-04 prepared in Example 1-G-04, WSCI, HOBt and 2-methoxy-ethylamine, the desired compound was obtained.

$^1$H-NMR (400 MHz, DMSO-$d_6$) δ (ppm): 8.66 (1H, t, J=4.8 Hz), 8.46 (2H, d, J=6.1 Hz), 8.37 (1H, s), 8.09 (1H, d, J=7.8 Hz), 7.94 (1H, d, J=8.0 Hz), 7.84 (2H, d, J=6.3 Hz), 7.60 (1H, t, J=7.8 Hz), 4.12 (2H, t, J=8.1 Hz), 3.75 (8H, dd, J=16.7, 4.7 Hz), 3.42-3.52 (4H, m), 3.37-3.40 (2H, m), 3.28 (3H, s).

ESI (LC-MS positive mode) m/z 461 [(M+H)$^+$].

Example 1-G-22

N-(2-morpholin-4-yl-ethyl)-3-(2-morpholin-4-yl-7-pyridin-4-yl-6,7-dihydro-5H-pyrrolo[2,3-d]pyrimidin-4-yl)-benzamide (G-22)

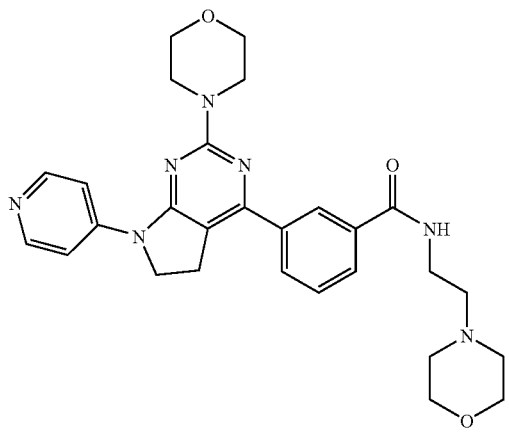

In the same manner as Example 1-G-05, from Compound G-04 prepared in Example 1-G-04, WSCI, HOBt and 2-morpholin-4-yl-ethylamine, the desired compound was obtained.

$^1$H-NMR (270 MHz, DMSO-$d_6$) δ (ppm): 8.54 (1H, t, J=5.7 Hz), 8.47 (2H, d, J=6.8 Hz), 8.36 (1H, t, J=1.2 Hz), 8.09 (1H, d, J=8.7 Hz), 7.92 (1H, d, J=7.7 Hz), 7.85 (2H, d, J=6.8 Hz), 7.61 (1H, t, J=7.7 Hz), 4.13 (2H, t, J=8.1 Hz), 3.80-3.70 (8H, m), 3.58 (4H, t, J=4.3 Hz), 3.41 (4H, m), 2.43 (4H, t, J=4.3 Hz).

ESI (LC-MS positive mode) m/z 516 [(M+H)$^+$].

Example 1-G-23

N-carbamoylmethyl-3-(2-morpholin-4-yl-7-pyridin-4-yl-6,7-dihydro-5H-pyrrolo[2,3-d]pyrimidin-4-yl)-benzamide (G-23)

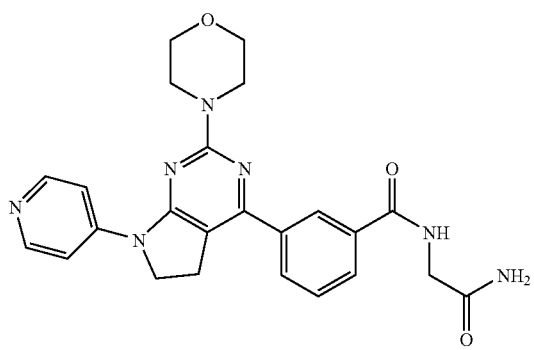

In the same manner as Example 1-G-05, from Compound G-04 prepared in Example 1-G-04, WSCI, HOBt and 2-aminoacetamide, the desired compound was obtained.

$^1$H-NMR (250 MHz, DMSO-$d_6$) δ (ppm): 8.89 (1H, t, J=5.7 Hz), 8.65 (2H, d, J=7.1 Hz), 8.42 (1H, s), 8.28 (2H, brs), 8.12 (1H, d, J=7.8 Hz), 8.02 (1H, d, J=7.8 Hz), 7.63 (1H, t, J=7.8 Hz), 7.47 (1H, brs), 7.08 (1H, brs), 4.24 (2H, t, J=7.6 Hz), 3.69-3.97 (10H, m), 3.38-3.54 (2H, m).

ESI (LC-MS positive mode) m/z 460 [(M+H)$^+$].

Example 1-G-24

N-(2-carbamoyl-ethyl)-3-(2-morpholin-4-yl-7-pyridin-4-yl-6,7-dihydro-5H-pyrrolo[2,3-d]pyrimidin-4-yl)-benzamide (G-24)

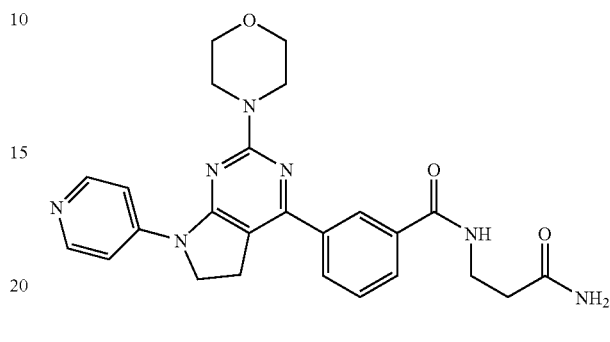

In the same manner as Example 1-G-05, from Compound G-04 prepared in Example 1-G-04, WSCI, HOBt and 3-aminopropionamide, the desired compound was obtained.

$^1$H-NMR (250 MHz, DMSO-$d_6$) δ (ppm): 8.57-8.83 (3H, m), 8.38 (1H, s), 8.28 (2H, brs), 8.11 (1H, d, J=7.9 Hz), 7.96 (1H, d, J=7.9 Hz), 7.61 (1H, t, J=7.8 Hz), 7.41 (1H, brs), 6.88 (1H, brs), 4.24 (2H, t, J=7.8 Hz), 3.77 (8H, d, J=8.6 Hz), 3.43-3.57 (4H, m), 2.38 (2H, t, J=7.1 Hz).

ESI (LC-MS positive mode) m/z 474 [(M+H)$^+$].

Example 1-G-25

3-(2-Morpholin-4-yl-7-pyridin-4-yl-6,7-dihydro-5H-pyrrolo[2,3-d]pyrimidin-4-yl)-N-phenethyl-benzamide (G-25)

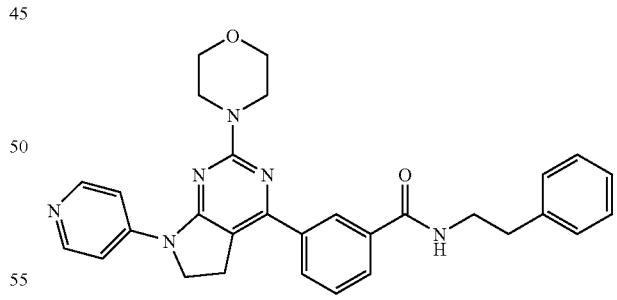

In the same manner as Example 1-G-05, from Compound G-04 prepared in Example 1-G-04, WSCI, HOBt and phenethylamine, the desired compound was obtained.

$^1$H-NMR (270 MHz, CDCl$_3$) δ (ppm): 8.52 (2H, d, J=6.5 Hz), 8.25 (1H, s), 8.05 (1H, m), 7.75 (2H, d, J=6.5 Hz), 7.75 (1H, m), 7.51 (1H, m), 7.32 (5H, m), 6.21 (1H, m), 4.08 (2H, t, J=8.4 Hz), 3.86 (8H, m), 3.76 (2H, t, J=6.8 Hz), 3.36 (2H, t, J=8.4 Hz), 2.97 (2H, t, J=6.8 Hz).

ESI (LC-MS positive mode) m/z 507 [(M+H)$^+$].

Example 1-G-26

N-isobutyl-3-(2-morpholin-4-yl-7-pyridin-3-yl-6,7-dihydro-5H-pyrrolo[2,3-d]pyrimidin-4-yl)-benzamide (G-26)

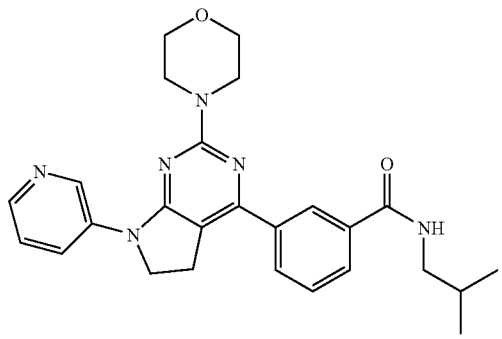

In the same manner as Example 1-G-05, from Compound G-03 prepared in Example 1-G-03, WSCI, HOBt and isobutylamine, the desired compound was obtained.

$^1$H-NMR (400 MHz, DMSO-$d_6$) δ (ppm): 9.10 (1H, s), 8.58 (1H, t, J=5.6 Hz), 8.37 (1H, s), 8.26 (2H, d, J=5.3 Hz), 8.08 (1H, d, J=7.6 Hz), 7.92 (1H, d, J=7.7 Hz), 7.59 (1H, t, J=7.8 Hz), 7.43 (1H, dd, J=8.1, 5.1 Hz), 4.15 (2H, t, J=8.2 Hz), 3.73 (8H, dd, J=13.8, 3.3 Hz), 3.36-3.43 (2H, m), 3.11 (2H, t, J=6.4 Hz), 1.74-1.97 (1H, m), 0.91 (6H, d, J=6.7 Hz).

ESI (LC-MS positive mode) m/z 459 [(M+H)$^+$].

Example 1-G-27

3-(2-Morpholin-4-yl-7-pyridin-3-yl-6,7-dihydro-5H-pyrrolo[2,3-d]pyrimidin-4-yl)-benzoic acid 2-dimethylamino-ethyl ester (G-27)

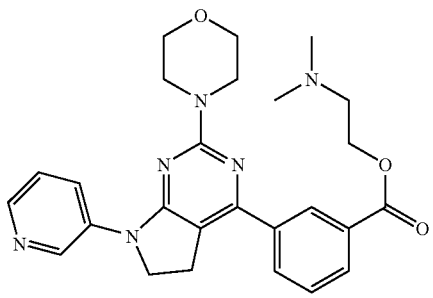

In the same manner as Example 1-G-05, from Compound G-03 prepared in Example 1-G-03, WSCI, HOBt and N,N-dimethylethanolamine, the desired compound was obtained.

$^1$H-NMR (400 MHz, DMSO-$d_6$) δ (ppm): 9.08 (1H, d, J=2.4 Hz), 8.53 (1H, s), 8.26-8.18 (3H, m), 8.03 (1H, d, J=7.8 Hz), 7.66 (1H, t, J=7.8 Hz), 7.42 (1H, dd, J=8.3, 4.9 Hz), 4.38 (2H, t, J=5.6 Hz), 4.14 (2H, t, J=8.1 Hz), 3.76-3.68 (8H, m), 3.45-3.40 (2H, m), 2.64 (2H, t, J=5.6 Hz), 2.23 (6H, s).

ESI (LC-MS positive mode) m/z 475 [(M+H)$^+$].

Example 1-G-28

3-(2-Morpholin-4-yl-7-pyridin-3-yl-6,7-dihydro-5H-pyrrolo[2,3-d]pyrimidin-4-yl)-benzamide (G-28)

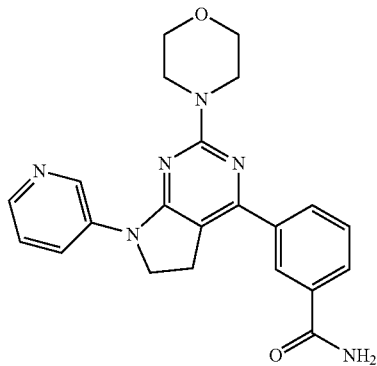

In the same manner as Example 1-G-05, from Compound G-03 prepared in Example 1-G-03, WSCI, HOBt, triethylamine and ammonium chloride, the desired compound was obtained.

$^1$H-NMR (270 MHz, CDCl$_3$) δ (ppm): 9.07 (1H, d, J=2.5 Hz), 8.37 (1H, s), 8.28 (1H, d, J=3.8 Hz), 8.23-8.19 (1H, m), 8.08 (1H, d, J=7.9 Hz), 7.86 (1H, d, J=7.1 Hz), 7.56 (1H, t, J=7.9 Hz), 7.35 (1H, dd, J=8.5, 4.5 Hz), 4.11 (2H, t, J=7.8 Hz), 3.86-3.82 (8H, m), 3.41 (2H, t, J=7.8 Hz).

ESI (LC-MS positive mode) m/z 403 [(M+H)$^+$].

Example 1-G-29

4-(2-Morpholin-4-yl-7-pyridin-4-yl-6,7-dihydro-5H-pyrrolo[2,3-d]pyrimidin-4-yl)-benzoic acid methyl ester hydrochloride (G-29)

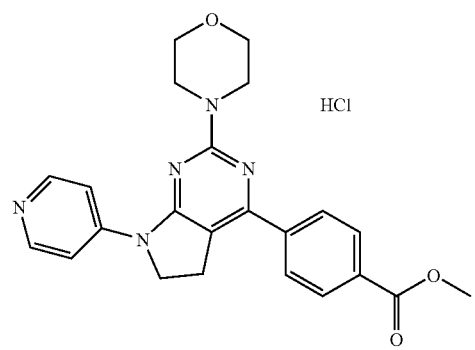

In the same manner as Example 1-G-02, from 4-carbomethoxyphenylboronic acid, 4-(2-morpholin-4-yl-7-pyridin-4-yl-6,7-dihydro-5H-pyrrolo[2,3-d]pyrimidin-4-yl)-benzoic acid methyl ester was obtained. To this, 1M hydrochloric acid (1.0 equivalent) was added, followed by stirring at room temperature, and subsequently concentration was carried out under reduced pressure, to obtain the desired compound.

$^1$H-NMR (270 MHz, DMSO-$d_6$) δ (ppm): 8.68 (2H, d, J=7.4 Hz), 8.26-8.38 (2H, m), 8.11 (4H, s), 4.27 (2H, t, J=7.2 Hz), 3.90 (3H, s), 3.73-3.82 (8H, m), 3.38-3.46 (2H, br).

ESI (LC-MS positive mode) m/z 418 [(M+H)$^+$].

Example 1-G-30

N-(2-dimethylamino-ethyl)-4-(2-morpholin-4-yl-7-pyridin-3-yl-6,7-dihydro-5H-pyrrolo[2,3-d]pyrimidin-4-yl)-benzamide (G-30)

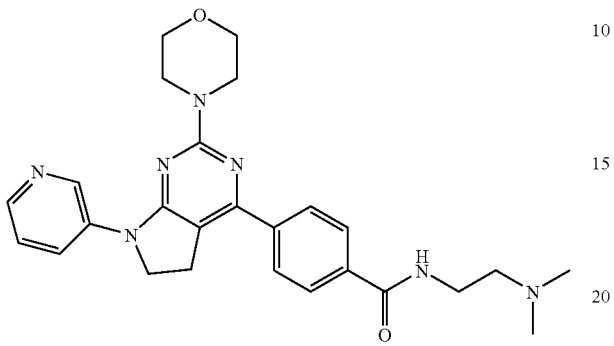

Compound G-32 obtained in Example 1-G-32 was treated with sodium hydroxide in methanol, and the resulting carboxylic acid was reacted with WSCI, HOBt and N,N-dimethyl ethylenediamine in the same manner as Example 1-G-05, whereby the desired compound was obtained.

$^1$H-NMR (270 MHz, CD$_3$OD) δ (ppm): 9.21 (1H, m), 8.22 (2H, m), 8.02 (2H, d, J=8.7 Hz), 7.93 (2H, d, J=8.7 Hz), 7.44 (1H, dd, J=8.5, 4.9 Hz), 4.12 (2H, t, J=8.2 Hz), 3.85-3.77 (8H, m), 3.69-3.54 (3H, m), 3.37 (2H, t, J=8.2 Hz), 2.75 (2H, t, J=6.8 Hz), 2.46 (6H, s).

ESI (LC-MS positive mode) m/z 474 [(M+H)$^+$].

Example 1-G-31

3-(2-Morpholin-4-yl-7-pyridin-4-yl-6,7-dihydro-5H-pyrrolo[2,3-d]pyrimidin-4-yl)-benzamide (G-31)

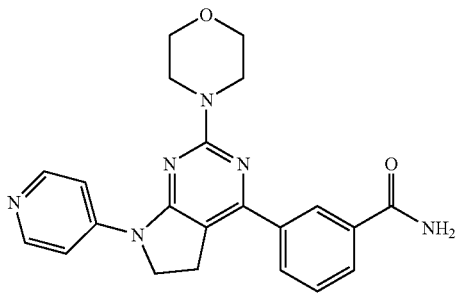

In the same manner as Example 1-G-05, from Compound G-04 prepared in Example 1-G-04, WSCI, HOBt, ammonium chloride and triethylamine, the desired compound was obtained.

$^1$H-NMR (270 MHz, DMSO-d$_6$) δ (ppm): 8.47 (2H, d, J=6.8 Hz), 8.39 (1H, t, J=1.3 Hz), 8.10 (1H, s), 8.09 (1H, dt, J=7.7, 1.3 Hz), 7.97 (1H, dt, J=7.7, 1.3 Hz), 7.84 (2H, d, J=6.8 Hz), 7.59 (1H, t, J=7.7 Hz), 7.50 (1H, s), 4.12 (2H, t, J=7.8 Hz), 3.80-3.73 (8H, m), 3.37 (2H, t, J=7.8 Hz).

ESI (LC-MS positive mode) m/z 403 [(M+H)$^+$].

Example 1-G-32

4-(2-Morpholin-4-yl-7-pyridin-3-yl-6,7-dihydro-5H-pyrrolo[2,3-d]pyrimidin-4-yl)-benzoic acid methyl ester (G-32)

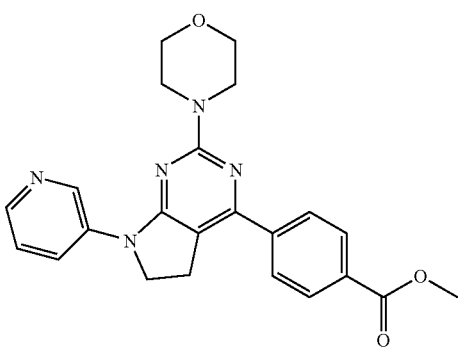

In the same manner as Example 1-G-01, using 4-carbomethoxyphenylboronic acid, the desired compound was obtained.

$^1$H-NMR (270 MHz, DMSO-d$_6$) δ (ppm): 9.10 (1H, d, J=2.7 Hz), 8.26 (1H, d, J=4.9 Hz), 8.08 (4H, s), 8.23 (2H, m), 4.15 (2H, t, J=8.2 Hz), 7.43 (1H, m), 3.89 (3H, s), 3.65-3.75 (8H, m), 3.37 (2H, t, J=8.2 Hz).

ESI (LC-MS positive mode) m/z 418 [(M+H)$^+$].

Example 1-G-33

4-(2-Morpholin-4-yl-7-pyridin-4-yl-6,7-dihydro-5H-pyrrolo[2,3-d]pyrimidin-4-yl)-benzamide (G-33)

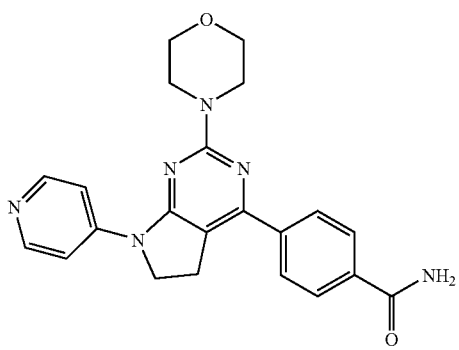

In the same manner as Example 1-G-05, Compound G-29 prepared in Example 1-G-29 was treated with sodium hydroxide in methanol, and the resulting carboxylic acid was reacted with WSCI, HOBt, ammonium chloride and triethylamine, whereby the desired compound was obtained.

$^1$H-NMR (270 MHz, DMSO-d$_6$) δ (ppm): 8.47 (2H, d, J=6.5 Hz), 8.08 (1H, brs), 7.99 (4H, s), 7.83 (2H, d, J=6.5 Hz), 7.46 (1H, brs), 4.12 (2H, t, J=7.8 Hz), 3.74-3.76 (8H, m), 3.37 (2H, t, J=7.8 Hz).

ESI (LC-MS positive mode) m/z 403 [(M+H)$^+$].

Example 1-G-34

N-(2-morpholin-4-yl-ethyl)-4-(2-morpholin-4-yl-7-pyridin-3-yl-6,7-dihydro-5H-pyrrolo[2,3-d]pyrimidin-4-yl)-benzamide (G-34)

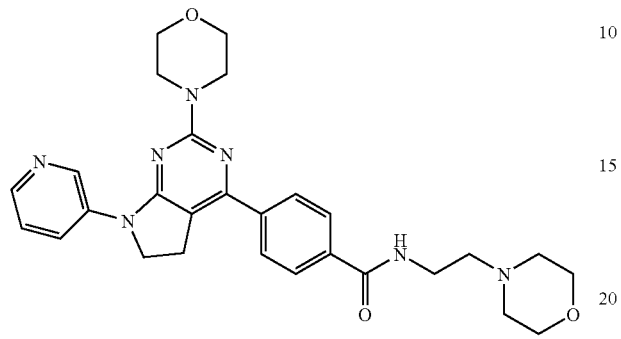

In the same manner as Example 1-G-30, using morpholinoethylamine, the desired compound was obtained.

$^1$H-NMR (270 MHz, CDCl$_3$) δ (ppm): 9.12 (1H, d, J=2.6 Hz), 8.31 (1H, dd, J=4.5, 1.4 Hz), 8.15 (1H, dq, J=8.4, 1.4 Hz), 8.00 (2H, d, J=8.6 Hz), 7.89 (2H, d, J=8.6 Hz), 7.33 (1H, dd, J=8.4, 4.5 Hz), 6.95 (1H, s), 4.12 (2H, t, J=8.2 Hz), 3.89-3.81 (8H, m), 3.77 (4H, t, J=4.6 Hz), 3.65-3.58 (2H, m), 3.38 (2H, t, J=8.2 Hz), 2.67 (2H, t, J=5.9 Hz), 2.56 (4H, t, J=4.5 Hz).

ESI (LC-MS positive mode) m/z 516 [(M+H)$^+$].

Example 1-G-35

N-(2-morpholin-4-yl-ethyl)-4-(2-morpholin-4-yl-7-pyridin-4-yl-6,7-dihydro-5H-pyrrolo[2,3-d]pyrimidin-4-yl)-benzamide (G-35)

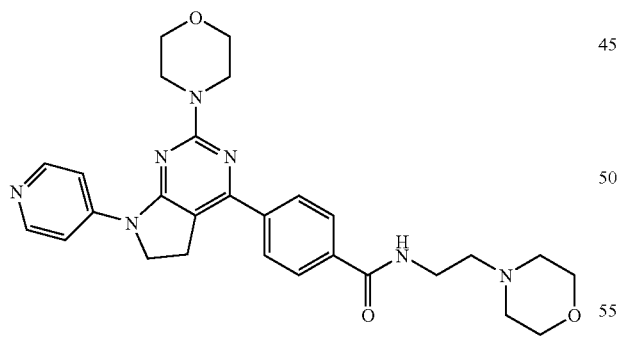

In the same manner as Example 1-G-34, from morpholinoethylamine, the desired compound was obtained.

$^1$H-NMR (270 MHz, CDCl$_3$) δ (ppm): 8.52 (2H, d, J=6.4 Hz), 7.99 (2H, d, J=8.6 Hz), 7.89 (2H, d, J=8.6 Hz), 7.74 (2H, d, J=6.4 Hz), 6.95 (1H, t, J=4.3 Hz), 4.09 (2H, t, J=8.2 Hz), 3.91-3.81 (8H, m), 3.76 (4H, t, J=4.4 Hz), 3.61 (2H, dt, J=15.9, 5.9 Hz), 3.37 (2H, t, J=8.2 Hz), 2.66 (2H, t, J=5.9 Hz), 2.56 (4H, t, J=4.4 Hz).

ESI (LC-MS positive mode) m/z 516 [(M+H)$^+$].

Example 1-G-36

4-(2-Morpholin-4-yl-7-pyridin-3-yl-6,7-dihydro-5H-pyrrolo[2,3-d]pyrimidin-4-yl)-benzamide (G-36)

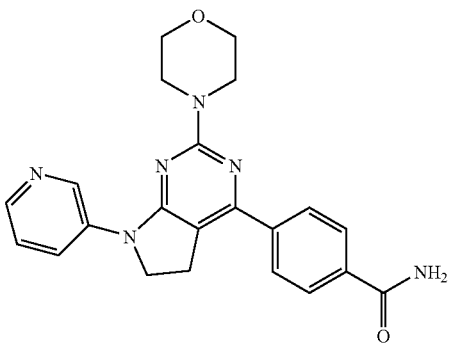

In the same manner as Example 1-G-34, from ammonium chloride, the desired compound was obtained.

$^1$H-NMR (270 MHz, DMSO-d$_6$) δ (ppm): 9.09 (1H, d, J=2.3 Hz), 8.27-8.23 (1H, m), 8.06 (1H, s), 7.87-7.95 (3H, m), 7.45-7.40 (2H, m), 4.13 (2H, t, J=8.3 Hz), 3.72 (8H, m), 3.36 (2H, t, J=8.3 Hz).

ESI (LC-MS positive mode) m/z 403 [(M+H)$^+$].

Example 1-G-37

3-(2-Morpholin-4-yl-7-pyridin-4-yl-6,7-dihydro-5H-pyrrolo[2,3-d]pyrimidin-4-yl)-benzoic acid 2-dimethylamino-ethyl ester (G-37)

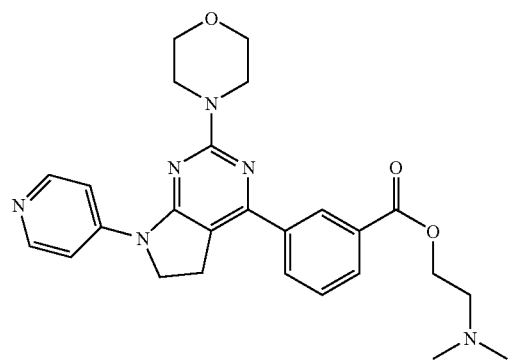

In the same manner as Example 1-G-05, using Compound G-04 prepared in Example 1-G-04 and N,N-dimethylaminoethanol, the desired compound was obtained.

$^1$H-NMR (270 MHz, CD$_3$OD) δ (ppm): 8.62 (1H, t, J=1.6 Hz), 8.50 (2H, d, J=7.3 Hz), 8.27-8.21 (4H, m), 7.66 (1H, t, J=7.7 Hz), 4.76-4.73 (2H, m), 4.25 (2H, t, J=8.0 Hz), 3.85 (8H, m), 3.69-3.65 (2H, m), 3.45 (2H, t, J=8.0 Hz), 3.03 (6H, s).

ESI (LC-MS positive mode) m/z 475 [(M+H)$^+$].

Example 1-G-38

N,N-dimethyl-3-(2-morpholin-4-yl-7-pyridin-4-yl-6,7-dihydro-5H-pyrrolo[2,3-d]pyrimidin-4-yl)-benzamide trifluoroacetic acid salt (G-38)

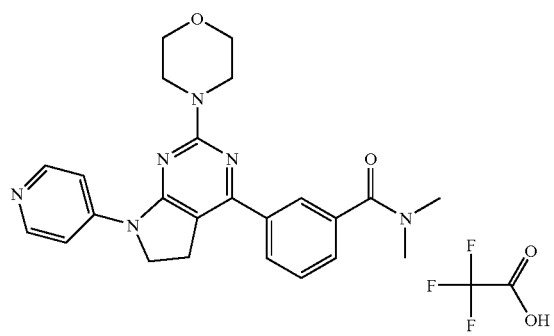

In the same manner as Example 1-G-05, from Compound G-04 prepared in Example 1-G-04 and dimethylamine, the desired compound was obtained.

$^1$H-NMR (400 MHz, DMSO-$d_6$) δ (ppm): 8.68 (2H, d, J=7.3 Hz), 8.32 (2H, br), 8.02 (1H, d, J=7.7 Hz), 7.94 (1H, s), 7.60 (1H, t, J=7.6 Hz), 7.55 (1H, d, J=6.4 Hz), 4.24 (2H, t, J=8.0 Hz), 3.77 (8H, dd, J=20.6, 5.0 Hz), 3.42 (2H, t, J=7.9 Hz), 3.02 (3H, s), 2.95 (3H, s).

ESI (LC-MS positive mode) m/z 431 ([M+H]$^+$).

Example 1-G-39

N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-39)

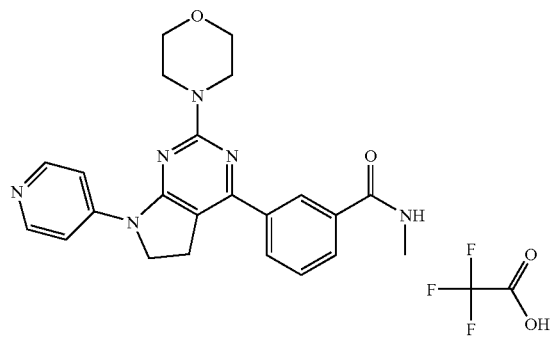

In the same manner as Example 1-G-05, from Compound G-04 prepared in Example 1-G-04 and methylamine-tetrahydrofuran, the desired compound was obtained.

$^1$H-NMR (400 MHz, DMSO-$d_6$) δ (ppm): 8.67 (2H, d, J=7.3 Hz), 8.59 (1H, d, J=4.6 Hz), 8.37 (1H, s), 8.29 (2H, brs), 8.11 (1H, d, J=8.1 Hz), 7.96 (1H, d, J=8.0 Hz), 7.62 (1H, t, J=7.8 Hz), 4.25 (2H, t, J=8.1 Hz), 3.78 (8H, dd, J=23.3, 5.0 Hz), 3.40-3.50 (2H, m), 2.82 (3H, d, J=4.6 Hz).

ESI (LC-MS positive mode) m/z 417 ([M+H]$^+$).

Example 1-G-40

3-(2-Morpholin-4-yl-7-pyridin-4-yl-6,7-dihydro-5H-pyrrolo[2,3-d]pyrimidin-4-yl)-N-phenyl-benzamide trifluoroacetic acid salt (G-40)

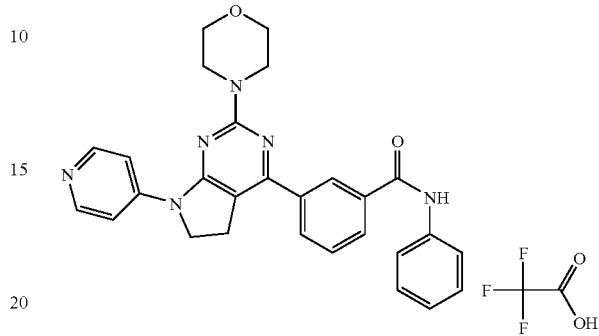

In the same manner as Example 1-G-05, from Compound G-04 prepared in Example 1-G-04 and aniline, the desired compound was obtained.

$^1$H-NMR (400 MHz, DMSO-$d_6$) δ (ppm): 10.41 (1H, s), 8.67 (2H, d, J=7.3 Hz), 8.47 (1H, s), 8.30 (2H, brs), 8.19 (1H, d, J=8.3 Hz), 8.09 (1H, d, J=8.1 Hz), 7.79 (2H, d, J=7.6 Hz), 7.70 (1H, t, J=7.8 Hz), 7.37 (2H, t, J=7.5 Hz), 7.12 (1H, t, J=7.4 Hz), 4.26 (2H, t, J=8.1 Hz), 3.78 (8H, dd, J=26.7, 4.5 Hz), 3.43-3.50 (2H, m).

ESI (LC-MS positive mode) m/z 479 ([M+H]$^+$).

Example 1-G-41

N-(3-dimethylamino-propyl)-3-(2-morpholin-4-yl-7-pyridin-4-yl-6,7-dihydro-5H-pyrrolo[2,3-d]pyrimidin-4-yl)-benzamide trifluoroacetic acid salt (G-41)

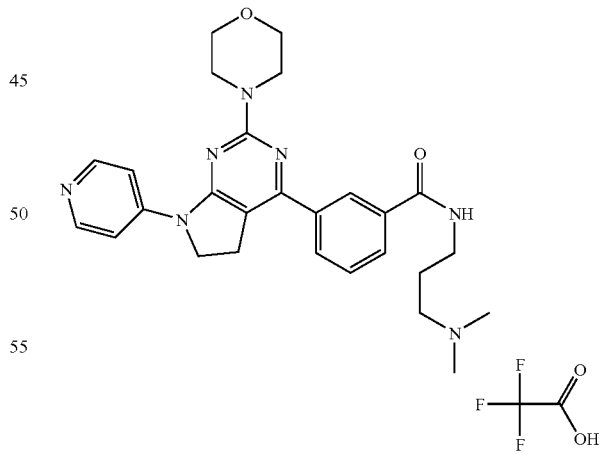

In the same manner as Example 1-G-05, from Compound G-04 prepared in Example 1-G-04 and N,N-dimethylpropan-1,3-diamine, the desired compound was obtained.

$^1$H-NMR (400 MHz, DMSO-$d_6$) δ (ppm): 9.51 (1H, brs), 8.79 (1H, t, J=5.7 Hz), 8.69 (2H, d, J=7.4 Hz), 8.41 (1H, s), 8.33 (2H, brs), 8.13 (1H, d, J=7.9 Hz), 7.99 (1H, d, J=8.1 Hz), 7.65 (1H, t, J=7.8 Hz), 4.27 (2H, t, J=8.1 Hz), 3.78 (8H, dd, 24.6, J=4.8 Hz), 3.43 (2H, t, J=8.1 Hz), 3.32-3.40 (2H, m), 3.04-3.18 (2H, m), 2.79 (6H, d, J=4.4 Hz), 1.75-2.02 (2H, m). ESI (LC-MS positive mode) m/z 488 ([M+H]⁺).

Example 1-G-42

N-carbamoylmethyl-3-(2-morpholin-4-yl-7-pyridin-3-yl-6,7-dihydro-5H-pyrrolo[2,3-d]pyrimidin-4-yl)-benzamide trifluoroacetic acid salt (G-42)

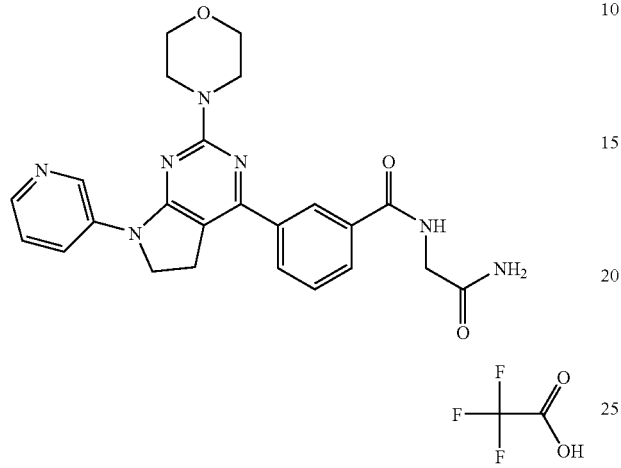

In the same manner as Example 1-G-05, from Compound G-03 prepared in Example 1-G-03 and 2-aminoacetamide, the desired compound was obtained.

¹H-NMR (400 MHz, DMSO-d₆) δ (ppm): 9.29 (1H, brs), 8.81 (1H, t, J=5.9 Hz), 8.48 (1H, d, J=10.1 Hz), 8.37-8.43 (2H, m), 8.11 (1H, d, J=7.9 Hz), 7.99 (1H, d, J=7.9 Hz), 7.71 (1H, dd, J=8.5, 5.0 Hz), 7.62 (1H, t, J=7.8 Hz), 7.42 (1H, s), 7.06 (1H, s), 4.18 (2H, t, J=8.1 Hz), 3.85 (2H, d, J=5.9 Hz), 3.75 (8H, dd, J=18.2, 5.0 Hz), 3.40 (2H, t, J=8.1 Hz).
ESI (LC-MS positive mode) m/z 460 ([M+H]⁺).

Example 1-G-43

3-(2-Morpholin-4-yl-7-pyridin-3-yl-6,7-dihydro-5H-pyrrolo[2,3-d]pyrimidin-4-yl)-N-phenyl-benzamide trifluoroacetic acid salt (G-43)

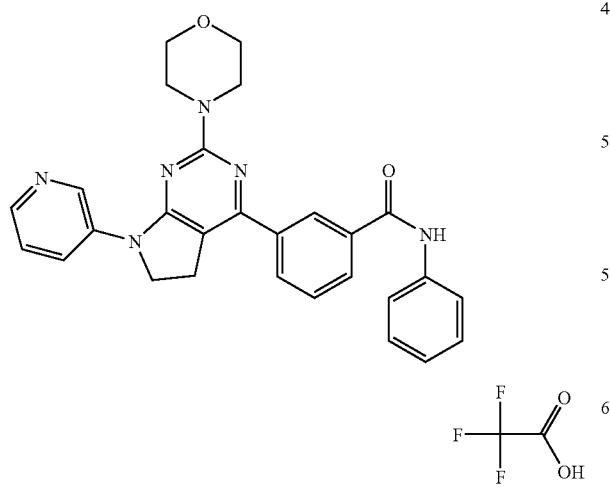

In the same manner as Example 1-G-05, from Compound G-03 prepared in Example 1-G-03 and aniline, the desired compound was obtained.

¹H-NMR (400 MHz, DMSO-d₆) δ (ppm): 9.28 (1H, brs), 8.43-8.52 (2H, m), 8.38 (1H, d, J=4.4 Hz), 8.16 (1H, d, J=8.1 Hz), 8.05 (1H, d, J=8.2 Hz), 7.79 (2H, d, J=7.5 Hz), 7.68 (2H, t, J=7.7 Hz), 7.37 (2H, t, J=7.5 Hz), 7.12 (1H, t, J=7.4 Hz), 4.19 (2H, t, J=8.1 Hz), 3.75 (8H, dd, J=20.3, 5.0 Hz), 3.43 (2H, t, J=8.2 Hz).
ESI (LC-MS positive mode) m/z 479 ([M+H]⁺).

Example 1-G-44

3-(2-Morpholin-4-yl-7-pyridin-3-yl-6,7-dihydro-5H-pyrrolo[2,3-d]pyrimidin-4-yl)-N-phenethyl-benzamide (G-44)

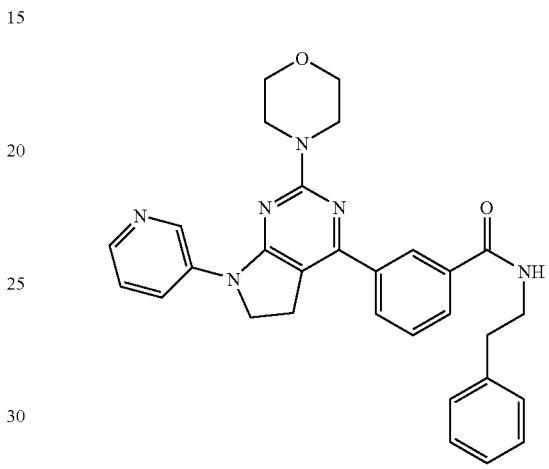

In the same manner as Example 1-G-05, from Compound G-03 prepared in Example 1-G-03 and phenethylamine, the desired compound was obtained.

¹H-NMR (400 MHz, DMSO-d₆) δ (ppm): 9.10 (1H, s), 8.68 (1H, t, J=5.5 Hz), 8.32 (1H, s), 8.25 (2H, d, J=5.3 Hz), 8.08 (1H, d, J=8.0 Hz), 7.89 (1H, d, J=7.8 Hz), 7.58 (1H, t, J=7.7 Hz), 7.43 (1H, dd, J=8.1, 5.1 Hz), 7.15-7.36 (5H, m), 4.14 (2H, t, J=8.2 Hz), 3.73 (8H, d, J=8.0 Hz), 3.46-3.57 (2H, m), 3.35-3.39 (2H, m), 2.87 (2H, t, J=7.2 Hz).
ESI (LC-MS positive mode) m/z 507 ([M+H]⁺).

Example 1-G-45

N-(2-methoxy-ethyl)-3-(2-morpholin-4-yl-7-pyridin-3-yl-6,7-dihydro-5H-pyrrolo[2,3-d]pyrimidin-4-yl)-benzamide (G-45)

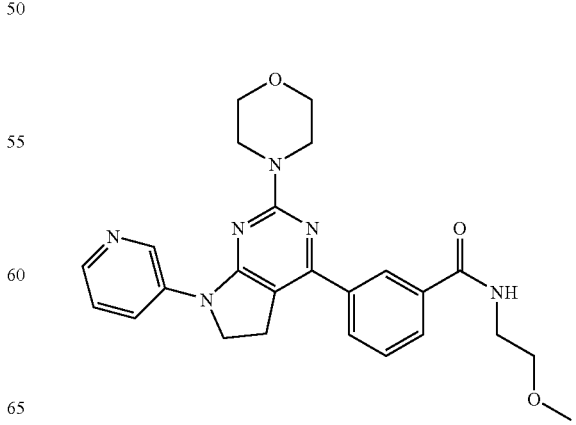

In the same manner as Example 1-G-05, using Compound G-03 prepared in Example 1-G-03 and 2-methoxyethylamine, the desired compound was obtained.

$^1$H-NMR (400 MHz, DMSO-d$_6$) δ (ppm): 9.09 (1H, brs), 8.58-8.73 (1H, m), 8.37 (1H, s), 8.25 (2H, d, J=4.9 Hz), 8.08 (1H, d, J=7.7 Hz), 7.93 (1H, d, J=7.7 Hz), 7.59 (1H, t, J=7.7 Hz), 7.42 (1H, dd, J=8.1, 4.8 Hz), 4.13 (2H, t, J=8.0 Hz), 3.73 (8H, d, J=8.9 Hz), 3.42-3.55 (4H, m), 3.36-3.40 (2H, m), 3.28 (3H, s).

ESI (LC-MS positive mode) m/z 461 ([M+H]$^+$).

Example 1-G-46

3-(2-Morpholin-4-yl-7-pyridin-4-yl-6,7-dihydro-5H-pyrrolo[2,3-d]pyrimidin-4-yl)-N-(2-piperidin-1-yl-ethyl)-benzamide (G-46)

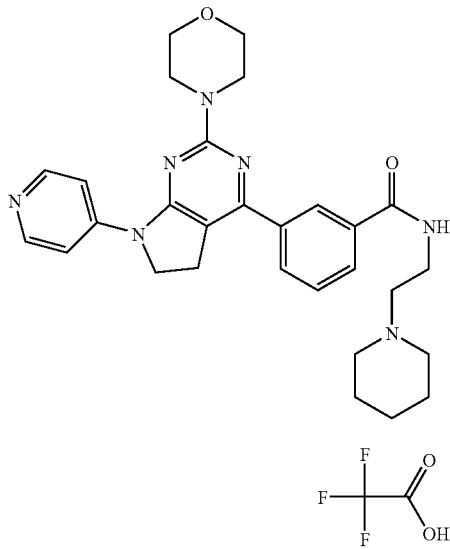

In the same manner as Example 1-G-05, from Compound G-04 prepared in Example 1-G-04 and 2-piperidin-1-yl-ethylamine, the desired compound was obtained.

$^1$H-NMR (400 MHz, DMSO-d$_6$) δ (ppm): 9.28 (1H, brs), 8.91 (1H, t, J=5.6 Hz), 8.70 (2H, d, J=7.5 Hz), 8.43 (1H, s), 8.34 (2H, brs), 8.15 (1H, d, J=8.1 Hz), 8.00 (1H, d, J=7.9 Hz), 7.67 (1H, t, J=7.8 Hz), 4.27 (2H, t, J=8.1 Hz), 3.78 (8H, dd, J=25.7, 4.1 Hz), 3.66 (2H, q, J=6.1 Hz), 3.56 (2H, d, J=11.5 Hz), 3.43 (2H, t, J=8.0 Hz), 3.27 (2H, d, J=3.5 Hz), 2.90-3.05 (2H, m), 1.84 (2H, d, J=14.1 Hz), 1.57-1.76 (3H, m), 1.39 (1H, q, J=12.3 Hz).

ESI (LC-MS positive mode) m/z 514 ([M+H]$^+$).

Example 1-G-47

N-(3-hydroxy-propyl)-3-(2-morpholin-4-yl-7-pyridin-3-yl-6,7-dihydro-5H-pyrrolo[2,3-d]pyrimidin-4-yl)-benzamide (G-47)

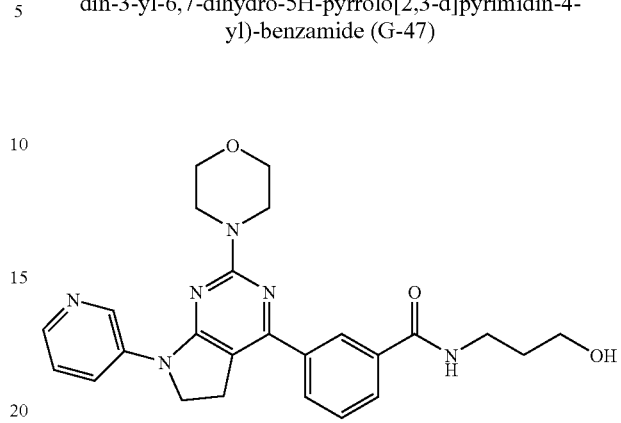

In the same manner as Example 1-G-05, from Compound G-03 prepared in Example 1-G-03 and 3-aminopropanol, the desired compound was obtained.

$^1$H-NMR (400 MHz, DMSO-d$_6$) δ (ppm): 9.10 (1H, s), 8.56 (1H, t, J=5.6 Hz), 8.35 (1H, s), 8.19-8.29 (2H, m), 8.07 (1H, d, J=8.1 Hz), 7.91 (1H, d, J=8.1 Hz), 7.58 (1H, t, J=7.8 Hz), 7.39-7.46 (1H, m), 4.51 (1H, t, J=5.2 Hz), 4.14 (2H, t, J=8.2 Hz), 3.65-3.81 (8H, m), 3.43-3.54 (2H, m), 3.35-3.41 (2H, m), 3.27-3.33 (2H, m), 1.62-1.80 (2H, m).

ESI (LC-MS positive mode) m/z 461 ([M+H]$^+$).

Example 1-G-48

N-(1-methyl-butyl)-3-(2-morpholin-4-yl-7-pyridin-3-yl-6,7-dihydro-5H-pyrrolo[2,3-d]pyrimidin-4-yl)-benzamide (G-48)

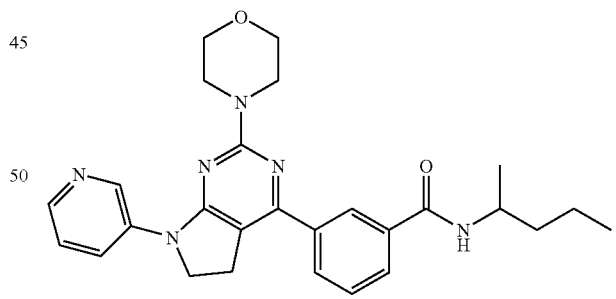

In the same manner as Example 1-G-05, from Compound G-03 prepared in Example 1-G-03 and 1-methylbutylamine, the desired compound was obtained.

$^1$H-NMR (400 MHz, DMSO-d$_6$) δ (ppm): 9.10 (1H, brs), 8.36 (1H, brs), 8.19-8.33 (3H, m), 8.07 (1H, d, J=8.5 Hz), 7.91 (1H, d, J=7.2 Hz), 7.58 (1H, t, J=8.0 Hz), 7.40-7.49 (1H, m), 4.11-4.26 (2H, m), 3.95-4.09 (1H, m), 3.73 (8H, d, J=12.1 Hz), 3.27 (2H, m), 1.25-1.67 (4H, m), 1.15 (3H, d, J=6.4 Hz), 0.89 (2H, t, J=7.0 Hz).

ESI (LC-MS positive mode) m/z 473 ([M+H]$^+$).

Example 1-G-49

N-(2-methoxy-ethyl)-N-methyl-3-(2-morpholin-4-yl-7-pyridin-3-yl-6,7-dihydro-5H-pyrrolo[2,3-d]pyrimidin-4-yl)-benzamide (G-49)

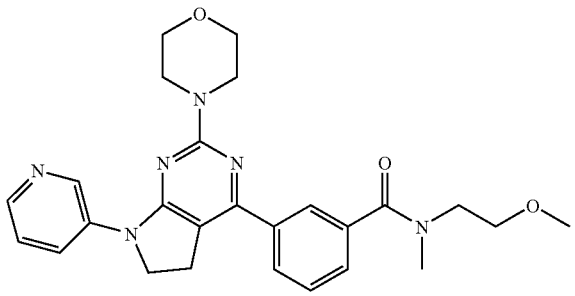

In the same manner as Example 1-G-05, from Compound G-03 prepared in Example 1-G-03 and (2-methoxyethyl)methylamine, the desired compound was obtained.

$^1$H-NMR (400 MHz, DMSO-$d_6$) δ (ppm): 9.09 (1H, s), 8.18-8.36 (2H, m), 7.98 (1H, brs), 7.91 (1H, s), 7.56 (1H, brs), 7.34-7.49 (2H, m), 4.13 (2H, t, J=8.1 Hz), 3.72 (8H, d, J=7.0 Hz), 3.62 (2H, d, J=19.7 Hz), 3.42 (3H, brs), 3.28-3.33 (2H, m), 3.18 (2H, brs), 2.99 (3H, d, J=10.3 Hz).

ESI (LC-MS positive mode) m/z 475 ([M+H]$^+$).

Example 1-G-50 (4-Methyl-piperazin-1-yl)-[3-(2-morpholin-4-yl-7-pyridin-3-yl-6,7-dihydro-5H-pyrrolo[2,3-d]pyrimidin-4-yl)-phenyl]-methanone (G-50)

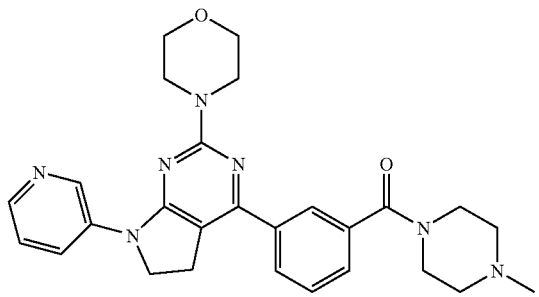

In the same manner as Example 1-G-05, from Compound G-03 prepared in Example 1-G-03 and N-methylpiperazine, the desired compound was obtained.

$^1$H-NMR (400 MHz, DMSO-$d_6$) δ (ppm): 9.09 (1H, s), 8.25 (2H, d, 5.1 Hz), 7.99 (1H, d, J=8.0 Hz), 7.92 (1H, s), 7.58 (1H, t, J=7.7 Hz), 7.48 (1H, d, J=7.6 Hz), 7.42 (1H, dd, J=8.3, 4.8 Hz), 4.13 (2H, t, J=8.1 Hz), 3.72 (8H, d, J=7.0 Hz), 3.65 (2H, brs), 3.36-3.47 (4H, m), 2.36 (4H, d, J=23.3 Hz), 2.22 (3H, s).

ESI (LC-MS positive mode) m/z 486 ([M+H]$^+$).

Example 1-G-51

(4-Hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone (G-51)

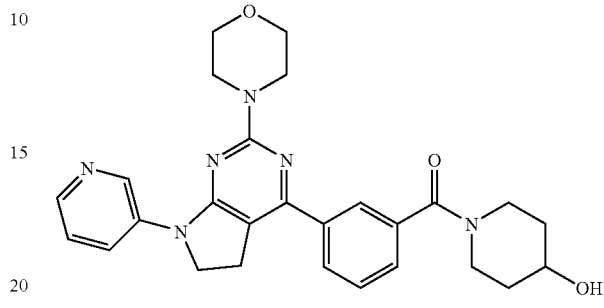

In the same manner as Example 1-G-05, from Compound G-03 prepared in Example 1-G-03 and 4-hydroxypiperidine, the desired compound was obtained.

$^1$H-NMR (400 MHz, DMSO-$d_6$) δ (ppm): 9.09 (1H, s), 8.20-8.32 (2H, m) 7.99 (1H, d, J=8.0 Hz), 7.90 (1H, s), 7.57 (1H, t, 7.7 Hz), 7.36-7.51 (2H, m), 4.82 (1H, d, J=4.0 Hz), 4.13 (2H, t, J=8.2 Hz), 4.04 (1H, brs), 3.72 (9H, d, J=7.3 Hz), 3.53 (1H, brs), 3.36-3.41 (2H, m), 3.20 (2H, brs), 1.77 (2H, d, J=34.4 Hz), 1.38 (2H, brs).

ESI (LC-MS positive mode) m/z 487 ([M+H]$^+$).

Example 1-G-52

N-(3,3-dimethyl-butyl)-3-(2-morpholin-4-yl-7-pyridin-3-yl-6,7-dihydro-5H-pyrrolo[2,3-d]pyrimidin-4-yl)-benzamide (G-52)

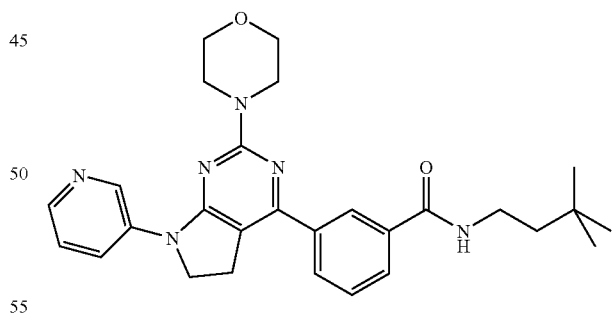

In the same manner as Example 1-G-05, from Compound G-03 prepared in Example 1-G-03 and 3,3-dimethylbutylamine, the desired compound was obtained.

$^1$H-NMR (400 MHz, DMSO-$d_6$) δ (ppm): 9.10 (1H, s), 8.53 (1H, t, J=5.5 Hz), 8.35 (1H, s), 8.22-8.28 (2H, m), 8.07 (1H, d, J=8.0 Hz), 7.90 (1H, d, J=8.0 Hz), 7.58 (1H, t, J=7.8 Hz), 7.43 (1H, dd, J=8.1, 4.9 Hz), 4.14 (2H, t, J=8.2 Hz), 3.73 (8H, d, J=8.5 Hz), 3.35-3.43 (2H, m), 3.26-3.33 (2H, m), 1.35-1.56 (2H, m), 0.94 (9H, s).

ESI (LC-MS positive mode) m/z 487 ([M+H]$^+$).

Example 1-G-53

N-cyclopropylmethyl-3-(2-morpholin-4-yl-7-pyridin-3-yl-6,7-dihydro-5H-pyrrolo[2,3-d]pyrimidin-4-yl)-N-propyl-benzamide (G-53)

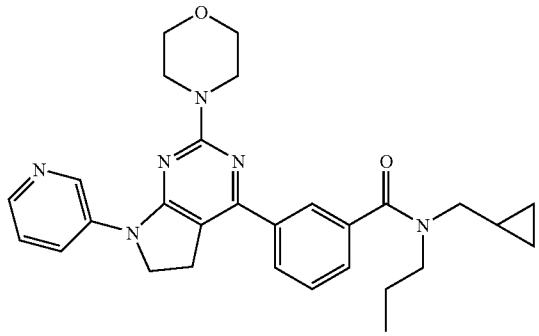

In the same manner as Example 1-G-05, from Compound G-03 prepared in Example 1-G-03 and cyclopropylmethyl-propylamine, the desired compound was obtained.

$^1$H-NMR (400 MHz, DMSO-$d_6$) δ (ppm): 9.09 (1H, s), 8.18-8.35 (2H, m), 7.97 (1H, d, J=7.9 Hz), 7.87 (1H, s), 7.57 (1H, t, J=7.7 Hz), 7.31-7.46 (2H, m), 4.13 (2H, t, J=8.1 Hz), 3.71 (8H, d, J=7.0 Hz), 3.50 (1H, brs), 3.34-3.41 (3H, m), 3.24 (1H, brs), 3.10 (1H, brs), 1.61 (2H, d, J=43.9 Hz), 0.62-1.21 (4H, m), 0.48 (2H, d, J=19.4 Hz), 0.31 (1H, brs), 0.06 (1H, brs).

ESI (LC-MS positive mode) m/z 499 ([M+H]$^+$).

Example 1-G-54

N—((S)-2-hydroxy-1-phenyl-ethyl)-3-(2-morpholin-4-yl-7-pyridin-3-yl-6,7-dihydro-5H-pyrrolo[2,3-d]pyrimidin-4-yl)-benzamide (G-54)

Chiral

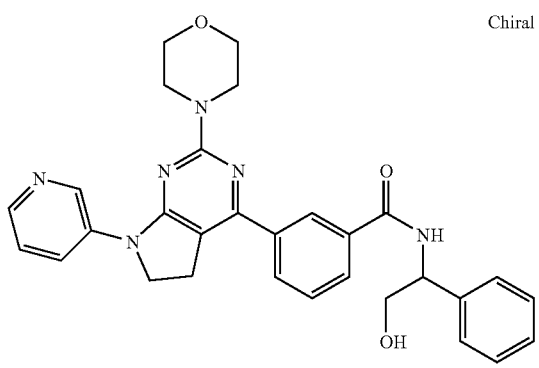

In the same manner as Example 1-G-05, from Compound G-03 prepared in Example 1-G-03 and (S)-2-amino-2-phenylethanol, the desired compound was obtained.

$^1$H-NMR (400 MHz, DMSO-$d_6$) δ (ppm): 9.10 (1H, d, J=2.5 Hz), 8.85 (1H, d, J=8.1 Hz), 8.41 (1H, s), 8.22-8.30 (2H, m), 8.09 (1H, d, J=8.0 Hz), 8.01 (1H, d, J=7.9 Hz), 7.61 (1H, t, J=7.8 Hz), 7.38-7.47 (3H, m), 7.33 (2H, t, J=7.5 Hz), 7.24 (1H, t, J=7.3 Hz), 5.04-5.16 (1H, m), 4.96 (1H, t, J=5.8 Hz), 4.14 (2H, t, J=8.2 Hz), 3.73 (8H, dd, J=14.2, 4.8 Hz), 3.63-3.69 (2H, m), 3.35-3.40 (2H, m).

ESI (LC-MS positive mode) m/z 523 ([M+H]$^+$).

Example 1-G-55

N-(3-morpholin-4-yl-propyl)-3-(2-morpholin-4-yl-7-pyridin-3-yl-6,7-dihydro-5H-pyrrolo[2,3-d]pyrimidin-4-yl)-benzamide (G-55)

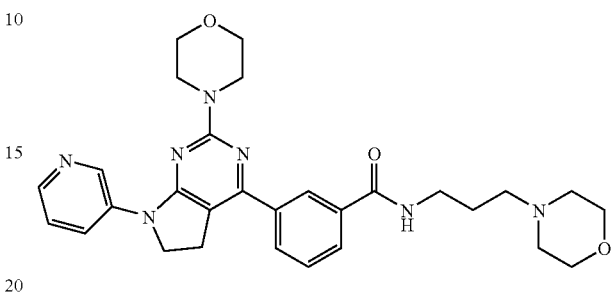

In the same manner as Example 1-G-05, from Compound G-03 prepared in Example 1-G-03 and 3-morpholin-4-yl-propylamine, the desired compound was obtained.

$^1$H-NMR (400 MHz, DMSO-$d_6$) δ (ppm): 9.09 (1H, d, J=2.5 Hz), 8.61 (1H, t, J=5.5 Hz), 8.35 (1H, s), 8.21-8.30 (2H, m), 8.07 (1H, d, J=7.9 Hz), 7.90 (1H, d, J=7.9 Hz), 7.59 (1H, t, J=7.8 Hz), 7.43 (1H, dd, J=8.1, 4.9 Hz), 4.14 (2H, t, J=8.2 Hz), 3.73 (8H, d, J=9.0 Hz), 3.57 (4H, t, J=4.6 Hz), 3.35-3.41 (2H, m), 3.28-3.32 (2H, m), 2.35 (6H, t, J=7.0 Hz), 1.62-1.79 (2H, m).

ESI (LC-MS positive mode) m/z 530 ([M+H]$^+$).

Example 1-G-56

N-(3-dimethylamino-propyl)-3-(2-morpholin-4-yl-7-pyridin-3-yl-6,7-dihydro-5H-pyrrolo[2,3-d]pyrimidin-4-yl)-benzamide (G-56)

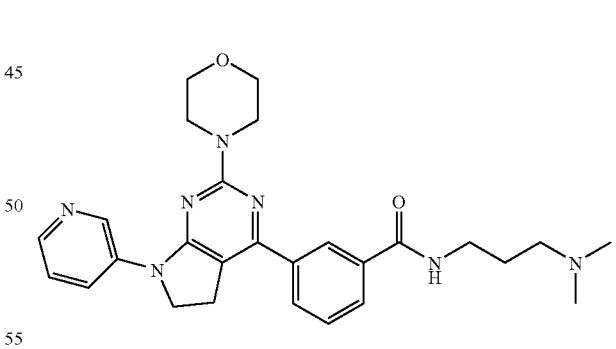

In the same manner as Example 1-G-05, from Compound G-03 prepared in Example 1-G-03 and N,N-dimethyl-propan-1,3-diamine, the desired compound was obtained.

$^1$H-NMR (250 MHz, DMSO-$d_6$) δ (ppm): 9.08 (1H, d, J=2.9 Hz), 8.71-8.79 (1H, m), 8.37 (1H, s), 8.18-8.30 (2H, m), 8.07 (1H, d, J=7.9 Hz), 7.94 (1H, d, J=7.8 Hz), 7.59 (1H, t, J=7.7 Hz), 7.42 (1H, dd, J=8.2, 5.0 Hz), 4.13 (2H, t, J=8.1 Hz), 3.72 (8H, d, J=3.3 Hz), 3.36 (4H, t, J=7.4 Hz), 2.77-2.90 (2H, m), 2.56 (6H, s), 1.76-1.96 (2H, m).

ESI (LC-MS positive mode) m/z 488 ([M+H]$^+$).

Example 1-G-57

3-(2-Morpholin-4-yl-7-pyridin-3-yl-6,7-dihydro-5H-pyrrolo[2,3-d]pyrimidin-4-yl)-N-pyridin-4-ylmethyl-benzamide (G-57)

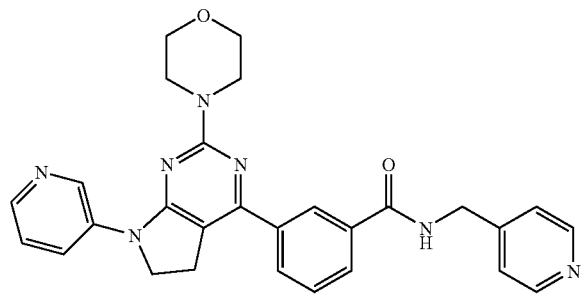

In the same manner as Example 1-G-05, from Compound G-03 prepared in Example 1-G-03 and 4-aminomethylpyridine, the desired compound was obtained.

$^1$H-NMR (250 MHz, DMSO-d$_6$) δ (ppm): 9.27 (1H, t, J=5.8 Hz), 9.10 (1H, s), 8.51 (2H, d, J=5.7 Hz), 8.43 (1H, s), 8.25 (2H, d, J=5.4 Hz), 8.11 (1H, d, J=7.8 Hz), 8.00 (1H, d, J=7.8 Hz), 7.63 (1H, t, 7.8 Hz), 7.42 (1H, dd, J=8.1, 5.0 Hz), 7.33 (2H, d, J=5.6 Hz), 4.53 (2H, d, J=5.7 Hz), 4.07-4.22 (2H, m), 3.72 (8H, brs), 3.40 (2H, brs).

ESI (LC-MS positive mode) m/z 494 ([M+H]$^+$).

Example 1-G-58

N-cyclohexylmethyl-3-(2-morpholin-4-yl-7-pyridin-3-yl-6,7-dihydro-5H-pyrrolo[2,3-d]pyrimidin-4-yl)-benzamide (G-58)

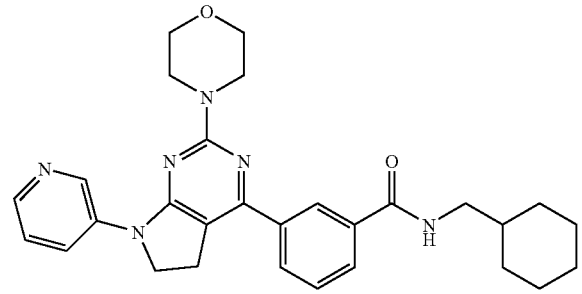

In the same manner as Example 1-G-05, from Compound G-03 prepared in Example 1-G-03 and C-cyclohexylmethylamine, the desired compound was obtained.

$^1$H-NMR (400 MHz, DMSO-d$_6$) δ (ppm): 9.09 (1H, d, J=2.4 Hz), 8.56 (1H, t, J=5.8 Hz), 8.37 (1H, s), 8.21-8.29 (2H, m), 8.07 (1H, d, J=8.0 Hz), 7.91 (1H, d, J=7.9 Hz), 7.58 (1H, t, J=7.8 Hz), 7.43 (1H, dd, J=8.1, 5.0 Hz), 4.08-4.20 (2H, m), 3.73 (8H, dd, J=14.5, 4.8 Hz), 3.16 (2H, d, J=5.2 Hz), 3.13 (2H, t, J=6.4 Hz), 1.70 (4H, t, J=13.0 Hz), 1.49-1.63 (2H, m), 1.06-1.30 (3H, m), 0.85-0.99 (2H, m).

ESI (LC-MS positive mode) m/z 499 ([M+H]$^+$).

Example 1-G-59

N-(2-diethylamino-ethyl)-3-(2-morpholin-4-yl-7-pyridin-3-yl-6,7-dihydro-5H-pyrrolo[2,3-d]pyrimidin-4-yl)-benzamide (G-59)

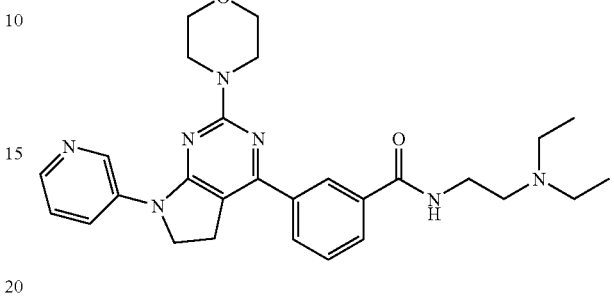

In the same manner as Example 1-G-05, from Compound G-03 prepared in Example 1-G-03 and N,N-diethyl ethylenediamine, the desired compound was obtained.

$^1$H-NMR (400 MHz, DMSO-d$_6$) δ (ppm): 9.09 (1H, d, J=2.7 Hz), 8.51 (1H, t, 5.6 Hz), 8.35 (1H, s), 8.20-8.27 (2H, m), 8.06 (1H, d, J=8.1 Hz), 7.90 (1H, d, J=7.9 Hz), 7.58 (1H, t, J=7.8 Hz), 7.38-7.46 (1H, m), 4.13 (2H, t, J=8.2 Hz), 3.66-3.79 (8H, m), 3.28-3.44 (6H, m), 2.51-2.66 (4H, m), 0.98 (6H, t, J=7.0 Hz).

ESI (LC-MS positive mode) m/z 502 ([M+H]$^+$).

Example 1-G-60

N-isopropyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-60)

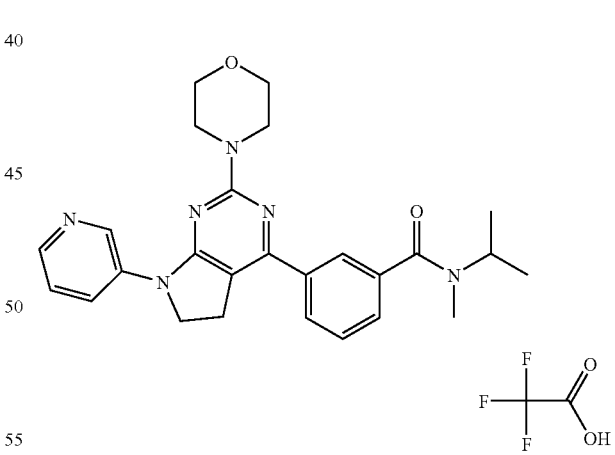

In the same manner as Example 1-G-05, from Compound G-03 prepared in Example 1-G-03 and isopropylmethylamine, the desired compound was obtained.

$^1$H-NMR (400 MHz, DMSO-d$_6$) δ (ppm): 9.45 (1H, d, J=2.4 Hz), 8.65 (1H, d, J=8.6 Hz), 8.50 (1H, d, J=5.3 Hz), 7.84-8.03 (3H, m), 7.60 (1H, t, J=7.7 Hz), 7.45-7.52 (1H, m), 4.19 (2H, t, J=8.1 Hz), 3.87 (1H, brs), 3.75 (8H, dd, J=18.6, 5.0 Hz), 3.40 (2H, t, J=8.1 Hz), 2.72-2.93 (3H, m), 1.14 (6H, brs).

ESI (LC-MS positive mode) m/z 459 ([M+H]$^+$).

Example 1-G-61

N-isobutyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-61)

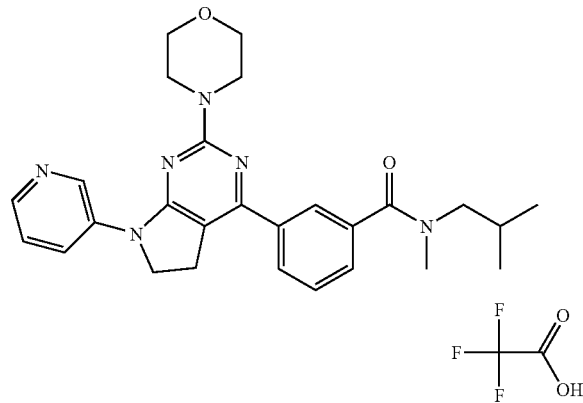

In the same manner as Example 1-G-05, from Compound G-03 prepared in Example 1-G-03 and isobutylmethylamine, the desired compound was obtained.

$^1$H-NMR (400 MHz, DMSO-d$_6$) δ (ppm): 9.47 (1H, d, J=2.6 Hz), 8.65 (1H, d, J=8.6 Hz), 8.50 (1H, d, J=5.3 Hz), 7.84-8.05 (3H, m), 7.59 (1H, t, J=7.6 Hz), 7.42-7.54 (1H, m), 4.19 (2H, t, J=8.1 Hz), 3.74 (8H, dd, J=17.8, 4.9 Hz), 3.39 (2H, t, J=8.0 Hz), 3.32 (1H, d, J=7.5 Hz), 3.09 (1H, d, J=7.1 Hz), 2.94 (3H, d J=25.1 Hz), 1.86-2.14 (1H, m), 0.82 (6H, m).

ESI (LC-MS positive mode) m/z 473 ([M+H]$^+$).

Example 1-G-62

N-ethyl-N-(2-hydroxy-ethyl)-3-(2-morpholin-4-yl-7-pyridin-3-yl-6,7-dihydro-5H-pyrrolo[2,3-d]pyrimidin-4-yl)-benzamide (G-62)

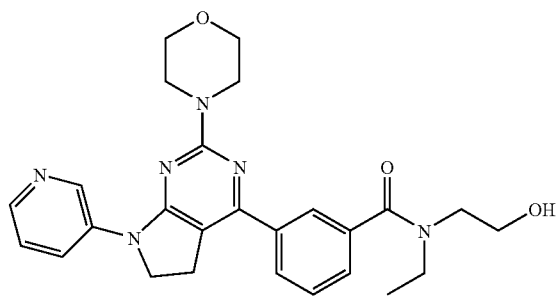

In the same manner as Example 1-G-05, from Compound G-03 prepared in Example 1-G-03 and 2-ethylaminoethanol, the desired compound was obtained.

$^1$H-NMR (400 MHz, DMSO-d$_6$) δ (ppm): 9.09 (1H, s), 8.19-8.31 (2H, m), 7.96 (1H, d, J=7.9 Hz), 7.90 (1H, brs), 7.55 (1H, brs), 7.39-7.49 (2H, m), 4.82 (1H, t, J=5.1 Hz), 4.12 (2H, t, J=8.1 Hz), 3.67-3.79 (8H, m), 3.44-3.65 (4H, m), 3.24-3.33 (4H, m), 1.03-1.22 (3H, m).

ESI (LC-MS positive mode) m/z 475 ([M+H]$^+$).

Example 1-G-63

(3-Hydroxy-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-63)

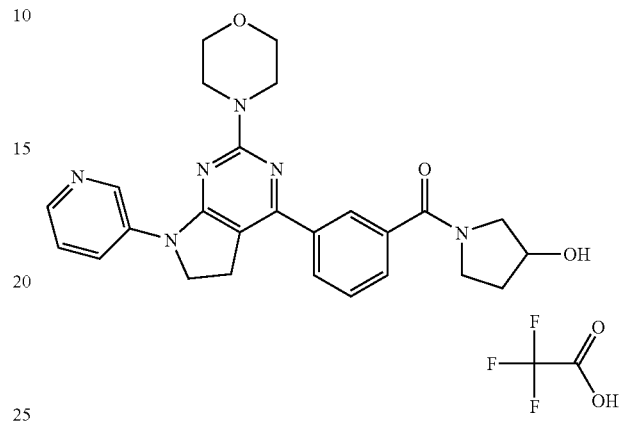

In the same manner as Example 1-G-05, from Compound G-03 prepared in Example 1-G-03 and 3-hydroxypyrrolidine, the desired compound was obtained.

$^1$H-NMR (400 MHz, DMSO-d$_6$) δ (ppm): 9.48 (1H, brs), 8.64 (1H, d, J=8.8 Hz), 8.50 (1H, d, J=5.1 Hz), 8.07-7.99 (2H, m), 7.94 (1H, dd, J=8.4, 5.5 Hz), 7.66-7.53 (2H, m), 4.29-4.14 (3H, m), 3.74 (8H, dd, J=17.93, 4.9 Hz), 3.66-3.52 (3H, m), 3.48-3.35 (3H, m), 2.05-1.73 (2H, m).

ESI (LC-MS positive mode) m/z 473 ([M+H]$^+$).

Example 1-G-64

N-indan-2-yl-3-(2-morpholin-4-yl-7-pyridin-3-yl-6,7-dihydro-5H-pyrrolo[2,3-d]pyrimidin-4-yl)-benzamide (G-64)

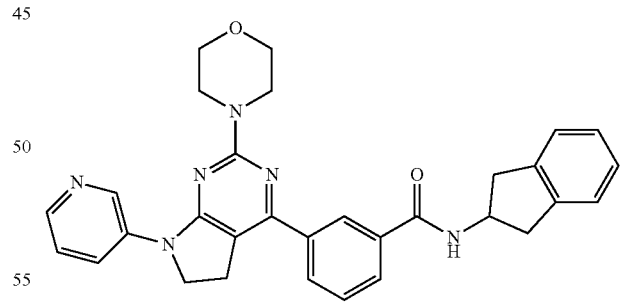

In the same manner as Example 1-G-05, from Compound G-03 prepared in Example 1-G-03 and indan-2-ylamine, the desired compound was obtained.

$^1$H-NMR (250 MHz, DMSO-d$_6$) δ (ppm): 9.10 (1H, brs), 8.79 (1H, d, J=6.6 Hz), 8.38 (1H, s), 8.26 (2H, d, J=5.5 Hz), 8.08 (1H, d, J=8.0 Hz), 7.94 (1H, d, J=7.4 Hz), 7.58 (1H, t, J=7.8 Hz), 7.43 (1H, dd, J=8.5, 4.3 Hz), 7.08-7.29 (4H, m), 4.62-4.91 (1H, m), 3.93-4.29 (4H, m), 3.73 (8H, brs), 3.20-3.30 (2H, m), 2.98 (2H, dd, J=15.9, 6.4 Hz).

ESI (LC-MS positive mode) m/z 519 ([M+H]$^+$).

Example 1-G-65

Azetidine-1-yl-[3-(2-morpholin-4-yl-7-pyridin-3-yl-6,7-dihydro-5H-pyrrolo[2,3-d]pyrimidin-4-yl)-phenyl]-methanone (G-65)

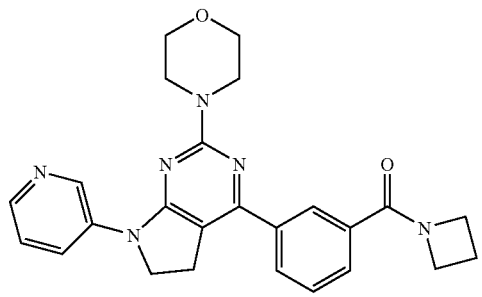

In the same manner as Example 1-G-05, from Compound G-03 prepared in Example 1-G-03 and azetidine, the desired compound was obtained.

$^1$H-NMR (400 MHz, DMSO-d$_6$) δ (ppm): 9.09 (1H, d, J=2.3 Hz), 8.21-8.30 (2H, m), 8.13 (1H, s), 8.06 (1H, d, J=7.9 Hz), 7.67-7.74 (1H, m), 7.58 (1H, t, J=7.7 Hz), 7.42 (1H, dd, J=8.6, 4.6 Hz), 4.34 (2H, t, J=7.6 Hz), 4.01-4.18 (4H, m), 3.72 (8H, d, J=6.3 Hz), 3.36-3.40 (2H, m), 2.23-2.36 (2H, m).

ESI (LC-MS positive mode) m/z 443 ([M+H]$^+$).

Example 1-G-66

(4-Ethyl-piperazin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-66)

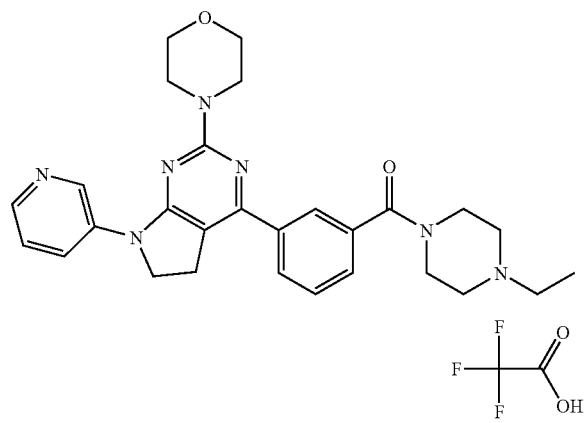

In the same manner as Example 1-G-05, from Compound G-03 prepared in Example 1-G-03 and N-ethylpiperazine, the desired compound was obtained.

$^1$H-NMR (400 MHz, CD$_3$OD) δ (ppm): 9.16 (1H, brs), 8.16 (2H, brs), 7.98 (2H, brs), 7.31-7.64 (3H, m), 4.03 (2H, brs), 3.75 (8H, brs), 3.53 (2H, brs), 3.28 (4H, brs), 2.62 (4H, brs), 2.51 (2H, q, J=7.0 Hz), 1.14 (3H, t, J=7.2 Hz).

ESI (LC-MS positive mode) m/z 500 ([M+H]$^+$).

Example 1-G-67

N,N-diethyl-3-(2-morpholin-4-yl-7-pyridin-3-yl-6,7-dihydro-5H-pyrrolo[2,3-d]pyrimidin-4-yl)-benzamide (G-67)

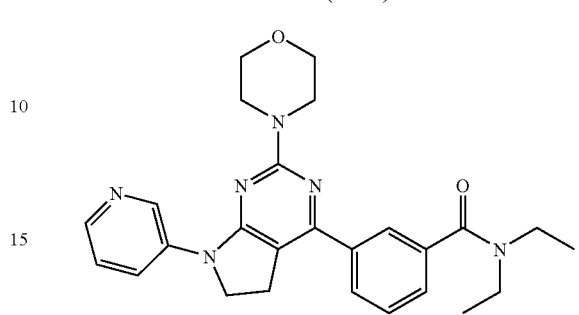

In the same manner as Example 1-G-05, from Compound G-03 prepared in Example 1-G-03 and diethylamine, the desired compound was obtained.

$^1$H-NMR (400 MHz, DMSO-d$_6$) δ (ppm): 9.09 (1H, d, J=2.2 Hz), 8.18-8.31 (2H, m), 7.97 (1H, d, J=8.0 Hz), 7.87 (1H, s), 7.57 (1H, t, J=7.7 Hz), 7.37-7.47 (2H, m), 4.12 (2H, t, J=8.2 Hz), 3.71 (8H, d, J=7.4 Hz), 3.46 (2H, brs), 3.35-3.38 (2H, m), 3.23 (2H, brs), 1.13 (6H, d, J=24.0 Hz).

ESI (LC-MS positive mode) m/z 459 ([M+H]$^+$).

Example 1-G-68

((R)-2-hydroxymethyl-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-68)

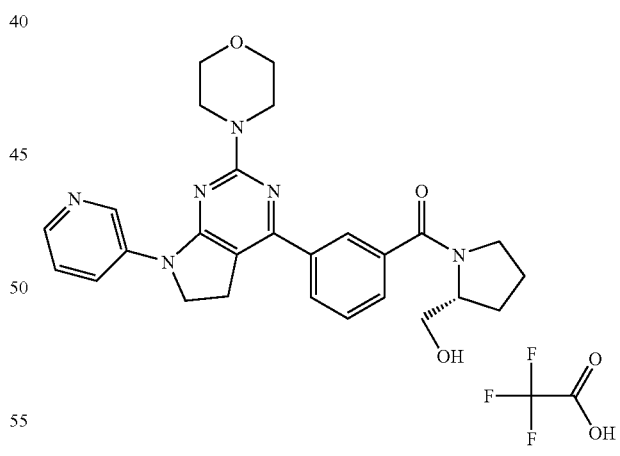

In the same manner as Example 1-G-05, from Compound G-03 prepared in Example 1-G-03 and (R)-1-pyrrolidin-2-yl-methanol, the desired compound was obtained.

$^1$H-NMR (400 MHz, DMSO-d$_6$) δ (ppm): 9.46 (1H, s), 8.63 (1H, d, J=8.9 Hz), 8.50 (1H, d, J=5.1 Hz), 7.96-8.07 (2H, m), 7.92 (1H, dd, J=8.7, 5.3 Hz), 7.55-7.68 (2H, m), 4.19 (2H, t, 8.1 Hz), 3.75 (8H, dd, J=18.2, 4.7 Hz), 3.52-3.66 (2H, m), 3.31-3.50 (4H, m), 1.79-2.07 (4H, m), 1.59-1.77 (1H, m).

ESI (LC-MS positive mode) m/z 487 ([M+H]$^+$).

Example 1-G-69

[3-(2-Morpholin-4-yl-7-pyridin-3-yl-6,7-dihydro-5H-pyrrolo[2,3-d]pyrimidin-4-yl)-phenyl]-(4-pyrrolidin-1-yl-piperidin-1-yl)-methanone (G-69)

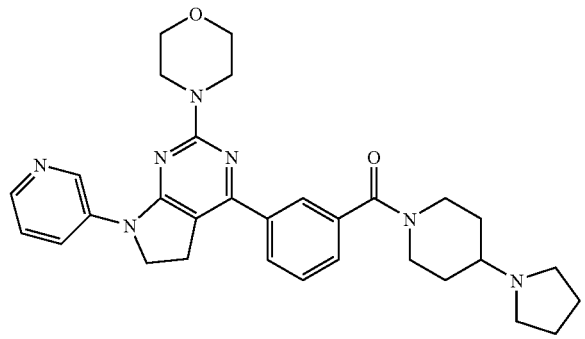

In the same manner as Example 1-G-05, from Compound G-03 prepared in Example 1-G-03 and 4-pyrrolidin-1-yl-piperidine, the desired compound was obtained.

$^1$H-NMR (400 MHz, DMSO-d$_6$) δ (ppm): 9.09 (1H, s), 8.19-8.33 (2H, m), 7.98 (1H, d, J=8.0 Hz), 7.91 (1H, s), 7.57 (1H, t, J=7.7 Hz), 7.47 (1H, d, J=7.6 Hz), 7.42 (1H, dd, J=8.3, 4.8 Hz), 4.30 (1H, brs), 4.13 (2H, t, J=8.1 Hz), 3.72 (8H, d, J=7.7 Hz), 3.60 (2H, brs), 3.24-3.43 (4H, m), 3.05 (2H, d, J=41.7 Hz), 2.50 (1H, brs), 2.28 (1H, brs), 1.87 (2H, d, J=44.0 Hz), 1.68 (4H, brs), 1.40 (2H, brs).

ESI (LC-MS positive mode) m/z 540 ([M+H]$^+$).

Example 1-G-70

(3-Hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-70)

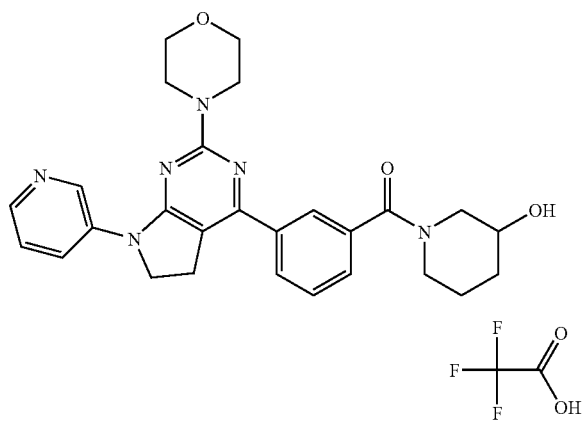

In the same manner as Example 1-G-05, from Compound G-03 prepared in Example 1-G-03 and 3-hydroxypiperidine, the desired compound was obtained.

$^1$H-NMR (400 MHz, DMSO-d$_6$) δ (ppm): 9.42 (1H, s), 8.60 (1H, d, J=7.8 Hz), 8.47 (1H, d, J=5.1 Hz), 8.00 (1H, d, J=8.0 Hz), 7.92 (1H, brs), 7.87 (1H, d, J=13.9 Hz), 7.59 (1H, t, J=7.7 Hz), 7.52 (1H, brs), 4.18 (2H, t, J=8.1 Hz), 3.83 (1H, brs), 3.74 (8H, dd, J=18.0, 5.0 Hz), 3.54 (2H, brs), 3.39 (2H, t, J=8.1 Hz), 2.84-3.32 (2H, m), 1.60-1.93 (2H, m), 1.45 (2H, brs).

ESI (LC-MS positive mode) m/z 487 ([M+H]$^+$).

Example 1-G-71

N-cyclopentyl-3-(2-morpholin-4-yl-7-pyridin-3-yl-6,7-dihydro-5H-pyrrolo[2,3-d]pyrimidin-4-yl)-benzamide (G-71)

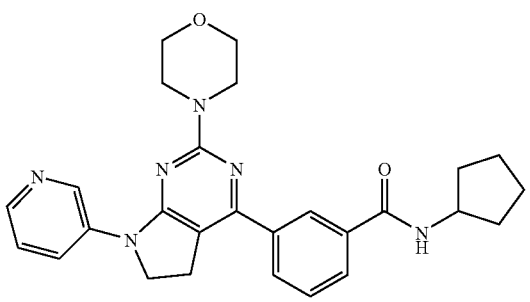

In the same manner as Example 1-G-05, from Compound G-03 prepared in Example 1-G-03 and cyclopentylamine, the desired compound was obtained.

$^1$H-NMR (250 MHz, DMSO-d$_6$) δ (ppm): 9.10 (1H, d, J=1.5 Hz), 8.42 (1H, d, J=7.0 Hz), 8.34 (1H, s), 8.26 (2H, d, J=5.4 Hz), 8.07 (1H, d, J=8.7 Hz), 7.91 (1H, d, J=7.8 Hz), 7.58 (1H, t, J=7.7 Hz), 7.43 (1H, dd, J=8.0, 5.2 Hz), 4.15 (2H, t, J=7.2 Hz), 4.06 (1H, s), 3.73 (8H, d, J=3.7 Hz), 3.37-3.43 (2H, m), 1.90 (2H, brs), 1.71 (2H, brs), 1.54 (4H, brs).

ESI (LC-MS positive mode) m/z 471 ([M+H]$^+$).

Example 1-G-72

(2,5-Dihydro-pyrrol-1-yl)-[3-(2-morpholin-4-yl-7-pyridin-3-yl-6,7-dihydro-5H-pyrrolo[2,3-d]pyrimidin-4-yl)-phenyl]-methanone (G-72)

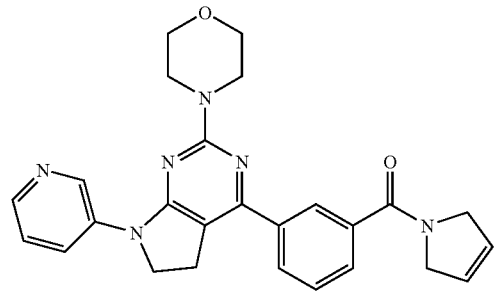

In the same manner as Example 1-G-05, from Compound G-03 prepared in Example 1-G-03 and 2,5-dihydro-1H-pyrrole, the desired compound was obtained.

$^1$H-NMR (400 MHz, DMSO-d$_6$) δ (ppm): 9.09 (1H, s), 8.19-8.32 (2H, m), 7.98-8.10 (2H, m), 7.62-7.70 (1H, m), 7.58 (1H, t, J=7.6 Hz), 7.42 (1H, dd, J=8.3, 4.8 Hz), 5.94-6.04 (1H, m), 4.32 (2H, brs), 4.24 (2H, brs), 4.12 (2H, t, J=8.2 Hz), 3.72 (8H, d, J=7.1 Hz), 3.36-3.42 (2H, m).

ESI (LC-MS positive mode) m/z 455 ([M+H]$^+$).

Example 1-G-73

[3-(2-Morpholin-4-yl-7-pyridin-3-yl-6,7-dihydro-5H-pyrrolo[2,3-d]pyrimidin-4-yl)-phenyl]-(4-phenyl-piperazin-1-yl)-methanone (G-73)

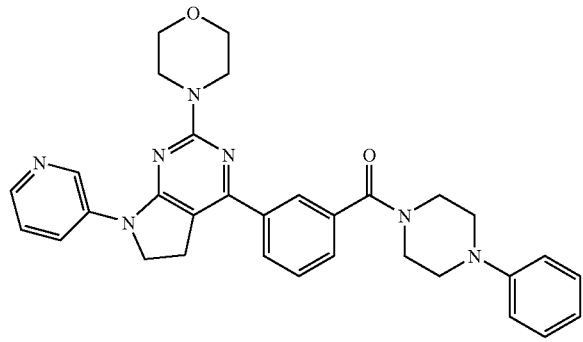

In the same manner as Example 1-G-05, from Compound G-03 prepared in Example 1-G-03 and N-phenylpiperazine, the desired compound was obtained.

$^1$H-NMR (400 MHz, DMSO-$d_6$) δ (ppm): 9.08 (1H, s), 8.18-8.33 (2H, m), 7.95-8.04 (2H, m), 7.51-7.65 (2H, m), 7.41 (1H, dd, J=8.3, 4.7 Hz), 7.23 (2H, t, J=8.0 Hz), 6.96 (2H, d, J=8.0 Hz), 6.81 (1H, t, J=7.3 Hz), 4.11 (2H, t, J=8.1 Hz), 3.79 (2H, brs), 3.70 (8H, dd, J=16.0, 4.7 Hz), 3.53 (2H, brs), 3.29-3.36 (2H, m), 3.11-3.25 (4H, m).

ESI (LC-MS positive mode) m/z 548 ([M+H]$^+$).

Example 1-G-74

N-cyclohexyl-3-(2-morpholin-4-yl-7-pyridin-3-yl-6,7-dihydro-5H-pyrrolo[2,3-d]pyrimidin-4-yl)-benzamide (G-74)

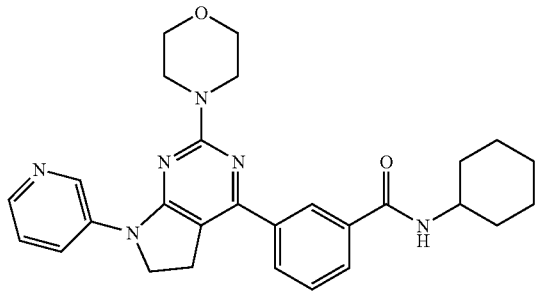

In the same manner as Example 1-G-05, from Compound G-03 prepared in Example 1-G-03 and cyclohexylamine, the desired compound was obtained.

$^1$H-NMR (250 MHz, DMSO-$d_6$) δ (ppm): 9.09 (1H, d, J=1.8 Hz), 8.30-8.44 (2H, m), 8.26 (2H, d, J=5.3 Hz), 8.05 (1H, d, J=0.7 Hz), 7.91 (1H, d, J=8.1 Hz), 7.57 (1H, t, J=7.7 Hz), 7.43 (1H, dd, J=8.3, 5.1 Hz), 4.14 (2H, t, J=8.1 Hz), 3.73 (9H, d, J=3.3 Hz), 3.36-3.43 (2H, m), 1.48-1.93 (5H, m), 0.99-1.45 (5H, m).

ESI (LC-MS positive mode) m/z 485 ([M+H]$^+$).

Example 1-G-75 (2,6-Dimethyl-morpholin-4-yl)-[3-(2-morpholin-4-yl-7-pyridin-3-yl-6,7-dihydro-5H-pyrrolo[2,3-d]pyrimidin-4-yl)-phenyl]-methanone (G-75)

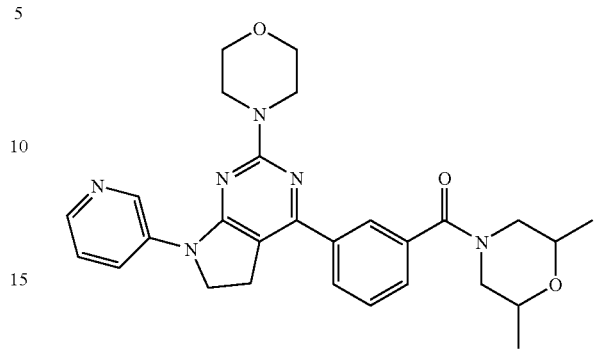

In the same manner as Example 1-G-05, from Compound G-03 prepared in Example 1-G-03 and 2,6-dimethylmorpholine, the desired compound was obtained.

$^1$H-NMR (400 MHz, DMSO-$d_6$) δ (ppm): 9.10 (1H, s), 8.18-8.30 (2H, m), 8.01 (1H, d, J=7.9 Hz), 7.92 (1H, s), 7.59 (1H, t, J=7.7 Hz), 7.50 (1H, d, J=7.7 Hz), 7.43 (1H, dd, J=8.2, 4.8 Hz), 4.40 (1H, brs), 4.14 (2H, t, J=8.6 Hz), 3.78 (1H, brs), 3.72 (8H, d, J=7.0 Hz), 3.43-3.64 (3H, m), 3.27-3.38 (2H, m), 2.86 (1H, brs), 1.16 (3H, brs), 1.00 (3H, brs).

ESI (LC-MS positive mode) m/z 501 ([M+H]$^+$).

Example 1-G-76

N-methyl-N-(3-methyl-butyl)-3-(2-morpholin-4-yl-7-pyridin-3-yl-6,7-dihydro-5H-pyrrolo[2,3-d]pyrimidin-4-yl)-benzamide trifluoroacetic acid salt (G-76)

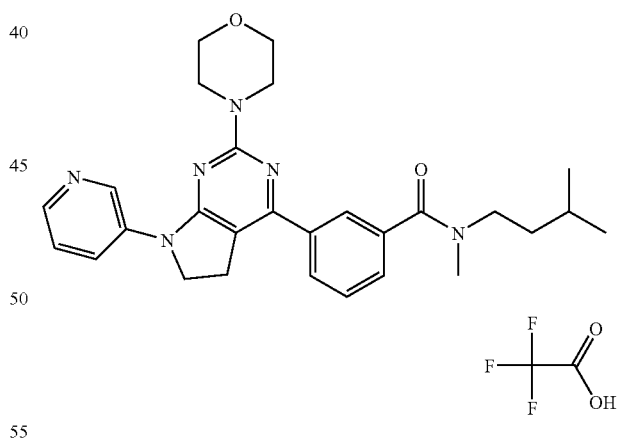

In the same manner as Example 1-G-05, from Compound G-03 prepared in Example 1-G-03 and methyl-(3-methylbutyl)amine, the desired compound was obtained.

$^1$H-NMR (400 MHz, DMSO-$d_6$) δ (ppm): 9.09 (1H, d, J=2.7 Hz), 8.17-8.31 (2H, m), 7.98 (1H, d, J=8.0 Hz), 7.90 (1H, s), 7.57 (1H, t, J=7.7 Hz), 7.36-7.50 (2H, m), 4.13 (2H, t, J=8.2 Hz), 3.72 (8H, d, J=6.8 Hz), 3.49 (2H, t, J=6.9 Hz), 3.35-3.40 (2H, m), 3.18-3.25 (2H, m), 2.94 (3H, d, J=26.7 Hz), 1.25-1.69 (3H, m), 0.95 (3H, d, J=6.1 Hz), 0.68 (3H, d, J=5.8 Hz).

ESI (LC-MS positive mode) m/z 487 ([M+H]$^+$).

Example 1-G-77

N-(2-dimethylamino-ethyl)-N-ethyl-3-(2-morpholin-4-yl-7-pyridin-3-yl-6,7-dihydro-5H-pyrrolo[2,3-d]pyrimidin-4-yl)-benzamide trifluoroacetic acid salt (G-77)

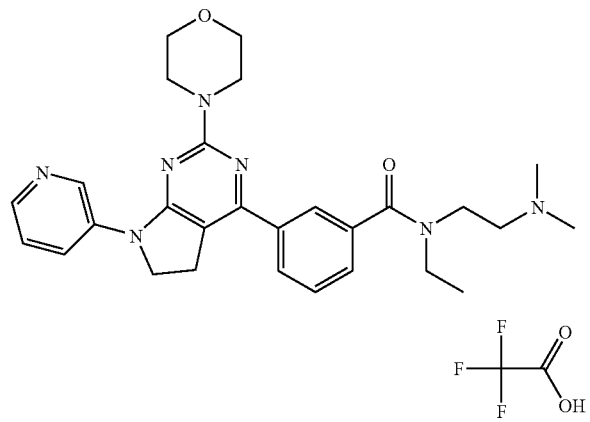

In the same manner as Example 1-G-05, from Compound G-03 prepared in Example 1-G-03 and N'-ethyl-N,N-dimethylethane-1,2-diamine, the desired compound was obtained.

$^1$H-NMR (400 MHz, CD$_3$OD) δ (ppm): 9.69 (1H, s), 8.66 (1H, d, J=8.5 Hz), 8.50 (1H, d, J=5.0 Hz), 7.93-8.11 (3H, m), 7.59-7.74 (2H, m), 4.30 (2H, t, J=8.0 Hz), 3.91-4.00 (2H, m), 3.85 (8H, dd, J=20.8, 5.1 Hz), 3.38-3.58 (6H, m), 3.05 (6H, s), 1.21 (3H, t, J=6.9 Hz).

ESI (LC-MS positive mode) m/z 502 ([M+H]$^+$).

Example 1-G-78

Azetidine-1-yl-[3-(2-morpholin-4-yl-7-pyridin-4-yl-6,7-dihydro-5H-pyrrolo[2,3-d]pyrimidin-4-yl)-phenyl]-methanone (G-78)

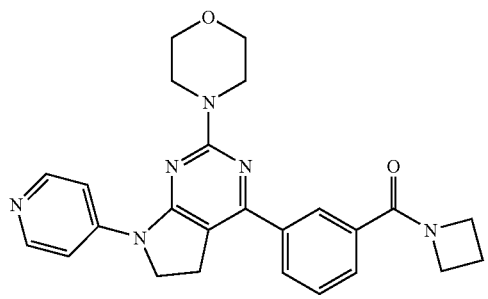

In the same manner as Example 1-G-05, from Compound G-04 prepared in Example 1-G-04 and azetidine, the desired compound was obtained.

$^1$H-NMR (400 MHz, DMSO-d$_6$) δ (ppm): 8.46 (2H, d, J=6.4 Hz), 8.13 (1H, s), 8.07 (1H, d, J=8.0 Hz), 7.83 (2H, d, J=6.4 Hz), 7.72 (1H, d, J=7.9 Hz), 7.59 (1H, t, J=7.7 Hz), 4.34 (2H, t, J=7.6 Hz), 4.09 (4H, q, J=8.8 Hz), 3.74 (8H, dd, J=14.0, 4.8 Hz), 3.36-3.42 (2H, m), 2.21-2.36 (2H, m).

ESI (LC-MS positive mode) m/z 443 ([M+H]$^+$).

Example 1-G-79

N-(3-hydroxy-propyl)-3-(2-morpholin-4-yl-7-pyridin-4-yl-6,7-dihydro-5H-pyrrolo[2,3-d]pyrimidin-4-yl)-benzamide (G-79)

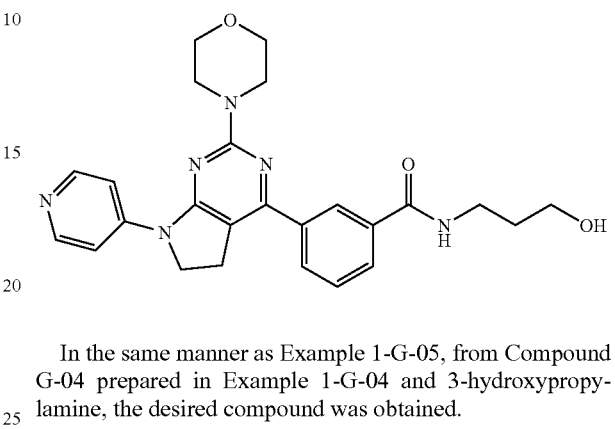

In the same manner as Example 1-G-05, from Compound G-04 prepared in Example 1-G-04 and 3-hydroxypropylamine, the desired compound was obtained.

$^1$H-NMR (400 MHz, DMSO-d$_6$) δ (ppm): 8.57 (1H, t, J=5.6 Hz), 8.46 (2H, d, J=6.4 Hz), 8.35 (1H, s), 8.07 (1H, d, J=8.1 Hz), 7.92 (1H, d, J=8.0 Hz), 7.83 (2H, d, J=6.5 Hz), 7.59 (1H, t, J=7.8 Hz), 4.51 (1H, t, J=5.2 Hz), 4.11 (2H, t, J=8.2 Hz), 3.75 (8H, dd, J=6.0, 4.8 Hz), 3.44-3.53 (2H, m), 3.35-3.40 (2H, m), 3.29-3.33 (2H, m), 1.62-1.78 (2H, m).

ESI (LC-MS positive mode) m/z 461 ([M+H]$^+$).

Example 1-G-80

N-cyclopentyl-3-(2-morpholin-4-yl-7-pyridin-4-yl-6,7-dihydro-5H-pyrrolo[2,3-d]pyrimidin-4-yl)-benzamide (G-80)

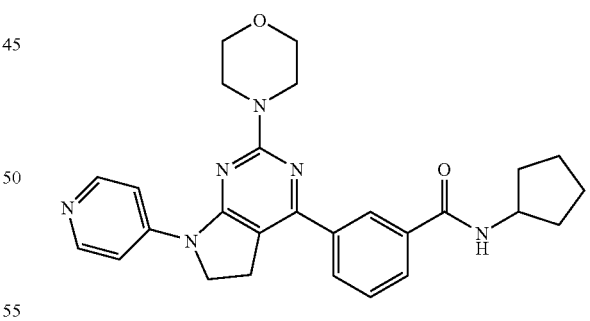

In the same manner as Example 1-G-05, from Compound G-04 prepared in Example 1-G-04 and cyclopentylamine, the desired compound was obtained.

$^1$H-NMR (400 MHz, DMSO-d$_6$) δ (ppm): 8.46 (2H, d, J=6.3 Hz), 8.41 (1H, d, J=7.1 Hz), 8.34 (1H, s), 8.07 (1H, d, J=7.9 Hz), 7.92 (1H, d, J=7.9 Hz), 7.83 (2H, d, J=6.4 Hz), 7.58 (1H, t, J=7.7 Hz), 4.17-4.32 (1H, m), 4.11 (2H, t, J=8.2 Hz), 3.75 (8H, dd, J=16.1, 4.7 Hz), 3.27-3.43 (2H, m), 1.90 (2H, brs), 1.71 (2H, brs), 1.54 (4H, brs).

ESI (LC-MS positive mode) m/z 471 ([M+H]$^+$).

Example 1-G-81

(3-Hydroxy-pyrrolidin-1-yl)-[3-(2-morpholin-4-yl-7-pyridin-4-yl-6,7-dihydro-5H-pyrrolo[2,3-d]pyrimidin-4-yl)-phenyl]-methanone trifluoroacetic acid salt (G-81)

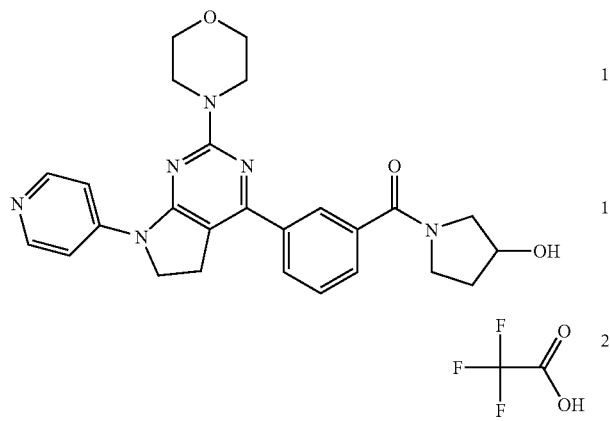

In the same manner as Example 1-G-05, from Compound G-04 prepared in Example 1-G-04 and 3-hydroxypyrrolidine, the desired compound was obtained.

$^1$H-NMR (400 MHz, CD$_3$OD) δ (ppm): 8.52 (2H, d, J=7.2 Hz), 8.39 (2H, brs), 8.14 (1H, brs), 8.08 (1H, d, J=7.8 Hz), 7.54-7.73 (2H, m), 4.46 (1H, d, J=48.2 Hz), 4.27 (2H, t, J=7.9 Hz), 3.78-3.94 (8H, m), 3.50-3.77 (3H, m), 3.47 (2H, t, J=7.9 Hz), 3.35-3.43 (1H, m), 1.91-2.27 (2H, m).

ESI (LC-MS positive mode) m/z 473 ([M+H]$^+$).

Example 1-G-82

N-(2-methoxy-ethyl)-N-methyl-3-(2-morpholin-4-yl-7-pyridin-4-yl-6,7-dihydro-5H-pyrrolo[2,3-d]pyrimidin-4-yl)-benzamide (G-82)

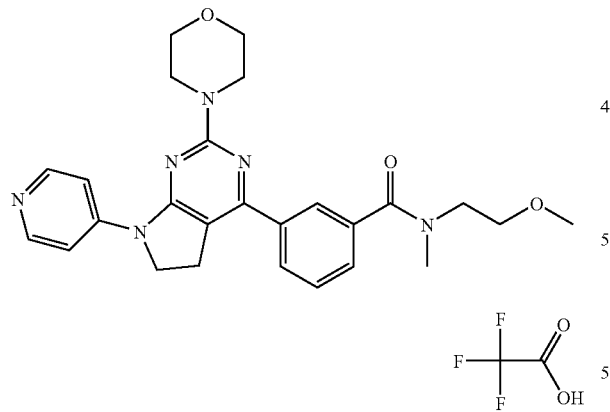

In the same manner as Example 1-G-05, from Compound G-04 prepared in Example 1-G-04 and (2-methoxyethyl)methylamine, the desired compound was obtained.

$^1$H-NMR (400 MHz, CD$_3$OD) δ (ppm): 8.52 (2H, d, J=7.3 Hz), 8.38 (2H, brs), 7.94-8.12 (2H, m), 7.45-7.67 (2H, m), 4.28 (2H, t, J=8.1 Hz), 3.79-3.93 (8H, m), 3.74 (2H, dd, J=20.4, 4.9 Hz), 3.52 (2H, s), 3.46 (2H, t, J=7.8 Hz), 3.35 (3H, d, J=54.3 Hz), 3.11 (3H, d, J=24.4 Hz).

ESI (LC-MS positive mode) m/z 475 ([M+H]$^+$).

Example 1-G-83

(4-Methyl-piperazin-1-yl)-[3-(2-morpholin-4-yl-7-pyridin-4-yl-6,7-dihydro-5H-pyrrolo[2,3-d]pyrimidin-4-yl)-phenyl]-methanone (G-83)

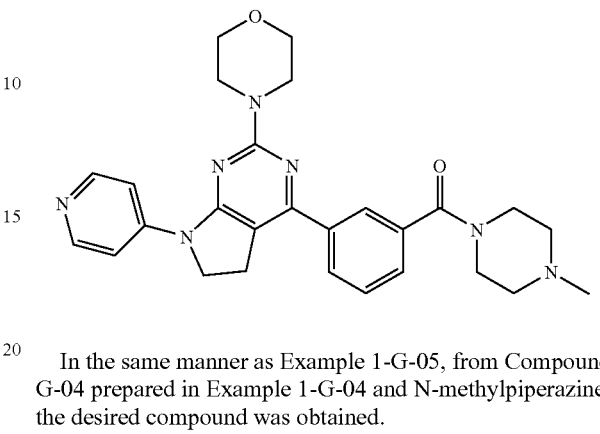

In the same manner as Example 1-G-05, from Compound G-04 prepared in Example 1-G-04 and N-methylpiperazine, the desired compound was obtained.

$^1$H-NMR (400 MHz, DMSO-d$_6$) δ (ppm): 8.46 (2H, d, J=6.4 Hz), 8.00 (1H, d, J=8.1 Hz), 7.92 (1H, s), 7.83 (2H, d, J=6.5 Hz), 7.59 (1H, t, J=7.7 Hz), 7.49 (1H, d, J=7.6 Hz), 4.10 (2H, t, J=8.2 Hz), 3.74 (8H, dd, J=13.9, 4.7 Hz), 3.64 (2H, brs), 3.37-3.42 (4H, m), 2.35 (4H, d, J=22.0 Hz), 2.21 (3H, s).

ESI (LC-MS positive mode) m/z 486 ([M+H]$^+$).

Example 1-G-84

(4-Hydroxy-piperidin-1-yl)-[3-(2-morpholin-4-yl-7-pyridin-4-yl-6,7-dihydro-5H-pyrrolo[2,3-d]pyrimidin-4-yl)-phenyl]-methanone trifluoroacetic acid salt (G-84)

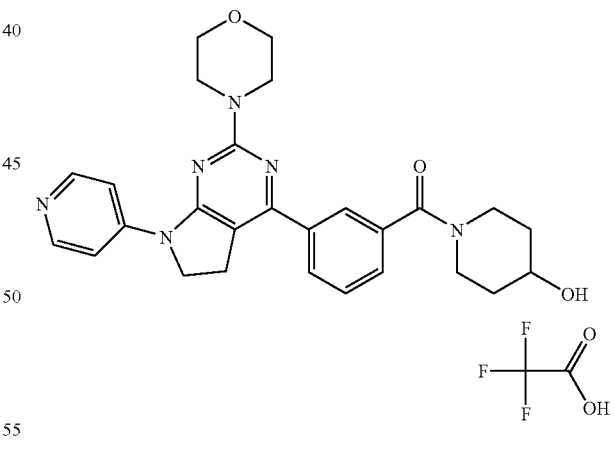

In the same manner as Example 1-G-05, from Compound G-04 prepared in Example 1-G-04 and 4-hydroxypiperidine, the desired compound was obtained.

$^1$H-NMR (400 MHz, CD$_3$OD) δ (ppm): 8.56 (2H, d, J=7.6 Hz), 8.42 (2H, brs), 8.06-8.15 (1H, m), 8.04 (1H, s), 7.54-7.68 (2H, m), 4.31 (2H, t, J=8.1 Hz), 4.24 (1H, brs), 3.81-3.93 (8H, m), 3.65-3.97 (2H, m), 3.50 (2H, t, J=7.8 Hz), 3.25-3.45 (2H, m), 1.36-2.28 (4H, m).

ESI (LC-MS positive mode) m/z 487 ([M+H]$^+$).

Example 1-G-85

N-methyl-N-(3-methyl-butyl)-3-(2-morpholin-4-yl-7-pyridin-4-yl-6,7-dihydro-5H-pyrrolo[2,3-d]pyrimidin-4-yl)-benzamide (G-85)

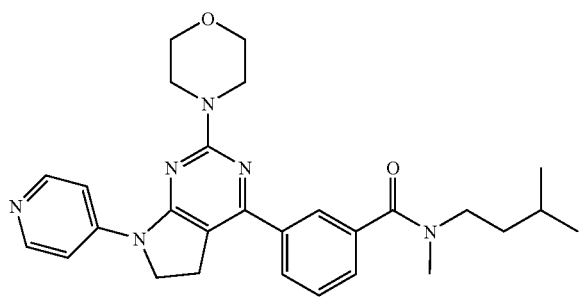

In the same manner as Example 1-G-05, from Compound G-04 prepared in Example 1-G-04 and methyl-(3-methyl-butyl)amine, the desired compound was obtained.

$^1$H-NMR (400 MHz, DMSO-$d_6$) δ (ppm): 8.46 (2H, d, J=6.4 Hz), 7.98 (1H, d, J=8.0 Hz), 7.90 (1H, s), 7.83 (2H, d, J=6.5 Hz), 7.57 (1H, t, J=7.7 Hz), 7.47 (1H, brs), 4.10 (2H, t, J=8.2 Hz), 3.74 (8H, dd, J=14.0, 4.7 Hz), 3.44-3.55 (1H, m), 3.36-3.42 (1H, m), 3.17-3.26 (2H, m), 2.94 (3H, d, J=27.5 Hz), 1.25-1.72 (3H, m), 0.95 (3H, d, J=6.0 Hz), 0.68 (3H, d, J=6.0 Hz).

ESI (LC-MS positive mode) m/z 487 ([M+H]$^+$).

Example 1-G-86

3-(2-Morpholin-4-yl-7-pyridin-4-yl-6,7-dihydro-5H-pyrrolo[2,3-d]pyrimidin-4-yl)-N-pyridin-4-ylmethyl-benzamide (G-86)

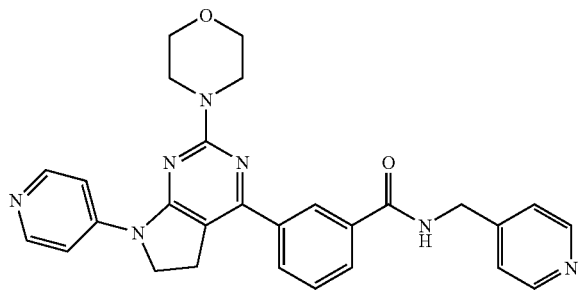

In the same manner as Example 1-G-05, from Compound G-04 prepared in Example 1-G-04 and 4-aminomethylpyridine, the desired compound was obtained.

$^1$H-NMR (400 MHz, DMSO-$d_6$) δ (ppm): 9.26 (1H, t, J=5.9 Hz), 8.51 (2H, d, J=6.0 Hz), 8.46 (2H, d, J=6.3 Hz), 8.43 (1H, s), 8.12 (1H, d, J=7.9 Hz), 8.01 (1H, d, J=7.9 Hz), 7.83 (2H, d, J=6.4 Hz), 7.63 (1H, t, J=7.8 Hz), 7.33 (2H, d, J=5.9 Hz), 4.53 (2H, d, J=5.9 Hz), 4.11 (2H, t, J=8.1 Hz), 3.75 (8H, dd, J=17.3, 4.8 Hz), 3.35-3.41 (2H, m).

ESI (LC-MS positive mode) m/z 494 ([M+H]$^+$).

Example 1-G-87

(4-Ethyl-piperazin-1-yl)-[3-(2-morpholin-4-yl-7-pyridin-4-yl-6,7-dihydro-5H-pyrrolo[2,3-d]pyrimidin-4-yl)-phenyl]-methanone (G-87)

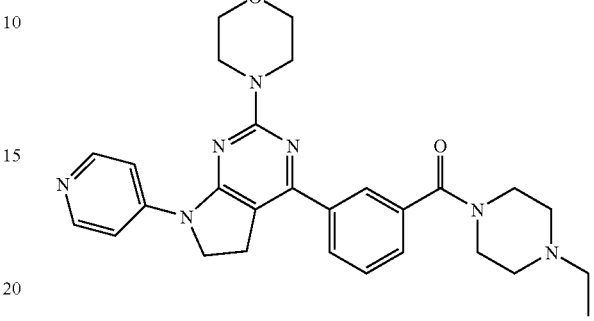

In the same manner as Example 1-G-05, from Compound G-04 prepared in Example 1-G-04 and N-ethylpiperazine, the desired compound was obtained.

$^1$H-NMR (400 MHz, DMSO-$d_6$) δ (ppm): 8.46 (2H, d, J=6.4 Hz), 7.99 (1H, d, J=8.0 Hz), 7.92 (1H, s), 7.83 (2H, d, J=6.5 Hz), 7.58 (1H, t, J=7.7 Hz), 7.49 (1H, d, J=7.6 Hz), 4.09 (2H, t, J=8.2 Hz), 3.74 (8H, dd, J=14.2, 4.7 Hz), 3.64 (2H, brs), 3.35-3.43 (4H, m), 2.43 (4H, brs), 2.36 (2H, q, J=7.1 Hz), 1.01 (3H, t, J=7.2 Hz).

ESI (LC-MS positive mode) m/z 500 ([M+H]$^+$).

Example 1-G-88

N-(2-diethylamino-ethyl)-3-(2-morpholin-4-yl-7-pyridin-4-yl-6,7-dihydro-5H-pyrrolo[2,3-d]pyrimidin-4-yl)-benzamide trifluoroacetic acid salt (G-88)

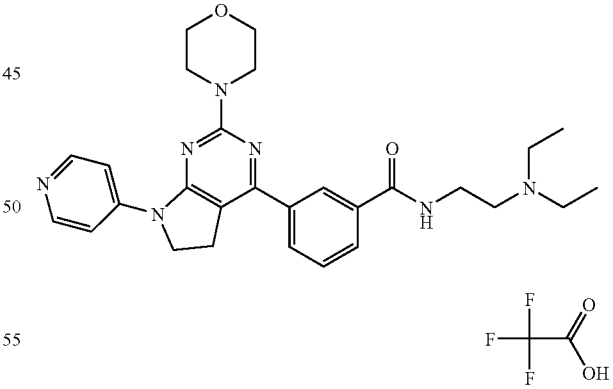

In the same manner as Example 1-G-05, from Compound G-04 prepared in Example 1-G-04 and N,N-diethyl ethylenediamine, the desired compound was obtained.

$^1$H-NMR (400 MHz, CD$_3$OD) δ (ppm): 8.54 (2H, d, J=7.5 Hz), 8.48 (1H, s), 8.39 (2H, brs), 8.16 (1H, d, J=7.9 Hz), 7.98 (1H, d, J=7.9 Hz), 7.64 (1H, t, J=7.8 Hz), 4.29 (2H, t, J=8.0 Hz), 3.48 (2H, t, J=8.1 Hz), 3.43 (2H, t, J=6.3 Hz), 3.32-3.39 (4H, m), 1.37 (6H, t, J=7.3 Hz).

ESI (LC-MS positive mode) m/z 502 ([M+H]$^+$).

Example 1-G-89

N-(2-dimethylamino-ethyl)-N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-89)

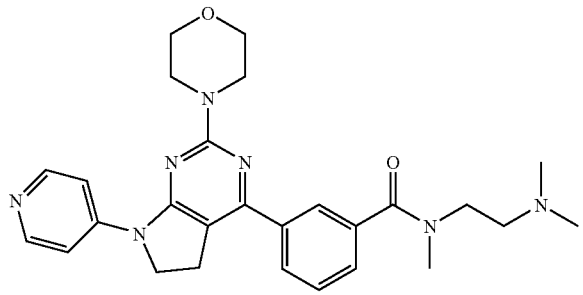

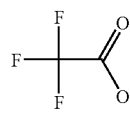

In the same manner as Example 1-G-05, from Compound G-04 prepared in Example 1-G-04 and N,N,N'-trimethyl ethylenediamine, the desired compound was obtained.

$^1$H-NMR (400 MHz, CD$_3$OD) δ (ppm): 8.53 (2H, brs), 8.39 (2H, brs), 8.09 (2H, brs), 7.56-7.70 (2H, m), 4.27 (2H, brs), 3.97 (2H, brs), 3.84 (8H, d, J=26.3 Hz), 3.40-3.59 (4H, m), 3.11 (3H, s), 3.05 (6H, s).

ESI (LC-MS positive mode) m/z 488 ([M+H]$^+$).

Example 1-G-90

3-(2-Morpholin-4-yl-7-pyridin-4-yl-6,7-dihydro-5H-pyrrolo[2,3-d]pyrimidin-4-yl)-N-(2-pyrrolidin-1-yl-ethyl)-benzamide (G-90)

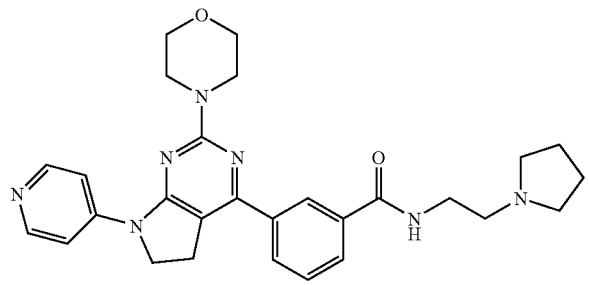

In the same manner as Example 1-G-05, from Compound G-04 prepared in Example 1-G-04 and 2-pyrrolidin-1-yl-ethylamine, the desired compound was obtained.

$^1$H-NMR (400 MHz, DMSO-d$_6$) δ (ppm): 8.56 (1H, t, J=5.6 Hz), 8.46 (2H, d, J=6.4 Hz), 8.36 (1H, s), 8.08 (1H, d, J=8.0 Hz), 7.92 (1H, d, J=7.9 Hz), 7.83 (2H, d, J=6.5 Hz), 7.59 (1H, t, J=7.8 Hz), 4.11 (2H, t, J=8.2 Hz), 3.75 (8H, dd, J=16.1, 4.8 Hz), 3.36-3.48 (8H, m), 2.60 (2H, t, J=7.0 Hz), 1.62-1.75 (4H, m).

ESI (LC-MS positive mode) m/z 500 ([M+H]$^+$).

Example 1-G-91

3-(2-Morpholin-4-yl-7-pyridin-3-yl-6,7-dihydro-5H-pyrrolo[2,3-d]pyrimidin-4-yl)-N-(2-pyrrolidin-1-yl-ethyl)-benzamide (G-91)

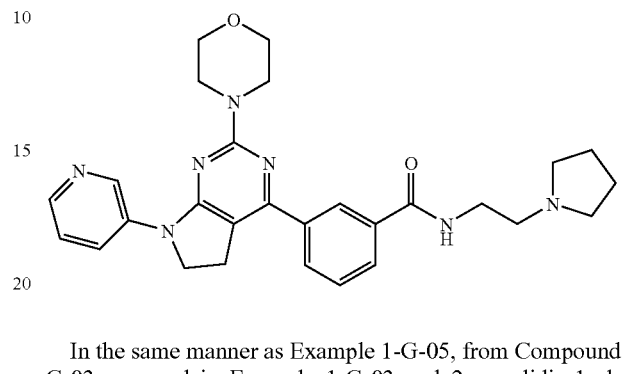

In the same manner as Example 1-G-05, from Compound G-03 prepared in Example 1-G-03 and 2-pyrrolidin-1-yl-ethylamine, the desired compound was obtained.

$^1$H-NMR (400 MHz, DMSO-d$_6$) δ (ppm): 9.09 (1H, d, J=2.6 Hz), 8.60 (1H, t, J=5.4 Hz), 8.36 (1H, s), 8.20-8.29 (2H, m), 8.08 (1H, d, J=8.1 Hz), 7.92 (1H, d, J=8.0 Hz), 7.59 (1H, t, J=7.8 Hz), 7.37-7.47 (1H, m), 4.14 (2H, t, J=8.2 Hz), 3.73 (8H, dd, J=13.5, 4.6 Hz), 3.40-3.48 (2H, m), 3.36-3.40 (2H, m), 2.55-2.77 (6H, m), 1.72 (4H, brs).

ESI (LC-MS positive mode) m/z 500 ([M+H]$^+$).

Example 1-G-92

N-(4,5-dimethyl-thiazol-2-yl)-3-(2-morpholin-4-yl-7-pyridin-3-yl-6,7-dihydro-5H-pyrrolo[2,3-d]pyrimidin-4-yl)-benzamide (G-92)

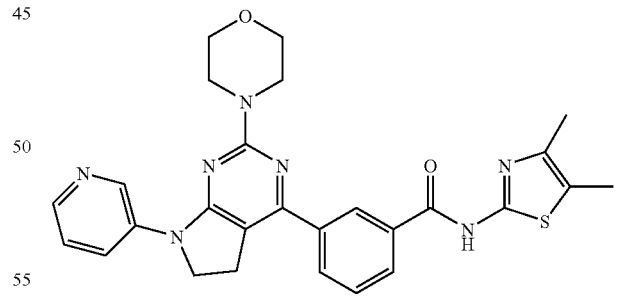

In the same manner as Example 1-G-05, from Compound G-03 prepared in Example 1-G-03 and 2-amino-4,5-dimethylthiazole, the desired compound was obtained.

$^1$H-NMR (400 MHz, DMSO-d$_6$) δ (ppm): 9.45 (1H, s), 8.66 (1H, d, J=8.8 Hz), 8.55 (1H, s), 8.49 (1H, d, J=5.1 Hz), 8.19 (2H, d, J=8.8 Hz), 7.91 (1H, dd, J=8.6, 5.3 Hz), 7.67 (1H, t, J=7.8 Hz), 4.21 (2H, t, J=8.1 Hz), 3.77 (8H, dd, J=21.0, 5.0 Hz), 3.42-3.48 (2H, m), 2.27 (3H, s), 2.21 (3H, s).

ESI (LC-MS positive mode) m/z 514 ([M+H]$^+$).

Example 1-G-93

N-indan-2-yl-3-(2-morpholin-4-yl-7-pyridin-4-yl-6,7-dihydro-5H-pyrrolo[2,3-d]pyrimidin-4-yl)-benzamide (G-93)

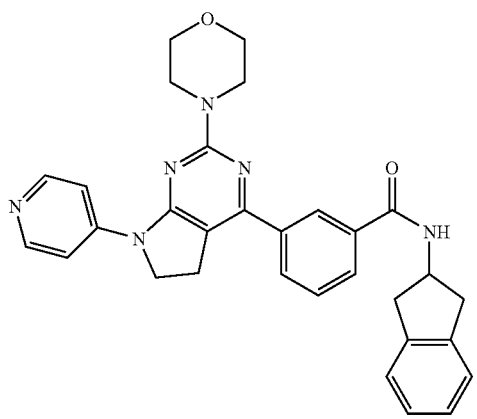

In the same manner as Example 1-G-05, from Compound G-04 prepared in Example 1-G-04 and indan-2-ylamine, the desired compound was obtained.

$^1$H-NMR (400 MHz, DMSO-$d_6$) δ (ppm): 8.43-8.52 (2H, m), 8.38 (1H, s), 8.08 (1H, d, J=10.6 Hz), 7.92-7.99 (1H, m), 7.84 (2H, d, J=7.5 Hz), 7.24 (3H, d, 4.8 Hz), 7.16 (3H, d, J=3.5 Hz), 4.06-4.16 (2H, m), 3.69-3.82 (8H, m), 3.23-3.30 (4H, m), 3.16 (1H, d, J=5.3 Hz), 2.91-3.04 (2H, m).

ESI (LC-MS positive mode) m/z 519 ([M+H]$^+$).

Example 1-G-94

(3-Hydroxy-piperidin-1-yl)-[3-(2-morpholin-4-yl-7-pyridin-4-yl-6,7-dihydro-5H-pyrrolo[2,3-d]pyrimidin-4-yl)-phenyl]-methanone (G-94)

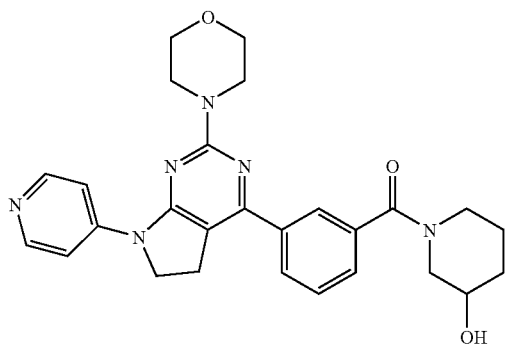

In the same manner as Example 1-G-05, from Compound G-04 prepared in Example 1-G-04 and 3-hydroxy-piperidine, the desired compound was obtained.

$^1$H-NMR (400 MHz, DMSO-$d_6$) δ (ppm): 8.45 (2H, d, J=6.0 Hz), 7.99 (1H, d, J=7.8 Hz), 7.90 (1H, J=brs), 7.82 (2H, d, J=6.4 Hz), 7.57 (1H, t, J=7.7 Hz), 7.49 (1H, brs), 4.85-5.06 (1H, m), 4.09 (2H, t, J=8.2 Hz), 3.67-3.80 (8H, m), 3.45-3.60 (2H, m), 3.20-3.29 (2H, m), 2.91-3.11 (2H, m), 1.35-1.93 (4H, m).

ESI (LC-MS positive mode) m/z 487 ([M+H]$^+$).

Example 1-H

Bis-(4-methoxy-benzyl)-[5-(2-morpholin-4-yl-6,7-dihydro-5H-pyrrolo[2,3-d]pyrimidin-4-yl)-pyrimidin-2-yl]-amine to be used in Step A in the following Example 1-H-31 was prepared according to Example 1-J-02 described below. Further, in the following Examples 1-H-02, 1-H-08 to 10, 1-H-13 to 20 and 1-H-24 to 30, a resulting crude reaction product was subjected to HPLC purification using a developing solvent containing trifluoroacetic acid, to obtain the desired compound as a trifluoroacetic acid salt.

Example 1-H-01

7-(2-Chloro-pyridin-4-yl)-4-(3-methoxy-phenyl)-2-morpholin-4-yl-6,7-dihydro-5H-pyrrolo[2,3-d]pyrimidine trifluoroacetic acid salt (H-01)

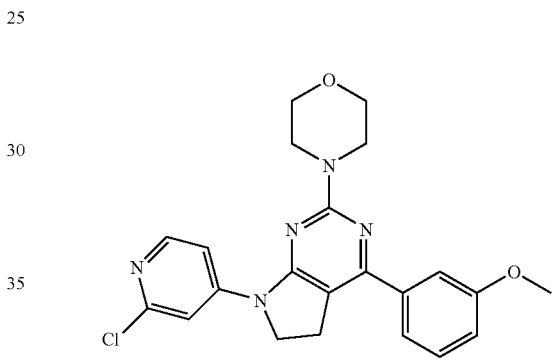

Sodium hydride (844 mg, 60% mineral oil dispersion, 21.1 mmol) was placed in a dried flask under a nitrogen atmosphere, followed by sequential addition of anhydrous tetrahydrofuran (75 ml) and 4-amino-2-chloropyridine (648 mg, 5.06 mmol) with a syringe. This mixture was heated to reflux for 1.5 hours, and subsequently 4-[4-chloro-5-(2-chloroethyl)-6-(3-methoxyphenyl)-pyrimidin-2-yl]morpholine (1.55 g, 4.22 mmol) obtained in Step C in Example 1-A-01 was added. After heating to reflux for further 1.5 hours, the reaction mixture was cooled, which was added dropwise slowly onto ice water. Filtration of the deposited precipitate afforded the desired compound as a pale brown solid (808 mg, 49% yield). The filtrate was extracted three times with ethyl acetate (30 ml), and the organic layer was dried over sodium sulfate, followed by distilling off under reduced pressure. The obtained crude product was recrystallized (ethyl acetate), whereby the desired compound was obtained as a pale brown solid (250 mg, 15% yield, total 64%).

$^1$H-NMR (400 MHz, DMSO-$d_6$) δ (ppm) 8.27 (1H, d, J=6.40 Hz), 7.85-7.96 (2H, m), 7.36-7.56 (3H, m), 7.06 (1H, d, J=2.38 Hz), 4.10 (2H, t, J=8.14 Hz), 3.82 (3H, s), 3.68-3.78 (8H, m), 3.27-3.34 (2H, m).

ESI (LC-MS positive mode) m/z 424 [M+H].

Example 1-H-02

3-{7-[2-(3-Hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-02)

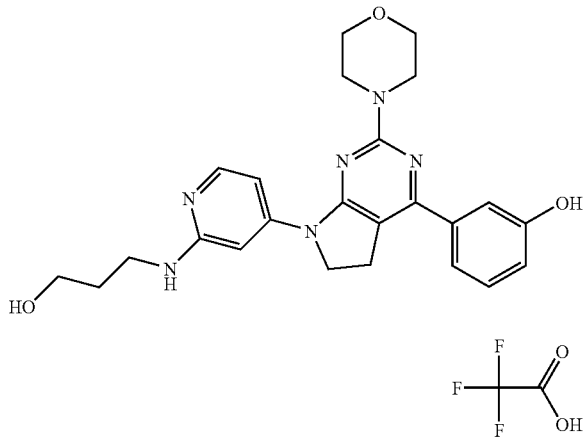

Compound H-01 (70 mg, 0.165 mmol) obtained in Example 1-H-01 was dissolved in 1,3-propanolamine (2 ml), followed by heating in a sealed tube at 180° C. for 16 hours. The mixture was cooled to room temperature, and subsequently saturated aqueous sodium hydrogencarbonate solution (4 ml) was added, followed by extraction three times with ethyl acetate (5 ml). The organic layer was dried over sodium sulfate, and distilled off under reduced pressure, whereby a yellow oil was obtained (80 mg). A solution of this crude product (80 mg) in dimethylformamide (1 ml) was heated to 150° C., and sodium ethanethiolate (275 mg, 3.3 mmol) was added for every 15 minutes in 3 portions. After heating at 150° C. for further 15 minutes followed by cooling, water (1 ml) was added. After extraction with ethyl acetate (2 ml), the organic layer was separated, followed by concentration under reduced pressure. The obtained crude product was purified by preparative HPLC, to obtain a trifluoroacetic acid salt of the desired compound as a pale yellow solid (9 mg, 10% yield).

$^1$H-NMR (400 MHz, DMSO-d$_6$) δ (ppm) 12.54 (1H, br.s.), 9.64 (1H, s), 8.11 (1H, br.s.), 7.88 (1H, d, J=7.32 Hz), 7.6 (1H, br.s.), 7.22-7.44 (3H, m), 7.06 (1H, br.s.), 6.85-6.92 (1H, m), 6.55 (1H, br.s.), 4.69 (1H, br.s.), 4.12 (2H, t, J=7.87 Hz), 3.68-3.83 (8H, m), 3.52 (2H, t, J=5.95 Hz), 3.29-3.33 (4H, m), 1.70-1.82 (2H, m).

ESI (LC-MS positive mode) m/z 449 [M+H].

Example 1-H-03

3-{7-[2-(Isobutyl-methyl-amino)-pyridin-4-yl]-2-morpholin-4-yl-6,7-dihydro-5H-pyrrolo[2,3-d]pyrimidin-4-yl}-phenol (H-03)

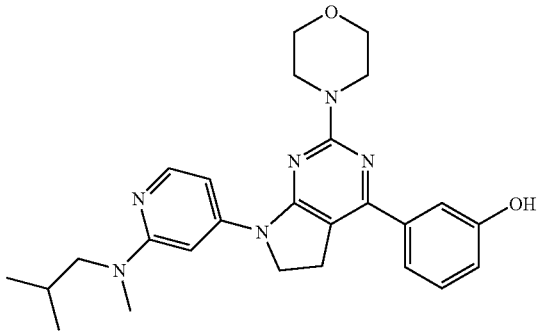

Compound H-01 (70 mg, 0.165 mmol) obtained in Example 1-H-01, n-butanol (1.5 ml), N-methylisobutylamine (0.2 ml) and 1-butyl-3-methyl imidazolium trifluoromethanesulfonate (1 drop) were mixed in a microwave tube, followed by irradiation of microwave (300 W, 210° C., 280 psi) for 3 hours. After the mixture was cooled to room temperature, ethyl acetate (3 ml) was added, and the organic layer was washed with saturated aqueous sodium hydrogencarbonate solution (3 ml). The organic layer was distilled off under reduced pressure, to obtain a brown oil (45 mg, 57% yield). A solution of this crude product (45 mg) in dimethylformamide (1 ml) was heated to 150° C., and sodium ethanethiolate (275 mg, 3.3 mmol) was added for every 15 minutes in 3 portions. After heating at 150° C. for further 15 minutes followed by cooling, water (1 ml) was added. The deposited precipitate was filtered, followed by washing with cooled diethyl ether, whereby the desired compound was obtained as a pale yellow solid (25 mg, 33% yield).

$^1$H-NMR (400 MHz, DMSO-d$_6$) δ (ppm) 7.96 (1H, d, J=5.85 Hz), 7.37 (1H, s), 7.23-7.33 (2H, m), 7.13 (1H, s), 6.93 (1H, d, J=5.85 Hz), 6.83 (1H, d, J=7.68 Hz), 4.06 (2H, t, J=8.32 Hz), 3.72 (8H, dd, J=19.49, 5.03 Hz), 3.37 (2H, d, J=7.50 Hz), 3.25 (2H, t, J=8.23 Hz), 3.00 (3H, s), 1.97-2.11 (1H, m), 0.85 (6H, d, J=6.77 Hz).

ESI (LC-MS positive mode) m/z 461 [M+H].

Example 1-H-04

3-{7-[2-(4-Ethyl-piperazin-1-yl)-pyridin-4-yl]-2-morpholin-4-yl-6,7-dihydro-5H-pyrrolo[2,3-d]pyrimidin-4-yl}-phenol (H-04)

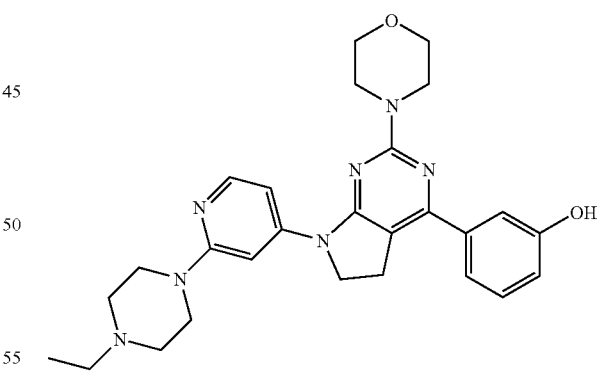

In the same manner as Example 1-H-03, using N-ethylpiperazine, the desired compound was obtained.

$^1$H-NMR (250 MHz, DMSO-d$_6$) δ (ppm) 9.59 (1H, s), 8.02 (1H, d, J=5.8 Hz), 7.22-7.48 (4H, m), 7.09 (1H, dd, J=5.4, 1.1 Hz), 6.85 (1H, d, J=7.6 Hz) 4.07 (2H, t, J=8.3 Hz), 3.73 (8H, d, J=4.3 Hz), 3.47 (4H, t, J=4.8 Hz), 3.21-3.31 (2H, m), 2.42-2.48 (4H, m), 2.36 (2H, q, J=7.1 Hz), 1.04 (3H, t, J=7.2 Hz).

ESI (LC-MS positive mode) m/z 488 [M+H].

Example 1-H-05

4'-[4-(3-Hydroxy-phenyl)-2-morpholin-4-yl-5,6-dihydro-pyrrolo[2,3-d]pyrimidin-7-yl]-3,4,5,6-tetrahydro-2H-[1,2']bipyridinyl-4-ol (H-05)

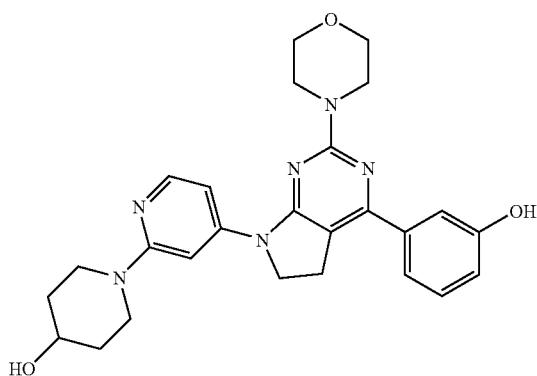

In the same manner as Example 1-H-03, using 4-hydroxypiperidine, the desired compound was obtained.

$^1$H-NMR (360 MHz, CD$_3$OD) δ (ppm) 7.95 (1H, d, J=5.9 Hz), 7.61 (1H, s), 7.40 (1H, s), 7.32 (1H, d, J=7.7 Hz), 7.25 (1H, t, J=7.8 Hz), 6.79-6.93 (2H, m), 3.90-4.06 (4H, m), 3.81-3.87 (1H, m), 3.77 (8H, d, J=5.2 Hz), 3.20 (2H, t, J=8.1 Hz), 3.03-3.14 (2H, m), 1.85-1.97 (2H, m), 1.46-1.62 (2H, m).

ESI (LC-MS positive mode) m/z 475 [M+H].

Example 1-H-06

4-[4-(3-Hydroxy-phenyl)-2-morpholin-4-yl-5,6-dihydro-pyrrolo[2,3-d]pyrimidin-7-yl]-pyridin-2-ol (H-06)

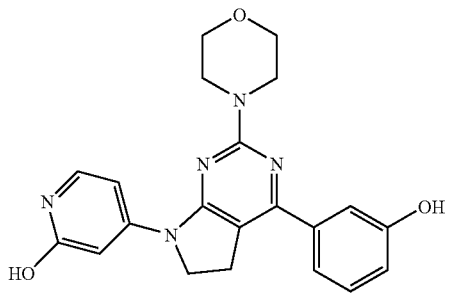

In the same manner as Example 1-H-03, using 1M aqueous sodium hydroxide solution, the desired compound was obtained.

$^1$H-NMR (400 MHz, DMSO-d$_6$) δ (ppm): 7.38 (1H, s), 7.24-7.34 (4H, m), 6.85 (1H, d, J=7.7 Hz), 6.20 (1H, s), 3.99 (2H, t, J=8.1 Hz), 3.67-3.74 (8H, m), 3.24 (2H, t, J=8.2 Hz).

ESI (LC-MS positive mode) m/z 392 ([M+H]$^+$).

Example 1-H-07

1-(4-{4-[4-(3-Hydroxy-phenyl)-2-morpholin-4-yl-5,6-dihydro-pyrrolo[2,3-d]pyrimidin-7-yl]-pyridin-2-yl}-piperazin-1-yl)-ethanone (H-07)

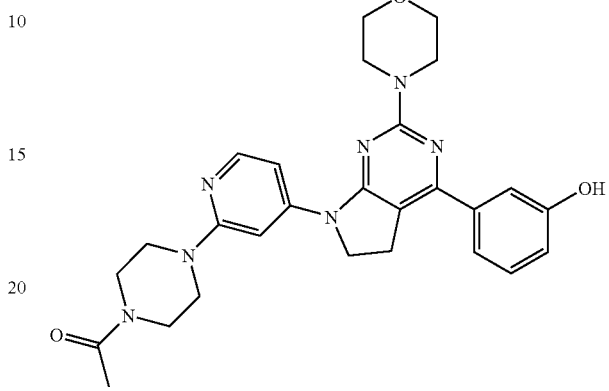

In the same manner as Example 1-H-03, using N-acetylpiperazine, the desired compound was obtained.

$^1$H-NMR (400 MHz, DMSO-d$_6$) δ (ppm): 8.04 (1H, d, J=5.7 Hz), 7.24-7.42 (4H, m), 7.17 (1H, dd, J=5.9, 1.7 Hz), 6.85 (1H, dd, J=7.8, 1.3 Hz), 4.08 (2H, t, J=8.1 Hz), 3.68-3.80 (8H, m), 3.55 (4H, s), 3.45-3.50 (2H, m), 3.23-3.30 (2H, m), 2.05 (3H, s).

ESI (LC-MS positive mode) m/z 502 ([M+H]$^+$).

Example 1-H-08

3-{7-[2-(2-Hydroxy-ethylamino)-pyridin-4-yl]-2-morpholin-4-yl-6,7-dihydro-5H-pyrrolo[2,3-d]pyrimidin-4-yl}-phenol trifluoroacetic acid salt (H-08)

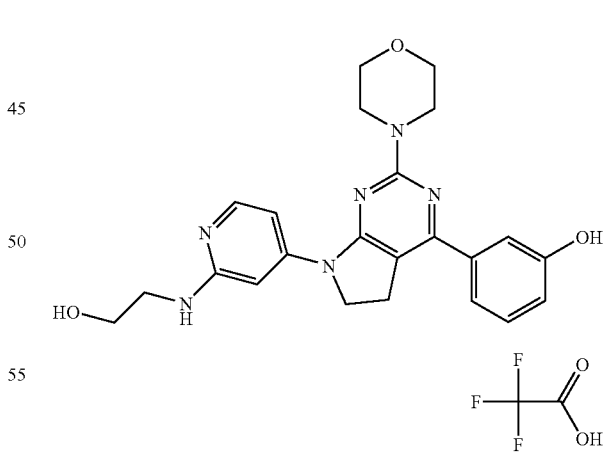

In the same manner as Example 1-H-03, using 2-hydroxyethylamine, the desired compound was obtained.

$^1$H-NMR (400 MHz, DMSO-d$_6$) δ (ppm): 9.65 (1H, brs), 8.20 (1H, brs), 7.88 (1H, d, J=7.5 Hz), 7.69 (1H, brs), 7.26-7.42 (3H, m), 7.11 (1H, brs), 6.89 (1H, d, J=7.9 Hz), 4.12 (2H, t, J=8.0 Hz), 3.74 (8H, dd, J=12.3, 3.7 Hz), 3.62 (2H, t, J=5.4 Hz), 3.27-3.42 (4H, m).

ESI (LC-MS positive mode) m/z 435 ([M+H]$^+$).

Example 1-H-09

3-{7-[2-(2-Hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-09)

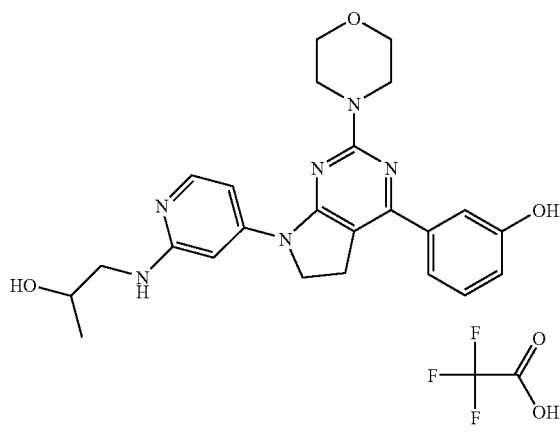

In the same manner as Example 1-H-03, using 1-aminopropan-2-ol, the desired compound was obtained.

¹H-NMR (400 MHz, DMSO-d₆) δ (ppm): 12.53 (1H, brs), 9.66 (1H, brs), 8.13 (1H, brs), 7.90 (1H, d, J=7.5 Hz), 7.72 (1H, brs), 7.25-7.46 (3H, m), 7.10 (1H, brs), 6.89 (1H, d, J=7.9 Hz), 4.12 (2H, t, J=8.1 Hz), 3.83-3.92 (1H, m), 3.69-3.81 (8H, m), 3.27-3.36 (3H, m), 3.12-3.22 (1H, m), 1.15 (3H, d, J=6.2 Hz).

ESI (LC-MS positive mode) m/z 449 ([M+H]⁺).

Example 1-H-10

3-{7-[2-(2-Hydroxy-1-methyl-ethylamino)-pyridin-4-yl]-2-morpholin-4-yl-6,7-dihydro-5H-pyrrolo[2,3-d]pyrimidin-4-yl}-phenol trifluoroacetic acid salt (H-10)

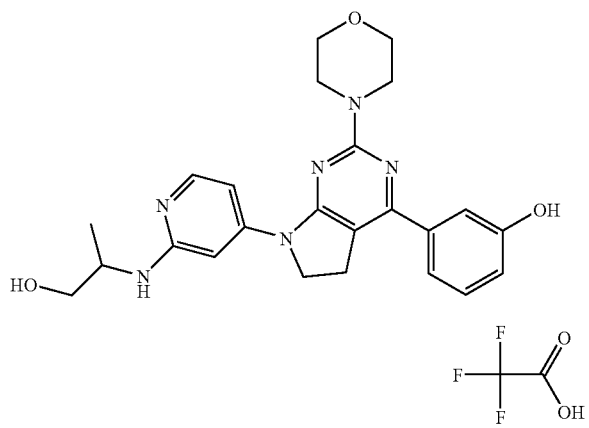

In the same manner as Example 1-H-03, using 2-aminopropan-1-ol, the desired compound was obtained.

¹H-NMR (400 MHz, DMSO-d₆) δ (ppm): 12.44 (1H, brs), 9.66 (1H, s), 7.98 (1H, brs), 7.88 (1H, d, J=7.3 Hz), 7.74 (1H, brs), 7.27-7.43 (3H, m), 7.03 (1H, brs), 6.89 (1H, d, J=10.4 Hz), 6.57 (1H, brs), 4.11 (2H, t, J=8.1 Hz), 3.66-3.87 (9H, m), 3.50-3.57 (1H, m), 3.41-3.47 (1H, m), 3.30-3.33 (2H, m), 1.18 (3H, d, J=6.4 Hz).

ESI (LC-MS positive mode) m/z 449 ([M+H]⁺).

Example 1-H-11

4'-[4-(3-Hydroxy-phenyl)-2-morpholin-4-yl-5,6-dihydro-pyrrolo[2,3-d]pyrimidin-7-yl]-3,4,5,6-tetrahydro-2H-[1,2']bipyridinyl-3-ol (H-11)

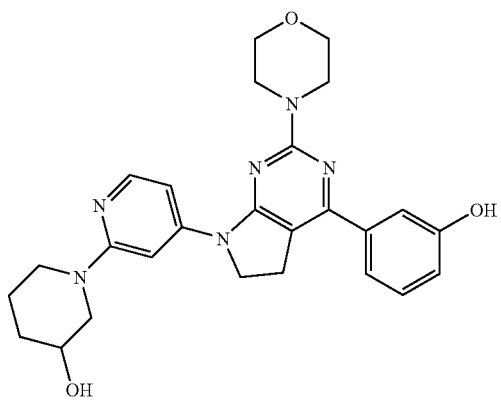

In the same manner as Example 1-H-03, using 3-hydroxypiperidine, the desired compound was obtained.

¹H-NMR (400 MHz, DMSO-d₆) δ (ppm): 9.68 (1H, brs), 7.98 (1H, d, J=5.9 Hz), 7.52 (1H, d, J=1.3 Hz), 7.23-7.41 (3H, m), 6.81-6.90 (2H, m), 4.84 (1H, brs), 4.16 (1H, dd, J=12.2, 3.8 Hz), 3.99-4.10 (3H, m), 3.72 (8H, dd, J=15.6, 4.9 Hz), 3.47 (1H, brs), 3.26 (2H, t, J=8.2 Hz), 2.78-2.88 (1H, m), 2.66 (1H, dd, J=12.3, 9.3 Hz), 1.87-1.95 (1H, m), 1.65-1.75 (1H, m), 1.28-1.48 (2H, m).

ESI (LC-MS positive mode) m/z 475 ([M+H]⁺).

Example 1-H-12

3-{7-[2-(3-Dimethylamino-propylamino)-pyridin-4-yl]-2-morpholin-4-yl-6,7-dihydro-5H-pyrrolo[2,3-d]pyrimidin-4-yl}-phenol (H-12)

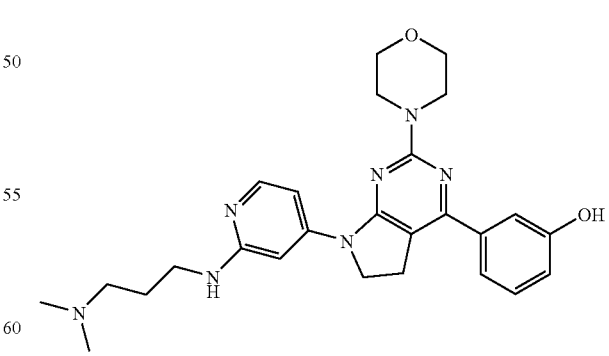

In the same manner as Example 1-H-03, using N,N-dimethyl-propan-1,3-diamine, the desired compound was obtained.

¹H-NMR (400 MHz, DMSO-d₆) δ (ppm): 9.59 (1H, brs), 7.87 (1H, d, J=5.9 Hz), 7.21-7.41 (3H, m), 7.04 (1H, dd, J=6.0, 1.7 Hz), 6.80-6.89 (2H, m), 6.34 (1H, t, J=5.6 Hz), 4.01 (2H, t, J=8.2 Hz), 3.65-3.79 (8H, m), 3.16-3.29 (4H, m), 2.26 (2H, t, J=7.0 Hz), 2.12 (6H, s), 1.60-1.70 (2H, m).
ESI (LC-MS positive mode) m/z 476 ([M+H]$^+$).

Example 1-H-13

3-{7-[2-(3-Hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-13)

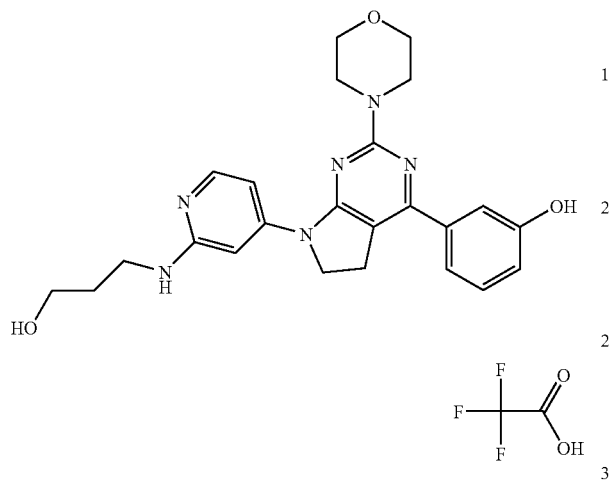

Using 3-hydroxypropylamine instead of N-methylisobutylamine in Example 1-H-03, the desired compound was obtained.
$^1$H-NMR (400 MHz, DMSO-d$_6$) δ (ppm): 12.54 (1H, brs), 9.64 (1H, s), 8.11 (1H, brs), 7.88 (1H, d, J=7.3 Hz), 7.69 (1H, brs), 7.22-7.44 (3H, m), 7.06 (1H, brs), 6.85-6.92 (1H, m), 6.55 (1H, brs), 4.69 (1H, brs), 4.12 (2H, t, J=7.9 Hz), 3.68-3.83 (8H, m), 3.52 (2H, t, J=6.0 Hz), 3.29-3.33 (4H, m), 1.70-1.82 (2H, m).
ESI (LC-MS positive mode) m/z 449 ([M+H]$^+$).

Example 1-H-14

3-(7-{2-[(2-Hydroxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-14)

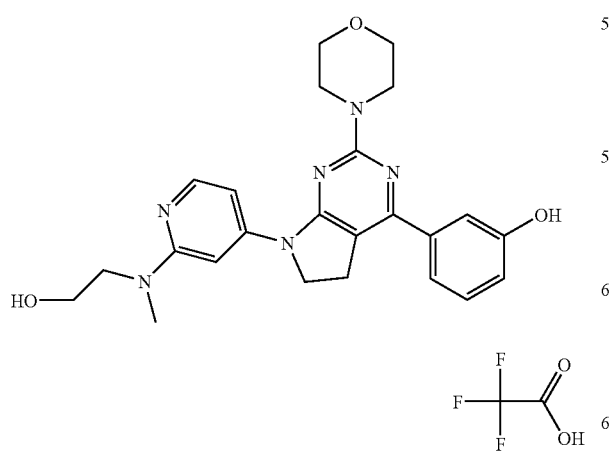

In the same manner as Example 1-H-03, using (2-hydroxyethyl)methylamine, the desired compound was obtained.
$^1$H-NMR (400 MHz, DMSO-d$_6$) δ (ppm): 9.67 (1H, brs), 7.92 (1H, d, J=7.3 Hz), 7.62 (1H, brs), 7.24-7.43 (4H, m), 6.86-6.93 (1H, m), 4.19 (2H, t, J=8.1 Hz), 3.75 (8H, dd, J=17.4, 5.0 Hz), 3.67 (4H, s), 3.34 (2H, t, J=8.1 Hz), 3.19 (3H, s).
ESI (LC-MS positive mode) m/z 449 ([M+H]$^+$).

Example 1-H-15

3-(7-{2-[(2-Methoxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-15)

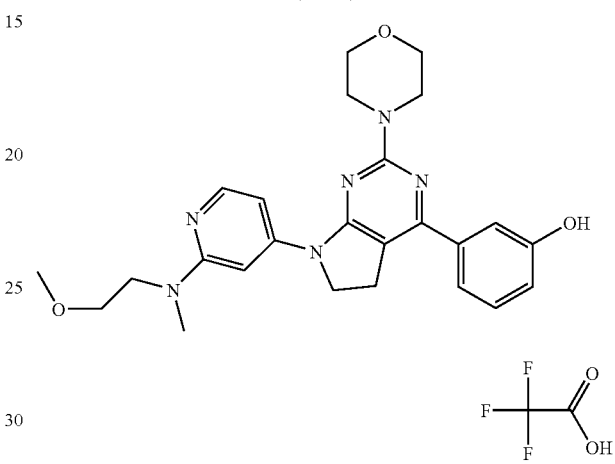

In the same manner as Example 1-H-03, using (2-methoxyethyl)methylamine, the desired compound was obtained.
$^1$H-NMR (400 MHz, DMSO-d$_6$) δ (ppm): 12.52 (1H, brs), 9.65 (1H, s), 7.92 (1H, d, J=7.2 Hz), 7.61 (1H, brs), 7.25-7.44 (3H, m), 7.24 (1H, brs), 6.86-6.92 (1H, m), 4.18 (2H, t, J=8.0 Hz), 3.68-3.82 (10H, m), 3.57 (2H, t, J=5.3 Hz), 3.33 (2H, t, J=8.1 Hz), 3.27 (3H, s), 3.17 (3H, s).
ESI (LC-MS positive mode) m/z 463 ([M+H]$^+$).

Example 1-H-16

3-(7-{2-[(2-Dimethylamino-ethyl)-ethyl-amino]-pyridin-4-yl}-2-morpholin-4-yl-6,7-dihydro-5H-pyrrolo[2,3-d]pyrimidin-4-yl)-phenol trifluoroacetic acid salt (H-16)

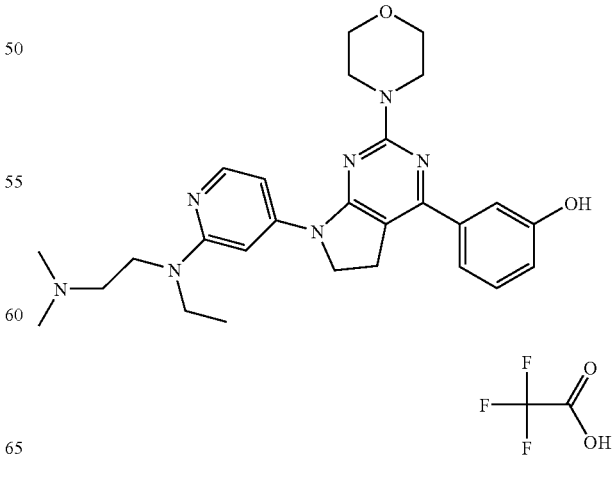

In the same manner as Example 1-H-03, using N,N-dimethyl-N'-ethyl-ethylenediamine, the desired compound was obtained.

¹H-NMR (400 MHz, DMSO-d₆) δ (ppm): 9.66 (1H, brs), 8.03 (1H, d, J=6.8 Hz), 7.23-7.50 (3H, m), 7.07 (1H, brs), 6.84-6.92 (1H, m), 4.16 (2H, t, J=8.1 Hz), 3.89 (2H, t, J=6.7 Hz), 3.74 (8H, dd, J=14.9, 4.8 Hz), 3.52-3.61 (2H, m), 3.28-3.39 (4H, m), 2.88 (6H, s), 1.16 (3H, t, J=7.0 Hz).

ESI (LC-MS positive mode) m/z 490 ([M+H]⁺).

Example 1-H-17

3-{7-[2-((R)-2-hydroxymethyl-pyrrolidin-1-yl)-pyridin-4-yl]-2-morpholin-4-yl-6,7-dihydro-5H-pyrrolo[2,3-d]pyrimidin-4-yl}-phenol trifluoroacetic acid salt (H-17)

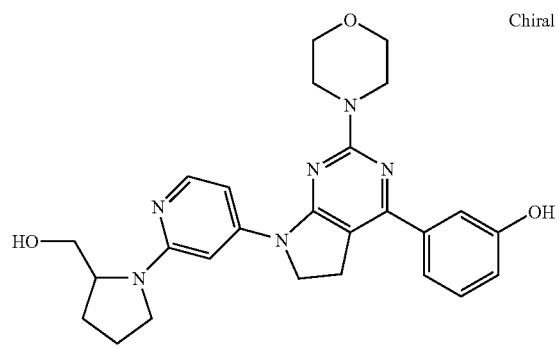

In the same manner as Example 1-H-03, using (R)-pyrrolidin-2-yl-methanol, the desired compound was obtained.

¹H-NMR (400 MHz, DMSO-d₆) δ (ppm): 7.92 (1H, d, J=7.5 Hz), 7.65 (1H, brs), 7.27-7.43 (3H, m), 7.21 (1H, brs), 6.89 (1H, d, J=7.9 Hz), 4.13-4.23 (3H, m), 3.75 (8H, dd, J=15.7, 4.8 Hz), 3.37-3.65 (4H, m), 3.33 (2H, t, J=8.1 Hz), 1.94-2.16 (4H, m).

ESI (LC-MS positive mode) m/z 475 [M+H]⁺.

Example 1-H-18

3-[2-Morpholin-4-yl-7-(4-pyrrolidin-1-yl-3,4,5,6-tetrahydro-2H-[1,2']bipyridinyl-4'-yl)-6,7-dihydro-5H-pyrrolo[2,3-d]pyrimidin-4-yl]-phenol trifluoroacetic acid salt (H-18)

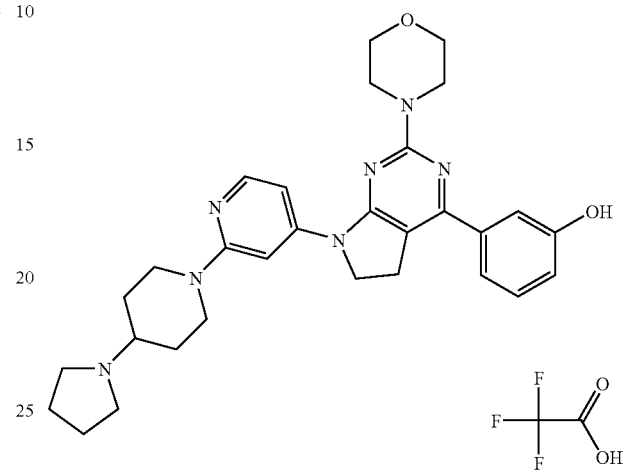

In the same manner as Example 1-H-03, using 4-pyrrolidin-1-yl-piperidine, the desired compound was obtained.

¹H-NMR (400 MHz, DMSO-d₆) δ (ppm): 10.13 (1H, brs), 8.05 (1H, d, J=7.1 Hz), 7.74 (1H, brs), 7.28-7.44 (4H, m), 6.89 (1H, d, J=7.9 Hz), 4.13-4.30 (4H, m), 3.75 (8H, d, J=7.1 Hz), 3.53-3.63 (2H, m), 3.39-3.49 (1H, m), 3.34 (2H, t, J=8.1 Hz), 3.06-3.22 (4H, m), 2.21 (2H, d, J=10.6 Hz), 1.97-2.08 (2H, m), 1.82-1.93 (2H, m), 1.60-1.76 (2H, m).

ESI (LC-MS positive mode) m/z 528 ([M+H]⁺).

Example 1-H-19

3-{7-[2-(Cyclohexylmethyl-amino)-pyridin-4-yl]-2-morpholin-4-yl-6,7-dihydro-5H-pyrrolo[2,3-d]pyrimidin-4-yl}-phenol trifluoroacetic acid salt (H-19)

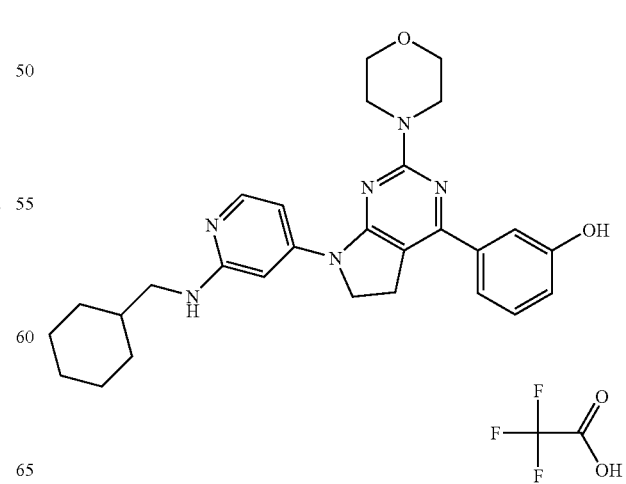

In the same manner as Example 1-H-03, using C-cyclohexylmethylamine, the desired compound was obtained.

¹H-NMR (400 MHz, DMSO-d₆) δ (ppm): 12.40 (1H, brs), 9.64 (1H, s), 7.87 (1H, d, J=7.3 Hz), 7.24-7.45 (3H, m), 6.84-6.99 (2H, m), 4.11 (2H, t, J=8.1 Hz), 3.66-3.82 (8H, m), 3.27-3.32 (2H, m), 3.13 (2H, t, J=6.2 Hz), 1.52-1.84 (6H, m), 1.10-1.33 (3H, m), 0.92-1.04 (2H, m).

ESI (LC-MS positive mode) m/z 487 ([M+H]⁺).

Example 1-H-20

3-{7-[2-(3,3-Dimethyl-butylamino)-pyridin-4-yl]-2-morpholin-4-yl-6,7-dihydro-5H-pyrrolo[2,3-d]pyrimidin-4-yl}-phenol trifluoroacetic acid salt (H-20)

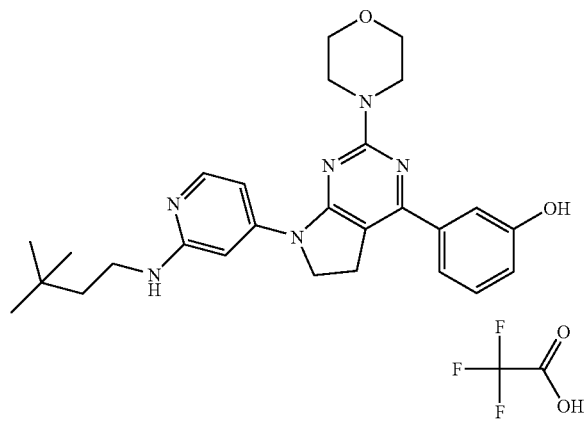

In the same manner as Example 1-H-03, using 3,3-dimethylbutylamine, the desired compound was obtained.

¹H-NMR (400 MHz, DMSO-d₆) δ (ppm): 12.51 (1H, brs), 9.64 (1H, brs), 8.09 (1H, brs), 7.89 (1H, d, J=7.5 Hz), 7.75-7.86 (1H, m), 7.25-7.48 (3H, m), 6.89 (2H, d, J=6.6 Hz), 4.12 (2H, t, J=8.1 Hz), 3.64-3.86 (8H, m), 3.22-3.32 (4H, m), 1.47-1.63 (2H, m), 0.96 (9H, s).

ESI (LC-MS positive mode) m/z 475 ([M+H]⁺).

Example 1-H-21

3-{7-[2-(Isobutyl-methyl-amino)-pyridin-4-yl]-2-morpholin-4-yl-6,7-dihydro-5H-pyrrolo[2,3-d]pyrimidin-4-yl}-phenol (H-21)

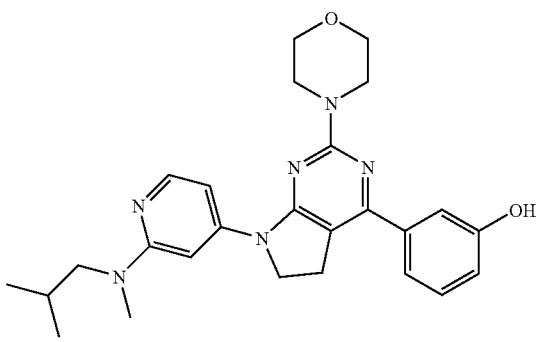

Using isobutylmethylamine instead of N-methylisobutylamine in Example 1-H-03, the desired compound was obtained.

¹H-NMR (400 MHz, DMSO-d₆) δ (ppm): 7.96 (1H, d, J=5.9 Hz), 7.37 (1H, s), 7.23-7.33 (2H, m), 7.13 (1H, s), 6.93 (1H, d, J=5.9 Hz), 6.83 (1H, d, J=7.7 Hz), 4.06 (2H, t, J=8.3 Hz), 3.72 (8H, dd, J=19.5, 5.0 Hz), 3.37 (2H, d, J=7.5 Hz), 3.25 (2H, t, J=8.2 Hz), 3.00 (3H, s), 1.97-2.11 (1H, m), 0.85 (6H, d, J=6.8 Hz).

ESI (LC-MS positive mode) m/z 461 ([M+H]⁺).

Example 1-H-22

3-(7-{2-[Methyl-(3-methyl-butyl)-amino]-pyridin-4-yl}-2-morpholin-4-yl-6,7-dihydro-5H-pyrrolo[2,3-d]pyrimidin-4-yl)-phenol (H-22)

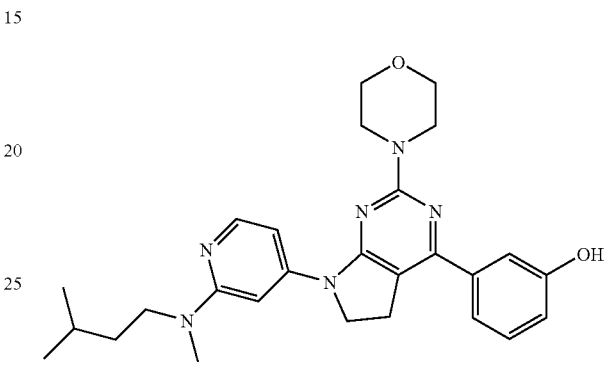

In the same manner as Example 1-H-03, using methyl-(3-methyl-butyl)-amine, the desired compound was obtained.

¹H-NMR (400 MHz, DMSO-d₆) δ (ppm): 7.97 (1H, d, J=5.7 Hz), 7.38 (1H, s), 7.23-7.34 (2H, m), 7.10 (1H, s), 6.94 (1H, dd, J=5.7, 1.8 Hz), 6.80-6.86 (1H, m), 4.05 (2H, t, J=8.2 Hz), 3.72 (8H, dd, J=18.1, 4.9 Hz), 3.51-3.59 (2H, m), 3.25 (2H, t, J=8.2 Hz), 2.96 (3H, s), 1.48-1.60 (1H, m), 1.36-1.45 (2H, m), 0.91 (6H, d, J=6.6 Hz).

ESI (LC-MS positive mode) m/z 475 ([M+H]⁺).

Example 1-H-23

1-{4-[4-(3-Hydroxy-phenyl)-2-morpholin-4-yl-5,6-dihydro-pyrrolo[2,3-d]pyrimidin-7-yl]-pyridin-2-yl}-pyrrolidin-3-ol (H-23)

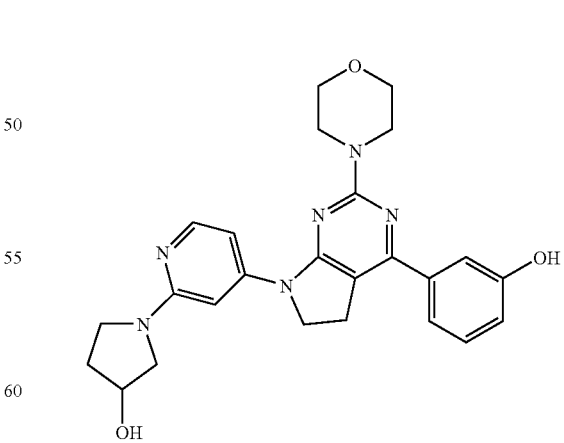

In the same manner as Example 1-H-03, using 3-hydroxypyrrolidine, the desired compound was obtained.

¹H-NMR (400 MHz, DMSO-d₆) δ (ppm): 7.96 (1H, d, J=5.9 Hz), 7.39 (1H, s), 7.23-7.36 (2H, m), 7.11 (1H, s), 6.82-6.93 (2H, m), 4.98 (1H, brs), 4.39 (1H, brs), 4.06 (2H, t, J=8.1 Hz), 3.66-3.81 (8H, m), 3.40-3.51 (2H, m), 3.21-3.31 (4H, m), 1.98-2.08 (1H, m), 1.85-1.94 (1H, m).

ESI (LC-MS positive mode) m/z 461 ([M+H]$^+$).

Example 1-H-24

3-{2-Morpholin-4-yl-7-[2-(4-phenyl-piperazin-1-yl)-pyridin-4-yl]-6,7-dihydro-5H-pyrrolo[2,3-d]pyrimidin-4-yl}-phenol trifluoroacetic acid salt (H-24)

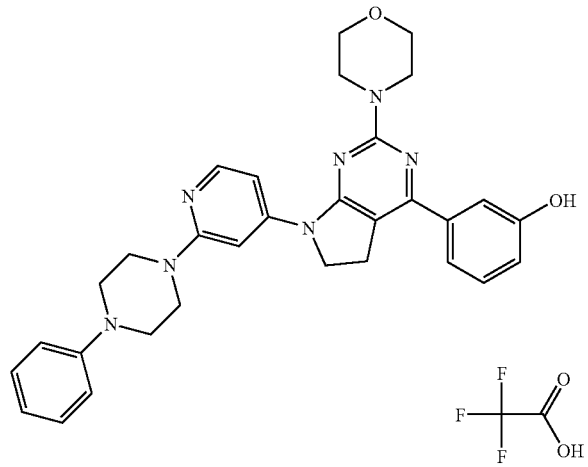

In the same manner as Example 1-H-03, using N-phenylpiperazine, the desired compound was obtained.

$^1$H-NMR (400 MHz, DMSO-d$_6$) δ (ppm): 8.03 (1H, d, J=7.3 Hz), 7.80 (1H, brs), 7.21-7.44 (6H, m), 7.02 (2H, d, J=8.9 Hz), 6.89 (1H, d, J=9.0 Hz), 6.84 (1H, t, J=7.3 Hz), 4.15-4.24 (2H, m), 3.71-3.82 (12H, m), 3.30-3.40 (6H, m).

ESI (LC-MS positive mode) m/z 536 ([M+H]$^+$).

Example 1-H-25

3-{7-[2-(Cyclopropylmethyl-propyl-amino)-pyridin-4-yl]-2-morpholin-4-yl-6,7-dihydro-5H-pyrrolo[2,3-d]pyrimidin-4-yl}-phenol trifluoroacetic acid salt (H-25)

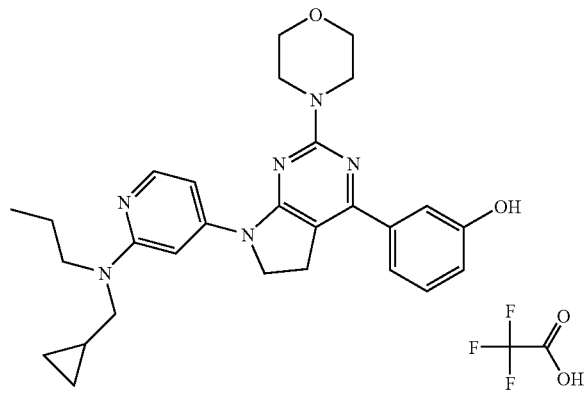

In the same manner as Example 1-H-03, using cyclopropylmethylpropylamine, the desired compound was obtained.

$^1$H-NMR (400 MHz, DMSO-d$_6$) δ (ppm): 9.66 (1H, brs), 7.92 (1H, d, J=7.3 Hz), 7.26-7.43 (4H, m), 6.89 (1H, d, J=9.0 Hz), 4.20 (2H, t, J=8.2 Hz), 3.68-3.84 (8H, m), 3.55 (2H, t, J=7.7 Hz), 3.46 (2H, d, J=6.6 Hz), 3.28-3.33 (2H, m), 1.55-1.68 (2H, m), 1.07-1.17 (1H, m), 0.91 (3H, t, J=7.3 Hz), 0.51-0.58 (2H, m), 0.39 (2H, q, J=4.8 Hz).

ESI (LC-MS positive mode) m/z 487 ([M+H]$^+$).

Example 1-H-26

3-{7-[2-(2,6-Dimethyl-morpholin-4-yl)-pyridin-4-yl]-2-morpholin-4-yl-6,7-dihydro-5H-pyrrolo[2,3-d]pyrimidin-4-yl}-phenol trifluoroacetic acid salt (H-26)

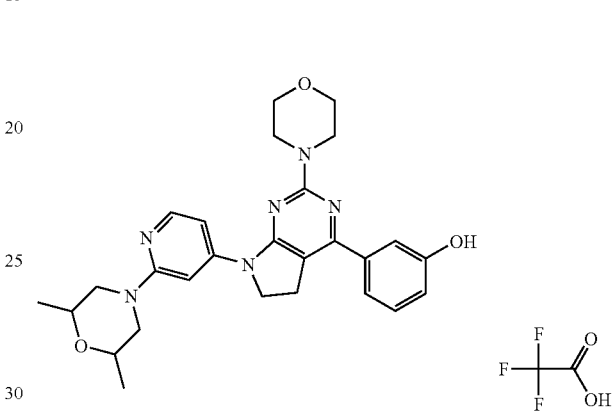

In the same manner as Example 1-H-03, using 2,6-dimethylmorpholine, the desired compound was obtained.

$^1$H-NMR (400 MHz, DMSO-d$_6$) δ (ppm): 9.67 (1H, brs), 8.02 (1H, d, J=7.1 Hz), 7.77 (1H, brs), 7.25-7.46 (4H, m), 6.89 (1H, d, J=7.9 Hz), 4.19 (2H, t, J=8.2 Hz), 3.98 (2H, d, J=11.9 Hz), 3.68-3.82 (10H, m), 3.27-3.40 (2H, m), 2.68-2.79 (2H, m), 1.18 (6H, d, J=6.2 Hz).

ESI (LC-MS positive mode) m/z 489 ([M+H]$^+$).

Example 1-H-27

3-{2-Morpholin-4-yl-7-[2-(3-morpholin-4-yl-propylamino)-pyridin-4-yl]-6,7-dihydro-5H-pyrrolo[2,3-d]pyrimidin-4-yl}-phenol trifluoroacetic acid salt (H-27)

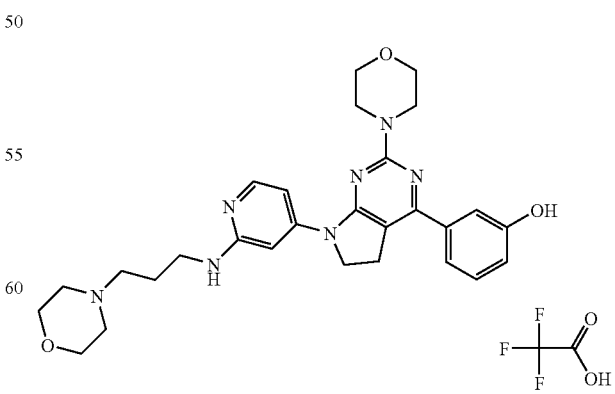

In the same manner as Example 1-H-03, using 3-morpholin-4-yl-propylamine, the desired compound was obtained.

¹H-NMR (400 MHz, DMSO-d₆) δ (ppm): 8.42 (1H, brs), 7.95 (1H, d, J=7.3 Hz), 7.77 (1H, brs), 7.26-7.47 (3H, m), 6.84-7.09 (2H, m), 4.13 (2H, t, J=7.8 Hz), 3.99 (1H, brs), 3.70-3.82 (8H, m), 3.46-3.58 (8H, m), 3.29-3.44 (4H, m), 3.10-3.24 (2H, m), 1.92-2.06 (2H, m).
ESI (LC-MS positive mode) m/z 518 ([M+H]⁺).

Example 1-H-28

3-{7-[2-(Indan-2-ylamino)-pyridin-4-yl]-2-morpholin-4-yl-6,7-dihydro-5H-pyrrolo[2,3-d]pyrimidin-4-yl}-phenol trifluoroacetic acid salt (H-28)

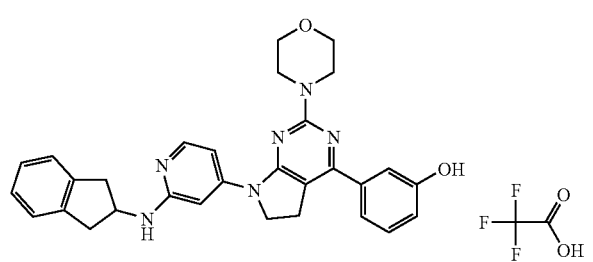

In the same manner as Example 1-H-03, using indan-2-ylamine, the desired compound was obtained.
¹H-NMR (400 MHz, DMSO-d₆) δ (ppm): 12.55 (1H, brs), 9.65 (1H, s), 8.49 (1H, brs), 7.90-8.00 (1H, m), 7.15-7.44 (7H, m), 6.89 (1H, d, J=7.9 Hz), 4.42-4.59 (1H, m), 4.01-4.18 (2H, m), 3.55-3.80 (8H, m), 3.38-3.47 (2H, m), 3.26-3.30 (2H, m), 2.92 (2H, dd, J=15.9, 5.3 Hz).
ESI (LC-MS positive mode) m/z 507 ([M+H]⁺).

Example 1-H-29

3-{7-[2-(2,5-Dihydro-pyrrol-1-yl)-pyridin-4-yl]-2-morpholin-4-yl-6,7-dihydro-5H-pyrrolo[2,3-d]pyrimidin-4-yl}-phenol trifluoroacetic acid salt (H-29)

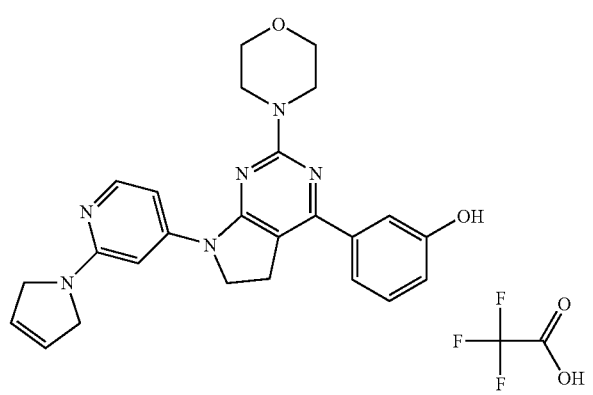

In the same manner as Example 1-H-03, using 2,5-dihydro-1H-pyrrole, the desired compound was obtained.
¹H-NMR (400 MHz, DMSO-d₆) δ (ppm): 9.65 (1H, s), 7.97 (1H, d, J=7.3 Hz), 7.59-7.68 (1H, m), 7.26-7.44 (4H, m), 6.89 (1H, d, J=9.0 Hz), 6.11 (2H, s), 4.33 (4H, s), 4.20 (2H, t, J=8.0 Hz), 3.76 (8H, dd, J=16.7, 4.9 Hz), 3.27-3.32 (2H, m).
ESI (LC-MS positive mode) m/z 443 ([M+H]⁺).

Example 1-H-30

3-[7-(2-Cyclohexylamino-pyridin-4-yl)-2-morpholin-4-yl-6,7-dihydro-5H-pyrrolo[2,3-d]pyrimidin-4-yl]-phenol trifluoroacetic acid salt (H-30)

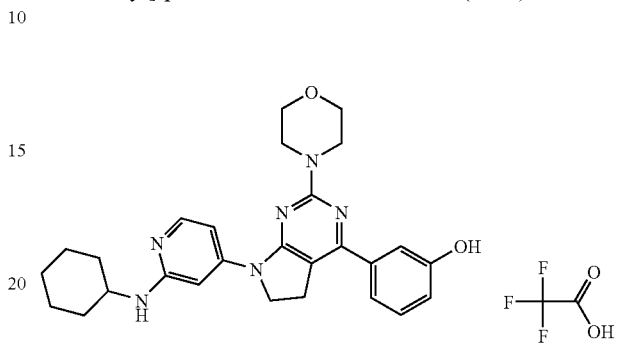

In the same manner as Example 1-H-03, using cyclohexylamine, the desired compound was obtained.
¹H-NMR (400 MHz, DMSO-d₆) δ (ppm): 9.66 (1H, s), 8.16 (1H, brs), 7.78-7.92 (2H, m), 7.23-7.44 (3H, m), 6.76-6.92 (2H, m), 4.09 (2H, t, J=8.1 Hz), 3.74 (8H, d, J=6.8 Hz), 3.56 (1H, brs), 3.25-3.33 (2H, m), 1.87-1.97 (2H, m), 1.70-1.79 (2H, m), 1.09-1.43 (6H, m).
ESI (LC-MS positive mode) m/z 473 ([M+H]⁺).

Example 1-H-31

5-[2-Morpholin-4-yl-7-(2-morpholin-4-yl-pyridin-4-yl)-6,7-dihydro-5-pyrrolo[2,3-d]pyrimidin-4-yl]-pyrimidin-2-ylamine (H-31)

Step A

{5-[7-(2-Chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine

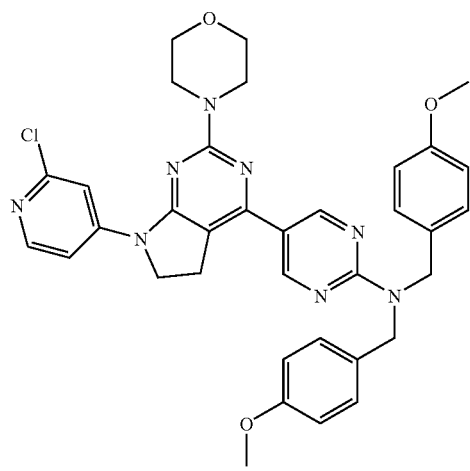

Bis-(4-methoxybenzyl)-[5-(2-morpholin-4-yl-6,7-dihydro-5H-pyrrolo[2,3-d]pyrimidin-4-yl)-pyrimidin-2-yl]- amine (1.65 g) was suspended in dimethylformamide (20 ml), followed by addition of 2-chloro-4-iodopyridine (805 mg), palladium acetate (35 mg), triphenylphosphine (81 mg) and potassium phosphate (1.95 g), and argon gas was blown for 10 minutes while irradiating ultrasonic wave. The reaction mixture was stirred at 100° C. for 1 hour, and cooled to room temperature, followed by addition of water (50 ml). The mixture was extracted with ethyl acetate (100 ml) and dichloromethane (100 ml), and the combined organic layers were washed with brine, followed by drying over sodium sulfate. After filtering off the drying agent, the filtrate was concentrated under reduced pressure, and the resulting residue was purified by silica gel column chromatography (dichloromethane/methanol=50/1), followed by suspension of the residue in ethyl acetate/hexane (10 ml/50 ml). The precipitate was filtered, and washed with hexane, followed by drying under reduced pressure, to obtain a yellow powder (1.75 g, 88%).

$^1$H-NMR (300 MHz, CDCl$_3$) δ (ppm): 8.99 (2H, s), 8.27 (1H, d, J=5.7 Hz), 7.82 (1H, d, J=1.9 Hz), 7.71 (1H, dd, J=5.7, 1.9 Hz), 7.20 (4H, d, J=8.4 Hz), 6.86 (4H, d, J=8.4 Hz), 4.84 (4H, s), 4.08 (2H, t, J=8.4 Hz), 3.81-3.89 (8H, m), 3.80 (6H, s), 3.36 (2H, t, J=8.4 Hz).

ESI (LC-MS positive mode) m/z 651 [(M+H)$^+$].

Step B

Bis-(4-methoxy-benzyl)-{5-[2-morpholin-4-yl-7-(2-morpholin-4-yl-pyridin-4-yl)-6,7-dihydro-5H-pyrrolo[2,3-d]pyrimidin-4-yl]-pyrimidin-2-yl}-amine

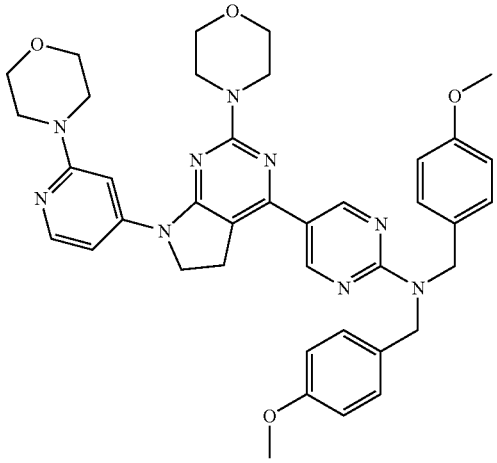

To a solution of {5-[7-(2-chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine (50 mg) obtained in Step A, sodium t-butoxide (50 mg) and palladium dibenzylideneacetone complex (6 mg) suspended in toluene (1.5 ml), argon gas was blown for 5 minutes. Morpholine (10 μl) and 2,8,9-triisobutyl-2,5,8,9-tetraaza-1-phospha-bicyclo[3.3.3]undecane (6.9 mg) were added, followed by stirring at 110° C. for 6 hours. The reaction mixture was cooled to room temperature, and water (5 ml) was added, followed by extraction with dichloromethane (10 ml×2). The combined organic layers were washed with brine, and dried over sodium sulfate. After the drying agent was filtered off, the filtrate was concentrated under reduced pressure, and the resulting residue was purified by silica gel column chromatography (dichloromethane/methanol=50/1), to obtain a yellow amorphous (46 mg, 85%).

$^1$H-NMR (300 MHz, CDCl$_3$) δ (ppm): 8.99 (2H, s), 8.14 (1H, d, J=6.2 Hz), 7.40-7.46 (1H, m), 7.20 (4H, d, J=8.4 Hz), 7.02-7.10 (1H, m), 6.86 (4H, d, J=8.7 Hz), 4.84 (4H, s), 4.11 (2H, t, J=8.4 Hz), 3.76-3.89 (18H, m), 3.55-3.62 (4H, m), 3.34 (2H, t, J=8.4 Hz).

ESI (LC-MS positive mode) m/z 702 [(M+H)$^+$].

Step C

5-[2-Morpholin-4-yl-7-(2-morpholin-4-yl-pyridin-4-yl)-6,7-dihydro-5-pyrrolo[2,3-d]pyrimidin-4-yl]-pyrimidin-2-ylamine

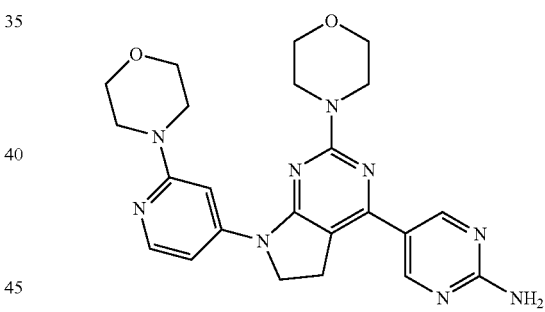

Bis-(4-methoxy-benzyl)-{5-[2-morpholin-4-yl-7-(2-morpholin-4-yl-pyridin-4-yl)-6,7-dihydro-5H-pyrrolo[2,3-d]pyrimidin-4-yl]-pyrimidin-2-yl}-amine (48 mg) obtained in Step B was stirred in TFA (0.5 ml) at 80° C. for 2.5 hours. After the reaction mixture was cooled to room temperature, the solvent was distilled off under reduced pressure. The reaction mixture was basified with sodium bicarbonate water (pH 8 to 9), followed by extraction with dichloromethane/methanol (10/1, 20 ml×3). The combined organic layers were washed with brine, and dried over sodium sulfate. After the drying agent was filtered off, the filtrate was concentrated under reduced pressure, and the resulting residue was purified by silica gel column chromatography (dichloromethane/methanol=20/1), to obtain a yellow solid (16 mg, 51%).

¹H-NMR (300 MHz, TFA-d) δ (ppm): 9.24 (2H, s), 8.04-8.10 (2H, m), 7.16-7.18 (1H, m), 4.53-4.58 (2H, m), 4.10-4.26 (12H, m), 3.84-3.95 (4H, m), 3.45-3.51 (2H, m).

ESI (LC-MS positive mode) m/z 462 [(M+H)⁺].

Example 1-H-32

5-[7-(2-Dimethylaminoethoxy-pyridin-4-yl)-2-morpholin-4-yl-6,7-dihydro-5H-pyrrolo[2,3-d]pyrimidin-4-yl]-pyrimidin-2-ylamine (H-32)

Step A (5-{7-[2-(2-Dimethylaminoethoxy)-pyridin-4-yl]-2-morpholin-4-yl-6,7-dihydro-5H-pyrrolo[2,3-d]pyrimidin-4-yl}-pyrimidin-2-yl)-bis-(4-methoxy-benzyl)-amine

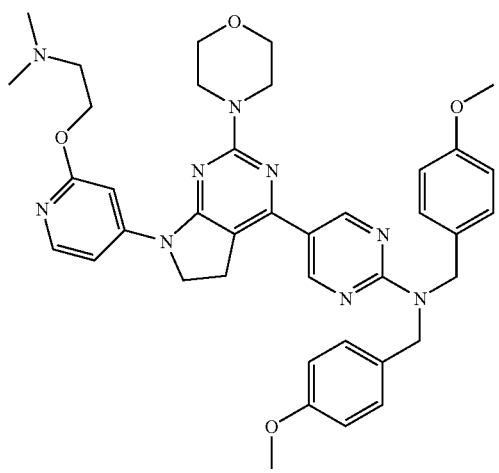

Sodium hydride (15 mg, 60% mineral oil dispersion, 5 equivalents) and N,N-dimethylaminoethanol (39 μl, 5 equivalents) were added to toluene (1.3 ml). After refluxing for 5 minutes, stirring was carried out at 50° C. for 15 minutes. {5-[7-(2-Chloro-pyridin-4-yl)-2-morpholin-4-yl-6,7-dihydro-5H-pyrrolo[2,3-d]pyrimidin-4-yl]-pyrimidin-2-yl}-bis-(4-methoxy-benzyl)-amine (50 mg) obtained in Step A in Example 1-H-31 was added, followed by refluxing overnight, and the reaction mixture was concentrated under reduced pressure. The resulting residue was purified by silica gel column chromatography (dichloromethane/methanol=30/1 to 10/1), to obtain a colorless solid (54 mg, 100%).

¹H-NMR (300 MHz, CDCl₃) δ (ppm): 8.99 (2H, s), 8.05 (1H, d, J=6.1 Hz), 7.77 (1H, dd, J=6.1, 1.9 Hz), 7.17-7.21 (4H, m), 6.84-6.90 (5H, m), 4.84 (4H, s), 4.56 (2H, bs), 4.03-4.08 (2H, m), 3.80-3.85 (14H, m), 3.30-3.35 (2H, m), 2.96 (2H, brs), 2.52 (6H, brs).

ESI (LC-MS positive mode) m/z 705 [(M+H)⁺].

Step B

5-[7-(2-Dimethylaminoethoxy-pyridin-4-yl)-2-morpholin-4-yl-6,7-dihydro-5H-pyrrolo[2,3-d]pyrimidin-4-yl]-pyrimidin-2-ylamine

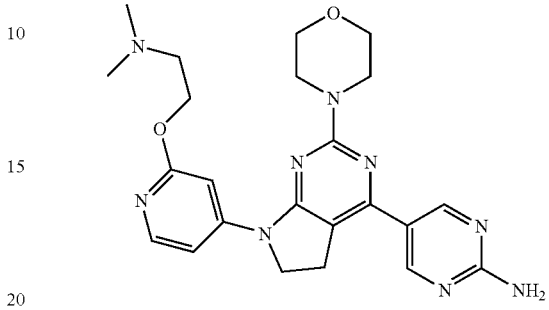

The same operation as Step C in Example 1-H-31 was carried out, followed by purification by amino silica gel column chromatography (dichloromethane/methanol=100/1), to obtain a colorless solid (12 mg, 36%).

¹H-NMR (300 MHz, CDCl₃) δ (ppm): 8.88 (2H, s), 8.06 (1H, d, J=6.1 Hz), 7.76 (1H, dd, J=6.1, 1.9 Hz), 6.84-6.87 (1H, m), 5.31 (2H, s), 4.43-4.46 (2H, m), 4.01-4.07 (2H, m), 3.84 (8H, m), 3.27-3.32 (2H, m), 2.75-2.79 (2H, m), 2.38 (6H, s).

ESI (LC-MS positive mode) m/z 464 [(M+H)⁺].

Example 1-H-33

N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (H-33)

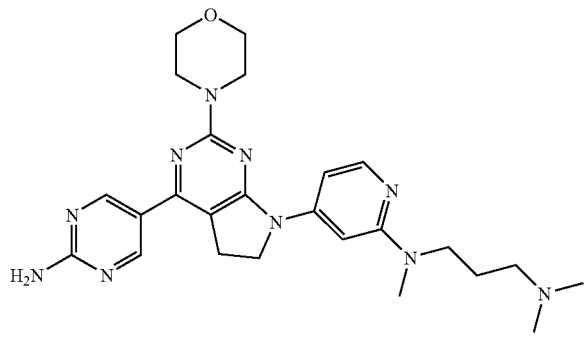

In Step B in Example 1-H-31, using N,N',N'-trimethyl-propan-1,3-diamine instead of morpholine, the same operation was carried out, and subsequently the same operation as Step C in Example 1-H-31 was carried out, to obtain the desired compound.

¹H-NMR (CDCl₃) δ (ppm): 8.89 (2H, s), 8.08 (1H, d, J=5.7 Hz), 7.11 (1H, s), 6.88 (1H, dd, J=5.7 Hz, 1.9 Hz), 5.26 (2H, s), 4.09 (2H, m), 3.83 (8H, m), 3.61 (2H, m), 3.28 (2H, m), 3.06 (3H, s), 2.31 (2H, m), 2.22 (6H, s), 1.78 (2H, m).

LCMS (ESI+) m/z 491 ([M+H]⁺).

Example 1-H-34

5-{7-[2-(4-Ethyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-34)

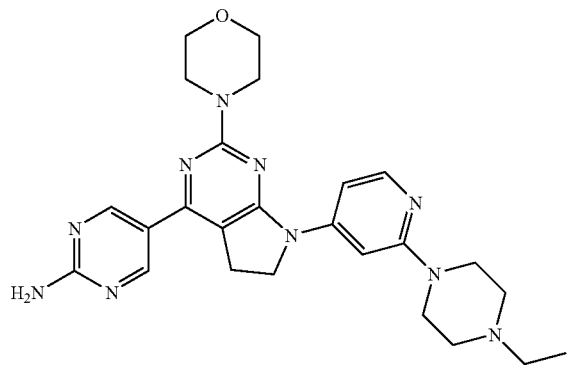

In Step B in Example 1-H-31, using 4-ethyl-piperazine instead of morpholine, the same operation was carried out, and subsequently the same operation as Step C in Example 1-H-31 was carried out, to obtain the desired compound.

$^1$H-NMR (CDCl$_3$) δ (ppm): 8.89 (2H, s), 8.13 (1H, d, J=5.7 Hz), 7.43 (1H, s), 6.92 (1H, d, J=5.3 Hz), 5.26 (2H, s), 4.09 (2H, m), 3.83 (8H, m), 3.63 (4H, m), 3.29 (2H, m), 2.65 (4H, m), 2.64 (2H, m), 1.17 (3H, m).

LCMS (ESI+) m/z 489 ([M+H]$^+$).

Example 1-H-35

{4'-[4-(2-Amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (H-35)

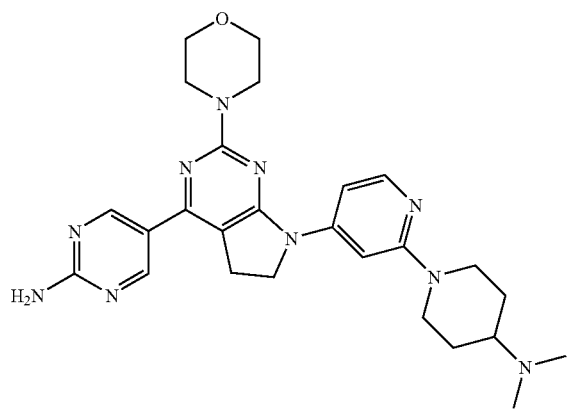

In Step B in Example 1-H-31, using 4-dimethylamino-piperidine instead of morpholine, the same operation was carried out, and subsequently the same operation as Step C in Example 1-H-31 was carried out, to obtain the desired compound.

$^1$H-NMR (CDCl$_3$) δ (ppm): 8.89 (2H, s), 8.11 (1H, d, J=5.7 Hz), 7.49 (1H, s), 6.83 (1H, d, J=5.3 Hz), 5.23 (2H, s), 4.35 (2H, m), 4.09 (2H, m), 3.83 (8H, m), 3.29 (2H, m), 2.86 (2H, m), 2.31 (6H, s), 1.91 (2H, m), 1.53 (2H, m).

LCMS (ESI+) m/z 503 ([M+H]$^+$).

Example 1-H-36

5-{7-[2-(4-Methyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-36)

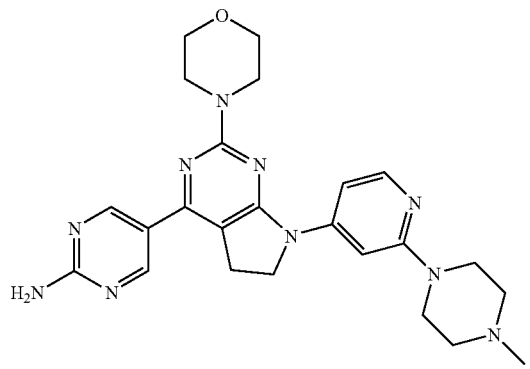

In Step B in Example 1-H-31, using 1-methyl-piperazine instead of morpholine, the same operation was carried out, and subsequently the same operation as Step C in Example 1-H-31 was carried out, to obtain the desired compound.

$^1$H-NMR (CDCl$_3$) δ (ppm): 8.89 (2H, s), 8.13 (1H, d, J=6.1 Hz), 7.42 (1H, s), 6.93 (1H, m), 5.24 (2H, s), 4.09 (2H, t, J=7.6 Hz), 3.83 (8H, m), 3.67 (4H, m), 3.29 (2H, t, J=7.6 Hz), 2.65 (4H, m), 2.43 (3H, s).

LCMS (ESI+) m/z 475 ([M+H]$^+$).

Example 1-I

Bis-(4-methoxy-benzyl)-[5-(2-morpholin-4-yl-6,7-dihydro-5H-pyrrolo[2,3-d]pyrimidin-4-yl)-pyrimidin-2-yl]-amine to be used in the following Example 1-I-01 was prepared according to Example 1-J-02 described later.

Example 1-I-01

N-{3-[4-(2-amino-pyrimidin-5-yl)-2-morpholin-4-yl-5,6-dihydro-pyrrolo[2,3-d]pyrimidin-7-yl]-phenyl}-methane sulfonamide (I-01)

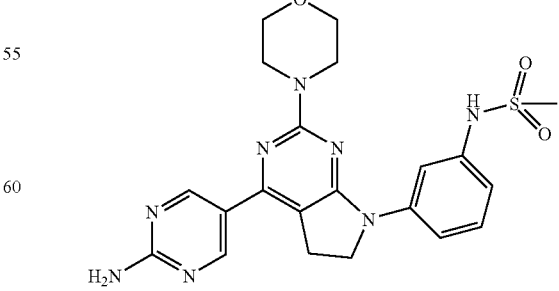

Bis-(4-methoxybenzyl)-[5-(2-morpholin-4-yl-6,7-dihydro-5H-pyrrolo[2,3-d]pyrimidin-4-yl)-pyrimidin-2-yl]- amine (162 mg), palladium acetate (1.0 mg, 0.015 equivalents), S-Phos (3.7 mg, 0.03 equivalents), 3-iodo-nitrobenzene (82 mg, 1.1 equivalents) and potassium phosphate (128 mg, 2 equivalents) were stirred in dimethylformamide (3 ml) at 100° C. for 1 hour under an argon air stream. After the reaction mixture was cooled to room temperature, water (20 ml) was added, and the resulting precipitate was filtered, followed by washing with ether, to obtain bis-(4-methoxy-benzyl)-{5-[2-morpholin-4-yl-7-(3-nitro-phenyl)-6,7-dihydro-5H-pyrrolo[2,3-d]pyrimidin-4-yl]-pyrimidin-2-yl}-amine as a yellow powder (138 mg, 70%). The above yellow powder was suspended in ethanol/water (5 ml/5 ml), and sodium hydrosulfite (110 mg, 3 equivalents) was added, followed by refluxing for 3 hours. The reaction mixture was concentrated under reduced pressure and diluted with 20 ml of water, and subsequently the resulting precipitate was filtered and dried, to obtain {5-[7-(3-amino-phenyl)-2-morpholin-4-yl-6,7-dihydro-5H-pyrrolo[2,3-d]pyrimidin-4-yl]-pyrimidin-2-yl}-bis-(4-methoxy-benzyl)-amine as a yellow powder (122 mg, 93%). The above yellow powder (50 mg) was dissolved in pyridine (1 ml), and mesyl chloride (13 μl, 2 equivalents) was added, followed by stirring for 5 hours. Saturated aqueous ammonium chloride solution (10 ml) was added, followed by extraction with ethyl acetate (10 ml×2), and the combined organic layers were washed with brine and dried over sodium sulfate. After the drying agent was filtered off, the filtrate was concentrated under reduced pressure, and subsequently the resulting residue was purified by amino silica gel column chromatography (dichloromethane), to obtain N-[3-(4-{2-[bis-(4-methoxy-benzyl)-amino]-pyrimidin-5-yl}-2-morpholin-4-yl-5,6-dihydro-pyrrolo[2,3-d]pyrimidin-7-yl)-phenyl]-methanesulfonamide as a pale yellow solid (38 mg, 68%). The above solid (38 mg) was dissolved in trifluoroacetic acid (2 ml), followed by refluxing for 5 hours in the presence of N-acetylcysteine (20 mg, 2.2 equivalents). The reaction mixture was concentrated under reduced pressure, and the resulting residue was diluted with methanol (500 μl) and water (3 ml), whereby the resulting precipitate was filtered and washed with ether, to obtain the title compound as a grayish white powder (24 mg, 96%).

$^1$H-NMR (DMSO-d$_6$) δ (ppm): 8.81 (2H, s), 7.81 (1H, s), 7.37 (1H, d, J=7.7 Hz), 7.27 (1H, t, J=8.1 Hz), 7.09 (2H, s), 6.81 (1H, d, J=7.7 Hz), 4.05 (2H, t, J=8.6 Hz), 3.75-3.65 (8H, m), 3.28 (2H, t, J=8.6 Hz), 2.92 (3H, s).

ESI (LC-MS positive mode) m/z 469 [(M+H)$^+$].

Example 2

The following compounds can be synthesized in the same manner as the above each Example.

| Structural formula | Compound name |
|---|---|
| 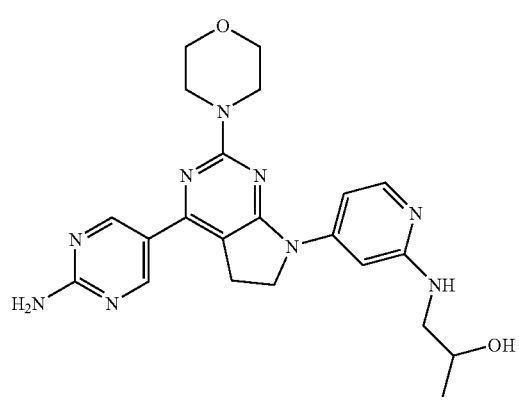 | 1-{4-[4-(2-amino-pyrimidin-5-yl)-2-morpholin-4-yl-5,6-dihydro-pyrrolo[2,3-d]pyrimidin-7-yl]-pyridin-2-ylamino}-propan-2-ol |
| 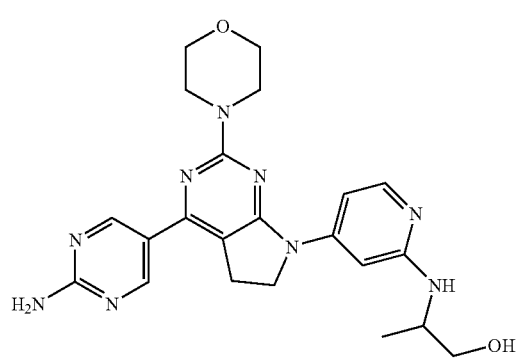 | 2-{4-[4-(2-amino-pyrimidin-5-yl)-2-morpholin-4-yl-5,6-dihydro-pyrrolo[2,3-d]pyrimidin-7-yl]-pyridin-2-ylamino}-propan-1-ol |

| Structural formula | Compound name |
| --- | --- |
| | N-{4-[4-(2-amino-pyrimidin-5-yl)-2-morpholin-4-yl-5,6-dihydro-pyrrolo[2,3-d]pyrimidin-7-yl]-pyridin-2-yl}-N',N'-dimethyl-propan-1,3-diamine |
| | 1-{4-[4-(2-amino-pyrimidin-5-yl)-2-morpholin-4-yl-5,6-dihydro-pyrrolo[2,3-d]pyrimidin-7-yl]-pyridin-2-yl}-pyrrolidin-3-ol |
| | 4-(2-amino-pyrimidin-5-yl)-2-morpholin-4-yl-5,6-dihydro-pyrrolo[2,3-d]pyrimidin-7-carbothio acid methylamide |
| | 1-[4-(2-amino-pyrimidin-5-yl)-2-morpholin-4-yl-5,6-dihydro-pyrrolo[2,3-d]pyrimidin-7-yl]-2,2-dimethyl-propan-1-one |

-continued

| Structural formula | Compound name |
| --- | --- |
| | 3-{4-[4-(2-amino-pyrimidin-5-yl)-2-morpholin-4-yl-5,6-dihydro-pyrrolo[2,3-d]pyrimidin-7-yl]-pyridin-2-yl}-benzoic acid methyl ester |
| | 3-{4-[4-(2-amino-pyrimidin-5-yl)-2-morpholin-4-yl-5,6-dihydro-pyrrolo[2,3-d]pyrimidin-7-yl]-pyridin-2-yl}-N-(3-carbamoyl-propyl)-benzamide |
| | 2-(2-morpholin-4-yl-7-pyridin-4-yl-6,7-dihydro-5H-pyrrolo[2,3-d]-pyrimidin-4-yl)-thiazole-5-carboxylic acid amide |
| | 2-(2-morpholin-4-yl-7-pyridin-3-yl-6,7-dihydro-5H-pyrrolo[2,3-d]-pyrimidin-4-yl)-thiazole-5-carboxylic acid amide |

| Structural formula | Compound name |
|---|---|
| | 2-(2-morpholin-4-yl-7-pyridin-4-yl-6,7-dihydro-5H-pyrrolo[2,3-d]-pyrimidin-4-yl)-thiazol-5-ylamine |
| | 2-(2-morpholin-4-yl-7-pyridin-3-yl-6,7-dihydro-5H-pyrrolo[2,3-d]-pyrimidin-4-yl)-thiazol-5-ylamine |
| | 2-(2-morpholin-4-yl-7-pyridin-4-yl-6,7-dihydro-5H-pyrrolo[2,3-d]-pyrimidin-4-yl)-thiazole-4-carboxylic acid amide |
| | 2-(2-morpholin-4-yl-7-pyridin-3-yl-6,7-dihydro-5H-pyrrolo[2,3-d]-pyrimidin-4-yl)-thiazole-4-carboxylic acid amide |
| | 2-(2-morpholin-4-yl-7-pyridin-4-yl-6,7-dihydro-5H-pyrrolo[2,3-d]-pyrimidin-4-yl)-thiazol-4-ylamine |

| Structural formula | Compound name |
|---|---|
| | 2-(2-morpholin-4-yl-7-pyridin-3-yl-6,7-dihydro-5H-pyrrolo[2,3-d]-pyrimidin-4-yl)-thiazol-4-ylamine |
| | 5-(2-morpholin-4-yl-7-pyridin-4-yl-6,7-dihydro-5H-pyrrolo[2,3-d]-pyrimidin-4-yl)-thiazol-2-ylamine |
| | 5-(2-morpholin-4-yl-7-pyridin-3-yl-6,7-dihydro-5H-pyrrolo[2,3-d]-pyrimidin-4-yl)-thiazol-2-ylamine |
| | 2-({4-[4-(2-amino-pyrimidin-5-yl)-2-morpholin-4-yl-5,6-dihydro-pyrrolo[2,3-d]pyrimidin-7-yl]-pyridin-2-yl}-methyl-amino)-ethanol |
| | 5-(7-{2-[(2-methoxy-ethyl)-methyl-amino]-pyridin-4-yl}-2-morpholin-4-yl-6,7-dihydro-5H-pyrrolo[2,3-d]pyrimidin-4-yl)-pyrimidin-2-ylamine |

| Structural formula | Compound name |
|---|---|
| | 3-{4-[4-(2-amino-pyrimidin-5-yl)-2-morpholin-4-yl-5,6-dihydro-pyrrolo[2,3-d]pyrimidin-7-yl]-pyridin-2-ylamino}-propan-1-ol |
| | N-(2-{4-[4-(2-amino-pyrimidin-5-yl)-2-morpholin-4-yl-5,6-dihydro-pyrrolo[2,3-d]pyrimidin-7-yl]-pyridin-2-ylsulfanyl}-ethyl)-acetamide |
| | 3-{4-[4-(2-amino-pyrimidin-5-yl)-2-morpholin-4-yl-5,6-dihydro-pyrrolo[2,3-d]pyrimidin-7-yl]-pyridin-2-ylsulfanyl}-propionamide |
| | N-(2-{4-[4-(2-amino-pyrimidin-5-yl)-2-morpholin-4-yl-5,6-dihydro-pyrrolo[2,3-d]pyrimidin-7-yl]-6-methanesulfonylamino-pyridin-2-ylsulfanyl}-ethyl)-acetamide |

-continued

| Structural formula | Compound name |
| --- | --- |
| | 5-(7-methyl-2-morpholin-4-yl-6,7-dihydro-5H-pyrrolo[2,3-d]-pyrimidin-4-yl)-pyrimidin-2-ylamine |
| | 5-(7-allyl-2-morpholin-4-yl-6,7-dihydro-5H-pyrrolo[2,3-d]-pyrimidin-4-yl)-pyrimidin-2-ylamine |
| | 4-[4-(2-amino-pyrimidin-5-yl)-2-morpholin-4-yl-5,6-dihydro-pyrrolo[2,3-d]pyrimidin-7-yl]-butyric acid methyl ester |
| | 4-[4-(2-amino-pyrimidin-5-yl)-2-morpholin-4-yl-5,6-dihydro-pyrrolo[2,3-d]pyrimidin-7-yl]-butyric acid |

-continued

| Structural formula | Compound name |
|---|---|
| | 4-[4-(2-amino-pyrimidin-5-yl)-2-morpholin-4-yl-5,6-dihydro-pyrrolo[2,3-d]pyrimidin-7-yl]-butyramide |
| | [5-(2-morpholin-4-yl-7-pyridin-4-yl-6,7-dihydro-5H-pyrrolo[2,3-d]-pyrimidin-4-yl)-pyrimidin-2-yl]-hydrazine |
| | 2-(2-morpholin-4-yl-4-pyridin-4-yl-5,6-dihydro-pyrrolo[2,3-d]-pyrimidin-7-yl)-thiazole-5-carboxylic acid amide |
| | 2-(2-morpholin-4-yl-4-pyridin-4-yl-5,6-dihydro-pyrrolo[2,3-d]-pyrimidin-7-yl)-thiazole-4-carboxylic acid amide |
| | 5-(2-morpholin-4-yl-4-pyridin-4-yl-5,6-dihydro-pyrrolo[2,3-d]-pyrimidin-7-yl)-thiazol-2-ylamine |

| Structural formula | Compound name |
|---|---|
|  | 5-(2-morpholin-4-yl-7-{4-[4-(2,2,2-trifluoroethyl)piperazin-1-ylmethyl]-phenyl}-6,7-dihydro-5H-pyrrolo[2,3-d]pyrimidin-4-yl}-pyrimidin-2-ylamine |

Hereinafter, there is described a process for the preparation of an intermediate compound to be used for the preparation of a compound of the formula (I) of the present invention.

Example 1-J-01

4-(3-t-Butoxyphenyl)-2-morpholin-4-yl-6,7-dihydro-5H-pyrrolo[2,3-d]pyrimidine (J-01)

Step A1

{[6-Chloro-5-(2-chloroethyl)-2-morpholin-4-yl]-pyrimidin-4-yl}-(4-methoxybenzyl)-amine (J-01-A1)

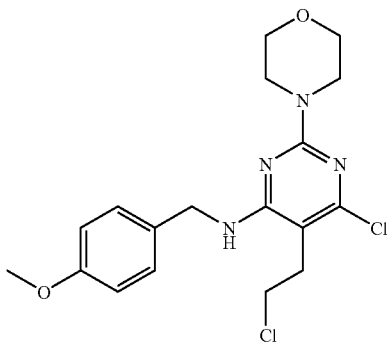

4-[4,6-Dichloro-5-(2-chloroethyl)-pyrimidin-2-yl]-morpholine (2.9 g) obtained in Step B in Example 1-B-01, 4-methoxybenzylamine (1.91 ml) and diisopropylethylamine (3.40 ml) were dissolved in acetonitrile (40 ml), followed by refluxing for 10 hours. Further, 4-methoxybenzylamine (0.64 ml) and diisopropylethylamine (0.85 ml) were added, followed by refluxing for 1 hour. After the solvent was concentrated under reduced pressure, the residue was dissolved in ethyl acetate (150 ml), which was washed with saturated aqueous ammonium chloride solution (200 ml) and brine (200 ml), followed by drying over sodium sulfate. The drying agent was filtered off, followed by concentration, and the resulting residue was purified by silica gel column chromatography (dichloromethane/methanol=100/0 to 100/1), to obtain the desired compound as a yellow solid (2.13 g, 55%).

$^1$H-NMR (270 MHz, CDCl$_3$) δ (ppm): 7.23 (2H, d, J=8.7 Hz), 6.87 (2H, d, J=8.7 Hz), 5.16 (1H, t, J=5.4 Hz), 4.55 (2H, d, J=5.4 Hz), 3.80 (3H, s), 3.68-3.78 (8H, m), 3.62 (2H, t, J=7.3 Hz), 2.91 (2H, t, J=7.3 Hz).

ESI (LC-MS positive mode) m/z 361 [(M+H)$^+$].

Step A2

{[6-Chloro-5-(2-chloroethyl)-2-morpholin-4-yl]}-pyrimidin-4-yl}-(2,4-dimethoxybenzyl)-amine (J-01-A2)

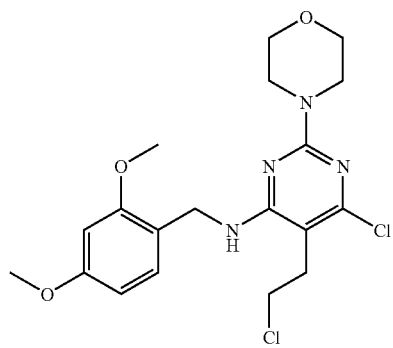

In the same manner as Step A1, from 4-[4,6-dichloro-5-(2-chloroethyl)-pyrimidin-2-yl]-morpholine and 2,4-dimethoxybenzylamine, the desired compound was obtained as a yellow solid.

$^1$H-NMR (270 MHz, CDCl$_3$) δ (ppm): 7.16 (1H, d, J=8.2 Hz), 6.48 (1H, d, J=2.3 Hz), 6.42 (1H, dd, J=8.2, 2.3 Hz), 5.43 (1H, t, J=5.6 Hz), 4.52 (2H, d, J=5.6 Hz), 3.86 (3H, s), 3.80 (3H, s), 3.70-3.77 (8H, m), 3.55 (2H, t, J=7.6 Hz), 2.89 (2H, t, J=7.6 Hz).

ESI (LC-MS positive mode) m/z 427 [(M+H)$^+$].

Step B1

4-Chloro-7-(4-methoxybenzyl)-2-morpholin-4-yl-6,7-dihydro-5H-pyrrolo[2,3-d]pyrimidine (J-01-B1)

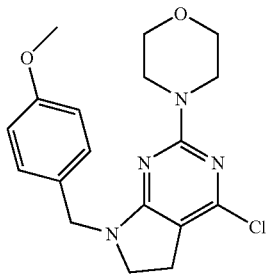

Compound J-01-A1 (2.30 g) prepared as in the above was dissolved in acetonitrile (290 ml), and cesium carbonate (5.65 g) and sodium iodide (1.83 g) were added, followed by refluxing for 10 hours. The reaction mixture was diluted with water (200 ml), followed by extraction with ethyl acetate (200 ml×2). After the organic layer was washed with brine and dried over sodium sulfate, the drying agent was filtered off, and the filtrate was concentrated under reduced pressure, to obtain a pale yellow powder (2.10 g). The crude product was used for the next reaction without purification.

$^1$H-NMR (270 MHz, CDCl$_3$) δ (ppm): 7.19 (2H, d, J=8.5 Hz), 6.86 (2H, d, J=8.5 Hz), 4.48 (2H, s), 3.80 (3H, s), 3.70-3.80 (8H, m), 3.43 (2H, t, J=8.4 Hz), 2.87 (2H, t, J=8.4 Hz).

ESI (LC-MS positive mode) m/z 361 [(M+H)$^+$].

Step B2

4-Chloro-7-(2,4-dimethoxybenzyl)-2-morpholin-4-yl-6,7-dihydro-5H-pyrrolo[2,3-d]pyrimidine (J-01-B2)

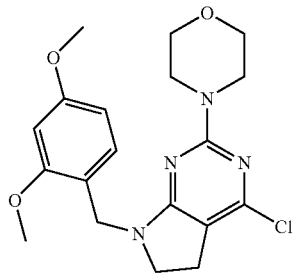

In the same manner as Step B1, from Compound J-01-A2 prepared as in the above, the desired compound was obtained as a pale yellow powder. The crude product was used for the next reaction without purification.

$^1$H-NMR (270 MHz, CDCl$_3$) δ (ppm): 7.14 (1H, d, J=7.9 Hz), 6.46 (1H, d, J=2.2 Hz), 6.42 (1H, dd, J=7.9, 2.2 Hz), 4.49 (2H, s), 3.81 (3H, s), 3.80 (3H, s), 3.61-3.81 (8H, m), 3.50 (2H, t, J=8.7 Hz), 2.86 (2H, t, J=8.7 Hz).

ESI (LC-MS positive mode) m/z 391 [(M+H)$^+$].

Step C

4-Chloro-2-morpholin-4-yl-6,7-dihydro-5H-pyrrolo[2,3-d]pyrimidine (J-01-C)

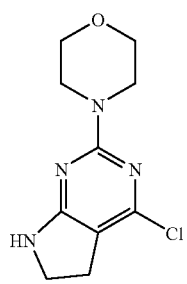

[Method C-1]

Compound J-01-B1 (1.87 g) prepared as in the above was dissolved in trifluoroacetic acid (5.2 ml), and concentrated sulfuric acid (290 μl, 1.05 equivalents) was added, followed by refluxing for 3 hours. Excess amount of solvent was removed under reduced pressure, and the resulting residue was poured onto ice water (ca. 25 ml), followed by neutralization with 5M sodium hydroxide with ice cooling. The reaction mixture was extracted twice with ethyl acetate/tetrahydrofuran (4/1, 150 ml), and the organic layer was washed with brine, followed by drying over sodium sulfate. After the drying agent was filtered off, the filtrate was concentrated under reduced pressure, to obtain a pale brown powder (1.78 g). The crude product was used for the next reaction without purification.

[Method C-2]

Compound J-01-B2 (2.6 g) prepared as in the above was dissolved in trifluoroacetic acid (6.7 ml), followed by refluxing for 1 hour. Excess amount of solvent was removed under reduced pressure, and the resulting residue was poured onto ice water (ca. 70 ml), followed by neutralization with saturated sodium bicarbonate water with ice cooling. The resulting precipitate was filtered, washed with water, and subsequently azeotroped with toluene, followed by drying under reduced pressure, to obtain a violet powder (2.94 g). The crude product was used for the next reaction without purification.

$^1$H-NMR (270 MHz, CDCl$_3$) δ (ppm): 4.91 (1H, brs), 3.70 (8H, s), 3.64 (2H, t, J=8.4 Hz), 2.99 (2H, t, J=8.4 Hz).

ESI (LC-MS positive mode) m/z 241 [(M+H)$^+$].

Step D 1-(4-Chloro-2-morpholin-4-yl-5,6-dihydro-pyrrolo[2,3-d]pyrimidin-7-yl)-ethanone (J-01-D)

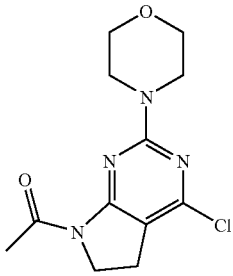

Compound J-01-C (2.94 g) prepared as in the above, dimethylaminopyridine (28 mg) and pyridine (2.48 ml) were added to acetonitrile (50 ml), and acetyl chloride (1.67 ml) was added dropwise slowly with ice cooling. The reaction mixture was raised to room temperature, followed by stirring for 30 minutes. The reaction mixture was diluted with water (200 ml) and ethyl acetate (200 ml), and insolubles were filtered off through Celite pad, and the Celite pad was washed with ethyl acetate. The organic layer of the filtrate was separated, and the aqueous layer was extracted with ethyl acetate (200 ml). The organic layers were combined, and washed with brine, followed by drying over sodium sulfate. After the drying agent was filtered off, the filtrate was concentrated under reduced pressure, and the resulting residue was purified by silica gel column chromatography (ethyl acetate/hexane=3/0 to 2/1), to obtain the desired compound (1.67 g) as a pale yellow powder.

$^1$H-NMR (270 MHz, CDCl$_3$) δ (ppm): 4.04 (2H, t, J=8.5 Hz), 3.66-3.78 (8H, brs), 2.92 (2H, t, J=8.5 Hz), 2.62 (3H, s).

ESI (LC-MS positive mode) m/z 283 [(M+H)$^+$].

Step E

1-[4-(3-t-Butoxyphenyl)-2-morpholin-4-yl-5,6-dihydro-pyrrolo[2,3-d]pyrimidin-7-yl)-ethanone (J-01-E)

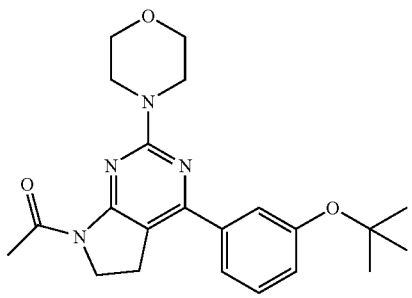

Compound J-01-D (2.94 g) prepared as in the above, palladium acetate (23 mg), S-Phos (87 mg), potassium phosphate (6.61 g) and 3-t-butoxyphenylboronic acid pinacol ester (3.15 g) were dissolved in dimethylformamide (20 ml). Then, argon substitution was carried out three times under ultrasonic irradiation under reduced pressure. The reaction mixture was stirred at 100° C. for 1 hour, and after allowing to cool, the mixture was diluted with ethyl acetate/water (100 ml/150 ml), and then the organic layer was separated. The aqueous layer was extracted with ethyl acetate (150 ml×2), and the combined organic layers were washed with brine, followed by drying over sodium sulfate. After the drying agent was filtered off, the filtrate was concentrated under reduced pressure, and the resulting residue was purified by silica gel column chromatography (ethyl acetate/hexane=3/0 to 2/1), to obtain a colorless solid (3.5 g, 85%).

$^1$H-NMR (270 MHz, CDCl$_3$) δ (ppm): 7.59 (1H, d, J=7.9 Hz), 7.49 (1H, t, J=1.9 Hz), 7.34 (1H, t, J=7.9 Hz), 7.06 (1H, dd, J=7.9, 1.9 Hz), 4.05 (2H, t, J=8.3 Hz), 3.73-3.86 (8H, m), 3.16 (2H, t, J=8.3 Hz), 2.69 (3H, s), 1.37 (9H, s).

ESI (LC-MS positive mode) m/z 397 [(M+H)$^+$].

Step E 4-(3-t-Butoxyphenyl)-2-morpholin-4-yl-6,7-dihydro-5H-pyrrolo[2,3-d]pyrimidine (J-01)

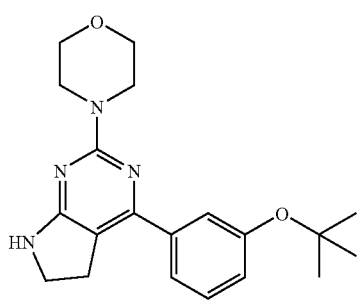

Compound prepared as in the above (J-01-E) (3.5 g) was dissolved in methanol (45 ml), and 5M aqueous sodium hydroxide solution (3.8 ml, 2 equivalents) was added, followed by refluxing for 1 hour. After the reaction mixture was allowed to cool, methanol (50 ml) was added to the suspension, to dissolve the insolubles, followed by neutralization with 5M hydrochloric acid (ca. 4 ml) with ice cooling. The precipitate was filtered, followed by washing with water, and the resulting powder was dried under reduced pressure, to obtain a colorless powder (2.87 g, 92%).

$^1$H-NMR (270 MHz, CDCl$_3$) δ (ppm): 7.65 (1H, m), 7.52 (1H, m), 7.34 (1H, t, J=7.9 Hz), 7.03 (1H, ddd, J=7.9, 2.5, 1.0 Hz), 4.69 (1H, brs), 3.74-3.82 (8H, m), 3.65 (2H, t, J=8.4 Hz), 3.26 (2H, t, J=8.4 Hz), 1.38 (9H, s).

ESI (LC-MS positive mode) m/z 355 [(M+H)$^+$].

Example 1-J-02

Bis-(4-methoxy-benzyl)-[5-(2-morpholin-4-yl-6,7-dihydro-5H-pyrrolo[2,3-d]pyrimidin-4-yl)-pyrimidin-2-yl]-amine (J-02)

Step A 1-(4-{2-[Bis-(4-methoxy-benzyl)-amino]-pyrimidin-5-yl}-2-morpholin-4-yl-5,6-dihydro-pyrrolo[2,3-d]pyrimidin-7-yl)-ethanone (J-02-A)

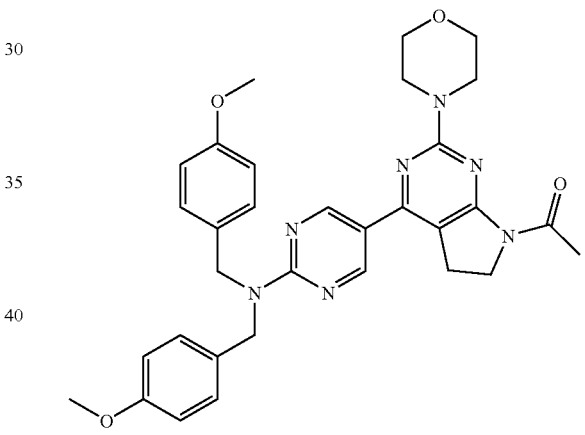

To Compound J-01-D (300 mg, 1.06 mmol, 1.0 equivalent) prepared as in the above, bis-(4-methoxybenzyl)-[5-(4,4,5,5-tetramethyl-[1,3,2]dioxaborolan-2-yl)-pyrimidin-2-yl]amine (538 mg, 1.17 mmol, 1.1 equivalents), palladium acetate (2.4 mg, 0.0106 mmol, 1 mol %), S-Phos (8.7 mg, 0.0212 mmol, 2 mol %) and potassium phosphate (450 mg, 2.12 mmol, 2.0 equivalents), dimethylformamide (5 ml) was added. The mixture was degassed under ultrasonic irradiation. This was stirred at 100° C. for 1.5 hours, followed by addition of water, to filter the solid, which was dissolved in dichloromethane, and dried over anhydrous sodium sulfate. Concentration was carried out under reduced pressure, followed by purification by column chromatography (dichloromethane/methanol=50/1), to obtain the desired compound as a colorless solid (560 mg, yield 91%).

$^1$H-NMR (CDCl$_3$) δ (ppm): 8.98 (2H, s), 7.19 (4H, d, J=8.8 Hz), 6.85 (4H, d, J=8.8 Hz), 4.84 (4H, s), 4.10 (2H, t, J=8.5 Hz), 3.84-3.76 (8.0H, m), 3.80 (6H, s), 3.18 (2H, t, J=8.5 Hz), 2.69 (3.0H, s).

ESI (LC-MS positive mode) m/z 582 [(M+H)$^+$].

Step B

Bis-(4-methoxy-benzyl)-[5-(2-morpholin-4-yl-6,7-dihydro-5H-pyrrolo[2,3-d]pyrimidin-4-yl)-pyrimidin-2-yl]-amine (J-02)

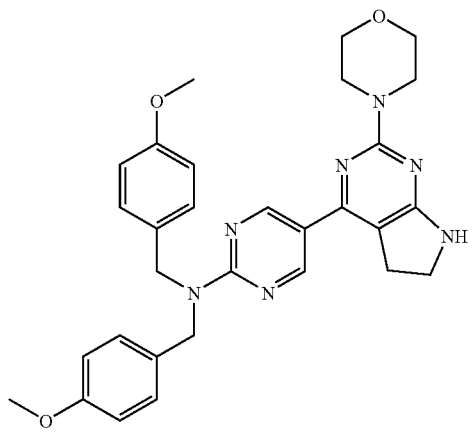

To a solution of Compound J-02-A (335 mg, 0.576 mmol) prepared as in the above in tetrahydrofuran (12 ml), 5M aqueous sodium hydroxide solution (6 ml) was added, followed by refluxing overnight. To this, 1M hydrochloric acid was added for neutralization, and the resulting solid was filtered, which was washed with acetonitrile, to obtain the desired compound as a colorless solid (290 mg, yield 93%).

$^1$H-NMR (CDCl$_3$) δ (ppm): 8.97 (2H, s), 7.18 (4H, d, J=8.3 Hz), 6.85 (4H, d, J=8.3 Hz), 4.83 (4H, s), 3.79 (6H, s), 3.79-3.73 (8H, m), 3.68 (2H, t, J=8.3 Hz), 3.24 (2H, t, J=8.3 Hz).

ESI (LC-MS positive mode) m/z 540 [(M+H)$^+$].

Test Example 1

Measurement of PI3K Inhibitory Activity

The inhibitory activity of compounds of the present invention represented by formula (I) were measured with human PI3K(p110α/p85α) prepared in a baculovirus expression system using the AlphaScreen GST Detection Kit (Perkin Elmer, Inc.). A predetermined concentration of the compound dissolved in dimethylsulfoxide (DMSO) and PI3K were mixed in a 384-well assay plate and after allowing to stand for 20 minutes at room temperature, 4 µM PI(4,5)P2 (Echelon Corporation) and 10 µM ATP (5 mM Hepes, pH 7.5, 2.5 mM MgCl$_2$) were added to initiate the reaction. After reacting for 15 minutes at 37° C., GST-GRP1 expressed and purified from *Escherichia coli*, Anti-GST Acceptor Beads (Perkin Elmer, Inc.), Streptavidin Donor Beads (Perkin Elmer, Inc.) and biotin-PI(3,4,5) P3 (Echelon Corporation) (10 mM Tris-HCl pH 7.4, 150 mM NaCl, 7.5 mM EDTA, 1 mM DTT, 0.1% Tween 20) were added, and after allowing to stand for 1 hour at room temperature, light at 520 to 620 nm emitted as a result of exciting with light at 680 nm was measured with the Envision measuring instrument (Perkin Elmer, Inc.).

The inhibitory activity of the compounds was calculated by assigning a value of 0% inhibitory activity to the measured value following addition of DMSO alone, assigning a value of 100% inhibitory activity to the measured value in the absence of ATP, and defining the concentration that resulted in 50% inhibitory activity as the IC$_{50}$ value (µM).

Test Example 1 described above can be performed according to "Analytical Biochemistry, 2003, 313, 234-245; Alexander Gray et al".

Test Example 2

Measurement of Cell Proliferation Inhibitory Activity

The cell proliferation inhibitory activity was measured for compounds of the present invention represented by formula (I). Cancer cell proliferation inhibitory activity was measured using the Cell Counting Kit-8 (Dojindo). 2000 cells each of human colon cancer cell line HCT116 purchased from the American Type Culture Collection (Virginia, USA) were seeded into each well of a 96-well culture plate followed by the addition of a predetermined concentration of the compounds and cultivating in a CO$_2$ environment for 4 days at 37° C. On the fourth day of cultivating, the Cell Counting Kit-8 solution was added and absorbance (measuring wavelength: 450 nm, reference wavelength: 615 nm) was measured in accordance with the protocol provided with the kit. The percentage of cell proliferation inhibition at 2.5 µM was calculated by assigning a value of 0% inhibition to the measured value in the case of not containing a test compound, and assigning a value of 100% inhibition to the measured value in the case of not containing a test compound and cells.

Cancer cell proliferation inhibitory activity was also measured for human lung cancer cell line NCI-H460 and human prostate cancer cell line PC3 purchased from the American Type Culture Collection. 1000 and 3000 cells of NCI-H460 and PC3, respectively, were seeded into each well of a 96-well culture plate followed by testing in the same manner as the human colon cancer cell line and calculating the percentage of cell proliferation inhibition at 2.5 µM.

The enzyme inhibitory activities and cell proliferation inhibitory activities are shown in the following tables. As shown in Tables 11-1, 11-2, 11-3 and 11-4 the compounds of the present invention demonstrated satisfactory enzyme inhibitory activity and cell proliferation inhibitory activity.

| | Enzyme inhibitory activity (IC50, µM) | Cell proliferation inhibitory activity (% Inhibition at 2.5 µM) | | |
|---|---|---|---|---|
| Compound No. | PI3K α | Colon cancer (HCT116) | Prostate cancer (PC3) | Non-small cell lung cancer (NCI-H460) |
| (A-09) | 0.009 | 83 | 96 | 84 |
| (A-14) | 0.08 | 76 | 98 | 95 |
| (A-32) | 0.24 | 81 | 81 | 79 |
| (A-44) | 0.05 | 69 | 79 | 82 |
| (A-48) | 0.02 | 55 | 62 | 67 |
| (B-02) | 0.03 | 87 | 96 | 95 |
| (B-03) | 0.24 | 100 | 95 | 97 |
| (B-09) | 0.26 | 45 | 56 | 67 |
| (B-22) | 0.30 | 71 | 22 | 72 |
| (B-32) | 0.47 | 78 | 29 | 67 |
| (B-35) | 0.87 | 78 | 61 | 71 |
| (B-55) | 0.34 | 79 | 47 | 58 |
| (C-55) | 0.05 | 72 | 87 | 89 |
| (D-01) | 0.04 | 83 | 89 | 92 |
| (D-02) | 0.02 | 81 | 87 | 83 |
| (D-03) | 0.02 | 92 | 88 | 92 |
| (D-16) | 0.23 | 74 | 73 | 76 |
| (D-17) | 0.024 | 96 | 93 | 97 |
| (D-18) | 0.022 | 100 | 93 | 102 |

-continued

| Compound No. | Enzyme inhibitory activity (IC50, μM) PI3K α | Cell proliferation inhibitory activity (% Inhibition at 2.5 μM) | | |
|---|---|---|---|---|
| | | Colon cancer (HCT116) | Prostate cancer (PC3) | Non-small cell lung cancer (NCI-H460) |
| (D-19) | 0.060 | 73 | 102 | 97 |
| (D-20) | 0.046 | 83 | 99 | 99 |
| (D-21) | 0.010 | 77 | 100 | 79 |
| (D-22) | 0.042 | 82 | 79 | 83 |
| (D-23) | 0.0060 | 99 | 89 | 100 |
| (D-24) | 0.034 | 88 | 91 | 94 |
| (D-25) | 0.22 | 61 | 55 | 57 |
| (D-26) | 0.048 | 87 | 82 | 84 |
| (D-42) | 0.014 | 91 | 88 | 94 |
| (D-95) | 0.007 | 93 | 91 | 83 |
| (D-101) | 0.009 | 92 | 89 | 67 |
| (D-102) | 0.007 | 72 | 70 | 94 |
| (D-103) | 0.006 | 74 | 80 | 92 |
| (D-104) | 0.006 | 37 | 34 | 67 |
| (D-108) | 0.007 | 92 | 90 | 95 |
| (D-128) | 0.008 | 81 | 60 | 95 |
| (D-137) | 0.092 | 60 | 71 | 52 |
| (D-138) | 0.11 | 82 | 85 | 86 |
| (D-139) | 0.009 | 90 | 89 | 72 |
| (D-172) | 0.008 | 86 | 86 | 79 |
| (D-223) | 0.007 | 95 | 95 | 92 |
| (D-231) | 0.011 | 33 | 37 | 71 |
| (D-237) | 0.005 | 95 | 97 | 84 |
| (D-242) | 0.010 | 99 | 100 | 55 |
| (D-264) | 0.007 | 63 | 72 | 82 |
| (D-265) | 0.006 | 98 | 96 | 71 |
| (D-273) | 0.010 | 83 | 79 | 67 |
| (D-286) | 0.008 | 94 | 89 | 97 |
| (D-290) | 0.009 | 99 | 99 | 18 |
| (D-307) | 0.009 | 87 | 89 | 58 |
| (D-318) | 0.007 | 96 | 94 | 89 |
| (D-325) | 0.11 | 78 | 73 | 81 |
| (D-326) | 0.24 | 72 | 81 | 83 |
| (D-327) | 0.07 | 78 | 79 | 85 |
| (D-328) | 0.06 | 84 | 84 | 91 |
| (D-329) | 0.26 | 73 | 65 | 81 |
| (D-330) | 0.02 | 25 | 0 | −13 |
| (D-332) | 0.21 | 60 | 43 | 54 |
| (D-333) | 0.16 | 99 | 43 | 102 |
| (D-334) | 0.20 | 93 | 90 | 94 |
| (G-27) | 0.33 | 44 | 48 | 18 |
| (G-05) | 0.36 | 38 | 49 | 55 |
| (H-12) | 0.02 | 82 | 76 | 71 |
| (H-32) | 0.018 | 82 | 89 | 86 |
| (H-34) | 0.011 | 81 | 91 | 89 |

The invention claimed is:
1. A compound, represented by the following formula (I):

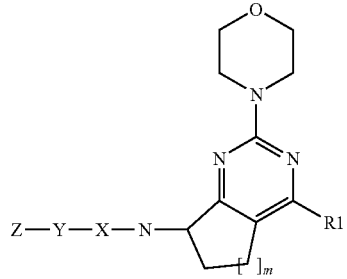

(I)

wherein,
X represents a single bond, or a linking group selected from —CO—, —SO$_2$—, —CS— or —CH$_2$—;
Y represents a single bond or a divalent linking group derived from a ring selected from benzene, pyridine, pyrimidine, pyrazole, imidazole, oxazole, thiazole, furan, thiophene, quinoline, benzoimidazole, benzothiazole, benzopyrazole, naphthalene and benzothiophene (said linking group may be unsubstituted or substituted at 1 to 6 locations by a halogen atom, —C$_{1-6}$alkyl or —OC$_{1-6}$ alkyl);
X and Y are not simultaneously single bonds;
Z represents a hydrogen atom or a substituent selected from the following group A:
Group A:
—C$_{1-6}$alkyl,
-ethynyl,
-halogenoC$_{1-6}$alkyl,
-Cyc,
—C$_{1-6}$alkylene-OR,
—C$_{1-6}$alkylene-COR,
—C$_{1-6}$alkylene-COOR,
—C$_{1-6}$alkylene-CONRR',
—C$_{1-6}$alkylene-NRR',
—C$_{1-6}$alkylene-Cyc,
—C$_{1-6}$alkylene-CO-Cyc,
—C$_{1-6}$alkylene-O—C$_{1-6}$alkylene-Cyc,
—C$_{1-6}$alkylene-SO$_2$R,
—C$_{1-6}$alkylene-SO$_2$-Cyc,
-halogen,
—CN,
—SO$_2$R,
—SO$_2$—NRR',
—SO$_2$—NR-Cyc,
—SO$_2$—NR—C$_{1-6}$alkylene-Cyc,
—SO$_2$-Cyc,
—COR,
—CO-Cyc,
—CO-Cyc-C$_{1-6}$alkylene-Cyc,
—CO—C$_{1-6}$alkylene-Cyc,
—CO-Cyc-Cyc,
—COOR,
—CONRR',
—CONR—C$_{1-6}$alkylene-OR',
—CONR—C$_{1-6}$alkylene-CONR'R",
—CONR-Cyc,
—CONR—C$_{1-6}$alkylene-Cyc,
—OR,
—O-allyl,
—O-halogenoC$_{1-6}$alkyl,
—O—C$_{1-6}$alkylene-NRR',
—O—C$_{1-6}$alkylene-CONRR',
—O—C$_{1-6}$alkylene-NRCOR',
—NRR',
—NH—NH$_2$,
—NRCOR',
—NRCO-Cyc,
—NRCO—C$_{1-6}$alkylene-Cyc,
—NRCO—C$_{1-6}$alkylene-OR',
—NR—C$_{1-6}$alkylene-COOR',
—NR—C$_{1-6}$alkylene-CONR'R",
—NR—C$_{1-6}$alkylene-NR'R",
—NR—C$_{1-6}$alkylene-NR'COR",
—NR—C$_{1-6}$alkylene-OR',
—NR-Cyc,
—NR-Cyc-Cyc,
—NR-Cyc-CO-Cyc,
—NR-Cyc-CO—C$_{1-6}$alkylene-Cyc,
—NR-Cyc-NR'-Cyc,
—NR-Cyc-NR'—C$_{1-6}$alkylene-Cyc,
—NR—C$_{1-6}$alkylene-Cyc,
—NR—C$_{1-6}$alkylene-Cyc-CO-Cyc, —NR—C$_{1-6}$alkylene-Cyc-NR'-Cyc,
—NRSO$_2$R',
—S—C$_{1-6}$alkylene-CO-Cyc,
—S—C$_{1-6}$alkylene-COOR',
—S—C$_{1-6}$alkylene-NRCOR', and
—S—C$_{1-6}$alkylene-CONRR';

m represents an integer of 1 or 2;
R$^1$ represents a cyclic substituent selected from the following group having n substituents T;

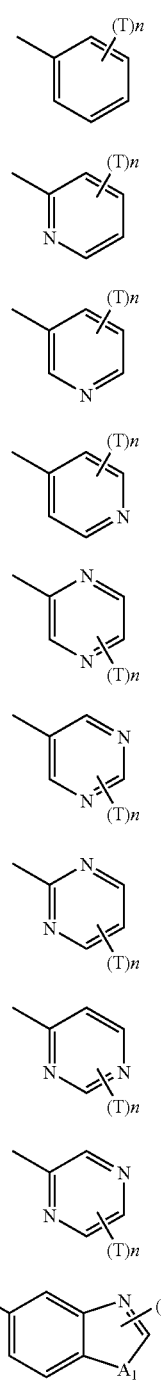

R$_1$a

R$_1$b1

R$_1$b2

R$_1$b3

R$_1$c1

R$_1$c2

R$_1$c3

R$_1$c4

R$_1$c5

R$_1$d

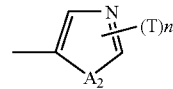

R$_1$e

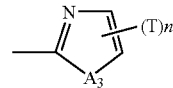

R$_1$f

A$_1$, A$_2$ and A$_3$ are respectively and independently selected from NH, S or O;
T represents a substituent selected from the following group B:
Group B:
—Cyc,
—C$_{1-6}$alkyl,
—C$_{1-6}$alkylene-OR,
—C$_{1-6}$alkylene-NRR',
—C$_{1-6}$alkylene-CONRR',
—C$_{1-6}$alkylene-NRCOR',
—C$_{1-6}$alkylene-Cyc,
—OR,
—O-halogenoC$_{1-6}$alkyl,
—O—C$_{1-6}$alkylene-Cyc,
—O—COOR,
—O—COR,
—O—CONRR',
—NRR',
—NR—C$_{1-6}$alkylene-NR'R",
—NR—C$_{1-6}$alkylene-OR',
-halogen,
—CO-Cyc,
—CO-Cyc-Cyc,
—CO—C$_{1-6}$alkylene-Cyc,
—COOR,
—COO—C$_{1-6}$alkylene-OR,
—COO—C$_{1-6}$alkylene-NRR',
—COO—C$_{1-6}$alkylene-Cyc,
—CONRR',
—CONR—C$_{1-6}$alkylene-OR',
—CONR—C$_{1-6}$alkylene-NR'R",
—CONR—C$_{1-6}$alkylene-CONR'R",
—CONR-Cyc,
—CONR—C$_{1-6}$alkylene-Cyc,
—SO$_2$NRR',
—NRSO$_2$R',
—CN, and
—NH—NH$_2$;
n represents an integer of 0, 1, 2, 3, 4 or 5 (T may be the same or different when n is 2 to 5);
in the aforementioned group A and group B,
R, R' and R" may be respectively and independently the same or different and represent a hydrogen atom or a —C$_{1-6}$ alkyl (said —C$_{1-6}$ alkyl may be substituted by a group selected from —OH, —O(C$_{1-6}$ alkyl), —COOH, —COO(C$_{1-6}$ alkyl), —CONH$_2$, —CONH (C$_{1-6}$ alkyl), —CON(C$_{1-6}$ alkyl)$_2$, —NHCO(C$_{1-6}$ alkyl), —NH$_2$, —NH(C$_{1-6}$ alkyl) and —N(C$_{1-6}$ alkyl)$_2$);
Cyc represents a hydrocarbon ring or nitrogen-containing heterocyclic ring (said hydrocarbon ring and nitrogen-containing heterocylic ring may be substituted at 1 to 3 locations by a group selected from —R(R is not a hydrogen atom at this time), —CO—R, —COOR, —CONRR', —NRCOR', -halogeno C$_{1-6}$ alkyl, halogen atom, —OR, —O-halogeno C$_{1-6}$ alkyl, —NRR' and —SO$_2$R);

said C$_{1-6}$ alkylene in the groups A and B may be substituted at 1 to 3 locations by a group selected from —C$_{1-6}$ alkyl, —OH, —CONH$_2$, —NH$_2$, —NH(C$_{1-6}$ alkyl) and —N(C$_{1-6}$ alkyl)$_2$; and R, R' and R" in said —NRR', —NR'R" or —CONRR' in the group A, group B and Cyc may form a 3- to 7-member nitrogen-containing saturated hydrocarbon ring together with an adjacent N;

or a pharmaceutically acceptable salt thereof.

2. The compound according to claim 1, wherein Y is either a single bond or a divalent linking group selected from the following (said linking group may be unsubstituted or substituted at 1 to 6 locations by a halogen atom, —C$_{1-6}$ alkyl or —OC$_{1-6}$ alkyl, and an asterisk (*) in the following group of linking groups represents a bond with Z), or a pharmaceutically acceptable salt thereof;

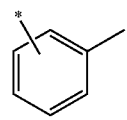
Ya

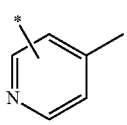
Yb$_1$

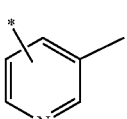
Yb$_2$

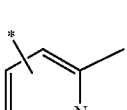
Yb$_3$

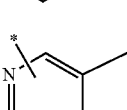
Yb$_4$

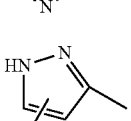
Yc$_1$

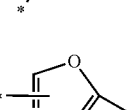
Yc$_2$

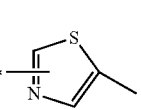
Yc$_3$

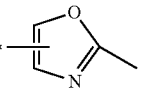
Yc$_4$

-continued

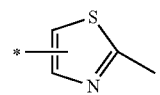
Yc$_5$

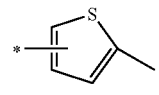
Yc$_6$

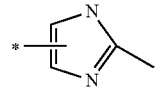
Yc$_7$

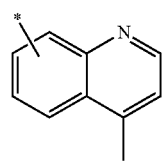
Yd

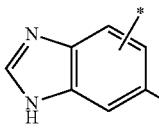
Ye

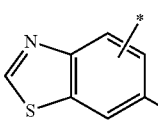
Yf

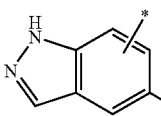
Yg

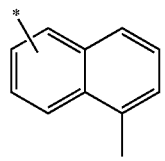
Yi$_1$

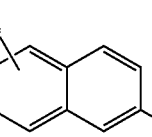
Yi$_2$

Yh

3. The compound according to claim 1, wherein X is a single bond, —CO— or —CS—,
or a pharmaceutically acceptable salt thereof.

4. The compound according to claim 1, wherein the linking group in Y is an unsubstituted linking group or a linking group substituted at 1 or 2 locations by -fluoro, -methyl or -methoxy,
or a pharmaceutically acceptable salt thereof.

5. The compound according to claim 2, wherein Y is a single bond or a linking group according to claim 2 selected from Ya, Yb$_1$, Yb$_2$, Yb$_3$ or Yb$_4$,
or a pharmaceutically acceptable salt thereof.

6. The compound according to claim 1, wherein m is 1, or a pharmaceutically acceptable salt thereof.

7. The compound according to claim 1, wherein n is 0, 1 or 2, or a pharmaceutically acceptable salt thereof.

8. The compound according to claim 1, wherein Cyc in the group A is a monovalent or divalent group derived from a hydrocarbon ring or nitrogen-containing heterocyclic ring selected from benzene, naphthalene, cyclopropane, cyclobutane, cyclopentane, cyclohexane, spiro[2,3]hexane, spiro[3,3]heptane, indane, tetrahydronaphthalene, cyclopropene, cyclobutene, cyclopentene, cyclohexene, pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, quinoline, isoquinoline, quinoxaline, quinazoline, phthalazine, purine, pteridine, aziridine, azetidine, pyrrolidine, imidazoline, oxazoline, imidazolidine, oxazolidine, thiazine, piperidine, piperazine, morpholine or azepane (said Cyc may be respectively substituted at 1 to 3 locations by —OH, —O($C_{1-6}$ alkyl), —O—$C_{1-6}$ alkylene-OH, —$C_{1-6}$ alkyl, —$C_{1-6}$ alkylene-OH, —$C_{1-6}$ alkyl fluoride, —COO ($C_{1-6}$ alkyl), —$CONH_2$, —CONH($C_{1-6}$ alkyl), —CON($C_{1-6}$ alkyl)$_2$, —$NH_2$, —NH($C_{1-6}$ alkyl), —N($C_{1-6}$ alkyl)$_2$, —$SO_2$ ($C_{1-6}$ alkyl) or —CO($C_{1-6}$ alkyl)),
or a pharmaceutically acceptable salt thereof.

9. The compound according to claim 1, wherein $R^1$ is $R_1$a, $R_1b_1$, $R_1b_2$, $R_1b_3$, $R_1c_1$, $R_1c_2$, $R_1c_3$, $R_1c_4$, $R_1c_5$, $R_1$d, $R_1$e or $R_1$f, and $A_3$ is S or O,
or a pharmaceutically acceptable salt thereof.

10. The compound according to claim 1, wherein R, R' and R" in group B of T, which are the same or different, are a hydrogen atom or $C_{1-6}$ alkyl,
or a pharmaceutically acceptable salt thereof.

11. The compound according to claim 1, wherein Cyc in the group B is a monovalent or divalent group derived from a hydrocarbon ring or nitrogen-containing heterocyclic ring selected from benzene, naphthalene, cyclopropane, cyclobutane, cyclopentane, cyclohexane, spiro[2.3]hexane, spiro[3.3]heptane, indane, tetrahydronaphthalene, cyclopropene, cyclobutene, cyclopentene, cyclohexene, pyrrole, pyrazole, imidazole, triazole, oxazole, isoxazole, indazole, thiazole, pyridine, pyridazine, pyrimidine, pyrazine, oxazine, triazine, indole, benzimidazole, benzoxazole, benzothiazole, benzopyrazole, quinoline, isoquinoline, quinoxaline, quinazoline, phthalazine, purine, pteridine, aziridine, azetidine, pyrrolidine, imidazoline, oxazoline, imidazolidine, oxazolidine, thiazine, 2,5-dihydropyrrole, piperidine, piperazine, morpholine or azepane (said Cyc may be unsubstituted or respectively substituted at 1 to 3 locations by —OH, —O($C_{1-6}$ alkyl), —$C_{1-6}$ alkyl, —$NH_2$, —NH($C_{1-6}$ alkyl), —N($C_{1-6}$ alkyl)$_2$ or —CO($C_{1-6}$ alkyl)),
or a pharmaceutically acceptable salt thereof.

12. The compound according to claim 1, wherein X is a linking group selected from —CO— or —CS—, and Z is a group selected from the following groups when Y is a single bond:
—Cyc,
—$C_{1-6}$ alkylene-Cyc,
—$C_{1-6}$ alkylene-CO-Cyc,
—$C_{1-6}$ alkylene-O—$C_{1-6}$ alkylene-Cyc,
—$C_{1-6}$ alkylene-$SO_2$-Cyc,
—NRCO-Cyc,
—NRCO—$C_{1-6}$ alkylene-Cyc,
—NR-Cyc,
—NR-Cyc-Cyc,
—NR-Cyc-CO-Cyc,
—NR—$C_{1-6}$ alkylene-Cyc-CO-Cyc,
—NR-Cyc-CO—$C_{1-6}$ alkylene-Cyc,
—NR-Cyc-NR'-Cyc,
—NR—$C_{1-6}$ alkylene-Cyc-NR'-Cyc,
—NR-Cyc-NR'—$C_{1-6}$ alkylene-Cyc, and
—NR—$C_{1-6}$ alkylene-Cyc,
or a pharmaceutically acceptable salt thereof.

13. The compound according to claim 1, wherein $R^1$ is a substituent selected from the following group of substituents,

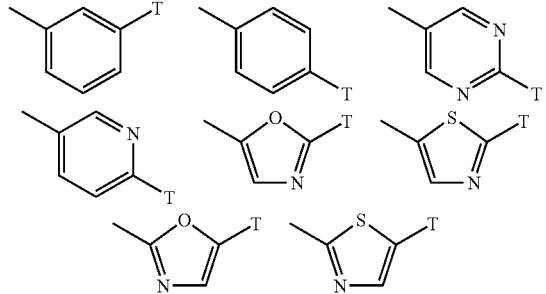

or a pharmaceutically acceptable salt thereof.

14. The compound according to claim 1, wherein $R^1$ is -3-hydroxyphenyl or -2-amino-pyrimidin-5-yl,
or a pharmaceutically acceptable salt thereof.

15. A compound, selected from the following compounds:
4-(3-methoxy-phenyl)-2-morpholin-4-yl-7-pyridin-4-yl-6,7-dihydro-5H-pyrrolo[2,3-d]pyrimidine (A-01);
4-(3-methoxy-phenyl)-2-morpholin-4-yl-7-pyridin-3-yl-6,7-dihydro-5H-pyrrolo[2,3-d]pyrimidine (A-02);
5-[4-(3-methoxy-phenyl)-2-morpholin-4-yl-5,6-dihydro-pyrrolo[2,3-d]pyrimidin-7-yl]-pyridin-2-ol (A-03);
4-(3-methoxy-phenyl)-2-morpholin-4-yl-7-pyridin-3-yl-methyl-6,7-dihydro-5H-pyrrolo[2,3-d]pyrimidine (A-04);
7-(1H-indazol-5-yl)-4-(3-methoxy-phenyl)-2-morpholin-4-yl-6,7-dihydro-5H-pyrrolo[2,3-d]pyrimidine (A-05);
7-(1H-benzimidazol-5-yl)-4-(3-methoxy-phenyl)-2-morpholin-4-yl-6,7-dihydro-5H-pyrrolo[2,3-d]pyrimidine (A-06);
4-(3-methoxy-phenyl)-7-methyl-2-morpholin-4-yl-6,7-dihydro-5H-pyrrolo[2,3-d]pyrimidine (A-07);
4-(3-methoxy-phenyl)-7-(6-methoxy-pyridin-3-yl)-2-morpholin-4-yl-6,7-dihydro-5H-pyrrolo[2,3-d]pyrimidine (A-08);
3-(2-morpholin-4-yl-7-pyridin-4-yl-6,7-dihydro-5H-pyrrolo[2,3-d]pyrimidin-4-yl)-phenol (A-09);
3-(2-morpholin-4-yl-7-pyridin-3-yl-6,7-dihydro-5H-pyrrolo[2,3-d]pyrimidin-4-yl)-phenol (A-10);
5-[4-(3-hydroxy-phenyl)-2-morpholin-4-yl-5,6-dihydro-pyrrolo[2,3-d]pyrimidin-7-yl]-pyridin-2-ol (A-11);
3-(2-morpholin-4-yl-7-pyridin-3-ylmethyl-6,7-dihydro-5H-pyrrolo[2,3-d]pyrimidin-4-yl)-phenol trifluoroacetic acid salt (A-12);
3-[7-(1H-indazol-5-yl)-2-morpholin-4-yl-6,7-dihydro-5H-pyrrolo[2,3-d]pyrimidin-4-yl]-phenol (A-13);
3-[7-(1H-benzimidazol-5-yl)-2-morpholin-4-yl-6,7-dihydro-5H-pyrrolo[2,3-d]pyrimidin-4-yl]-phenol (A-14);
3-(7-methyl-2-morpholin-4-yl-6,7-dihydro-5H-pyrrolo[2,3-d]pyrimidin-4-yl)-phenol (A-15);
3-[7-(2-methyl-pyridin-4-yl)-2-morpholin-4-yl-6,7-dihydro-5H-pyrrolo[2,3-d]pyrimidin-4-yl]-phenol (A-16);
3-[7-(1-methyl-1H-pyrazol-3-yl)-2-morpholin-4-yl-6,7-dihydro-5H-pyrrolo[2,3-d]pyrimidin-4-yl]-phenol (A-17);

3-[4-(3-hydroxy-phenyl)-2-morpholin-4-yl-5,6-dihydro-pyrrolo[2,3-d]pyrimidin-7-yl]-benzonitrile (A-18);
3-[7-(2-methyl-quinolin-4-yl)-2-morpholin-4-yl-6,7-dihydro-5H-pyrrolo[2,3-d]pyrimidin-4-yl]-phenol (A-19);
3-[7-(3-dimethylamino-phenyl)-2-morpholin-4-yl-6,7-dihydro-5H-pyrrolo[2,3-d]pyrimidin-4-yl]-phenol (A-20);
3-[2-morpholin-4-yl-7-(4-trifluoromethoxy-phenyl)-6,7-dihydro-5H-pyrrolo[2,3-d]pyrimidin-4-yl]-phenol (A-21);
3-(2-morpholin-4-yl-7-o-tolyl-6,7-dihydro-5H-pyrrolo[2,3-d]pyrimidin-4-yl)-phenol (A-22);
3-[7-(2,4-dimethyl-phenyl)-2-morpholin-4-yl-6,7-dihydro-5H-pyrrolo[2,3-d]pyrimidin-4-yl]-phenol (A-23);
3-[7-(3-dimethylamino-propyl)-2-morpholin-4-yl-6,7-dihydro-5H-pyrrolo[2,3-d]pyrimidin-4-yl]-phenol (A-24);
3-[7-(4-isopropyl-phenyl)-2-morpholin-4-yl-6,7-dihydro-5H-pyrrolo[2,3-d]pyrimidin-4-yl]-phenol (A-25);
3-[7-(3-chloro-phenyl)-2-morpholin-4-yl-6,7-dihydro-5H-pyrrolo[2,3-d]pyrimidin-4-yl]-phenol trifluoroacetic acid salt (A-26);
3-[7-(4-chloro-3-methyl-phenyl)-2-morpholin-4-yl-6,7-dihydro-5H-pyrrolo[2,3-d]pyrimidin-4-yl]-phenol trifluoroacetic acid salt (A-27);
3-[7-(2-chloro-phenyl)-2-morpholin-4-yl-6,7-dihydro-5H-pyrrolo[2,3-d]pyrimidin-4-yl]-phenol trifluoroacetic acid salt (A-28);
3-(2-morpholin-4-yl-7-pyridin-2-yl-6,7-dihydro-5H-pyrrolo[2,3-d]pyrimidin-4-yl)-phenol (A-29);
3-[7-(5-methyl-pyridin-2-yl)-2-morpholin-4-yl-6,7-dihydro-5H-pyrrolo[2,3-d]pyrimidin-4-yl]-phenol (A-30);
3-[7-(4-chloro-phenyl)-2-morpholin-4-yl-6,7-dihydro-5H-pyrrolo[2,3-d]pyrimidin-4-yl]-phenol trifluoroacetic acid salt (A-31);
2-fluoro-5-(2-morpholin-4-yl-7-pyridin-4-yl-6,7-dihydro-5H-pyrrolo[2,3-d]pyrimidin-4-yl)-phenol trifluoroacetic acid salt (A-32);
2-fluoro-3-(2-morpholin-4-yl-7-pyridin-4-yl-6,7-dihydro-5H-pyrrolo[2,3-d]pyrimidin-4-yl)-phenol trifluoroacetic acid salt (A-33);
2-methyl-5-(2-morpholin-4-yl-7-pyridin-4-yl-6,7-dihydro-5H-pyrrolo[2,3-d]pyrimidin-4-yl)-phenol (A-34);
2-methyl-3-(2-morpholin-4-yl-7-pyridin-4-yl-6,7-dihydro-5H-pyrrolo[2,3-d]pyrimidin-4-yl)-phenol (A-35);
3-[4-(3-methoxy-phenyl)-2-morpholin-4-yl-5,6-dihydro-pyrrolo[2,3-d]pyrimidin-7-yl]-propan-1-ol (A-36);
2-morpholin-4-yl-4,7-di-pyridin-3-yl-6,7-dihydro-5H-pyrrolo[2,3-d]pyrimidine (A-37); 2-morpholin-4-yl-4-pyridin-3-yl-7-pyridin-4-yl-6,7-dihydro-5H-pyrrolo[2,3-d]pyrimidine (A-38);
N-methyl-3-(2-morpholin-4-yl-7-pyridin-3-yl-6,7-dihydro-5H-pyrrolo[2,3-d]pyrimidin-4-yl)-benzenesulfonamide (A-39);
N-methyl-3-(2-morpholin-4-yl-7-pyridin-4-yl-6,7-dihydro-5H-pyrrolo[2,3-d]pyrimidin-4-yl)-benzenesulfonamide (A-40);
3-{7-[2-(4-methyl-piperazin-1-yl)-pyridin-4-yl]-2-morpholin-4-yl-6,7-dihydro-5H-pyrrolo[2,3-d]pyrimidin-4-yl}-phenol (A-41);
3-{7-[2-(2-dimethylamino-ethoxy)-pyridin-4-yl]-2-morpholin-4-yl-6,7-dihydro-5H-pyrrolo[2,3-d]pyrimidin-4-yl}-phenol (A-42);
3-[7-(4-dimethylamino-3,4,5,6-tetrahydro-2H-[1,2']bipyridinyl-4'-yl)-2-morpholin-4-yl-6,7-dihydro-5H-pyrrolo[2,3-d]pyrimidin-4-yl]-phenol (A-43);
3-[2-morpholin-4-yl-7-(2-morpholin-4-yl-pyridin-4-yl)-6,7-dihydro-5H-pyrrolo[2,3-d]pyrimidin-4-yl]-phenol (A-44);
3-(7-{2-[(3-dimethylamino-propyl)-methyl-amino]-pyridin-4-yl}-2-morpholin-4-yl-6,7-dihydro-5H-pyrrolo[2,3-d]pyrimidin-4-yl)-phenol (A-45);
3-(7-{2-[(2-dimethylamino-ethyl)-methyl-amino]-pyridin-4-yl}-2-morpholin-4-yl-6,7-dihydro-5H-pyrrolo[2,3-d]pyrimidin-4-yl)-phenol (A-46);
3-[7-(4-dimethylamino-phenyl)-2-morpholin-4-yl-6,7-dihydro-5H-pyrrolo[2,3-d]pyrimidin-4-yl]-phenol (A-47);
N-{3-[4-(3-hydroxy-phenyl)-2-morpholin-4-yl-5,6-dihydro-pyrrolo[2,3-d]pyrimidin-7-yl]-phenyl}-methanesulfonamide trifluoroacetic acid salt (A-48);
3-(2-morpholin-4-yl-7-thiazol-2-yl-6,7-dihydro-5H-pyrrolo[2,3-d]pyrimidin-4-yl)-phenol (A-49);
3-[7-(4-methanesulfonyl-phenyl)-2-morpholin-4-yl-6,7-dihydro-5H-pyrrolo[2,3-d]pyrimidin-4-yl]-phenol (A-50);
4-[4-(3-hydroxy-phenyl)-2-morpholin-4-yl-5,6-dihydro-pyrrolo[2,3-d]pyrimidin-7-yl]-benzenesulfonamide (A-51);
3-(7-benzothiazol-6-yl-2-morpholin-4-yl-6,7-dihydro-5H-pyrrolo[2,3-d]pyrimidin-4-yl)-phenol trifluoroacetic acid salt (A-52);
3-[4-(3-hydroxy-phenyl)-2-morpholin-4-yl-5,6-dihydro-pyrrolo[2,3-d]pyrimidin-7-yl]-benzenesulfonamide (A-53);
3-(2-morpholin-4-yl-8-pyridin-4-yl-5,6,7,8-tetrahydro-pyrido[2,3-d]pyrimidin-4-yl)-phenol (A-54);
5-(2-morpholin-4-yl-7-pyridin-4-yl-6,7-dihydro-5H-pyrrolo[2,3-d]pyrimidin-4-yl)-pyrimidin-2-ylamine (B-01);
5-(2-morpholin-4-yl-7-pyridin-3-yl-6,7-dihydro-5H-pyrrolo[2,3-d]pyrimidin-4-yl)-pyrimidin-2-ylamine (B-02);
5-(2-morpholin-4-yl-7-pyridin-4-yl-6,7-dihydro-5H-pyrrolo[2,3-d]pyrimidin-4-yl)-pyridin-2-ylamine (B-03);
5-(2-morpholin-4-yl-7-pyridin-3-yl-6,7-dihydro-5H-pyrrolo[2,3-d]pyrimidin-4-yl)-pyridin-2-ylamine (B-04);
4-methoxy-5-(2-morpholin-4-yl-7-pyridin-3-yl-6,7-dihydro-5H-pyrrolo[2,3-d]pyrimidin-4-yl)-pyrimidin-2-ylamine (B-05);
2-fluoro-4-(2-morpholin-4-yl-7-pyridin-4-yl-6,7-dihydro-5H-pyrrolo[2,3-d]pyrimidin-4-yl)-phenylamine (B-06);
2,6-difluoro-4-(2-morpholin-4-yl-7-pyridin-4-yl-6,7-dihydro-5H-pyrrolo[2,3-d]pyrimidin-4-yl)-phenylamine (B-07);
4-(2,4-dimethoxy-pyrimidin-5-yl)-2-morpholin-4-yl-7-pyridin-4-yl-6,7-dihydro-5H-pyrrolo[2,3-d]pyrimidine (B-08);
4-(2,4-dimethoxy-pyrimidin-5-yl)-2-morpholin-4-yl-7-pyridin-3-yl-6,7-dihydro-5H-pyrrolo[2,3-d]pyrimidine (B-09);
4-(6-methoxy-pyridin-3-yl)-2-morpholin-4-yl-7-pyridin-3-yl-6,7-dihydro-5H-pyrrolo[2,3-d]pyrimidine (B-10);
4-(6-methoxy-pyridin-3-yl)-2-morpholin-4-yl-7-pyridin-4-yl-6,7-dihydro-5H-pyrrolo[2,3-d]pyrimidine (B-11);
4-(2-morpholin-4-yl-7-pyridin-3-yl-6,7-dihydro-5H-pyrrolo[2,3-d]pyrimidin-4-yl)-benzoic acid methyl ester (B-12);
4-(2-morpholin-4-yl-7-pyridin-3-yl-6,7-dihydro-5H-pyrrolo[2,3-d]pyrimidin-4-yl)-benzoic acid methyl ester hydrochloride (B-13);

4-(2-morpholin-4-yl-7-pyridin-3-yl-6,7-dihydro-5H-pyrrolo[2,3-d]pyrimidin-4-yl)-benzonitrile (B-14);
4-(2-morpholin-4-yl-7-pyridin-4-yl-6,7-dihydro-5H-pyrrolo[2,3-d]pyrimidin-4-yl)-benzonitrile hydrochloride (B-15);
4-(3-fluoro-phenyl)-2-morpholin-4-yl-7-pyridin-4-yl-6,7-dihydro-5H-pyrrolo[2,3-d]pyrimidine (B-16);
4-(5-methoxy-pyridin-3-yl)-2-morpholin-4-yl-7-pyridin-4-yl-6,7-dihydro-5H-pyrrolo[2,3-d]pyrimidine (B-17);
2-morpholin-4-yl-7-pyridin-4-yl-4-pyrimidin-5-yl-6,7-dihydro-5H-pyrrolo[2,3-d]pyrimidine (B-18);
N-[4-(2-morpholin-4-yl-7-pyridin-4-yl-6,7-dihydro-5H-pyrrolo[2,3-d]pyrimidin-4-yl)-phenyl]-methanesulfonamide (B-19);
[2,6-difluoro-3-(2-morpholin-4-yl-7-pyridin-4-yl-6,7-dihydro-5H-pyrrolo[2,3-d]pyrimidin-4-yl)-phenyl]-methanol (B-20);
4-(1H-benzimidazol-5-yl)-2-morpholin-4-yl-7-pyridin-3-yl-6,7-dihydro-5H-pyrrolo[2,3-d]pyrimidine (B-21);
4-(1H-benzimidazol-5-yl)-2-morpholin-4-yl-7-pyridin-4-yl-6,7-dihydro-5H-pyrrolo[2,3-d]pyrimidine (B-22);
[3-(2-morpholin-4-yl-7-pyridin-3-yl-6,7-dihydro-5H-pyrrolo[2,3-d]pyrimidin-4-yl)-phenyl]-methanol (B-23);
4-(2-methoxy-pyridin-3-yl)-2-morpholin-4-yl-7-pyridin-3-yl-6,7-dihydro-5H-pyrrolo[2,3-d]pyrimidine (B-24);
4-(3-benzyloxy-2,6-difluoro-phenyl)-2-morpholin-4-yl-7-pyridin-4-yl-6,7-dihydro-5H-pyrrolo[2,3-d]pyrimidine (B-25);
2,4-difluoro-3-(2-morpholin-4-yl-7-pyridin-4-yl-6,7-dihydro-5H-pyrrolo[2,3-d]pyrimidin-4-yl)-phenol (B-26);
4-(2-methoxy-pyrimidin-5-yl)-2-morpholin-4-yl-7-pyridin-4-yl-6,7-dihydro-5H-pyrrolo[2,3-d]pyrimidine (B-27);
2-morpholin-4-yl-4,7-di-pyridin-4-yl-6,7-dihydro-5H-pyrrolo[2,3-d]pyrimidine (B-28);
2-morpholin-4-yl-4-pyridin-4-yl-7-pyridin-3-yl-6,7-dihydro-5H-pyrrolo[2,3-d]pyrimidine (B-29);
[4-(2-morpholin-4-yl-7-pyridin-4-yl-6,7-dihydro-5H-pyrrolo[2,3-d]pyrimidin-4-yl)-phenyl]-methanol (B-30);
[4-(2-morpholin-4-yl-7-pyridin-3-yl-6,7-dihydro-5H-pyrrolo[2,3-d]pyrimidin-4-yl)-phenyl]-methanol (B-31);
4-(2-morpholin-4-yl-7-pyridin-4-yl-6,7-dihydro-5H-pyrrolo[2,3-d]pyrimidin-4-yl)-benzylamine hydrochloride (B-32);
4-(2-morpholin-4-yl-7-pyridin-3-yl-6,7-dihydro-5H-pyrrolo[2,3-d]pyrimidin-4-yl)-benzylamine hydrochloride (B-33);
2-fluoro-5-(2-morpholin-4-yl-7-pyridin-4-yl-6,7-dihydro-5H-pyrrolo[2,3-d]pyrimidin-4-yl)-benzonitrile (B-34);
[2-fluoro-5-(2-morpholin-4-yl-7-pyridin-4-yl-6,7-dihydro-5H-pyrrolo[2,3-d]pyrimidin-4-yl)-phenyl]-methanol (B-35);
[3-(2-morpholin-4-yl-7-pyridin-4-yl-6,7-dihydro-5H-pyrrolo[2,3-d]pyrimidin-4-yl)-phenyl]-methanol (B-36);
2-morpholin-4-yl-7-pyridin-4-yl-4-(3-trifluoromethoxy-phenyl)-6,7-dihydro-5H-pyrrolo[2,3-d]pyrimidine (B-37);
2-morpholin-4-yl-7-pyridin-4-yl-4-(4-trifluoromethoxy-phenyl)-6,7-dihydro-5H-pyrrolo[2,3-d]pyrimidine (B-38);
4-(2-morpholin-4-yl-7-pyridin-4-yl-6,7-dihydro-5H-pyrrolo[2,3-d]pyrimidin-4-yl)-phenol (B-39);
2-morpholin-4-yl-7-pyridin-4-yl-4-(3,4,5-trimethoxy-phenyl)-6,7-dihydro-5H-pyrrolo[2,3-d]pyrimidine (B-40);
2-morpholin-4-yl-4-phenyl-7-pyridin-4-yl-6,7-dihydro-5H-pyrrolo[2,3-d]pyrimidine (B-41);
5-(2-morpholin-4-yl-7-pyridin-3-yl-6,7-dihydro-5H-pyrrolo[2,3-d]pyrimidin-4-yl)-pyridin-2-ol (B-42);
5-(2-morpholin-4-yl-7-pyridin-4-yl-6,7-dihydro-5H-pyrrolo[2,3-d]pyrimidin-4-yl)-pyridin-2-ol (B-43);
3-(2-morpholin-4-yl-7-pyridin-3-yl-6,7-dihydro-5H-pyrrolo[2,3-d]pyrimidin-4-yl)-pyridin-2-ol (B-44);
5-(2-morpholin-4-yl-7-pyridin-4-yl-6,7-dihydro-5H-pyrrolo[2,3-d]pyrimidin-4-yl)-pyrimidin-2-ol (B-45);
3-(2-morpholin-4-yl-7-phenyl-6,7-dihydro-5H-pyrrolo[2,3-d]pyrimidin-4-yl)-phenol (B-46);
3-[7-(2,4-difluoro-phenyl)-2-morpholin-4-yl-6,7-dihydro-5H-pyrrolo[2,3-d]pyrimidin-4-yl]-phenol (B-47);
4-(3-methoxy-phenyl)-7-(4-methoxy-phenyl)-2-morpholin-4-yl-6,7-dihydro-5H-pyrrolo[2,3-d]pyrimidine (B-48);
7-(4-methoxy-benzyl)-4-(3-methoxy-phenyl)-2-morpholin-4-yl-6,7-dihydro-5H-pyrrolo[2,3-d]pyrimidine (B-49);
3-(2-morpholin-4-yl-7-pyridin-3-yl-6,7-dihydro-5H-pyrrolo[2,3-d]pyrimidin-4-yl)-benzenesulfonamide (B-50);
3-(2-morpholin-4-yl-7-pyridin-4-yl-6,7-dihydro-5H-pyrrolo[2,3-d]pyrimidin-4-yl)-benzenesulfonamide (B-51);
2-fluoro-4-(2-morpholin-4-yl-7-pyridin-3-yl-6,7-dihydro-5H-pyrrolo[2,3-d]pyrimidin-4-yl)-phenylamine (B-52);
2,6-difluoro-4-(2-morpholin-4-yl-7-pyridin-3-yl-6,7-dihydro-5H-pyrrolo[2,3-d]pyrimidin-4-yl)-phenylamine (B-53);
4-(2-morpholin-4-yl-7-pyridin-3-yl-6,7-dihydro-5H-pyrrolo[2,3-d]pyrimidin-4-yl)-phenylamine (B-54);
6-(2-morpholin-4-yl-7-pyridin-4-yl-6,7-dihydro-5H-pyrrolo[2,3-d]pyrimidin-4-yl)-pyridin-3-ylamine (B-55);
4-(3-hydroxyphenyl)-2-(morpholin-4-yl)-7-(ethylaminocarbonyl)-6,7-dihydro-5H-pyrrolo[2,3-d]pyrimidine (C-01);
1-[4-(3-hydroxy-phenyl)-2-morpholin-4-yl-5,6-dihydro-pyrrolo[2,3-d]pyrimidin-7-yl]-ethanone (C-02);
[4-(3-t-butoxyphenyl)-2-morpholin-4-yl-5,6-dihydropyrrolo[2,3-d]pyrimidin-7-yl]-phenylmethanone (C-03);
[4-(3-hydroxyphenyl)-2-morpholin-4-yl-5,6-dihydropyrrolo[2,3-d]pyrimidin-7-yl]-phenylmethanone (C-04);
1-[4-(3-hydroxyphenyl)-2-morpholin-4-yl-5,6-dihydro-pyrrolo[2,3-d]pyrimidin-7-yl]propan-1-one (C-05);
1-[4-(3-hydroxyphenyl)-2-morpholin-4-yl-5,6-dihydro-pyrrolo[2,3-d]pyrimidin-7-yl]-2,2-dimethyl-propan-1-one (C-06);
4-(3-t-butoxy-phenyl)-2-morpholin-4-yl-7-(toluene-4-sulfonyl)-6,7-dihydro-5H-pyrrolo[2,3-d]pyrimidine (C-07);
3-[2-morpholin-4-yl-7-(toluene-4-sulfonyl)-6,7-dihydro-5H-pyrrolo[2,3-d]pyrimidin-4-yl]-phenol (C-08);
4-(3-hydroxy-phenyl)-2-morpholin-4-yl-5,6-dihydro-pyrrolo[2,3-d]pyrimidin-7-carbaldehyde (C-09);
3-(7-methanesulfonyl-2-morpholin-4-yl-6,7-dihydro-5H-pyrrolo[2,3-d]pyrimidin-4-yl)-phenol (C-10);
3-(7-ethanesulfonyl-2-morpholin-4-yl-6,7-dihydro-5H-pyrrolo[2,3-d]pyrimidin-4-yl)-phenol (C-11);
3-[2-morpholin-4-yl-7-(toluene-2-sulfonyl)-6,7-dihydro-5H-pyrrolo[2,3-d]pyrimidin-4-yl]-phenol (C-12);
[4-(3-hydroxy-phenyl)-2-morpholin-4-yl-5,6-dihydro-pyrrolo[2,3-d]pyrimidin-7-yl]-acetic acid ethyl ester (C-13);

3-(7-benzenesulfonyl-2-morpholin-4-yl-6,7-dihydro-5H-pyrrolo[2,3-d]pyrimidin-4-yl)-phenol (C-14);
3-[2-morpholin-4-yl-7-(thiophene-2-sulfonyl)-6,7-dihydro-5H-pyrrolo[2,3-d]pyrimidin-4-yl]-phenol (C-15);
3-[7-(3-methoxy-benzenesulfonyl)-2-morpholin-4-yl-6,7-dihydro-5H-pyrrolo[2,3-d]pyrimidin-4-yl]-phenol (C-16);
4-(3-hydroxy-phenyl)-2-morpholin-4-yl-5,6-dihydro-pyrrolo[2,3-d]pyrimidine-7-carboxylic acid phenyl amide (C-17);
4-(3-hydroxy-phenyl)-2-morpholin-4-yl-5,6-dihydro-pyrrolo[2,3-d]pyrimidine-7-carboxylic acid (2,4-difluoro-phenyl)-amide (C-18);
4-(3-hydroxy-phenyl)-2-morpholin-4-yl-5,6-dihydro-pyrrolo[2,3-d]pyrimidine-7-carboxylic acid p-tolyl amide (C-19);
4-(3-hydroxy-phenyl)-2-morpholin-4-yl-5,6-dihydro-pyrrolo[2,3-d]pyrimidine-7-carboxylic acid (4-trifluoromethyl-phenyl)-amide (C-20);
3-[7-(4-fluoro-benzenesulfonyl)-2-morpholin-4-yl-6,7-dihydro-5H-pyrrolo[2,3-d]pyrimidin-4-yl]-phenol (C-21);
3-[7-(2,4-difluoro-benzenesulfonyl)-2-morpholin-4-yl-6,7-dihydro-5H-pyrrolo[2,3-d]pyrimidin-4-yl]-phenol (C-22);
4-[4-(3-hydroxy-phenyl)-2-morpholin-4-yl-5,6-dihydro-pyrrolo[2,3-d]pyrimidine-7-sulfonyl]-benzonitrile (C-23);
3-[2-morpholin-4-yl-7-(toluene-3-sulfonyl)-6,7-dihydro-5H-pyrrolo[2,3-d]pyrimidin-4-yl]-phenol (C-24);
3-[7-(4-tert-butyl-benzenesulfonyl)-2-morpholin-4-yl-6,7-dihydro-5H-pyrrolo[2,3-d]pyrimidin-4-yl]-phenol (C-25);
3-[2-morpholin-4-yl-7-(4-trifluoromethyl-benzenesulfonyl)-6,7-dihydro-5H-pyrrolo[2,3-d]pyrimidin-4-yl]-phenol (C-26);
3-[2-morpholin-4-yl-7-(3-trifluoromethyl-benzenesulfonyl)-6,7-dihydro-5H-pyrrolo[2,3-d]pyrimidin-4-yl]-phenol (C-27);
3-[2-morpholin-4-yl-7-(4-trifluoromethoxy-benzenesulfonyl)-6,7-dihydro-5H-pyrrolo[2,3-d]pyrimidin-4-yl]-phenol (C-28);
[4-(3-hydroxy-phenyl)-2-morpholin-4-yl-5,6-dihydro-pyrrolo[2,3-d]pyrimidin-7-yl]-p-tolyl-methanone (C-29);
[4-(3-hydroxy-phenyl)-2-morpholin-4-yl-5,6-dihydro-pyrrolo[2,3-d]pyrimidin-7-yl]-m-tolyl-methanone (C-30);
[4-(3-hydroxy-phenyl)-2-morpholin-4-yl-5,6-dihydro-pyrrolo[2,3-d]pyrimidin-7-yl]-(4-trifluoromethyl-phenyl)-methanone (C-31);
2-(4-fluoro-phenyl)-1-[4-(3-hydroxy-phenyl)-2-morpholin-4-yl-5,6-dihydro-pyrrolo[2,3-d]pyrimidin-7-yl]-ethanone (C-32);
1-[4-(3-hydroxy-phenyl)-2-morpholin-4-yl-5,6-dihydro-pyrrolo[2,3-d]pyrimidin-7-yl]-3-phenyl-propan-1-one (C-33);
[4-(3-hydroxy-phenyl)-2-morpholin-4-yl-5,6-dihydro-pyrrolo[2,3-d]pyrimidin-7-yl]-(3-trifluoromethyl-phenyl)-methanone (C-34);
1-[4-(3-hydroxy-phenyl)-2-morpholin-4-yl-5,6-dihydro-pyrrolo[2,3-d]pyrimidin-7-yl]-2-phenyl-ethanone (C-35);
N-{4-[4-(3-hydroxy-phenyl)-2-morpholin-4-yl-5,6-dihydro-pyrrolo[2,3-d]pyrimidine-7-carbonyl]-phenyl}-acetamide (C-36);
[4-(3-hydroxy-phenyl)-2-morpholin-4-yl-5,6-dihydro-pyrrolo[2,3-d]pyrimidin-7-yl]-pyridin-2-yl-methanone (C-37);
(2,4-difluoro-phenyl)-[4-(3-hydroxy-phenyl)-2-morpholin-4-yl-5,6-dihydro-pyrrolo[2,3-d]pyrimidin-7-yl]-methanone (C-38);
[4-(3-hydroxy-phenyl)-2-morpholin-4-yl-5,6-dihydro-pyrrolo[2,3-d]pyrimidin-7-yl]-pyridin-4-yl-methanone (C-39);
[4-(3-hydroxy-phenyl)-2-morpholin-4-yl-5,6-dihydro-pyrrolo[2,3-d]pyrimidin-7-yl]-o-tolyl-methanone (C-40);
(4-tert-butyl-phenyl)-[4-(3-hydroxy-phenyl)-2-morpholin-4-yl-5,6-dihydro-pyrrolo[2,3-d]pyrimidin-7-yl]-methanone (C-41);
4-[4-(3-hydroxy-phenyl)-2-morpholin-4-yl-5,6-dihydro-pyrrolo[2,3-d]pyrimidine-7-carbonyl]-benzonitrile trifluoroacetic acid salt (C-42);
[4-(3-hydroxy-phenyl)-2-morpholin-4-yl-5,6-dihydro-pyrrolo[2,3-d]pyrimidin-7-yl]-naphthalen-2-yl-methanone trifluoroacetic acid salt (C-43);
[4-(3-hydroxy-phenyl)-2-morpholin-4-yl-5,6-dihydro-pyrrolo[2,3-d]pyrimidin-7-yl]-naphthalen-1-yl-methanone trifluoroacetic acid salt (C-44);
1-[4-(3-hydroxy-phenyl)-2-morpholin-4-yl-5,6-dihydro-pyrrolo[2,3-d]pyrimidin-7-yl]-3,3-dimethyl-butan-1-one (C-45);
1-[4-(3-hydroxy-phenyl)-2-morpholin-4-yl-5,6-dihydro-pyrrolo[2,3-d]pyrimidin-7-yl]-pentan-1-one (C-46);
4-[4-(3-hydroxy-phenyl)-2-morpholin-4-yl-5,6-dihydro-pyrrolo[2,3-d]pyrimidin-7-yl]-4-oxo-butyric acid methyl ester (C-47);
5-[4-(3-hydroxy-phenyl)-2-morpholin-4-yl-5,6-dihydro-pyrrolo[2,3-d]pyrimidin-7-yl]-5-oxo-pentanoic acid methyl ester (C-48);
1-[4-(3-hydroxy-phenyl)-2-morpholin-4-yl-5,6-dihydro-pyrrolo[2,3-d]pyrimidin-7-yl]-heptan-1-one (C-49);
4-(3-hydroxy-phenyl)-2-morpholin-4-yl-5,6-dihydro-pyrrolo[2,3-d]pyrimidine-7-carboxylic acid isopropylamide trifluoroacetic acid salt (C-50);
4-(3-hydroxy-phenyl)-2-morpholin-4-yl-5,6-dihydro-pyrrolo[2,3-d]pyrimidine-7-carboxylic acid phenethylamide trifluoroacetic acid salt (C-51);
1-[4-(3-hydroxy-phenyl)-2-morpholin-4-yl-5,6-dihydro-pyrrolo[2,3-d]pyrimidin-7-yl]-2-naphthalen-1-yl-ethanone (C-52);
[4-(3-hydroxy-phenyl)-2-morpholin-4-yl-5,6-dihydro-pyrrolo[2,3-d]pyrimidin-7-yl]-thiophen-2-yl-methanone trifluoroacetic acid salt (C-53);
benzo[b]thiophen-2-yl-[4-(3-hydroxy-phenyl)-2-morpholin-4-yl-5,6-dihydro-pyrrolo[2,3-d]pyrimidin-7-yl]-methanone trifluoroacetic acid salt (C-54);
4-(3-hydroxy-phenyl)-2-morpholin-4-yl-5,6-dihydro-pyrrolo[2,3-d]pyrimidine-7-carbothioic acid methyl amide trifluoroacetic acid salt (C-55);
4-(3-hydroxy-phenyl)-2-morpholin-4-yl-5,6-dihydro-pyrrolo[2,3-d]pyrimidine-7-carbothioic acid butyl amide trifluoroacetic acid salt (C-56);
3-[7-(butane-1-sulfonyl)-2-morpholin-4-yl-6,7-dihydro-5H-pyrrolo[2,3-d]pyrimidin-4-yl]-phenol (C-57);
1-[4-(2-amino-pyrimidin-5-yl)-2-morpholin-4-yl-5,6-dihydro-pyrrolo[2,3-d]pyrimidin-7-yl]-ethanone (D-01);
5-(7-methanesulfonyl-2-morpholin-4-yl-6,7-dihydro-5H-pyrrolo[2,3-d]pyrimidin-4-yl)-pyrimidin-2-ylamine (D-02);

4-(2-amino-pyrimidin-5-yl)-2-morpholin-4-yl-5,6-dihydro-pyrrolo[2,3-d]pyrimidine-7-carboxylic acid ethyl amide (D-03);

5-(7-ethyl-2-morpholin-4-yl-6,7-dihydro-5H-pyrrolo[2,3-d]pyrimidin-4-yl)-pyrimidin-2-ylamine (D-04);

5-(7-benzyl-2-morpholin-4-yl-6,7-dihydro-5H-pyrrolo[2,3-d]pyrimidin-4-yl)-pyrimidin-2-ylamine (D-05);

1-[4-(2-amino-pyrimidin-5-yl)-2-morpholin-4-yl-5,6-dihydro-pyrrolo[2,3-d]pyrimidin-7-yl]-propan-1-one (D-06);

4-[4-(2-amino-pyrimidin-5-yl)-2-morpholin-4-yl-5,6-dihydro-pyrrolo[2,3-d]pyrimidin-7-yl]-pyridine-2-carboxylic acid tert-butyl amide (D-07);

4-[4-(2-amino-pyrimidin-5-yl)-2-morpholin-4-yl-5,6-dihydro-pyrrolo[2,3-d]pyrimidin-7-yl]-benzoic acid methyl ester (D-08);

4-[4-(2-amino-pyrimidin-5-yl)-2-morpholin-4-yl-5,6-dihydro-pyrrolo[2,3-d]pyrimidin-7-yl]-benzoic acid sodium salt (D-09);

4-[4-(2-amino-pyrimidin-5-yl)-2-morpholin-4-yl-5,6-dihydro-pyrrolo[2,3-d]pyrimidin-7-yl]-benzamide (D-10);

1-[4-(2-amino-pyrimidin-5-yl)-2-morpholin-4-yl-5,6-dihydro-pyrrolo[2,3-d]pyrimidin-7-yl]-3-phenylpropan-1-one (D-11);

4-[4-(2-amino-pyrimidin-5-yl)-2-morpholin-4-yl-5,6-dihydro-pyrrolo[2,3-d]pyrimidin-7-yl]-4-oxo-butyric acid methyl ester (D-12);

4-(2-amino-pyrimidin-5-yl)-2-morpholin-4-yl-5,6-dihydro-pyrrolo[2,3-d]pyrimidine-7-carboxylic acid isopropylamide (D-13);

4-(2-amino-pyrimidin-5-yl)-2-morpholin-4-yl-5,6-dihydro-pyrrolo[2,3-d]pyrimidine-7-thiocarboxylic acid ethyl amide (D-14);

4-(2-amino-pyrimidin-5-yl)-2-morpholin-4-yl-5,6-dihydro-pyrrolo[2,3-d]pyrimidine-7-carboxylic acid ethyl ester (D-15);

{3-[4-(2-amino-pyrimidin-5-yl)-2-morpholin-4-yl-5,6-dihydro-pyrrolo[2,3-d]pyrimidin-7-yl]-4-fluoro-phenyl}-morpholin-4-yl-methanone (D-16);

4-(2-amino-pyrimidin-5-yl)-2-morpholin-4-yl-5,6-dihydro-pyrrolo[2,3-d]pyrimidine-7-carbothioic acid [5-(4-ethyl-piperazine-1-carbonyl)-2-methyl-phenyl]-amide (D-17);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-2,6-difluoro-phenyl]-amide (D-18);

4-[4-(2-amino-pyrimidin-5-yl)-2-morpholin-4-yl-5,6-dihydro-pyrrolo[2,3-d]pyrimidin-7-yl]-N-pyridin-3-ylmethyl-benzamide (D-19);

{4-[4-(2-amino-pyrimidin-5-yl)-2-morpholin-4-yl-5,6-dihydro-pyrrolo[2,3-d]pyrimidin-7-yl]-phenyl}-(4-pyridin-3-yl-piperazin-1-yl)-methanone (D-20);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-3-yl-piperazin-1-yl)-methanone (D-21);

{4-[4-(2-amino-pyrimidin-5-yl)-2-morpholin-4-yl-5,6-dihydro-pyrrolo[2,3-d]pyrimidin-7-yl]-3-fluoro-phenyl}-morpholin-4-yl-methanone (D-22);

4-(2-amino-pyrimidin-5-yl)-2-morpholin-4-yl-5,6-dihydro-pyrrolo[2,3-d]pyrimidine-7-carboxylic acid [4-(4-methyl-piperazin-1-yl)-2,6-difluoro-phenyl]-amide (D-23);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2,6-difluoro-phenyl]-amide (D-24);

{3-[4-(2-amino-pyrimidin-5-yl)-2-morpholin-4-yl-5,6-dihydro-pyrrolo[2,3-d]pyrimidin-7-yl]-4-methyl-phenyl}-morpholin-4-yl-methanone (D-25);

5-{7-[4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-26);

[4-(2-amino-pyrimidin-5-yl)-2-morpholin-4-yl-5,6-dihydro-pyrrolo[2,3-d]pyrimidin-7-yl]-phenyl-methanone (D-27);

4-(2-amino-pyrimidin-5-yl)-2-morpholin-4-yl-5,6-dihydro-pyrrolo[2,3-d]pyrimidine-7-carboxylic acid phenylamide (D-28);

{[4-(2-amino-pyrimidin-5-yl)-2-morpholin-4-yl-5,6-dihydro-pyrrolo[2,3-d]pyrimidine-7-carbonyl]-amino}-acetic acid ethyl ester (D-29);

3-{[4-(2-amino-pyrimidin-5-yl)-2-morpholin-4-yl-5,6-dihydro-pyrrolo[2,3-d]pyrimidine-7-carbonyl]-amino}-propionic acid ethyl ester (D-30);

4-(2-amino-pyrimidin-5-yl)-2-morpholin-4-yl-5,6-dihydro-pyrrolo[2,3-d]pyrimidine-7-carboxylic acid carbamoylmethyl-amide (D-31);

4-(2-amino-pyrimidin-5-yl)-2-morpholin-4-yl-5,6-dihydro-pyrrolo[2,3-d]pyrimidine-7-carboxylic acid (2-carbamoyl-ethyl)-amide (D-32);

{[4-(2-amino-pyrimidin-5-yl)-2-morpholin-4-yl-5,6-dihydro-pyrrolo[2,3-d]pyrimidine-7-carbonyl]-amino}-acetic acid (D-33);

3-{[4-(2-amino-pyrimidin-5-yl)-2-morpholin-4-yl-5,6-dihydro-pyrrolo[2,3-d]pyrimidine-7-carbonyl]-amino}-propionic acid (D-34);

4-[4-(2-amino-pyrimidin-5-yl)-2-morpholin-4-yl-5,6-dihydro-pyrrolo[2,3-d]pyrimidin-7-yl]-4-oxo-butyric acid (D-35);

5-[7-(5-bromo-pyridin-2-yl)-2-morpholin-4-yl-6,7-dihydro-5H-pyrrolo[2,3-d]pyrimidin-4-yl]-pyrimidin-2-ylamine (D-36);

5-[7-(6-fluoro-pyridin-3-yl)-2-morpholin-4-yl-6,7-dihydro-5H-pyrrolo[2,3-d]pyrimidin-4-yl]-pyrimidin-2-ylamine (D-37);

4-[4-(2-amino-pyrimidin-5-yl)-2-morpholin-4-yl-5,6-dihydro-pyrrolo[2,3-d]pyrimidin-7-yl]-4-oxo-butyramide (D-38);

4-(2-amino-pyrimidin-5-yl)-2-morpholin-4-yl-5,6-dihydro-pyrrolo[2,3-d]pyrimidine-7-carboxylic acid 2-methoxy-ethyl ester (D-39);

4-(2-amino-pyrimidin-5-yl)-2-morpholin-4-yl-5,6-dihydro-pyrrolo[2,3-d]pyrimidine-7-carboxylic acid allyl ester (D-40);

4-[4-(2-amino-pyrimidin-5-yl)-2-morpholin-4-yl-5,6-dihydro-pyrrolo[2,3-d]pyrimidin-7-yl]-N-(2-dimethylamino-ethyl)-benzamide (D-41);

{4-[4-(2-amino-pyrimidin-5-yl)-2-morpholin-4-yl-5,6-dihydro-pyrrolo[2,3-d]pyrimidin-7-yl]-phenyl}-(4-methyl-piperazin-1-yl)-methanone (D-42);

N-{4-[4-(2-amino-pyrimidin-5-yl)-2-morpholin-4-yl-5,6-dihydro-pyrrolo[2,3-d]pyrimidin-7-yl]-phenyl}-acetamide (D-43);

N-{4-[4-(2-amino-pyrimidin-5-yl)-2-morpholin-4-yl-5,6-dihydro-pyrrolo[2,3-d]pyrimidin-7-yl]-phenyl}-methanesulfonamide (D-44);

N-{3-[4-(2-amino-pyrimidin-5-yl)-2-morpholin-4-yl-5,6-dihydro-pyrrolo[2,3-d]pyrimidin-7-yl]-phenyl}-acetamide (D-45);

4-(2-amino-pyrimidin-5-yl)-2-morpholin-4-yl-5,6-dihydro-pyrrolo[2,3-d]pyrimidine-7-carbothioic acid (2-morpholin-4-yl-ethyl)-amide (D-46);

4-(2-amino-pyrimidin-5-yl)-2-morpholin-4-yl-5,6-dihydro-pyrrolo[2,3-d]pyrimidine-7-carboxylic acid (3-trifluoromethyl-phenyl)-amide (D-47);

N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-48);

5-{7-[6-(4-ethyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-49);

5-(7-ethanesulfonyl-2-morpholin-4-yl-6,7-dihydro-5H-pyrrolo[2,3-d]pyrimidin-4-yl)-pyrimidin-2-ylamine (D-50);

5-[2-morpholin-4-yl-7-(propane-1-sulfonyl)-6,7-dihydro-5H-pyrrolo[2,3-d]pyrimidin-4-yl]-pyrimidin-2-ylamine (D-51);

3-[4-(2-amino-pyrimidin-5-yl)-2-morpholin-4-yl-5,6-dihydro-pyrrolo[2,3-d]pyrimidin-7-yl]-benzoic acid methyl ester (D-52);

{3-[4-(2-amino-pyrimidin-5-yl)-2-morpholin-4-yl-5,6-dihydro-pyrrolo[2,3-d]pyrimidin-7-yl]-phenyl}-morpholin-4-yl-methanone (D-53);

{3-[4-(2-amino-pyrimidin-5-yl)-2-morpholin-4-yl-5,6-dihydro-pyrrolo[2,3-d]pyrimidin-7-yl]-phenyl}-(4-methyl-piperazin-1-yl)-methanone (D-54);

3-[4-(2-amino-pyrimidin-5-yl)-2-morpholin-4-yl-5,6-dihydro-pyrrolo[2,3-d]pyrimidin-7-yl]-N-(2-dimethylamino-ethyl)-benzamide (D-55);

4-{[4-(2-amino-pyrimidin-5-yl)-2-morpholin-4-yl-5,6-dihydro-pyrrolo[2,3-d]pyrimidine-7-carbonyl]-amino}-benzoic acid ethyl ester (D-56);

5-(2-morpholin-4-yl-7-phenyl-6,7-dihydro-5H-pyrrolo[2,3-d]pyrimidin-4-yl)-pyrimidin-2-ylamine (D-57);

5-[7-(2,4-difluoro-phenyl)-2-morpholin-4-yl-6,7-dihydro-5H-pyrrolo[2,3-d]pyrimidin-4-yl]-pyrimidin-2-ylamine (D-58);

4-(2-amino-pyrimidin-5-yl)-2-morpholin-4-yl-5,6-dihydro-pyrrolo[2,3-d]pyrimidine-7-carboxylic acid (2-morpholin-4-yl-ethyl)-amide (D-59);

4-(2-amino-pyrimidin-5-yl)-2-morpholin-4-yl-5,6-dihydro-pyrrolo[2,3-d]pyrimidine-7-carboxylic acid [3-(4-methyl-piperazin-1-yl)-propyl]-amide (D-60);

4-(2-amino-pyrimidin-5-yl)-2-morpholin-4-yl-5,6-dihydro-pyrrolo[2,3-d]pyrimidine-7-carboxylic acid (2-piperidin-1-yl-ethyl)-amide (D-61);

5-{7-[3-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-62);

5-{7-[4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-63);

[4-(2-amino-pyrimidin-5-yl)-2-morpholin-4-yl-5,6-dihydro-pyrrolo[2,3-d]pyrimidin-7-yl]-piperidin-4-yl-methanone (D-64);

4-(2-amino-pyrimidin-5-yl)-2-morpholin-4-yl-5,6-dihydro-pyrrolo[2,3-d]pyrimidine-7-carboxylic acid (4-pyridin-3-yl-phenyl)-amide (D-65);

4-(2-amino-pyrimidin-5-yl)-2-morpholin-4-yl-5,6-dihydro-pyrrolo[2,3-d]pyrimidine-7-carboxylic acid (4-pyridin-4-yl-phenyl)-amide (D-66);

4-(2-amino-pyrimidin-5-yl)-2-morpholin-4-yl-5,6-dihydro-pyrrolo[2,3-d]pyrimidine-7-carboxylic acid piperidin-4-ylamide (D-67);

4-(2-amino-pyrimidin-5-yl)-2-morpholin-4-yl-5,6-dihydro-pyrrolo[2,3-d]pyrimidine-7-carboxylic acid (2-dimethylamino-ethyl)-amide (D-68);

5-{2-morpholin-4-yl-7-[2-(3-morpholin-4-yl-propylamino)-pyridin-4-yl]-6,7-dihydro-5H-pyrrolo[2,3-d]pyrimidin-4-yl}-pyrimidin-2-ylamine (D-69);

1-(4-{4-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-70);

5-{7-[6-(4-methyl-piperazin-1-yl)-pyridin-3-yl]-2-morpholin-4-yl-6,7-dihydro-5H-pyrrolo[2,3-d]pyrimidin-4-yl}-pyrimidin-2-ylamine (D-71);

5-{7-[6-(2-dimethylamino-ethoxy)-pyridin-3-yl]-2-morpholin-4-yl-6,7-dihydro-5H-pyrrolo[2,3-d]pyrimidin-4-yl}-pyrimidin-2-ylamine (D-72);

{5'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (D-73);

N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-ethane-1,2-diamine (D-74);

4'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-ol (D-75);

[4-(2-amino-pyrimidin-5-yl)-2-morpholin-4-yl-5,6-dihydro-pyrrolo[2,3-d]pyrimidin-7-yl]-(4-methyl-piperazin-1-yl)-methanone (D-76);

4-(2-amino-pyrimidin-5-yl)-2-morpholin-4-yl-5,6-dihydro-pyrrolo[2,3-d]pyrimidine-7-carboxylic acid (3-dimethylamino-propyl)-amide (D-77);

4-(2-amino-pyrimidin-5-yl)-2-morpholin-4-yl-5,6-dihydro-pyrrolo[2,3-d]pyrimidine-7-carboxylic acid (piperidin-4-ylmethyl)-amide (D-78);

{5-[4-(2-amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-79);

3-[4-(2-amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-80);

4-(2-amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-amide (D-81);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-amide (D-82);

{4-[4-(2-amino-pyrimidin-5-yl)-2-morpholin-4-yl-5,6-dihydro-pyrrolo[2,3-d]pyrimidin-7-yl]-phenyl}-(4-ethyl-piperazin-1-yl)-methanone (D-83);

4-[4-(2-amino-pyrimidin-5-yl)-2-morpholin-4-yl-5,6-dihydro-pyrrolo[2,3-d]pyrimidin-7-yl]-N-(2-dimethylamino-ethyl)-N-methyl-benzamide (D-84);

{5-[4-(2-amino-pyrimidin-5-yl)-2-morpholin-4-yl-5,6-dihydro-pyrrolo[2,3-d]pyrimidin-7-yl]-pyridin-2-yl}-morpholin-4-yl-methanone (D-85):

5-{7-[3-(morpholine-4-sulfonyl)-phenyl]-2-morpholin-4-yl-6,7-dihydro-5H-pyrrolo[2,3-d]pyrimidin-4-yl}-pyrimidin-2-ylamine (D-86);

5-{7-[4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-87);

4-(2-amino-pyrimidin-5-yl)-2-morpholin-4-yl-5,6-dihydro-pyrrolo[2,3-d]pyrimidine-7-carboxylic acid (1-methyl-piperidin-4-yl)-amide (D-88);

1-[4-(2-amino-pyrimidin-5-yl)-2-morpholin-4-yl-5,6-dihydro-pyrrolo[2,3-d]pyrimidin-7-yl]-4-(4-ethyl-piperazin-1-yl)-butane-1,4-dione (D-89);

1-[4-(2-amino-pyrimidin-5-yl)-2-morpholin-4-yl-5,6-dihydro-pyrrolo[2,3-d]pyrimidin-7-yl]-4-morpholin-4-yl-butane-1,4-dione (D-90);

4-[4-(2-amino-pyrimidin-5-yl)-2-morpholin-4-yl-5,6-dihydro-pyrrolo[2,3-d]pyrimidin-7-yl]-N-(3-dimethylamino-propyl)-benzamide (D-91);

4-[4-(2-amino-pyrimidin-5-yl)-2-morpholin-4-yl-5,6-dihydro-pyrrolo[2,3-d]pyrimidin-7-yl]-N-(3-dimethylamino-propyl)-N-methyl-benzamide (D-92);

4-[4-(2-amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-93);

4-[4-(2-amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-94);

{5-[4-(2-amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-95);

5-{7-[3-(4-ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-96);

5-{7-[4-(4-ethyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-97);

4-[4-(2-amino-pyrimidin-5-yl)-2-morpholin-4-yl-5,6-dihydro-pyrrolo[2,3-d]pyrimidin-7-yl]-N-(3-hydroxy-propyl)-benzenesulfonamide (D-98);

3-[4-(2-amino-pyrimidin-5-yl)-2-morpholin-4-yl-5,6-dihydro-pyrrolo[2,3-d]pyrimidin-7-yl]-N-(2-hydroxy-ethyl)-benzene sulfonamide (D-99);

4-[4-(2-amino-pyrimidin-5-yl)-2-morpholin-4-yl-5,6-dihydro-pyrrolo[2,3-d]pyrimidin-7-yl]-N-(2-hydroxy-ethyl)-benzene sulfonamide (D-100);

4-(2-amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-phenyl]-amide (D-101);

4-(2-amino-pyrimidin-5-yl)-2-morpholin-4-yl-5,6-dihydro-pyrrolo[2,3-d]pyrimidine-7-carboxylic acid [3-(morpholine-4-carbonyl)-phenyl]-amide (D-102);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-phenyl]-amide (D-103);

4-(2-amino-pyrimidin-5-yl)-2-morpholin-4-yl-5,6-dihydro-pyrrolo[2,3-d]pyrimidine-7-carboxylic acid [4-(morpholine-4-carbonyl)-phenyl]-amide (D-104);

4-(2-amino-pyrimidin-5-yl)-2-morpholin-4-yl-5,6-dihydro-pyrrolo[2,3-d]pyrimidine-7-carboxylic acid (3-morpholin-4-yl-phenyl)-amide (D-105);

4-(2-amino-pyrimidin-5-yl)-2-morpholin-4-yl-5,6-dihydro-pyrrolo[2,3-d]pyrimidine-7-carboxylic acid [3-(2-morpholin-4-yl-ethylamino)-phenyl]-amide (D-106);

4-(2-amino-pyrimidin-5-yl)-2-morpholin-4-yl-5,6-dihydro-pyrrolo[2,3-d]pyrimidine-7-carboxylic acid (4-morpholin-4-yl-phenyl)-amide (D-107);

4-(2-amino-pyrimidin-5-yl)-2-morpholin-4-yl-5,6-dihydro-pyrrolo[2,3-d]pyrimidine-7-carboxylic acid [4-(2-morpholin-4-yl-ethylamino)-phenyl]-amide (D-108);

1-(4-{5-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl)-ethanone (D-109);

5-[2-morpholin-4-yl-7-(6-morpholin-4-yl-pyridin-3-yl)-6,7-dihydro-5H-pyrrolo[2,3-d]pyrimidin-4-yl]-pyrimidin-2-ylamine (D-110);

{4-[4-(2-amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-111);

{4-[4-(2-amino-pyrimidin-5-yl)-2-morpholin-4-yl-5,6-dihydro-pyrrolo[2,3-d]pyrimidin-7-yl]-phenyl}-piperazin-1-yl-methanone (D-112);

{4-[4-(2-amino-pyrimidin-5-yl)-2-morpholin-4-yl-5,6-dihydro-pyrrolo[2,3-d]pyrimidin-7-yl]-phenyl}-(4-isopropyl-piperazin-1-yl)-methanone (D-113);

5-[7-(1-benzyloxymethyl-1H-benzimidazol-5-yl)-2-morpholin-4-yl-6,7-dihydro-5H-pyrrolo[2,3-d]pyrimidin-4-yl]-pyrimidin-2-ylamine (D-114);

5-[7-(1H-benzimidazol-5-yl)-2-morpholin-4-yl-6,7-dihydro-5H-pyrrolo[2,3-d]pyrimidin-4-yl]-pyrimidin-2-ylamine (D-115);

N-{5-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (D-116);

{5-[4-(2-amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-117);

2-(4-{3-[4-(2-amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-118);

2-(4-{4-[4-(2-amino-pyrimidin-5-yl)-2-morpholin-4-yl-5,6-dihydro-pyrrolo[2,3-d]pyrimidin-7-yl]-benzenesulfonyl}-piperazin-1-yl)-ethanol (D-119);

{2-[4-(2-amino-pyrimidin-5-yl)-2-morpholin-4-yl-5,6-dihydro-pyrrolo[2,3-d]pyrimidin-7-yl]-thiazol-4-yl}-(4-ethyl-piperazin-1-yl)-methanone (D-120);

{2-[4-(2-amino-pyrimidin-5-yl)-2-morpholin-4-yl-5,6-dihydro-pyrrolo[2,3-d]pyrimidin-7-yl]-thiazol-4-yl}-[4-(2-hydroxy-ethyl)-piperazin-1-yl]-methanone (D-121);

4-(2-amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazine-1-carbonyl]-phenyl}-amide (D-122);

3-[4-(2-amino-pyrimidin-5-yl)-2-morpholin-4-yl-5,6-dihydro-pyrrolo[2,3-d]pyrimidin-7-yl]-N-(2-morpholin-4-yl-ethyl)-benzamide (D-123);

3-[4-(2-amino-pyrimidin-5-yl)-2-morpholin-4-yl-5,6-dihydro-pyrrolo[2,3-d]pyrimidin-7-yl]-N-(3-morpholin-4-yl-propyl)-benzamide (D-124);

{3-[4-(2-amino-pyrimidin-5-yl)-2-morpholin-4-yl-5,6-dihydro-pyrrolo[2,3-d]pyrimidin-7-yl]-phenyl}-[4-(2-hydroxy-ethyl)-piperazin-1-yl]-methanone (D-125);

5-[2-morpholin-4-yl-7-(4-morpholin-4-ylmethyl-phenyl)-6,7-dihydro-5H-pyrrolo[2,3-d]pyrimidin-4-yl]-pyrimidin-2-ylamine (D-126);

2-{4-[4-(2-amino-pyrimidin-5-yl)-2-morpholin-4-yl-5,6-dihydro-pyrrolo[2,3-d]pyrimidin-7-yl]-phenylsulfanyl}-1-(4-ethyl-piperazin-1-yl)-ethanone (D-127);

{5-[4-(2-amino-pyrimidin-5-yl)-2-morpholin-4-yl-5,6-dihydro-pyrrolo [2,3-d]pyrimidin-7-yl]-pyridin-2-yl}-piperazin-1-yl-methanone (D-128);

5-{2-morpholin-4-yl-7-[3-(2-piperazin-1-yl-ethyl)-phenyl]-6,7-dihydro-5H-pyrrolo[2,3-d]pyrimidin-4-yl}-pyrimidin-2-ylamine (D-129);

{3-[4-(2-amino-pyrimidin-5-yl)-2-morpholin-4-yl-5,6-dihydro-pyrrolo [2,3-d]pyrimidin-7-yl]-4-methyl-phenyl}-(4-methyl-piperazin-1-yl)-methanone (D-130);

5-{2-morpholin-4-yl-7-[4-(2-piperazin-1-yl-ethyl)-phenyl]-6,7-dihydro-5H-pyrrolo[2,3-d]pyrimidin-4-yl}-pyrimidin-2-ylamine (D-131);

5-{2-morpholin-4-yl-7-[3-(piperazine-1-sulfonyl)-phenyl]-6,7-dihydro-5H-pyrrolo[2,3-d]pyrimidin-4-yl}-pyrimidin-2-ylamine (D-132);

5-{2-morpholin-4-yl-7-[4-(piperazine-1-sulfonyl)-phenyl]-6,7-dihydro-5H-pyrrolo[2,3-d]pyrimidin-4-yl}-pyrimidin-2-ylamine (D-133);

1-[4-(2-{3-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-134);

4-(2-amino-pyrimidin-5-yl)-2-morpholin-4-yl-5,6-dihydro-pyrrolo[2,3-d]pyrimidine-7-carboxylic acid [3-(4-ethyl-piperazin-1-yl)-phenyl]-methyl-amide (D-135);

5-(7-{3-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-136);

{4-[4-(2-amino-pyrimidin-5-yl)-2-morpholin-4-yl-5,6-dihydro-pyrrolo[2,3-d]pyrimidin-7-yl]-3-methyl-phenyl}-morpholin-4-yl-methanone (D-137);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-ethyl-piperazin-1-yl)-methanone (D-138);

4-[4-(2-amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzamide (D-139);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-methyl-piperazin-1-yl)-methanone (D-140);

{4-[4-(2-amino-pyrimidin-5-yl)-2-morpholin-4-yl-5,6-dihydro-pyrrolo[2,3-d]pyrimidin-7-yl]-3-fluoro-phenyl}-piperazin-1-yl-methanone (D-141);

{4-[4-(2-amino-pyrimidin-5-yl)-2-morpholin-4-yl-5,6-dihydro-pyrrolo[2,3-d]pyrimidin-7-yl]-3-methyl-phenyl}-(4-methyl-piperazin-1-yl)-methanone (D-142);

1-[4-(2-{4-[4-(2-amino-pyrimidin-5-yl)-2-morpholin-4-yl-5,6-dihydro-pyrrolo[2,3-d]pyrimidin-7-yl]-phenyl}-ethyl)-piperazin-1-yl]-ethanone (D-143);

5-(7-{4-[2-(4-methanesulfonyl-piperazin-1-yl)-ethyl]-phenyl}-2-morpholin-4-yl-6,7-dihydro-5H-pyrrolo[2,3-d]pyrimidin-4-yl)-pyrimidin-2-ylamine (D-144);

{4-[4-(2-amino-pyrimidin-5-yl)-2-morpholin-4-yl-5,6-dihydro-pyrrolo[2,3-d]pyrimidin-7-yl]-3-fluoro-phenyl}-[4-(2-hydroxy-ethyl)-piperazin-1-yl]-methanone (D-145);

{4-[4-(2-amino-pyrimidin-5-yl)-2-morpholin-4-yl-5,6-dihydro-pyrrolo[2,3-d]pyrimidin-7-yl]-3-methyl-phenyl}-(4-ethyl-piperazin-1-yl)-methanone (D-146);

{4-[4-(2-amino-pyrimidin-5-yl)-2-morpholin-4-yl-5,6-dihydro-pyrrolo[2,3-d]pyrimidin-7-yl]-3-methyl-phenyl}-[4-(2-hydroxy-ethyl)-piperazin-1-yl]-methanone (D-147);

{3-[4-(2-amino-pyrimidin-5-yl)-2-morpholin-4-yl-5,6-dihydro-pyrrolo [2,3-d]pyrimidin-7-yl]-2-methyl-phenyl}-(4-methyl-piperazin-1-yl)-methanone (D-148);

5-{7-[2-fluoro-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-149);

5-{7-[4-(4-ethyl-piperazine-1-sulfonyl)-2-fluoro-phenyl]-2-morpholin-4-yl-6,7-dihydro-5H-pyrrolo[2,3-d]pyrimidin-4-yl}-pyrimidin-2-ylamine (D-150);

5-{7-[5-(4-ethyl-piperazin-1-ylmethyl)-2-fluoro-phenyl]-2-morpholin-4-yl-6,7-dihydro-5H-pyrrolo[2,3-d]pyrimidin-4-yl}-pyrimidin-2-ylamine (D-151);

2-(4-{4-[4-(2-amino-pyrimidin-5-yl)-2-morpholin-4-yl-5,6-dihydro-pyrrolo[2,3-d]pyrimidin-7-yl]-3-fluoro-benzenesulfonyl}-piperazin-1-yl)-ethanol (D-152);

4-(2-amino-pyrimidin-5-yl)-2-morpholin-4-yl-5,6-dihydro-pyrrolo[2,3-d]pyrimidine-7-carboxylic acid {3-[4-(2-hydroxy-ethyl)-piperazin-1-yl]-phenyl}-methyl-amide (D-153);

4-(2-amino-pyrimidin-5-yl)-2-morpholin-4-yl-5,6-dihydro-pyrrolo[2,3-d]pyrimidine-7-carboxylic acid methyl-(3-piperazin-1-yl-phenyl)-amide (D-154);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-phenyl]-methyl-amide (D-155);

1-(4-{3-[4-(2-amino-pyrimidin-5-yl)-2-morpholin-4-yl-5,6-dihydro-pyrrolo[2,3-d]pyrimidin-7-yl]-4-fluoro-benzyl}-piperazin-1-yl)-ethanone (D-156);

{3-[4-(2-amino-pyrimidin-5-yl)-2-morpholin-4-yl-5,6-dihydro-pyrrolo [2,3-d]pyrimidin-7-yl]-2-methyl-phenyl}-morpholin-4-yl-methanone (D-157);

{3-[4-(2-amino-pyrimidin-5-yl)-2-morpholin-4-yl-5,6-dihydro-pyrrolo [2,3-d]pyrimidin-7-yl]-2-methyl-phenyl}-(4-ethyl-piperazin-1-yl)-methanone (D-158);

{3-[4-(2-amino-pyrimidin-5-yl)-2-morpholin-4-yl-5,6-dihydro-pyrrolo [2,3-d]pyrimidin-7-yl]-2-methyl-phenyl}-[4-(2-hydroxy-ethyl)-piperazin-1-yl]-methanone (D-159);

4-(2-amino-pyrimidin-5-yl)-2-morpholin-4-yl-5,6-dihydro-pyrrolo[2,3-d]pyrimidine-7-carboxylic acid methyl-[4-(4-methyl-piperazin-1-yl)-phenyl]-amide (D-160);

4-(2-amino-pyrimidin-5-yl)-2-morpholin-4-yl-5,6-dihydro-pyrrolo[2,3-d]pyrimidine-7-carboxylic acid methyl-(4-piperazin-1-yl-phenyl)-amide (D-161);

4-(2-amino-pyrimidin-5-yl)-2-morpholin-4-yl-5,6-dihydro-pyrrolo[2,3-d]pyrimidine-7-carboxylic acid {4-[4-(2-hydroxy-ethyl)-piperazin-1-yl]-phenyl}-methyl-amide (D-162);

4-(2-amino-pyrimidin-5-yl)-2-morpholin-4-yl-5,6-dihydro-pyrrolo[2,3-d]pyrimidine-7-carboxylic acid methyl-phenyl-amide (D-163);

5-{7-[2-methyl-4-(4-methyl-piperazine-1-sulfonyl)-phenyl]-2-morpholin-4-yl-6,7-dihydro-5H-pyrrolo[2,3-d]pyrimidin-4-yl}-pyrimidin-2-ylamine (D-164);

5-{7-[4-(4-ethyl-piperazine-1-sulfonyl)-2-methyl-phenyl]-2-morpholin-4-yl-6,7-dihydro-5H-pyrrolo[2,3-d]pyrimidin-4-yl}-pyrimidin-2-ylamine (D-165);

2-(4-{4-[4-(2-amino-pyrimidin-5-yl)-2-morpholin-4-yl-5,6-dihydro-pyrrolo[2,3-d]pyrimidin-7-yl]-3-methyl-benzenesulfonyl}-piperazin-1-yl)-ethanol (D-166);

2-{4-[4-(2-amino-pyrimidin-5-yl)-2-morpholin-4-yl-5,6-dihydro-pyrrolo[2,3-d]pyrimidin-7-yl]-pyridin-2-ylamino}-ethanol (D-167);

3-{4-[4-(2-amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-168);

3-{4-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-169);

3-{4-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-170);

2-{3-[4-(2-amino-pyrimidin-5-yl)-2-morpholin-4-yl-5,6-dihydro-pyrrolo[2,3-d]pyrimidin-7-yl]-phenyl}-1-piperazin-1-yl-ethanone (D-171);

2-{4-[4-(2-amino-pyrimidin-5-yl)-2-morpholin-4-yl-5,6-dihydro-pyrrolo[2,3-d]pyrimidin-7-yl]-phenyl}-1-piperazin-1-yl-ethanone (D-172);

5-[7-(2-fluoro-5-morpholin-4-ylmethyl-phenyl)-2-morpholin-4-yl-6,7-dihydro-5H-pyrrolo[2,3-d]pyrimidin-4-yl]-pyrimidin-2-ylamine (D-173);

5-(2-morpholin-4-yl-7-o-tolyl-6,7-dihydro-5H-pyrrolo[2,3-d]pyrimidin-4-yl)-pyrimidin-2-ylamine (D-174);

5-{7-[2-fluoro-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-175);

5-{7-[2-methyl-4-(piperazine-1-sulfonyl)-phenyl]-2-morpholin-4-yl-6,7-dihydro-5H-pyrrolo[2,3-d]pyrimidin-4-yl}-pyrimidin-2-ylamine (D-176);

4-(2-amino-pyrimidin-5-yl)-2-morpholin-4-yl-5,6-dihydro-pyrrolo[2,3-d]pyrimidine-7-carboxylic acid methyl-[3-(4-methyl-piperazin-1-yl)-phenyl]-amide (D-177);

5-[7-(3-methyl-pyridin-2-yl)-2-morpholin-4-yl-6,7-dihydro-5H-pyrrolo [2,3-d]pyrimidin-4-yl]-pyrimidin-2-ylamine (D-178);

4-[4-(2-amino-pyrimidin-5-yl)-2-morpholin-4-yl-5,6-dihydro-pyrrolo[2,3-d]pyrimidin-7-yl]-N-[2-(2-hydroxy-ethoxy)-ethyl]-benzamide (D-179);

4-(2-amino-pyrimidin-5-yl)-2-morpholin-4-yl-5,6-dihydro-pyrrolo[2,3-d]pyrimidine-7-carboxylic acid o-tolylamide (D-180);

4-(2-amino-pyrimidin-5-yl)-2-morpholin-4-yl-5,6-dihydro-pyrrolo[2,3-d]pyrimidine-7-carboxylic acid (2-isopropyl-phenyl)-amide (D-181);

2-{3-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-182);

2-{4-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-ethanone (D-183);

2-{3-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-184);

2-{4-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-ethanone (D-185);

2-{3-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-186);

2-{4-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-ethanone (D-187);

3-{4-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-188);

3-{3-[4-(2-amino-pyrimidin-5-yl)-2-morpholin-4-yl-5,6-dihydro-pyrrolo[2,3-d]pyrimidin-7-yl]-phenyl}-1-piperazin-1-yl-propan-1-one (D-189);

3-{3-[4-(2-amino-pyrimidin-5-yl)-2-morpholin-4-yl-5,6-dihydro-pyrrolo[2,3-d]pyrimidin-7-yl]-phenyl}-1-(4-methyl-piperazin-1-yl)-propan-1-one (D-190);

3-{3-[4-(2-amino-pyrimidin-5-yl)-2-morpholin-4-yl-5,6-dihydro-pyrrolo[2,3-d]pyrimidin-7-yl]-phenyl}-1-(4-ethyl-piperazin-1-yl)-propan-1-one (D-191);

3-{3-[4-(2-amino-pyrimidin-5-yl)-2-morpholin-4-yl-5,6-dihydro-pyrrolo[2,3-d]pyrimidin-7-yl]-phenyl}-1-[4-(2-hydroxy-ethyl)-piperazin-1-yl]-propan-1-one (D-192);

5-[7-(4-methyl-pyridin-3-yl)-2-morpholin-4-yl-6,7-dihydro-5H-pyrrolo[2,3-d]pyrimidin-4-yl]-pyrimidin-2-ylamine (D-193);

4-(2-amino-pyrimidin-5-yl)-2-morpholin-4-yl-5,6-dihydro-pyrrolo[2,3-d]pyrimidine-7-carboxylic acid (4-{-methyl-[3-(4-methyl-piperazin-1-yl)-propyl]-amino}-phenyl)-amide (D-194);

{3-[4-(2-amino-pyrimidin-5-yl)-2-morpholin-4-yl-5,6-dihydro-pyrrolo[2,3-d]pyrimidin-7-yl]-2-fluoro-phenyl}-morpholin-4-yl-methanone (D-195);

5-{7-[2-methyl-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-196);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzamide (D-197);

5-{7-[2-fluoro-4-(morpholine-4-sulfonyl)-phenyl]-2-morpholin-4-yl-6,7-dihydro-5H-pyrrolo[2,3-d]pyrimidin-4-yl}-pyrimidin-2-ylamine (D-198);

{4-[4-(2-amino-pyrimidin-5-yl)-2-morpholin-4-yl-5,6-dihydro-pyrrolo[2,3-d]pyrimidin-7-yl]-pyridin-2-yl}-piperazin-1-yl-methanone (D-199);

{4-[4-(2-amino-pyrimidin-5-yl)-2-morpholin-4-yl-5,6-dihydro-pyrrolo[2,3-d]pyrimidin-7-yl]-pyridin-2-yl}-(4-methyl-piperazin-1-yl)-methanone (D-200);

{4-[4-(2-amino-pyrimidin-5-yl)-2-morpholin-4-yl-5,6-dihydro-pyrrolo[2,3-d]pyrimidin-7-yl]-pyridin-2-yl}-(4-ethyl-piperazin-1-yl)-methanone (D-201);

{4-[4-(2-amino-pyrimidin-5-yl)-2-morpholin-4-yl-5,6-dihydro-pyrrolo[2,3-d]pyrimidin-7-yl]-pyridin-2-yl}-[4-(2-hydroxy-ethyl)-piperazin-1-yl]-methanone (D-202);

{3-[4-(2-amino-pyrimidin-5-yl)-2-morpholin-4-yl-5,6-dihydro-pyrrolo[2,3-d]pyrimidin-7-yl]-4-fluoro-phenyl}-(4-ethyl-piperazin-1-yl)-methanone (D-203);

5-[7-(1-methyl-1H-imidazol-2-yl)-2-morpholin-4-yl-6,7-dihydro-5H-pyrrolo[2,3-d]pyrimidin-4-yl]-pyrimidin-2-ylamine (D-204);

4-[4-(2-amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzamide (D-205);

4-(2-amino-pyrimidin-5-yl)-2-morpholin-4-yl-5,6-dihydro-pyrrolo[2,3-d]pyrimidine-7-carboxylic acid {4-[methyl-(2-morpholin-4-yl-ethyl)-amino]-phenyl}-amide (D-206);

4-(2-amino-pyrimidin-5-yl)-2-morpholin-4-yl-5,6-dihydro-pyrrolo[2,3-d]pyrimidine-7-carboxylic acid {4-[methyl-(3-morpholin-4-yl-propyl)-amino]-phenyl}-amide (D-207);

4-(2-amino-pyrimidin-5-yl)-2-morpholin-4-yl-5,6-dihydro-pyrrolo[2,3-d]pyrimidine-7-carboxylic acid [4-(3-morpholin-4-yl-propylamino)-phenyl]-amide (D-208);

4-[4-(2-amino-pyrimidin-5-yl)-2-morpholin-4-yl-5,6-dihydro-pyrrolo[2,3-d]pyrimidin-7-yl]-N-methyl-N-(2-morpholin-4-yl-ethyl)-benzenesulfonamide (D-209);

4-(2-amino-pyrimidin-5-yl)-2-morpholin-4-yl-5,6-dihydro-pyrrolo[2,3-d]pyrimidine-7-carbothioic acid o-tolylamide (D-210);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-morpholin-4-yl-ethyl)-benzenesulfonamide (D-211);

4-[4-(2-amino-pyrimidin-5-yl)-2-morpholin-4-yl-5,6-dihydro-pyrrolo[2,3-d]pyrimidin-7-yl]-3,N-dimethyl-N-(2-morpholin-4-yl-ethyl)-benzenesulfonamide (D-212);

4-(2-amino-pyrimidin-5-yl)-2-morpholin-4-yl-5,6-dihydro-pyrrolo[2,3-d]pyrimidine-7-carboxylic acid (2-ethyl-phenyl)-amide (D-213);

4-(2-amino-pyrimidin-5-yl)-2-morpholin-4-yl-5,6-dihydro-pyrrolo[2,3-d]pyrimidine-7-carboxylic acid (2-propyl-phenyl)-amide (D-214);

4-(2-amino-pyrimidin-5-yl)-2-morpholin-4-yl-5,6-dihydro-pyrrolo[2,3-d]pyrimidine-7-carboxylic acid (2,6-difluoro-phenyl)-amide (D-215);

4-(2-amino-pyrimidin-5-yl)-2-morpholin-4-yl-5,6-dihydro-pyrrolo[2,3-d]pyrimidine-7-carbothioic acid phenylamide (D-216);

4-(2-amino-pyrimidin-5-yl)-2-morpholin-4-yl-5,6-dihydro-pyrrolo[2,3-d]pyrimidine-7-carboxylic acid (2-chloro-phenyl)-amide (D-217);

4-(2-amino-pyrimidin-5-yl)-2-morpholin-4-yl-5,6-dihydro-pyrrolo[2,3-d]pyrimidine-7-carboxylic acid [2-methyl-5-(morpholine-4-carbonyl)-phenyl]-amide (D-218);

4-(2-amino-pyrimidin-5-yl)-2-morpholin-4-yl-5,6-dihydro-pyrrolo[2,3-d]pyrimidine-7-carboxylic acid [2-methyl-4-(morpholine-4-carbonyl)-phenyl]-amide (D-219);

4-(2-amino-pyrimidin-5-yl)-2-morpholin-4-yl-5,6-dihydro-pyrrolo[2,3-d]pyrimidine-7-carboxylic acid [2-methyl-4-(4-methyl-piperazine-1-carbonyl)-phenyl]-amide (D-220);

4-(2-amino-pyrimidin-5-yl)-2-morpholin-4-yl-5,6-dihydro-pyrrolo[2,3-d]pyrimidine-7-carboxylic acid [4-(4-ethyl-piperazine-1-carbonyl)-2-methyl-phenyl]-amide (D-221);

4-(2-amino-pyrimidin-5-yl)-2-morpholin-4-yl-5,6-dihydro-pyrrolo[2,3-d]pyrimidine-7-carbothioic acid (2-fluoro-phenyl)-amide (D-222);

4-(2-amino-pyrimidin-5-yl)-2-morpholin-4-yl-5,6-dihydro-pyrrolo[2,3-d]pyrimidine-7-carboxylic acid [2-methyl-5-(4-methyl-piperazine-1-carbonyl)-phenyl]-amide (D-223);

4-(2-amino-pyrimidin-5-yl)-2-morpholin-4-yl-5,6-dihydro-pyrrolo[2,3-d]pyrimidine-7-carboxylic acid [5-(4-ethyl-piperazine-1-carbonyl)-2-methyl-phenyl]-amide (D-224);

4-(2-amino-pyrimidin-5-yl)-2-morpholin-4-yl-5,6-dihydro-pyrrolo[2,3-d]pyrimidine-7-carbothioic acid (2,6-difluoro-phenyl)-amide (D-225);

4-(2-amino-pyrimidin-5-yl)-2-morpholin-4-yl-5,6-dihydro-pyrrolo[2,3-d]pyrimidine-7-carboxylic acid methyl-(3-morpholin-4-yl-phenyl)-amide (D-226);

4-(2-amino-pyrimidin-5-yl)-2-morpholin-4-yl-5,6-dihydro-pyrrolo[2,3-d]pyrimidine-7-carboxylic acid methyl-{3-[methyl-(2-morpholin-4-yl-ethyl)-amino]-phenyl}-amide (D-227);

{5-[4-(2-amino-pyrimidin-5-yl)-2-morpholin-4-yl-5,6-dihydro-pyrrolo[2,3-d]pyrimidin-7-yl]-pyridin-3-yl}-morpholin-4-yl-methanone (D-228);

{5-[4-(2-amino-pyrimidin-5-yl)-2-morpholin-4-yl-5,6-dihydro-pyrrolo[2,3-d]pyrimidin-7-yl]-pyridin-3-yl}-(4-methyl-piperazin-1-yl)-methanone (D-229);

{5-[4-(2-amino-pyrimidin-5-yl)-2-morpholin-4-yl-5,6-dihydro-pyrrolo[2,3-d]pyrimidin-7-yl]-pyridin-3-yl}-(4-ethyl-piperazin-1-yl)-methanone (D-230);

4-(2-amino-pyrimidin-5-yl)-2-morpholin-4-yl-5,6-dihydro-pyrrolo[2,3-d]pyrimidine-7-carbothioic acid [4-(4-methyl-piperazine-1-carbonyl)-phenyl]-amide (D-231);

4-(2-amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-phenyl]-amide (D-232);

4-(2-amino-pyrimidin-5-yl)-2-morpholin-4-yl-5,6-dihydro-pyrrolo[2,3-d]pyrimidine-7-carbothioic acid [3-(4-methyl-piperazine-1-carbonyl)-phenyl]-amide (D-233);

4-[4-(2-amino-pyrimidin-5-yl)-2-morpholin-4-yl-5,6-dihydro-pyrrolo[2,3-d]pyrimidin-7-yl]-3-methyl-benzonitrile (D-234);

4-(2-amino-pyrimidin-5-yl)-2-morpholin-4-yl-5,6-dihydro-pyrrolo[2,3-d]pyrimidine-7-carbothioic acid [3-(4-ethyl-piperazine-1-carbonyl)-phenyl]-amide (D-235);

4-(2-amino-pyrimidin-5-yl)-2-morpholin-4-yl-5,6-dihydro-pyrrolo[2,3-d]pyrimidine-7-carbothioic acid [2-methyl-5-(4-methyl-piperazine-1-carbonyl)-phenyl]-amide (D-236);

4-(2-amino-pyrimidin-5-yl)-2-morpholin-4-yl-5,6-dihydro-pyrrolo[2,3-d]pyrimidine-7-carboxylic acid (2-methyl-5-morpholin-4-yl-phenyl)-amide (D-237);

4-(2-amino-pyrimidin-5-yl)-2-morpholin-4-yl-5,6-dihydro-pyrrolo[2,3-d]pyrimidine-7-carboxylic acid [2-methyl-5-(4-methyl-piperazin-1-yl)-phenyl]-amide (D-238);

4-(2-amino-pyrimidin-5-yl)-2-morpholin-4-yl-5,6-dihydro-pyrrolo[2,3-d]pyrimidine-7-carboxylic acid [5-(4-ethyl-piperazin-1-yl)-2-methyl-phenyl]-amide (D-239);

4-(2-amino-pyrimidin-5-yl)-2-morpholin-4-yl-5,6-dihydro-pyrrolo[2,3-d]pyrimidine-7-carboxylic acid (2-methyl-4-morpholin-4-yl-phenyl)-amide (D-240);

4-(2-amino-pyrimidin-5-yl)-2-morpholin-4-yl-5,6-dihydro-pyrrolo[2,3-d]pyrimidine-7-carboxylic acid [2-methyl-4-(4-methyl-piperazin-1-yl)-phenyl]-amide (D-241);

4-(2-amino-pyrimidin-5-yl)-2-morpholin-4-yl-5,6-dihydro-pyrrolo[2,3-d]pyrimidine-7-carboxylic acid [4-(4-ethyl-piperazin-1-yl)-2-methyl-phenyl]-amide (D-242);

4-(2-amino-pyrimidin-5-yl)-2-morpholin-4-yl-5,6-dihydro-pyrrolo[2,3-d]pyrimidine-7-carboxylic acid [2-methyl-3-(morpholine-4-carbonyl)-phenyl]-amide (D-243);

4-(2-amino-pyrimidin-5-yl)-2-morpholin-4-yl-5,6-dihydro-pyrrolo[2,3-d]pyrimidine-7-carboxylic acid [2-methyl-3-(4-methyl-piperazine-1-carbonyl)-phenyl]-amide (D-244);

4-(2-amino-pyrimidin-5-yl)-2-morpholin-4-yl-5,6-dihydro-pyrrolo[2,3-d]pyrimidine-7-carboxylic acid [3-(4-ethyl-piperazine-1-carbonyl)-2-methyl-phenyl]-amide (D-245);

{4-[4-(2-amino-pyrimidin-5-yl)-2-morpholin-4-yl-5,6-dihydro-pyrrolo[2,3-d]pyrimidin-7-yl]-3-methyl-phenyl}-((2R,6S)-2,6-dimethyl-morpholin-4-yl)-methanone (D-246);

4-(2-amino-pyrimidin-5-yl)-2-morpholin-4-yl-5,6-dihydro-pyrrolo[2,3-d]pyrimidine-7-carbothioic acid [3-(morpholine-4-carbonyl)-phenyl]-amide (D-247);

5-{7-[5-(morpholine-4-sulfonyl)-pyridin-3-yl]-2-morpholin-4-yl-6,7-dihydro-5H-pyrrolo[2,3-d]pyrimidin-4-yl}-pyrimidin-2-ylamine (D-248);

5-{7-[5-(4-methyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-249);

5-{7-[5-(4-ethyl-piperazine-1-sulfonyl)-pyridin-3-yl]-2-morpholin-4-yl-6,7-dihydro-5H-pyrrolo[2,3-d]pyrimidin-4-yl}-pyrimidin-2-ylamine (D-250);

4-(2-amino-pyrimidin-5-yl)-2-morpholin-4-yl-5,6-dihydro-pyrrolo[2,3-d]pyrimidine-7-carbothioic acid [4-(morpholine-4-carbonyl)-phenyl]-amide (D-251);

4-(2-amino-pyrimidin-5-yl)-2-morpholin-4-yl-5,6-dihydro-pyrrolo[2,3-d]pyrimidine-7-carbothioic acid [2-methyl-4-(morpholine-4-carbonyl)-phenyl]-amide (D-252);

4-(2-amino-pyrimidin-5-yl)-2-morpholin-4-yl-5,6-dihydro-pyrrolo[2,3-d]pyrimidine-7-carbothioic acid [2-methyl-4-(4-methyl-piperazine-1-carbonyl)-phenyl]-amide (D-253);

4-(2-amino-pyrimidin-5-yl)-2-morpholin-4-yl-5,6-dihydro-pyrrolo[2,3-d]pyrimidine-7-carbothioic acid [4-(4-ethyl-piperazine-1-carbonyl)-2-methyl-phenyl]-amide (D-254);

4-(2-amino-pyrimidin-5-yl)-2-morpholin-4-yl-5,6-dihydro-pyrrolo[2,3-d]pyrimidine-7-carbothioic acid [2-methyl-5-(morpholine-4-carbonyl)-phenyl]-amide (D-255);

4-(2-amino-pyrimidin-5-yl)-2-morpholin-4-yl-5,6-dihydro-pyrrolo[2,3-d]pyrimidine-7-carboxylic acid [2,6-difluoro-4-(4-methyl-piperazine-1-carbonyl)-phenyl]-amide (D-256);

4-(2-amino-pyrimidin-5-yl)-2-morpholin-4-yl-5,6-dihydro-pyrrolo[2,3-d]pyrimidine-7-carboxylic acid [2,6-difluoro-4-(morpholine-4-carbonyl)-phenyl]-amide (D-257);

4-[4-(2-amino-pyrimidin-5-yl)-2-morpholin-4-yl-5,6-dihydro-pyrrolo[2,3-d]pyrimidin-7-yl]-3-methyl-N-pyridin-4-yl-benzamide (D-258);

4-[4-(2-amino-pyrimidin-5-yl)-2-morpholin-4-yl-5,6-dihydro-pyrrolo[2,3-d]pyrimidin-7-yl]-3-methyl-N-pyridin-4-ylmethyl-benzamide (D-259);

4-methyl-5-(2-morpholin-4-yl-7-pyridin-3-yl-6,7-dihydro-5H-pyrrolo[2,3-d]pyrimidin-4-yl)-pyrimidin-2-ylamine (D-260);

4-methyl-5-(2-morpholin-4-yl-7-pyridin-4-yl-6,7-dihydro-5H-pyrrolo[2,3-d]pyrimidin-4-yl)-pyrimidin-2-ylamine (D-261);

4-(2-amino-pyrimidin-5-yl)-2-morpholin-4-yl-5,6-dihydro-pyrrolo[2,3-d]pyrimidine-7-carboxylic acid benzyl-methyl-amide (D-262);

4-(2-amino-pyrimidin-5-yl)-2-morpholin-4-yl-5,6-dihydro-pyrrolo[2,3-d]pyrimidine-7-carboxylic acid methyl-phenethyl-amide (D-263);

4-[4-(2-amino-pyrimidin-5-yl)-2-morpholin-4-yl-5,6-dihydro-pyrrolo[2,3-d]pyrimidin-7-yl]-N-pyridin-4-ylmethyl-benzamide (D-264);

{4-[4-(2-amino-pyrimidin-5-yl)-2-morpholin-4-yl-5,6-dihydro-pyrrolo[2,3-d]pyrimidin-7-yl]-phenyl}-(4-pyridin-4-yl-piperazin-1-yl)-methanone (D-265);

5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-266);

{4-[4-(2-amino-pyrimidin-5-yl)-2-morpholin-4-yl-5,6-dihydro-pyrrolo[2,3-d]pyrimidin-7-yl]-3-methyl-phenyl}-pyrrolidin-1-yl-methanone (D-267);

{4-[4-(2-amino-pyrimidin-5-yl)-2-morpholin-4-yl-5,6-dihydro-pyrrolo[2,3-d]pyrimidin-7-yl]-3-methyl-phenyl}-piperidin-1-yl-methanone (D-268);

4-methyl-piperazine-1-carboxylic acid {3-[4-(2-amino-pyrimidin-5-yl)-2-morpholin-4-yl-5,6-dihydro-pyrrolo[2,3-d]pyrimidin-7-yl]-phenyl}-amide (D-269);

4-[4-(2-amino-pyrimidin-5-yl)-2-morpholin-4-yl-5,6-dihydro-pyrrolo[2,3-d]pyrimidin-7-yl]-3-fluoro-N-thiazol-2-yl-benzamide (D-270);

4-[4-(2-amino-pyrimidin-5-yl)-2-morpholin-4-yl-5,6-dihydro-pyrrolo[2,3-d]pyrimidin-7-yl]-3-fluoro-N-pyridin-4-ylmethyl-benzamide (D-271);

{4-[4-(2-amino-pyrimidin-5-yl)-2-morpholin-4-yl-5,6-dihydro-pyrrolo[2,3-d]pyrimidin-7-yl]-3-methyl-phenyl}-azepan-1-yl-methanone (D-272);

4-(2-amino-pyrimidin-5-yl)-2-morpholin-4-yl-5,6-dihydro-pyrrolo[2,3-d]pyrimidine-7-carboxylic acid (2,6-difluoro-4-morpholin-4-yl-phenyl)-amide (D-273);

4-(2-amino-pyrimidin-5-yl)-2-morpholin-4-yl-5,6-dihydro-pyrrolo[2,3-d]pyrimidine-7-carboxylic acid (2-methyl-pyridin-3-yl)-amide (D-274);

4-(2-amino-pyrimidin-5-yl)-2-morpholin-4-yl-5,6-dihydro-pyrrolo[2,3-d]pyrimidine-7-carboxylic acid (pyridin-3-ylmethyl)-amide (D-275);

4-(2-amino-pyrimidin-5-yl)-2-morpholin-4-yl-5,6-dihydro-pyrrolo[2,3-d]pyrimidine-7-carboxylic acid (4-methyl-pyridin-3-yl)-amide (D-276);

N-{4-[4-(2-amino-pyrimidin-5-yl)-2-morpholin-4-yl-5,6-dihydro-pyrrolo[2,3-d]pyrimidin-7-yl]-phenyl}-isonicotinamide (D-277);

{4-[4-(2-amino-pyrimidin-5-yl)-2-morpholin-4-yl-5,6-dihydro-pyrrolo[2,3-d]pyrimidin-7-yl]-phenyl}-(4-pyridin-2-yl-piperazin-1-yl)-methanone (D-278);

4-[4-(2-amino-pyrimidin-5-yl)-2-morpholin-4-yl-5,6-dihydro-pyrrolo[2,3-d]pyrimidin-7-yl]-N-(2-pyridin-3-yl-ethyl)-benzamide (D-279);

4-(2-amino-pyrimidin-5-yl)-2-morpholin-4-yl-5,6-dihydro-pyrrolo[2,3-d]pyrimidine-7-carboxylic acid (2-methyl-2H-pyrazol-3-yl)-amide (D-280);

4-(2-amino-pyrimidin-5-yl)-2-morpholin-4-yl-5,6-dihydro-pyrrolo[2,3-d]pyrimidine-7-carboxylic acid (5-methyl-2-phenyl-2H-pyrazol-3-yl)-amide (D-281);

4-[4-(2-amino-pyrimidin-5-yl)-2-morpholin-4-yl-5,6-dihydro-pyrrolo[2,3-d]pyrimidin-7-yl]-N-pyridin-2-ylmethyl-benzamide (D-282);

4-(2-amino-pyrimidin-5-yl)-2-morpholin-4-yl-5,6-dihydro-pyrrolo[2,3-d]pyrimidine-7-carboxylic acid (2,6-dimethyl-phenyl)-amide (D-283);

{4-[4-(2-amino-pyrimidin-5-yl)-2-morpholin-4-yl-5,6-dihydro-pyrrolo[2,3-d]pyrimidin-7-yl]-phenyl}-(4-pyrimidin-2-yl-piperazin-1-yl)-methanone (D-284);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-2-yl-piperazin-1-yl)-methanone (D-285);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-4-yl-piperazin-1-yl)-methanone (D-286);

4-(2-amino-pyrimidin-5-yl)-2-morpholin-4-yl-5,6-dihydro-pyrrolo[2,3-d]pyrimidine-7-carboxylic acid 3-(4-methyl-piperazine-1-carbonyl)-benzylamide (D-287);

{4-[4-(2-amino-pyrimidin-5-yl)-2-morpholin-4-yl-5,6-dihydro-pyrrolo[2,3-d]pyrimidin-7-yl]-3-methyl-phenyl}-(4-pyridin-4-yl-piperazin-1-yl)-methanone (D-288);

4-(2-amino-pyrimidin-5-yl)-2-morpholin-4-yl-5,6-dihydro-pyrrolo[2,3-d]pyrimidine-7-carbothioic acid [2-methyl-5-(4-methyl-piperazin-1-yl)-phenyl]-amide (D-289);

4-(2-amino-pyrimidin-5-yl)-2-morpholin-4-yl-5,6-dihydro-pyrrolo[2,3-d]pyrimidine-7-carbothioic acid [5-(4-ethyl-piperazin-1-yl)-2-methyl-phenyl]-amide (D-290);

4-(2-amino-pyrimidin-5-yl)-2-morpholin-4-yl-5,6-dihydro-pyrrolo[2,3-d]pyrimidine-7-carbothioic acid [2-methyl-4-(4-methyl-piperazin-1-yl)-phenyl]-amide (D-291);

4-(2-amino-pyrimidin-5-yl)-2-morpholin-4-yl-5,6-dihydro-pyrrolo[2,3-d]pyrimidine-7-carbothioic acid [4-(4-ethyl-piperazin-1-yl)-2-methyl-phenyl]-amide (D-292);

4-(2-amino-pyrimidin-5-yl)-2-morpholin-4-yl-5,6-dihydro-pyrrolo[2,3-d]pyrimidine-7-carboxylic acid 4-(4-methyl-piperazine-1-carbonyl)-benzylamide (D-293);

4-(2-amino-pyrimidin-5-yl)-2-morpholin-4-yl-5,6-dihydro-pyrrolo[2,3-d]pyrimidine-7-carboxylic acid {2-[4-(4-methyl-piperazine-1-carbonyl)-phenyl]-ethyl}-amide (D-294);

4-(2-amino-pyrimidin-5-yl)-2-morpholin-4-yl-5,6-dihydro-pyrrolo[2,3-d]pyrimidine-7-carboxylic acid methyl-{2-[4-(4-methyl-piperazine-1-carbonyl)-phenyl]-ethyl}-amide (D-295);

5-(7-{4-[2-(4-methyl-piperazine-1-sulfonyl)-ethyl]-phenyl}-2-morpholin-4-yl-6,7-dihydro-5H-pyrrolo[2,3-d]pyrimidin-4-yl)-pyrimidin-2-ylamine (D-296);

4-(2-amino-pyrimidin-5-yl)-2-morpholin-4-yl-5,6-dihydro-pyrrolo[2,3-d]pyrimidine-7-carboxylic acid methyl-[4-(4-methyl-piperazine-1-carbonyl)-benzyl]-amide (D-297);

4-(2-amino-pyrimidin-5-yl)-2-morpholin-4-yl-5,6-dihydro-pyrrolo[2,3-d]pyrimidine-7-carboxylic acid methyl-[3-(4-methyl-piperazine-1-carbonyl)-benzyl]-amide (D-298);

4-(2-amino-pyrimidin-5-yl)-2-morpholin-4-yl-5,6-dihydro-pyrrolo[2,3-d]pyrimidine-7-carboxylic acid (4-diethylamino-2-methyl-phenyl)-amide (D-299);

{3-[4-(2-amino-pyrimidin-5-yl)-2-morpholin-4-yl-5,6-dihydro-pyrrolo[2,3-d]pyrimidin-7-yl]-4-methoxy-phenyl}-morpholin-4-yl-methanone (D-300);

4-[4-(2-amino-pyrimidin-5-yl)-2-morpholin-4-yl-5,6-dihydro-pyrrolo[2,3-d]pyrimidin-7-yl]-3-methyl-N-pyridin-3-ylmethyl-benzamide (D-301);

4-[4-(2-amino-pyrimidin-5-yl)-2-morpholin-4-yl-5,6-dihydro-pyrrolo[2,3-d]pyrimidin-7-yl]-3-methyl-N-(2-pyridin-3-yl-ethyl)-benzamide (D-302);

3-[4-(2-amino-pyrimidin-5-yl)-2-morpholin-4-yl-5,6-dihydro-pyrrolo[2,3-d]pyrimidin-7-yl]-4-methyl-N-pyridin-3-ylmethyl-benzamide (D-303);

3-[4-(2-amino-pyrimidin-5-yl)-2-morpholin-4-yl-5,6-dihydro-pyrrolo[2,3-d]pyrimidin-7-yl]-4-methyl-N-(2-pyridin-3-yl-ethyl)-benzamide (D-304);

4-[4-(2-amino-pyrimidin-5-yl)-2-morpholin-4-yl-5,6-dihydro-pyrrolo[2,3-d]pyrimidin-7-yl]-3-fluoro-N-pyridin-3-ylmethyl-benzamide (D-305);

4-[4-(2-amino-pyrimidin-5-yl)-2-morpholin-4-yl-5,6-dihydro-pyrrolo[2,3-d]pyrimidin-7-yl]-3-fluoro-N-(2-pyridin-3-yl-ethyl)-benzamide (D-306);

{4-[4-(2-amino-pyrimidin-5-yl)-2-morpholin-4-yl-5,6-dihydro-pyrrolo[2,3-d]pyrimidin-7-yl]-phenyl}-(4-morpholin-4-yl-piperidin-1-yl)-methanone (D-307);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-morpholin-4-yl-piperidin-1-yl)-methanone (D-308);

{4-[4-(2-amino-pyrimidin-5-yl)-2-morpholin-4-yl-5,6-dihydro-pyrrolo[2,3-d]pyrimidin-7-yl]-3-chloro-phenyl}-morpholin-4-yl-methanone (D-309);

{3-[4-(2-amino-pyrimidin-5-yl)-2-morpholin-4-yl-5,6-dihydro-pyrrolo[2,3-d]pyrimidin-7-yl]-4-chloro-phenyl}-morpholin-4-yl-methanone (D-310);

{4-[4-(2-amino-pyrimidin-5-yl)-2-morpholin-4-yl-5,6-dihydro-pyrrolo[2,3-d]pyrimidin-7-yl]-3-methyl-phenyl}-(4-pyridin-3-yl-piperazin-1-yl)-methanone (D-311);

4-(2-amino-pyrimidin-5-yl)-2-morpholin-4-yl-5,6-dihydro-pyrrolo[2,3-d]pyrimidine-7-carboxylic acid (4-methyl-biphenyl-3-yl)-amide (D-312);

4-(2-amino-pyrimidin-5-yl)-2-morpholin-4-yl-5,6-dihydro-pyrrolo[2,3-d]pyrimidine-7-carboxylic acid (2-methyl-5-pyridin-3-yl-phenyl)-amide (D-313);

5-[2-morpholin-4-yl-7-(5-trifluoromethyl-pyridin-3-yl)-6,7-dihydro-5H-pyrrolo[2,3-d]pyrimidin-4-yl]-pyrimidin-2-ylamine (D-314);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-3-ylmethyl-piperazin-1-yl)-methanone (D-315);

{4-[4-(2-amino-pyrimidin-5-yl)-2-morpholin-4-yl-5,6-dihydro-pyrrolo[2,3-d]pyrimidin-7-yl]-3-fluoro-phenyl}-(4-pyridin-4-ylmethyl-piperazin-1-yl)-methanone (D-316);

4-[4-(2-amino-pyrimidin-5-yl)-2-morpholin-4-yl-5,6-dihydro-pyrrolo[2,3-d]pyrimidin-7-yl]-N-methyl-N-pyridin-3-ylmethyl-benzamide (D-317);

4-[4-(2-amino-pyrimidin-5-yl)-2-morpholin-4-yl-5,6-dihydro-pyrrolo[2,3-d]pyrimidin-7-yl]-3-fluoro-N-methyl-N-pyridin-3-ylmethyl-benzamide (D-318);

4-[4-(2-amino-pyrimidin-5-yl)-2-morpholin-4-yl-5,6-dihydro-pyrrolo[2,3-d]pyrimidin-7-yl]-N-methyl-N-(2-pyridin-3-yl-ethyl)-benzamide (D-319);

4-[4-(2-amino-pyrimidin-5-yl)-2-morpholin-4-yl-5,6-dihydro-pyrrolo[2,3-d]pyrimidin-7-yl]-3-fluoro-N-methyl-N-(2-pyridin-3-yl-ethyl)-benzamide (D-320);

{4-[4-(2-amino-pyrimidin-5-yl)-2-morpholin-4-yl-5,6-dihydro-pyrrolo[2,3-d]pyrimidin-7-yl]-phenyl}-(4-pyridin-3-ylmethyl-piperazin-1-yl)-methanone (D-321);

{4-[4-(2-amino-pyrimidin-5-yl)-2-morpholin-4-yl-5,6-dihydro-pyrrolo[2,3-d]pyrimidin-7-yl]-phenyl}-(4-pyridin-4-ylmethyl-piperazin-1-yl)-methanone (D-322);

5-(2-morpholin-4-yl-4-pyridin-4-yl-5,6-dihydro-pyrrolo[2,3-d]pyrimidin-7-yl)-pyrimidin-2-ylamine (D-323);

{6-[4-(2-amino-pyrimidin-5-yl)-2-morpholin-4-yl-5,6-dihydro-pyrrolo[2,3-d]pyrimidin-7-yl]-naphthalen-2-yl}-(4-methyl-piperazin-1-yl)-methanone (D-324);

5-{7-[3-fluoro-4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-325);

5-{7-[2-fluoro-4-(4-methyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-326);

5-{2-morpholin-4-yl-7-[4-(4-propyl-piperazin-1-ylmethyl)-phenyl]-6,7-dihydro-5H-pyrrolo[2,3-d]pyrimidin-4-yl}-pyrimidin-2-ylamine (D-327);

5-{7-[4-(4-isopropyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-328);

5-(7-{4-[4-(2-fluoroethyl)-piperazin-1-ylmethyl]-phenyl}-2-morpholin-4-yl-6,7-dihydro-5H-pyrrolo[2,3-d]pyrimidin-4-yl)-pyrimidin-2-ylamine (D-329);

5-(7-{4-[4-(4-fluorobutyl)-piperazin-1-ylmethyl]-phenyl}-2-morpholin-4-yl-6,7-dihydro-5H-pyrrolo[2,3-d]pyrimidin-4-yl)-pyrimidin-2-ylamine (D-330);

5-(2-morpholin-4-yl-7-{4-[4-(3,3,3-trifluoropropyl)piperazin-1-ylmethyl]-phenyl}-6,7-dihydro-5H-pyrrolo[2,3-d]pyrimidin-4-yl)-pyrimidin-2-ylamine (D-332);

5-{7-[6-(4-methyl-piperazin-1-ylmethyl)naphthalen-2-yl]-2-morpholin-4-yl-6,7-dihydro-5H-pyrrolo[2,3-d]pyrimidin-4-yl}-pyrimidin-2-ylamine (D-333);

5-{7-[4-(4-ethyl-piperazin-1-ylmethyl)-phenyl]-2-morpholin-4-yl-6,7-dihydro-5H-pyrrolo[2,3-d]pyrimidin-4-yl}-pyrimidin-2-ylamine (D-334);

5-[7-(2-fluoro-4-morpholin-4-ylmethyl-phenyl)-2-morpholin-4-yl-6,7-dihydro-5H-pyrrolo[2,3-d]pyrimidin-4-yl]-pyrimidin-2-ylamine (D-335)

4-(3-ethylaminocarbonyloxyphenyl)-2-(morpholin-4-yl)-7-(pyridin-4-yl)-6,7-dihydro-5H-pyrrolo [2,3-d]pyrimidine (E-01);

4-(3-methylaminocarbonyloxyphenyl)-2-(morpholin-4-yl)-7-(pyridin-4-yl)-6,7-dihydro-5H-pyrrolo [2,3-d]pyrimidine (E-02);

4-(3-acetoxyphenyl)-2-(morpholin-4-yl)-7-(pyridin-4-yl)-6,7-dihydro-5H-pyrrolo[2,3-d]pyrimidine (E-03);
2-morpholin-4-yl-7-pyridin-4-yl-4-[3-(2-pyridin-2-ylethoxy)phenyl]-6,7-dihydro-5H-pyrrolo[2,3-d]pyrimidine (E-04);
2-morpholin-4-yl-7-pyridin-4-yl-4-[3-(3-pyridin-3-yl-propoxy)-phenyl]-6,7-dihydro-5H-pyrrolo [2,3-d]pyrimidine (E-05);
2-morpholin-4-yl-7-pyridin-4-yl-4-[3-(pyridin-4-yl-methoxy)-phenyl]-6,7-dihydro-5H-pyrrolo [2,3-d]pyrimidine (E-06);
3-(2-morpholin-4-yl-7-pyridin-4-yl-6,7-dihydro-5H-pyrrolo[2,3-d]pyrimidin-4-yl)benzonitrile (E-07);
3-(2-morpholin-4-yl-7-pyridin-4-yl-6,7-dihydro-5H-pyrrolo[2,3-d]pyrimidin-4-yl)benzylamine (E-08);
N-[3-(2-morpholin-4-yl-7-pyridin-4-yl-6,7-dihydro-5H-pyrrolo[2,3-d]pyrimidin-4-yl)benzyl]acetamide (E-9);
5-(2-morpholin-4-yl-7-pyridin-4-yl-6,7-dihydro-5H-pyrrolo[2,3-d]pyrimidin-4-yl)-2-pyrrolidin-1-ylmethylphenol (E-10);
2-diethylaminomethyl-5-(2-morpholin-4-yl-7-pyridin-4-yl-6,7-dihydro-5H-pyrrolo [2,3-d]pyrimidin-4-yl)phenol (E-11);
5-(2-morpholin-4-yl-7-pyridin-4-yl-6,7-dihydro-5H-pyrrolo[2,3-d]pyrimidin-4-yl)-2-piperidin-1-ylmethylphenol (E-12);
3-(2-morpholin-4-yl-7-pyridin-4-yl-6,7-dihydro-5H-pyrrolo[2,3-d]pyrimidin-4-yl)-phenylamine (F-01);
3-(2-morpholin-4-yl-7-pyridin-3-yl-6,7-dihydro-5H-pyrrolo[2,3-d]pyrimidin-4-yl)-benzoic acid methyl ester (G-01);
3-(2-morpholin-4-yl-7-pyridin-4-yl-6,7-dihydro-5H-pyrrolo[2,3-d]pyrimidin-4-yl)-benzoic acid methyl ester (G-02);
3-(2-morpholin-4-yl-7-pyridin-3-yl-6,7-dihydro-5H-pyrrolo[2,3-d]pyrimidin-4-yl)-benzoic acid (G-03);
3-(2-morpholin-4-yl-7-pyridin-4-yl-6,7-dihydro-5H-pyrrolo[2,3-d]pyrimidin-4-yl)-benzoic acid (G-04);
N-(2-dimethylaminoethyl)-3-(2-morpholin-4-yl-7-pyridin-3-yl-6,7-dihydro-5H-pyrrolo [2,3-d]pyrimidin-4-yl)-benzamide (G-05);
N-(2-morpholin-4-yl-ethyl)-3-(2-morpholin-4-yl-7-pyridin-3-yl-6,7-dihydro-5H-pyrrolo [2,3-d]pyrimidin-4-yl)-benzamide (G-06);
3-(2-morpholin-4-yl-7-pyridin-3-yl-6,7-dihydro-5H-pyrrolo[2,3-d]pyrimidin-4-yl)-N-(2-pyridin-3-yl-ethyl)-benzamide (G-07);
N-methyl-3-(2-morpholin-4-yl-7-pyridin-3-yl-6,7-dihydro-5H-pyrrolo[2,3-d]pyrimidin-4-yl)-benzamide (G-08);
3-(2-morpholin-4-yl-7-pyridin-3-yl-6,7-dihydro-5H-pyrrolo[2,3-d]pyrimidin-4-yl)-N-pyridin-3-ylmethyl-benzamide (G-09);
N-(2-dimethylamino-ethyl)-3-(2-morpholin-4-yl-7-pyridin-4-yl-6,7-dihydro-5H-pyrrolo[2,3-d]pyrimidin-4-yl)-benzamide (G-10);
3-(2-morpholin-4-yl-7-pyridin-3-yl-6,7-dihydro-5H-pyrrolo[2,3-d]pyrimidin-4-yl)-N-(2-pyridin-4-yl-ethyl)-benzamide (G-11);
N-(2-carbamoyl-ethyl)-3-(2-morpholin-4-yl-7-pyridin-3-yl-6,7-dihydro-5H-pyrrolo[2,3-d]pyrimidin-4-yl)-benzamide (G-12);
N-(2-morpholin-4-yl-ethyl)-3-(2-morpholin-4-yl-7-pyridin-3-yl-6,7-dihydro-5H-pyrrolo[2,3-d]pyrimidin-4-yl)-benzamide (G-13);
3-(2-morpholin-4-yl-7-pyridin-4-yl-6,7-dihydro-5H-pyrrolo[2,3-d]pyrimidin-4-yl)-N-(2-pyridin-3-yl-ethyl)-benzamide (G-14);
N-isobutyl-3-(2-morpholin-4-yl-7-pyridin-4-yl-6,7-dihydro-5H-pyrrolo[2,3-d]pyrimidin-4-yl)-benzamide (G-15);
3-(2-morpholin-4-yl-7-pyridin-4-yl-6,7-dihydro-5H-pyrrolo[2,3-d]pyrimidin-4-yl)-N-pyridin-3-ylmethyl-benzamide (G-16);
3-(2-morpholin-4-yl-7-pyridin-3-yl-6,7-dihydro-5H-pyrrolo[2,3-d]pyrimidin-4-yl)-N-propyl-benzamide (G-17);
3-(2-morpholin-4-yl-7-pyridin-4-yl-6,7-dihydro-5H-pyrrolo[2,3-d]pyrimidin-4-yl)-N-propyl-benzamide (G-18);
3-(2-morpholin-4-yl-7-pyridin-4-yl-6,7-dihydro-5H-pyrrolo[2,3-d]pyrimidin-4-yl)-N-(2-pyridin-4-yl-ethyl)-benzamide (G-19);
N-benzyl-3-(2-morpholin-4-yl-7-pyridin-3-yl-6,7-dihydro-5H-pyrrolo[2,3-d]pyrimidin-4-yl)-benzamide (G-20);
N-(2-methoxy-ethyl)-3-(2-morpholin-4-yl-7-pyridin-4-yl-6,7-dihydro-5H-pyrrolo[2,3-d]pyrimidin-4-yl)-benzamide (G-21);
N-(2-morpholin-4-yl-ethyl)-3-(2-morpholin-4-yl-7-pyridin-4-yl-6,7-dihydro-5H-pyrrolo[2,3-d]pyrimidin-4-yl)-benzamide (G-22);
N-carbamoylmethyl-3-(2-morpholin-4-yl-7-pyridin-4-yl-6,7-dihydro-5H-pyrrolo[2,3-d]pyrimidin-4-yl)-benzamide (G-23);
N-(2-carbamoyl-ethyl)-3-(2-morpholin-4-yl-7-pyridin-4-yl-6,7-dihydro-5H-pyrrolo[2,3-d]pyrimidin-4-yl)-benzamide (G-24);
3-(2-morpholin-4-yl-7-pyridin-4-yl-6,7-dihydro-5H-pyrrolo[2,3-d]pyrimidin-4-yl)-N-phenethyl-benzamide (G-25);
N-isobutyl-3-(2-morpholin-4-yl-7-pyridin-3-yl-6,7-dihydro-5H-pyrrolo[2,3-d]pyrimidin-4-yl)-benzamide (G-26);
3-(2-morpholin-4-yl-7-pyridin-3-yl-6,7-dihydro-5H-pyrrolo[2,3-d]pyrimidin-4-yl)-benzoic acid 2-dimethylamino-ethyl ester (G-27);
3-(2-morpholin-4-yl-7-pyridin-3-yl-6,7-dihydro-5H-pyrrolo[2,3-d]pyrimidin-4-yl)-benzamide (G-28);
4-(2-morpholin-4-yl-7-pyridin-4-yl-6,7-dihydro-5H-pyrrolo[2,3-d]pyrimidin-4-yl)-benzoic acid methyl ester hydrochloride (G-29);
N-(2-dimethylamino-ethyl)-4-(2-morpholin-4-yl-7-pyridin-3-yl-6,7-dihydro-5H-pyrrolo[2,3-d]pyrimidin-4-yl)-benzamide (G-30);
3-(2-morpholin-4-yl-7-pyridin-4-yl-6,7-dihydro-5H-pyrrolo[2,3-d]pyrimidin-4-yl)-benzamide (G-31);
4-(2-morpholin-4-yl-7-pyridin-3-yl-6,7-dihydro-5H-pyrrolo[2,3-d]pyrimidin-4-yl)-benzoic acid methyl ester (G-32);
4-(2-morpholin-4-yl-7-pyridin-4-yl-6,7-dihydro-5H-pyrrolo[2,3-d]pyrimidin-4-yl)-benzamide (G-33);
N-(2-morpholin-4-yl-ethyl)-4-(2-morpholin-4-yl-7-pyridin-3-yl-6,7-dihydro-5H-pyrrolo[2,3-d]pyrimidin-4-yl)-benzamide (G-34);
N-(2-morpholin-4-yl-ethyl)-4-(2-morpholin-4-yl-7-pyridin-4-yl-6,7-dihydro-5H-pyrrolo[2,3-d]pyrimidin-4-yl)-benzamide (G-35);
4-(2-morpholin-4-yl-7-pyridin-3-yl-6,7-dihydro-5H-pyrrolo[2,3-d]pyrimidin-4-yl)-benzamide (G-36)

3-(2-morpholin-4-yl-7-pyridin-4-yl-6,7-dihydro-5H-pyrrolo[2,3-d]pyrimidin-4-yl)-benzoic acid 2-dimethylamino-ethyl ester (G-37);

N,N-dimethyl-3-(2-morpholin-4-yl-7-pyridin-4-yl-6,7-dihydro-5H-pyrrolo[2,3-d]pyrimidin-4-yl)-benzamide trifluoroacetic acid salt (G-38);

N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-39);

3-(2-morpholin-4-yl-7-pyridin-4-yl-6,7-dihydro-5H-pyrrolo[2,3-d]pyrimidin-4-yl)-N-phenyl-benzamide trifluoroacetic acid salt (G-40);

N-(3-dimethylamino-propyl)-3-(2-morpholin-4-yl-7-pyridin-4-yl-6,7-dihydro-5H-pyrrolo[2,3-d]pyrimidin-4-yl)-benzamide trifluoroacetic acid salt (G-41);

N-carbamoylmethyl-3-(2-morpholin-4-yl-7-pyridin-3-yl-6,7-dihydro-5H-pyrrolo[2,3-d]pyrimidin-4-yl)-benzamide trifluoroacetic acid salt (G-42);

3-(2-morpholin-4-yl-7-pyridin-3-yl-6,7-dihydro-5H-pyrrolo[2,3-d]pyrimidin-4-yl)-N-phenyl-benzamide trifluoroacetic acid salt (G-43);

3-(2-morpholin-4-yl-7-pyridin-3-yl-6,7-dihydro-5H-pyrrolo[2,3-d]pyrimidin-4-yl)-N-phenethyl-benzamide (G-44);

N-(2-methoxy-ethyl)-3-(2-morpholin-4-yl-7-pyridin-3-yl-6,7-dihydro-5H-pyrrolo[2,3-d]pyrimidin-4-yl)-benzamide (G-45);

3-(2-morpholin-4-yl-7-pyridin-4-yl-6,7-dihydro-5H-pyrrolo[2,3-d]pyrimidin-4-yl)-N-(2-piperidin-1-yl-ethyl)-benzamide (G-46);

N-(3-hydroxy-propyl)-3-(2-morpholin-4-yl-7-pyridin-3-yl-6,7-dihydro-5H-pyrrolo[2,3-d]pyrimidin-4-yl)-benzamide (G-47);

N-(1-methyl-butyl)-3-(2-morpholin-4-yl-7-pyridin-3-yl-6,7-dihydro-5H-pyrrolo[2,3-d]pyrimidin-4-yl)-benzamide (G-48);

N-(2-methoxy-ethyl)-N-methyl-3-(2-morpholin-4-yl-7-pyridin-3-yl-6,7-dihydro-5H-pyrrolo[2,3-d]pyrimidin-4-yl)-benzamide (G-49);

(4-methyl-piperazin-1-yl)-[3-(2-morpholin-4-yl-7-pyridin-3-yl-6,7-dihydro-5H-pyrrolo[2,3-d]pyrimidin-4-yl)-phenyl]-methanone (G-50);

(4-hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone (G-51);

N-(3,3-dimethyl-butyl)-3-(2-morpholin-4-yl-7-pyridin-3-yl-6,7-dihydro-5H-pyrrolo[2,3-d]pyrimidin-4-yl)-benzamide (G-52);

N-cyclopropylmethyl-3-(2-morpholin-4-yl-7-pyridin-3-yl-6,7-dihydro-5H-pyrrolo[2,3-d]pyrimidin-4-yl)-N-propyl-benzamide (G-53);

N—((S)-2-hydroxy-1-phenyl-ethyl)-3-(2-morpholin-4-yl-7-pyridin-3-yl-6,7-dihydro-5H-pyrrolo[2,3-d]pyrimidin-4-yl)-benzamide (G-54);

N-(3-morpholin-4-yl-propyl)-3-(2-morpholin-4-yl-7-pyridin-3-yl-6,7-dihydro-5H-pyrrolo[2,3-d]pyrimidin-4-yl)-benzamide (G-55);

N-(3-dimethylamino-propyl)-3-(2-morpholin-4-yl-7-pyridin-3-yl-6,7-dihydro-5H-pyrrolo[2,3-d]pyrimidin-4-yl)-benzamide (G-56);

3-(2-morpholin-4-yl-7-pyridin-3-yl-6,7-dihydro-5H-pyrrolo[2,3-d]pyrimidin-4-yl)-N-pyridin-4-ylmethyl-benzamide (G-57);

N-cyclohexylmethyl-3-(2-morpholin-4-yl-7-pyridin-3-yl-6,7-dihydro-5H-pyrrolo[2,3-d]pyrimidin-4-yl)-benzamide (G-58);

N-(2-diethylamino-ethyl)-3-(2-morpholin-4-yl-7-pyridin-3-yl-6,7-dihydro-5H-pyrrolo[2,3-d]pyrimidin-4-yl)-benzamide (G-59);

N-isopropyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-60);

N-isobutyl-N-methyl-3-(2-morpholin-4-yl-7-pyridin-3-yl-6,7-dihydro-5H-pyrrolo[2,3-d]pyrimidin-4-yl)-benzamide trifluoroacetic acid salt (G-61);

N-ethyl-N-(2-hydroxy-ethyl)-3-(2-morpholin-4-yl-7-pyridin-3-yl-6,7-dihydro-5H-pyrrolo[2,3-d]pyrimidin-4-yl)-benzamide (G-62);

(3-hydroxy-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-63);

N-indan-2-yl-3-(2-morpholin-4-yl-7-pyridin-3-yl-6,7-dihydro-5H-pyrrolo[2,3-d]pyrimidin-4-yl)-benzamide (G-64);

azetidin-1-yl-[3-(2-morpholin-4-yl-7-pyridin-3-yl-6,7-dihydro-5H-pyrrolo[2,3-d]pyrimidin-4-yl)-phenyl]-methanone (G-65);

(4-ethyl-piperazin-1-yl)-[3-(2-morpholin-4-yl-7-pyridin-3-yl-6,7-dihydro-5H-pyrrolo [2,3-d]pyrimidin-4-yl)-phenyl]-methanone trifluoroacetic acid salt (G-66);

N,N-diethyl-3-(2-morpholin-4-yl-7-pyridin-3-yl-6,7-dihydro-5H-pyrrolo[2,3-d]pyrimidin-4-yl)-benzamide (G-67);

((R)-2-hydroxymethyl-pyrrolidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-68);

[3-(2-morpholin-4-yl-7-pyridin-3-yl-6,7-dihydro-5H-pyrrolo[2,3-d]pyrimidin-4-yl)-phenyl]-(4-pyrrolidin-1-yl-piperidin-1-yl)-methanone (G-69);

(3-hydroxy-piperidin-1-yl)-[3-(2-morpholin-4-yl-7-pyridin-3-yl-6,7-dihydro-5H-pyrrolo[2,3-d]pyrimidin-4-yl)-phenyl]-methanone trifluoroacetic acid salt (G-70);

N-cyclopentyl-3-(2-morpholin-4-yl-7-pyridin-3-yl-6,7-dihydro-5H-pyrrolo[2,3-d]pyrimidin-4-yl)-benzamide (G-71);

(2,5-dihydro-pyrrol-1-yl)-[3-(2-morpholin-4-yl-7-pyridin-3-yl-6,7-dihydro-5H-pyrrolo[2,3-d]pyrimidin-4-yl)-phenyl]-methanone (G-72);

[3-(2-morpholin-4-yl-7-pyridin-3-yl-6,7-dihydro-5H-pyrrolo[2,3-d]pyrimidin-4-yl)-phenyl]-(4-phenyl-piperazin-1-yl)-methanone (G-73);

N-cyclohexyl-3-(2-morpholin-4-yl-7-pyridin-3-yl-6,7-dihydro-5H-pyrrolo[2,3-d]pyrimidin-4-yl)-benzamide (G-74);

(2,6-dimethyl-morpholin-4-yl)-[3-(2-morpholin-4-yl-7-pyridin-3-yl-6,7-dihydro-5H-pyrrolo[2,3-d]pyrimidin-4-yl)-phenyl]-methanone (G-75);

N-methyl-N-(3-methyl-butyl)-3-(2-morpholin-4-yl-7-pyridin-3-yl-6,7-dihydro-5H-pyrrolo[2,3-d]pyrimidin-4-yl)-benzamide trifluoroacetic acid salt (G-76);

N-(2-dimethylamino-ethyl)-N-ethyl-3-(2-morpholin-4-yl-7-pyridin-3-yl-6,7-dihydro-5H-pyrrolo[2,3-d]pyrimidin-4-yl)-benzamide trifluoroacetic acid salt (G-77);

azetidin-1-yl-[3-(2-morpholin-4-yl-7-pyridin-4-yl-6,7-dihydro-5H-pyrrolo[2,3-d]pyrimidin-4-yl)-phenyl]-methanone (G-78);

N-(3-hydroxy-propyl)-3-(2-morpholin-4-yl-7-pyridin-4-yl-6,7-dihydro-5H-pyrrolo[2,3-d]pyrimidin-4-yl)-benzamide (G-79);

N-cyclopentyl-3-(2-morpholin-4-yl-7-pyridin-4-yl-6,7-dihydro-5H-pyrrolo[2,3-d]pyrimidin-4-yl)-benzamide (G-80);

(3-hydroxy-pyrrolidin-1-yl)-[3-(2-morpholin-4-yl-7-pyridin-4-yl-6,7-dihydro-5H-pyrrolo[2,3-d]pyrimidin-4-yl)-phenyl]-methanone trifluoroacetic acid salt (G-81);
N-(2-methoxy-ethyl)-N-methyl-3-(2-morpholin-4-yl-7-pyridin-4-yl-6,7-dihydro-5H-pyrrolo[2,3-d]pyrimidin-4-yl)-benzamide (G-82);
(4-methyl-piperazin-1-yl)-[3-(2-morpholin-4-yl-7-pyridin-4-yl-6,7-dihydro-5H-pyrrolo[2,3-d]pyrimidin-4-yl)-phenyl]-methanone (G-83);
(4-hydroxy-piperidin-1-yl)-[3-(2-morpholin-4-yl-7-pyridin-4-yl-6,7-dihydro-5H-pyrrolo [2,3-d]pyrimidin-4-yl)-phenyl]-methanone trifluoroacetic acid salt (G-84);
N-methyl-N-(3-methyl-butyl)-3-(2-morpholin-4-yl-7-pyridin-4-yl-6,7-dihydro-5H-pyrrolo[2,3-d]pyrimidin-4-yl)-benzamide (G-85); 3-(2-morpholin-4-yl-7-pyridin-4-yl-6,7-dihydro-5H-pyrrolo[2,3-d]pyrimidin-4-yl)-N-pyridin-4-ylmethyl-benzamide (G-86);
(4-ethyl-piperazin-1-yl)-[3-(2-morpholin-4-yl-7-pyridin-4-yl-6,7-dihydro-5H-pyrrolo [2,3-d]pyrimidin-4-yl)-phenyl]-methanone (G-87);
N-(2-diethylamino-ethyl)-3-(2-morpholin-4-yl-7-pyridin-4-yl-6,7-dihydro-5H-pyrrolo[2,3-d]pyrimidin-4-yl)-benzamide trifluoroacetic acid salt (G-88);
N-(2-dimethylamino-ethyl)-N-methyl-3-(2-morpholin-4-yl-7-pyridin-4-yl-6,7-dihydro-5H-pyrrolo[2,3-d]pyrimidin-4-yl)-benzamide trifluoroacetic acid salt (G-89);
3-(2-morpholin-4-yl-7-pyridin-4-yl-6,7-dihydro-5H-pyrrolo[2,3-d]pyrimidin-4-yl)-N-(2-pyrrolidin-1-yl-ethyl)-benzamide (G-90);
3-(2-morpholin-4-yl-7-pyridin-3-yl-6,7-dihydro-5H-pyrrolo[2,3-d]pyrimidin-4-yl)-N-(2-pyrrolidin-1-yl-ethyl)-benzamide (G-91);
N-(4,5-dimethyl-thiazol-2-yl)-3-(2-morpholin-4-yl-7-pyridin-3-yl-6,7-dihydro-5H-pyrrolo[2,3-d]pyrimidin-4-yl)-benzamide (G-92);
N-indan-2-yl-3-(2-morpholin-4-yl-7-pyridin-4-yl-6,7-dihydro-5H-pyrrolo[2,3-d]pyrimidin-4-yl)-benzamide (G-93);
(3-hydroxy-piperidin-1-yl)-[3-(2-morpholin-4-yl-7-pyridin-4-yl-6,7-dihydro-5H-pyrrolo [2,3-d]pyrimidin-4-yl)-phenyl]-methanone (G-94);
7-(2-chloro-pyridin-4-yl)-4-(3-methoxy-phenyl)-2-morpholin-4-yl-6,7-dihydro-5H-pyrrolo[2,3-d]pyrimidine trifluoroacetic acid salt (H-01);
3-{7-[2-(3-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-02);
3-{7-[2-(isobutyl-methyl-amino)-pyridin-4-yl]-2-morpholin-4-yl-6,7-dihydro-5H-pyrrolo[2,3-d]pyrimidin-4-yl}-phenol (H-03);
3-{7-[2-(4-ethyl-piperazin-1-yl)-pyridin-4-yl]-2-morpholin-4-yl-6,7-dihydro-5H-pyrrolo[2,3-d]pyrimidin-4-yl}-phenol (H-04);
4'-[4-(3-hydroxy-phenyl)-2-morpholin-4-yl-5,6-dihydro-pyrrolo[2,3-d]pyrimidin-7-yl]-3,4,5,6-tetrahydro-2H-[1,2']bipyridinyl-4-ol (H-05);
4-[4-(3-hydroxy-phenyl)-2-morpholin-4-yl-5,6-dihydro-pyrrolo[2,3-d]pyrimidin-7-yl]-pyridin-2-ol (H-06);
1-(4-{4-[4-(3-hydroxy-phenyl)-2-morpholin-4-yl-5,6-dihydro-pyrrolo[2,3-d]pyrimidin-7-yl]-pyridin-2-yl}-piperazin-1-yl)-ethanone (H-07);
3-{7-[2-(2-hydroxy-ethylamino)-pyridin-4-yl]-2-morpholin-4-yl-6,7-dihydro-5H-pyrrolo[2,3-d]pyrimidin-4-yl}-phenol trifluoroacetic acid salt (H-08);
3-{7-[2-(2-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-09);
3-{7-[2-(2-hydroxy-1-methyl-ethylamino)-pyridin-4-yl]-2-morpholin-4-yl-6,7-dihydro-5H-pyrrolo[2,3-d]pyrimidin-4-yl}-phenol trifluoroacetic acid salt (H-10);
4'-[4-(3-hydroxy-phenyl)-2-morpholin-4-yl-5,6-dihydro-pyrrolo[2,3-d]pyrimidin-7-yl]-3,4,5,6-tetrahydro-2H-[1,2']bipyridinyl-3-ol (H-11);
3-{7-[2-(3-dimethylamino-propylamino)-pyridin-4-yl]-2-morpholin-4-yl-6,7-dihydro-5H-pyrrolo[2,3-d]pyrimidin-4-yl}-phenol (H-12);
3-{7-[2-(3-hydroxy-propylamino)-pyridin-4-yl]-2-morpholin-4-yl-6,7-dihydro-5H-pyrrolo[2,3-d]pyrimidin-4-yl}-phenol trifluoroacetic acid salt (H-13);
3-(7-{2-[(2-hydroxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-14);
3-(7-{2-[(2-methoxy-ethyl)-methyl-amino]-pyridin-4-yl}-2-morpholin-4-yl-6,7-dihydro-5H-pyrrolo[2,3-d]pyrimidin-4-yl)-phenol trifluoroacetic acid salt (H-15);
3-(7-{2-[(2-dimethylamino-ethyl)-ethyl-amino]-pyridin-4-yl}-2-morpholin-4-yl-6,7-dihydro-5H-pyrrolo[2,3-d]pyrimidin-4-yl)-phenol trifluoroacetic acid salt (H-16);
3-{7-[2-((R)-2-hydroxymethyl-pyrrolidin-1-yl)-pyridin-4-yl]-2-morpholin-4-yl-6,7-dihydro-5H-pyrrolo[2,3-d]pyrimidin-4-yl}-phenol trifluoroacetic acid salt (H-17);
3-[2-morpholin-4-yl-7-(4-pyrrolidin-1-yl-3,4,5,6-tetrahydro-2H-[1,2']bipyridinyl-4'-yl)-6,7-dihydro-5H-pyrrolo[2,3-d]pyrimidin-4-yl]-phenol trifluoroacetic acid salt (H-18);
3-{7-[2-(cyclohexylmethyl-amino)-pyridin-4-yl]-2-morpholin-4-yl-6,7-dihydro-5H-pyrrolo[2,3-d]pyrimidin-4-yl}-phenol trifluoroacetic acid salt (H-19);
3-{7-[2-(3,3-dimethyl-butylamino)-pyridin-4-yl]-2-morpholin-4-yl-6,7-dihydro-5H-pyrrolo[2,3-d]pyrimidin-4-yl}-phenol trifluoroacetic acid salt (H-20);
3-{7-[2-(isobutyl-methyl-amino)-pyridin-4-yl]-2-morpholin-4-yl-6,7-dihydro-5H-pyrrolo[2,3-d]pyrimidin-4-yl}-phenol (H-21);
3-(7-{2-[methyl-(3-methyl-butyl)-amino]-pyridin-4-yl}-2-morpholin-4-yl-6,7-dihydro-5H-pyrrolo[2,3-d]pyrimidin-4-yl)-phenol (H-22);
1-{4-[4-(3-hydroxy-phenyl)-2-morpholin-4-yl-5,6-dihydro-pyrrolo[2,3-d]pyrimidin-7-yl]-pyridin-2-yl}-pyrrolidin-3-ol (H-23);
3-{2-morpholin-4-yl-7-[2-(4-phenyl-piperazin-1-yl)-pyridin-4-yl]-6,7-dihydro-5H-pyrrolo[2,3-d]pyrimidin-4-yl}-phenol trifluoroacetic acid salt (H-24);
3-{7-[2-(cyclopropylmethyl-propyl-amino)-pyridin-4-yl]-2-morpholin-4-yl-6,7-dihydro-5H-pyrrolo[2,3-d]pyrimidin-4-yl}-phenol trifluoroacetic acid salt (H-25);
3-{7-[2-(2,6-dimethyl-morpholin-4-yl)-pyridin-4-yl]-2-morpholin-4-yl-6,7-dihydro-5H-pyrrolo[2,3-d]pyrimidin-4-yl}-phenol trifluoroacetic acid salt (H-26);
3-{2-morpholin-4-yl-7-[2-(3-morpholin-4-yl-propylamino)-pyridin-4-yl]-6,7-dihydro-5H-pyrrolo[2,3-d]pyrimidin-4-yl}-phenol trifluoroacetic acid salt (H-27);
3-{7-[2-(indan-2-ylamino)-pyridin-4-yl]-2-morpholin-4-yl-6,7-dihydro-5H-pyrrolo[2,3-d]pyrimidin-4-yl}-phenol trifluoroacetic acid salt (H-28);
3-{7-[2-(2,5-dihydro-pyrrol-1-yl)-pyridin-4-yl]-2-morpholin-4-yl-6,7-dihydro-5H-pyrrolo[2,3-d]pyrimidin-4-yl}-phenol trifluoroacetic acid salt (H-29);
3-[7-(2-cyclohexylamino-pyridin-4-yl)-2-morpholin-4-yl-6,7-dihydro-5H-pyrrolo[2,3-d]pyrimidin-4-yl]-phenol trifluoroacetic acid salt (H-30);
5-[2-morpholin-4-yl-7-(2-morpholin-4-yl-pyridin-4-yl)-6,7-dihydro-5 pyrrolo[2,3-d]pyrimidin-4-yl]-pyrimidin-2-ylamine (H-31);

5-[7-(2-dimethylaminoethoxy-pyridin-4-yl)-2-morpholin-4-yl-6,7-dihydro-5H-pyrrolo[2,3-d]pyrimidin-4-yl]-pyrimidin-2-ylamine (H-32)

N-{4-[4-(2-amino-pyrimidin-5-yl)-2-morpholin-4-yl-5,6-dihydro-pyrrolo[2,3-d]pyrimidin-7-yl]-pyridin-2-yl}-N,N',N'-trimethyl-propan-1,3-diamine (H-33);

5-{7-[2-(4-ethyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-34);

{4'-[4-(2-amino-pyrimidin-5-yl)-2-morpholin-4-yl-5,6-dihydro-pyrrolo[2,3-d]pyrimidin-7-yl]-3,4,5,6-tetrahydro-2H-[1,2']bipyridinyl-4-yl}-dimethyl-amine (H-35);

5-{7-[2-(4-methyl-piperazin-1-yl)-pyridin-4-yl]-2-morpholin-4-yl-6,7-dihydro-5H-pyrrolo[2,3-d]pyrimidin-4-yl}-pyrimidin-2-ylamine (H-36); and N-{3-[4-(2-amino-pyrimidin-5-yl)-2-morpholin-4-yl-5,6-dihydro-pyrrolo[2,3-d]pyrimidin-7-yl]-phenyl}-methanesulfonamide (I-01);

or a pharmaceutically acceptable salt thereof.

16. A compound represented by the following general formula (II):

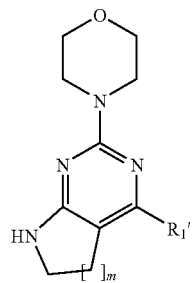

(II)

wherein, m represents an integer of 1 or 2;

$R^1$, represents a cyclic substituent selected from the following group having n substituents T;

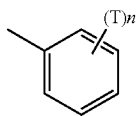 $R_1a$

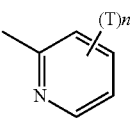 $R_1b1$

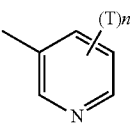 $R_1b2$

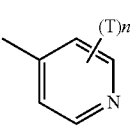 $R_1b3$

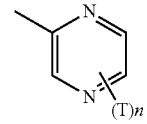 $R_1c1$

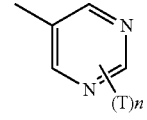 $R_1c2$

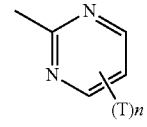 $R_1c3$

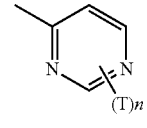 $R_1c4$

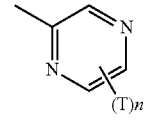 $R_1c5$

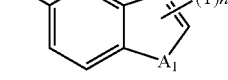 $R_1d$

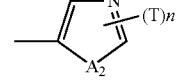 $R_1e$

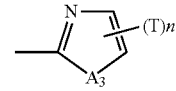 $R_1f$ $A_1$, $A_2$ and $A_3$ are respectively and independently selected from NH, S or O;

T represents a substituent selected from the following group B:

Group B:
- -Cyc,
- —$C_{1-6}$alkyl,
- —$C_{1-6}$alkylene-OR,
- —$C_{1-6}$alkylene-NRR',
- —$C_{1-6}$alkylene-CONRR',
- —$C_{1-6}$alkylene-NRCOR',
- —$C_{1-6}$alkylene-Cyc,
- —OR,
- —O-halogeno$C_{1-6}$alkyl,
- —O—$C_{1-6}$alkylene-Cyc,
- —O—COOR
- —O—COR,
- —O—CONRR',
- —NRR'
- —NR—$C_{1-6}$alkylene-NR'R",
- —NR—$C_{1-6}$alkylene-OR',
- -halogen,
- —CO-Cyc, —CO-Cyc-Cyc,
—CO—$C_{1-6}$alkylene-Cyc,
—COOR,
—COO—$C_{1-6}$alkylene-OR,
—COO—$C_{1-6}$alkylene-NRR',
—COO—$C_{1-6}$alkylene-Cyc,
—CONRR'
—CONR—$C_{1-6}$alkylene-OR',
—CONR—$C_{1-6}$alkylene-NR'R'',
—CONR—$C_{1-6}$alkylene-CONR'R'',
—CONR-Cyc,
—CONR—$C_{1-6}$alkylene-Cyc,
—$SO_2NRR'$
—$NRSO_2R'$
—CN, and n represents an integer of 0, 1, 2, 3, 4 or 5 (T may be the same or different when n is 2 to 5);

in the aforementioned group B,

R, R' and R'' may be respectively and independently the same or different and represent a hydrogen atom or a —$C_{1-6}$ alkyl (said —$C_{1-6}$ alkyl may be substituted by a group selected from —OH, —O($C_{1-6}$ alkyl), —COOH, —COO($C_{1-6}$ alkyl), —$CONH_2$, —CONH ($C_{1-6}$ alkyl), —CON($C_{1-6}$ alkyl)$_2$, —NHCO($C_{1-6}$ alkyl), —$NH_2$, —NH($C_{1-6}$ alkyl) and —N($C_{1-6}$ alkyl)$_2$);

Cyc represents a hydrocarbon ring or nitrogen-containing heterocyclic ring (said hydrocarbon ring and nitrogen-containing heterocylic ring may be substituted at 1 to 3 locations by a group selected from —R(R is not a hydrogen atom at this time), —CO—R, —COOR, —CONRR', —NRCOR', -halogeno $C_{1-6}$ alkyl, halogen atom, —OR, —O-halogeno $C_{1-6}$ alkyl, —NRR' and —$SO_2R$);

said $C_{1-6}$ alkylene in the group B may be substituted at 1 to 3 locations by a group selected from —$C_{1-6}$ alkyl, —OH, —$CONH_2$—$NH_2$, —NH($C_{1-6}$ alkyl) and —N($C_{1-6}$ alkyl)$_7$; and R, R' and R'' in said —NRR', —NR'R'' or —CONRR' in the group B and Cyc may form a 3- to 7-member nitrogen-containing saturated hydrocarbon ring together with an adjacent N;

or $R^1$, is the selected from the following group:

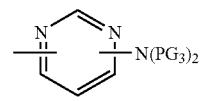

R1'a

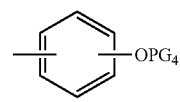

R1'b wherein, $PG_3$ represents an amine-protecting group selected from methoxycarbonyl, ethoxycarbonyl, t-butoxycarbonyl, benzyloxycarbonyl, 9-fluorenylmethyloxycarbonyl (Fmoc), formyl, acetyl, chloroacetyl, trichloroacetyl, trifluoroacetyl, benzoyl, methyl, allyl, benzyl, 2-methoxybenzyl, 4-methoxybenzyl or 2,4-dimethoxybenzyl; and $PG_4$ represents a hydroxyl group-protecting group selected from methyl, t-butyl, methoxymethyl, methylthiomethyl, 2-methoxyethoxymethyl, benzyloxymethyl, tetrahydropyranyl (THP), tetrahydrofuranyl, trimethylsilyl, triethylsilyl, t-butyldimethylsilyl, formyl, acetyl, pivaloyl, benzoyl, methoxycarbonyl, ethoxycarbonyl or vinyloxycarbonyl.

17. A pharmaceutical composition comprising as an active ingredient thereof the compound according to claim 1 and at least one pharmaceutically acceptable carrier, excipient, diluent or vehicle; or pharmaceutically acceptable salt thereof.

18. A pharmaceutical composition comprising as an active ingredient thereof the compound according to claim 1 and at least one pharmaceutically acceptable diluent or vehicle;

or pharmaceutically acceptable salt thereof.

* * * * *